(12) United States Patent
Nasveschuk et al.

(10) Patent No.: US 12,371,442 B2
(45) Date of Patent: *Jul. 29, 2025

(54) ISOINDOLINONE AND INDAZOLE COMPOUNDS FOR THE DEGRADATION OF EGFR

(71) Applicant: C4 Therapeutics, Inc., Watertown, MA (US)

(72) Inventors: Christopher G. Nasveschuk, Stoneham, MA (US); Martin Duplessis, Somerville, MA (US); Jae Young Ahn, Somerville, MA (US); Alexander W. Hird, Belmont, MA (US); Ryan E. Michael, Erie, CO (US); Kiel Lazarski, Boston, MA (US); Yanke Liang, Belmont, MA (US); Georg Jaeschke, Basel (CH); Antonio Ricci, Biel-Benken (CH); Annick Goergler, Colmar (FR); Daniel Rueher, Raedersdorf (FR)

(73) Assignee: C4 Therapeutics, Inc., Watertown, MA (US)

( * ) Notice: Subject to any disclaimer, the term of this patent is extended or adjusted under 35 U.S.C. 154(b) by 80 days.

This patent is subject to a terminal disclaimer.

(21) Appl. No.: 18/144,800

(22) Filed: May 8, 2023

(65) Prior Publication Data

US 2024/0076300 A1    Mar. 7, 2024

Related U.S. Application Data

(63) Continuation of application No. 17/843,769, filed on Jun. 17, 2022, now Pat. No. 11,673,902, which is a continuation of application No. PCT/US2020/066211, filed on Dec. 18, 2020.

(60) Provisional application No. 62/951,464, filed on Dec. 20, 2019, provisional application No. 62/951,467, filed on Dec. 20, 2019.

(51) Int. Cl.
| | |
|---|---|
| C07D 519/00 | (2006.01) |
| A61K 9/00 | (2006.01) |
| A61K 9/02 | (2006.01) |
| A61K 9/08 | (2006.01) |
| A61K 9/20 | (2006.01) |
| A61K 9/48 | (2006.01) |
| A61K 47/10 | (2017.01) |
| A61K 47/12 | (2006.01) |
| A61K 47/26 | (2006.01) |
| A61K 47/32 | (2006.01) |
| A61K 47/38 | (2006.01) |
| C07D 487/04 | (2006.01) |

(52) U.S. Cl.
CPC .......... *C07D 519/00* (2013.01); *A61K 9/009* (2013.01); *A61K 9/02* (2013.01); *A61K 9/08* (2013.01); *A61K 9/2013* (2013.01); *A61K 9/2018* (2013.01); *A61K 9/2054* (2013.01); *A61K 9/4825* (2013.01); *A61K 9/485* (2013.01); *A61K 9/4858* (2013.01); *A61K 9/4866* (2013.01); *A61K 47/10* (2013.01); *A61K 47/12* (2013.01); *A61K 47/26* (2013.01); *A61K 47/32* (2013.01); *A61K 47/38* (2013.01); *C07D 487/04* (2013.01)

(58) Field of Classification Search
CPC ...... C07D 495/04; A61K 9/0014; A61K 9/06; A61K 47/12; A61K 47/38

See application file for complete search history.

(56) References Cited

U.S. PATENT DOCUMENTS

| | | |
|---|---|---|
| 5,635,517 A | 6/1997 | Muller et al. |
| 6,306,663 B1 | 10/2001 | Kenten et al. |
| 8,008,332 B2 | 8/2011 | Cao et al. |
| 2014/0302523 A1 | 10/2014 | Crews et al. |
| 2014/0356322 A1 | 12/2014 | Crews et al. |
| 2015/0291562 A1 | 10/2015 | Crew et al. |
| 2016/0022642 A1 | 1/2016 | Crews et al. |
| 2016/0045607 A1 | 2/2016 | Crew et al. |
| 2016/0046661 A1 | 2/2016 | Gray et al. |
| 2016/0058872 A1 | 3/2016 | Crew et al. |
| 2016/0176916 A1 | 6/2016 | Bradner et al. |
| 2016/0272639 A1 | 9/2016 | Crew et al. |
| 2018/0085465 A1 | 3/2018 | Bradner et al. |
| 2018/0290975 A1 | 10/2018 | Gray et al. |
| 2019/0247509 A1 | 8/2019 | Buckley et al. |

FOREIGN PATENT DOCUMENTS

| | | |
|---|---|---|
| WO | WO 2016/065139 A1 | 4/2016 |
| WO | WO 2016/105518 A1 | 6/2016 |
| WO | WO 2016/197032 A1 | 12/2016 |
| WO | WO 2017/024317 A2 | 2/2017 |
| WO | WO 2017/079267 A1 | 5/2017 |
| WO | WO 2017/161119 A1 | 9/2017 |
| WO | WO 2017/185036 A1 | 10/2017 |
| WO | WO 2017/197051 A1 | 11/2017 |

(Continued)

OTHER PUBLICATIONS

U.S. Pat. No. 10,646,575, B2, U.S. Appl. No. 16/186,339, Phillips et al., May 12, 2020.

(Continued)

*Primary Examiner* — Genevieve S Alley

(74) *Attorney, Agent, or Firm* — Knowles Intellectual Property Strategies, LLC

(57) ABSTRACT

The invention provides compounds that degrade the epidermal growth factor receptor (EGFR) including mutant forms via the ubiquitination of the EGFR protein and subsequent proteasomal degradation. The compounds are useful for the treatment of various cancers.

28 Claims, No Drawings

(56) References Cited

FOREIGN PATENT DOCUMENTS

| WO | WO 2017/197055 A1 | 11/2017 |
|---|---|---|
| WO | WO 2017/201069 A1 | 11/2017 |
| WO | WO 2018/111902 A1 | 6/2018 |
| WO | WO 2018/115218 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/144649 A1 | 8/2018 |
| WO | WO 2018/220149 A1 | 12/2018 |
| WO | WO 2018/237026 A1 | 12/2018 |
| WO | WO 2019/060742 A1 | 3/2019 |
| WO | WO 2019/140387 A1 | 7/2019 |
| WO | WO 2019/149922 A1 | 8/2019 |
| WO | WO 2020/002487 A1 | 1/2020 |

OTHER PUBLICATIONS

U.S. Pat. No. 10,660,968, B2, U.S. Appl. No. 16/186,334, Phillips et al., May 26, 2020.
U.S. Pat. No. 10,849,982, B2, U.S. Appl. No. 16/186,341, Phillips et al., Dec. 1, 2020.
U.S. Pat. No. 10,905,768, B2, U.S. Appl. No. 16/872,225, Phillips et al., Feb. 2, 2021.
U.S. Pat. No. 11,185,592, B2, U.S. Appl. No. 16/882,236, Phillips et al., Nov. 30, 3021.
U.S. Pat. No. 11,254,672, B2, U.S. Appl. No. 16/809,325, Norcross et al., Feb. 22, 2022.
U.S. Pat. No. 11,401,256, B2, U.S. Appl. No. 16/809,345, Norcross et al., Aug. 2, 2022.
U.S. Pat. No. 11,407,732, B2, U.S. Appl. No. 17/498,617, Henderson et al., Aug. 9, 2022.
U.S. Pat. No. 11,459,335, A1, U.S. Appl. No. 16/721,650, Phillips et al., Oct. 4, 2022.
U.S. Pat. No. 11,524,949, A1, U.S. Appl. No. 16/874,475, Phillips et al., Dec. 13, 2022.
U.S. Pat. No. 11,584,748, A1, U.S. Appl. No. 17/072,896, Nasveschuk et al., Feb. 21, 2023.
U.S. Pat. No. 11,623,929, A1, U.S. Appl. No. 17/103,621, Nasveschuk et al., Apr. 11, 2023.
U.S. Pat. No. 11,673,902, B2, U.S. Appl. No. 17/843,769, Nasveschuk et al., Jun. 13, 2023.
U.S. Pat. No. 11,691,972, A1, U.S. Appl. No. 17/541,035, Nasveschuk et al., Jul. 4, 2023.
US, 2020/0207783, A1, U.S. Appl. No. 16/809,336, Norcross et al., Jul. 2, 2020.
US, 2020/0207733, A1, U.S. Appl. No. 16/809,345, Norcross et al., Jul. 2, 2020.
US, 2021/0009559, A1, U.S. Appl. No. 17/031,550, Henderson et al., Jan. 14, 2021.
US, 2021/0198256, A1, U.S. Appl. No. 17/192,634, Nasveschuk et al., Jul. 1, 2021.
US, 2022/0289738, A1, U.S. Appl. No. 17/576,582, Norcross et al., Sep. 15, 2022.
US, 2022/0313826, A1, U.S. Appl. No. 17/107,781, Phillips et al., Oct. 6, 2022.
US, 2022/0313827, A1, U.S. Appl. No. 17/121,389, Phillips et al., Oct. 6, 2022.
US, 2022/0372016, A1, U.S. Appl. No. 17/351,935, Phillips et al., Nov. 24, 2022.
US, 2023/0014124, A1, U.S. Appl. No. 17/164,446, Phillips et al., Jan. 19, 2023.
US, 2023/0019060, A1, U.S. Appl. No. 17/465,583, Nasveschuk et al., Jan. 19, 2023.
US, 2023/0060334, A1, U.S. Appl. No. 17/901,775, Nasveschuk et al., Mar. 2, 2023.
US, 2023/0082430, A1, U.S. Appl. No. 17/723,199, Henderson et al., Mar. 16, 2023.
US, 2023/0095223, A1, U.S. Appl. No. 17/524,558, Phillips et al., Mar. 30, 2023.
US, 2023/0145336, A1, U.S. Appl. No. 18/084,380, Nasveschuk et al., May 11, 2023.
US, 2023/0190760, A1, U.S. Appl. No. 18/106,893, Proia et al., Jun. 22, 2023.
US, 2023/0192643, A1, U.S. Appl. No. 17/878,753, Norcross et al., Jun. 22, 2023.
US, 2023/0233692, A1, U.S. Appl. No. 18/105,735, Henderson et al., Jul. 27, 2023.
U.S. Pat. No. 10,660,968, B2, U.S. Appl. No. 16/186,334, Phillips et al., May 12, 2020.
U.S. Pat. No. 11,185,592, B2, U.S. Appl. No. 16/882,236, Phillips et al., Nov. 30, 2021.
U.S. Pat. No. 11,254,672, B2, U.S. Appl. No. 16/809,325, Norcorss et al., Feb. 22, 2022.
US, 2020/0140456, A1, U.S. Appl. No. 16/721,650, Phillips et al., May 7, 2020.
US, 2020/0308171, A1, U.S. Appl. No. 16/903,237, Jaeschke et al., Oct. 1, 2020.
US, 2021/0032245, A1, U.S. Appl. No. 17/072,896, Nasveschuk et al., Feb. 4, 2021.
US, 2021/0070763, A1, U.S. Appl. No. 17/103,621, Nasveschuk et al., Mar. 11, 2021.
US, 2022/0098194, A1, U.S. Appl. No. 17/541,035, Nasveschuk et al., Mar. 31, 2022.
US, 2023/0279023, A1, U.S. Appl. No. 17/959,144, Phillips et al., Sep. 7, 2023.
U.S. Appl. No. 18/240,231, Henderson et al., Aug. 30, 2023.
U.S. Appl. No. 18/100,992, Nasveschuk et al., Jan. 24, 2023.
U.S. Appl. No. 18/117,978, Nasveschuk et al., Mar. 6, 2023.
U.S. Appl. No. 18/134,971, Nasveschuk et al., Apr. 14, 2023.
U.S. Appl. No. 18/134,985, Nasveschuk et al., Apr. 14, 2023.
U.S. Appl. No. 18/134,990, Nasveschuk et al., Apr. 14, 2023.
U.S. Appl. No. 17/965,569, Nasveschuk et al., Oct. 13, 2022.
U.S. Appl. No. 18/079,815, Phillips et al., Dec. 12, 2022.
U.S. Appl. No. 18/370,186, Norcross et al., Sep. 19, 2023.
U.S. Pat. No. 11,802,131, A1, U.S. Appl. No. 16/809,336, Norcross et al., Oct. 31, 2023.
U.S. Pat. No. 11,401,256, A1, U.S. Appl. No. 16/809,345, Norcross et al., Aug. 2, 2022.
U.S. Pat. No. 11,753,397, A1, U.S. Appl. No. 17/031,550, Henderson et al., Sep. 12, 2023.
U.S. Pat. No. 11,787,802, A1, U.S. Appl. No. 17/576,582, Norcross et al., Oct. 17, 2023.
U.S. Appl. No. 18/534,395, Nasveshuk et al., Dec. 8, 2023.
U.S. Appl. No. 18/516,589, Nasveshuk et al., Nov. 21, 2023.
U.S. Appl. No. 18/385,277, Norcross et al., Oct. 30, 2023.
Li, P. et al. "The next generation of EGFR inhibitors: a patenting perspective of PROTACs based EGFR degraders," Expert Opinion on Therapeutic Patents, vol. 33, Nos. 7-8, p. 477-492, (Nov. 6, 2023).
Ayatia, Adileh et al., "A review on progression of epidermal growth factor receptor (EGFR) inhibitors as an efficient approach in cancer targeted therapy." Bioorganic Chemistry 99 (2020) 103811.
Bartlett, et al. "The evolution of thalidomide and its IMiD derivatives as anticancer agents," Nat Rev Cancer, Apr. 2004, 4(4):314-322.
Berndsen et al. "New insights into ubiquitin E3 ligase mechanism," Nat. Struct. Mol. Biol. Nature America, Inc. Apr. 2014, 21:4, 301-307.
Bondeson et al. "Catalytic in vivo protein knockdown by small-molecule PROTACs" Nature Chemical Biology Jun. 10, 2015, 11:611-617.
C4 Therapeutics Presentation Phillips—"Small Molecule Driven Targeted Protein Degradation", ChemBio in the Hub 47, Cambridge, MA, 47 pages (Oct. 22, 2018).
C4 Therapeutics Presentation Fisher—"Targeted Protein Degradation", Targeted Protein Degradation Summit, Boston, MA, 39 pages, Oct. 24-25, 2018.
C4 Therapeutics Presentation Fisher—"Degrader Drugs: From cellular activity to in vivo pharmacology Discovery on Target," Boston, MA, 21 pages, Sep. 18, 2019.

(56) References Cited

OTHER PUBLICATIONS

C4 Therapeutics Presentation Nasveschuk—"Degrader Drug Space: What Rules?" HT-ADME Conference Cambridge, MA, Jun. 20, 2019; 20 pages.

Chamberlain et al. "Structure of the human cereblon-DDB1-lenalidomide complex reveals basis for responsiveness to thalidomide analogs" Nature Structural and Molecule Biology, Nature American, Inc., Sep. 2014, 21(9):803-809.

Corson et al. "Design and applications of bifunctional small molecules: Why two heads are better than one" ACS Chemical Biology Nov. 21, 2008, 3(11): 677-692.

Fischer et al. "Structure of the DDB1-CRBN E3 ubiquitin ligase in complex with thalidomide" Nature Aug. 7, 2014, Macmillan Publisher Limited, 512:49-53.

Fischer et al. "The Molecular Basis of $CRL4^{DDB2/CSA}$ Ubiquitin Ligase Architecture, Targeting, and Activation," Cell Nov. 23, 2011, 147:1024-1039.

International Search Report and Written Opinion for PCT/US2020/066211, filed Dec. 18, 2020.

Jang, Jaebong et al., "Mutant-Selective Allosteric EGFR Degraders are Effective Against a Broad Range of Drug-Resistant Mutations," Angew Chem Int Ed Engl. Aug. 17, 2020; 59(34): 14481-14489.

Zhang, Hao et al., "Discovery of potent epidermal growth factor receptor (EGFR) degraders by proteolysis targeting chimera (PROTAC)," European Journal of Medicinal Chemistry, European Journal of Medicinal Chemistry 189 (2020) 112061.

ISOINDOLINONE AND INDAZOLE COMPOUNDS FOR THE DEGRADATION OF EGFR

CROSS-REFERENCE TO RELATED APPLICATIONS

This application is a continuation of U.S. patent application Ser. No. 17/843,769, filed on Jun. 17, 2022, which is a continuation of International Application No. PCT/US2020/066211 filed in the U.S. Receiving Office on Dec. 18, 2020, which claims the benefit of U.S. Provisional Application 62/951,464 filed Dec. 20, 2019, and U.S. Provisional Application 62/951,467 filed Dec. 20, 2019, the entirety of each of these applications is incorporated by reference for all purposes.

FIELD OF THE INVENTION

The invention provides compounds that degrade the epidermal growth factor receptor (EGFR) including mutant forms via the ubiquitination of the EGFR protein and subsequent proteasomal degradation. The compounds are useful for the treatment of various cancers.

BACKGROUND OF THE INVENTION

The HER family receptor tyrosine kinases are mediators of cell growth, differentiation, and survival. The receptor family includes four distinct members, i.e. epidermal growth factor receptor (EGFR, ErbB1, or HER1), HER2 (ErbB2), HER3 (ErbB3) and HER4 (ErbB4). Upon ligand binding, the receptors form homo and heterodimers and subsequent activation of the intrinsic tyrosine kinase activity leads to receptor auto-phosphorylation and the activation of downstream signaling molecules (Yarden, Y., Sliwkowski, MX. Untangling the ErbB signaling network. Nature Review Mol Cell Biol. 2001 February; 2(2): 127-37). These signaling molecules promote cell growth and proliferation. Deregulation of EGFR by overexpression or mutation has been implicated in many types of human cancer including colorectal, pancreatic, gliomas, head and neck and lung cancer, in particular non-small cell lung cancer (NSCLC). Several EGFR targeting agents have been developed over the years (Ciardiello, F., and Tortora, G. (2008). EGFR antagonists in cancer treatment. The New England journal of medicine 358, 1160-1174). Erlotinib (Tarceva®), a reversible inhibitor of the EGFR tyrosine kinase is approved in numerous countries for the treatment of recurrent NSCLC.

An impressive single agent activity of EGFR tyrosine kinase inhibitors is observed in a subset of NSCLC patients whose tumors harbor somatic kinase domain mutations, whereas clinical benefit in wild-type EGFR patients is greatly diminished (Paez, J. et al. (2004). EGFR mutations in lung cancer: correlation with clinical response to gefitinib therapy. Science (New York, NY 304, 1497-1500). The most common somatic mutations of EGFR are exon 19 deletions with delta 746-750 the most prevalent mutation and the exon 21 amino acid substitutions with L858R the most frequent mutation (Sharma S V, Bell D W, Settleman J, Haber D A. Epidermal growth factor receptor mutations in lung cancer. Nat Rev Cancer. 2007 March; 7(3): 169-81).

Treatment resistance arises frequently, often due to the secondary T790M mutation within the ATP site of the receptor. Some developed mutant-selective irreversible inhibitors are highly active against the T790M mutant, but their efficacy can be compromised by acquired mutation of C797S, that is the cysteine residue with which they form a key covalent bond (Thress, K. S. et al. Acquired EGFR C797S mutation mediates resistance to AZD9291 in non-small cell lung cancer harboring EGFR T790M. Nat. Med. 21, 560-562 (2015)). C797S mutation was further reported by Wang to be a major mechanism for resistance to T790M-targeting EGFR inhibitors (Wang et al. EGFR C797S mutation mediates resistance to third-generation inhibitors in T790M-positive non-small cell lung cancer, J Hematol Oncol. 2016; 9: 59). Additional mutations that cause resistance to Osimertinib are described by Yang, for example L718Q. (Yang et al, Investigating Novel Resistance Mechanisms to Third-Generation EGFR Tyrosine Kinase Inhibitor Osimertinib in Non-Small Cell Lung Cancer Patients, Clinical Cancer Research, DOI: 10.1158/1078-0432.CCR-17-2310). Additional mutations targeting strategies are also known including Targeting EGFRL858R/T790M and EGFRL858R/T790M/C797S resistance mutations in NSCLC treatment (Lu et al. Targeting EGFR$^{L858R/T790M}$ and EGFR$^{L858R/T790M/C797S}$ resistance mutations in NSCLC: Current developments in medicinal chemistry, Med Res Rev 2018; 1-32).

Additional examples of EGFR inhibitors, in particular selective inhibitors of T790M containing EGFR mutants, have also been described including those described in WO2014081718, WO2014210354, WO2018/115218, WO2018220149, WO2020002487, and ZHOU et al., "Novel mutant-selective EGFR kinase inhibitors against EGFR T790M", NATURE, (20091224), vol. 462, no. 7276, doi:10.1038/nature08622, ISSN 0028-0836, pages 1070-1074.

As most available EGFR tyrosine kinase inhibitors target the ATP-site of the kinase, there is a need for new therapeutic agents that work differently, for example through targeting drug-resistant EGFR mutants.

Recent studies suggest that purposefully targeting allosteric sites might lead to mutant-selective inhibitors (Jia et al. Overcoming EGFR (T790M) and EGFR(C797S) resistance with mutant-selective allosteric inhibitors, June 2016, Nature 534, 129-132).

The field of targeted protein degradation promoted by small molecules has been intensively studied (Collins et al., Biochem J, 2017, 474(7), 1127-47). Protein degradation plays a role in various cellular functions. For example, the body uses protein degradation to adjust the concentrations of regulatory proteins through degradation into small peptides to maintain health and productivity of the cells.

Cereblon is a protein that forms an E3 ubiquitin ligase complex, which ubiquitinates various other proteins. Cereblon is known as the primary target for the anticancer thalidomide analogs. A higher expression of cereblon has been linked to the efficiency of thalidomide analogs in cancer therapy.

Compounds have been described as useful modulators of targeted ubiquitination, for example the compounds described in. WO2013020557, WO2013063560, WO2013106643, WO/2013170147, WO2016011906, and WO/2019183523 can be used for targeted ubiquitination. Additional modulators for targeted ubiquitination include those described by Ranok Therapeutics Hangzhou WO2020206608 and WO2020207396; those described by Arvinas in WO2015160845, WO2016149668, WO2016197032, WO2017011590, WO2017030814, WO2018144649, WO2018226542, and WO2019199816; those described by Dana-Farber Cancer Institute in WO2016105518, WO2017007612, WO2017024317, WO2017024318, WO2017117473, WO2017117474, WO2018148443, WO2018148440, and WO2019165229; those described by Kymera in WO2019/060742, WO2019/140387, and WO2020/01022; and those described by C4 Therapeutics Inc. in WO2017197036, WO2017197046, WO2017197051, WO2017197055, WO2018237026, WO2019099868, WO2019191112, WO2019204353, WO2019236483, WO2020132561, WO2020181232, and WO2020210630.

Some specific molecules for the degradation of EGFR have also been described, for example, Dana-Farber Cancer Institute described EGFR degraders in WO2017185036. F. Hoffman-La-Roche described EGFR degraders in WO2019121562 and WO2019149922. Arvinas has described EGFR degraders in WO2018119441.

Despite these efforts, there remains a need for new EGFR modulators to treat disorders mediated by EGFR in hosts, and in particular humans, in need thereof.

SUMMARY OF THE INVENTION

Compounds and their uses and manufacture are provided that degrade the epidermal growth factor receptor protein (EGFR) via the ubiquitin proteasome pathway (UPP). The present invention provides compounds of Formula I, II, III, or IV or a pharmaceutically acceptable salt thereof that include a Targeting Ligand that binds to EGFR, an E3 Ligase binding portion (typically via a cereblon subunit), and a Linker that covalently links the Targeting Ligand to the E3 Ligase binding portion. In certain embodiments the E3 Ligase binding portion is a moiety of A or A*, the Linker is a moiety of $L^1$ or $L^2$, and the remainder of the molecule is the EGFR Targeting Ligand portion. In certain embodiments a compound of the present invention degrades EGFR with a mutation or combination of mutations, for example a mutation selected from T790M, L858R, and C797S; the combination of two mutations selected from T790M, L858R, and C797S; or the combination of three mutations selected from T790M, L858R, and C797S. In certain embodiments a compound of the present invention is a selective degrader of T790M/L858R, T790M/L858R/C797S, L858R, or L858R/C797S containing EGFR mutants.

A compound of the present invention provided herein or its pharmaceutically acceptable salt and/or its pharmaceutically acceptable composition can be used to treat a disorder which is mediated by EGFR. In some embodiments a method to treat a patient with a disorder mediated by EGFR is provided that includes administering an effective amount of one or more compounds as described herein, or a pharmaceutically acceptable salt thereof, to the patient, typically a human, optionally in a pharmaceutically acceptable composition.

In one aspect the present invention provides a compound of Formula I

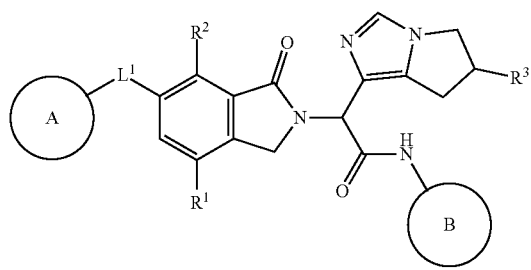

(I)

or a pharmaceutically acceptable salt thereof;
wherein:
A is selected from the ring systems AF and AG;

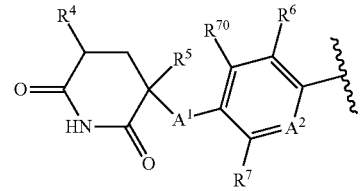

AF

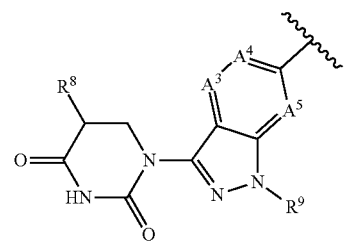

AG $A^1$ is selected from
  i) —NH—, and
  ii) —O—;
$A^2$ is selected from
  i) —N—, and
  ii) —$CR^{52}$—;
$A^3$ is selected from
  i) —N—, and
  ii) —$CR^{53}$—;
$A^4$ is selected from
  i) —N—, and
  ii) —$CR^{54}$—;
$A^5$ is selected from
  i) —N—, and
  ii) —$CR^{55}$—;
$R^1$ is selected from
  i) H,
  ii) halogen
  iii) $C_{1-6}$-alkyl;
$R^{52}$ is selected from
  i) H,
  ii) halogen,
  iii) cyano,
  iv) $C_{1-6}$-alkoxy,
  v) halo-$C_{1-6}$-alkoxy,
  vi) $C_{1-6}$-alkyl,
  vii) halo-$C_{1-6}$-alkyl,
  viii) $C_{3-8}$-cycloalkyl, and
  ix) halo-$C_{3-8}$-cycloalkyl;
$R^{53}$, $R^{54}$ and $R^{55}$ are independently selected from
  i) H,
  ii) halogen,
  iii) $C_{1-6}$-alkyl,
  iv) halo-$C_{1-6}$-alkyl,
  v) $C_{3-8}$-cycloalkyl, and
  vi) halo-$C_{3-8}$-cycloalkyl;
$R^2$ is selected from
  i) H,
  ii) halogen,
  iii) $C_{1-6}$-alkyl,
  iv) halo-$C_{1-6}$-alkyl,
  v) $C_{3-8}$-cycloalkyl, and
  vi) halo-$C_{3-8}$-cycloalkyl;

$R^3$ is selected from
i) H,
ii) halogen,
iii) $C_{1-6}$-alkyl,
iv) halo-$C_{1-6}$-alkyl,
v) $C_{3-8}$-cycloalkyl, and
vi) halo-$C_{3-8}$-cycloalkyl;
$R^4$ and $R^5$ are H;
or $R^4$ and $R^5$ together form —$(CH_2)_q$—;
q is 1 or 2;
$R^6$ is selected from
i) H,
ii) halogen,
iii) cyano,
iv) $C_{1-6}$-alkoxy,
v) halo-$C_{1-6}$-alkoxy,
vi) $C_{1-6}$-alkyl,
vii) halo-$C_{1-6}$-alkyl,
viii) $C_{3-8}$-cycloalkyl, and
ix) halo-$C_{3-8}$-cycloalkyl;
$R^7$ is selected from
i) H,
ii) halogen,
iii) cyano,
iv) $C_{1-6}$-alkyl,
v) halo-$C_{1-6}$-alkyl,
vi) $C_{3-8}$-cycloalkyl, and
vii) halo-$C_{3-8}$-cycloalkyl;
$R^{70}$ is selected from
i) H,
ii) halogen,
iii) cyano,
iv) $C_{1-6}$-alkyl,
v) halo-$C_{1-6}$-alkyl,
vi) $C_{3-8}$-cycloalkyl, and
vii) halo-$C_{3-8}$-cycloalkyl;
$R^8$ is H;
$R^9$ is selected from
i) H, and
ii) $C_{1-6}$-alkyl;
$L^1$ is

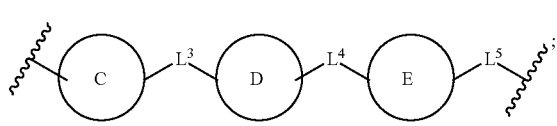

C is absent or selected from the ring systems F, G and H;

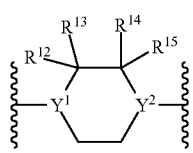
F

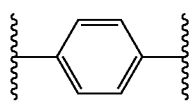
G

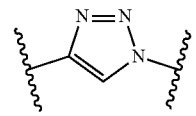
H $Y^1$ is selected from
i) —N—, and
ii) —CH—;
$Y^2$ is selected from
i) —N—, and
ii) —$CR^{16}$—;
$R^{12}$, $R^{13}$, $R^{14}$ and $R^{15}$ are independently selected from
i) —H—,
ii) halogen, and
iii) hydroxy-$C_{1-6}$-alkyl;
$R^{16}$ is selected from
i) —H—,
ii) hydroxy, and
iii) fluoro;
$L^3$ is absent or selected from
i) —$(CH_2)_m$—C(O)—,
ii) —C(O)—$(CH_2)_p$—,
iii) —C(O)—C(O)—,
iv) —$NR^{10}$—C(O)—,
v) —C(O)—$NR^{10}$—,
vi) —C(O)O—,
vii) —$CH_2$—$CF_2$—$CH_2$—,
viii) —$CH_2$—,
ix)

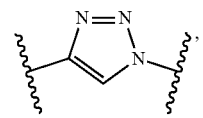

x)

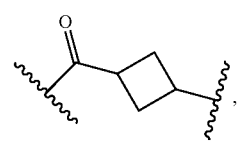 [SMILES: *C(=O)C1CC(*)C1]

and
xi)

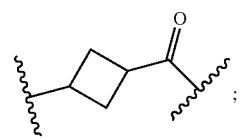 [SMILES: *C(=O)C1CC(*)C1]

m is 0, 1 or 2;
p is 0, 1, 2 or 3;
$R^{10}$ is selected from
i) H, and
ii) $C_{1-6}$-alkyl;
D is selected from the ring systems I, J, K, L, M, N, O, P, Q, R, S, T, U, V, W and X, all ring systems being optionally substituted by one to three substituents selected from $R^{80}$, $R^{81}$ and $R^{82}$;

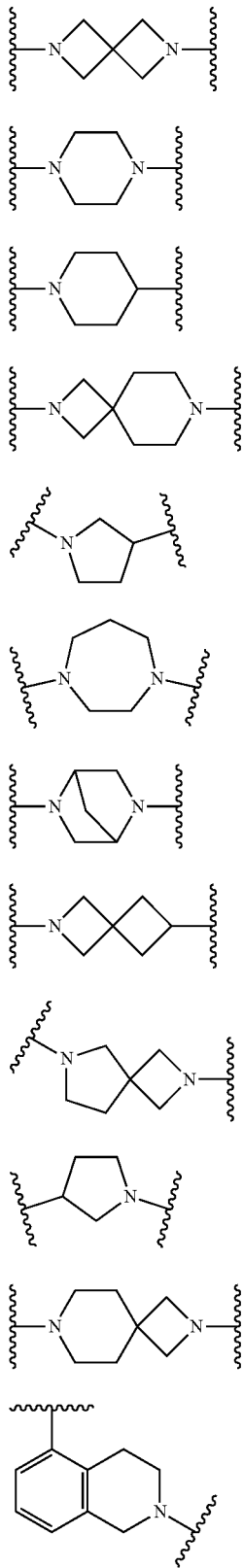

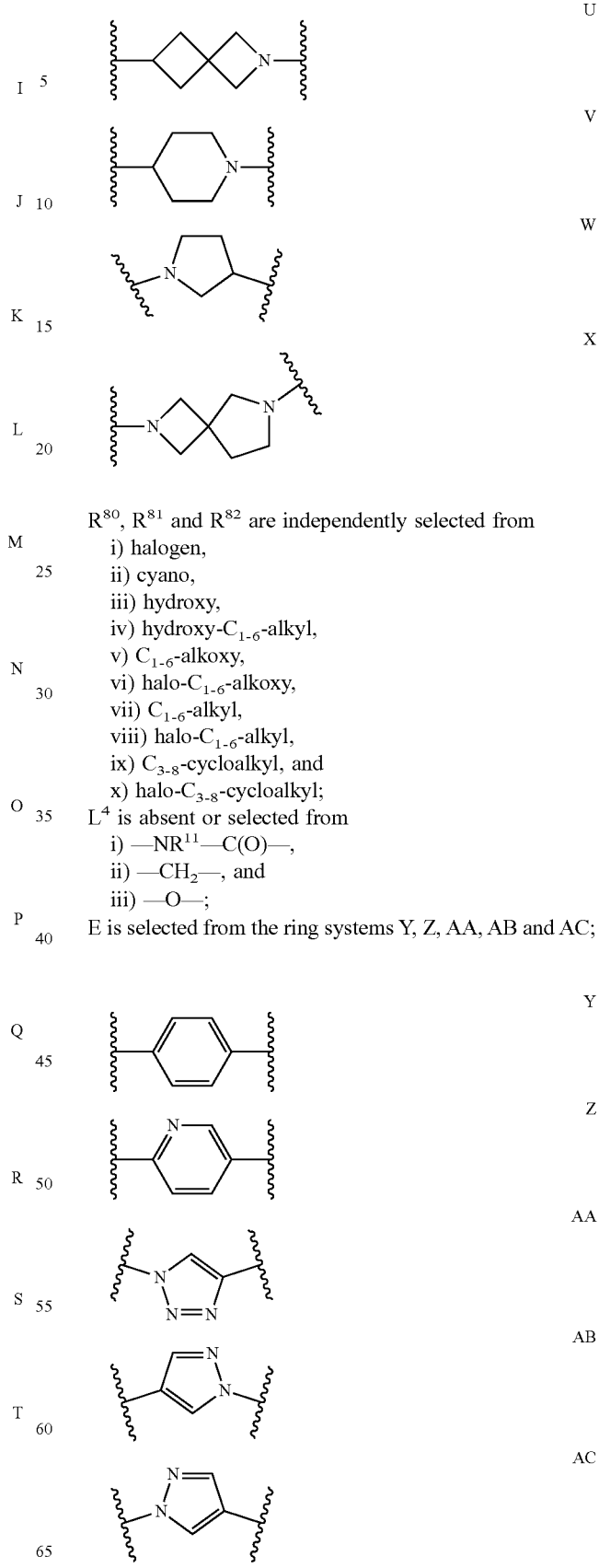

$R^{80}$, $R^{81}$ and $R^{82}$ are independently selected from
i) halogen,
ii) cyano,
iii) hydroxy,
iv) hydroxy-$C_{1-6}$-alkyl,
v) $C_{1-6}$-alkoxy,
vi) halo-$C_{1-6}$-alkoxy,
vii) $C_{1-6}$-alkyl,
viii) halo-$C_{1-6}$-alkyl,
ix) $C_{3-8}$-cycloalkyl, and
x) halo-$C_{3-8}$-cycloalkyl;

$L^4$ is absent or selected from
i) —$NR^{11}$—C(O)—,
ii) —$CH_2$—, and
iii) —O—;

E is selected from the ring systems Y, Z, AA, AB and AC;

$L^5$ is absent or

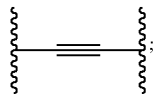

B is selected from the ring system AD and AE;

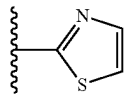
AD

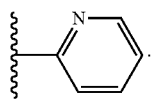
AE

In another aspect of the invention a compound of Formula II, or a pharmaceutically acceptable salt thereof is provided

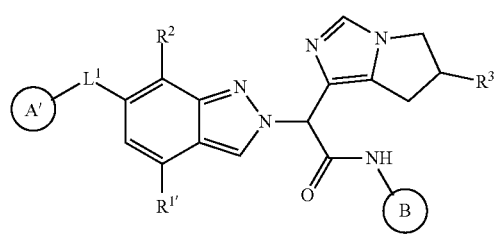
(II)

wherein
A' is selected from the ring systems AF, AG and AH;

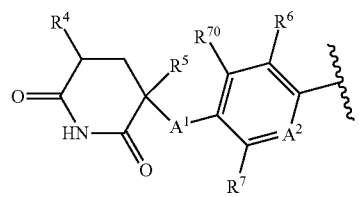
AF

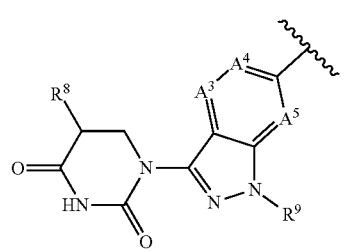
AG

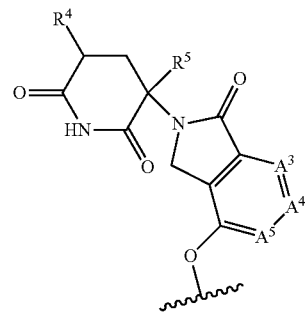
AH $R^{1'}$ is selected from
i) H,
ii) halogen,
iii) $C_{1-6}$-alkyl
iv) cyano,
v) $C_{1-6}$-alkoxy,
vi) halo-$C_{1-6}$-alkoxy,
vii) $C_{1-6}$-alkyl,
viii) halo-$C_{1-6}$-alkyl,
ix) $C_{3-8}$-cycloalkyl, and
x) halo-$C_{3-8}$-cycloalkyl;

and the remaining variables are as defined herein.

In certain aspects an isotope, N-oxide, or stereoisomer of Formula I is provided, or a pharmaceutically acceptable salt or composition thereof. In other aspects an isotope, N-oxide, or stereoisomer of Formula II is provided, or a pharmaceutically acceptable salt or composition thereof.

Other aspects of the present invention provide a compound of Formula III or Formula IV:

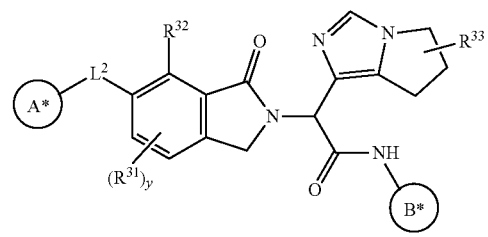
(III)

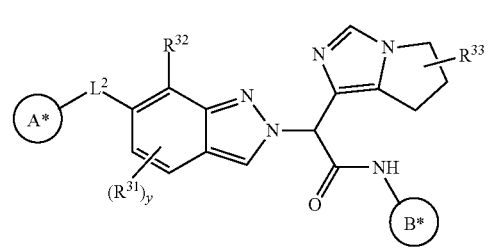
(IV)

or a pharmaceutically acceptable salt, isotope, N-oxide, stereoisomer thereof, optionally as part of a pharmaceutical composition;

wherein:
A* is selected from:

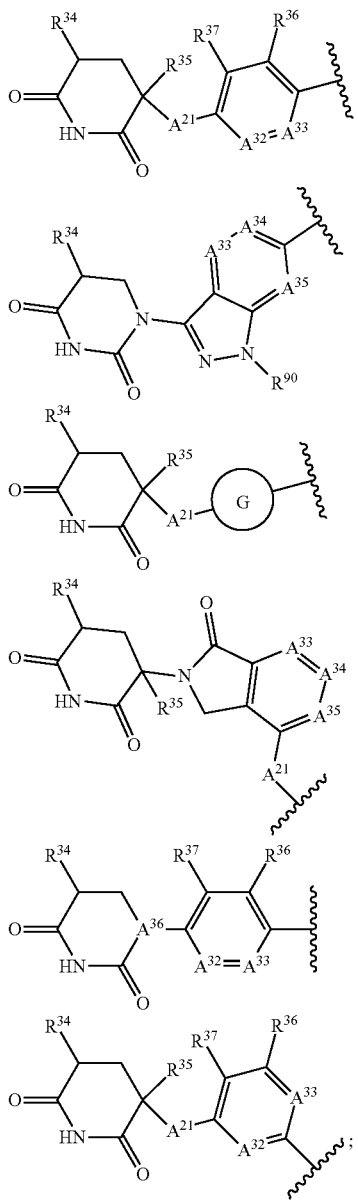

B* is heteroaryl or aryl which is optionally substituted with 1, 2, or 3 $R^{31}$ substituents; in certain embodiments B* is selected from

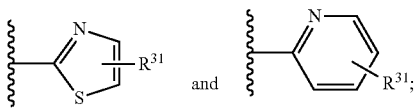

y is 0, 1, 2, or 3;
$R^{31}$ is independently selected at each occurrence from H, halogen (F, Cl, Br, or I), $C_{1-6}$-alkyl, cyano, $C_{1-6}$-alkoxy, halo-$C_{1-6}$-alkoxy, halo-$C_{1-6}$-alkyl, $C_{3-8}$-cycloalkyl, and halo-$C_{3-8}$-cycloalkyl and can be located on either ring where present on a bicycle, for example

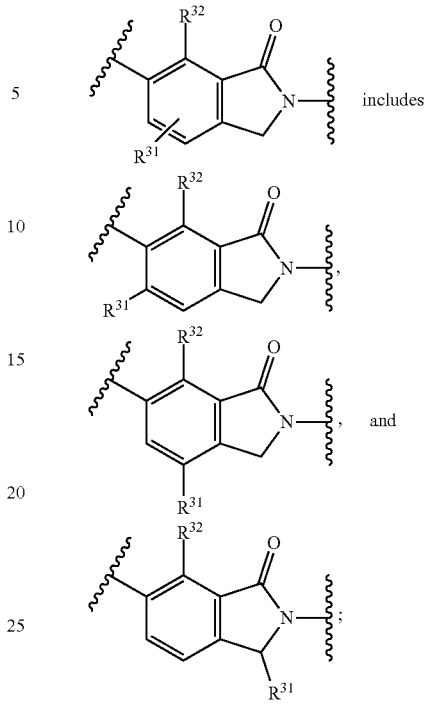 includes $R^{32}$ is hydrogen, halogen (F, Cl, Br, or I), $C_{1-6}$-alkyl, halo-$C_{1-6}$-alkyl, $C_{3-8}$-cycloalkyl, or halo-$C_{3-8}$-cycloalkyl;
$R^{33}$ is hydrogen, halogen (F, Cl, Br, or I), $C_{1-6}$-alkyl, halo-$C_{1-6}$-alkyl, $C_{3-8}$-cycloalkyl, or halo-$C_{3-8}$-cycloalkyl and can be located on the dihydropyrrole or imidazole ring;
$R^{34}$ is independently selected at each occurrence from H, F, $C_{1-6}$-alkyl, halo-$C_{1-6}$-alkyl, $C_{3-8}$-cycloalkyl, and halo-$C_{3-8}$-cycloalkyl;
$R^{35}$ is selected at each occurrence from H, halogen (F, Cl, Br, or I), $C_{1-6}$-alkyl, halo-$C_{1-6}$-alkyl, and $C_{3-8}$-cycloalkyl;
or $R^{34}$ and $R^{35}$ combine to form —$(CH_2)_q$—;
$R^{36}$ and $R^{37}$ are independently selected from H, halogen (F, Cl, Br, or I), cyano, $C_{1-6}$-alkoxy, halo-$C_{1-6}$-alkoxy (for example F, Cl, or Br), $C_{1-6}$-alkyl, halo-$C_{1-6}$-alkyl (for example F, Cl, or Br), $C_{3-8}$-cycloalkyl, and halo-$C_{3-8}$-cycloalkyl;
or $R^{36}$ and $R^{37}$ together are combined to form a 5- or 6-membered cycle optionally substituted with 1, 2, or 3 $R^{31}$ substituents;
$R^{42}$ is independently selected at each occurrence from H, halogen (F, Cl, Br, or I), cyano, $C_{1-6}$-alkoxy, halo-$C_{1-6}$-alkoxy, $C_{1-6}$-alkyl, halo-$C_{1-6}$-alkyl, $C_{3-8}$-cycloalkyl, and halo-$C_{3-8}$-cycloalkyl;
$R^{90}$ is H, $C_{1-6}$-alkyl, or $C_{3-6}$-cycloalkyl;
Ring G is a heteroaryl optionally substituted with 1 or 2 $R^{42}$ substituents, for example a 5- or 6-membered heteroaryl ring with 1, 2, or 3 N heteroatoms;
$A^{21}$ is —NH—, —O—, —$CH_2$—, or —$NR^{100}$—;
$R^{100}$ is alkyl, cycloalkyl, aryl, or heteroaryl; or as allowed by valence $R^{100}$ may combine with $R^{37}$ to form a 5-8 membered heterocycle or 5 membered heteroaryl;
$A^{32}$, $A^{33}$, $A^{34}$, and $A^{35}$ are independently selected from —N— and —$CR^{42}$—;
$A^{36}$ is —N— or —$CR^{35}$—;

L² is a bivalent linking group (a linker) that connects A* and either the isoindolinone or indazole, for example but not limited to a bivalent linking group of Formula LI; and wherein the remaining variables are as defined herein.

In certain embodiments L² is of formula:

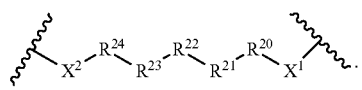
(LI)

wherein,
- $X^1$ and $X^2$ are independently at each occurrence selected from bond, heterocycle, aryl, heteroaryl, bicycle, alkyl, aliphatic, heteroaliphatic, —$NR^{27}$—, —$CR^{40}R^{41}$—, —O—, —C(O)—, —C($NR^{27}$)—, —C(S)—, —S(O)—, —S(O)$_2$— and —S—; each of which heterocycle, aryl, heteroaryl, and bicycle is optionally substituted with 1, 2, 3, or 4 substituents independently selected from $R^{40}$;
- $R^{20}$, $R^{21}$, $R^{22}$, $R^{23}$, and $R^{24}$ are independently at each occurrence selected from the group consisting of a bond, alkyl, —C(O)—, —C(O)O—, —OC(O)—, —SO$_2$—, —S(O)—, —C(S)—, —C(O)$NR^{27}$—, —$NR^{27}$C(O)—, —O—, —S—, —$NR^{27}$—, oxyalkylene, —C($R^{40}R^{40}$)—, —P(O)($OR^{26}$)O—, —P(O)($OR^{26}$)—, bicycle, alkene, alkyne, haloalkyl, alkoxy, aryl, heterocycle, aliphatic, heteroaliphatic, heteroaryl, lactic acid, glycolic acid, and carbocycle; each of which is optionally substituted with 1, 2, 3, or 4 substituents independently selected from $R^{40}$;
- $R^{26}$ is independently at each occurrence selected from the group consisting of hydrogen, alkyl, arylalkyl, heteroarylalkyl, alkene, alkyne, aryl, heteroaryl, heterocycle, aliphatic and heteroaliphatic;
- $R^{27}$ is independently at each occurrence selected from the group consisting of hydrogen, alkyl, aliphatic, heteroaliphatic, heterocycle, aryl, heteroaryl, —C(O)(aliphatic, aryl, heteroaliphatic or heteroaryl), —C(O)O (aliphatic, aryl, heteroaliphatic, or heteroaryl), alkene, and alkyne;
- $R^{40}$ is independently at each occurrence selected from the group consisting of hydrogen, $R^{27}$, alkyl, alkene, alkyne, fluoro, bromo, chloro, hydroxyl, alkoxy, azide, amino, cyano, —NH (aliphatic, including alkyl), —N(aliphatic, including alkyl)$_2$, —NHSO$_2$(aliphatic, including alkyl), —N(aliphatic, including alkyl)SO$_2$alkyl, —NHSO$_2$(aryl, heteroaryl or heterocycle), —N(alkyl)SO$_2$(aryl, heteroaryl or heterocycle), —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, aryl, heteroaryl, heterocycle, oxo, and cycloalkyl; additionally, where allowed by valence two $R^{40}$ groups bound to the same carbon may be joined together to form a 3-8 membered spirocycle; and
- $R^{41}$ is aliphatic, aryl, heteroaryl, or hydrogen.

Every combination of variables, substituents, embodiments and the compounds that result from these combinations, is deemed specifically and individually disclosed, as such depiction is for convenience of space only and not intended to describe only a genus or even a subgenus of compounds.

A compound of the present invention may be used to treat an EGFR-mediated disorders such as colon cancer; rectal cancer; lung cancer, including non-small cell lung cancer; breast cancer, including HER-2 positive breast cancer, ER+ (estrogen positive) breast cancer, PR+ (progesterone positive) breast cancer, or triple negative breast cancer; head and neck cancer; glioblastoma; pancreatic cancer; thyroid cancer; astrocytoma; esophageal cancer; cervical cancer; synovial sarcoma; ovarian cancer; liver cancer; bladder cancer; or kidney cancer.

In certain embodiments, a method of treatment is provided comprising administering an effective amount of a compound of Formula I, II, III, or IV, or a pharmaceutically acceptable salt thereof to a patient in need thereof, for example a human, optionally in a pharmaceutically acceptable carrier. For example, in certain embodiments, a compound of Formula I, II, III, or IV is administered to a human to treat a cancer.

In certain embodiments a compound of the present invention is used to treat lung cancer. In certain embodiments, the lung cancer is non-small cell lung cancer.

In certain embodiments a compound of the present invention is used to treat breast cancer. In certain embodiments, the breast cancer is HER-2 positive breast cancer. In certain embodiments, the breast cancer is ER+ breast cancer. In certain embodiments, the breast cancer is PR+ breast cancer. In certain embodiments, the breast cancer is triple negative breast cancer.

In certain embodiments a compound of the present invention is used to treat colorectal or rectal cancer.

In certain embodiments a compound of the present invention is used to treat head and neck cancer or esophageal cancer.

In certain embodiments a compound of the present invention is used to treat glioblastoma. In certain embodiments a compound of the present invention is used to treat pancreatic cancer.

In certain embodiments a compound of the present invention is used to treat thyroid cancer.

In certain embodiments a compound of the present invention is used to treat ovarian cancer, uterine cancer, or cervical cancer.

In certain embodiments a compound of the present invention is used to treat kidney cancer, liver cancer, or bladder cancer.

In certain embodiments, the compound of the present invention provides one or more, and even may provide multiple advantages over traditional treatment with an EGFR ligand.

For example, the EGFR degrading compound of the present invention may a) overcome resistance in certain cases; b) prolong the kinetics of drug effect by destroying the protein, thus requiring resynthesis of the protein even after the compound has been metabolized; c) target all functions of a protein at once rather than a specific catalytic activity or binding event; and/or d) have increased potency compared to inhibitors due to the possibility of the small molecule acting catalytically.

In one aspect, a compound of the present invention is used to treat an EGFR mediated cancer, wherein the EGFR has mutated from the wild-type. There are a number of possibilities for EGFR mutations. In certain non-limiting embodiments, the mutation is found in exon 18, exon 19, exon 20, or exon 21, or any combination thereof. In certain nonlimiting embodiments, the mutation is at position L858, E709, G719, C797, L861, T790, or L718 or any combination thereof. In certain embodiments the mutation is a L858R, T790M, L718Q, L792H, and/or a C797S mutation or any combination thereof.

In certain aspects, the cancer has developed one or more EGFR mutations following treatment with at least one EGFR inhibitor that can be a non-covalent inhibitor (including but not limited to gefitinib, erlotinib, lapatinib or vandetanib) or a covalent inhibitor (such as afatinib, osimertinib or dacomitinib). In another aspect, the cancer has developed one or more EGFR mutations following treatment with an antibody such as cetuximab, panitumab or necitumab. In yet another aspect, the cancer has one or more EGFR mutations or non-EGFR mutations that renders the cancer intrinsically resistant to EGFR inhibitor treatment, for example, a somatic exon 20 insertion, asomatic PIK3CA mutation, loss of PTEN expression, MET amplification, or a KRAS mutation.

In certain embodiments, a compound of the present invention is used to treat a cancer that is resistant to, or has acquired a resistance to, a first generation EGFR inhibitor such as erlotinib, gefitinib, and/or lapatinib. In certain embodiments, a compound of the present invention is used to treat a cancer that is resistant to, or has acquired a resistance to a second generation EGFR inhibitor such as afatinib and/or dacomitinib. In certain embodiments, a compound of the present invention is used to treat a cancer that is resistant to, or acquired a resistance to a third generation EGFR inhibitor such as osimertinib.

In some embodiments, the mutated EGFR protein in the diseased tissue has an L858 mutation, for example L858R.

In certain embodiments the compound of the present invention is used to treat a mutant EGFR mediated disorder, wherein EGFR has a mutation of at least one of the below listed amino acid sites, or a combination thereof. The mutation may, for example, be selected from one of the listed exemplary mutations, or may be a different mutation.

| Amino Acid | Exemplary Mutations |
| --- | --- |
| C797 | C797S |
| E709 | E709A, E709G, E709K, E709V |
| G719 | G719A, G719S, G719C, G719D |
| G724 | G724S |
| G119 | G119A |
| G796 | G796S, G796C |
| L718 | L718V, L718Q |
| L792 | L792H; L792V |
| L858 | L858R |
| L861 | L861Q |
| S768 | S768I |
| T790 | T790M |

In certain embodiments the mutant EGFR mediated disorder has two mutations selected from the table above. In other embodiments the mutant EGFR mediated disorder has three mutations selected from the table above. In other embodiments the mutant EGFR mediated disorder has four or more mutations, which may optionally be selected from the table above.

In certain embodiments the mutant EGFR mediated disorder has an L858R mutation and one additional mutation which may optionally be selected from the table above. In some of these embodiments the mutant EGFR mediated disorder has an L858R mutation and two additional mutation that may optionally be selected from the table above. In other embodiments the mutant EGFR mediated disorder has a L858R mutation and three additional mutation that may optionally be selected from the table above.

In certain embodiments the mutant EGFR mediated disorder has a T790M mutation and one additional mutation optionally selected from the table above. In other embodiments the mutant EGFR mediated disorder has a T790M mutation and two additional mutation optionally selected from the table above. In other embodiments the mutant EGFR mediated disorder has a T790M mutation and three additional mutation optionally selected from the table above.

In certain embodiments the mutant EGFR mediated disorder has a L718Q mutation and one additional mutation optionally selected from the table above. In other embodiments the mutant EGFR mediated disorder has a L718Q mutation and two additional mutation optionally selected from the table above. In other embodiments the mutant EGFR mediated disorder has a L718Q mutation and three additional mutation optionally selected from the table above.

In certain embodiments the EGFR mediated disorder is mutant EGFR mediated cancer.

In certain embodiments the EGFR mediated cancer has a mutation of S768I, L718V, L792H, L792V, G796S, G796C, G724S, and/or G719A.

In certain embodiments, a compound of the present invention is used to treat an EGFR mediated cancer that has a frameshift mutation, for example a short in-frame deletion. In certain embodiments, a compound of the present invention is used to treat an EGFR mediated cancer wherein the EGFR has an exon 19 deletion. In certain embodiments, the exon 19 deletion is a deletion which includes the amino acids LREA (L747-A750). In certain embodiments, the exon 19 deletion is a deletion which includes the amino acids ELREA (E746-A750).

In certain embodiments a compound of the present invention is used to treat an EGFR mediated cancer wherein the EGFR has an L858R mutation in exon 21.

In certain embodiments a compound of the present invention is more active against a disorder driven by a mutated EGFR than wild-type EGFR.

In certain embodiments, a compound of the present invention is used to treat an EGFR mediated cancer wherein the EGFR has one or more exon 18 deletions.

In certain embodiments a compound of the present invention is used to treat EGFR with a E709 mutation, for example E709A, E709G, E709K, or E709V.

In certain embodiments a compound of the present invention is used to treat EGFR with a L718 mutation, for example L718Q.

In certain embodiments a compound of the present invention is used to treat EGFR with a G719 mutation, for example G719S, G719A, G719C, or G719D.

In certain embodiments, a compound of the present invention is used to treat an EGFR mediated cancer wherein the EGFR has one or more exon 19 insertions and/or one or more exon 20 insertions.

In certain embodiments, a compound of the present invention is used to treat S768I mutant EGFR cancer. In certain embodiments a compound of the present invention is used to treat EGFR L861Q mutant EGFR cancer. In certain embodiments, a compound of the present invention is used to treat C797S mutant EGFR cancer.

In certain embodiments a compound of the present invention is used to treat a T790M, L858R mutant EGFR cancer.

In certain embodiments a compound of the present invention is used to treat a L718Q, L858R mutant EGFR cancer.

In certain embodiments a compound of the present invention is used to treat a L792H, L858R mutant EGFR cancer.

In certain embodiments a compound of the present invention is used to treat a C797S, L858R mutant EGFR cancer.

In certain embodiments, the compound of the present invention provides an improved efficacy and/or safety profile relative to at least one known EGFR inhibitor. For example, the degrader of the present invention has the efficiency of an inhibitor only protein binding moiety combined with the catalytic degradation activity of the cereblon-activated proteasomal degradation. This provides rapid activity against the target overexpressed EGFR by an active moiety that can quickly "return to action" and repeat the catalytic function. In this way, the EGFR is quickly destroyed as done with a covalent suicide inhibitor, like osimertinib, but without at the same time destroying the active drug.

In certain embodiments, the degrader compound of the present invention has one or more advantages in the treatment of an EGFR mediated disorders than using an enzyme inhibitor only.

In certain embodiments, less of the compounds described herein is needed for the treatment of an EGFR mediated disorder, than by mole of the EGFR Targeting Ligand portion alone.

In certain embodiments, the compound of the present invention has less of at least one side-effect in the treatment of an EGFR mediated disorder, than by mole of the EGFR Targeting Ligand portion alone.

In certain embodiments, a less frequent dose regimen of a selected compound described herein is needed for the treatment of an EGFR mediated disorder, than the dose by mole of the EGFR Targeting Ligand portion alone.

Another aspect of the present invention provides a compound as described herein, or an enantiomer, diastereomer, or stereoisomer thereof, or pharmaceutically acceptable salt, hydrate, or solvate thereof, or a pharmaceutical composition, for use in the manufacture of a medicament for inhibiting or preventing a disorder mediated by EGFR or for modulating or decreasing the amount of EGFR.

Another aspect of the present invention provides a compound as described herein, or an enantiomer, diastereomer, or stereoisomer thereof, or pharmaceutically acceptable salt, hydrate, or solvate thereof, or its pharmaceutical composition, for use in the manufacture of a medicament for treating or preventing a disease mediated by EGFR.

In certain embodiments, a selected compound as described herein is useful to treat a disorder comprising an abnormal cellular proliferation, such as a tumor or cancer, wherein EGFR is an oncogenic protein or a signaling mediator of the abnormal cellular proliferative pathway and its degradation decreases abnormal cell growth.

In certain embodiments, the selected compound of Formula I, II, III, or IV, or its pharmaceutically acceptable salt thereof, has at least one desired isotopic substitution of an atom, at an amount above the natural abundance of the isotope, i.e., enriched.

In certain embodiments, the compound of Formula I, II, III, or IV, or its pharmaceutically acceptable salt thereof, includes a deuterium atom or multiple deuterium atoms.

In certain embodiments a compound of the present invention is useful for the therapeutic and/or prophylactic treatment of cancer.

In certain embodiments a compound of the present invention has an E3 Ubiquitin Ligase-binding moiety that is linked to a moiety that binds to the target protein EGFR, where the target protein is proximate to the ubiquitin ligase to effect degradation of said protein.

Other features and advantages of the present application will be apparent from the following detailed description.

The present invention thus includes at least the following features:

(a) A compound of Formula I, II, III, or IV, as described herein, or a pharmaceutically acceptable salt or isotopic derivative (including a deuterated derivative) thereof;

(b) A method for treating an EGFR mediated disorder, such as an abnormal cellular proliferation, including cancer, comprising administering an effective amount of a compound of Formula I, II, III, or IV, or pharmaceutically acceptable salt thereof, as described herein, to a patient in need thereof;

(c) A compound of Formula I, II, III, or IV, or a pharmaceutically acceptable salt, or isotopic derivative (including a deuterated derivative) thereof for use in the treatment of a disorder that is mediated by EGFR, for example an abnormal cellular proliferation such as a tumor or cancer;

(d) Use of a compound of Formula I, II, III, or IV, or a pharmaceutically acceptable salt thereof, in an effective amount in the treatment of a patient in need thereof, typically a human, with an EGFR mediated disorder, for example an abnormal cellular proliferation such as a tumor or cancer;

(e) Use of a compound of Formula I, II, III, or IV, or a pharmaceutically acceptable salt or isotopic derivative (including a deuterated derivative) thereof in the manufacture of a medicament for the treatment of an EGFR mediated disorder, for example an abnormal cellular proliferation such as a tumor or cancer;

(f) A method for treating a mutant EGFR mediated disorder, such as an abnormal cellular proliferation, including cancer, comprising administering an effective amount of a compound of Formula I, II, III, or IV, or pharmaceutically acceptable salt thereof, as described herein, to a patient in need thereof;

(g) A compound of Formula I, II, III, or IV, or a pharmaceutically acceptable salt, or isotopic derivative (including a deuterated derivative) thereof for use in the treatment of a disorder that is mediated by mutant EGFR, for example an abnormal cellular proliferation such as a tumor or cancer;

(h) Use of a compound of Formula I, II, III, or IV, or a pharmaceutically acceptable salt thereof, in an effective amount in the treatment of a patient in need thereof, typically a human, with a mutant EGFR mediated disorder, for example an abnormal cellular proliferation such as a tumor or cancer;

(i) Use of a compound of Formula I, II, III, or IV, or a pharmaceutically acceptable salt or isotopic derivative (including a deuterated derivative) thereof in the manufacture of a medicament for the treatment of a mutant EGFR mediated disorder, for example an abnormal cellular proliferation such as a tumor or cancer;

(j) A pharmaceutical composition comprising an effective patient-treating amount of a compound of Formula I, II, III, or IV, or a pharmaceutically acceptable salt, isotopic derivative thereof; and optionally a pharmaceutically acceptable carrier or diluent;

(k) A compound Formula I, II, III, or IV, as described herein as a mixture of enantiomers or diastereomers (as relevant), including as a racemate;

(l) A compound of Formula I, II, III, or IV, as described herein in enantiomerically or diastereomerically (as relevant) enriched form, including as an isolated enantiomer or diastereomer (i.e., about greater than 85, 90, 95, 97, or 99% pure); and (m) A process for the preparation of therapeutic products that contain an effective amount of a compound of Formula I, II, III, or IV, or a pharmaceutically acceptable salt thereof, as described herein.

DETAILED DESCRIPTION OF THE INVENTION

Compounds and their uses and manufacture are provided that degrade the epidermal growth factor receptor protein (EGFR) via the ubiquitin proteasome pathway (UPP). The present invention provides compounds of Formula I, II, III, or IV or a pharmaceutically acceptable salt thereof that include a Targeting Ligand that binds to EGFR, an E3 Ligase binding portion (typically via a cereblon subunit), and a Linker that covalently links the Targeting Ligand to the E3 Ligase binding portion. In certain embodiments the E3 Ligase binding portion is a moiety of A or A*, the Linker is a moiety of $L^1$ or $L^2$, and the remainder of the molecule is the EGFR Targeting Ligand portion. In certain embodiments a compound of the present invention degrades EGFR with a mutation or combination of mutations, for example a mutation selected from T790M, L858R, and C797S; the combination of two mutations selected from T790M, L858R, and C797S; or the combination of two mutations selected from T790M, L858R, and C797S In certain embodiments a compound of the present invention is a selective degrader of T790M/L858R, T790M/L858R/C797S, L858R, and/or L858R/C797S containing EGFR mutants.

In certain embodiments, a compound of the present invention provides an improved efficacy and/or safety profile relative to at least one known EGFR inhibitor. For example, the degrader of the present invention has the efficiency of an inhibitor only protein binding moiety combined with the catalytic degradation activity of the cereblon-activated proteasomal degradation. This provides rapid activity against the target overexpressed EGFR by an active moiety that can quickly "return to action" and repeat the catalytic function. In this way, the EGFR is quickly destroyed as done with a covalent suicide inhibitor, like osimertinib, but without at the same time destroying the active drug.

I. Definitions

The following definitions of the general terms used in the present description apply whether the terms appear alone or in combination with other groups.

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

The term "$C_{1-6}$-alkoxy" denotes a group of the formula —O—R', wherein R' is an $C_{1-6}$-alkyl group, particularly $C_{1-3}$-alkyl. Examples of $C_{1-6}$-alkoxy groups include methoxy, ethoxy, n-propoxy, isopropoxy, n-butoxy, isobutoxy and tert-butoxy. Particular examples are methoxy, ethoxy and isopropoxy. More particular example is methoxy.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. A specific group is methyl.

The term "cyano" denotes a —C≡N group.

The term "$C_{3-8}$-cycloalkoxy" denotes a group of the formula —O—R', wherein R' is a $C_{3-8}$-cycloalkyl group. Examples of cycloalkoxy group include cyclopropoxy, cyclobutoxy, cyclopentyloxy, cyclohexyloxy, cycloheptyloxy and cyclooctyloxy. Particular example is cyclopropoxy.

The term "$C_{3-8}$-cycloalkyl" denotes a monovalent saturated monocyclic or bicyclic hydrocarbon group of 3 to 8 ring carbon atoms. Bicyclic means a ring system consisting of two saturated carbocycles having one or two carbon atoms in common. Examples of monocyclic $C_{3-8}$-cycloalkyl are cyclopropyl, cyclobutanyl, cyclopentyl, cyclohexyl or cycloheptyl. Example of bicyclic $C_{3-8}$-cycloalkyl is spiro[3.3]heptanyl. Particular monocyclic $C_{3-8}$-cycloalkyl groups are cyclopropyl, cyclobutanyl. More particular monocyclic $C_{3-8}$-cycloalkyl groups include cyclopropyl.

The term "halo-$C_{1-6}$-alkoxy" denotes an $C_{1-6}$-alkoxy group wherein at least one of the hydrogen atoms of the $C_{1-6}$-alkoxy group has been replaced by same or different halogen atoms. The term "perhalo-$C_{1-6}$-alkoxy" denotes an $C_{1-6}$-alkoxy group where all hydrogen atoms of the $C_{1-6}$-alkoxy group have been replaced by the same or different halogen atoms. Examples of halo-$C_{1-6}$-alkoxy include fluoromethoxy, difluoromethoxy, trifluoromethoxy, fluoroethoxy, difluoroethoxy, trifluoroethoxy, trifluoromethylethoxy, trifluorodimethylethoxy and pentafluoroethoxy. Particular halo-$C_{1-6}$-alkoxy groups include fluoromethoxy, rifluoroethoxy, difluoromethoxy, difluoroethoxy, trifluoromethoxy, trifluoromethylethoxy and trifluorodimethylethoxy. More particular examples are fluoromethoxy, difluoromethoxy and trifluoromethoxy.

The term "halo-$C_{1-6}$-alkyl" denotes an $C_{1-6}$-alkyl group wherein at least one of the hydrogen atoms of the $C_{1-6}$-alkyl group has been replaced by the same or different halogen atoms. The term "perhalo-$C_{1-6}$-alkyl-$C_{1-6}$-alkyl" denotes an-$C_{1-6}$-alkyl-$C_{1-6}$-alkyl group where all hydrogen atoms of the alkyl group have been replaced by the same or different halogen atoms. Examples of halo-$C_{1-6}$-alkyl include fluoromethyl, difluoromethyl, trifluoromethyl, trifluoroethyl, trifluoromethylethyl and pentafluoroethyl. Particular halo-$C_{1-6}$-alkyl groups include fluoromethyl, difluoromethyl, trifluoromethyl, fluoroethyl, trifluoroethyl and difluoroethyl. More particular halo-$C_{1-6}$-alkyl groups include fluoromethyl.

The term "halo-$C_{3-8}$-cycloalkoxy" denotes an $C_{3-8}$-cycloalkoxy group wherein at least one of the hydrogen atoms of the $C_{3-8}$-cycloalkoxy group has been replaced by same or different halogen atoms. The term "perhalo-$C_{3-8}$-cycloalkoxy" denotes an $C_{3-8}$-cycloalkoxy group where all hydrogen atoms of the $C_{3-8}$-cycloalkoxy group have been replaced by the same or different halogen atoms. Examples of halo-$C_{3-8}$-cycloalkoxy include fluorocyclopropoxy, fluorocyclobutoxy, fluorocyclopentyloxy, fluorocyclohexyloxy, fluorocycloheptyloxy, difluorocyclopropoxy, difluorocyclobutoxy, difluorocyclopentyloxy, difluorocyclohexyloxy and difluorocycloheptyloxy.

The term "halo-$C_{3-8}$-cycloalkyl" denotes an $C_{3-8}$-cycloalkyl group wherein at least one of the hydrogen atoms of the $C_{3-8}$-cycloalkyl group has been replaced by the same or different halogen atoms. The term "perhalo-$C_{3-8}$-cycloalkyl" denotes an-$C_{3-8}$-cycloalkyl group where all hydrogen atoms of the alkyl group have been replaced by the same or different halogen atoms. Examples of halo-$C_{3-8}$-cycloalkyl include fluorocyclopropyl, fluorocyclobutanyl, fluorocyclopentyl, fluorocyclohexyl, fluorocycloheptyl, difluorocyclopropyl, difluorocyclobutanyl, difluorocyclopentyl, difluorocyclohexyl or difluorocycloheptyl.

The term "halogen", alone or in combination with other groups, denotes chloro (Cl), iodo (I), fluoro (F) and bromo (Br). Specific groups are F and Cl.

The term "hydroxy" denotes a —OH group.

The term "hydroxy-$C_{1-6}$-alkyl alkyl" denotes an $C_{1-6}$-alkyl alkyl group wherein at least one of the hydrogen atoms of the $C_{1-6}$-alkyl alkyl group has been replaced by a hydroxy group. Examples of hydroxy-$C_{1-6}$-alkyl include hydroxymethyl, hydroxyethyl and hydroxypropyl. Particular example is hydroxymentyl.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. A specific acid is trifluoroacetic acid.

The terms "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (–log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant ($K_i$) using the Cheng-Prusoff equation (Biochem. Pharmacol. (1973) 22:3099).

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "aromatic" denotes the conventional idea of aromaticity as defined in the literature, in particular in IUPAC-Compendium of Chemical Terminology, 2nd, A. D. McNaught & A. Wilkinson (Eds). Blackwell Scientific Publications, Oxford (1997).

Whenever a chiral carbon is present in a chemical structure, it is intended that all stereoisomers associated with that chiral carbon are encompassed by the structure as pure stereoisomers as well as mixtures thereof.

In certain embodiments, isotopes are incorporated into the compounds of the invention. These isotopes include, but are not limited to, isotopes of hydrogen, carbon, nitrogen, oxygen, fluorine, and chlorine such as $^2H$, $^3H$, $^{11}C$, $^{13}C$, $^{14}C$, $^{15}N$, $^{17}O$, $^{18}O$, $^{18}F$, $^{35}S$, and $^{36}Cl$ respectively. In one non-limiting embodiment, isotopically labelled compounds can be used in metabolic studies (with, for example $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. Additionally, any hydrogen atom present in the compound of the invention may be substituted with an $^{18}$F atom, a substitution that may be particularly desirable for PET or SPECT studies.

In one non-limiting embodiment, the substitution of a hydrogen atom for a deuterium atom can be provided in any compound described herein. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated. In certain embodiments, at least one deuterium is placed on an atom that has a bond which is broken during metabolism of the compound in vivo, or is one, two or three atoms remote form the metabolized bond (e.g., which may be referred to as an α, β or γ, or primary, secondary or tertiary isotope effect).

In certain embodiments a compound of the present invention is isotopically labeled. In certain embodiments at least one R group independently selected from $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^1$, $R^{16}$, $R^{17}$, $R^{20}$, $R^{21}$, $R^{22}$, $R^{23}$, $R^{24}$, $R^{26}$, $R^{27}$, $R^{31}$, $R^{32}$, $R^{33}$, $R^{34}$, $R^{35}$, $R^{36}$, $R^{37}$, $R^{40}$, $R^{41}$, $R^{42}$, $R^{52}$, $R^{53}$, $R^{54}$, $R^{55}$, $R^{70}$, $R^{80}$, $R^{81}$, $R^{82}$, $R^{90}$, or $R^{100}$ is isotopically labeled with 1, 2, or more isotopes as allowed by valence. In certain embodiments the isotopic label is deuterium. In certain embodiments, at least one deuterium is placed on an atom that has a bond which is broken during metabolism of the compound in vivo, or is one, two or three atoms remote form the metabolized bond (e.g., which may be referred to as an α, β or γ, or primary, secondary or tertiary isotope effect). In another embodiment the isotopic label is $^{13}$C. In other embodiments the isotopic label is $^{18}$F.

In certain embodiments the compounds of the present invention may form a solvate with a solvent (including water). Therefore, in one non-limiting embodiment, the invention includes a solvated form of the compounds described herein. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents.

In certain embodiments "alkenyl" is a linear or branched aliphatic hydrocarbon groups having one or more carbon-carbon double bonds that may occur at a stable point along the chain. In one non-limiting embodiment, the alkenyl contains from 2 to about 12 carbon atoms, more generally from 2 to about 6 carbon atoms or from 2 to about 4 carbon atoms. In certain embodiments the alkenyl is $C_2$, $C_2$-$C_3$, $C_2$-$C_4$, $C_2$-$C_5$, or $C_2$-$C_6$. In certain embodiments, examples of alkenyl radicals include, but are not limited to ethenyl, propenyl, allyl, propenyl, butenyl and 4-methylbutenyl. In certain embodiments the term "alkenyl" also embodies "cis" and "trans" alkenyl geometry, or alternatively, "E" and "Z" alkenyl geometry. In certain embodiments the term "alkenyl" also encompasses cycloalkyl or carbocyclic groups having at least one point of unsaturation.

In certain embodiments "alkynyl" is a branched or straight chain aliphatic hydrocarbon group having one or more carbon-carbon triple bonds that may occur at any stable point along the chain. In one non-limiting embodiment, the alkynyl contains from 2 to about 12 carbon atoms, more generally from 2 to about 6 carbon atoms or from 2 to about 4 carbon atoms. In certain embodiments the alkynyl is $C_2$, $C_2$-$C_3$, $C_2$-$C_4$, $C_2$-$C_5$, or $C_2$-$C_6$. In certain embodiments, examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In certain embodiments, the term "alkynyl" also encompasses cycloalkyl or carbocyclic groups having at least one point of triple bond unsaturation.

II. Compounds of Formula I, II, III, and IV

The invention provides compounds of Formulas I, II, III, and IV pharmaceutical compositions, methods of using, and methods of preparing these compounds.

Embodiments of Formula I

All separate embodiments may be combined.
E1: One embodiment of the invention is a compound of formula I, or a pharmaceutically acceptable salt thereof,

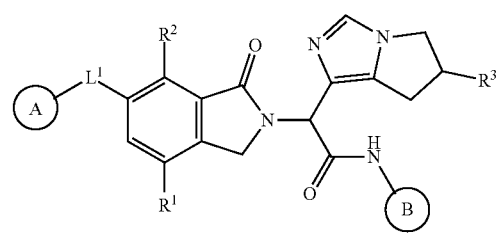

(I)

wherein
A is selected from the ring systems AF and AG;

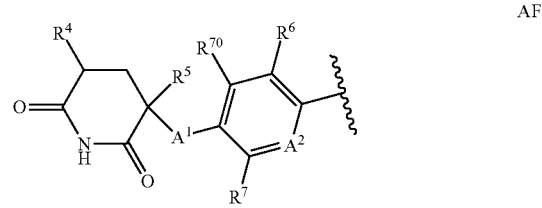

AF

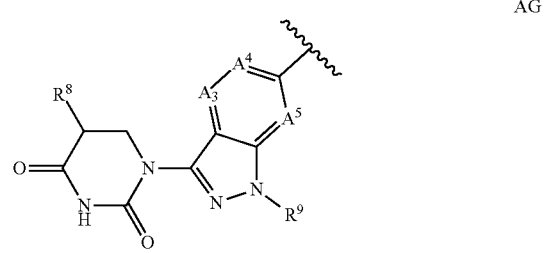

AG $A^1$ is selected from
  i) —NH—, and
  ii) —O—;
$A^2$ is selected from
  i) —N—, and
  ii) —$CR^{52}$—;
$A^3$ is selected from
  i) —N—, and
  ii) —$CR^{53}$—;
$A^4$ is selected from
  i) —N—, and
  ii) —$CR^{54}$—;

$A^5$ is selected from
i) —N—, and
ii) —$CR^{55}$—;
$R^1$ is selected from
i) H,
ii) halogen
iii) $C_{1-6}$-alkyl;
$R^{52}$ is selected from
i) H,
ii) halogen,
iii) cyano,
iv) $C_{1-6}$-alkoxy,
v) halo-$C_{1-6}$-alkoxy,
vi) $C_{1-6}$-alkyl,
vii) halo-$C_{1-6}$-alkyl,
viii) $C_{3-8}$-cycloalkyl, and
ix) halo-$C_{3-8}$-cycloalkyl;
$R^{53}$, $R^{54}$ and $R^{55}$ are independently selected from
i) H,
ii) halogen,
iii) $C_{1-6}$-alkyl,
iv) halo-$C_{1-6}$-alkyl,
v) $C_{3-8}$-cycloalkyl, and
vi) halo-$C_{3-8}$-cycloalkyl;
$R^2$ is selected from
i) H,
ii) halogen,
iii) $C_{1-6}$-alkyl,
iv) halo-$C_{1-6}$-alkyl,
v) $C_{3-8}$-cycloalkyl, and
vi) halo-$C_{3-8}$-cycloalkyl;
$R^3$ is selected from
i) H,
ii) halogen,
iii) $C_{1-6}$-alkyl,
iv) halo-$C_{1-6}$-alkyl,
v) $C_{3-8}$-cycloalkyl, and
vi) halo-$C_{3-8}$-cycloalkyl;
$R^4$ and $R^5$ are H;
or $R^4$ and $R^5$ together form —$(CH_2)_q$—;
q is 1 or 2;
$R^6$ is selected from
i) H,
ii) halogen,
iii) cyano,
iv) $C_{1-6}$-alkoxy,
v) halo-$C_{1-6}$-alkoxy,
vi) $C_{1-6}$-alkyl,
vii) halo-$C_{1-6}$-alkyl,
viii) $C_{3-8}$-cycloalkyl, and
ix) halo-$C_{3-8}$-cycloalkyl;
$R^7$ is selected from
i) H,
ii) halogen,
iii) cyano,
iv) $C_{1-6}$-alkyl,
v) halo-$C_{1-6}$-alkyl,
vi) $C_{3-8}$-cycloalkyl, and
vii) halo-$C_{3-8}$-cycloalkyl;
$R^{70}$ is selected from
i) H,
ii) halogen,
iii) cyano,
iv) $C_{1-6}$-alkyl,
v) halo-$C_{1-6}$-alkyl,
vi) $C_{3-8}$-cycloalkyl, and
vii) halo-$C_{3-8}$-cycloalkyl;

$R^8$ is H;
$R^9$ is selected from
iii) H, and
iv) $C_{1-6}$-alkyl;
$L^1$ is

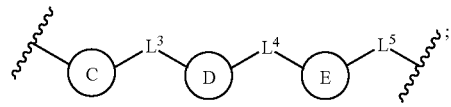

C is absent or selected from the ring systems F, G and H;

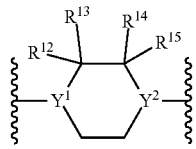

F

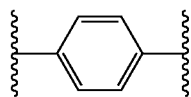

G

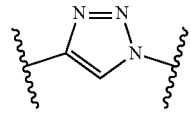

H $Y^1$ is selected from
i) —N—, and
ii) —CH—;
$Y^2$ is selected from
i) —N—, and
ii) —$CR^{16}$—;
$R^{12}$, $R^{13}$, $R^{14}$ and $R^{15}$ are independently selected from
i) —H—,
ii) halogen, and
iii) hydroxy-$C_{1-6}$-alkyl;
$R^{16}$ is selected from
i) —H—,
ii) hydroxy, and
iii) fluoro;
$L^3$ is absent or selected from
i) —$(CH_2)_m$—C(O)—,
ii) —C(O)—$(CH_2)_p$—,
iii) —C(O)—C(O)—,
iv) —$NR^{10}$—C(O)—,
v) —C(O)—$NR^{10}$—,
vi) —C(O)O—,
vii) —$CH_2$—$CF_2$—$CH_2$—,
viii) —$CH_2$—,
ix)

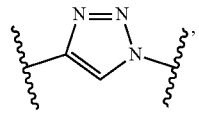 [SMILES: *c1cn(*)nn1], x)

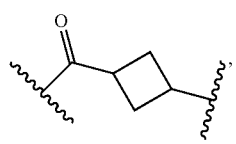 [SMILES: *C(=O)C1CC(*)C1]

and xi)

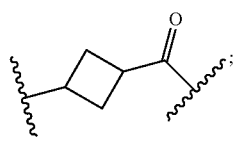 [SMILES: *C(=O)C1CC(*)C1]

m is 0, 1 or 2;
p is 0, 1, 2 or 3;
R$^{10}$ is selected from
  i) H, and
  ii) C$_{1-6}$-alkyl;
D is selected from the ring systems I, J, K, L, M, N, O, P, Q, R, S, T, U, V, W and X, all ring system being optionally substituted by one to three substituents selected from R$^{80}$, R$^{81}$ and R$^{82}$;

I

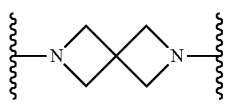

J

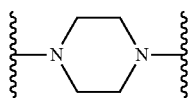

K

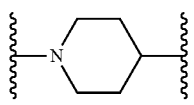

L

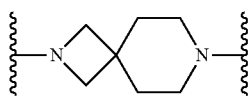

M

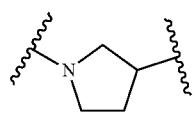

N

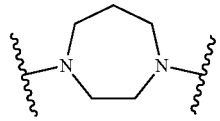

O

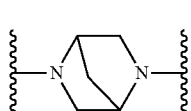

P

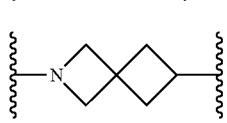

Q

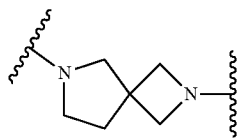

R

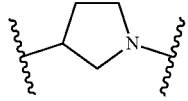

S

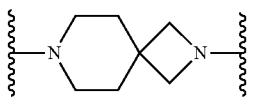

T

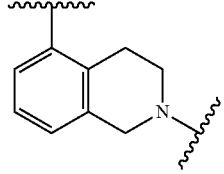

U

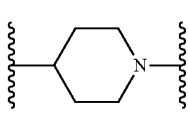

V

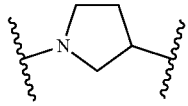

W

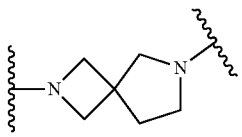

X

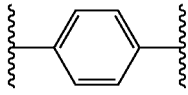

R$^{80}$, R$^{81}$ and R$^{82}$ are independently selected from
  i) halogen,
  ii) cyano,
  iii) hydroxy,
  iv) hydroxy-C$_{1-6}$-alkyl,
  v) C$_{1-6}$-alkoxy,
  vi) halo-C$_{1-6}$-alkoxy,
  vii) C$_{1-6}$-alkyl,
  viii) halo-C$_{1-6}$-alkyl,
  ix) C$_{3-8}$-cycloalkyl, and
  x) halo-C$_{3-8}$-cycloalkyl;
L$^4$ is absent or selected from
  i) —NR$^{11}$—C(O)—,
  ii) —CH$_2$—, and
  iii) —O—;
E is selected from the ring systems Y, Z, AA, AB and AC;

Y

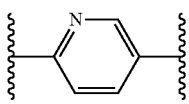

Z

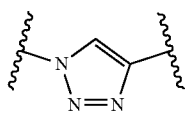

AA

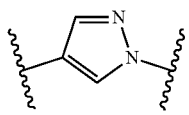

AB

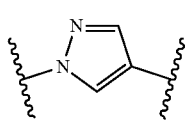

AC

L⁵ is absent or

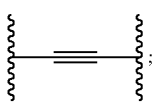

B is selected from the ring system AD and AE;

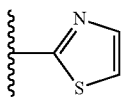

AD

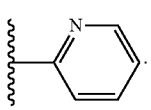

AE

E2: A certain embodiment of the invention is the compound of formula I as described herein, or a pharmaceutically acceptable salt thereof, wherein A is selected from the ring systems AF and AG;

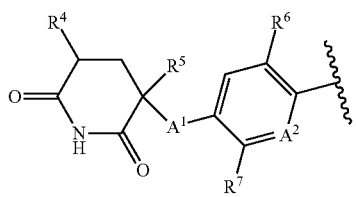

AF

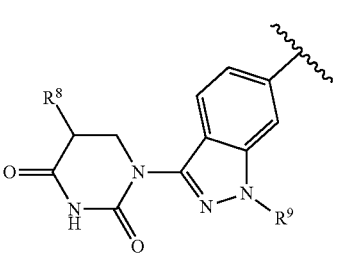

AG $A^1$ is selected from
  i) —NH—, and
  ii) —O—;
$A^2$ is selected from
  i) —N—, and
  ii) —CH—;
$R^1$ is selected from
  i) H, and
  ii) halogen;
$R^2$ is H;
$R^3$ is selected from
  i) H, and
  ii) halogen;
$R^4$ is H
$R^5$ is H;
or $R^4$ and $R^5$ together form —(CH$_2$)$_n$—;
n is 1;
$R^6$ is selected from
  i) H,
  ii) halogen,
  iii) cyano, and
  iv) halo-C$_{1-6}$-alkyl;
$R^7$ is H;
$R^8$ is H;
$R^9$ is C$_{1-6}$-alkyl;
$L^1$ is

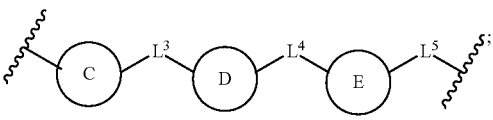

C is absent or the ring system F;

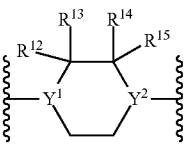

F $Y^1$ is selected from
  i) —N—, and
  ii) —CH—;
$Y^2$ is selected from
  i) —N—, and
  ii) —CR$^{16}$—;
$R^{12}$, $R^{13}$, $R^{14}$ and $R^{15}$ are independently selected from
  i) H, and
  ii) halogen;

$R^{16}$ is selected from
  i) H, and
  ii) hydroxy;
$L^3$ is selected from
  i) —(CH$_2$)$_m$—C(O)—,
  ii) —C(O)—(CH$_2$)$_p$—,
  iii) —C(O)—C(O)—, and
  iv) —NR$^{10}$—C(O)—;
m is 1;
p is 1 or 3;
$R^{10}$ is selected from
  i) H, and
  ii) $C_{1-6}$-alkyl;
D is selected from the ring systems I, J, K, L and M;

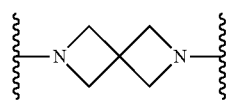  I

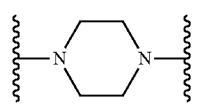  J

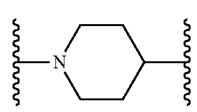  K

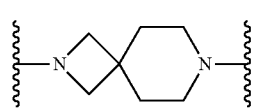  L

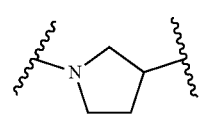  M $L^4$ is selected from
  i) —NR$^{11}$—C(O)—,
  ii) —CH$_2$—, and
  iii) —O—;
E is selected from the ring systems Y, Z and AA, AB and AC;

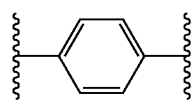  Y

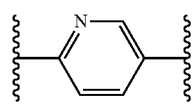  Z

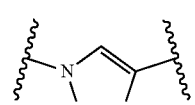  AA

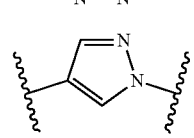  AB

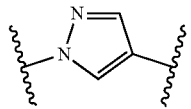  AC $L^5$ is

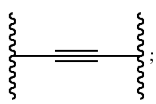

B is selected from the ring system AD and AE;

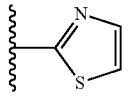  AD

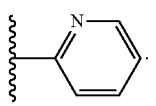  AE

E3: A certain embodiment of the invention is the compound of formula I as described herein, or a pharmaceutically acceptable salt thereof, wherein
A is selected from the ring systems AF and AG;

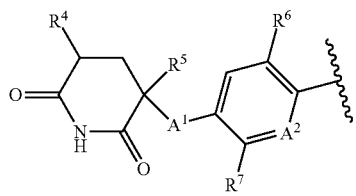  AF

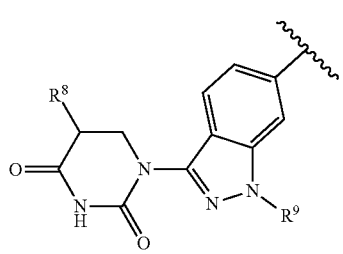  AG $A^1$ is selected from
  i) —NH—, and
  ii) —O—;
$A^2$ is selected from
  i) —N—, and
  ii) —CH—;
$R^1$ is selected from
  i) H, and
  ii) fluoro;
$R^2$ is H;
$R^3$ is selected from
  i) H, and
  ii) fluoro;

$R^4$ is H
$R^5$ is H;
or $R^4$ and $R^5$ together form —$(CH_2)_q$—;
q is 1;
$R^6$ is selected from
  i) H,
  ii) fluoro,
  iii) cyano,
  iv) difluoromethyl, and
  v) trifluoromethyl;
$R^7$ is H;
$R^8$ is H;
$R^9$ is methyl;
$L^1$ is

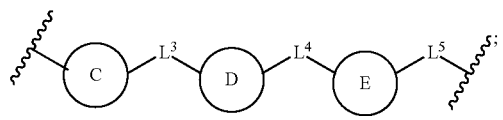

C is the ring system F;

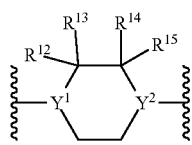 F $Y^1$ is selected from
  i) —N—, and
  ii) —CH—;
$Y^2$ is selected from
  i) —N—, and
  ii) —$CR^{16}$—;
$R^{12}$ and $R^{13}$ are fluoro;
$R^{14}$ and $R^{15}$ are H;
$R^{16}$ is selected from
  i) H, and
  ii) hydroxy;
$L^3$ is selected from
  i) —$(CH_2)_m$—C(O)—,
  ii) —C(O)—$(CH_2)_p$—,
  iii) —C(O)—C(O)—, and
  iv) —$NR^{10}$—C(O)—;
m is 1;
p is 1 or 3;
$R^{10}$ is H;
D is selected from the ring systems I, J, K, L and M;

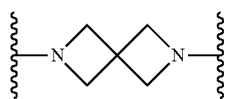 I

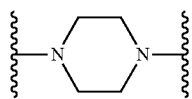 J

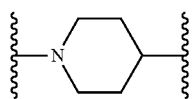 K

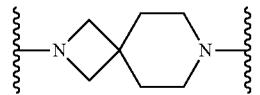 L

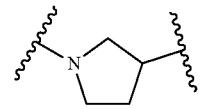 M $L^4$ is selected from
  i) —$NR^{11}$—C(O)—,
  ii) —$CH_2$—, and
  iii) —O—;
E is selected from the ring systems Y, Z, AA, AB and AC;

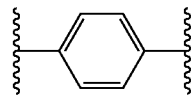 Y

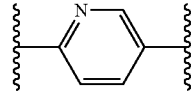 Z

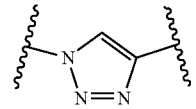 AA

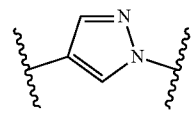 AB

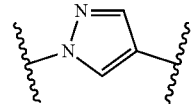 AC $L^5$ is

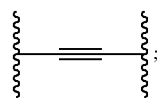

B is selected from the ring system AD and AE;

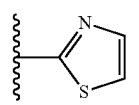 AD

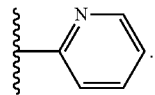 AE

E4: A certain embodiment of the invention is the compound of formula I as described herein, or a pharmaceutically acceptable salt thereof, wherein A is the ring system AF.

E5: A certain embodiment of the invention is the compound of formula I as described herein, or a pharmaceutically acceptable salt thereof, wherein $A^1$ is —N—.

E6: A certain embodiment of the invention is the compound of formula I as described herein, or a pharmaceutically acceptable salt thereof, wherein $A^2$ is —CH—.

E7: A certain embodiment of the invention is the compound of formula I as described herein, or a pharmaceutically acceptable salt thereof, wherein $R^1$ is selected from
i) H, and
ii) halogen.

E8: A certain embodiment of the invention is the compound of formula I as described herein, or a pharmaceutically acceptable salt thereof, wherein $R^1$ is selected from
i) H, and
ii) fluoro.

E9: A certain embodiment of the invention is the compound of formula I as described herein, or a pharmaceutically acceptable salt thereof, wherein $R^1$ is fluoro.

E10: A certain embodiment of the invention is the compound of formula I as described herein, or a pharmaceutically acceptable salt thereof, wherein $R^2$ is H.

E11: A certain embodiment of the invention is the compound of formula I as described herein, or a pharmaceutically acceptable salt thereof, wherein $R^3$ is selected from
i) H, and
ii) halogen.

E12: A certain embodiment of the invention is the compound of formula I as described herein, or a pharmaceutically acceptable salt thereof, wherein $R^3$ is selected from
i) H, and
ii) fluoro.

E13: A certain embodiment of the invention is the compound of formula I as described herein, or a pharmaceutically acceptable salt thereof, wherein $R^4$ is H.

E14: A certain embodiment of the invention is the compound of formula I as described herein, or a pharmaceutically acceptable salt thereof, wherein $R^5$ is H.

E15: A certain embodiment of the invention is the compound of formula I as described herein, or a pharmaceutically acceptable salt thereof, wherein $R^6$ is selected from
i) H,
ii) halogen,
iii) cyano, and
iv) halo-$C_{1-6}$-alkyl.

E16: A certain embodiment of the invention is the compound of formula I as described herein, or a pharmaceutically acceptable salt thereof, wherein $R^7$ is H.

E17: A certain embodiment of the invention is the compound of formula I as described herein, or a pharmaceutically acceptable salt thereof, wherein $R^8$ is H.

E18: A certain embodiment of the invention is the compound of formula I as described herein, or a pharmaceutically acceptable salt thereof, wherein $R^9$ is $C_{1-6}$-alkyl.

E19: A certain embodiment of the invention is the compound of formula I as described herein, or a pharmaceutically acceptable salt thereof, wherein $R^9$ is methyl.

E20: A certain embodiment of the invention is the compound of formula I as described herein, or a pharmaceutically acceptable salt thereof, wherein n is 1.

E21: A certain embodiment of the invention is the compound of formula I as described herein, or a pharmaceutically acceptable salt thereof, wherein C is absent or the ring system F.

E22: A certain embodiment of the invention is the compound of formula I as described herein, or a pharmaceutically acceptable salt thereof, wherein C is the ring system F.

E23: A certain embodiment of the invention is the compound of formula I as described herein, or a pharmaceutically acceptable salt thereof, wherein $R^{12}$ and $R^{13}$ are fluoro.

E24: A certain embodiment of the invention is the compound of formula I as described herein, or a pharmaceutically acceptable salt thereof, wherein $R^{14}$ and $R^{15}$ are H.

E25: A certain embodiment of the invention is the compound of formula I as described herein, or a pharmaceutically acceptable salt thereof, wherein $R^{16}$ is selected from
i) H, and
ii) hydroxy.

E26: A certain embodiment of the invention is the compound of formula I as described herein, or a pharmaceutically acceptable salt thereof, wherein $R^{16}$ is H.

E27: A certain embodiment of the invention is the compound of formula I as described herein, or a pharmaceutically acceptable salt thereof, wherein $L^3$ is selected from
i) —$(CH_2)_m$—C(O)—,
ii) —C(O)—$(CH_2)_p$—,
iii) —C(O)—C(O)—, and
iv) —$NR^{10}$—C(O)—.

E28: A certain embodiment of the invention is the compound of formula I as described herein, or a pharmaceutically acceptable salt thereof, wherein m is 1.

E29: A certain embodiment of the invention is the compound of formula I as described herein, or a pharmaceutically acceptable salt thereof, wherein p is 1 or 3.

E30: A certain embodiment of the invention is the compound of formula I as described herein, or a pharmaceutically acceptable salt thereof, wherein $R^{10}$ is selected from
i) H, and
ii) $C_{1-6}$-alkyl.

E31: A certain embodiment of the invention is the compound of formula I as described herein, or a pharmaceutically acceptable salt thereof, wherein D is selected from the ring systems I, J, K, L and M.

E32: A certain embodiment of the invention is the compound of formula I as described herein, or a pharmaceutically acceptable salt thereof, wherein $L^4$ is selected from
i) —$NR^{11}$—C(O)—,
ii) —$CH_2$—, and
iii) —O—.

E33: A certain embodiment of the invention is the compound of formula I as described herein, or a pharmaceutically acceptable salt thereof, wherein $L^4$ is

E34: A certain embodiment of the invention is the compound of formula I as described herein, or a pharmaceutically acceptable salt thereof, which is selected from the group consisting of 5-((2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)ethynyl)-N-(1-(2-(4-(4-((2,6-dioxopiperidin-3-yl)amino)phenyl)piperidin-1-yl)acetyl)piperidin-4-yl)picolinamide;

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[(2,6-dioxo-3-piperidyl)amino]phenyl]acetyl]-4-piperidyl]pyridine-2-carboxamide;

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[4-[(2,6-dioxo-3-piperidyl)oxy]phenyl]piperazin-1-yl]acetyl]-4-piperidyl]pyridine-2-carboxamide;

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[4-[[(3S)-2,6-dioxo-3-piperidyl]amino]-2-fluoro-phenyl]-1-piperidyl]acetyl]-4-piperidyl]pyridine-2-carboxamide;

2-(6,7-dihydro-5H-pyrrolo[1,2-c]imidazol-1-yl)-2-[6-[4-[4-[2-[4-[4-[(2,6-dioxo-3-piperidyl)amino]phenyl]-1-piperidyl]acetyl]piperazin-1-yl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[4-[2-[4-[4-[[(3S)-2,6-dioxo-3-piperidyl]amino]phenyl]-1-piperidyl]acetyl]piperazin-1-yl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[4-[2-[4-[4-[[(3R)-2,6-dioxo-3-piperidyl]amino]phenyl]-1-piperidyl]acetyl]piperazin-1-yl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-(6-(4-(4-(4-(4-(4-((2,6-dioxopiperidin-3-yl)amino)phenyl)piperidin-1-yl)-4-oxobutyl)piperazin-1-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-(4-(2-(4-(4-((2,6-dioxopiperidin-3-yl)amino)phenyl)cyclohexyl)acetyl)piperazin-1-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-(1-(2-(4-(4-((2,6-dioxopiperidin-3-yl)amino)phenyl)piperidin-1-yl)-2-oxoethyl)piperidin-4-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-[6-[4-[4-[2-[4-[5-[(2,6-dioxo-3-piperidyl)amino]-2-pyridyl]-1-piperidyl]acetyl]piperazin-1-yl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[4-[2-[4-[4-[(2,6-dioxo-3-piperidyl)amino]-2-fluoro-phenyl]-1-piperidyl]acetyl]piperazin-1-yl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[4-[2-[4-[4-[(2,6-dioxo-3-piperidyl)amino]-3-fluoro-phenyl]-1-piperidyl]acetyl]piperazin-1-yl]phenyl]-4-fluoro-1-oxo-isoindolin-2-yl]-N-thiazol-2-yl-acetamide;

2-[6-[4-[4-[2-[4-[2-cyano-4-[(2,6-dioxo-3-piperidyl)amino]phenyl]-1-piperidyl]acetyl]piperazin-1-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide;

2-[6-[4-[4-[2-[4-[2-(difluoromethyl)-4-[(2,6-dioxo-3-piperidyl)amino]phenyl]-1-piperidyl]acetyl]piperazin-1-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide;

2-(6,7-dihydro-5H-pyrrolo[1,2-c]imidazol-1-yl)-2-(6-(4-(4-(2-(4-(3-((2,6-dioxopiperidin-3-yl)amino)phenyl)piperidin-1-yl)acetyl)piperazin-1-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-(4-(2-(4-(3-(2,4-dioxotetrahydropyrimidin-1(2H)-yl)-1-methyl-1H-indazol-6-yl)piperidin-1-yl)acetyl)piperazin-1-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-(4-(2-(1-(4-((2,6-dioxopiperidin-3-yl)amino)-2-(trifluoromethyl)phenyl)-4-hydroxypiperidin-4-yl)acetyl)piperazin-1-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-(4-(2-(4-(4-((2,6-dioxopiperidin-3-yl)amino)phenyl)piperidin-1-yl)acetyl)piperazin-1-yl)phenyl)-4-fluoro-1-oxoisoindolin-2-yl)-N-(pyridin-2-yl)acetamide;

2-(6,7-dihydro-5H-pyrrolo[1,2-c]imidazol-1-yl)-2-[6-[4-[4-[2-[4-[4-[(2,6-dioxo-3-piperidyl)amino]-2-fluoro-phenyl]-1-piperidyl]acetyl]piperazin-1-yl]phenyl]-4-fluoro-1-oxo-isoindolin-2-yl]-N-(2-pyridyl)acetamide;

2-(6,7-dihydro-5H-pyrrolo[1,2-c]imidazol-1-yl)-2-(6-(4-(1-(2-(4-(4-((2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-(1-(2-(4-(4-(((S)-2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-(1-(2-(4-(4-(((R)-2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-(1-(2-(4-(4-(((S)-2,6-dioxopiperidin-3-yl)amino)-2-fluorophenyl)piperidin-1-yl)acetyl)piperidin-4-yl)phenyl)-4-fluoro-1-oxoisoindolin-2-yl)-N-(thiazol-2-yl)acetamide;

2-(6-(4-(1-(2-(4-(2-cyano-4-((2,6-dioxopiperidin-3-yl)amino)phenyl)piperidin-1-yl)acetyl)piperidin-4-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide;

2-(6,7-dihydro-5H-pyrrolo[1,2-c]imidazol-1-yl)-2-[6-[4-[1-[2-[4-[4-[(2,6-dioxo-3-piperidyl)amino]phenyl]-1-piperidyl]-2-oxo-ethyl]-4-piperidyl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]acetyl]piperazin-1-yl]-3-pyridyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[1-[1-[2-[4-[4-[[(3S)-2,6-dioxo-3-piperidyl]amino]phenyl]-1-piperidyl]acetyl]-4-piperidyl]pyrazol-4-yl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[1-[2-[4-[4-[[(3S)-2,6-dioxo-3-piperidyl]amino]phenyl]-1-piperidyl]acetyl]-4-piperidyl]pyrazol-1-yl]-4-fluoro-1-oxo-isoindolin-2-yl]-N-thiazol-2-yl-acetamide;

2-(6,7-Dihydro-5H-pyrrolo[1,2-c]imidazol-1-yl)-2-(6-(1-(1-(2-(4-(4-(((S)-2,6-dioxopiperidin-3-yl)amino)phenyl)piperidin-1-yl)acetyl)piperidin-4-yl)-1H-1,2,3-triazol-4-yl)-4-fluoro-1-oxoisoindolin-2-yl)-N-(thiazol-2-yl)acetamide;

2-(6,7-dihydro-5H-pyrrolo[1,2-c]imidazol-1-yl)-2-[6-[4-[[1-[2-[4-[4-[(2,6-dioxo-3-piperidyl)amino]phenyl]-1-piperidyl]acetyl]-4-piperidyl]oxy]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[[1-[2-[4-[4-[[(3S)-2,6-dioxo-3-piperidyl]amino]phenyl]-1-piperidyl]acetyl]-4-piperidyl]oxy]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[[1-[2-[4-[4-[[(3R)-2,6-dioxo-3-piperidyl]amino]phenyl]-1-piperidyl]acetyl]-4-piperidyl]oxy]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-(6-(4-((1-(2-(4-(4-((2,6-dioxopiperidin-3-yl)amino)-3-fluorophenyl)piperidin-1-yl)acetyl)piperidin-4-yl)oxy)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-((1-(2-(4-(4-((2,6-dioxopiperidin-3-yl)amino)-2-fluorophenyl)piperidin-1-yl)acetyl)piperidin-4-yl)oxy)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-((1-(2-(4-(5-((2,6-dioxopiperidin-3-yl)amino)pyridin-2-yl)piperidin-1-yl)acetyl)piperidin-4-yl)oxy)phenyl)-4-fluoro-1-oxoisoindolin-2-yl)-N-(thiazol-2-yl)acetamide;

2-(6-(4-((1-(2-(4-(2-cyano-4-((2,6-dioxopiperidin-3-yl)amino)phenyl)piperidin-1-yl)acetyl)piperidin-4-yl)oxy)phenyl)-4-fluoro-1-oxoisoindolin-2-yl)-2-(6,7-dihydro-5H-pyrrolo[1,2-c]imidazol-1-yl)-N-(thiazol-2-yl)acetamide;

2-(6,7-dihydro-5H-pyrrolo[1,2-c]imidazol-1-yl)-2-(6-(4-((1-(2-(4-(4-((2,4-dioxo-3-azabicyclo[3.1.1]heptan-1-yl)amino)phenyl)piperidin-1-yl)acetyl)piperidin-4-yl)oxy)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-(6-(4-((1-(2-(4-(4-(((S)-2,6-dioxopiperidin-3-yl)amino)-2-fluorophenyl)piperidin-1-yl)acetyl)piperidin-4-yl)oxy)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-[6-[4-[[1-[2-[4-[4-[(2,6-dioxo-3-piperidyl)amino]phenyl]-1-piperidyl]-2-oxo-acetyl]-4-piperidyl]oxy]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[(3R)-1-[2-[4-[4-[[(3S)-2,6-dioxo-3-piperidyl]amino]phenyl]-1-piperidyl]acetyl]pyrrolidin-3-yl]oxyphenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[(3S)-1-[2-[4-[4-[[(3S)-2,6-dioxo-3-piperidyl]amino]phenyl]-1-piperidyl]acetyl]pyrrolidin-3-yl]oxyphenyl]-4-fluoro-1-oxo-isoindolin-2-yl]-N-thiazol-2-yl-acetamide;

2-(6-(4-(4-(2-(4-(4-((2,6-dioxopiperidin-3-yl)amino)phenyl)piperidin-1-yl)acetyl)piperazin-1-yl)phenyl)-4-fluoro-1-oxoisoindolin-2-yl)-2-((R)-6-fluoro-6,7-dihydro-5H-pyrrolo[1,2-c]imidazol-1-yl)-N-(thiazol-2-yl)acetamide;

2-[6-[4-[4-[2-[4-[4-[[(3S)-2,6-dioxo-3-piperidyl]amino]-2-fluoro-phenyl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide;

2-[6-[4-[4-[2-[4-[3-(2,4-dioxohexahydropyrimidin-1-yl)-1-methyl-indazol-6-yl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide;

2-(6,7-dihydro-5H-pyrrolo[1,2-c]imidazol-1-yl)-2-(6-(4-(2-(2-(4-(4-(((S)-2,6-dioxopiperidin-3-yl)amino)-2-fluorophenyl)piperidin-1-yl)acetyl)-2,7-diazaspiro[3.5]nonan-7-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-[6-[4-[2-[2-[4-[4-[(2,6-dioxo-3-piperidyl)amino]phenyl]-1-piperidyl]acetyl]-2,6-diazaspiro[3.3]heptan-6-yl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-1-piperidyl]acetyl]-2,6-diazaspiro[3.3]heptan-6-yl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-(6-(4-(6-(2-(4-(4-((2,6-dioxopiperidin-3-yl)amino)phenyl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide;

2-(6,7-dihydro-5H-pyrrolo[1,2-c]imidazol-1-yl)-2-[6-[4-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]phenyl]-4-fluoro-1-oxo-isoindolin-2-yl]-N-(2-pyridyl)acetamide;

2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-1-piperidyl]acetyl]-2,6-diazaspiro[3.3]heptan-6-yl]phenyl]-4-fluoro-1-oxo-isoindolin-2-yl]-N-(2-pyridyl)acetamide;

2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-(2-pyridyl)acetamide;

2-(6,7-dihydro-5H-pyrrolo[1,2-c]imidazol-1-yl)-2-[6-[4-[[4-[2-[4-[4-[(2,6-dioxo-3-piperidyl)amino]phenyl]-1-piperidyl]acetyl]piperazin-1-yl]methyl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[[4-[2-[4-[4-[(2,6-dioxo-3-piperidyl)amino]-2-fluorophenyl]-1-piperidyl]acetyl]piperazin-1-yl]methyl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[[4-[2-[4-[4-[[(3S)-2,6-dioxo-3-piperidyl]amino]-2-fluoro-phenyl]-1-piperidyl]acetyl]piperazin-1-yl]methyl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[[4-[2-[4-[4-[[(3S)-2,6-dioxo-3-piperidyl]amino]-2-fluoro-phenyl]-1-piperidyl]-2-oxo-ethyl]piperazin-1-yl]methyl]phenyl]-4-fluoro-1-oxo-isoindolin-2-yl]-N-thiazol-2-yl-acetamide;

2-(6,7-dihydro-5H-pyrrolo[1,2-c]imidazol-1-yl)-2-[6-[4-[[1-[2-[4-[4-[[(3S)-2,6-dioxo-3-piperidyl]amino]-2-fluoro-phenyl]-1-piperidyl]acetyl]-4-piperidyl]methyl]phenyl]-4-fluoro-1-oxo-isoindolin-2-yl]-N-thiazol-2-yl-acetamide.

E35: A certain embodiment of the invention is the compound of formula I as described herein, or a pharmaceutically acceptable salt thereof, for use as therapeutically active substance.

E36: A certain embodiment of the invention is the compound of formula I as described herein, or a pharmaceutically acceptable salt thereof, for the use in the therapeutic and/or prophylactic treatment of cancer, in particular non-small-cell lung cancer, more particularly EGFR-mutant non-small lung cancer wherein the activating mutation is L858R.

E37: A certain embodiment of the invention is the compound of formula I as described herein, or a pharmaceutically acceptable salt thereof, for the use in the therapeutic and/or prophylactic treatment of non-small-cell lung cancer, more particularly EGFR-mutant non-small lung cancer wherein the activating mutation is L858R.

E38: A certain embodiment of the invention is the compound of formula I as described herein, or a pharmaceutically acceptable salt thereof, for the manufacture of a medicament for the therapeutic and/or prophylactic treatment of cancer, in particular non-small-cell lung cancer, more particularly EGFR-mutant non-small lung cancer wherein the activating mutation is L858R.

E39: A certain embodiment of the invention is a pharmaceutical composition comprising the compound of formula I as described herein, or a pharmaceutically acceptable salt thereof, and a pharmaceutically acceptable auxiliary substance.

E40: A certain embodiment of the invention is a method for the therapeutic and/or prophylactic treatment of cancer, in particular non-small-cell lung cancer, more particularly EGFR-mutant non-small lung cancer wherein the activating mutation is L858R, by administering the compound of formula I as described herein, or a pharmaceutically acceptable salt thereof, to a patient.

E41: A certain embodiment of the invention is the compound of formula I as described herein, or a pharmaceutically acceptable salt thereof, for the use as a medicament in therapeutic and/or prophylactic treatment of a patient with EGFR activating mutations suffering from cancer, in particular non-small-cell lung cancer, comprising determining the EGFR activating mutations status in said patient and then administering the compound of formula I as described herein, or a pharmaceutically acceptable salt thereof, to said patient.

E42: A certain embodiment of the invention is the compound of formula I as described herein, or a pharmaceutically acceptable salt thereof, for the use as a medicament in therapeutic and/or prophylactic treatment of a patient with EGFR mutations T790M/L858R, T790M/L858R/C797S, L858R and/or L858R/C797S suffering from cancer, in particular non-small-cell lung cancer, comprising determining the EGFR activating mutations status in said patient and then administering the compound of formula I as described herein, or a pharmaceutically acceptable salt thereof, to said patient.

E43: A certain embodiment of the invention is the compound of formula I as described herein, or a pharmaceutically acceptable salt thereof, for the use as a medicament in therapeutic and/or prophylactic treatment of a patient with EGFR activating mutations as determined with a Cobas® EGFR Mutation Test v2 suffering from cancer, in particular non-small-cell lung cancer, comprising determining the EGFR activating mutations status in said patient and then administering the compound of formula I as described herein, or a pharmaceutically acceptable salt thereof, to said patient.

E44: The invention includes all substituents in its corresponding deuterated form, wherever applicable, of the compounds of formula I.

E45: The invention includes all optical isomers, i.e. diastereoisomers, diastereomeric mixtures, racemic mixtures, all their corresponding enantiomers and/or tautomers as well as their solvates, wherever applicable, of the compounds of formula I.

Embodiments of Formula II

All separate embodiments may be combined.

E1: One embodiment of the invention is a compound of formula II, or a pharmaceutically acceptable salt thereof,

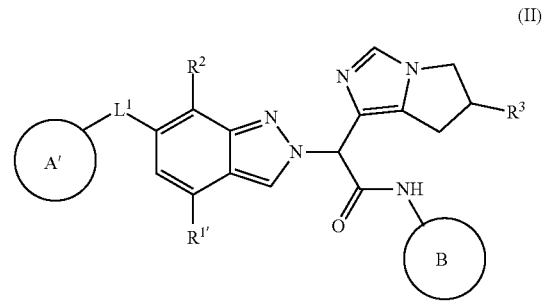

(II)

wherein
A' is selected from the ring systems AF, AG and AH;

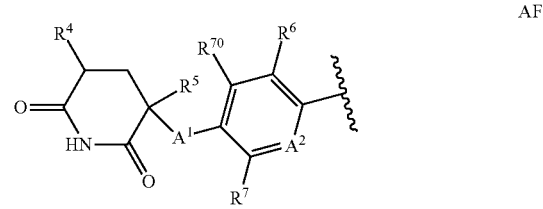

AF

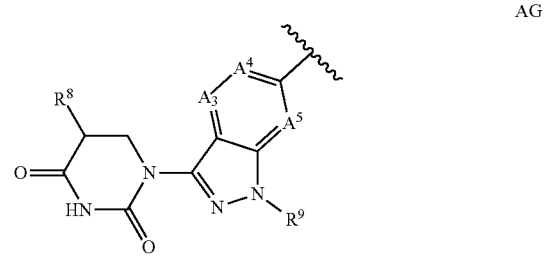

AG

-continued

AH

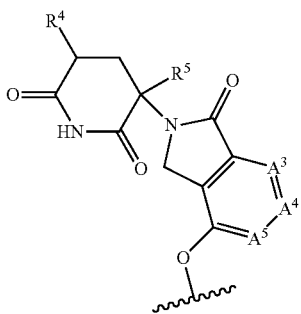

A¹ is selected from
i) —NH—, and
ii) —O—;
A² is selected from
i) —N—, and
ii) —CR$^{52}$—;
A³ is selected from
i) —N—, and
ii) —CR$^{53}$—;
A⁴ is selected from
i) —N—, and
ii) —CR$^{54}$—;
A⁵ is selected from
i) —N—, and
ii) —CR$^{55}$—;
R$^{1'}$ is selected from
i) H,
ii) halogen,
iii) C$_{1-6}$-alkyl
iv) cyano,
v) C$_{1-6}$-alkoxy,
vi) halo-C$_{1-6}$-alkoxy,
vii) C$_{1-6}$-alkyl,
viii) halo-C$_{1-6}$-alkyl,
ix) C$_{3-8}$-cycloalkyl, and
x) halo-C$_{3-8}$-cycloalkyl;
R$^{52}$ is selected from
i) H,
ii) halogen,
iii) cyano,
iv) C$_{1-6}$-alkoxy,
v) halo-C$_{1-6}$-alkoxy,
vi) C$_{1-6}$-alkyl,
vii) halo-C$_{1-6}$-alkyl,
viii) C$_{3-8}$-cycloalkyl, and
ix) halo-C$_{3-8}$-cycloalkyl;
R$^{53}$, R$^{54}$ and R$^{55}$ are independently selected from
i) H,
ii) halogen,
iii) C$_{1-6}$-alkyl,
iv) halo-C$_{1-6}$-alkyl,
v) C$_{3-8}$-cycloalkyl, and
vi) halo-C$_{3-8}$-cycloalkyl;
R² is selected from
i) H,
ii) halogen,
iii) cyano,
iv) C$_{1-6}$-alkyl,
v) halo-C$_{1-6}$-alkyl,
vi) C$_{3-8}$-cycloalkyl, and
vii) halo-C$_{3-8}$-cycloalkyl;

R³ is selected from
i) H,
ii) halogen,
iii) C$_{1-6}$-alkyl,
iv) halo-C$_{1-6}$-alkyl,
v) C$_{3-8}$-cycloalkyl, and
vi) halo-C$_{3-8}$-cycloalkyl;
R⁴ and R⁵ are H;
or R⁴ and R⁵ together form —(CH$_2$)$_q$—;
q is 1 or 2;
R⁶ is selected from
i) H,
ii) halogen,
iii) cyano,
iv) C$_{1-6}$-alkoxy,
v) halo-C$_{1-6}$-alkoxy,
vi) C$_{1-6}$-alkyl,
vii) halo-C$_{1-6}$-alkyl,
viii) C$_{3-8}$-cycloalkyl, and
ix) halo-C$_{3-8}$-cycloalkyl;
R⁷ is selected from
i) H,
ii) halogen,
iii) cyano,
iv) C$_{1-6}$-alkyl,
v) halo-C$_{1-6}$-alkyl,
vi) C$_{3-8}$-cycloalkyl, and
vii) halo-C$_{3-8}$-cycloalkyl;
R$^{70}$ is selected from
i) H,
ii) halogen,
iii) cyano,
iv) C$_{1-6}$-alkyl,
v) halo-C$_{1-6}$-alkyl,
vi) C$_{3-8}$-cycloalkyl, and
vii) halo-C$_{3-8}$-cycloalkyl;
R⁸ is H;
R⁹ is selected from
i) H, and
ii) C$_{1-6}$-alkyl;
L¹ is

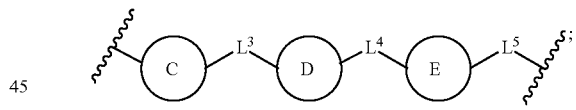

C is absent or selected from the ring systems F, G and H;

F

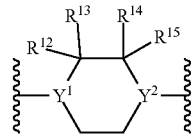

G

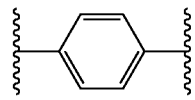

H

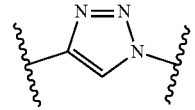

$Y^1$ is selected from
i) —N—, and
ii) —CH—;
$Y^2$ is selected from
i) —N—, and
ii) —CR$^{16}$—;
$R^{12}$, $R^{13}$, $R^{14}$ and $R^{15}$ are independently selected from
i) —H—,
ii) halogen, and
iii) hydroxy-C$_{1-6}$-alkyl;
$R^{16}$ is selected from
i) —H—,
ii) hydroxy, and
iii) fluoro;
$L^3$ is absent or selected from
i) —(CH$_2$)$_m$—C(O)—,
ii) —C(O)—(CH$_2$)$_p$—,
iii) —C(O)—C(O)—,
iv) —NR$^{10}$—C(O)—,
v) —C(O)—NR$^{10}$—,
vi) —C(O)O—,
vii) —CH$_2$—CF$_2$—CH$_2$—,
viii) —CH$_2$—,
ix)

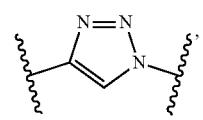 [SMILES: *c1cn(*)nn1]

x)

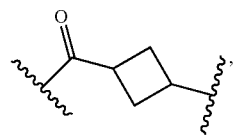 [SMILES: *C(=O)C1CC(*)C1]

and
xi)

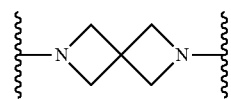

m is 0, 1 or 2;
p is 0, 1, 2 or 3;
$R^{10}$ is selected from
i) H, and
ii) C$_{1-6}$-alkyl;
D is selected from the ring systems I, J, K, L, M, N, O, P, Q, R, S, T, U, V, W and X, all ring system being optionally substituted by one to three substituents selected from $R^{80}$, $R^{81}$ and $R^{82}$;

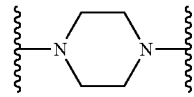

I

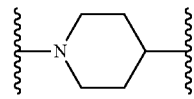

J

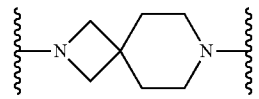

K

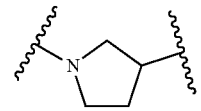

L

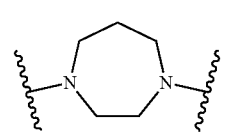

M

N

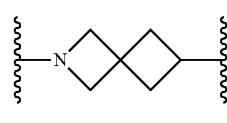

O

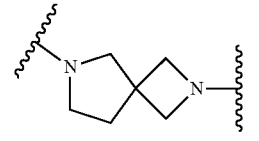

P

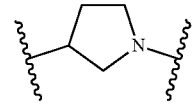

Q

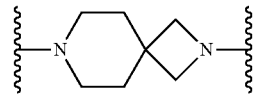

R

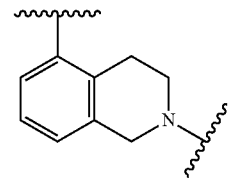

S

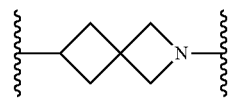

T

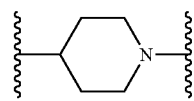

U

V

-continued

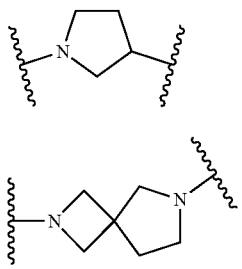
W

X $R^{80}$, $R^{81}$ and $R^{82}$ are independently selected from
  i) halogen,
  ii) cyano,
  iii) hydroxy,
  iv) hydroxy-$C_{1-6}$-alkyl,
  v) $C_{1-6}$-alkoxy,
  vi) halo-$C_{1-6}$-alkoxy,
  vii) $C_{1-6}$-alkyl,
  viii) halo-$C_{1-6}$-alkyl,
  ix) $C_{3-8}$-cycloalkyl, and
  x) halo-$C_{3-8}$-cycloalkyl;
$L^4$ is absent or selected from
  i) —$NR^{11}$—C(O)—,
  ii) —$CH_2$—, and
  iii) —O—;
E is selected from the ring systems Y, Z, AA, AB and AC;

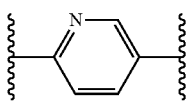
Y

Z

AA

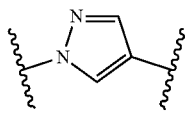
AB

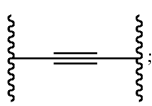 [SMILES: *C#C*]
AC $L^5$ is absent or

B is selected from the ring system AD and AE;

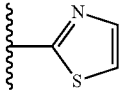
AD

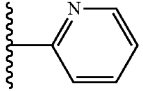
AE or a pharmaceutically acceptable salt thereof.
E2: A certain embodiment of the invention is the compound of formula II as described herein, or a pharmaceutically acceptable salt thereof, wherein
A' is selected from the ring systems AF, AG and AH;

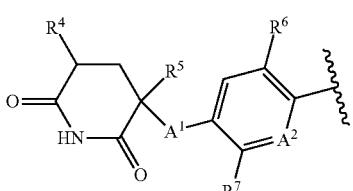
AF

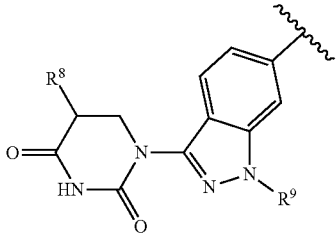
AG

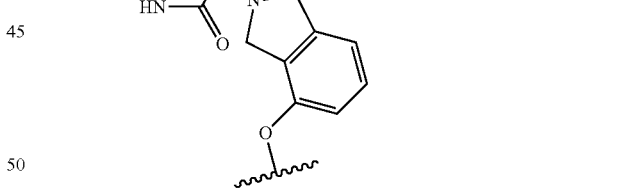
AH $A^1$ is —NH—;
$A^2$ is selected from
  i) —N—, and
  ii) —CH—;
$R^{1'}$ is selected from
  i) H, and
  ii) halogen;
$R^2$ is selected from
  i) H, and
  ii) halogen;
$R^3$ is H;
$R^4$ is H;
$R^5$ is H;

$R^6$ is selected from
i) H, and
ii) halogen;
$R^7$ is H;
$R^8$ is H;
$R^9$ is $C_{1-6}$-alkyl;
$L^1$ is

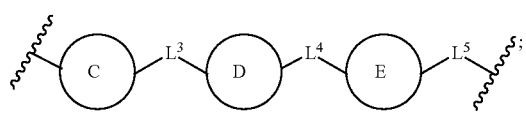 (II)

C is the ring system F;

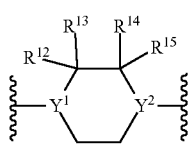 F $Y^1$ is —CH—;
$Y^2$ is —N—;
$R^{12}$, $R^{13}$, $R^{14}$ and $R^{15}$ are H;
$L^3$ is selected from
i) —$(CH_2)_m$—C(O)—, and
ii) —C(O)—$(CH_2)_p$—;
m is 1;
p is 3;
D is selected from the ring systems I and J;

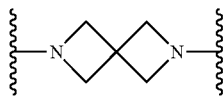 I

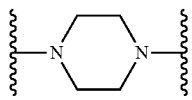 J $L^4$ is absent;
E is selected from the ring systems Y and Z;

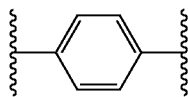 Y

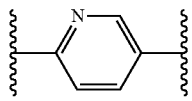 Z $L^5$ is absent;
or a pharmaceutically acceptable salt thereof.

E3: A certain embodiment of the invention is the compound of formula II as described herein, or a pharmaceutically acceptable salt thereof, wherein A is selected from the ring systems AG and AF.

E4: A certain embodiment of the invention is the compound of formula II as described herein, or a pharmaceutically acceptable salt thereof, wherein A is the ring system AF.

E5: A certain embodiment of the invention is the compound of formula II as described herein, or a pharmaceutically acceptable salt thereof, wherein $A^1$ is —NH—.

E6: A certain embodiment of the invention is the compound of formula II as described herein, or a pharmaceutically acceptable salt thereof, wherein $A^2$ is —CH—.

E7: A certain embodiment of the invention is the compound of formula II as described herein, or a pharmaceutically acceptable salt thereof, wherein $R^{1'}$ is selected from
i) H, and
ii) halogen.

E8: A certain embodiment of the invention is the compound of formula II as described herein, or a pharmaceutically acceptable salt thereof, wherein $R^{1'}$ is selected from
i) H,
ii) chloro, and
iii) fluoro.

E9: A certain embodiment of the invention is the compound of formula II as described herein, or a pharmaceutically acceptable salt thereof, wherein $R^2$ is selected from
i) H, and
ii) halogen.

E10: A certain embodiment of the invention is the compound of formula II as described herein, or a pharmaceutically acceptable salt thereof, wherein $R^2$ is selected from
i) H,
ii) chloro, and
iii) fluoro.

E11: A certain embodiment of the invention is the compound of formula II as described herein, or a pharmaceutically acceptable salt thereof, wherein $R^3$ is selected from
i) H, and
ii) halogen.

E12: A certain embodiment of the invention is the compound of formula II as described herein, or a pharmaceutically acceptable salt thereof, wherein $R^3$ is H.

E13: A certain embodiment of the invention is the compound of formula II as described herein, or a pharmaceutically acceptable salt thereof, wherein $R^4$ is H.

E14: A certain embodiment of the invention is the compound of formula II as described herein, or a pharmaceutically acceptable salt thereof, wherein $R^5$ is H.

E15: A certain embodiment of the invention is the compound of formula II as described herein, or a pharmaceutically acceptable salt thereof, wherein $R^6$ is selected from
i) H,
ii) halogen.

E16: A certain embodiment of the invention is the compound of formula II as described herein, or a pharmaceutically acceptable salt thereof, wherein $R^7$ is H.

E17: A certain embodiment of the invention is the compound of formula II as described herein, or a pharmaceutically acceptable salt thereof, wherein $R^8$ is H.

E18: A certain embodiment of the invention is the compound of formula II as described herein, or a pharmaceutically acceptable salt thereof, wherein $R^9$ is $C_{1-6}$-alkyl.

E19: A certain embodiment of the invention is the compound of formula II as described herein, or a pharmaceutically acceptable salt thereof, wherein $R^9$ is methyl.

E20: A certain embodiment of the invention is the compound of formula II as described herein, or a pharmaceutically acceptable salt thereof, wherein C is the ring system F.

E21: A certain embodiment of the invention is the compound of formula II as described herein, or a pharmaceutically acceptable salt thereof, wherein $Y^1$ is —CH—.

E22: A certain embodiment of the invention is the compound of formula II as described herein, or a pharmaceutically acceptable salt thereof, wherein $Y^2$ is —N—.

E23: A certain embodiment of the invention is the compound of formula II as described herein, or a pharmaceutically acceptable salt thereof, wherein $R^{12}$, $R^{13}$, $R^{14}$ and $R^{15}$ are H.

E24: A certain embodiment of the invention is the compound of formula II as described herein, or a pharmaceutically acceptable salt thereof, wherein $L^3$ is selected from
  i) —(CH$_2$)$_m$—C(O)—, and
  ii) —C(O)—(CH$_2$)$_p$—.

E25: A certain embodiment of the invention is the compound of formula II as described herein, or a pharmaceutically acceptable salt thereof, wherein m is 1.

E26: A certain embodiment of the invention is the compound of formula II as described herein, or a pharmaceutically acceptable salt thereof, wherein p is 1 or 3.

E27: A certain embodiment of the invention is the compound of formula II as described herein, or a pharmaceutically acceptable salt thereof, wherein D is selected from the ring systems I and J.

E28: A certain embodiment of the invention is the compound of formula II as described herein, or a pharmaceutically acceptable salt thereof, wherein D is the ring system J.

E29: A certain embodiment of the invention is the compound of formula II as described herein, or a pharmaceutically acceptable salt thereof, wherein $L^4$ is absent.

E30: A certain embodiment of the invention is the compound of formula II as described herein, or a pharmaceutically acceptable salt thereof, wherein E is selected from the ring systems Y and Z.

E31: A certain embodiment of the invention is the compound of formula II as described herein, or a pharmaceutically acceptable salt thereof, wherein $L^5$ is absent.

E32: A certain embodiment of the invention is the compound of formula II as described herein, or a pharmaceutically acceptable salt thereof, which is selected from the group consisting of
2-(6,7-dihydro-5H-pyrrolo[1,2-c]imidazol-1-yl)-2-(6-(6-(4-(4-(4-((2-(2,6-dioxopiperidin-3-yl)-1-oxoisoindolin-4-yl)oxy)piperidin-1-yl)-4-oxobutyl)piperazin-1-yl)pyridin-3-yl)-7-fluoro-2H-indazol-2-yl)-N-(thiazol-2-yl)acetamide;
2-(6,7-dihydro-5H-pyrrolo[1,2-c]imidazol-1-yl)-2-(6-(6-(4-(2-(4-(4-((2,6-dioxopiperidin-3-yl)amino)phenyl)piperidin-1-yl)acetyl)piperazin-1-yl)pyridin-3-yl)-7-fluoro-2H-indazol-2-yl)-N-(thiazol-2-yl)acetamide;
2-[4,7-dichloro-6-[4-[4-[2-[4-[4-[(2,6-dioxo-3-piperidyl)amino]phenyl]-1-piperidyl]acetyl]piperazin-1-yl]phenyl]indazol-2-yl]-2-(6,7-dihydro-5H-pyrrolo[1,2-c]imidazol-1-yl)-N-thiazol-2-yl-acetamide;
2-(6,7-dihydro-5H-pyrrolo[1,2-c]imidazol-1-yl)-2-[6-[6-[4-[2-[4-[4-[(2,6-dioxo-3-piperidyl)amino]-2-fluoro-phenyl]-1-piperidyl]acetyl]piperazin-1-yl]-3-pyridyl]-4-fluoro-indazol-2-yl]-N-thiazol-2-yl-acetamide;
2-(6,7-dihydro-5H-pyrrolo[1,2-c]imidazol-1-yl)-2-[6-[6-[4-[2-[4-[4-[(2,6-dioxo-3-piperidyl)amino]phenyl]-1-piperidyl]acetyl]piperazin-1-yl]-3-pyridyl]-4-fluoro-indazol-2-yl]-N-thiazol-2-yl-acetamide;
2-(6,7-dihydro-5H-pyrrolo[1,2-c]imidazol-1-yl)-2-[6-[6-[4-[2-[4-[5-[(2,6-dioxo-3-piperidyl)amino]-2-pyridyl]-1-piperidyl]acetyl]piperazin-1-yl]-3-pyridyl]-4-fluoro-indazol-2-yl]-N-thiazol-2-yl-acetamide;
2-(6,7-dihydro-5H-pyrrolo[1,2-c]imidazol-1-yl)-2-[6-[6-[4-[2-[4-[3-(2,4-dioxohexahydropyrimidin-1-yl)-1-methyl-indazol-6-yl]-1-piperidyl]acetyl]piperazin-1-yl]-3-pyridyl]-4-fluoro-indazol-2-yl]-N-thiazol-2-yl-acetamide;
2-(6,7-dihydro-5H-pyrrolo[1,2-c]imidazol-1-yl)-2-(6-(6-(4-(2-(4-(4-(((S)-2,6-dioxopiperidin-3-yl)amino)-2-fluoro-phenyl)piperidin-1-yl)acetyl)piperazin-1-yl)pyridin-3-yl)-4-fluoro-2H-indazol-2-yl)-N-(thiazol-2-yl)acetamide;
or a pharmaceutically acceptable salt thereof.

E33: A certain embodiment of the invention is the compound of formula II as described herein, or a pharmaceutically acceptable salt thereof, for use as therapeutically active substance.

E34: A certain embodiment of the invention is the compound of formula II as described herein, or a pharmaceutically acceptable salt thereof, for the use in the therapeutic and/or prophylactic treatment of cancer, in particular non-small-cell lung cancer, more particularly EGFR-mutant non-small lung cancer wherein the activating mutation is L858R.

E35: A certain embodiment of the invention is the compound of formula II as described herein, or a pharmaceutically acceptable salt thereof, for the use in the therapeutic and/or prophylactic treatment of non-small-cell lung cancer, more particularly EGFR-mutant non-small lung cancer wherein the activating mutation is L858R.

E36: A certain embodiment of the invention is the compound of formula II as described herein, or a pharmaceutically acceptable salt thereof, for the manufacture of a medicament for the therapeutic and/or prophylactic treatment of cancer, in particular non-small-cell lung cancer, more particularly EGFR-mutant non-small lung cancer wherein the activating mutation is L858R.

E37: A certain embodiment of the invention is a pharmaceutical composition comprising the compound of formula II as described herein, or a pharmaceutically acceptable salt thereof, and a pharmaceutically acceptable auxiliary substance.

E38: A certain embodiment of the invention is a method for the therapeutic and/or prophylactic treatment of cancer, in particular non-small-cell lung cancer, more particularly EGFR-mutant non-small lung cancer wherein the activating mutation is L858R, by administering the compound of formula II as described herein, or a pharmaceutically acceptable salt thereof, to a patient.

E39: A certain embodiment of the invention is the compound of formula II as described herein, or a pharmaceutically acceptable salt thereof, for the use as a medicament in therapeutic and/or prophylactic treatment of a patient with EGFR activating mutations suffering from cancer, in particular non-small-cell lung cancer, comprising determining the EGFR activating mutations status in said patient and then administering the compound of formula II as described herein, or a pharmaceutically acceptable salt thereof, to said patient.

E40: A certain embodiment of the invention is the compound of formula II as described herein, or a pharmaceutically acceptable salt thereof, for the use as a medicament in therapeutic and/or prophylactic treatment of a patient with EGFR mutations T790M/L858R, T790M/L858R/C797S, L858R and/or L858R/C797S suffering from cancer, in particular non-small-cell lung cancer, comprising determining the EGFR activating mutations status in said patient and then administering the compound of formula II as described herein, or a pharmaceutically acceptable salt thereof, to said patient.

E41: A certain embodiment of the invention is the compound of formula II as described herein, or a pharmaceutically acceptable salt thereof, for the use as a medicament in therapeutic and/or prophylactic treatment of a patient with EGFR activating mutations as determined with a Cobas® EGFR Mutation Test v2 suffering from cancer, in particular non-small-cell lung cancer, comprising determining the EGFR activating mutations status in said patient and then administering the compound of formula II as described herein, or a pharmaceutically acceptable salt thereof, to said patient.

E42: The invention includes all substituents in its corresponding deuterated form, wherever applicable, of the compounds of formula II.

E43: The invention includes all optical isomers, i.e. diastereoisomers, diastereomeric mixtures, racemic mixtures, all their corresponding enantiomers and/or tautomers as well as their solvates, wherever applicable, of the compounds of formula II.

Embodiments of Formula III and Formula IV

E1: In certain embodiments the present invention provides a compound of Formula III or Formula IV:

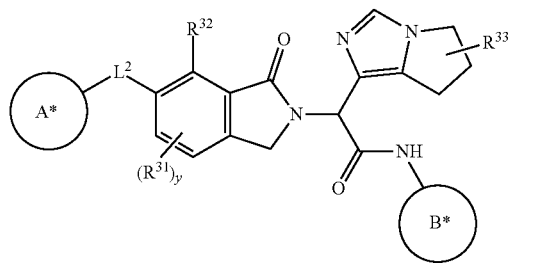

(III)

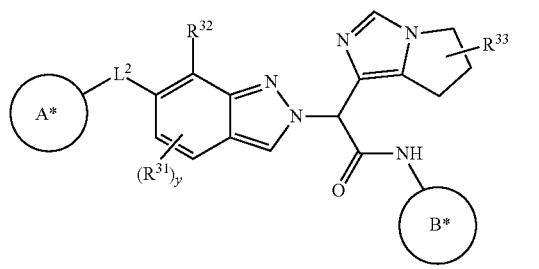

(IV)

or a pharmaceutically acceptable salt, isotope, N-oxide, stereoisomer thereof, optionally as part of a pharmaceutical composition;

wherein:

A* is selected from:

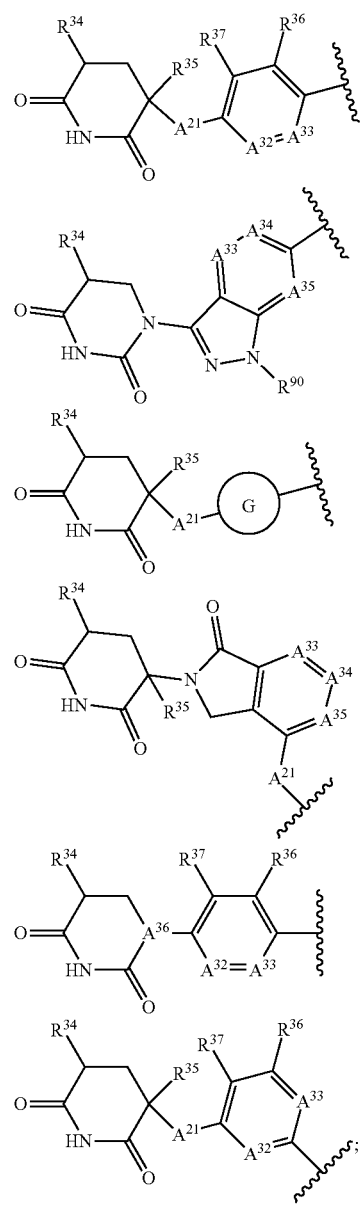

B* is heteroaryl or aryl each of which is optionally substituted with 1, 2, or 3 $R^{31}$ substituents;

y is 0, 1, 2, or 3;

$R^{31}$ is independently selected at each occurrence from H, halogen (F, Cl, Br, or I), $C_{1-6}$-alkyl, cyano, $C_{1-6}$-alkoxy, halo-$C_{1-6}$-alkoxy, halo-$C_{1-6}$-alkyl, $C_{3-8}$-cycloalkyl, and halo-$C_{3-8}$-cycloalkyl and can be located on either ring where present on a bicycle;

$R^{32}$ is hydrogen, halogen (F, Cl, Br, or I), $C_{1-6}$-alkyl, halo-$C_{1-6}$-alkyl, $C_{3-8}$-cycloalkyl, or halo-$C_{3-8}$-cycloalkyl;

$R^{33}$ is hydrogen, halogen (F, Cl, Br, or I), $C_{1-6}$-alkyl, halo-$C_{1-6}$-alkyl, $C_{3-8}$-cycloalkyl, or halo-$C_{3-8}$-cycloalkyl and can be located on the dihydropyrrole or imidazole ring;

$R^{34}$ is independently selected at each occurrence from H, F, $C_{1-6}$-alkyl, halo-$C_{1-6}$-alkyl, $C_{3-8}$-cycloalkyl, and halo-$C_{3-8}$-cycloalkyl;

$R^{35}$ is independently selected at each occurrence from H, halogen (F, Cl, Br, or I), $C_{1-6}$-alkyl, halo-$C_{1-6}$-alkyl, and $C_{3-8}$-cycloalkyl;

or $R^{34}$ and $R^{35}$ combine to form —$(CH_2)_q$—;

q is 1 or 2;

$R^{36}$ and $R^{37}$ are independently selected from H, halogen (F, Cl, Br, or I), cyano, $C_{1-6}$-alkoxy, halo-$C_{1-6}$-alkoxy, $C_{1-6}$-alkyl, halo-$C_{1-6}$-alkyl, $C_{3-8}$-cycloalkyl, and halo-$C_{3-8}$-cycloalkyl;

or $R^{36}$ and $R^{37}$ together are combined to form a 5- or 6-membered cycle optionally substituted with 1, 2, or 3 $R^{31}$ substituents;

$R^{90}$ is H, $C_{1-6}$-alkyl, or $C_{3-6}$-cycloalkyl;

Ring G is a heteroaryl optionally substituted with 1 or 2 $R^{42}$ substituents;

$A^{21}$ is —NH—, —O—, —$CH_2$—, or —$NR^{100}$—;

$R^{100}$ is alkyl, cycloalkyl, aryl, or heteroaryl; or as allowed by valence $R^{100}$ may combine with $R^{37}$ to form a 5-8 membered heterocycle or 5 membered heteroaryl;

$A^{32}$, $A^{33}$, $A^{34}$, and $A^{35}$ are independently selected from —N— and —$CR^{42}$—;

$R^{42}$ is independently selected at each occurrence from H, halogen (F, Cl, Br, or I), cyano, $C_{1-6}$-alkoxy, halo-$C_{1-6}$-alkoxy, $C_{1-6}$-alkyl, halo-$C_{1-6}$-alkyl, $C_{3-8}$-cycloalkyl, and halo-$C_{3-8}$-cycloalkyl;

$A^{36}$ is —N— or —$CR^{35}$—;

$L^2$ is a bivalent linking group that connects A* and either the isoindolinone or indazole.

E2: The compound of embodiment 1, wherein the compound is selected from:

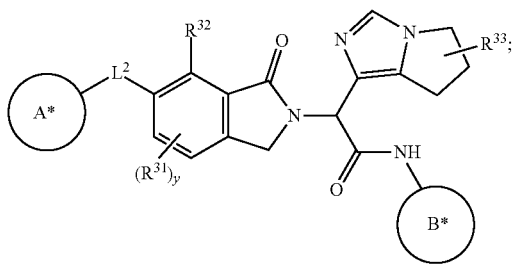

(III)

or a pharmaceutically acceptable salt thereof.

E3: The compound of embodiment 1, wherein the compound is selected from:

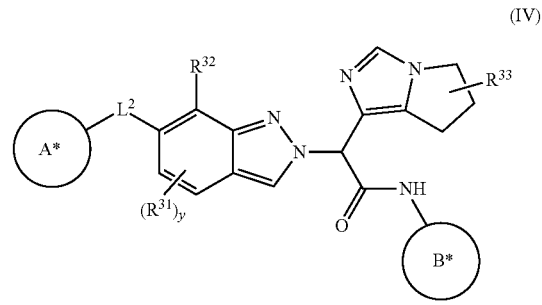

(IV)

or a pharmaceutically acceptable salt thereof.

E4: The compound of any one of embodiments 1-3, wherein $R^{33}$ is H.

E5: The compound of any one of embodiments 1-3, wherein $R^{33}$ is F.

E6: The compound of any one of embodiments 1-5, wherein y is 1.

E7: The compound of any one of embodiments 1-5, wherein y is 2.

E8: The compound of any one of embodiments 1-7, wherein at least one $R^{31}$ is halo.

E9: The compound of any one of embodiments 1-7, wherein at least one $R^{31}$ is F E10: The compound of any one of embodiments 1-5, wherein y is 0.

E11: The compound of any one of embodiments 1-10, wherein $R^{32}$ is H.

E12: The compound of any one of embodiments 1-10, wherein $R^{32}$ is F.

E13: The compound of embodiment 1, wherein the compound is selected from:

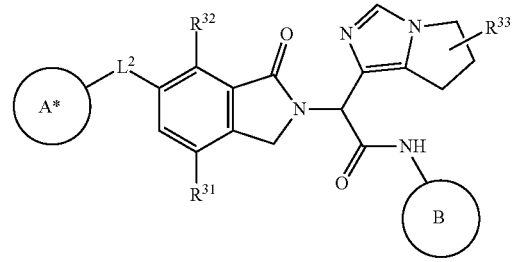

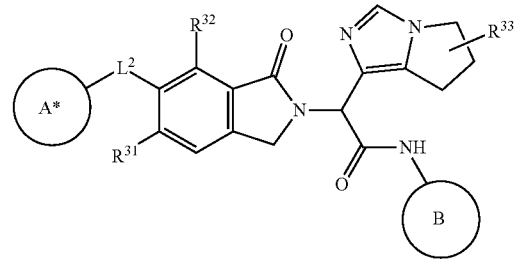

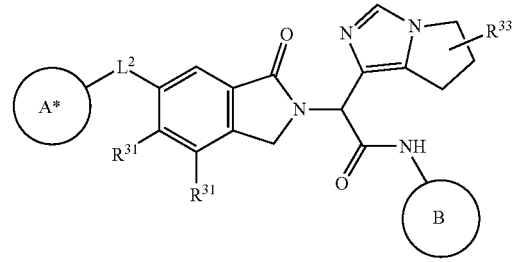

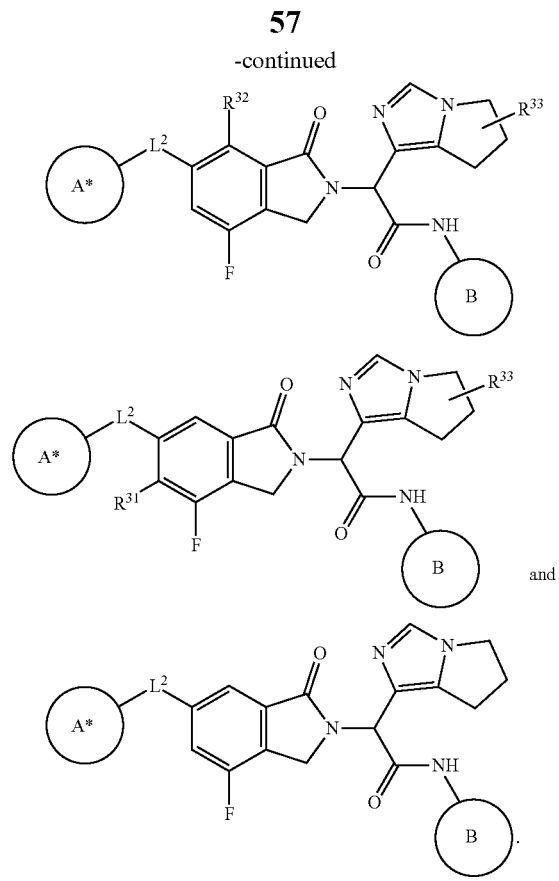

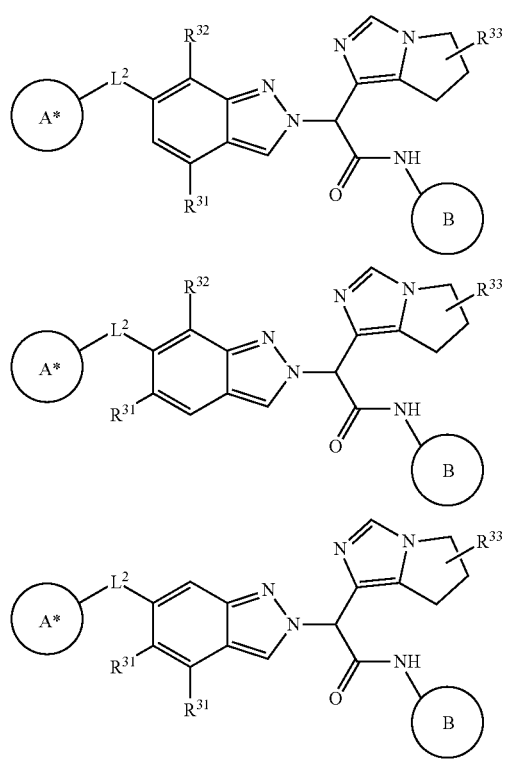

E14: The compound of embodiment 1, wherein the compound is selected from:

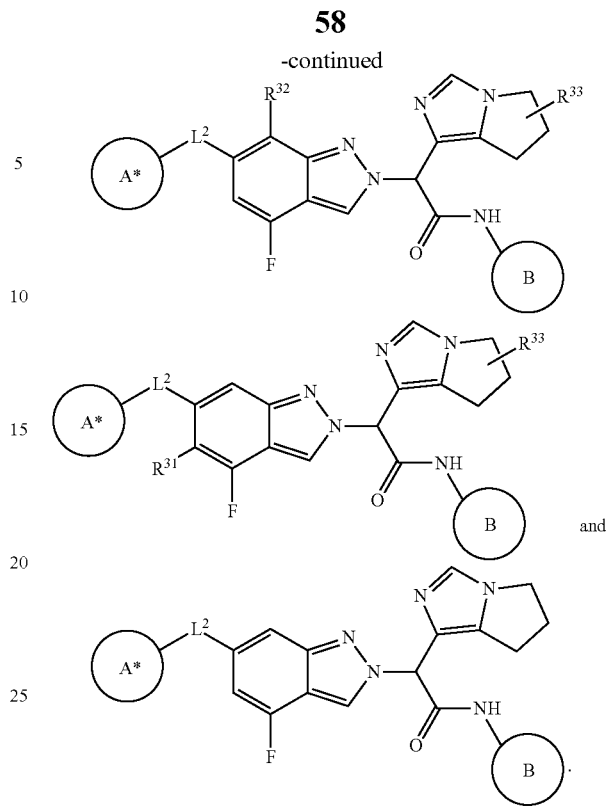

E15: The compound of any one of embodiments 1-14, wherein A* is:

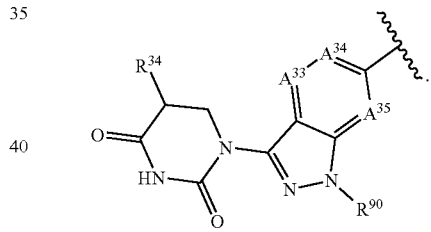

E16: The compound of any one of embodiments 1-14, wherein A* is:

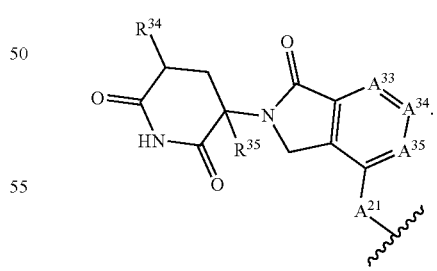

E17: The compound of any one of embodiments 1-16, wherein $A^{34}$ is CH.
E18: The compound of any one of embodiments 1-16, wherein $A^{34}$ is N.
E19: The compound of any one of embodiments 1-16, wherein $A^{34}$ is $CR^{42}$.
E20: The compound of any one of embodiments 1-16, wherein $A^{34}$ is CF.

E21: The compound of any one of embodiments 1-20, wherein $A^{35}$ is CH.

E22: The compound of any one of embodiments 1-20, wherein $A^{35}$ is N.

E23: The compound of any one of embodiments 1-20, wherein $A^{35}$ is $CR^{42}$.

E24: The compound of any one of embodiments 1-20, wherein $A^{35}$ is CF.

E25: The compound of any one of embodiments 1-14, wherein A* is:

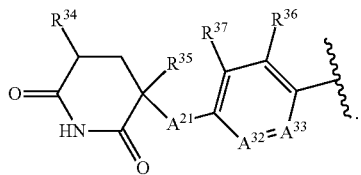

E26: The compound of any one of embodiments 1-14, wherein A* is:

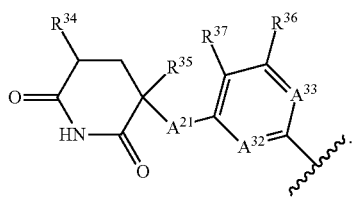

E27: The compound of embodiment 25 or 26, wherein $A^{21}$ is NH.

E28: The compound of embodiment 25 or 26, wherein $A^{21}$ is O.

E29: The compound of any one of embodiments 1-14, wherein A* is:

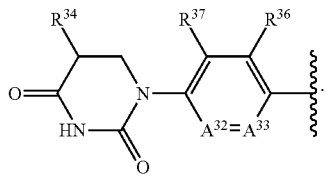

E30: The compound of any one of embodiments 1-29, wherein $A^{32}$ is CH.

E31: The compound of any one of embodiments 1-29, wherein $A^{32}$ is N.

E32: The compound of any one of embodiments 1-29, wherein $A^{32}$ is $CR^{42}$.

E33: The compound of any one of embodiments 1-29, wherein $A^{32}$ is CF.

E34: The compound of any one of embodiments 1-33, wherein $A^{33}$ is CH.

E35: The compound of any one of embodiments 1-33, wherein $A^{33}$ is N.

E36: The compound of any one of embodiments 1-33, wherein $A^{33}$ is $CR^{42}$.

E37: The compound of any one of embodiments 1-33, wherein $A^{33}$ is CF.

E38: The compound of any one of embodiments 1-14, wherein A* is:

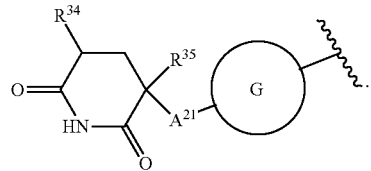

E39: The compound of embodiment 38, wherein $A^{21}$ is N.

E40: The compound of embodiment 38, wherein $A^{21}$ is O.

E41: The compound of any one of embodiments 1-40, wherein $R^{34}$ is H.

E42: The compound of any one of embodiments 1-40, wherein $R^{34}$ is F.

E43: The compound of any one of embodiments 1-40, wherein $R^{34}$ is $CH_3$.

E44: The compound of any one of embodiments 1-43, wherein $R^{35}$ is H.

E45: The compound of any one of embodiments 1-43, wherein $R^{35}$ is F.

E46: The compound of any one of embodiments 1-43, wherein $R^{35}$ is $CH_3$.

E47: The compound of any one of embodiments 1-40, wherein $R^{34}$ and $R^{35}$ combine to form a —$CH_2$—.

E48: The compound of any one of embodiments 1-47, wherein $R^{31}$ is independently selected at each occurrence from H, halogen (F, Cl, Br, or I), and $C_{1-6}$-alkyl.

E49: The compound of any one of embodiments 1-48, wherein $R^{42}$ is independently selected at each occurrence from H, halogen (F, Cl, Br, or I), and $C_{1-6}$-alkyl.

E50: The compound of any one of embodiments 1-49, wherein B* is

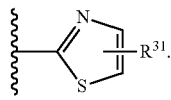

E51: The compound of any one of embodiments 1-49, wherein B* is

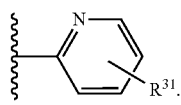

E52: The compound of any one of embodiments 1-49, wherein B* is

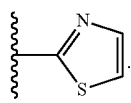

E53: The compound of any one of embodiments 1-49, wherein B* is

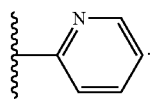

E54: The compound of any one of embodiments 1-53, wherein $L^2$ is of formula:

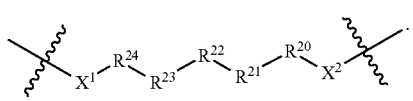

(LI)

wherein, $X^1$ and $X^2$ are independently at each occurrence selected from bond, heterocycle, aryl, heteroaryl, bicycle, alkyl, aliphatic, heteroaliphatic, —$NR^{27}$—, —$CR^{40}R^{41}$—, —O—, —C(O)—, —C($NR^{27}$)—, —C(S)—, —S(O)—, —S(O)$_2$— and —S—; each of which heterocycle, aryl, heteroaryl, and bicycle is optionally substituted with 1, 2, 3, or 4 substituents independently selected from $R^{40}$;

$R^{20}$, $R^{21}$, $R^{22}$, $R^{23}$, and $R^{24}$ are independently at each occurrence selected from the group consisting of a bond, alkyl, —C(O)—, —C(O)O—, —OC(O)—, —SO$_2$—, —S(O)—, —C(S)—, —C(O)$NR^{27}$—, —$NR^{27}$C(O)—, —O—, —S—, —$NR^{27}$—, oxyalkylene, —C($R^{40}R^{40}$)—, —P(O)($OR^{26}$)O—, —P(O)($OR^{26}$)—, bicycle, alkene, alkyne, haloalkyl, alkoxy, aryl, heterocycle, aliphatic, heteroaliphatic, heteroaryl, lactic acid, glycolic acid, and carbocycle; each of which is optionally substituted with 1, 2, 3, or 4 substituents independently selected from $R^{40}$;

$R^{26}$ is independently at each occurrence selected from the group consisting of hydrogen, alkyl, arylalkyl, heteroarylalkyl, alkene, alkyne, aryl, heteroaryl, heterocycle, aliphatic and heteroaliphatic;

$R^{27}$ is independently at each occurrence selected from the group consisting of hydrogen, alkyl, aliphatic, heteroaliphatic, heterocycle, aryl, heteroaryl, —C(O)(aliphatic, aryl, heteroaliphatic or heteroaryl), —C(O)O (aliphatic, aryl, heteroaliphatic, or heteroaryl), alkene, and alkyne;

$R^{40}$ is independently at each occurrence selected from the group consisting of hydrogen, $R^{27}$, alkyl, alkene, alkyne, fluoro, bromo, chloro, hydroxyl, alkoxy, azide, amino, cyano, —NH (aliphatic), —N(aliphatic)$_2$, —NHSO$_2$(aliphatic), —N(aliphatic)SO$_2$alkyl, —NHSO$_2$(aryl, heteroaryl or heterocycle), —N(alkyl)SO$_2$(aryl, heteroaryl or heterocycle), —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, aryl, heteroaryl, heterocycle, oxo, and cycloalkyl; additionally, where allowed by valence two $R^{40}$ groups bound to the same carbon may be joined together to form a 3-8 membered spirocycle; and $R^{41}$ is aliphatic, aryl, heteroaryl, or hydrogen.

E55: The compound of embodiment 54, wherein $L^2$ is of formula:

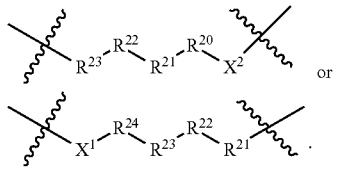

or

E56: The compound of embodiment 54 or 55, wherein $X^1$ is bond.
E57: The compound of embodiment 54 or 55, wherein $X^1$ is heterocycle.
E58: The compound of embodiment 54 or 55, wherein $X^1$ is $NR^2$.
E59: The compound of embodiment 54 or 55, wherein $X^1$ is C(O).
E60: The compound of any one of embodiments 54-59, wherein $X^2$ is bond.
E61: The compound of any one of embodiments 54-59, wherein $X^2$ is heterocycle.
E62: The compound of any one of embodiments 54-59, wherein $X^2$ is $NR^2$.
E63: The compound of any one of embodiments 54-59, wherein $X^2$ is C(O).
E64: The compound of any one of embodiments 54-63, wherein $R^{20}$ is bond.
E65: The compound of any one of embodiments 54-63, wherein $R^{20}$ is $CH_2$.
E66: The compound of any one of embodiments 54-63, wherein $R^{20}$ is heterocycle.
E67: The compound of any one of embodiments 54-63, wherein $R^{20}$ is aryl.
E68: The compound of any one of embodiments 54-63, wherein $R^{20}$ is phenyl.
E69: The compound of any one of embodiments 54-63, wherein $R^{20}$ is bicycle.
E70: The compound of any one of embodiments 54-69, wherein $R^{21}$ is bond.
E71: The compound of any one of embodiments 54-69, wherein $R^{21}$ is $CH_2$.
E72: The compound of any one of embodiments 54-69, wherein $R^{21}$ is heterocycle.
E73: The compound of any one of embodiments 54-69, wherein $R^{21}$ is aryl.
E74: The compound of any one of embodiments 54-69, wherein $R^{21}$ is phenyl.
E75: The compound of any one of embodiments 54-69, wherein $R^{21}$ is bicycle.
E76: The compound of embodiment 54, wherein L is a linker of formula:

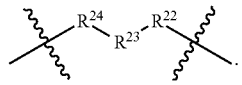

E77: The compound of any one of embodiments 54-76, wherein $R^{22}$ is bond.
E78: The compound of any one of embodiments 54-76, wherein $R^{22}$ is $CH_2$.
E79: The compound of any one of embodiments 54-76, wherein $R^{22}$ is heterocycle.
E80: The compound of any one of embodiments 54-76, wherein $R^{22}$ is aryl.
E81: The compound of any one of embodiments 54-69, wherein $R^{22}$ is phenyl.
E82: The compound of any one of embodiments 54-76, wherein $R^{22}$ is bicycle.
E83: The compound of embodiment 54, wherein L is a linker of formula:

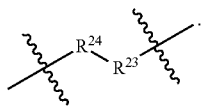

E84: The compound of any one of embodiments 54-83, wherein $R^{23}$ is bond.

E85: The compound of any one of embodiments 54-83, wherein $R^{23}$ is $CH_2$.

E86: The compound of any one of embodiments 54-83, wherein $R^{23}$ is heterocycle.

E87: The compound of any one of embodiments 54-83, wherein $R^{23}$ is aryl.

E88: The compound of any one of embodiments 54-83, wherein $R^{23}$ is phenyl.

E89: The compound of any one of embodiments 54-83, wherein $R^{23}$ is bicycle.

E90: The compound of any one of embodiments 54-89, wherein $R^{24}$ is bond.

E91: The compound of any one of embodiments 54-89, wherein $R^{24}$ is $CH_2$.

E92: The compound of any one of embodiments 54-89, wherein $R^{24}$ is heterocycle.

E93: The compound of any one of embodiments 54-89, wherein $R^{24}$ is aryl.

E94: The compound of any one of embodiments 54-89, wherein $R^{24}$ is phenyl.

E95: The compound of any one of embodiments 54-89, wherein $R^{24}$ is bicycle.

E96: The compound of any one of embodiments 54-89, wherein $R^{24}$ is C(O).

E97: In certain embodiments a compound is provided selected from:

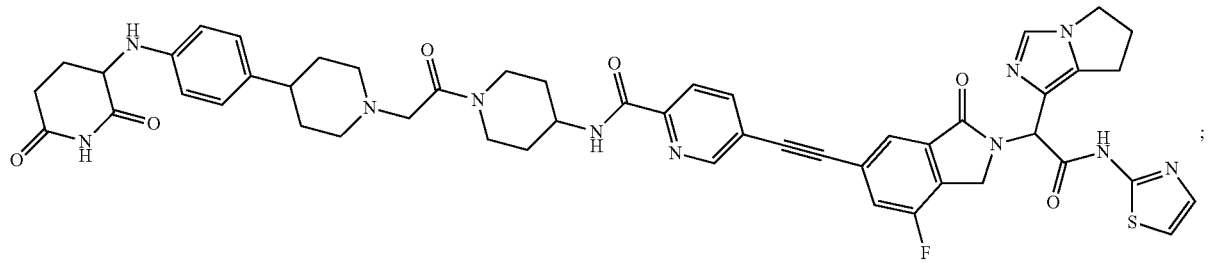

5-((2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)ethynyl)-N-(1-(2-(4-(4-((2,6-dioxopiperidine-3-yl)amino)phenyl)piperidin-1-yl)acetyl)piperidin-4-yl)picolinamide

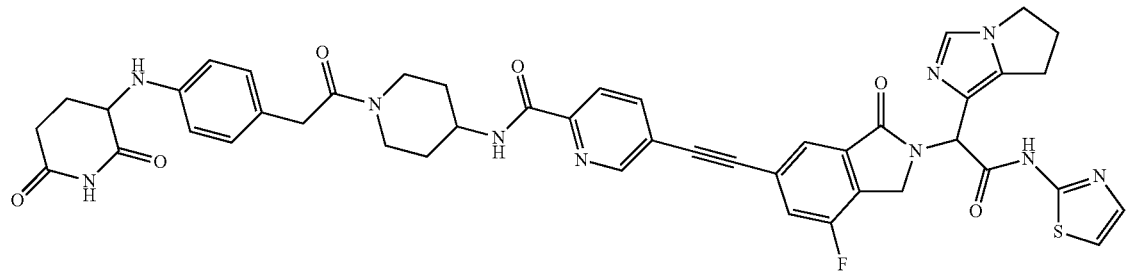

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[(2,6-dioxo-3-piperidyl)amino]phenyl]acetyl]-4-piperidyl]pyridine-2-carboxamide

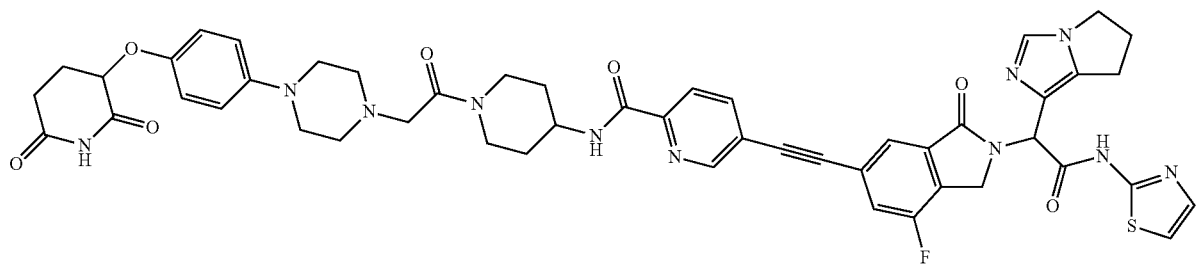

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[4-[(2,6-dioxo-3-piperidyl)oxy]phenyl]piperazin-1-yl]acetyl]-4-piperidyl]pyridine-2-carboxamide

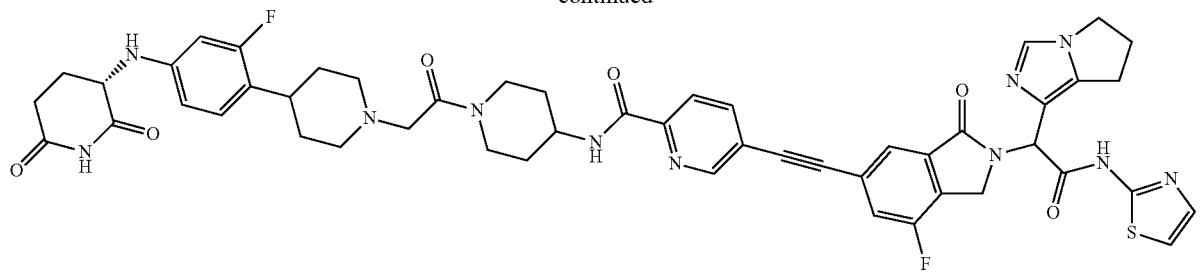

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[4-[[(3S)-2,6-dioxo-3-piperidyl]amino]-2-fluoro-phenyl]-1-piperidyl]acetyl]-4-piperidyl]pyridine-2-carboxamide

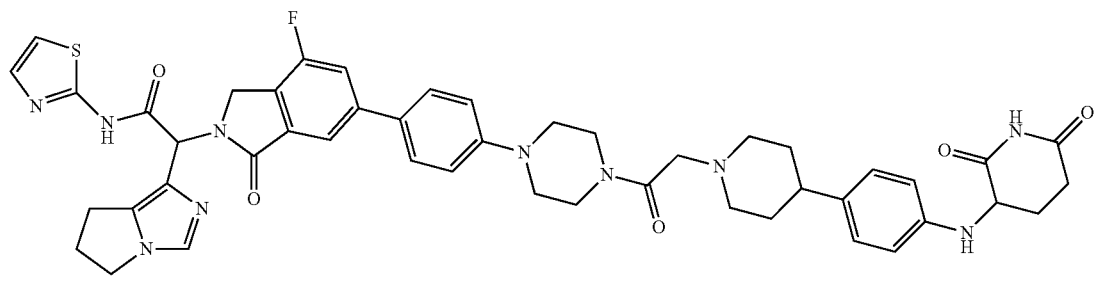

2-(6,7-dihydro-5H-pyrrolo[1,2-c]imidazol-1-yl)-2-[6-[4-[4-[2-[4-[4-[(2,6-dioxo-3-piperidyl)amino]phenyl]-1-piperidyl]acetyl]piperazin-1-yl]pheyl]-4-fluoro-1-oxo-isoindolin-2-yl]-N-thiazol-2-yl-acetamide

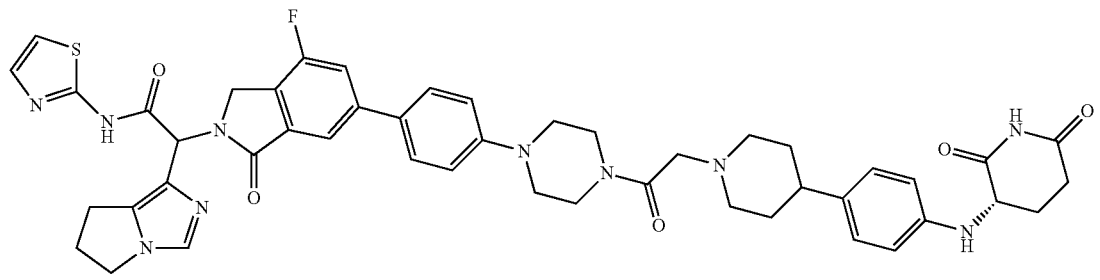

2-(6,7-dihydro-5H-pyrrolo[1,2-c]imidazol-1-yl)-2-[6-[4-[4-[2-[4-[4-[[(3S)-2,6-dioxo-3-piperidyl]amino]phenyl]-1-piperidyl]acetyl]piperazin-1-yl]pheyl]-4-fluoro-1-oxo-isoindolin-2-yl]-N-thiazol-2-yl-acetamide

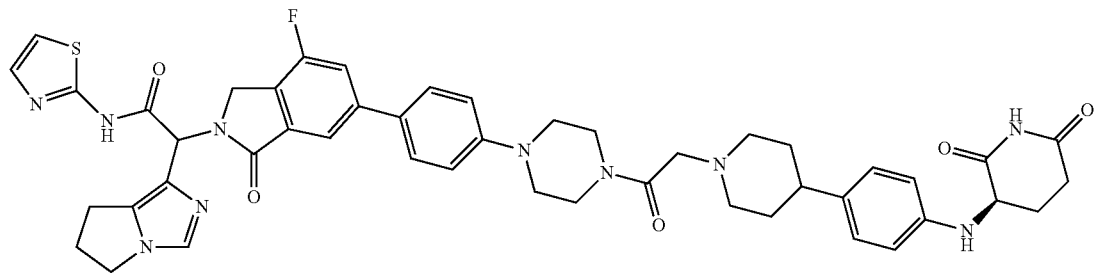

2-(6,7-dihydro-5H-pyrrolo[1,2-c]imidazol-1-yl)-2-[6-[4-[4-[2-[4-[4-[[(3R)-2,6-dioxo-3-piperidyl]amino]phenyl]-1-piperidyl]acetyl]piperazin-1-yl]pheyl]-4-fluoro-1-oxo-isoindolin-2-yl]-N-thiazol-2-yl-acetamide

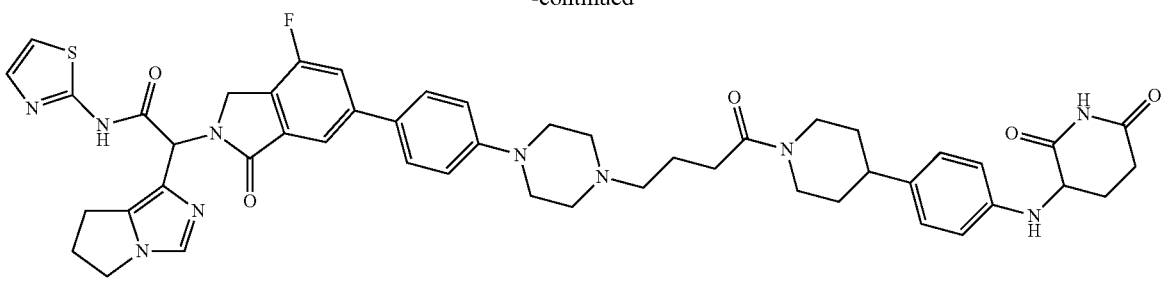

2-(6,7-dihydro-5H-pyrrolo[1,2-c]imidazol-1-yl)-2-(6-(4-(4-(4-(4-((2,6-dioxopiperidin-3-yl)amino)phenyl)piperidin-1-yl)-4-oxobutyl)piperazin-1-yl)phenyl)-4-fluoro-1-oxoisoindolin-2-yl)-N-(thiazol-2-yl)acetamide

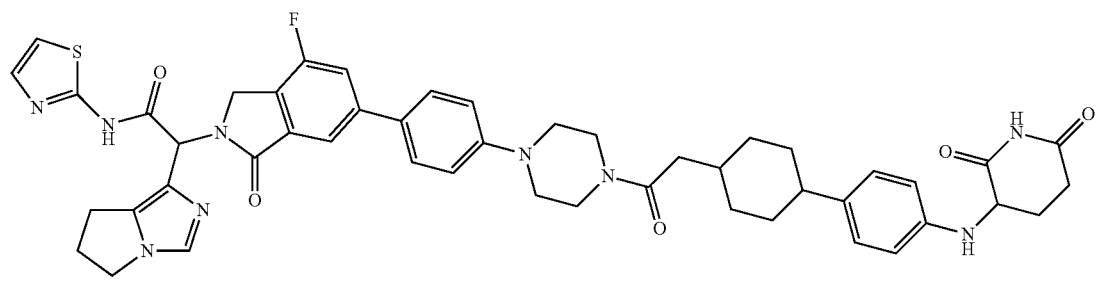

2-(6,7-dihydro-5H-pyrrolo[1,2-c]imidazol-1-yl)-2-(6-(4-(4-(2-(4-(4-((2,6-dioxopiperidin-3-yl)amino)phenyl)cyclohexyl)acetyl)piperazin-1-yl)phenyl)-4-fluoro-1-oxoisoindolin-2-yl)-N-(thiazol-2-yl)acetamide

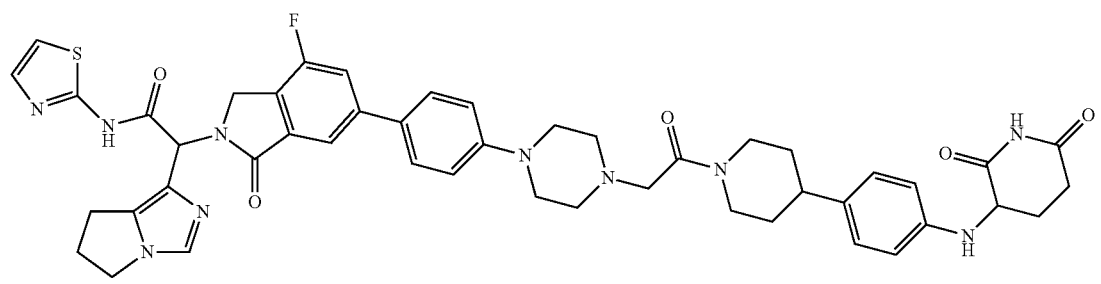

2-(6,7-dihydro-5H-pyrrolo[1,2-c]imidazol-1-yl)-2-(6-(4-(4-(2-(4-(4-((2,6-dioxopiperidin-3-yl)amino)phenyl)piperidin-1-yl)-2-oxoethyl)piperazin-1-yl)phenyl)-4-fluoro-1-oxoisoindolin-2-yl)-N-(thiazol-2-yl)acetamide

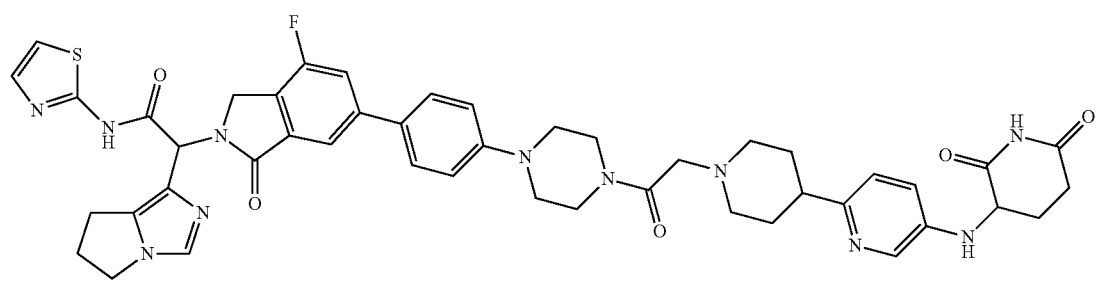

2-(6,7-dihydro-5H-pyrrolo[1,2-c]imidazol-1-yl)-2-[6-[4-[4-[2-[4-[5-[(2,6-dioxo-3-piperidyl)amino]-2-pyridyl]-1-piperidyl]acetyl]piperazin-1-yl]phenyl]-4-fluoro-1-oxo-isoindolin-2-yl]-N-thiazol-2-yl-acetamide

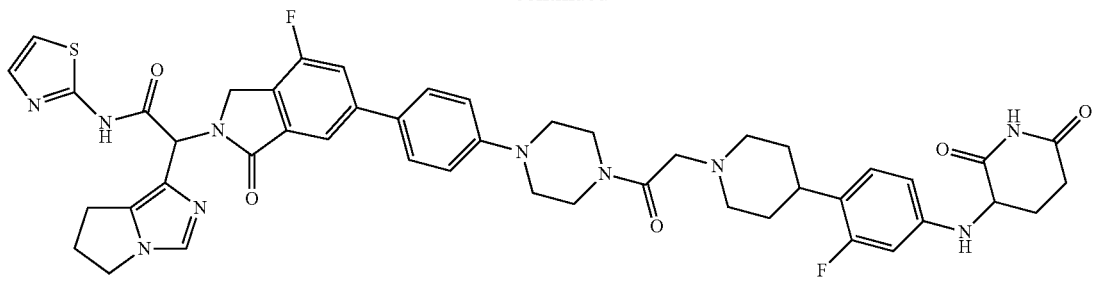

2-(6,7-dihydro-5H-pyrrolo[1,2-c]imidazol-1-yl)-2-[6-[4-[4-[2-[4-[4-[(2,6-dioxo-3-piperidyl)amino]-2-fluoro-phenyl]-1-piperidyl]acetyl]piperazin-1-yl]phenyl]-4-fluoro-1-oxo-isoindolin-2-yl]-N-thiazol-2-yl-acetamide

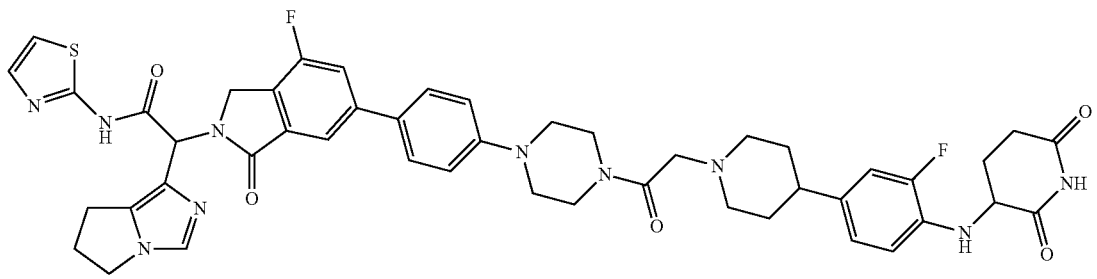

2-(6,7-dihydro-5H-pyrrolo[1,2-c]imidazol-1-yl)-2-[6-[4-[4-[2-[4-[4-[(2,6-dioxo-3-piperidyl)amino]-3-fluoro-phenyl]-1-piperidyl]acetyl]piperazin-1-yl]phenyl]-4-fluoro-1-oxo-isoindolin-2-yl]-N-thiazol-2-yl-acetamide

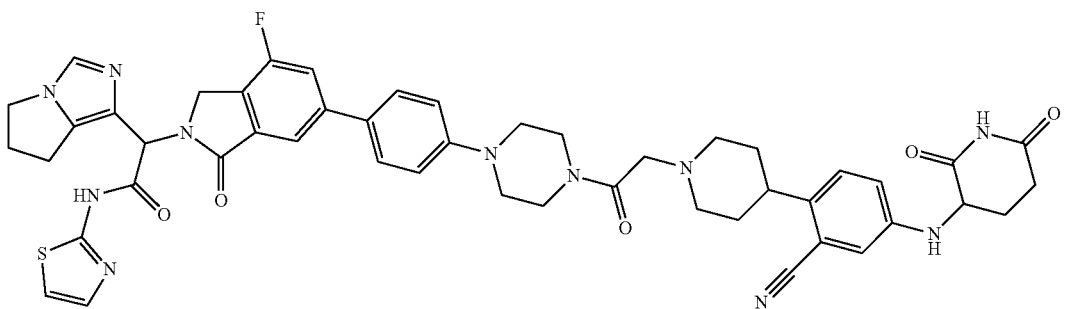

2-[6-[4-[4-[2-[4-[2-cyano-4-[(2,6-dioxo-3-piperidyl)amino]phenyl]-1-piperidyl]acetyl]piperazin-1-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

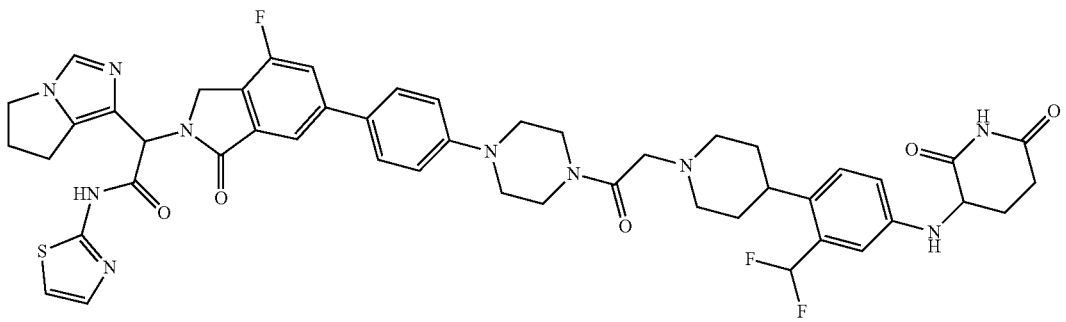

2-[6-[4-[4-[2-[4-[2-(difluoromethyl)-4-[(2,6-dioxo-3-piperidyl)amino]phenyl]-1-piperidyl]acetyl]piperazin-1-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

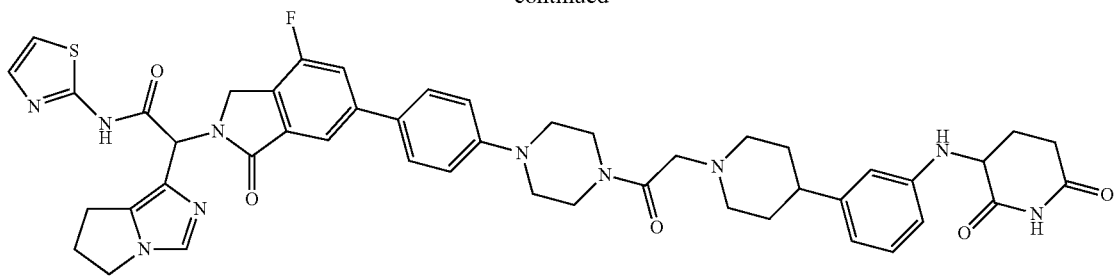

2-(6,7-dihydro-5H-pyrrolo[1,2-c]imidazol-1-yl)-2-(6-(4-(4-(2-(4-(3-((2,6-dioxopiperidin-3-yl)amino)phenyl)piperidin-1-yl)acetyl)piperazin-1-yl)phenyl)-4-fluoro-1-oxoisoindolin-2-yl)-N-(thiazol-2-yl)acetamide

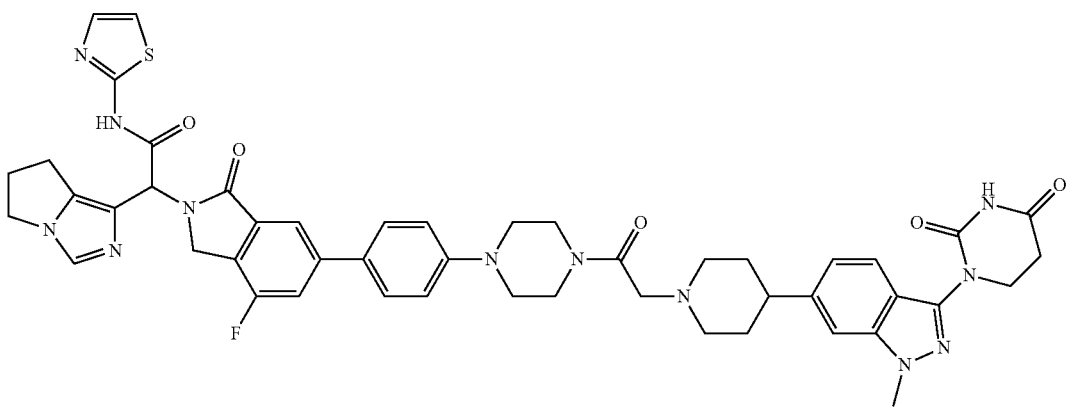

2-(6,7-dihydro-5H-pyrrolo[1,2-c]imidazol-1-yl)-2-(6-(4-(4-(2-(4-(3-(2,4-dioxotetrahydropyrimidin-1(2H)-yl)-1-methyl-1H-indazol-6-yl)piperidin-1-yl)acetyl)piperazin-1-yl)phenyl)-4-fluoro-1-oxoisoindolin-2-yl)-N-(thiazol-2-yl)acetamide

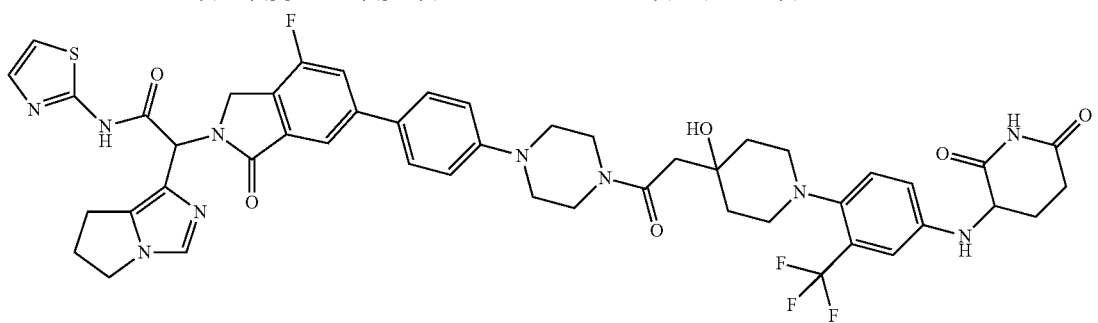

2-(6,7-dihydro-5H-pyrrolo[1,2-c]imidazol-1-yl)-2-(6-(4-(4-(2-(1-(4-((2,6-dioxopiperidin-3-yl)amino)-2-(trifluoromethyl)phenyl)-4-hydroxypiperidin-4-yl)acetyl)piperazin-1-yl)phenyl)-4-fluoro-1-oxoisoindolin-2-yl)-N-(thiazol-2-yl)acetamide

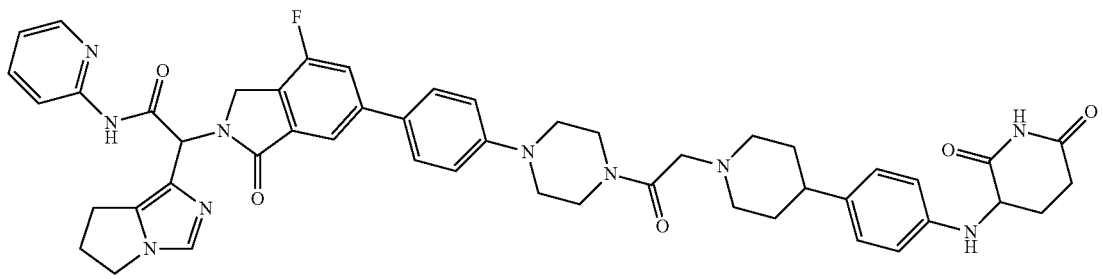

2-(6,7-dihydro-5H-pyrrolo[1,2-c]imidazol-1-yl)-2-(6-(4-(4-(2-(4-(4-((2,6-dioxopiperidin-3-yl)amino)phenyl)piperidin-1-yl)acetyl)piperazin-1-yl)phenyl)-4-fluoro-1-oxoisoindolin-2-yl)-N-(pyridin-2-yl)acetamide

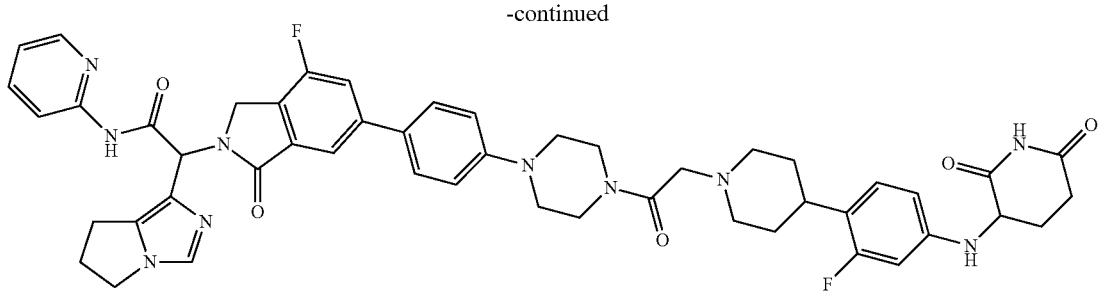

2-(6,7-dihydro-5H-pyrrolo[1,2-c]imidazol-1-yl)-2-[6-[4-[4-[2-[4-[4-[(2,6-dioxo-3-piperidyl)amino]-2-fluoro-phenyl]-1-piperidyl]acetyl]piperazin-1-yl]phenyl]-4-fluoro-1-oxo-isoindolin-2-yl]-N-(2-pyridyl)acetamide

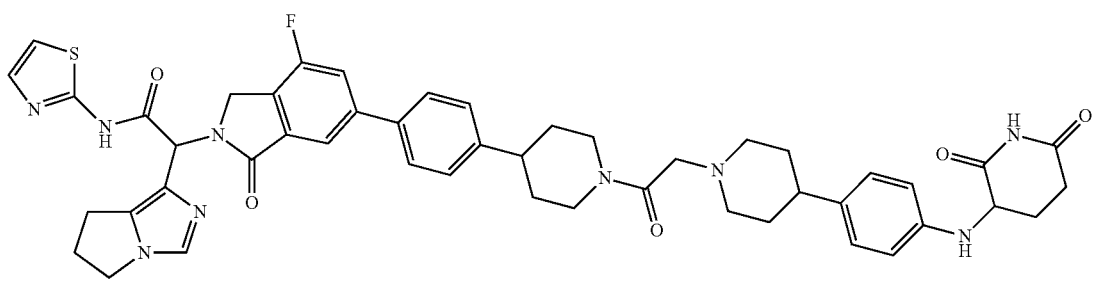

2-(6,7-dihydro-5H-pyrrolo[1,2-c]imidazol-1-yl)-2-(6-(4-(1-(2-(4-(4-((2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide

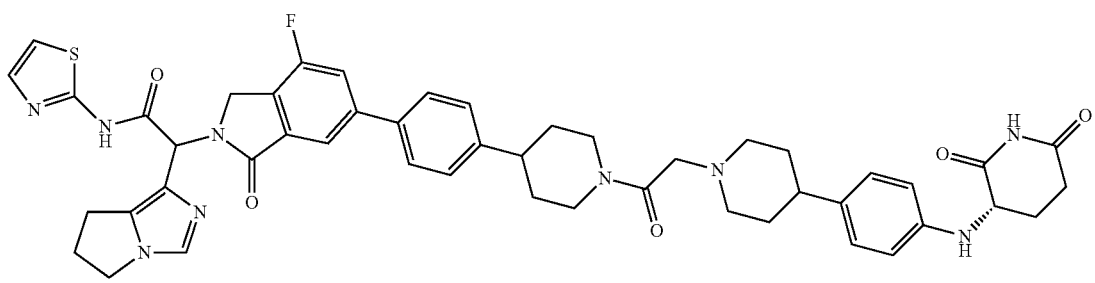

2-(6,7-dihydro-5H-pyrrolo[1,2-c]imidazol-1-yl)-2-(6-(4-(1-(2-(4-(4-(((S)-2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide

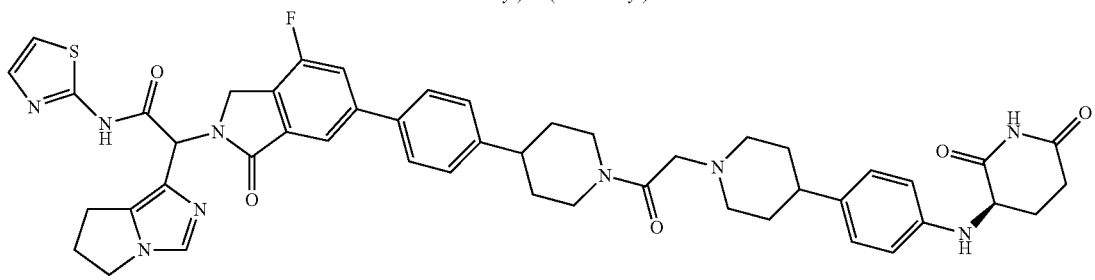

2-(6,7-dihydro-5H-pyrrolo[1,2-c]imidazol-1-yl)-2-(6-(4-(1-(2-(4-(4-(((R)-2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide

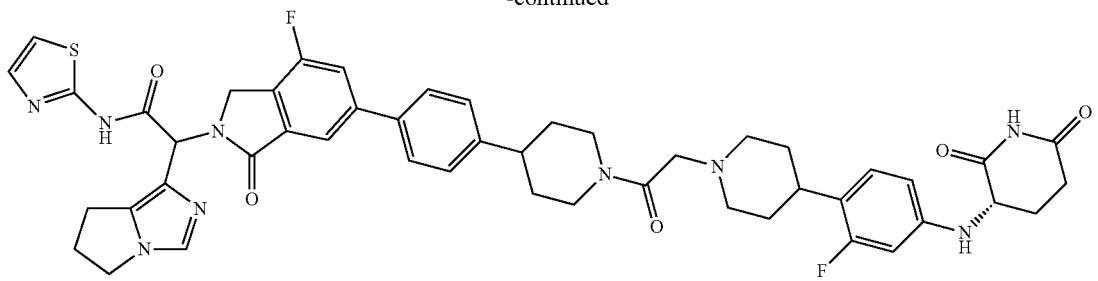

2-(6,7-dihydro-5H-pyrrolo[1,2-c]imidazol-1-yl)-2-(6-(4-(1-(2-(4-(4-(((S)-2,6-dioxopiperidin-3-yl)amino)-2-fluorophenyl)piperidin-1-yl)acetyl)piperidin-4-yl)phenyl)-4-fluoro-1-oxoisoindolin-2-yl)-N-(thiazol-2-yl)acetamide

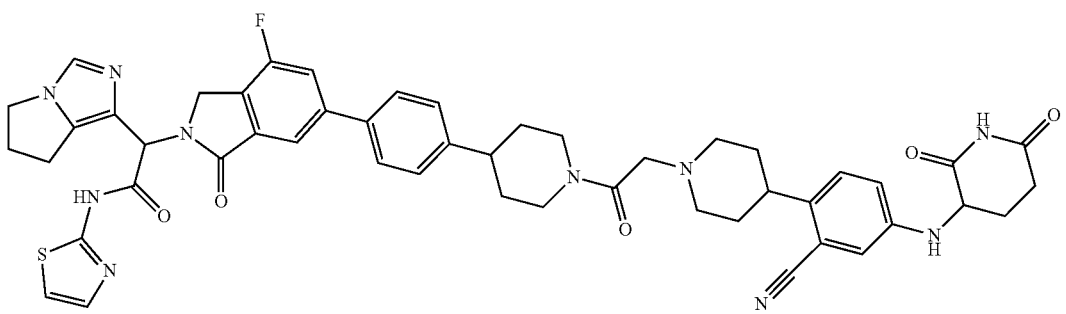

2-(6-(4-(1-(2-(4-(2-cyano-4-((2,6-dioxopiperidin-3-yl)amino)phenyl)piperidin-1-yl)acetyl)piperidin-4-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide

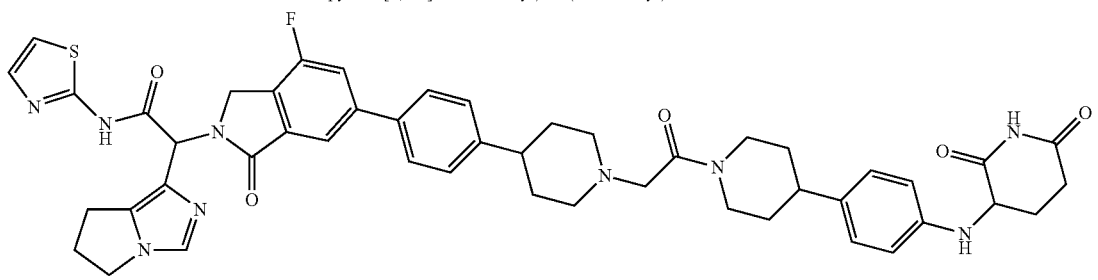

2-(6,7-dihydro-5H-pyrrolo[1,2-c]imidazol-1-yl)-2-[6-[4-[1-[2-[4-[4-[(2,6-dioxo-3-piperidyl)amino]phenyl]-1-piperidyl]-2-oxo-ethyl]-4-piperidyl]phenyl]-4-fluoro-1-oxo-isoindolin-2-yl]-N-thiazol-2-yl-acetamide

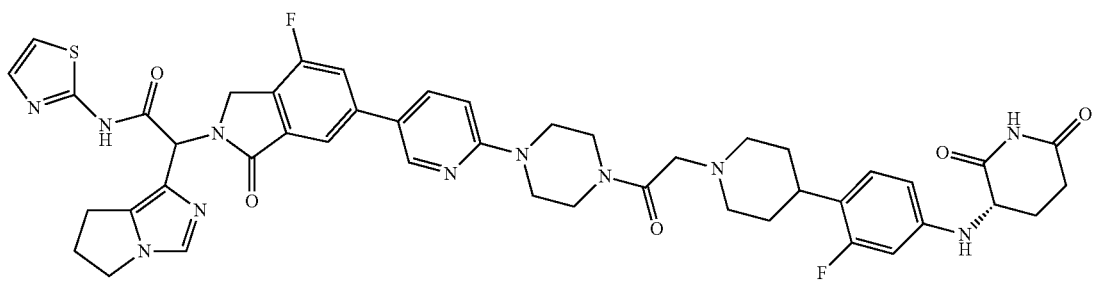

2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]acetyl]piperazin-1-yl]-3-pyridyl]-4-fluoro-1-oxo-isoindolin-2-yl]-N-thiazol-2-yl-acetamide

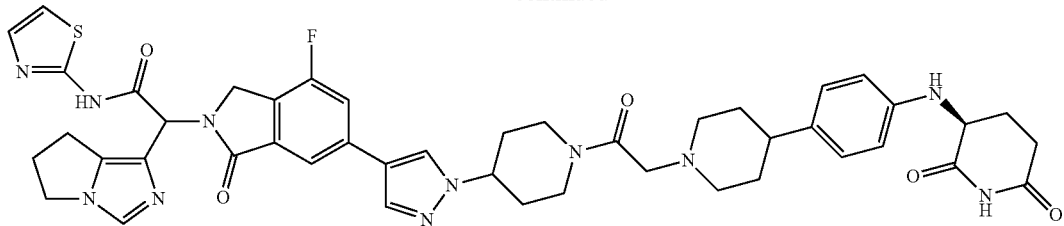

2-(6,7-dihydro-5H-pyrrolo[1,2-c]imidazol-1-yl)-2-[6-[1-[1-[2-[4-[4-[[(3S)-2,6-dioxo-3-piperidyl]amino]phenyl]-1-piperidyl]acetyl]-4-piperidyl]pyrazol-4-yl]-4-fluoro-1-oxo-isoindolin-2-yl]-N-thiazol-2-yl-acetamide

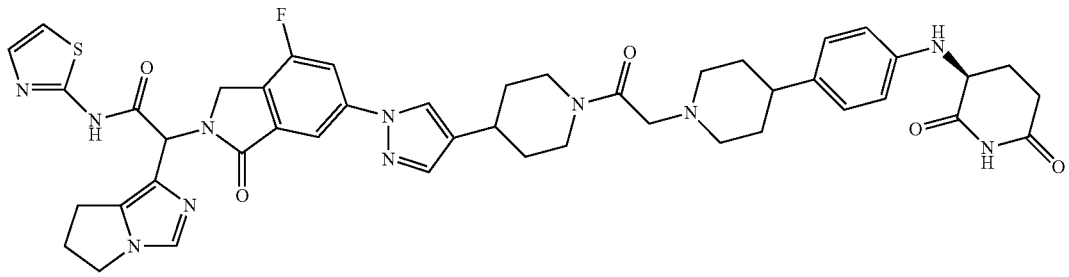

2-(6,7-dihydro-5H-pyrrolo[1,2-c]imidazol-1-yl)-2-[6-[4-[1-[2-[4-[4-[[(3S)-2,6-dioxo-3-piperidyl]amino]phenyl]-1-piperidyl]acetyl]-4-piperidyl]pyrazol-1-yl]-4-fluoro-1-oxo-isoindolin-2-yl]-N-thiazol-2-yl-acetamide

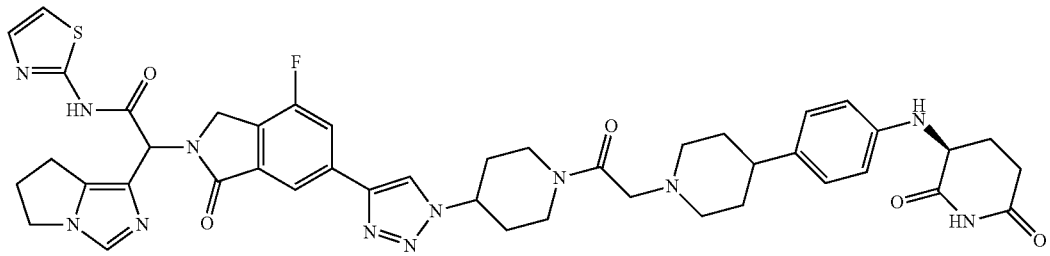

2-(6,7-dihydro-5H-pyrrolo[1,2-c]imidazol-1-yl)-2-(6-(1-(1-(2-(4-(4-(((S)-2,6-dioxopiperidin-3-yl)amino)phenyl)piperidin-1-yl)acetyl)piperidin-4-yl)-1H-1,2,3-triazol-4-yl)-4-fluoro-1-oxoisoindolin-2-yl)-N-(thiazol-2-yl)acetamide

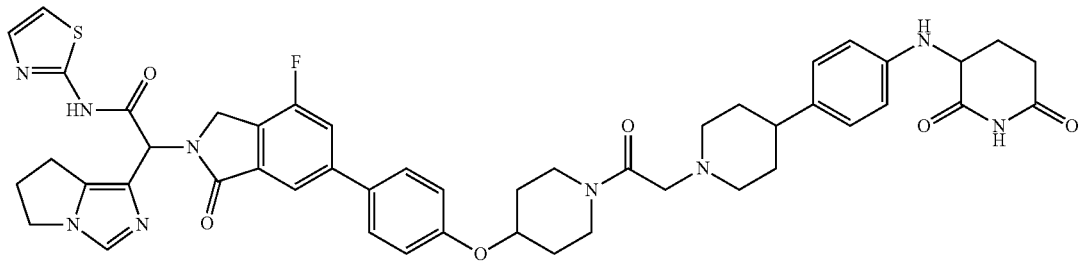

2-(6,7-dihydro-5H-pyrrolo[1,2-c]imidazol-1-yl)-2-[6-[4-[[1-[2-[4-[4-[(2,6-dioxo-3-piperidyl)amino]phenyl]-1-piperidyl]acetyl]-4-piperidyl]oxy]phenyl]-4-fluoro-1-oxo-isoindolin-2-yl]-N-thiazol-2-yl-acetamide

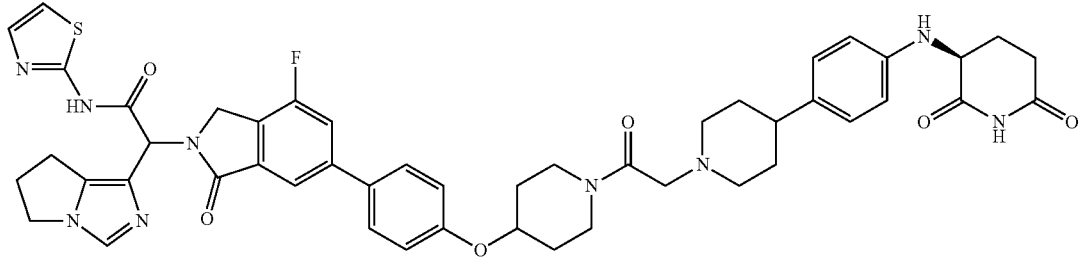

2-(6,7-dihydro-5H-pyrrolo[1,2-c]imidazol-1-yl)-2-[6-[4-[[1-[2-[4-[4-[[(3S)-2,6-dioxo-3-piperidyl]amino]phenyl]-1-piperidyl]acetyl]-4-piperidyl]oxy]phenyl]-4-fluoro-1-oxo-isoindolin-2-yl]-N-thiazol-2-yl-acetamide

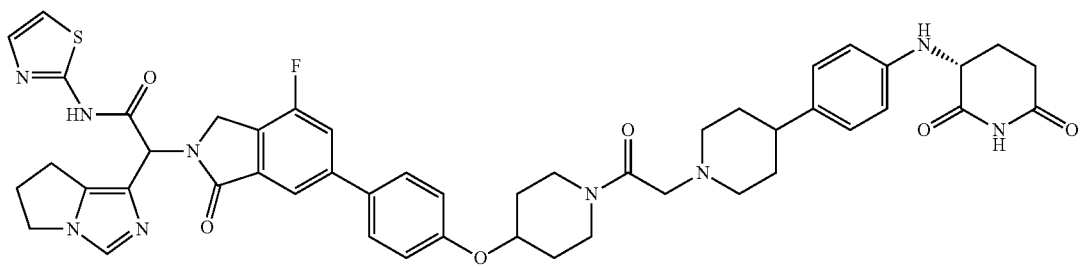

2-(6,7-dihydro-5H-pyrrolo[1,2-c]imidazol-1-yl)-2-[6-[4-[[1-[2-[4-[4-[[(3R)-2,6-dioxo-3-piperidyl]amino]phenyl]-1-piperidyl]acetyl]-4-piperidyl]oxy]phenyl]-4-fluoro-1-oxo-isoindolin-2-yl]-N-thiazol-2-yl-acetamide

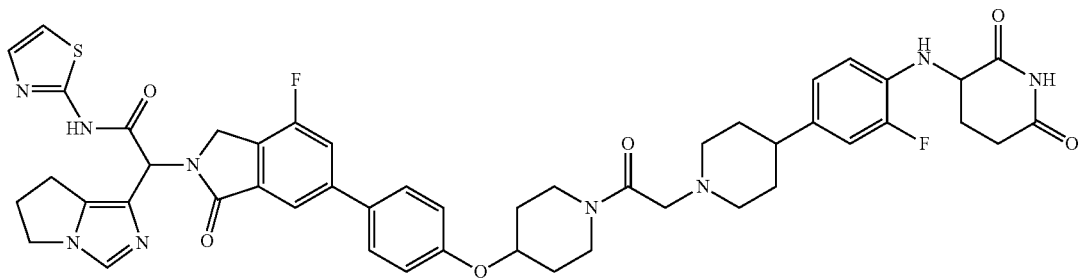

2-(6,7-dihydro-5H-pyrrolo[1,2-c]imidazol-1-yl)-2-(6-(4-((1-(2-(4-(4-((2,6-dioxopiperidin-3-yl)amino)-3-fluorophenyl)piperidin-1-yl)acetyl)piperidin-4-yl)oxy)phenyl)-4-fluoro-1-oxoisoindolin-2-yl)-N-(thiazol-2-yl)acetamide

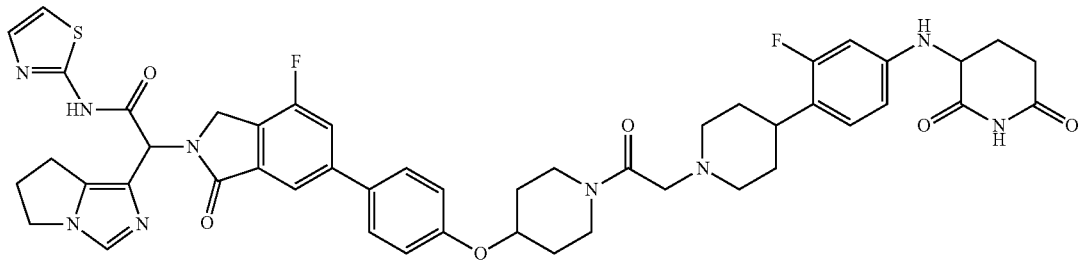

2-(6,7-dihydro-5H-pyrrolo[1,2-c]imidazol-1-yl)-2-(6-(4-((1-(2-(4-(4-((2,6-dioxopiperidin-3-yl)amino)-2-fluorophenyl)piperidin-1-yl)acetyl)piperidin-4-yl)oxy)phenyl)-4-fluoro-1-oxoisoindolin-2-yl)-N-(thiazol-2-yl)acetamide

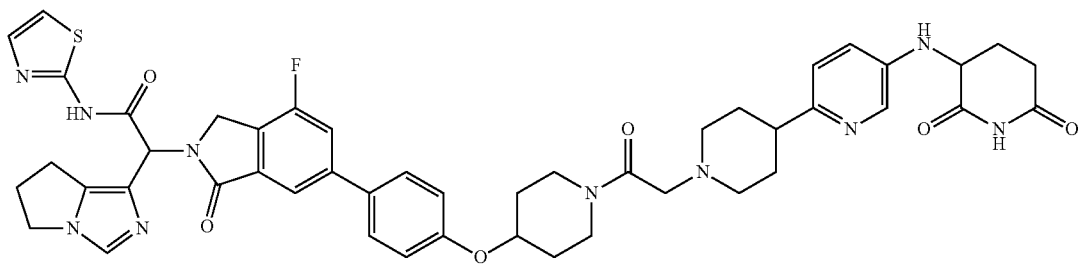

2-(6,7-dihydro-5H-pyrrolo[1,2-c]imidazol-1-yl)-2-(6-(4-((1-(2-(4-(5-((2,6-dioxopiperidin-3-yl)amino)pyridin-2-yl)piperidin-1-yl)acetyl)piperidin-4-yl)oxy)phenyl)-4-fluoro-1-oxoisoindolin-2-yl)-N-(thiazol-2-yl)acetamide -continued

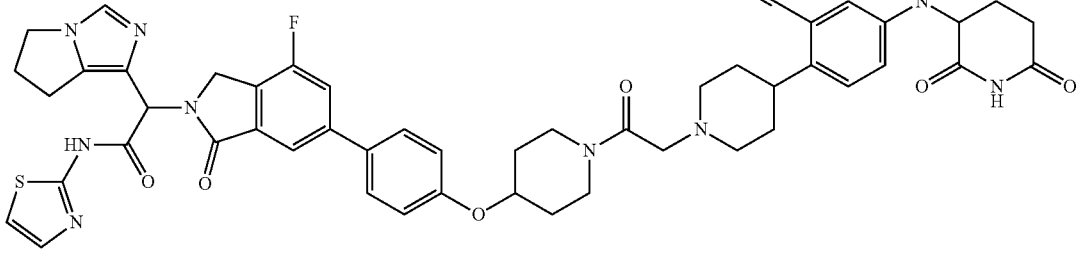

2-(6-(4-((1-(2-(4-(2-cyano-4-((2,6-dioxopiperidin-3-yl)amino)phenyl)piperidin-1-yl)acetyl)piperidin-4-yl)oxy)phenyl)-4-fluoro-1-oxoisoindolin-2-yl)-2-(6,7-dihydro-5H-pyrrolo[1,2-c]imidazol-1-yl)-N-(thiazol-2-yl)acetamide

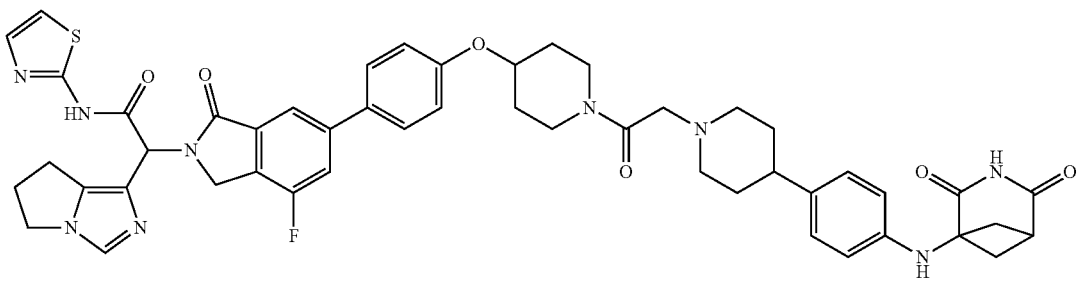

2-(6,7-dihydro-5H-pyrrolo[1,2-c]imidazol-1-yl)-2-(6-(4-((1-(2-(4-(4-((2,4-dioxo-3-azabicyclo[3.1.1]heptan-1-yl)amino)phenyl)piperidin-1-yl)acetyl)piperidin-4-yl)oxy)phenyl)-4-fluoro-1-oxoisoindolin-2-yl)-N-(thiazol-2-yl)acetamide

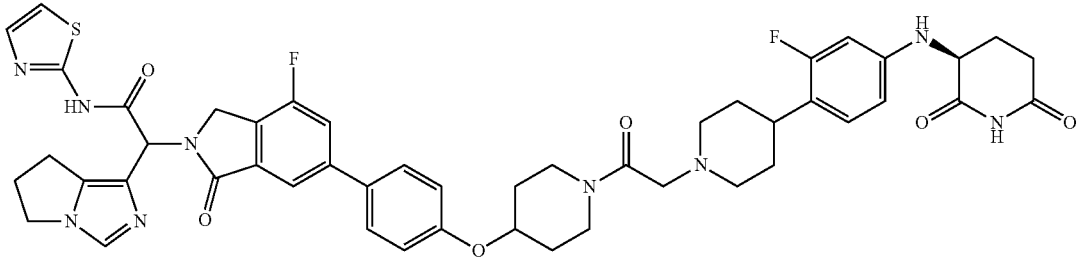

2-(6,7-dihydro-5H-pyrrolo[1,2-c]imidazol-1-yl)-2-(6-(4-((1-(2-(4-(4-(((S)-2,6-dioxopiperidin-3-yl)amino)-2-fluorophenyl)piperidin-1-yl)acetyl)piperidin-4-yl)oxy)phenyl)-4-fluoro-1-oxoisoindolin-2-yl)-N-(thiazol-2-yl)acetamide

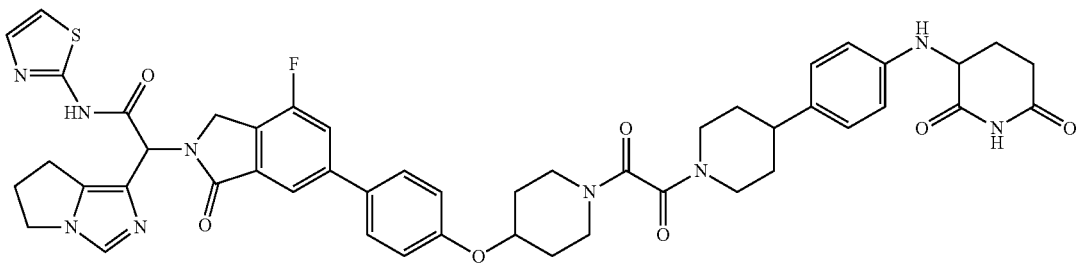

2-(6,7-dihydro-5H-pyrrolo[1,2-c]imidazol-1-yl)-2-[6-[4-[[1-[2-[4-[4-[(2,6-dioxo-3-piperidyl)amino]phenyl]-1-piperidyl]-2-oxo-acetyl]-4-piperidyl]oxy]phenyl]-4-fluoro-1-oxo-isoindolin-2-yl]-N-thiazol-2-yl-acetamide

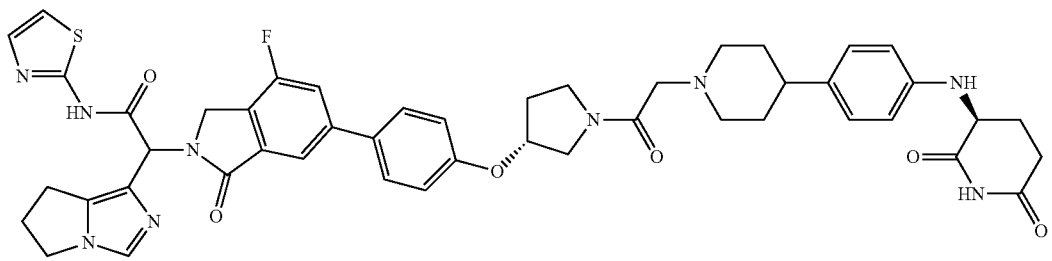

2-(6,7-dihydro-5H-pyrrolo[1,2-c]imidazol-1-yl)-2-[6-[4-[(3R)-1-[2-[4-[4-[[(3S)-2,6-dioxo-3-piperidyl]amino]phenyl]-1-piperidyl]acetyl]pyrrolidin-3-yl]oxyphenyl]-4-fluoro-1-oxo-isoindolin-2-yl]-N-thiazol-2-yl-acetamide

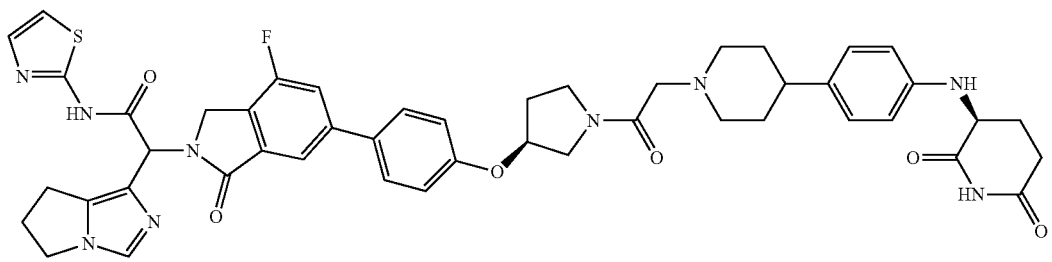

2-(6,7-dihydro-5H-pyrrolo[1,2-c]imidazol-1-yl)-2-[6-[4-[(3R)-1-[2-[4-[4-[[(3S)-2,6-dioxo-3-piperidyl]amino]phenyl]-1-piperidyl]acetyl]pyrrolidin-3-yl]oxyphenyl]-4-fluoro-1-oxo-isoindolin-2-yl]-N-thiazol-2-yl-acetamide

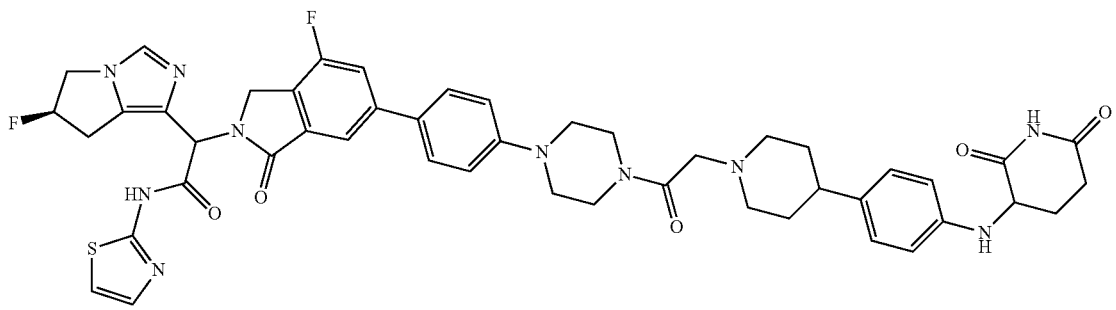

2-(6-(4-(4-(2-(4-(4-((2,6-dioxopiperidin-3-yl)amino)phenyl)piperidin-1-yl)acetyl)piperazin-1-yl)phenyl)-4-fluoro-1-oxoisoindolin-2-yl)-2-((R)-6-fluoro-6,7-dihydro-5H-pyrrolo[1,2-c]imidazol-1-yl)-N-(thiazol-2-yl)acetamide

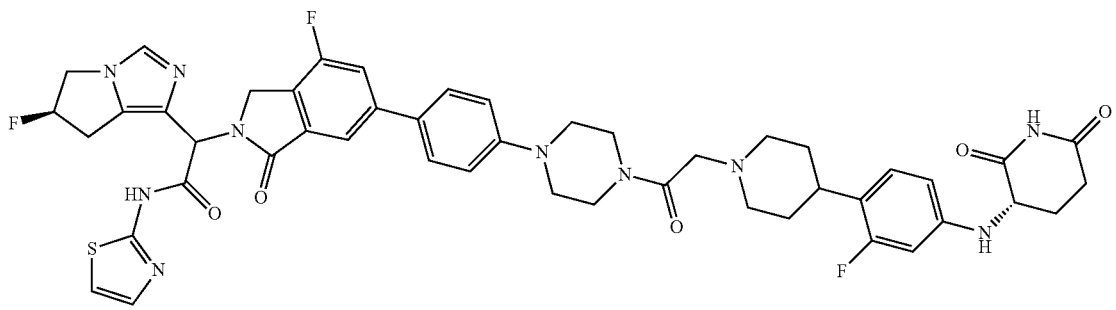

2-[6-[4-[4-[2-[4-[4-[[(3S)-2,6-dioxo-3-piperidyl]amino]-2-fluoro-phenyl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide

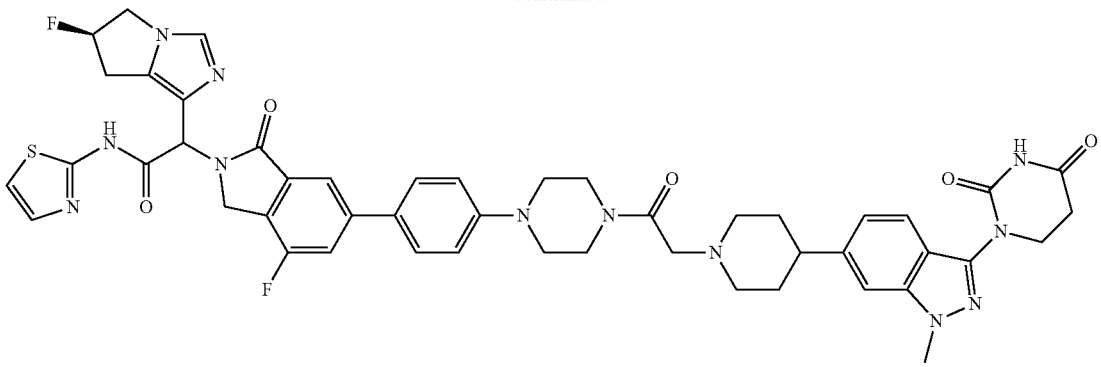

2-[6-[4-[4-[2-[4-[3-(2,4-dioxohexahydropyrimidin-1-yl)-1-methyl-indazol-6-yl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide

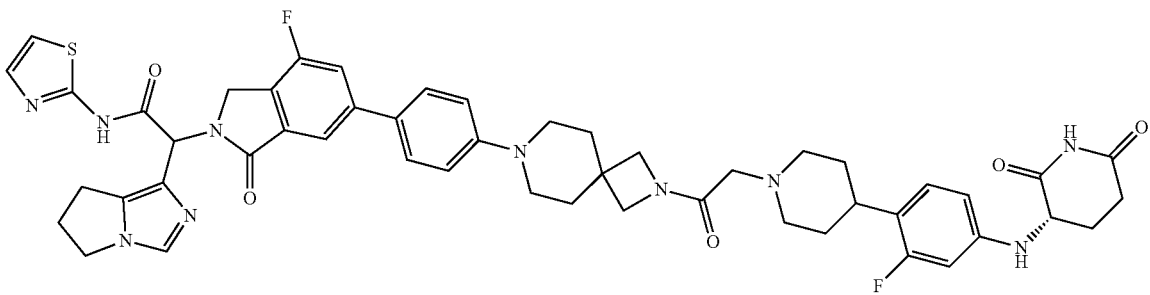

2-(6,7-dihydro-5H-pyrrolo[1,2-c]imidazol-1-yl)-2-(6-(4-(2-(2-(4-(4-(((S)-2,6-dioxopiperidin-3-yl)amino)-2-fluorophenyl)piperidin-1-yl)acetyl)-2,7-diazaspiro[3.5]nonan-7-yl)phenyl)-4-fluoro-1-oxoisoindolin-2-yl)-N-(thiazol-2-yl)acetamide

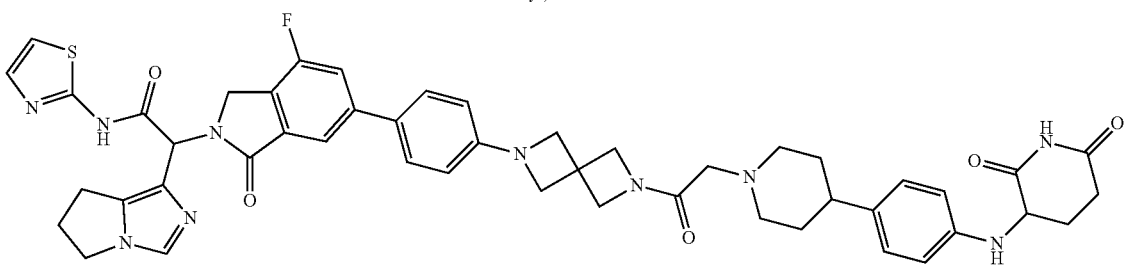

2-(6,7-dihydro-5H-pyrrolo[1,2-c]imidazol-1-yl)-2-[6-[4-[2-[2-[4-[4-[(2,6-dioxo-3-piperidyl)amino]phenyl]-1-piperidyl]acetyl]-2,6-diazaspiro[3.3]heptan-6-yl]phenyl]-4-fluoro-1-oxo-isoindolin-2-yl]-N-thiazol-2-yl-acetamide

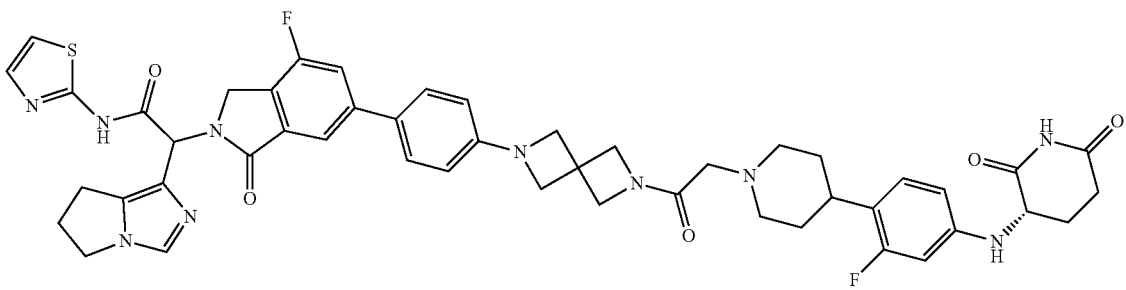

2-(6,7-dihydro-5H-pyrrolo[1,2-c]imidazol-1-yl)-2-[6-[4-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]phenyl]-4-fluoro-1-oxo-isoindolin-2-yl]-N-thiazol-2-yl-acetamide

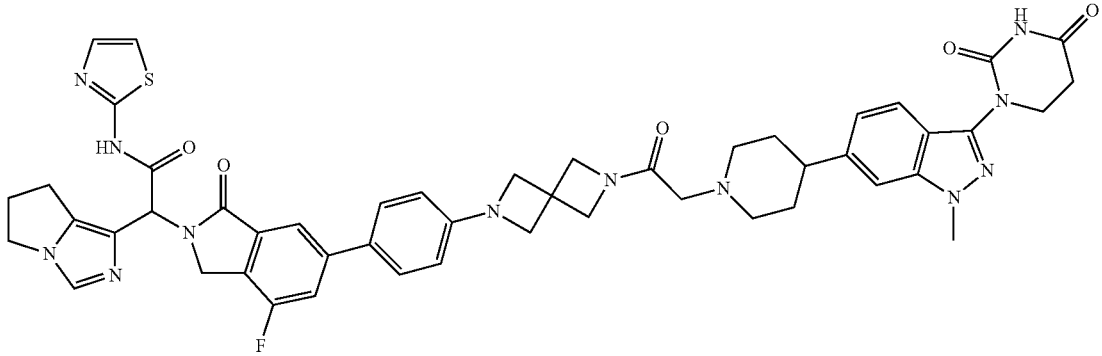

2-(6,7-dihydro-5H-pyrrolo[1,2-c]imidazol-1-yl)-2-[6-[4-[2-[2-[4-[3-[(2,4-dioxohexahydropyrimidin-1-yl)-1-methyl-indazol-6-yl]-1-piperidyl]acetyl]-2,6-diazaspiro[3.3]heptan-6-yl]phenyl]-4-fluoro-1-oxo-isoindolin-2-yl]-N-thiazol-2-yl-acetamide

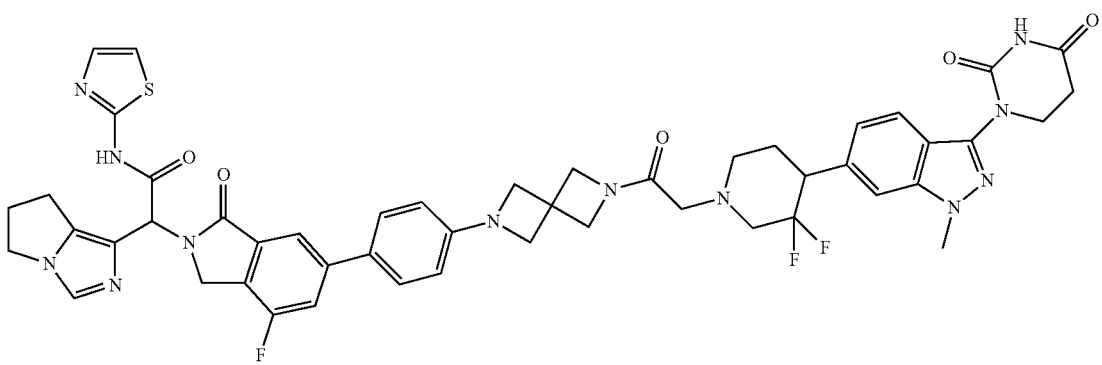

2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide

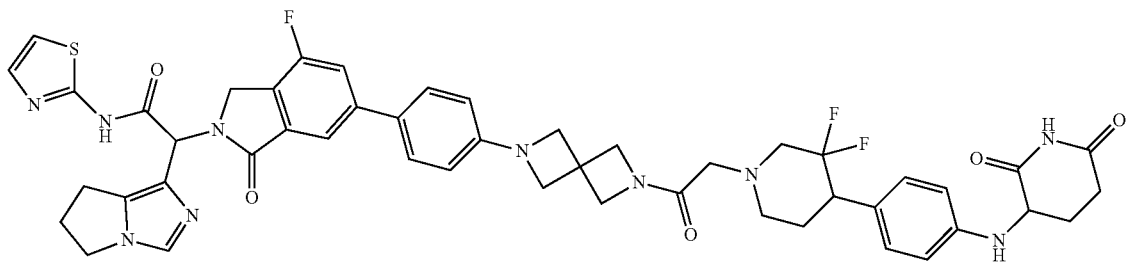

2-(6,7-dihydro-5H-pyrrolo[1,2-c]imidazol-1-yl)-2-(6-(4-(6-(2-(4-(4-((2,6-dioxopiperidin-3-yl)amino)phenyl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide

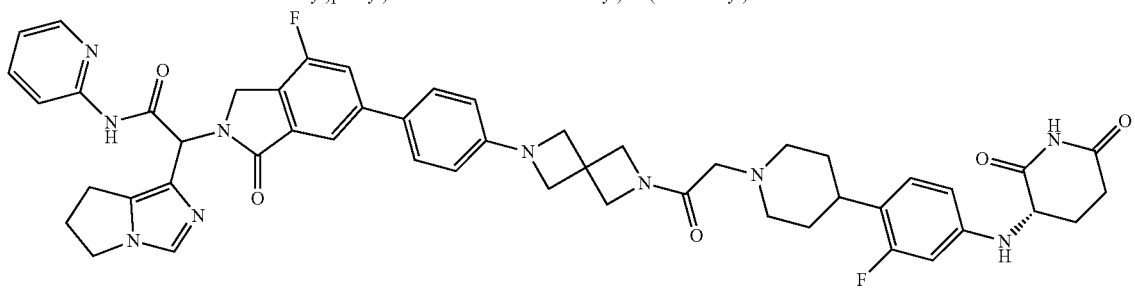

2-(6,7-dihydro-5H-pyrrolo[1,2-c]imidazol-1-yl)-2-[6-[4-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]phenyl]-4-fluoro-1-oxo-isoindolin-2-yl]-N-(2-pyridyl)acetamide

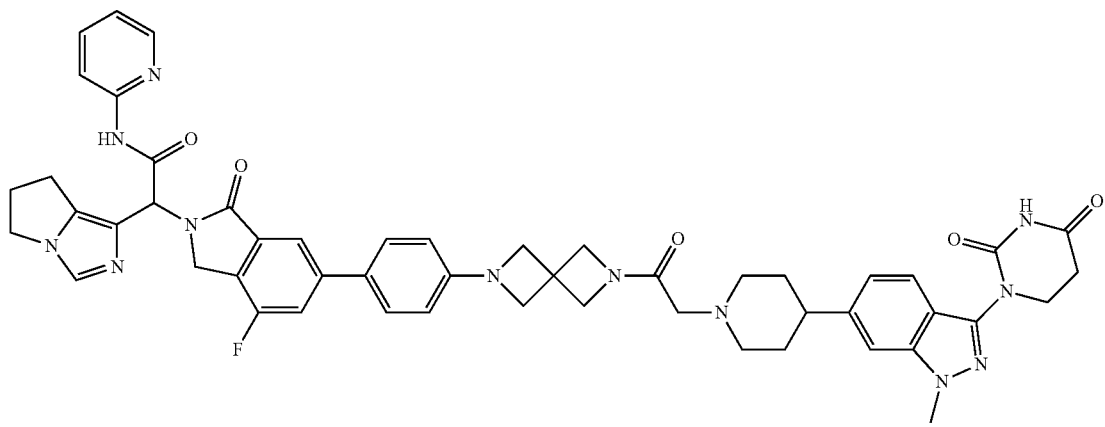

2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-1-piperidyl]acetyl]-2,6-diazaspiro[3.3]heptan-6-yl]phenyl]-4-fluoro-1-oxo-isoindolin-2-yl]-N-(2-pyridyl)acetamide

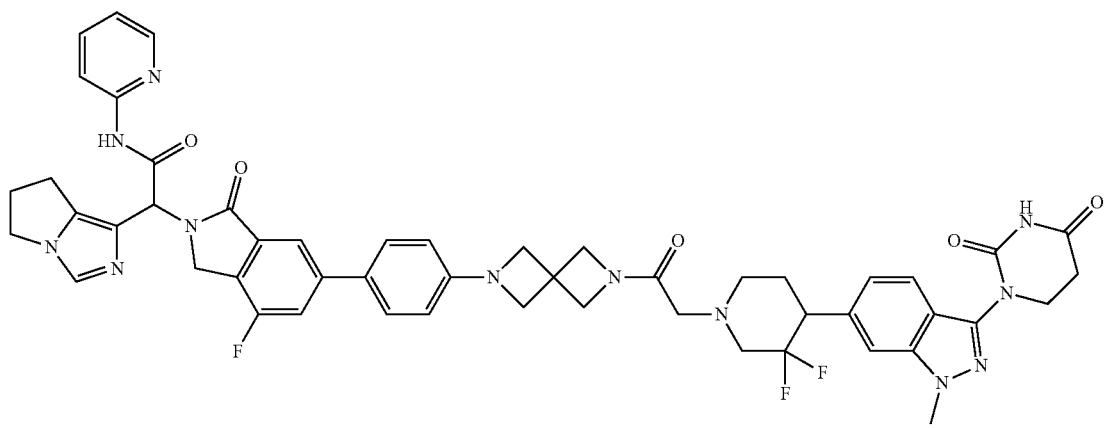

2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-(2-pyridyl)acetamide

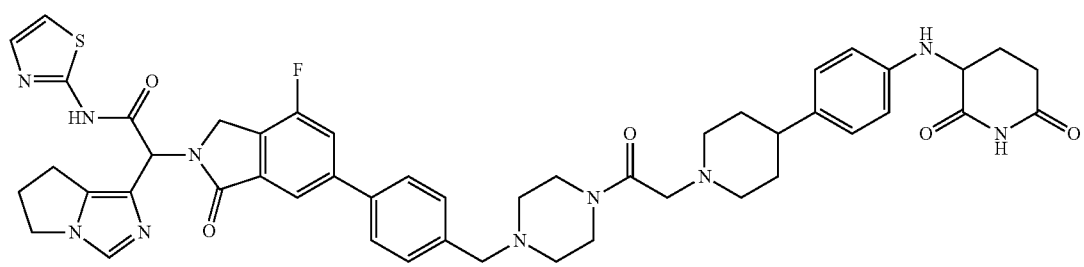

2-(6,7-dihydro-5H-pyrrolo[1,2-c]imidazol-1-yl)-2-[6-[4-[[4-[2-[4-[4-(2,6-dioxo-3-piperidyl)amino]phenyl]-1-piperidyl]acetyl]piperazin-1-yl]methyl]phenyl]-4-fluoro-1-oxo-isoindolin-2-yl]-N-thiazol-2-yl-acetamide

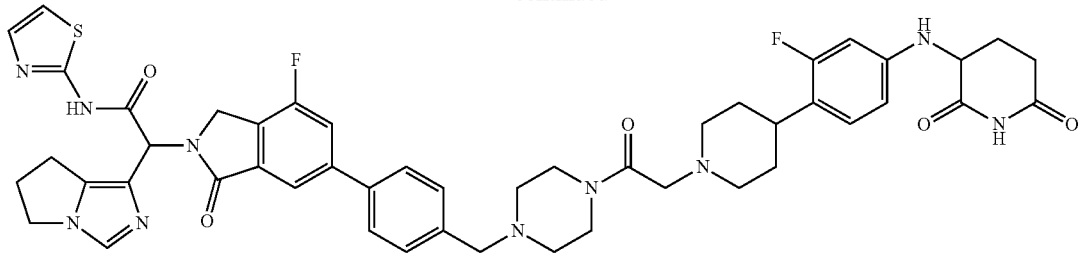

2-(6,7-dihydro-5H-pyrrolo[1,2-c]imidazol-1-yl)-2-[6-[4-[[4-[2-[4-[4-[(2,6-dioxo-3-piperidyl)amino]phenyl]-2-fluoro-phenyl]-1-piperidyl]acetyl]piperazin-1-yl]methyl]phenyl]-4-fluoro-1-oxo-isoindolin-2-yl]-N-thiazol-2-yl-acetamide

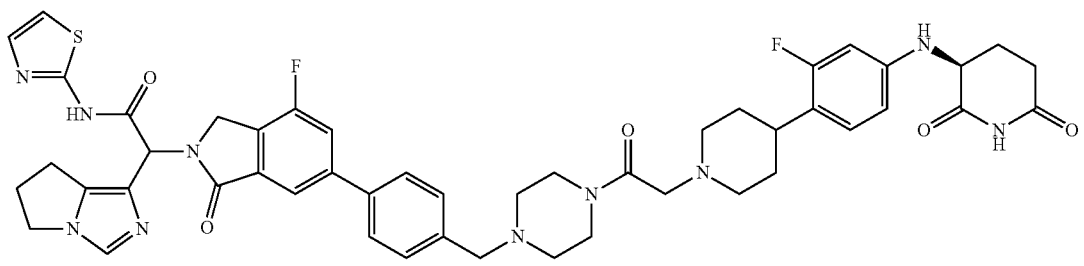

2-(6,7-dihydro-5H-pyrrolo[1,2-c]imidazol-1-yl)-2-[6-[4-[[4-[2-[4-[4-[[(3S)-2,6-dioxo-3-piperidyl]amino]-2-fluoro-phenyl]-1-piperidyl]acetyl]piperazin-1-yl]methyl]phenyl]-4-fluoro-1-oxo-isoindolin-2-yl]-N-thiazol-2-yl-acetamide

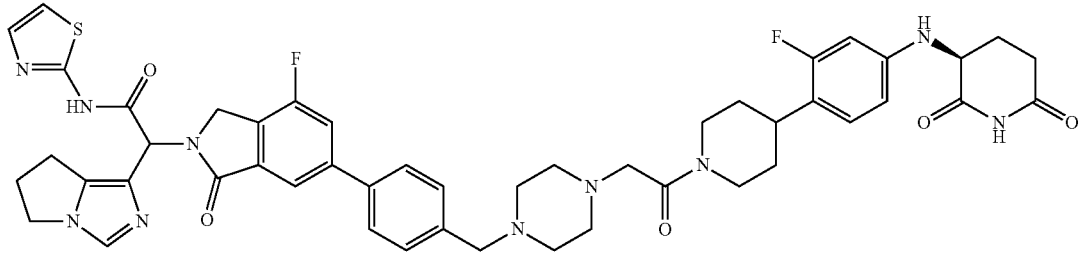

2-(6,7-dihydro-5H-pyrrolo[1,2-c]imidazol-1-yl)-2-[6-[4-[[4-[2-[4-[4-[[(3S)-2,6-dioxo-3-piperidyl]amino]-2-fluoro-phenyl]-1-piperidyl]-2-oxo-ethyl]piperazin-1-yl]methyl]phenyl]-4-fluoro-1-oxo-isoindolin-2-yl]-N-thiazol-2-yl-acetamide

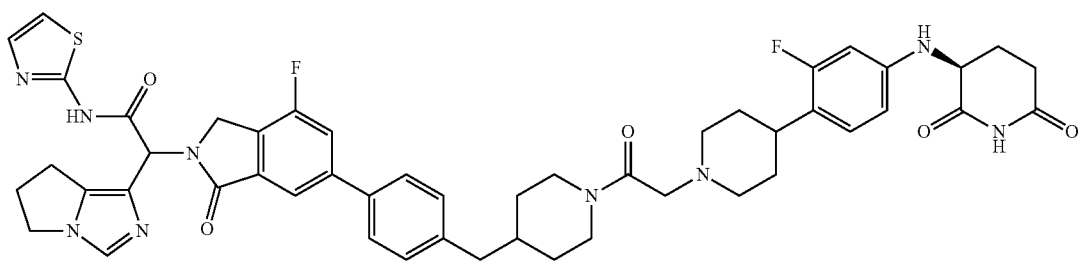

2-(6,7-dihydro-5H-pyrrolo[1,2-c]imidazol-1-yl)-2-[6-[4-[[1-[2-[4-[4-[[(3S)-2,6-dioxo-3-piperidyl]amino]-2-fluoro-phenyl]-1-piperidyl]acetyl]-4-piperidyl]methyl]phenyl]-4-fluoro-1-oxo-isoindolin-2-yl]-N-thiazol-2-yl-acetamide -continued

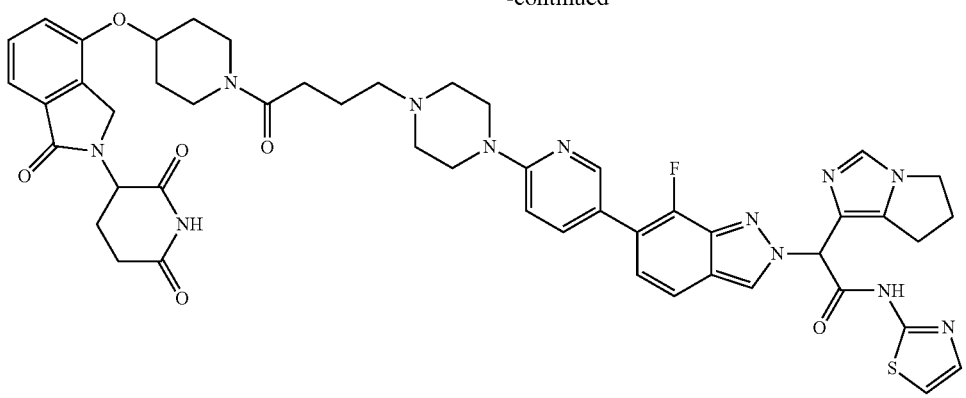

2-[4,7-dichloro-6-[4-[4-[2-[4-[4-[(2,6-dioxo-3-piperidyl)amino]phenyl]-1-piperidyl]acetyl]piperazin-1-yl]phenyl]indazol-2-yl]-2-(6,7-dihydro-5H-pyrrolo[1,2-c]imidazol-1-yl)-N-thiazol-2-yl-acetamide

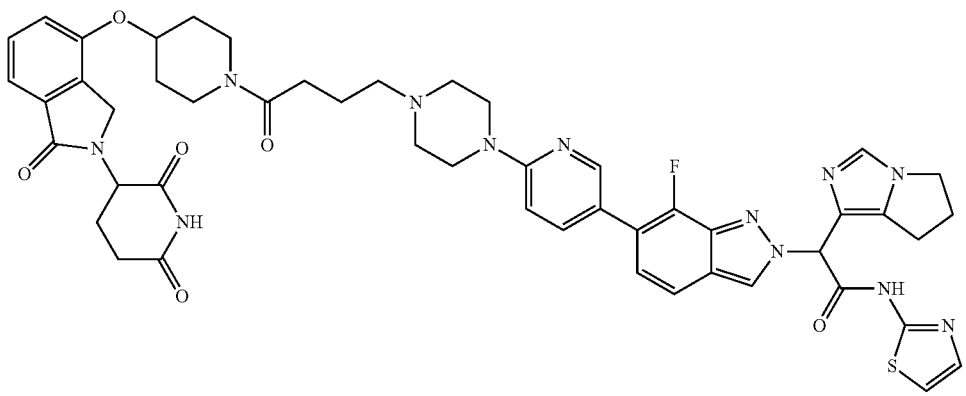

2-(6,7-dihydro-5H-pyrrolo[1,2-c]imidazol-1-yl)-2-(6-(6-(4-(4-(4-((2-(2,6-dioxopiperidin-3-yl)-1-oxoisoindolin-4-yl)oxy)piperidin-1-yl)-4-oxobutyl)piperazin-1-yl)pyridin-3-yl)-7-fluoro-2H-indazol-2-yl)-N-(thiazol-2-yl)acetamide

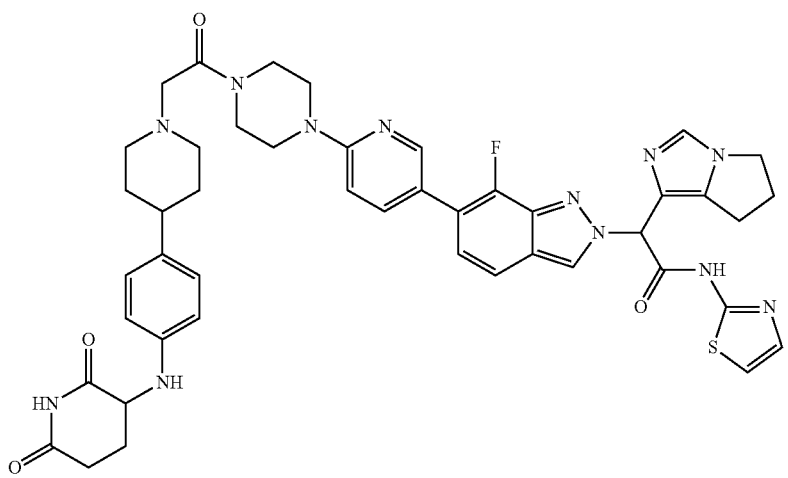

2-(6,7-dihydro-5H-pyrrolo[1,2-c]imidazol-1-yl)-2-(6-(6-(4-(2-(4-(4-((2,6-dioxopiperidin-3-yl)amino)phenyl)piperidin-1-yl)acetyl)piperazin-1-yl)pyridin-3-yl)-7-fluoro-2H-indazol-2-yl)-N-(thiazol-2-yl)acetamide -continued

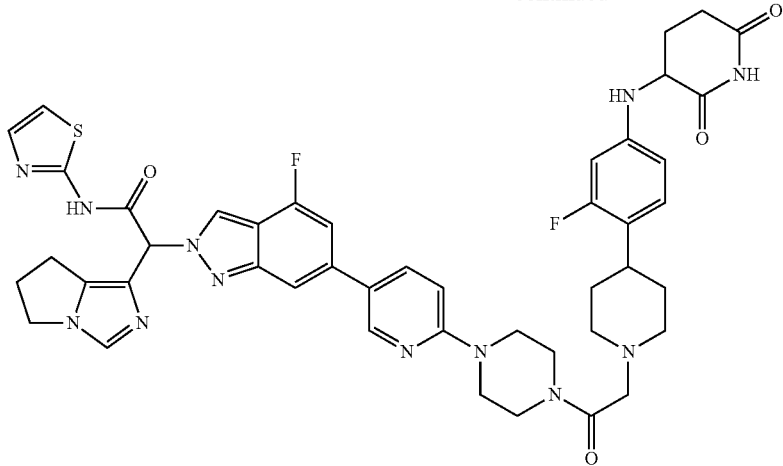

2-(6,7-dihydro-5H-pyrrolo[1,2-c]imidazol-1-yl)-2-[6-[6-[4-[2-[4-[4-[(2,6-dioxo-3-piperidyl)amino]-2-fluoro-phenyl]-1-piperidyl]acetyl]piperazin-1-yl]-3-pyridyl]-4-fluoro-indazol-2-yl]-N-thiazol-2-yl-acetamide

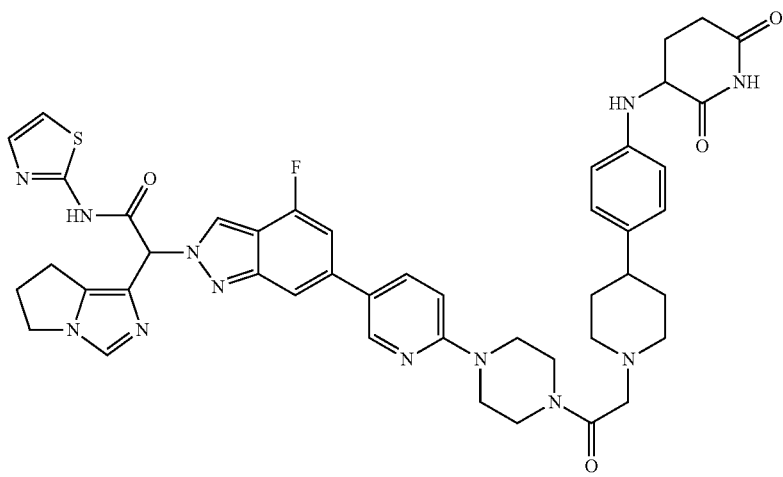

2-(6,7-dihydro-5H-pyrrolo[1,2-c]imidazol-1-yl)-2-[6-[6-[4-[2-[4-[4-[(2,6-dioxo-3-piperidyl)amino]phenyl]-1-piperidyl]acetyl]piperazin-1-yl]-3-pyridyl]-4-fluoro-indazol-2-yl]-N-thiazol-2-yl-acetamide

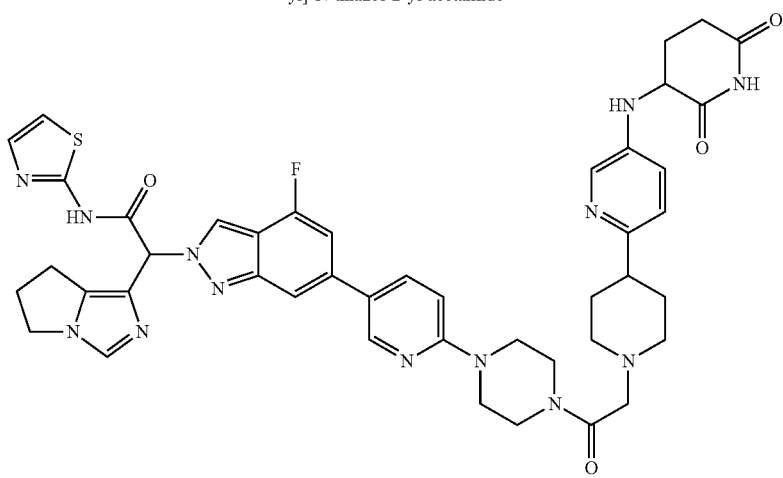

2-(6,7-dihydro-5H-pyrrolo[1,2-c]imidazol-1-yl)-2-[6-[6-[4-[2-[4-[5-[(2,6-dioxo-3-piperidyl)amino]-2-pyridyl]-1-piperidyl]acetyl]piperazin-1-yl]-3-pyridyl]-4-fluoro-indazol-2-yl]-N-thiazol-2-yl-acetamide

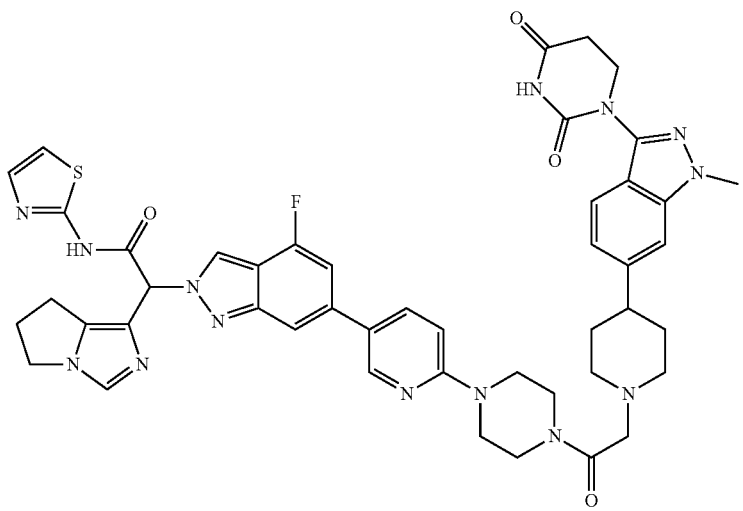

2-(6,7-dihydro-5H-pyrrolo[1,2-c]imidazol-1-yl)-2-[6-[6-[4-[2-[4-[3-(2,4-dioxohexahydropyrimidin-1-yl)-1-methyl-indazol-6-yl]-1-piperidyl]acetyl]piperazin-1-yl]-3-pyridyl]-4-fluoro-indazol-2-yl]-N-thiazol-2-yl-acetamide

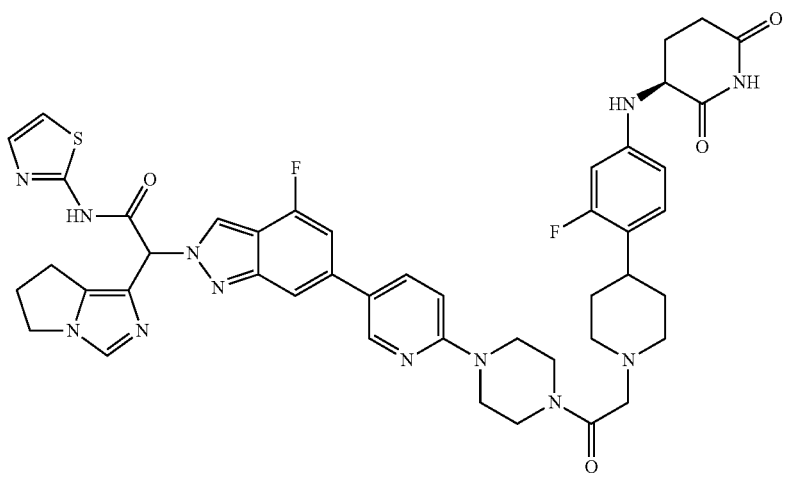

2-(6,7-dihydro-5H-pyrrolo[1,2-c]imidazol-1-yl)-2-(6-(6-(4-(2-(4-(4-(((S)-2,6-dioxopiperidin-3-yl)amino)-2-flurophenyl)piperidin-1-yl)acetyl)piperazin-1-yl)pyridin-3-yl)-4-fluoro-2H-indazol-2-yl)-N-(thiazol-2-yl)acetamide or a pharmaceutically acceptable salt thereof.

E98: In certain embodiments a compound is provided selected from:

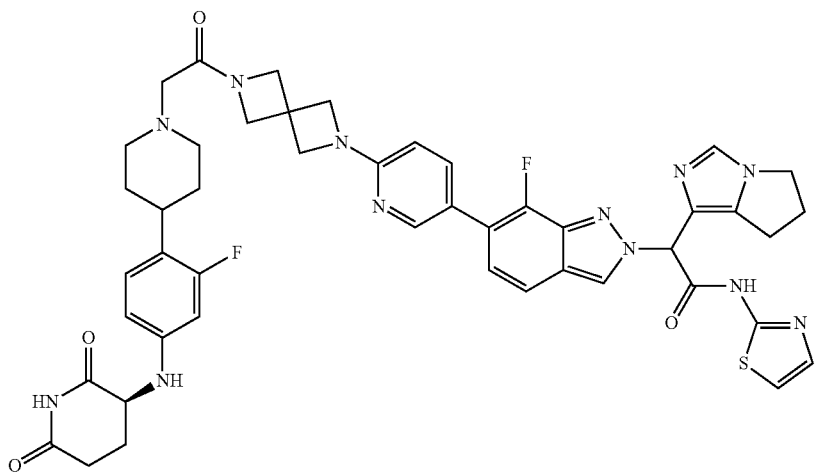

2-(6,7-dihydro-5H-pyrrolo[1,2-c]imidazol-1-yl)-2-(6-(6-(6-(2-(4-(4-(((S)-2,6-dioxopiperidin-3-yl)amino)-2-fluorophenyl)piperidin-1-yl)acetyl)-2,6-diazaspiro[3.3]heptan-2-yl)pyridin-3-yl)-7-fluoro-2H-indazol-2-yl)-N-(thiazol-2-yl)acetamide

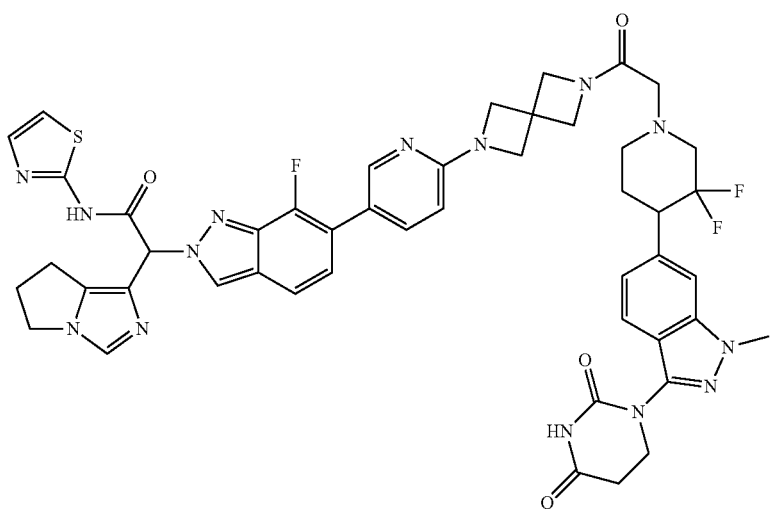

2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)pyridin-3-yl)-7-fluoro-2H-indazol-2-yl)-N-(thiazol-2-yl)acetamide

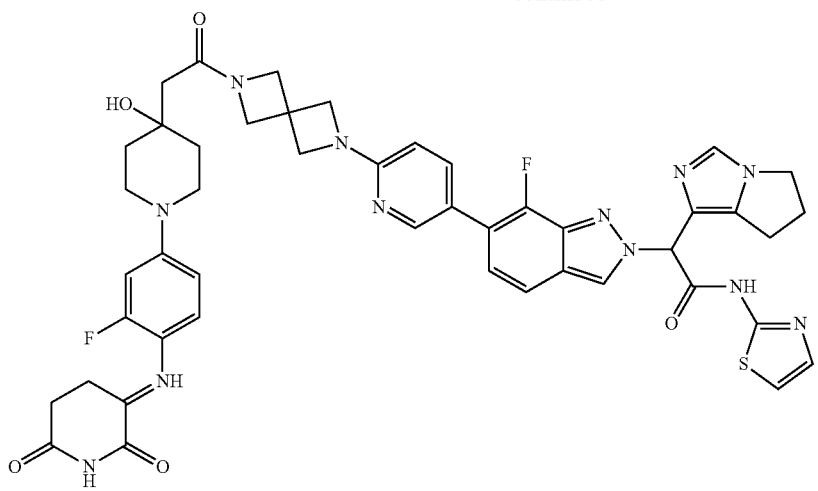
2-(6,7-dihydro-5H-pyrrolo[1,2-c]imidazol-1-yl)-2-(6-(6-(6-(2-(1-(4-((2,6-dioxopiperidin-3-yl)amino)-2-fluorophenyl)-4-hydroxypiperidin-4-yl)acetyl)-2,6-diazaspiro[3.3]heptan-2-yl)pyridin-3-yl)-7-fluoro-2H-indazol-2-yl)-N-(thiazol-2-yl)acetamide
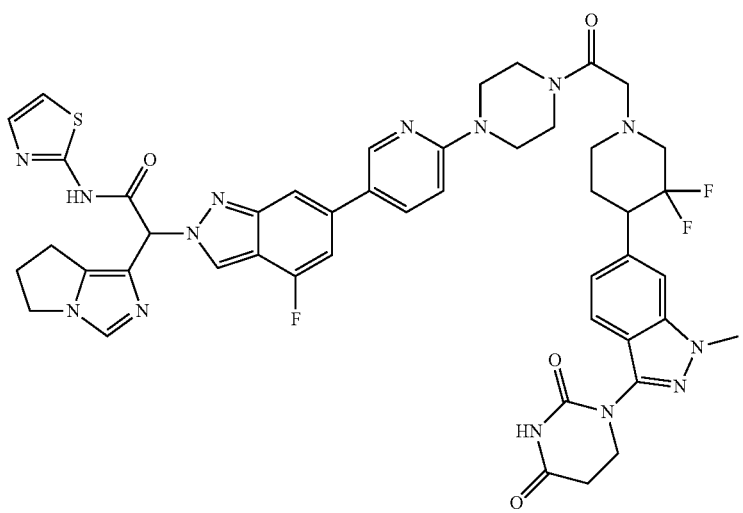
2-(6,7-dihydro-5H-pyrrolo[1,2-c]imidazol-1-yl)-2-(6-(6-(4-(2-(4-(3-(2,4-dioxotetrahydropyrimidin-1(2H)-yl)-1-methyl-1H-indazol-6-yl)-3,3-difluoropiperidin-1-yl)acetyl)piperazin-1-yl)pyridin-3-yl)-4-fluoro-2H-indazol-2-yl)-N-(thiazol-2-yl)acetamide

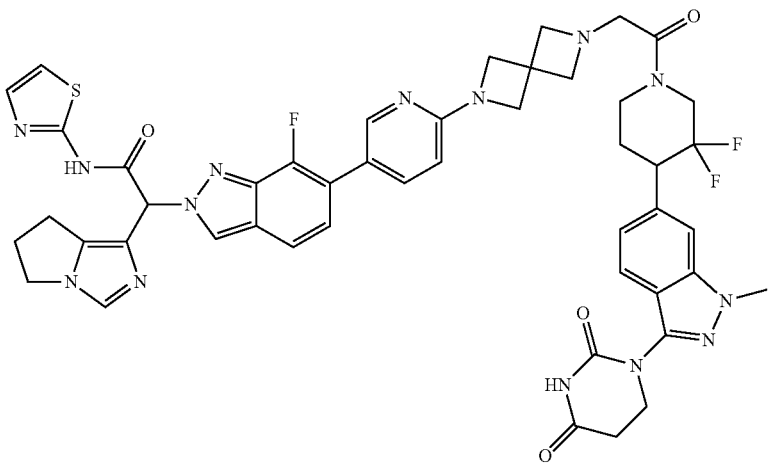

2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)-2-oxoethyl)-2,6-diazaspiro[3.3]heptan-2-yl)pyridin-3-yl)-7-fluoro-2H-indazol-2-yl)-N-(thiazol-2-yl)acetamide

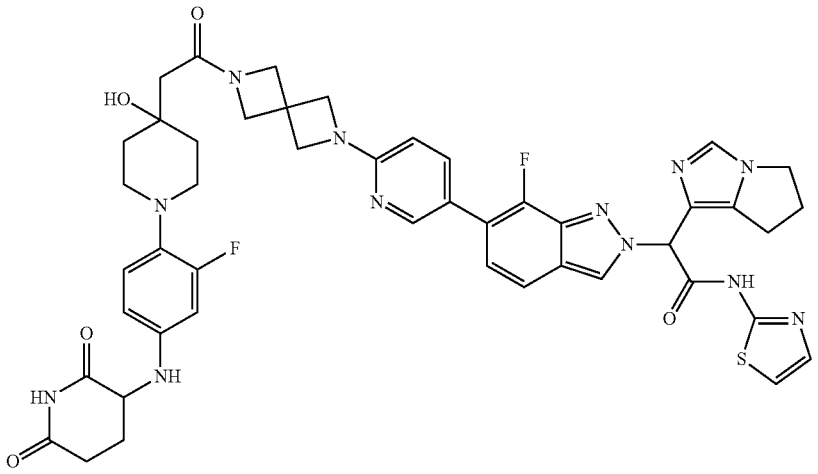

2-(6,7-dihydro-5H-pyrrolo[1,2-c]imidazol-1-yl)-2-(6-(6-(6-(2-(1-(4-((2,6-dioxopiperidin-3-yl)amino)-2-fluorophenyl)-4-hydroxypiperidin-4-yl)acetyl)-2,6-diazaspiro[3.3]heptan-2-yl)pyridin-3-yl)-7-fluoro-2H-indazol-2-yl)-N-(thiazol-2-yl)acetamide

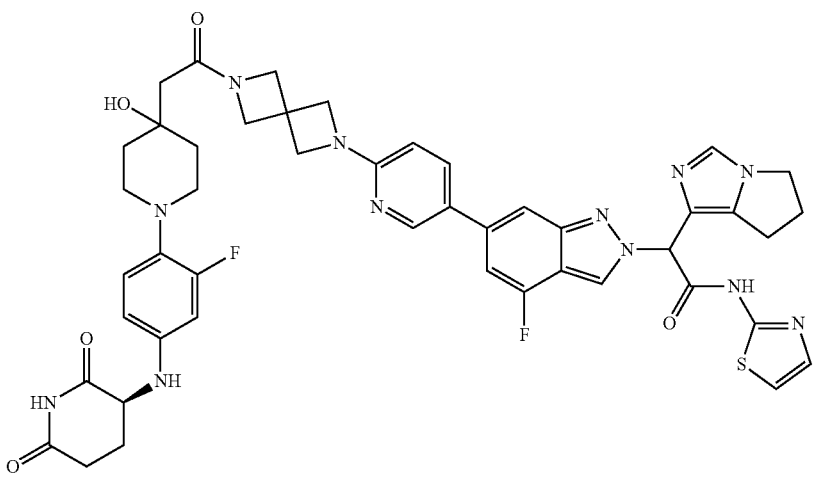

2-(6,7-dihydro-5H-pyrrolo[1,2-c]imidazol-1-yl)-2-(6-(6-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)pyridin-3-yl)-4-fluoro-2H-indazol-2-yl)-N-(thiazol-2-yl)acetamide

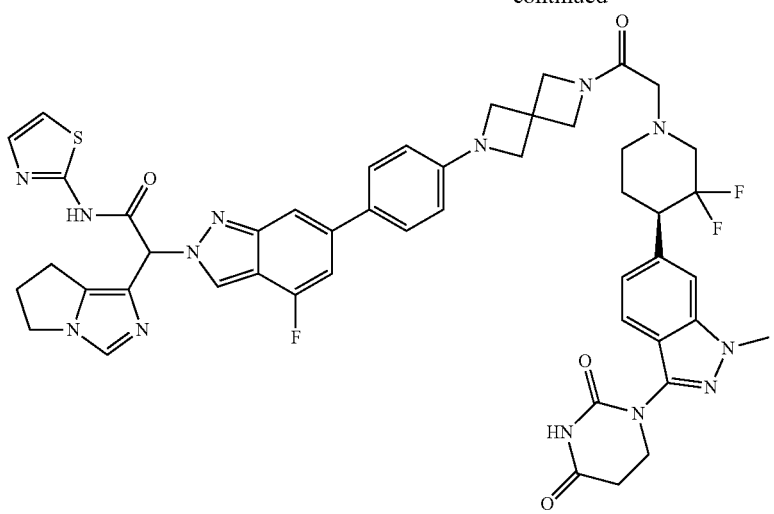

2-(6,7-dihydro-5H-pyrrolo[1,2-c]imidazol-1-yl)-2-(6-(4-(6-(2-((R)-4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)phenyl)-4-fluoro-2H-indazol-2-yl)-N-(thiazol-2-yl)acetamide

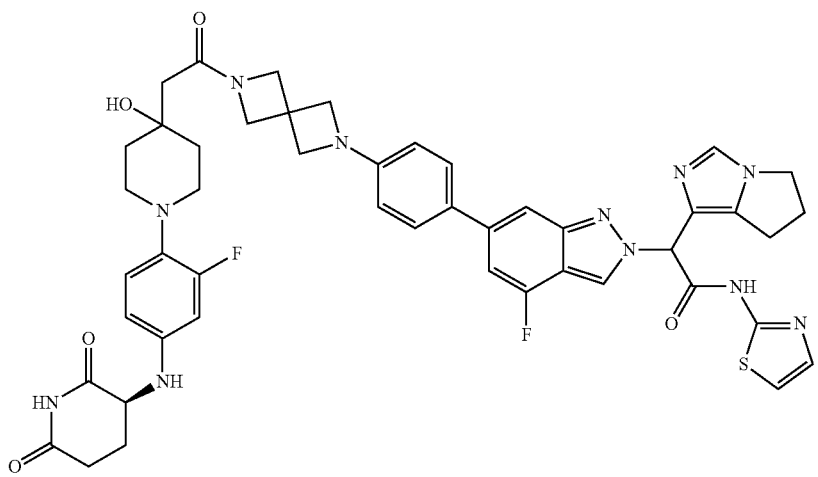

2-(6,7-dihydro-5H-pyrrolo[1,2-c]imidazol-1-yl)-2-(6-(4-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-2H-indazol-2-yl)-N-(thiazol-2-yl)acetamide

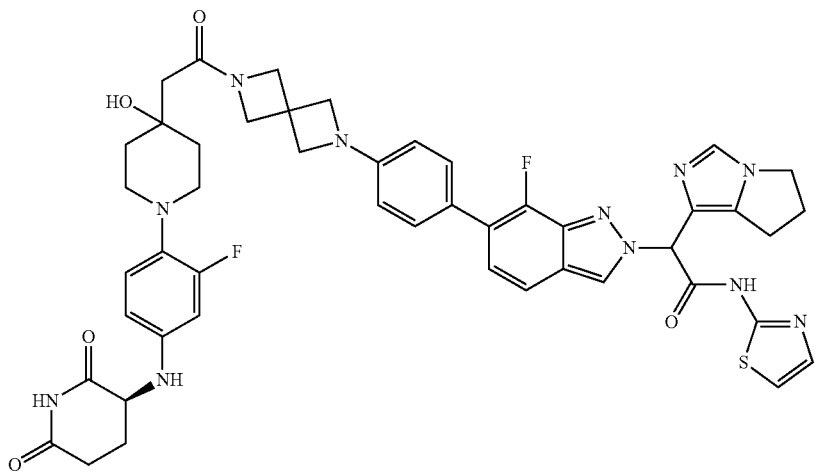

2-(6,7-dihydro-5H-pyrrolo[1,2-c]imidazol-1-yl)-2-(6-(4-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)phenyl)-7-fluoro-2H-indazol-2-yl)-N-(thiazol-2-yl)acetamide

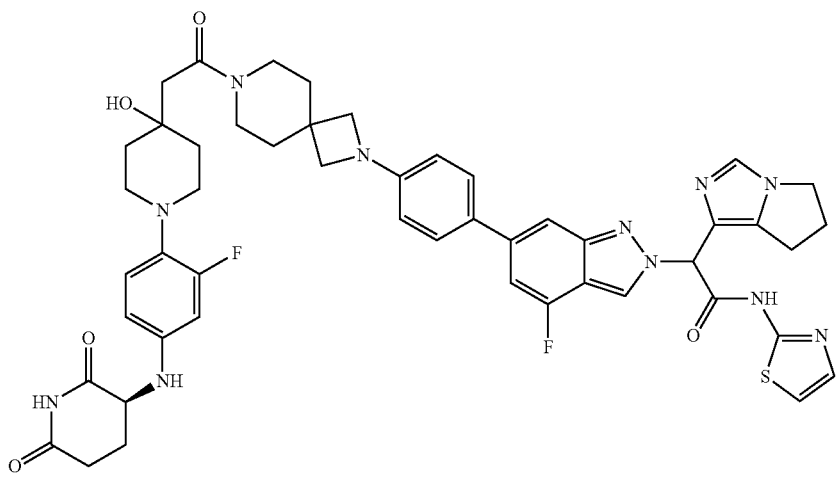
2-(6,7-dihydro-5H-pyrrolo[1,2-c]imidazol-1-yl)-2-(6-(4-(7-(2-(1-(4-(((S)-2,6-dioxopiperidin-3-yl)amino)-2-fluorophenyl)-4-hydroxypiperidin-4-yl)acetyl)-2,7-diazaspiro[3.3]nonan-2-yl)phenyl)-4-fluoro-2H-indazol-2-yl)-N-(thiazol-2-yl)acetamide
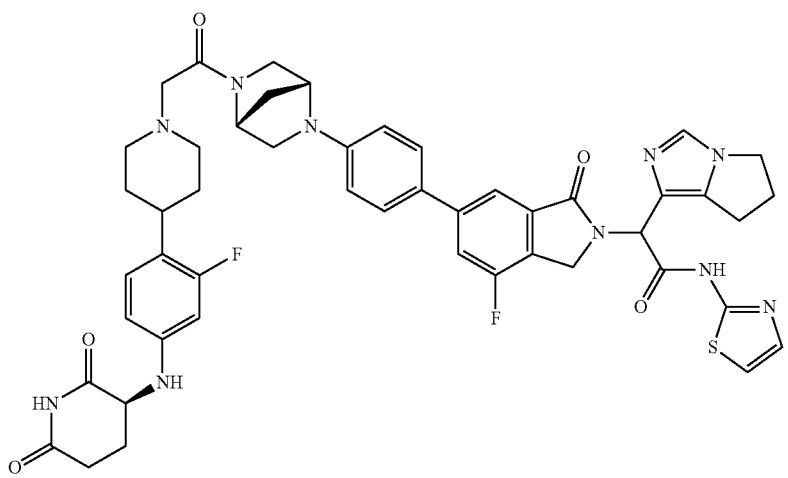
2-(6,7-dihydro-5H-pyrrolo[1,2-c]imidazol-1-yl)-2-(6-(4-((1R,4R)-5-(2-(4-(4-(((S)-2,6-dioxopiperidin-3-yl)amino)-2-fluorophenyl)piperidin-1-yl)acetyl-2,5-diazabicyclo[2.2.1]heptan-2-yl)phenyl)-4-fluoro-1-oxoisoindolin-2-yl)-N-(thiazol-2-yl)acetamide

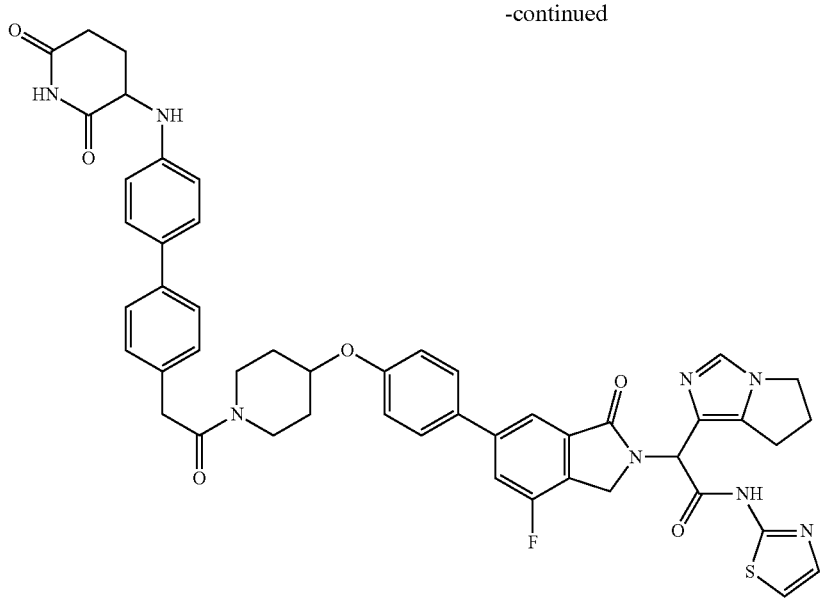
2-(6,7-dihydro-5H-pyrrolo[1,2-c]imidazol-1-yl)-2-(6-(4-((1-(2-(4'-((2,6-dioxopiperidin-3-yl)amino)-[1,1'-biphenyl]-4-yl)acetyl)piperidin-4-yl)oxy)phenyl)-4-fluoro-1-oxoisoindolin-2-yl)-N-(thiazol-2-yl)acetamide
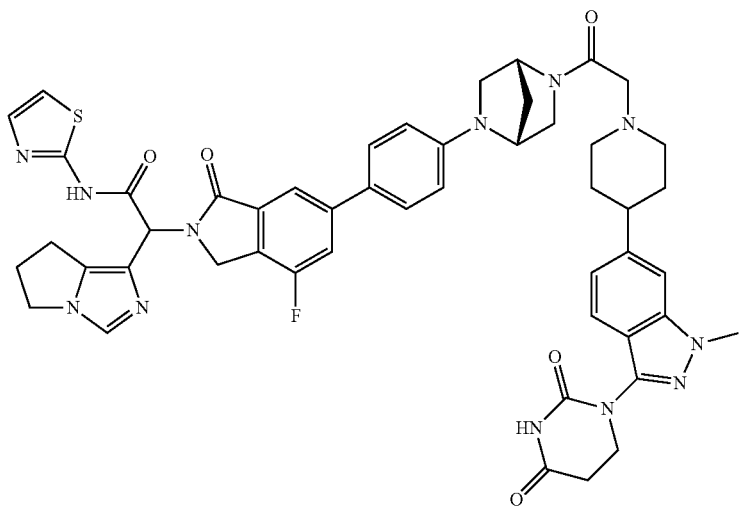
2-(6,7-dihydro-5H-pyrrolo[1,2-c]imidazol-1-yl)-2-(6-(4-((1R,4R)-5-(2-(4-(3-(2,4-dioxotetrahydropyrimidin-1(2H)-yl)-1-methyl-1H-indazol-6-yl)piperidin-1-yl)acetyl-2,5-diazabicyclo[2.2.1]heptan-2-yl)phenyl)-4-fluoro-1-oxoisoindolin-2-yl)-N-(thiazol-2-yl)acetamide -continued

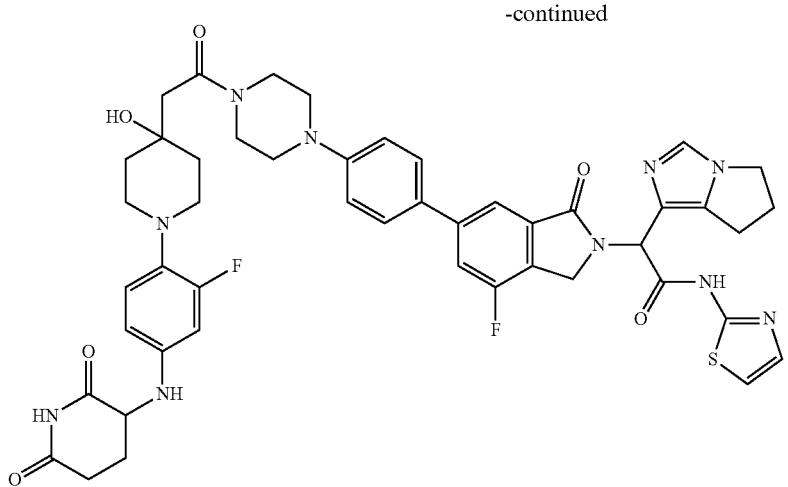

2-(6,7-dihydro-5H-pyrrolo[1,2-c]imidazol-1-yl)-2-(6-(4-(4-(2-(1-(4-((2,6-dioxopiperidin-3-yl)amino)-2-fluorophenyl)-4-hydroxypiperidin-4-yl)acetyl)piperazin-1-yl)phenyl)-4-fluoro-1-oxoisoindolin-2-yl)-N-(thiazol-2-yl)acetamide

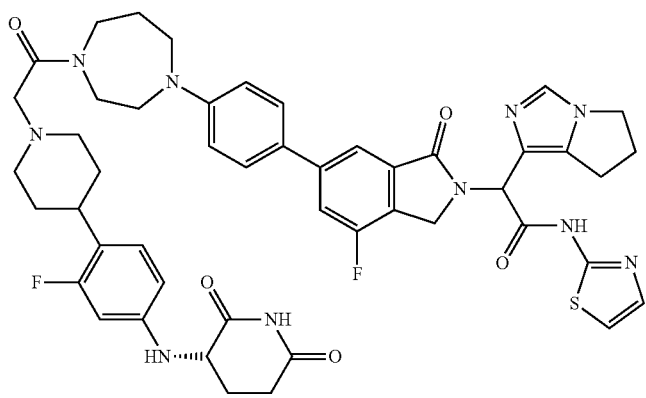

2-(6,7-dihydro-5H-pyrrolo[1,2-c]imidazol-1-yl)-2-(6-(4-(4-(2-(4-(4-(((S)-2,6-dioxopiperidin-3-yl)amino)-2-fluorophenyl)piperidin-1-yl)acetyl)-1,4-diazepan-1-yl)phenyl)-4-fluoro-1-oxoisoindolin-2-yl)-N-(thiazol-2-yl)acetamide

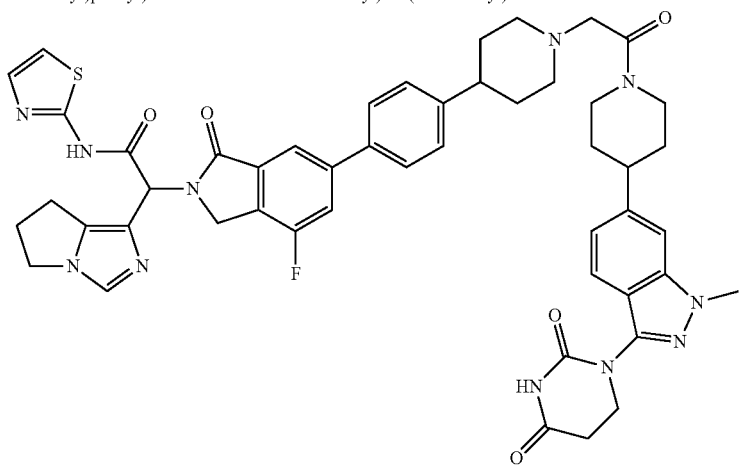

2-(6,7-dihydro-5H-pyrrolo[1,2-c]imidazol-1-yl)-2-(6-(4-(1-(2-(4-(3-(2,4-dioxotetrahydropyrimidin-1(2H)-yl)-1-methyl-1H-indazol-6-yl)piperidin-1-yl)-2-oxoethyl)piperidin-4-yl)phenyl)-4-fluoro-1-oxoisoindolin-2-yl)-N-(thiazol-2-yl)acetamide

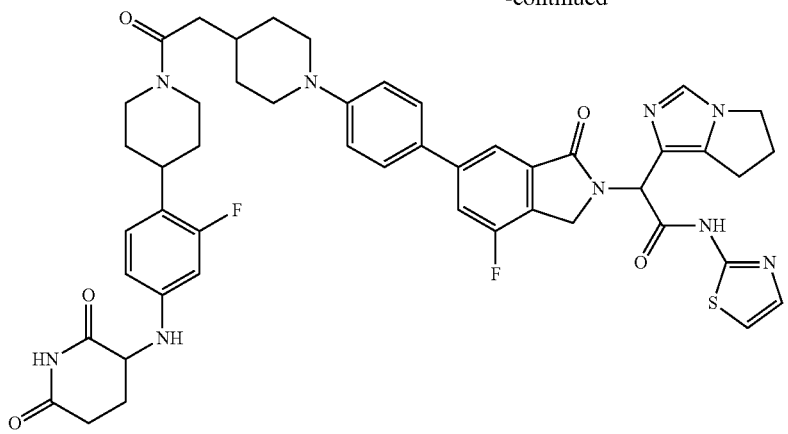
2-(6,7-dihydro-5H-pyrrolo[1,2-c]imidazol-1-yl)-2-(6-(4-(4-(2-(4-(4-((2,6-dioxopiperidin-3-yl)amino)-2-fluorophenyl)piperidin-1-yl)-2-oxoethyl)piperidin-1-yl)phenyl)-4-fluoro-1-oxoisoindolin-2-yl)-N-(thiazol-2-yl)acetamide
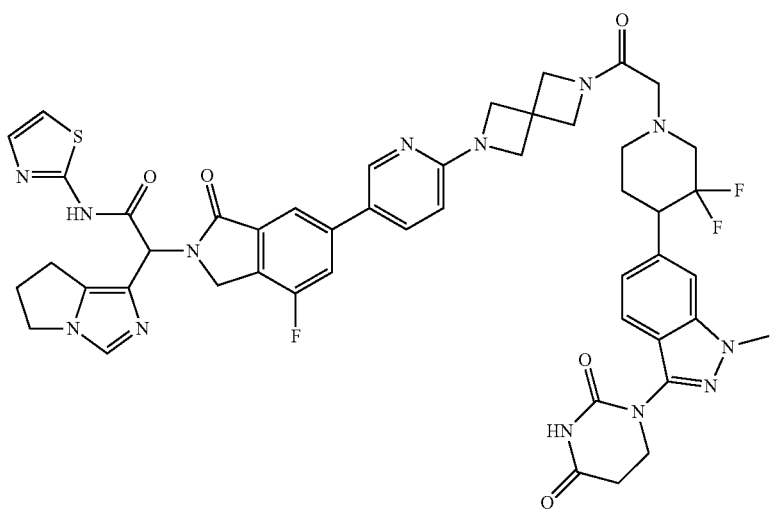
2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)pyridin-3-yl)-4-fluoro-1-oxoisoindolin-2-yl)-N-(thiazol-2-yl)acetamide

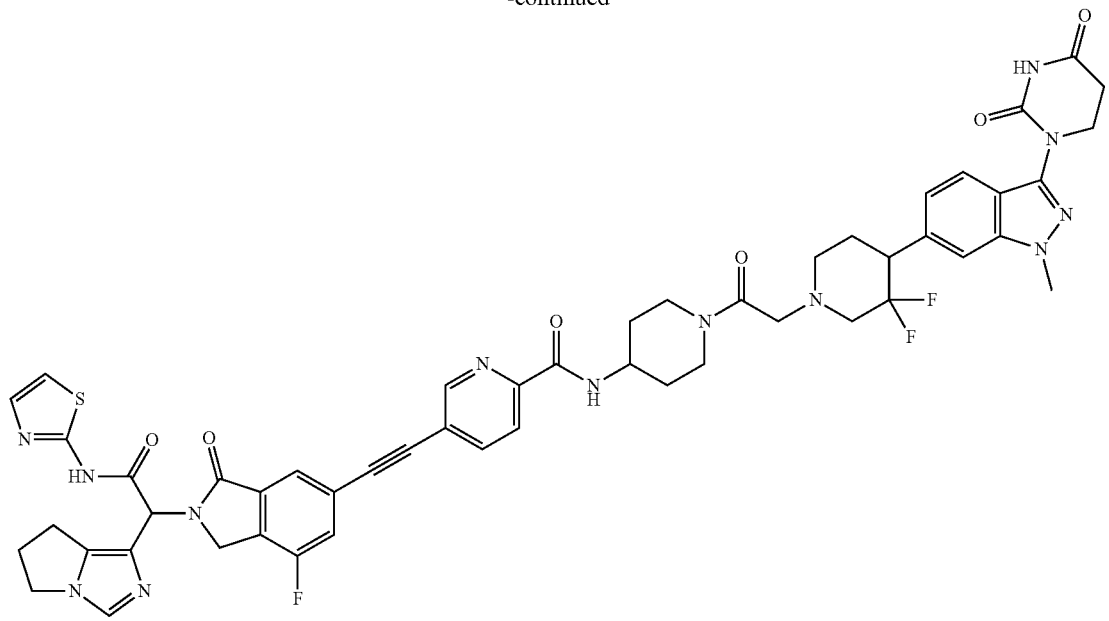

5-((2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)ethynyl)-N-(1-(2-(4-(3-(2,4-dioxotetrahydropyrimidin-1(2H)-yl)-1-methyl-1H-indazol-6-yl)-3,3-difluoropiperidin-1-yl)acetyl)piperidin-4-yl)picolinamide

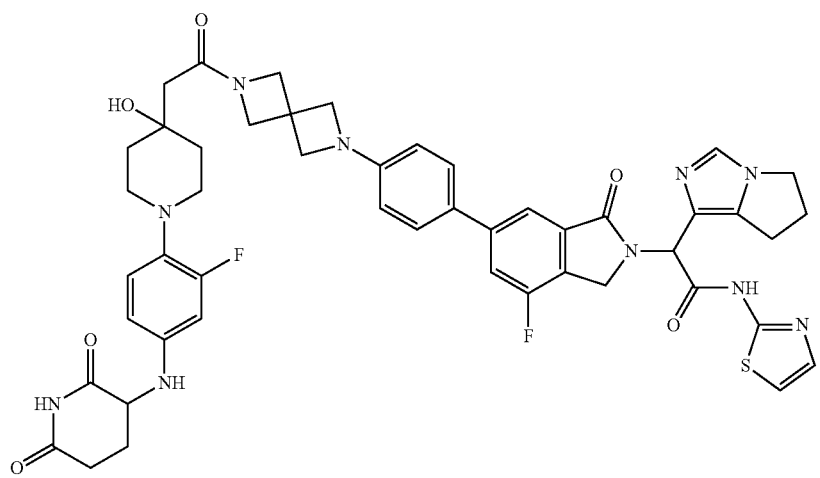

2-(6,7-dihydro-5H-pyrrolo[1,2-c]imidazol-1-yl)-2-(6-(4-(6-(2-(1-(4-((2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide

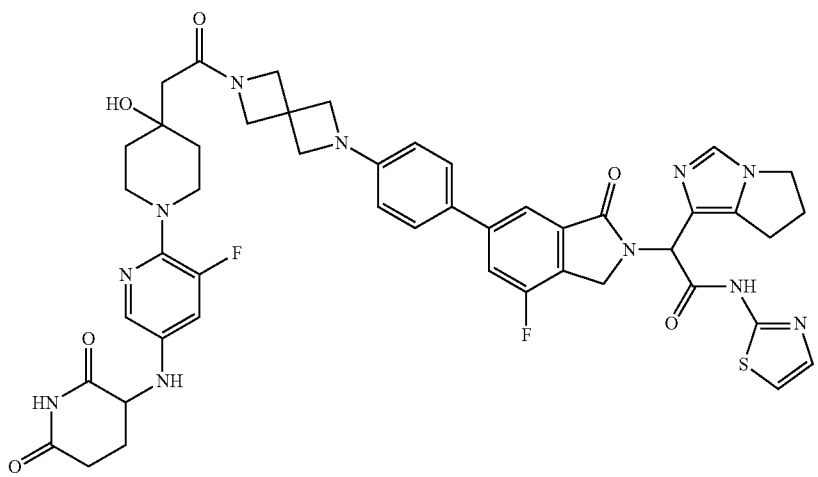

2-(6,7-dihydro-5H-pyrrolo[1,2-c]imidazol-1-yl)-2-(6-(4-(6-(2-(1-(5-(2,6-dioxopiperidin-3-yl)amino)-3-fluoropyridin-2-yl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide

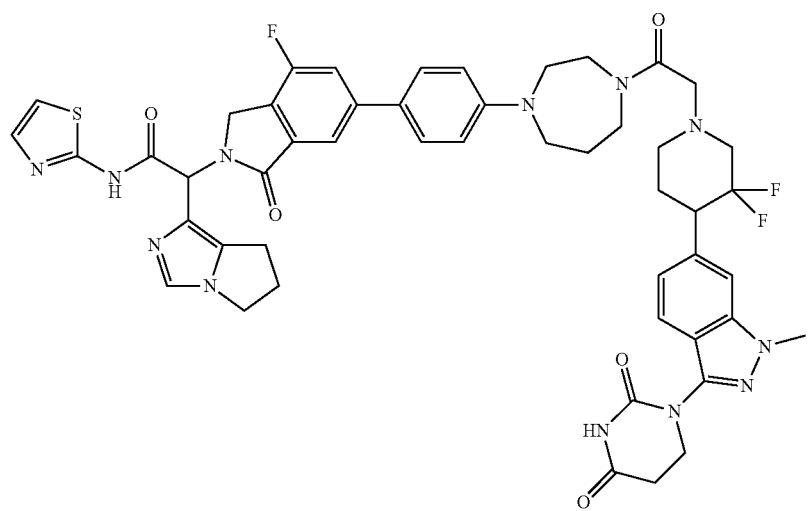

2-(6,7-dihydro-5H-pyrrolo[1,2-c]imidazol-1-yl)-2-(6-(4-(4-(2-(4-(3-(2,4-dioxotetrahydropyrimidin-1(2H)-yl)-1-methyl-1H-indazol-6-yl)-3,3-difluoropiperidin-1-yl)acetyl)-1,4-diazepan-1-yl)phenyl)-4-fluoro-1-oxoisoindolin-2-yl)-N-(thiazol-2-yl)acetamide -continued

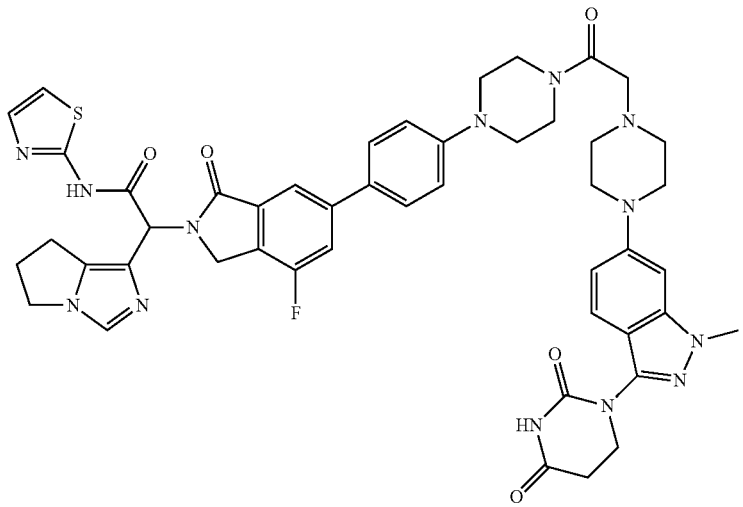

2-(6,7-dihydro-5H-pyrrolo[1,2-c]imidazol-1-yl)-2-(6-(4-(4-(2-(4-(3-(2,4-dioxotetrahydropyrimidin-1(2H)-yl)-1-methyl-1H-indazol-6-yl)piperazin-1-yl)acetyl)piperazin-1-yl)phenyl)-4-fluoro-1-oxoisoindolin-2-yl)-N-(thiazol-2-yl)acetamide

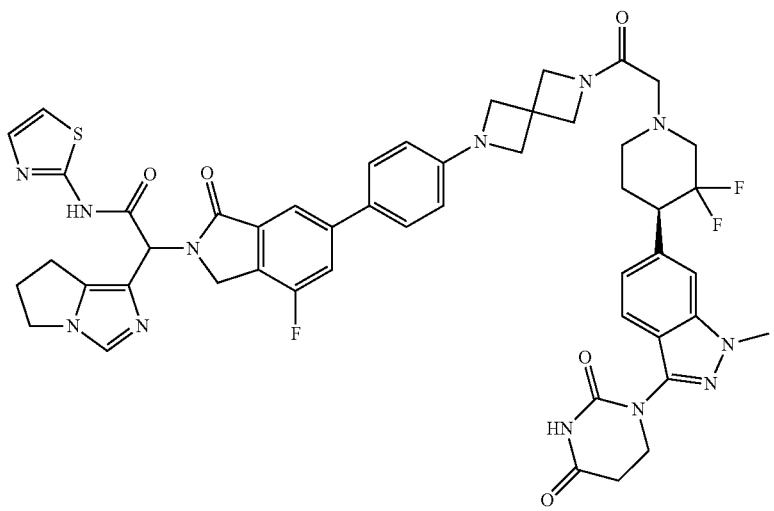

2-(6,7-dihydro-5H-pyrrolo[1,2-c]imidazol-1-yl)-2-(6-(4-(6-(2-((R)-4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide -continued

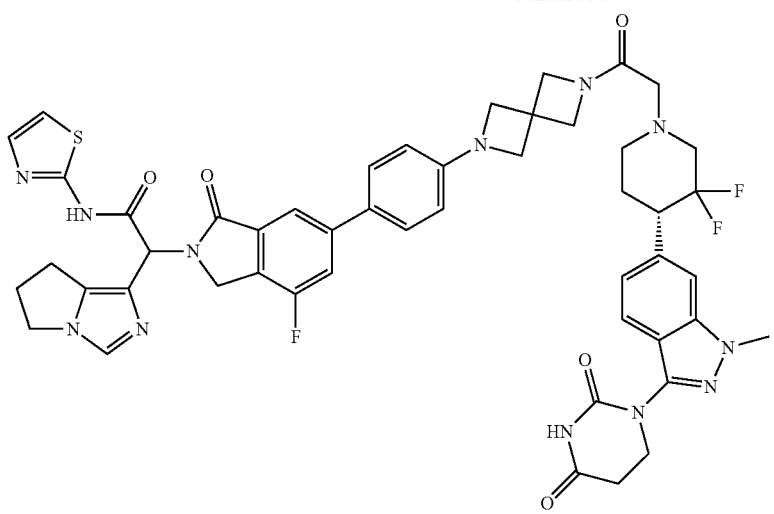

2-(6,7-dihydro-5H-pyrrolo[1,2-c]imidazol-1-yl)-2-(6-(4-(6-(2-((S)-4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide

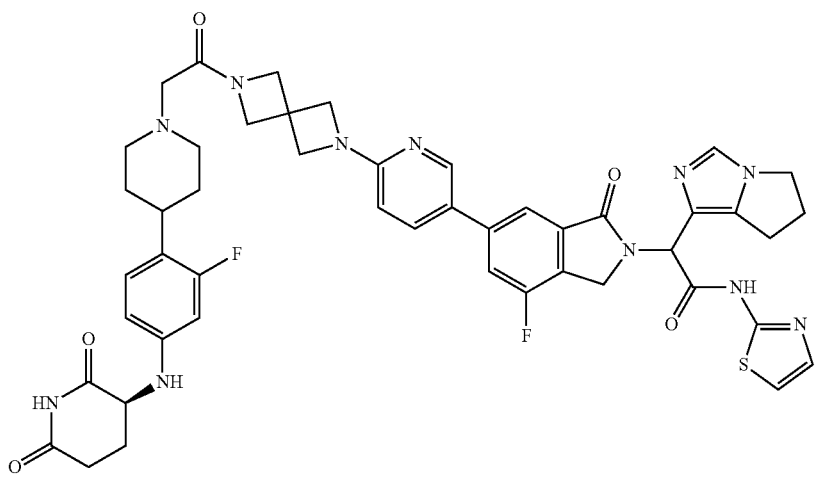

2-(6,7-dihydro-5H-pyrrolo[1,2-c]imidazol-1-yl)-2-(6-(6-(6-(2-(4-(4-(((S)-2,6-dioxopiperidin-3-yl)amino)-2-fluorophenyl)piperidin-1-yl)acetyl)-2,6-diazaspiro[3.3]heptan-2-yl)pyridin-3-yl)-4-fluoro-1-oxoisoindolin-2-yl)-N-(thiazol-2-yl)acetamide -continued

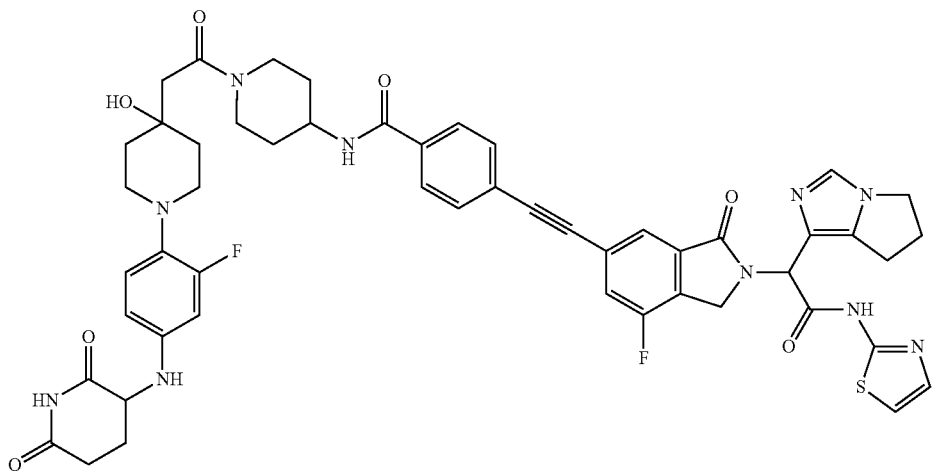

5-((2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)ethynyl)-N-(1-(2-(1-(4-((2,6-dioxopiperidin-3-yl)amino)-2-fluorophenyl)-4-hydroxypiperidin-4-yl)acetyl)piperidin-4-yl)picolinamide

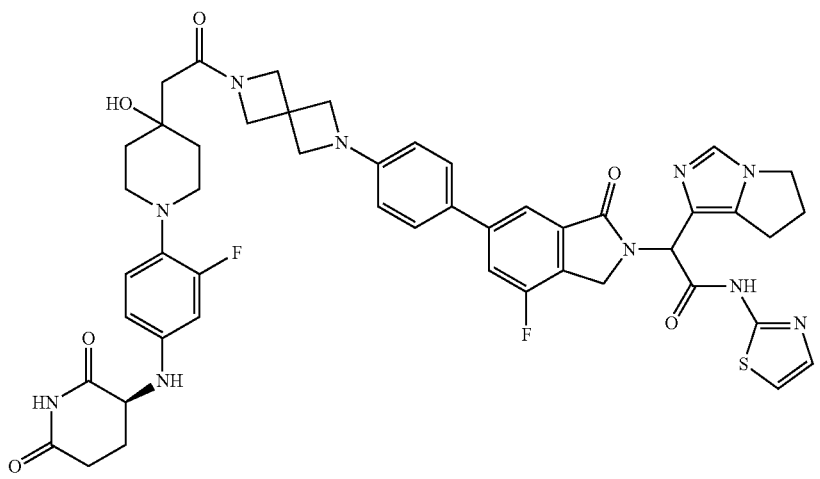

2-(6,7-dihydro-5H-pyrrolo[1,2-c]imidazol-1-yl)-2-(6-(4-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide

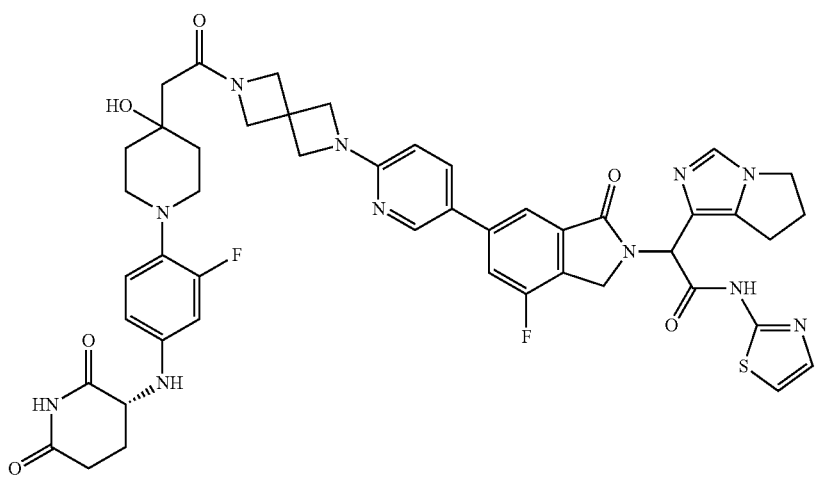

2-(6,7-dihydro-5H-pyrrolo[1,2-c]imidazol-1-yl)-2-(6-(4-(6-(2-(1-(4-(((R)-2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide

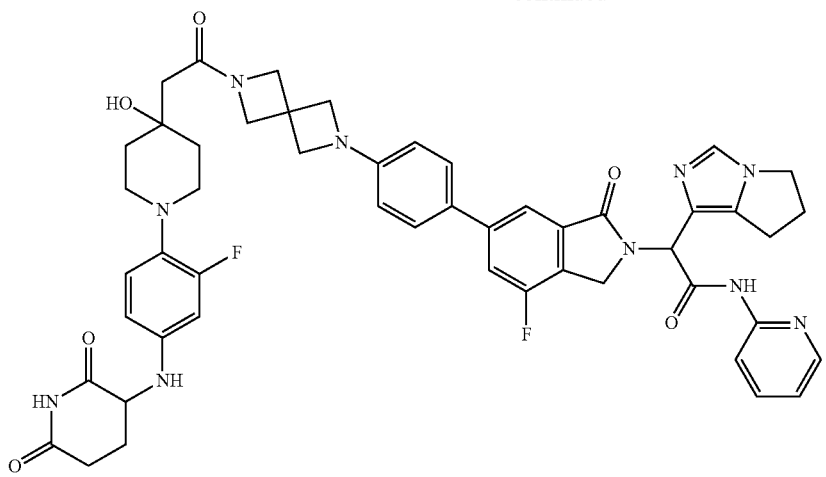

2-(6,7-dihydro-5H-pyrrolo[1,2-c]imidazol-1-yl)-2-(6-(4-(6-(2-(1-(4-((2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(pyridin-2-yl)acetamide

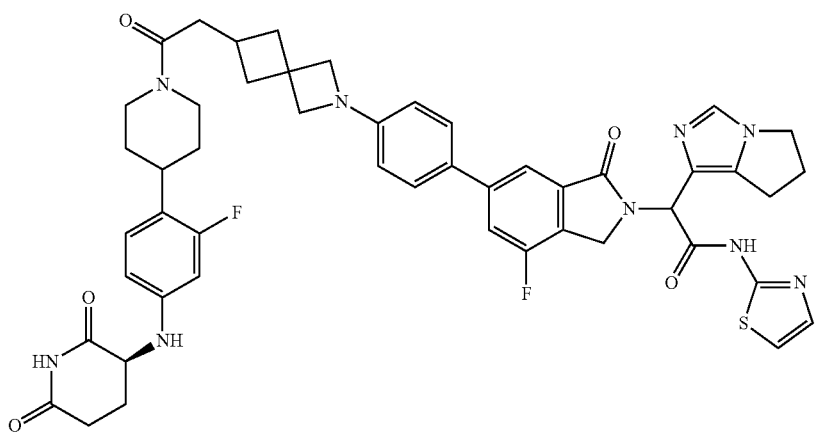

2-(6,7-dihydro-5H-pyrrolo[1,2-c]imidazol-1-yl)-2-(6-(4-(6-(2-(4-(4-(((S)-2,6-dioxopiperidin-3-yl)amino)-2-fluorophenyl)piperidin-1-yl)-2-oxoethyl)-2-azaspiro[3.3]heptan-2-yl)phenyl)-4-fluoro-1-oxoisoindolin-2-yl)-N-(thiazol-2-yl)acetamide

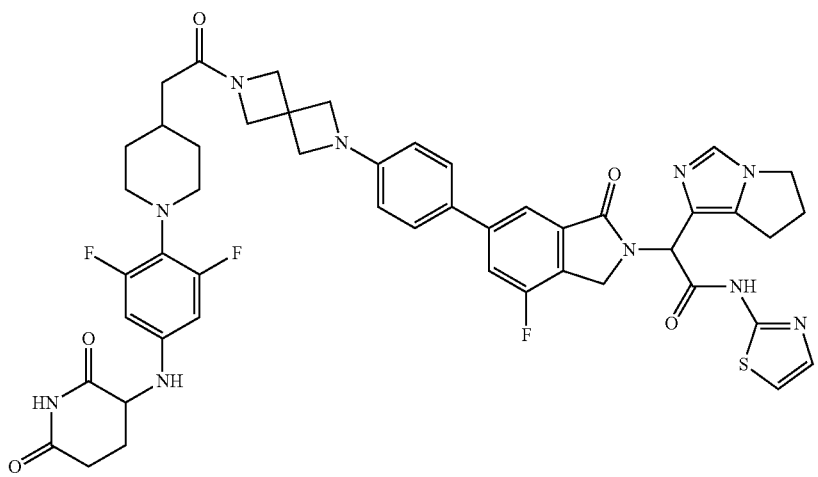

2-(6,7-dihydro-5H-pyrrolo[1,2-c]imidazol-1-yl)-2-(6-(4-(6-(2-(1-(4-((2,6-dioxopiperidin-3-yl)amino)-2,6-fluorophenyl)piperidin-4-yl)acetyl)-2,6-diazaspiro[3.3]heptan-2-yl)phenyl)-4-fluoro-1-oxoisoindolin-2-yl)-N-(thiazol-2-yl)acetamide -continued

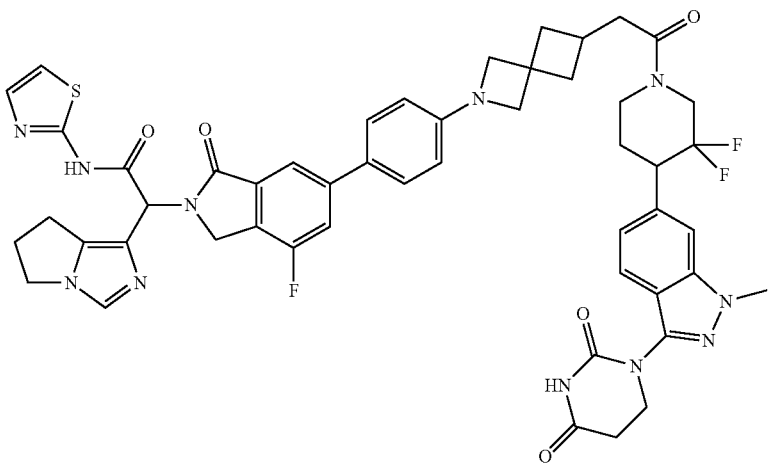

2-(6,7-dihydro-5H-pyrrolo[1,2-c]imidazol-1-yl)-2-(6-(4-(6-(2-(4-(3-(2,4-dioxotetrahydropyrimidin-1(2H)-yl)-1-methyl-1H-indazol-6-yl)-3,3-difluoropiperidin-1-yl)-2-oxoethyl)-2-azaspiro[3.3]heptan-2-yl)phenyl)-4-fluoro-1-oxoisoindolin-2-yl)-N-(thiazol-2-yl)acetamide

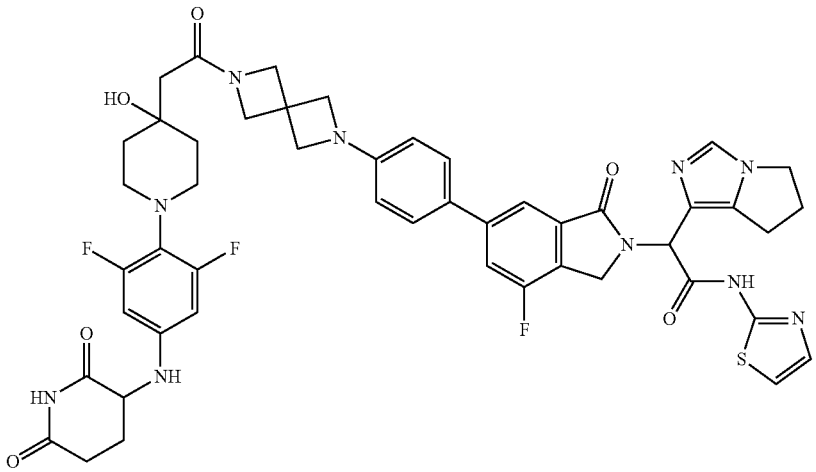

2-(6,7-dihydro-5H-pyrrolo[1,2-c]imidazol-1-yl)-2-(6-(4-(6-(2-(1-(4-((2,6-dioxopiperidin-3-yl)amino)-2,6-difluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide

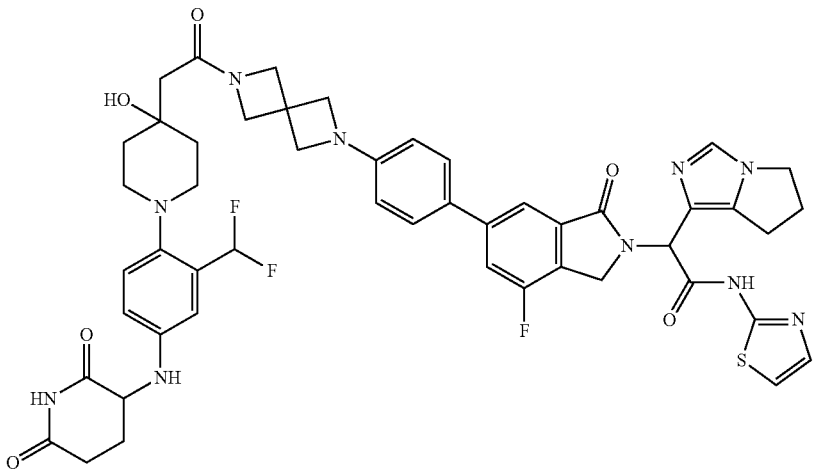

2-(6-(4-(6-(2-(1-(2-(difluoromethyl)-4-((2,6-dioxopiperidin-3-yl)amino)phenyl)-4-hydroxypiperidin-4-yl)acetyl)-2,6-diazaspiro[3.3]heptan-2-yl)phenyl)-4-fluoro-1-oxoisoindolin-2-yl)-2-(6,7-dihydro-5H-pyrrolo[1,2-c]imidazol-1-yl)-N-(thiazol-2-yl(acetamide -continued

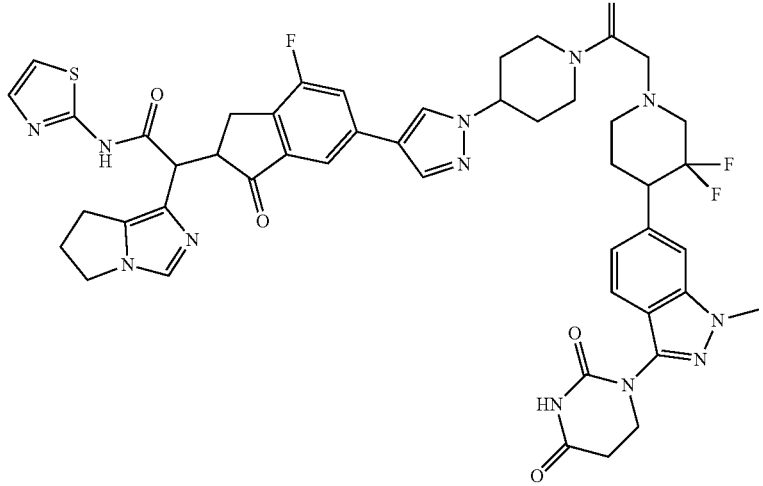

2-(6,7-dihydro-5H-pyrrolo[1,2-c]imidazol-1-yl)-2-(6-(1-(1-(2-(4-(3-(2,4-dioxotetrahydropyrimidin-1(2H)-yl)-1-methyl-1H-indazol-6-yl)-3,3-difluoropiperidin-1-yl)acetyl)piperidin-4-yl)-1H-pyrazol-4-yl)-4-fluoro-1-oxoisoindolin-2-yl)-N-(thiazol-2-yl)acetamide

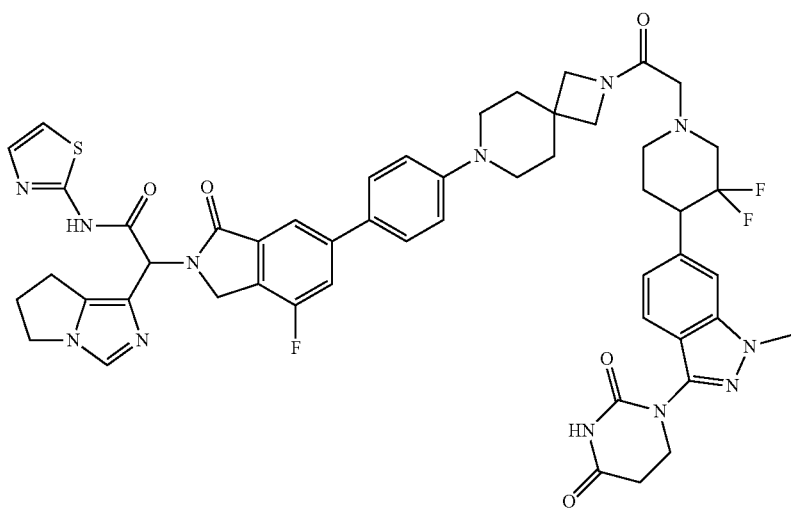

2-(6,7-dihydro-5H-pyrrolo[1,2-c]imidazol-1-yl)-2-(6-(4-(2-(2-(4-(3-(2,4-dioxotetrahydropyrimidin-1(2H)-yl)-1-methyl-1H-indazol-6-yl)-3,3-difluoropiperidin-1-yl)acetyl)-2,7-diazaspiro[3.5]nonan-7-yl)phenyl)-4-fluoro-1-oxoisoindolin-2-yl)-N-(thiazol-2-yl)acetamide

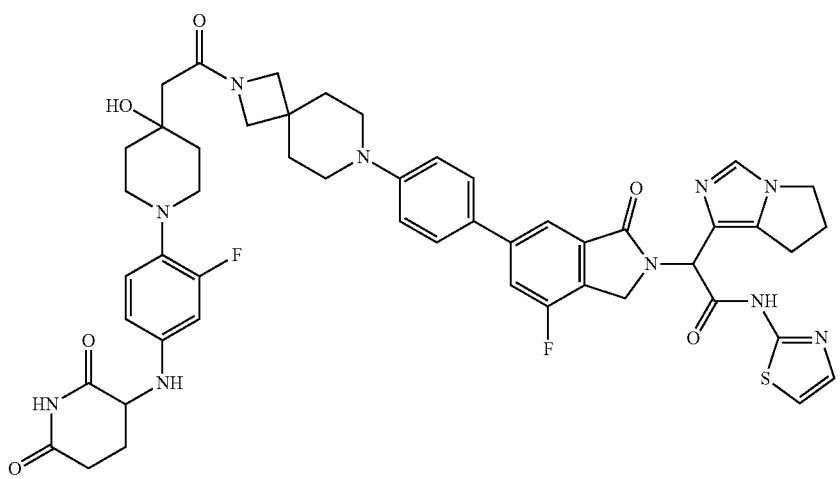

2-(6,7-dihydro-5H-pyrrolo[1,2-c]imidazol-1-yl)-2-(6-(4-(2-(2-(1-(4-((2,6-dioxopiperidin-3-yl)amino)-2-fluorophenyl)-4-hydroxypiperidin-4-yl)acetyl)-2,7-diazaspiro[3.5]nonan-7-yl)phenyl)-4-fluoro-1-oxoisoindolin-2-yl)-N-(thiazol-2-yl)acetamide

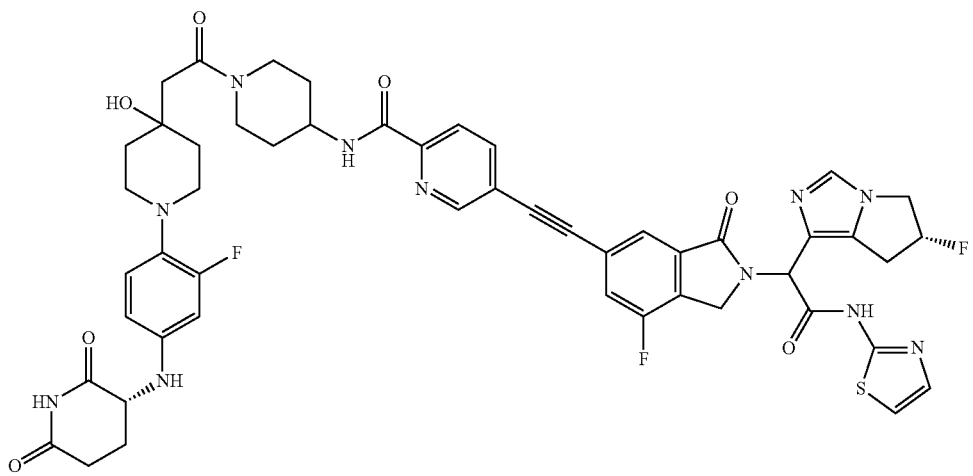

N-(1-(2-(1-(4-(((R)-2,6-dioxopiperidin-3-yl)amino)-2-fluorophenyl)-4-hydroxypiperidin-4-yl)acetyl)piperidin-4-yl)-5-((7-fluoro-2-(1-((R)-6-fluoro-6,7-dihydro-5H-pyrrolo[1,2-c]imidazol-1-yl)-2-oxo-2-(thiazol-2-ylamino)ethyl)-3-oxoisoindolin-5-yl)ethynyl)picolinamide

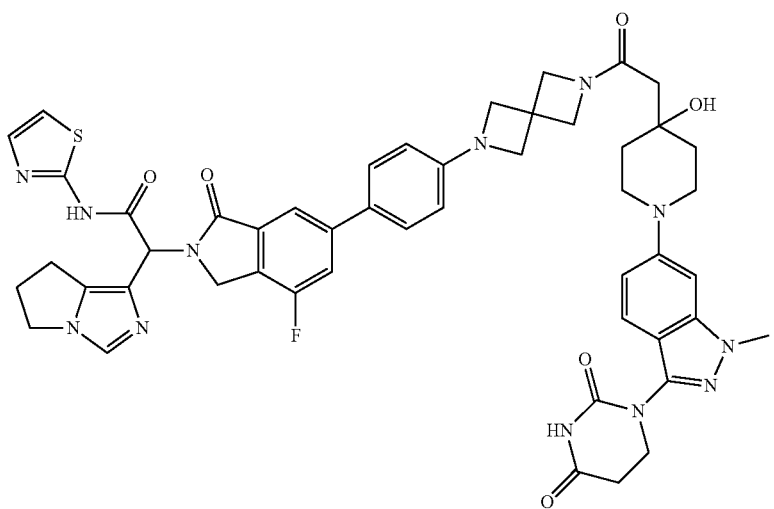

2-(6,7-dihydro-5H-pyrrolo[1,2-c]imidazol-1-yl)-2-(6-(4-(6-(2-(1-(3-(2,4-dioxotetrahydropyrimidin-1(2H)-yl)-1-methyl-1H-indazol-6-yl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide

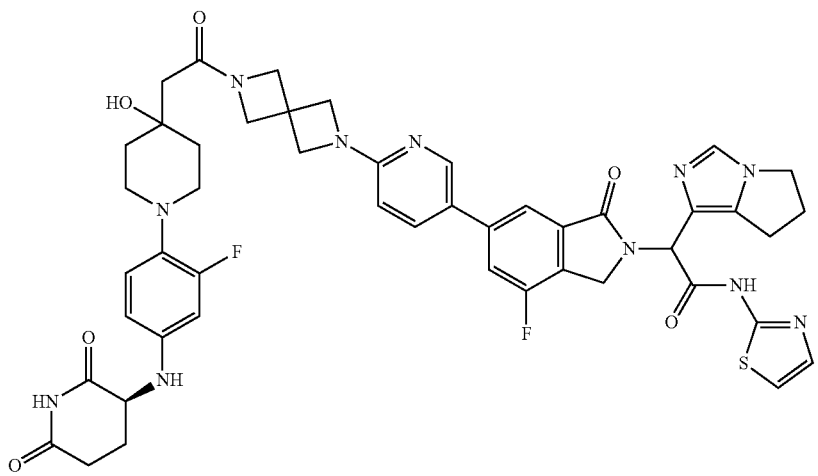

2-(6,7-dihydro-5H-pyrrolo[1,2-c]imidazol-1-yl)-2-(6-(6-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)pyridin-3-yl)-4-fluoro-1-oxoisoindolin-2-yl)-N-(thiazol-2-yl)acetamide

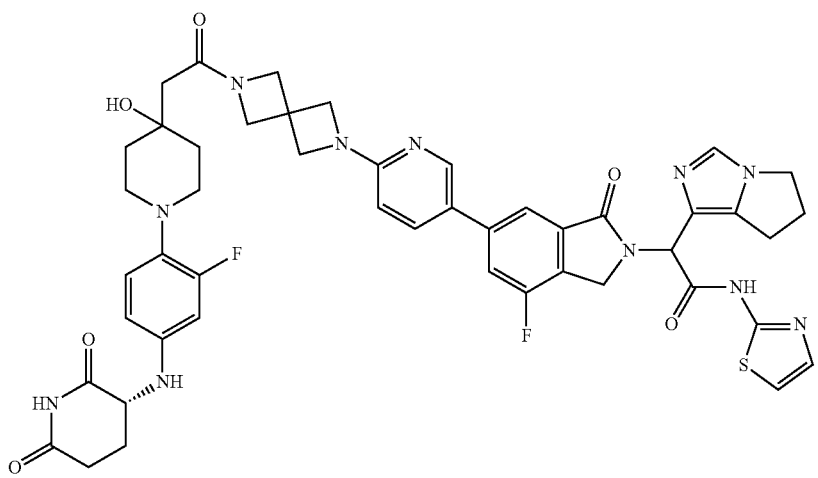

2-(6,7-dihydro-5H-pyrrolo[1,2-c]imidazol-1-yl)-2-(6-(6-(6-(2-(1-(4-(((R)-2,6-dioxopiperidin-3-yl)amino)-2-fluorophenyl)-4-hydroxypiperidin-4-yl)acetyl)-2,6-diazaspiro[3.3]heptan-2-yl)pyridin-3-yl)-4-fluoro-1-oxoisoindolin-2-yl)-N-(thiazol-2-yl)acetamide

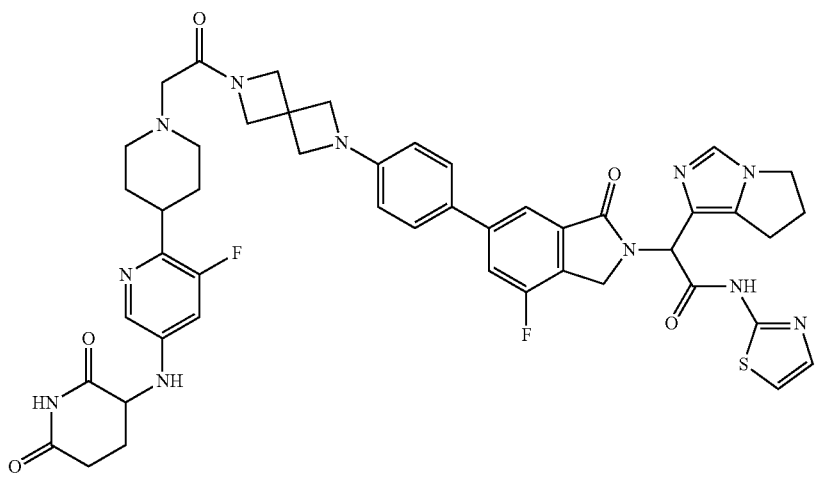

2-(6,7-dihydro-5H-pyrrolo[1,2-c]imidazol-1-yl)-2-(6-(4-(6-(2-(4-(5-((2,6-dioxopiperidin-3-yl)amino)-3-fluoropyridin-2-yl)piperidin-1-yl)acetyl)-2,6-diazaspiro[3.3]heptan-2-yl)phenyl)-4-fluoro-1-oxoisoindolin-2-yl)-N-(thiazol-2-yl)acetamide

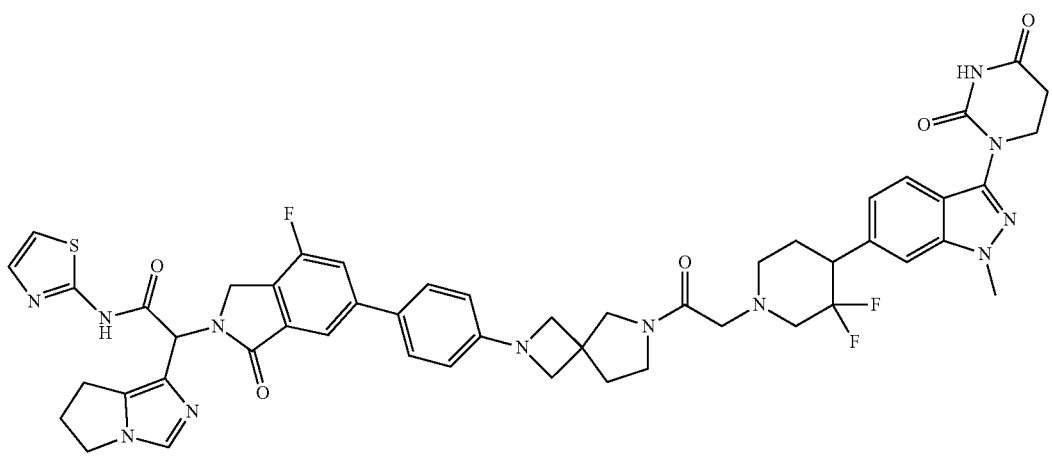

2-(6,7-dihydro-5H-pyrrolo[1,2-c]imidazol-1-yl)-2-(6-(4-(6-(2-(4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.4]octan-2-yl)phenyl)-4-fluoro-1-oxoisoindolin-2-yl)-N-(thiazol-2-yl)acetamide

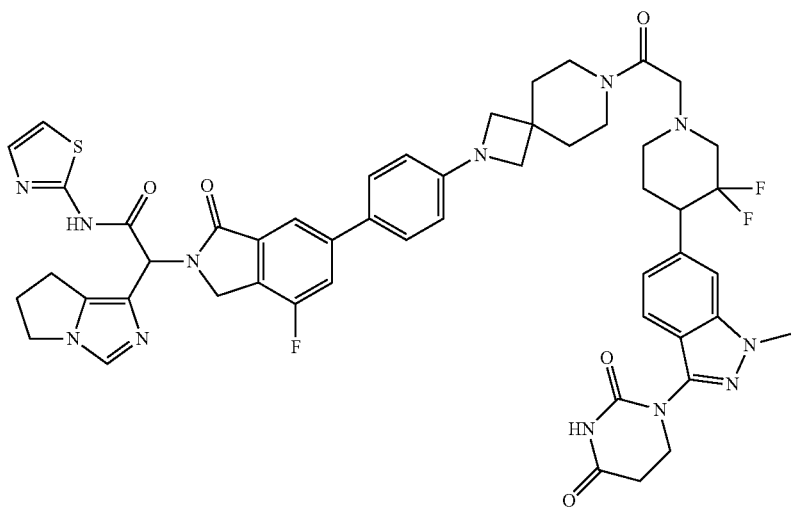

2-(6,7-dihydro-5H-pyrrolo[1,2-c]imidazol-1-yl)-2-(6-(4-(7-(2-(4-(3-(2,4-dioxotetrahydropyrimidin-1(2H)-yl)-1-methyl-1H-indazol-6-yl)-3,3-difluoropiperidin-1-yl)-acetyl)-2,7-diazaspiro[3.5]nonan-2-yl)phenyl)-4-fluoro-1-oxoisoindolin-2-yl)-N-(thiazol-2-yl)acetamide

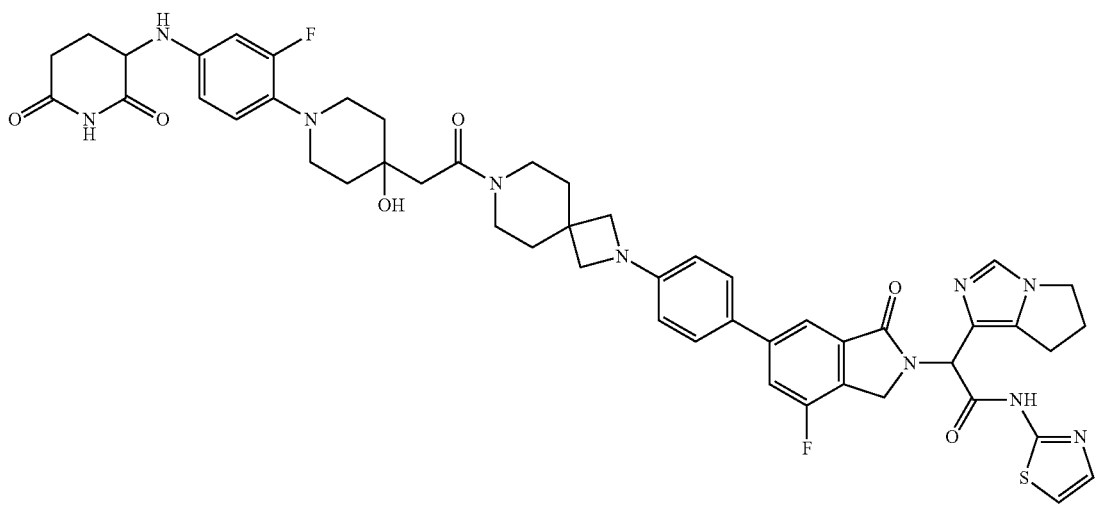

2-(6,7-dihydro-5H-pyrrolo[1,2-c]imidazol-1-yl)-2-(6-(4-(7-(2-(1-(4-((2,6-dioxopiperidin-3-yl)amino)-2-fluorophenyl)-4-hydroxypiperidin-4-yl)acetyl)-2,7-diazaspiro[3.5]nonan-2-yl)phenyl)-4-fluoro-1-oxoisoindolin-2-yl)-N-(thiazol-2-yl)acetamide

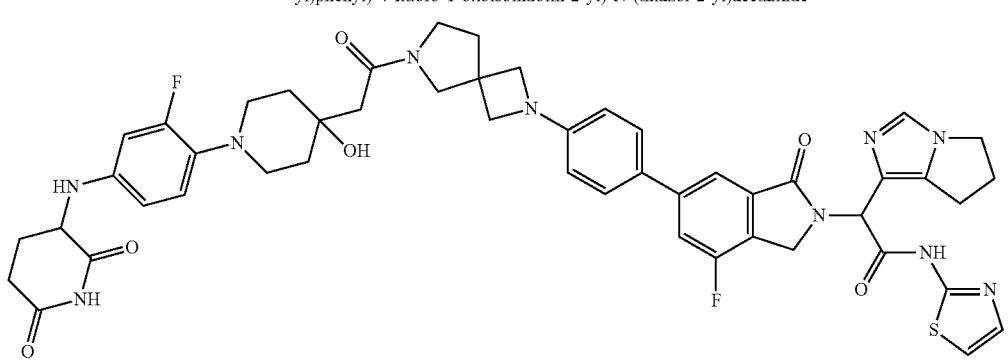

2-(6,7-dihydro-5H-pyrrolo[1,2-c]imidazol-1-yl)-2-(6-(4-(6-(2-(1-(4-((2,6-dioxopiperidin-3-yl)amino)-2-fluorophenyl)-4-hydroxypiperidin-4-yl)acetyl)-2,6-diazaspiro[3.4]octan-2-yl)phenyl)-4-fluoro-1-oxoisoindolin-2-yl)-N-(thiazol-2-yl)acetamide -continued

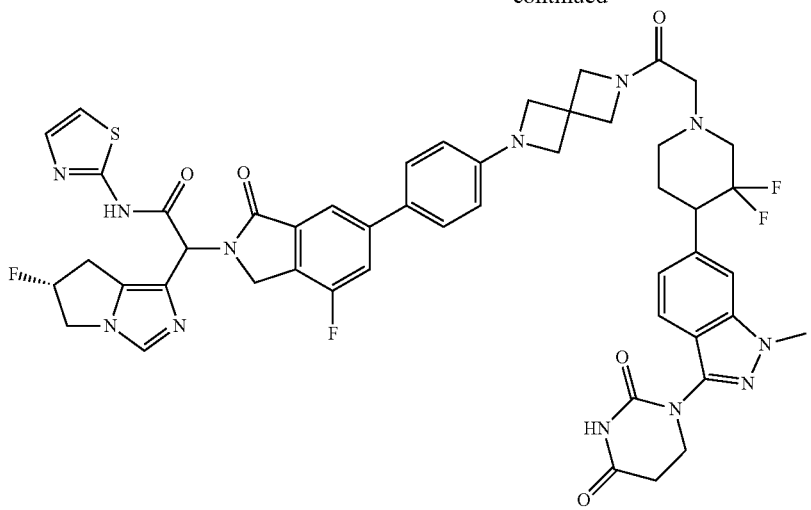

2-(6-(4-(6-(2-(4-(3-(2,4-dioxotetrahydropyrimidin-1(2H)-yl)-1-methyl-1H-indazol-6-yl)-3,3-difluoropiperidin-1-yl)-acetyl)-2,6-diazaspiro[3.3]heptan-2-yl)phenyl)-4-fluoro-1-oxoisoindolin-2-yl)-2-((R)-6-fluoro-6,7-dihydro-5H-pyrrolo[1,2-c]imidazol-1-yl)-N-(thiazol-2-yl)acetamide

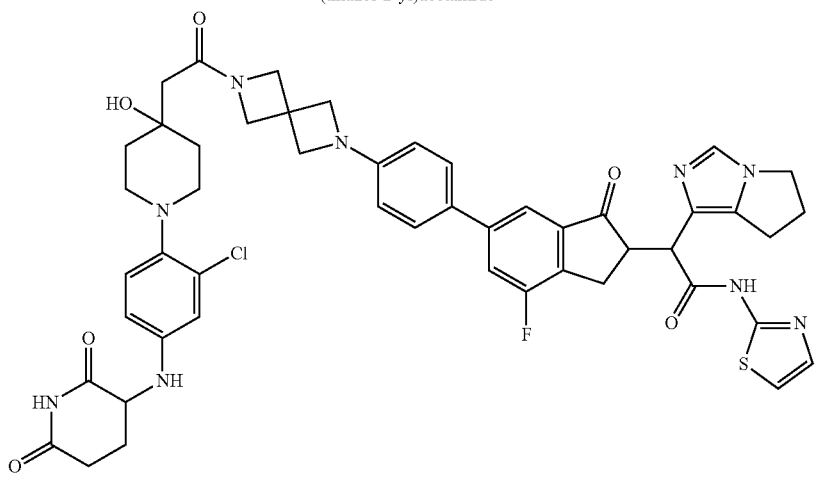

2-(6-(4-(6-(2-(1-(2-chloro-4-((2,6-dioxotpiperidin-3-yl)amino)phenyl)-4-hydroxypiperidin-4-yl)acetyl)-2,6-diazaspiro[3.3]heptan-2-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide

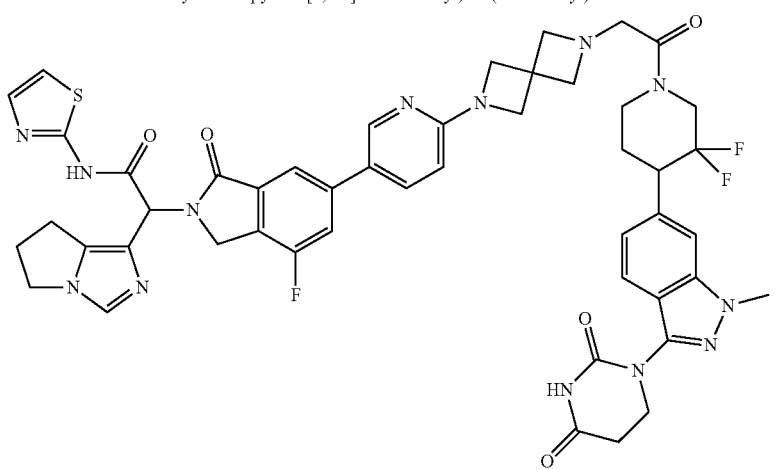

2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)-2-oxoethyl)-2,6-diazaspiro[3.3]heptan-2-yl)pyridin-3-yl)-4-fluoro-1-oxoisoindolin-2-yl)-N-(thiazol-2-yl)acetamide

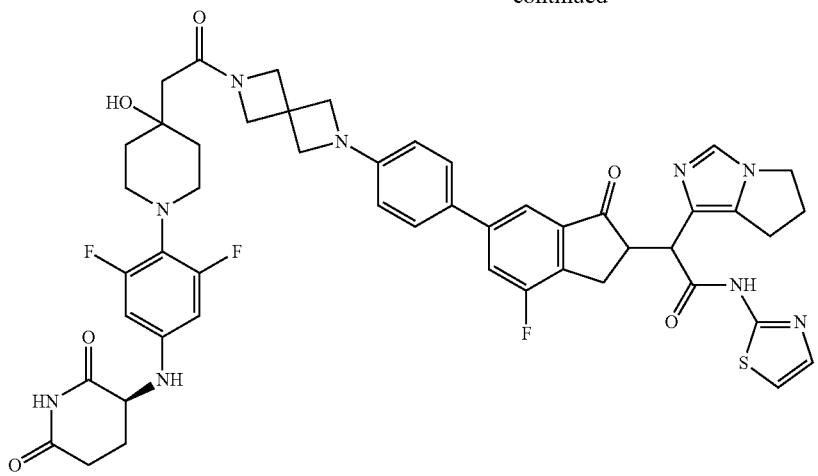
2-(6,7-dihydro-5H-pyrrolo[1,2-c]imidazol-1-yl)-2-(6-(4-(6-(2-(1-(4-(((S)-2,6-dioxopiperidin-3-yl)amino)-2,6-difluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide
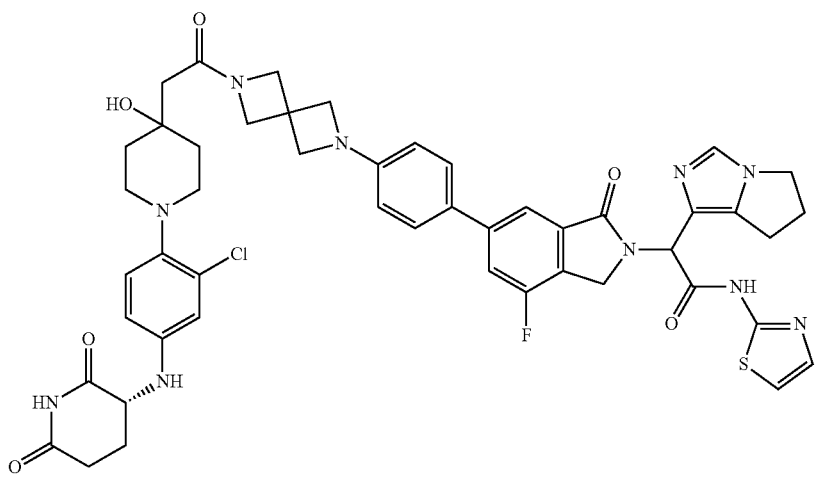
2-(6-(4-(6-(2-(1-(2-chloro-4-(((R)-2,6-dioxopiperidin-3-yl)amino)phenyl)-4-hydroxypiperidin-4-yl)acetyl)-2,6-diazaspiro[3.3]heptan-2-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide

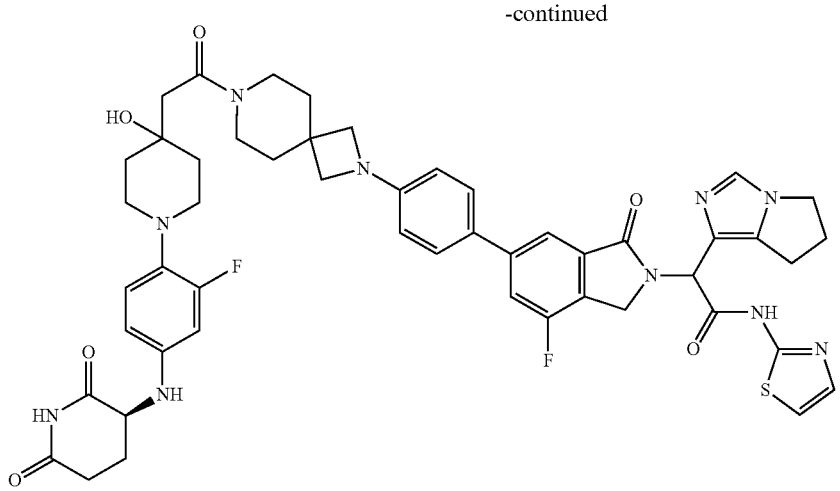

2-(6,7-dihydro-5H-pyrrolo[1,2-c]imidazol-1-yl)-2-(6-(4-(7-(2-(1-(4-(((S)-2,6-dioxopiperidin-3-yl)amino)-2-fluorophenyl)-4-hydroxypiperidin-4-yl)acetyl)-2,7-diazaspiro[3.5]nonan-2-yl)phenyl)-4-fluoro-1-oxoisoindolin-2-yl)-N-(thiazol-2-yl)acetamide

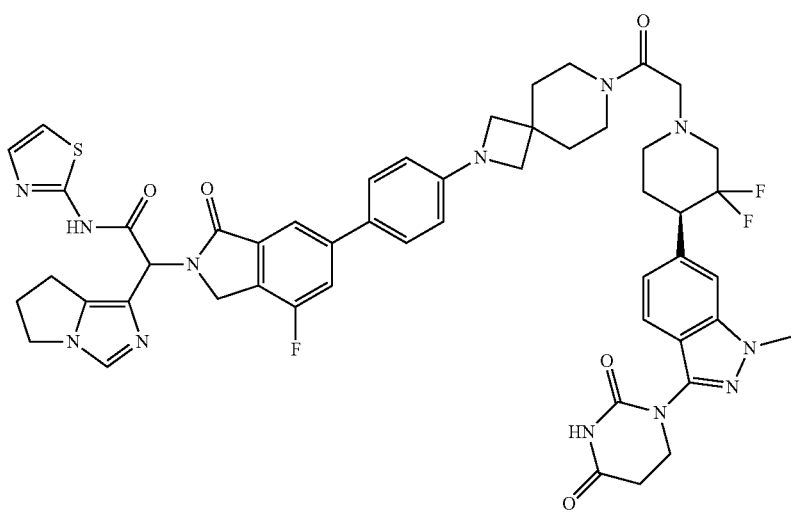

2-(6,7-dihydro-5H-pyrrolo[1,2-c]imidazol-1-yl)-2-(6-(4-(7-(2-((R)-4-(3-(2,4-dioxotetrahydropyrimidin-1(2H)-yl)-1-methyl-1H-indazol-6-yl)-3,3-difluoropiperidin-1-yl)acetyl)-2,7-diazaspiro[3.5]nonan-2-yl)phenyl)-4-fluoro-1-oxoisoindolin-2-yl)-N-(thiazol-2-yl)acetamide

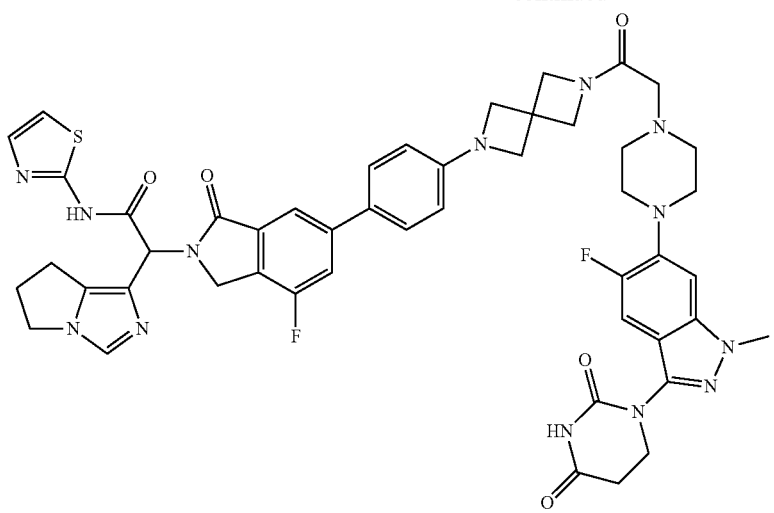

2-(6,7-dihydro-5H-pyrrolo[1,2-c]imidazol-1-yl)-2-(6-(4-(6-(2-(4-(3-(2,4-dioxotetrahydropyrimidin-1(2H)-yl)-5-fluoro-1-methyl-1H-indazol-6-yl)piperazin-1-yl)acetyl)-2,6-diazaspiro[3.3]heptan-2-yl)phenyl)-4-fluoro-1-oxoisoindolin-2-yl)-N-(thiazol-2-yl)acetamide

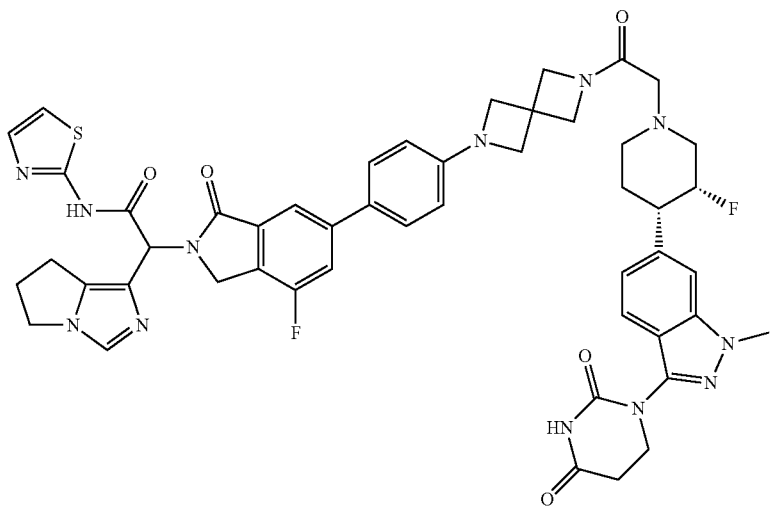

2-(6,7-dihydro-5H-pyrrolo[1,2-c]imidazol-1-yl)-2-(6-(4-(6-(2-((3R,4S)-4-(3-(2,4-dioxotetrahydropyrimidin-1(2H)-yl)-1-methyl-1H-indazol-6-yl)-3-fluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide

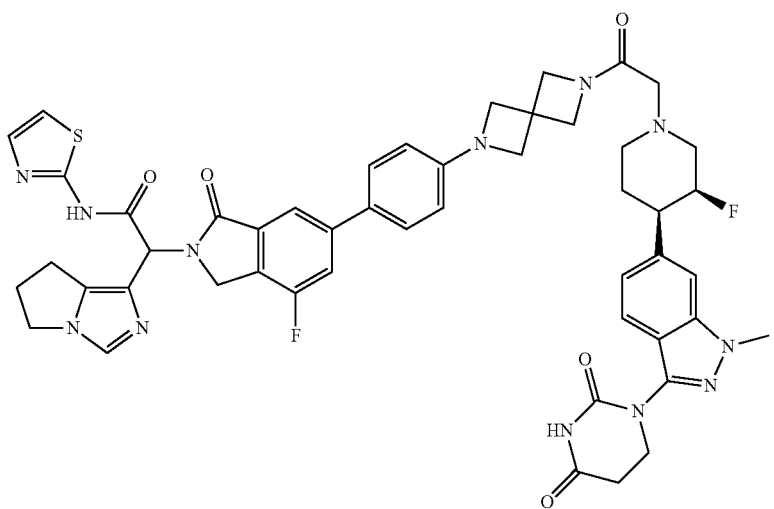

2-(6,7-dihydro-5H-pyrrolo[1,2-c]imidazol-1-yl)-2-(6-(4-(6-(2-((3R,4R)-4-(3-(2,4-dioxotetrahydropyrimidin-1(2H)-yl)-1-methyl-1H-indazol-6-yl)-3-fluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide

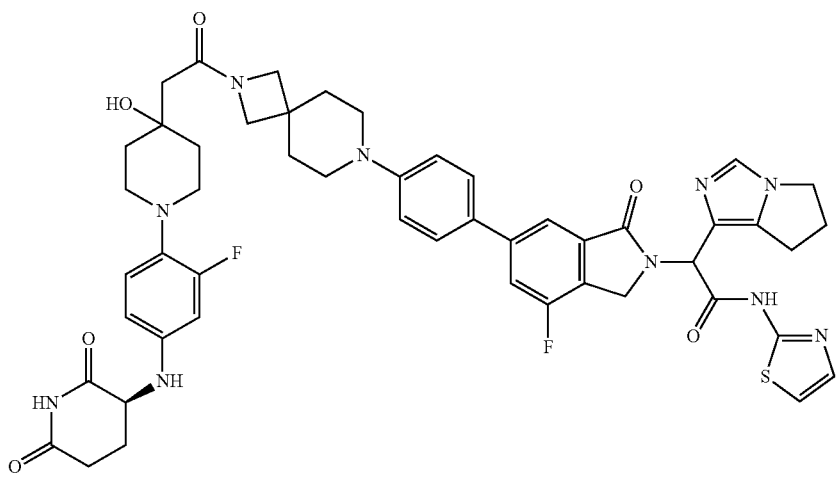

2-(6,7-dihydro-5H-pyrrolo[1,2-c]imidazol-1-yl)-2-(6-(4-(2-(2-(1-(4-(((S)-2,6-dioxopiperidin-3-yl)amino)-2-fluorophenyl)-4-hydroxypiperidin-4-yl)acetyl)-2,7-diazaspiro[3.5]nonan-7-yl)phenyl)-4-fluoro-1-oxoisoindolin-2-yl)-N-(thiazol-2-yl)acetamide

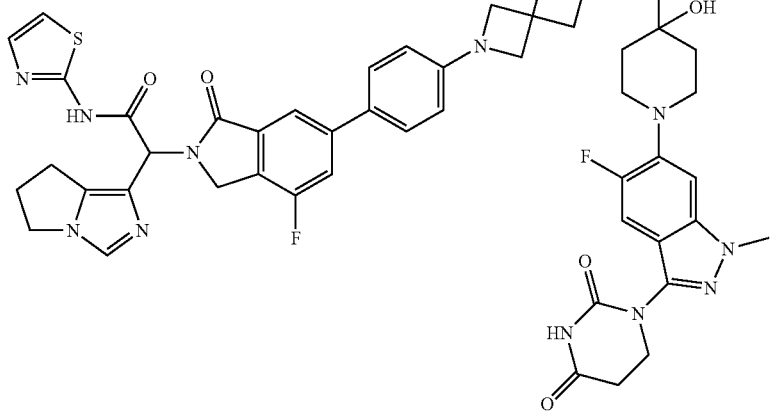

2-(6,7-dihydro-5H-pyrrolo[1,2-c]imidazol-1-yl)-2-(6-(4-(6-(2-(1-(3-(2,4-dioxotetrahydropyrimidin-1(2H)-yl)-5-fluoro-1-methyl-1H-indazol-6-yl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide

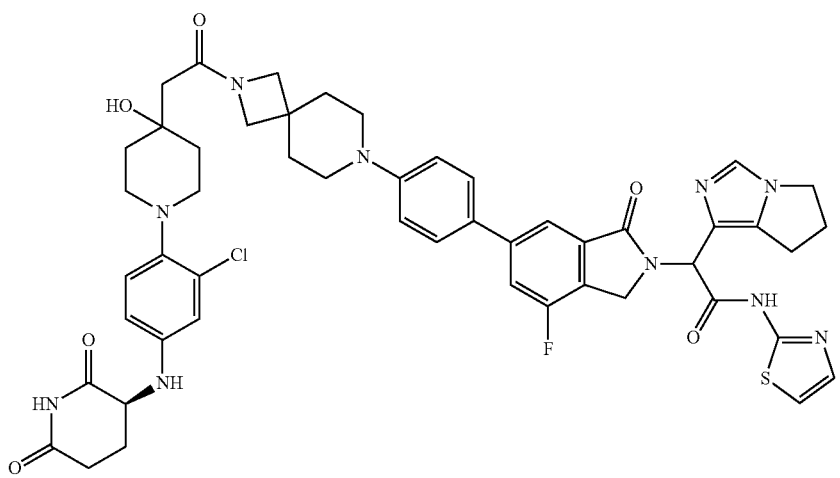

2-(6-(4-(2-(2-(1-(2-chloro-4-(((S)-2,6-dioxopiperidin-3-yl)amino)phenyl)-4-hydroxypiperidin-4-yl)acetyl)-2,7-diazaspiro[3.5]nonan-7-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide

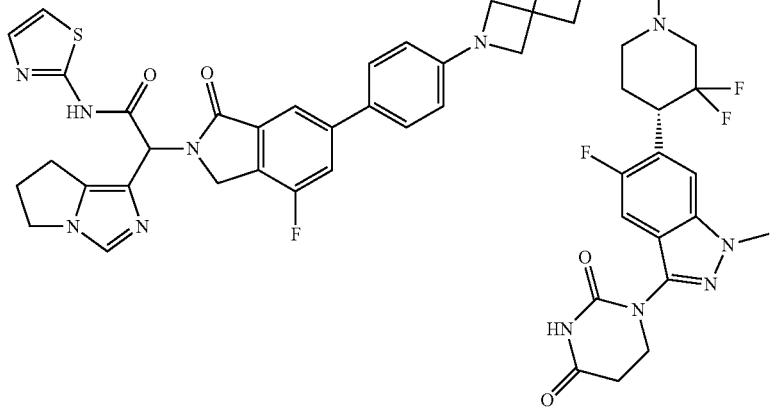

2-(6,7-dihydro-5H-pyrrolo[1,2-c]imidazol-1-yl)-2-(6-(4-(6-(2-((S)-4-(3-(2,4-dioxotetrahydropyrimidin-1(2H)-yl)-5-fluoro-1-methyl-1H-indazol-6-yl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide

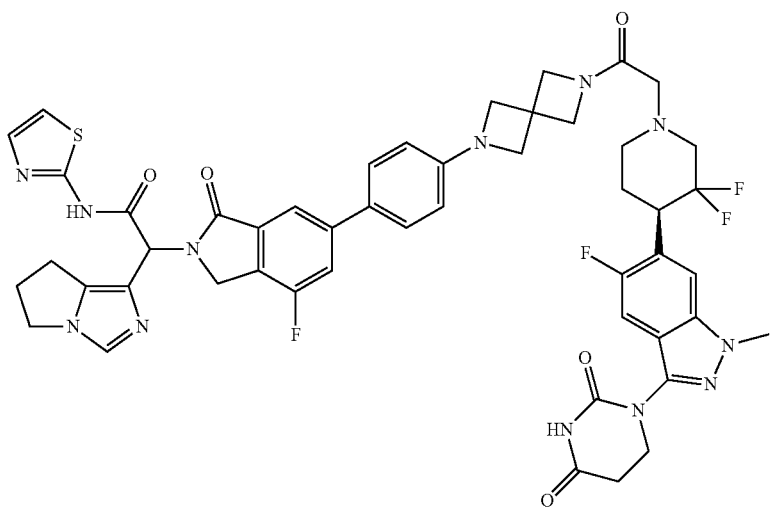

2-(6,7-dihydro-5H-pyrrolo[1,2-c]imidazol-1-yl)-2-(6-(4-(6-(2-((R)-4-(3-(2,4-dioxotetrahydropyrimidin-1(2H)-yl)-5-fluoro-1-methyl-1H-indazol-6-yl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide -continued

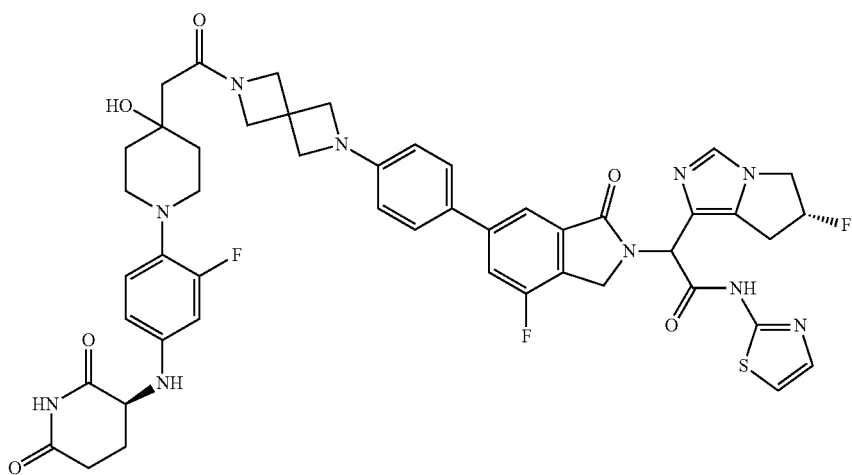

2-(6-(4-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-2-((R)-6-fluoro-6,7-dihydro-5H-pyrrolop[1,2-c]imidazol-1-yl)-N-(thiazol-2-yl)acetamide

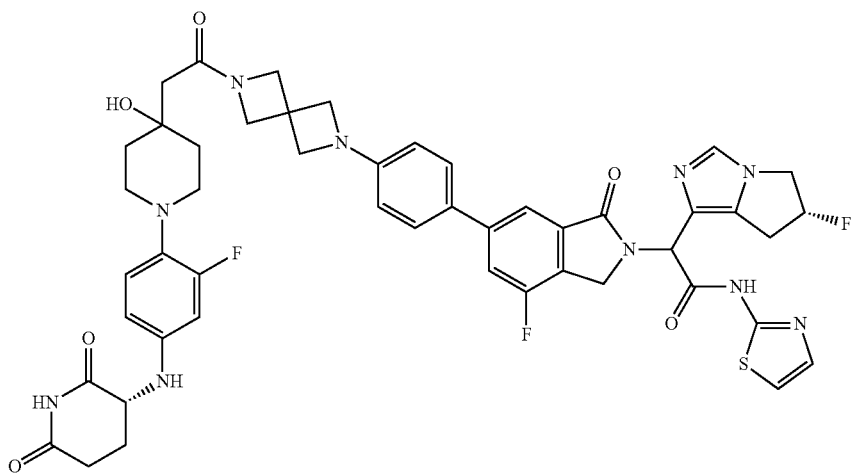

2-(6-(4-(6-(2-(1-(4-(((R)-2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-2-((R)-6-fluoro-6,7-dihydro-5H-pyrrolo[1,2-c]imidazol-1-yl)-N-(thiazol-2-yl)acetamide

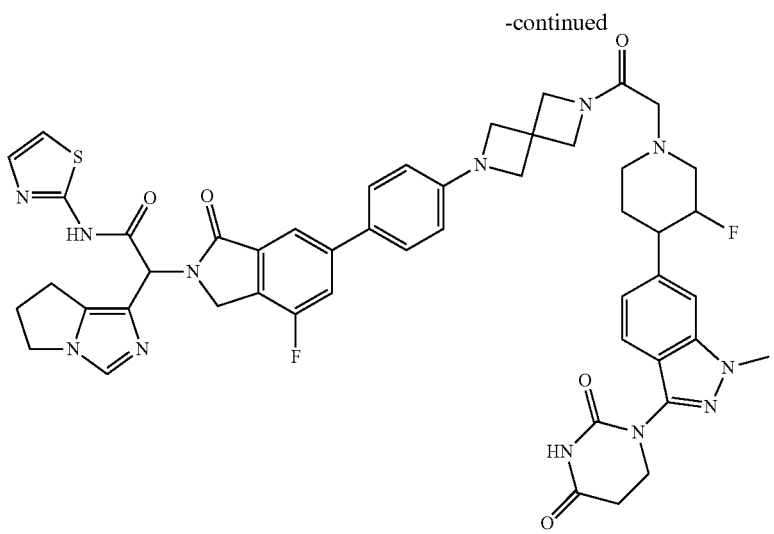

2-(6,7-dihydro-5H-pyrrolo[1,2-c]imidazol-1-yl)-2-(6-(4-(6-(2-(4-(3-(2,4-dioxotetrahydropyrimidin-1(2H)-yl)-1-methyl-1H-indazol-6-yl)-3-fluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide

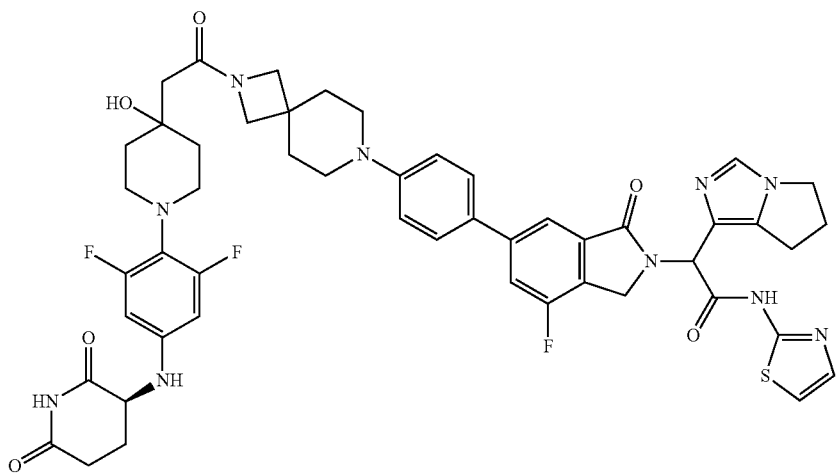

2-(6,7-dihydro-5H-pyrrolo[1,2-c]imidazol-1-yl)-2-(6-(4-(2-(2-(1-(4-(((S)-(2,6-dioxopiperidin-3-yl)amino)-2,6-difluorophenyl)-4-hydroxypiperidin-4-yl)acetyl)-2,7-diazaspiro[3.5]nonan-7-yl)phenyl)-4-fluoro-1-oxoisoindolin-2-yl)-N-(thiazol-2-yl)acetamide

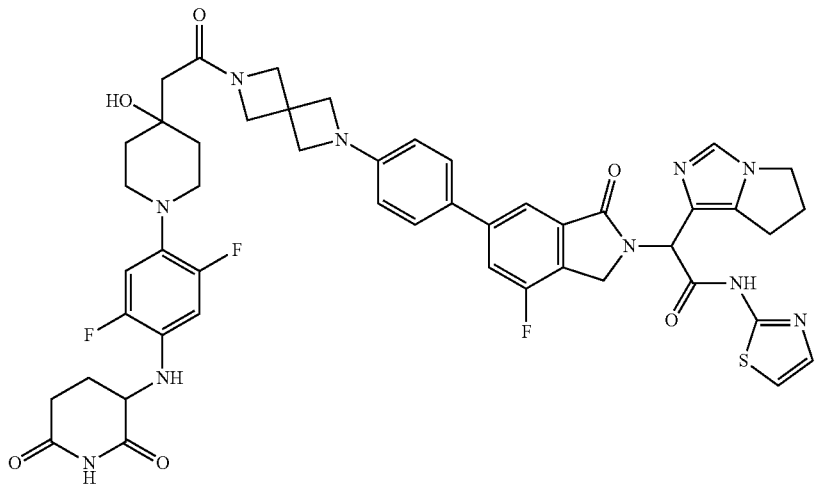

2-(6,7-dihydro-5H-pyrrolo[1,2-c]imidazol-1-yl)-2-(6-(4-(6-(2-(1-(4-((2,6-dioxopiperidin-3-yl)amino)-2,5-difluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide

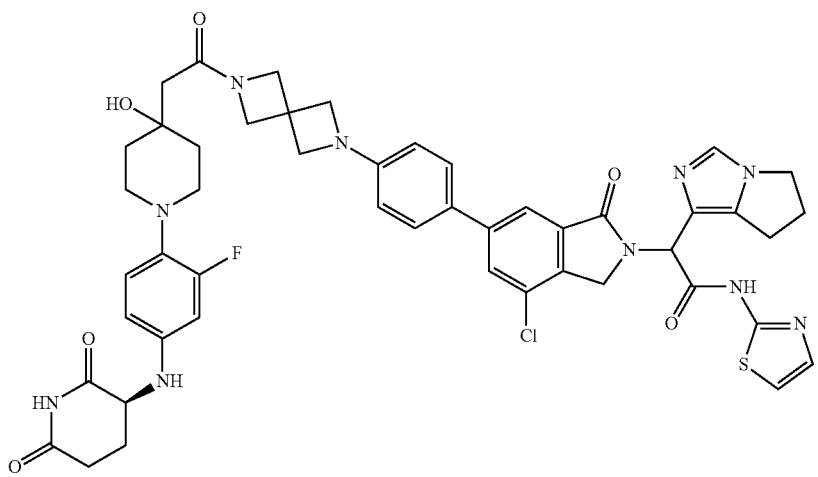

2-(4-chloro-6-(4-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)phenyl)-1-oxoisoindolin-2-yl)-2-(6,7-dihydro-5H-pyrrolo[1,2-c]imidazol-1-yl)-N-(thiazol-2-yl)acetamide

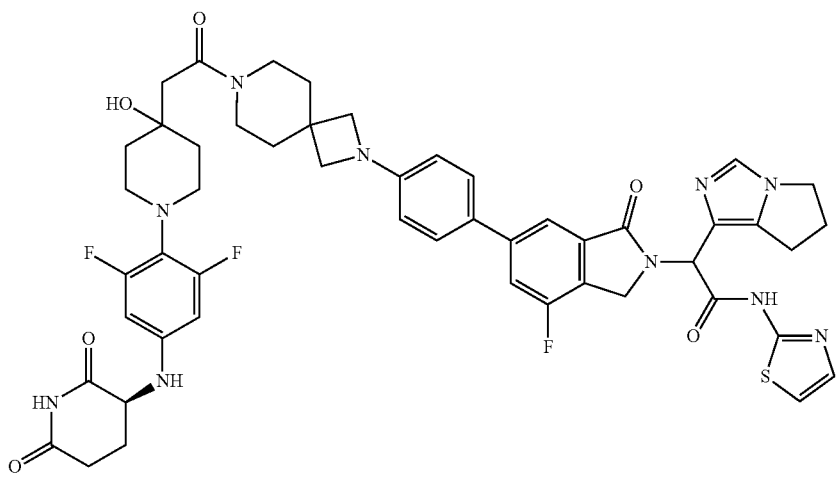

2-(6,7-dihydro-5H-pyrrolo[1,2-c]imidazol-1-yl)-2-(6-(4-(7-(2-(1-(4-(((S)-2,6-dioxopiperidin-3-yl)amino)-2,6-difluorophenyl)-4-hydroxypiperidin-4-yl)acetyl)-2,7-diazaspiro[3.5]nonan-2-yl)phenyl)-4-fluoro-1-oxoisoindolin-2-yl)-N-(thiazol-2-yl)acetamide -continued

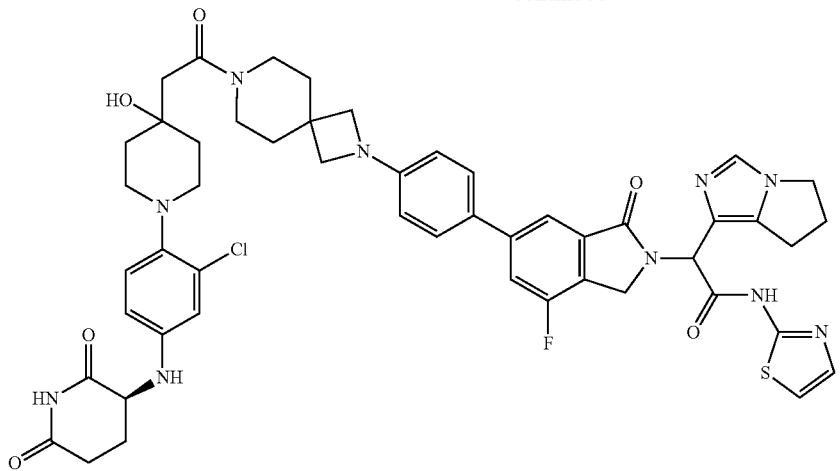

2-(6-(4-(7-(2-(1-(2-chloro-4-(((S)-2,6-dioxopiperidin-3-yl)amino)phenyl)-4-hydroxypiperidin-4-yl)acetyl)-2,7-diazaspiro[3.5]nonan-2-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide

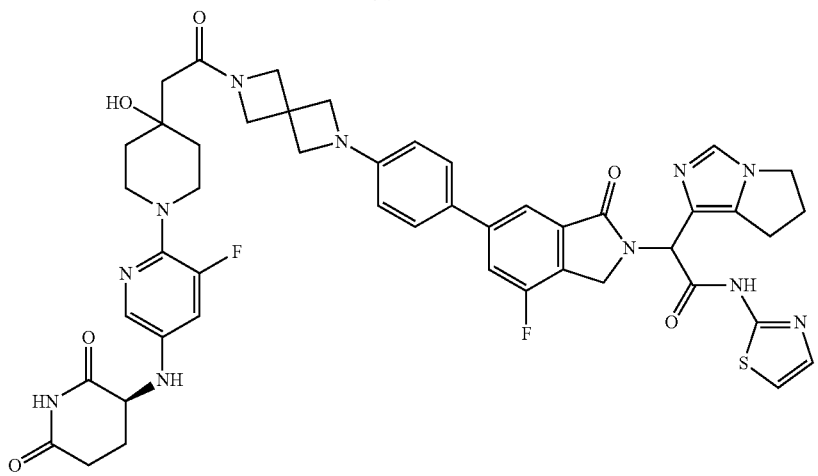

2-(6,7-dihydro-5H-pyrrolo[1,2-c]imidazol-1-yl)-2-(6-(4-(6-(2-(1-(5-(((S)-2,6-dioxopiperidin-3-yl)amino)-3-fluoropyridin-2-yl)-4-hydroxypiperidin-4-yl)acetyl)-2,6-diazaspiro[3.3]heptan-2-yl)phenyl)-4-fluoro-1-osoixoindolin-2-yl)-N-(thiazol-2-yl)acetamide

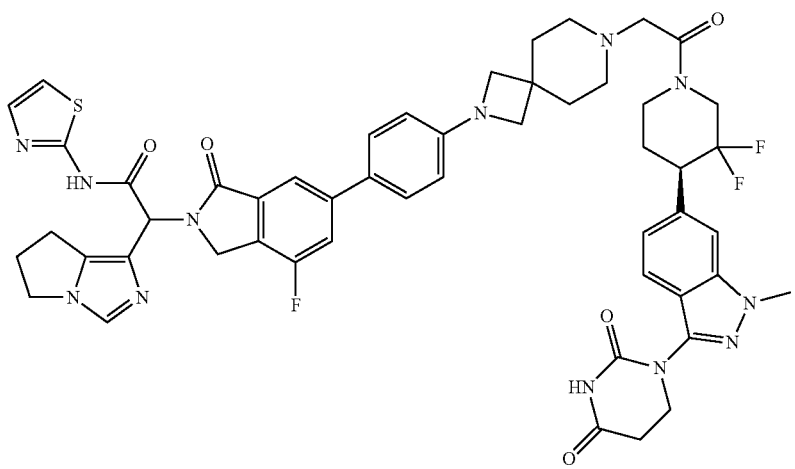

2-(6,7-dihydro-5H-pyrrolo[1,2-c]imidazol-1-yl)-2-(6-(4-(7-(2-((R)-4-(3-(2,4-dioxotetrahydropyrimidin-1(2H)-yl)-1-methyl-1H-indazol-6-yl)-3,3-difluoropiperidin-1-yl)-2-oxoethyl)-2,7-diazaspiro[3.5]nonan-2-yl)phenyl)-4-fluoro-1-oxoisoindolin-2-yl)-N-(thiazol-2-yl)acetamide

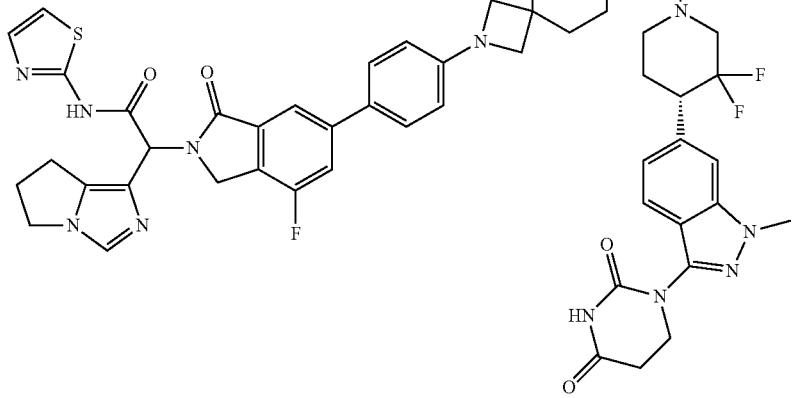

2-(6,7-dihydro-5H-pyrrolo[1,2-c]imidazol-1-yl)-2-(6-(4-(7-(2-((S)-4-(3-(2,4-dioxotetrahydropyrimidin-1(2H)-yl)-1-methyl-1H-indazol-6-yl)-3,3-difluoropiperidin-1-yl)-2-oxoethyl)-2,7-diazaspiro[3.5]nonan-2-yl)phenyl)-4-fluoro-1-oxoisoindolin-2-yl)-N-(thiazol-2-yl)acetamide

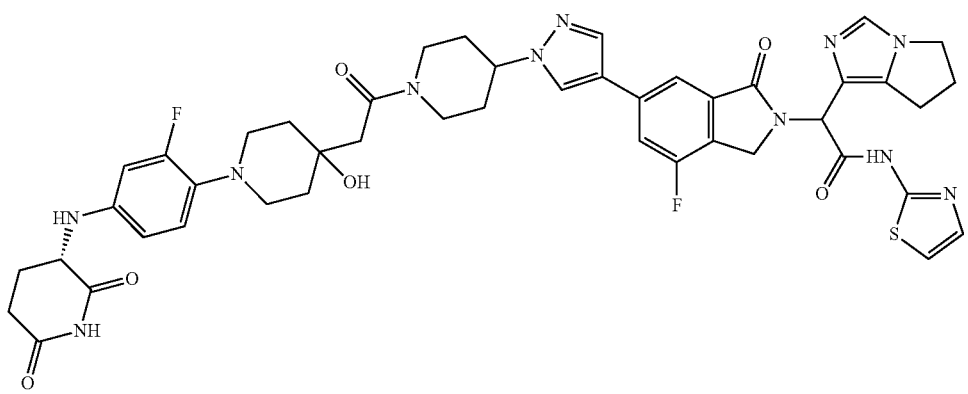

2-(6,7-dihydro-5H-pyrrolo[1,2-c]imidazol-1-yl)-2-(6-(1-(1-(2-(1-(4-(((S)-2,6-dioxopiperidin-3-yl)amino)-2-fluorophenyl)-4-hydroxypiperidin-4-yl)acetyl)piperidin-4-yl)-1H-pyrazol-4-yl)-4-fluoro-1-oxoisoindolin-2-yl)-N-(thiazol-2-yl)acetamide

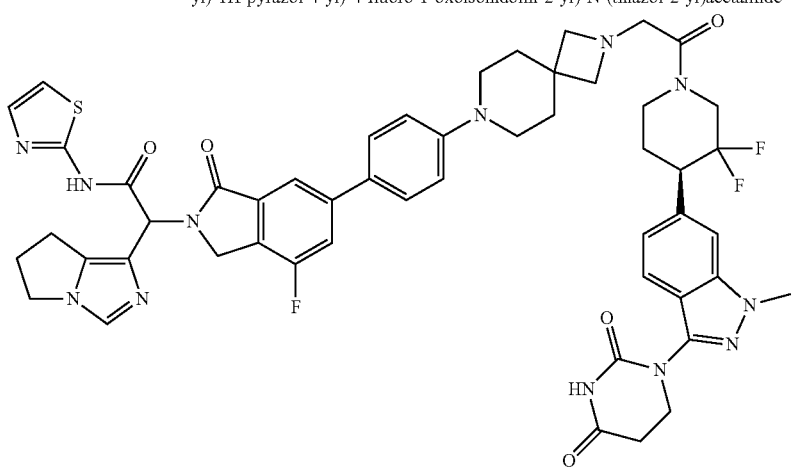

2-(6,7-dihydro-5H-pyrrolo[1,2-c]imidazol-1-yl)-2-(6-(4-(2-(2-((R)-4-(3-(2,4-dioxotetrahydropyrimidin-1(2H)-yl)-1-methyl-1H-indazol-6-yl)-3,3-difluoropiperidin-1-yl)-2-oxoethyl)-2,7-diazaspiro[3.5]nonan-7-yl)phenyl)-4-fluoro-1-oxoisoindolin-2-yl)-N-(thiazol-2-yl)acetamide

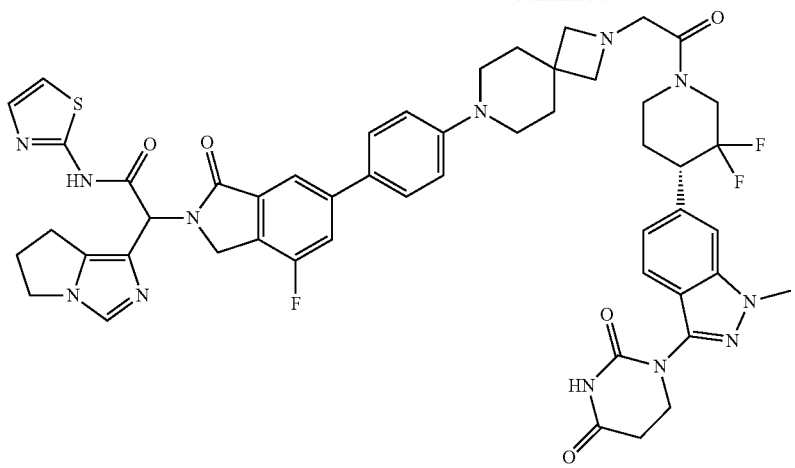

2-(6,7-dihydro-5H-pyrrolo[1,2-c]imidazol-1-yl)-2-(6-(4-(2-(2-((S)-4-(3-(2,4-dioxotetrahydropyrimidin-1(2H)-yl)-1-methyl-1H-indazol-6-yl)-3,3-difluoropiperidin-1-yl)-2-oxoethyl)-2,7-diazaspiro[3.5]nonan-7-yl)phenyl)-4-fluoro-1-oxoisoindolin-2-yl)-N-(thiazol-2-yl)acetamide

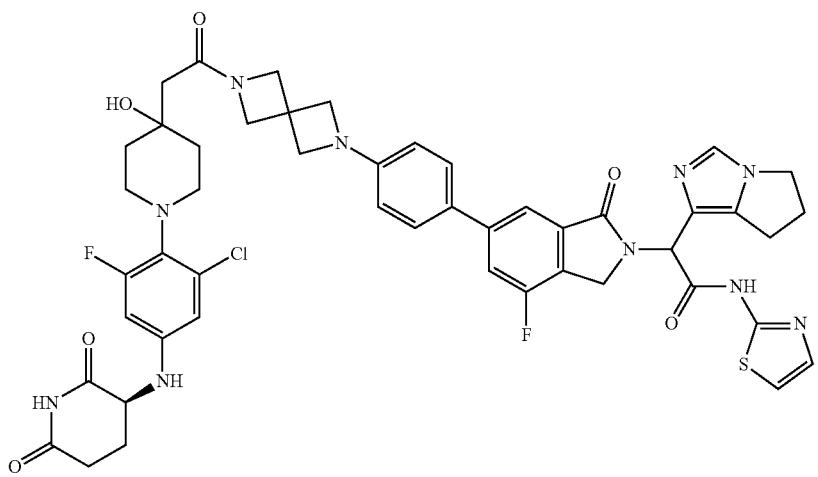

2-(6-(4-(6-(2-(1-(2-chloro-4-(((S)-2,6-dioxopiperidin-3-yl)amino)-6-fluorophenyl)-4-hydroxypiperidin-4-yl)acetyl)-2,6-diazaspiro[3.3]heptan-2-yl)phenyl)-4-fluoro-1-oxoisoindolin-2-yl)-2-(6,7-dihydro-5H-pyrrolo[1,2-c]imidazol-1-yl)-N-(thiazol-2-yl-acetamide

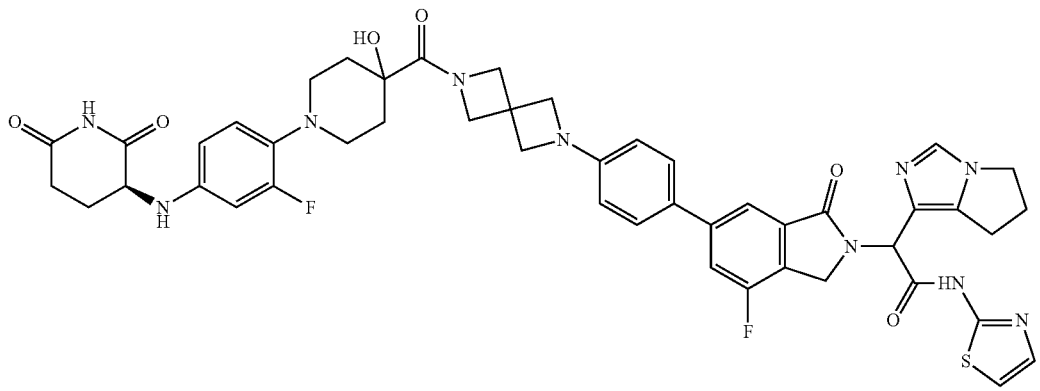

2-(6,7-dihydro-5H-pyrrolo[1,2-c]imidazol-1-yl)-2-(6-(4-(6-(1-(4-(((S)-2,6-dioxopiperidin-3-yl)amino)-2-fluorophenyl)-4-hydroxypiperidine-4-carbonyl)-2,6-diazaspiro[3.3]heptan-2-yl)phenyl)-4-fluoro-1-oxoisoindolin-2-yl)-N-(thiazol-2-yl)acetamide -continued

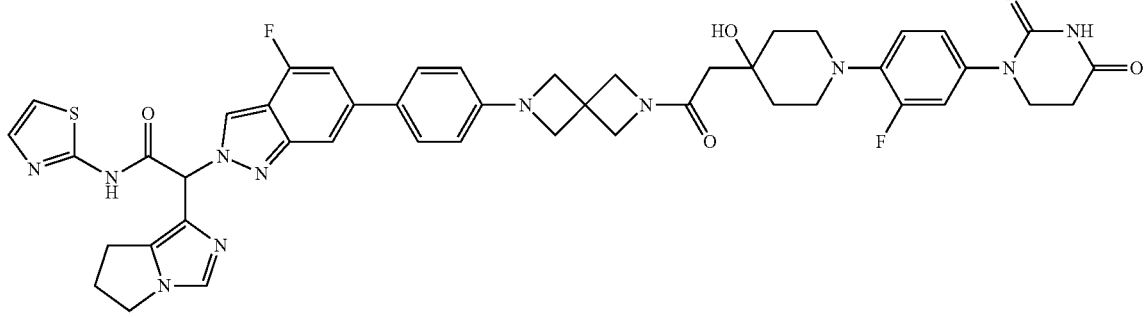

2-(6,7-dihydro-5H-pyrrolo[1,2-c]imidazol-1-yl)-2-[6-[4-[2-[2-[1-[4-(2,4-dioxohexahydropyrimidin-1-yl)-2-fluoro-phenyl]-4-hydroxy-4-piperidyl]acetyl]2,6-diazaspiro[3.3]heptan-6-yp]phenyl]-4-fluoro-indazol-2-yl]-N-thiazol-2-yl-acetamide

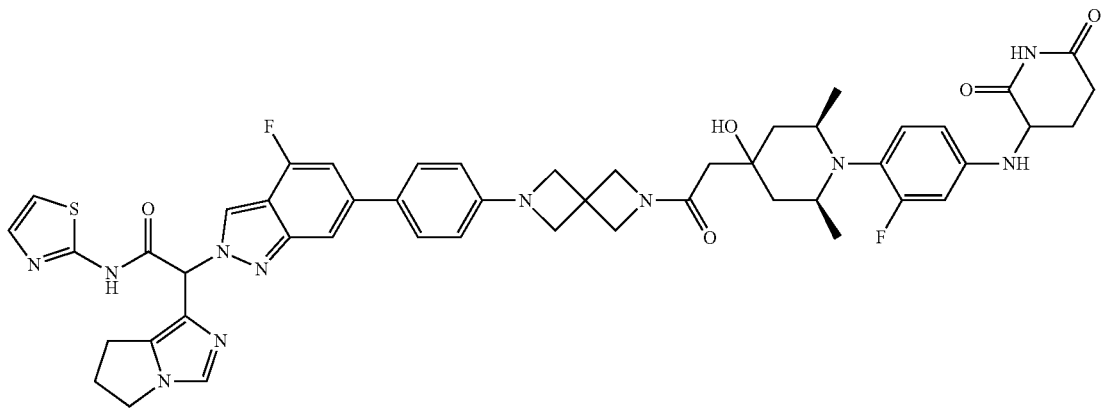

2-(6,7-dihydro-5H-pyrrolo[1,2-c]imidazol-1-yl)-2-[6-[4-[2-[2-[(2s,6r)-1-[4-[(2,6-dioxo-3-piperidyl)amino]-2-fluoro-phenyl]-4-hydroxy-2,6-dimethyl-4-piperidyl]acetyl]-2,6-diazaspiro[3.3]heptan-6-yl]phenyl]-4-fluoro-indazol-2-yl]-N-thiazol-2-yl-acetamide

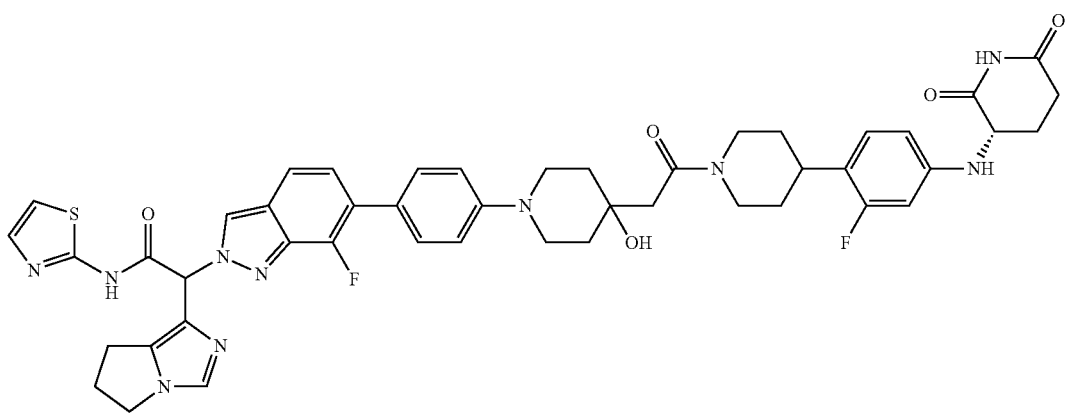

2-(6,7-dihydro-5H-pyrrolo[1,2-c]imidazol-1-yl)-2-[6-[4-[4-[2-[4-[4-[[(3S)-2,6-dioxo-3-piperidyl]amino]-2-fluoro-phenyl]-1-piperidyl]-2-oxo-ethyl]-4-hydroxy-1-piperidyl]phenyl]-7-fluoro-indazol-2-yl]-N-thiazol-2-yl-acetamide -continued

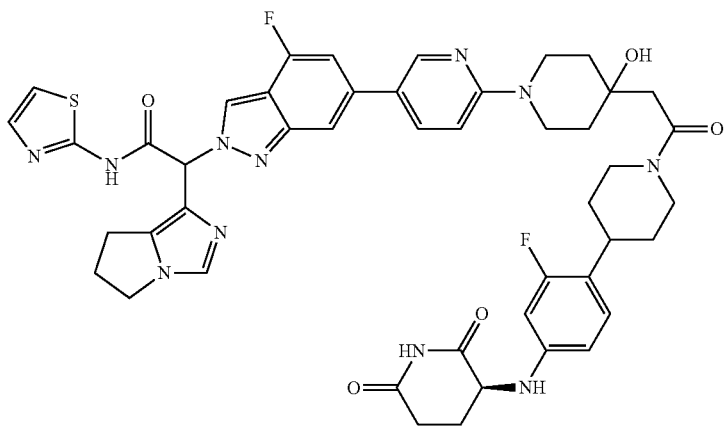

2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]-2-oxo-ethyl]-4-hydroxy-1-piperidyl]-3-pyridyl]-4-fluoro-indazol-2-yl]-N-thiazol-2-yl-acetamide

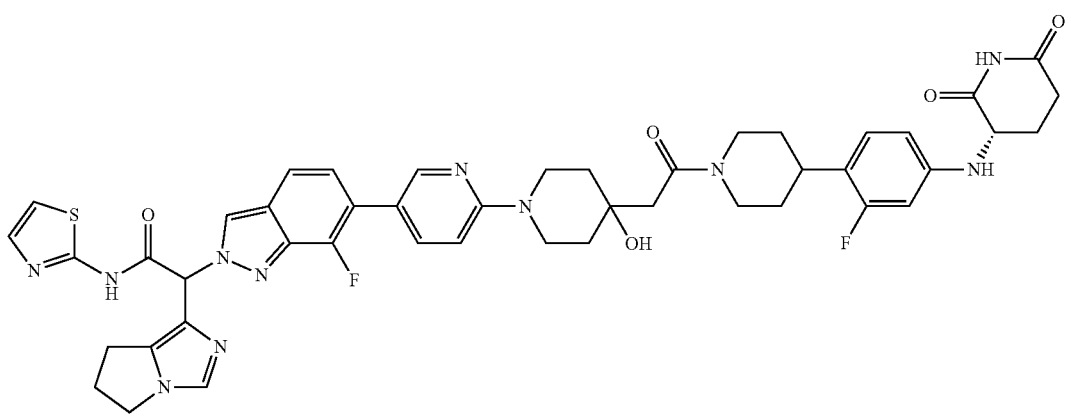

2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]-2-oxo-ethyl]-4-hydroxy-1-piperidyl]-3-pyridyl]-7-fluoro-indazol-2-yl]-N-thiazol-2-yl-acetamide

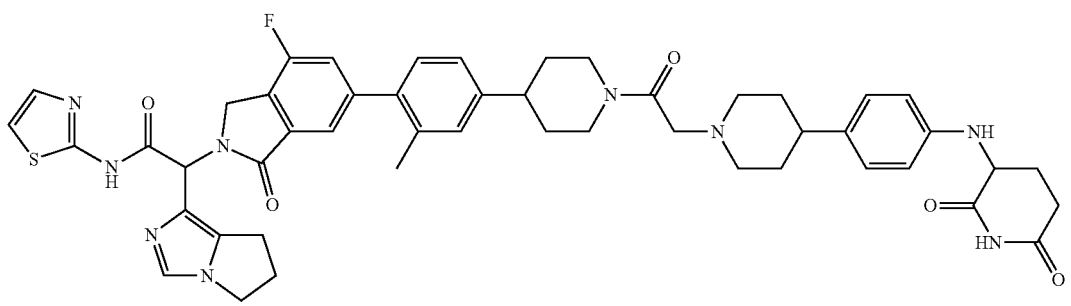

2-(6,7-dihydro-5H-pyrrolo[1,2-c]imidazol-1-yl)-2-[6-[4-[1-[2-[4-[4-[(2,6-dioxo-3-piperidyl)amino]phenyl]-1-piperidyl]acetyl]-4-piperidyl]-2-methyl-phenyl]-4-fluoro-1-oxo-isoindolin-2-yl]-N-thiazol-2-yl-acetamide

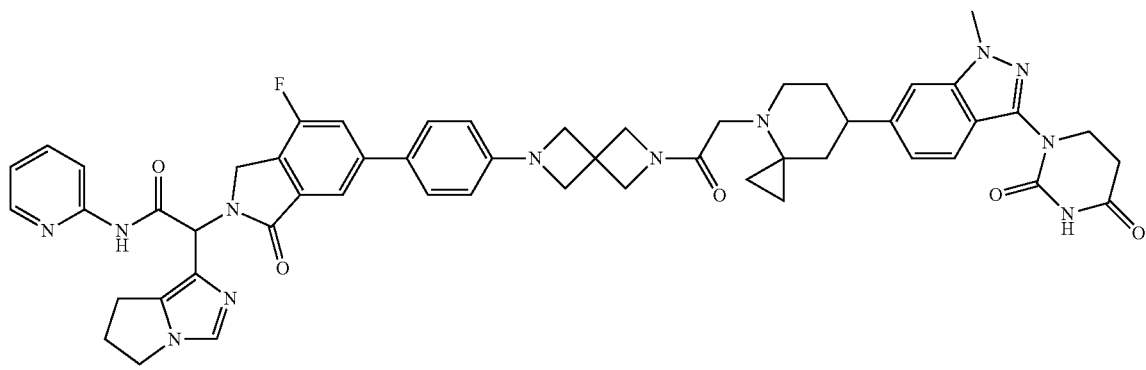

2-(6,7-dihydro-5H-pyrrolo[1,2-c]imidazol-1-yl)-2-[6-[4-[2-[2-[7-[3-[(2,4-dioxohexahydropyrimidin-1-yl)-1-methyl-indazol-6-yl]-4-azaspiro[2.5]octan-4-yl]acetyl]-2,6-diazaspiro[3.3]heptan-6-yl]phenyl]-4-fluoro-1-oxo-isoindolin-2-yl]-N-(2-pyridyl)acetamide

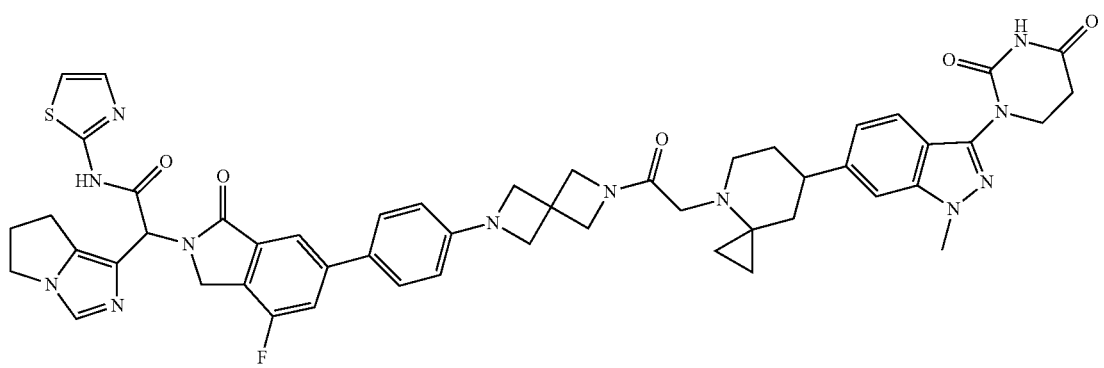

2-(6,7-dihydro-5H-pyrrolo[1,2-c]imidazol-1-yl)-2-[6-[4-[2-[2-[7-[3-(2,4-dioxohexahydropyrimidin-1-yl)-1-methyl-indazol-6-yl]-4-azaspiro[2.5]octan-4-yl]acetyl]-2,6-diazaspiro[3.3]heptan-6-yl]phenyl]-4-fluoro-1-oxo-isoindolin-2-yl]-N-thiazol-2-yl-acetamide

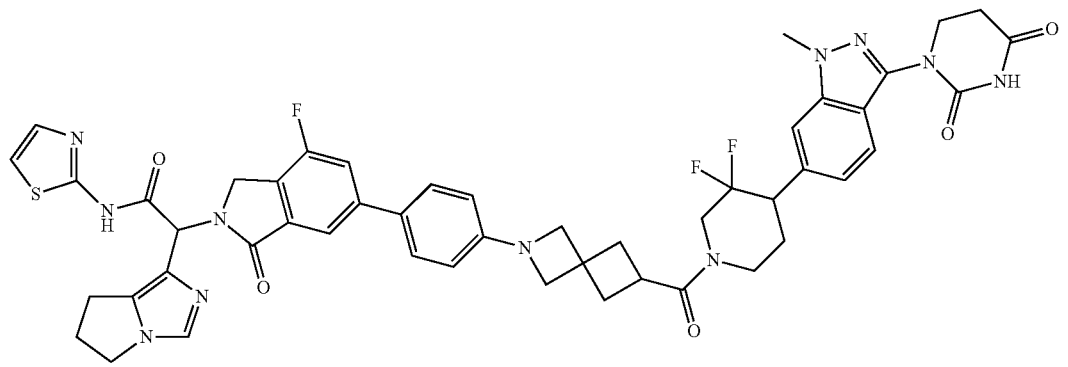

2-(6,7-dihydro-5H-pyrrolo[1,2-c]imidazol-1-yl)-2-[6-[4-[6-[4-[3-(2,4-dioxohexahydropyrimidin-1-yl)-1-methyl-indazol-6-yl]-3,3-difluoro-piperidine-1-carbonyl]-2-azaspiro[3.3]heptan-2-yl]phenyl]-4-fluoro-1-oxo-isoindolin-2-yl]-N-thiazol-2-yl-acetamide

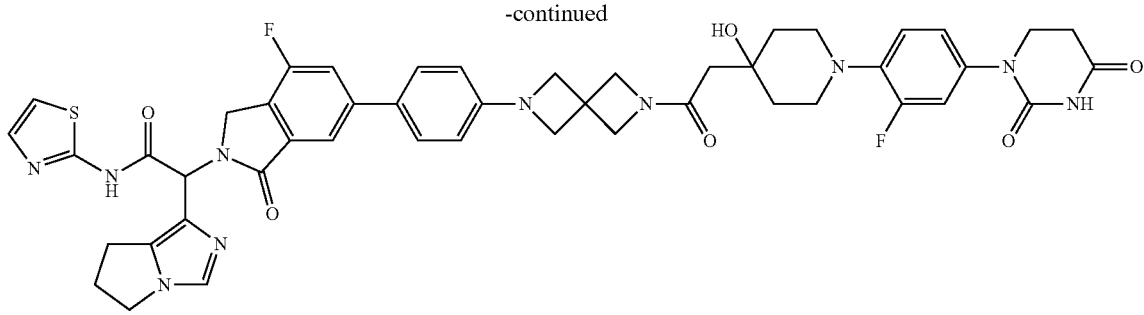

2-(6,7-dihydro-5H-pyrrolo[1,2-c]imidazol-1-yl)-2-[6-[4-[2-[2-[1-[4-(2,4-dioxohexahydropyrimidin-1-yl)-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide

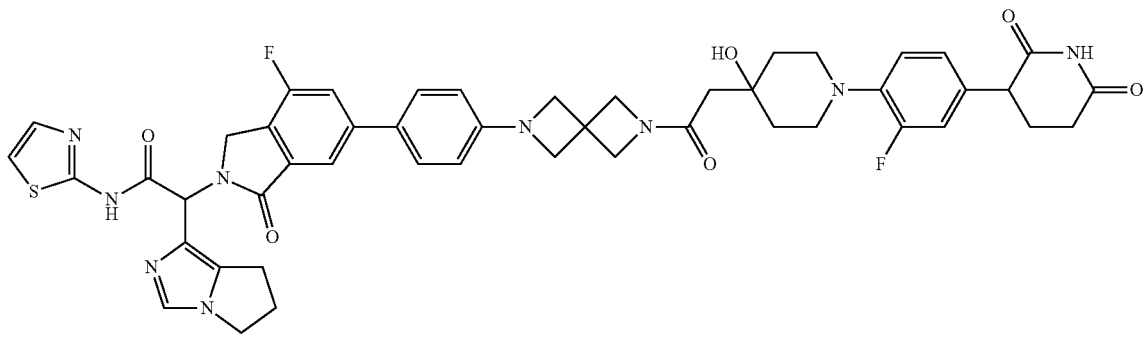

2-(6,7-dihydro-5H-pyrrolo[1,2-c]imidazol-1-yl)-2-(6-(4-(6-(2-(1-(4-(2,6-dioxopiperidin-3-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide

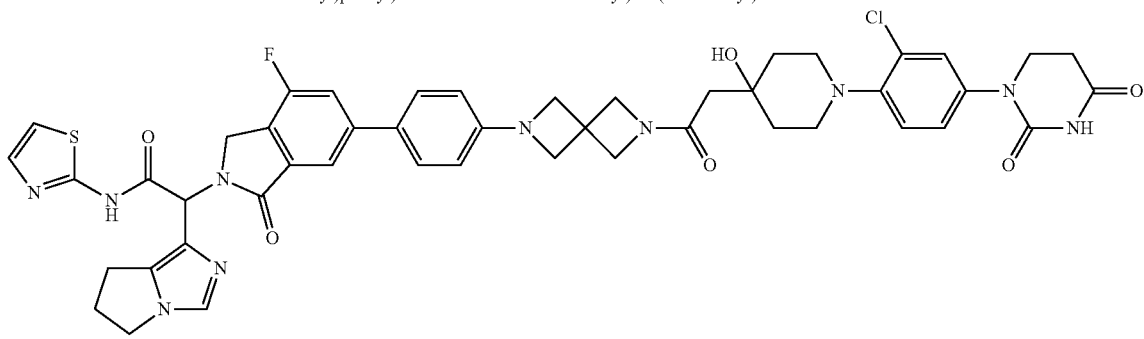

2-[6-[4-[2-[2-[1-[2-chloro-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

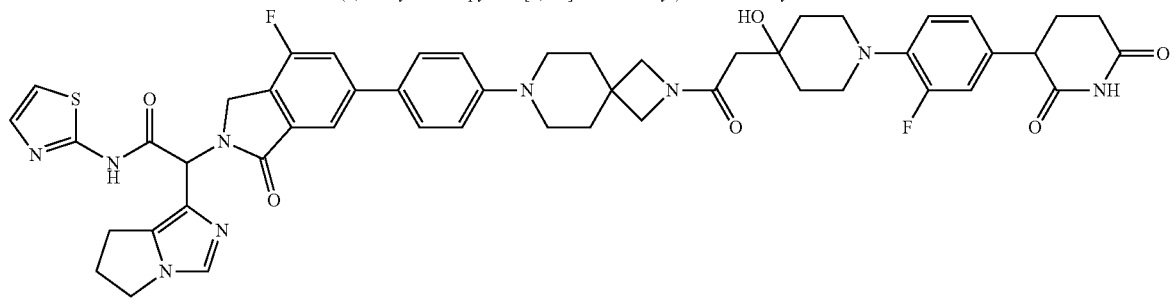

2-(6,7-dihydro-5H-pyrrolo[1,2-c]imidazol-1-yl)-2-[6-[4-[2-[2-[1-[4-(2,6-dioxo-3-piperidyl)-2-fluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide

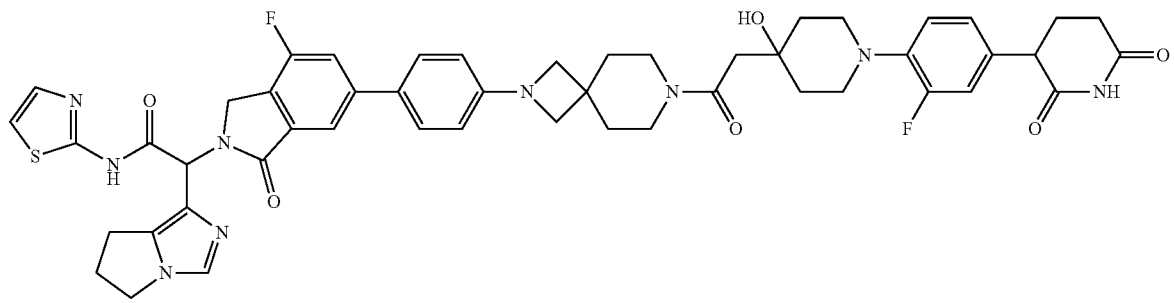

2-(6,7-dihydro-5H-pyrrolo[1,2-c]imidazol-1-yl)-2-[6-[4-[7-[2-[1-[4-(2,6-dioxo-3-piperidyl)-2-fluoro-phenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide

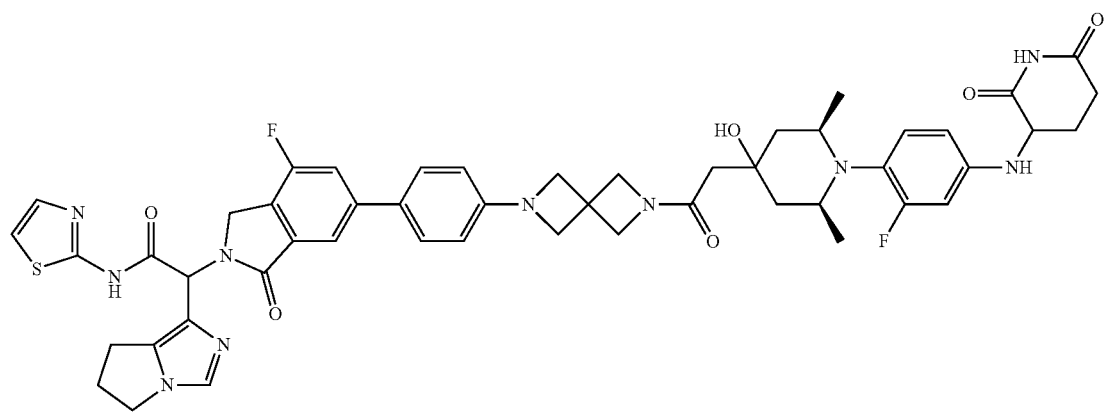

2-(6,7-dihydro-5H-pyrrolo[1,2-c]imidazol-1-yl)-2-[6-[4-[2-[2-[(2s,6r)-1-[4-[(2,6-dioxo-3-piperidyl)amino]-2-fluoro-phenyl]-4-hydroxy-2,6-dimethyl-4-piperidyl]acetyl]-2,6-diazaspiro[3.3]heptan-6-yl]phenyl]-4-fluoro-1-oxo-isoindolin-2-yl]-N-thiazol-2-yl-acetamide

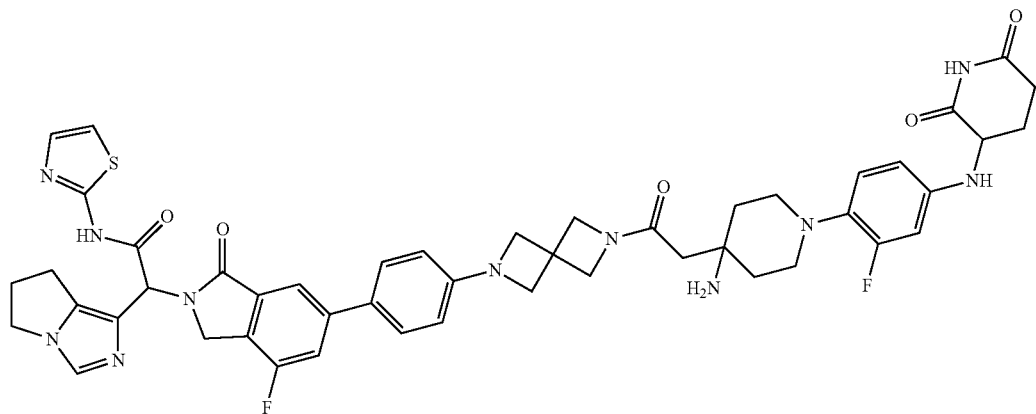

2-[6-[4-[2-[2-[4-amino-1-[4-[(2,6-dioxo-3-piperidyl)amino]-2-fluoro-phenyl]-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide 175 176

-continued

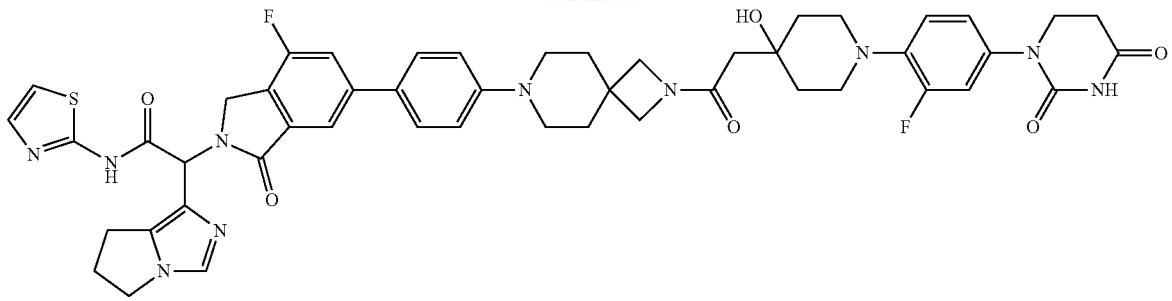

2-(6,7-dihydro-5H-pyrrolo[1,2-c]imidazol-1-yl)-2-[6-[4-[2-[2-[1-[4-[(2,4-dioxohexahydropyrimidin-1-yl)-2-fluoro-phenyl]-4-hydroxy-piperidyl]acetyl]-2,7-diazaspiro[3.5]nonan-7-yl]phenyl]-4-fluoro-1-oxo-isoindolin-2-yl]-N-thiazol-2-yl-acetamide Isomer A1

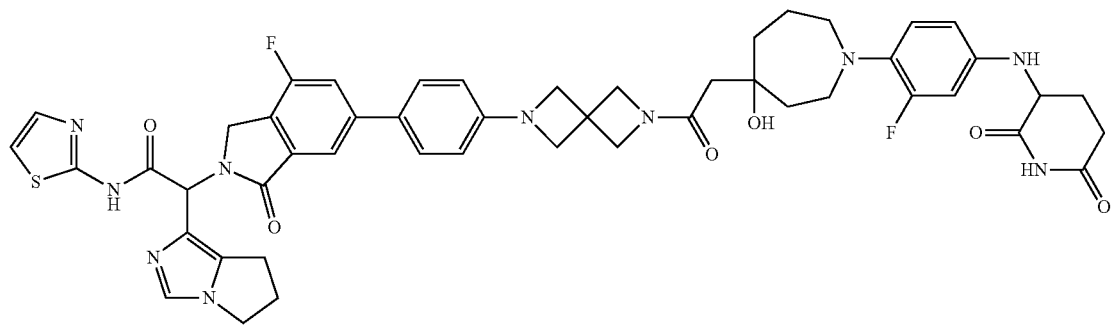

2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, isomer A1

Isomer A2

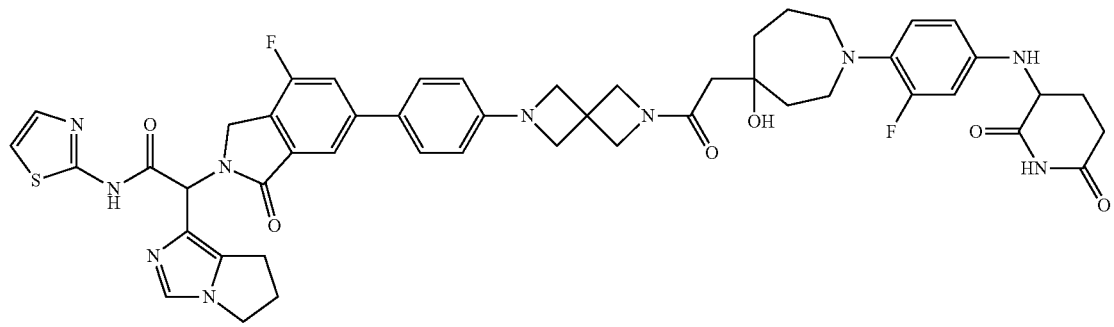

2-(6,7-dihydro-5H-pyrrolo[1,2-c]imidazol-1-yl)-2-(6-(4-(6-(2-(1-(4-((2,6-dioxopiperidin-3-yl)amino)-2-fluorophenyl)-4-hydroxyazepan-4-yl)acetyl)-2,6-diazaspiro[3.3]heptan-2-yl)phenyl)-4-fluoro-1-oxoisoindolin-2-yl)-N-(thiazol-2-yl)acetamide, isomer A2

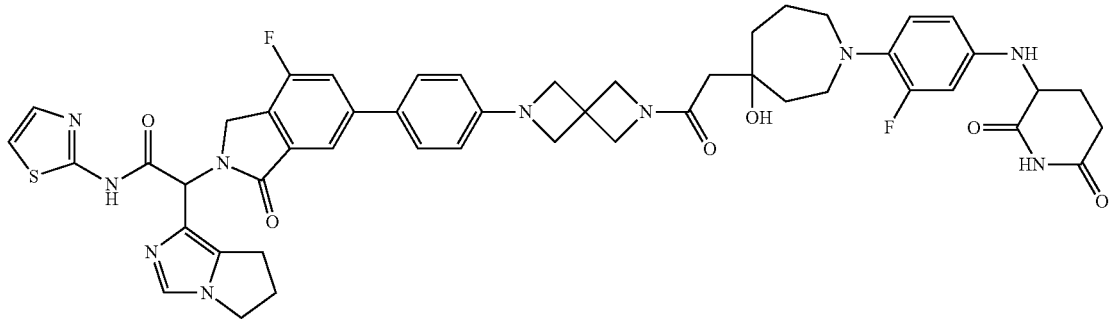

2-(6,7-dihydro-5H-pyrrolo[1,2-c]imidazol-1-yl)-2-(6-(4-(6-(2-(1-(4-((2,6-dioxopiperidin-3-yl)amino)-2-fluorophenyl)-4-hydroxyazepan-4-yl)acetyl)-2,6-diazaspiro[3.3]heptan-2-yl)phenyl)-4-fluoro-1-oxoisoindolin-2-yl)-N-(thiazol-2-yl)acetamide, isomer B1

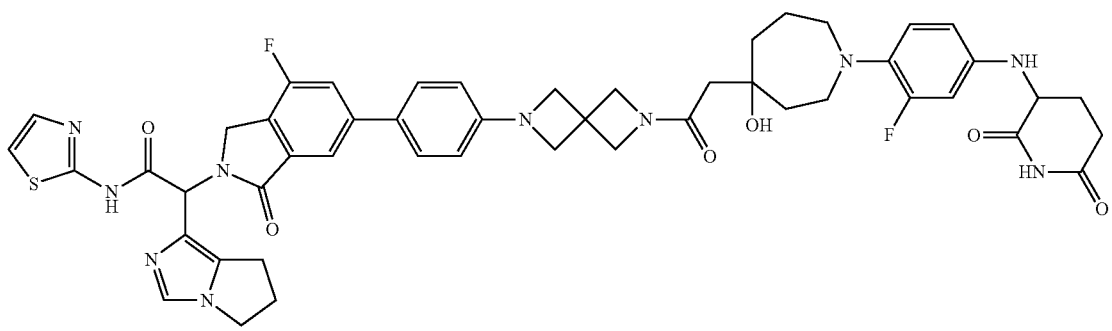

2-(6,7-dihydro-5H-pyrrolo[1,2-c]imidazol-1-yl)-2-(6-(4-(6-(2-(1-(4-((2,6-dioxopiperidin-3-yl)amino)-2-fluorophenyl)-4-hydroxyazepan-4-yl)acetyl)-2,6-diazaspiro[3.3]heptan-2-yl)phenyl)-4-fluoro-1-oxoisoindolin-2-yl)-N-(thiazol-2-yl)acetamide, isomer B2

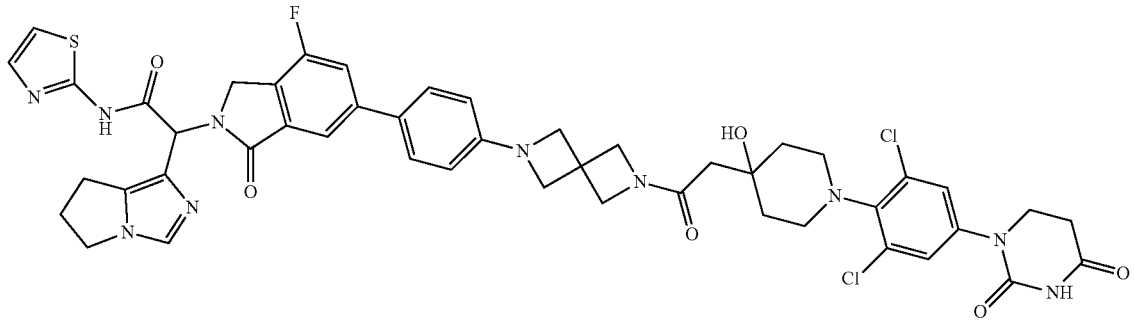

2-(6,7-dihydro-5H-pyrrolo[1,2-c]imidazol-1-yl)-2-[6-[4-[2-[2-[1-[4-(2,4-dioxohexahydropyrimidin-1-yl)-2-(trifluoromethyl)phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide

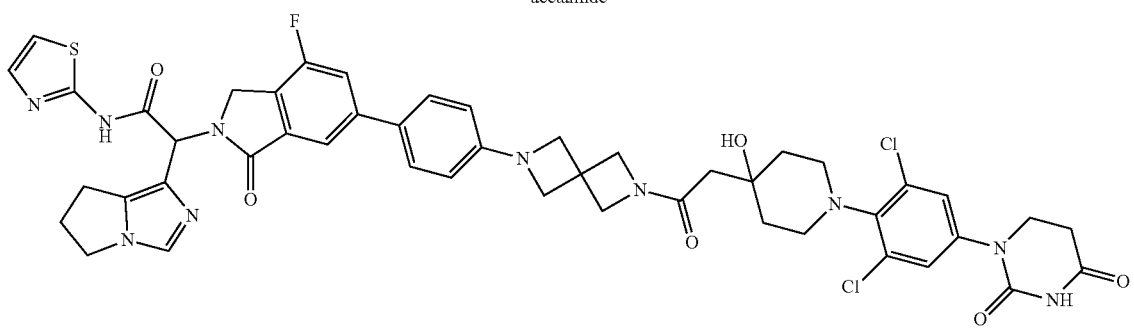

2-[6-[4-[2-[2-[1-[2,6-dichloro-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide -continued

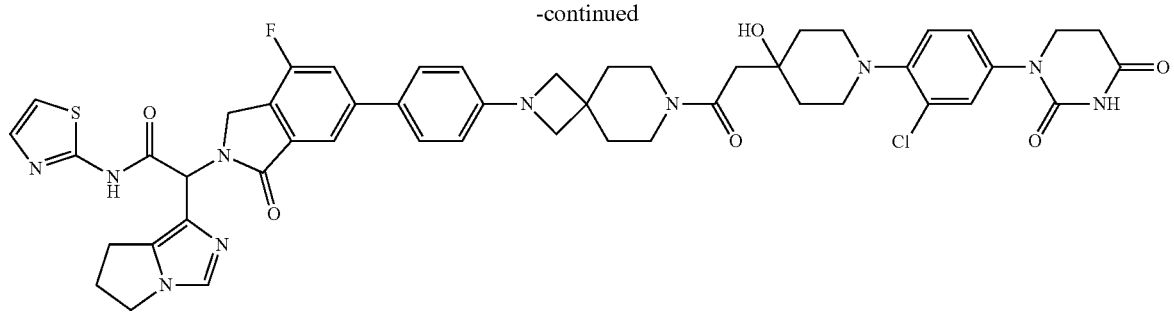

2-[6-[4-[7-[2-[1-[2-chloro-4-(2,4-dioxohexahydropyrimidin-1-yl)phenyl]-4-hydroxy-4-piperidyl]acetyl]-2,7-diazaspiro[3.5]nonan-2-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

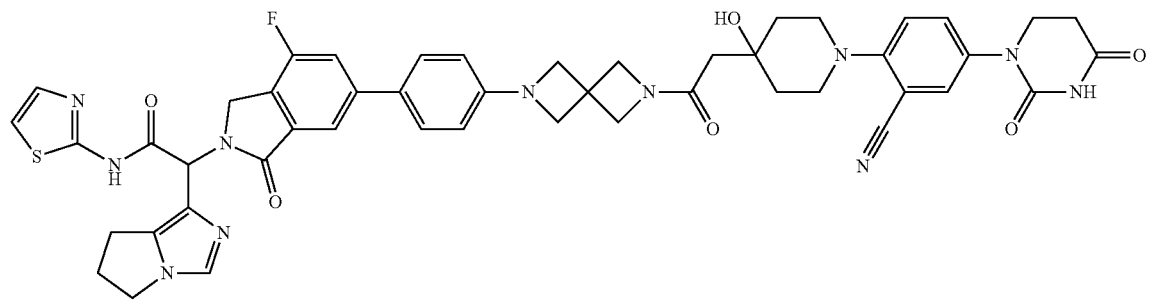

2-[6-[4-[2-[2-[1-[2-cyano-4-(2,4-dioxohexahydropyrimidin-1-yl)phenyl]-4-hydroxy-4-piperidyl]acetyl]-2,6-diazaspiro[3.3]nonan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

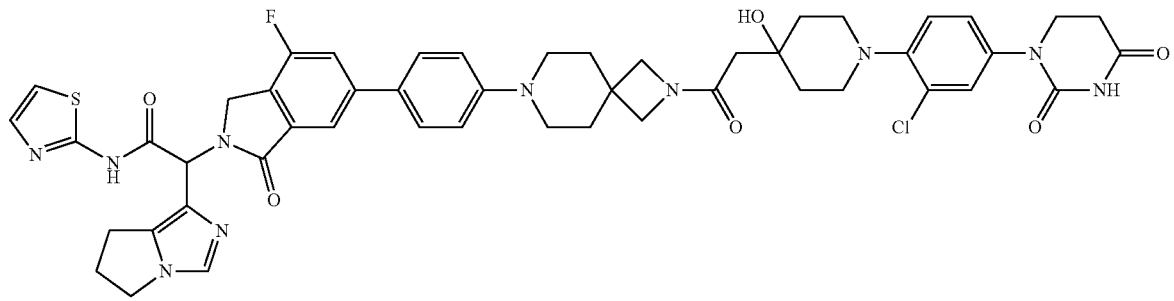

2-[6-[4-[2-[2-[1-[2-chloro-4-(2,4-dioxohexahydropyrimidin-1-yl)phenyl]-4-hydroxy-4-piperidyl]acetyl]-2,7-diazaspiro[3.5]nonan-7-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide Isomer 1

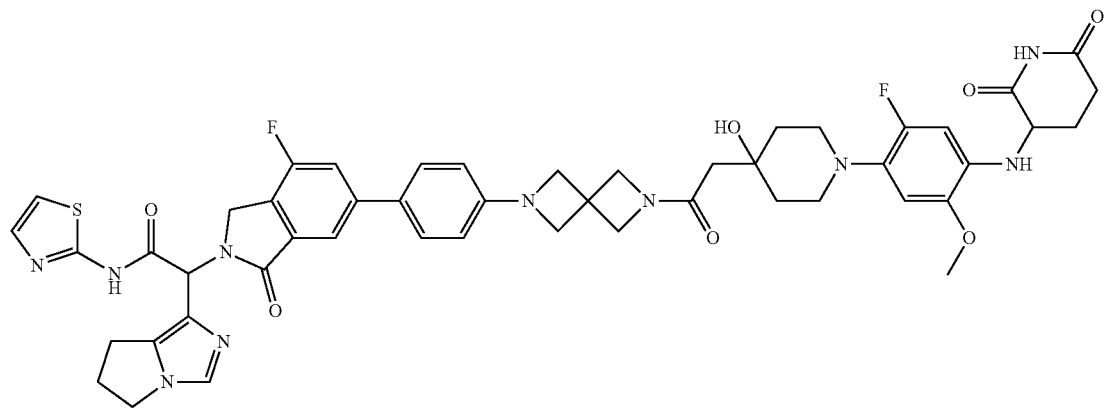

2-(6,7-dihydro-5H-pyrrolo[1,2-c]imidazol-1-yl)-2-[6-[4-[2-[2-[1-[4-[[2,6-dioxo-3-piperidyl]amino]-2-fluoro-5-methoxy-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1 or a pharmaceutically acceptable salt thereof.

E99: In certain embodiments the invention is a compound of any one of embodiments 1-98, or a pharmaceutically acceptable salt thereof, optionally in a pharmaceutical composition, for use as a therapeutically active substance.

E100: In certain embodiments the invention is a compound of any one of embodiments 1-98, or a pharmaceutically acceptable salt thereof, optionally in a pharmaceutical composition, for the use in the therapeutic and/or prophylactic treatment of cancer.

E101: In certain embodiments the invention is a method of treating a patient with an EGFR mediated disorder, comprising administering a compound of any one of embodiments 1-98, or a pharmaceutically acceptable salt thereof, optionally in a pharmaceutical composition.

E102: The method of embodiment 101 wherein the patient is a human.

E103: The method of embodiment 101 or 102, wherein the EGFR mediated disorder is a cancer, tumor, or abnormal cellular proliferation.

E104: The method of embodiment 103, wherein the EGFR mediated disorder is a cancer or a tumor.

E105: The method of embodiment 103, wherein the EGFR mediated disorder is an abnormal cellular proliferation.

E106: The method of embodiment 104, wherein the cancer is lung cancer.

E107: The method of embodiment 106, wherein the lung cancer is non-small cell lung cancer.

E108: The method of any one of embodiments 103-107, wherein the cancer, tumor, or abnormal cellular proliferation has an EGFR protein with at least one mutation.

E109: The method of any one of embodiments 103-108, wherein the cancer, tumor, or abnormal cellular proliferation has an EGFR protein with the L858R mutation.

E110: The method of any one of embodiments 103-109, wherein the cancer, tumor, or abnormal cellular proliferation has an EGFR protein with the T790M mutation.

E111: The method of any one of embodiments 103-110, wherein the cancer, tumor, or abnormal cellular proliferation has an EGFR protein with the C797S mutation.

E112: The method of any one of embodiments 103-111, wherein the cancer, tumor, or abnormal cellular proliferation has an EGFR protein with the L792H mutation.

E113: The method of any one of embodiments 103-112, wherein the cancer, tumor, or abnormal cellular proliferation has an EGFR protein with the L718Q mutation.

E114: The method of any one of embodiments 103-108, wherein the cancer, tumor, or abnormal cellular proliferation has an EGFR protein with the T790M/L858R mutation.

E115: The method of any one of embodiments 103-108, wherein the cancer, tumor, or abnormal cellular proliferation has an EGFR protein with the T790M/L858R/C797S mutation.

E116: The method of any one of embodiments 103-108, wherein the cancer, tumor, or abnormal cellular proliferation has an EGFR protein with the L858R/C797S mutation.

E117: The method of any one of embodiments 101-116, wherein an additional EGFR inhibitor is administered.

E118: The method of embodiment 117, wherein the additional EGFR inhibitor is a tyrosine kinase inhibitor.

E119: The method of embodiment 118, wherein the additional EGFR inhibitor is osimertinib.

E120: The method of embodiment 118, wherein the additional EGFR inhibitor is rociletinib.

E121: The method of embodiment 118, wherein the additional EGFR inhibitor is avitinib.

E122: The method of embodiment 118, wherein the additional EGFR inhibitor is lazertinib.

E123: The method of embodiment 118, wherein the additional EGFR inhibitor is nazartinib.

E124: The method of embodiment 117, wherein the additional EGFR inhibitor is an antibody to a mutated form of EGFR.

E125: The method of embodiment 124, wherein the additional EGFR inhibitor is cetuximab.

E126: The method of embodiment 124, wherein the additional EGFR inhibitor is panitumab.

E127: The method of embodiment 124, wherein the additional EGFR inhibitor is necitumab.

E128: The method of any one of embodiments 101-127, wherein a MET inhibitor is also administered.

E129: The method of any one of embodiments 101-128, wherein the patient receives an additional chemotherapeutic agent.

E130: In certain embodiments the invention is a compound of any one of embodiments 1-98, or a pharmaceutically acceptable salt thereof in the manufacture of a medicament to treat an EGFR mediated disorder in a patient.

E131: The use of embodiment 130, wherein the patient is a human.

E132: The use of embodiment 130 or 131, wherein the EGFR mediated disorder is a cancer, tumor, or abnormal cellular proliferation.

E133: The use of embodiment 132, wherein the EGFR mediated disorder is a cancer or a tumor.

E134: The use of embodiment 132, wherein the EGFR mediated disorder is an abnormal cellular proliferation.

E135: The use of embodiment 132, wherein the cancer is lung cancer.

E136: The use of embodiment 135, wherein the lung cancer is non-small cell lung cancer.

E137: The use of any one of embodiments 132-136, wherein the cancer, tumor, or abnormal cellular proliferation has an EGFR protein with at least one mutation.

E138: The use of any one of embodiments 132-137, wherein the cancer, tumor, or abnormal cellular proliferation has an EGFR protein with the L858R mutation.

E139: The use of any one of embodiments 132-138, wherein the cancer, tumor, or abnormal cellular proliferation has an EGFR protein with the T790M mutation.

E140: The use of any one of embodiments 132-139, wherein the cancer, tumor, or abnormal cellular proliferation has an EGFR protein with the C797S mutation.

E141: The use of any one of embodiments 132-140, wherein the cancer, tumor, or abnormal cellular proliferation has an EGFR protein with the L792H mutation.

E142: The use of any one of embodiments 132-141, wherein the cancer, tumor, or abnormal cellular proliferation has an EGFR protein with the L718Q mutation.

E143: The use of any one of embodiments 132-136, wherein the cancer, tumor, or abnormal cellular proliferation has an EGFR protein with the T790M/L858R mutation.

E144: The use of any one of embodiments 132-136, wherein the cancer, tumor, or abnormal cellular proliferation has an EGFR protein with the T790M/L858R/C797S mutation.

E145: The use of any one of embodiments 132-136, wherein the cancer, tumor, or abnormal cellular proliferation has an EGFR protein with the L858R/C797S mutation.
E146: The use of any one of embodiments 130-145, wherein an additional EGFR inhibitor is administered.
E147: The use of embodiment 146, wherein the additional EGFR inhibitor is a tyrosine kinase inhibitor.
E148: The use of embodiment 147, wherein the additional EGFR inhibitor is osimertinib.
E149: The use of embodiment 147, wherein the additional EGFR inhibitor is rociletinib.
E150: The use of embodiment 147, wherein the additional EGFR inhibitor is avitinib.
E151: The use of embodiment 147, wherein the additional EGFR inhibitor is lazertinib.
E152: The use of embodiment 147, wherein the additional EGFR inhibitor is nazartinib.
E153: The use of embodiment 146, wherein the additional EGFR inhibitor is an antibody to a mutated form of EGFR.
E154: The use of embodiment 153, wherein the additional EGFR inhibitor is cetuximab.
E155: The use of embodiment 153, wherein the additional EGFR inhibitor is panitumab.
E156: The use of embodiment 153, wherein the additional EGFR inhibitor is necitumab.
E157: The use of any one of embodiments 130-156, wherein a MET inhibitor is also administered.
E158: The use of any one of embodiments 130-157, wherein the patient receives an additional chemotherapeutic agent.
E159: In certain embodiments the invention is a compound of any one of embodiments 1-98, or a pharmaceutically acceptable salt thereof, optionally in a pharmaceutical composition, for the use in the treatment of an EGFR mediated disorder in a patient.
E160: The compound of embodiment 159, wherein the patient is a human.
E161: The compound of embodiment 159 or 160, wherein the EGFR mediated disorder is a cancer, tumor, or abnormal cellular proliferation.
E162: The compound of embodiment 161, wherein the EGFR mediated disorder is a cancer or a tumor.
E163: The compound of embodiment 161, wherein the EGFR mediated disorder is an abnormal cellular proliferation.
E164: The compound of embodiment 162, wherein the cancer is lung cancer.
E165: The compound of embodiment 164, wherein the lung cancer is non-small cell lung cancer.
E166: The compound of any one of embodiments 161-165, wherein the cancer, tumor, or abnormal cellular proliferation has an EGFR protein with at least one mutation.
E167: The compound of any one of embodiments 161-166, wherein the cancer, tumor, or abnormal cellular proliferation has an EGFR protein with the L858R mutation.
E168: The compound of any one of embodiments 161-167, wherein the cancer, tumor, or abnormal cellular proliferation has an EGFR protein with the T790M mutation.
E169: The compound of any one of embodiments 161-168, wherein the cancer, tumor, or abnormal cellular proliferation has an EGFR protein with the C797S mutation.
E170: The compound of any one of embodiments 161-169, wherein the cancer, tumor, or abnormal cellular proliferation has an EGFR protein with the L792H mutation.
E171: The compound of any one of embodiments 161-170, wherein the cancer, tumor, or abnormal cellular proliferation has an EGFR protein with the L718Q mutation.
E172: The compound of any one of embodiments 161-166, wherein the cancer, tumor, or abnormal cellular proliferation has an EGFR protein with the T790M/L858R mutation.
E173: The compound of any one of embodiments 161-166, wherein the cancer, tumor, or abnormal cellular proliferation has an EGFR protein with the T790M/L858R/C797S mutation.
E174: The compound of any one of embodiments 161-166, wherein the cancer, tumor, or abnormal cellular proliferation has an EGFR protein with the L858R/C797S mutation.
E175: The compound of any one of embodiments 159-174, wherein an additional EGFR inhibitor is administered.
E176: The compound of embodiment 175, wherein the additional EGFR inhibitor is a tyrosine kinase inhibitor.
E177: The compound of embodiment 175, wherein the additional EGFR inhibitor is osimertinib.
E178: The compound of embodiment 175, wherein the additional EGFR inhibitor is rociletinib.
E179: The compound of embodiment 175, wherein the additional EGFR inhibitor is avitinib.
E180: The compound of embodiment 175, wherein the additional EGFR inhibitor is lazertinib.
E181: The compound of embodiment 175, wherein the additional EGFR inhibitor is nazartinib E182: The compound of embodiment 174, wherein the additional EGFR inhibitor is an antibody to a mutated form of EGFR.
E183: The compound of embodiment 182, wherein the additional EGFR inhibitor is cetuximab.
E184: The compound of embodiment 182, wherein the additional EGFR inhibitor is panitumab.
E185: The compound of embodiment 182, wherein the additional EGFR inhibitor is necitumab.
E186: The compound of any one of embodiments 159-185, wherein a MET inhibitor is also administered.
E187: The compound of any one of embodiments 159-186, wherein the patient receives an additional chemotherapeutic agent.
E188: In certain embodiments the invention is a compound of any one of embodiments 1-98, or a pharmaceutically acceptable salt thereof, optionally in a pharmaceutical composition, for the use as a medicament in therapeutic and/or prophylactic treatment of a patient with EGFR activating mutations as determined with a Cobas® EGFR Mutation Test v2, suffering from cancer, in particular non-small-cell lung cancer, comprising determining the EGFR activating mutations status in said patient and then administering the compound of any one of embodiments 1-98, or a pharmaceutically acceptable salt thereof, optionally in a pharmaceutical composition to said patient.
E189: In certain embodiments the invention is a pharmaceutical composition comprising a compound of any one of embodiments 1-98 and a pharmaceutically acceptable excipient.

Additional Embodiments of the Present Invention

Chirality Embodiments

The compounds of the present invention may have multiple stereocenters (e.g., chiral carbon atoms) including for example one or more stereocenters in the E3 ligase binding moiety (for example

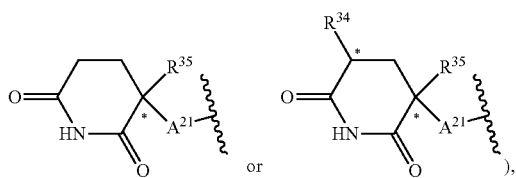

one or more stereocenters in the linker, and/or at least one stereocenter in the EGFR binding ligand moiety of the molecule

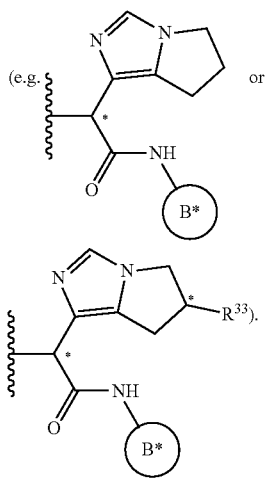

In certain embodiments, the EGFR-degrading compound of the present invention is provided without regard to stereochemistry. In other embodiments, the EGFR-degrading compound may have one or more chiral carbons presented in an enantiomerically enriched (i.e., greater than about 50%, 60%, 70%, 80% or 90% pure) or even substantially pure form (greater than about 95%, 98% or 99% pure) of R and S stereochemistry. In certain aspects, the EGFR-degrading compound has two enantiomerically enriched and/or substantially pure stereocenters. In one sub-aspect of this, the two enantiomerically enriched and/or substantially pure stereocenters are located in the ligase-binding moiety of the compound and the linker; or alternatively there are two in the linker. In another sub-aspect, there are three enantiomerically enriched and/or substantially pure stereocenters, with one in the ligase-binding moiety of the compound and two in the linker. In yet another sub-aspect of this, there are three enantiomerically enriched and/or substantially pure stereocenters, with one in the ligase-binding moiety of the compound and two in the linker. In another aspect, in any of these embodiments, aspects or sub-aspects, in addition, the EGFR binding ligand moiety is enantiomerically enriched or in substantially pure form.

It has been observed that in some embodiments, the chiral carbon in the EGFR binding ligand moiety adjacent to the amide may easily racemize between stereoisomers under the conditions of use, and therefore in certain embodiments, is not considered for purposes of stereochemistry designation.

In certain embodiments one stereocenter is in the R configuration and any others present are either enantiomerically enriched or substantially pure. In certain embodiments one stereocenter is in the S configuration and any others present are either enantiomerically enriched or substantially pure.

In certain embodiments one stereocenter is in the R configuration and any others present are without regard to stereochemistry, enantiomerically enriched or substantially pure. In certain embodiments one stereocenter is in the S configuration and any others present are without regard to stereochemistry, enantiomerically enriched or substantially pure.

In certain embodiments there is one stereocenter in the E3 ligase binding moiety (disregarding the stereocenter in the EGFR binding ligand moiety) and it is enantiomerically enriched or substantially pure in the R-configuration, as indicated below. In another embodiment there is one stereocenter in the E3 ligase binding moiety (disregarding the stereocenter in the EGFR binding ligand moiety) and it enantiomerically enriched or substantially pure in the S-configuration, as indicated below.

In certain embodiments

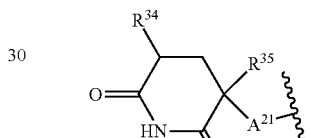

is

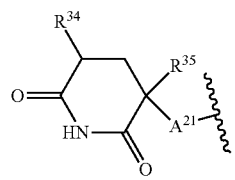

wherein $R^{34}$ is hydrogen.

In certain embodiments

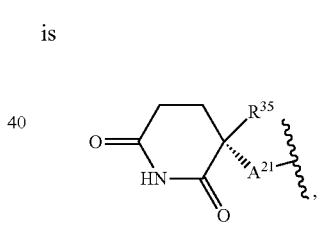

is

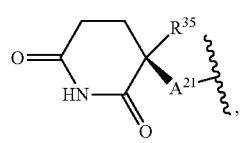

wherein $R^{34}$ is hydrogen.

In certain embodiments

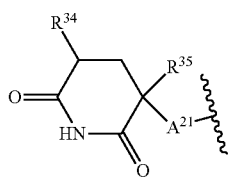

is

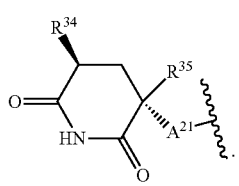

In certain embodiments

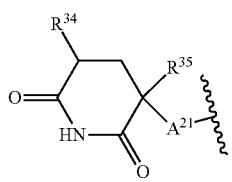

is

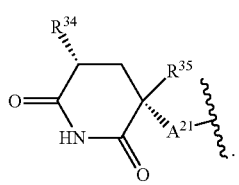

In certain embodiments

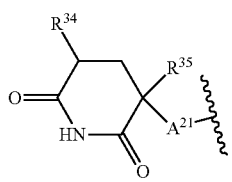

is

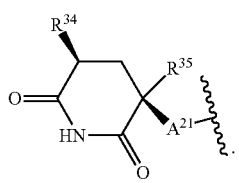

In certain embodiments

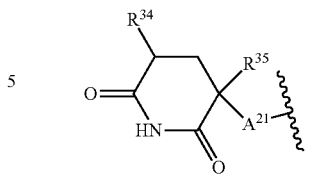

is

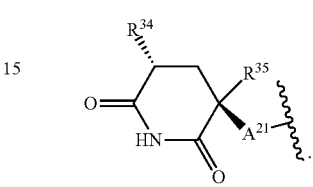

In certain embodiments there is one stereocenter in the linker portion and it is a mixture of R- and S-configuration. In another embodiment there is one stereocenter in the linker portion and it is enantiomerically enriched or substantially pure R-configuration. In another embodiment there is one stereocenter in the linker portion and it is enantiomerically enriched or substantially pure S-configuration.

In certain embodiments the linker contains one or more moieties with a chiral center. Non-limiting examples include heterocycle with an enantiomerically enriched or substantially pure stereocenter for example piperidine with a substituent meta- or ortho to the nitrogen or linking in the meta- or ortho-configuration; piperazine with a substituent or linking in the meta- or ortho-configuration; pyrrolidinone with or without a substituent; and pyrrolidine with or without a substituent.

Additional non-limiting examples of linker moieties with at least one chiral center include an alkyl with an enantiomerically enriched or substantially pure stereocenter; an alkene with an enantiomerically enriched or substantially pure stereocenter; an alkyne with an enantiomerically enriched or substantially pure stereocenter; a haloalkyl with an enantiomerically enriched or substantially pure stereocenter; an alkoxy with an enantiomerically enriched or substantially pure stereocenter; an aliphatic group with an enantiomerically enriched or substantially pure stereocenter; a heteroaliphatic group with an enantiomerically enriched or substantially pure stereocenter; and a cycloalkyl with an enantiomerically enriched or substantially pure stereocenter In certain embodiments the linker includes

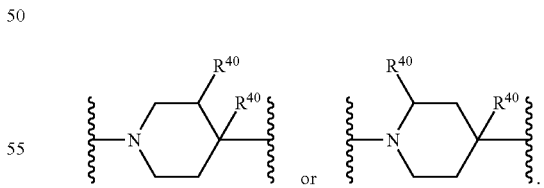

In certain embodiments the linker includes

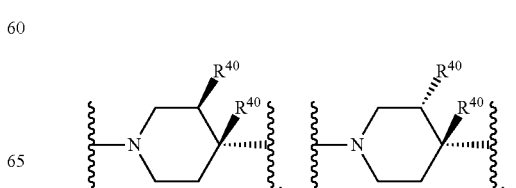

-continued

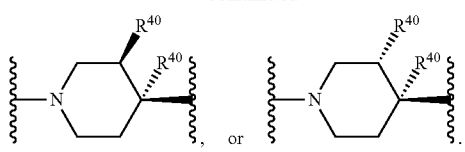

In certain embodiments the linker includes

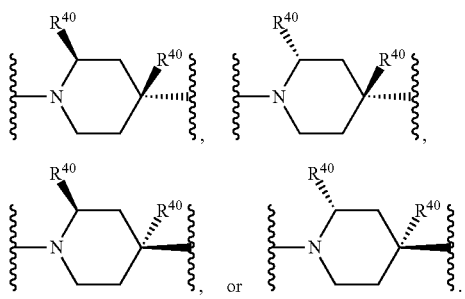

In certain embodiments the linker includes

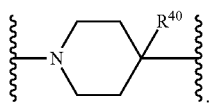

In certain embodiments the linker includes

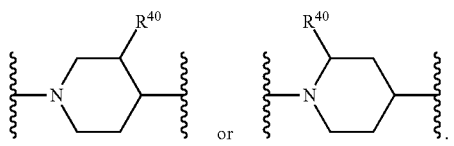

In certain embodiments the linker includes

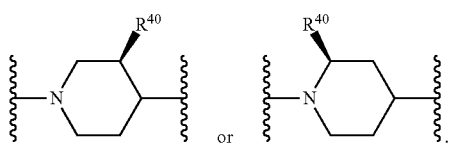

In certain embodiments the linker includes

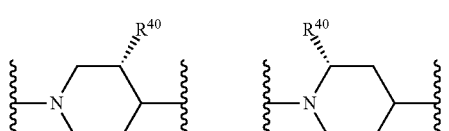

In certain embodiments the linker includes

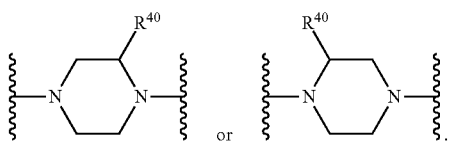

In certain embodiments the linker includes

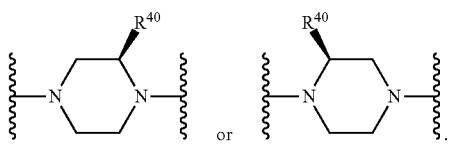

In certain embodiments the linker includes

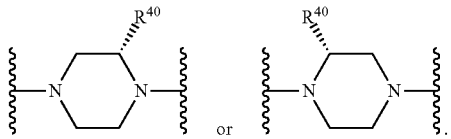

In certain embodiments the linker includes

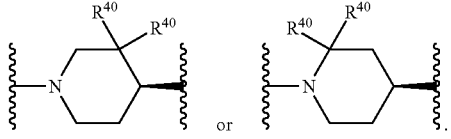

In certain embodiments the linker includes

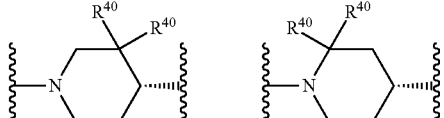

In certain embodiments the linker includes

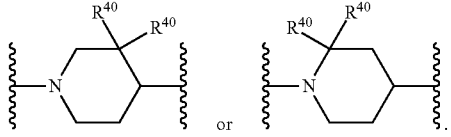

In certain embodiments, there is at least one stereocenter in the EGFR ligand portion which is a mixture of R and S. In another embodiment there is at least one stereocenter in the EGFR ligand portion and it is enantiomerically enriched or substantially pure in the R-configuration. In another embodiment there is at least one stereocenter in the EGFR ligand portion and it is enantiomerically enriched or substantially pure in the S-configuration.

In certain embodiments

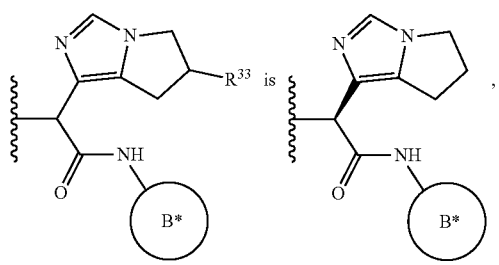

wherein R³³ is hydrogen.
In certain embodiments

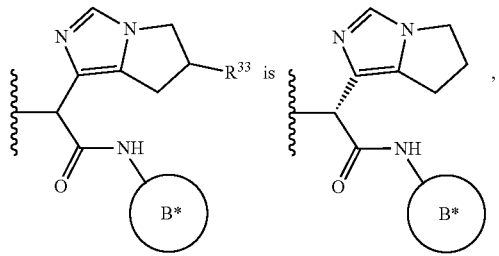

wherein R³³ is hydrogen.
In certain embodiments

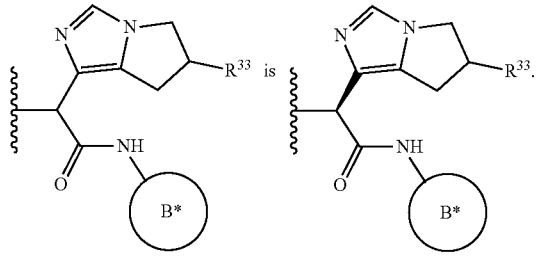

In certain embodiments

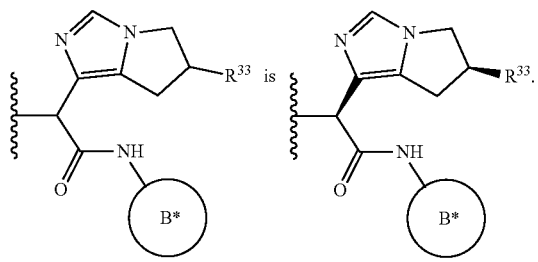

In certain embodiments

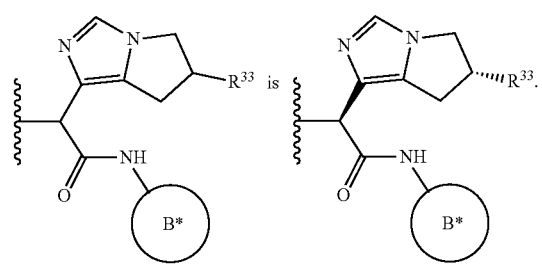

In certain embodiments

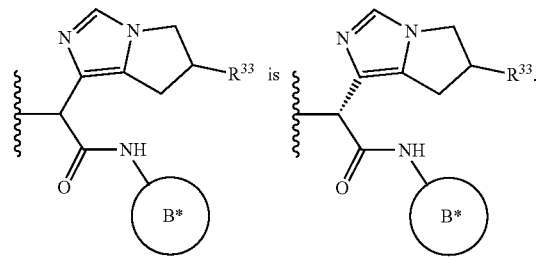

In certain embodiments

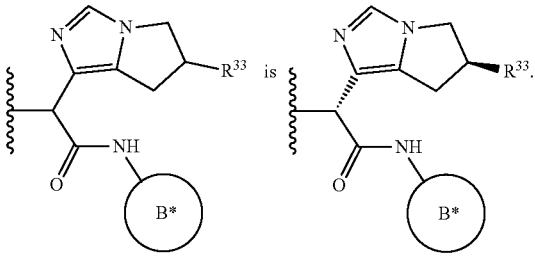

In certain embodiments

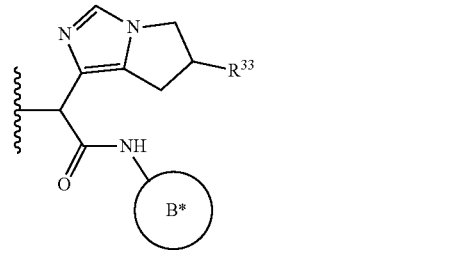

Embodiments of Alkyl
In certain embodiments "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.
In certain embodiments "alkyl" has one carbon.
In certain embodiments "alkyl" has two carbons.
In certain embodiments "alkyl" has three carbons.
In certain embodiments "alkyl" has four carbons.
In certain embodiments "alkyl" has five carbons.
In certain embodiments "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In an alternative embodiment "alkyl" is "optionally substituted" with 1, 2, 3, or 4 $R^{31}$ substituents.

Embodiments of Cycloalkyl

In certain embodiments "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In certain embodiments "cycloalkyl" has three carbons.
In certain embodiments "cycloalkyl" has four carbons.
In certain embodiments "cycloalkyl" has five carbons.
In certain embodiments "cycloalkyl" has six carbons.
In certain embodiments "cycloalkyl" has seven carbons.
In certain embodiments "cycloalkyl" has eight carbons.
In certain embodiments "cycloalkyl" has nine carbons.
In certain embodiments "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

In an alternative embodiment "cycloalkyl" is "optionally substituted" with 1, 2, 3, or 4 $R^{31}$ substituents.

Embodiments of Haloalkyl

In certain embodiments "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In certain embodiments "haloalkyl" has one carbon.
In certain embodiments "haloalkyl" has one carbon and one halogen.
In certain embodiments "haloalkyl" has one carbon and two halogens.
In certain embodiments "haloalkyl" has one carbon and three halogens.
In certain embodiments "haloalkyl" has two carbons.
In certain embodiments "haloalkyl" has three carbons.
In certain embodiments "haloalkyl" has four carbons.
In certain embodiments "haloalkyl" has five carbons.
In certain embodiments "haloalkyl" has six carbons.

Non-limiting examples of "haloalkyl" include:

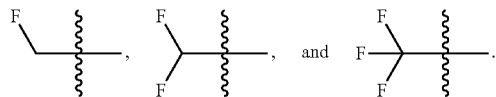

Additional non-limiting examples of "haloalkyl" include:

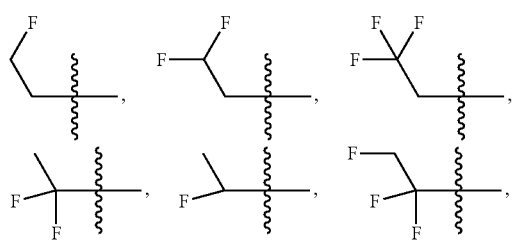

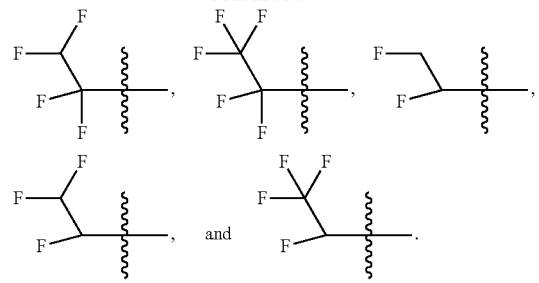

Additional non-limiting examples of "haloalkyl" include:

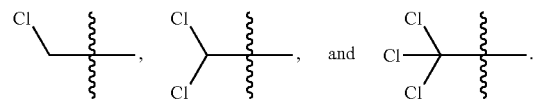

Additional non-limiting examples of "haloalkyl" include:

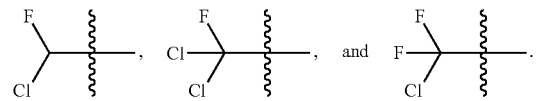

Embodiments of Heterocycle

In certain embodiments "heterocycle" refers to a cyclic ring with one nitrogen and 3, 4, 5, 6, 7, or 8 carbon atoms.

In certain embodiments "heterocycle" refers to a cyclic ring with one nitrogen and one oxygen and 3, 4, 5, 6, 7, or 8 carbon atoms.

In certain embodiments "heterocycle" refers to a cyclic ring with two nitrogens and 3, 4, 5, 6, 7, or 8 carbon atoms.

In certain embodiments "heterocycle" refers to a cyclic ring with one oxygen and 3, 4, 5, 6, 7, or 8 carbon atoms.

In certain embodiments "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocycle ring.

Non-limiting examples of "heterocycle" also include:

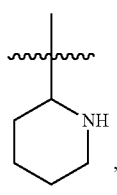 , 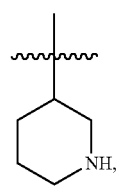 , 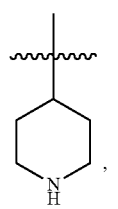 , 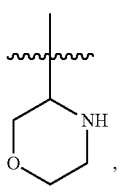 ,

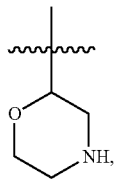 , 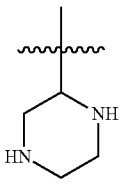 , 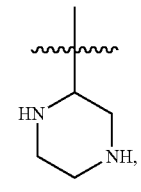 ,

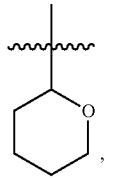 , 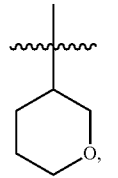 , and 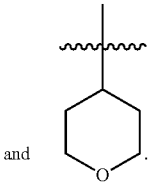 .

Additional non-limiting examples of "heterocycle" include:

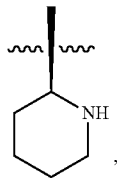 , 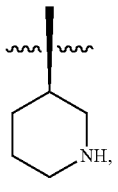 , 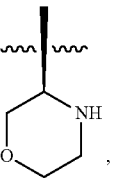 ,

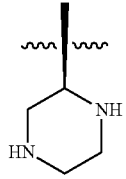 , 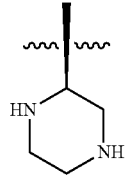 , 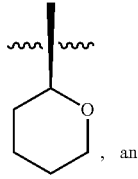 , and

Additional non-limiting examples of "heterocycle" include:

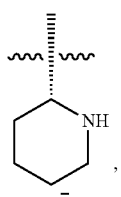 , 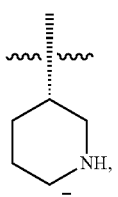 , 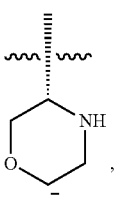 ,

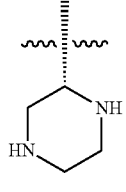 , 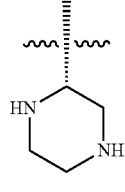 , 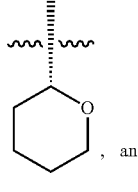 , and

Non-limiting examples of "heterocycle" also include:

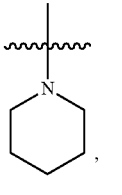 , 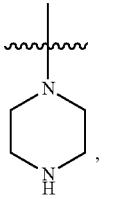 , and 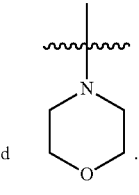 .

Non-limiting examples of "heterocycle" also include:

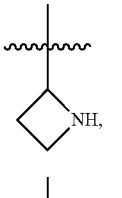 , 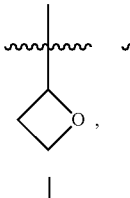 , 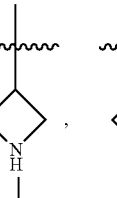 ,

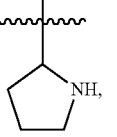 , 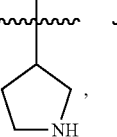 , 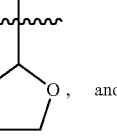 , and

Additional non-limiting examples of "heterocycle" include:

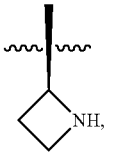 ,  , 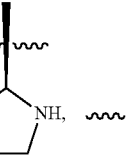 ,

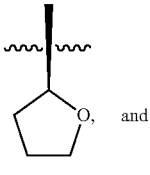 , and  ,  .

Additional non-limiting examples of "heterocycle" include:

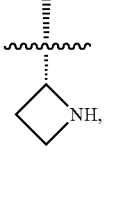 , 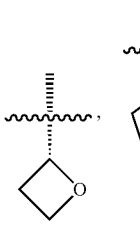 , 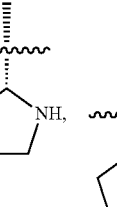 .

-continued

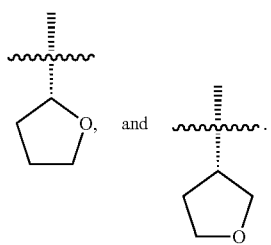

In an alternative embodiment "heterocycle" is "optionally substituted" with 1, 2, 3, or 4 $R^{31}$ substituents.

Embodiments of Heteroaryl

In certain embodiments "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

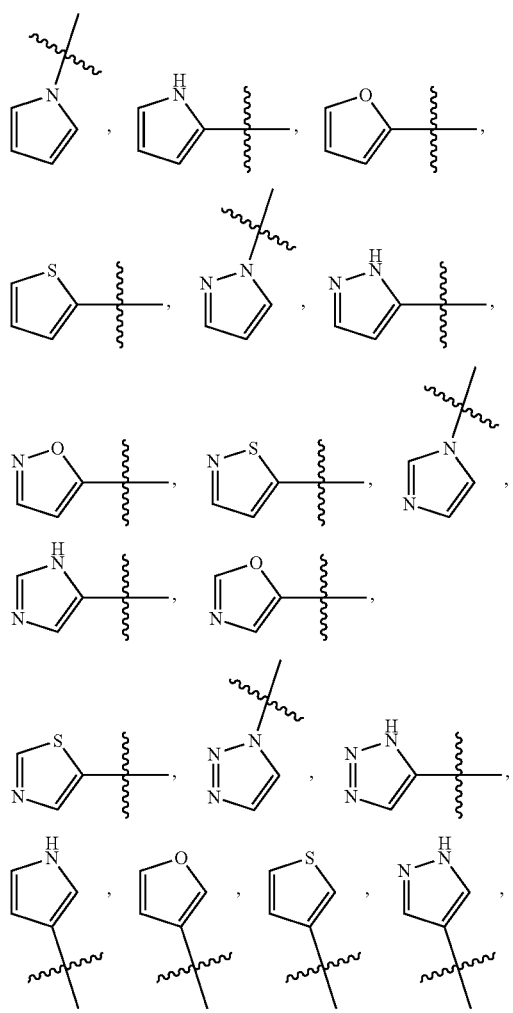

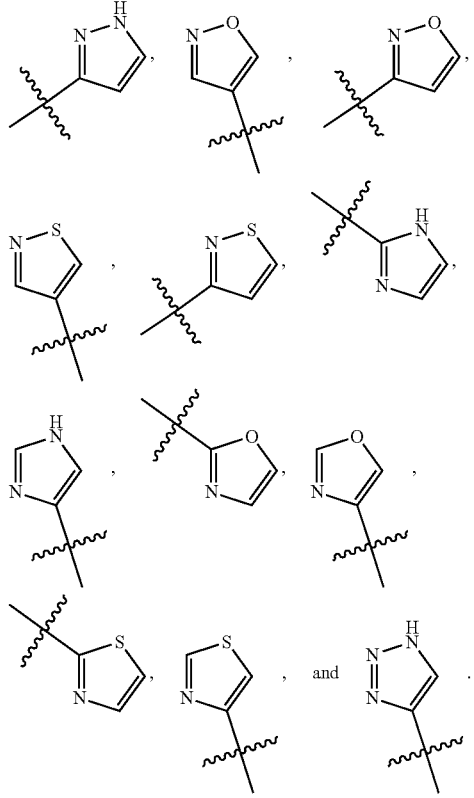

In certain embodiments "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

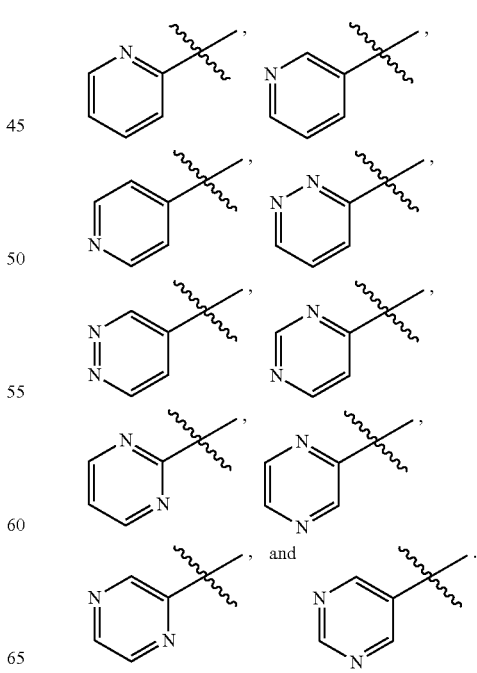

In certain embodiments "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

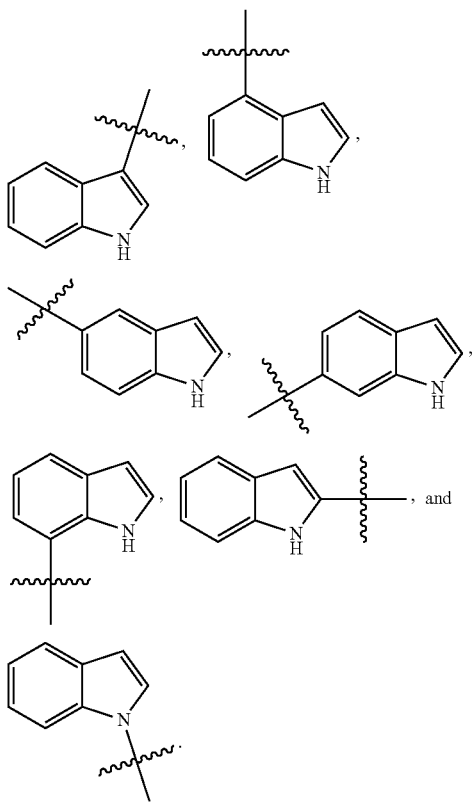

Additional non-limiting examples of "heteroaryl" groups that are bicyclic include:

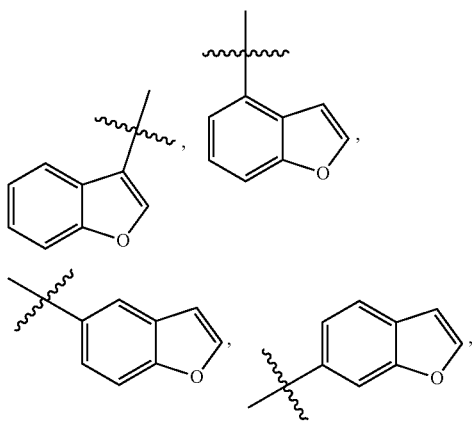

-continued

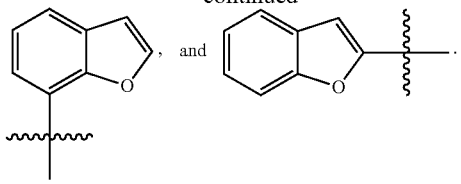

Additional non-limiting examples of "heteroaryl" groups that are bicyclic include:

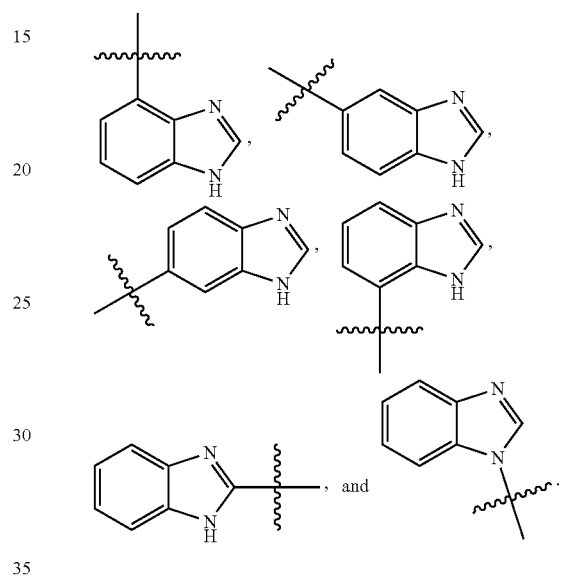

In certain embodiments "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

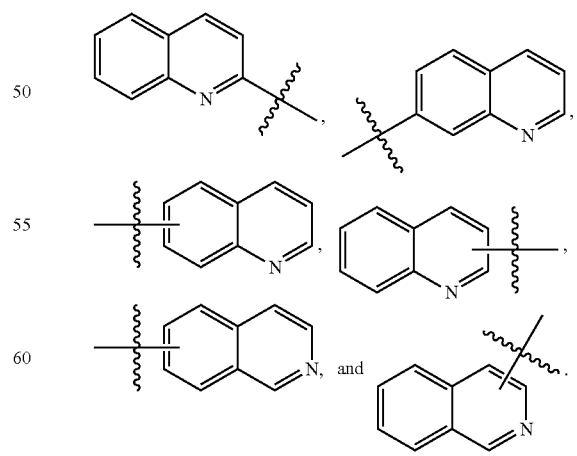

In an alternative embodiment "heteroaryl" is "optionally substituted" with 1, 2, 3, or 4 $R^{31}$ substituents.

Embodiments of Aryl

In certain embodiments aryl is phenyl.
In certain embodiments aryl is napthyl.
In an alternative embodiment "aryl" is "optionally substituted" with 1, 2, 3, or 4 $R^{31}$ substituents.

Embodiments of Bicycle

The term "bicycle" refers to a ring system wherein two rings share at least one atom in common. These rings can be spirocyclic or fused together and each ring is independently selected from carbocycle, heterocycle, aryl, and heteroaryl. Non-limiting examples of bicycle groups include:

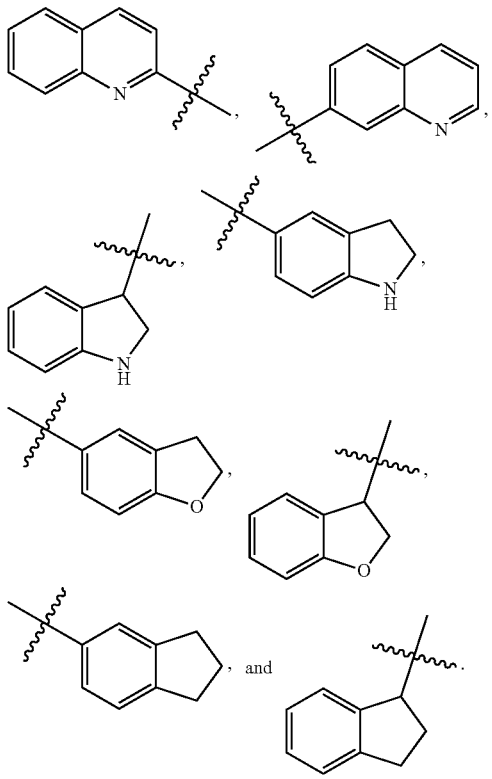

When the term "bicycle" is used in the context of a bivalent residue such as Linker the attachment points can be on separate rings or on the same ring. In certain embodiments both attachment points are on the same ring. In certain embodiments both attachment points are on different rings. Non-limiting examples of bivalent bicycle groups include:

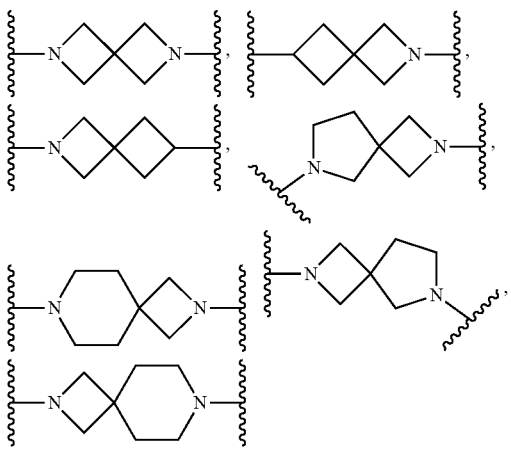

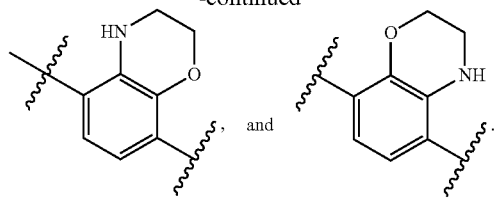

Additional non-limiting examples of bivalent bicycle include:

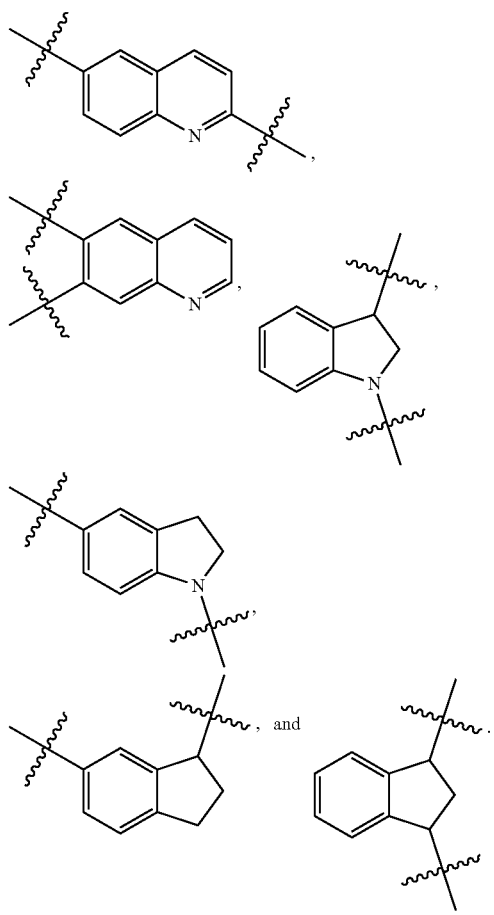

In an alternative embodiment "bicycle" is "optionally substituted" with 1, 2, 3, or 4 $R^{31}$ substituents.

Embodiments of Optional Substituents

In certain embodiments wherein a variable can be optionally substituted it is not substituted.
In certain embodiments wherein a variable can be optionally substituted it is substituted with 1 substituent.
In certain embodiments wherein a variable can be optionally substituted it is substituted with 2 substituents.
In certain embodiments wherein a variable can be optionally substituted it is substituted with 3 substituents.
In certain embodiments wherein a variable can be optionally substituted it is substituted with 4 substituents.
In one alternative embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino.

Embodiments of Aliphatic and Heteroaliphatic

In certain embodiments "aliphatic" refers to a saturated or unsaturated, straight, branched, or cyclic hydrocarbon. In these embodiments aliphatic is intended to include, but is not limited to, alkyl, alkenyl, alkynyl, cycloalkyl, cycloalkenyl, and cycloalkynyl moieties, and thus incorporates each of these definitions. In certain embodiments, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In certain embodiments, the aliphatic group contains from 1 to about 12 carbon atoms, more generally from 1 to about 6 carbon atoms or from 1 to about 4 carbon atoms. In certain embodiments, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In certain embodiments, the aliphatic group is substituted with one or more functional groups that results in the formation of a stable moiety.

In certain embodiments "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In certain embodiments, the only heteroatom is nitrogen. In certain embodiments, the only heteroatom is oxygen. In certain embodiments, the only heteroatom is sulfur. In certain embodiments "heteroaliphatic" is intended herein to include, but is not limited to, heteroalkyl, heteroalkenyl, heteroalkynyl, heterocycloalkyl, heterocycloalkenyl, and heterocycloalkynyl moieties. In certain embodiments, "heteroaliphatic" is used to indicate a heteroaliphatic group (cyclic, acyclic, substituted, unsubstituted, branched or unbranched) having 1-20 carbon atoms.

In certain embodiments, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

Embodiments of A and A*

In certain embodiments A* is

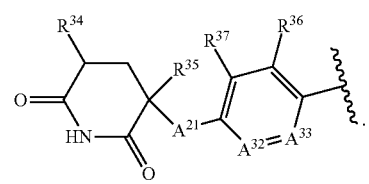

In certain embodiments A* is

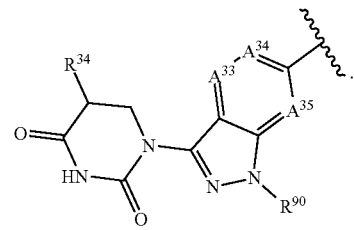

In certain embodiments A* is

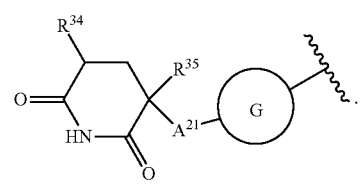

In certain embodiments A* is

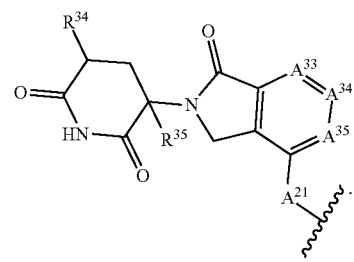

In certain embodiments A* is

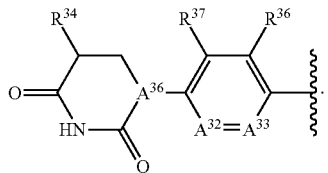

In certain embodiments A* is

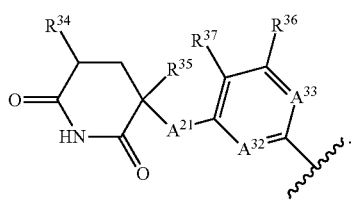

In certain embodiments $R^{34}$ and $R^{35}$ combine to form a $CH_2$.
In certain embodiments $R^{34}$ is H.
In certain embodiments $R^{35}$ is H.
In certain embodiments $A^1$ is NH.
In certain embodiments $A^1$ is O.
In certain embodiments $A^{21}$ is NH.
In certain embodiments $A^{21}$ is O.
In certain embodiments $A^{21}$ is $CH_2$.
In certain embodiments $A^{21}$ is $NR^{100}$.
In certain embodiments $A^{32}$, $A^{33}$, $A^{34}$, and $A^{35}$ are each selected from CH, C-halogen, and CF.
In certain embodiments $A^{32}$ is CH.
In certain embodiments $A^{32}$ is CF.
In certain embodiments $A^{32}$ is $CR^{42}$.
In certain embodiments $A^{32}$ is N.
In certain embodiments $A^{33}$ is CH.
In certain embodiments $A^{33}$ is CF.
In certain embodiments $A^{33}$ is $CR^{42}$.
In certain embodiments $A^{33}$ is N.
In certain embodiments $A^{34}$ is CH.
In certain embodiments $A^{34}$ is CF.
In certain embodiments $A^{34}$ is $CR^{42}$.
In certain embodiments $A^{34}$ is N.
In certain embodiments $A^{35}$ is CH.
In certain embodiments $A^{35}$ is CF.
In certain embodiments $A^{35}$ is $CR^{42}$.
In certain embodiments $A^{35}$ is N.
In certain embodiments $A^{36}$ is N.
In certain embodiments $R^{90}$ is hydrogen.
In certain embodiments $R^{90}$ is $C_1$-$C_3$ alkyl.
In certain embodiments $R^{90}$ is $C_{3-6}$-cycloalkyl.
In certain embodiments $R^{90}$ is methyl.
In certain embodiments A or A* is

AF

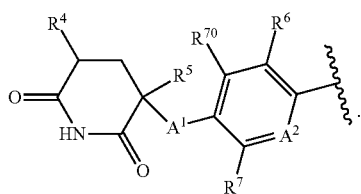

In certain embodiments A or A* is

AG

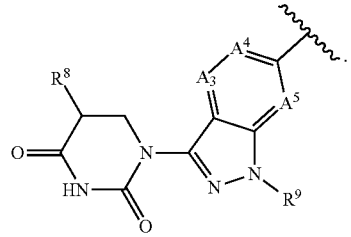

In certain embodiments A or A* is

AH

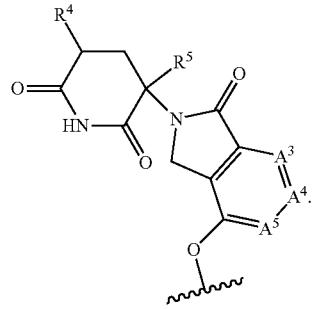

In certain embodiments, A or A* is selected from:

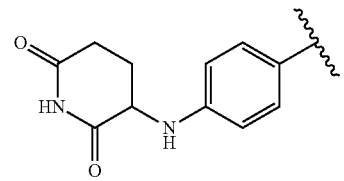

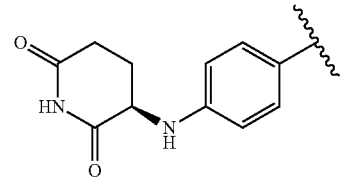

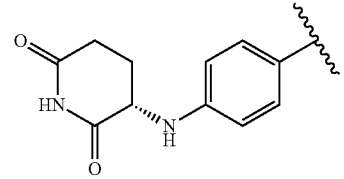

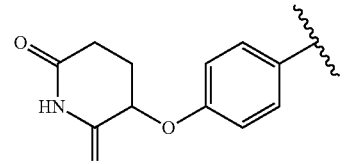

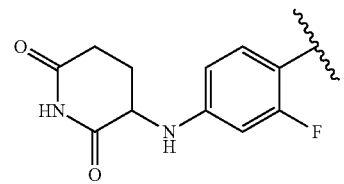

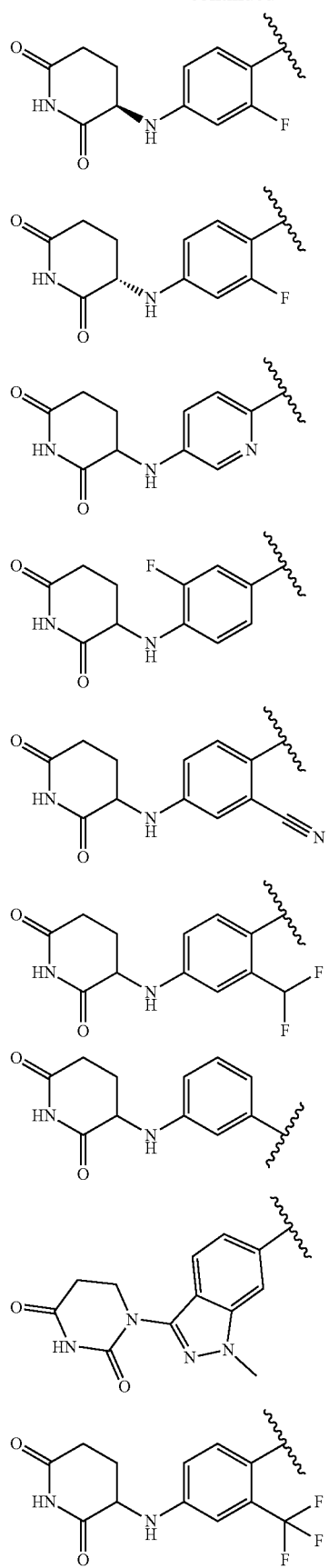
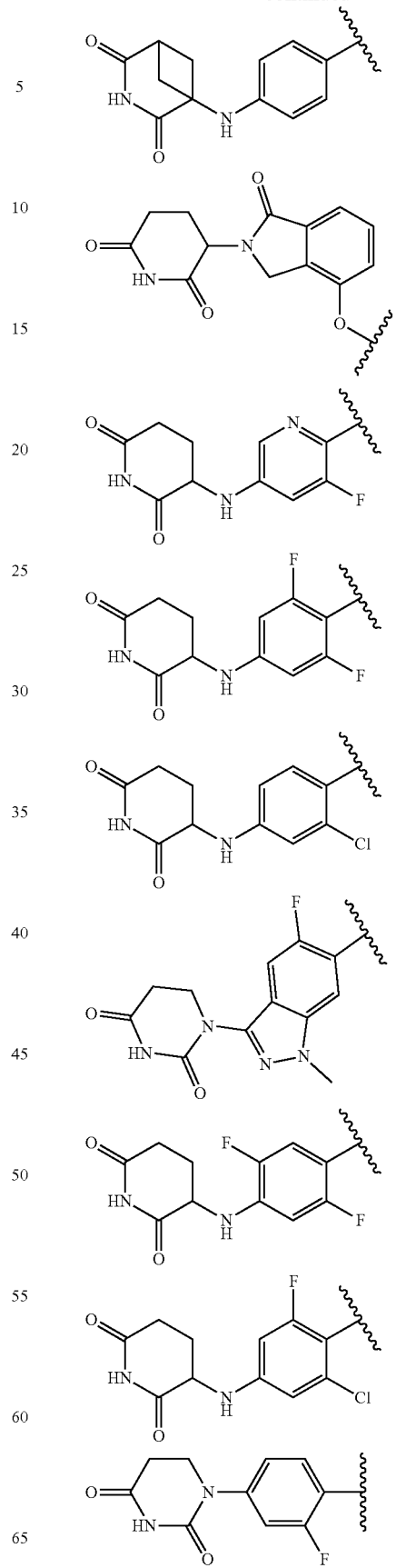

-continued

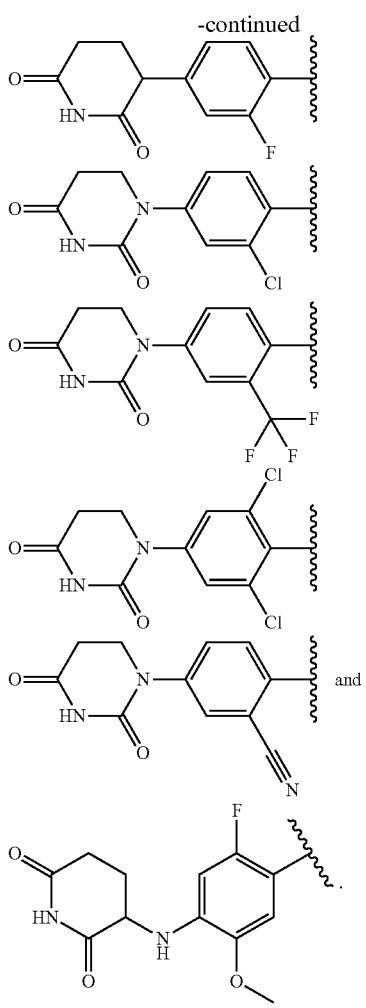

and

Embodiments of B and B*

In certain embodiments B or B* is

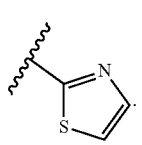

In certain embodiments B or B* is

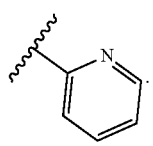

In certain embodiments B* is heteroaryl.
In certain embodiments B* is heteroaryl substituted with one $R^{31}$ group.
In certain embodiments B* is aryl.
In certain embodiments B* is aryl substituted with one $R^{31}$ group.

In certain embodiments B* is

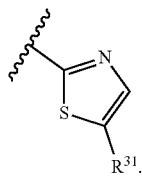

In certain embodiments B* is

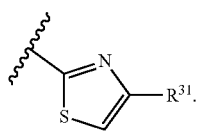

In certain embodiments B* is

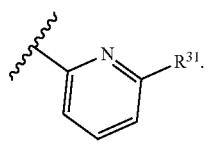

In certain embodiments B* is

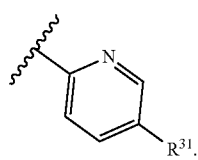

In certain embodiments B* is

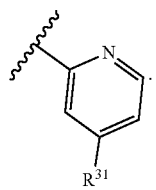

In certain embodiments B* is

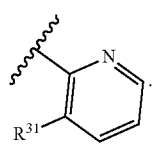

Embodiments of y
In certain embodiments y is 0.
In certain embodiments y is 1.
In certain embodiments y is 2.
In certain embodiments y is 3.
Embodiments of $R^{31}$
In certain embodiments at least one $R^{31}$ is halogen.

In certain embodiments at least one $R^{31}$ is F.

In certain embodiments at least one $R^{31}$ is Cl.

In certain embodiments at least one $R^{31}$ is $C_{1-6}$-alkyl.

In certain embodiments at least one $R^{31}$ is halo-$C_{1-6}$-alkyl.

In certain embodiments one $R^{31}$ is halogen.

In certain embodiments one $R^{31}$ is F.

In certain embodiments one $R^{31}$ is Cl.

In certain embodiments one $R^{31}$ is $C_{1-6}$-alkyl.

In certain embodiments one $R^{31}$ is cyano.

In certain embodiments one $R^{31}$ is $C_{1-6}$-alkoxy.

In certain embodiments one $R^{31}$ is halo-$C_{1-6}$-alkoxy.

In certain embodiments one $R^{31}$ is $C_{3-8}$-cycloalkyl.

In certain embodiments one $R^{31}$ is halo-$C_{3-8}$-cycloalkyl.

In certain embodiments $R^{31}$ is selected from halogen, $C_{1-6}$-alkoxy, and $C_{1-6}$-alkyl.

In certain embodiments $R^{31}$ is selected from F, Cl, methoxy, and methyl.

Embodiments of $R^{36}$ and $R^{37}$

In certain embodiments $R^{36}$ and $R^{37}$ together are combined to form a 5-membered cycle optionally substituted with 1, 2, or 3 $R^{31}$ substituents.

In certain embodiments $R^{36}$ and $R^{37}$ together are combined to form a 6-membered cycle optionally substituted with 1, 2, or 3 $R^{31}$ substituents.

In certain embodiments $R^{36}$ and $R^{37}$ together are combined to form a 5-membered cycloalkyl optionally substituted with 1, 2, or 3 $R^{31}$ substituents.

In certain embodiments $R^{36}$ and $R^{37}$ together are combined to form a 6-membered cycloalkyl optionally substituted with 1, 2, or 3 $R^{31}$ substituents.

In certain embodiments $R^{36}$ and $R^{37}$ together are combined to form a 5-membered heteroaryl optionally substituted with 1, 2, or 3 $R^{31}$ substituents.

In certain embodiments $R^{36}$ and $R^{37}$ together are combined to form a 6-membered heteroaryl optionally substituted with 1, 2, or 3 $R^{31}$ substituents.

In certain embodiments $R^{36}$ and $R^{37}$ together are combined to form a 5-membered heterocycle optionally substituted with 1, 2, or 3 $R^{31}$ substituents.

In certain embodiments $R^{36}$ and $R^{37}$ together are combined to form a 6-membered heterocycle optionally substituted with 1, 2, or 3 $R^{31}$ substituents.

In certain embodiments $R^{36}$ and $R^{37}$ together are combined to form a morpholine optionally substituted with 1, 2, or 3 $R^{31}$ substituents.

In certain embodiments $R^{36}$ and $R^{37}$ together are combined to form phenyl optionally substituted with 1, 2, or 3 $R^{31}$ substituents.

In certain embodiments the cycle formed by combining $R^{36}$ and $R^{37}$ is not substituted.

In certain embodiments the cycle formed by combining $R^{36}$ and $R^{37}$ is substituted with 1 $R^{31}$ substituent.

In certain embodiments the cycle formed by combining $R^{36}$ and $R^{37}$ is substituted with 2 $R^{31}$ substituents.

In certain embodiments the cycle formed by combining $R^{36}$ and $R^{37}$ is substituted with 3 $R^{31}$ substituents.

In certain embodiments $R^{36}$ is hydrogen.

In certain embodiments $R^{36}$ is halogen.

In certain embodiments $R^{36}$ is F.

In certain embodiments $R^{36}$ is Cl.

In certain embodiments $R^{36}$ is $C_{1-6}$-alkyl.

In certain embodiments $R^{36}$ is cyano.

In certain embodiments $R^{36}$ is $C_{1-6}$-alkoxy.

In certain embodiments $R^{36}$ is halo-$C_{1-6}$-alkoxy.

In certain embodiments $R^{36}$ is $C_{3-8}$-cycloalkyl.

In certain embodiments $R^{36}$ is halo-$C_{3-8}$-cycloalkyl.

In certain embodiments $R^{36}$ is selected from hydrogen, halogen, $C_{1-6}$-alkoxy, and $C_{1-6}$-alkyl.

In certain embodiments $R^{36}$ is selected from hydrogen, F, Cl, methoxy, and methyl.

In certain embodiments $R^{37}$ is hydrogen.

In certain embodiments $R^{37}$ is halogen.

In certain embodiments $R^{37}$ is F.

In certain embodiments $R^{37}$ is Cl.

In certain embodiments $R^{37}$ is $C_{1-6}$-alkyl.

In certain embodiments $R^{37}$ is cyano.

In certain embodiments $R^{37}$ is $C_{1-6}$-alkoxy.

In certain embodiments $R^{37}$ is halo-$C_{1-6}$-alkoxy.

In certain embodiments $R^{37}$ is $C_{3-8}$-cycloalkyl.

In certain embodiments $R^{37}$ is halo-$C_{3-8}$-cycloalkyl.

In certain embodiments $R^{37}$ is selected from hydrogen, halogen, $C_{1-6}$-alkoxy, and $C_{1-6}$-alkyl.

In certain embodiments $R^{37}$ is selected from hydrogen, F, Cl, methoxy, and methyl.

Embodiments of $R^{42}$

In certain embodiments at least one $R^{42}$ is halogen.

In certain embodiments at least one $R^{42}$ is F.

In certain embodiments at least one $R^{42}$ is Cl.

In certain embodiments at least one $R^{42}$ is $C_{1-6}$-alkyl.

In certain embodiments at least one $R^{42}$ is halo-$C_{1-6}$-alkyl.

In certain embodiments $R^{42}$ is hydrogen.

In certain embodiments $R^{42}$ is halogen.

In certain embodiments $R^{42}$ is F.

In certain embodiments $R^{42}$ is Cl.

In certain embodiments $R^{42}$ is $C_{1-6}$-alkyl.

In certain embodiments $R^{42}$ is cyano.

In certain embodiments $R^{42}$ is $C_{1-6}$-alkoxy.

In certain embodiments $R^{42}$ is halo-$C_1$-s-alkoxy.

In certain embodiments $R^{42}$ is $C_{3-8}$-cycloalkyl.

In certain embodiments $R^{42}$ is halo-$C_{3-8}$-cycloalkyl.

In certain embodiments $R^{42}$ is selected from hydrogen, halogen, $C_{1-6}$-alkoxy, and $C_{1-6}$-alkyl.

In certain embodiments $R^{42}$ is selected from hydrogen, F, Cl, methoxy, and methyl.

Embodiments of Ring G

In certain embodiments Ring G is a 5-membered heteroaryl ring optionally substituted with 1 or 2 $R^{42}$ substituents.

In certain embodiments Ring G is a 6-membered heteroaryl ring optionally substituted with 1 or 2 $R^{42}$ substituents.

In certain embodiments Ring G is selected from:

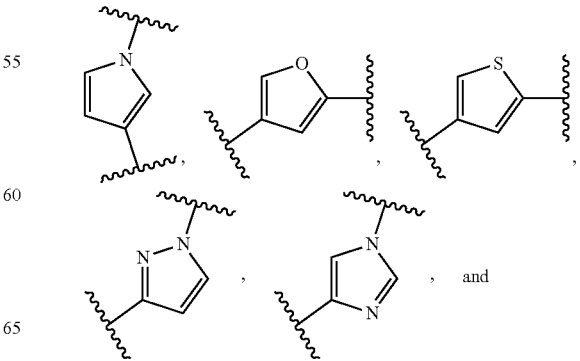

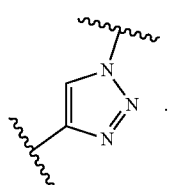
Embodiments of EGFR Targeting Ligand
In certain embodiments the compound of the present invention is selected from:
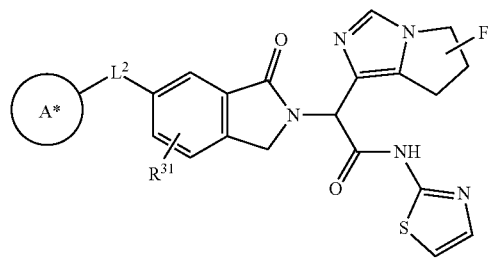
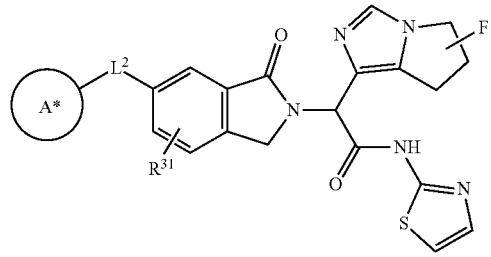
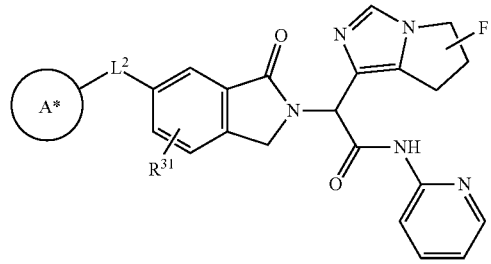
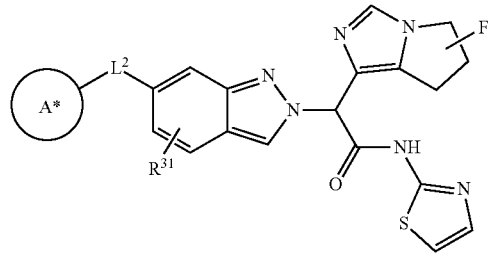
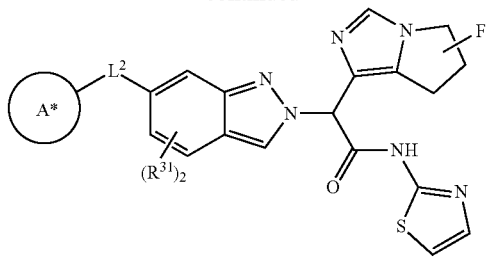
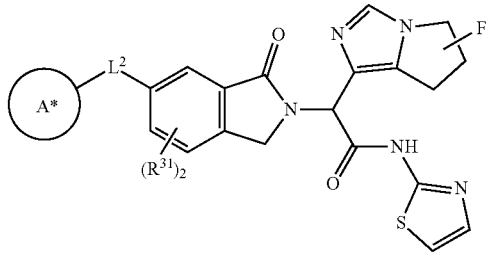
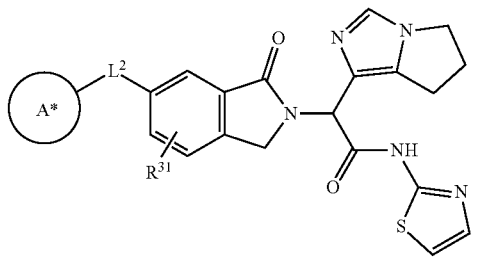
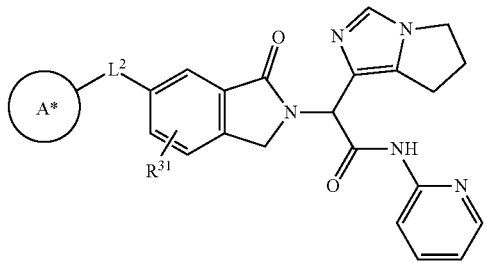
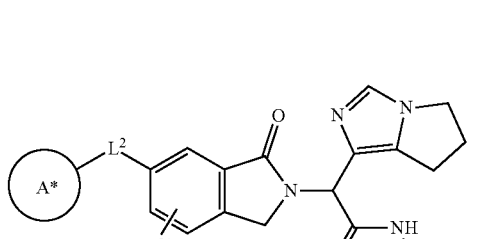
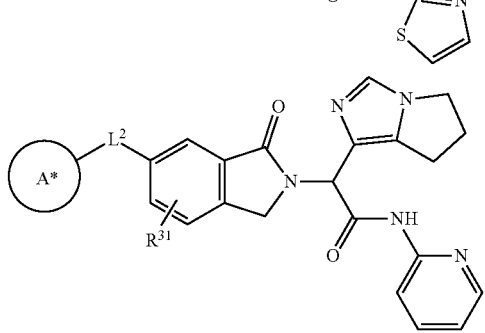

-continued
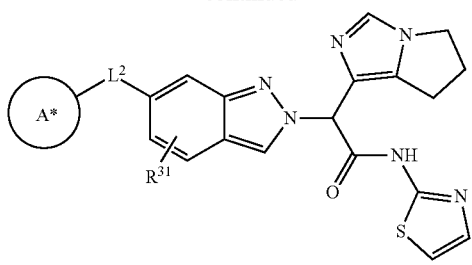
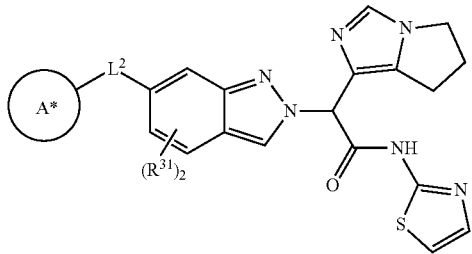
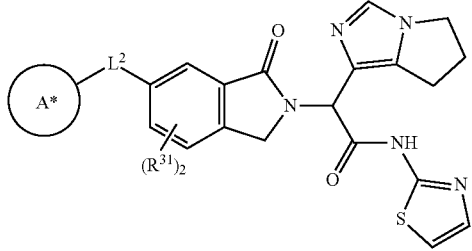
In certain embodiments the compound of the present invention is selected from:
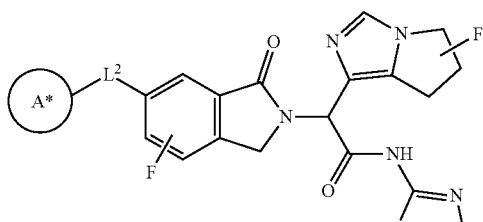
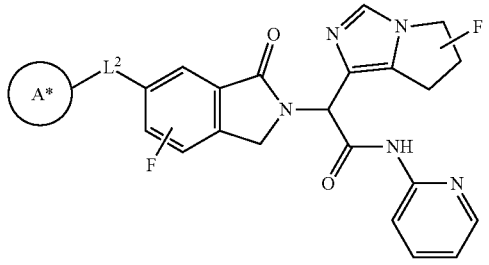
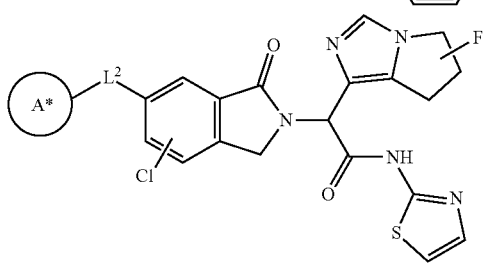
-continued
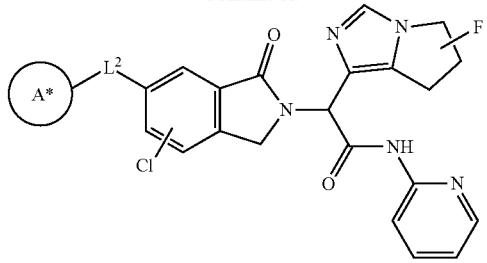
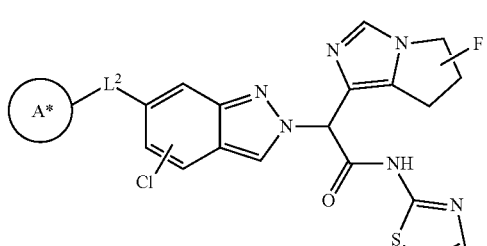
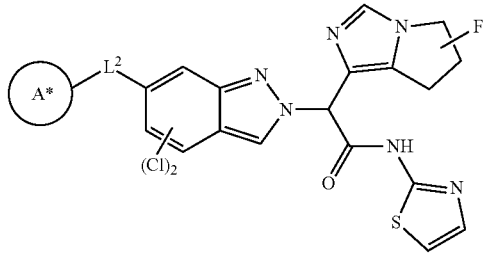
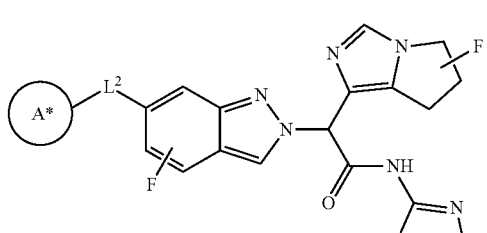
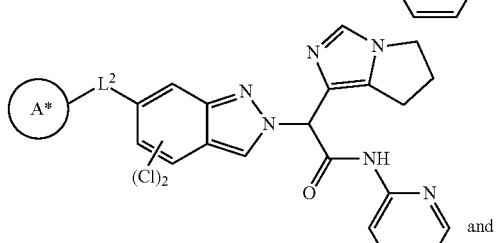
and -continued
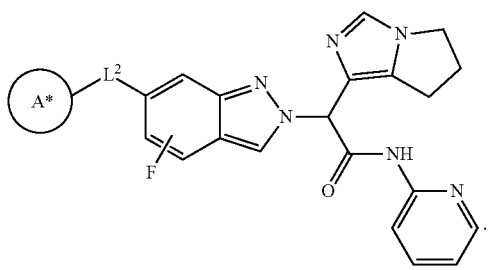
In certain embodiments the compound of the present invention is selected from:
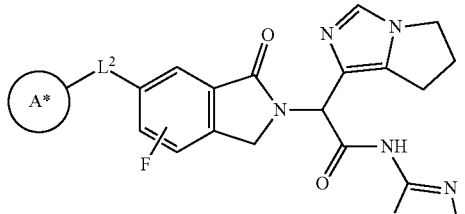
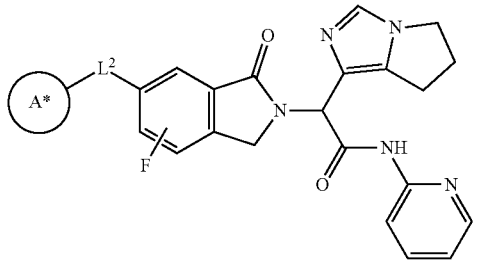
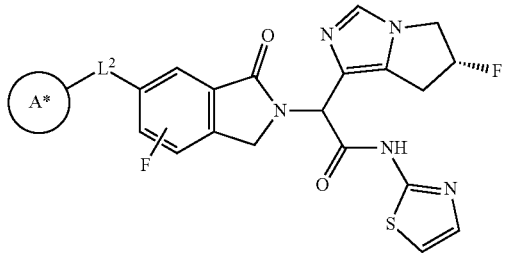
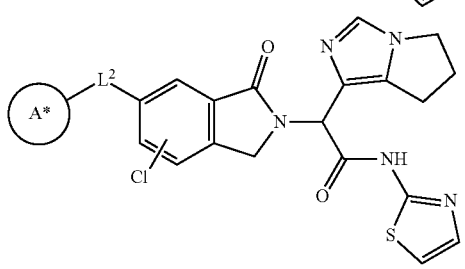
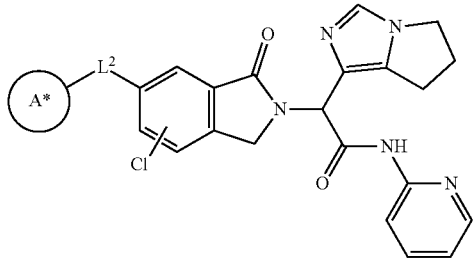
-continued
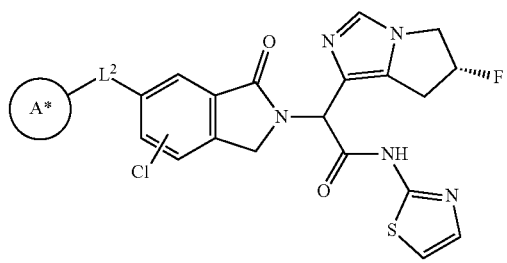
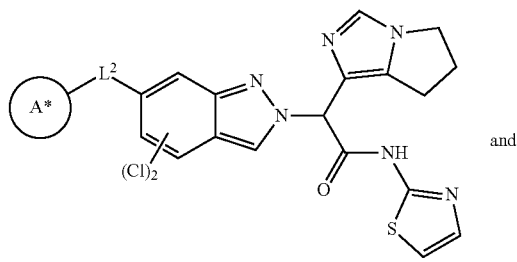 and
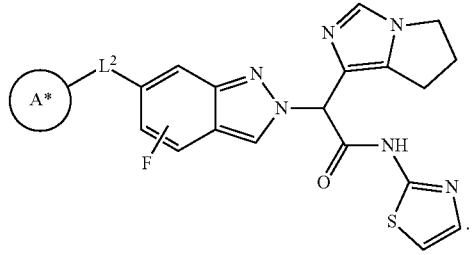
In certain embodiments the compound of the present invention is selected from:
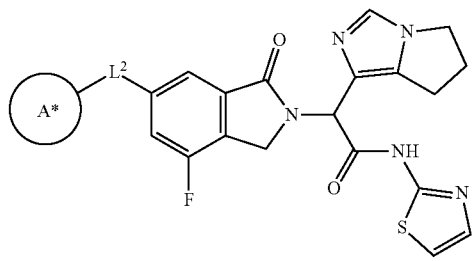
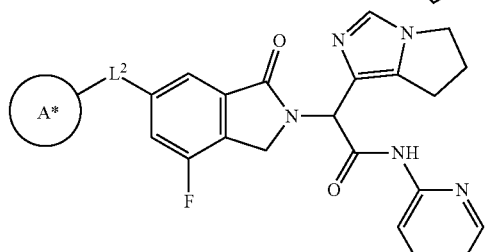
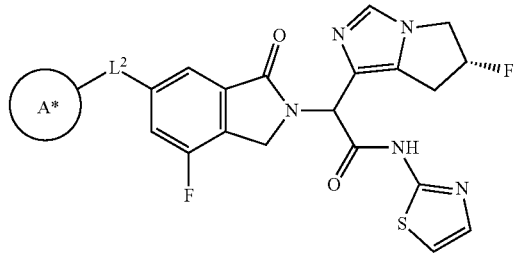

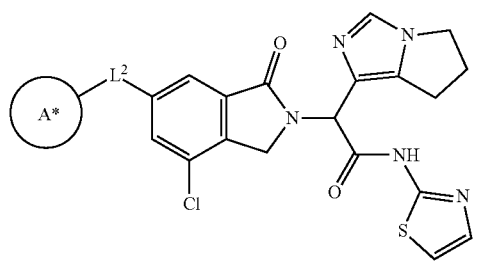
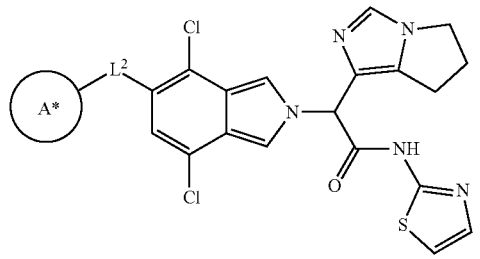
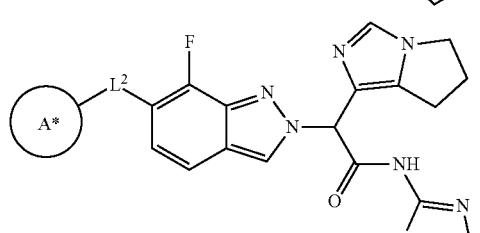
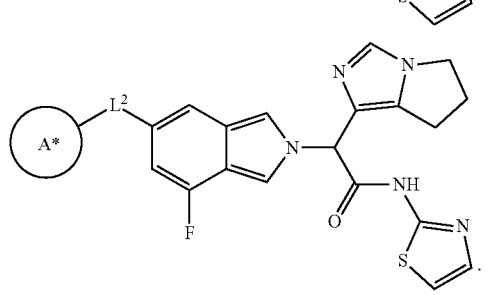
and
In certain embodiments the compound of the present invention is selected from:
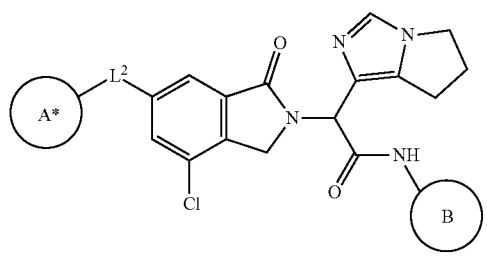
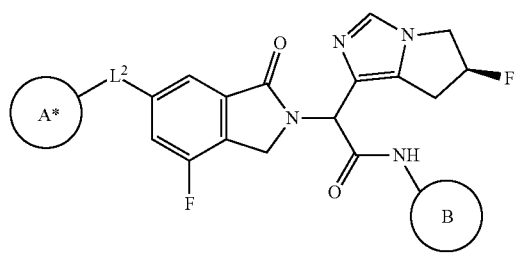
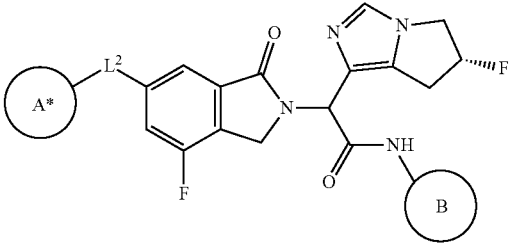
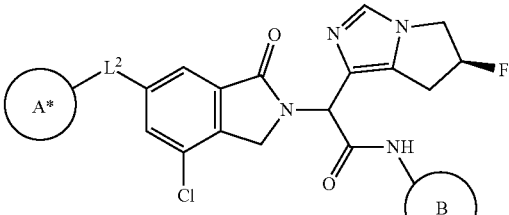
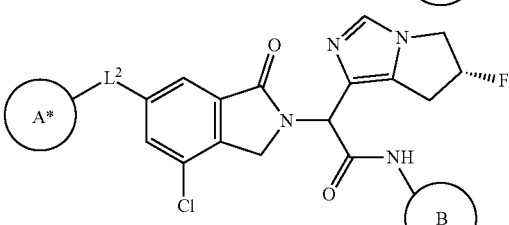
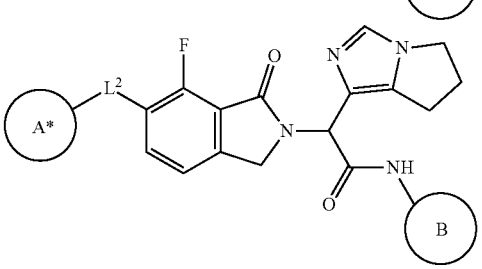
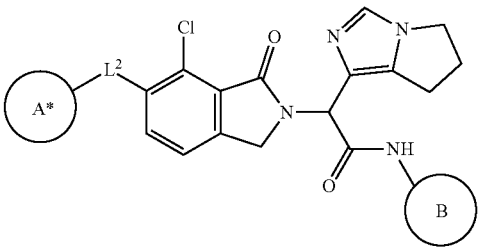

221
-continued
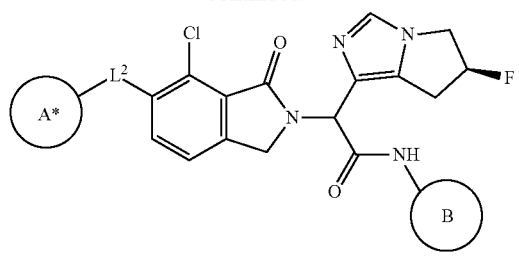
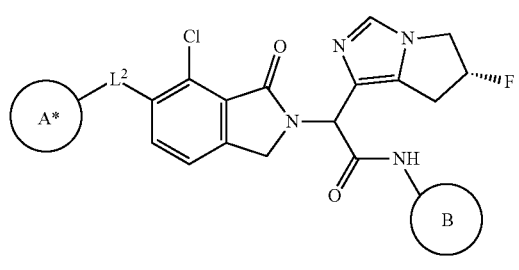
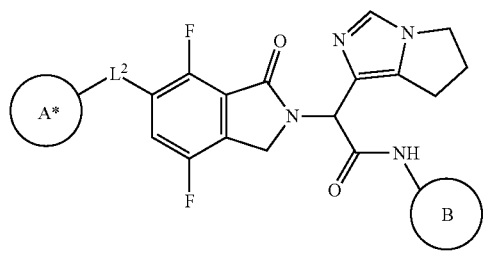
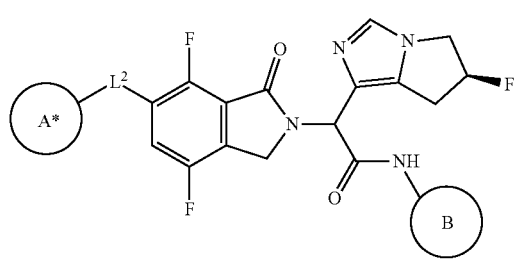
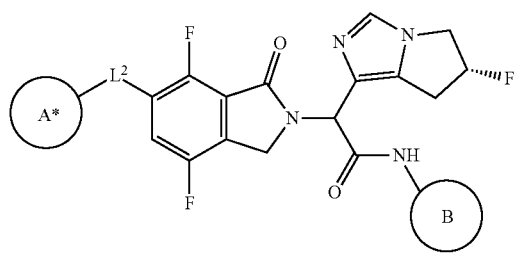
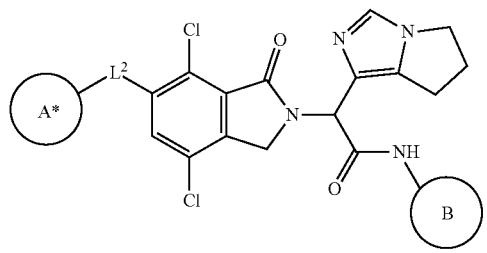
222
-continued
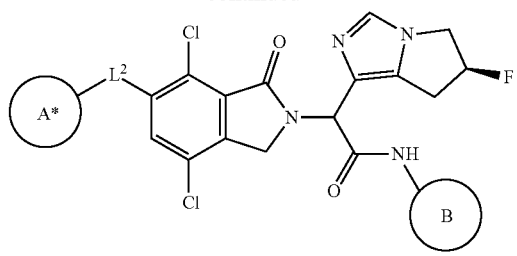
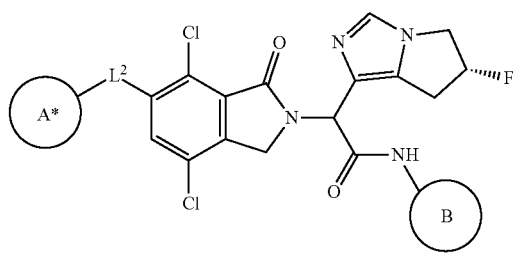
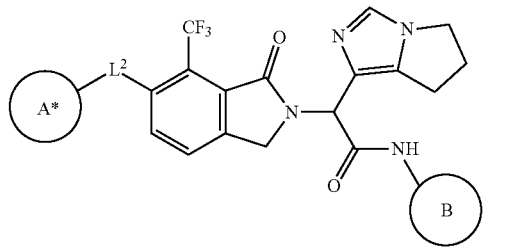
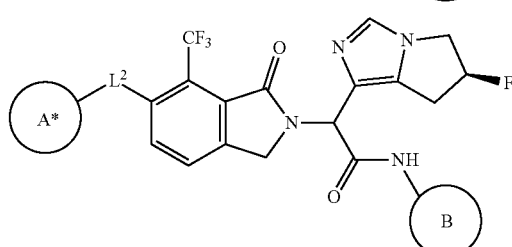
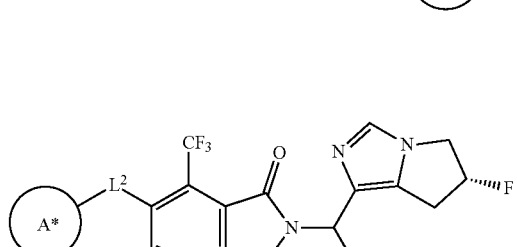
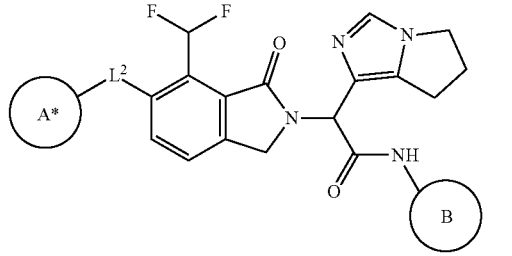

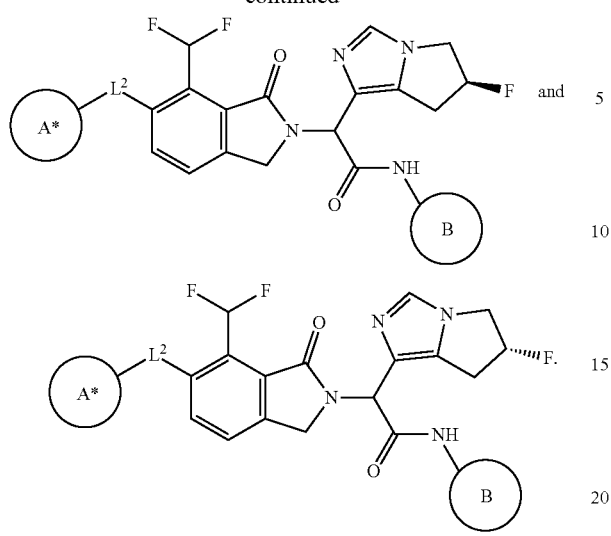
In certain embodiments the compound of the present invention is selected from:
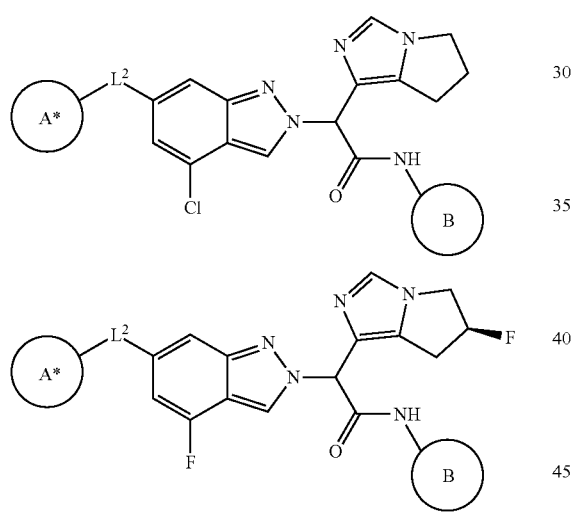
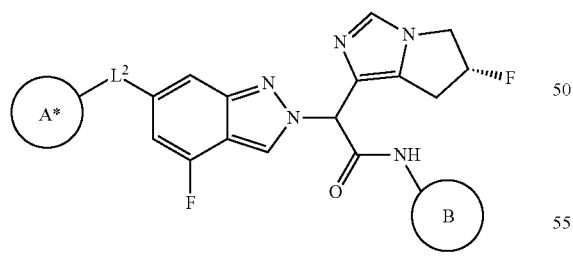
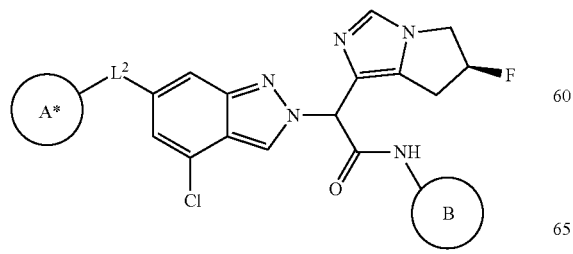
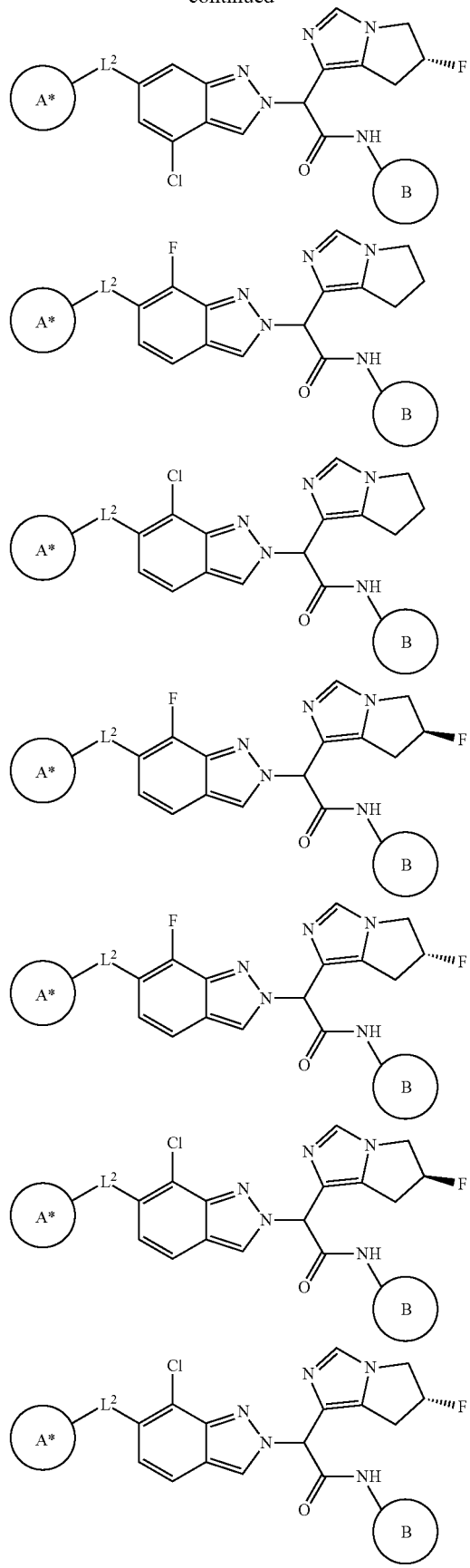

225
-continued
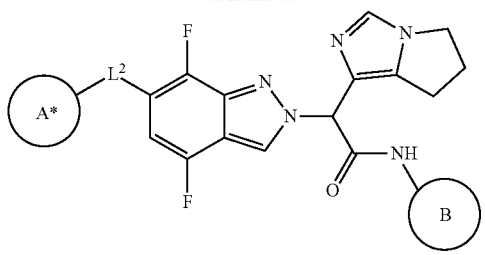
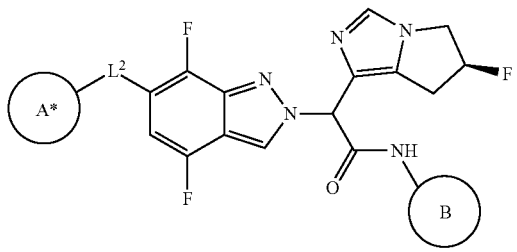
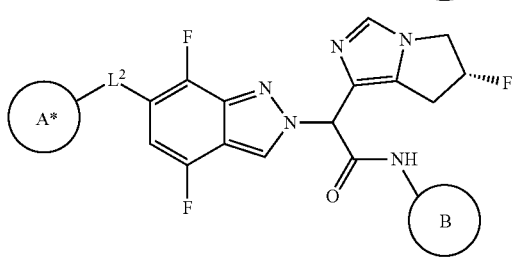
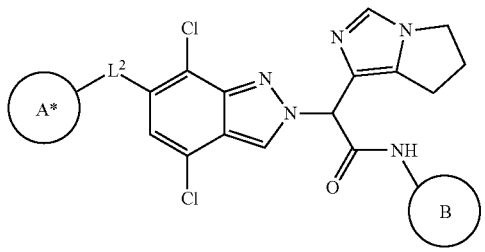
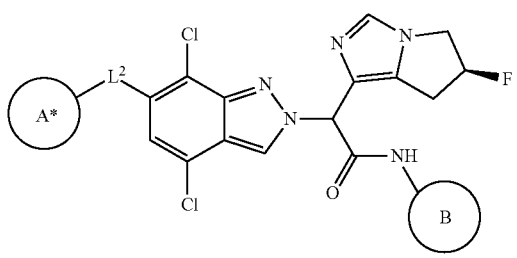
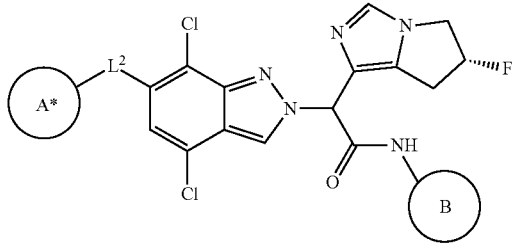
226
-continued
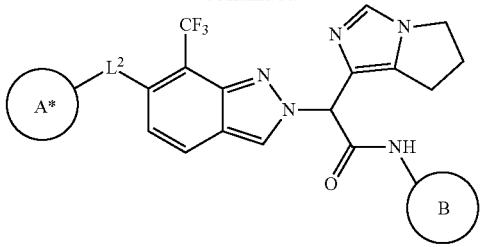
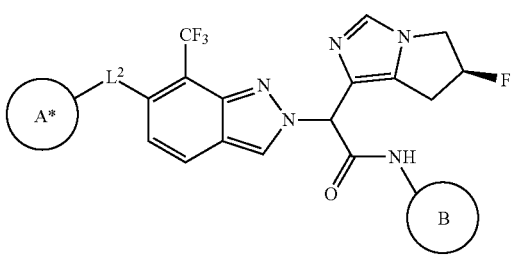
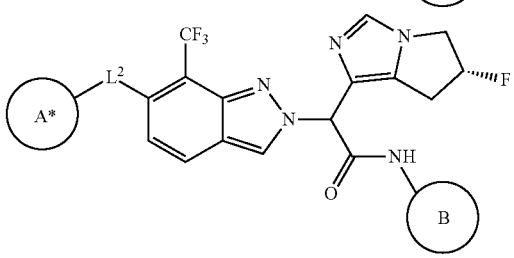
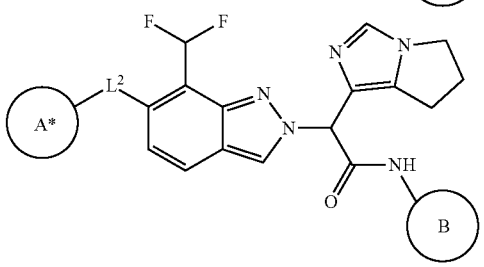
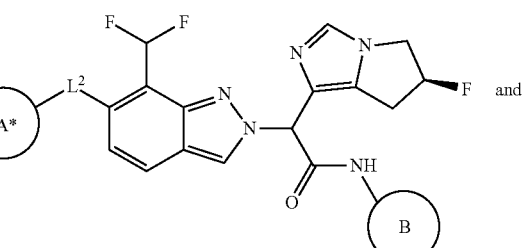 and
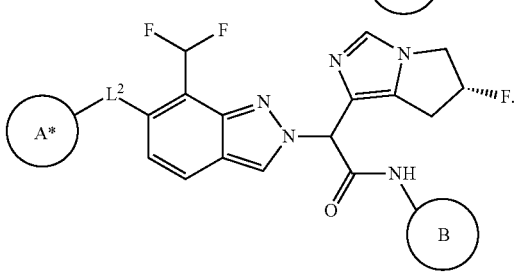

Compounds of Formula III
In certain embodiments the compound of the present invention is selected from:
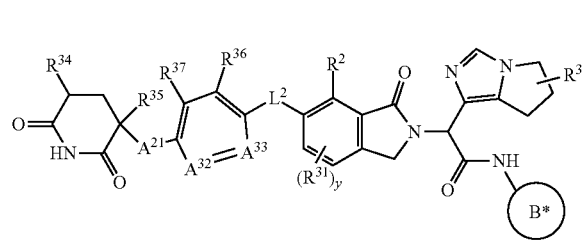
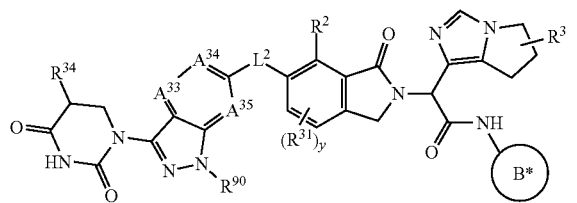
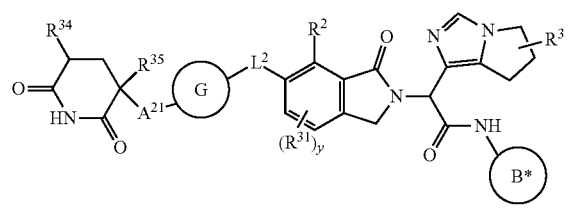
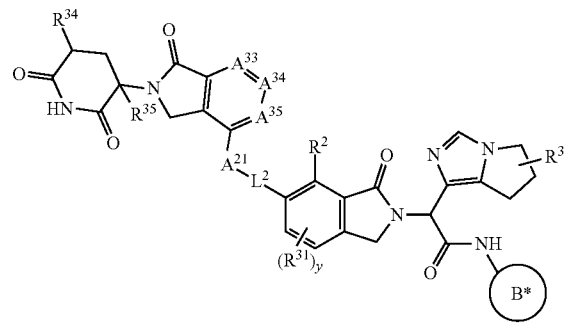
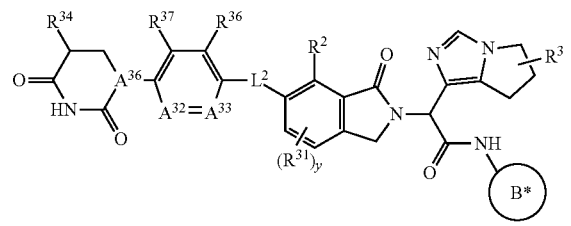
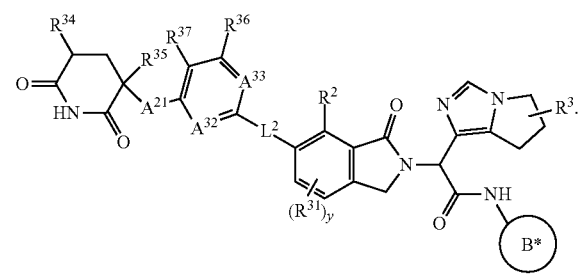
In certain embodiments the compound of the present invention is selected from:
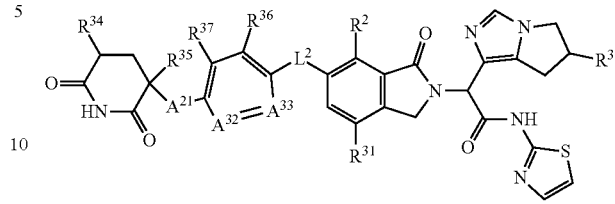
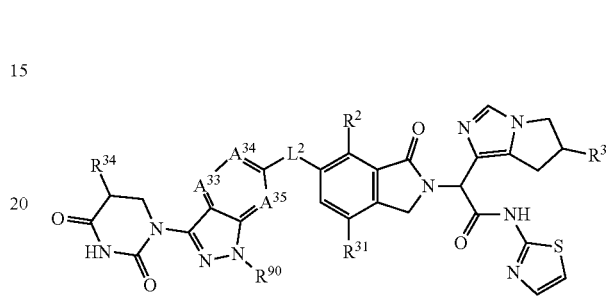
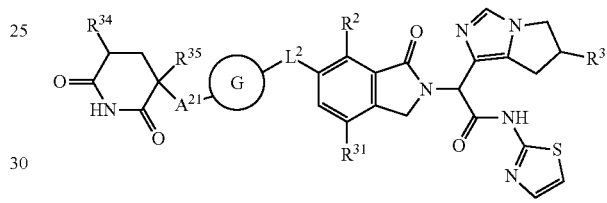
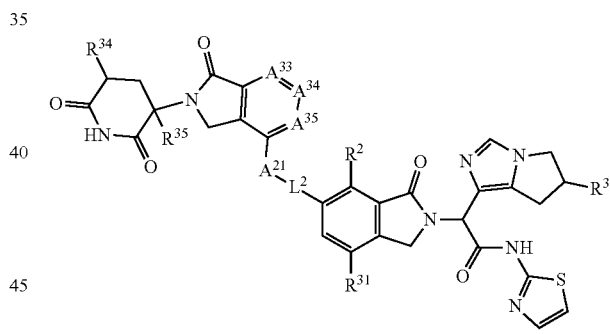
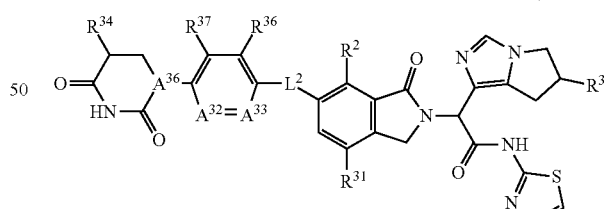
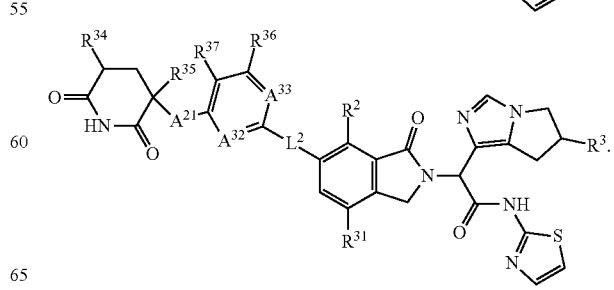

Compounds of Formula IV
In certain embodiments the compound of the present invention is selected from:
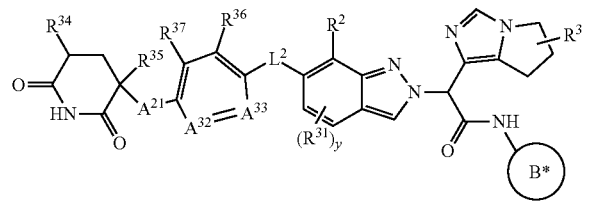
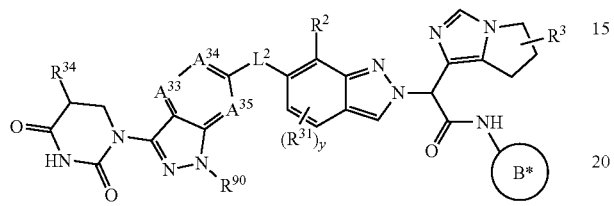
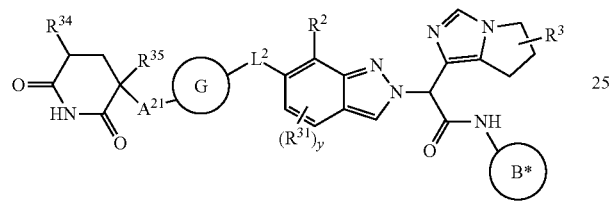
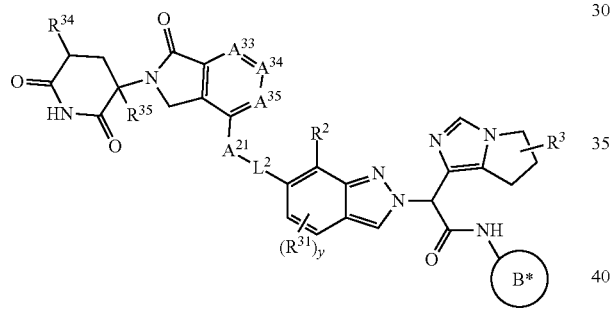
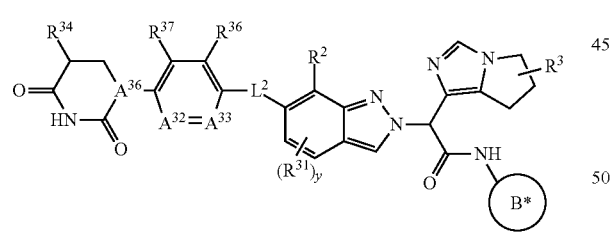
and
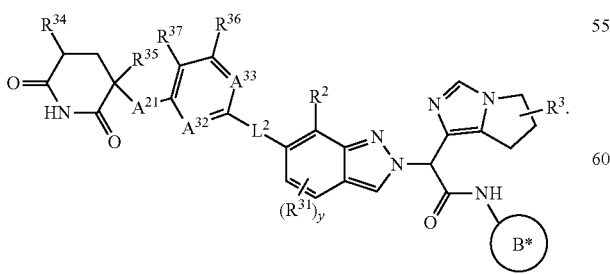
III. Additional Compounds of the Present Invention
In certain embodiments the compound of the present invention is selected from:
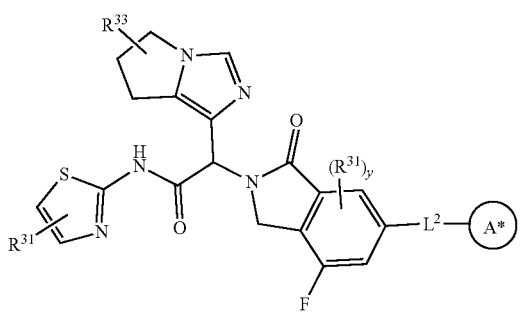
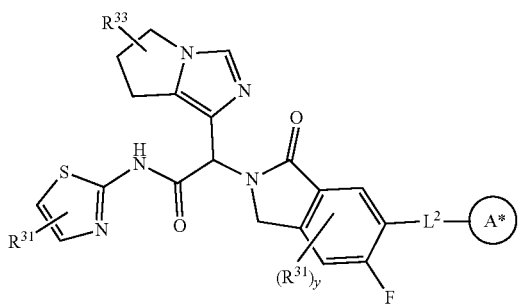
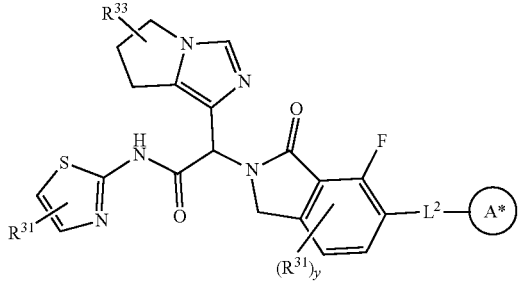
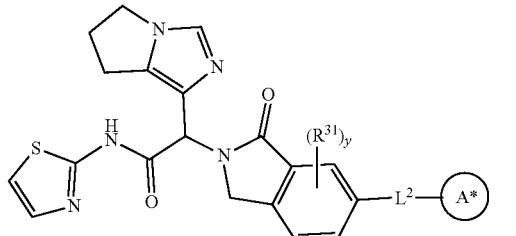
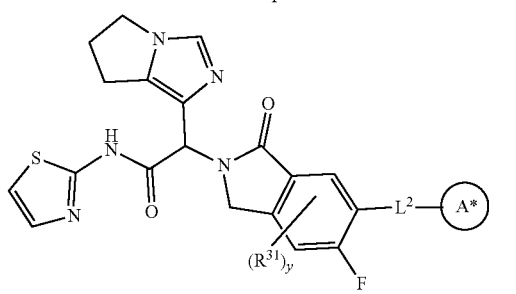

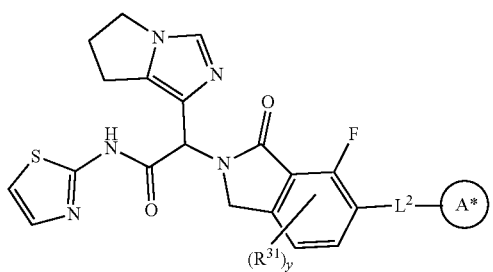
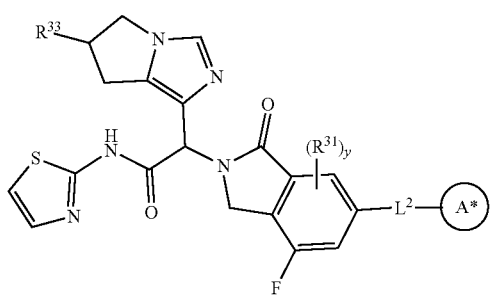
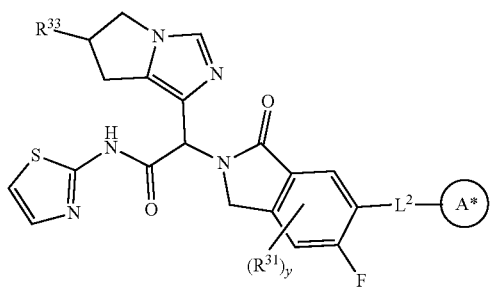
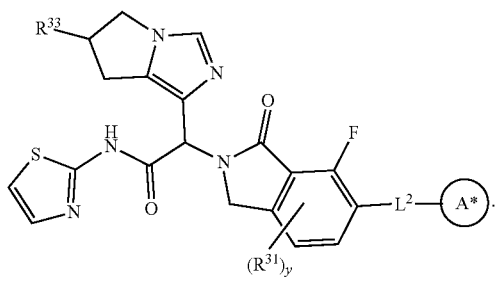
In certain embodiments the compound of the present invention is selected from:
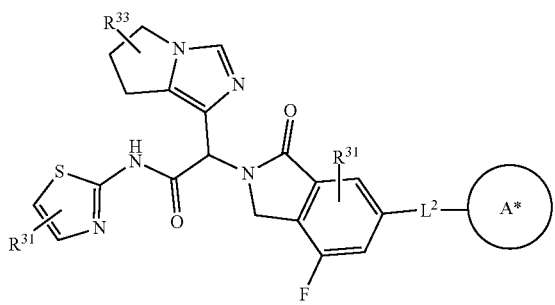
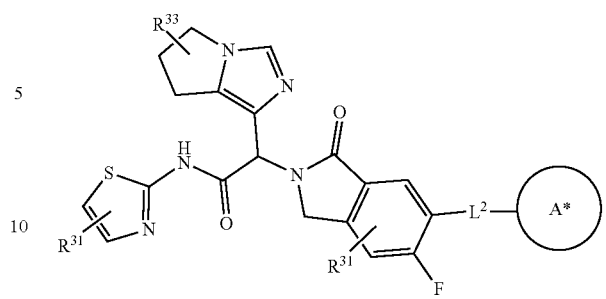
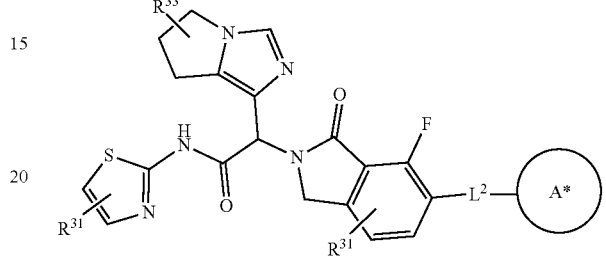
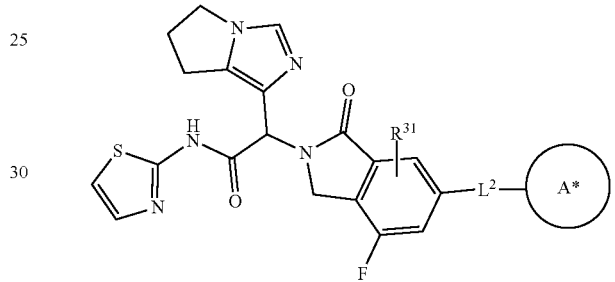
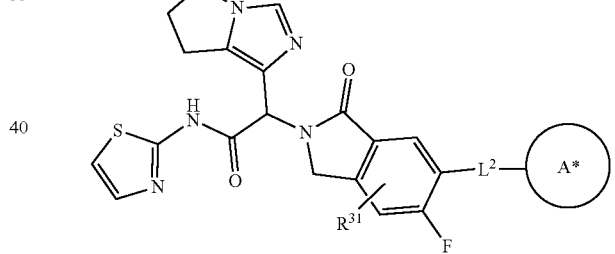
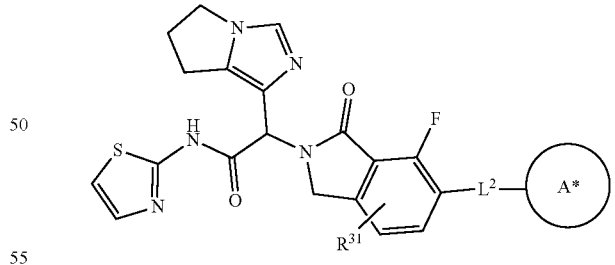
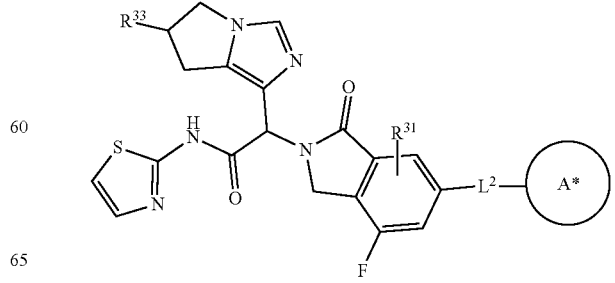

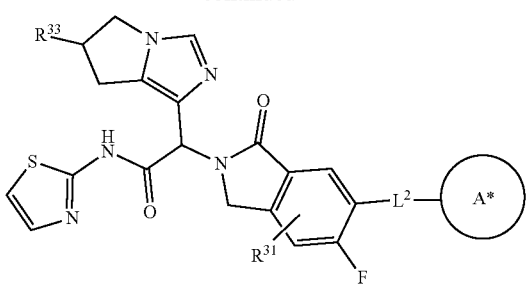
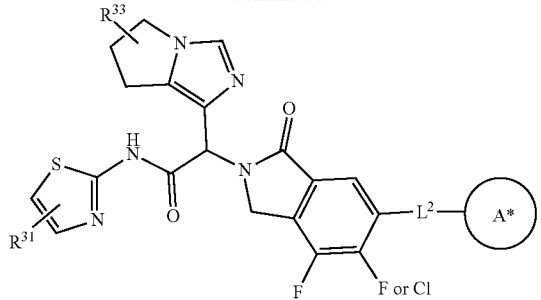
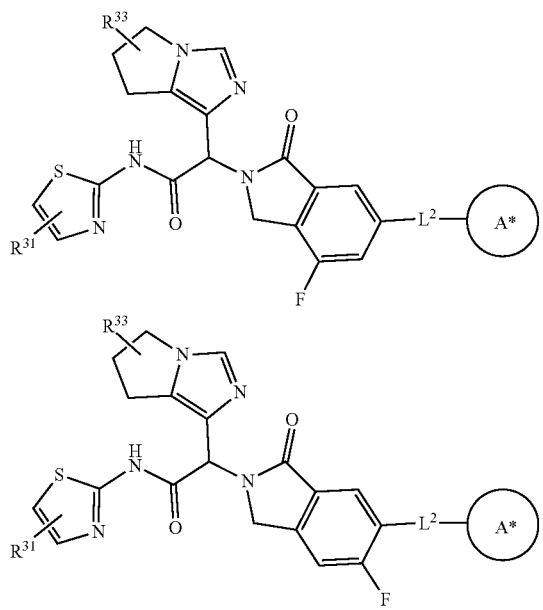
In certain embodiments the compound of the present invention is selected from:
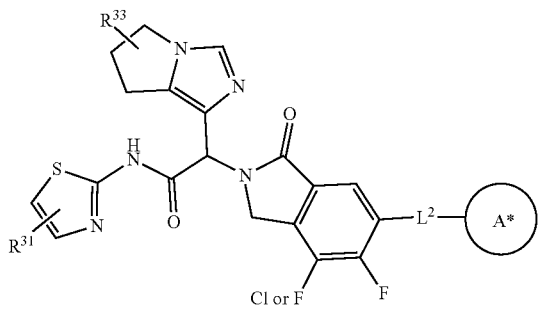
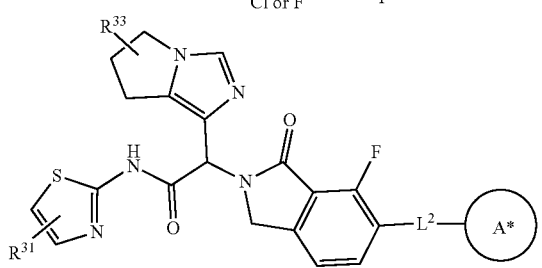
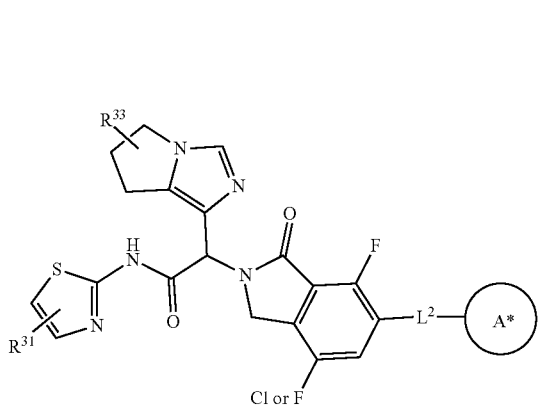
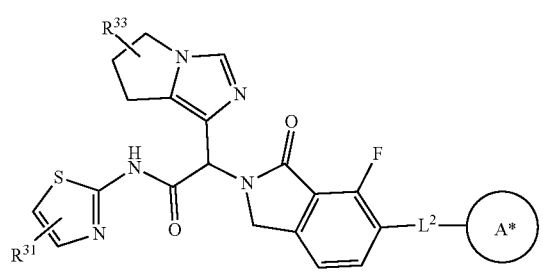
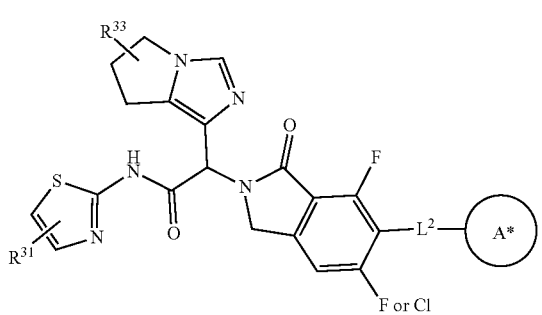

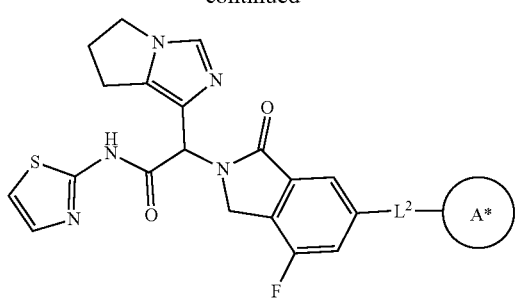
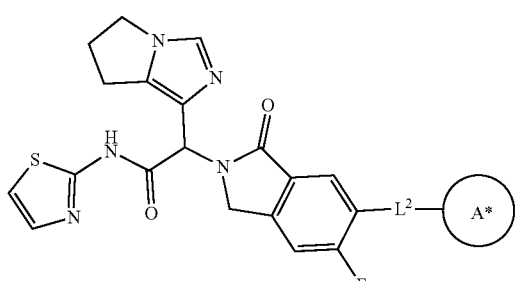
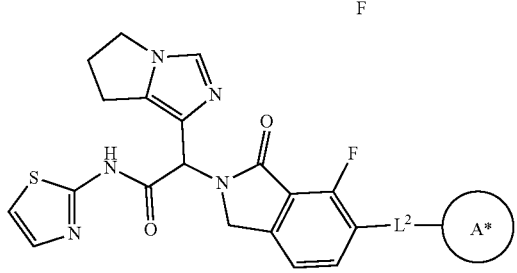
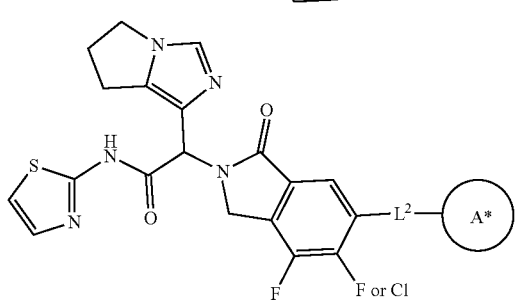
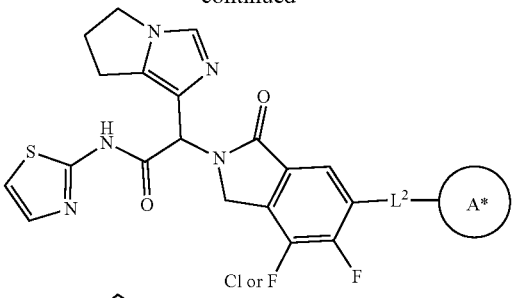
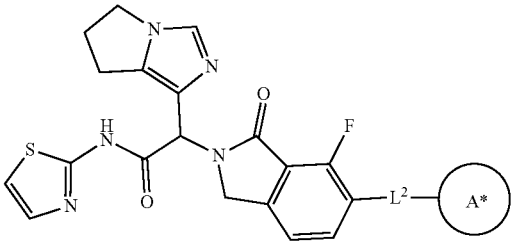
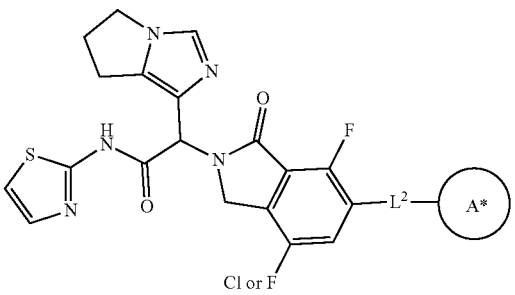
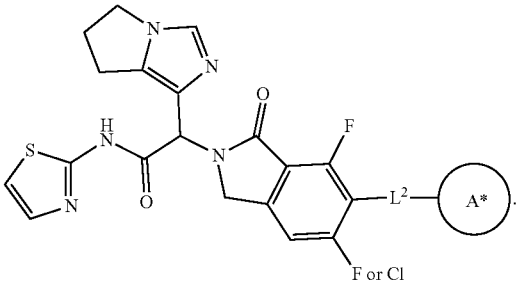
In certain embodiments the compound of the present invention is selected from:
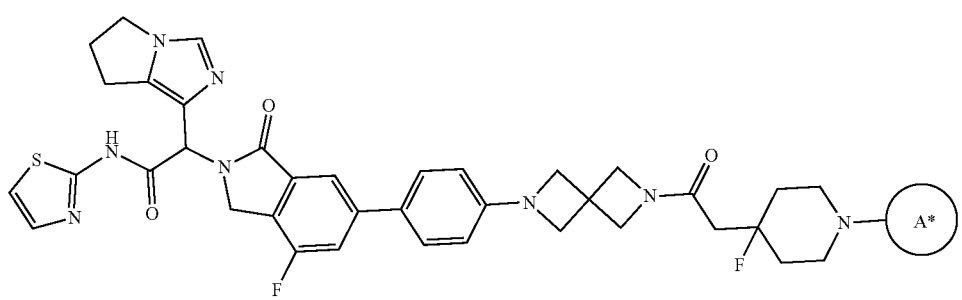

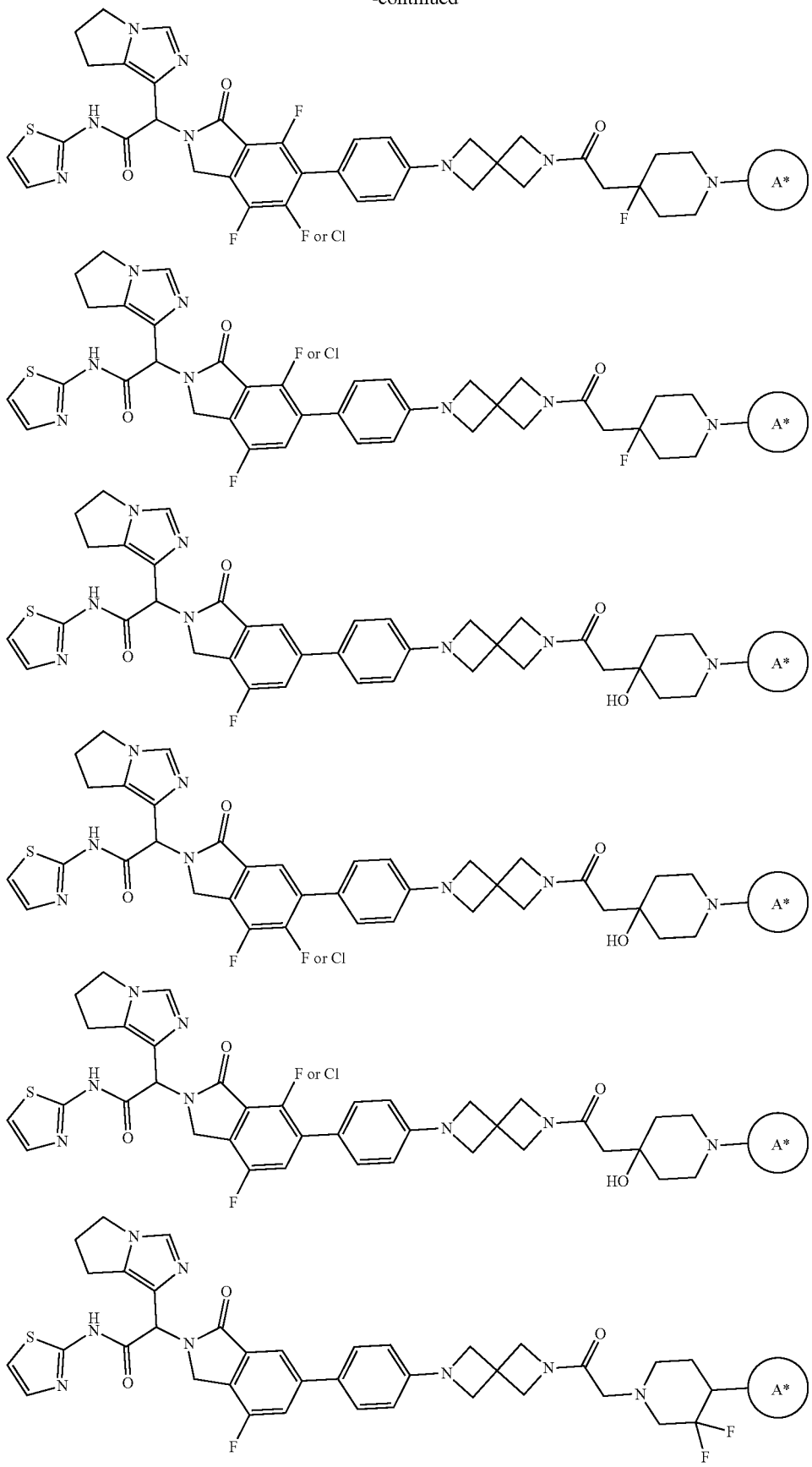

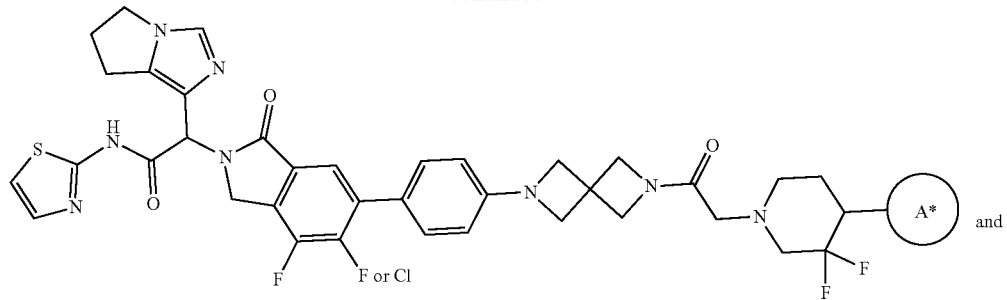
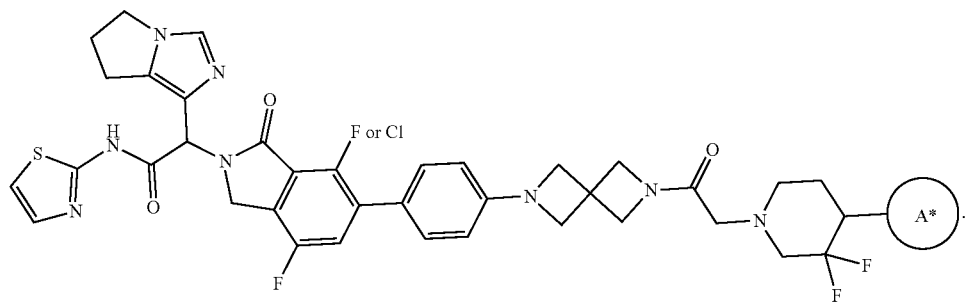
In certain embodiments the compound of the present invention is selected from:
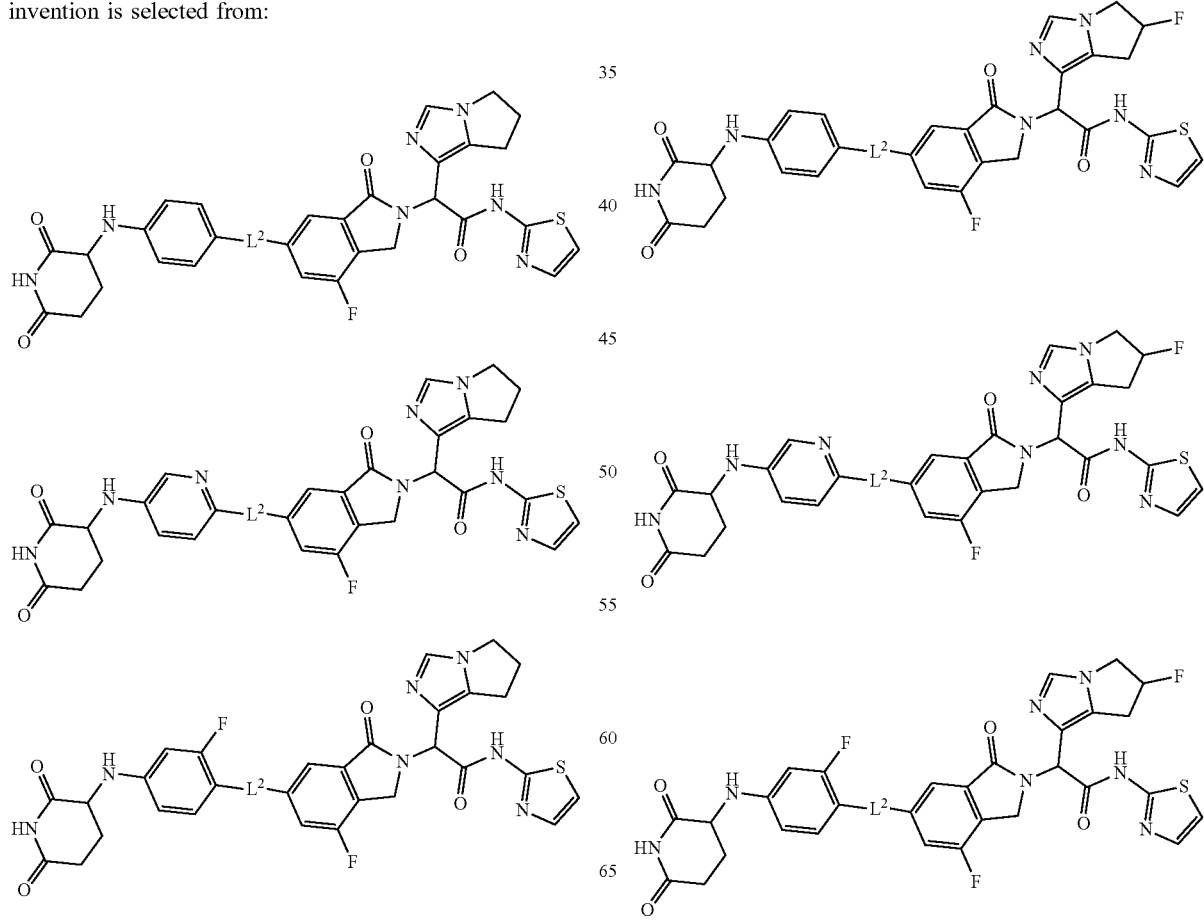

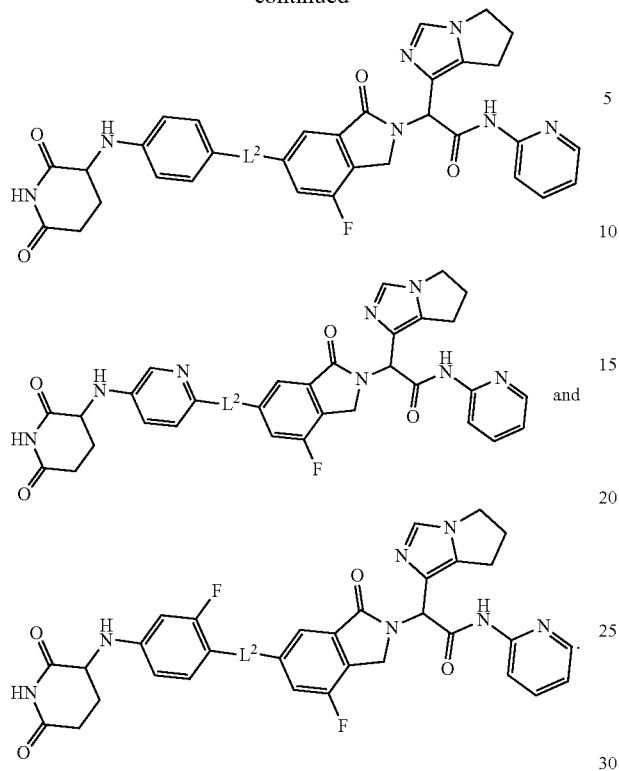
In certain embodiments the compound of the present invention is selected from:
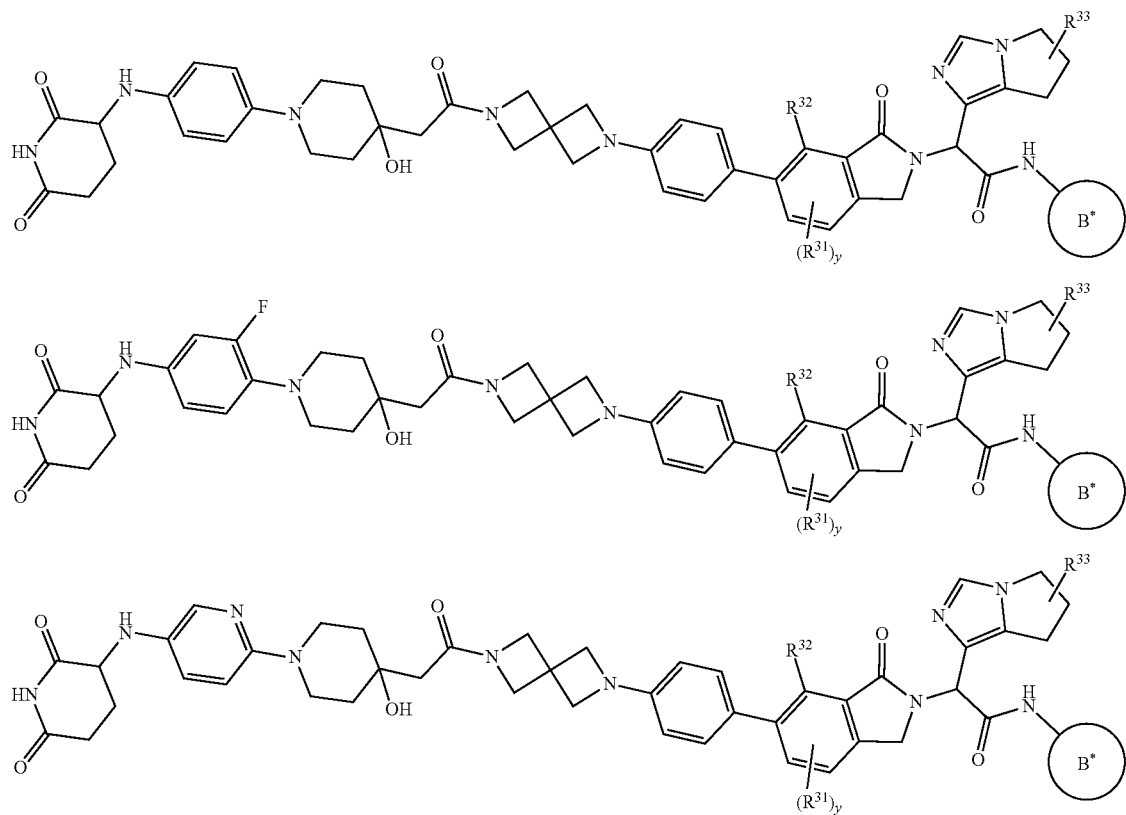

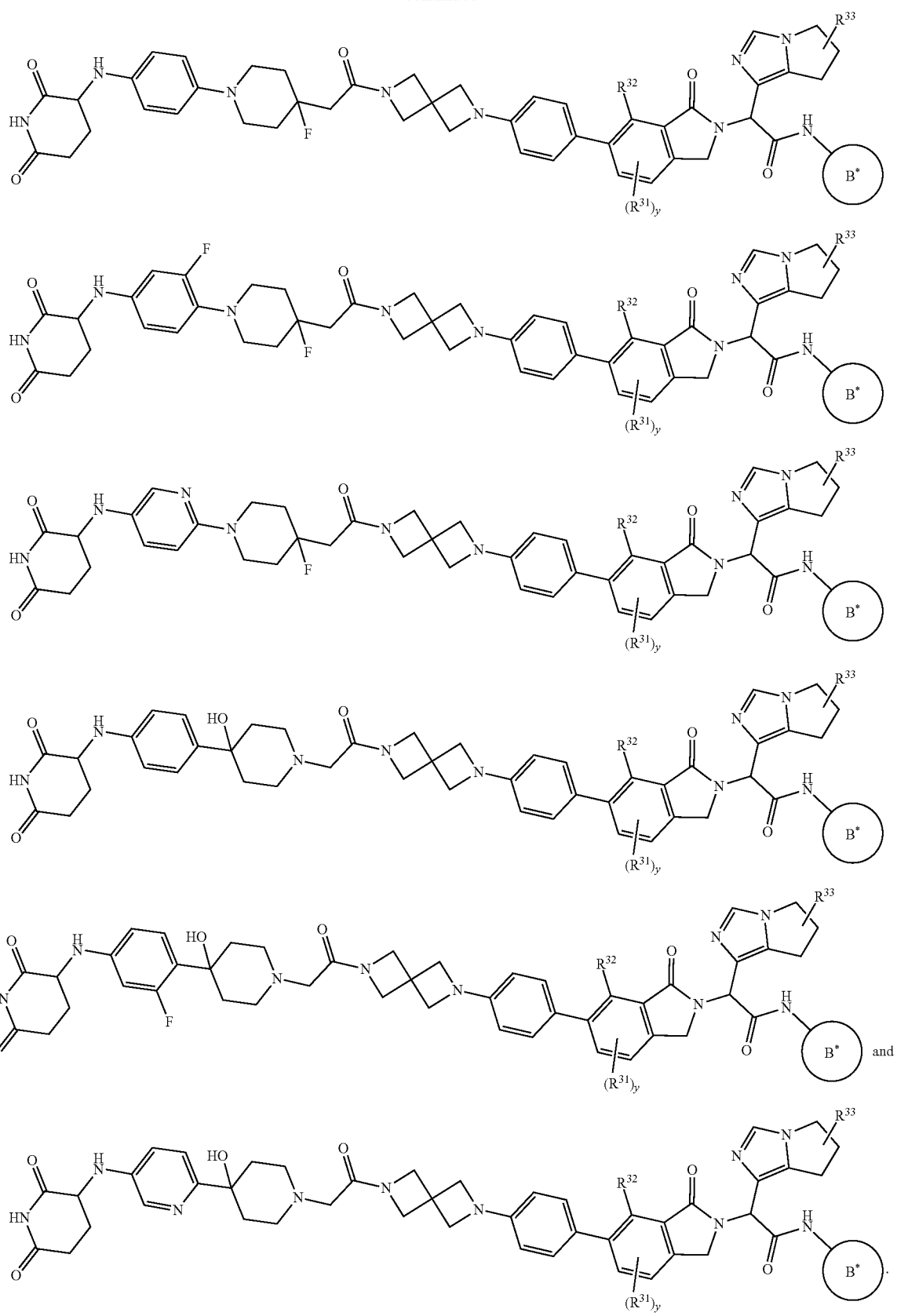

In certain embodiments the compound of the present invention is selected from:
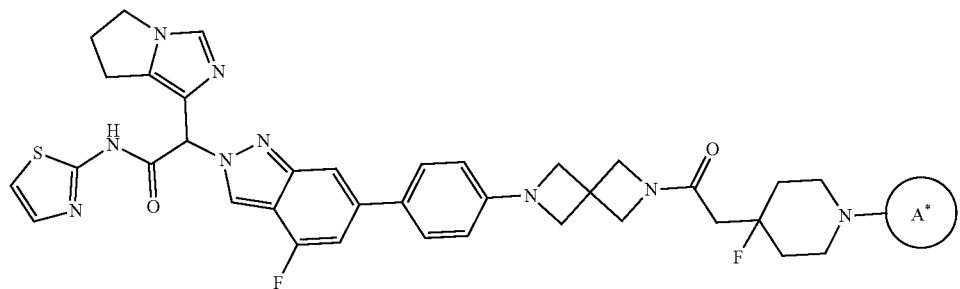
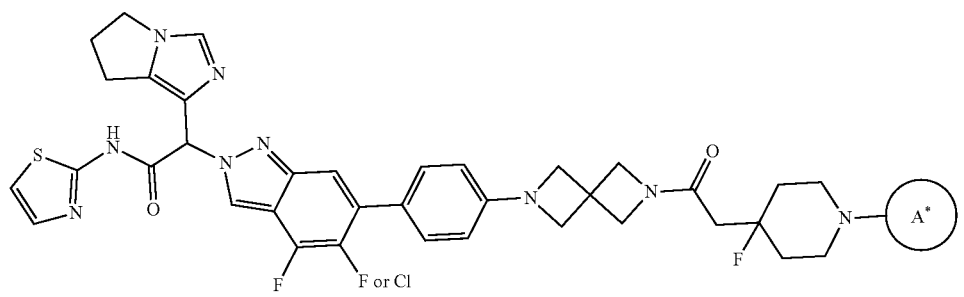
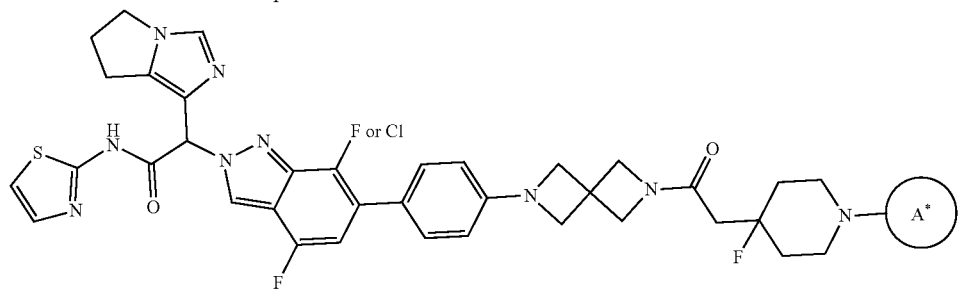
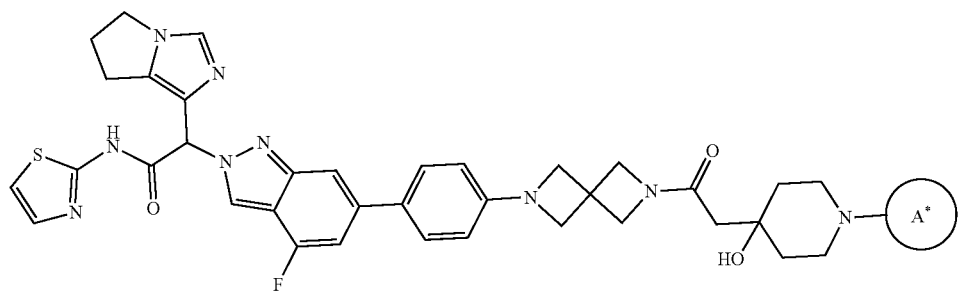
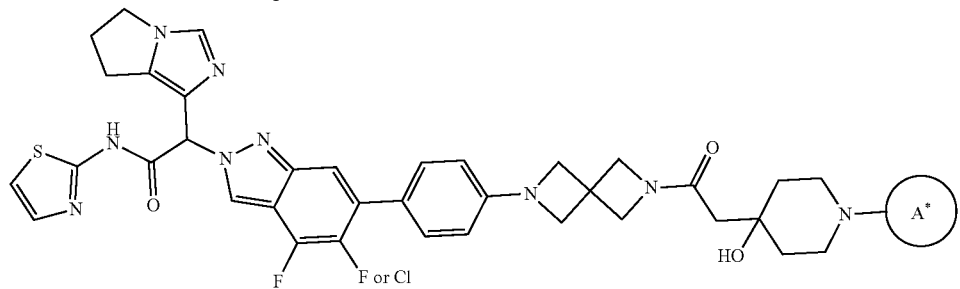

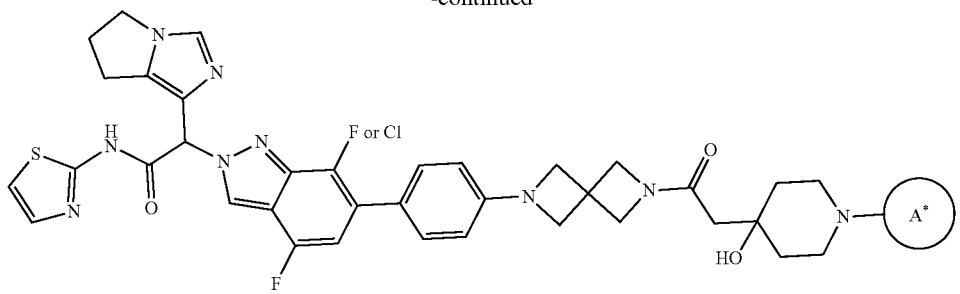
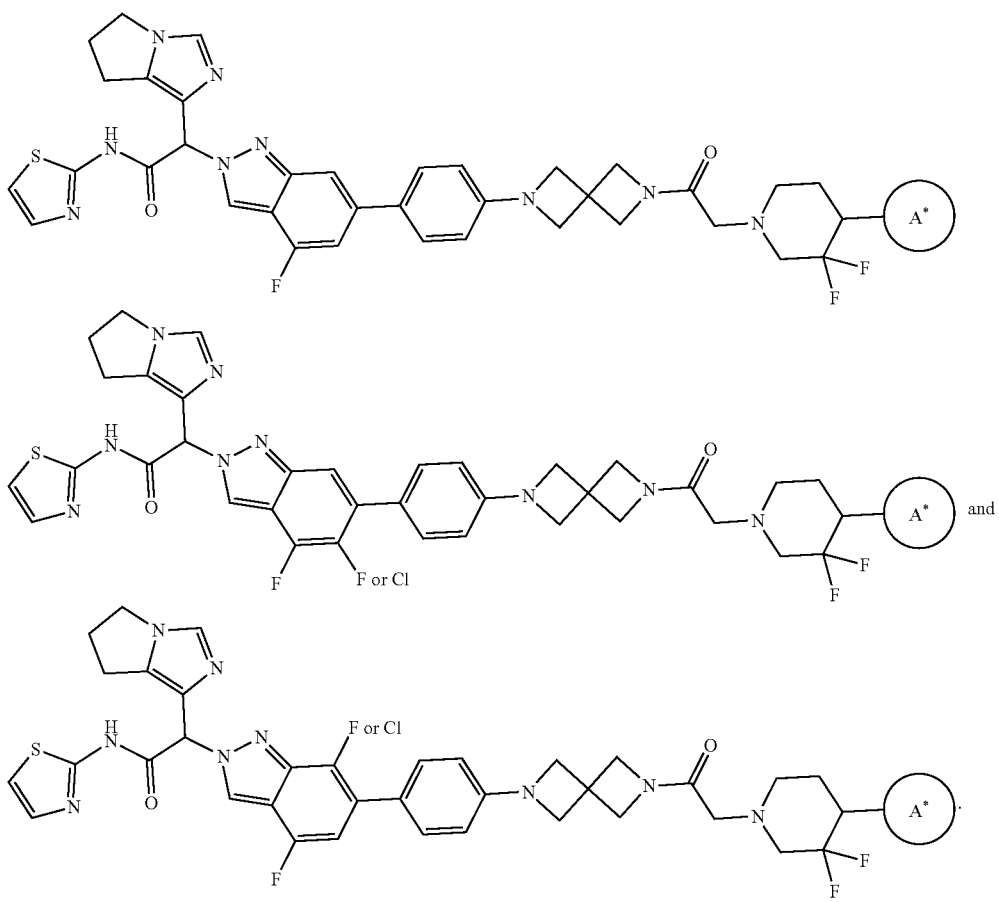
In certain embodiments the compound of the present invention is selected from:
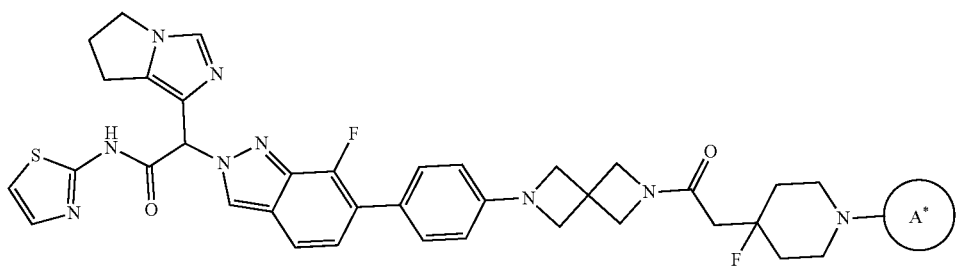

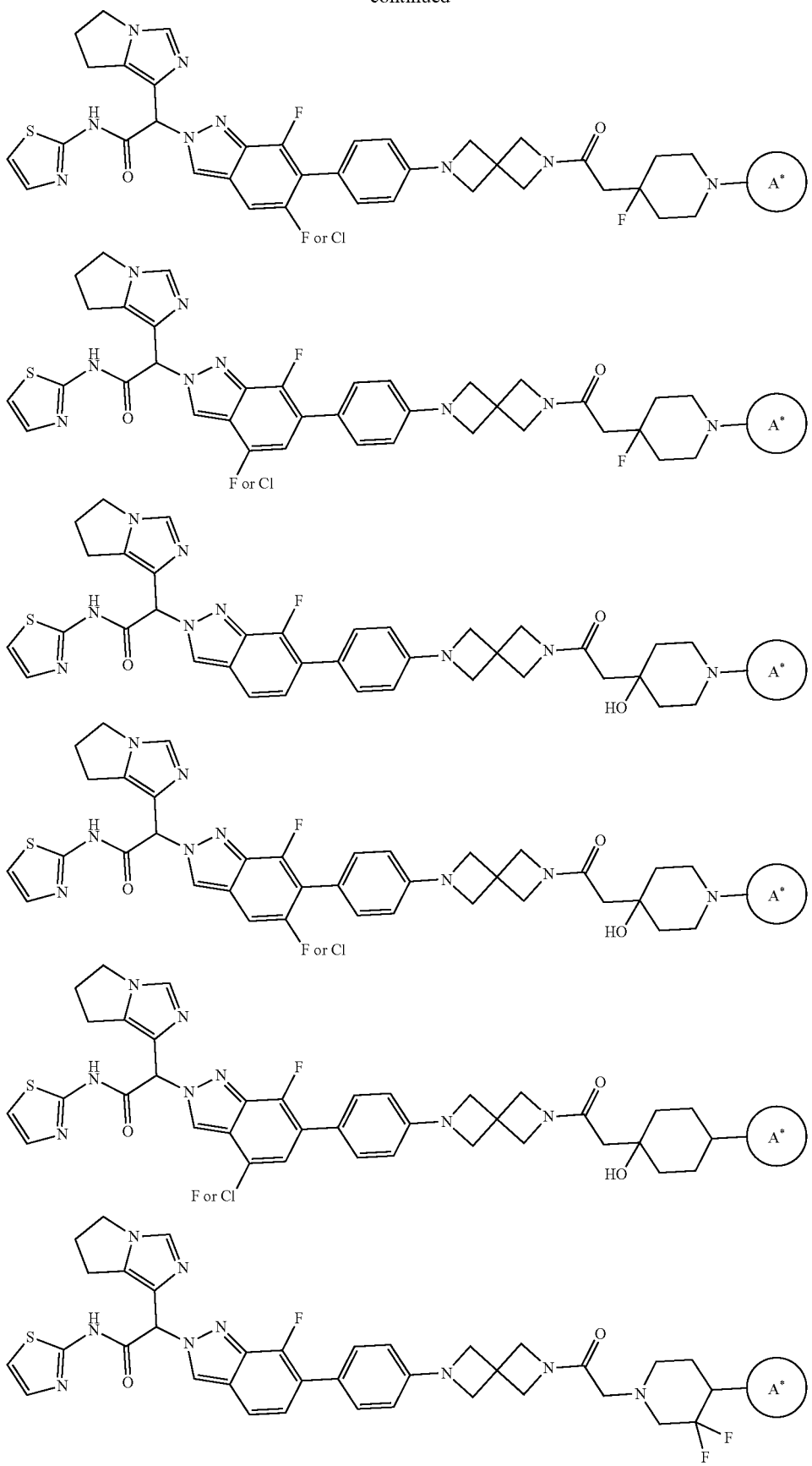

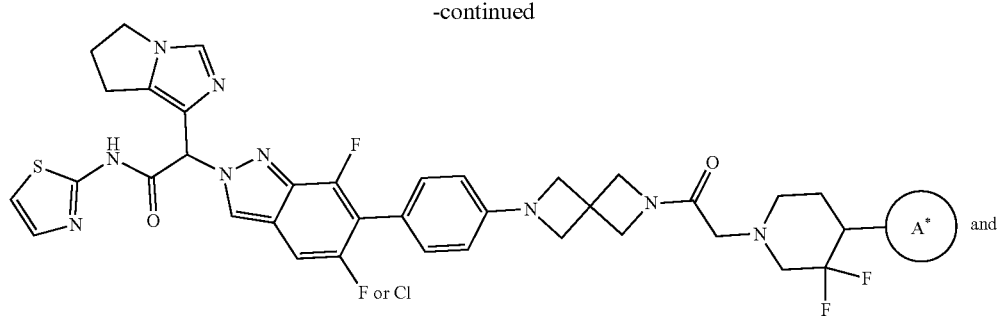
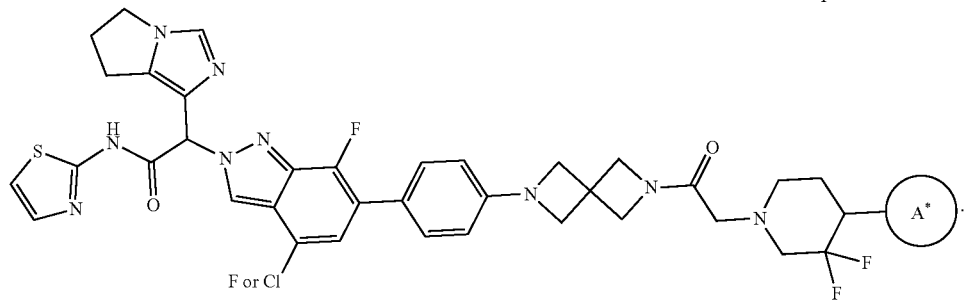
In certain embodiments the compound of the present invention is selected from:
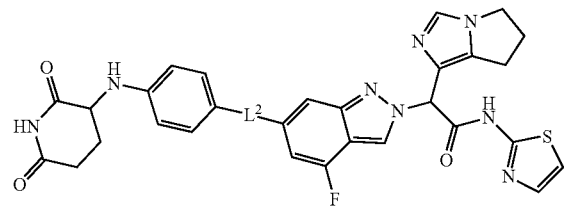
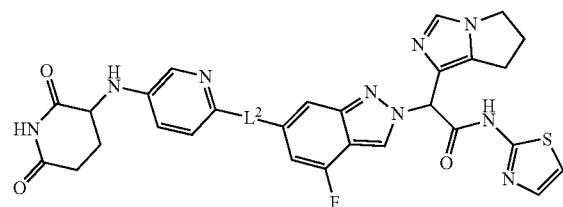
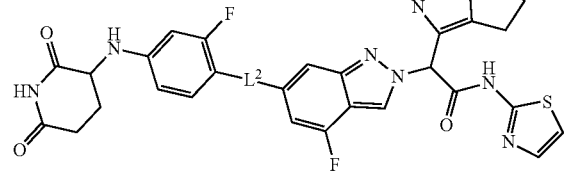
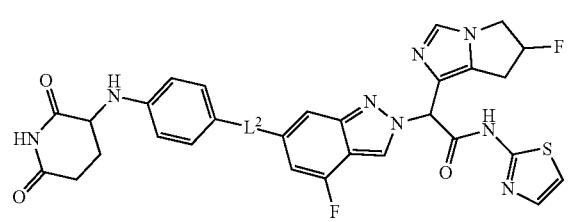
-continued
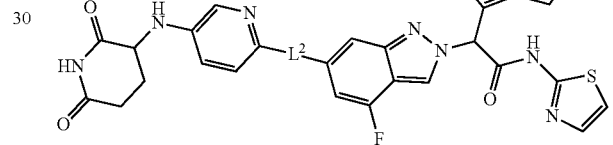
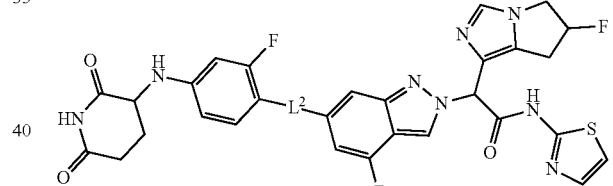
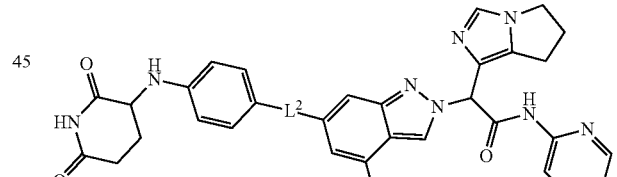
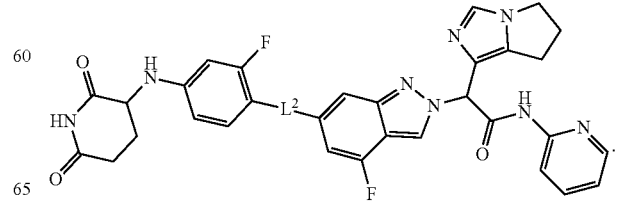

In certain embodiments the compound of the present invention is selected from:
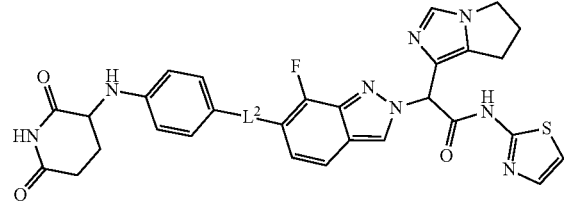
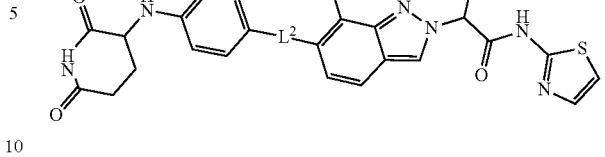
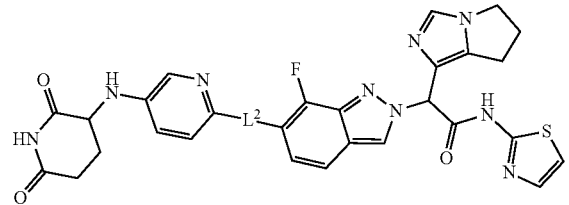
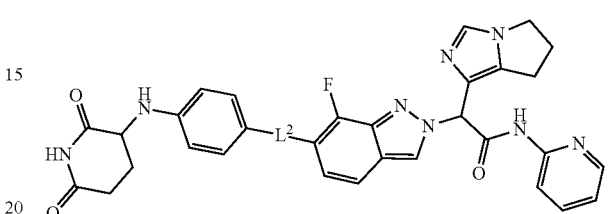
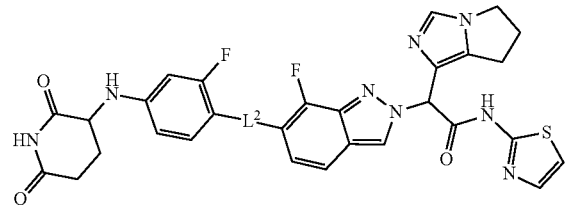
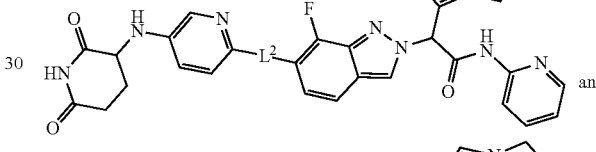
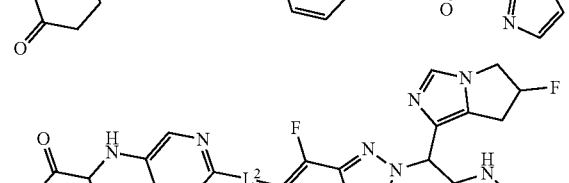
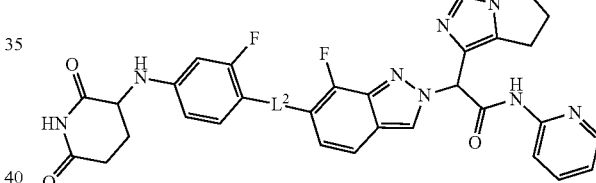
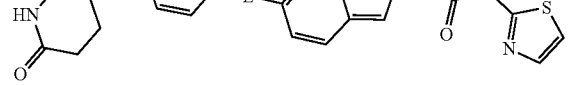
In certain embodiments the compound of the present invention is selected from:
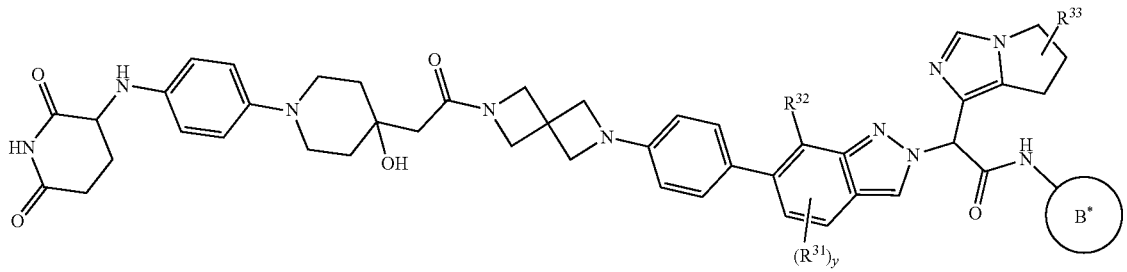
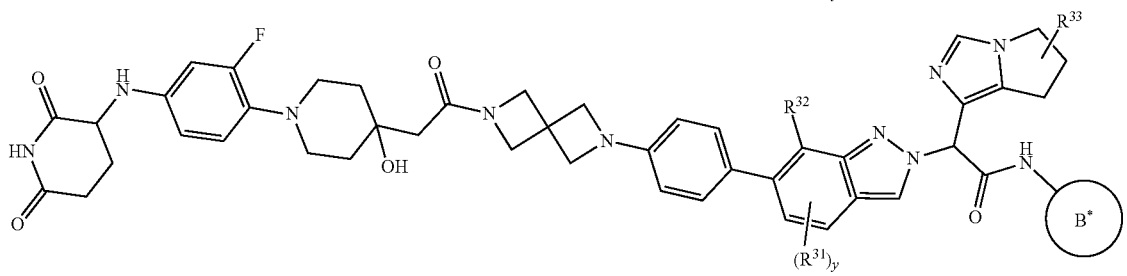

-continued
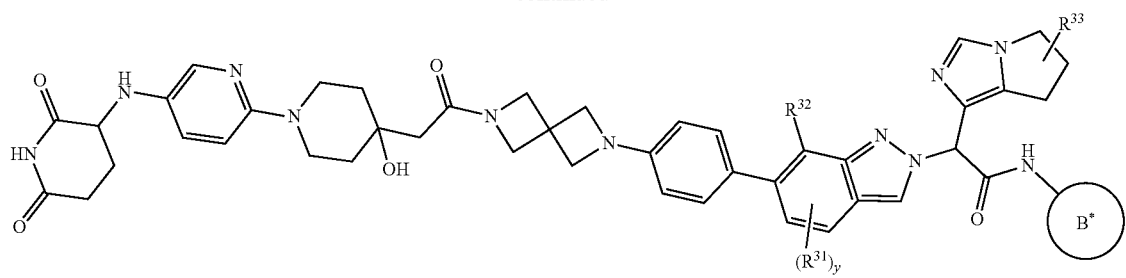
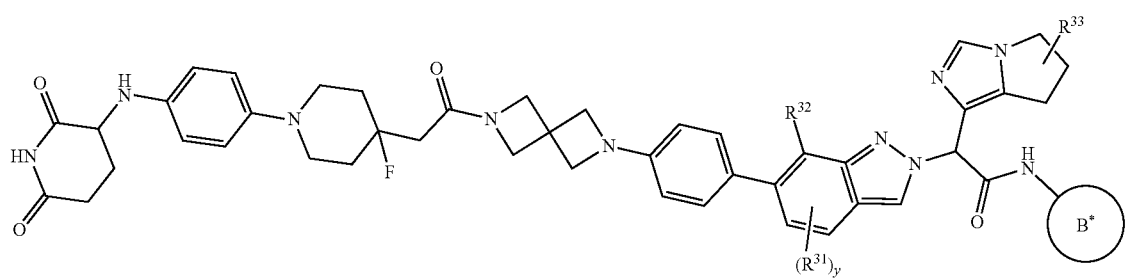
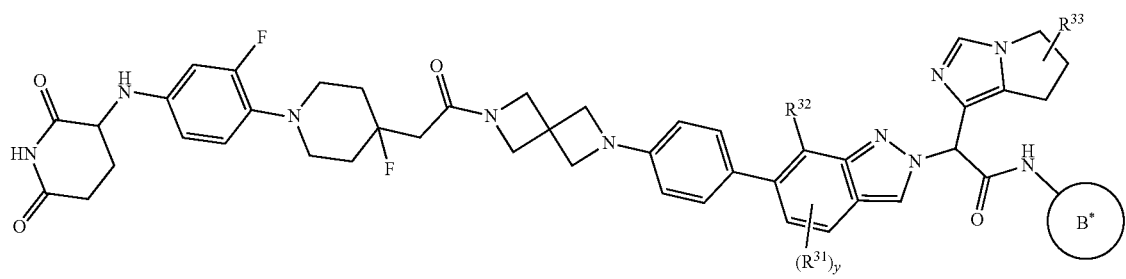
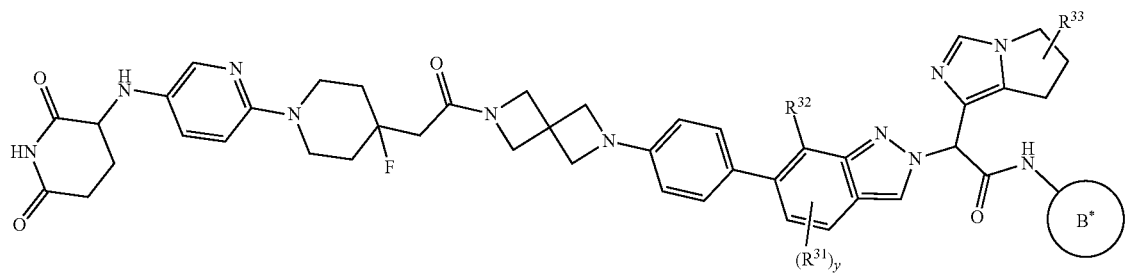
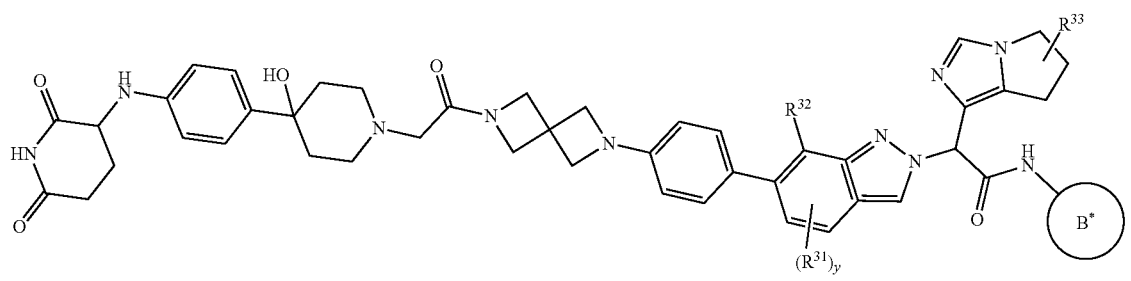
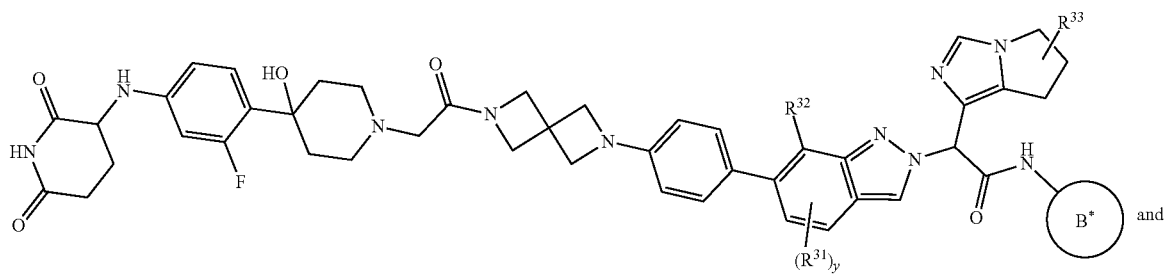
and

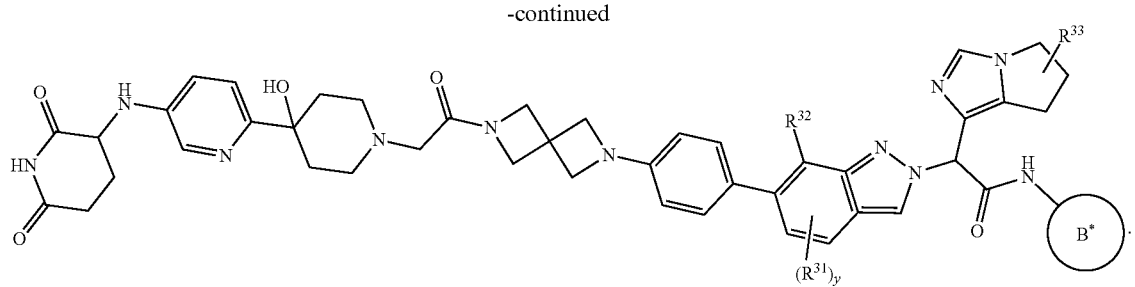
In certain embodiments the compound of the present invention is selected from:
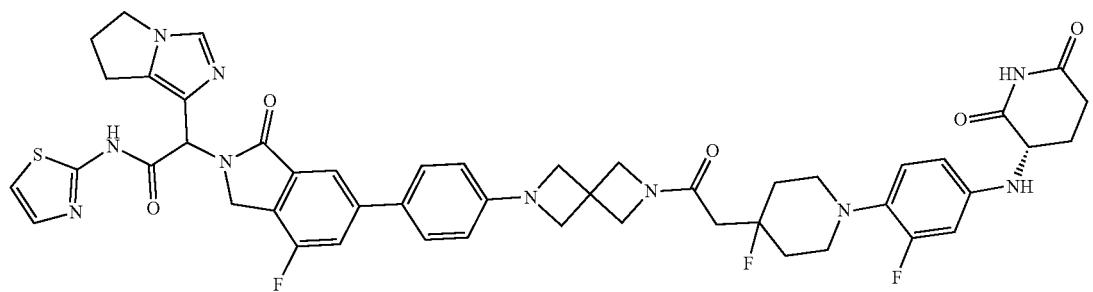
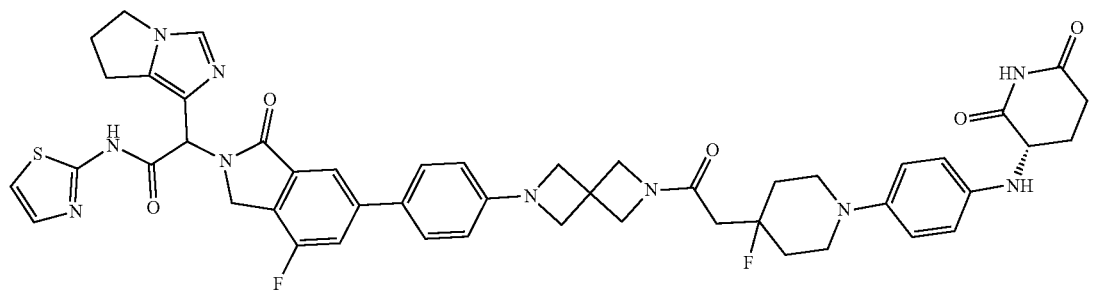
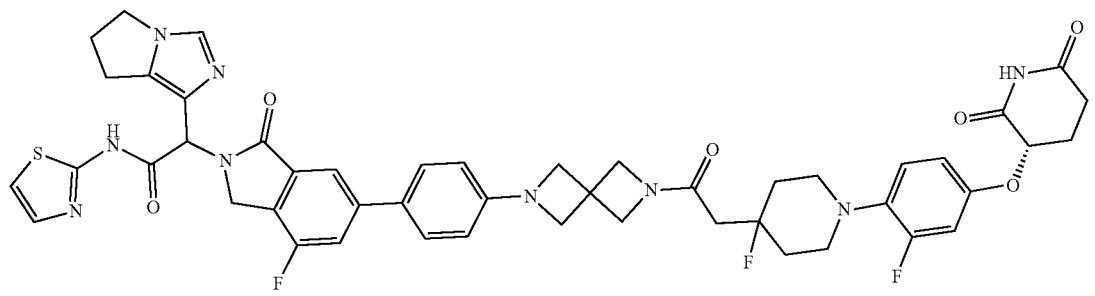
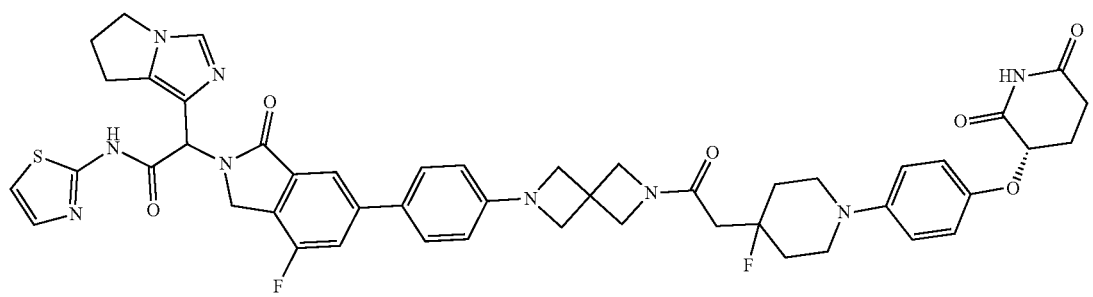

-continued
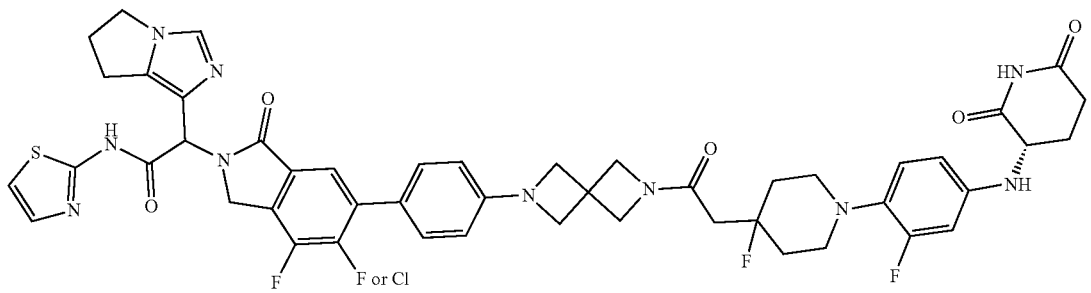
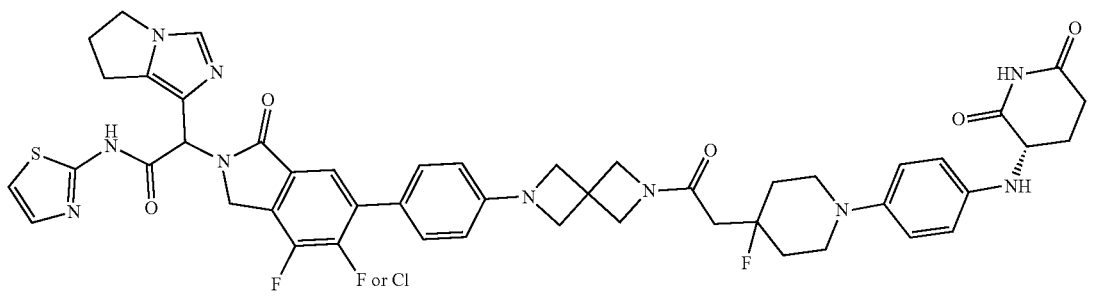
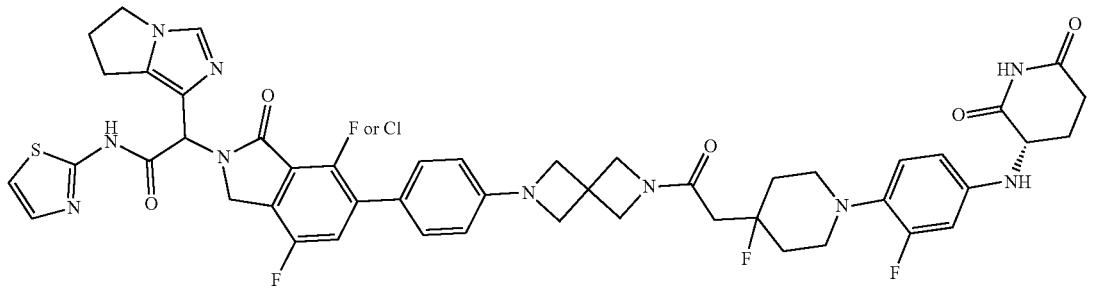
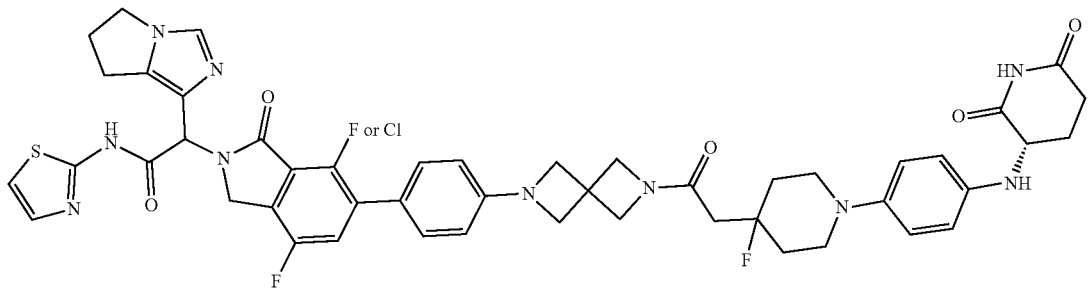
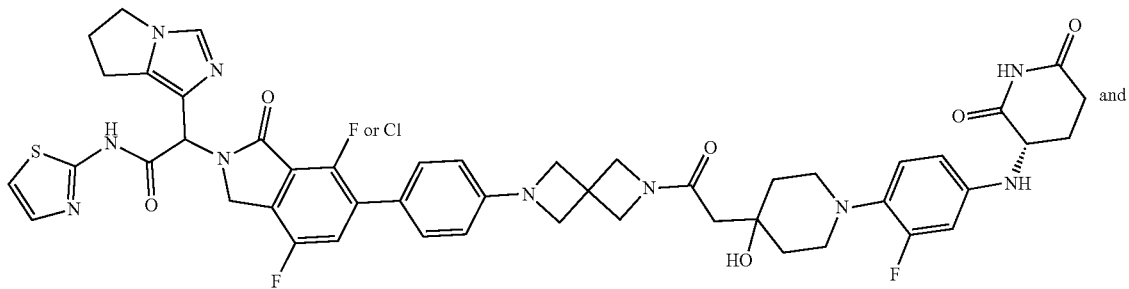
and

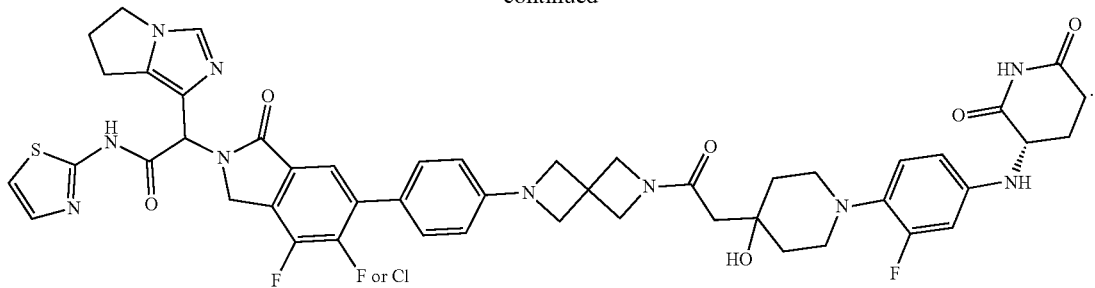
In certain embodiments the compound of the present invention is selected from:
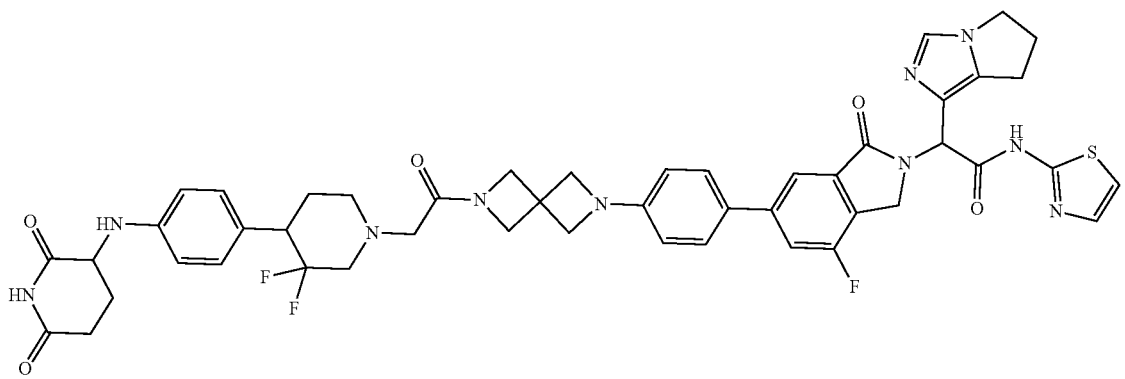
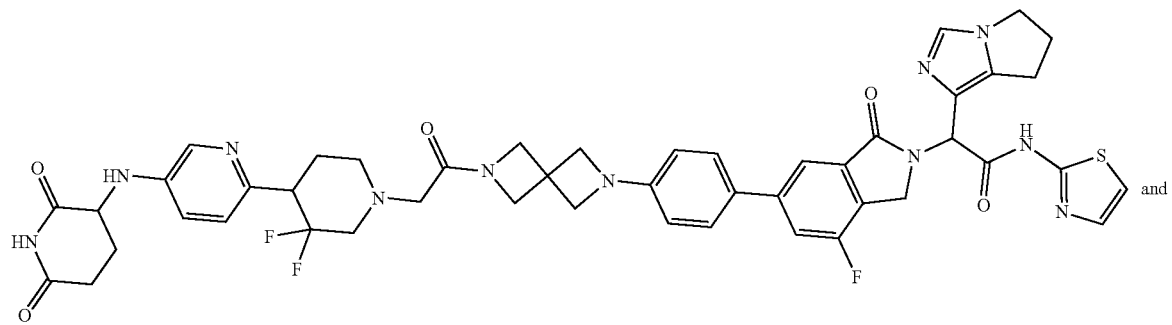
and
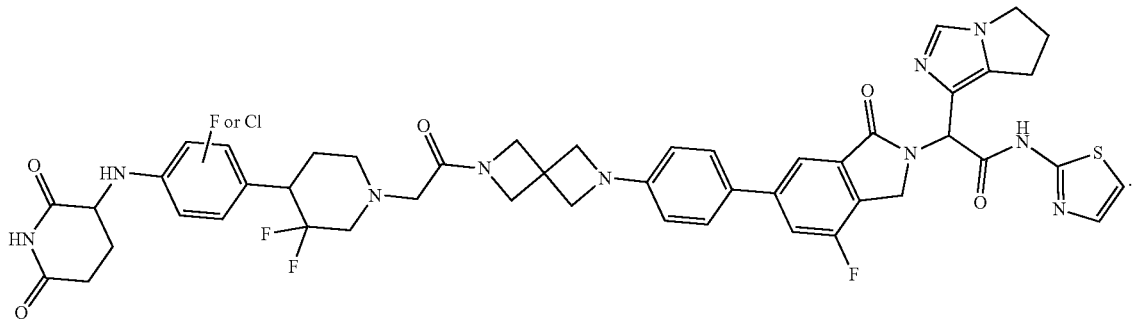

In certain embodiments the compound of the present invention is selected from:
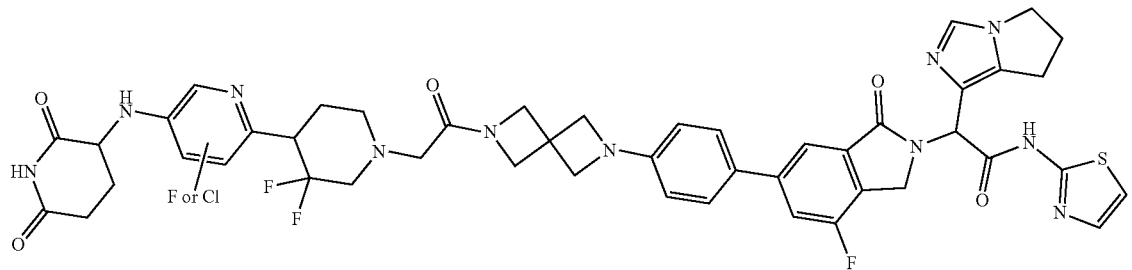
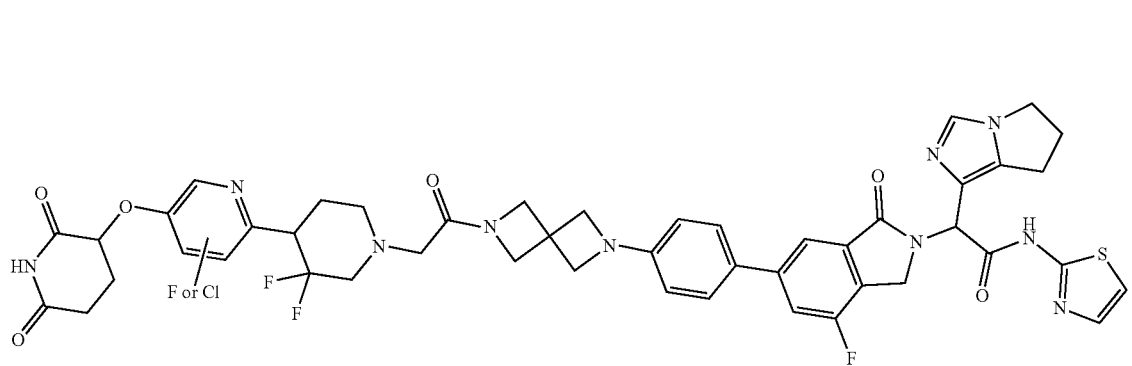
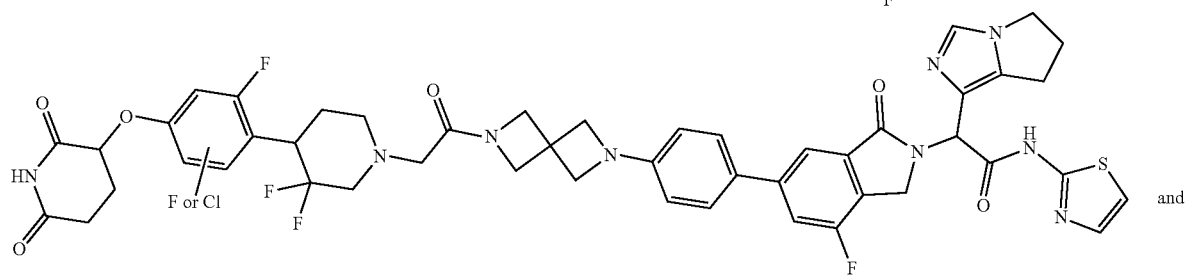
and
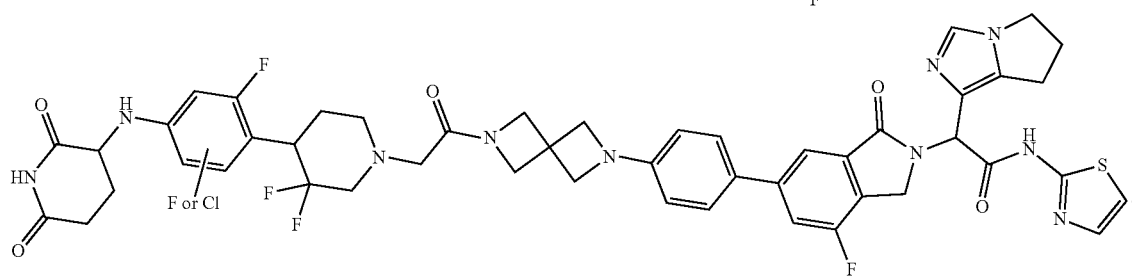
In certain embodiments the compound of the present invention is selected from:
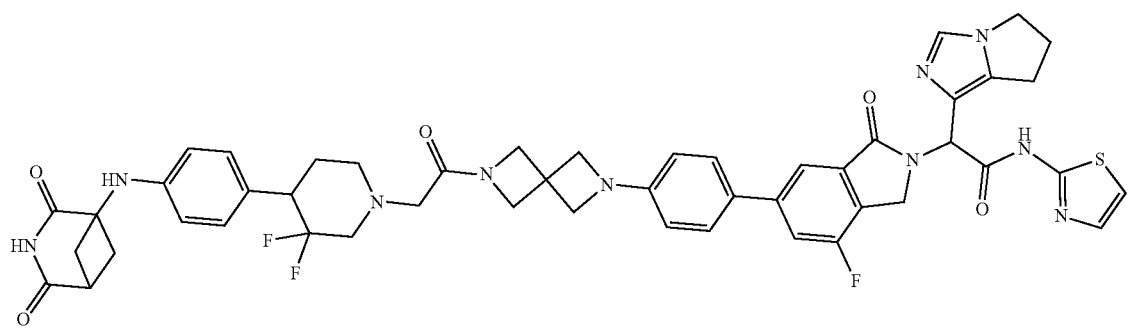

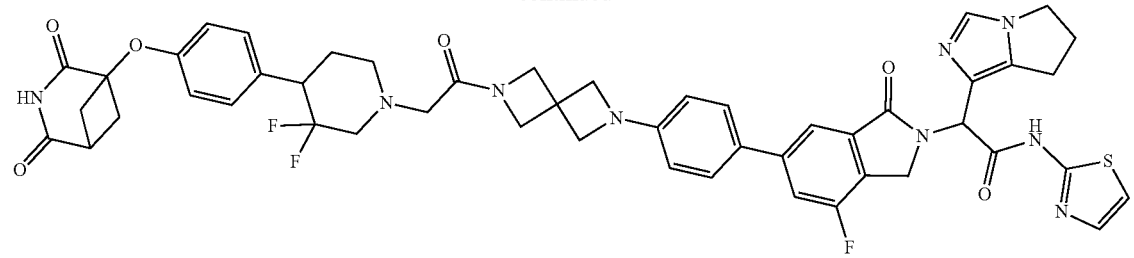
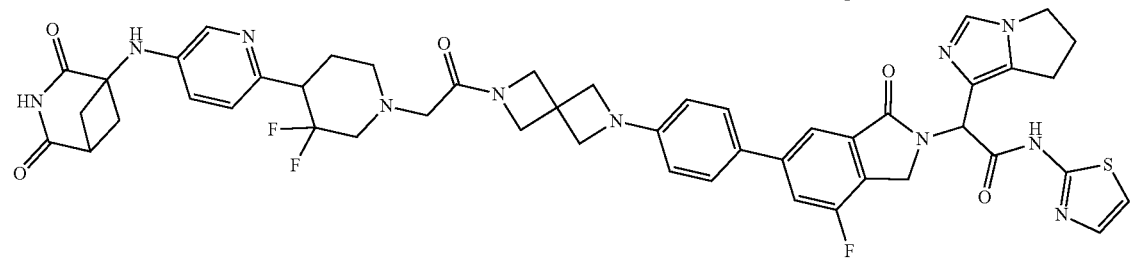
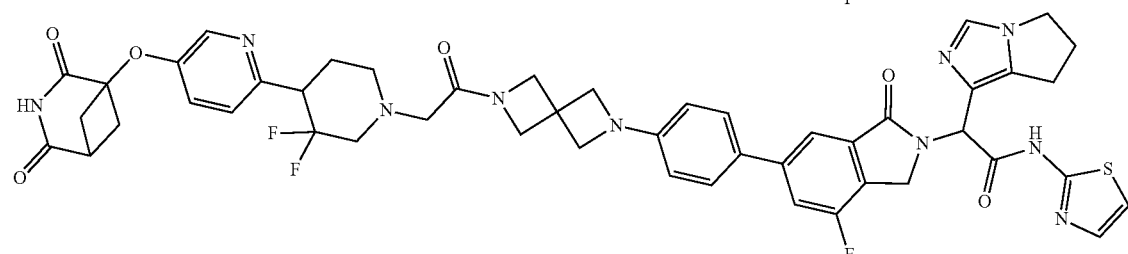
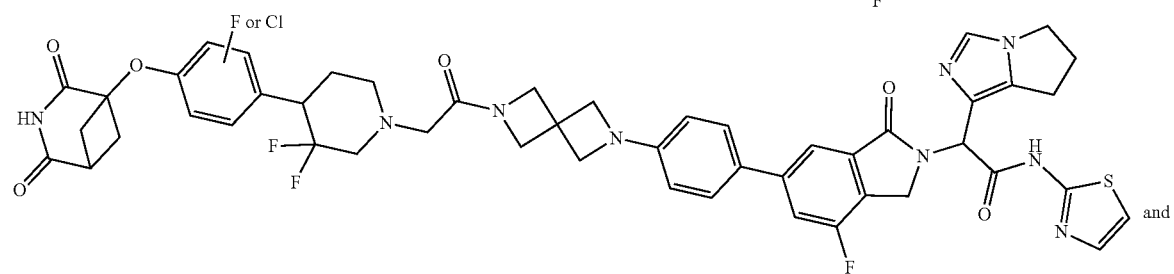
and
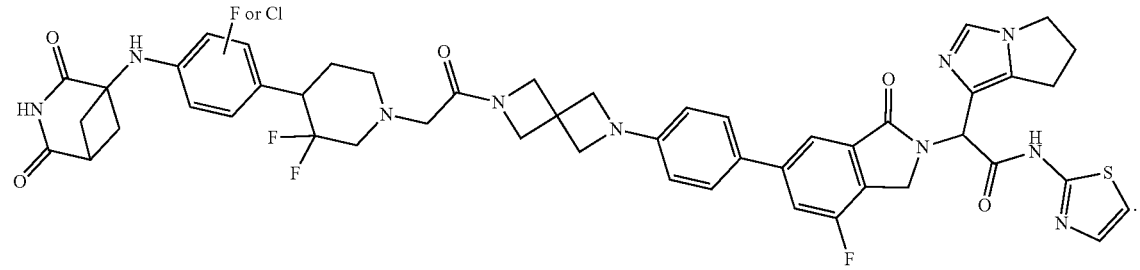
In certain embodiments the compound of the present invention is selected from:
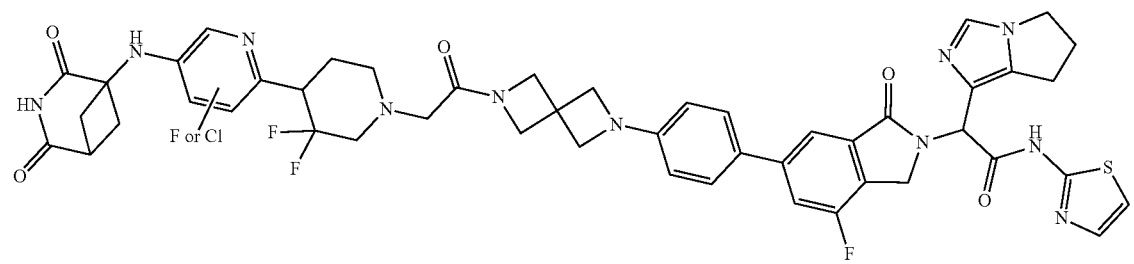

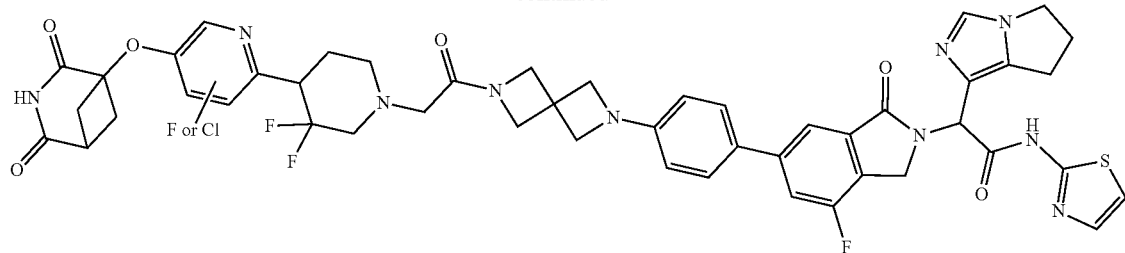
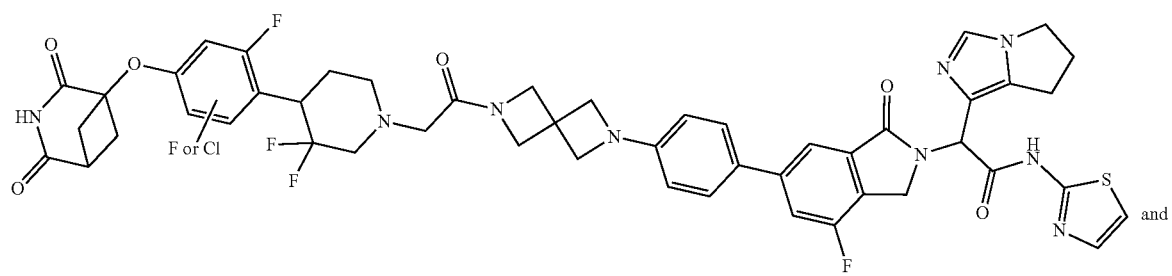
and
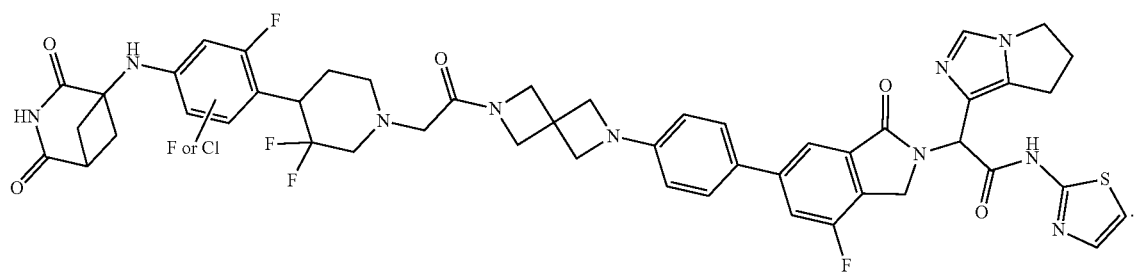
In certain embodiments the compound of the present invention is selected from:
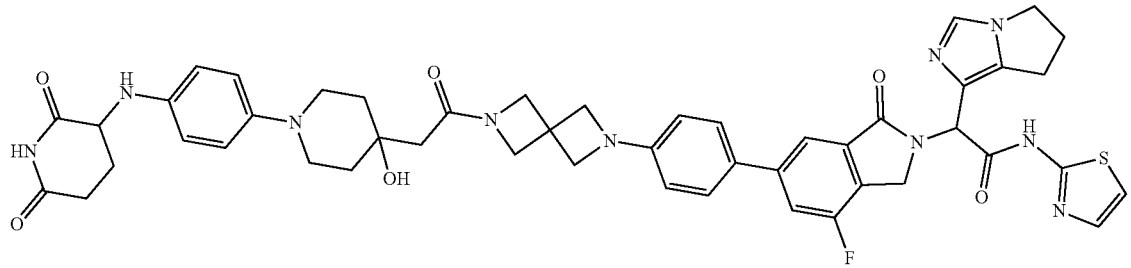
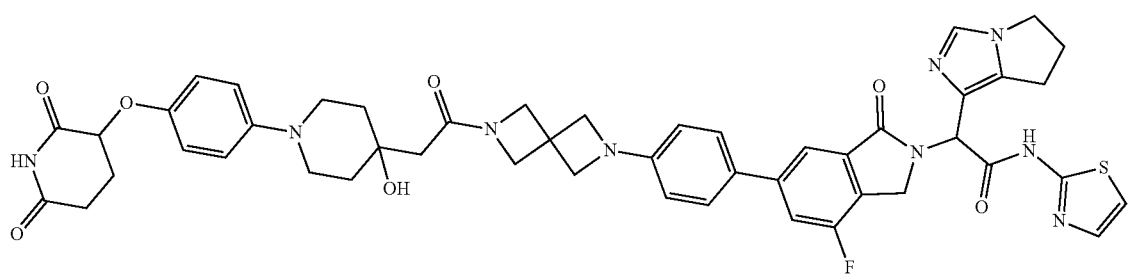

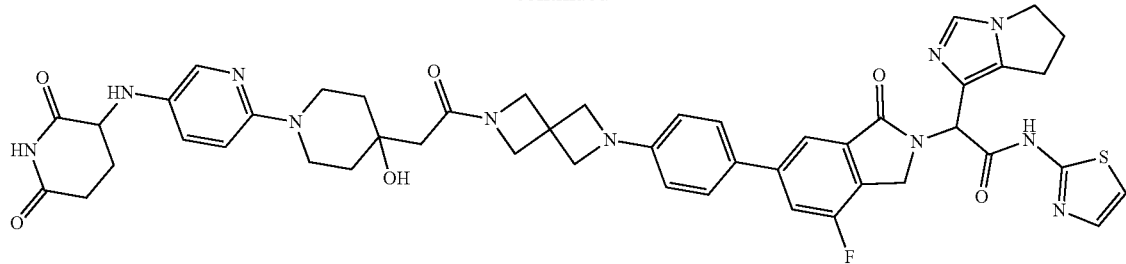
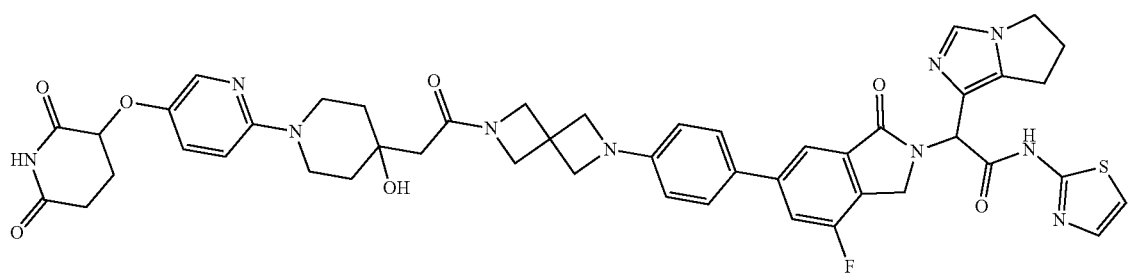
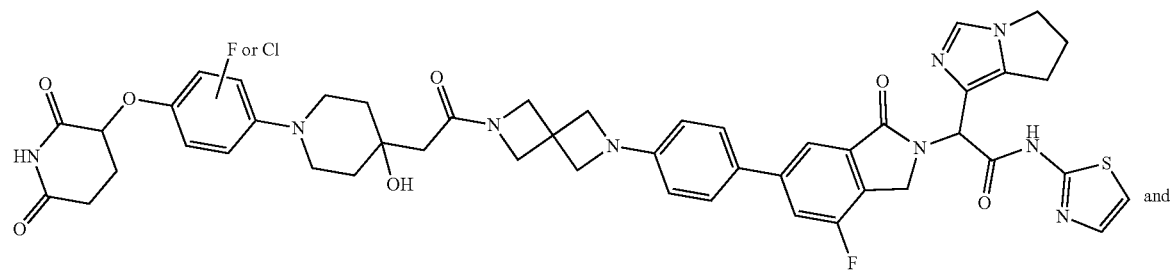
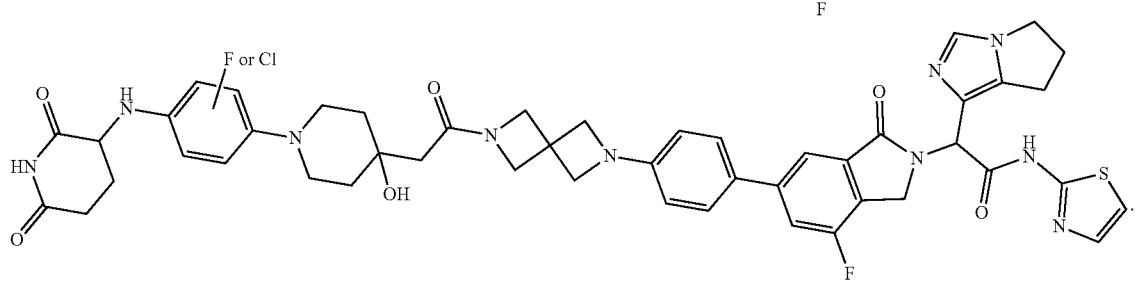
In certain embodiments the compound of the present invention is selected from:
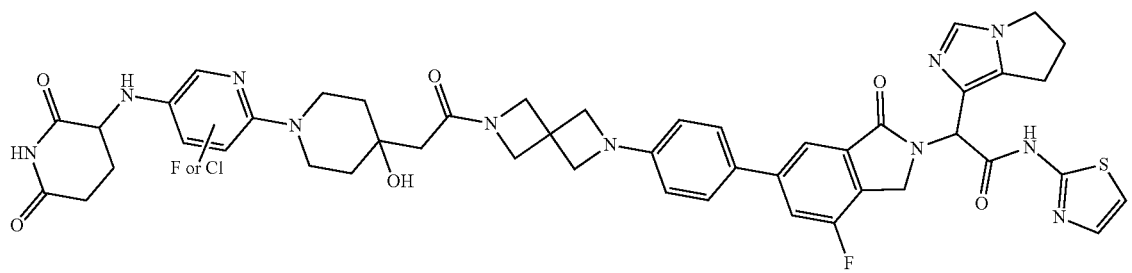

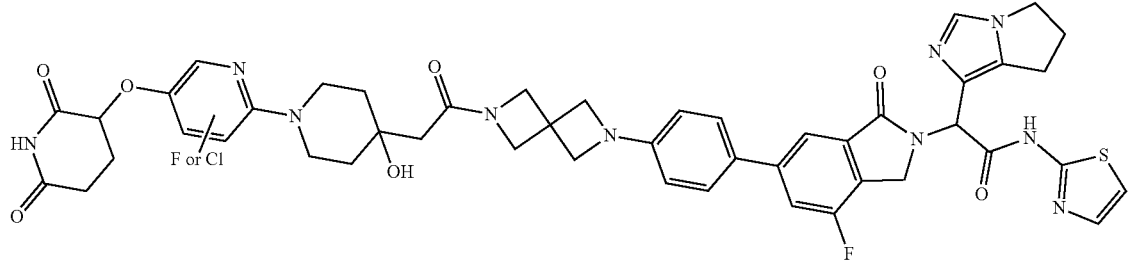
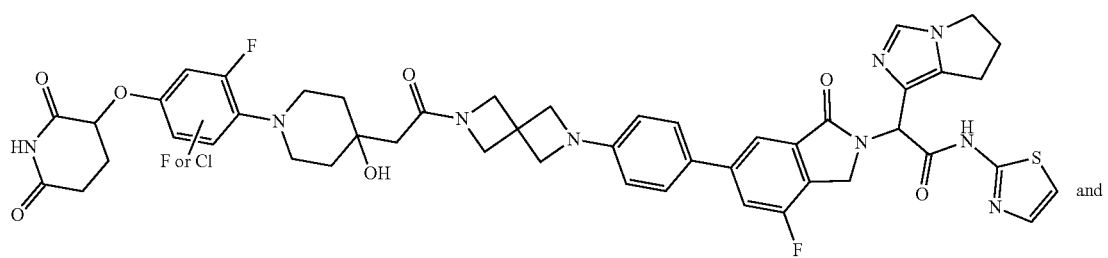 and
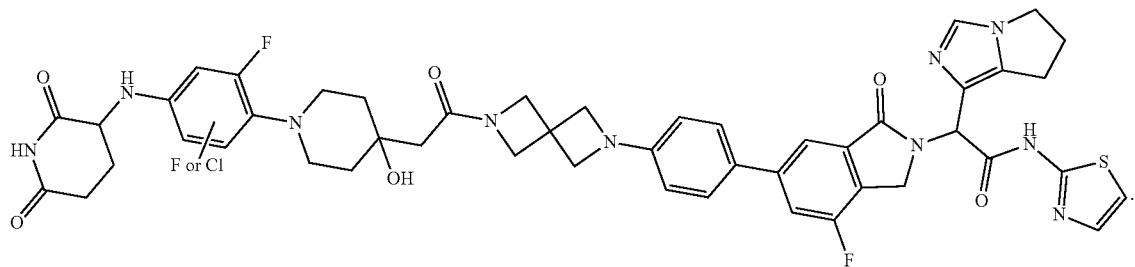
In certain embodiments the compound of the present invention is selected from:
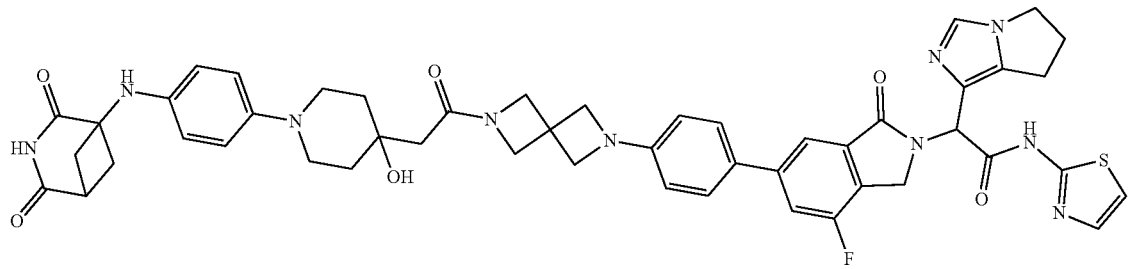
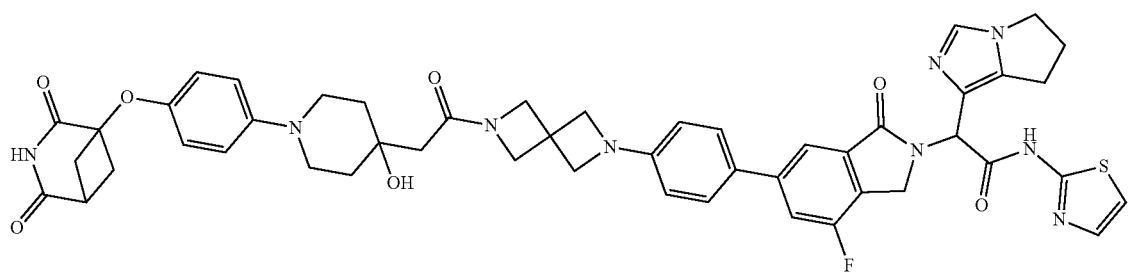

-continued
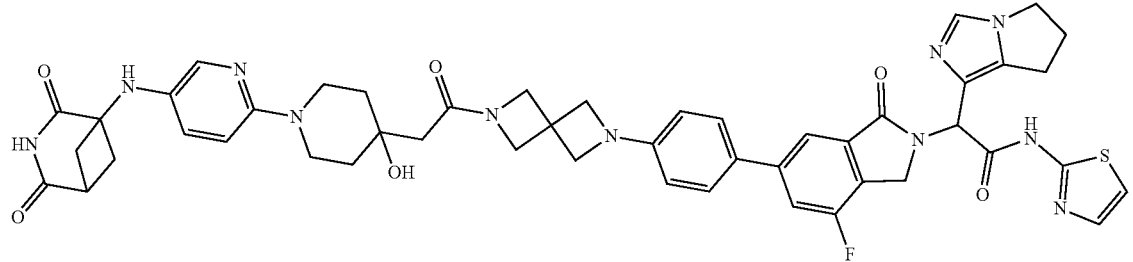
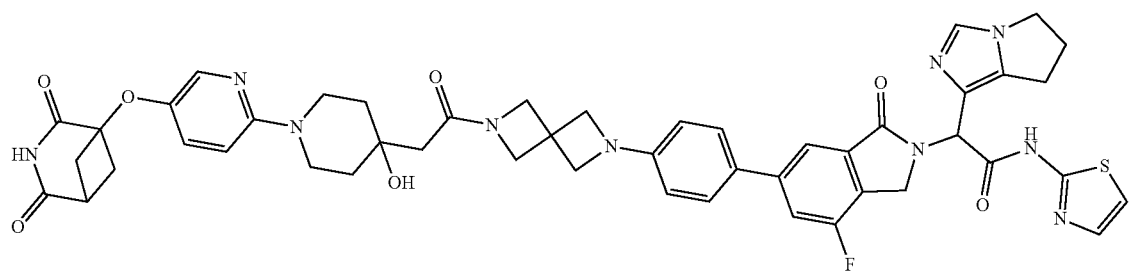
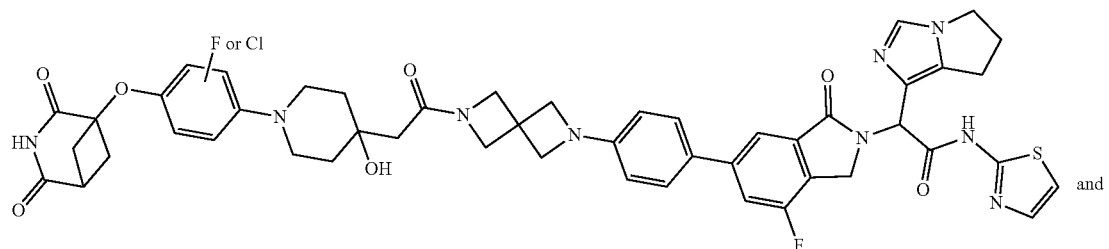
and
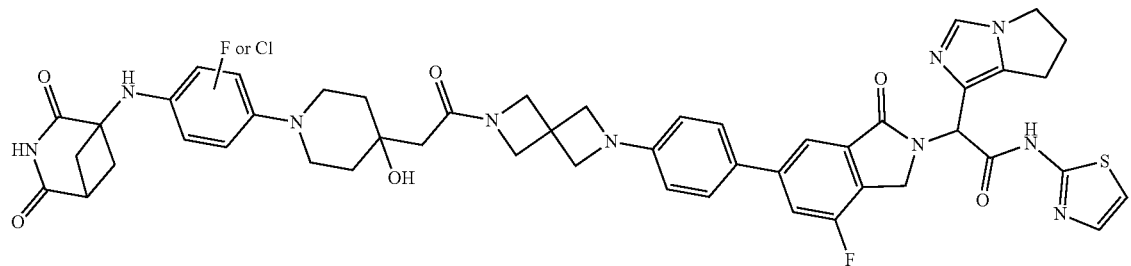
In certain embodiments the compound of the present invention is selected from:
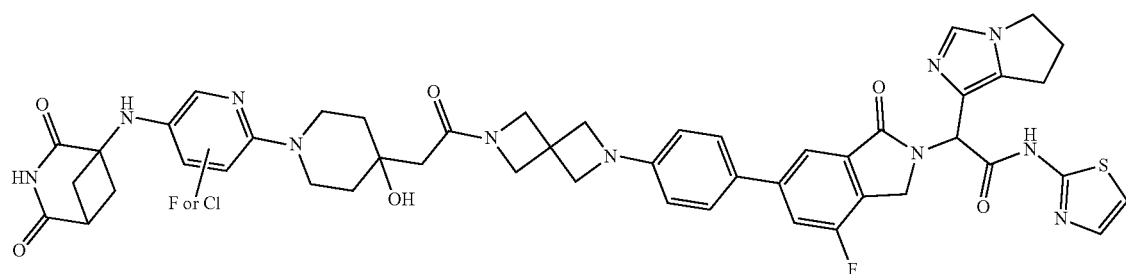

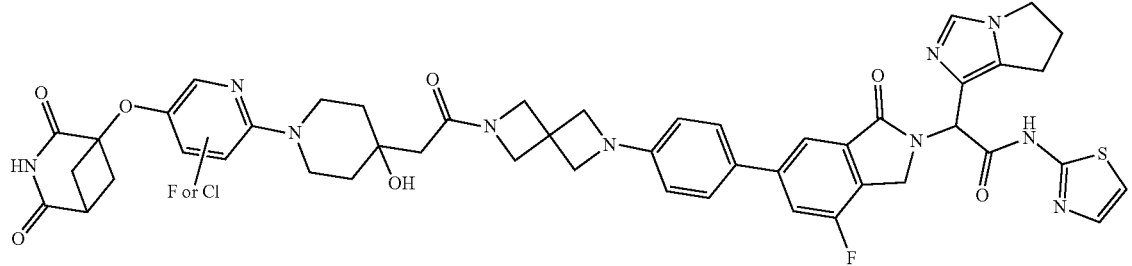
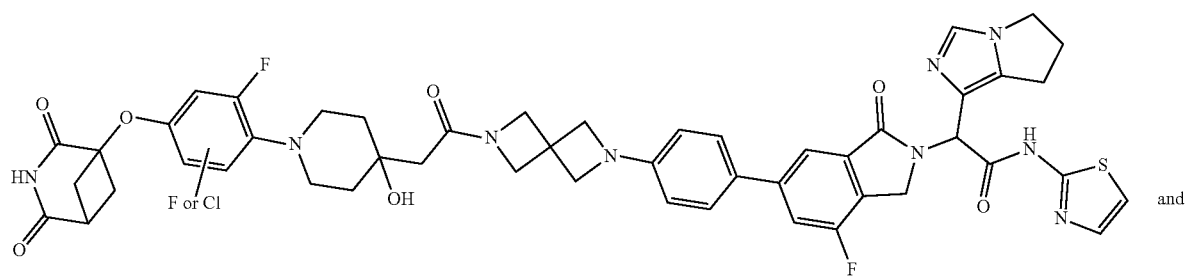
and
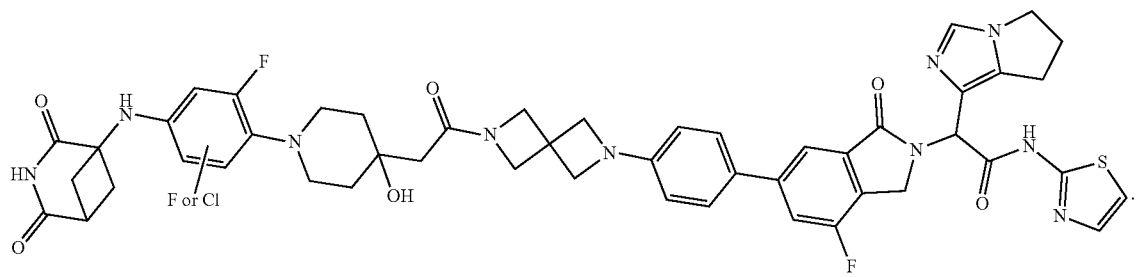
In certain embodiments the compound of the present invention is selected from:
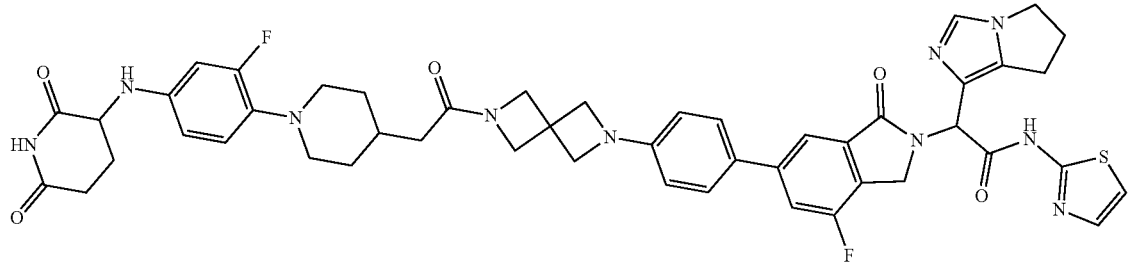
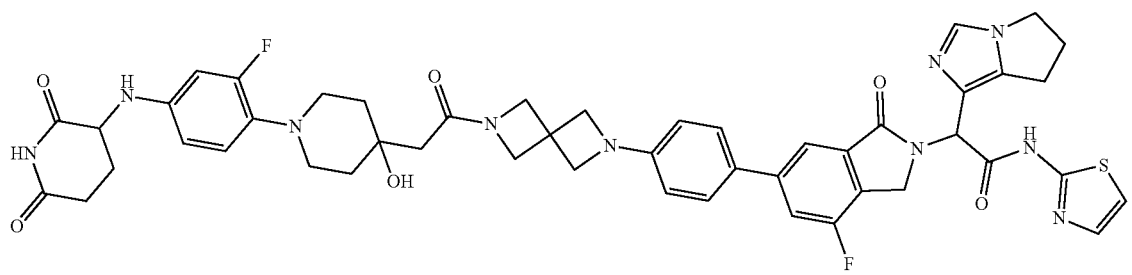

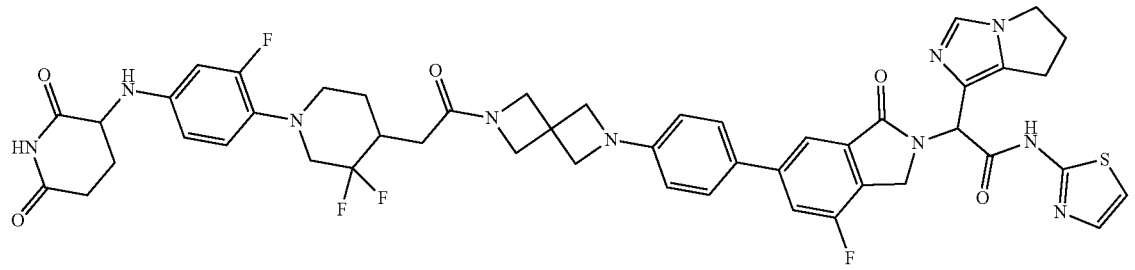
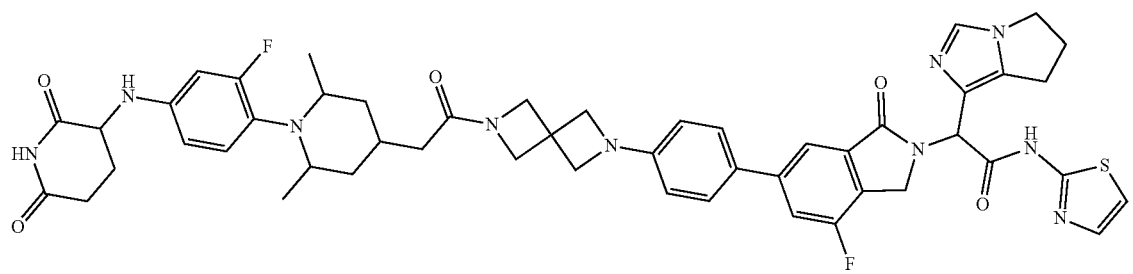
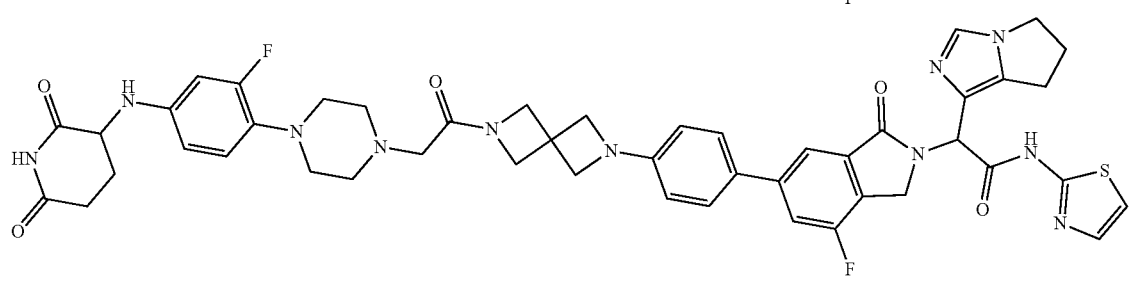
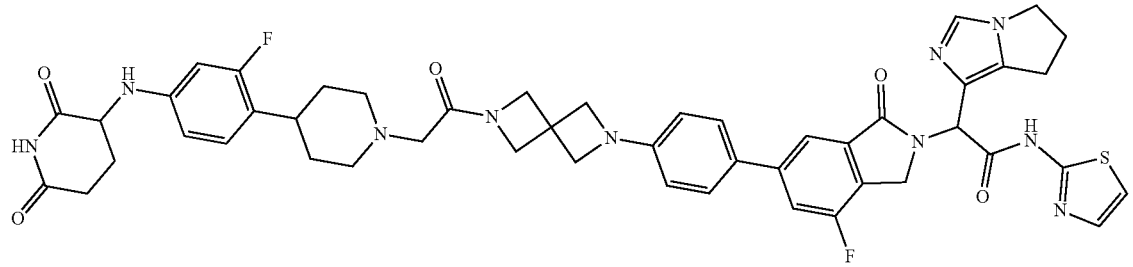
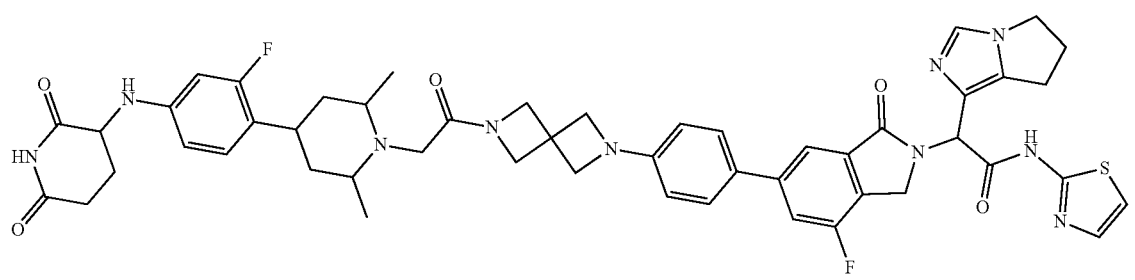
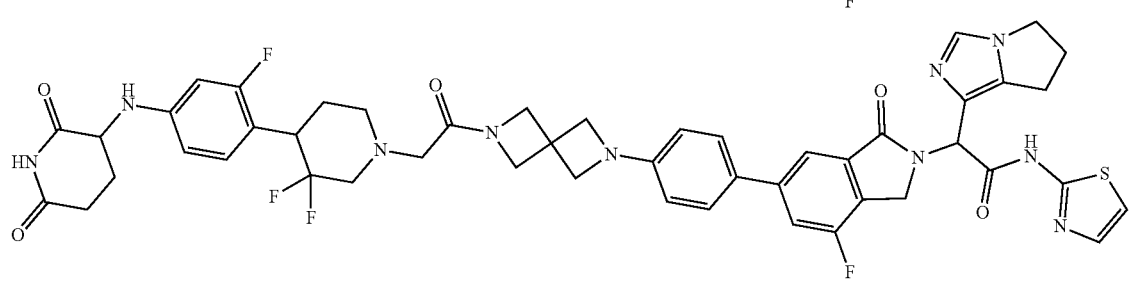

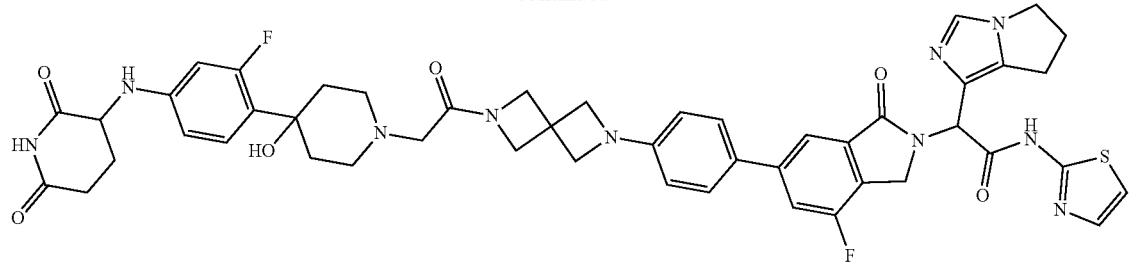
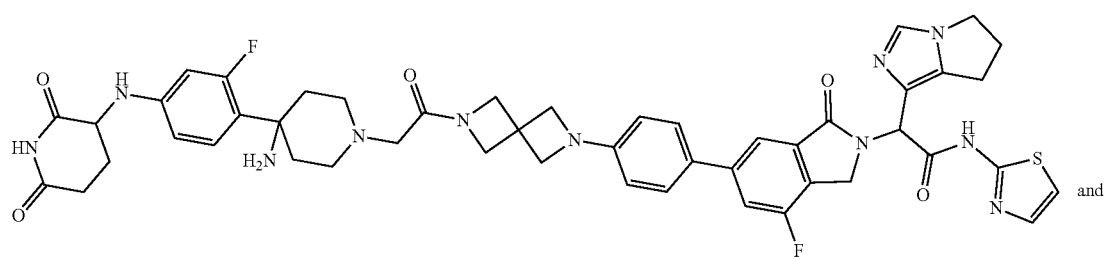
and
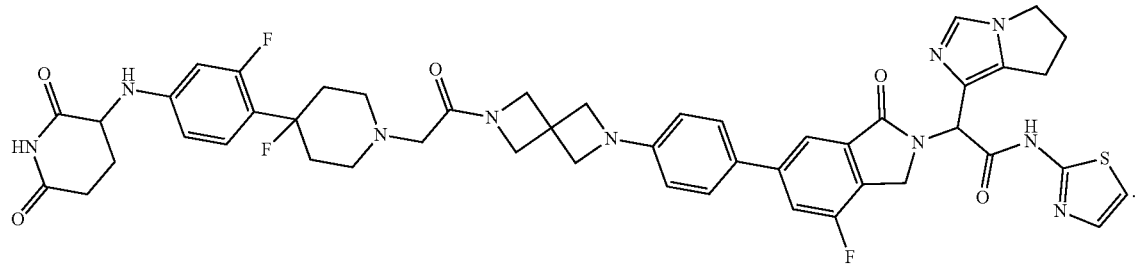
In certain embodiments the compound of the present invention is selected from:
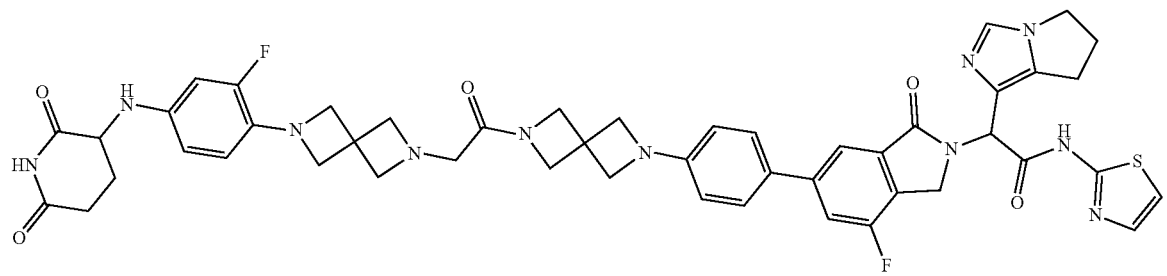
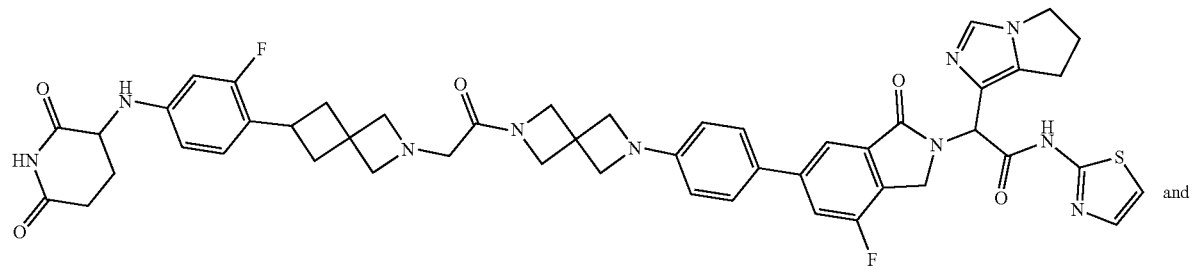
and -continued
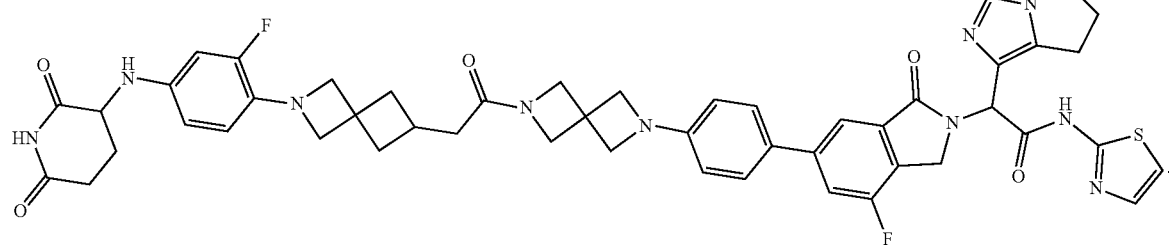
In certain embodiments the compound of the present invention is selected from:
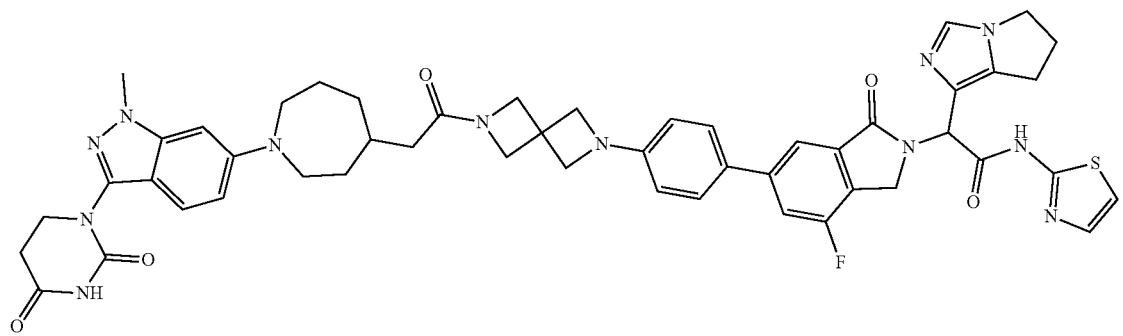
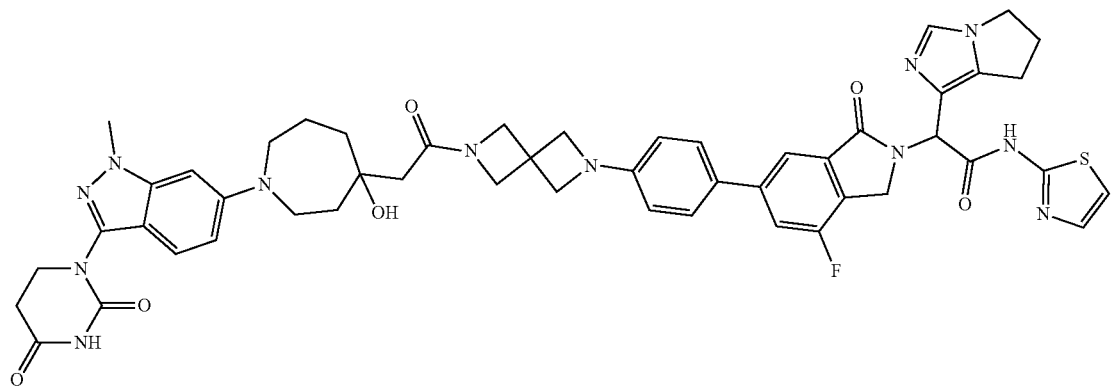
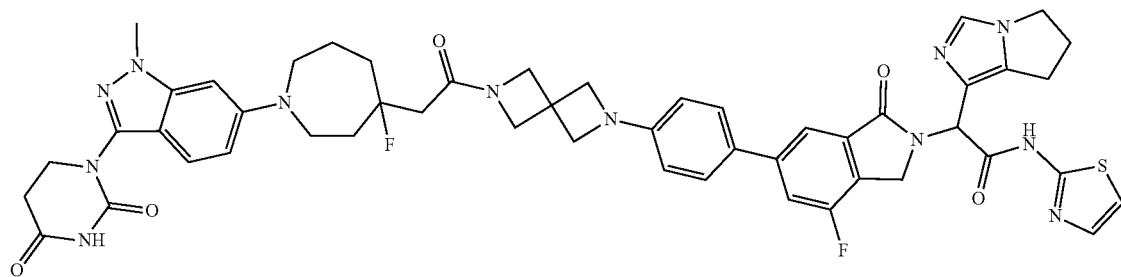

-continued
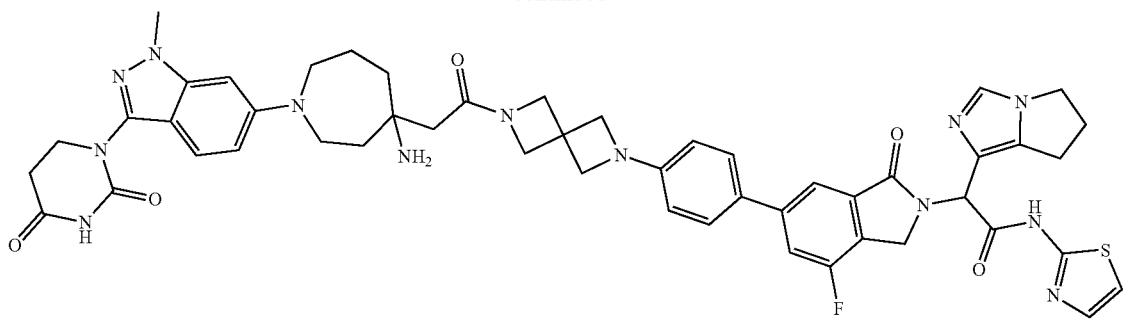
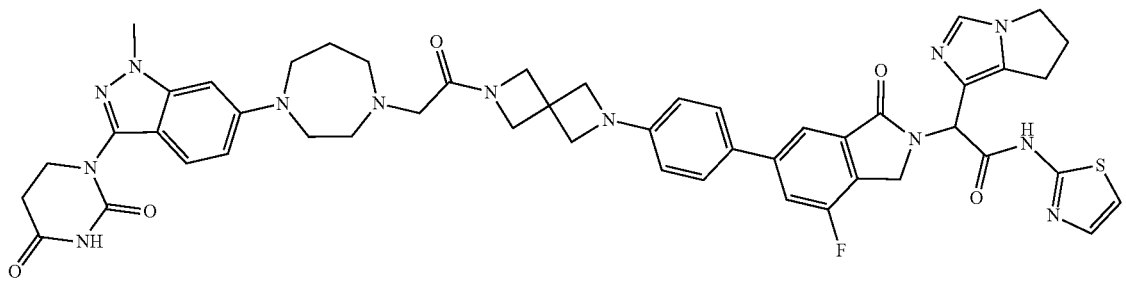
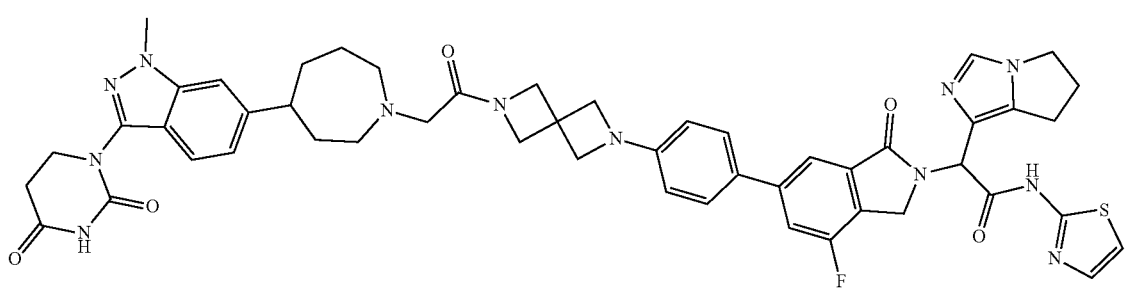
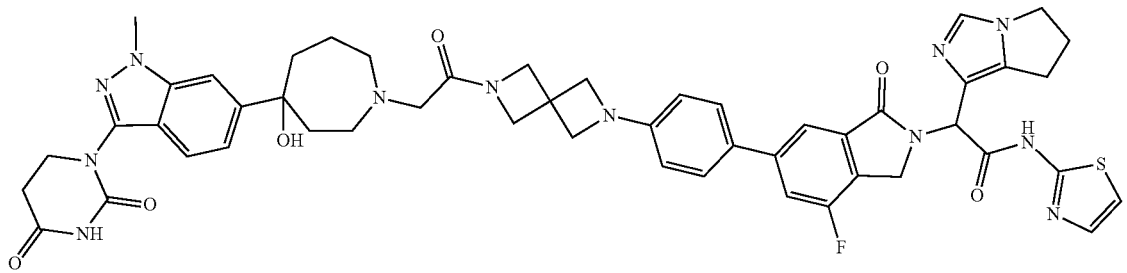
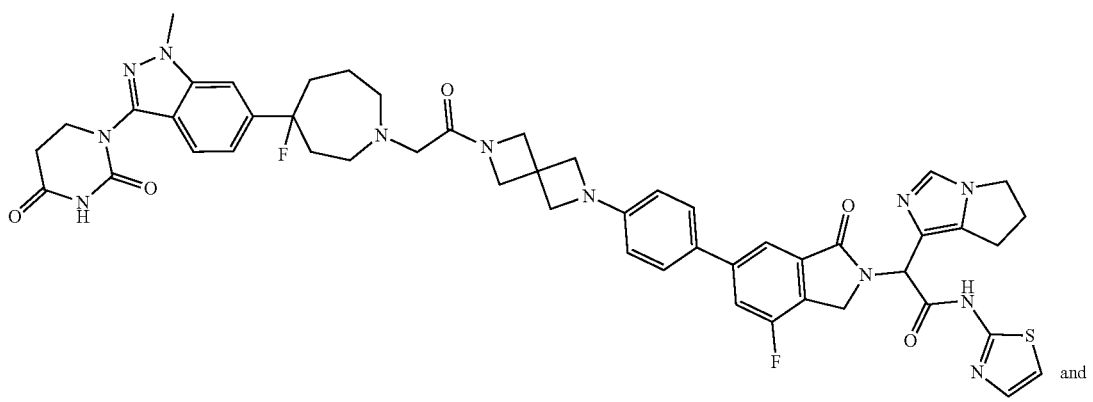
and

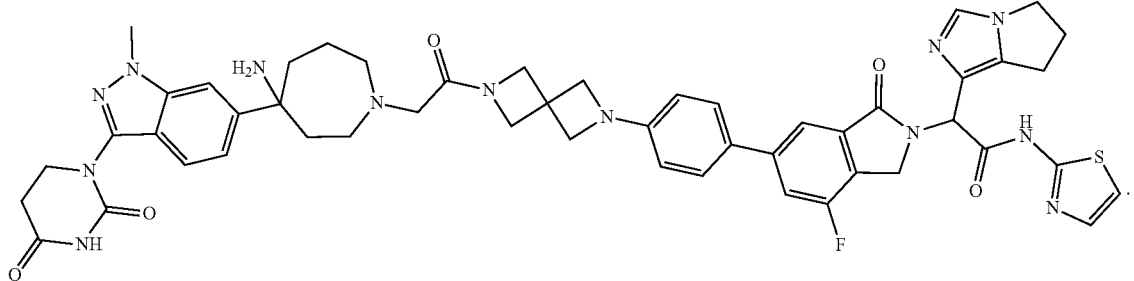
In certain embodiments the compound of the present invention is selected from:
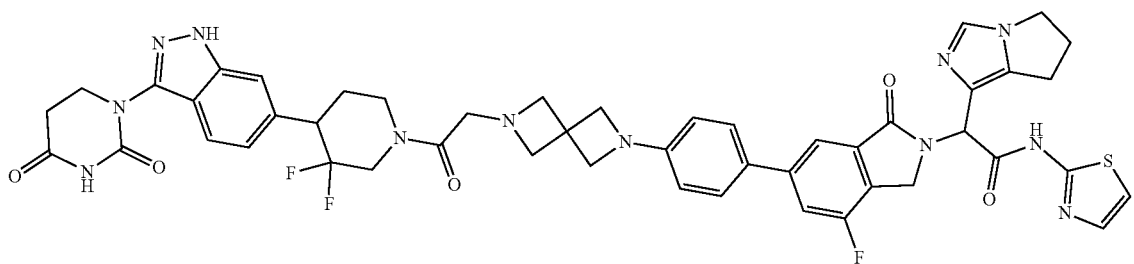
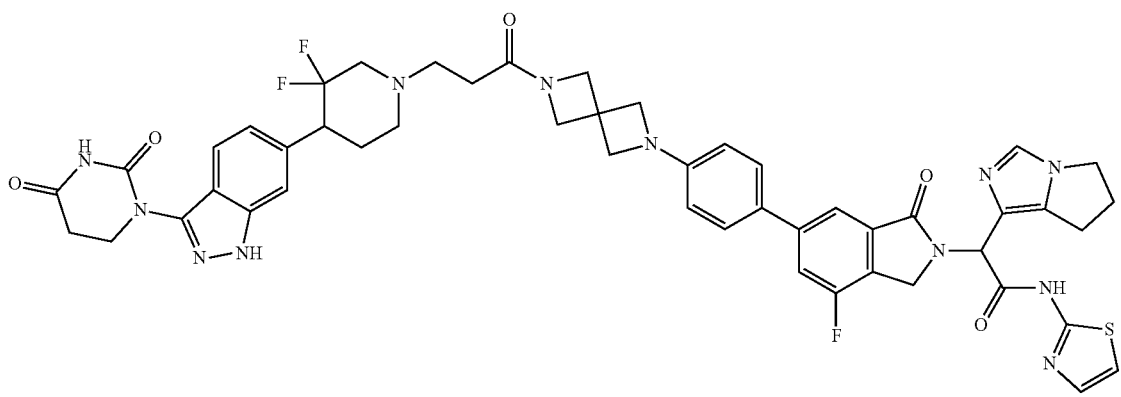
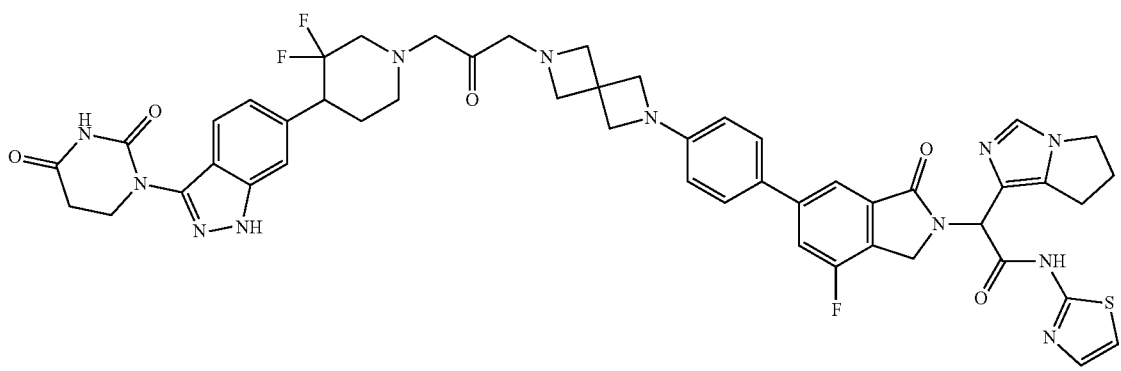

-continued
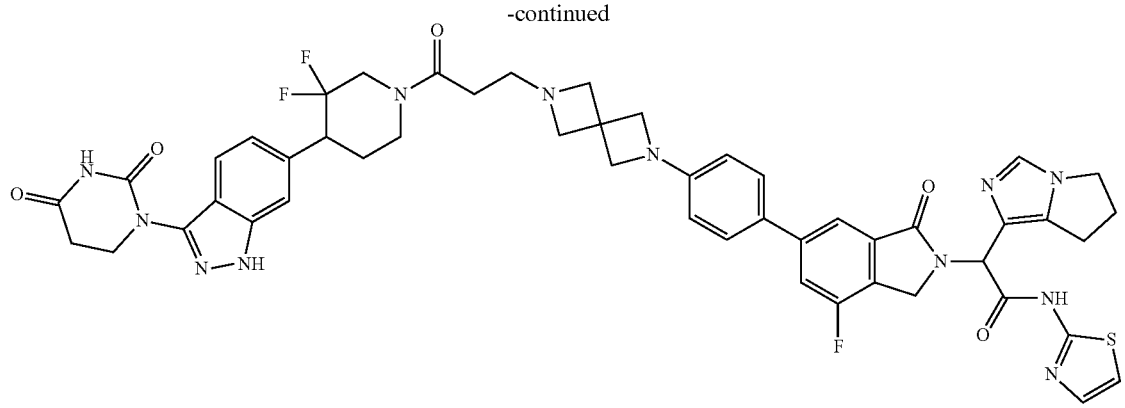
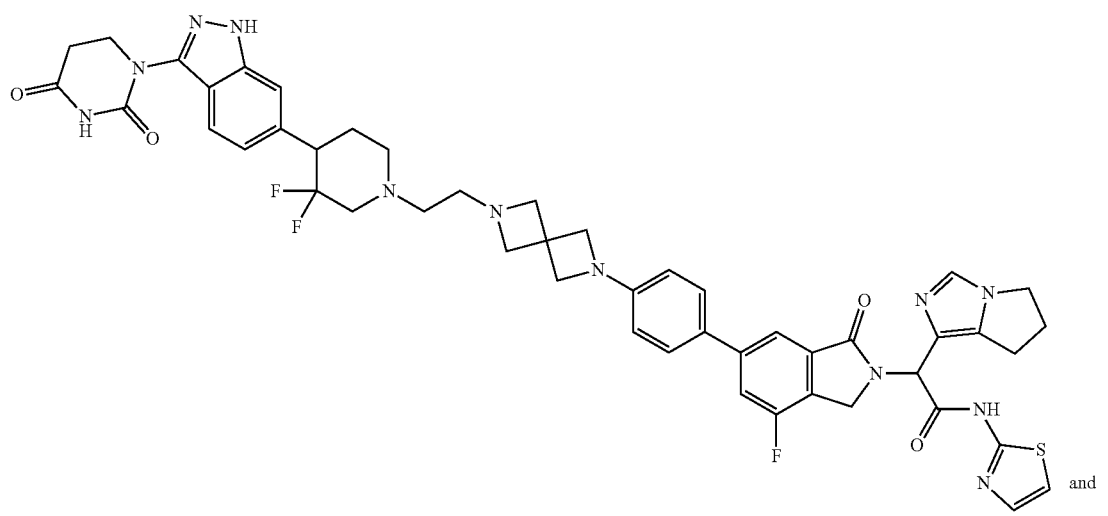
and
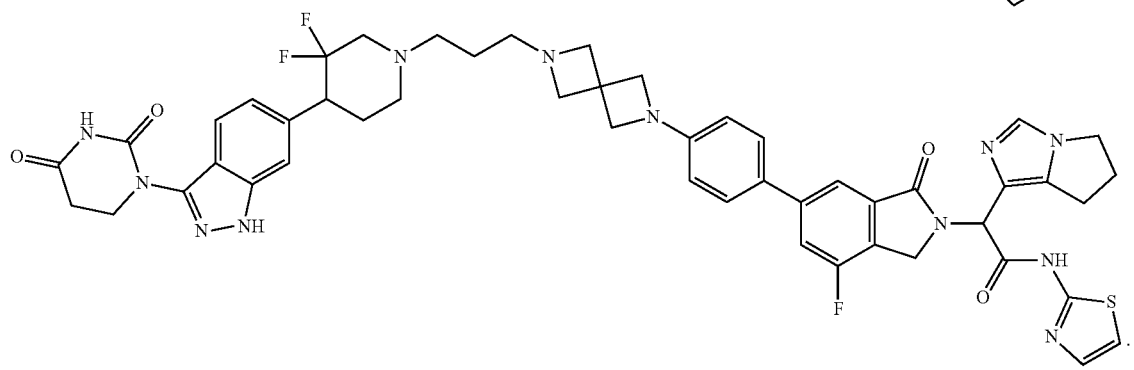
In certain embodiments the compound of the present invention is selected from:
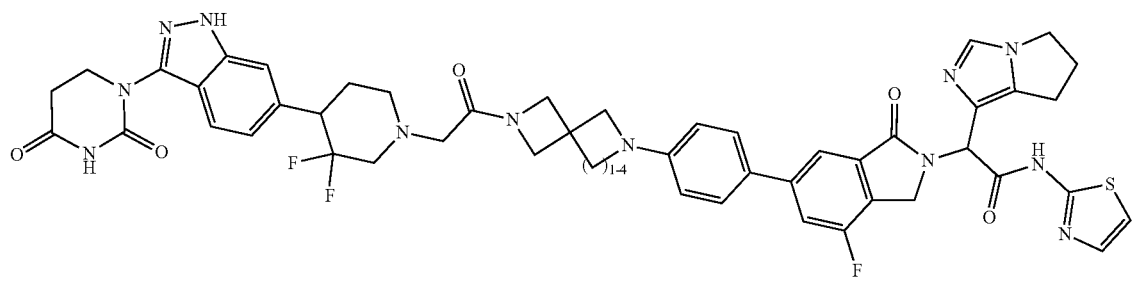

-continued
289
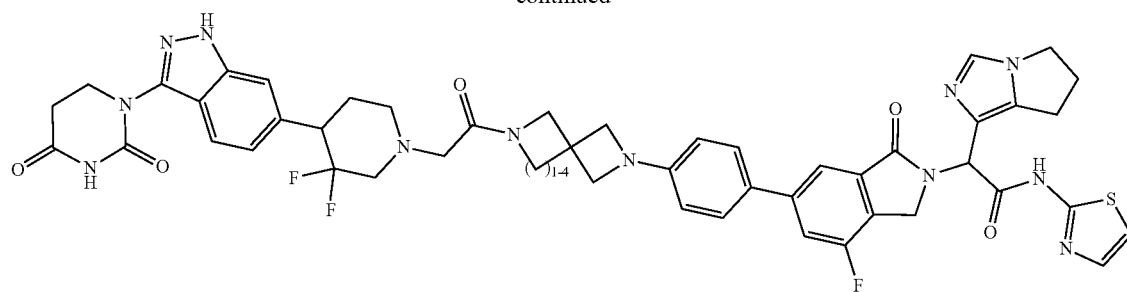
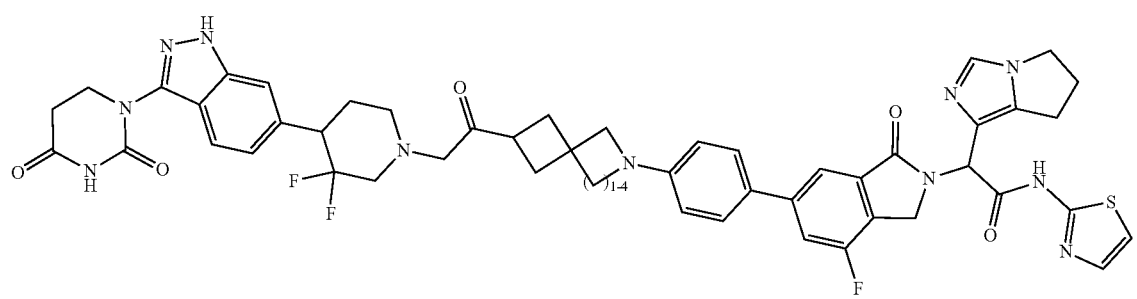
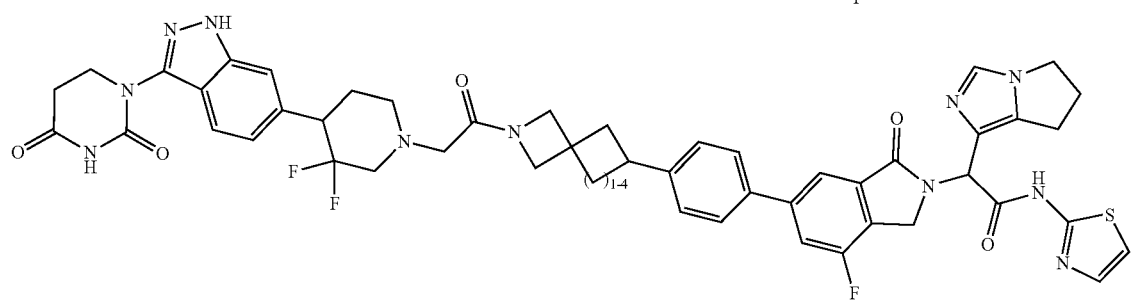
290
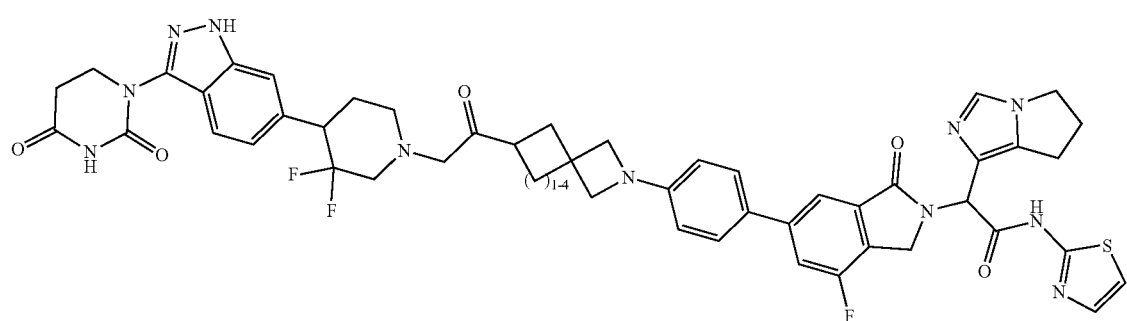
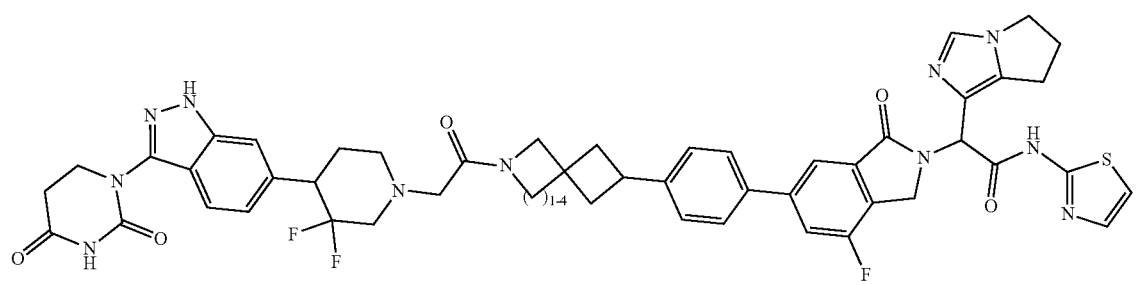

291
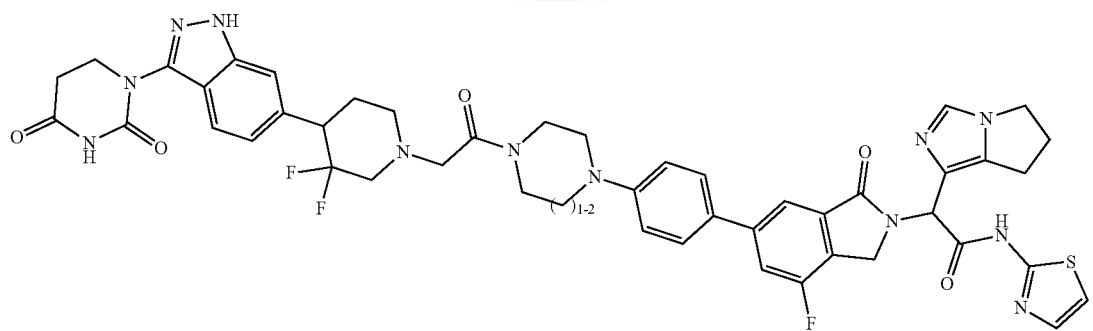
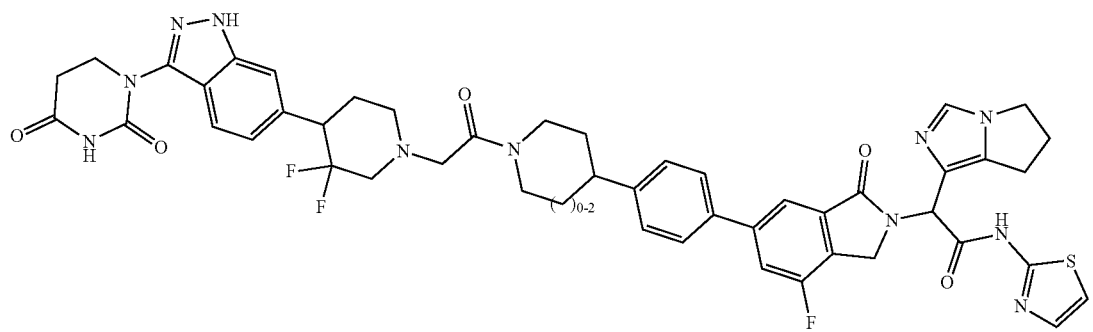
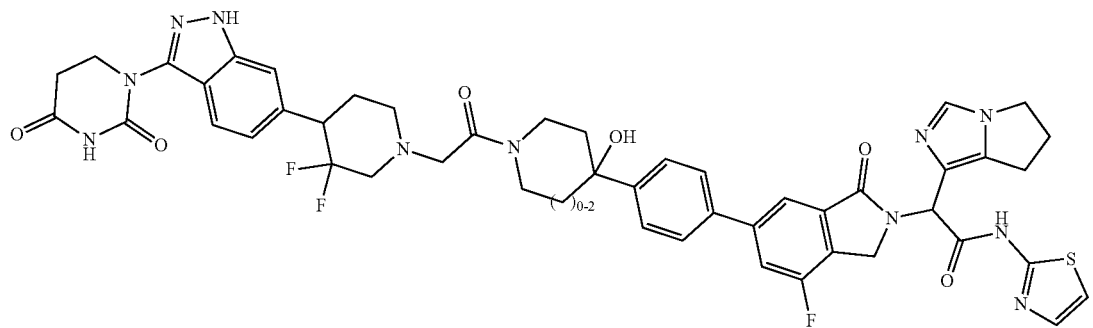
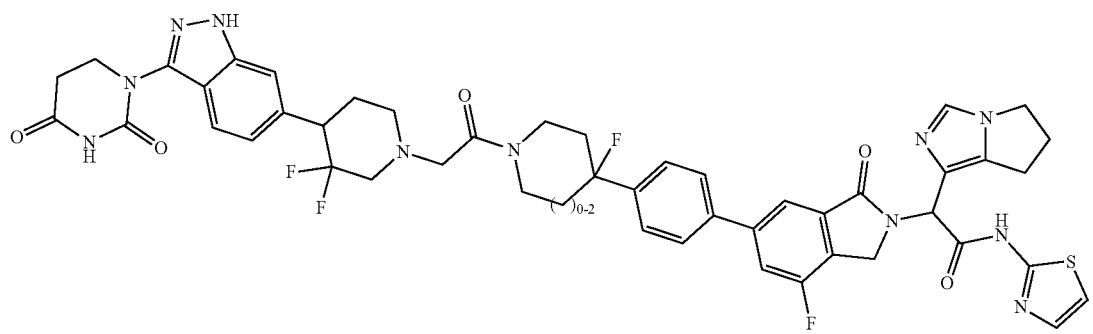
292
-continued
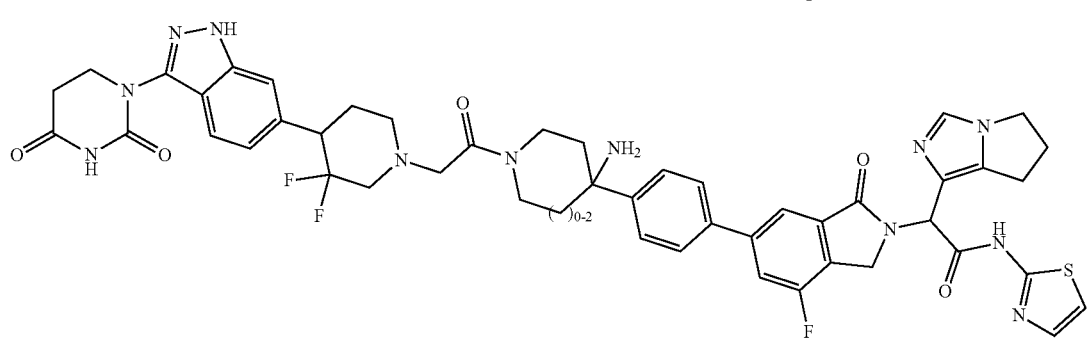

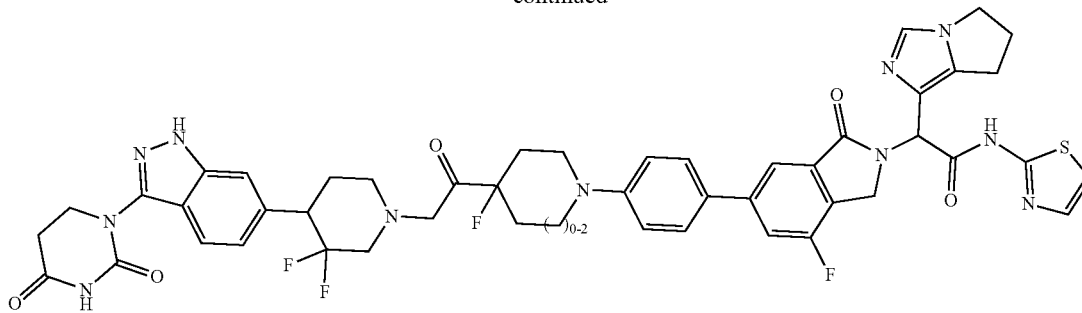
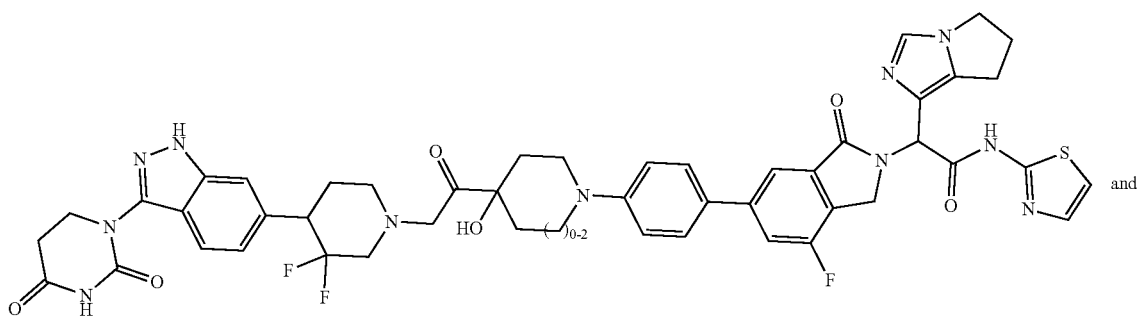
and
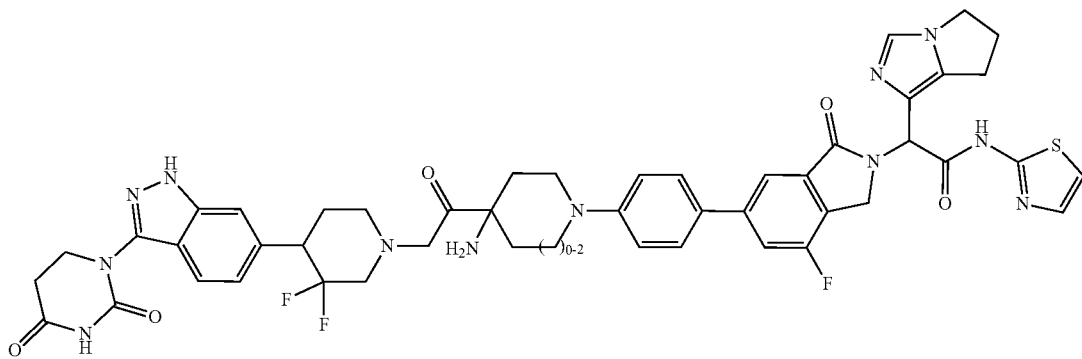
In certain embodiments the compound of the present invention is selected from:
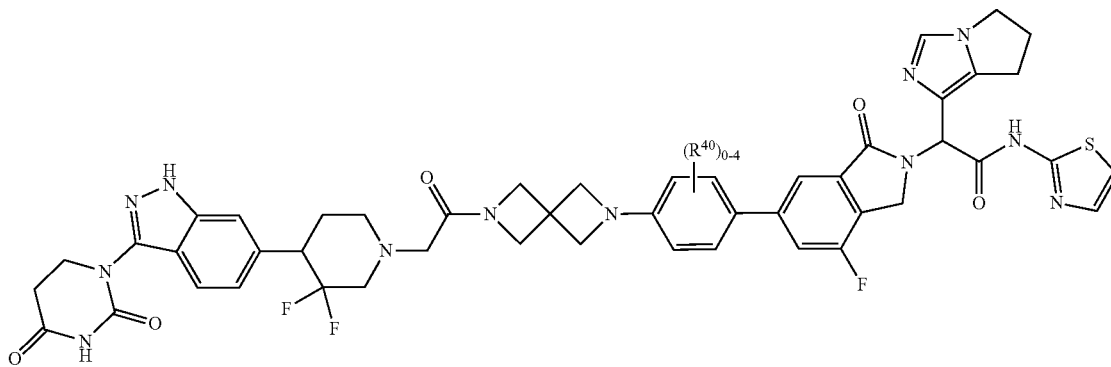

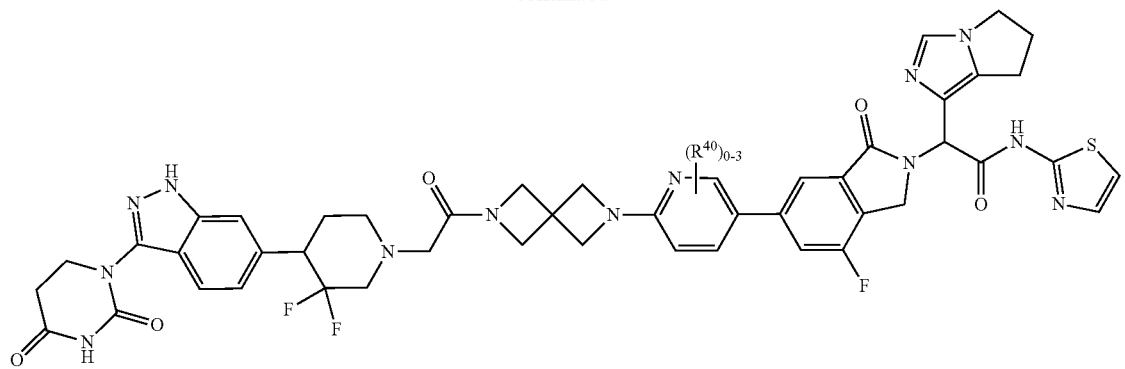
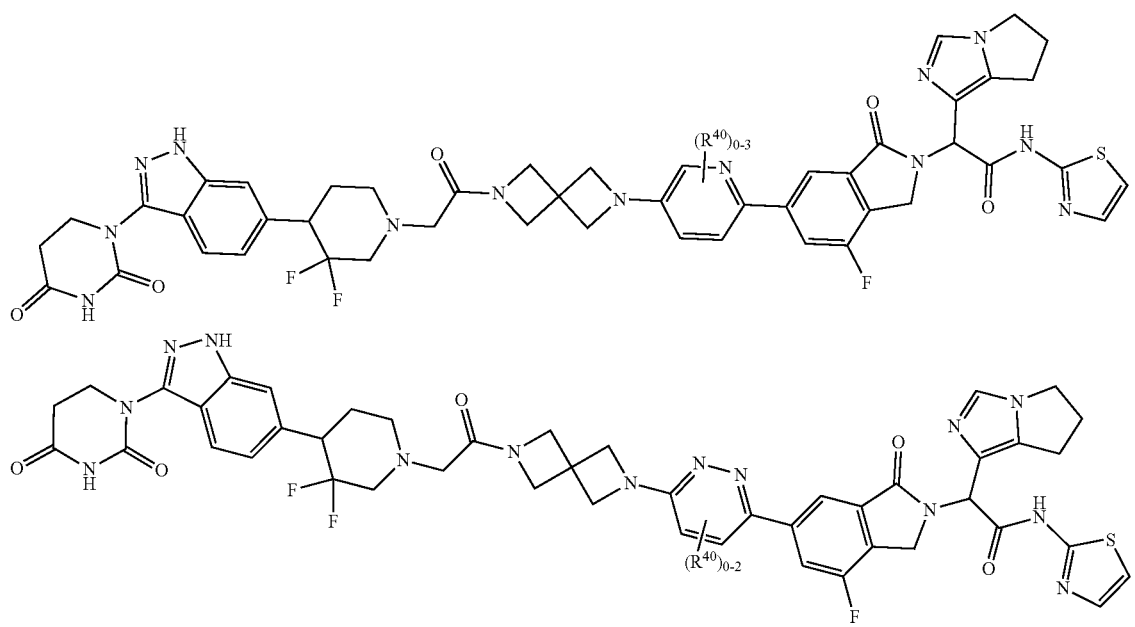
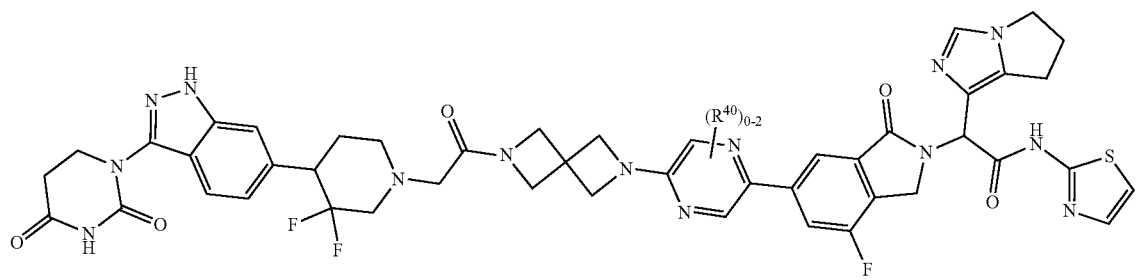
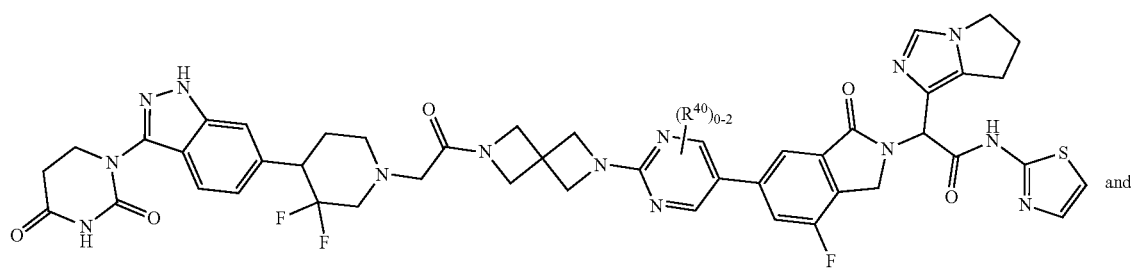

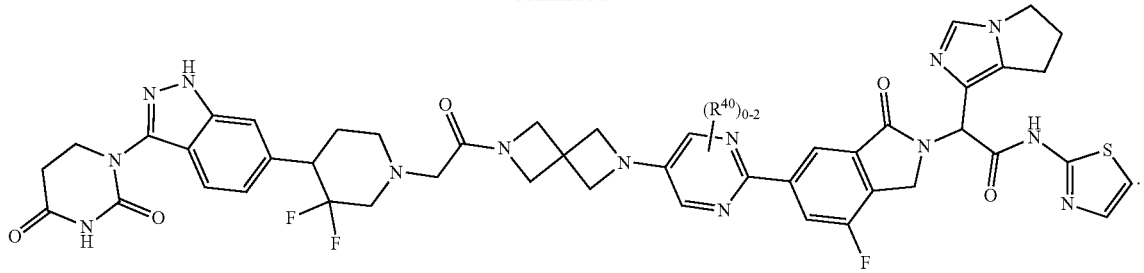
In certain embodiments the compound of the present invention is selected from:
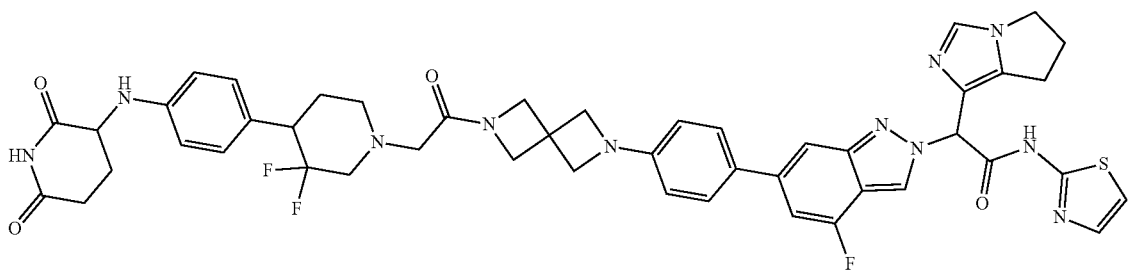
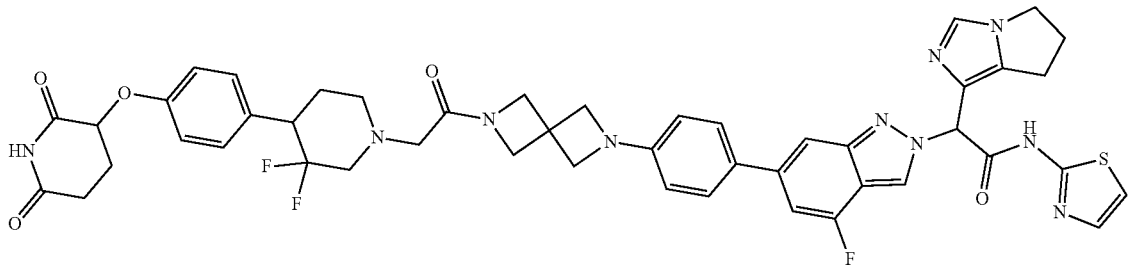
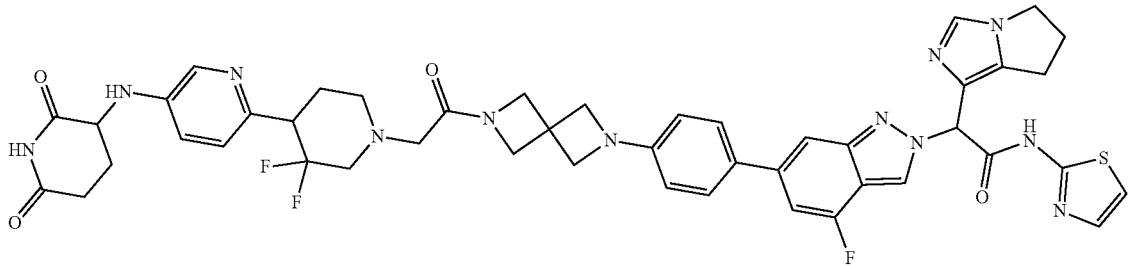
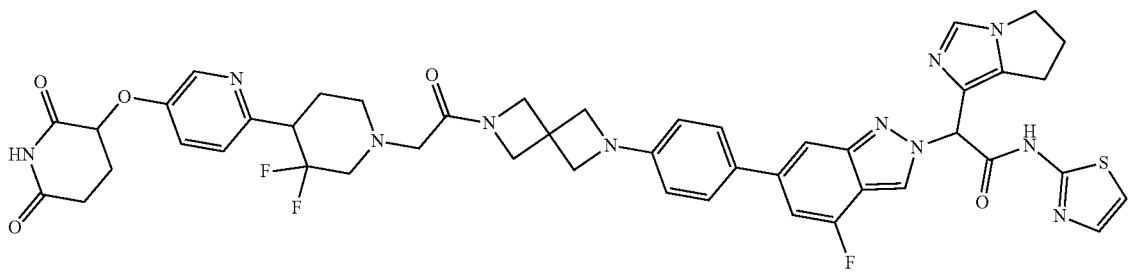

-continued
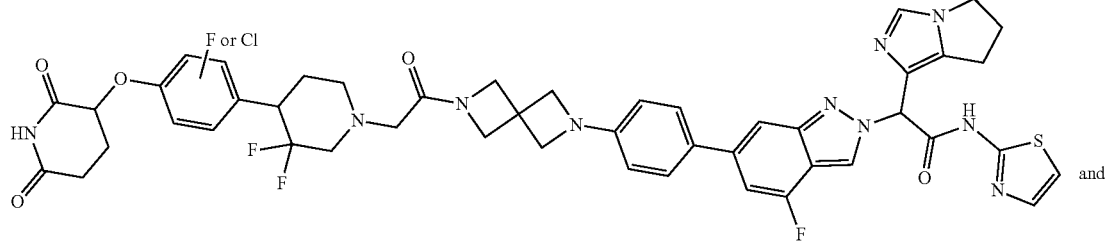
and
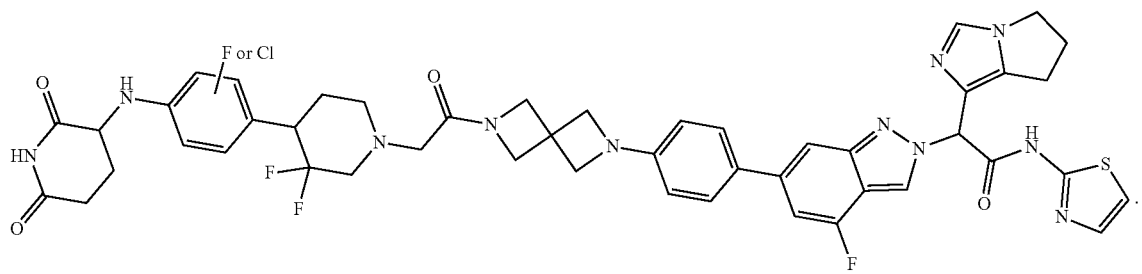
In certain embodiments the compound of the present invention is selected from:
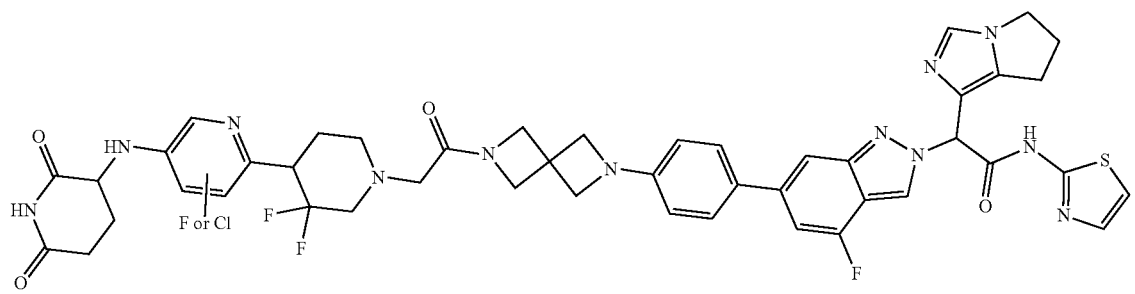
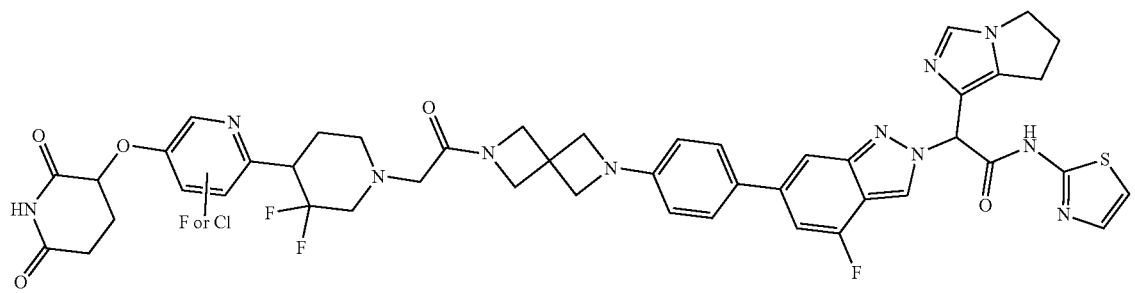
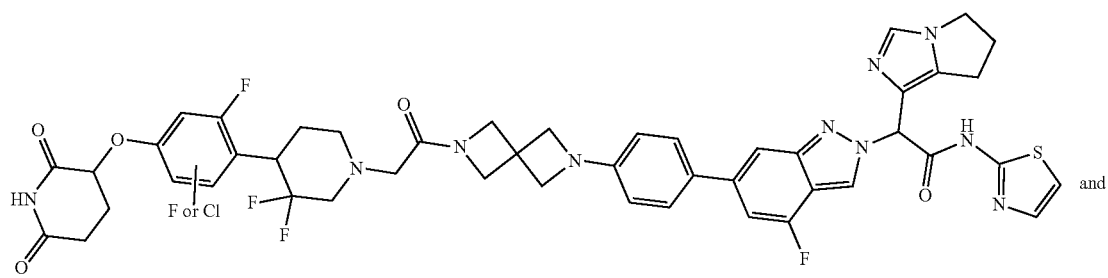
and

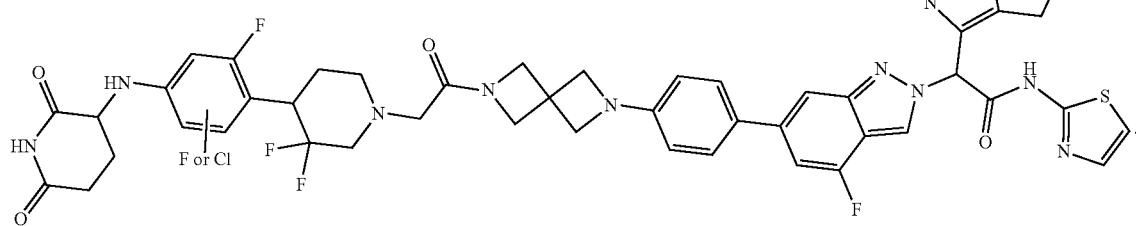
In certain embodiments the compound of the present invention is selected from:
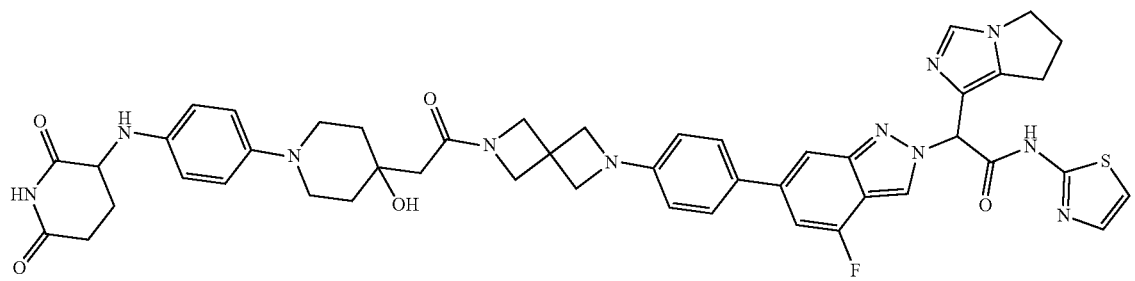
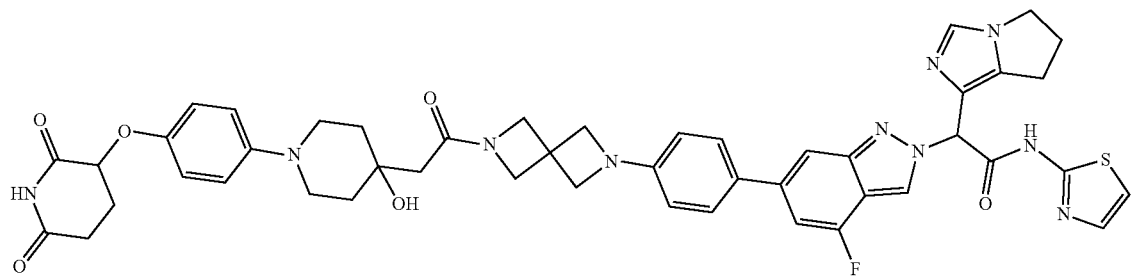
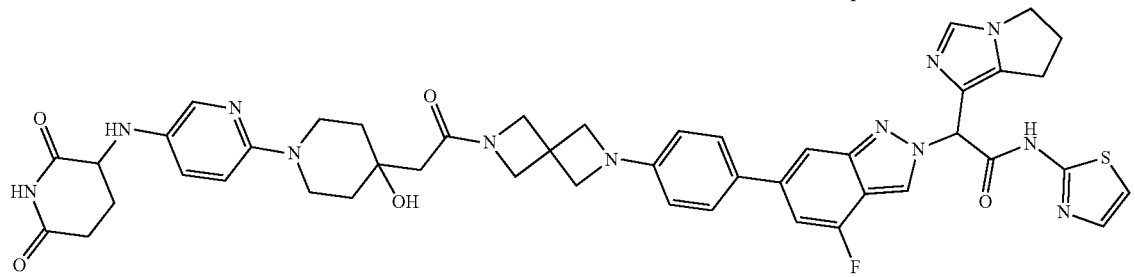
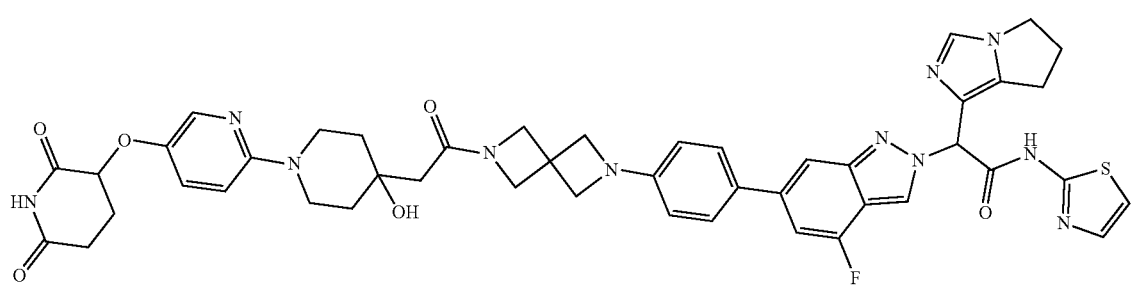

-continued
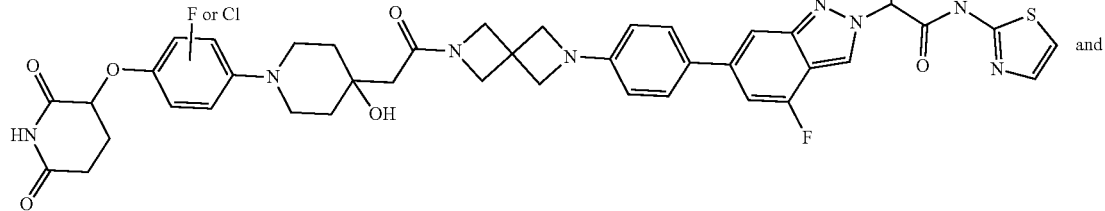
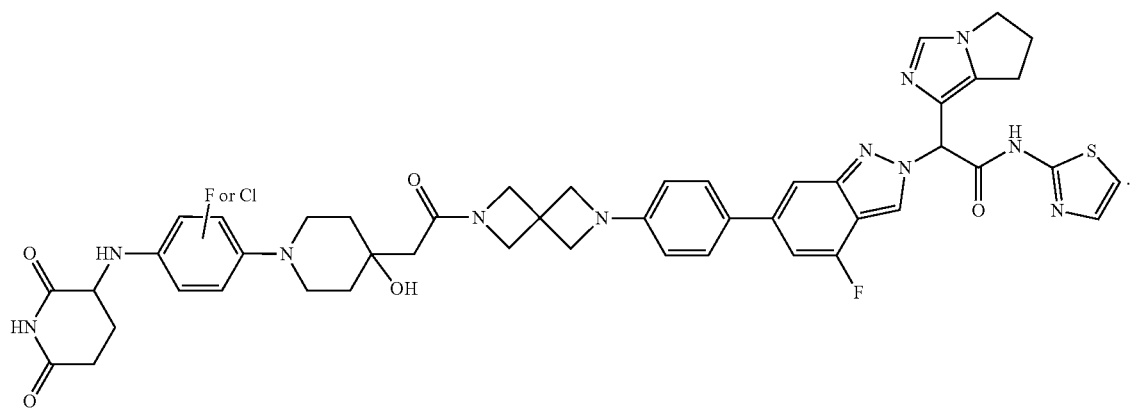
In certain embodiments the compound of the present invention is selected from:
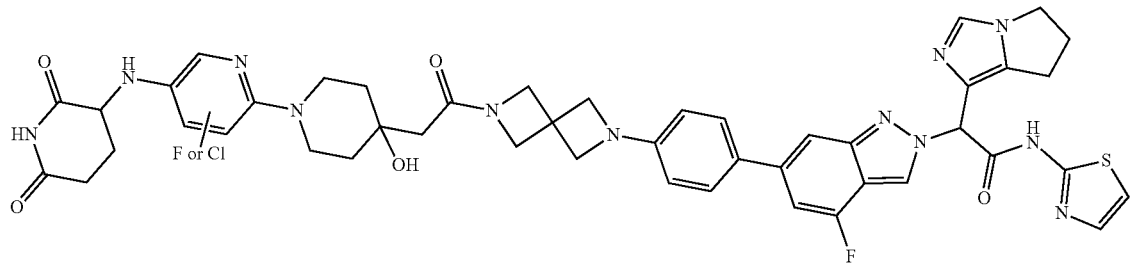
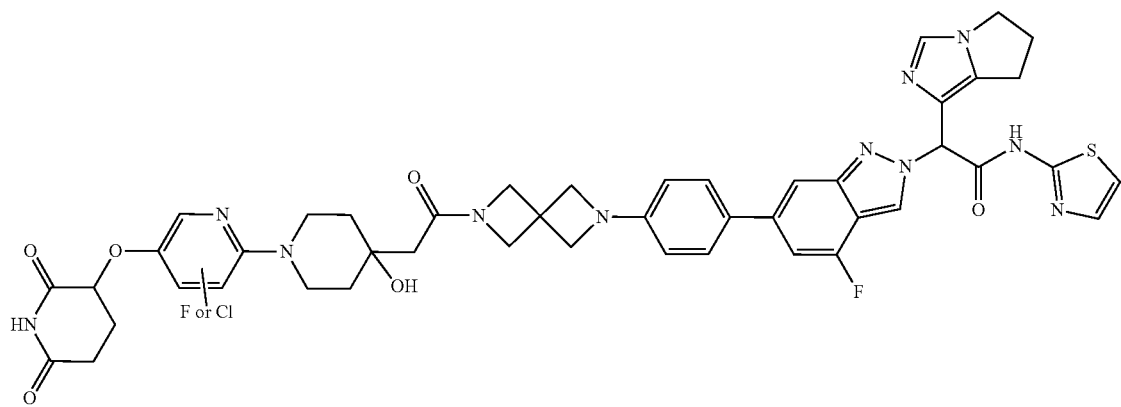

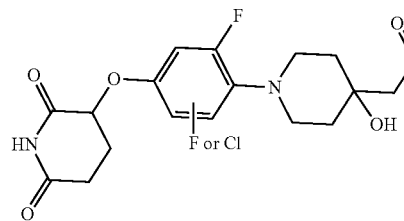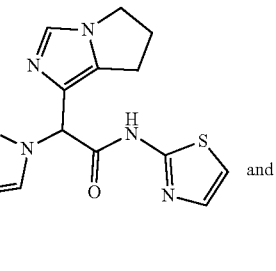
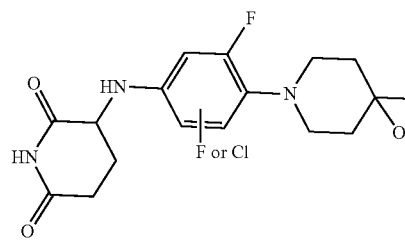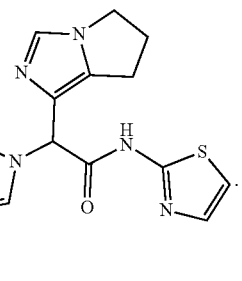
In certain embodiments the compound of the present invention is selected from:
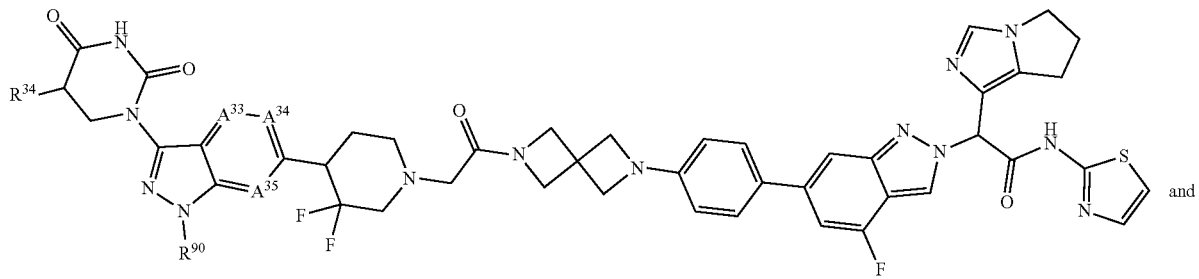
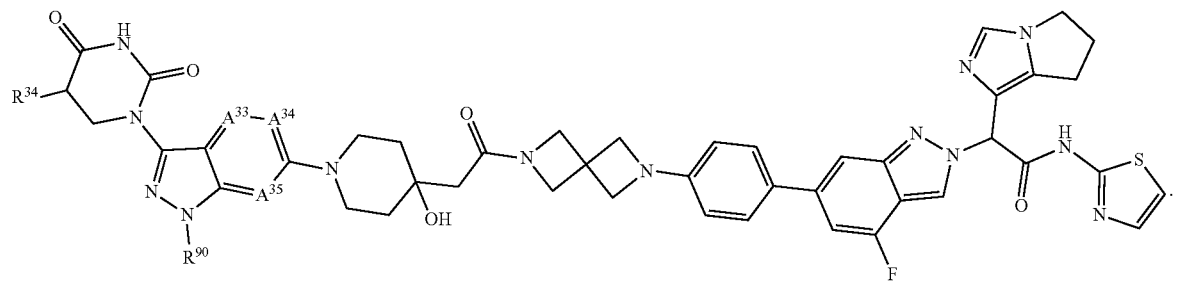

In certain embodiments the compound of the present invention is selected from:
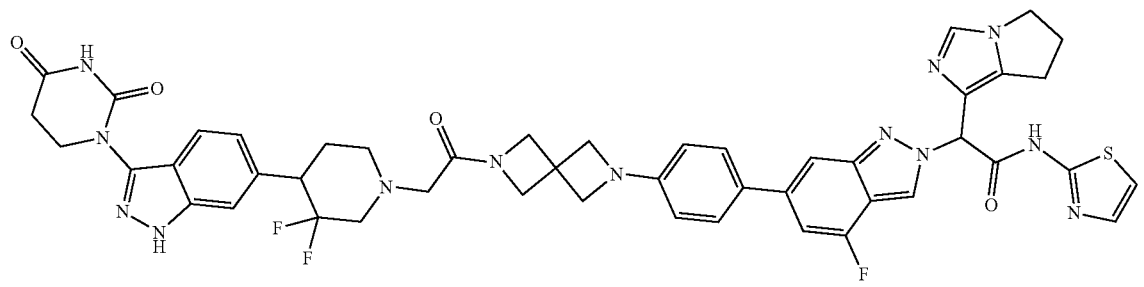
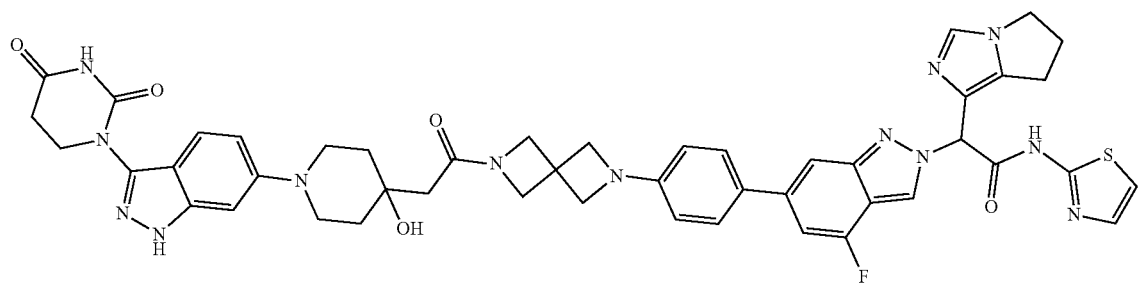
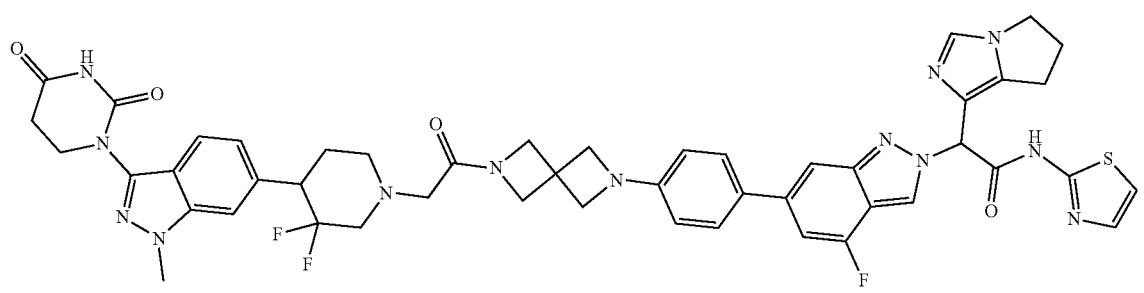
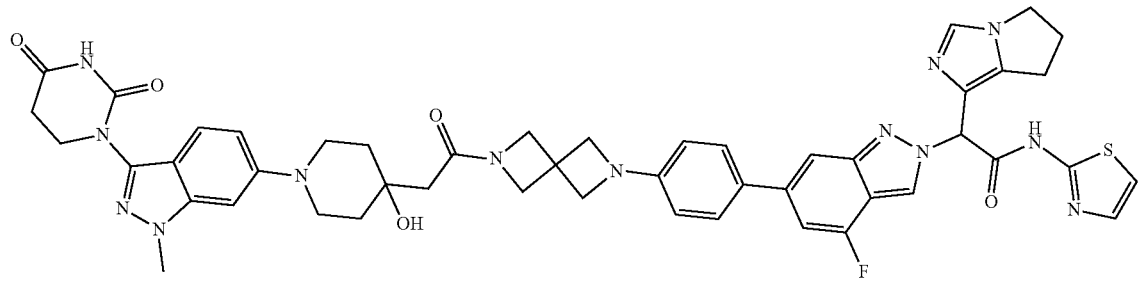
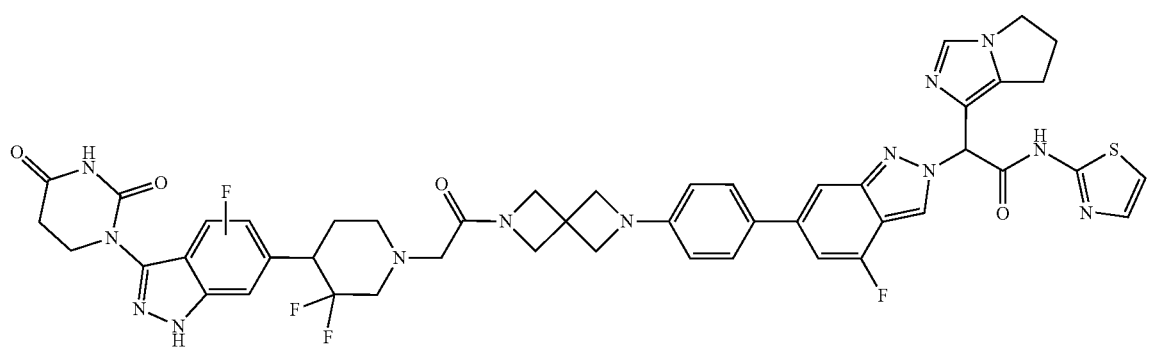

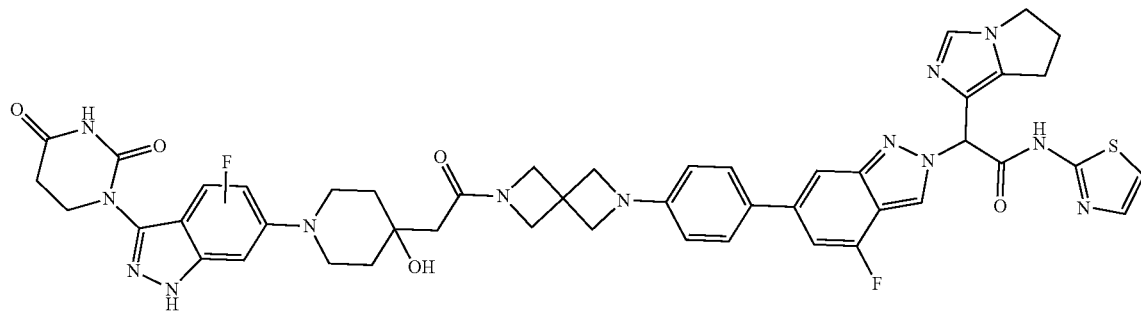
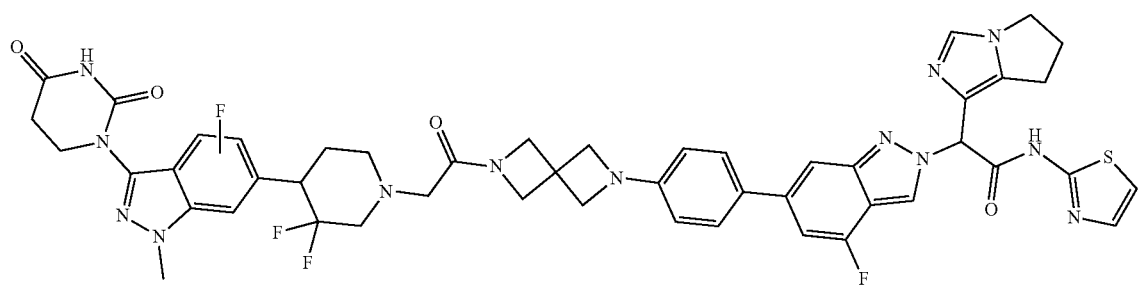
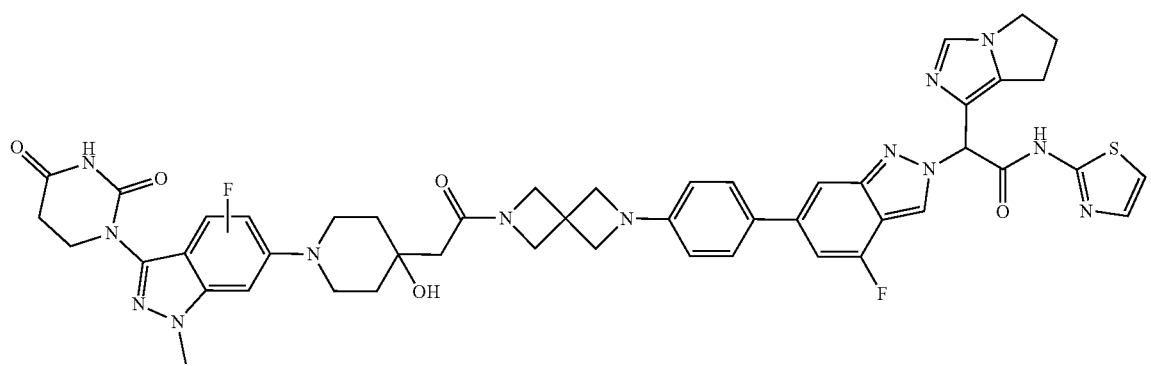
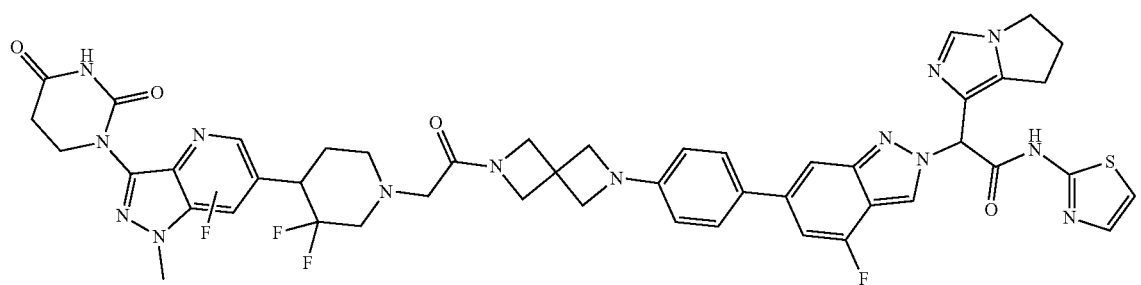
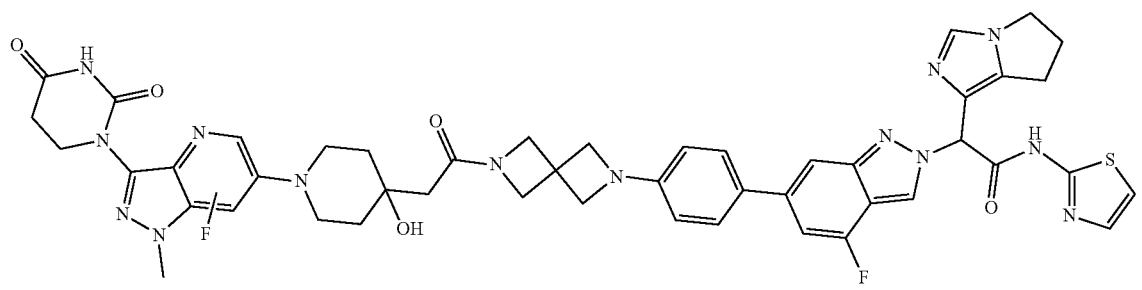

-continued
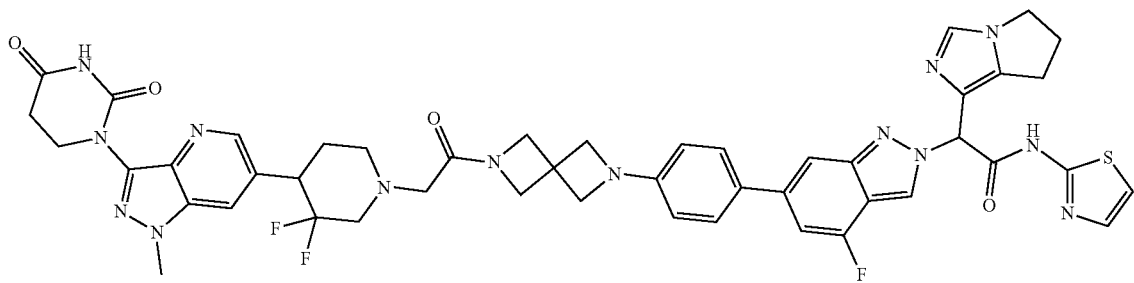
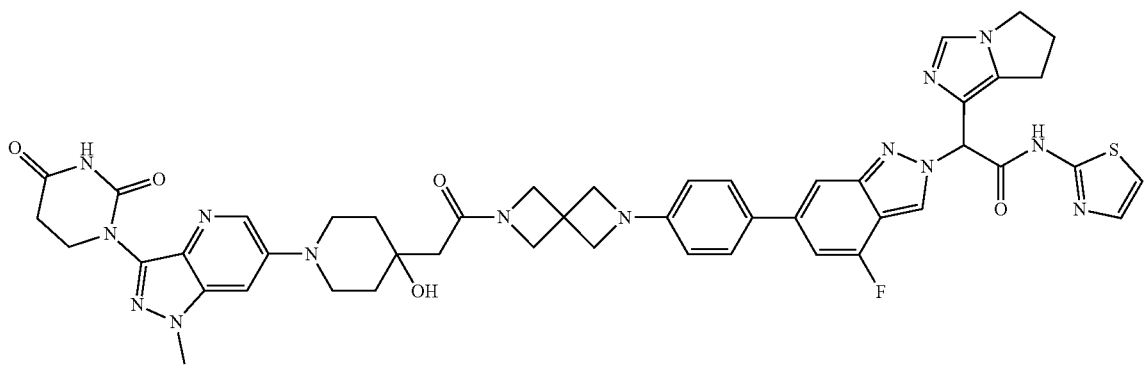
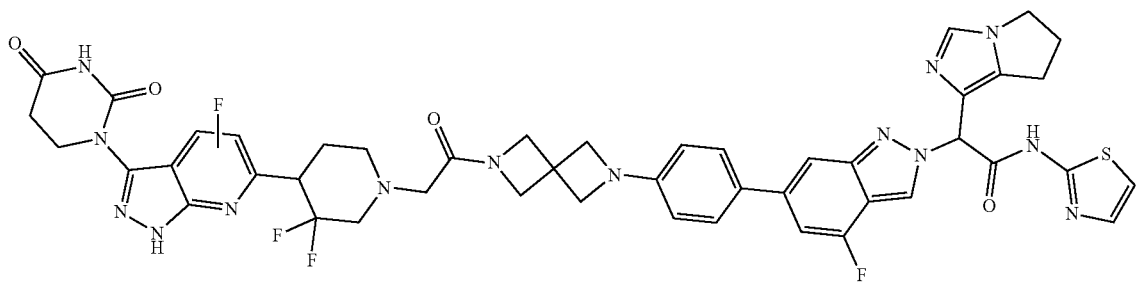
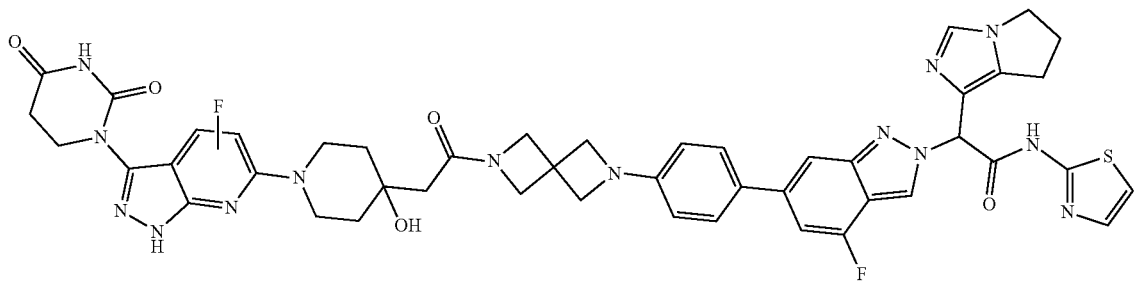
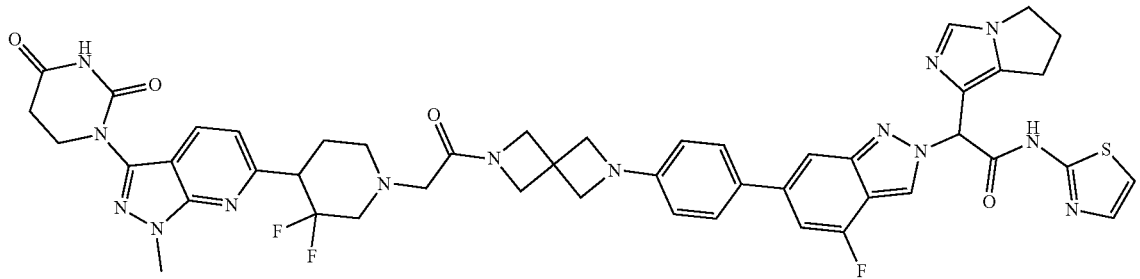

-continued
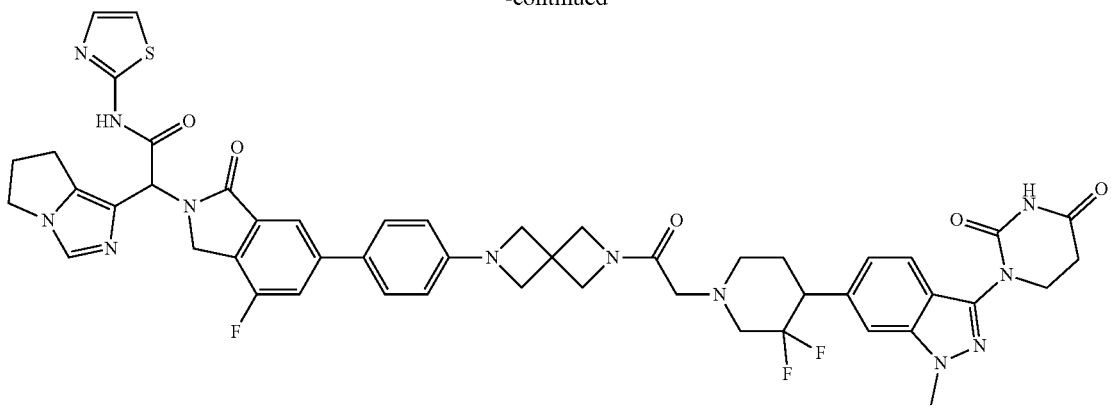
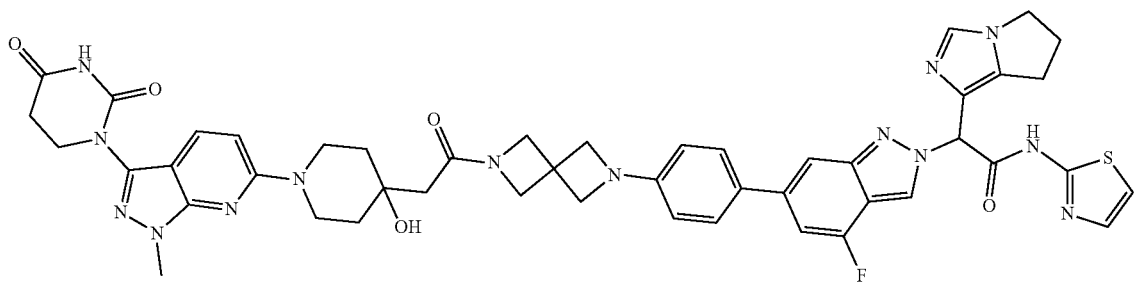
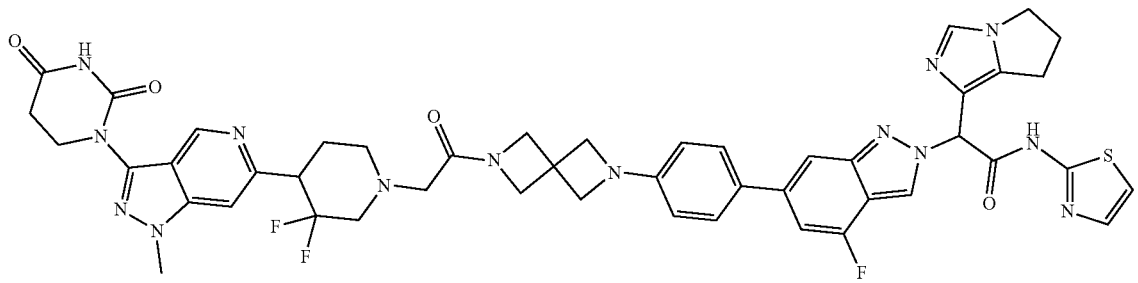
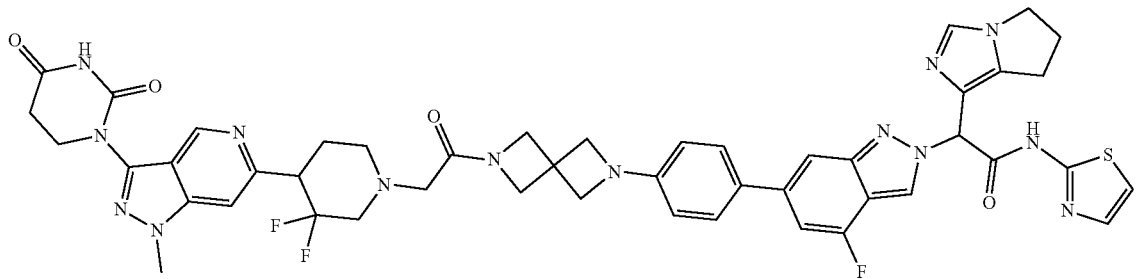
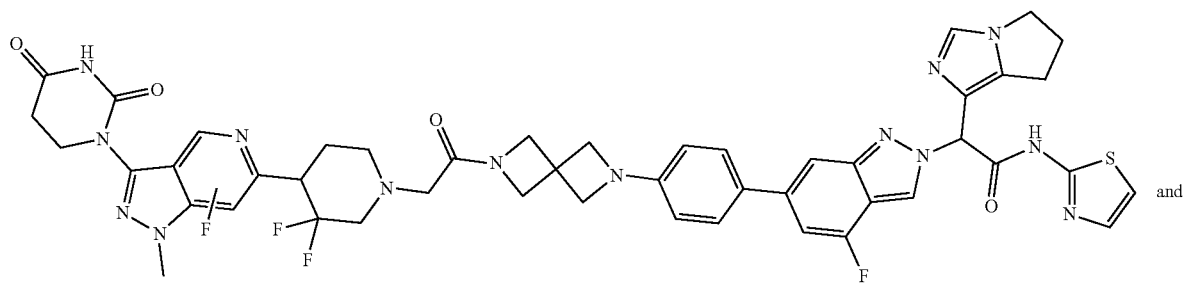
and

-continued

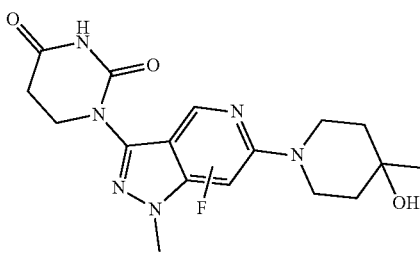

IV. Linkers

A Linker ($L^1$ or $L^2$) or a bond is included in the compounds of the present invention. Linker is a chemically stable bivalent group that attaches an E3 Ligase binding portion to an EGFR Targeting Ligand. According to the invention, any desired linker, as described herein, can be used as long as the resulting compound has a stable shelf life, for example at least 1 month, 2 months, 3 months, 6 months or 1 year as part of a pharmaceutically acceptable dosage form, and itself is pharmaceutically acceptable.

Linker as described herein can be used in either direction, i.e., either the left end is linked to the E3 Ligase binding portion and the right end to the EGFR Targeting Ligand, or the left end is linked to the EGFR Targeting Ligand and the right end is linked to the E3 Ligase binding portion.

In certain embodiments Linker is a bond.

In certain embodiments, the Linker has a chain of 2 to 14, 15, 16, 17, 18 or 20 or more carbon atoms of which one or more carbons can be replaced by a heteroatom such as O, N, S, or P.

In certain embodiments the chain has 2, 3, 4, 5, 6, 7, 8, 9, 10, 11, 12, 13, 14, 15, 16, 17, 18, 19 or 20 contiguous atoms in the chain. For example, the chain may include 1 or more ethylene glycol units that can be contiguous, partially contiguous or non-contiguous (for example, 2, 3, 4, 5, 6, 7, 8, 9, 10, 11 or 12 ethylene glycol units).

In certain embodiments the chain has at least 1, 2, 3, 4, 5, 6, 7, or 8 contiguous chains which can have branches which can be independently alkyl, aryl, heteroaryl, alkenyl, or alkynyl, aliphatic, heteroaliphatic, cycloalkyl or heterocycle substituents.

In other embodiments, the linker can include or be comprised of one or more of ethylene glycol, propylene glycol, lactic acid and/or glycolic acid. Lactic acid segments tend to have a longer half-life than glycolic acid segments. Block and random lactic acid-co-glycolic acid moieties, as well as ethylene glycol and propylene glycol, are known in the art to be pharmaceutically acceptable and can be modified or arranged to obtain the desired half-life and hydrophilicity. In certain aspects, these units can be flanked or interspersed with other moieties, such as aliphatic, including alkyl, heteroaliphatic, aryl, heteroaryl, heterocycle, cycloalkyl, etc., as desired to achieve the appropriate drug properties.

In certain embodiments, $L^2$ is a linker selected from:

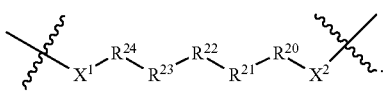
(LI)

In one aspect, Linker ($L^2$) is selected from the group consisting of a moiety of Formula LI, Formula LII, Formula LIII, Formula LIV, Formula LV, Formula LVI, Formula LVII Formula LVIII, Formula IX and Formula LX:

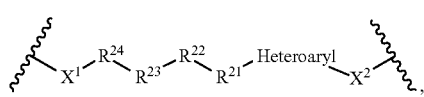
(LII)

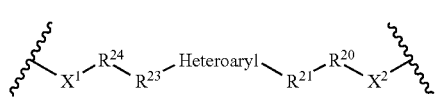
(LIII)

(LIV)

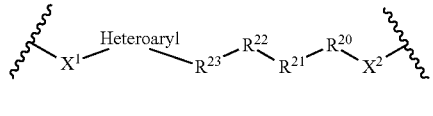
(LV)

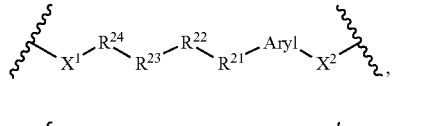
(LVI)

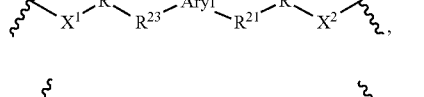
(LVII)

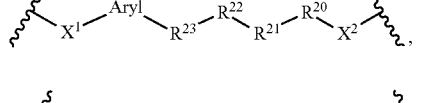
(LVIII)

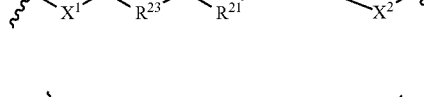
(LIX)

and

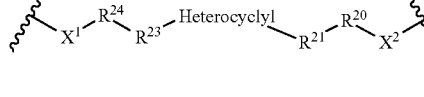
(LX)

wherein all variables are as defined herein.

In certain embodiments, Linker (L²) is selected from:

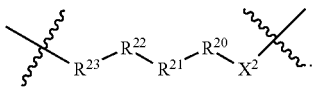

In one aspect, Linker (L²) is selected from the group consisting of a moiety of Formula LDI, Formula LDII, Formula LDIII, Formula LDIV, Formula LDV, Formula LDVI, and Formula LDVII:

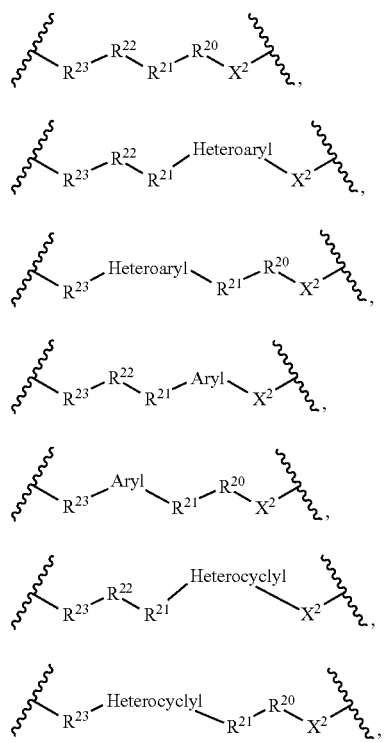

wherein all variables are described herein.

The following are non-limiting examples of Linkers that can be used in this invention. Based on this elaboration, those of skill in the art will understand how to use the full breadth of Linkers that will accomplish the goal of the invention.

In certain embodiments L² is selected from:

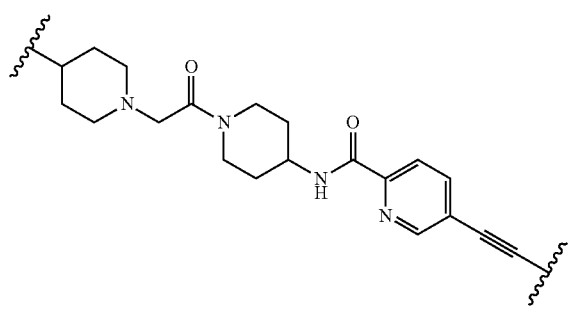

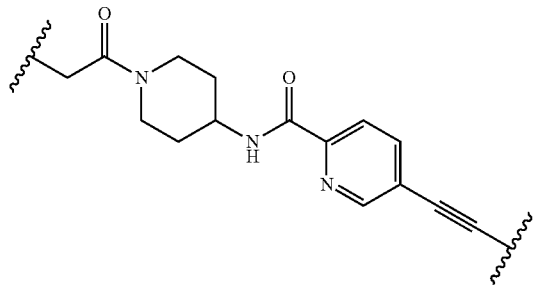

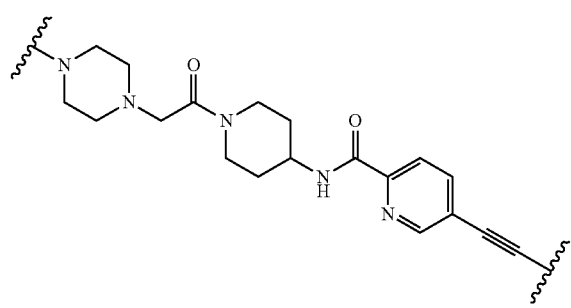

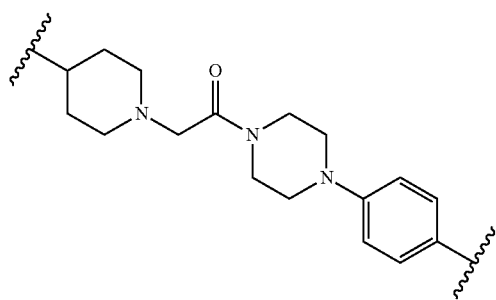

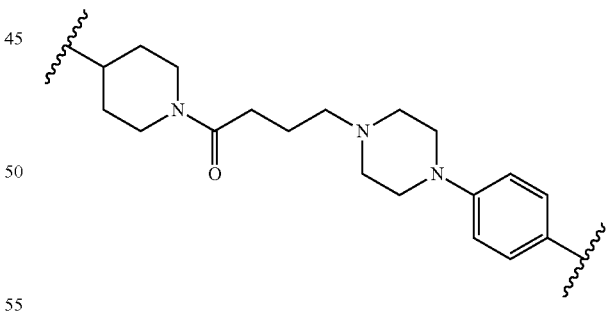

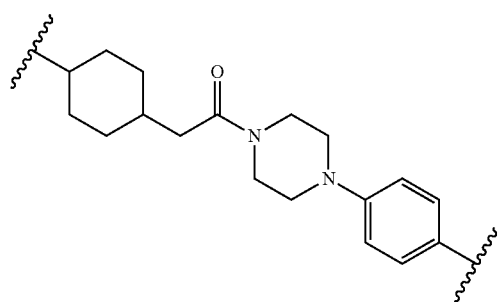

319
-continued
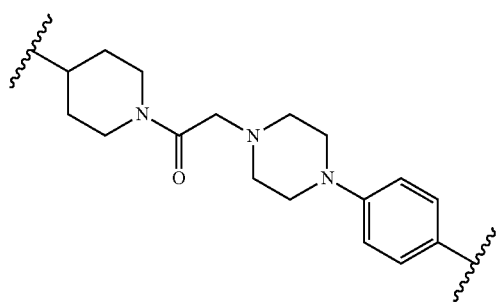
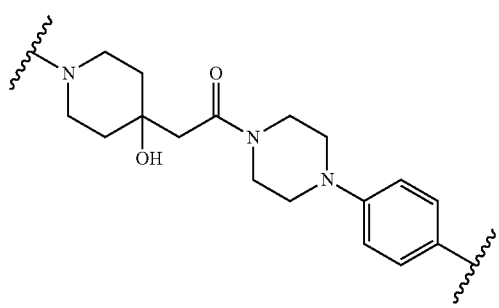
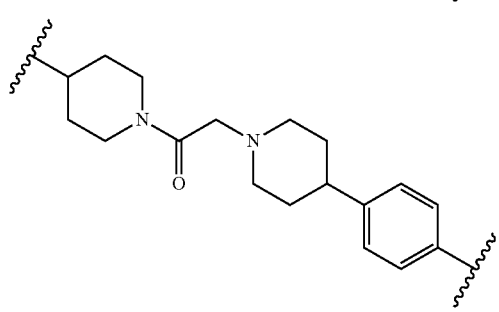
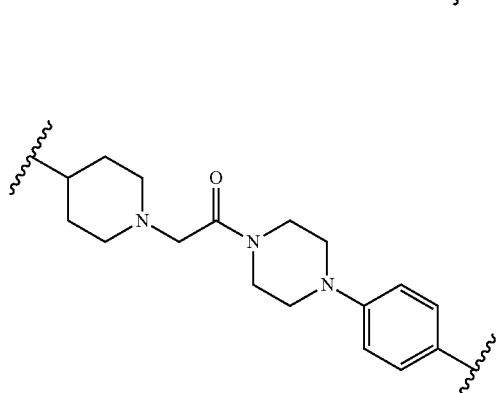
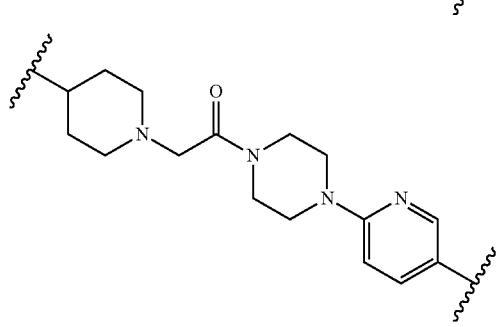
320
-continued
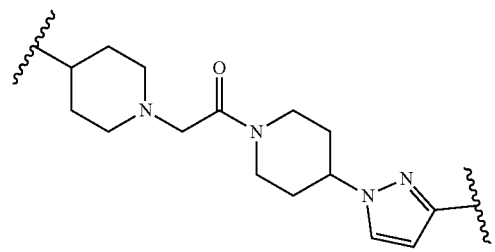
In certain embodiments L² is selected from:
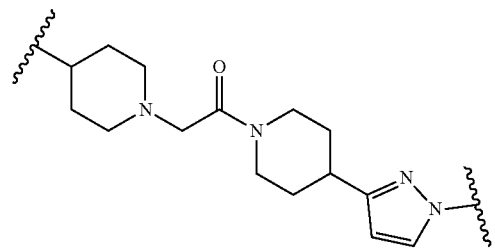
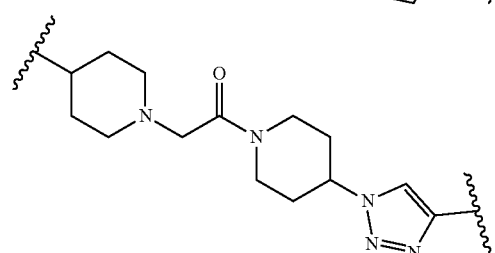
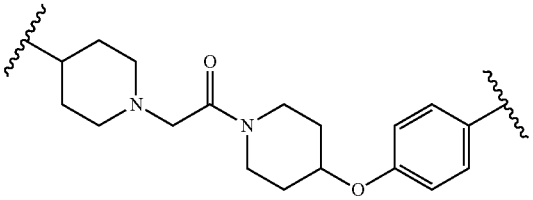
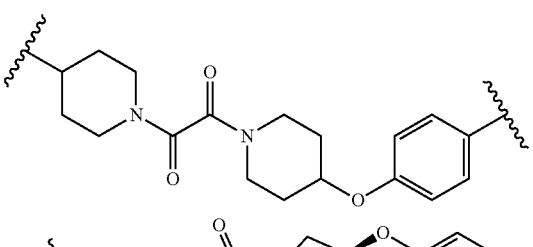
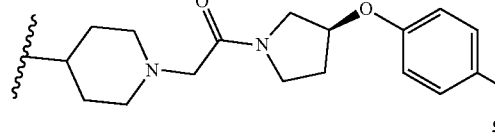
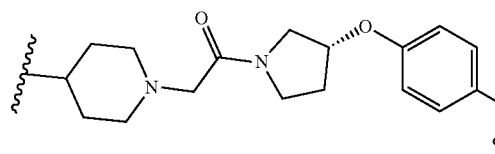

321
-continued
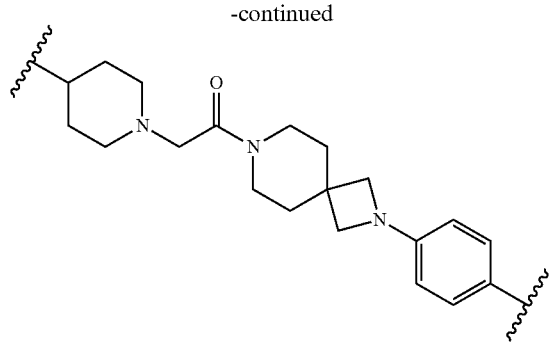
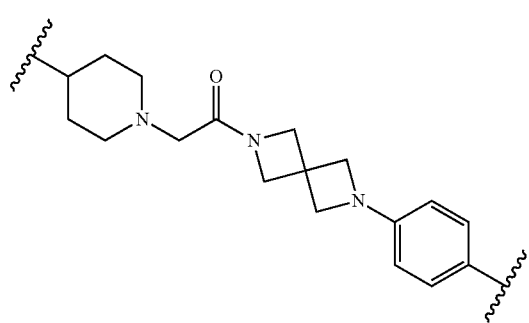
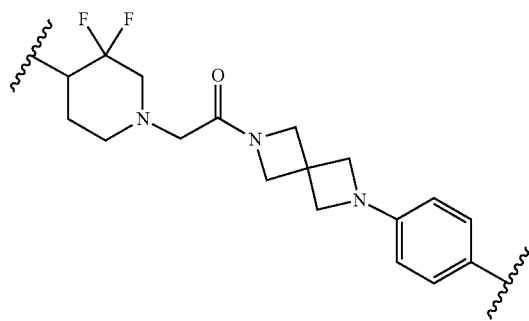
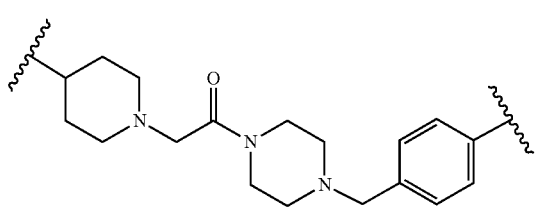
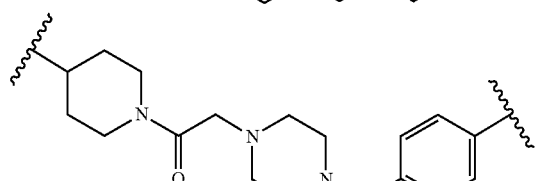
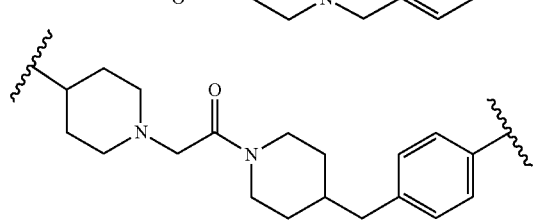
322
-continued
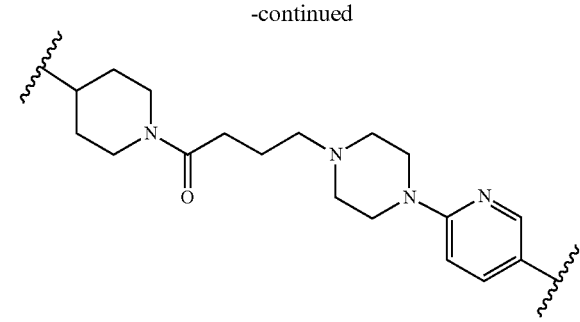
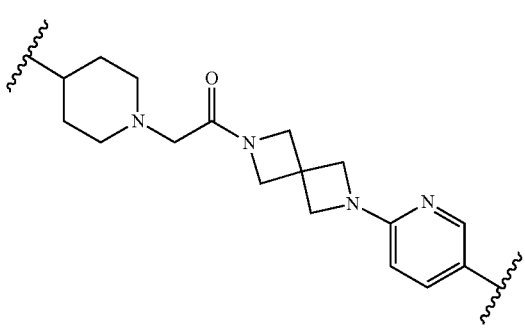
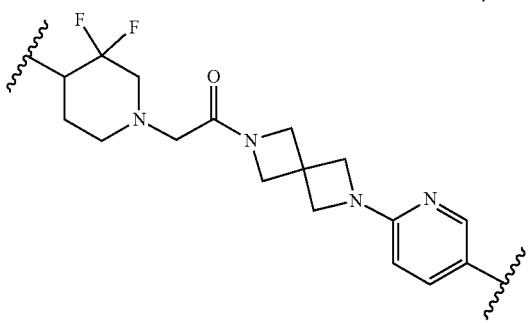
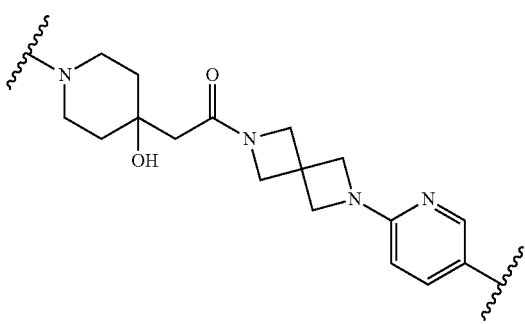
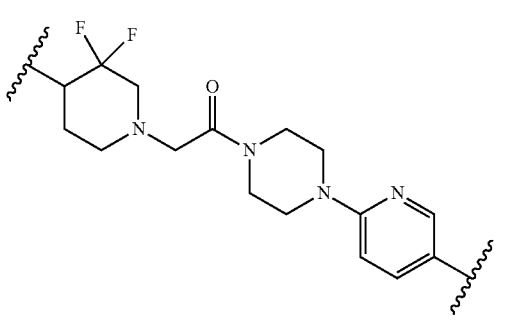

323
-continued
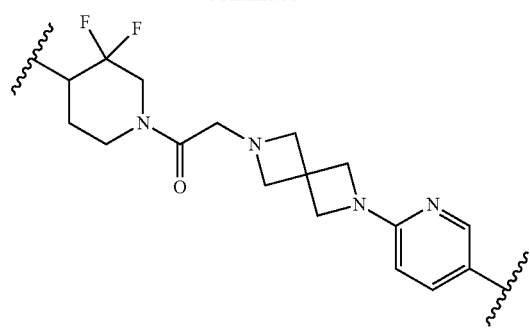
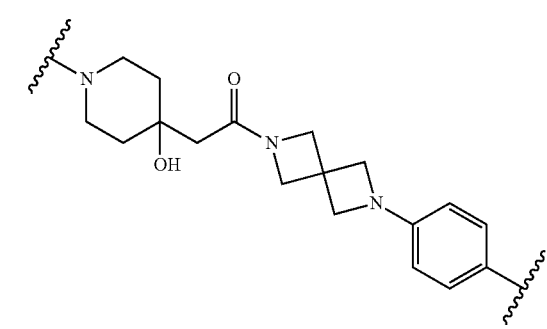
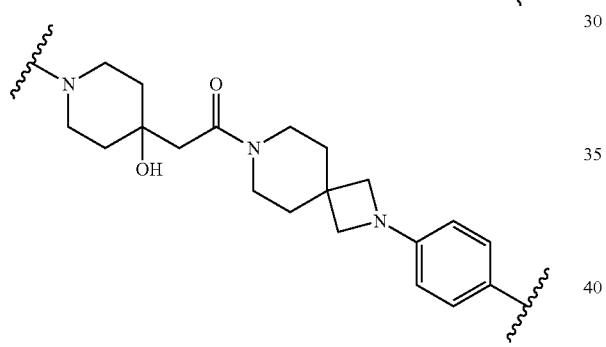
In certain embodiments L² is selected from:
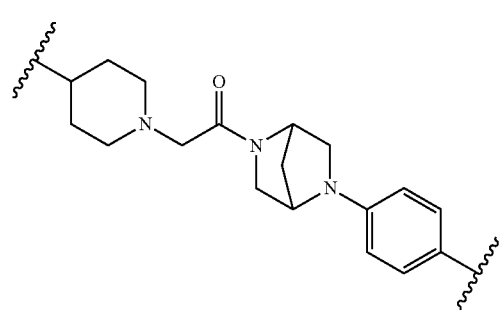
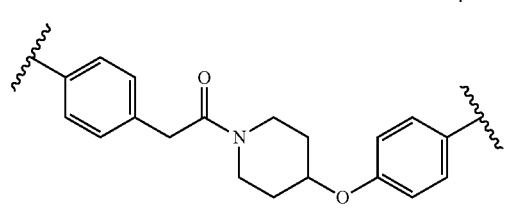
324
-continued
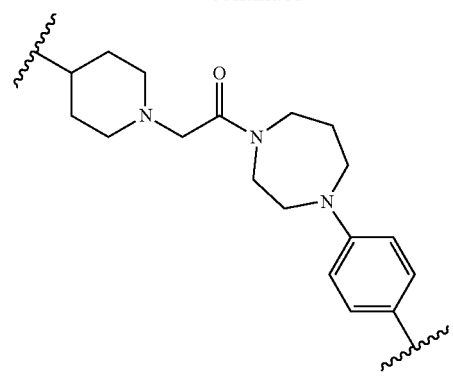
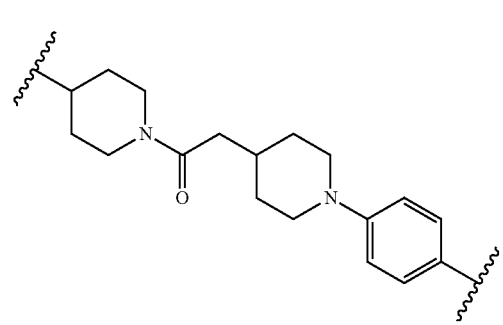
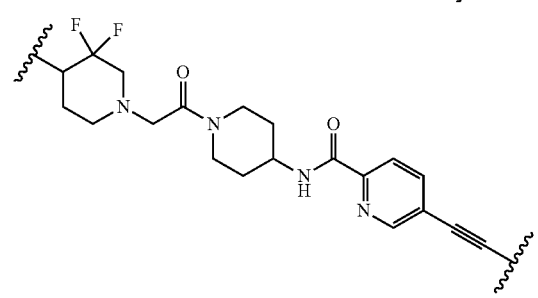
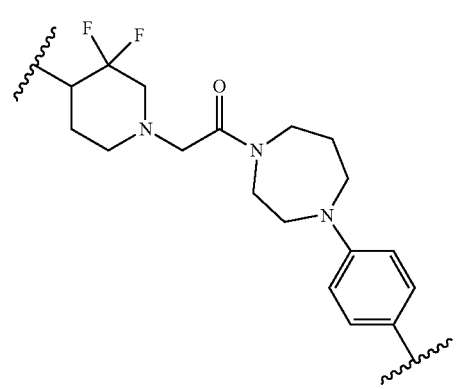
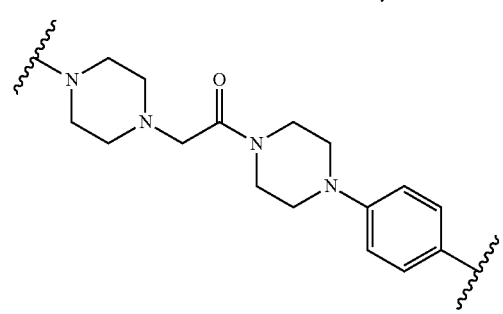

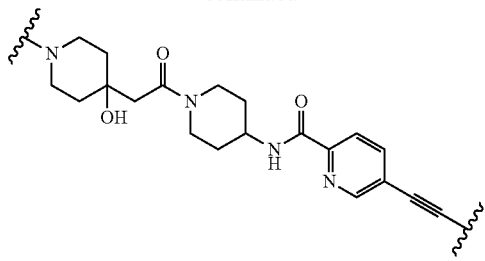
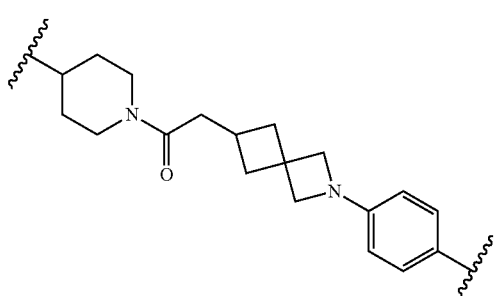
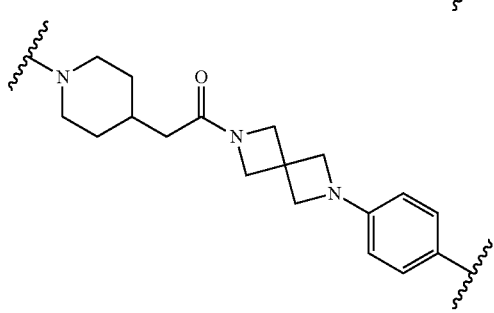
In certain embodiments L² is selected from:
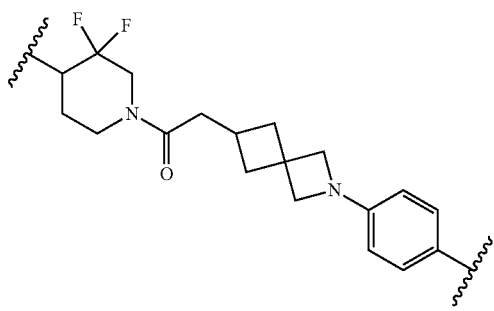
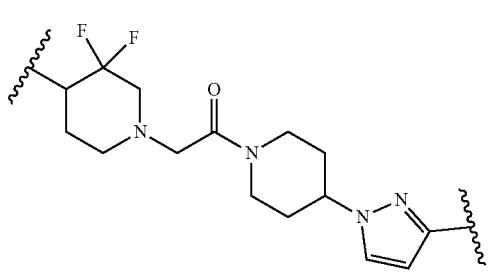
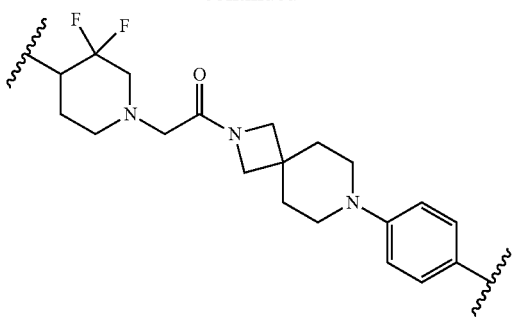
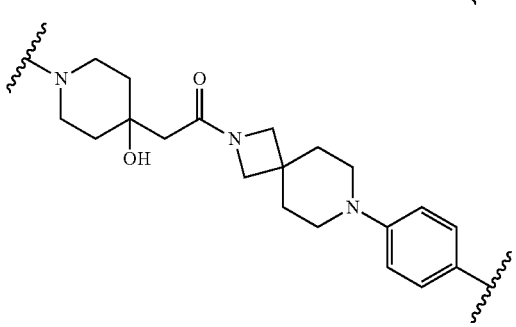
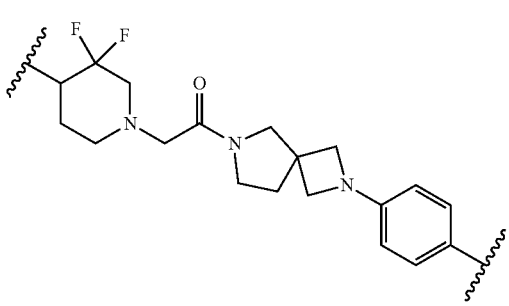
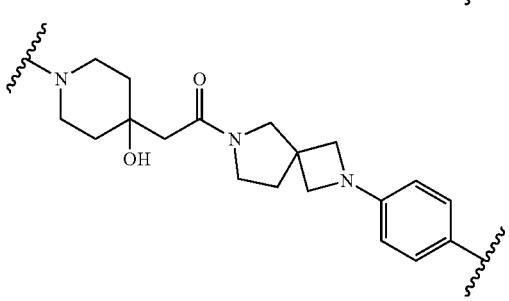
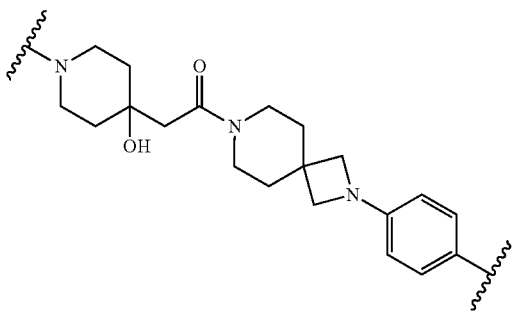

327
-continued
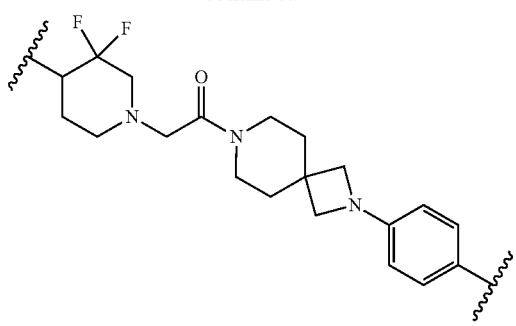
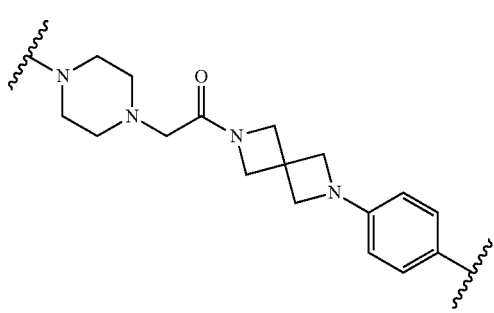
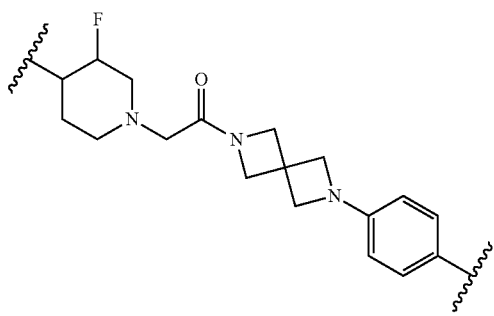
328
-continued
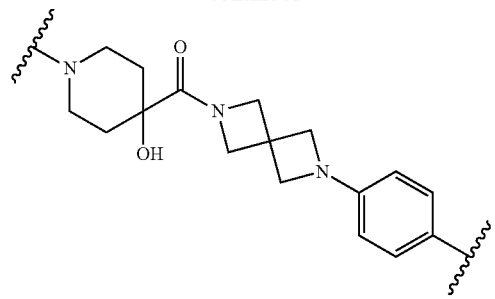
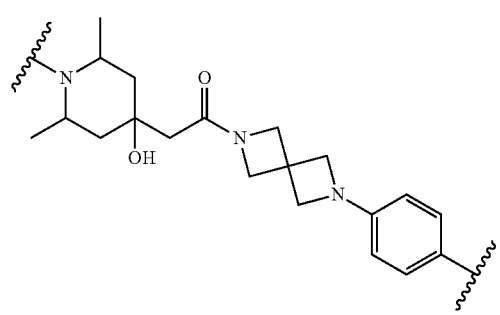
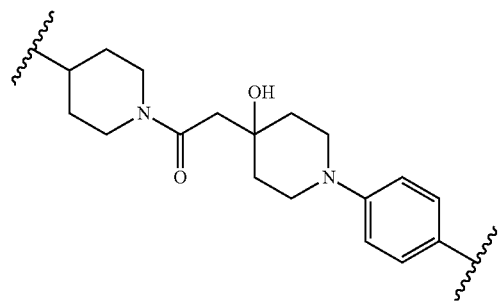
In certain embodiments L² is selected from:
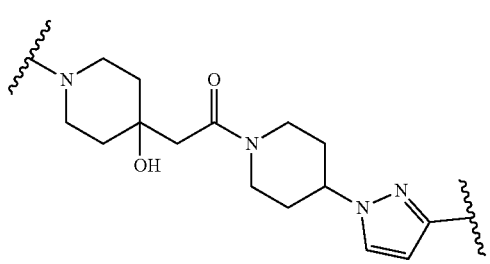
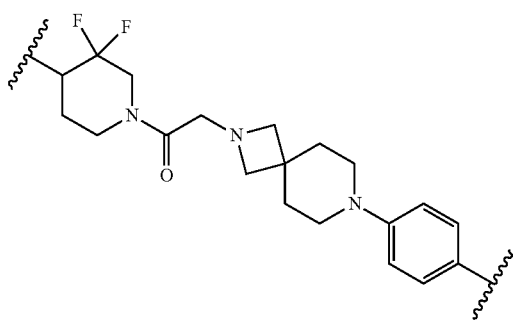
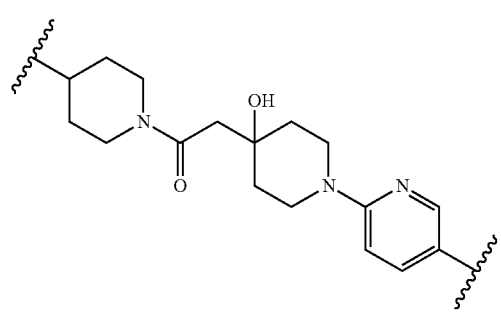
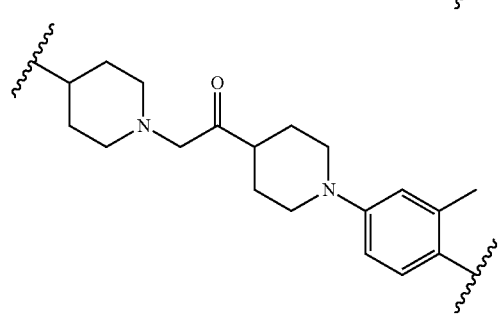

329
-continued
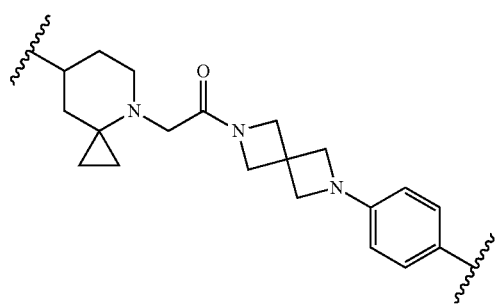
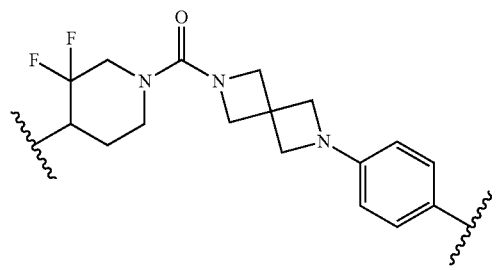
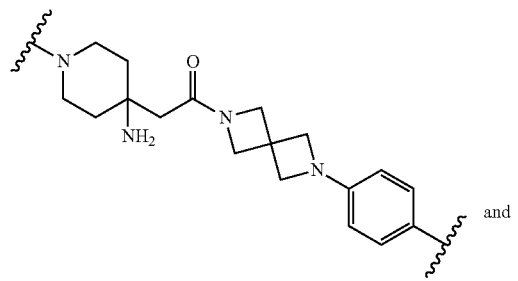
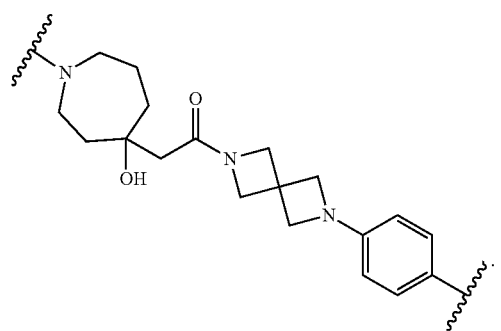
In certain embodiments L² is selected from:
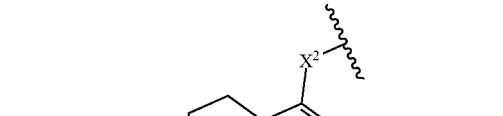
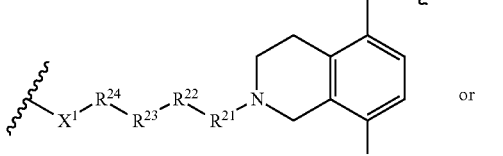
330
-continued
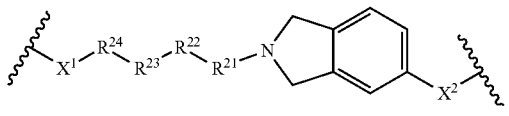
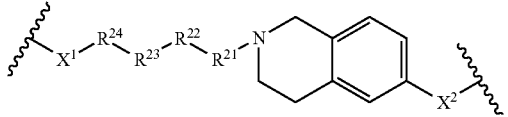
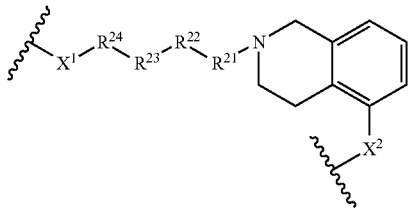
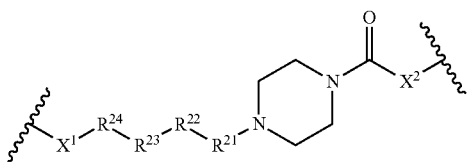
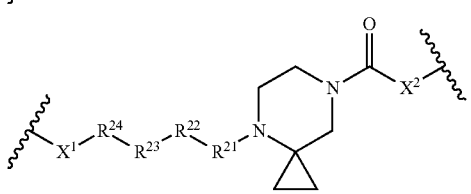
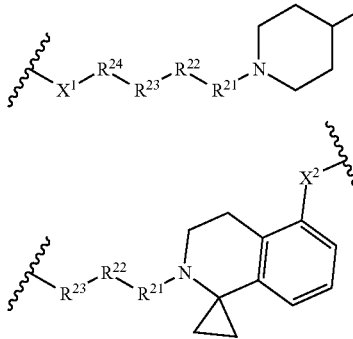
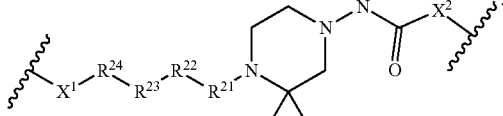
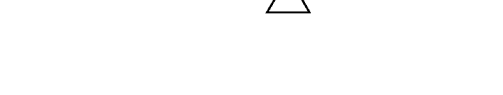

In certain embodiments $L^2$ is selected from:
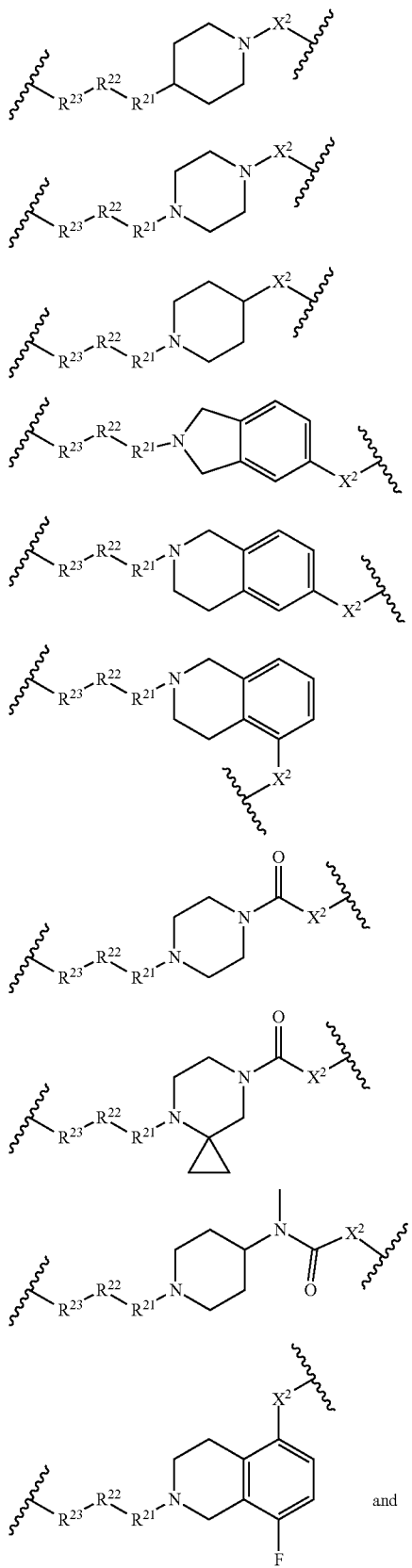
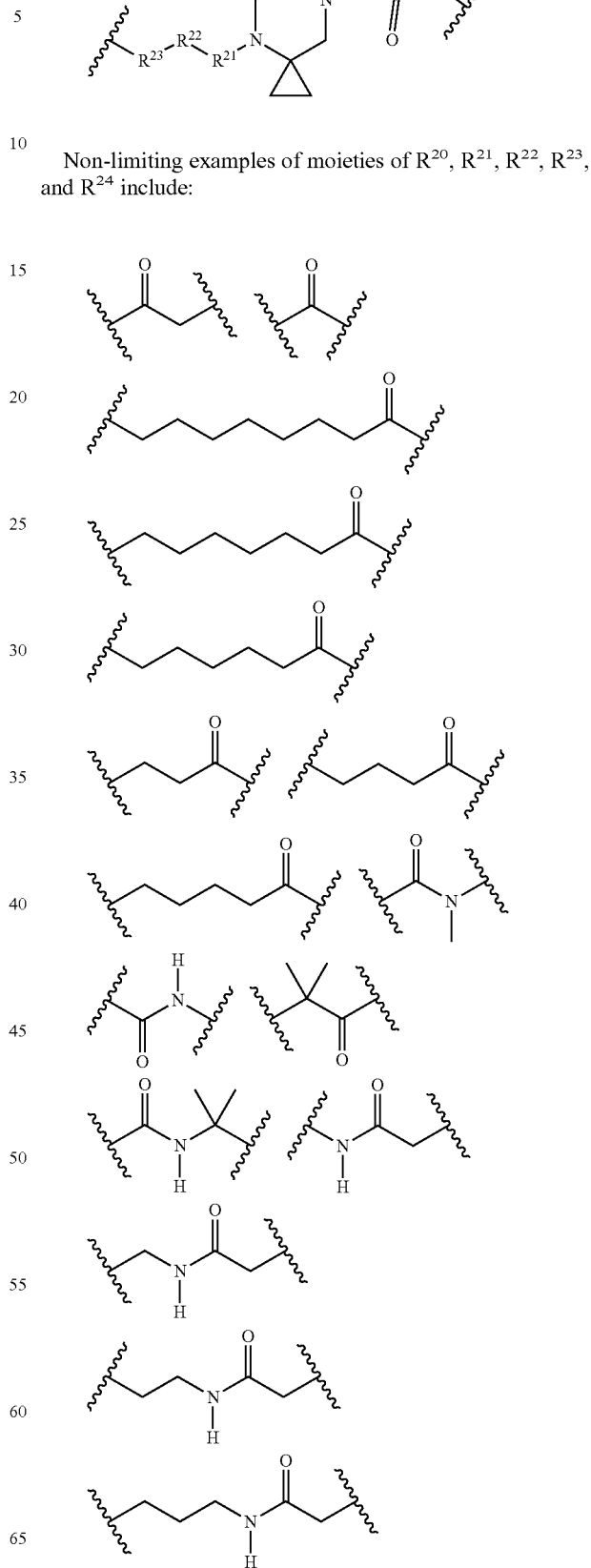
Non-limiting examples of moieties of $R^{20}$, $R^{21}$, $R^{22}$, $R^{23}$, and $R^{24}$ include:

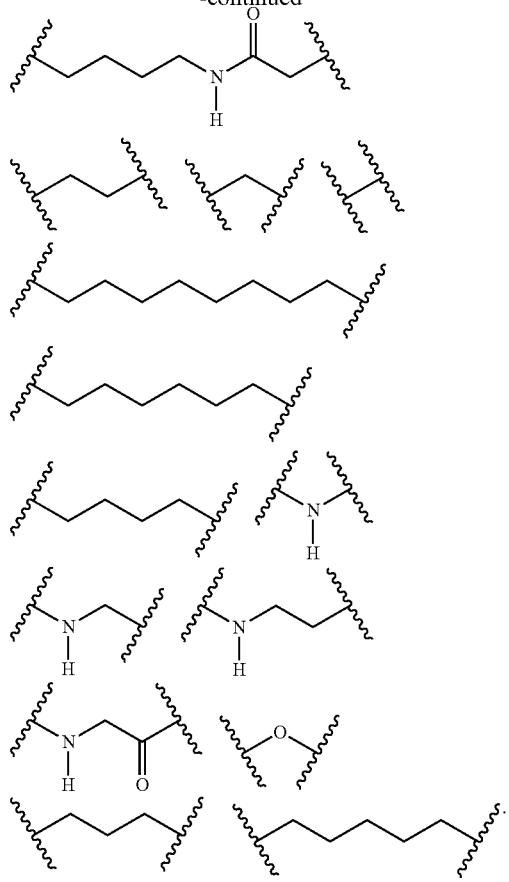
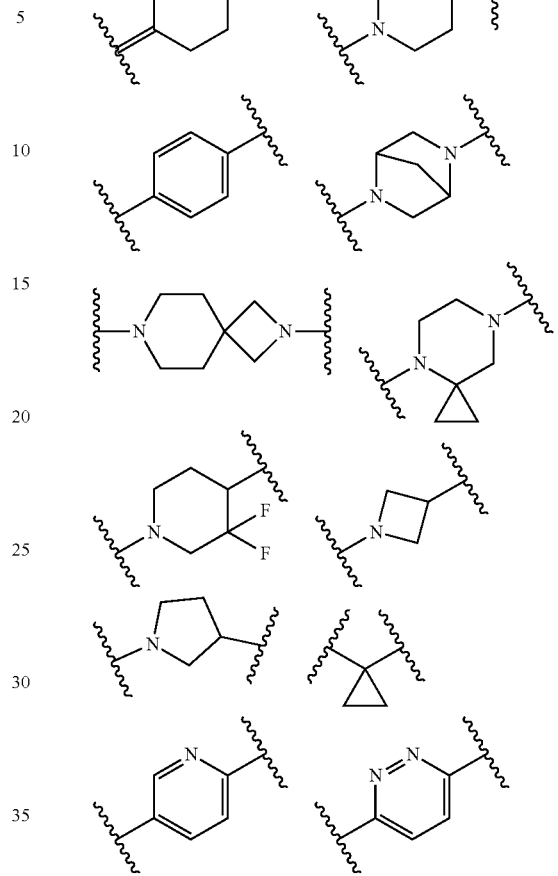
Additional non-limiting examples of moieties of $R^{20}$, $R^{21}$, $R^{22}$, $R^{23}$, and $R^{24}$ include:
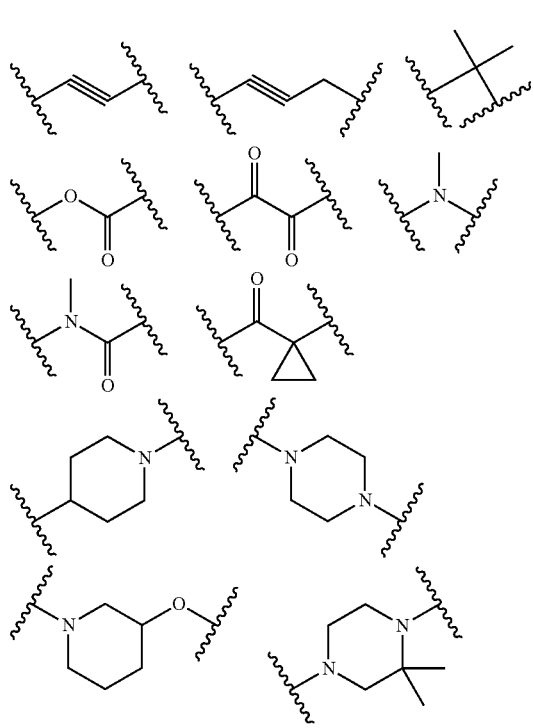
Additional non-limiting examples of moieties of $R^{20}$, $R^{21}$, $R^{22}$, $R^{23}$, and $R^{24}$ include:
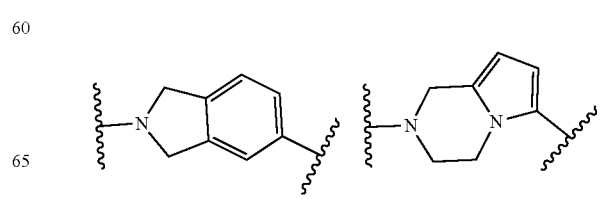

-continued

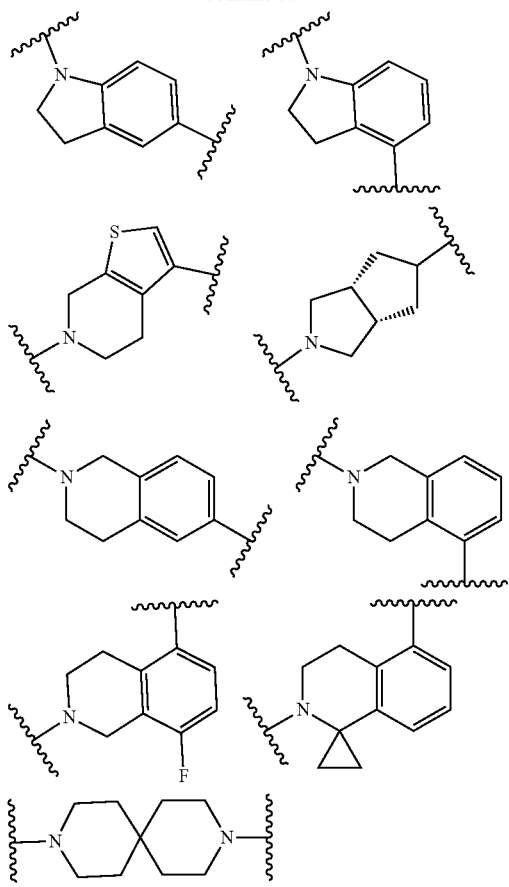

In additional embodiments, the Linker (L²) moiety is an optionally substituted (poly)ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms.

In certain embodiments, the Linker (L²) is flanked, substituted, or interspersed with an aryl, phenyl, benzyl, alkyl, alkylene, or heterocycle group.

In certain embodiments, the Linker (L²) may be asymmetric or symmetrical.

In certain embodiments, Linker (L²) can be a nonlinear chain, and can be, or include, aliphatic or aromatic or heteroaromatic cyclic moieties.

In any of the embodiments of the compounds described herein, the Linker group may be any suitable moiety as described herein.

In certain embodiments, the Linker (L²) is selected from the group consisting of:

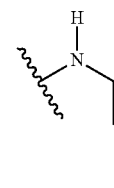

-continued

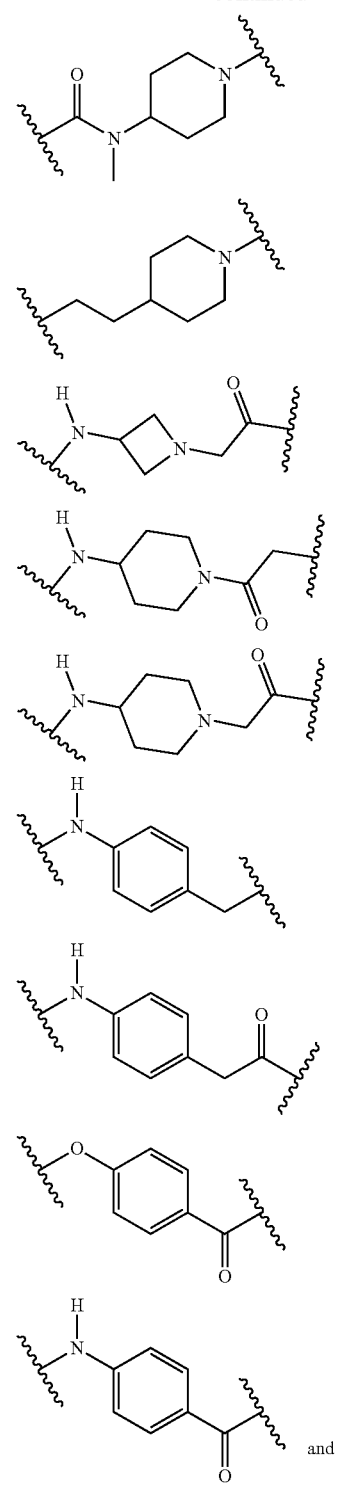

In certain embodiments, the linker ($L^2$) is selected from the group consisting of:
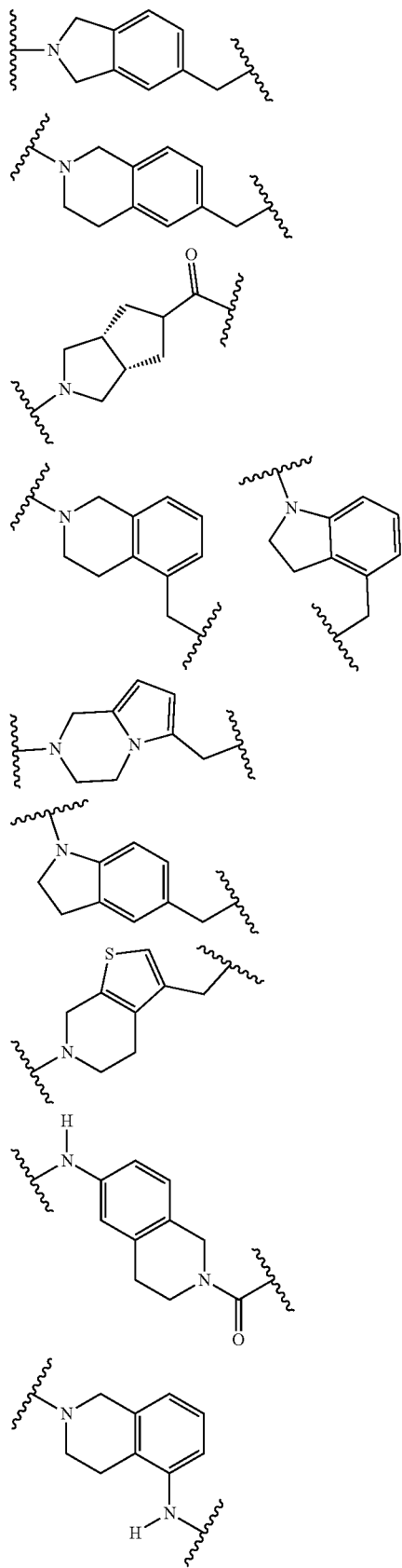
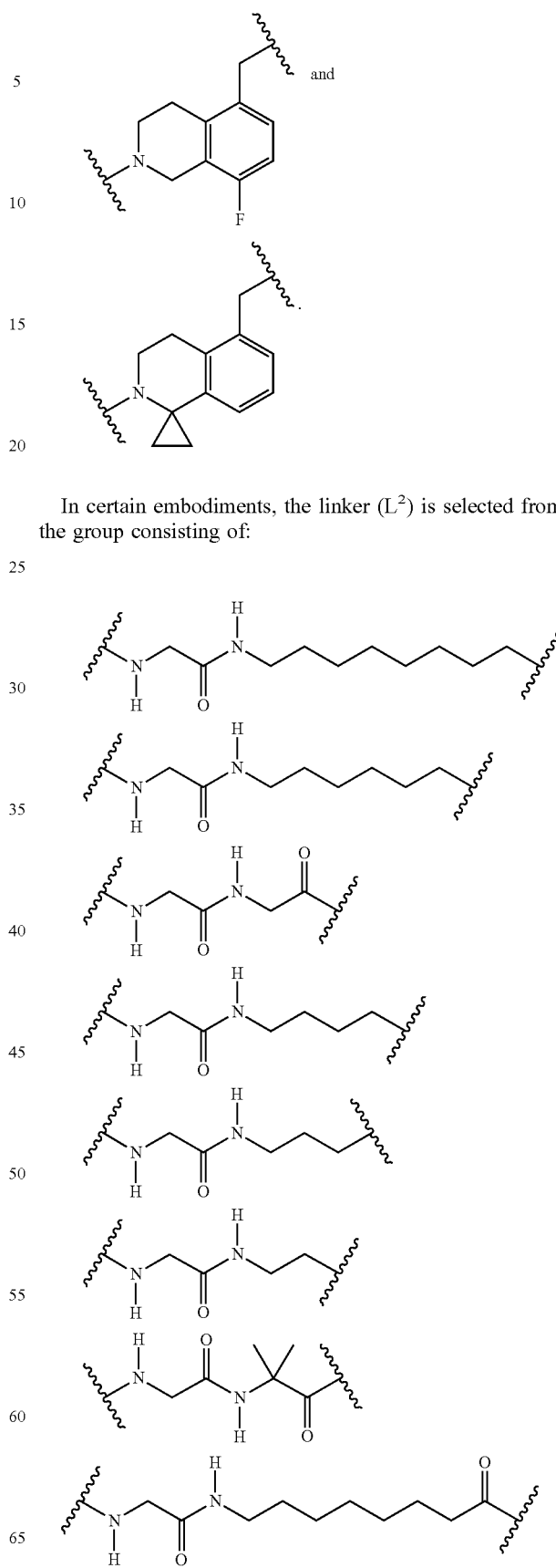
In certain embodiments, the linker ($L^2$) is selected from the group consisting of:

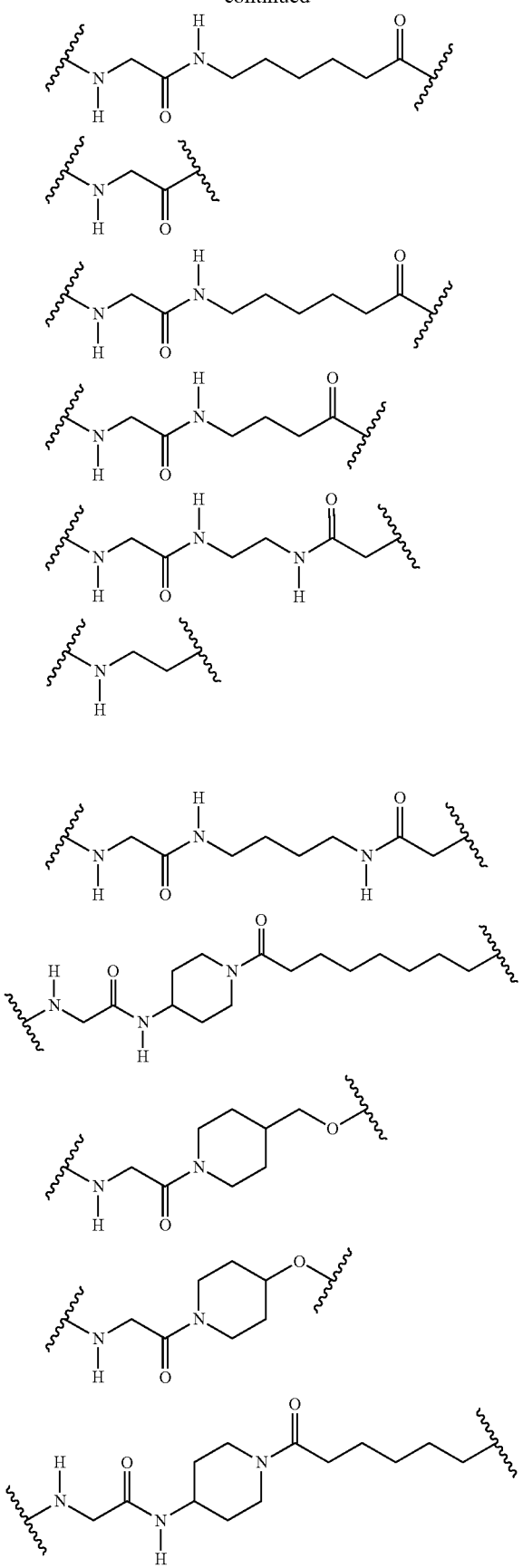
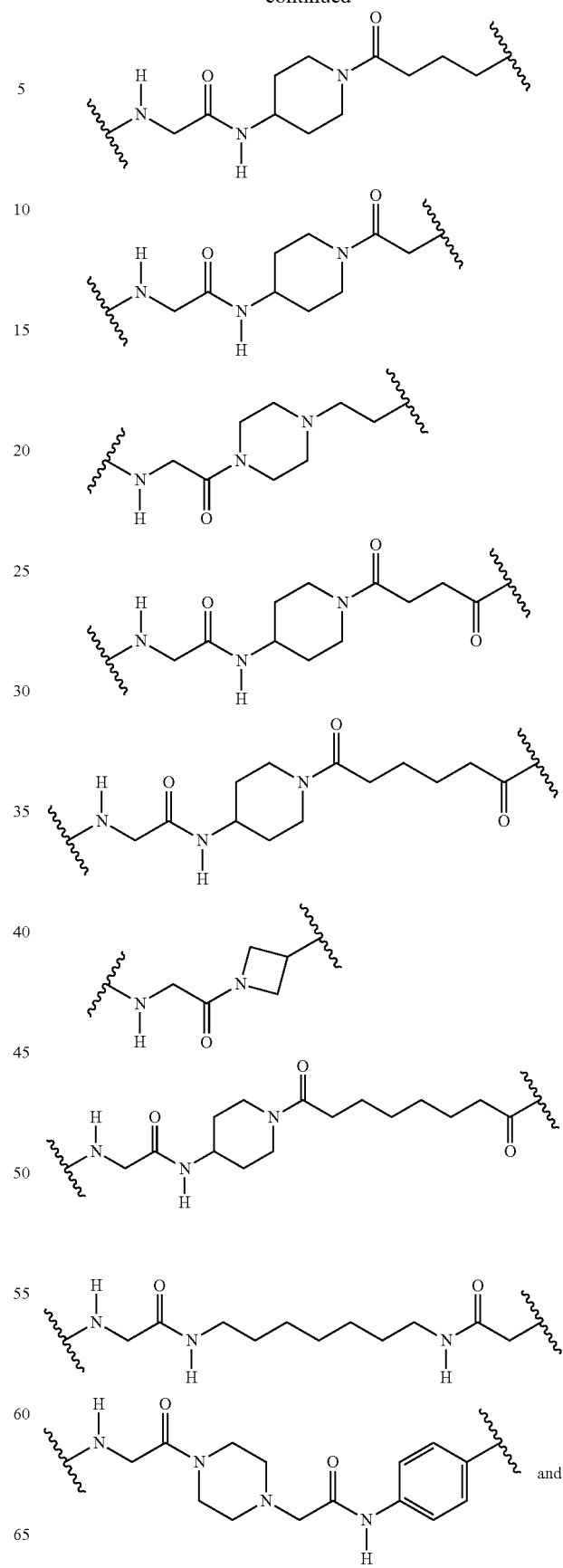

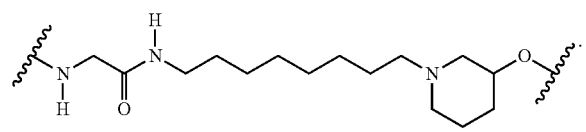
In certain embodiments, the linker (L²) is selected from the group consisting of
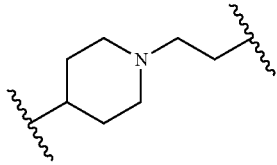
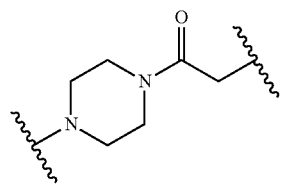
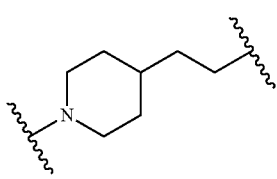
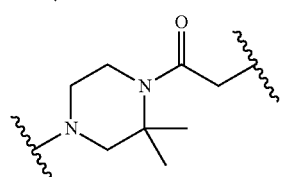
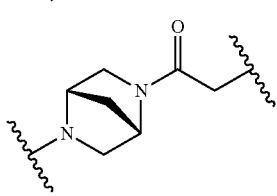
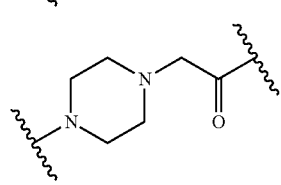
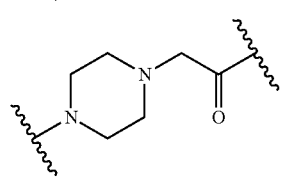
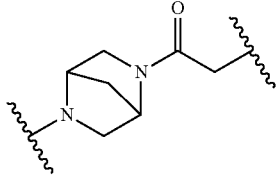
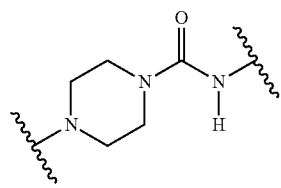 [SMILES: *N1CCN(C(=O)C(*)(C)C)CC1]
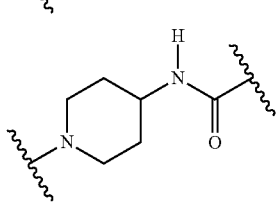
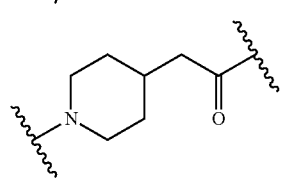
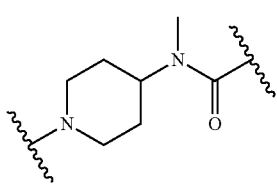
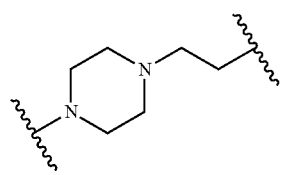

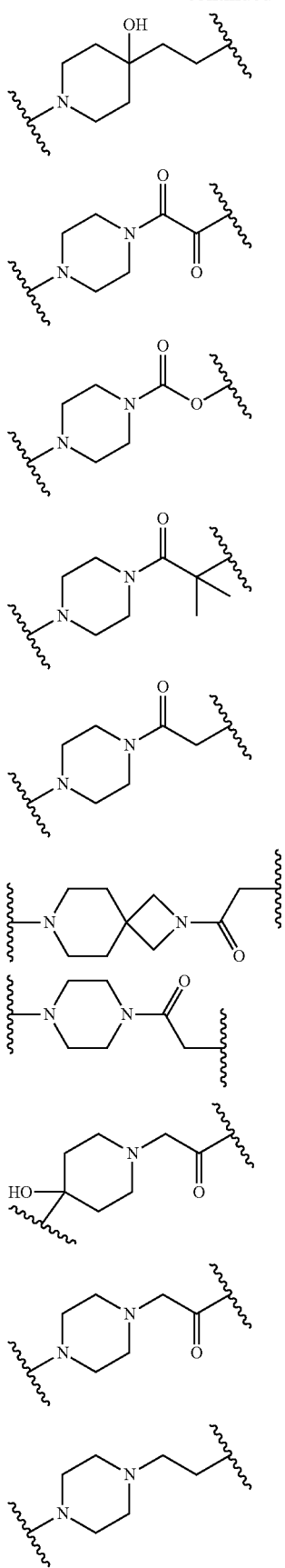
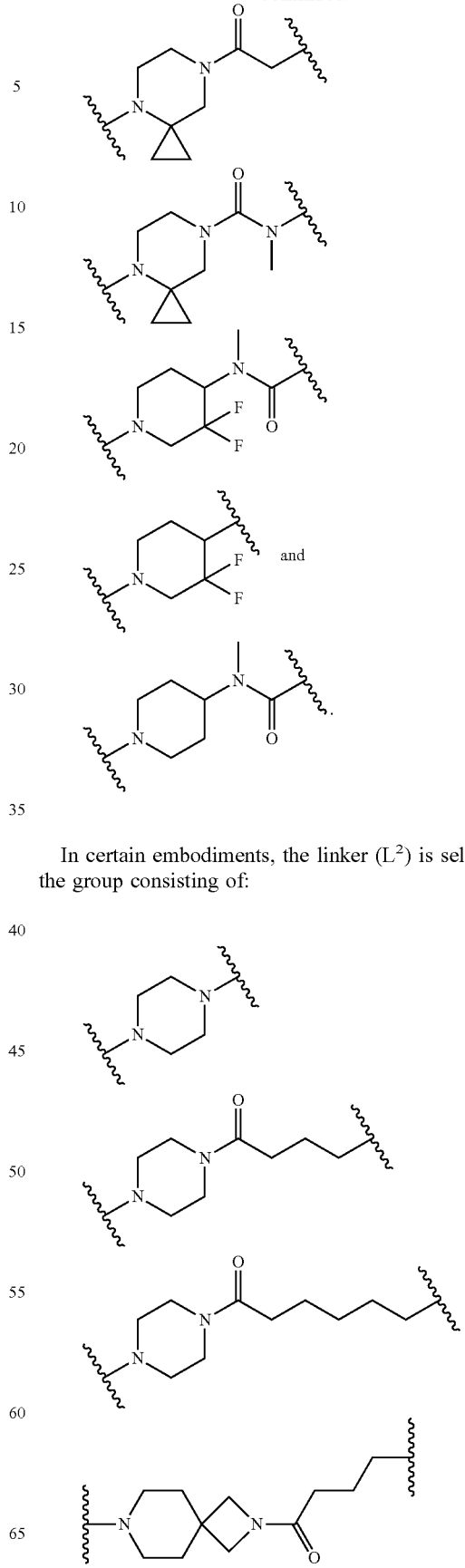
In certain embodiments, the linker ($L^2$) is selected from the group consisting of:

-continued
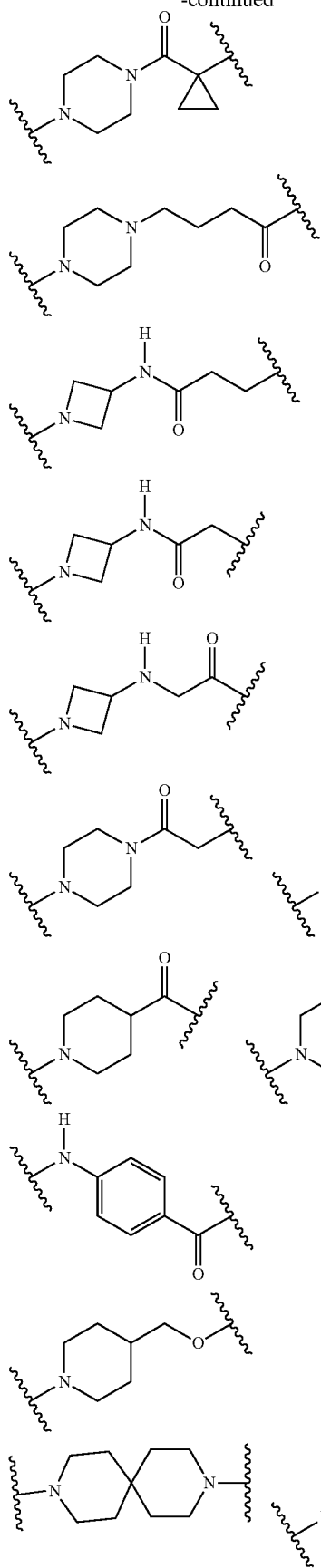
-continued
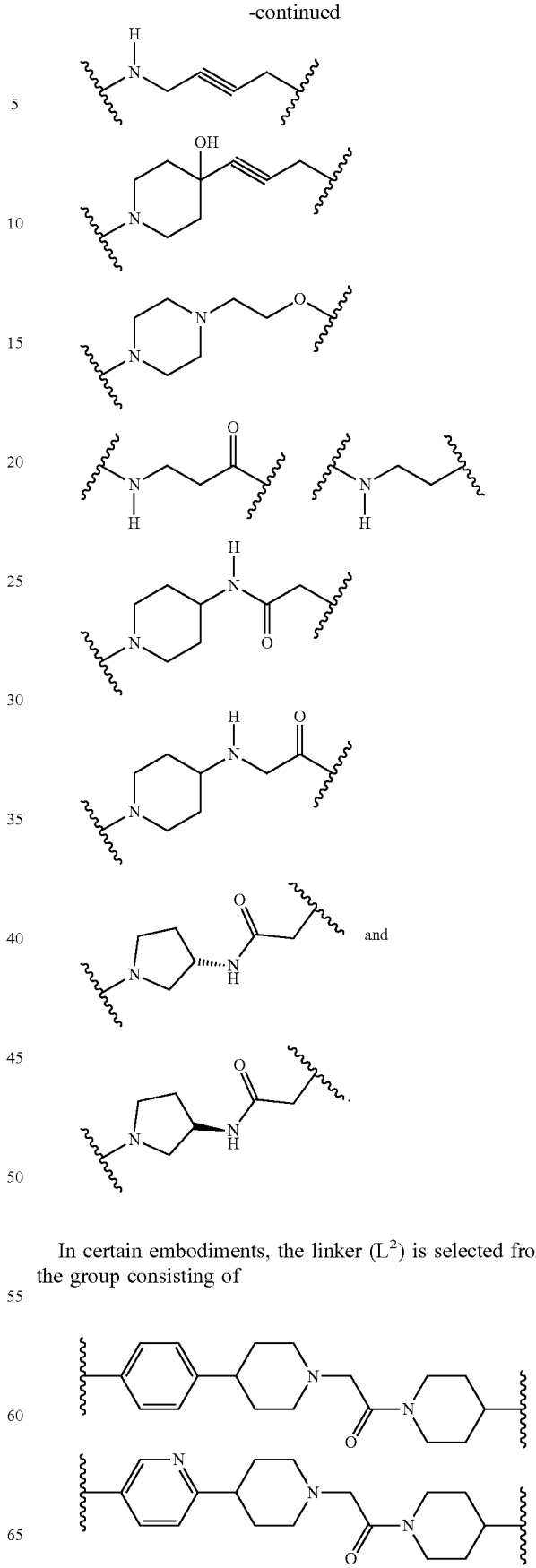
In certain embodiments, the linker ($L^2$) is selected from the group consisting of -continued
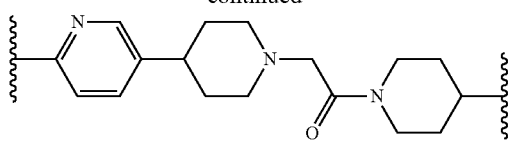
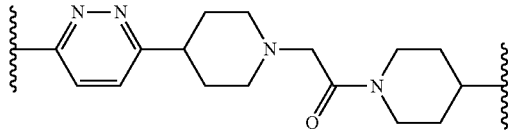
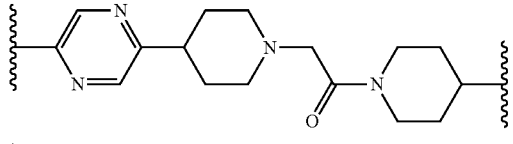
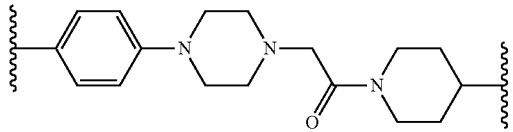
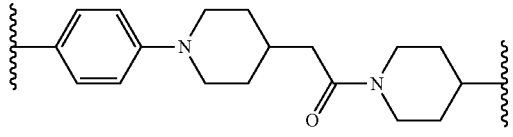
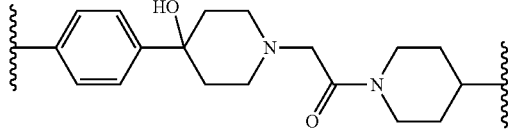
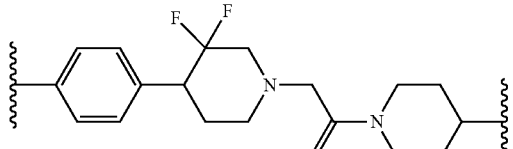
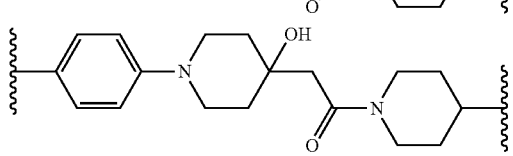
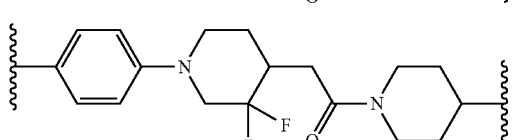
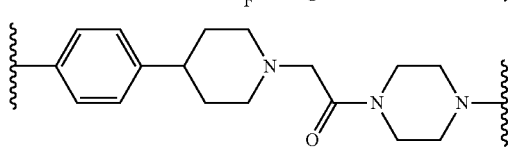
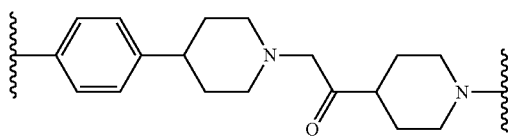
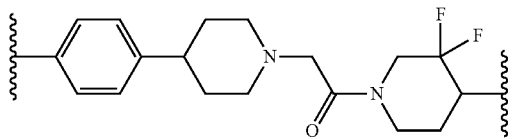
-continued
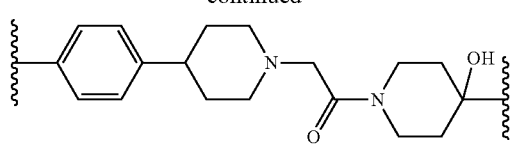
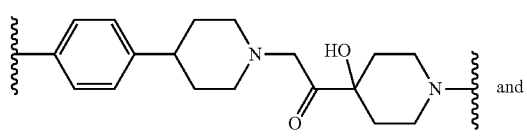
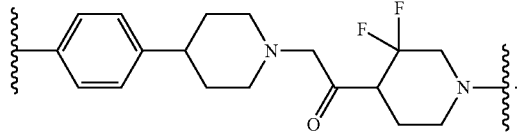
In certain embodiments, the linker ($L^2$) is selected from the group consisting of
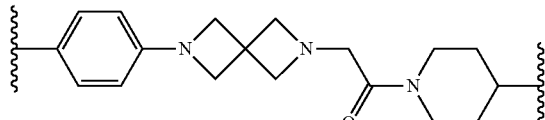
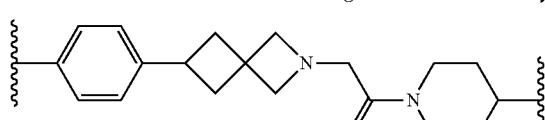
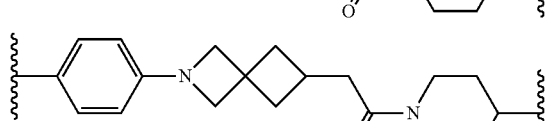
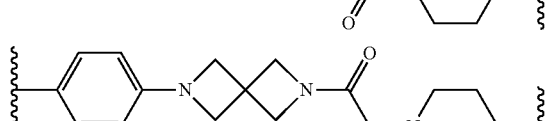
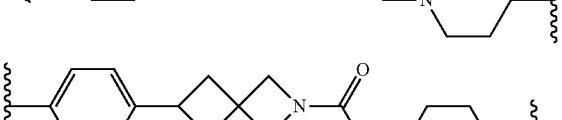
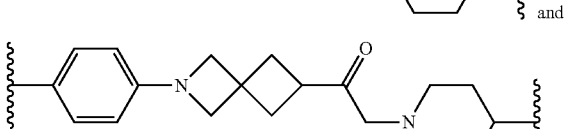
In certain embodiments linker ($L^2$) or a portion thereof is selected from:
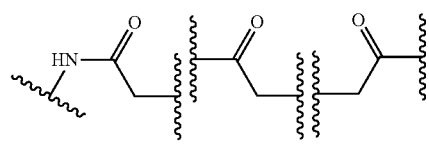

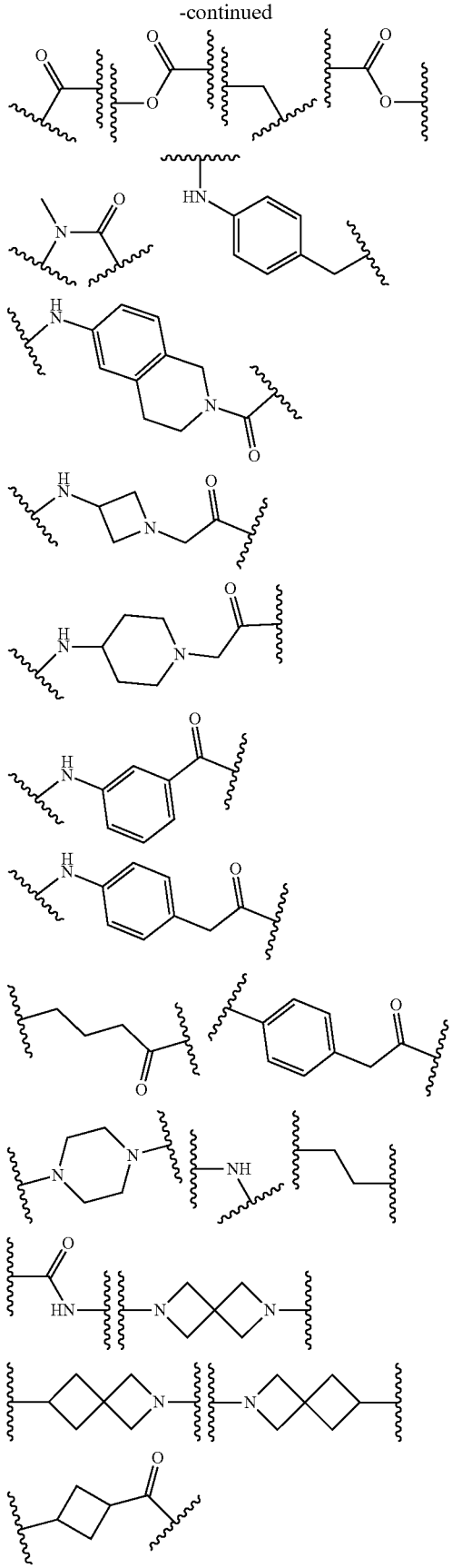

V. Methods of Treatment

A compound of the present invention can be used in an effective amount to treat a patient, in need thereof, or to treat any disorder mediated by EGFR.

Another aspect of the present invention provides a compound as described herein, or an enantiomer, diastereomer, or stereoisomer thereof, or pharmaceutically acceptable salt, hydrate, or solvate thereof, or a pharmaceutical composition, for use in the manufacture of a medicament for treating or preventing cancer in a patient in need thereof; wherein there is a need of EGFR inhibition for the treatment or prevention of cancer.

In one aspect, a compound of the present invention is used to treat an EGFR mediated cancer, wherein the EGFR has mutated from the wild-type. There are a number of possibilities for EGFR mutations. In certain non-limiting embodiments, the mutation is found in exon 18, exon 19, exon 20, or exon 21, or any combination thereof. In certain nonlimiting embodiments, the mutation is at position L858, E709, G719, C797, L861, T790, or L718 or any combination thereof. In certain embodiments the mutation is a L858R, T790M, L718Q, L792H, and/or a C797S mutation or any combination thereof.

In certain aspects, the cancer has developed one or more EGFR mutations following treatment with at least one EGFR inhibitor that can be a non-covalent inhibitor (including but not limited to gefitinib, erlotinib, lapatinib or vandetanib) or a covalent inhibitor (such as afatinib, osimertinib or dacomitinib). In another aspect, the cancer has developed one or more EGFR mutations following treatment with an antibody such as cetuximab, panitumab or necitumab. In yet another aspect, the cancer has one or more EGFR mutations or non-EGFR mutations that renders the cancer intrinsically resistant to EGFR inhibitor treatment, for example, a somatic exon 20 insertion, asomatic PIK3CA mutation, loss of PTEN expression, MET amplification, or a KRAS mutation.

In certain embodiments, a compound of the present invention is used to treat a cancer that is resistant to, or has acquired a resistance to, a first generation EGFR inhibitor such as erlotinib, gefitinib, and/or lapatinib. In certain embodiments, a compound of the present invention is used to treat a cancer that is resistant to, or has acquired a resistance to a second generation EGFR inhibitor such as afatinib and/or dacomitinib. In certain embodiments, a compound of the present invention is used to treat a cancer that is resistant to, or acquired a resistance to a third generation EGFR inhibitor such as osimertinib.

In some embodiments, the mutated EGFR protein in the diseased tissue has an L858 mutation, for example L858R.

In certain embodiments the compound of the present invention is used to treat a mutant EGFR mediated disorder, wherein EGFR has a mutation at one of the below listed amino acid sites. The mutation may, for example, be selected from one of the listed exemplary mutations, or may be a different mutation.

| Amino Acid | Exemplary Mutations |
|---|---|
| C797 | C797S |
| E709 | E709A, E709G, E709K, E709V |
| G719 | G719A, G719S, G719C, G719D |
| G724 | G724S |
| G119 | G119A |
| G796 | G796S, G796C |

-continued

| Amino Acid | Exemplary Mutations |
|---|---|
| L718 | L718V, L718Q |
| L792 | L792H; L792V |
| L858 | L858R |
| L861 | L861Q |
| S768 | S768I |
| T790 | T790M |

In certain embodiments the mutant EGFR mediated disorder has two mutations selected from the table above. In other embodiments the mutant EGFR mediated disorder has three mutations selected from the table above. In other embodiments the mutant EGFR mediated disorder has four or more mutations, which may optionally be selected from the table above.

In certain embodiments the mutant EGFR mediated disorder has an L858R mutation and one additional mutation which may optionally be selected from the table above. In some of these embodiments the mutant EGFR mediated disorder has an L858R mutation and two additional mutation that may optionally be selected from the table above. In other embodiments the mutant EGFR mediated disorder has a L858R mutation and three additional mutation that may optionally be selected from the table above.

In certain embodiments the mutant EGFR mediated disorder has a T790M mutation and one additional mutation optionally selected from the table above. In other embodiments the mutant EGFR mediated disorder has a T790M mutation and two additional mutation optionally selected from the table above. In other embodiments the mutant EGFR mediated disorder has a T790M mutation and three additional mutation optionally selected from the table above.

In certain embodiments the mutant EGFR mediated disorder has a L718Q mutation and one additional mutation optionally selected from the table above. In other embodiments the mutant EGFR mediated disorder has a L718Q mutation and two additional mutation optionally selected from the table above. In other embodiments the mutant EGFR mediated disorder has a L718Q mutation and three additional mutation optionally selected from the table above.

In certain embodiments the EGFR mediated disorder is mutant EGFR mediated cancer.

In certain embodiments the EGFR mediated cancer has a mutation of S768I, L718V, L792H, L792V, G796S, G796C, G724S, and/or G719A.

In certain embodiments, a compound of the present invention is used to treat an EGFR mediated cancer that has a frameshift mutation, for example a short in-frame deletion. In certain embodiments, a compound of the present invention is used to treat an EGFR mediated cancer wherein the EGFR has an exon 19 deletion. In certain embodiments, the exon 19 deletion is a deletion which includes the amino acids LREA (L747-A750). In certain embodiments, the exon 19 deletion is a deletion which includes the amino acids ELREA (E746-A750).

In certain embodiments a compound of the present invention is used to treat an EGFR mediated cancer wherein the EGFR has an L858R mutation in exon 21.

In certain embodiments a compound of the present invention is more active against a disorder driven by a mutated EGFR than wild-type EGFR.

In certain embodiments, a compound of the present invention is used to treat an EGFR mediated cancer wherein the EGFR has one or more exon 18 deletions.

In certain embodiments a compound of the present invention is used to treat EGFR with a E709 mutation, for example E709A, E709G, E709K, or E709V.

In certain embodiments a compound of the present invention is used to treat EGFR with a L718 mutation, for example L718Q.

In certain embodiments a compound of the present invention is used to treat EGFR with a G719 mutation, for example G719S, G719A, G719C, or G719D.

In certain embodiments, a compound of the present invention is used to treat an EGFR mediated cancer wherein the EGFR has one or more exon 19 insertions and/or one or more exon 20 insertions.

In certain embodiments, a compound of the present invention is used to treat S768I mutant EGFR cancer. In certain embodiments a compound of the present invention is used to treat EGFR L861Q mutant EGFR cancer. In certain embodiments, a compound of the present invention is used to treat C797S mutant EGFR cancer.

In certain embodiments a compound of the present invention is used to treat a T790M, L858R mutant EGFR cancer.

In certain embodiments a compound of the present invention is used to treat a L718Q, L858R mutant EGFR cancer.

In certain embodiments a compound of the present invention is used to treat a L792H, L858R mutant EGFR cancer.

In certain embodiments a compound of the present invention is used to treat a C797S, L858R mutant EGFR cancer.

In certain embodiments, a compound of the present invention is used to treat a cancer that is resistant to at least one EGFR inhibitor, for example a cancer that is resistant to a first generation EGFR inhibitor such as erlotinib, gefitinib, and/or lapatinib. In certain embodiments, a compound of the present invention is used to treat a cancer that has acquired resistance to a first generation EGFR inhibitor, for example a cancer that has acquired resistance to a first generation EGFR inhibitor such as erlotinib, gefitinib, and/or lapatinib.

In certain embodiments, a compound of the present invention is used to treat a cancer that is resistant to a second generation EGFR inhibitor such as afatinib and/or dacomitinib. In certain embodiments, a compound of the present invention is used to treat a cancer that has acquired resistance to a second generation EGFR inhibitor, for example a cancer that has acquired resistance to a second generation EGFR inhibitor such as afatinib and/or dacomitinib.

In certain embodiments, a compound of the present invention is used to treat a cancer that is resistant to a third generation EGFR inhibitor such as osimertinib. In certain embodiments, a compound of the present invention is used to treat a cancer that has acquired resistance to a third generation EGFR inhibitor, for example a cancer that has acquired resistance to a third generation EGFR inhibitor such as osimertinib.

In certain embodiments, the method comprises administering an effective amount of the active compound or its salt as described herein, optionally including a pharmaceutically acceptable excipient, carrier, or adjuvant (i.e., a pharmaceutically acceptable composition), or optionally in combination or alternation with another bioactive agent or combination of agents, to a patient in need thereof.

In certain embodiments, the present invention provides a method of treating any of the disorders described herein, in a patient in need thereof.

In other embodiments, the patient is administered an additional therapeutic agent. In other embodiments, the compound as described herein, and the additional therapeutic agent are administered simultaneously or sequentially.

In certain embodiments, the application provides a method of preventing any of the disorders described herein, in a patient in need thereof.

In certain embodiments, the patient is a human.

As degraders of EGFR, the compounds and compositions of this application are particularly useful for treating or lessening the severity of a disease, condition, or disorder where a EGFR is implicated in the disease, condition, or disorder.

In one aspect, the present invention provides a method for treating or lessening the severity of a disease, condition, or disorder where EGFR is implicated in the disease state.

Another aspect of the present invention provides a method of treating or preventing a proliferative disease. The method comprises administering an effective amount of a pharmaceutical composition comprising a compound as described herein, or an enantiomer, diastereomer, or stereoisomer thereof, or pharmaceutically acceptable salt, hydrate, or solvate thereof and optionally a pharmaceutically acceptable carrier to a patient in need thereof.

In some embodiments, the disease is mediated by EGFR. In other embodiments, EGFR plays a role in the initiation or development of the disease.

In certain embodiments, the disease or disorder is cancer or a proliferation disease.

In certain embodiments, the EGFR mediated disorder is an abnormal cell proliferation, including, but not limited to, a solid or hematoligical cancer.

In certain embodiments, the hematological cancer is acute myelogenous leukemia (AML), acute lymphoblastic leukemia (ALL), lymphoblastic T-cell leukemia, chronic myelogenous leukemia (CML), chronic lymphocytic leukemia (CLL), hairy-cell leukemia, chronic neutrophilic leukemia (CNL), acute lymphoblastic T-cell leukemia, acute monocytic leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukemia (MLL), erythroleukemia, malignant lymphoma, Hodgkins lymphoma, non-Hodgkins lymphoma, lymphoblastic T-cell lymphoma, Burkitt's lymphoma, follicular lymphoma, B cell acute lymphoblastic leukemia, diffuse large B cell lymphoma, Myc and B-Cell Leukemia (BCL)2 and/or BCL6 rearrangements/overexpression [double- and triple-hit lymphoma], myelodysplastic/myeloproliferative neoplasm, mantle cell lymphoma including bortezomib resistant mantle cell lymphoma.

Solid tumors that can be treated with the compounds described herein include, but are not limited to lung cancers, including small cell lung cancer (SCLC) and non-small cell lung cancer (NSCLC), breast cancers including inflammatory breast cancer, ER-positive breast cancer including tamoxifen resistant ER-positive breast cancer, and triple negative breast cancer, colon cancers, midline carcinomas, liver cancers, renal cancers, prostate cancers including castrate resistant prostate cancer (CRPC), brain cancers including gliomas, glioblastomas, neuroblastoma, and medulloblastoma including MYC-amplified medulloblastoma, colorectal cancers, Wilm's tumor, Ewing's sarcoma, rhabdomyosarcomas, ependymomas, head and neck cancers, melanomas, squamous cell carcinomas, ovarian cancers, pancreatic cancers including pancreatic ductal adenocarcinomas (PDAC) and pancreatic neuroendocrine tumors (PanNET), osteosarcomas, giant cell tumors of bone, thyroid cancers, bladder cancers, urothelial cancers, vulval cancers, cervical cancers, endometrial cancers, mesotheliomas, esophageal cancers, salivary gland cancers, gastric cancesr, nasopharangeal cancers, buccal cancers, cancers of the mouth, GIST (gastrointestinal stromal tumors), NUT-midline carcinomas, testicular cancers, squamous cell carcinomas, hepatocellular carcinomas (HCC), MYCN driven solid tumors, and NUT midline carcinomas (NMC).

In further embodiments, the disease or disorder is sarcoma of the bones, muscles, tendons, cartilage, nerves, fat, or blood vessels.

In further embodiments, the disease or disorder is soft tissue sarcoma, bone sarcoma, or osteosarcoma.

In further embodiments, the disease or disorder is angiosarcoma, fibrosarcoma, liposarcoma, leiomyosarcoma, Karposi's sarcoma, osteosarcoma, gastrointestinal stromal tumor, synovial sarcoma, pleomorphic sarcoma, chondrosarcoma, Ewing's sarcoma, reticulum cell sarcoma, meningiosarcoma, botryoid sarcoma, rhabdomyosarcoma, or embryonal rhabdomyosarcoma.

In certain embodiments the disorder is a bone, muscle, tendon, cartilage, nerve, fat, or blood vessel sarcoma.

In further embodiments, the disease or disorder is multiple myeloma.

In certain embodiments a compound of the present invention or a pharmaceutically acceptable salt thereof is used as a medicament in therapeutic and/or prophylactic treatment of a patient with EGFR activating mutations as determined by next-generation sequencing (NGS), suffering from cancer, in particular non-small-cell lung cancer, comprising determining the EGFR activating mutations status in said patient and then administering the compound of the present invention, or a pharmaceutically acceptable salt thereof, to said patient.

In other embodiments, the disease or disorder is inflammation, arthritis, rheumatoid arthritis, spondyiarthropathies, gouty arthritis, osteoarthritis, juvenile arthritis, and other arthritic conditions, neuroinflammation, allergy, pain, neuropathic pain, fever, pulmonary disorders, lung inflammation, adult respiratory distress chronic pulmonary inflammatory disease, and chronic obstructive pulmonary disease (COPD), liver disease and nephritis, gastrointestinal conditions, inflammatory bowel disease, Crohn's disease, gastritis, irritable bowel syndrome, ulcerative colitis, ulcerative diseases, gastric ulcers, autoimmune disease, graft vs. host reaction and allograft rejections, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, peripheral neuropathy, or B-Cell Lymphoma.

In other embodiments, the pharmaceutical composition comprising the compound as described herein and the additional therapeutic agent are administered simultaneously or sequentially.

In other embodiments, the disease or disorder is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, solid tumors, hematological cancers or solid cancers.

In some embodiments, said method is used to treat or prevent a condition selected from autoimmune diseases, inflammatory diseases, proliferative and hyperproliferative diseases, and immunologically-mediated diseases. In other embodiments, said condition is selected from a proliferative disorder.

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CMIL), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers, such as oral, laryngeal, nasopharyngeal and esophageal, genitourinary cancers, such as prostate, bladder, renal, uterine, ovarian, testicular, lung cancer, such as small-cell and non-small cell, breast cancer, pancreatic cancer, melanoma and other skin cancers, stomach cancer, brain tumors, tumors related to Gorlin's syndrome, such as medulloblastoma or meningioma, and liver cancer.

Additional exemplary forms of cancer include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more compound as described herein, in the manufacture of a medicament for the treatment of cancer, including without limitation the various types of cancer disclosed herein.

In some embodiments, the compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compound as described herein is useful for treating hematopoietic disorders, in particular, acute-myelogenous leukemia (AML), chronic-myelogenous leukemia (CML), acute-promyelocytic leukemia, and acute lymphocytic leukemia (ALL).

In certain embodiments, a compound or its corresponding pharmaceutically acceptable salt, or isotopic derivative, as described herein can be used in an effective amount to treat a host, for example a human, with a lymphoma or lymphocytic or myelocytic proliferation disorder or abnormality. For example, a compound as described herein can be administered to a host suffering from a Hodgkin's Lymphoma or a Non-Hodgkin's Lymphoma. For example, the host can be suffering from a Non-Hodgkin's Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); diffuse small-cleaved cell lymphoma (DSCCL); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; Langerhans cell histiocytosis; or Waldenstrom's Macroglobulinemia.

In another embodiment, a compound or its corresponding pharmaceutically acceptable salt, or isotopic derivative, as described herein can be used in an effective amount to treat a patient, for example a human, with a Hodgkin's lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin's Lymphoma; or Nodular Lymphocyte Predominant HL.

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

As inhibitors of EGFR protein, the compounds and compositions of this application are also useful in biological samples. One aspect of the application is inhibiting protein activity in a biological sample, which method comprises contacting said biological sample with a compound or composition as described herein. The term "biological sample", as used herein, means an in vitro or an ex vivo sample, including, without limitation, cell cultures or extracts thereof, biopsied material obtained from a mammal or extracts thereof, and blood, saliva, urine, feces, semen, tears, or other body fluids or extracts thereof. Inhibition of protein activity in a biological sample is useful for a variety of purposes that are known to one of skill in the art. Examples of such purposes include, but are not limited to, blood transfusion, organ-transplantation, and biological specimen storage.

Another aspect of this application is the study of EGFR protein in biological and pathological phenomena; the study of intracellular signal transduction pathways mediated by such proteins; and the comparative evaluation of new protein inhibitors. Examples of such uses include, but are not limited to, biological assays such as enzyme assays and cell-based assays.

In accordance with the foregoing, the present application further provides a method for preventing or treating any of the diseases or disorders described above in a patient in need of such treatment, which method comprises administering to said patient a therapeutically effective amount of a compound as described herein, or an enantiomer, diastereomer, or stereoisomer thereof, or pharmaceutically acceptable salt, hydrate, or solvate thereof. For any of the above uses, the required dosage will vary depending on the mode of administration, the particular condition to be treated and the effect desired.

VI. Combination Therapy

The disclosed compounds described herein can be used in an effective amount alone or in combination with another compound of the present invention or another bioactive agent or second therapeutic agent to treat a patient such as a human with an EGFR mediated disorder, including but not limited to those described herein.

The term "bioactive agent" is used to describe an agent, other than the selected compound according to the present invention, which can be used in combination or alternation with a compound of the present invention to achieve a desired result of therapy. In certain embodiments, the compound of the present invention and the bioactive agent are administered in a manner that they are active in vivo during overlapping time periods, for example, have time-period overlapping Cmax, Tmax, AUC or another pharmacokinetic parameter. In another embodiment, the compound of the present invention and the bioactive agent are administered to a patient in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In certain embodiments the checkpoint inhibitor is selected from nivolumab/OPDIVO®; pembrolizumab/KEYTRUDA®; and pidilizumab/CT-011, MPDL3280A/RG7446; MEDI4736; MSB0010718C; BMS 936559, a PDL2/1 g fusion protein such as AMP 224 or an inhibitor of B7-H3 (e.g., MGA271), B7-H4, BTLA, HVEM, TIM3, GAL9, LAG 3, VISTA, KIR, 2B4, CD160, CGEN-15049, CHK 1, CHK2, A2aR, B-7 family ligands, or a combination thereof.

In yet another embodiment, one of the active compounds described herein can be administered in an effective amount for the treatment of abnormal tissue of the female reproductive system such as breast, ovarian, endometrial, or uterine cancer, in combination or alternation with an effective amount of an estrogen inhibitor including, but not limited to, a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors.

Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138.

Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestratnt; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone.

Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In another embodiment, active compounds described herein can be administered in an effective amount for the treatment of abnormal tissue of the male reproductive system such as prostate or testicular cancer, in combination or alternation with an effective amount of an androgen (such as testosterone) inhibitor including, but not limited to a selective androgen receptor modulator, a selective androgen receptor degrader, a complete androgen receptor degrader, or another form of partial or complete androgen antagonist. In certain embodiments, the prostate or testicular cancer is androgen-resistant.

Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In certain embodiments, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In certain embodiments, the bioactive agent is an HER-2 inhibitor. Examples of HER-2 inhibitors include trastuzumab, lapatinib, ado-trastuzumab emtansine, and pertuzumab.

In certain embodiments, the bioactive agent is a CD20 inhibitor. Examples of CD20 inhibitors include obinutuzumab, rituximab, fatumumab, ibritumomab, tositumomab, and ocrelizumab.

In certain embodiments, the bioactive agent is a JAK3 inhibitor. Examples of JAK3 inhibitors include tasocitinib.

In certain embodiments, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N—[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl] amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N—((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In certain embodiments, the bioactive agent is a kinase inhibitor. In certain embodiments, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include, but are not limited to, Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-[(S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d] pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422).

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl)propenamide), GDC-0834 ([R-N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl) benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl) phenyl)-1H-imidazo[4,5-g]quinoxalin-6(5H)-one), GDC-0834 ((R)-N-(3-(6-((4-(1,4-dimethyl-3-oxopiperazin-2-yl) phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)-N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-f{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, but are not limited to, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl] methyl dihydrogen phosphate), fostamatinib disodium salt (sodium (6-((5-fluoro-2-((3,4,5-trimethoxyphenyl)amino) pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R, 2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl) bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In certain embodiments, the bioactive agent is a MEK inhibitor. MEK inhibitors are well known, and include, for example, trametinib/GSK1120212 (N-(3-{3-Cyclopropyl-5-

[(2-fluoro-4-iodophenyl)amino]-6,8-dimethyl-2,4,7-trioxo-3,4,6,7-tetrahydropyrido[4,3-d]pyrimidin-1(2H-yl)}phenyl) acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl) amino)-N-(2-hydroxyethoxy)-5-((3-oxo-1,2-oxazinan-2yl) methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In certain embodiments, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl] pyridin-4-yl]oxy-N-[4-(trifluoromethyl)phenyl] benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3-(trifluoroMethyl)phenyl]aMino]carbonyl]aMino] phenoxy]-N-Methyl-2pyridinecarboxaMide 1-Oxide), PLX-4720, dabrafenib (GSK2118436), GDC-0879, RAF265, AZ 628, Sf590885, ZM336372, GW5074, TAK-632, CEP-32496, LY3009120, and GX818 (Encorafenib).

In certain embodiments, the bioactive agent is an EGFR inhibitor, including, for example gefitinib (Iressa), erlotinib (Tarceva), lapatinib (Tykerb), osimertinib (Tagrisso), neratinib (Nerlynx), vandetanib (Caprelsa), dacomitinib (Vizimpro), rociletinib (Xegafri), afatinib (Glotriff, Giotriff, Afanix), lazertinib, or nazartib.

Additional examples of EGFR inhibitors include rociletinib (CO-1686), olmutinib (Olita), naquotinib (ASP8273), nazartinib (EGF816), PF-06747775, icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, dacomitinib (PF-00299804; Pfizer), brigatinib (Alunbrig), lorlatinib, and PF-06747775 (PF7775).

In certain embodiments, the bioactive agent is a first-generation EGFR inhibitor such as erlotinib, gefitinib, or lapatinib. In certain embodiments, the bioactive agent is a second-generation EGFR inhibitor such as afatinib and/or dacomitinib. In certain embodiments, the bioactive agent is a third-generation EGFR inhibitor such as osimertinib.

In certain embodiments a compound of the present invention is administered to a patient in need thereof in combination with osimertinib.

In certain embodiments a compound of the present invention is administered to a patient in need thereof in combination with rociletinib.

In certain embodiments a compound of the present invention is administered to a patient in need thereof in combination with avitinib.

In certain embodiments a compound of the present invention is administered to a patient in need thereof in combination with lazertinib.

In certain embodiments a compound of the present invention is administered to a patient in need thereof in combination with nazartinib.

In certain embodiments a compound of the present invention is administered to a patient in need thereof in combination with an EGFR antibody, for example, cetuximab, panitumab, or necitumab.

In certain embodiments a compound of the present invention is administered to a patient in need thereof in combination with cetuximab.

In certain embodiments a compound of the present invention is administered to a patient in need thereof in combination with panitumab.

In certain embodiments a compound of the present invention is administered to a patient in need thereof in combination with necitumab.

In certain embodiments, the bioactive agent is a c-MET inhibitor, for example, crizotinib (Xalkori, Crizonix), tepotinib (XL880, EXEL-2880, GSK1363089, GSK089), or tivantinib (ARQ 197).

In certain embodiments, the bioactive agent is an AKT inhibitor, including, but not limited to, MK-2206, GSK690693, Perifosine, (KRX-0401), GDC-0068, Triciribine, AZD5363, Honokiol, PF-04691502, and Miltefosine, a FLT-3 inhibitor, including, but not limited to, P406, Dovitinib, Quizartinib (AC220), Amuvatinib (MP-470), Tandutinib (MLN518), ENMD-2076, and KW-2449, or a combination thereof.

In certain embodiments, the bioactive agent is an mTOR inhibitor. Examples of mTOR inhibitors include, but are not limited to, rapamycin and its analogs, everolimus (Afinitor), temsirolimus, ridaforolimus, sirolimus, and deforolimus.

In certain embodiments, the bioactive agent is a RAS inhibitor. Examples of RAS inhibitors include but are not limited to Reolysin and siG12D LODER.

In certain embodiments, the bioactive agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ 197, MK-0457, MLN8054, PHA-739358, R-763, AT-9263, a FLT-3 inhibitor, a VEGFR inhibitor, an aurora kinase inhibitor, a PIK-1 modulator, an HDAC inhbitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, of atumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL 13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatinib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In certain embodiments the compound is administered in combination with ifosfamide.

In certain embodiments, the bioactive agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™).

Examples of additional suitable chemotherapeutic agents include, but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In some embodiments, the compound of the present invention is administered in combination with a chemotherapeutic agent (e.g., a cytotoxic agent or other chemical compound useful in the treatment of cancer). Examples of chemotherapeutic agents include alkylating agents, antimetabolites, folic acid analogs, pyrimidine analogs, purine analogs and related inhibitors, vinca alkaloids, epipodopyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Inti. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, NJ), ABRAXANE®, cremophor-free, albumin-engineered nanoparticle formulation of paclitaxel (American Pharmaceutical Partners, Schaumberg, IL), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-1 1); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the compound of the present invention. Suitable dosing regimens of combination chemotherapies are known in the ar. For example combination dosing regimes are described in Saltz et al., Proc. Am. Soc. Clin. Oncol. 18:233a (1999) and Douillard et al., Lancet 355(9209): 1041-1047 (2000).

Additional therapeutic agents that can be administered in combination with a Compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In certain embodiments, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a SiP receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (OR-THOCLONE OKT3®), Prednisone, ATGAM®, THYMO-GLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SVIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In some embodiments, the bioactive agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anticancer response, or antagonizes an antigen important for cancer. Such agents include RITUXAN® (rituximab); ZENAPAX® (daclizumab); SEVIULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-1-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOURIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The combination therapy may include a therapeutic agent which is a non-drug treatment. For example, the compound could be administered in addition to radiation therapy, cryotherapy, hyperthermia, and/or surgical excision of tumor tissue.

In certain embodiments the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

In certain embodiments the second therapeutic agent is administered on a different dosage schedule than the compound of the present invention. For example the second therapeutic agent may have a treatment holiday of 1 day, 2 days, 3 days, 4 days, 5 days, 6 days, 7 days, 8 days, 9 days, 10 days, 11 days, 12 days, 13 days, or 14 days per treatment cycle. In another embodiment the first therapeutic agent has a treatment holiday. For example the first therapeutic agent may have a treatment holiday of 1 day, 2 days, 3 days, 4 days, 5 days, 6 days, 7 days, 8 days, 9 days, 10 days, 11 days, 12 days, 13 days, or 14 days per treatment cycle. In certain embodiments both the first and second therapeutic have a treatment holiday.

VII. Pharmaceutical Compositions

A compound of Formula I, II, III, or IV or a pharmaceutically acceptable salt thereof can be used as a therapeutically active substance, e.g. in the form of a pharmaceutical preparations. The pharmaceutical preparations can be administered orally, e.g. in the form of tablets, coated tablets, dragées, hard and soft gelatin capsules, solutions, emulsions or suspensions. In other embodiments the compound is administered paternally, for example by intravaneous administration. The administration can, however, also be effected rectally, e.g. in the form of suppositories, or parenterally, e.g. in the form of injection solutions.

The compounds of Formula I, II, III, or IV and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of Formula I, II, III, or IV or a pharmaceutically acceptable salt thereof and a therapeutically inert carrier are also provided by the present invention, as is a process for their production, which comprises bringing one or more compounds of Formula I, II, III, or IV and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general Formula I, II, III, or IV or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of Formula I, II, III, or IV. Examples of compositions according to the invention are:

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt.

In some embodiments, compounds disclosed herein or used as described are administered once a day (QD), twice a day (BID), or three times a day (TID). In some embodiments, compounds disclosed herein or used as described are administered at least once a day for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a day, twice a day, three times a day, or four times a day.

In certain embodiments the compound of the present invention is administered orally once a day. In certain embodiments the compound of the present invention is administered orally twice a day. In certain embodiments the compound of the present invention is administered orally three times a day. In certain embodiments the compound of the present invention is administered orally four times a day.

In certain embodiments the compound of the present invention is administered intravenously once a day. In certain embodiments the compound of the present invention is administered intravenously twice a day. In certain embodiments the compound of the present invention is administered intravenously three times a day. In certain embodiments the compound of the present invention is administered intravenously four times a day.

In some embodiments the compound of the present invention is administered with a treatment holiday in between treatment cycles. For example the compound may have a treatment holiday of 1 day, 2 days, 3 days, 4 days, 5 days, 6 days, 7 days, 8 days, 9 days, 10 days, 11 days, 12 days, 13 days, or 14 days per treatment cycle.

In some embodiments a loading dose is administered to begin treatment. For example, the compound may be administered about 1.5×, about 2×, about 2.5×, about 3×, about 3.5×, about 4×, about 4.5×, about 5×, about 5.5×, about 6×, about 6.5×, about 7×, about 7.5×, about 8×, about 8.5×, about 9×, about 9.5×, or about 10× higher dose on the first day of treatment than the remaining days of treatment in the treatment cycle. Additional exemplary loading doses include about 1.5×, about 2×, about 2.5×, about 3×, about 3.5×, about 4×, about 4.5×, about 5×, about 5.5×, about 6×, about 6.5×, about 7×, about 7.5×, about 8×, about 8.5×, about 9×, about 9.5×, or about 10× higher dose on the first 2, 3, 4, 5, 6, 7, 8, 9, or 10 days of treatment than the remaining days of treatment in the treatment cycle.

The pharmaceutical composition may also include a molar ratio of the active compound and an additional active agent. For example the pharmaceutical composition may contain a molar ratio of about 0.5:1, about 1:1, about 2:1, about 3:1 or from about 1.5:1 to about 4:1 of an anti-inflammatory or immunosuppressing agent.

These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

A pharmaceutically or therapeutically effective amount of the composition will be delivered to the patient. The precise effective amount will vary from patient to patient, and will depend upon the species, age, the subject's size and health, the nature and extent of the condition being treated, recommendations of the treating physician, and the therapeutics or combination of therapeutics selected for administration. The effective amount for a given situation can be determined by routine experimentation. For purposes of the disclosure, a therapeutic amount may for example be in the range of about 0.01 mg/kg to about 250 mg/kg body weight, more typically about 0.1 mg/kg to about 10 mg/kg, in at least one dose. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

In certain embodiments the dose ranges from about 0.01-100 mg/kg of patient bodyweight, for example about 0.01 mg/kg, about 0.05 mg/kg, about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packed tablets, capsules, and powders in vials or ampoules. Also, the unit dosage form can be a capsule, tablet, cachet, or lozenge itself, or it can be the appropriate number of any of these in packaged form.

In certain embodiments the compound is administered as a pharmaceutically acceptable salt. Non-limiting examples of pharmaceutically acceptable salts include: acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

Thus, the composition of the disclosure can be administered as a pharmaceutical formulation including one suitable for oral (including buccal and sub-lingual), rectal, nasal, topical, transdermal, pulmonary, vaginal or parenteral (including intramuscular, intra-arterial, intrathecal, subcutaneous and intravenous), injections, inhalation or spray, intra-aortal, intracranial, subdermal, intraperitioneal, subcutaneous, or by other means of administration containing conventional pharmaceutically acceptable carriers. A typical manner of administration is oral, topical or intravenous, using a convenient daily dosage regimen which can be adjusted according to the degree of affliction.

Depending on the intended mode of administration, the pharmaceutical compositions can be in the form of solid, semi-solid or liquid dosage forms, such as, for example, tablets, suppositories, pills, capsules, powders, liquids, syrup, suspensions, creams, ointments, lotions, paste, gel, spray, aerosol, foam, or oil, injection or infusion solution, a transdermal patch, a subcutaneous patch, an inhalation formulation, in a medical device, suppository, buccal, or sub-lingual formulation, parenteral formulation, or an ophthalmic solution, or the like, preferably in unit dosage form suitable for single administration of a precise dosage.

Some dosage forms, such as tablets and capsules, are subdivided into suitably sized unit doses containing appropriate quantities of the active components, e.g., an effective amount to achieve the desired purpose. The compositions will include an effective amount of the selected drug in combination with a pharmaceutically acceptable carrier and, in addition, can include other pharmaceutical agents, adjuvants, diluents, buffers, and the like.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to adjuvants, binders, buffering agents, coloring agents, diluents, disintegrants, excipients, emulsifiers, flavorants, gels, glidents, lubricants, preservatives, stabilizers, surfactants, solubilizer, tableting agents, wetting agents or solidifying material.

Some carriers may be listed in more than one class, for example vegetable oil may be used as a lubricant in some formulations and a diluent in others.

Exemplary pharmaceutically acceptable carriers include sugars, starches, celluloses, powdered tragacanth, malt, gelatin; talc, petroleum jelly, lanoline, polyethylene glycols, alcohols, transdermal enhancers and vegetable oils. Optional active agents may be included in a pharmaceutical composition, which do not substantially interfere with the activity of the compound of the present invention.

Some excipients include, but are not limited to, liquids such as water, saline, glycerol, polyethylene glycol, hyaluronic acid, ethanol, and the like. The compound can be provided, for example, in the form of a solid, a liquid, spray dried material, a microparticle, nanoparticle, controlled release system, etc., as desired according to the goal of the therapy. Suitable excipients for non-liquid formulations are also known to those of skill in the art. A thorough discussion of pharmaceutically acceptable excipients and salts is available in Remington's Pharmaceutical Sciences, 18th Edition (Easton, Pennsylvania: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable, and which provides the formulation with the desired pH, i.e., a pH in the physiologically acceptable range. Examples of buffer solutions include saline, phosphate buffered saline, Tris buffered saline, Hank's buffered saline, and the like.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment provided is the use of permeation enhancer excipients including polymers such as: poly-cations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

In certain embodiments the excipient is selected from butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The pharmaceutical compositions/combinations can be formulated for oral administration. For oral administration, the composition will generally take the form of a tablet, capsule, a softgel capsule or can be an aqueous or nonaqueous solution, suspension or syrup.

Tablets and capsules are typical oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

Parenteral formulations can be prepared in conventional forms, either as liquid solutions or suspensions, solid forms suitable for solubilization or suspension in liquid prior to injection, or as emulsions. Typically, sterile injectable suspensions are formulated according to techniques known in the art using suitable carriers, dispersing or wetting agents and suspending agents. The sterile injectable formulation can also be a sterile injectable solution or a suspension in a acceptably nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, typical methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Formulations for buccal administration include tablets, lozenges, gels and the like. Alternatively, buccal administration can be effected using a transmucosal delivery system as known to those skilled in the art. The compounds of the disclosure can also be delivered through the skin or mucosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In certain embodiments, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like.

Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound may, for example generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve.

Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

Formulations suitable for rectal administration are typically presented as unit dose suppositories. These may be prepared by admixing the active compound with one or more conventional solid carriers, for example, cocoa butter, and then shaping the resulting mixture.

In certain embodiments, the pharmaceutical composition is suitable for topical application to the skin using a mode of administration and defined above.

In certain embodiments, the pharmaceutical composition is suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound.

In certain embodiments, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

In certain embodiments an oral formulation is provided.

Example A

Tablets of the following composition are manufactured in the usual manner:

TABLE 1 possible tablet composition

| ingredient | mg/tablet | | | |
|---|---|---|---|---|
| | 5 | 25 | 100 | 500 |
| Compound of Formula I, II, III, or IV | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 2 possible capsule ingredient composition

| ingredient | mg/capsule | | | |
|---|---|---|---|---|
| | 5 | 25 | 100 | 500 |
| Compound of Formula I, II, III, or IV | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of Formula I, II, III, or IV, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 3 possible soft gelatin capsule ingredient composition

| ingredient | mg/capsule |
|---|---|
| Compound of Formula I, II, III, or IV | 5 |
| Yellow wax | 8 |
| Hydrogenated Soya bean oil | 8 |
| Partially hydrogenated plant oils | 34 |
| Soya bean oil | 110 |
| Total | 165 |

TABLE 4 possible soft gelatin capsule composition

| ingredient | mg/capsule |
|---|---|
| Gelatin | 75 |
| Glycerol 85% | 32 |
| Karion 83 | 8 (dry matter) |

TABLE 4-continued possible soft gelatin capsule composition

| ingredient | mg/capsule |
|---|---|
| Titan dioxide | 0.4 |
| Iron oxide yellow | 1.1 |
| Total | 116.5 |

Manufacturing Procedure

The compound of Formula I, II, III, or IV is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 5 possible suppository composition

| ingredient | mg/supp. |
|---|---|
| Compound of Formula I, II, III, or IV | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of Formula I, II, III, or IV is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 6 possible injection solution composition

| ingredient | mg/injection solution. |
|---|---|
| Compound of Formula I, II, III, or IV | 3 |
| Polyethylene Glycol 400 | 150 |
| acetic acid | q.s. ad pH 5.0 |
| water for injection solutions | ad 1.0 ml |

Manufacturing Procedure

The compound of Formula I, II, III, or IV is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 7 possible sachet composition

| ingredient | mg/sachet |
|---|---|
| Compound of Formula I, II, III, or IV | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of Formula I, II, III, or IV is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

VIII. Pharmacological Tests

The compounds of Formula I, II, III, or IV and their pharmaceutically acceptable salts possess valuable pharmacological properties. The compounds were investigated in accordance with the test given hereinafter.

Materials

NCI-H1975 (harboring EGFR heterozygous T790M/L858R mutations) and NCI-H3255 (harboring EGFR heterozygous L858R mutation) were purchased from ATCC and NCI, respectively. NCI-H1975+CS (harboring EGFR heterozygous T/790M/L858R/C797S mutations) was generated using CRISPR technology to introduce the additional C797S mutation by Horizon Discovery. RPMI 1640 no-phenol red medium and fetal bovine serum (FBS) were purchased from Gibco (Grand Island, NY, USA). Cell culture flasks and 384-well microplates were acquired from VWR (Radnor, PA, USA). Total EGFR (L858R) HTRF assay kits were purchased from Cisbio (Bedford, MA, USA).

EGFR (L858R) Degradation Analysis

Degradation of EGFR protein containing L858R mutation was determined based on quantification of FRET signal using Total EGFR (L858R) HTRF assay kit. Test compounds were added to the 384-well plate from a top concentration of 10 μM with 11 points, half log titration in duplicates. NCI-H1975, NCI-H1975+CS or NCI-H3255 cells were added into 384-well plates at a cell density of 10000, 10000 or 1000 cells per well, respectively. The plates were kept at 37° C. with 5% C02 for 6 hours. Cells treated in the absence of the test compound were the negative control. Positive control was set by wells containing all reagents but no cells. FRET signal was acquired on EnVision™ Multilabel Reader (PerkinElmer, Santa Clara, CA, USA).

TABLE 8

$DC_{50}$ values

| Ex | Compound | H1975 EGFR DC50 [nM] | H3255 EGFR DC50 [nM] | H1975 C797S clone EGFR DC50 [nM] |
|---|---|---|---|---|
| 1 | 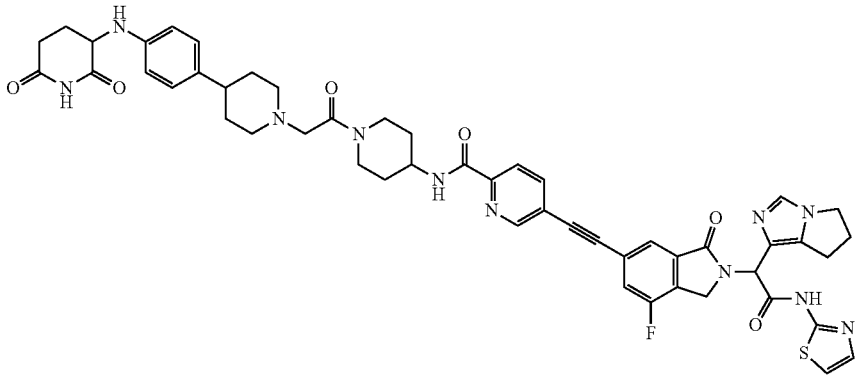 [SMILES: O=C1CCC(Nc2ccc(C3CCN(CC(=O)N4CCC(NC(=O)c5ccc(C#Cc6cc(F)c7c(c6)C(=O)N(C(C(=O)Nc6nccs6)c6ncn8c6CCC8)C7)cn5)CC4)CC3)cc2)C(=O)N1] 5-((2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)ethynyl)-N-(1-(2-(4-(4-((2,6-dioxopiperidin-3-yl)amino)phenyl)piperidin-1-yl)acetyl)piperidin-4-yl)picolinamide | 6 | 8 | 17 |

TABLE 8-continued

| | | DC$_{50}$ values | | |
|---|---|---|---|---|
| Ex | Compound | H1975 EGFR DC50 [nM] | H3255 EGFR DC50 [nM] | H1975 C797S clone EGFR DC50 [nM] |
| 2 | 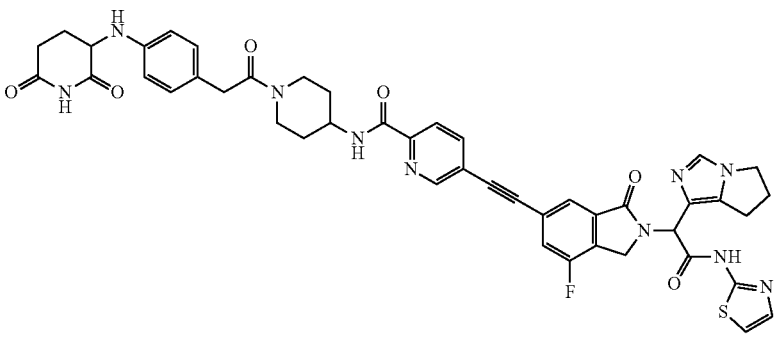 [SMILES: O=C1CCC(Nc2ccc(CC(=O)N3CCC(NC(=O)c4ccc(C#Cc5cc(F)c6c(c5)C(=O)N(C(C(=O)Nc5nccs5)c5ncn7c5CCC7)C6)cn4)CC3)cc2)C(=O)N1] 5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[(2,6-dioxo-3-piperidyl)amino]phenyl]acetyl]-4-piperidyl]pyridine-2-carboxamide | | 7 | |
| 3 | 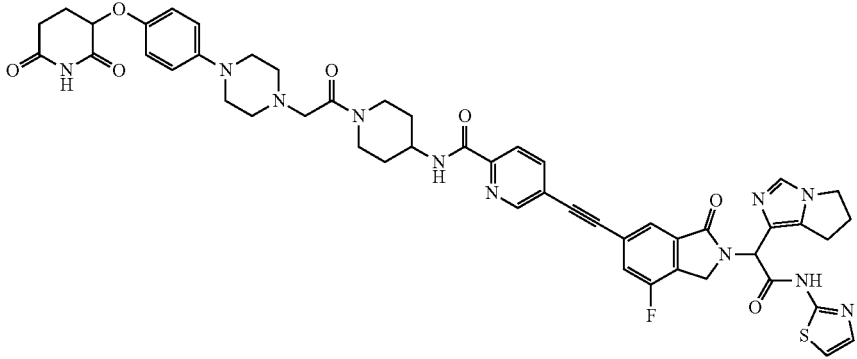 [SMILES: O=C1CCC(Oc2ccc(N3CCN(CC(=O)N4CCC(NC(=O)c5ccc(C#Cc6cc(F)c7c(c6)C(=O)N(C(C(=O)Nc6nccs6)c6ncn8c6CCC8)C7)cn5)CC4)CC3)cc2)C(=O)N1] 5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[4-[(2,6-dioxo-3-piperidyl)oxy]phenyl]piperazin-1-yl]acetyl]-4-piperidyl]pyridine-2-carboxamide | | 4 | |
| 4 | 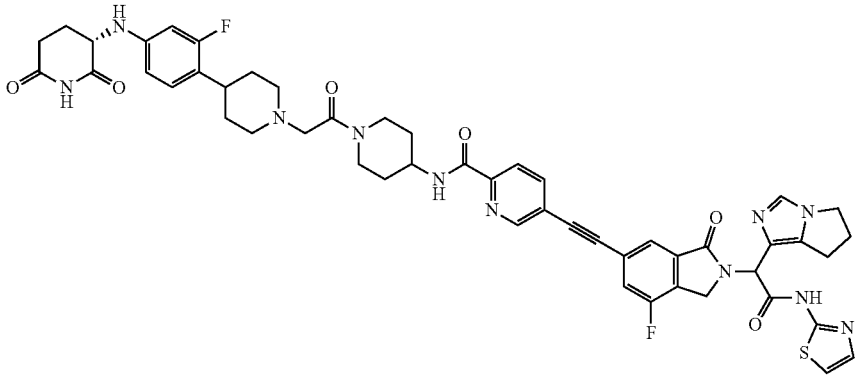 [SMILES: O=C1CC[C@H](Nc2ccc(C3CCN(CC(=O)N4CCC(NC(=O)c5ccc(C#Cc6cc(F)c7c(c6)C(=O)N(C(C(=O)Nc6nccs6)c6ncn8c6CCC8)C7)cn5)CC4)CC3)c(F)c2)C(=O)N1] 5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-4-[[(3S)-2,6-dioxo-3-piperidyl]amino]-2-fluoro-phenyl]-1-piperidyl]acetyl]-4-piperidyl]pyridine-2-carboxamide | | 10 | 9 |

TABLE 8-continued

| Ex | Compound | H1975 EGFR DC50 [nM] | H3255 EGFR DC50 [nM] | H1975 C797S clone EGFR DC50 [nM] |
|---|---|---|---|---|
| 5 | 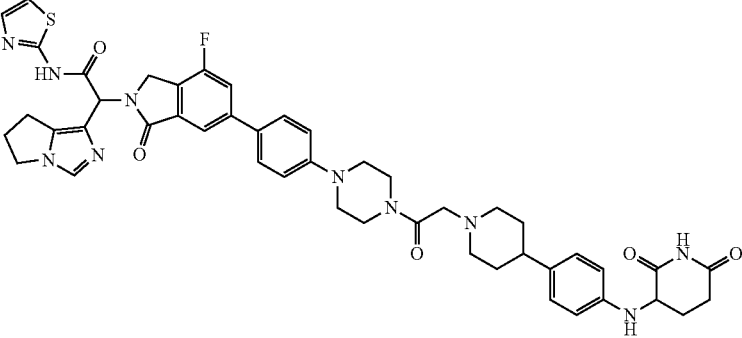 [SMILES: O=C1CCC(Nc2ccc(C3CCN(CC(=O)N4CCN(c5ccc(-c6cc(F)c7c(c6)C(=O)N(C(C(=O)Nc6nccs6)c6ncn8c6CCC8)C7)cc5)CC4)CC3)cc2)C(=O)N1]
2-(6,7-dihydro-5H-pyrrolo[1,2-c]imidazol-1-yl)-2-[6-[4-[4-[2-[4-[4-[(2,6-dioxo-3-piperidyl)amino]phenyl]-1-piperidyl]acetyl]piperazin-1-yl]phenyl]-4-fluoro-1-oxo-isoindolin-2-yl]-N-thiazol-2-yl-acetamide | 20 | 6 | 17 |
| 6 | 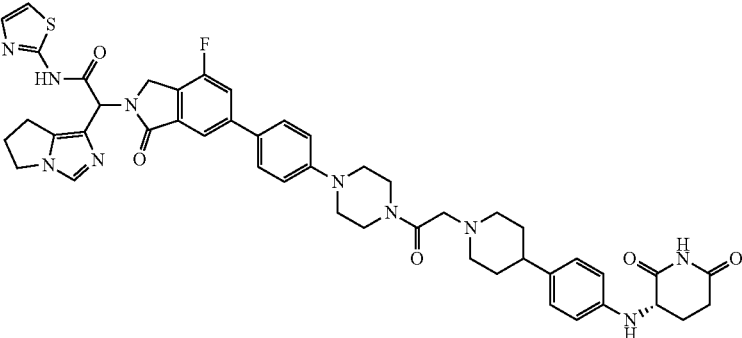
2-(6,7-dihydro-5H-pyrrolo[1,2-c]imidazol-1-yl)-2-[6-[4-[4-[2-[4-[4-[[(3S)-2,6-dioxo-3-piperidyl]amino]phenyl]-1-piperidyl]acetyl]piperazin-1-yl]phenyl]-4-fluoro-1-oxo-isoindolin-2-yl]-N-thiazol-2-yl-acetamide | 22 | 7 | 8 |
| 7 | 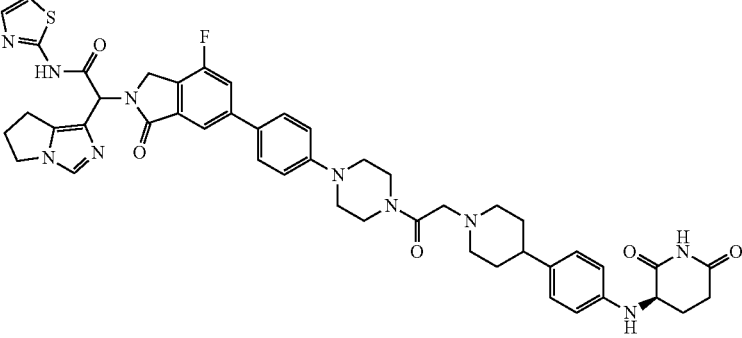
2-(6,7-dihydro-5H-pyrrolo[1,2-c]imidazol-1-yl)-2-[6-[4-[4-[2-[4-[4-[[(3R)-2,6-dioxo-3-piperidyl]amino]phenyl]-1-piperidyl]acetyl]piperazin-1-yl]phenyl]-4-fluoro-1-oxo-isoindolin-2-yl]-N-thiazol-2-yl-acetamide | 18 | | |

TABLE 8-continued

| | | DC$_{50}$ values | | |
|---|---|---|---|---|
| Ex | Compound | H1975 EGFR DC50 [nM] | H3255 EGFR DC50 [nM] | H1975 C797S clone EGFR DC50 [nM] |
| 8 | 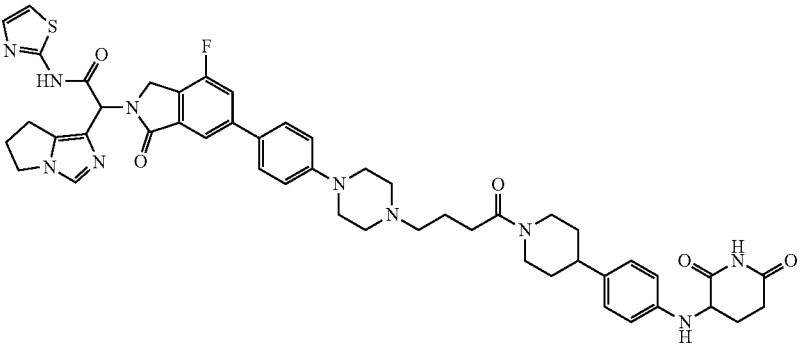 [SMILES: O=C1CCC(Nc2ccc(C3CCN(C(=O)CCCN4CCN(c5ccc(-c6cc(F)c7c(c6)C(=O)N(C(C(=O)Nc6nccs6)c6ncn8c6CCC8)C7)cc5)CC4)CC3)cc2)C(=O)N1] 2-(6,7-dihydro-5H-pyrrolo[1,2-c]imidazol-1-yl)-2-(6-(4-(4-(4-(4-(4-((2,6-dioxopiperidin-3-yl)amino)phenyl)piperidin-1-yl)-4-oxobutyl)piperazin-1-yl)phenyl)-4-fluoro-1-oxoisoindolin-2-yl)-N-(thiazol-2-yl)acetamide | | 17 | |
| 9 | 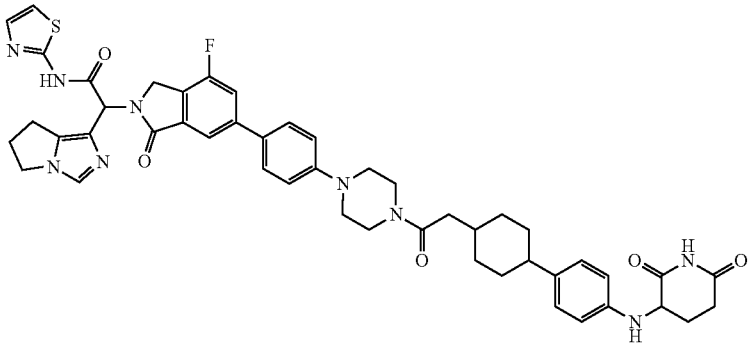 2-(6,7-dihydro-5H-pyrrolo[1,2-c]imidazol-1-yl)-2-(6-(4-(4-(2-(4-(4-((2,6-dioxopiperidin-3-yl)amino)phenyl)cyclohexyl)acetyl)piperazin-1-yl)phenyl)-4-fluoro-1-oxoisoindolin-2-yl)-N-(thiazol-2-yl)acetamide | | 30 | |
| 10 | 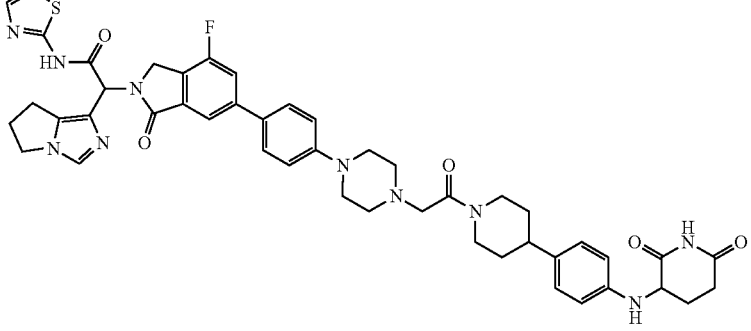 2-(6,7-dihydro-5H-pyrrolo[1,2-c]imidazol-1-yl)-2-(6-(4-(4-(2-(4-(4-((2,6-dioxopiperidin-3-yl)amino)phenyl)piperidin-1-yl)-2-oxoethyl)piperazin-1-yl)phenyl)-4-fluoro-1-oxoisoindolin-2-yl)-N-(thiazol-2-yl)acetamide | | 21 | 19 |

TABLE 8-continued

| | | DC50 values | | |
|---|---|---|---|---|
| Ex | Compound | H1975 EGFR DC50 [nM] | H3255 EGFR DC50 [nM] | H1975 C797S clone EGFR DC50 [nM] |
| 11 | 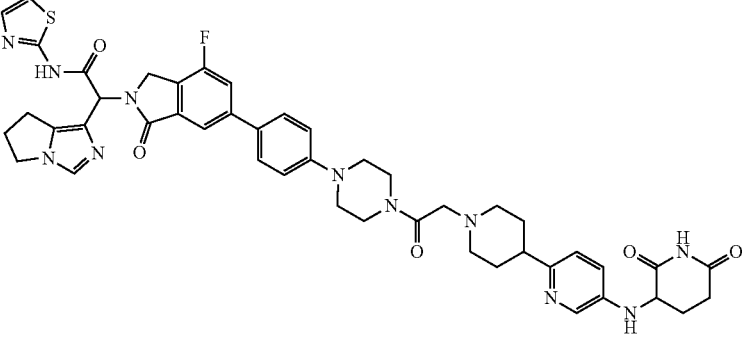<br>2-(6,7-dihydro-5H-pyrrolo[1,2-c]imidazol-1-yl)-2-[6-[4-[4-[2-[4-[5-[(2,6-dioxo-3-piperidyl)amino]-2-pyridyl]-1-piperidyl]acetyl]piperazin-1-yl]phenyl]-4-fluoro-1-oxo-isoindolin-2-yl]-N-thiazol-2-yl-acetamide | | 20 | 21 |
| 12 | 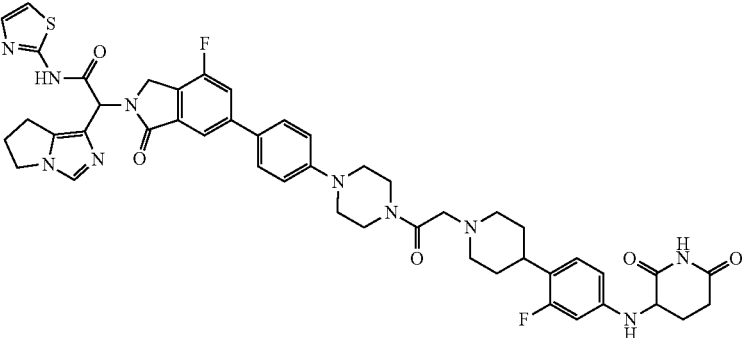 [SMILES: O=C1CCC(Nc2ccc(C3CCN(CC(=O)N4CCN(c5ccc(-c6cc(F)c7c(c6)C(=O)N(C(C(=O)Nc6nccs6)c6ncn8c6CCC8)C7)cc5)CC4)CC3)c(F)c2)C(=O)N1]<br>2-(6,7-dihydro-5H-pyrrolo[1,2-c]imidazol-1-yl)-2-[6-[4-[4-[2-[4-[4-[(2,6-dioxo-3-piperidyl)amino]-2-fluoro-phenyl]-1-piperidyl]acetyl]piperazin-1-yl]phenyl]-4-fluoro-1-oxo-isoindolin-2-yl]-N-thiazol-2-yl-acetamide | | 39 | 11 |
| 13 | 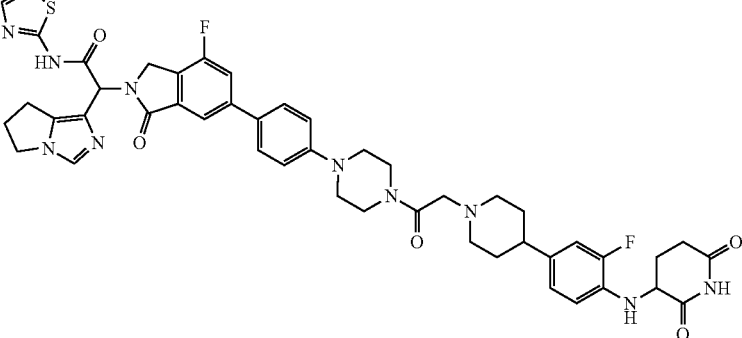<br>2-(6,7-dihydro-5H-pyrrolo[1,2-c]imidazol-1-yl)-2-[6-[4-[4-[2-[4-[4-[(2,6-dioxo-3-piperidyl)amino]-3-fluoro-phenyl]-1-piperidyl]acetyl]piperazin-1-yl]phenyl]-4-fluoro-1-oxo-isoindolin-2-yl]-N-thiazol-2-yl-acetamide | | 52 | |

TABLE 8-continued

| | | DC$_{50}$ values | | |
|---|---|---|---|---|
| Ex | Compound | H1975 EGFR DC50 [nM] | H3255 EGFR DC50 [nM] | H1975 C797S clone EGFR DC50 [nM] |
| 14 | 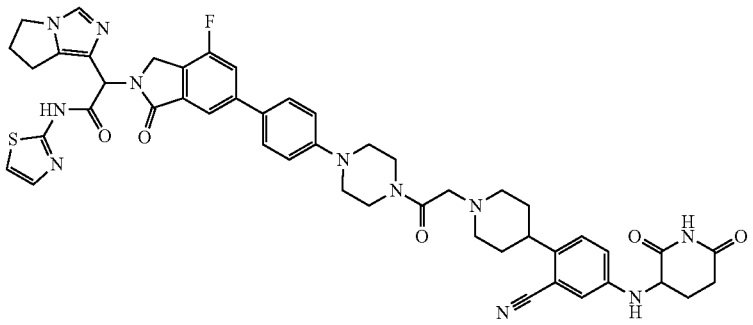 [SMILES: N#Cc1cc(NC2CCC(=O)NC2=O)ccc1C1CCN(CC(=O)N2CCN(c3ccc(-c4cc(F)c5c(c4)C(=O)N(C(C(=O)Nc4nccs4)c4ncn6c4CCC6)C5)cc3)CC2)CC1]  2-[6-[4-[4-[2-[4-[2-cyano-4-[(2,6-dioxo-3-piperidyl)amino]phenyl]-1-piperidyl]acetyl]piperazin-1-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide | 30 | 8 | 24 |
| 15 | 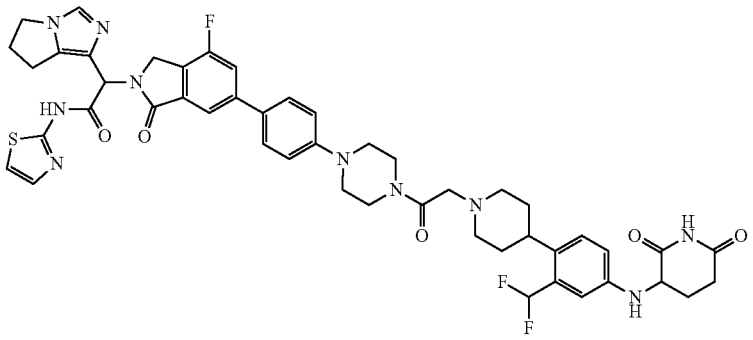 [SMILES: O=C1CCC(Nc2ccc(C3CCN(CC(=O)N4CCN(c5ccc(-c6cc(F)c7c(c6)C(=O)N(C(C(=O)Nc6nccs6)c6ncn8c6CCC8)C7)cc5)CC4)CC3)c(C(F)F)c2)C(=O)N1]  2-[6-[4-[4-[2-[4-[2-(difluoromethyl)-4-[(2,6-dioxo-3-piperidyl)amino]phenyl]-1-piperidyl]acetyl]piperazin-1-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide | 34 | 6 | 10 |
| 16 | 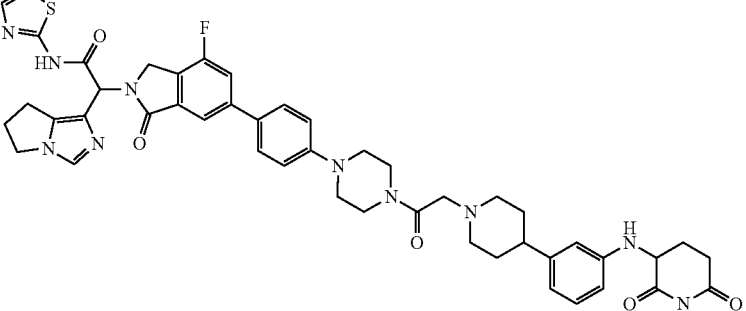  2-(6,7-dihydro-5H-pyrrolo[1,2-c]imidazol-1-yl)-2-(6-(4-(4-(2-(4-(3-((2,6-dioxopiperidin-3-yl)amino)phenyl)piperidin-1-yl)acetyl)piperazin-1-yl)phenyl)-4-fluoro-1-oxoisoindolin-2-yl)-N-(thiazol-2-yl)acetamide | 92 | | |

TABLE 8-continued

| | | DC50 values | | |
|---|---|---|---|---|
| Ex | Compound | H1975 EGFR DC50 [nM] | H3255 EGFR DC50 [nM] | H1975 C797S clone EGFR DC50 [nM] |
| 17 | 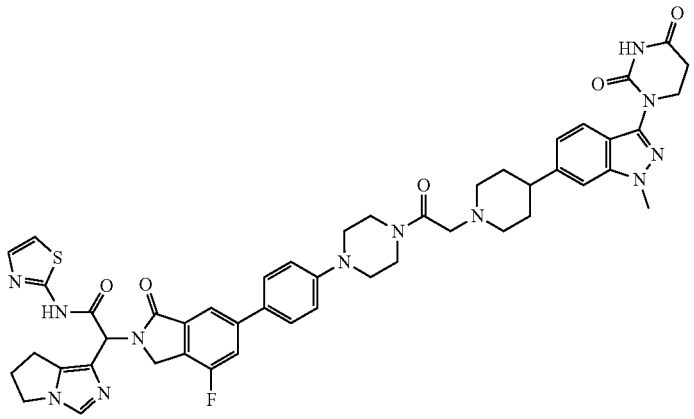 [SMILES: Cn1nc(N2CCC(=O)NC2=O)c2ccc(C3CCN(CC(=O)N4CCN(c5ccc(-c6cc(F)c7c(c6)C(=O)N(C(C(=O)Nc6nccs6)c6ncn8c6CCC8)C7)cc5)CC4)CC3)cc21] 2-(6,7-dihydro-5H-pyrrolo[1,2-c]imidazol-1-yl)-2-(6-(4-(4-(2-(4-(3-(2,4-dioxotetrahydropyrimidin-1(2H)-yl)-1-methyl-1H-indazol-6-yl)piperidin-1-yl)acetyl)piperazin-1-yl)phenyl)-4-fluoro-1-oxoisoindolin-2-yl)-N-(thiazol-2-yl)acetamide | 29 | 6 | 22 |
| 18 | 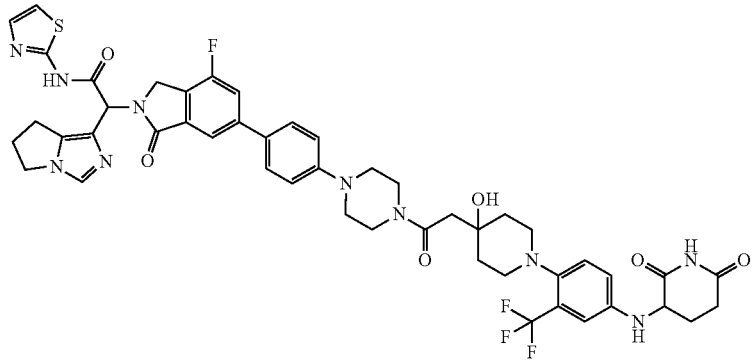 [SMILES: O=C1CCC(Nc2ccc(N3CCC(O)(CC(=O)N4CCN(c5ccc(-c6cc(F)c7c(c6)C(=O)N(C(C(=O)Nc6nccs6)c6ncn8c6CCC8)C7)cc5)CC4)CC3)c(C(F)(F)F)c2)C(=O)N1] 2-(6,7-dihydro-5H-pyrrolo[1,2-c]imidazol-1-yl)-2-(6-(4-(4-(2-(1-(4-((2,6-dioxopiperidin-3-yl)amino)-2-(trifluoromethyl)phenyl)-4-hydroxypiperidin-4-yl)acetyl)piperazin-1-yl)phenyl)-4-fluoro-1-oxoisoindolin-2-yl)-N-(thiazol-2-yl)acetamide | 46 | | |
| 19 | 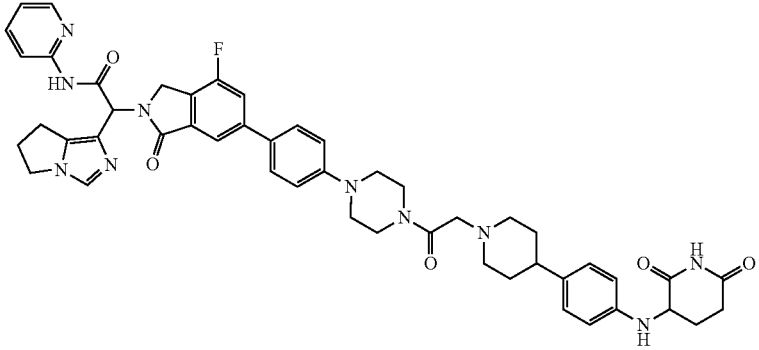 [SMILES: O=C1CCC(Nc2ccc(C3CCN(CC(=O)N4CCN(c5ccc(-c6cc(F)c7c(c6)C(=O)N(C(C(=O)Nc6ccccn6)c6ncn8c6CCC8)C7)cc5)CC4)CC3)cc2)C(=O)N1] | 50 | 13 | 20 |

TABLE 8-continued

| | | DC50 values | | |
|---|---|---|---|---|
| Ex | Compound | H1975 EGFR DC50 [nM] | H3255 EGFR DC50 [nM] | H1975 C797S clone EGFR DC50 [nM] |
| 20 | 2-(6,7-dihydro-5H-pyrrolo[1,2-c]imidazol-1-yl)-2-(6-(4-(4-(2-(4-(4-((2,6-dioxopiperidin-3-yl)amino)phenyl)piperidin-1-yl)acetyl)piperazin-1-yl)phenyl)-4-fluoro-1-oxoisoindolin-2-yl)-N-(pyridin-2-yl)acetamide | 59 | 25 | 34 |
| 21 | 2-(6,7-dihydro-5H-pyrrolo[1,2-c]imidazol-1-yl)-2-[6-[4-[4-[2-[4-[4-[(2,6-dioxo-3-piperidyl)amino]-2-fluoro-phenyl]-1-piperidyl]acetyl]piperazin-1-yl]phenyl]-4-fluoro-1-oxo-isoindolin-2-yl]-N-(2-pyridyl)acetamide | 31 | 11 | 17 |
| 22 | 2-(6,7-dihydro-5H-pyrrolo[1,2-c]imidazol-1-yl)-2-(6-(4-(1-(2-(4-(4-((2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide | 31 | 15 | |
| | 2-(6,7-dihydro-5H-pyrrolo[1,2-c]imidazol-1-yl)-2-(6-(4-(1-(2-(4-(4-(((S)-2,6-dioxopiperidin-3-yl)amino)phenyl)piperidin-1-yl)acetyl)piperidin-4- | | | |

TABLE 8-continued

| | | DC$_{50}$ values | | |
|---|---|---|---|---|
| Ex | Compound | H1975 EGFR DC50 [nM] | H3255 EGFR DC50 [nM] | H1975 C797S clone EGFR DC50 [nM] |
| | yl)phenyl)-4-fluoro-1-oxoisoindolin-2-yl)-N-(thiazol-2-yl)acetamide | | | |
| 23 | 2-(6,7-dihydro-5H-pyrrolo[1,2-c]imidazol-1-yl)-2-(6-(4-(1-(2-(4-(4-(((R)-2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide | 33 | | |
| 24 | 2-(6,7-dihydro-5H-pyrrolo[1,2-c]imidazol-1-yl)-2-(6-(4-(1-(2-(4-(4-(((S)-2,6-dioxopiperidin-3-yl)amino)-2-fluorophenyl)piperidin-1-yl)acetyl)piperidin-4-yl)phenyl)-4-fluoro-1-oxoisoindolin-2-yl)-N-(thiazol-2-yl)acetamide | 70 | 6 | 24 |
| 25 | 2-(6-(4-(1-(2-(4-(2-cyano-4-((2,6-dioxopiperidin-3-yl)amino)phenyl)piperidin-1-yl)acetyl)piperidin-4-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide | 25 | 6 | 17 |

TABLE 8-continued

| | | DC50 values | | |
|---|---|---|---|---|
| Ex | Compound | H1975 EGFR DC50 [nM] | H3255 EGFR DC50 [nM] | H1975 C797S clone EGFR DC50 [nM] |
| 26 | 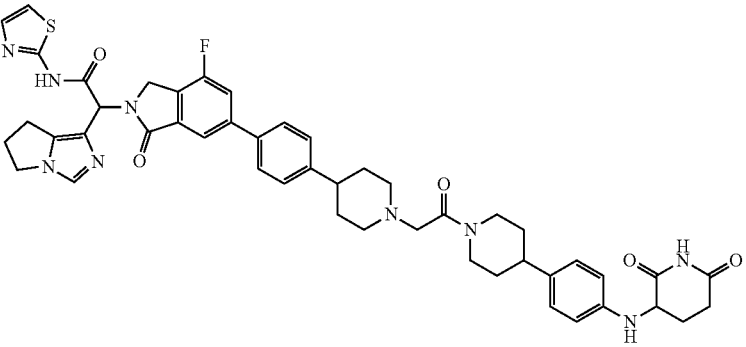 [SMILES: O=C1CCC(Nc2ccc(C3CCN(C(=O)CN4CCC(c5ccc(-c6cc(F)c7c(c6)C(=O)N(C(C(=O)Nc6nccs6)c6ncn8c6CCC8)C7)cc5)CC4)CC3)cc2)C(=O)N1]<br>2-(6,7-dihydro-5H-pyrrolo[1,2-c]imidazol-1-yl)-2-[6-[4-[1-[2-[4-[4-[(2,6-dioxo-3-piperidyl)amino]phenyl]-1-piperidyl]-2-oxo-ethyl]-4-piperidyl]phenyl]-4-fluoro-1-oxo-isoindolin-2-yl]-N-thiazol-2-yl-acetamide | 26 | | |
| 27 | 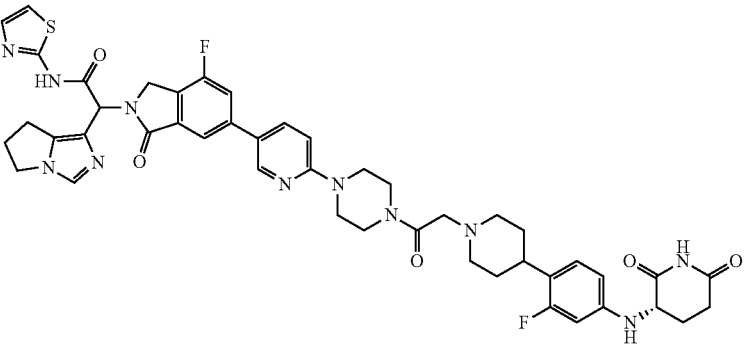 [SMILES: O=C1CC[C@H](Nc2ccc(C3CCN(CC(=O)N4CCN(c5ccc(-c6cc(F)c7c(c6)C(=O)N(C(C(=O)Nc6nccs6)c6ncn8c6CCC8)C7)cn5)CC4)CC3)c(F)c2)C(=O)N1]<br>2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]acetyl]piperazin-1-yl]-3-pyridyl]-4-fluoro-1-oxo-isoindolin-2-yl]-N-thiazol-2-yl-acetamide | | 36 | 20 |
| 28 | 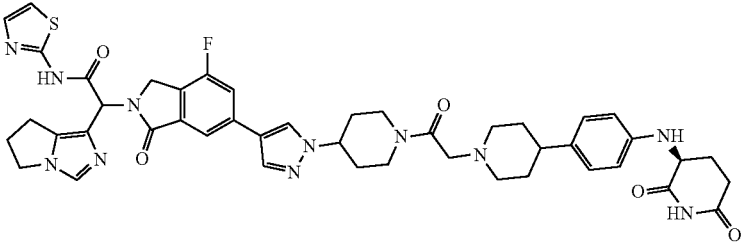 [SMILES: O=C1CC[C@H](Nc2ccc(C3CCN(CC(=O)N4CCC(n5cc(-c6cc(F)c7c(c6)C(=O)N(C(C(=O)Nc6nccs6)c6ncn8c6CCC8)C7)nn5)CC4)CC3)cc2)C(=O)N1]<br>2-(6,7-dihydro-5H-pyrrolo[1,2-c]imidazol-1-yl)-2-[6-[1-[1-[2-[4-[4-[[(3S)-2,6-dioxo-3-piperidyl]amino]phenyl]-1-piperidyl]acetyl]-4-piperidyl]pyrazol-4-yl]-4-fluoro-1-oxo-isoindolin-2-yl]-N-thiazol-2-yl-acetamide | | 16 | 17 |

TABLE 8-continued

| | | DC$_{50}$ values | | |
|---|---|---|---|---|
| Ex | Compound | H1975 EGFR DC50 [nM] | H3255 EGFR DC50 [nM] | H1975 C797S clone EGFR DC50 [nM] |
| 29 | 2-(6,7-dihydro-5H-pyrrolo[1,2-c]imidazol-1-yl)-2-[6-[4-[1-[2-[4-[4-[[(3S)-2,6-dioxo-3-piperidyl]amino]phenyl]-1-piperidyl]acetyl]-4-piperidyl]pyrazol-1-yl]-4-fluoro-1-oxo-isoindolin-2-yl]-N-thiazol-2-yl-acetamide | 24 | 20 | |
| 30 | 2-(6,7-Dihydro-5H-pyrrolo[1,2-c]imidazol-1-yl)-2-(6-(1-(1-(2-(4-(4-(((S)-2,6-dioxopiperidin-3-yl)amino)phenyl)piperidin-1-yl)acetyl)piperidin-4-yl)-1H-1,2,3-triazol-4-yl)-4-fluoro-1-oxoisoindolin-2 -yl)-N-(thiazol-2-yl)acetamide | 15 | 35 | |
| 31 | 2-(6,7-dihydro-5H-pyrrolo[1,2-c]imidazol-1-yl)-2-[6-[4-[[1-[2-[4-[4-[(2,6-dioxo-3-piperidyl)amino]phenyl]-1-piperidyl]acetyl]-4-piperidyl]oxy]phenyl]-4-fluoro-1-oxo-isoindolin-2-yl]-N-thiazol-2-yl-acetamide | 32 | | |
| 32 | 2-(6,7-dihydro-5H-pyrrolo[1,2-c]imidazol-1-yl)-2-[6-[4-[[1-[2-[4-[4-[[(3S)-2,6-dioxo-3-piperidyl]amino]phenyl]-1-piperidyl]acetyl]-4-piperidyl]oxy]phenyl]-4-fluoro-1-oxo-isoindolin-2-yl]-N-thiazol-2-yl-acetamide | 47 | 12 | 11 |

TABLE 8-continued

| | | H1975 EGFR DC50 [nM] | H3255 EGFR DC50 [nM] | H1975 C797S clone EGFR DC50 [nM] |
|---|---|---|---|---|
| Ex | Compound | | | |
| 33 | 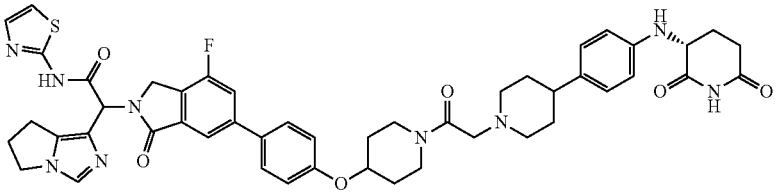 [SMILES: O=C1CCC(Nc2ccc(C3CCN(CC(=O)N4CCC(Oc5ccc(-c6cc(F)c7c(c6)C(=O)N(C(C(=O)Nc6nccs6)c6ncn8c6CCC8)C7)cc5)CC4)CC3)cc2)C(=O)N1]2-(6,7-dihydro-5H-pyrrolo[1,2-c]imidazol-1-yl)-2-[6-[4-[[1-[2-[4-[4-[[(3R)-2,6-dioxo-3-piperidyl]amino]phenyl]-1-piperidyl]acetyl]-4-piperidyl]oxy]phenyl]-4-fluoro-1-oxo-isoindolin-2-yl]-N-thiazol-2-yl-acetamide | 38 | 8 | 19 |
| 34 | 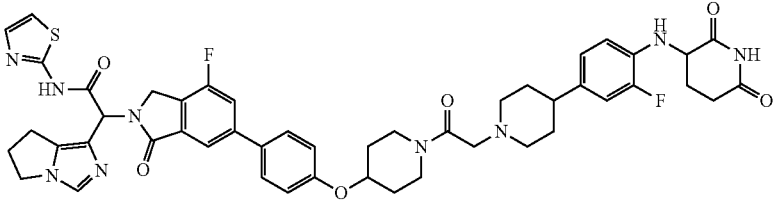 [SMILES: O=C1CCC(Nc2ccc(C3CCN(CC(=O)N4CCC(Oc5ccc(-c6cc(F)c7c(c6)C(=O)N(C(C(=O)Nc6nccs6)c6ncn8c6CCC8)C7)cc5)CC4)CC3)cc2F)C(=O)N1]2-(6,7-dihydro-5H-pyrrolo[1,2-c]imidazol-1-yl)-2-(6-(4-((1-(2-(4-(4-((2,6-dioxopiperidin-3-yl)amino)-3-fluorophenyl)piperidin-1-yl)acetyl)piperidin-4-yl)oxy)phenyl)-4-fluoro-1-oxoisoindolin-2-yl)-N-(thiazol-2-yl)acetamide | 57 | 13 | 22 |
| 35 | 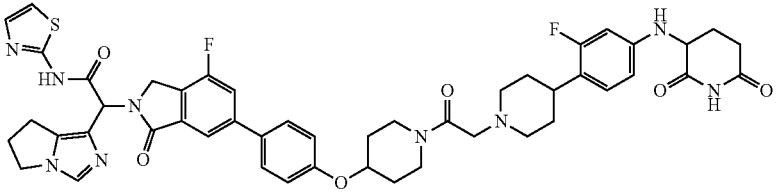 [SMILES: O=C1CCC(Nc2ccc(C3CCN(CC(=O)N4CCC(Oc5ccc(-c6cc(F)c7c(c6)C(=O)N(C(C(=O)Nc6nccs6)c6ncn8c6CCC8)C7)cc5)CC4)CC3)c(F)c2)C(=O)N1]2-(6,7-dihydro-5H-pyrrolo[1,2-c]imidazol-1-yl)-2-(6-(4-((1-(2-(4-(4-((2,6-dioxopiperidin-3-yl)amino)-2-fluorophenyl)piperidin-1-yl)acetyl)piperidin-4-yl)oxy)phenyl)-4-fluoro-1-oxoisoindolin-2-yl)-N-(thiazol-2-yl)acetamide | 46 | 9 | 12 |
| 36 | 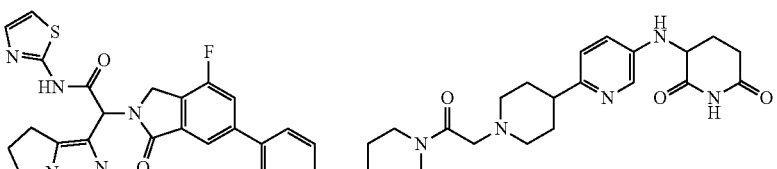2-(6,7-dihydro-5H-pyrrolo[1,2-c]imidazol-1-yl)-2-(6-(4-((1-(2-(4-(5-((2,6-dioxopiperidin-3-yl)amino)pyridin-2-yl)piperidin-1-yl)acetyl)piperidin-4-yl)oxy)phenyl)-4-fluoro-1-oxoisoindolin-2-yl)-N-(thiazol-2-yl)acetamide | 31 | | |

TABLE 8-continued

| | | DC50 values | | |
|---|---|---|---|---|
| Ex | Compound | H1975 EGFR DC50 [nM] | H3255 EGFR DC50 [nM] | H1975 C797S clone EGFR DC50 [nM] |
| 37 | 2-(6-(4-((1-(2-(4-(2-cyano-4-((2,6-dioxopiperidin-3-yl)amino)phenyl)piperidin-1-yl)acetyl)piperidin-4-yl)oxy)phenyl)-4-fluoro-1-oxoisoindolin-2-yl)-2-(6,7-dihydro-5H-pyrrolo[1,2-c]imidazol-1-yl)-N-(thiazol-2-yl)acetamide | 46 | 16 | 19 |
| 38 | 2-(6,7-dihydro-5H-pyrrolo[1,2-c]imidazol-1-yl)-2-(6-(4-((1-(2-(4-(4-((2,4-dioxo-3-azabicyclo[3.1.1]heptan-1-yl)amino)phenyl)piperidin-1-yl)acetyl)piperidin-4-yl)oxy)phenyl)-4-fluoro-1-oxoisoindolin-2-yl)-N-(thiazol-2-yl)acetamide | 52 | | |
| 39 | 2-(6,7-dihydro-5H-pyrrolo[1,2-c]imidazol-1-yl)-2-(6-(4-((1-(2-(4-(4-(((S)-2,6-dioxopiperidin-3-yl)amino)-2-fluorophenyl)piperidin-1-yl)acetyl)piperidin-4-yl)oxy)phenyl)-4-fluoro-1-oxoisoindolin-2-yl)-N-(thiazol-2-yl)acetamide | 88 | | |
| 40 | 2-(6,7-dihydro-5H-pyrrolo[1,2-c]imidazol-1-yl)-2-[6-[4-[[1-[2-[4-[4-[(2,6-dioxo-3-piperidyl)amino]phenyl]-1-piperidyl]-2-oxo-acetyl]-4-piperidyl]oxy]phenyl]-4-fluoro-1-oxo-isoindolin-2-yl]-N-thiazol-2-yl-acetamide | 21 | 14 | |

TABLE 8-continued

| | | DC$_{50}$ values | | |
|---|---|---|---|---|
| Ex | Compound | H1975 EGFR DC50 [nM] | H3255 EGFR DC50 [nM] | H1975 C797S clone EGFR DC50 [nM] |
| 41 | 2-(6,7-dihydro-5H-pyrrolo[1,2-c]imidazol-1-yl)-2-[6-[4-[(3R)-1-[2-[4-[4-[[(3S)-2,6-dioxo-3-piperidyl]amino]phenyl]-1-piperidyl]acetyl]pyrrolidin-3-yl]oxyphenyl]-4-fluoro-1-oxo-isoindolin-2-yl]-N-thiazol-2-yl-acetamide | | | 26 |
| 42 | 2-(6,7-dihydro-5H-pyrrolo[1,2-c]imidazol-1-yl)-2-[6-[4-[(3S)-1-[2-[4-[4-[[(3S)-2,6-dioxo-3-piperidyl]amino]phenyl]-1-piperidyl]acetyl]pyrrolidin-3-yl]oxyphenyl]-4-fluoro-1-oxo-isoindolin-2-yl]-N-thiazol-2-yl-acetamide | | | 20 |
| 43 | 2-(6-(4-(4-(2-(4-(4-((2,6-dioxopiperidin-3-yl)amino)phenyl)piperidin-1-yl)acetyl)piperazin-1-yl)phenyl)-4-fluoro-1-oxoisoindolin-2-yl)-2-((R)-6-fluoro-6,7-dihydro-5H-pyrrolo[1,2-c]imidazol-1-yl)-N-(thiazol-2-yl)acetamide | 13 | 6 | 18 |

TABLE 8-continued

| | | DC$_{50}$ values | | |
|---|---|---|---|---|
| Ex | Compound | H1975 EGFR DC50 [nM] | H3255 EGFR DC50 [nM] | H1975 C797S clone EGFR DC50 [nM] |
| 44 | 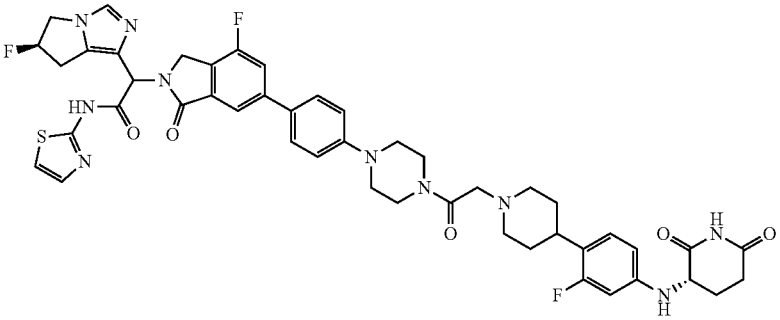 [SMILES: O=C1CC[C@H](Nc2ccc(C3CCN(CC(=O)N4CCN(c5ccc(-c6cc(F)c7c(c6)C(=O)N(C(C(=O)Nc6nccs6)c6ncn8c6C[C@@H](F)C8)C7)cc5)CC4)CC3)c(F)c2)C(=O)N1] 2-[6-[4-[4-[2-[4-[4-[[(3S)-2,6-dioxo-3-piperidyl]amino]-2-fluoro-phenyl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide | 22 | 6 | 12 |
| 45 | 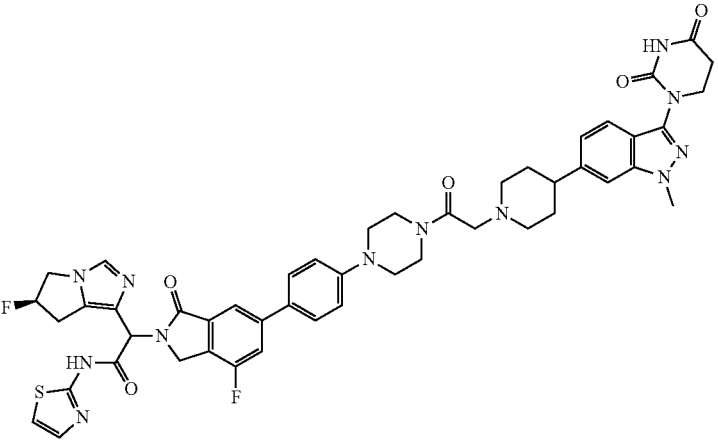 [SMILES: Cn1nc(N2CCC(=O)NC2=O)c2ccc(C3CCN(CC(=O)N4CCN(c5ccc(-c6cc(F)c7c(c6)C(=O)N(C(C(=O)Nc6nccs6)c6ncn8c6C[C@@H](F)C8)C7)cc5)CC4)CC3)cc21] 2-[6-[4-[4-[2-[4-[3-(2,4-dioxohexahydropyrimidin-1-yl)-1-methyl-indazol-6-yl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide | | 14 | 16 |
| 46 | 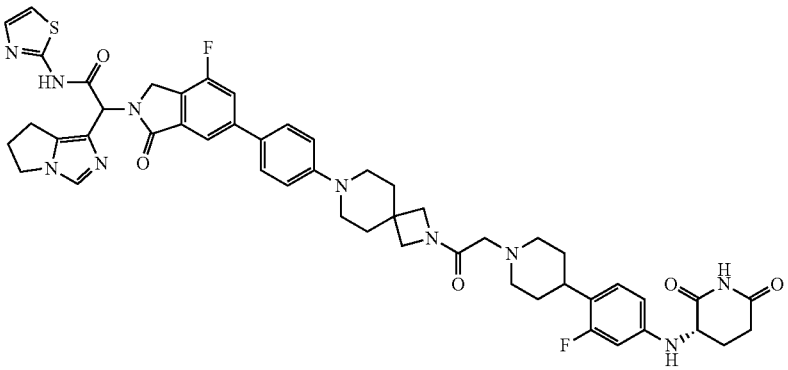 [SMILES: O=C1CC[C@H](Nc2ccc(C3CCN(CC(=O)N4CC5(CCN(c6ccc(-c7cc(F)c8c(c7)C(=O)N(C(C(=O)Nc7nccs7)c7ncn9c7CCC9)C8)cc6)CC5)C4)CC3)c(F)c2)C(=O)N1] | | 51 | 51 |

TABLE 8-continued

| | | DC50 values | | |
|---|---|---|---|---|
| Ex | Compound | H1975 EGFR DC50 [nM] | H3255 EGFR DC50 [nM] | H1975 C797S clone EGFR DC50 [nM] |
| | 2-(6,7-dihydro-5H-pyrrolo[1,2-c]imidazol-1-yl)-2-(6-(4-(2-(2-(4-(4-(((S)-2,6-dioxopiperidin-3-yl)amino)-2-fluorophenyl)piperidin-1-yl)acetyl)-2,7-diazaspiro[3.5]nonan-7-yl)phenyl)-4-fluoro-1-oxoisoindolin-2-yl)-N-(thiazol-2-yl)acetamide | | | |
| 47 | 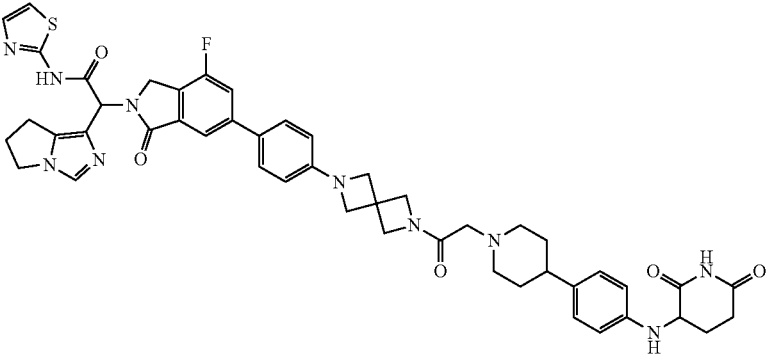 [SMILES: O=C1CCC(Nc2ccc(C3CCN(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)cc2)C(=O)N1] 2-(6,7-dihydro-5H-pyrrolo[1,2-c]imidazol-1-yl)-2-[6-[4-[2-[2-[4-[4-[(2,6-dioxo-3-piperidyl)amino]phenyl]-1-piperidyl]acetyl]-2,6-diazaspiro[3.3]heptan-6-yl]phenyl]-4-fluoro-1-oxo-isoindolin-2-yl]-N-thiazol-2-yl-acetamide | 18 | 10 | 9 |
| 48 | 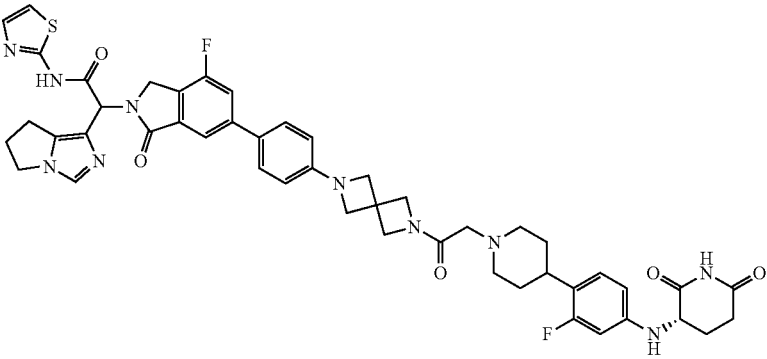 [SMILES: O=C1CC[C@H](Nc2ccc(C3CCN(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1] 2-(6,7-dihydro-5H-pyrrolo[1,2-c]imidazol-1-yl)-2-[6-[4-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]phenyl]-4-fluoro-1-oxo-isoindolin-2-yl]-N-thiazol-2-yl-acetamide | 28 | 7 | 11 |

TABLE 8-continued

| | | DC50 values | | |
|---|---|---|---|---|
| | | H1975 EGFR DC50 [nM] | H3255 EGFR DC50 [nM] | H1975 C797S clone EGFR DC50 [nM] |
| Ex | Compound | | | |
| 49 | 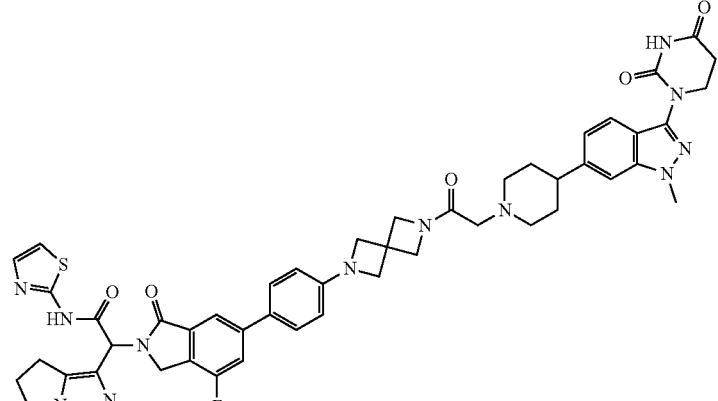
2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-1-piperidyl]acetyl]-2,6-diazaspiro[3.3]heptan-6-yl]phenyl]-4-fluoro-1-oxo-isoindolin-2-yl]-N-thiazol-2-yl-acetamide | 18 | 10 | |
| 50 | 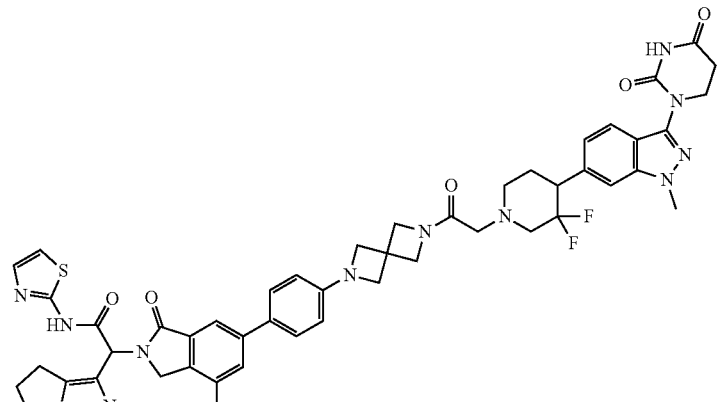
2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide | | 10 | |
| 51 | 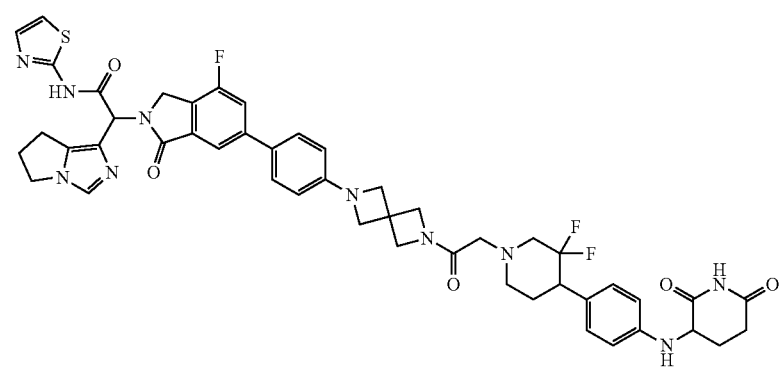 [SMILES: O=C1CCC(Nc2ccc(C3CCN(CC(=O)N4CC5(C4)CN(c4ccc(-c6cc(F)c7c(c6)C(=O)N(C(C(=O)Nc6nccs6)c6ncn8c6CCC8)C7)cc4)C5)CC3(F)F)cc2)C(=O)N1] | | 13 | |

TABLE 8-continued

| | | DC₅₀ values | | |
|---|---|---|---|---|
| Ex | Compound | H1975 EGFR DC50 [nM] | H3255 EGFR DC50 [nM] | H1975 C797S clone EGFR DC50 [nM] |
| 52 | 2-(6,7-dihydro-5H-pyrrolo[1,2-c]imidazol-1-yl)-2-(6-(4-(6-(2-(4-(4-((2,6-dioxopiperidin-3-yl)amino)phenyl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide, Isomer 1 | | 15 | |
| | 2-(6,7-dihydro-5H-pyrrolo[1,2-c]imidazol-1-yl)-2-(6-(4-(6-(2-(4-(4-((2,6-dioxopiperidin-3-yl)amino)phenyl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide, Isomer 2 | | | |
| 53 | 2-(6,7-dihydro-5H-pyrrolo[1,2-c]imidazol-1-yl)-2-[6-[4-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]phenyl]-4-fluoro-1-oxo-isoindolin-2-yl]-N-(2-pyridyl)acetamide | 64 | 37 | |

TABLE 8-continued

| | | DC$_{50}$ values | | |
|---|---|---|---|---|
| Ex | Compound | H1975 EGFR DC50 [nM] | H3255 EGFR DC50 [nM] | H1975 C797S clone EGFR DC50 [nM] |
| 54 | 2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-1-piperidyl]acetyl]-2,6-diazaspiro[3.3]heptan-6-yl]phenyl]-4-fluoro-1-oxo-isoindolin-2-yl]-N-(2-pyridyl)acetamide | 16 | | |
| 55 | 2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-(2-pyridyl)acetamide | 11 | | |
| 56 | 2-(6,7-dihydro-5H-pyrrolo[1,2-c]imidazol-1-yl)-2-[6-[4-[[4-[2-[4-[[(2,6-dioxo-3-piperidyl)amino]phenyl]-1-piperidyl]acetyl]piperazin-1-yl]methyl]phenyl]-4-fluoro-1-oxo-isoindolin-2-yl]-N-thiazol-2-yl-acetamide | | 20 | 14 |

TABLE 8-continued

| | | DC50 values | | |
|---|---|---|---|---|
| Ex | Compound | H1975 EGFR DC50 [nM] | H3255 EGFR DC50 [nM] | H1975 C797S clone EGFR DC50 [nM] |
| 57 | 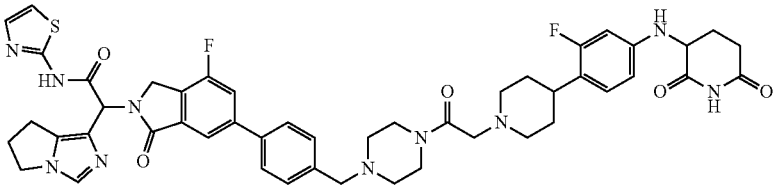 [SMILES: O=C1CCC(Nc2ccc(C3CCN(CC(=O)N4CCN(Cc5ccc(-c6cc(F)c7c(c6)C(=O)N(C(C(=O)Nc6nccs6)c6ncn8c6CCC8)C7)cc5)CC4)CC3)c(F)c2)C(=O)N1]<br>2-(6,7-dihydro-5H-pyrrolo[1,2-c]imidazol-1-yl)-2-[6-[4-[[4-[2-[4-[4-[(2,6-dioxo-3-piperidyl)amino]-2-fluoro-phenyl]-1-piperidyl]acetyl]piperazin-1-yl]methyl]phenyl]-4-fluoro-1-oxo-isoindolin-2-yl]-N-thiazol-2-yl-acetamide | 46 | 11 | 7 |
| 58 | 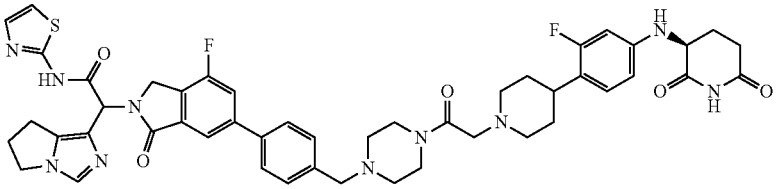 [SMILES: O=C1CC[C@H](Nc2ccc(C3CCN(CC(=O)N4CCN(Cc5ccc(-c6cc(F)c7c(c6)C(=O)N(C(C(=O)Nc6nccs6)c6ncn8c6CCC8)C7)cc5)CC4)CC3)c(F)c2)C(=O)N1]<br>2-(6,7-dihydro-5H-pyrrolo[1,2-c]imidazol-1-yl)-2-[6-[4-[[4-[2-[4-[4-[[(3S)-2,6-dioxo-3-piperidyl]amino]-2-fluoro-phenyl]-1-piperidyl]acetyl]piperazin-1-yl]methyl]phenyl]-4-fluoro-1-oxo-isoindolin-2-yl]-N-thiazol-2-yl-acetamide | 26 | 26 | 14 |
| 59 | 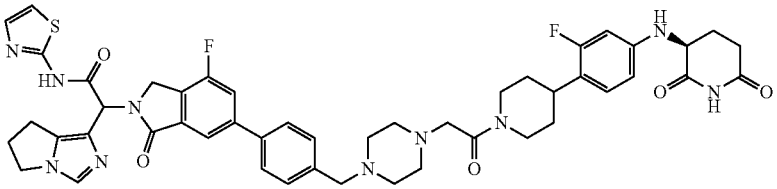 [SMILES: O=C1CC[C@H](Nc2ccc(C3CCN(C(=O)CN4CCN(Cc5ccc(-c6cc(F)c7c(c6)C(=O)N(C(C(=O)Nc6nccs6)c6ncn8c6CCC8)C7)cc5)CC4)CC3)c(F)c2)C(=O)N1]<br>2-(6,7-dihydro-5H-pyrrolo[1,2-c]imidazol-1-yl)-2-[6-[4-[[4-[2-[4-[4-[[(3S)-2,6-dioxo-3-piperidyl]amino]-2-fluoro-phenyl]-1-piperidyl]-2-oxo-ethyl]piperazin-1-yl]methyl]phenyl]-4-fluoro-1-oxo-isoindolin-2-yl]-N-thiazol-2-yl-acetamide | 19 | 12 | 8 |
| 60 | 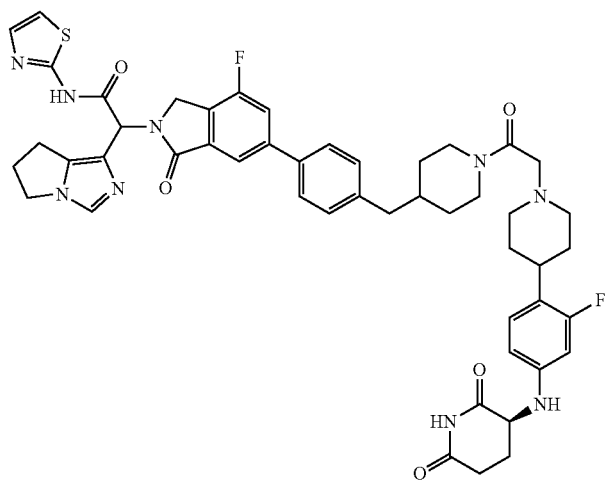 [SMILES: O=C1CC[C@H](Nc2ccc(C3CCN(CC(=O)N4CCC(Cc5ccc(-c6cc(F)c7c(c6)C(=O)N(C(C(=O)Nc6nccs6)c6ncn8c6CCC8)C7)cc5)CC4)CC3)c(F)c2)C(=O)N1]<br>2-(6,7-dihydro-5H-pyrrolo[1,2-c]imidazol-1-yl)-2-[6-[4-[[1-[2-[4-[4-[[(3S)-2,6-dioxo-3-piperidyl]amino]-2-fluoro- | 52 | 28 | |

TABLE 8-continued

| | | DC50 values | | |
|---|---|---|---|---|
| Ex | Compound | H1975 EGFR DC50 [nM] | H3255 EGFR DC50 [nM] | H1975 C797S clone EGFR DC50 [nM] |
| | phenyl]-1-piperidyl]acetyl]-4-piperidyl]methyl]phenyl]-4-fluoro-1-oxo-isoindolin-2-yl]-N-thiazol-2-yl-acetamide | | | |
| 61 | 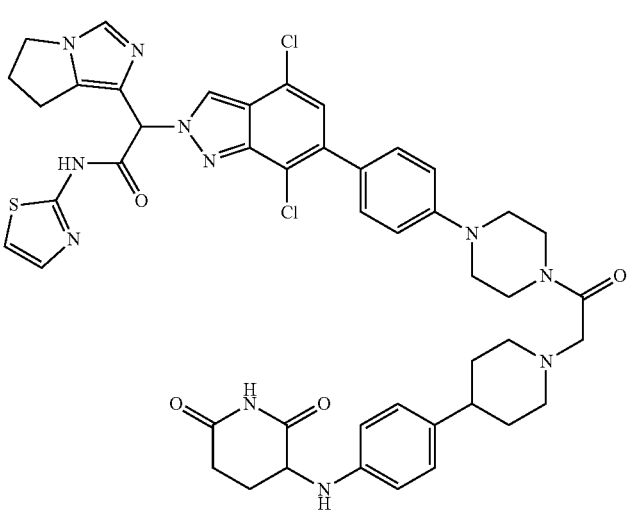 [SMILES: O=C1CCC(Nc2ccc(C3CCN(CC(=O)N4CCN(c5ccc(-c6cc(Cl)c7cn(C(C(=O)Nc8nccs8)c8ncn9c8CCC9)nc7c6Cl)cc5)CC4)CC3)cc2)C(=O)N1]
2-[4,7-dichloro-6-[4-[4-[2-[4-[4-[(2,6-dioxo-3-piperidyl)amino]phenyl]-1-piperidyl]acetyl]piperazin-1-yl]phenyl]indazol-2-yl]-2-(6,7-dihydro-5H-pyrrolo[1,2-c]imidazol-1-yl)-N-thiazol-2-yl-acetamide | | | 112 |
| 62 | 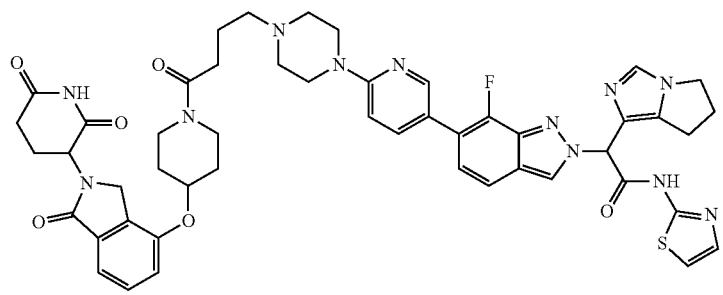 [SMILES: O=C1CCC(N2Cc3c(OC4CCN(C(=O)CCCN5CCN(c6ccc(-c7ccc8cn(C(C(=O)Nc9nccs9)c9ncn%10c9CCC%10)nc8c7F)cn6)CC5)CC4)cccc3C2=O)C(=O)N1]
2-(6,7-dihydro-5H-pyrrolo[1,2-c]imidazol-1-yl)-2-(6-(6-(4-(4-(4-((2-(2,6-dioxopiperidin-3-yl)-1-oxoisoindolin-4-yl)oxy)piperidin-1-yl)-4-oxobutyl)piperazin-1-yl)pyridin-3-yl)-7-fluoro-2H-indazol-2-yl)-N-(thiazol-2-yl)acetamide | | | 19 |
| 63 | 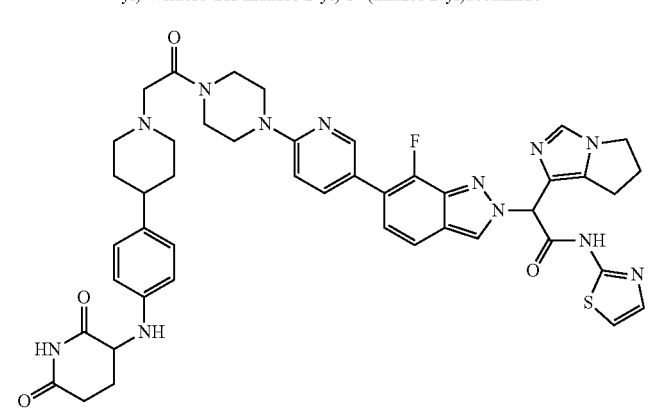 | | | 81 |

TABLE 8-continued

DC₅₀ values

| Ex | Compound | H1975 EGFR DC50 [nM] | H3255 EGFR DC50 [nM] | H1975 C797S clone EGFR DC50 [nM] |
|---|---|---|---|---|
| 64 | 2-(6,7-dihydro-5H-pyrrolo[1,2-c]imidazol-1-yl)-2-(6-(6-(4-(2-(4-(4-((2,6-dioxopiperidin-3-yl)amino)phenyl)piperidin-1-yl)acetyl)piperazin-1-yl)pyridin-3-yl)-7-fluoro-2H-indazol-2-yl)-N-(thiazol-2-yl)acetamide | 137 | | |
| 65 | 2-(6,7-dihydro-5H-pyrrolo[1,2-c]imidazol-1-yl)-2-[6-[6-[4-[2-[4-[4-[(2,6-dioxo-3-piperidyl)amino]-2-fluoro-phenyl]-1-piperidyl]acetyl]piperazin-1-yl]-3-pyridyl]-4-fluoro-indazol-2-yl]-N-thiazol-2-yl-acetamide | 36 | | |
| 66 | 2-(6,7-dihydro-5H-pyrrolo[1,2-c]imidazol-1-yl)-2-[6-[6-[4-[2-[4-[4-[(2,6-dioxo-3-piperidyl)amino]phenyl]-1-piperidyl]acetyl]piperazin-1-yl]-3-pyridyl]-4-fluoro-indazol-2-yl]-N-thiazol-2-yl-acetamide | 33 | 31 | |

TABLE 8-continued

| | | DC$_{50}$ values | | |
|---|---|---|---|---|
| Ex | Compound | H1975 EGFR DC50 [nM] | H3255 EGFR DC50 [nM] | H1975 C797S clone EGFR DC50 [nM] |
| | 2-(6,7-dihydro-5H-pyrrolo[1,2-c]imidazol-1-yl)-2-[6-[6-[4-[2-[4-[5-[(2,6-dioxo-3-piperidyl)amino]-2-pyridyl]-1-piperidyl]acetyl]piperazin-1-yl]-3-pyridyl]-4-fluoro-indazol-2-yl]-N-thiazol-2-yl-acetamide | | | |
| 67 | 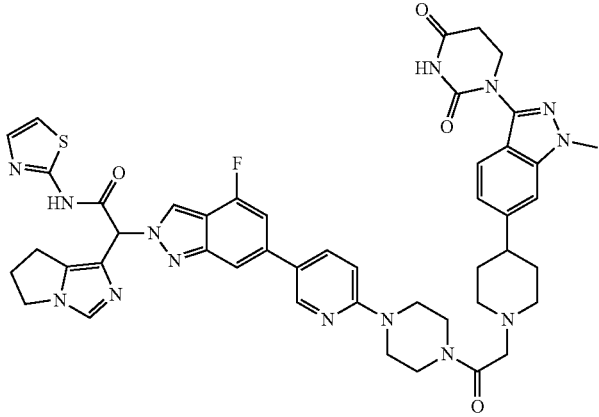 [SMILES: Cn1nc(N2CCC(=O)NC2=O)c2ccc(C3CCN(CC(=O)N4CCN(c5ccc(-c6cc(F)c7cn(C(C(=O)Nc8nccs8)c8ncn9c8CCC9)nc7c6)cn5)CC4)CC3)cc21] | 27 | 50 | |
| | 2-(6,7-dihydro-5H-pyrrolo[1,2-c]imidazol-1-yl)-2-[6-[6-[4-[2-[4-[3-(2,4-dioxohexahydropyrimidin-1-yl)-1-methyl-indazol-6-yl]-1-piperidyl]acetyl]piperazin-1-yl]-3-pyridyl]-4-fluoro-indazol-2-yl]-N-thiazol-2-yl-acetamide | | | |
| 68 | 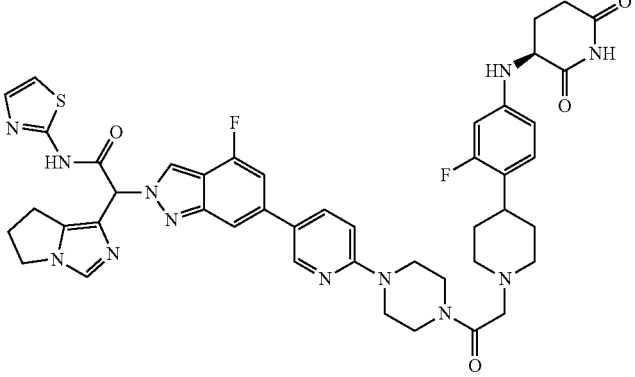 | 28 | 34 | |
| | 2-(6,7-dihydro-5H-pyrrolo[1,2-c]imidazol-1-yl)-2-(6-(6-(4-(2-(4-(4-(((S)-2,6-dioxopiperidin-3-yl)amino)-2-fluorophenyl)piperidin-1-yl)acetyl)piperazin-1-yl)pyridin-3-yl)-4-fluoro-2H-indazol-2-yl)-N-(thiazol-2-yl)acetamide | | | |

TABLE 2

| Ex | Compound | H1975 EGFR DC50 [nM] | H3255 EGFR DC50 [nM] | H1975 C797S clone EGFR DC50 [nM] |
|---|---|---|---|---|
| 69 | 2-(6,7-dihydro-5H-pyrrolo[1,2-c]imidazol-1-yl)-2-(6-(6-(6-(2-(4-(4-(((S)-2,6-dioxopiperidin-3-yl)amino)-2-fluorophenyl)piperidin-1-yl)acetyl)-2,6-diazaspiro[3.3]heptan-2-yl)pyridin-3-yl)-7-fluoro-2H-indazol-2-yl)-N-(thiazol-2-yl)acetamide | *** | | *** |
| 70 | 2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)pyridin-3-yl)-7-fluoro-2H-indazol-2-yl)-N-(thiazol-2-yl)acetamide | *** | | *** |
| 71 | 2-(6,7-dihydro-5H-pyrrolo[1,2-c]imidazol-1-yl)-2-(6-(6-(6-(2-(1-(4-(((2,6-dioxopiperidin-3-yl)amino)-3-fluorophenyl)-4-hydroxypiperidin-4-yl)acetyl)-2,6-diazaspiro[3.3]heptan-2-yl)pyridin-3-yl)-7-fluoro-2H-indazol-2-yl)-N-(thiazol-2-yl)acetamide | *** | | |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 72 | 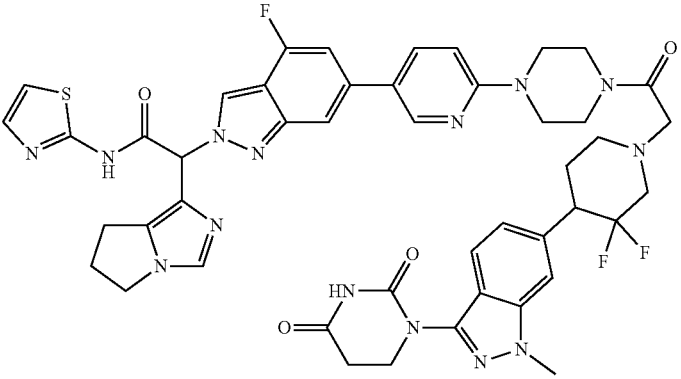 [SMILES: Cn1nc(N2CCC(=O)NC2=O)c2ccc(C3CCN(CC(=O)N4CCN(c5ccc(-c6cc(F)c7cn(C(C(=O)Nc8nccs8)c8ncn9c8CCC9)nc7c6)cn5)CC4)CC3(F)F)cc21] 2-(6,7-dihydro-5H-pyrrolo[1,2-c]imidazol-1-yl)-2-(6-(6-(4-(2-(4-(3-(2,4-dioxotetrahydropyrimidin-1(2H)-yl)-1-methyl-1H-indazol-6-yl)-3,3-difluoropiperidin-1-yl)acetyl)piperazin-1-yl)pyridin-3-yl)-4-fluoro-2H-indazol-2-yl)-N-(thiazol-2-yl)acetamide | *** | | |
| 73 | 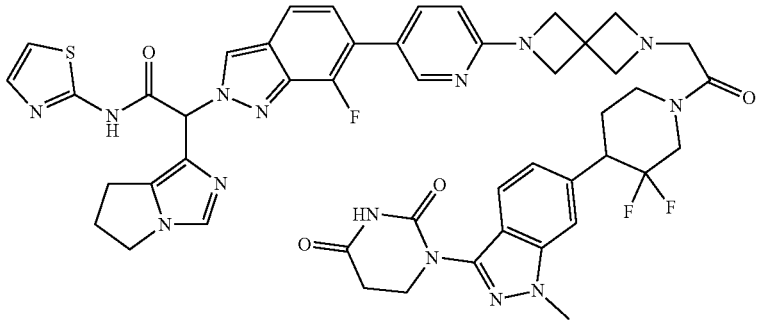 [SMILES: Cn1nc(N2CCC(=O)NC2=O)c2ccc(C3CCN(C(=O)CN4CC5(C4)CN(c4ccc(-c6ccc7cn(C(C(=O)Nc8nccs8)c8ncn9c8CCC9)nc7c6F)cn4)C5)CC3(F)F)cc21] 2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)-2-oxoethyl)-2,6-diazaspiro[3.3]heptan-2-yl)pyridin-3-yl)-7-fluoro-2H-indazol-2-yl)-N-(thiazol-2-yl)acetamide | * | * | |
| 74 | 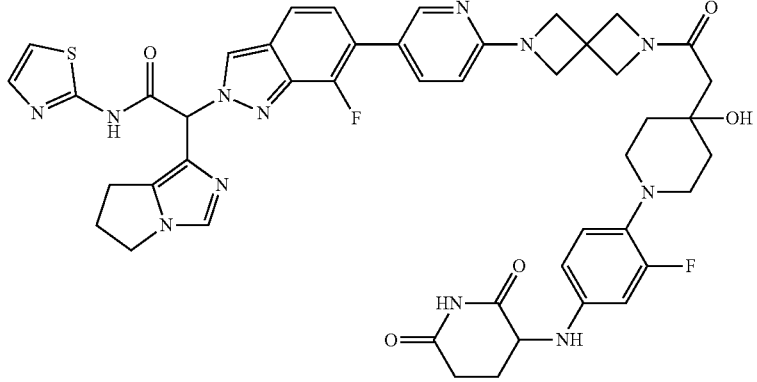 [SMILES: O=C1CCC(Nc2ccc(N3CCC(O)(CC(=O)N4CC5(C4)CN(c4ccc(-c6ccc7cn(C(C(=O)Nc8nccs8)c8ncn9c8CCC9)nc7c6F)cn4)C5)CC3)c(F)c2)C(=O)N1] 2-(6,7-dihydro-5H-pyrrolo[1,2-c]imidazol-1-yl)-2-(6-(6-(6-(2-(1-(4-((2,6-dioxopiperidin-3-yl)amino)-2-fluorophenyl)-4-hydroxypiperidin-4-yl)acetyl)-2,6-diazaspiro[3.3]heptan-2-yl)pyridin-3-yl)-7-fluoro-2H-indazol-2-yl)-N-(thiazol-2-yl)acetamide | *** | | |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 75 | 2-(6,7-dihydro-5H-pyrrolo[1,2-c]imidazol-1-yl)-2-(6-(6-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)pyridin-3-yl)-4-fluoro-2H-indazol-2-yl)-N-(thiazol-2-yl)acetamide | | | *** |
| 76 | 2-(6,7-dihydro-5H-pyrrolo[1,2-c]imidazol-1-yl)-2-(6-(4-(6-(2-((R)-4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)phenyl)-4-fluoro-2H-indazol-2-yl)-N-(thiazol-2-yl)acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 77 | 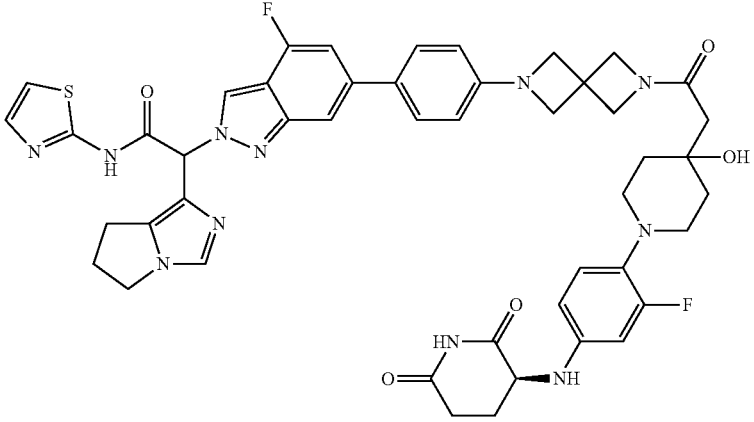 [SMILES: O=C1CC[C@H](Nc2ccc(N3CCC(O)(CC(=O)N4CC5(C4)CN(c4ccc(-c6cc(F)c7cn(C(C(=O)Nc8nccs8)c8ncn9c8CCC9)nc7c6)cc4)C5)CC3)c(F)c2)C(=O)N1]<br>2-(6,7-dihydro-5H-pyrrolo[1,2-c]imidazol-1-yl)-2-(6-(4-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-2H-indazol-2-yl)-N-(thiazol-2-yl)acetamide | | *** | |
| 78 | 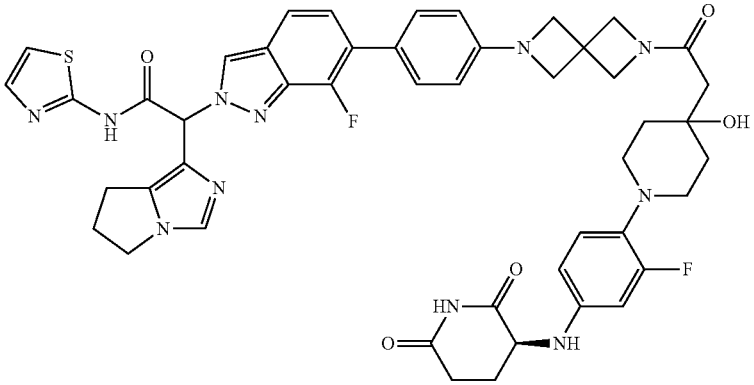 [SMILES: O=C1CC[C@H](Nc2ccc(N3CCC(O)(CC(=O)N4CC5(C4)CN(c4ccc(-c6ccc7cn(C(C(=O)Nc8nccs8)c8ncn9c8CCC9)nc7c6F)cc4)C5)CC3)c(F)c2)C(=O)N1]<br>2-(6,7-dihydro-5H-pyrrolo[1,2-c]imidazol-1-yl)-2-(6-(4-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)phenyl)-7-fluoro-2H-indazol-2-yl)-N-(thiazol-2-yl)acetamide | | *** | |
| 79 | 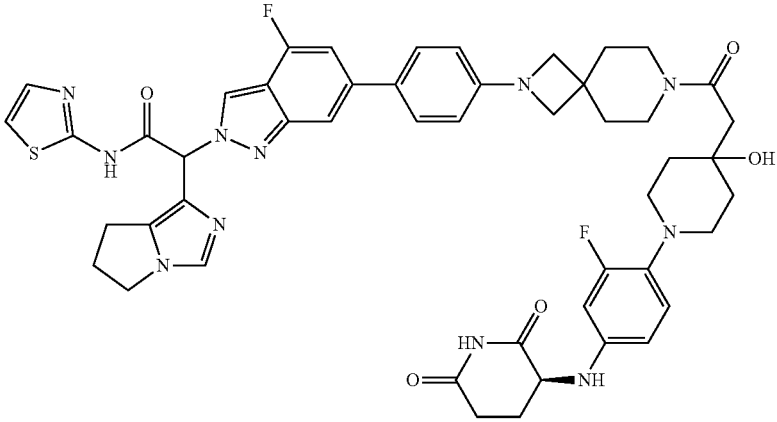 [SMILES: O=C1CC[C@H](Nc2ccc(N3CCC(O)(CC(=O)N4CCC5(CC4)CN(c4ccc(-c6cc(F)c7cn(C(C(=O)Nc8nccs8)c8ncn9c8CCC9)nc7c6)cc4)C5)CC3)c(F)c2)C(=O)N1] | | *** | |

| Ex | Compound | H1975 EGFR DC50 [nM] | H3255 EGFR DC50 [nM] | H1975 C797S clone EGFR DC50 [nM] |
|---|---|---|---|---|
|  | 2-(6,7-dihydro-5H-pyrrolo[1,2-c]imidazol-1-yl)-2-(6-(4-(7-(2-(1-(4-(((S)-2,6-dioxopiperidin-3-yl)amino)-2-fluorophenyl)-4-hydroxypiperidin-4-yl)acetyl)-2,7-diazaspiro[3.5]nonan-2-yl)phenyl)-4-fluoro-2H-indazol-2-yl)-N-(thiazol-2-yl)acetamide |  |  |  |
| 80 | 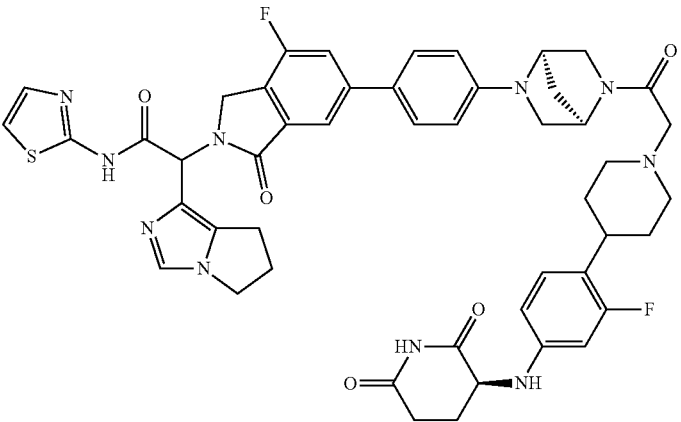 [SMILES: O=C1CC[C@H](Nc2ccc(C3CCN(CC(=O)N4C[C@H]5C[C@@H]4CN5c4ccc(-c5cc(F)c6c(c5)C(=O)N(C(C(=O)Nc5nccs5)c5ncn7c5CCC7)C6)cc4)CC3)c(F)c2)C(=O)N1] 2-(6,7-dihydro-5H-pyrrolo[1,2-c]imidazol-1-yl)-2-(6-(4-((1R,4R)-5-(2-(4-(4-(((S)-2,6-dioxopiperidin-3-yl)amino)-2-fluorophenyl)piperidin-1-yl)acetyl)-2,5-diazabicyclo[2.2.1]heptan-2-yl)phenyl)-4-fluoro-1-oxoisoindolin-2-yl)-N-(thiazol-2-yl)acetamide |  | | * |
| 81 | 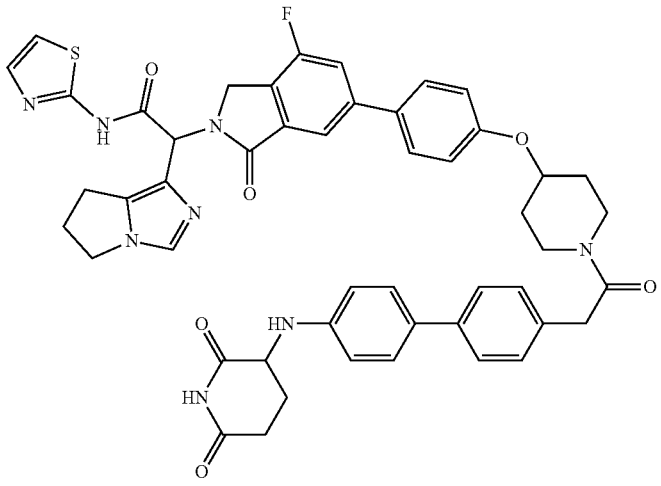 [SMILES: O=C1CCC(Nc2ccc(-c3ccc(CC(=O)N4CCC(Oc5ccc(-c6cc(F)c7c(c6)C(=O)N(C(C(=O)Nc6nccs6)c6ncn8c6CCC8)C7)cc5)CC4)cc3)cc2)C(=O)N1] 2-(6,7-dihydro-5H-pyrrolo[1,2-c]imidazol-1-yl)-2-(6-(4-((1-(2-(4'-((2,6-dioxopiperidin-3-yl)amino)-[1,1'-biphenyl]-4-yl)acetyl)piperidin-4-yl)oxy)phenyl)-4-fluoro-1-oxoisoindolin-2-yl)-N-(thiazol-2-yl)acetamide | ** | | |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 82 | 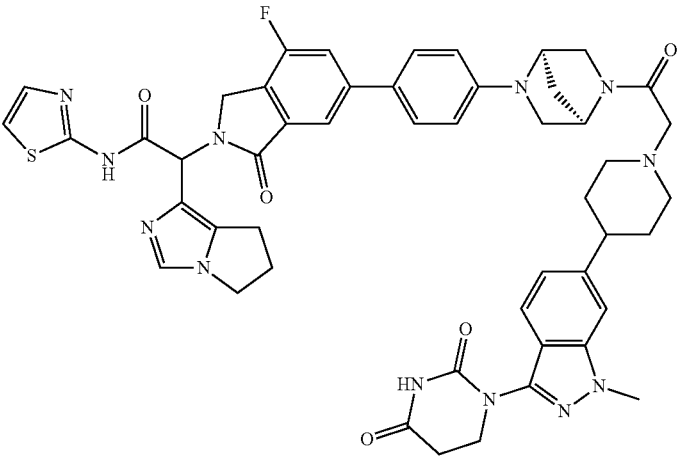 [SMILES: Cn1nc(N2CCC(=O)NC2=O)c2ccc(C3CCN(CC(=O)N4C[C@H]5C[C@@H]4CN5c4ccc(-c5cc(F)c6c(c5)C(=O)N(C(C(=O)Nc5nccs5)c5ncn7c5CCC7)C6)cc4)CC3)cc21] 2-(6,7-dihydro-5H-pyrrolo[1,2-c]imidazol-1-yl)-2-(6-(4-((1R,4R)-5-(2-(4-(3-(2,4-dioxotetrahydropyrimidin-1(2H)-yl)-1-methyl-1H-indazol-6-yl)piperidin-1-yl)acetyl)-2,5-diazabicyclo[2.2.1]heptan-2-yl)phenyl)-4-fluoro-1-oxoisoindolin-2-yl)-N-(thiazol-2-yl)acetamide | * | | |
| 83 | 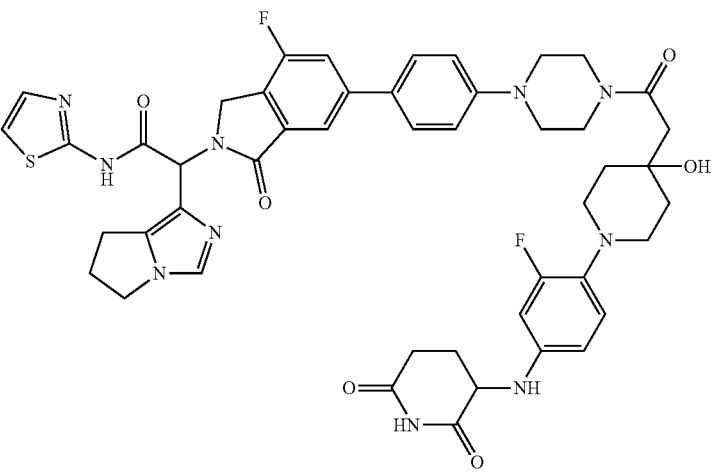 [SMILES: O=C1CCC(Nc2ccc(N3CCC(O)(CC(=O)N4CCN(c5ccc(-c6cc(F)c7c(c6)C(=O)N(C(C(=O)Nc6nccs6)c6ncn8c6CCC8)C7)cc5)CC4)CC3)c(F)c2)C(=O)N1] 2-(6,7-dihydro-5H-pyrrolo[1,2-c]imidazol-1-yl)-2-(6-(4-(4-(2-(1-(4-((2,6-dioxopiperidin-3-yl)amino)-2-fluorophenyl)-4-hydroxypiperidin-4-yl)acetyl)piperazin-1-yl)phenyl)-4-fluoro-1-oxoisoindolin-2-yl)-N-(thiazol-2-yl)acetamide | | * | * |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 84 | 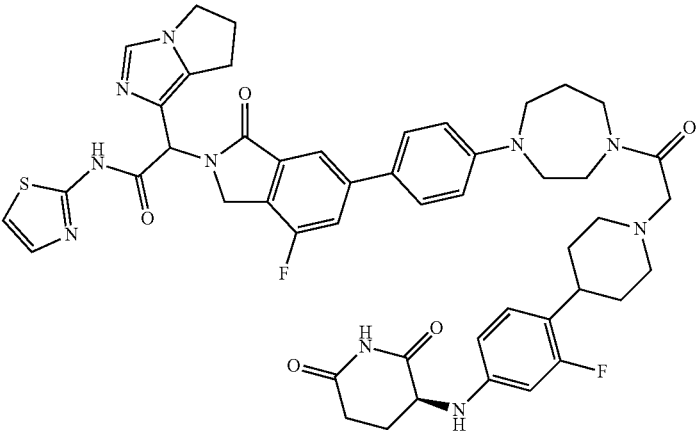 [SMILES: O=C1CC[C@H](Nc2ccc(C3CCN(CC(=O)N4CCCN(c5ccc(-c6cc(F)c7c(c6)C(=O)N(C(C(=O)Nc6nccs6)c6ncn8c6CCC8)C7)cc5)CC4)CC3)c(F)c2)C(=O)N1] 2-(6,7-dihydro-5H-pyrrolo[1,2-c]imidazol-1-yl)-2-(6-(4-(4-(2-(4-(4-(((S)-2,6-dioxopiperidin-3-yl)amino)-2-fluorophenyl)piperidin-1-yl)acetyl)-1,4-diazepan-1-yl)phenyl)-4-fluoro-1-oxoisoindolin-2-yl)-N-(thiazol-2-yl)acetamide |  |  | |
| 85 | 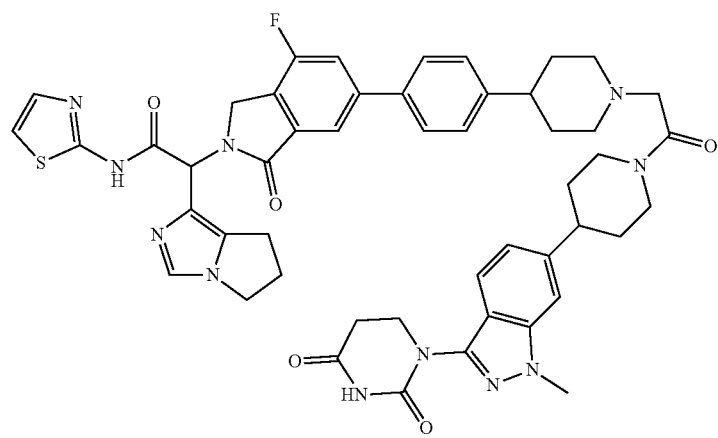 [SMILES: Cn1nc(N2CCC(=O)NC2=O)c2ccc(C3CCN(C(=O)CN4CCC(c5ccc(-c6cc(F)c7c(c6)C(=O)N(C(C(=O)Nc6nccs6)c6ncn8c6CCC8)C7)cc5)CC4)CC3)cc21] 2-(6,7-dihydro-5H-pyrrolo[1,2-c]imidazol-1-yl)-2-(6-(4-(1-(2-(4-(3-(2,4-dioxotetrahydropyrimidin-1(2H)-yl)-1-methyl-1H-indazol-6-yl)piperidin-1-yl)-2-oxoethyl)piperidin-4-yl)phenyl)-4-fluoro-1-oxoisoindolin-2-yl)-N-(thiazol-2-yl)acetamide | |  | * |
| 86 | 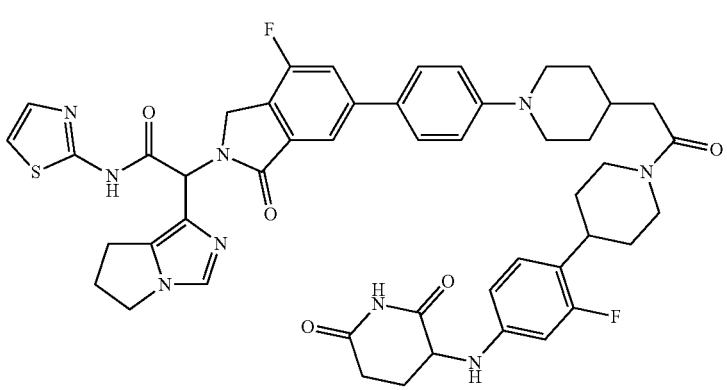 [SMILES: O=C1CCC(Nc2ccc(C3CCN(C(=O)CC4CCN(c5ccc(-c6cc(F)c7c(c6)C(=O)N(C(C(=O)Nc6nccs6)c6ncn8c6CCC8)C7)cc5)CC4)CC3)c(F)c2)C(=O)N1] | | ** | |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| | 2-(6,7-dihydro-5H-pyrrolo[1,2-c]imidazol-1-yl)-2-(6-(4-(4-(2-(4-(4-((2,6-dioxopiperidin-3-yl)amino)-2-fluorophenyl)piperidin-1-yl)-2-oxoethyl)piperidin-1-yl)phenyl)-4-fluoro-1-oxoisoindolin-2-yl)-N-(thiazol-2-yl)acetamide | | | |
| 87 | 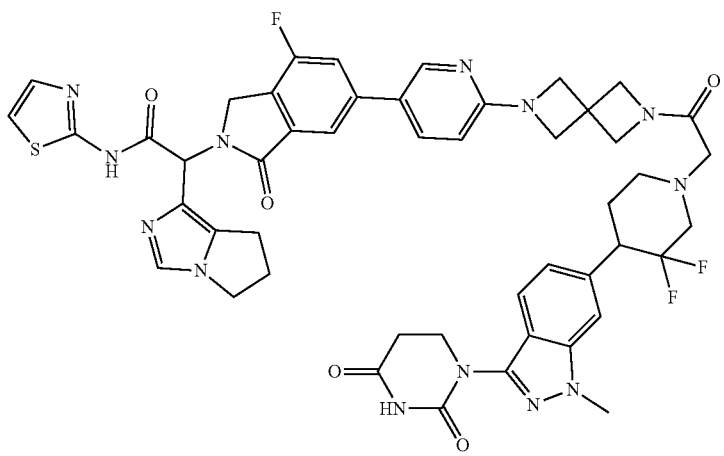 [SMILES: Cn1nc(N2CCC(=O)NC2=O)c2ccc(C3CCN(CC(=O)N4CC5(C4)CN(c4ccc(-c6cc(F)c7c(c6)C(=O)N(C(C(=O)Nc6nccs6)c6ncn8c6CCC8)C7)cn4)C5)CC3(F)F)cc21] 2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)pyridin-3-yl)-4-fluoro-1-oxoisoindolin-2-yl)-N-(thiazol-2-yl)acetamide | * | | * |
| 88 | 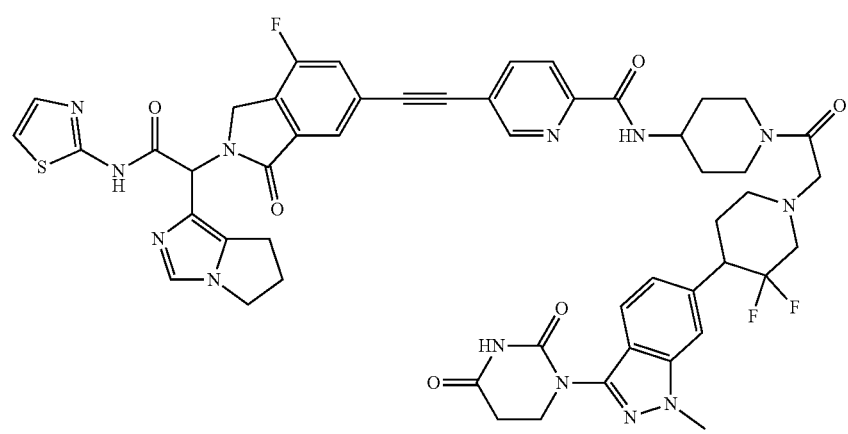 [SMILES: Cn1nc(N2CCC(=O)NC2=O)c2ccc(C3CCN(CC(=O)N4CCC(NC(=O)c5ccc(C#Cc6cc(F)c7c(c6)C(=O)N(C(C(=O)Nc6nccs6)c6ncn8c6CCC8)C7)cn5)CC4)CC3(F)F)cc21] 5-((2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)ethynyl)-N-(1-(2-(4-(3-(2,4-dioxotetrahydropyrimidin-1(2H)-yl)-1-methyl-1H-indazol-6-yl)-3,3-difluoropiperidin-1-yl)acetyl)piperidin-4-yl)picolinamide | * | | * |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 89 | 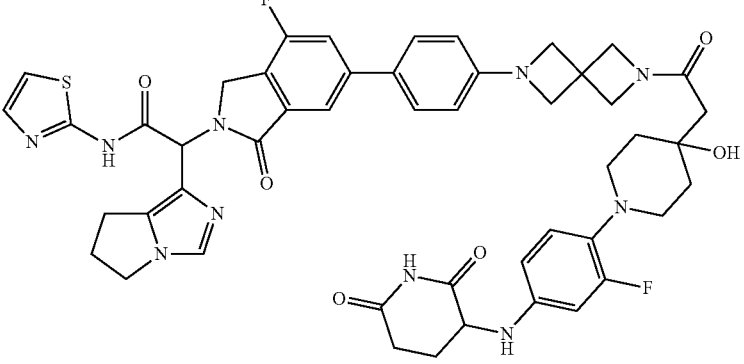 2-(6,7-dihydro-5H-pyrrolo[1,2-c]imidazol-1-yl)-2-(6-(4-(6-(2-(1-(4-((2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide | *** | | |
| 90 | 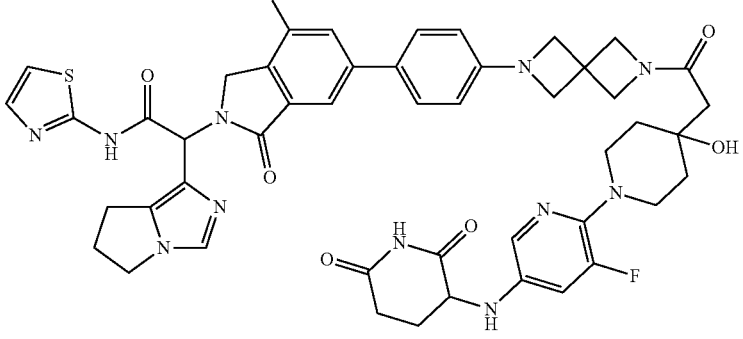 2-(6,7-dihydro-5H-pyrrolo[1,2-c]imidazol-1-yl)-2-(6-(4-(6-(2-(1-(5-((2,6-dioxopiperidin-3-yl)amino)-3-fluoropyridin-2-yl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide | *** | | |
| 91 | 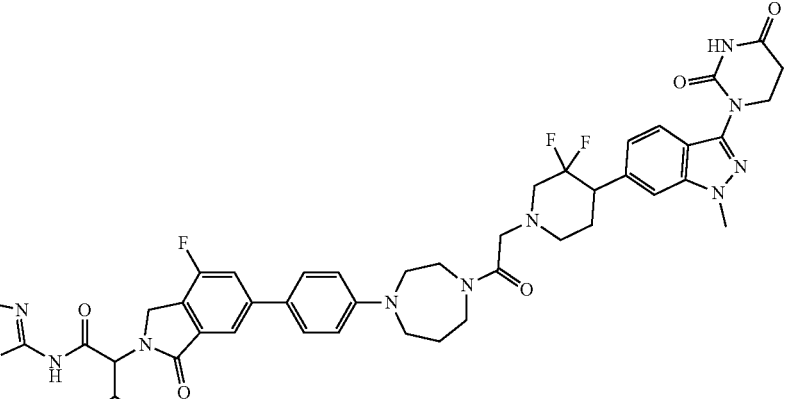 2-(6,7-dihydro-5H-pyrrolo[1,2-c]imidazol-1-yl)-2-(6-(4-(4-(2-(4-(3-(2,4-dioxotetrahydropyrimidin-1(2H)-yl)-1- | * | |  |

TABLE 2-continued

| | | H1975 EGFR DC50 [nM] | H3255 EGFR DC50 [nM] | H1975 C797S clone EGFR DC50 [nM] |
|---|---|---|---|---|
| Ex | Compound | | | | methyl-1H-indazol-6-yl)-3,3-difluoropiperidin-1-yl)acetyl)-1,4-diazepan-1-yl)phenyl)-4-fluoro-1-oxoisoindolin-2-yl)-N-(thiazol-2-yl)acetamide

| 92 | 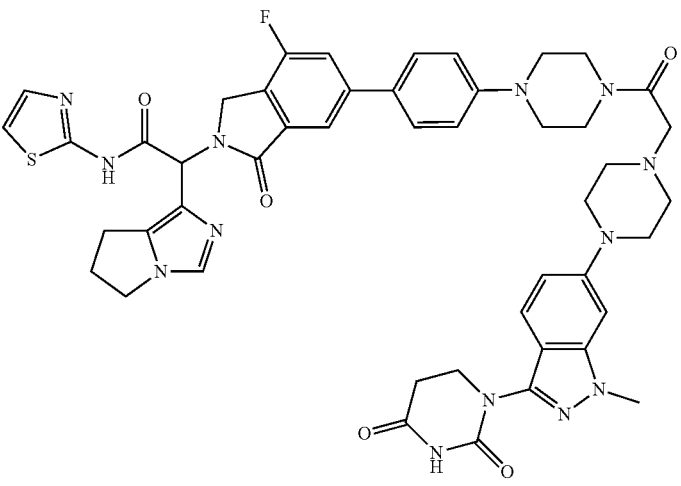 [SMILES: Cn1nc(N2CCC(=O)NC2=O)c2ccc(N3CCN(CC(=O)N4CCN(c5ccc(-c6cc(F)c7c(c6)C(=O)N(C(C(=O)Nc6nccs6)c6ncn8c6CCC8)C7)cc5)CC4)CC3)cc21] | * | | * |

2-(6,7-dihydro-5H-pyrrolo[1,2-c]imidazol-1-yl)-2-(6-(4-(4-(2-(4-(3-(2,4-dioxotetrahydropyrimidin-1(2H)-yl)-1-methyl-1H-indazol-6-yl)piperazin-1-yl)acetyl)piperazin-1-yl)phenyl)-4-fluoro-1-oxoisoindolin-2-yl)-N-(thiazol-2-yl)acetamide

| 93 | 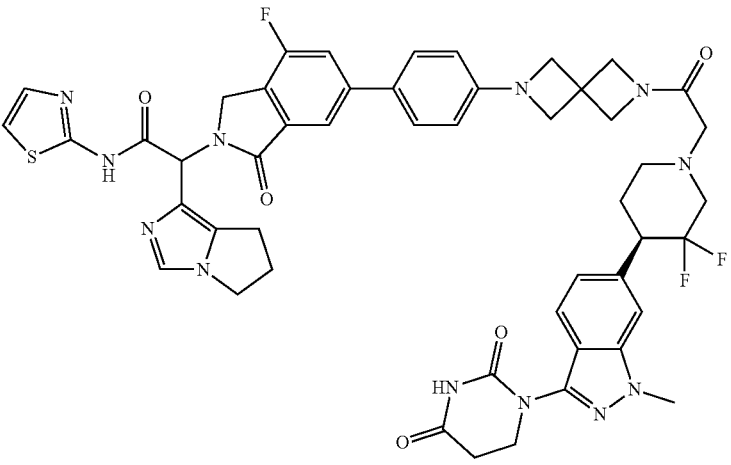 [SMILES: Cn1nc(N2CCC(=O)NC2=O)c2ccc([C@H]3CCN(CC(=O)N4CC5(C4)CN(c4ccc(-c6cc(F)c7c(c6)C(=O)N(C(C(=O)Nc6nccs6)c6ncn8c6CCC8)C7)cc4)C5)CC3(F)F)cc21] | * | * | *** |

2-(6,7-dihydro-5H-pyrrolo[1,2-c]imidazol-1-yl)-2-(6-(4-(6-(2-((R)-4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 94 | 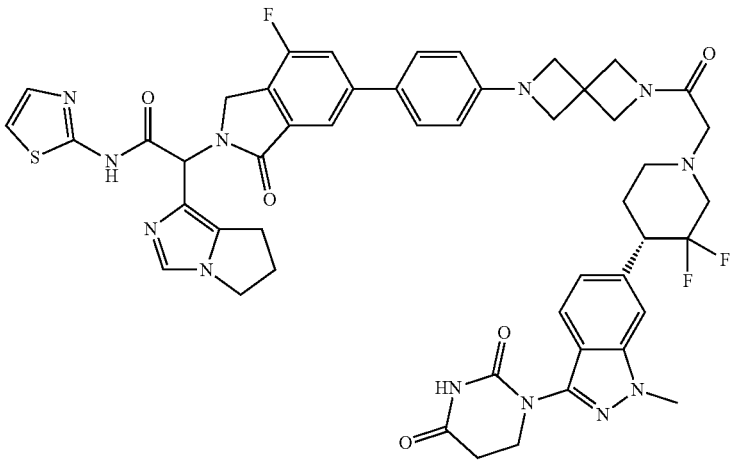 [SMILES: Cn1nc(N2CCC(=O)NC2=O)c2ccc([C@@H]3CCN(CC(=O)N4CC5(C4)CN(c4ccc(-c6cc(F)c7c(c6)C(=O)N(C(C(=O)Nc6nccs6)c6ncn8c6CCC8)C7)cc4)C5)CC3(F)F)cc21] 2-(6,7-dihydro-5H-pyrrolo[1,2-c]imidazol-1-yl)-2-(6-(4-(6-(2-((S)-4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide | * | * | *** |
| 95 | 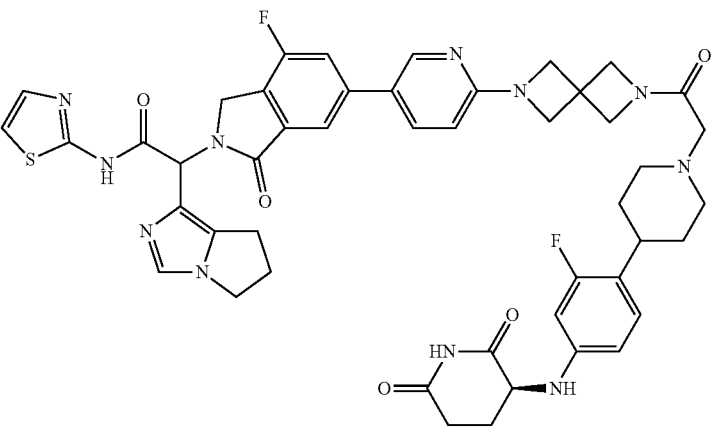 [SMILES: O=C1CC[C@H](Nc2ccc(C3CCN(CC(=O)N4CC5(C4)CN(c4ccc(-c6cc(F)c7c(c6)C(=O)N(C(C(=O)Nc6nccs6)c6ncn8c6CCC8)C7)cn4)C5)CC3)c(F)c2)C(=O)N1] 2-(6,7-dihydro-5H-pyrrolo[1,2-c]imidazol-1-yl)-2-(6-(6-(2-(4-(4-(((S)-2,6-dioxopiperidin-3-yl)amino)-2-fluorophenyl)piperidin-1-yl)acetyl)-2,6-diazaspiro[3.3]heptan-2-yl)pyridin-3-yl)-4-fluoro-1-oxoisoindolin-2-yl)-N-(thiazol-2-yl)acetamide | | *** | |

| Ex | Compound | H1975 EGFR DC50 [nM] | H3255 EGFR DC50 [nM] | H1975 C797S clone EGFR DC50 [nM] |
|---|---|---|---|---|
| 96 | 5-((2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)ethynyl)-N-(1-(2-(1-(4-((2,6-dioxopiperidin-3-yl)amino)-2-fluorophenyl)-4-hydroxypiperidin-4-yl)acetyl)piperidin-4-yl)picolinamide | | *** | *** |
| 97 | 2-(6,7-dihydro-5H-pyrrolo[1,2-c]imidazol-1-yl)-2-(6-(4-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide | *** | *** | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 98 | 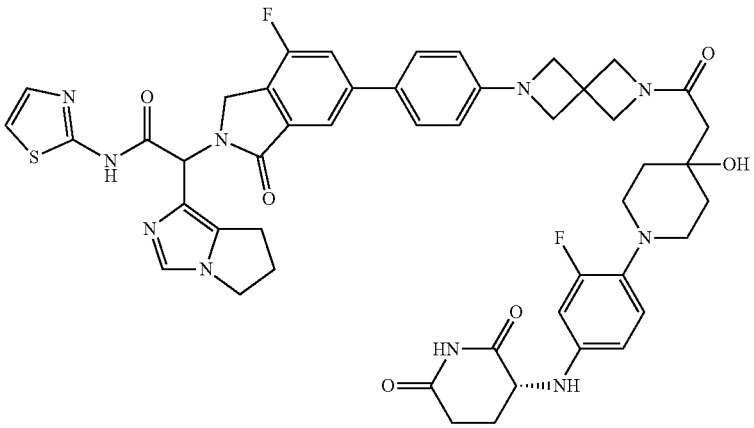 [SMILES: O=C1CC[C@@H](Nc2ccc(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1] 2-(6,7-dihydro-5H-pyrrolo[1,2-c]imidazol-1-yl)-2-(6-(4-(6-(2-(1-(4-(((R)-2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide | * | * | *** |
| 99 | 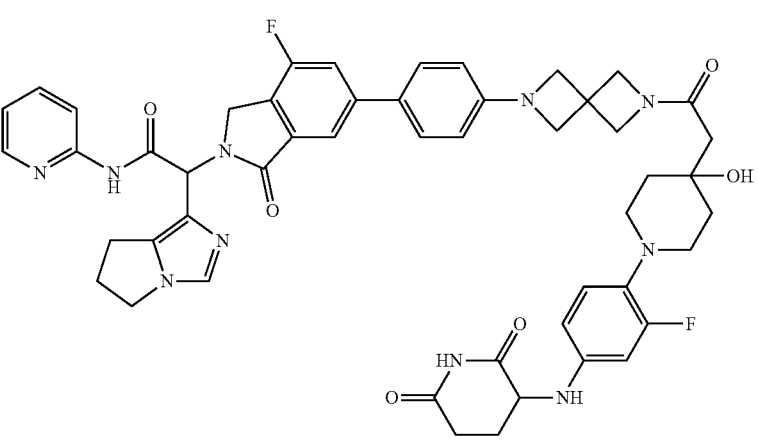 [SMILES: O=C1CCC(Nc2ccc(N3CCC(O)(CC(=O)N4CC5(C4)CN(c4ccc(-c6cc(F)c7c(c6)C(=O)N(C(C(=O)Nc6ccccn6)c6ncn8c6CCC8)C7)cc4)C5)CC3)c(F)c2)C(=O)N1] 2-(6,7-dihydro-5H-pyrrolo[1,2-c]imidazol-1-yl)-2-(6-(4-(6-(2-(1-(4-((2,6-dioxopiperidin-3-yl)amino)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(pyridin-2-yl)acetamide | | * | * |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 100 | 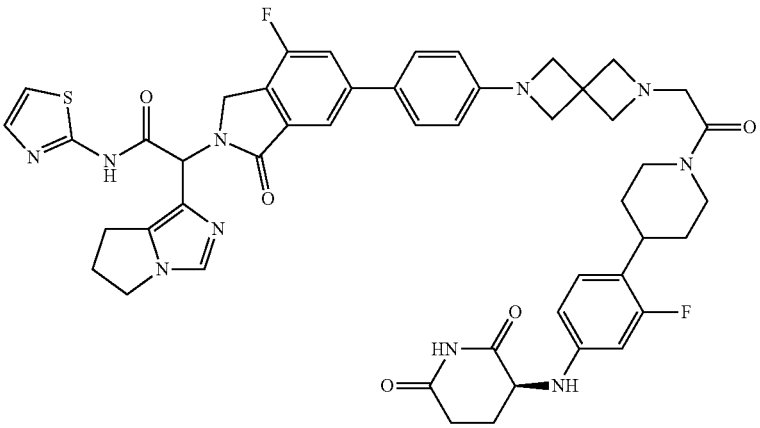 [SMILES: O=C1CC[C@H](Nc2ccc(C3CCN(C(=O)CN4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1]  2-(6,7-dihydro-5H-pyrrolo[1,2-c]imidazol-1-yl)-2-(6-(4-(6-(2-(4-(4-(((S)-2,6-dioxopiperidin-3-yl)amino)-2-fluorophenyl)piperidin-1-yl)-2-oxoethyl)-2-azaspiro[3.3]heptan-2-yl)phenyl)-4-fluoro-1-oxoisoindolin-2-yl)-N-(thiazol-2-yl)acetamide | | | *** |
| 101 | 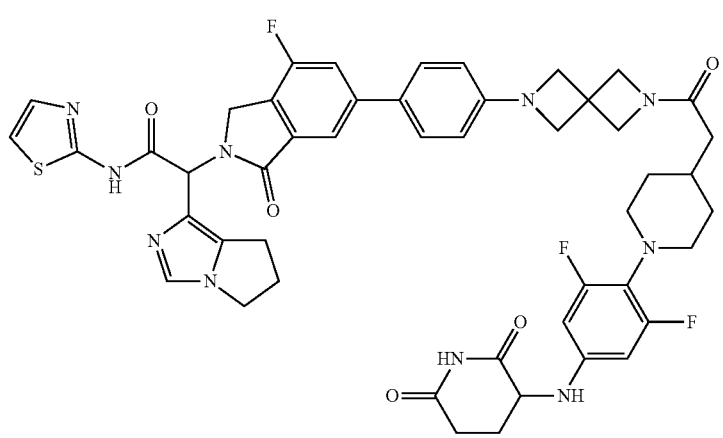 [SMILES: O=C1CCC(Nc2cc(F)c(N3CCC(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1]  2-(6,7-dihydro-5H-pyrrolo[1,2-c]imidazol-1-yl)-2-(6-(4-(6-(2-(1-(4-((2,6-dioxopiperidin-3-yl)amino)-2,6-difluorophenyl)piperidin-4-yl)acetyl)-2,6-diazaspiro[3.3]heptan-2-yl)phenyl)-4-fluoro-1-oxoisoindolin-2-yl)-N-(thiazol-2-yl)acetamide | | | ** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 102 | 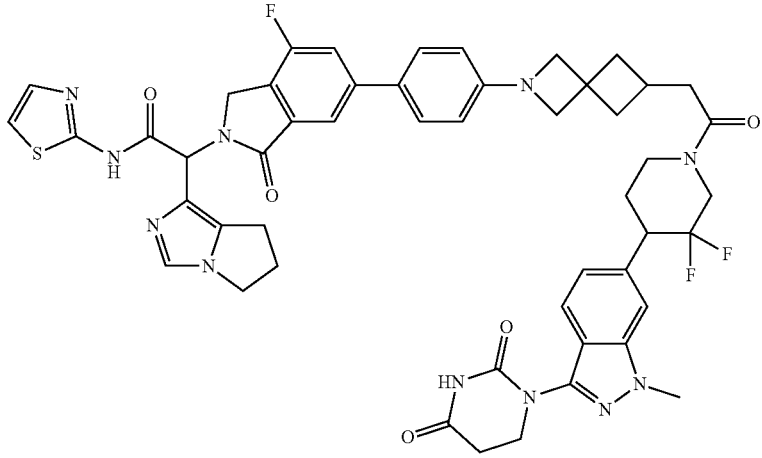 [SMILES: Cn1nc(N2CCC(=O)NC2=O)c2ccc(C3CCN(C(=O)CC4CC5(C4)CN(c4ccc(-c6cc(F)c7c(c6)C(=O)N(C(C(=O)Nc6nccs6)c6ncn8c6CCC8)C7)cc4)C5)CC3(F)F)cc21] 2-(6,7-dihydro-5H-pyrrolo[1,2-c]imidazol-1-yl)-2-(6-(4-(6-(2-(4-(3-(2,4-dioxotetrahydropyrimidin-1(2H)-yl)-1-methyl-1H-indazol-6-yl)-3,3-difluoropiperidin-1-yl)-2-oxoethyl)-2-azaspiro[3.3]heptan-2-yl)phenyl)-4-fluoro-1-oxoisoindolin-2-yl)-N-(thiazol-2-yl)acetamide | | | *** |
| 103 | 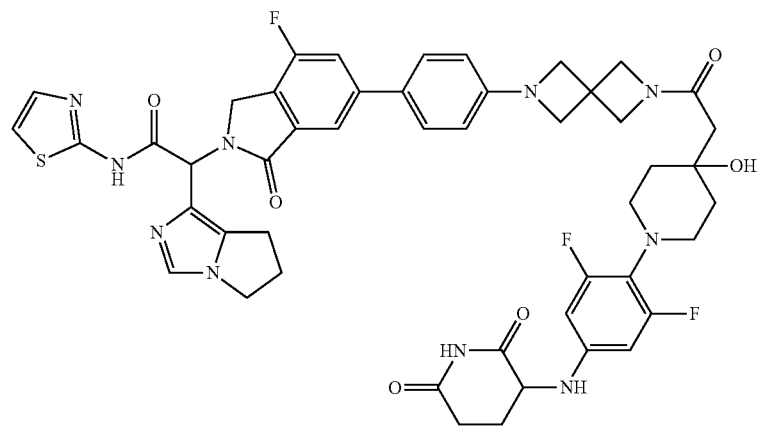 [SMILES: O=C1CCC(Nc2cc(F)c(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1] 2-(6,7-dihydro-5H-pyrrolo[1,2-c]imidazol-1-yl)-2-(6-(4-(6-(2-(1-(4-((2,6-dioxopiperidin-3-yl)amino)-2,6-difluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide | | * | * |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 104 | 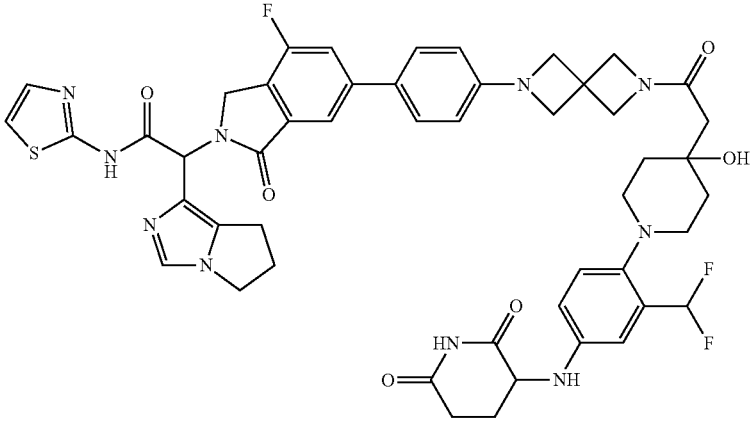 [SMILES: O=C1CCC(Nc2ccc(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(C(F)F)c2)C(=O)N1]  2-(6-(4-(6-(2-(1-(2-(difluoromethyl)-4-((2,6-dioxopiperidin-3-yl)amino)phenyl)-4-hydroxypiperidin-4-yl)acetyl)-2,6-diazaspiro[3.3]heptan-2-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide | * | * |  |
| 105 | 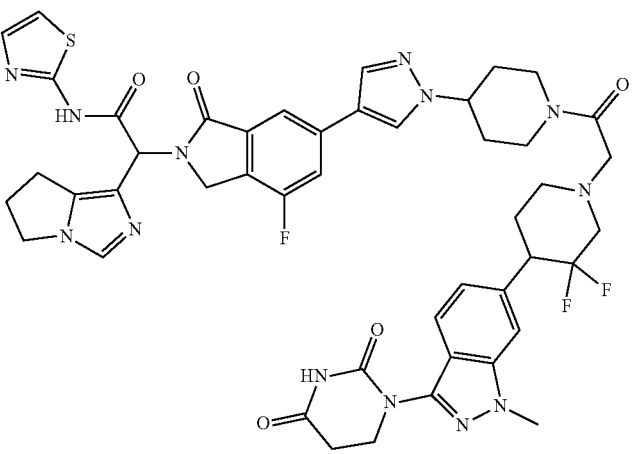 [SMILES: Cn1nc(N2CCC(=O)NC2=O)c2ccc(C3CCN(CC(=O)N4CCC(n5cc(-c6cc(F)c7c(c6)C(=O)N(C(C(=O)Nc6nccs6)c6ncn8c6CCC8)C7)cn5)CC4)CC3(F)F)cc21]  2-(6,7-dihydro-5H-pyrrolo[1,2-c]imidazol-1-yl)-2-(6-(1-(1-(2-(4-(3-(2,4-dioxotetrahydropyrimidin-1(2H)-yl)-1-methyl-1H-indazol-6-yl)-3,3-difluoropiperidin-1-yl)acetyl)piperidin-4-yl)-1H-pyrazol-4-yl)-4-fluoro-1-oxoisoindolin-2-yl)-N-(thiazol-2-yl)acetamide |  |  | *** |

| Ex | Compound | H1975 EGFR DC50 [nM] | H3255 EGFR DC50 [nM] | H1975 C797S clone EGFR DC50 [nM] |
|---|---|---|---|---|
| 106 | 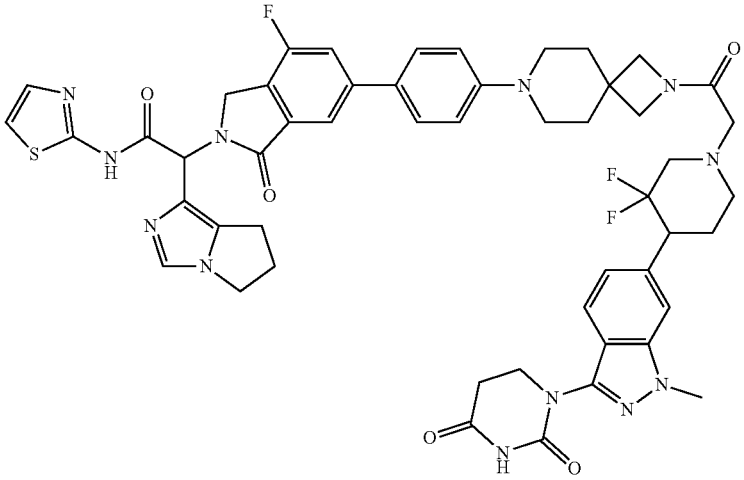 [SMILES: Cn1nc(N2CCC(=O)NC2=O)c2ccc(C3CCN(CC(=O)N4CC5(CCN(c6ccc(-c7cc(F)c8c(c7)C(=O)N(C(C(=O)Nc7nccs7)c7ncn9c7CCC9)C8)cc6)CC5)C4)CC3(F)F)cc21] 2-(6,7-dihydro-5H-pyrrolo[1,2-c]imidazol-1-yl)-2-(6-(4-(2-(2-(4-(3-(2,4-dioxotetrahydropyrimidin-1(2H)-yl)-1-methyl-1H-indazol-6-yl)-3,3-difluoropiperidin-1-yl)acetyl)-2,7-diazaspiro[3.5]nonan-7-yl)phenyl)-4-fluoro-1-oxoisoindolin-2-yl)-N-(thiazol-2-yl)acetamide | *** | | |
| 107 | 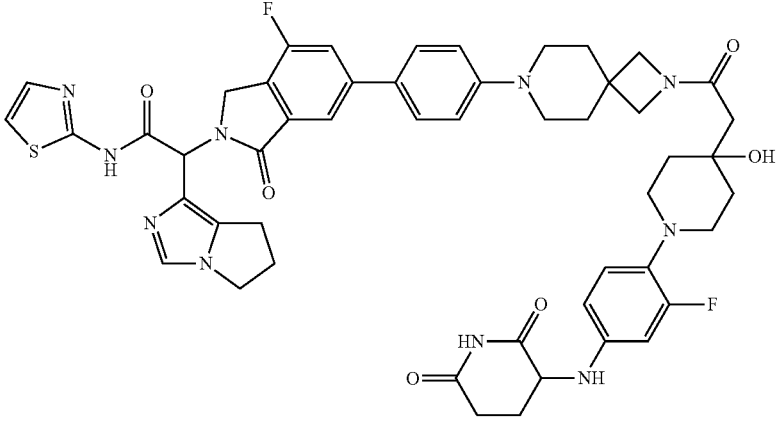 [SMILES: O=C1CCC(Nc2ccc(N3CCC(O)(CC(=O)N4CC5(CCN(c6ccc(-c7cc(F)c8c(c7)C(=O)N(C(C(=O)Nc7nccs7)c7ncn9c7CCC9)C8)cc6)CC5)C4)CC3)c(F)c2)C(=O)N1] 2-(6,7-dihydro-5H-pyrrolo[1,2-c]imidazol-1-yl)-2-(6-(4-(2-(2-(1-(4-((2,6-dioxopiperidin-3-yl)amino)-2-fluorophenyl)-4-hydroxypiperidin-4-yl)acetyl)-2,7-diazaspiro[3.5]nonan-7-yl)phenyl)-4-fluoro-1-oxoisoindolin-2-yl)-N-(thiazol-2-yl)acetamide | *** | | |
| 108 | 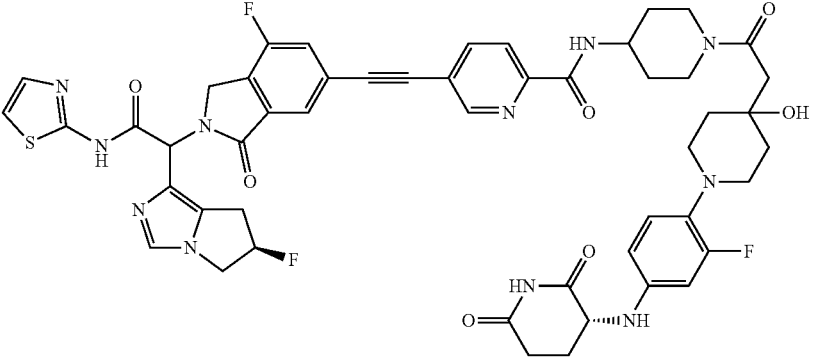 [SMILES: O=C1CC[C@@H](Nc2ccc(N3CCC(O)(CC(=O)N4CCC(NC(=O)c5ccc(C#Cc6cc(F)c7c(c6)C(=O)N(C(C(=O)Nc6nccs6)c6ncn8c6C[C@@H](F)C8)C7)cn5)CC4)CC3)c(F)c2)C(=O)N1] | *** | | |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| | N-(1-(2-(1-(4-(((R)-2,6-dioxopiperidin-3-yl)amino)-2-fluorophenyl)-4-hydroxypiperidin-4-yl)acetyl)piperidin-4-yl)-5-((7-fluoro-2-(1-((R)-6-fluoro-6,7-dihydro-5H-pyrrolo[1,2-c]imidazol-1-yl)-2-oxo-2-(thiazol-2-ylamino)ethyl)-3-oxoisoindolin-5-yl)ethynyl)picolinamide | | | |
| 109 | 2-(6,7-dihydro-5H-pyrrolo[1,2-c]imidazol-1-yl)-2-(6-(4-(6-(2-(1-(3-(2,4-dioxotetrahydropyrimidin-1(2H)-yl)-1-methyl-1H-indazol-6-yl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide | | | *** |
| 110 | 2-(6,7-dihydro-5H-pyrrolo[1,2-c]imidazol-1-yl)-2-(6-(6-(6-(2-(1-(4-(((S)-2,6-dioxopiperidin-3-yl)amino)-2-fluorophenyl)-4-hydroxypiperidin-4-yl)acetyl)-2,6-diazaspiro[3.3]heptan-2-yl)pyridin-3-yl)-4-fluoro-1-oxoisoindolin-2-yl)-N-(thiazol-2-yl)acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 111 | 2-(6,7-dihydro-5H-pyrrolo[1,2-c]imidazol-1-yl)-2-(6-(6-(6-(2-(1-(4-(((R)-2,6-dioxopiperidin-3-yl)amino)-2-fluorophenyl)-4-hydroxypiperidin-4-yl)acetyl)-2,6-diazaspiro[3.3]heptan-2-yl)pyridin-3-yl)-4-fluoro-1-oxoisoindolin-2-yl)-N-(thiazol-2-yl)acetamide | | | *** |
| 112 | 2-(6,7-dihydro-5H-pyrrolo[1,2-c]imidazol-1-yl)-2-(6-(4-(6-(2-(4-(5-((2,6-dioxopiperidin-3-yl)amino)-3-fluoropyridin-2-yl)piperidin-1-yl)acetyl)-2,6-diazaspiro[3.3]heptan-2-yl)phenyl)-4-fluoro-1-oxoisoindolin-2-yl)-N-(thiazol-2-yl)acetamide | | | *** |
| 113 | | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| | 2-(6,7-dihydro-5H-pyrrolo[1,2-c]imidazol-1-yl)-2-(6-(4-(6-(2-(4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.4]octan-2-yl)phenyl)-4-fluoro-1-oxoisoindolin-2-yl)-N-(thiazol-2-yl)acetamide | | | |
| 114 | 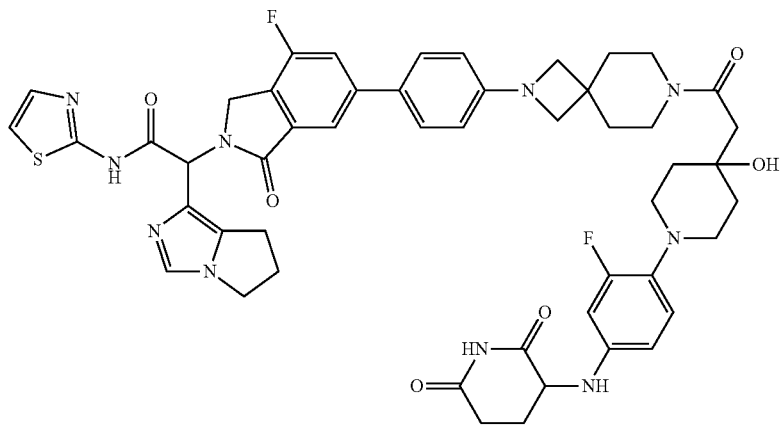 [SMILES: O=C1CCC(Nc2ccc(N3CCC(O)(CC(=O)N4CCC5(CC4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1] 2-(6,7-dihydro-5H-pyrrolo[1,2-c]imidazol-1-yl)-2-[6-[4-[7-[2-[1-[4-[(2,6-dioxo-3-piperidyl)amino]-2-fluoro-phenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide | | | *** |
| 115 | 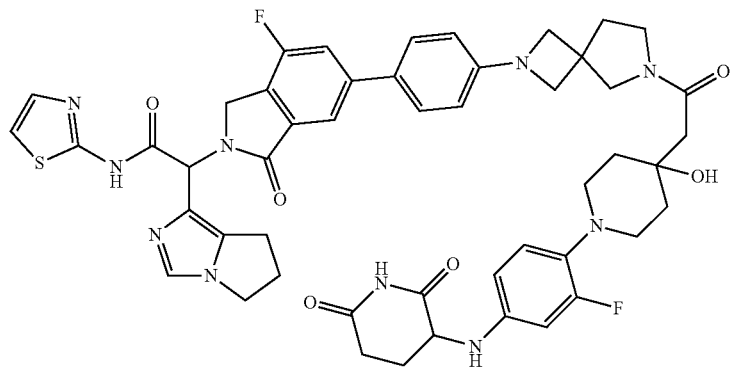 [SMILES: O=C1CCC(Nc2ccc(N3CCC(O)(CC(=O)N4CCC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1] 2-(6,7-dihydro-5H-pyrrolo[1,2-c]imidazol-1-yl)-2-[6-[4-[7-[2-[1-[4-[(2,6-dioxo-3-piperidyl)amino]-2-fluoro-phenyl]-4-hydroxy-4-piperidyl]acetyl]-2,7-diazaspiro[3.4]octan-2-yl]phenyl]-4-fluoro-1-oxo-isoindolin-2-yl]-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 116 | 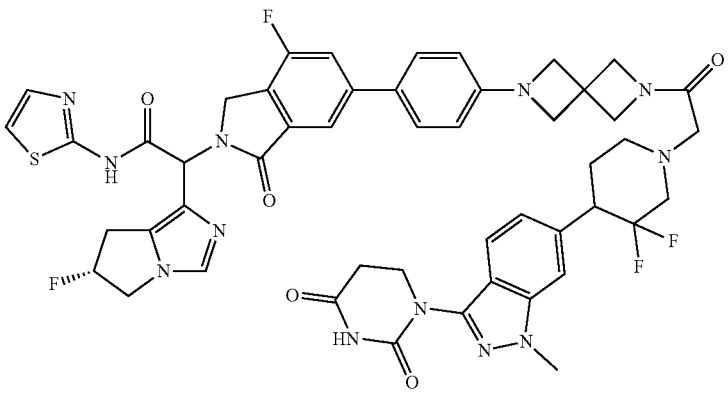 [SMILES: Cn1nc(N2CCC(=O)NC2=O)c2ccc(C3CCN(CC(=O)N4CC5(C4)CN(c4ccc(-c6cc(F)c7c(c6)C(=O)N(C(C(=O)Nc6nccs6)c6ncn8c6C[C@@H](F)C8)C7)cc4)C5)CC3(F)F)cc21] 2-[6-[4-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide | | | *** |
| 117 | 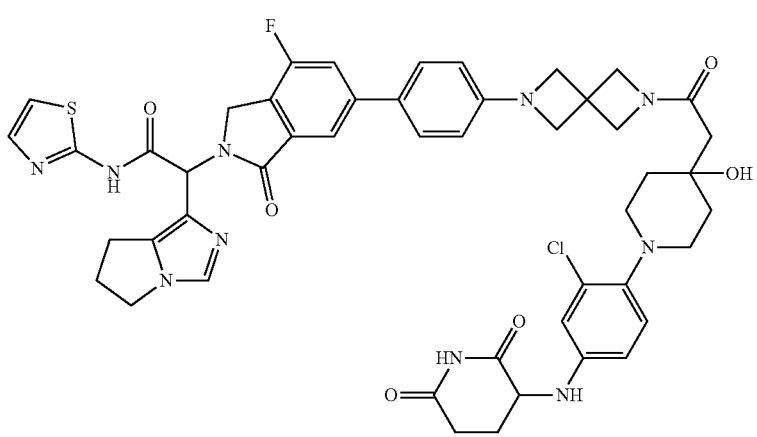 [SMILES: O=C1CCC(Nc2ccc(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(Cl)c2)C(=O)N1] 2-[6-[4-[2-[2-[1-[2-chloro-4-[(2,6-dioxo-3-piperidyl)amino]phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 118 | 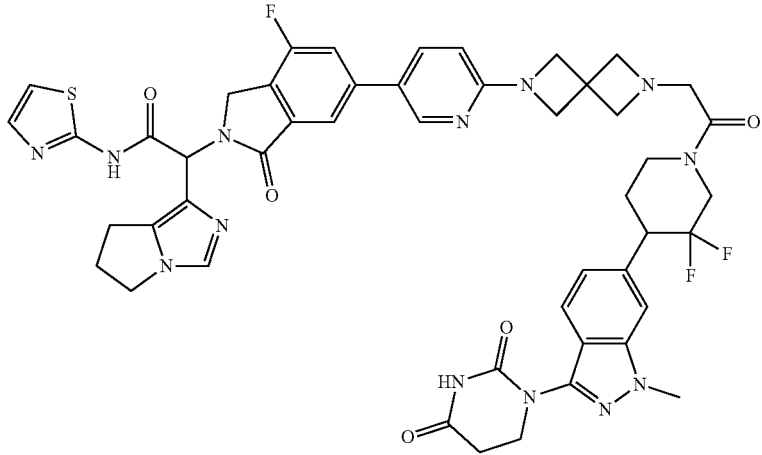 [SMILES: Cn1nc(N2CCC(=O)NC2=O)c2ccc(C3CCN(C(=O)CN4CC5(C4)CN(c4ccc(-c6cc(F)c7c(c6)C(=O)N(C(C(=O)Nc6nccs6)c6ncn8c6CCC8)C7)cn4)C5)CC3(F)F)cc21] 2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)-2-oxoethyl)-2,6-diazaspiro[3.3]heptan-2-yl)pyridin-3-yl)-4-fluoro-1-oxoisoindolin-2-yl)-N-(thiazol-2-yl)acetamide | | | *** |
| 119 | 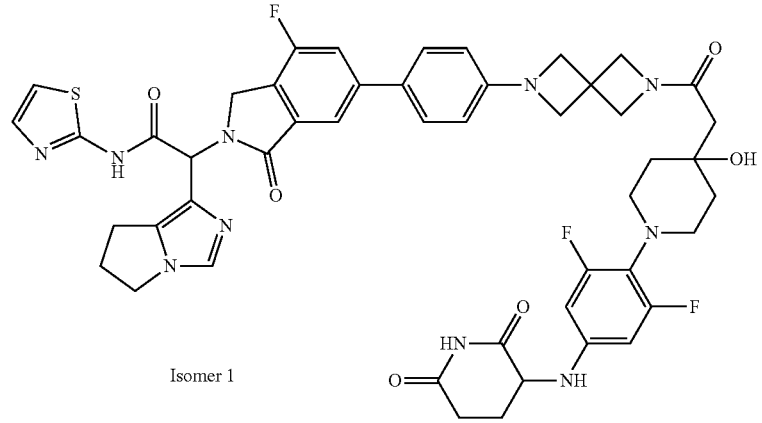 [SMILES: O=C1CCC(Nc2cc(F)c(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1] Isomer 1 2-(6,7-dihydro-5H-pyrrolo[1,2-c]imidazol-1-yl)-2-(6-(4-(6-(2-(1-(4-((2,6-dioxopiperidin-3-yl)amino)-2,6-difluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide, isomer 1 | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 120 | 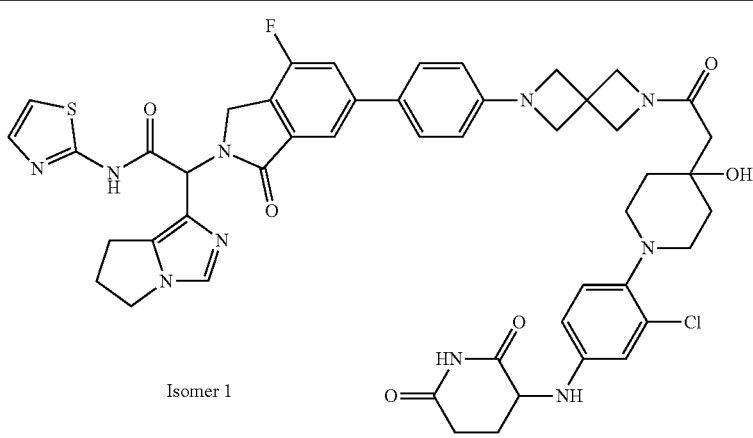 Isomer 1<br><br>2-(6-(4-(6-(2-(1-(2-chloro-4-((2,6-dioxopiperidin-3-yl)amino)phenyl)-4-hydroxypiperidin-4-yl)acetyl)-2,6-diazaspiro[3.3]heptan-2-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide, isomer 1 | | | *** |
| 121 | 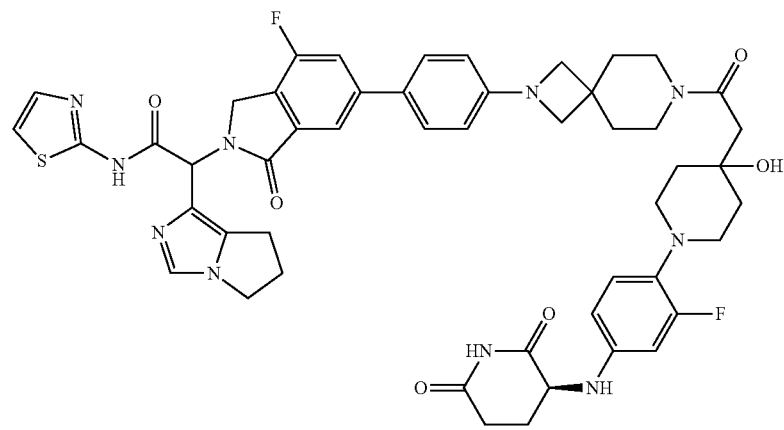 [SMILES: O=C1CC[C@H](Nc2ccc(N3CCC(O)(CC(=O)N4CCC5(CC4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1]<br><br>2-(6,7-dihydro-5H-pyrrolo[1,2-c]imidazol-1-yl)-2-[6-[4-[7-[2-[1-[4-[[(3S)-2,6-dioxo-3-piperidyl]amino]-2-fluoro-phenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 122 | 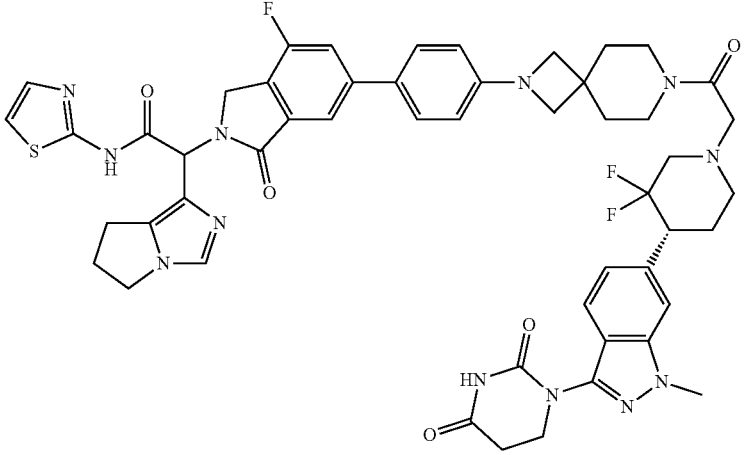 [SMILES: Cn1nc(N2CCC(=O)NC2=O)c2ccc([C@H]3CCN(CC(=O)N4CCC5(CC4)CN(c4ccc(-c6cc(F)c7c(c6)C(=O)N(C(C(=O)Nc6nccs6)c6ncn8c6CCC8)C7)cc4)C5)CC3(F)F)cc21]  2-(6,7-dihydro-5H-pyrrolo[1,2-c]imidazol-1-yl)-2-[6-[4-[7-[2-[(4R)-4-[3-(2,4-dioxohexahydropyrimidin-1-yl)-1-methyl-indazol-6-yl]-3,3-difluoro-1-piperidyl]acetyl]-2,7-diazaspiro[3.5]nonan-2-yl]phenyl]-4-fluoro-1-oxo-isoindolin-2-yl]-N-thiazol-2-yl-acetamide | | | *** |
| 123 | 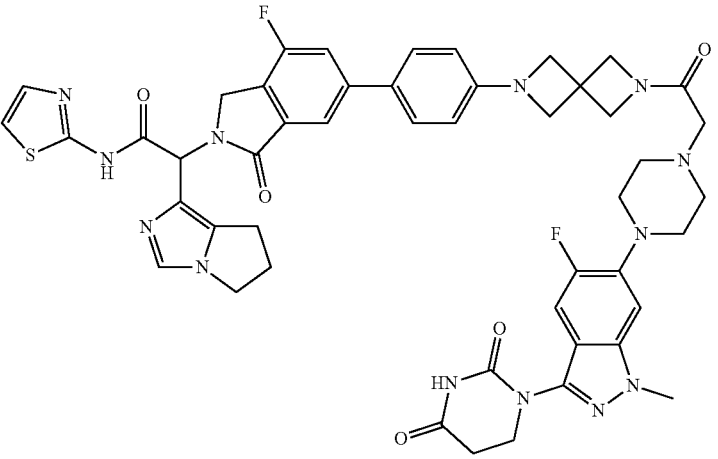 [SMILES: Cn1nc(N2CCC(=O)NC2=O)c2cc(F)c(N3CCN(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)cc21]  2-(6,7-dihydro-5H-pyrrolo[1,2-c]imidazol-1-yl)-2-[6-[4-[2-[2-[4-[3-(2,4-dioxohexahydropyrimidin-1-yl)-5-fluoro-1-methyl-indazol-6-yl]piperazin-1-yl]acetyl]-2,6-diazaspiro[3.3]heptan-6-yl]phenyl]-4-fluoro-1-oxo-isoindolin-2-yl]-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 124 | Isomer 1<br>2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3-fluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1 | | | *** |
| 125 | Isomer 2<br>2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3-fluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, isomer 2 | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 126 | 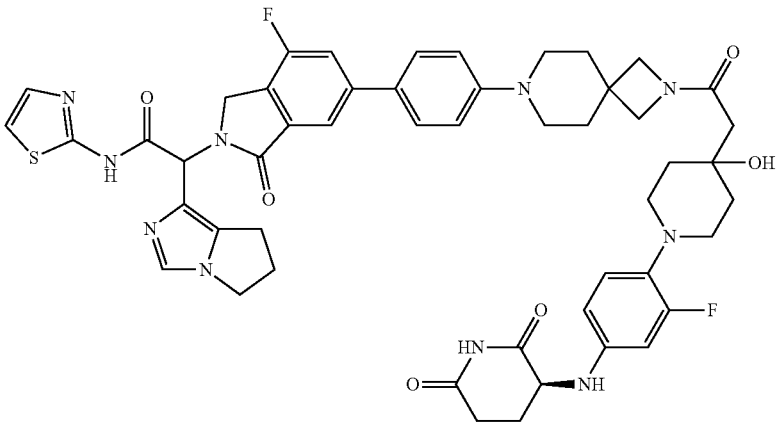 [SMILES: O=C1CC[C@H](Nc2ccc(N3CCC(O)(CC(=O)N4CC5(CCN(c6ccc(-c7cc(F)c8c(c7)C(=O)N(C(C(=O)Nc7nccs7)c7ncn9c7CCC9)C8)cc6)CC5)C4)CC3)c(F)c2)C(=O)N1]<br>2-(6,7-dihydro-5H-pyrrolo[1,2-c]imidazol-1-yl)-2-[6-[4-[2-[2-[1-[4-[[(3S)-2,6-dioxo-3-piperidyl]amino]-2-fluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide | | | *** |
| 127 | 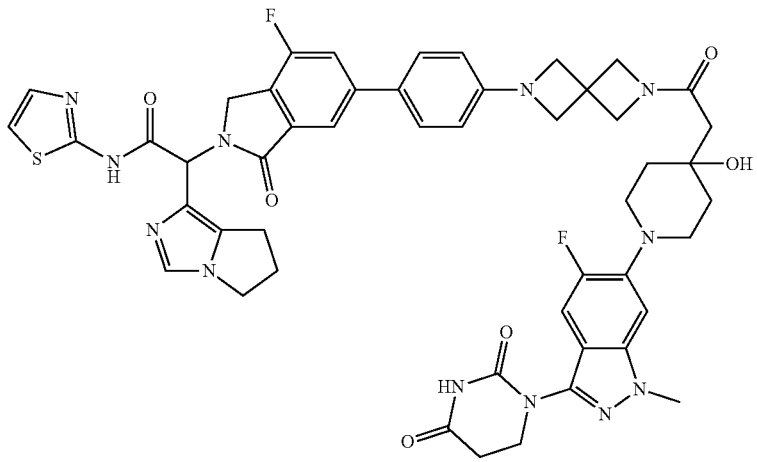 [SMILES: Cn1nc(N2CCC(=O)NC2=O)c2cc(F)c(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)cc21]<br>2-(6,7-dihydro-5H-pyrrolo[1,2-c]imidazol-1-yl)-2-[6-[4-[2-[2-[1-[3-(2,4-dioxohexahydropyrimidin-1-yl)-5-fluoro-1-methyl-indazol-6-yl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 128 | 2-[6-[4-[2-[2-[1-[2-chloro-4-[[2,6-dioxo-3-piperidyl]amino]phenyl]-4-hydroxy-4-piperidyl]acetyl]-2,7-diazaspiro[3.5]nonan-7-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, isomer 1 | | | *** |
| 129 | 2-(6,7-dihydro-5H-pyrrolo[1,2-c]imidazol-1-yl)-2-[6-[4-[2-[2-[4-[3-(2,4-dioxohexahydropyrimidin-1-yl)-5-fluoro-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1 | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 130 | Isomer 2<br>2-(6,7-dihydro-5H-pyrrolo[1,2-c]imidazol-1-yl)-2-[6-[4-[2-[2-[4-[3-(2,4-dioxohexahydropyrimidin-1-yl)-5-fluoro-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, isomer 2 | | | *** |
| 131 | 2-[6-[4-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 132 | 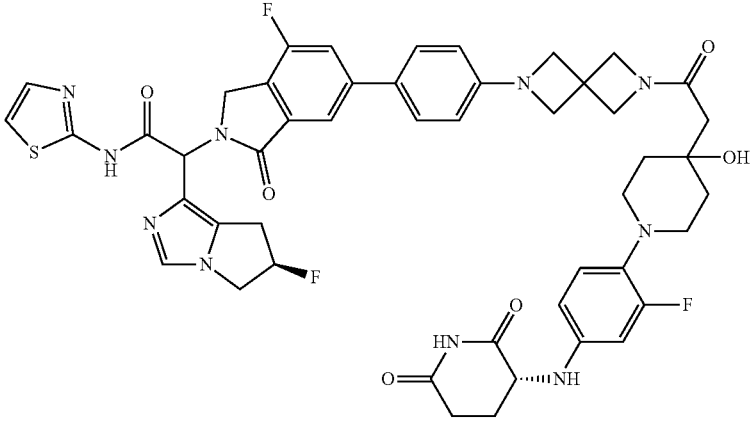 [SMILES: O=C1CC[C@@H](Nc2ccc(N3CCC(O)(CC(=O)N4CC5(C4)CN(c4ccc(-c6cc(F)c7c(c6)C(=O)N(C(C(=O)Nc6nccs6)c6ncn8c6C[C@@H](F)C8)C7)cc4)C5)CC3)c(F)c2)C(=O)N1] 2-[6-[4-[2-[2-[1-[4-[[(3R)-2,6-dioxo-3-piperidyl]amino]-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide | | | *** |
| 133 | 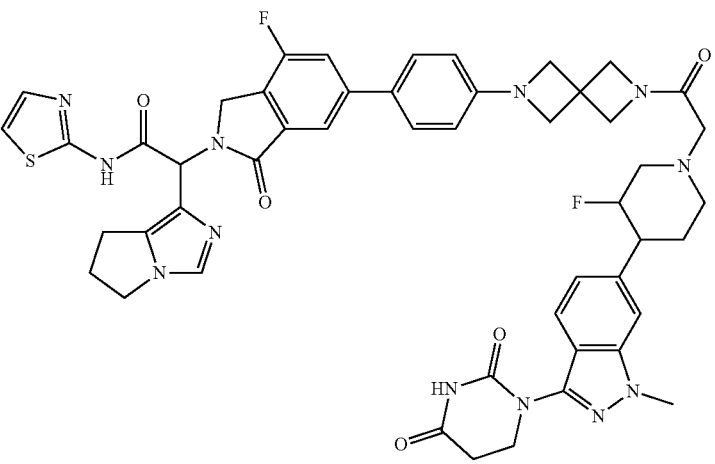 [SMILES: Cn1nc(N2CCC(=O)NC2=O)c2ccc(C3CCN(CC(=O)N4CC5(C4)CN(c4ccc(-c6cc(F)c7c(c6)C(=O)N(C(C(=O)Nc6nccs6)c6ncn8c6CCC8)C7)cc4)C5)CC3F)cc21] 2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3-fluoro-1-piperidyl]acetyl]-2,6-diazaspiro[3.3]heptan-6-yl]phenyl]-4-fluoro-1-oxo-isoindolin-2-yl]-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 134 | 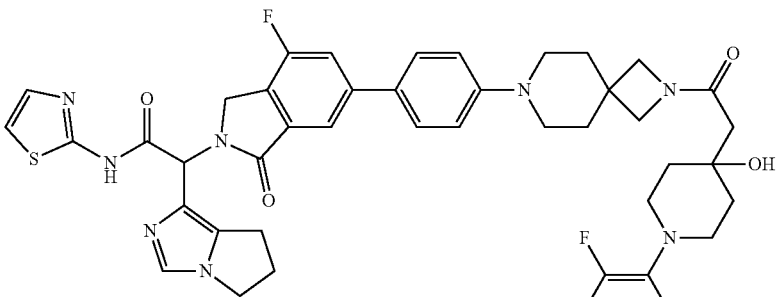<br>Isomer 1<br>2-(6,7-dihydro-5H-pyrrolo[1,2-c]imidazol-1-yl)-2-[6-[4-[2-[2-[1-[4-[[2,6-dioxo-3-piperidyl]amino]-2,6-difluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide, isomer 1 | | | *** |
| 135 | 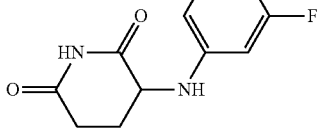<br>2-(6,7-dihydro-5H-pyrrolo[1,2-c]imidazol-1-yl)-2-[6-[4-[2-[2-[1-[4-[(2,6-dioxo-3-piperidyl)amino]-2,5-difluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 136 | 2-[4-chloro-6-[4-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]phenyl]-1-oxo-isoindolin-2-yl]-2-(6,7-dihydro-5H-pyrrolo[1,2-c]imidazol-1-yl)-N-thiazol-2-yl-acetamide | | | *** |
| 137 | 2-(6,7-dihydro-5H-pyrrolo[1,2-c]imidazol-1-yl)-2-[6-[4-[7-[2-[1-[4-[[2,6-dioxo-3-piperidyl]amino]-2,6-difluoro-phenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide, isomer 1 | | | ** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 138 | 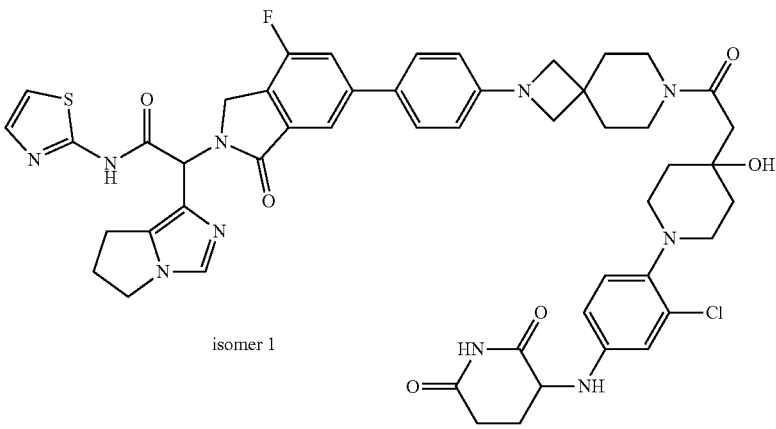 [SMILES: O=C1CCC(Nc2ccc(N3CCC(O)(CC(=O)N4CCC5(CC4)CN(c4ccc(-c6cc(F)c7c(c6)C(=O)N(C(C(=O)Nc6nccs6)c6ncn8c6CCC8)C7)cc4)C5)CC3)c(Cl)c2)C(=O)N1]<br>isomer 1<br><br>2-[6-[4-[7-[2-[1-[2-chloro-4-[[2,6-dioxo-3-piperidyl]amino]phenyl]-4-hydroxy-4-piperidyl]acetyl]-2,7-diazaspiro[3.5]nonan-2-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, isomer 1 | | | *** |
| 139 | 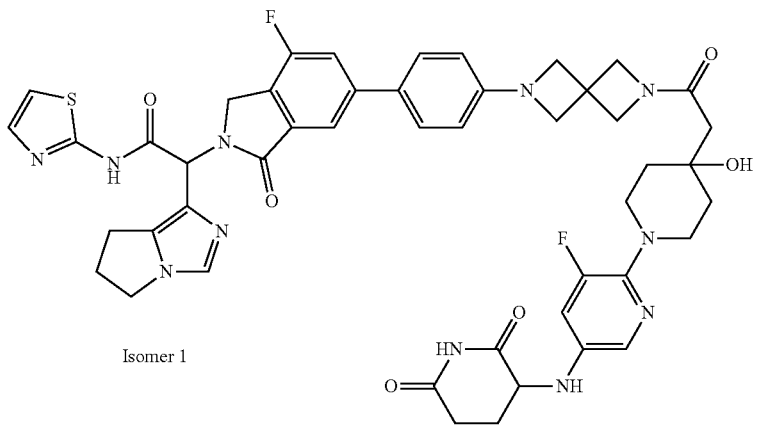 [SMILES: O=C1CCC(Nc2cnc(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1]<br>Isomer 1<br><br>2-(6,7-dihydro-5H-pyrrolo[1,2-c]imidazol-1-yl)-2-[6-[4-[2-[2-[1-[5-[[2,6-dioxo-3-piperidyl]amino]-3-fluoro-2-pyridyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1 | | | *** |

| Ex | Compound | H1975 EGFR DC50 [nM] | H3255 EGFR DC50 [nM] | H1975 C797S clone EGFR DC50 [nM] |
|---|---|---|---|---|
| 140 | 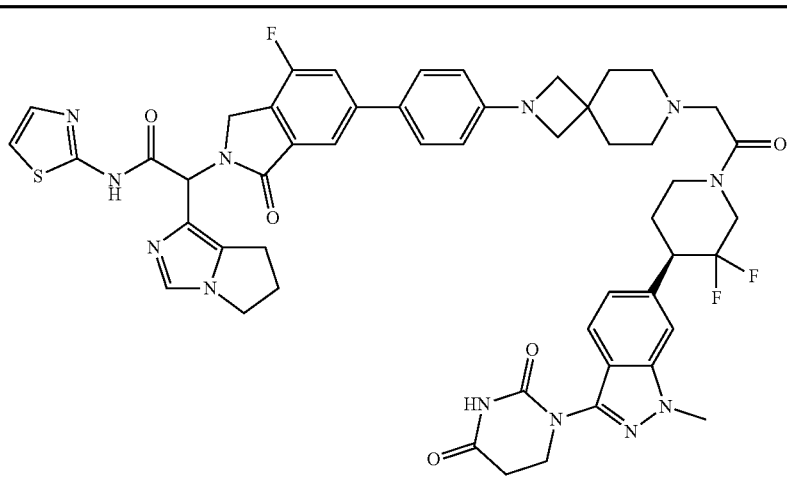 2-(6,7-dihydro-5H-pyrrolo[1,2-c]imidazol-1-yl)-2-[6-[4-[7-[2-[(4R)-4-[3-(2,4-dioxohexahydropyrimidin-1-yl)-1-methyl-indazol-6-yl]-3,3-difluoro-1-piperidyl]-2-oxo-ethyl]-2,7-diazaspiro[3.5]nonan-2-yl]phenyl]-4-fluoro-1-oxo-isoindolin-2-yl]-N-thiazol-2-yl-acetamide | | | *** |
| 141 | 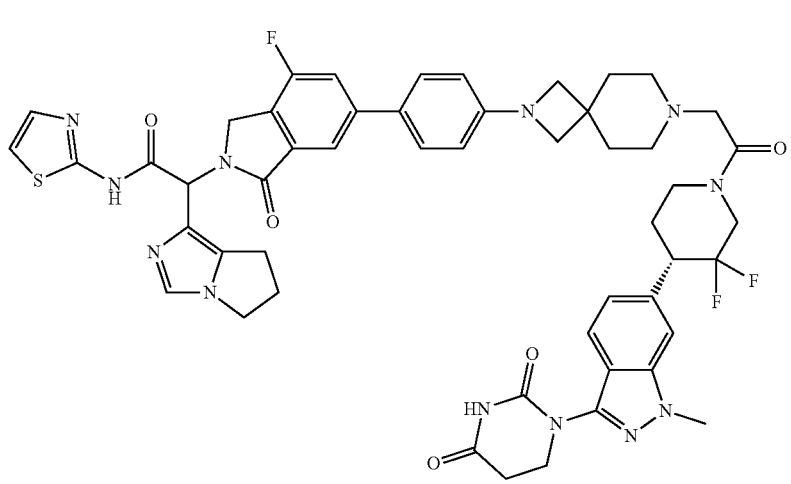 [SMILES: Cn1nc(N2CCC(=O)NC2=O)c2ccc([C@@H]3CCN(C(=O)CN4CCC5(CC4)CN(c4ccc(-c6cc(F)c7c(c6)C(=O)N(C(C(=O)Nc6nccs6)c6ncn8c6CCC8)C7)cc4)C5)CC3(F)F)cc21] 2-(6,7-dihydro-5H-pyrrolo[1,2-c]imidazol-1-yl)-2-[6-[4-[7-[2-[(4S)-4-[3-(2,4-dioxohexahydropyrimidin-1-yl)-1-methyl-indazol-6-yl]-3,3-difluoro-1-piperidyl]-2-oxo-ethyl]-2,7-diazaspiro[3.5]nonan-2-yl]phenyl]-4-fluoro-1-oxo-isoindolin-2-yl]-N-thiazol-2-yl-acetamide | | | ** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 142 | 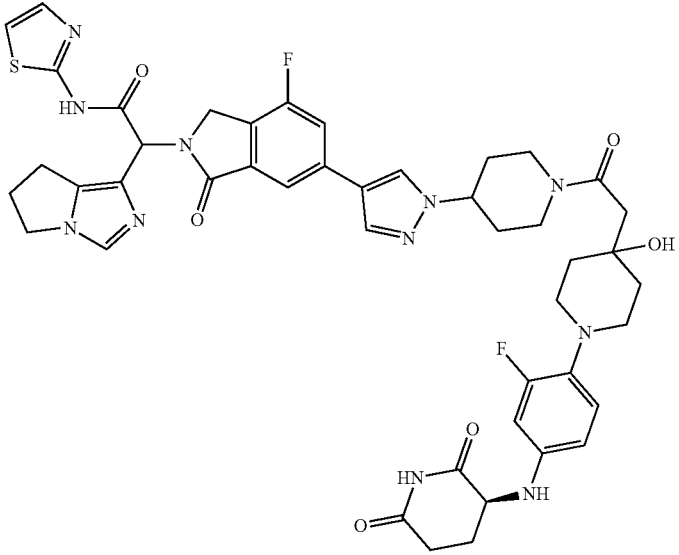 [SMILES: O=C1CC[C@H](Nc2ccc(N3CCC(O)(CC(=O)N4CCC(n5cc(-c6cc(F)c7c(c6)C(=O)N(C(C(=O)Nc6nccs6)c6ncn8c6CCC8)C7)cn5)CC4)CC3)c(F)c2)C(=O)N1] | | | *** |

2-(6,7-dihydro-5H-pyrrolo[1,2-c]imidazol-1-yl)-2-[6-[1-
[1-[2-[1-[4-[[(3S)-2,6-dioxo-3-piperidyl]amino]-2-fluoro-
phenyl]-4-hydroxy-4-piperidyl]acetyl]-4-
piperidyl]pyrazol-4-yl]-4-fluoro-1-oxo-isoindolin-2-yl]-
N-thiazol-2-yl-acetamide

| 143 | 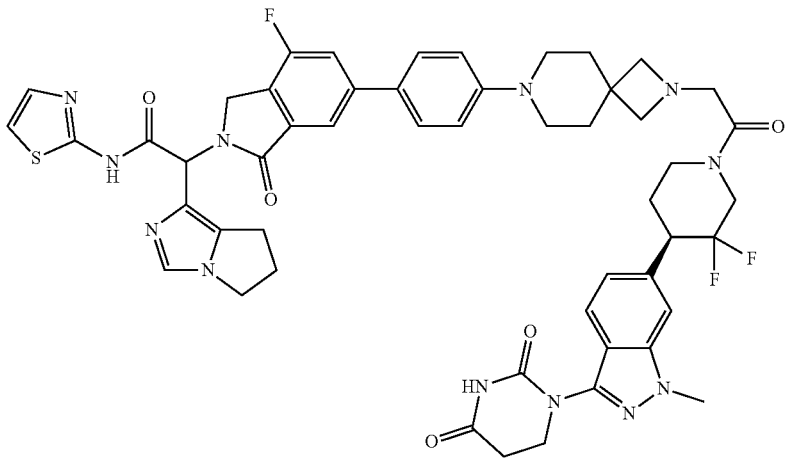 [SMILES: Cn1nc(N2CCC(=O)NC2=O)c2ccc([C@H]3CCN(C(=O)CN4CC5(CCN(c6ccc(-c7cc(F)c8c(c7)C(=O)N(C(C(=O)Nc7nccs7)c7ncn9c7CCC9)C8)cc6)CC5)C4)CC3(F)F)cc21] | | | ** |

2-(6,7-dihydro-5H-pyrrolo[1,2-c]imidazol-1-yl)-2-[6-[4-
[2-[2-[(4R)-4-[3-(2,4-dioxohexahydropyrimidin-1-yl)-1-
methyl-indazol-6-yl]-3,3-difluoro-1-piperidyl]-2-oxo-
ethyl]-2,7-diazaspiro[3.5]nonan-7-yl]phenyl]-4-fluoro-1-
oxo-isoindolin-2-yl]-N-thiazol-2-yl-acetamide TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 144 | 2-(6,7-dihydro-5H-pyrrolo[1,2-c]imidazol-1-yl)-2-[6-[4-[2-[2-[(4S)-4-[3-(2,4-dioxohexahydropyrimidin-1-yl)-1-methyl-indazol-6-yl]-3,3-difluoro-1-piperidyl]-2-oxo-ethyl]-2,7-diazaspiro[3.5]nonan-7-yl]phenyl]-4-fluoro-1-oxo-isoindolin-2-yl]-N-thiazol-2-yl-acetamide | | | *** |
| 145 | 2-[6-[4-[2-[2-[1-[2-chloro-4-[[2,6-dioxo-3-piperidyl]amino]-6-fluoro-phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, isomer 1 | | | ** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 146 | 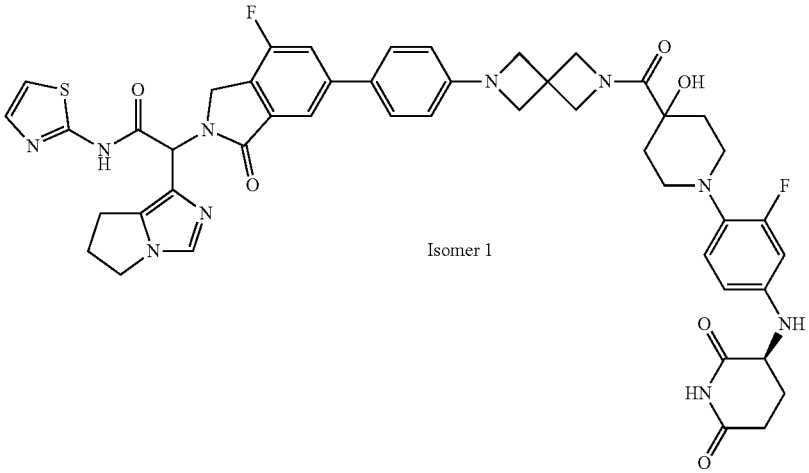 [SMILES: O=C1CC[C@H](Nc2ccc(N3CCC(O)(C(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1]  Isomer 1  2-(6,7-dihydro-5H-pyrrolo[1,2-c]imidazol-1-yl)-2-[6-[4-[2-[1-[4-[[2,6-dioxo-3-piperidyl]amino]-2-fluoro-phenyl]-4-hydroxy-piperidine-4-carbonyl]-2,6-diazaspiro[3.3]heptan-6-yl]phenyl]-4-fluoro-1-oxo-isoindolin-2-yl]-N-thiazol-2-yl-acetamide, isomer 1 | | | *** |
| 147 | 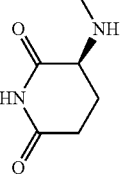  2-(6,7-dihydro-5H-pyrrolo[1,2-c]imidazol-1-yl)-2-[6-[4-[2-[2-[1-[4-(2,4-dioxohexahydropyrimidin-1-yl)-2-fluoro-phenyl]-4-hydroxy-4-piperidyl]acetyl]-2,6-diazaspiro[3.3]heptan-6-yl]phenyl]-4-fluoro-indazol-2-yl]-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 148 | 2-(6,7-dihydro-5H-pyrrolo[1,2-c]imidazol-1-yl)-2-[6-[4-[2-[2-[(2s,6r)-1-[4-[(2,6-dioxo-3-piperidyl)amino]-2-fluoro-phenyl]-4-hydroxy-2,6-dimethyl-4-piperidyl]acetyl]-2,6-diazaspiro[3.3]heptan-6-yl]phenyl]-4-fluoro-indazol-2-yl]-N-thiazol-2-yl-acetamide | | | *** |
| 149 | 2-(6,7-dihydro-5H-pyrrolo[1,2-c]imidazol-1-yl)-2-[6-[4-[4-[2-[4-[[(3S)-2,6-dioxo-3-piperidyl]amino]-2-fluoro-phenyl]-1-piperidyl]-2-oxo-ethyl]-4-hydroxy-1-piperidyl]phenyl]-7-fluoro-indazol-2-yl]-N-thiazol-2-yl-acetamide | | | *** |
| 150 | | | | *** |

| Ex | Compound | H1975 EGFR DC50 [nM] | H3255 EGFR DC50 [nM] | H1975 C797S clone EGFR DC50 [nM] |
|---|---|---|---|---|
| | 2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]-2-oxo-ethyl]-4-hydroxy-1-piperidyl]-3-pyridyl]-4-fluoro-indazol-2-yl]-N-thiazol-2-yl-acetamide | | | |
| 151 | 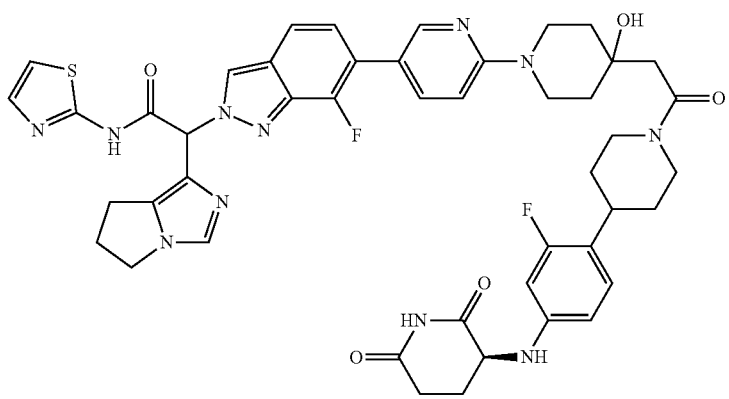 [SMILES: O=C1CC[C@H](Nc2ccc(C3CCN(C(=O)CC4(O)CCN(c5ccc(-c6ccc7cn(C(C(=O)Nc8nccs8)c8ncn9c8CCC9)nc7c6F)cn5)CC4)CC3)c(F)c2)C(=O)N1] | | | *** |
| | 2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]-2-oxo-ethyl]-4-hydroxy-1-piperidyl]-3-pyridyl]-7-fluoro-indazol-2-yl]-N-thiazol-2-yl-acetamide | | | |
| 152 | 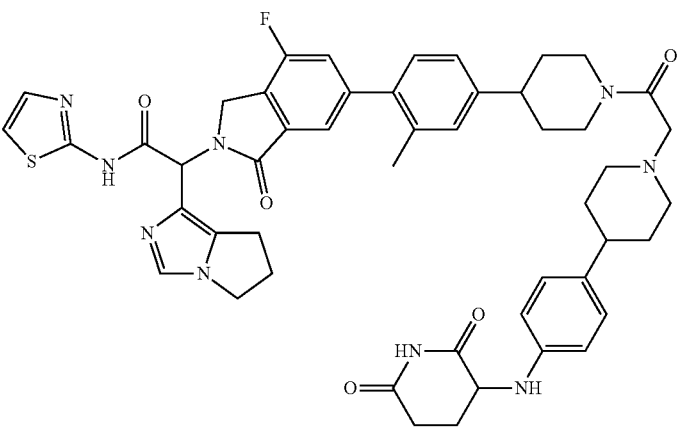 [SMILES: Cc1cc(C2CCN(C(=O)CN3CCC(c4ccc(NC5CCC(=O)NC5=O)cc4)CC3)CC2)ccc1-c1cc(F)c2c(c1)C(=O)N(C(C(=O)Nc1nccs1)c1ncn3c1CCC3)C2] | | | ** |
| | 2-(6,7-dihydro-5H-pyrrolo[1,2-c]imidazol-1-yl)-2-[6-[4-[1-[2-[4-[4-[(2,6-dioxo-3-piperidyl)amino]phenyl]-1-piperidyl]acetyl]-4-piperidyl]-2-methyl-phenyl]-4-fluoro-1-oxo-isoindolin-2-yl]-N-thiazol-2-yl-acetamide | | | |

| Ex | Compound | H1975 EGFR DC50 [nM] | H3255 EGFR DC50 [nM] | H1975 C797S clone EGFR DC50 [nM] |
|---|---|---|---|---|
| 153 | 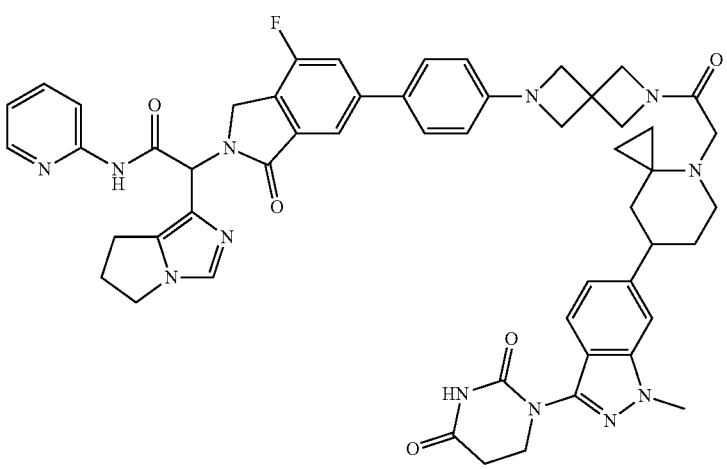 [SMILES: Cn1nc(N2CCC(=O)NC2=O)c2ccc(C3CCN(CC(=O)N4CC5(C4)CN(c4ccc(-c6cc(F)c7c(c6)C(=O)N(C(C(=O)Nc6ccccn6)c6ncn8c6CCC8)C7)cc4)C5)C4(CC4)C3)cc21]  2-(6,7-dihydro-5H-pyrrolo[1,2-c]imidazol-1-yl)-2-[6-[4-[2-[2-[7-[3-(2,4-dioxohexahydropyrimidin-1-yl)-1-methyl-indazol-6-yl]-4-azaspiro[2.5]octan-4-yl]acetyl]-2,6-diazaspiro[3.3]heptan-6-yl]phenyl]-4-fluoro-1-oxo-isoindolin-2-yl]-N-(2-pyridyl)acetamide | | | ** |
| 154 | 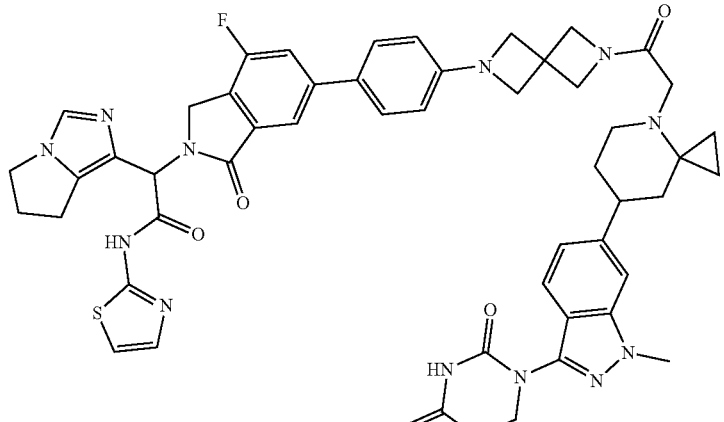  2-(6,7-dihydro-5H-pyrrolo[1,2-c]imidazol-1-yl)-2-[6-[4-[2-[2-[7-[3-(2,4-dioxohexahydropyrimidin-1-yl)-1-methyl-indazol-6-yl]-4-azaspiro[2.5]octan-4-yl]acetyl]-2,6-diazaspiro[3.3]heptan-6-yl]phenyl]-4-fluoro-1-oxo-isoindolin-2-yl]-N-thiazol-2-yl-acetamide | | * | * |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 155 | 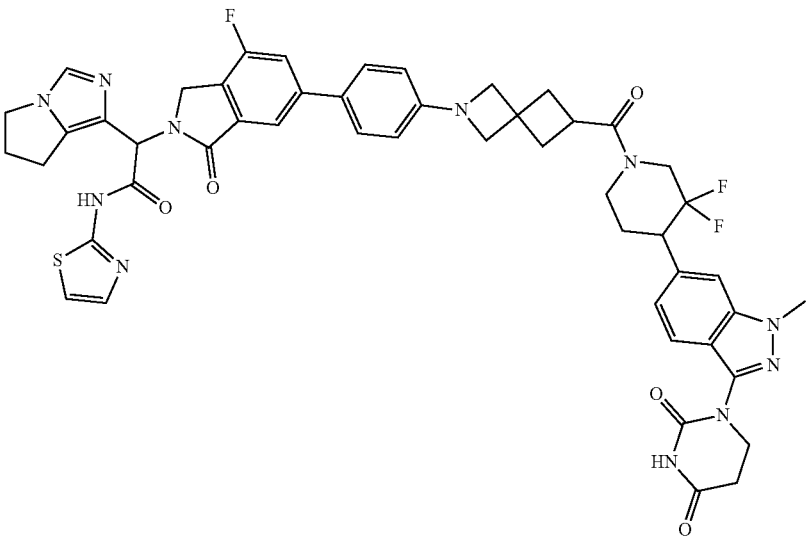 [SMILES: Cn1nc(N2CCC(=O)NC2=O)c2ccc(C3CCN(C(=O)C4CC5(C4)CN(c4ccc(-c6cc(F)c7c(c6)C(=O)N(C(C(=O)Nc6nccs6)c6ncn8c6CCC8)C7)cc4)C5)CC3(F)F)cc21] 2-(6,7-dihydro-5H-pyrrolo[1,2-c]imidazol-1-yl)-2-[6-[4-[6-[4-[3-(2,4-dioxohexahydropyrimidin-1-yl)-1-methyl-indazol-6-yl]-3,3-difluoro-piperidine-1-carbonyl]-2-azaspiro[3.3]heptan-2-yl]phenyl]-4-fluoro-1-oxo-isoindolin-2-yl]-N-thiazol-2-yl-acetamide | | | *** |
| 156 | 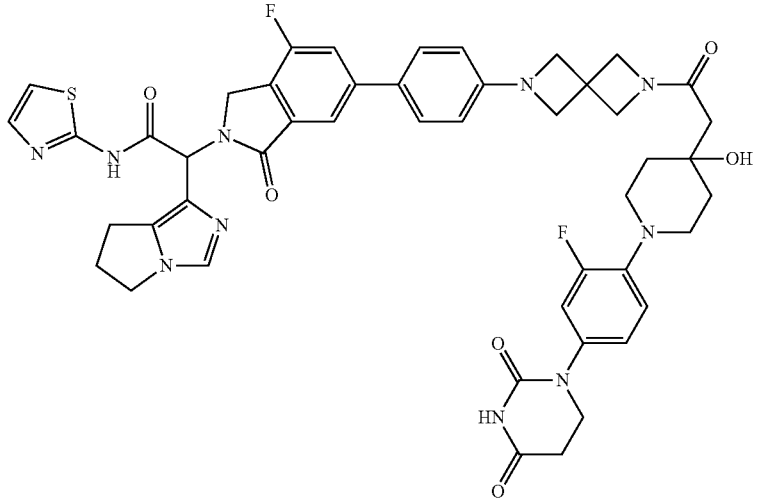 [SMILES: O=C1CCN(c2ccc(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1] 2-(6,7-dihydro-5H-pyrrolo[1,2-c]imidazol-1-yl)-2-[6-[4-[2-[2-[1-[4-(2,4-dioxohexahydropyrimidin-1-yl)-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide | | | ** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 157 | 2-(6,7-dihydro-5H-pyrrolo[1,2-c]imidazol-1-yl)-2-(6-(4-(6-(2-(1-(4-(2,6-dioxopiperidin-3-yl)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide | * | | |
| 158 | 2-[6-[4-[2-[2-[1-[2-chloro-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide | *** | | |

| | | H1975 EGFR DC50 [nM] | H3255 EGFR DC50 [nM] | H1975 C797S clone EGFR DC50 [nM] |
|---|---|---|---|---|
| Ex | Compound | | | |
| 159 | 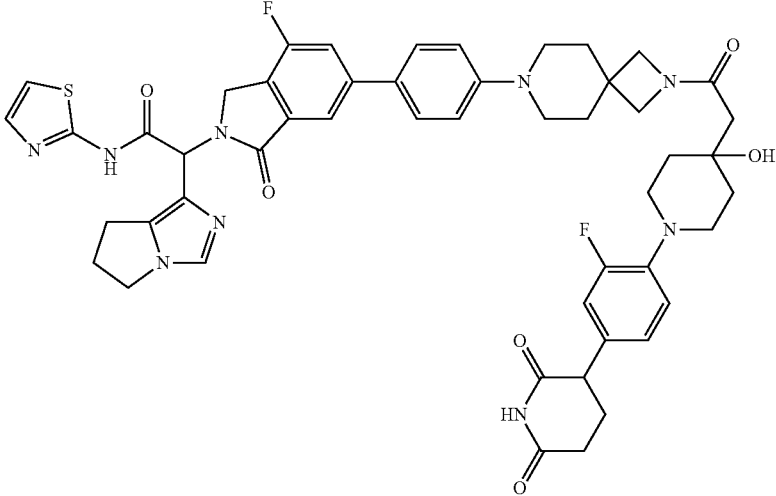 [SMILES: O=C1CCC(c2ccc(N3CCC(O)(CC(=O)N4CC5(CCN(c6ccc(-c7cc(F)c8c(c7)C(=O)N(C(C(=O)Nc7nccs7)c7ncn9c7CCC9)C8)cc6)CC5)C4)CC3)c(F)c2)C(=O)N1] | | | ** |

2-(6,7-dihydro-5H-pyrrolo[1,2-c]imidazol-1-yl)-2-[6-[4-[2-[2-[1-[4-(2,6-dioxo-3-piperidyl)-2-fluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide

| 160 | 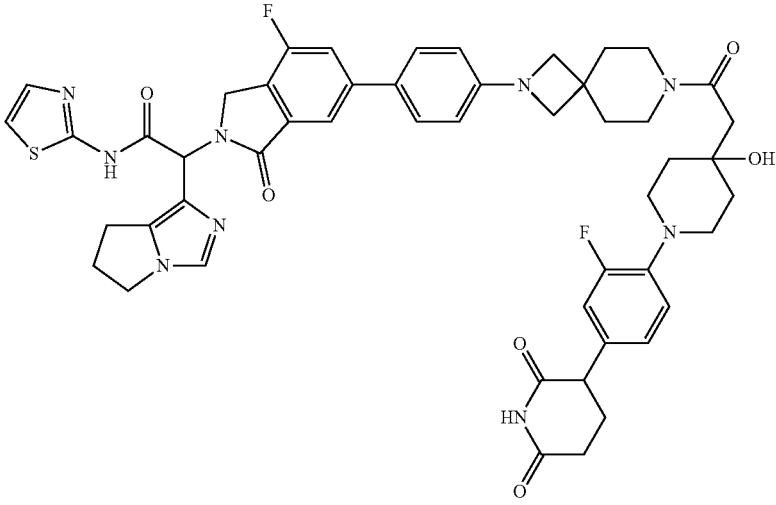 [SMILES: O=C1CCC(c2ccc(N3CCC(O)(CC(=O)N4CCC5(CC4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1] | | | ** |

2-(6,7-dihydro-5H-pyrrolo[1,2-c]imidazol-1-yl)-2-[6-[4-[7-[2-[1-[4-(2,6-dioxo-3-piperidyl)-2-fluoro-phenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 161 | 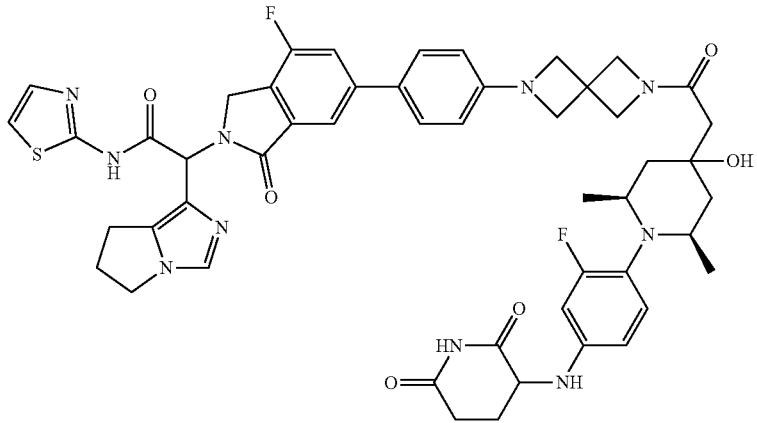 [SMILES: C[C@@H]1CC(O)(CC(=O)N2CC3(C2)CN(c2ccc(-c4cc(F)c5c(c4)C(=O)N(C(C(=O)Nc4nccs4)c4ncn6c4CCC6)C5)cc2)C3)C[C@H](C)N1c1ccc(NC2CCC(=O)NC2=O)cc1F] 2-(6,7-dihydro-5H-pyrrolo[1,2-c]imidazol-1-yl)-2-[6-[4-[2-[2-[((2s,6r)-1-[4-[(2,6-dioxo-3-piperidyl)amino]-2-fluoro-phenyl]-4-hydroxy-2,6-dimethyl-4-piperidyl]acetyl]-2,6-diazaspiro[3.3]heptan-6-yl]phenyl]-4-fluoro-1-oxo-isoindolin-2-yl]-N-thiazol-2-yl-acetamide | | | *** |
| 162 | 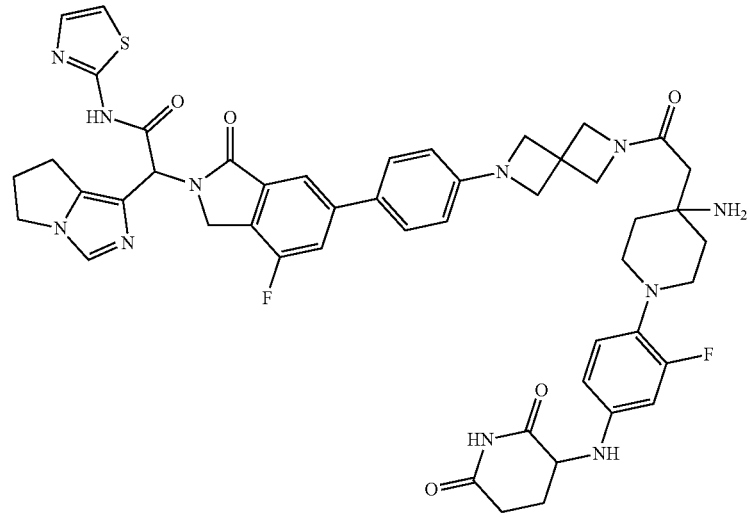 [SMILES: NC1(CC(=O)N2CC3(C2)CN(c2ccc(-c4cc(F)c5c(c4)C(=O)N(C(C(=O)Nc4nccs4)c4ncn6c4CCC6)C5)cc2)C3)CCN(c2ccc(NC3CCC(=O)NC3=O)cc2F)CC1] 2-[6-[4-[2-[2-[4-amino-1-[4-[(2,6-dioxo-3-piperidyl)amino]-2-fluoro-phenyl]-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 163 | 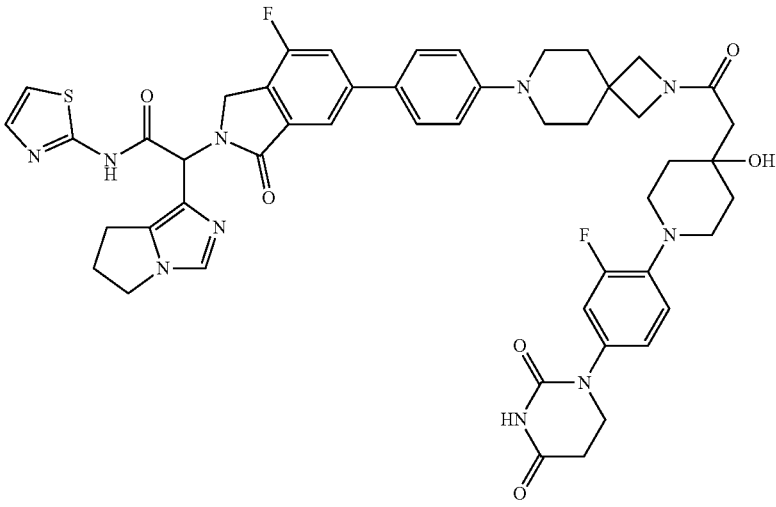2-(6,7-dihydro-5H-pyrrolo[1,2-c]imidazol-1-yl)-2-[6-[4-[2-[2-[1-[4-(2,4-dioxohexahydropyrimidin-1-yl)-2-fluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide | | | *** |
| 164 | 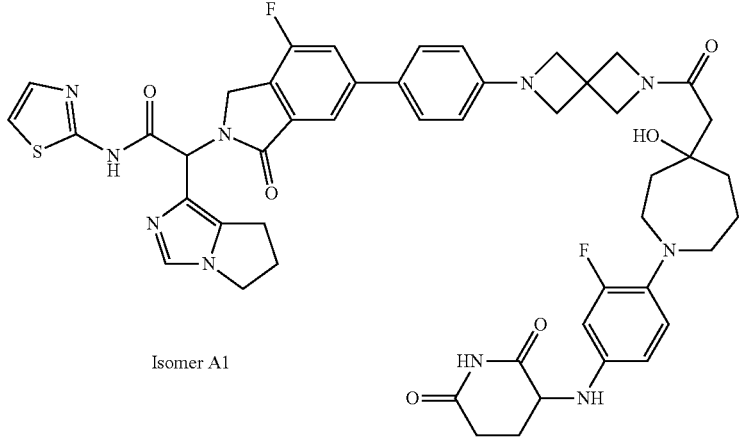 [SMILES: O=C1CCC(Nc2ccc(N3CCCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1]Isomer A1<br>2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, isomer A1 | | | ** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 165 | 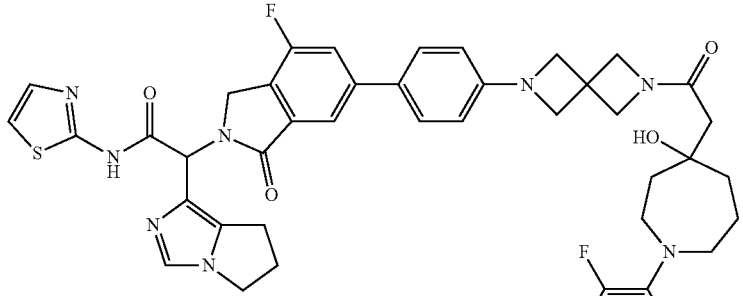<br>Isomer A2<br><br>2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, isomer A2 | | | *** |
| 166 | 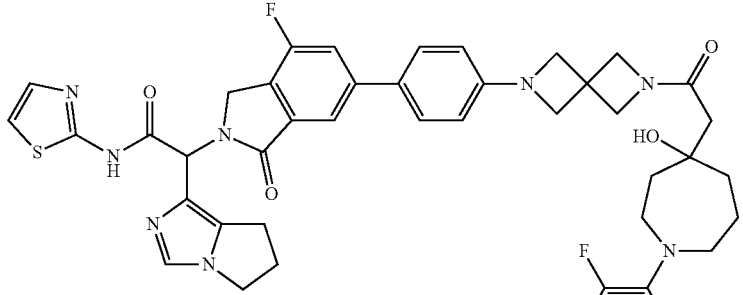<br>Isomer B1<br><br>2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, isomer B1 | | | ** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 167 | 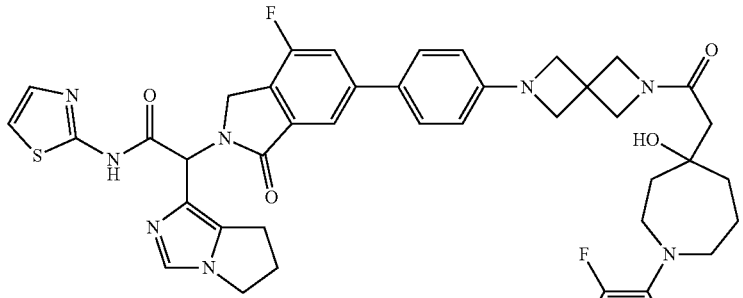<br>Isomer B2<br><br>2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, isomer B2 | | | ** |
| 168 | 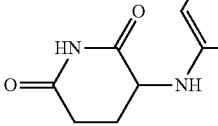<br><br>2-(6,7-dihydro-5H-pyrrolo[1,2-c]imidazol-1-yl)-2-[6-[4-[2-[2-[1-[4-(2,4-dioxohexahydropyrimidin-1-yl)-2-(trifluoromethyl)phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide | | | ** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 169 | 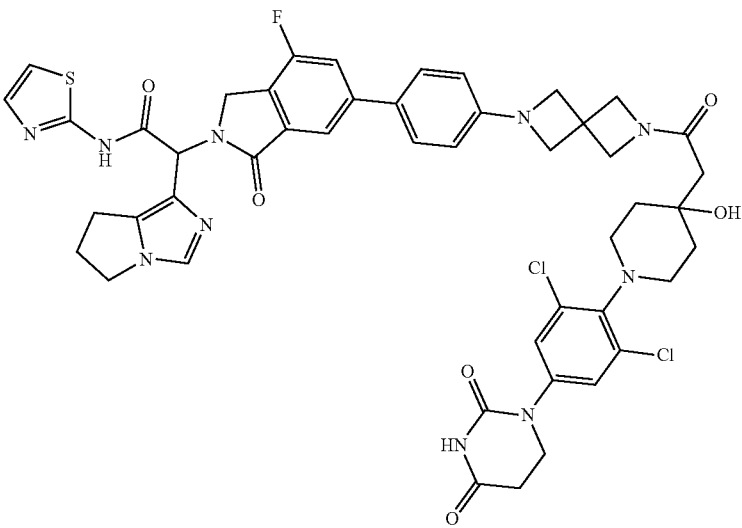 [SMILES: O=C1CCN(c2cc(Cl)c(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(Cl)c2)C(=O)N1] 2-[6-[4-[2-[2-[1-[2,6-dichloro-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide | | | *** |
| 170 | 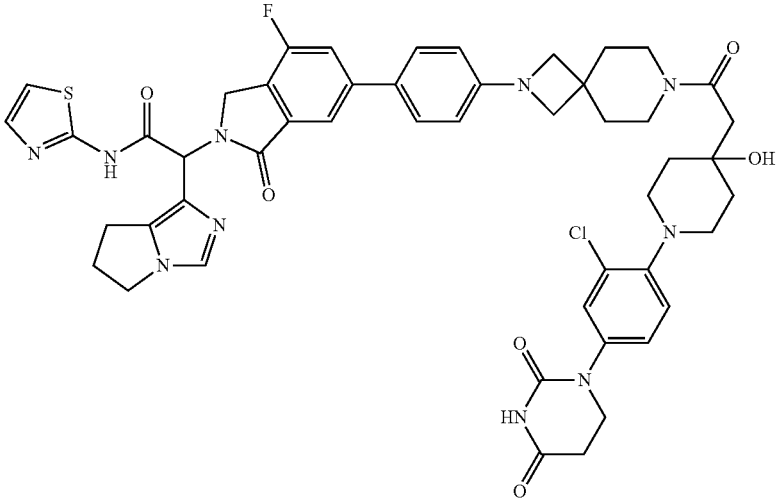 [SMILES: O=C1CCN(c2ccc(N3CCC(O)(CC(=O)N4CCC5(CC4)CN(c4ccc(-c6cc(F)c7c(c6)C(=O)N(C(C(=O)Nc6nccs6)c6ncn8c6CCC8)C7)cc4)C5)CC3)c(Cl)c2)C(=O)N1] 2-[6-[4-[7-[2-[1-[2-chloro-4-(2,4-dioxohexahydropyrimidin-1-yl)phenyl]-4-hydroxy-4-piperidyl]acetyl]-2,7-diazaspiro[3.5]nonan-2-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 171 | 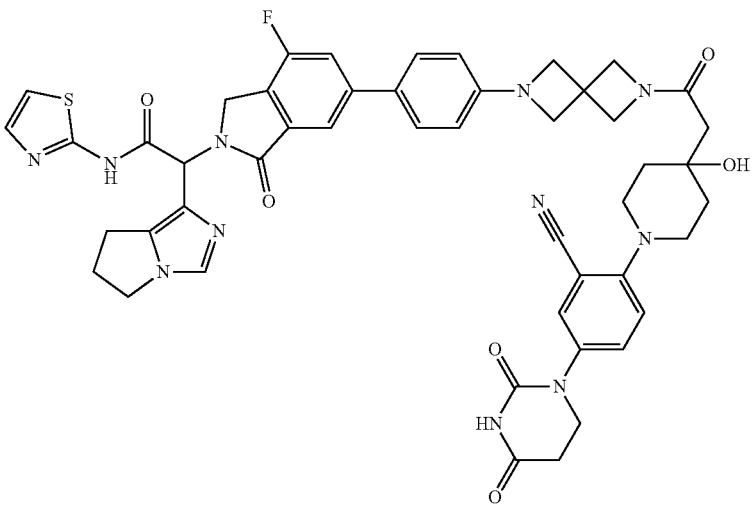 [SMILES: N#Cc1cc(N2CCC(=O)NC2=O)ccc1N1CCC(O)(CC(=O)N2CC3(C2)CN(c2ccc(-c4cc(F)c5c(c4)C(=O)N(C(C(=O)Nc4nccs4)c4ncn6c4CCC6)C5)cc2)C3)CC1] 2-[6-[4-[2-[2-[1-[2-cyano-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide | | | * |
| 172 | 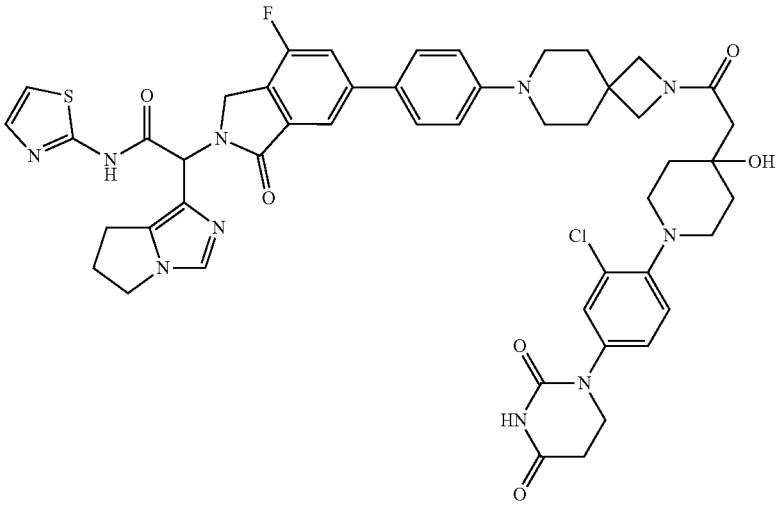 [SMILES: O=C1CCN(c2ccc(N3CCC(O)(CC(=O)N4CC5(CCN(c6ccc(-c7cc(F)c8c(c7)C(=O)N(C(C(=O)Nc7nccs7)c7ncn9c7CCC9)C8)cc6)CC5)C4)CC3)c(Cl)c2)C(=O)N1] 2-[6-[4-[2-[2-[1-[2-chloro-4-(2,4-dioxohexahydropyrimidin-1-yl)phenyl]-4-hydroxy-4-piperidyl]acetyl]-2,7-diazaspiro[3.5]nonan-7-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide | | | *** |

TABLE 2-continued

| Ex | Compound | H1975 EGFR DC50 [nM] | H3255 EGFR DC50 [nM] | H1975 C797S clone EGFR DC50 [nM] |
|---|---|---|---|---|
| 173 | 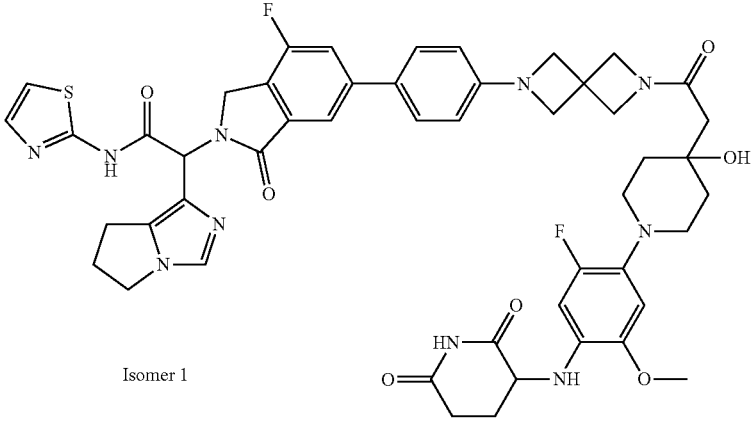 [SMILES: COc1cc(N2CCC(O)(CC(=O)N3CC4(C3)CN(c3ccc(-c5cc(F)c6c(c5)C(=O)N(C(C(=O)Nc5nccs5)c5ncn7c5CCC7)C6)cc3)C4)CC2)c(F)cc1NC1CCC(=O)NC1=O]<br>Isomer 1<br>2-(6,7-dihydro-5H-pyrrolo[1,2-c]imidazol-1-yl)-2-[6-[4-[2-[2-[1-[4-[[2,6-dioxo-3-piperidyl]amino]-2-fluoro-5-methoxy-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1 | | | *** |
| 174 | 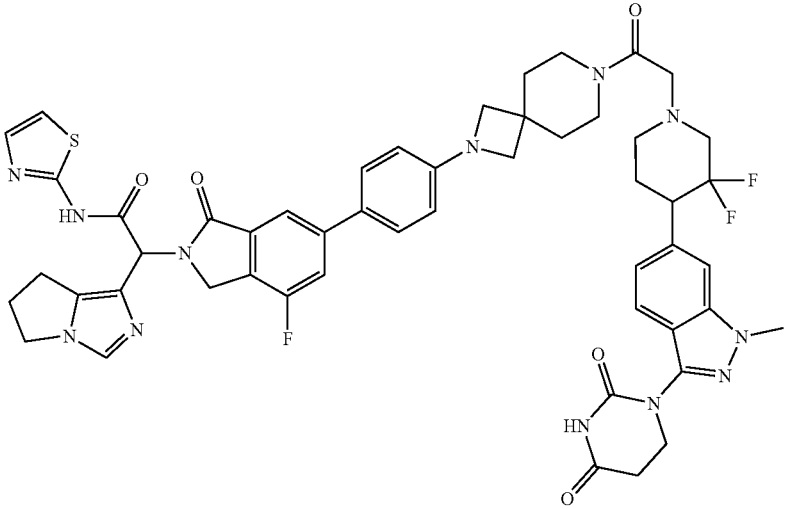 [SMILES: Cn1nc(N2CCC(=O)NC2=O)c2ccc(C3CCN(CC(=O)N4CCC5(CC4)CN(c4ccc(-c6cc(F)c7c(c6)C(=O)N(C(C(=O)Nc6nccs6)c6ncn8c6CCC8)C7)cc4)C5)CC3(F)F)cc21]<br>2-(6,7-dihydro-5H-pyrrolo[1,2-c]imidazol-1-yl)-2-(6-(4-(7-(2-(4-(3-(2,4-dioxotetrahydropyrimidin-1(2H)-yl)-1-methyl-1H-indazol-6-yl)-3,3-difluoropiperidin-1-yl)acetyl)-2,7-diazaspiro[3.5]nonan-2-yl)phenyl)-4-fluoro-1-oxoisoindolin-2-yl)-N-(thiazol-2-yl)acetamide | | | *** |

In the table above * is <50 nM;  is 50-150 nM; and * is >150 nM.

IX. Synthetic Methods

The compounds of Formula I, II, III, or IV may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The preparation of compounds of Formula I is further described in more detail in the scheme below.

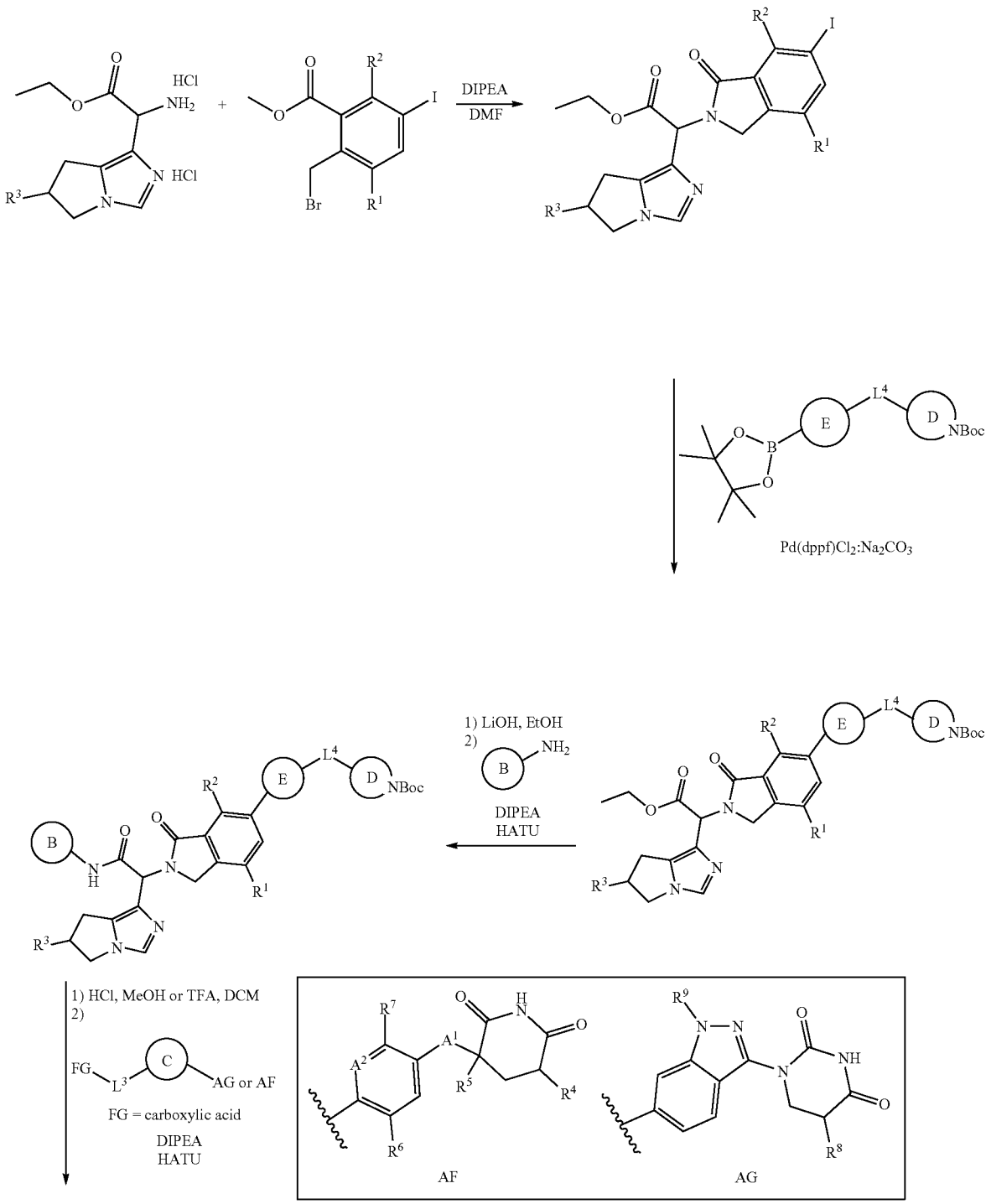

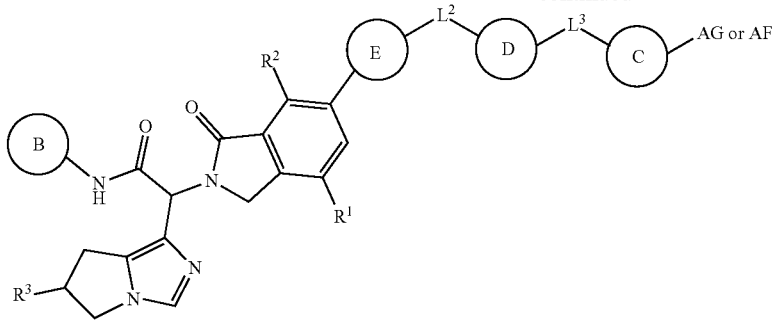
Generally speaking, the sequence of steps used to synthesize the compounds of Formula I can also be modified in certain cases.
The preparation of compounds of Formula II is further described in more detail in the scheme below.
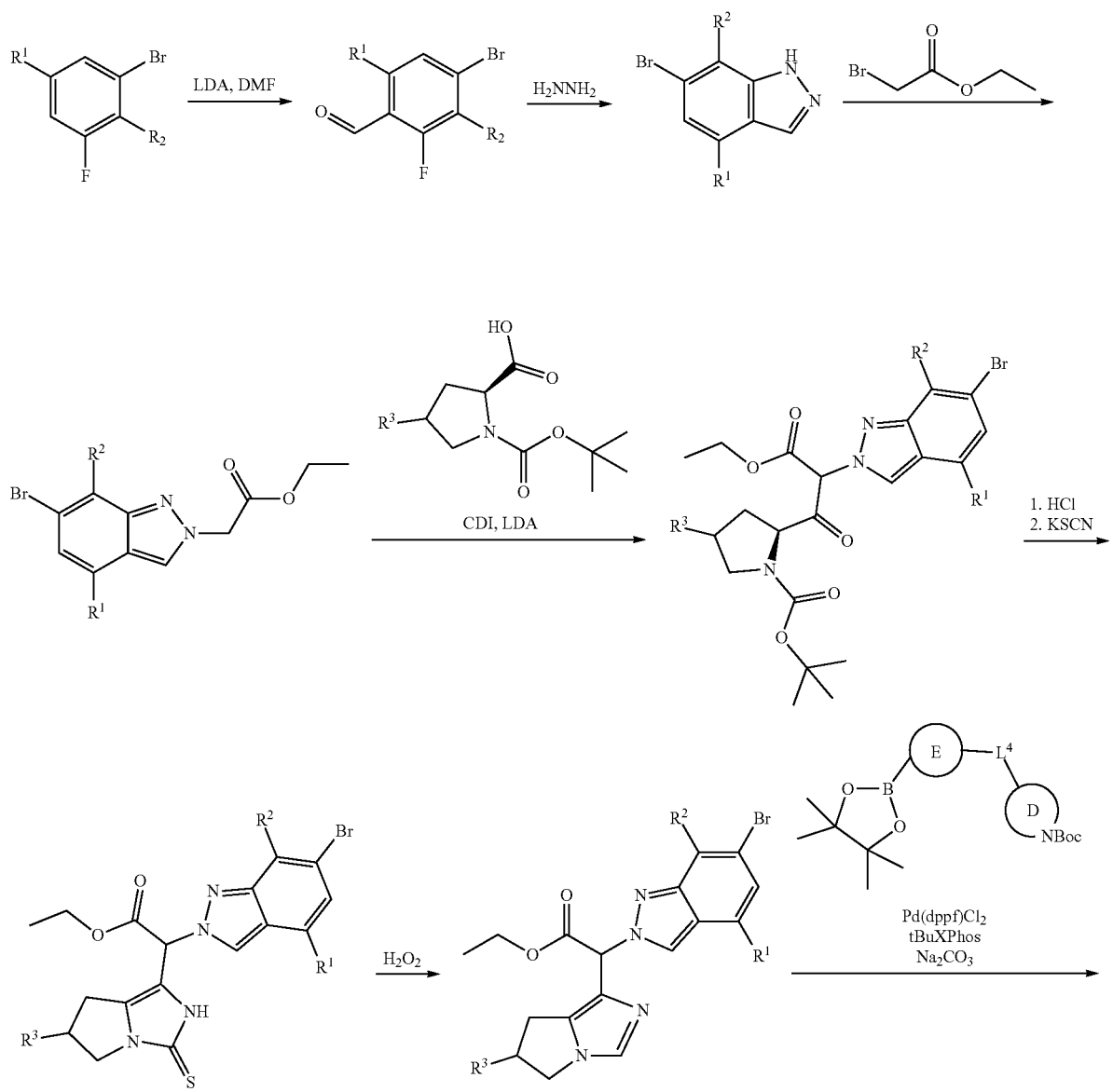

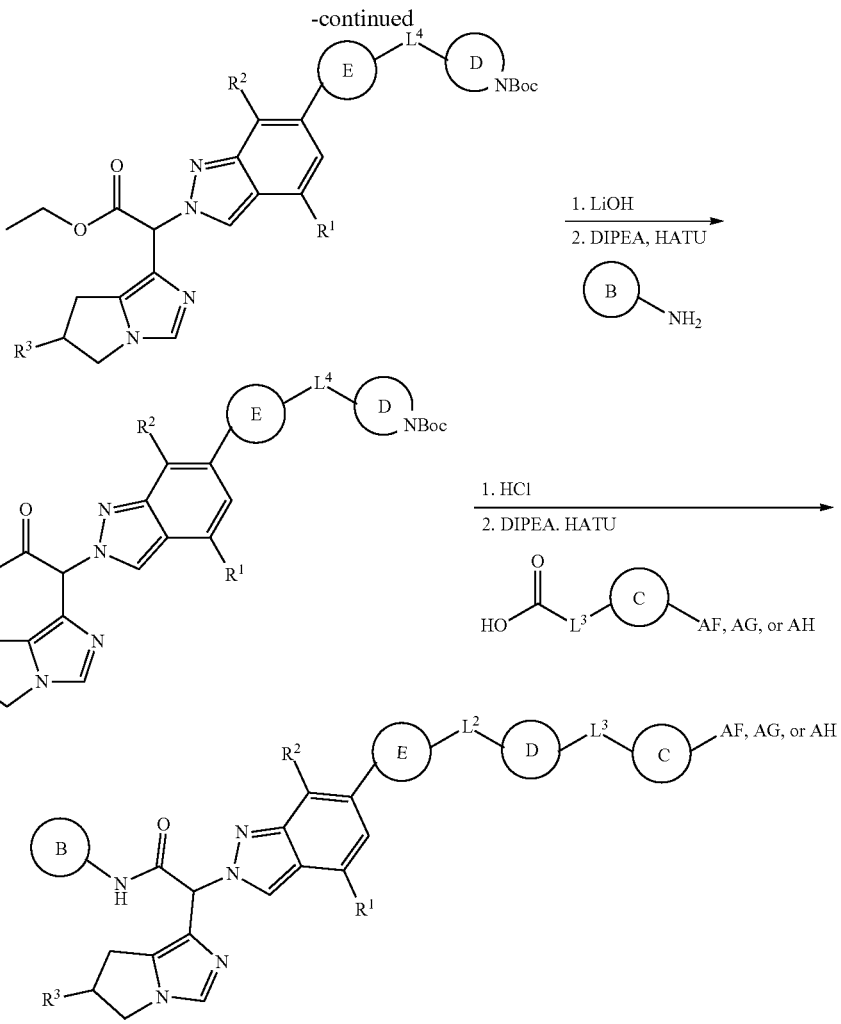
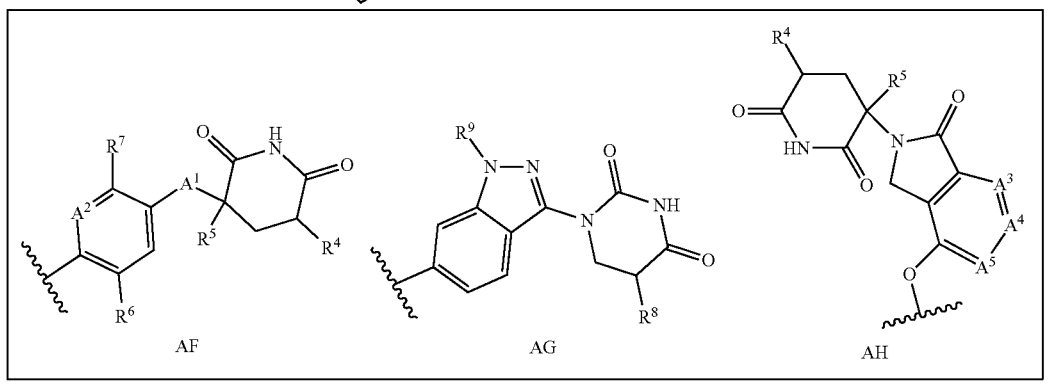

Generally speaking, the sequence of steps used to synthesize the compounds of Formula I can also be modified in certain cases. In certain cases the sequences of steps shown for Formula I or Formula II can be applied or modified for the synthesis of a compound of Formula III and Formula IV.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of Formula I, II, III, or IV can be separated using chiral HPLC. Racemic mixtures of chiral synthetic intermediates may also be separated using chiral HPLC.

Salts of Compounds of Formula I, II, III, or IV

In cases where the compounds of Formula I, II, III, or IV are basic they may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. A specific salt is the fumarate. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Insofar as their preparation is not described in the examples, the compounds of Formula I, II, III, or IV as well as all intermediate products can be prepared according to analogous methods or according to the methods set forth herein. Starting materials are commercially available, known in the art or can be prepared by methods known in the art or in analogy thereto.

It will be appreciated that the compounds of general Formula I, II, III, or IV in this invention may be derivatised at functional groups to provide derivatives which are capable of conversion back to the parent compound in vivo.

X. Experimental Procedures

Abbreviations

| | |
|---|---|
| ABPR | Automated back pressure regulator |
| AcCl | Acetyl Chloride |
| ACN | Acetonitrile |
| AIBN | Azobisisobutyronitrile |
| $AlCl_3$ | Aluminum trichloride |
| $Ag_2CO_3$ | Silver carbonate |
| Aq. | aqueous |
| AcOH | Acetic acid |
| $BBr_3$ | tribromoborane |
| $B_2pin_2$ | Bis(pinacolato)diboron |
| BINAP | 2,2'-bis(diphenylphosphino)-1,1'-binaphthyl |
| BnBr | Benzyl bromide |
| $Boc_2O$ | Di-tert-butyl dicarbonate |
| $Br_2$ | Bromine gas |
| ClCOOEt | Ethyl chloroformate |
| CAN | Ceric ammonium nitrate |
| CDI | Carbonyldiimidazole |
| CuI | Cuprous iodide |
| $CCl_4$ | Carbon tetrachloride |
| $CoCl_2$ | Cobalt (II) chloride |
| CO | Carbon monoxide |
| $CO_2$ | Carbon dioxide |
| COMU | (1-Cyano-2-ethoxy-2-oxoethylidenaminooxy) dimethylamino-morpholino-carbenium hexafluorophosphate |
| Cu | copper |
| $CH_3CN$ | Acetonitrile |
| $CHCl_3$ | Chloroform; trichloromethane |
| $CH_2Cl_2$, DCM | Methylene chloride; dichloromethane |
| $Cs_2CO_3$ | Cesium carbonate |
| CsF | Cesium fluoride |
| DAST | Diethylaminosulfur trifluoride |
| DBU | 1,8-Diazabicyclo[5.4.0]undec-7-ene |
| DCE | Dichloroethane; ethylene chloride |
| DIAD | Diisopropyl azodicarboxylate |
| DIEA, DIPEA | N,N-diisopropylethylamine |
| DMA; DMAc | N,N-dimethylacetamide |
| DMAP | 4-Dimethylaminopyridine |

-continued

| | |
|---|---|
| DMF | N,N-dimethylformamide |
| DMSO | Dimethylsulfoxide |
| DPPP | 1,3-Bis(diphenylphosphino)propane |
| EDCI | 1-Ethyl-3-(3-dimethylaminopropyl)carbodiimide |
| $Et_3SiH$ | Triethylsilane |
| EtOAc; EA | Ethyl acetate |
| EtOH | Ethanol |
| $FeBr_3$ | Iron (III) bromide |
| HATU | 1-[Bis(dimethylamino)methylene]-1H-1,2,3-triazolo[4,5-b]pyridinium 3-oxide hexafluorophosphate |
| HCl | Hydrochloric acid |
| $HCOONH_4$ | Ammonium formate |
| $H_2$ | hydrogen gas |
| $H_2O$ | Water |
| $H_2O_2$ | Hydrogen peroxide |
| HCOOH | Formic acid |
| $H_3PO_2$ | Hypophosphorous acid |
| $H_2SO_4$ | Sulfuric acid |
| HOBt | hydroxybenzotriazole |
| $InCl_3$ | Indium(III) chloride |
| IPA | Isopropyl alcohol |
| $KHCO_3$ | Potassium bicarbonate |
| KOAc | Potassium acetate |
| KOH | Potassium hydroxide |
| $KO^tBu$ | Potassium tert-butoxide |
| $K_2CO_3$ | Potassium carbonate |
| $KHSO_4$ | Potassium bisulfate |
| KI | Potassium iodide |
| KOCN | Potassium cyanate |
| $KMnO_4$ | Potassium permanganate |
| $K_3PO_4$ | Tribasic potassium phosphate |
| KSCN | Potassium thiocyanate |
| Lac | Lactic acid |
| LCMS | Liquid chromatography-mass spectrometry |
| $LiAlH_4$ | Lithium aluminum hydride |
| LiHMDS | Lithium bis(trimethylsilyl)amide |
| LiOH | Lithium hydroxide |
| LDA | Lithium diisopropylamide |
| Me | Methyl |
| MeCN | acetonitrile |
| MeI | Methyl iodide |
| MeOH | Methanol |
| $MnO_2$ | Manganese dioxide |
| $MgCl_2$ | Magnesium chloride |
| $MgSO_4$ | Magnesium sulfate |
| MsCl | Methanesulfonylchloride |
| MTBE | Methyl tert-butyl ether |
| $NH_4OAc$ | Ammonium acetate |
| $N_2$ | Nitrogen gas |
| NaCN | Sodium cyanide |
| $NH_4Cl$ | Ammonium chloride |
| $NH_4OH$ | Ammonium hydroxide |
| $NH_2OH$ | Hydroxylamine |
| $NaBH(OAc)_3$ | Sodium triacetoxyborohydride |
| $NaBH_4$ | Sodium borohydride |
| $NaClO_2$ | Sodium chlorite |
| $Na_2SO_4$ | Sodium sulfate |
| NaSMe | Sodium methanethiolate |
| $Na_2S_2O_3$ | Sodium thiosulfate |
| NaH | Sodium hydride |
| NaOH | Sodium hydroxide |
| $NaHCO_3$ | Sodium bicarbonate |
| $Na_2CO_3$ | Sodium carbonate |
| $NaNO_2$ | Sodium nitrite |
| $NaO^iPr$ | Sodium isopropoxide |
| $NaH_2PO_4$ | Sodium dihydrogen phosphate |
| $NaIO_4$ | Sodium periodate |
| NBS | N-bromo succinimide |
| $NH_3$ | Ammonia |
| $N_2H_2$ | Diazene |
| $N_2H_4$ | Hydrazine |
| $NaNO_2$ | Sodium nitrite |
| NMP | N-Methyl-2-pyrrolidone |
| $OsO_4$ | Osmium tetroxide |
| $Pd(OAc)_2$ | Palladium(II) acetate |
| $Pd(PPh_3)_2Cl_2$ | Bis(triphenylphosphine)palladium(II) dichloride |
| $Pd(PPh_3)_4$ | Tetrakis(triphenylphosphine)palladium(0) |
| $Pd(dppf)Cl_2$ | [1,1'-Bis(diphenylphosphino)ferrocene]dichloropalladium(II) |

| | |
|---|---|
| Pd/C | Palladium on carbon |
| Pd$_2$(dba)$_3$ | Tris(dibenzylideneacetone)dipalladium(0) |
| PhMe | toluene |
| PhNTF$_2$ | Bis(trifluoromethanesulfonyl)aniline |
| PPh$_3$ | Triphenylphosphine |
| P(pMeOPh)$_3$ | Tris(4-methoxyphenyl)phosphine |
| PCy$_3$ | Tricyclohexylphosphine |
| PET ether | Petroleum ether |
| PMB | Para-methoxybenzyl |
| POBr$_3$ | Phosphoryl bromide; phosphorus oxybromide |
| POCl$_3$ | Phosphoryl chloride; phosphorus oxychloride |
| PivOH | Pivalic acid |
| PtBu$_3$ | tritertbutylphosphine |
| PtO$_2$ | Platinum oxide |
| PTSA | p-toluenesulfonic acid |
| Py, py | Pyridine |
| PyBOP | (Benzotriazol-1-yloxy)tripyrrolidinophosphonium hexafluorophosphate |
| RBF | Round-bottom flask |
| RP | Reverse phase |
| rpm | Revolutions per minute |
| RT, rt | Room temperature |
| RuPhos | 2-Dicyclohexylphosphino-2',6'-diisopropoxybiphenyl |
| SFC | Supercritical fluid chromatography |
| SOCl$_2$ | Thionyl chloride |
| T3P | 1-Propanephosphonic anhydride |
| TBAB | Tetrabutylammonium bromide |
| TEA | Triethylamine |
| $^t$BuBrettPhos | 2-(Di-tert-butylphosphino)-2',4',6'-triisopropyl-3,6-dimethoxy-1,1'-biphenyl |
| $^t$BuOH | Tert-butyl alcohol |
| $^t$BuONO | Tert-butyl nitrite |
| $^t$BuXPhos | 2-Di-tert-butylphosphino-2',4',6'-triisopropylbiphenyl |
| $^t$BuXPhos Pd G3 | 3$^{rd}$ generation $^t$BuXPhos palladium precatalyst |
| TBAI | Tetrabutylammonium iodide |
| TBTU | 2-(1H-Benzotriazole-1-yl)-1,1,3,3-tetramethylaminium tetrafluoroborate |
| Tf$_2$O | Triflic anhydide |
| TFA | Trifluoroacetic acid |
| TFBen | Benzene-1,3,5-triyl triformate |
| TMSCN | Trimethylsilyl cyanide |
| THF | Tetrahydrofuran |
| TLC | Thin layer chromatography |
| XantPhos | 4,5-Bis(diphenylphosphino)-9,9-dimethylxanthene |
| XPhos | 2-Dicyclohexylphosphino-2',4',6'-triisopropylbiphenyl |
| Zn | zinc |

Synthetic Examples

The following examples are provided for illustration of the invention. They should not be considered as limiting the scope of the invention, but merely as being representative thereof.

Intermediates

Scheme 1

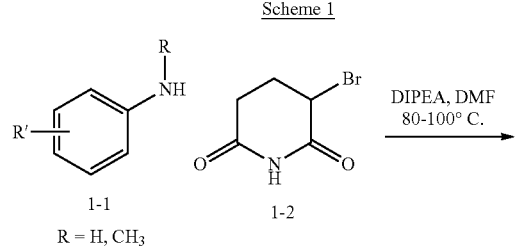

R = H, CH$_3$

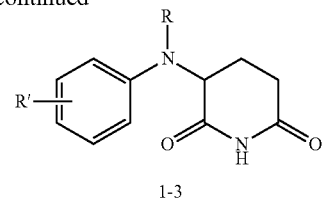

1-3

General Procedure—A

To a mixture of 1-1 (1 mmol) and 1-2 (2 mmol) in dioxane (3 mL) was added N,N-Diisopropylethylamine (2 mmol). The resulting solution was heated in a sealed tube at 70-110° C. for 24 hours to produce 1-3. Reaction mixture was then cooled to room temperature, diluted with water and extracted with Ethyl acetate. The combined Ethyl acetate extract was washed with brine, dried over anhydrous Na$_2$SO$_4$ and concentrated under reduced pressure. The residue was purified by column chromatography (silica, gradient: 0-3% methanol in dichloromethane) to afford 1-3.

Intermediate tert-butyl 4-(4-((2,6-dioxopiperidin-3-yl)amino)phenyl)piperidine-1-carboxylate

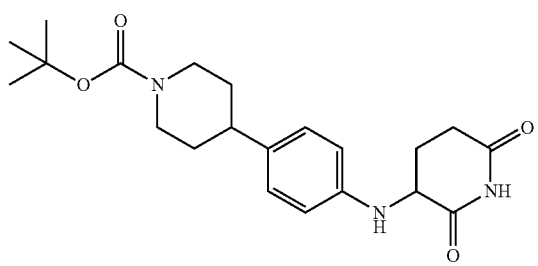 [SMILES: CC(C)(C)OC(=O)N1CCC(c2ccc(NC3CCC(=O)NC3=O)cc2)CC1]

tert-butyl 4-(4-((2,6-dioxopiperidin-3-yl)amino)phenyl)piperidine-1-carboxylate was synthesized from tert-Butyl 4-(4-aminophenyl)-1-piperidinecarboxylate (CAS #170011-57-1) following general procedure A (N,N-diisopropylethylamine/Dioxane). Yield-45%; $^1$H NMR (400 MHz, DMSO-d6) δ 10.75 (s, 1H), 6.94 (d, J=8.16 Hz, 2H), 6.60 (d, J=7.88 Hz, 2H), 5.64 (d, J=6.96 Hz, 1H), 4.28-4.24 (m, 1H), 4.07-4.00 (m, 2H), 2.79-2.64 (m, 4H), 2.53-2.48 (m, 2H), 2.11-2.05 (m, 1H), 1.89-1.81 (m, 1H), 1.71-1.64 (m, 2H0, 1.40-1.34 (m, 10H); LC MS: ES+ 386.3.

Intermediate 3-((3-(piperidin-4-yl)phenyl)amino)piperidine-2,6-dione hydrochloride

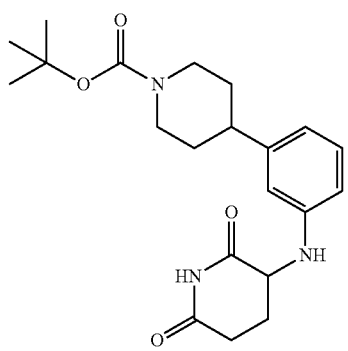 [SMILES: CC(C)(C)OC(=O)N1CCC(c2cccc(NC3CCC(=O)NC3=O)c2)CC1]

Tert-butyl 4-(3-((2,6-dioxopiperidin-3-yl)amino)phenyl)piperidine-1-carboxylate was synthesized from tert-Butyl 4-[3-aminophenyl]-1-piperidinecarboxylate (CAS #387827-19-2) following the general procedure A. Yield: 25% LCMS (ESI+): 388.2 (M+H) Intermediate 3-((6-(piperidin-4-yl)pyridin-3-yl)amino)piperidine-2,6-dione hydrochloride

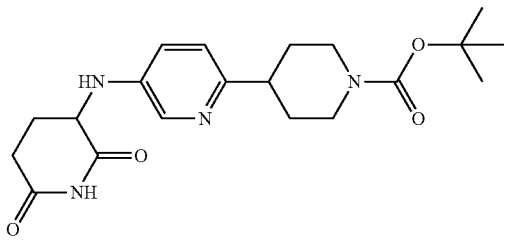 [SMILES: CC(C)(C)OC(=O)N1CCC(c2ccc(NC3CCC(=O)NC3=O)cn2)CC1]

Tert-butyl 4-(5-((2,6-dioxopiperidin-3-yl)amino)pyridin-2-yl)piperidine-1-carboxylate was synthesized from tert-butyl 4-(5-aminopyridin-2-yl)piperidine-1-carboxylate (CAS #885693-48-1) following the general procedure: Yield: 14%, LCMS (ESI+): 389.2 (M+H).

Scheme 2

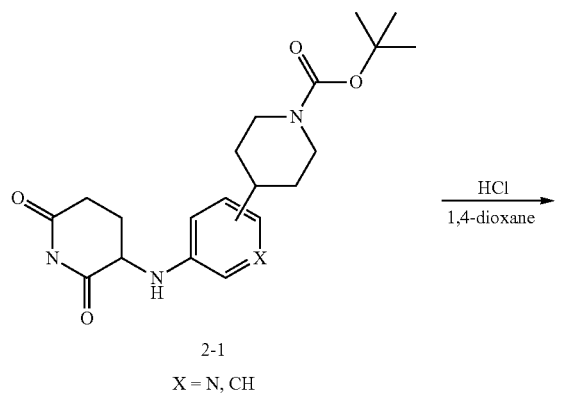

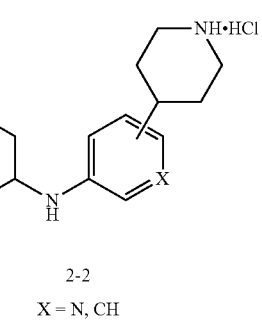

General Procedure B

To 2-1 dissolved in methanol (0.1 M) at room temperature was added hydrogen chloride (4M in 1,4-dioxane, 5 equiv.) and the reaction mixture was heated at 40° C. for 2 hours. The volatiles were evaporated under reduced pressure to afford 2-2.

Intermediate 3-((4-(piperidin-4-yl)phenyl)amino)piperidine-2,6-dione hydrochloride

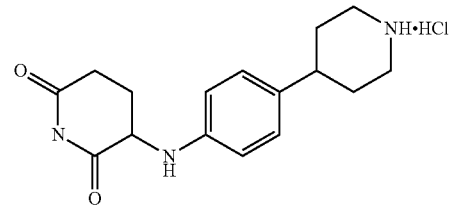

3-((4-(piperidin-4-yl)phenyl)amino)piperidine-2,6-dione hydrochloride was synthesized from tert-butyl 4-(4-((2,6-dioxopiperidin-3-yl)amino)phenyl)piperidine-1-carboxylate following general procedure (General procedure—B). Yield-88%; $^1$H NMR (400 MHz, DMSO-d6) δ 10.80 (s, 1H), 8.84 (brs, 1H), 8.77 (brs, 1H), 6.95 (d, J=8.44 Hz, 2H), 6.66 (d, J=8.48 Hz, 2H), 4.29 (dd, J=11.4, 4.72 Hz, 1H), 3.35-3.29 (m, 2H), 2.99-2.91 (m, 2H), 2.71-2.53 (m, 3H), 2.10-2.05 (m, 1H), 1.89-1.71 (m, 5H); LC MS: ES+288.2.

Intermediate 3-((3-(piperidin-4-yl)phenyl)amino)piperidine-2,6-dione hydrochloride

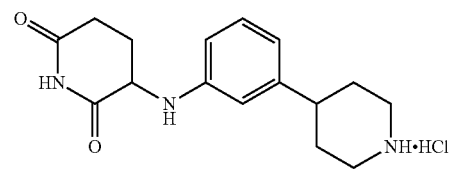

3-((3-(piperidin-4-yl)phenyl)amino)piperidine-2,6-dione hydrochloride was synthesized from tert-butyl 4-(3-((2,6-dioxopiperidin-3-yl)amino)phenyl)piperidine-1-carboxylate following the general procedure B. Yield: 76% $^1$H NMR (400 MHz, DMSO-d6) δ 10.80 (s, 1H), 9.00 (br.s, 1H), 8.85 (br. S, 1H), 1.02 (t, J=7.6 Hz, 1H), 6.57-6.55 (m, 2H), 6.47 (d, J=7.6 Hz, 1H), 4.32 (dd, J=11.2 Hz, 4.6 Hz, 1H), 3.45-3.39 (m, 2H), 2.80-2.65 (m, 2H), 2.79-2.67 (m, 2H), 2.61-2.53 (M, 1H), 2.11-2.07 (m, 1H), 1.94-1.80 (m, 5H). LCMS (ESI+): 288.2 (M+H).

Intermediate 3-((6-(piperidin-4-yl)pyridin-3-yl)amino)piperidine-2,6-dione

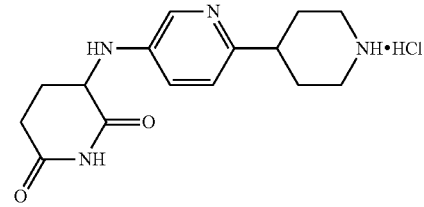

3-((6-(piperidin-4-yl)pyridin-3-yl)amino)piperidine-2,6-dione hydrochloride was synthesized from tert-butyl 4-(5-((2,6-dioxopiperidin-3-yl)amino)pyridin-2-yl)piperidine-1-carboxylate following the general procedure B. Yield: 83%, LCMS (ESI+): 289.0 (M+H).

Synthesis of Intermediate tert-butyl 4-[4-[[(3S)-2,6-dioxo-3-piperidyl]amino]phenyl]piperidine-1-carboxylate and tert-butyl 4-[4-[[(3R)-2,6-dioxo-3-piperidyl]amino]phenyl]piperidine-1-carboxylate by chiral SFC separation

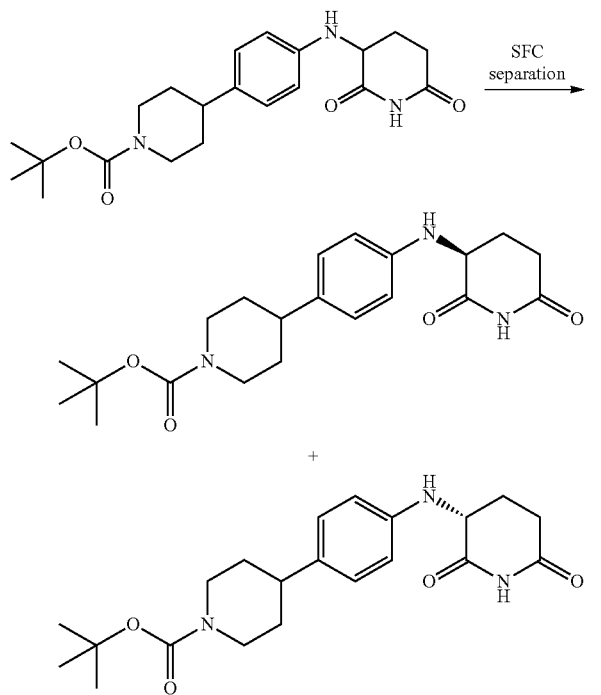

Separation of tert-butyl 4-[4-[(2,6-dioxo-3-piperidyl)amino]phenyl]piperidine-1-carboxylate (4 g, 10.32 mmol) by chiral SFC afforded two sets of fractions.

The following preparative scale SFC method was used to separate the enantiomers:

Column: Chiralpak ID (250×21 mm) 5 um

Flow: 35 g/min

Mobile Phase: 45% CO2+55% Isopropyl alcohol

ABPR: 100 bar

Temperature: 35° C.

The earlier eluting fractions were lyophilized to afford tert-butyl 4-[4-[[(3S)-2,6-dioxo-3-piperidyl]amino]phenyl]piperidine-1-carboxylate (1.44 g, 3.70 mmol, 35.88% yield, 99.66% enantiomeric excess, Chiral SFC Rt=4.31 min). $^1$H NMR (400 MHz, DMSO-D6) δ 10.77 (s, 1H), 6.94 (d, J=8.1 Hz, 2H), 6.60 (d, J=8.2 Hz, 2H), 5.68-5.66 (m, 1H), 4.29-4.23 (m, 1H), 4.05-4.02 (m, 2H), 2.78-2.54 (m, 5H), 2.11-2.07 (m, 1H), 1.89-1.83 (m, 1H), 1.69-1.66 (m, 2H), 1.40-1.36 (m 11H).

The later fractions were lyophilized to afford tert-butyl 4-[4-[[(3R)-2,6-dioxo-3-piperidyl]amino]phenyl]piperidine-1-carboxylate (1.56 g, 3.95 mmol, 38.24% yield, 98.06% enantiomeric excess, Chiral SFC Rt=5.96 min). $^1$H NMR (400 MHz, DMSO-D6) δ 10.77 (s, 1H), 6.94 (d, J=8.2 Hz, 2H), 6.60 (d, J=8.3 Hz, 2H), 5.68-5.66 (m, 1H), 4.29-4.23 (m, 1H), 4.05-4.02 (m, 2H), 2.78-2.58 (m, 5H), 2.11-2.07 (m, 1H), 1.87-1.83 (m, 1H), 1.70-1.67 (m, 2H), 1.40-1.35 (m 11H).

Synthesis of 2-[4-[4-[[(3S)-2,6-dioxo-3-piperidyl]amino]phenyl]-1-piperidyl]acetic acid trifluoroacetic acid salt and 2-[4-[4-[[(3R)-2,6-dioxo-3-piperidyl]amino]phenyl]-1-piperidyl]acetic acid trifluoroacetic acid salt Tert-butyl 2-[4-[4-[(2,6-dioxo-3-piperidyl)amino]phenyl]-1-piperidyl]acetate

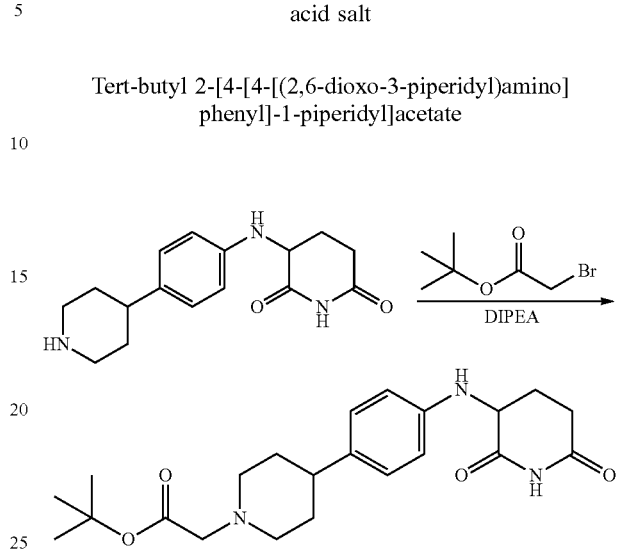

To a stirred solution of 3-[4-(4-piperidyl)anilino]piperidine-2,6-dione (2.0 g, 6.96 mmol) in DMF (20 mL) was added triethyl amine (3.52 g, 34.80 mmol, 4.85 mL) followed by tert-butyl 2-bromoacetate (1.49 g, 7.66 mmol, 1.12 mL) and stirred the reaction mixture at rt for 16 h. Water (75 mL) was added and the product was extracted with ethyl acetate (3×150 mL). The combined organic layers were dried over sodium sulphate, filtered and concentrated under reduced pressure. The residue was purified by silica gel chromatography using 30% ethyl acetate-pet ether as eluent to give tert-butyl 2-[4-[4-[(2,6-dioxo-3-piperidyl)amino]phenyl]-1-piperidyl]acetate (1.40 g, 3.36 mmol, 48.33% yield) as a green solid.

SFC Separation Conditions To Obtain Tert-butyl (S)-2-[4-[4-[(2,6-dioxo-3-piperidyl)amino]phenyl]-1-piperidyl]acetate and tert-butyl (R)-2-[4-[4-[(2,6-dioxo-3-piperidyl)amino]phenyl]-1-piperidyl]

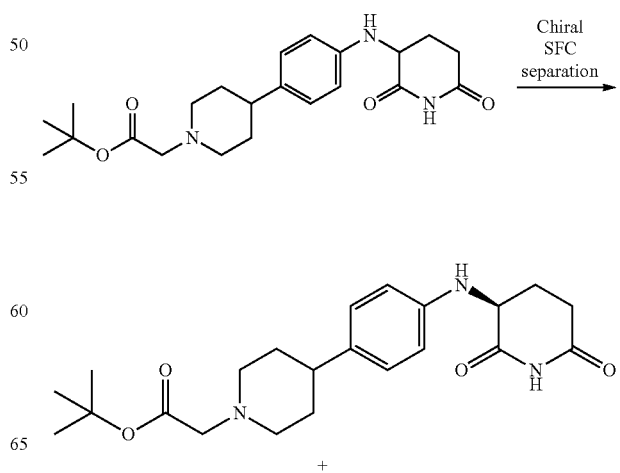

-continued

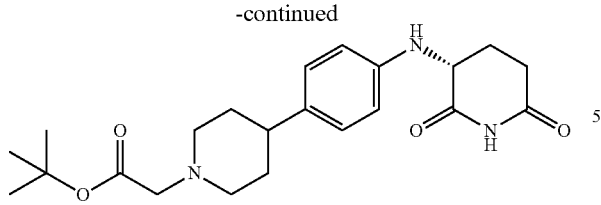

The racemic intermediate tert-butyl 2-[4-[4-[(2,6-dioxo-3-piperidyl)amino]phenyl]-1-piperidyl]acetate (1.40 g, 3.36 mmol) was resolved using chiral SFC method using Chiralcel OD-H column (250 mm×30 mm; 5 micron) eluting with 40% isopropyl alcohol/CO2 (Flow Rate: 3 ml/min; Outlet Pressure: 100 bar). The first eluting set of fractions was evaporated under reduced pressure to afford tert-butyl (S)-2-[4-[4-[(2,6-dioxo-3-piperidyl)amino]phenyl]-1-piperidyl]acetate (500 mg, 36% yield, Rt=3.36 min, 96.22% purity, >99% enantiomeric excess). The second set of fractions was evaporated under reduced pressure to afford 500 mg of tert-butyl (R)-2-[4-[4-[(2,6-dioxo-3-piperidyl)amino]phenyl]-1-piperidyl]acetate (500 mg, 36% yield, Rt=4.84 min., purity 96.22%, 99.04% enantiomeric excess). LCMS First eluted (m/z: 402.4 [M+H]), LCMS Second eluted (m/z: 402.2 [M+H]).

2-[4-[4-[[(3S)-2,6-dioxo-3-piperidyl]amino]phenyl]-1-piperidyl]acetic acid trifluoroacetic acid salt

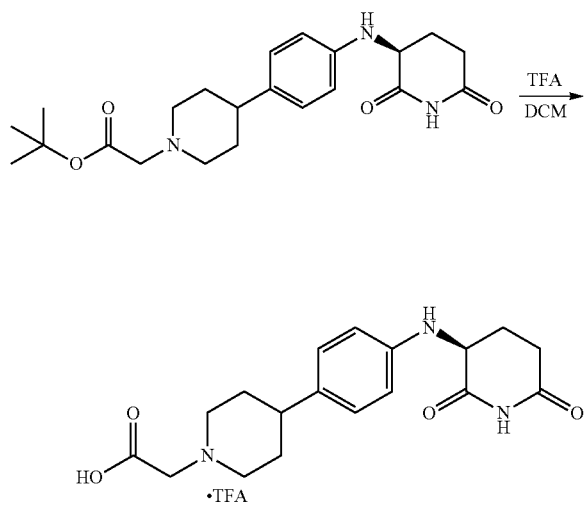 [SMILES: CC(C)(C)OC(=O)CN1CCC(c2ccc(N[C@H]3CCC(=O)NC3=O)cc2)CC1 ; O=C(O)CN1CCC(c2ccc(N[C@H]3CCC(=O)NC3=O)cc2)CC1]

tert-butyl 2-[4-[4-[[(3S)-2,6-dioxo-3-piperidyl]amino]phenyl]-1-piperidyl]acetate (500 mg, 1.25 mmol) was dissolved in dichloromethane (5 mL) and trifluoroacetic acid (12.26 g, 107.51 mmol, 8 mL) was added dropwise at 0° C. and the reaction was stirred at room temperature for 3 h. After completion of the reaction, reaction mixture was concentrated. The material was triturated with a methanol:MTBE mixture (1:4), solid was collected and the volatiles were evaporated under reduced pressure to give 2-[4-[4-[[(3S)-2,6-dioxo-3-piperidyl]amino]phenyl]-1-piperidyl]acetic acid trifluoroacetic acid salt (600 mg, 1.24 mmol, 99.6% yield) as an off white solid. LCMS (ESI+): 346.1 (M+H)

2-[4-[4-[[(3R)-2,6-dioxo-3-piperidyl]amino]phenyl]-1-piperidyl]acetic acid:trifluoroacetic acid salt

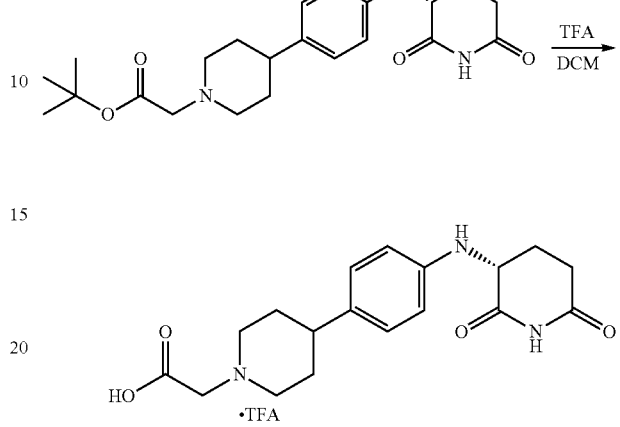

tert-butyl 2-[4-[4-[[(3R)-2,6-dioxo-3-piperidyl]amino]phenyl]-1-piperidyl]acetate (500.00 mg, 1.25 mmol) was treated in a way similar to 2-[4-[4-[[(3S)-2,6-dioxo-3-piperidyl]amino]phenyl]-1-piperidyl]acetic acid trifluoroacetic acid salt to yield 2-[4-[4-[[(3R)-2,6-dioxo-3-piperidyl]amino]phenyl]-1-piperidyl]acetic acid trifluoroacetic acid salt (600 mg, 1.24 mmol, 99.63% yield) as an off white solid. LCMS (ESI+): 346.1 (M+H)

Synthesis of Intermediate 3-(3-Fluoro-4-piperidin-4-yl-phenylamino)-piperidine-2,6-dione

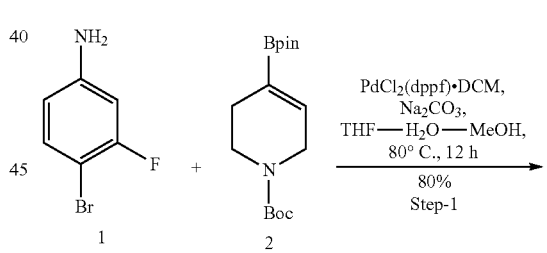

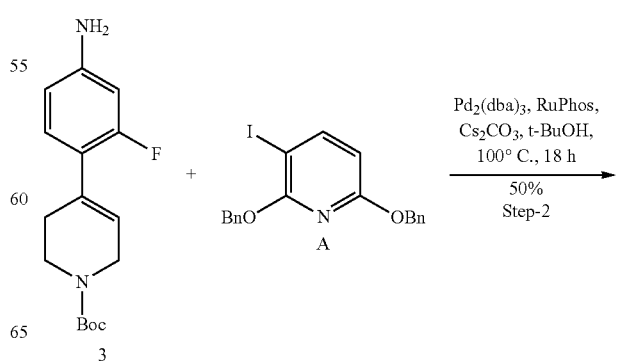

Step-2: Preparation of 4-[4-(2,6-Bis-benzyloxy-pyridin-3-ylamino)-2-fluoro-phenyl]-3,6-dihydro-2H-pyridine-1-carboxylic acid tert-butyl ester

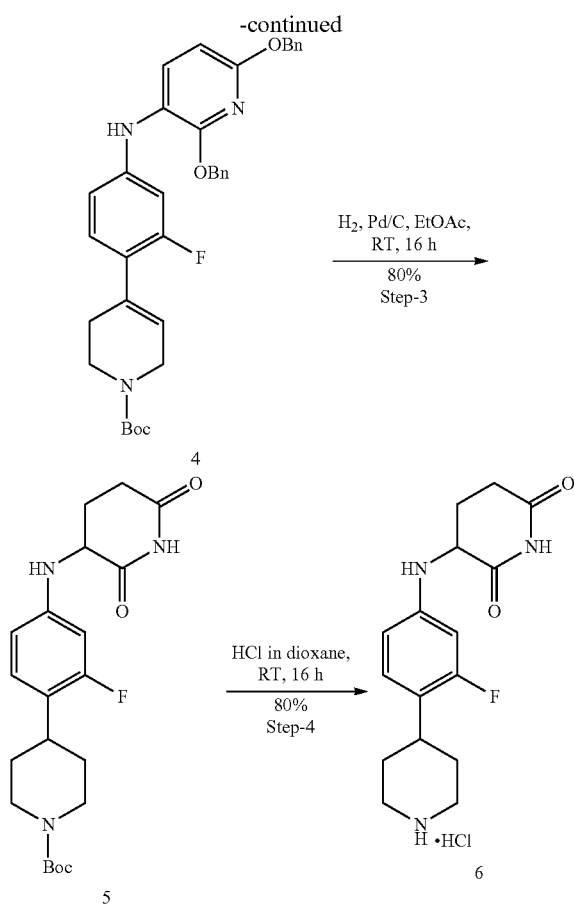

Cesium carbonate (19.73 g, 60.54 mmol) was added to a stirred solution of tert-butyl 4-(4-amino-2-fluoro-phenyl)-3,6-dihydro-2H-pyridine-1-carboxylate (5.9 g, 20.2 mmol) and 2,6-dibenzyloxy-3-iodo-pyridine (9.26 g, 22.2 mmol) in t-BuOH (60 mL) The resulting mixture was degassed with argon and $Pd_2(dba)_3$ (924 mg, 1.01 mmol), Ruphos (942 mg, 2.02 mmol) were added under inert atmosphere. The resulting mixture was heated at 100° C. for 18 h. The reaction mixture was diluted with ethyl acetate, filtered through a short pad of celite and washed with ethyl acetate. The combined organic extracts were washed with water and brine, dried over anhydrous sodium sulphate, filtered and concentrated under reduced pressure. The residue was purified by column chromatography (15% ethyl acetate-hexane) to get tert-butyl 4-[4-[(2,6-dibenzyloxy-3-pyridyl)amino]-2-fluoro-phenyl]-3,6-dihydro-2H-pyridine-1-carboxylate (5.9 g, 10.1 mmol, 50% yield) as pale yellow solid. LCMS: ES+582 (M+H$^+$)

Step-3: Preparation of 4-[4-(2,6-Dioxo-piperidin-3-ylamino)-2-fluoro-phenyl]-piperidine-1-carboxylic acid tert-butyl ester

Step-1: Preparation of 4-(4-Amino-2-fluoro-phenyl)-3,6-dihydro-2H-pyridine-1-carboxylic acid tert-butyl ester Sodium carbonate (6.14 g, 57.89 mmol, 2.43 mL) was added to a stirred solution of 4-bromo-3-fluoro-aniline (5.00 g, 26.3 mmol) and tert-butyl 4-(4,4,5,5-tetramethyl-1,3,2-dioxaborolan-2-yl)-3,6-dihydro-2H-pyridine-1-carboxylate (8.95 g, 29.0 mmol) in water (12 mL), THF (60 mL) and methanol (24 mL) and the flask was thoroughly purged with argon. $PdCl_2(dppf)$·dichloromethane (430 mg, 526 µmol) was added and the reaction mixture was degassed with nitrogen and then heated at 80° C. for 12 h. The reaction mixture was diluted with ethyl acetate, filtered through a short pad of celite and washed with ethyl acetate. The combined organic extracts were washed with water and brine, dried over anhydrous sodium sulphate, filtered and concentrated under reduced pressure. The residue was purified by column chromatography (15% ethyl acetate-hexane) to get tert-butyl 4-(4-amino-2-fluoro-phenyl)-3,6-dihydro-2H-pyridine-1-carboxylate (6.1 g, 20.9 mmol, 79% yield) as pale yellow solid. LCMS: ESI+293 (M+Hs)

10% Pd—C (50% wet, 4.6 g) was added to a stirred nitrogen-degassed solution of tert-butyl 4-[4-[(2,6-dibenzyloxy-3-pyridyl)amino]-2-fluoro-phenyl]-3,6-dihydro-2H- pyridine-1-carboxylate (4.6 g, 7.91 mmol) in ethyl acetate (40 mL). The resulting mixture was stirred at ambient temperature under hydrogen balloon pressure for 20 h. The reaction mixture was filtered through a small pad of celite and washed with ethyl acetate. The combined filtrate was evaporated under reduced pressure and purified by column chromatography (40% ethyl acetate in hexane) to afford tert-butyl 4-[4-[(2,6-dioxo-3-piperidyl)amino]-2-fluoro-phenyl]piperidine-1-carboxylate (2.6 g, 6.41 mmol, 81% yield) as a blue solid. LCMS: ES+406 (M+H⁺).

Step-4: Preparation of 3-(3-Fluoro-4-piperidin-4-yl-phenylamino)-piperidine-2,6-dione hydrochloride

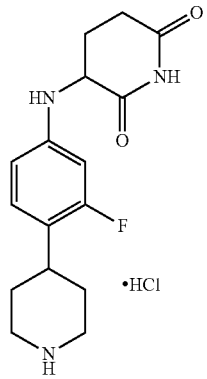 [SMILES: O=C1CCC(Nc2ccc(C3CCNCC3)c(F)c2)C(=O)N1 ; Cl]

Dioxane-HCl (4M, 30 mL, 130 mmol) was added to tert-butyl 4-[4-[(2,6-dioxo-3-piperidyl)amino]-2-fluoro-phenyl]piperidine-1-carboxylate (1.3 g, 3.21 mmol) at 10° C. the resulting mixture was warmed to ambient temperature and stirred for 16 h. The reaction mixture was concentrated under reduced pressure, triturated with ether and lyophilized to yield 3-[3-fluoro-4-(4-piperidyl)anilino]piperidine-2,6-dione (840 mg, 2.73 mmol, 85.25% yield) as green solid. LC MS: ES+306 (M+H⁺). ¹H NMR (400 MHz, DMSO-D6) δ 10.79 (s, 1H), 9.00 (br s, 1H), 8.85-8.83 (m, 1H), 6.96-6.91 (m, 1H), 6.50-6.45 (m, 2H), 4.34-4.30 (m, 1H), 3.32-3.29 (m, 2H), 2.98-2.93 (m, 3H), 2.77-2.69 (m, 1H), 2.60-2.56 (m, 1H), 2.08-2.05 (m, 1H), 1.92-1.81 (m, 5H).

Intermediate Synthesis of 3-(2-Fluoro-4-piperidin-4-yl-phenylamino)-piperidine-2,6-dione hydrochloride

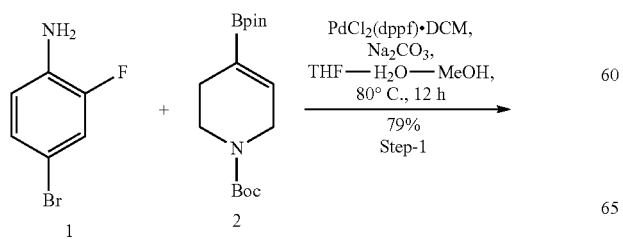

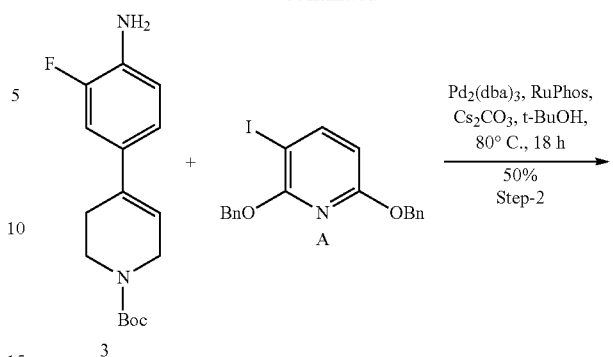

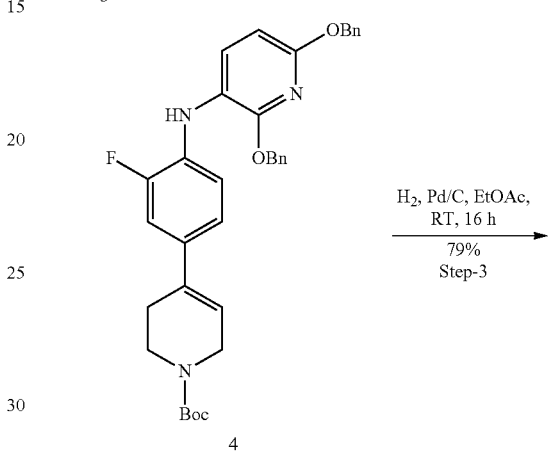

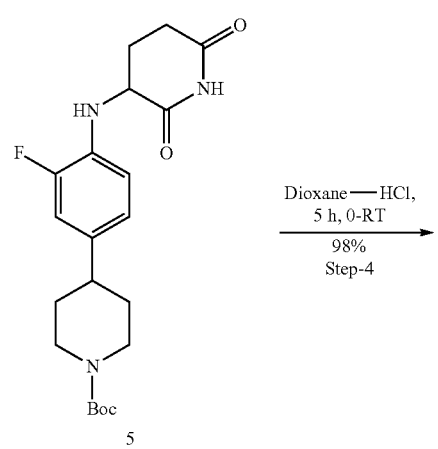

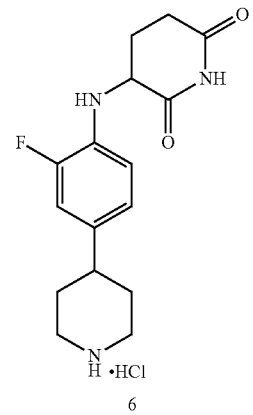

Step-1: Preparation of 4-(4-Amino-3-fluoro-phenyl)-3,6-dihydro-2H-pyridine-1-carboxylic acid tert-butyl ester

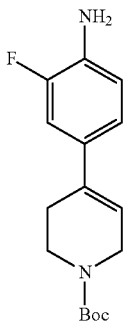

Sodium carbonate (6.14 g, 57.89 mmol) was added to a stirred solution of 4-bromo-2-fluoro-aniline (5.00 g, 26.3 mmol) and tert-butyl 4-(4,4,5,5-tetramethyl-1,3,2-dioxaborolan-2-yl)-3,6-dihydro-2H-pyridine-1-carboxylate (8.95 g, 29.0 mmol) in water (12 mL), THF (60 mL) and methanol (24 mL). The resulting mixture was degassed with argon and PdCl$_2$(dppf).dichloromethane (430 mg, 526 µmol) was added under inert atmosphere. The resulting mixture was heated at 80° C. for 12 h. The reaction mixture was diluted with ethyl acetate, filtered through a short pad of celite and washed with ethyl acetate. The combined organic extracts were washed with water, brine, dried over anhydrous sodium sulphate, filtered and concentrated under reduced pressure. The residue was purified by column chromatography (15% ethyl acetate-hexane) to yield tert-butyl 4-(4-amino-3-fluoro-phenyl)-3,6-dihydro-2H-pyridine-1-carboxylate (6.1 g, 20.9 mmol, 79% yield) as pale yellow solid. LC MS: ES+293 (M+H$^+$).

Step-2: Preparation of 4-[4-(2,6-Bis-benzyloxy-pyridin-3-ylamino)-3-fluoro-phenyl]-3,6-dihydro-2H-pyridine-1-carboxylic acid tert-butyl ester

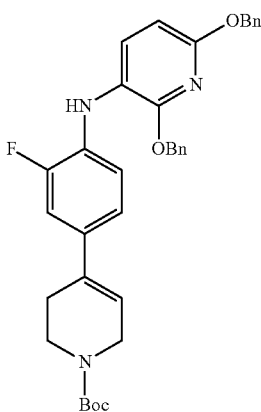 [SMILES: CC(C)(C)OC(=O)N1CC=C(c2ccc(Nc3ccc(OCc4ccccc4)nc3OCc3ccccc3)c(F)c2)CC1]

Cesium carbonate (19.73 g, 60.54 mmol) was added to a stirred solution of tert-butyl 4-(4-amino-3-fluoro-phenyl)-3,6-dihydro-2H-pyridine-1-carboxylate (5.9 g, 20.2 mmol) and 2,6-dibenzyloxy-3-iodo-pyridine (9.26 g, 22.2 mmol) in t-BuOH (60 mL). The resulting mixture was degassed with argon and Pd$_2$(dba)$_3$ (924 mg, 1.01 mmol) and RuPhos (942 mg, 2.02 mmol) were added under inert atmosphere. The resulting mixture was heated at 100° C. for 18 h. The reaction mixture was diluted with ethyl acetate, filtered through a short pad of celite and washed with ethyl acetate. The combined organic extracts were washed with water, brine, dried over anhydrous sodium sulphate, filtered and concentrated under reduced pressure. The residue was purified by column chromatography (10% ethyl acetate-hexane) to yield tert-butyl 4-[4-[(2,6-dibenzyloxy-3-pyridyl)amino]-3-fluoro-phenyl]-3,6-dihydro-2H-pyridine-1-carboxylate (5.9 g, 10.1 mmol, 50% yield) as pale yellow solid. LC MS: ES+582 (M+H$^+$).

Step-3: Preparation of 4-[4-(2,6-Dioxo-piperidin-3-ylamino)-3-fluoro-phenyl]-piperidine-1-carboxylic acid tert-butyl ester

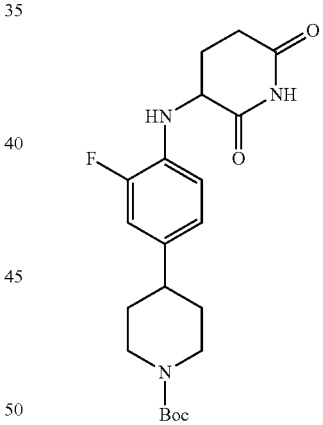

10% Pd—C (50% wet, 4.6 g) was added to a stirred degassed solution of tert-butyl 4-[4-[(2,6-dibenzyloxy-3-pyridyl)amino]-3-fluoro-phenyl]-3,6-dihydro-2H-pyridine-1-carboxylate (4.6 g, 7.91 mmol) in ethyl acetate (40 mL). The resulting mixture was stirred at ambient temperature under hydrogen balloon pressure for 20 h. The reaction mixture was filtered through a short pad of celite and washed with ethyl acetate. The combined filtrate was evaporated under reduced pressure and purified by column chromatography (40% ethyl acetate-hexane) to yield tert-butyl 4-[4-[(2,6-dioxo-3-piperidyl)amino]-3-fluoro-phenyl]piperidine-1-carboxylate (2.6 g, 6.41 mmol, 81% yield) as a blue solid. LC MS: ES+406 (M+H$^+$).

Step-4: Preparation of 3-(2-Fluoro-4-piperidin-4-yl-phenylamino)piperidine-2,6-dione hydrochloride

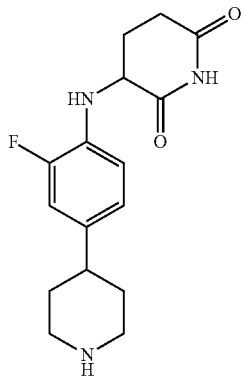

Dioxane HCl (4M, 10 mL, 40 mmol) was added to tert-butyl 4-[4-[(2,6-dioxo-3-piperidyl)amino]-3-fluorophenyl]piperidine-1-carboxylate (1.3 g, 3.21 mmol) at 10° C. The resulting mixture was warmed to ambient temperature and stirred for 16 h. The reaction mixture was concentrated under reduced pressure, triturated with ether and lyophilized to yield 3-[2-fluoro-4-(4-piperidyl)anilino]piperidine-2,6-dione hydrochloride (840 mg, 2.73 mmol, 85% yield) as a green solid. LC MS: ES+306 (M+H$^+$). $^1$H NMR (400 MHz, DMSO-D6) δ 10.82 (s, 1H), 8.85 (br s, 1H), 8.69-8.68 (m, 1H), 6.92-6.89 (m, 1H), 6.83-6.77 (m, 2H), 4.40-4.36 (m, 2H), 3.37-3.31 (m, 2H), 2.98-2.90 (m, 2H), 2.76-2.71 (m, 2H), 2.58-2.56 (m, 1H), 2.05-1.73 (m, 6H).

Synthesis of (S)-4-(4-((2,6-dioxopiperidin-3-yl)amino)-2-fluorophenyl)piperidine hydrochloride and (R)-4-(4-((2,6-dioxopiperidin-3-yl)amino)-2-fluorophenyl)piperidine hydrochloride

Step 1: Chiral separation to afford tert-butyl 4-(4-(((3S)-2,6-dioxopiperidin-3-yl)amino)-2-fluorophenyl)piperidine-1-carboxylate and tert-butyl 4-(4-(((3R)-2,6-dioxopiperidin-3-yl)amino)-2-fluorophenyl)piperidine-1-carboxylate

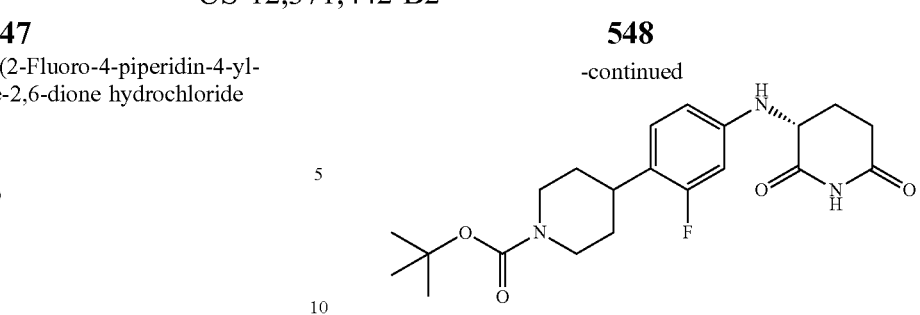

Separation of racemic tert-butyl 4-(4-((2,6-dioxopiperidin-3-yl)amino)-2-fluorophenyl)piperidine-1-carboxylate (5.96 g) by chiral SFC was performed using the following method.

Column: ChiralCel OJ-H (250×21 mm), 5 um silica
Flow: 70 mL/min
Mobile Phase: 65% CO2+35% Isopropyl alcohol
ABPR: 100 bar
Temperature: 35° C.

The SFC separation afforded two sets of fractions. The earlier eluting fractions were lyophilized to afford tert-butyl 4-(4-(((3S)-2,6-dioxopiperidin-3-yl)amino)-2-fluorophenyl)piperidine-1-carboxylate (2.51 g, 42% yield, >99% enantiomeric excess, Chiral SFC Retention time=0.91 min).

The later eluting fractions were lyophilized to afford tert-butyl 4-(4-(((3R)-2,6-dioxopiperidin-3-yl)amino)-2-fluorophenyl)piperidine-1-carboxylate (2.69 g, 45% yield, 99.6% enantiomeric excess, Chiral SFC Retention time=1.26 min).

The retention time and enantiomeric excess of the two isolated isomers were determined by analytical chiral SFC, using the following conditions:

Column: ChiralCel OJ-H (100×4.6 mm)
Flow rate: 4 mL/min
Pressure: 100 bar
Temperature: 40° C.

Step 2: Synthesis of (S)-4-(4-((2,6-dioxopiperidin-3-yl)amino)-2-fluorophenyl)piperidine hydrochloride

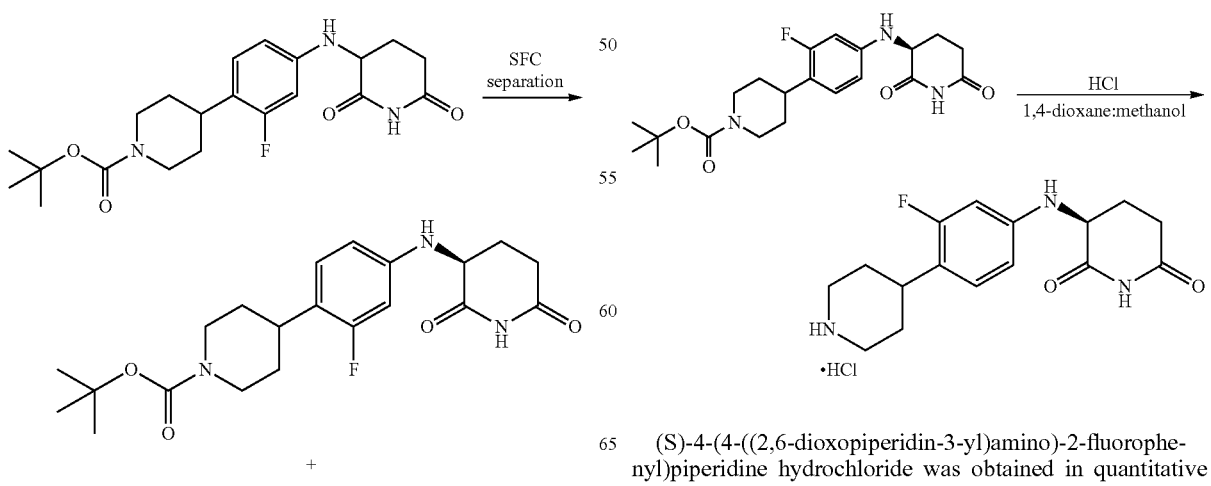

(S)-4-(4-((2,6-dioxopiperidin-3-yl)amino)-2-fluorophenyl)piperidine hydrochloride was obtained in quantitative yield from tert-butyl 4-(4-(((3S)-2,6-dioxopiperidin-3-yl)

amino)-2-fluorophenyl)piperidine-1-carboxylate using the General procedure B. LCMS (ESI+): 306.3 [M+H⁺]

Step 3: Synthesis of (R)-4-(4-((2,6-dioxopiperidin-3-yl)amino)-2-fluorophenyl)piperidine hydrochloride

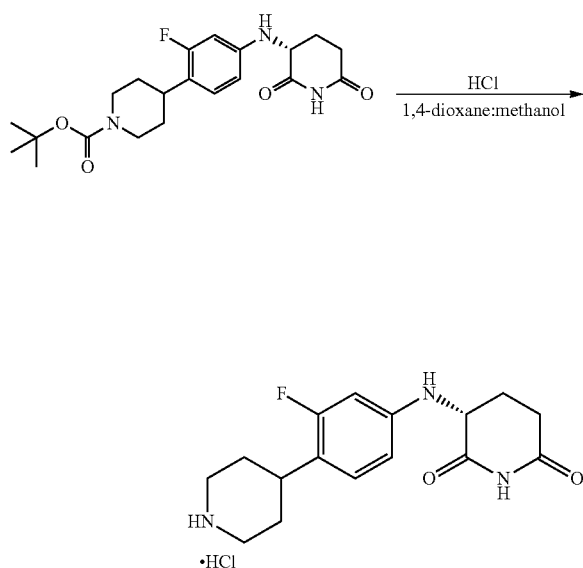

(R)-4-(4-((2,6-dioxopiperidin-3-yl)amino)-2-fluorophenyl)piperidine hydrochloride was obtained in quantitative yield from tert-butyl 4-(4-(((3S)-2,6-dioxopiperidin-3-yl)amino)-2-fluorophenyl)piperidine-1-carboxylate using the General procedure B. LCMS (ESI+): 306.3 (M+H⁺)

Intermediate: 2-[4-[(2,6-dioxo-3-piperidyl)amino]phenyl]acetic acid

Step-1: Preparation of tert-butyl 2-[4-[(2,6-dioxo-3-piperidyl)amino]phenyl]acetate

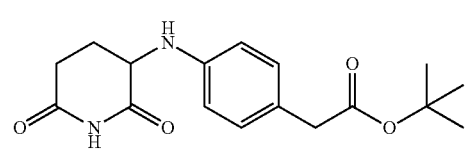 [SMILES: CC(C)(C)OC(=O)Cc1ccc(NC2CCC(=O)NC2=O)cc1]

3-Bromopiperidine-2,6-dione (13.9 g, 72.4 mmol), followed by sodium bicarbonate (12.2 g, 145 mmol) were added to a stirred solution of tert-butyl 2-(4-aminophenyl)acetate (10.0 g, 48.3 mmol) in DMF (80 mL) in a sealed tube. The resulting mixture was heated at 70° C. for 24 h. The reaction mixture was diluted with water and extracted with ethyl acetate. The combined organic extracts were washed with brine, dried over anhydrous sodium sulphate, filtered and evaporated under reduced pressure. The residue was purified by silica gel chromatography (35% ethyl acetate-hexane) to yield tert-butyl 2-[4-[(2,6-dioxo-3-piperidyl)amino]phenyl]acetate (7.5 g, 23.6 mmol, 49% yield). LC MS: ES+319 (M+H⁺)

Step-2: Preparation of 2-[4-[(2,6-dioxo-3-piperidyl)amino]phenyl]acetic acid

TFA (8.47 mL, 110 mmol) was added drop-wise at 0° C. to a stirred solution of tert-butyl 2-[4-[(2,6-dioxo-3-piperidyl)amino]phenyl]acetate (3.5 g, 10.99 mmol) in dichloromethane (45 mL. The resulting mixture was warmed to ambient temperature and stirred for 5 h. The reaction mixture was concentrated under reduced pressure, triturated with MTBE and lyophilized to yield 2-[4-[(2,6-dioxo-3-piperidyl)amino]phenyl]acetic acid (2.9 g, 10.9 mmol, 99% yield) as a grey solid. LC MS: ES+263 (M+H⁺). ¹H NMR (400 MHz, DMSO-D6) δ 10.79 (s, 1H), 6.97 (d, J=8.36 Hz, 2H), 6.63 (d, J=8.36 Hz, 2H), 4.32-4.28 (m, 1H), 3.37 (s, 2H), 2.78-2.71 (m, 1H), 2.61-2.54 (m, 1H), 2.13-2.07 (m, 1H), 1.92-1.81 (m, 1H)

Intermediate: Synthesis of 1-(6-bromo-1-methyl-indazol-3-yl)hexahydropyrimidine-2,4-dione

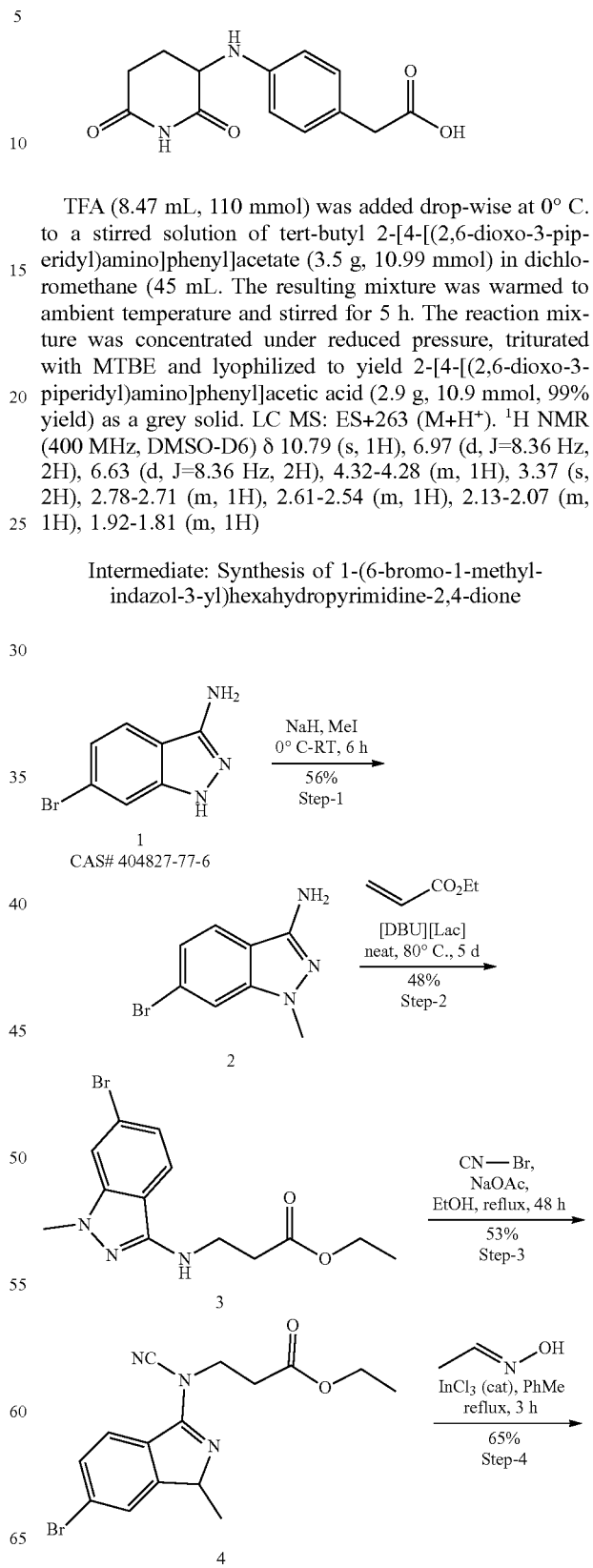

551

-continued

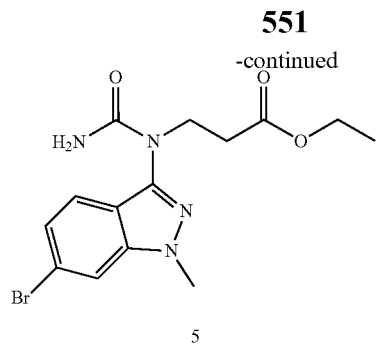

5

Triton B, MeCN
RT, 45 min
—————→
74%
Step-5

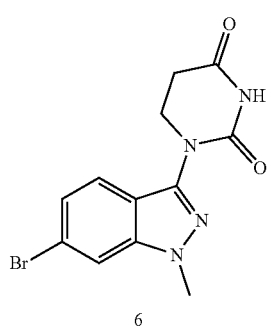

6

Step-1: Preparation of
6-bromo-1-methyl-indazol-3-amine

Sodium hydride (60% in oil 2.38 g, 59.4 mmol) was added portion wise at 0° C. to a stirred solution of 6-bromo-1H-indazol-3-amine (7 g, 33.0 mmol, 439 μL) in DMF (150 mL) and the mixture was stirred for 40 min. Iodomethane (5.15 g, 36.3 mmol, 2.26 mL) was added drop-wise under cooling and the resulting mixture was warmed to ambient temperature and stirred for 16 h. The reaction mixture was quenched with saturated ammonium chloride solution and extracted with ethyl acetate. The combined organic extracts were washed with water, brine, dried over anhydrous sodium sulphate, filtered and concentrated under reduced pressure. The residue was purified by silica gel chromatography (50% ethyl acetate-hexane) to yield 6-bromo-1-methyl-indazol-3-amine (4.2 g, 18.6 mmol, 56% yield). LC MS: ES+227 (M+H$^+$)

552

Step-2: Preparation of ethyl 3-[(6-bromo-1-methyl-indazol-3-yl)amino]propanoate

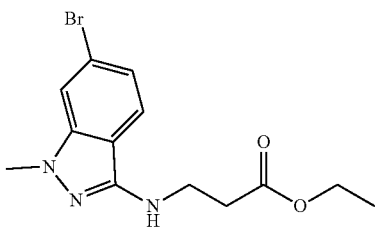 [SMILES: CCOC(=O)CCNc1nn(C)c2cc(Br)ccc12]

Ethyl acrylate (14.0 g, 139 mmol) was added in 5 portions (2.8 g each) over 5 days to a mixture of 6-bromo-1-methyl-indazol-3-amine (4.2 g, 18.6 mmol), [DBU][Lac] (prepared by mixing equimolar mixture of DBU and lactic acid with stirring for 16 h at ambient temperature, 2.09 g, 14.9 mmol) at 80° C. After completion (LCMS), the reaction mixture was quenched with sodium hypochlorite (30% aq, 5 mL) and diluted with ethyl acetate. The combined organics were washed with water, brine, dried over anhydrous sodium sulphate, filtered and concentrated under reduced pressure. The residue was purified by silica gel chromatography (50% ethyl acetate-hexane) to yield ethyl 3-[(6-bromo-1-methyl-indazol-3-yl)amino]propanoate (2.9 g, 8.89 mmol, 48% yield). LCMS (ESI+): 327 (M+H$^+$).

Step-3: Preparation of ethyl 3-[(6-bromo-1-methyl-indazol-3-yl)-cyano-amino]propanoate

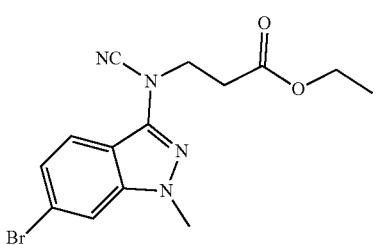 [SMILES: CCOC(=O)CCN(C#N)c1nn(C)c2cc(Br)ccc12]

Anhydrous sodium acetate (1.46 g, 17.8 mmol), followed by cyanogen bromide (1.41 g, 13.3 mmol) were added to a stirred solution of ethyl 3-[(6-bromo-1-methyl-indazol-3-yl)amino]propanoate (2.9 g, 8.89 mmol) in ethanol (40 mL) at ambient temperature. The resulting mixture was heated to reflux for 48 h. The reaction mixture was concentrated under reduced pressure and diluted with ethyl acetate. The combined organics were washed with water, brine, dried over anhydrous sodium sulphate, filtered and concentrated under reduced pressure. The residue was purified by column chromatography (45% ethyl acetate-hexane) to yield ethyl 3-[(6-bromo-1-methyl-indazol-3-yl)-cyano-amino]propanoate (1.65 g, 4.70 mmol, 53% yield). LC MS: ES+352 (M+H$^+$).

Step-4: Preparation of ethyl 3-[(6-bromo-1-methyl-indazol-3-yl)-carbamoyl-amino]propanoate

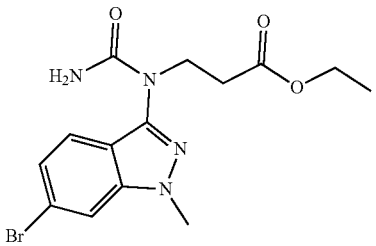 [SMILES: CCOC(=O)CCN(C(N)=O)c1nn(C)c2cc(Br)ccc12]

(1E)-Acetaldehyde oxime (1.01 g, 17.1 mmol), followed by indium (III) chloride (126 mg, 569 µmol) were added to a stirred solution of ethyl 3-[(6-bromo-1-methyl-indazol-3-yl)-cyano-amino]propanoate (2 g, 5.69 mmol) in toluene (60 mL) at ambient temperature. The resulting mixture was heated to reflux for 1 h. The reaction mixture was diluted with ethyl acetate, washed with water and brine. The organics were dried over anhydrous sodium sulphate, filtered and concentrated under reduced pressure. The residue was purified by column chromatography (60% ethyl acetate-hexane) to yield ethyl 3-[(6-bromo-1-methyl-indazol-3-yl)-carbamoyl-amino]propanoate (1.4 g, 3.79 mmol, 67% yield). LC MS: ES+370 (M+H$^+$).

Step-5: Preparation of 1-(6-bromo-1-methyl-indazol-3-yl)hexahydropyrimidine-2,4-dione

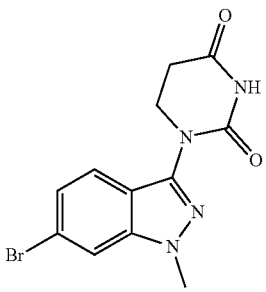 [SMILES: Cn1nc(N2CCC(=O)NC2=O)c2ccc(Br)cc21]

Triton-B (40% in methanol, 2.4 mL, 5.69 mmol) was added drop-wise to a stirred solution of ethyl 3-[(6-bromo-1-methyl-indazol-3-yl)-carbamoyl-amino]propanoate (1.40 g, 3.79 mmol) in MeCN (70 mL) at ambient temperature. The resulting mixture was stirred at ambient temperature for 45 minutes. The reaction mixture was concentrated under vacuum and diluted with ethyl acetate. The organic layer was washed with water, brine, dried over anhydrous sodium sulphate, filtered and concentrated under reduced pressure. The residue was purified by column chromatography (30% ethyl acetate-hexane) to yield 1-(6-bromo-1-methyl-indazol-3-yl)hexahydropyrimidine-2,4-dione (910 mg, 2.81 mmol, 74% yield) as white solid. LC MS: ES+324 (M+H$^+$). $^1$H NMR (400 MHz, DMSO-D6) δ 10.60 (s, 1H), 7.97 (s, 1H), 7.61 (d, J=8.6 Hz, 1H), 7.26-7.23 (m, 1H), 3.98 (s, 3H), 3.93 (t, J=6.6 Hz, 2H), 2.76 (t, J=6.6 Hz, 2H).

Preparation of 1-(1-methyl-6-(piperidin-4-yl)-1H-indazol-3-yl)dihydropyrimidine-2,4(1H,3H)-dione hydrochloride

Step 1: tert-butyl 4-[3-(2,4-dioxohexahydropyrimidin-1-yl)-1-methyl-indazol-6-yl]-3,6-dihydro-2H-pyridine-1-carboxylate

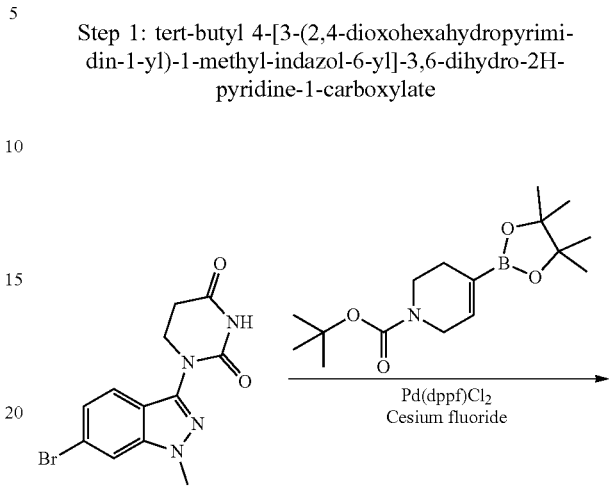

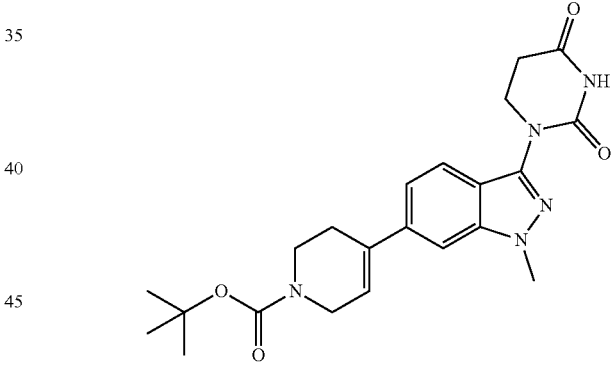

A solution of 1-(6-bromo-1-methyl-indazol-3-yl)hexahydropyrimidine-2,4-dione (1.25 g, 3.87 mmol) and tert-butyl 4-(4,4,5,5-tetramethyl-1,3,2-dioxaborolan-2-yl)-3,6-dihydro-2H-pyridine-1-carboxylate (2.39 g, 7.74 mmol) was bubbled with N$_2$ for 10 min. Then, cesium fluoride (1.18 g, 7.74 mmol) and Pd(dppf)Cl$_2$ (566 mg, 774 µmol) were added and the mixture was stirred at 85° C. for 2 h. The mixture was cooled to ambient temperature, diluted with ethyl acetate and filtered through Celite/silica gel. After washing with ethyl acetate, the filtrate was diluted with water and layers were separated, and the organic layer was washed with brine, dried over Na$_2$SO$_4$, filtered, and concentrated. The residue was purified by normal phase chromatography (5-100% ethyl acetate in Hexanes) to afford tert-butyl 4-[3-(2,4-dioxohexahydropyrimidin-1-yl)-1-methyl-indazol-6-yl]-3,6-dihydro-2H-pyridine-1-carboxylate (1.04 g, 2.44 mmol, 63% yield). LCMS (ESI+): 426.3 (M+H$^+$)

Step 2: tert-butyl 4-[3-(2,4-dioxohexahydropyrimidin-1-yl)-1-methyl-indazol-6-yl]piperidine-1-carboxylate

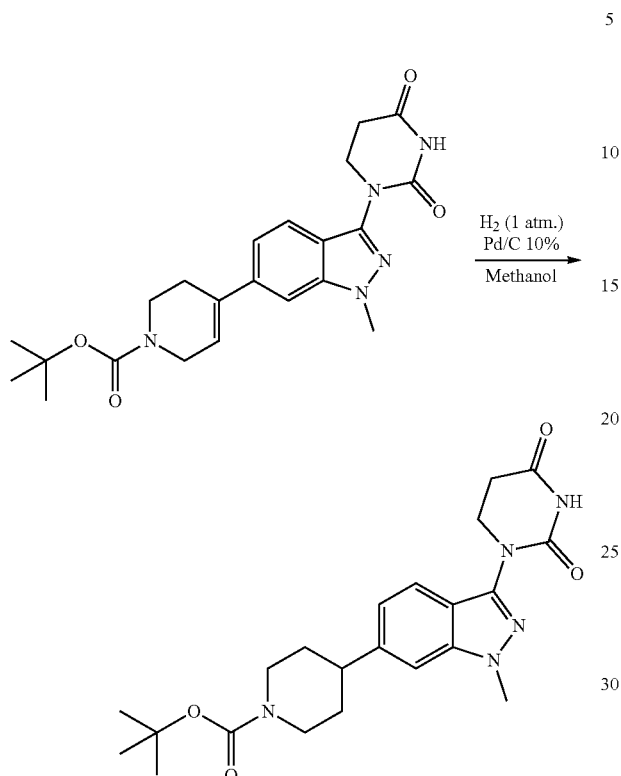

Palladium (10% on carbon, Type 487, dry, 1.08 g, 1.02 mmol) was added to a solution of tert-butyl 4-[3-(2,4-dioxohexahydropyrimidin-1-yl)-1-methyl-indazol-6-yl]-3,6-dihydro-2H-pyridine-1-carboxylate (1.44 g, 3.38 mmol) in methanol (30 mL) and the mixture was stirred at ambient temperature under a hydrogen balloon atmosphere. After 24 h, the reaction mixture was filtered through a pad of celite, washed with a mixture of dichloromethane/methanol (1:1), and concentrated in vacuo to yield tert-butyl 4-[3-(2,4-dioxohexahydropyrimidin-1-yl)-1-methyl-indazol-6-yl]piperidine-1-carboxylate (1.42 g, 3.32 mmol, 98% yield). LCMS (ESI+): 372.3 (M-tert-butyl+H$^+$).

Step 3: 1-(1-methyl-6-(piperidin-4-yl)-1H-indazol-3-yl)dihydropyrimidine-2,4(1H,3H)-dione hydrochloride

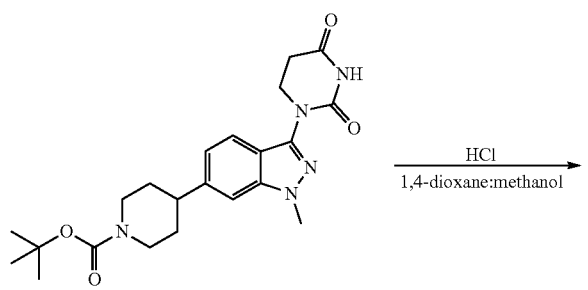

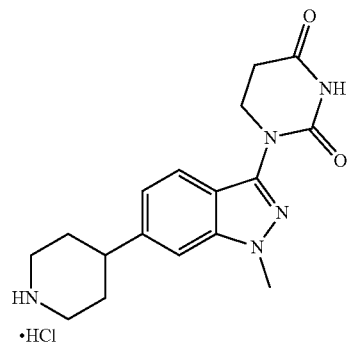

1-(1-methyl-6-(piperidin-4-yl)-1H-indazol-3-yl)dihydropyrimidine-2,4(1H,3H)-dione hydrochloride was obtained in quantitative yield from tert-butyl 4-[3-(2,4-dioxohexahydropyrimidin-1-yl)-1-methyl-indazol-6-yl]-3,6-dihydro-2H-pyridine-1-carboxylate using the general method B for tert-butoxycarbonyl protecting group deprotection. LCMS (ESI+): 328.1 (M+H$^+$).

Synthesis of 1-((4-(piperidin-4-yl)phenyl)amino)-3-azabicyclo[3.1.1]heptane-2,4-dione hydrochloride

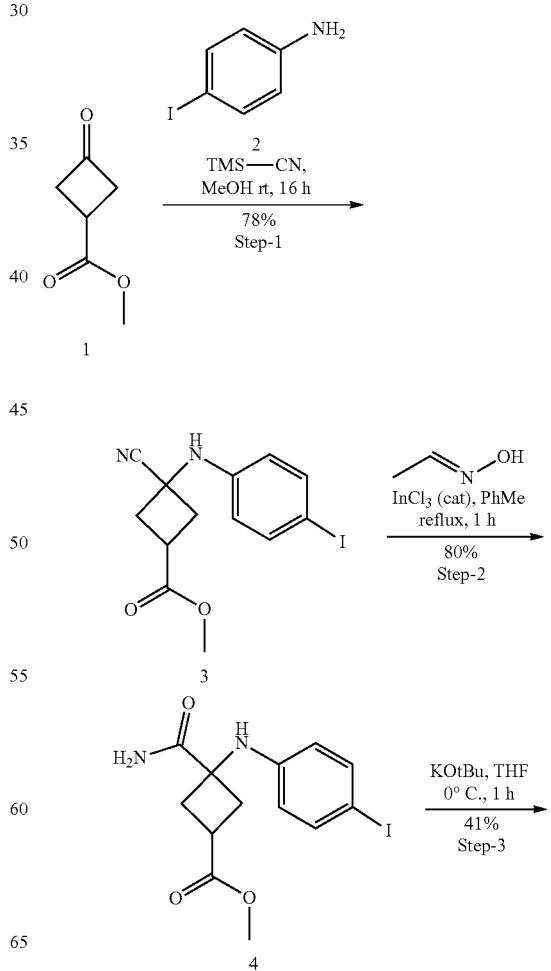

557

-continued

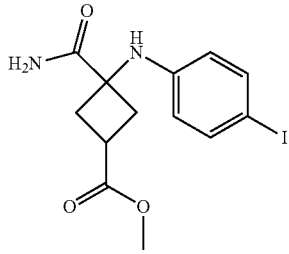

6

Pd(dppf)Cl$_2$, Na$_2$CO$_3$
DMF—water
(9:1), 80° C.
───────────────→
57%
Step-4

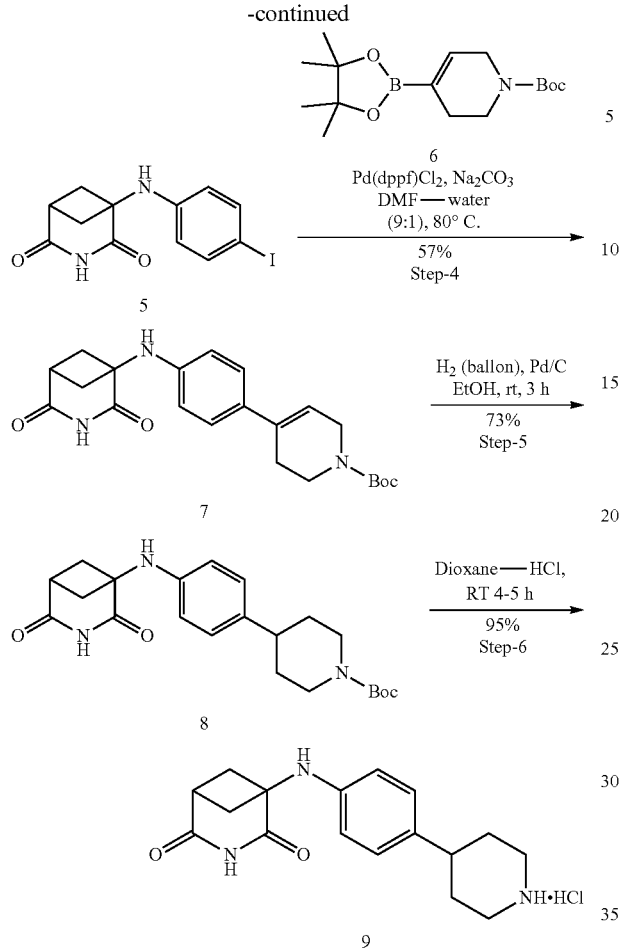

5

H$_2$ (ballon), Pd/C
EtOH, rt, 3 h
────────────→
73%
Step-5

7

Dioxane—HCl,
RT 4-5 h
──────────→
95%
Step-6

8

9

Step-1: Preparation of 3-Cyano-3-(4-iodo-phenylamino)-cyclobutane carboxylic acid methyl ester

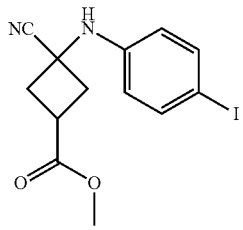 [SMILES: COC(=O)C1CC(C#N)(Nc2ccc(I)cc2)C1]

4-Iodoaniline (13.2 g, 60.1 mmol) followed by trimethylsilyl cyanide (10.8 g, 109 mmol, 13.7 mL) were added to a stirred solution of methyl 3-oxocyclobutanecarboxylate (7 g, 54.6 mmol) in methanol (270 mL). The resulting mixture was stirred at ambient temperature for 16 h. The reaction mixture was concentrated under reduced pressure and the residue was purified by silica gel chromatography (5-10% ethyl acetate-hexane) to afford methyl 3-cyano-3-(4-iodoanilino)cyclobutanecarboxylate (15.2 g, 42.7 mmol, 78% yield) as an off-white solid. LCMS ES+357 (M+H$^+$)

558

Step-2: Preparation of 3-Carbamoyl-3-(4-iodo-phenylamino)-cyclobutane carboxylic acid methyl ester Acetaldehyde oxime (4.98 g, 84.2 mmol), followed by indium chloride (62.1 mg, 281 μmol) were added to a stirred solution of methyl 3-cyano-3-(4-iodoanilino) cyclobutanecarboxylate (10 g, 28.1 mmol) in toluene (120 mL) at ambient temperature. The resulting mixture was heated to reflux for 1 h. After completion, the reaction mixture was cooled to ambient temperature and the precipitate thus formed was filtered, washed with toluene:ether (1:1) and dried to yield methyl 3-carbamoyl-3-(4-iodoanilino) cyclobutanecarboxylate (8.4 g, 22.5 mmol, 80% yield). It was used in the next step without further purification. LCMS (ESI+): 375 (M+H$^+$)

Step-3: Preparation of 1-(4-Iodo-phenylamino)-3-aza-bicyclo[3.1.1]heptane-2,4-dione Potassium tert-butoxide (4.62 g, 41.2 mmol) was added at 0° C. to a stirred solution of methyl 3-[2-amino-1-(4-iodoanilino)-2-oxo-ethyl]cyclobutanecarboxylate (8 g, 20.6 mmol) in THF (150 mL), and the reaction mixture was stirred for 1 h at 0° C. The reaction mixture was neutralized with 1M citric acid solution and adjusted to pH~6 and extracted with ethyl acetate. The combined organic layers were dried over sodium sulfate, filtered and concentrated under reduced pressure. The residue mass was purified by column chromatography (40% ethyl acetate/hexane) to afford 5-(4-iodoanilino)-3-azabicyclo[3.1.1]heptane-2,4-dione (2.9 g, 8.48 mmol, 41% yield). LCMS (ESI+): 343 (M+H$^+$)

Step-4: Preparation of 4-[4-(2,4-Dioxo-3-aza-bicyclo[3.1.1]hept-1-ylamino)-phenyl]-3,6-dihydro-2H-pyridine1-carboxylic acid tert-butyl ester

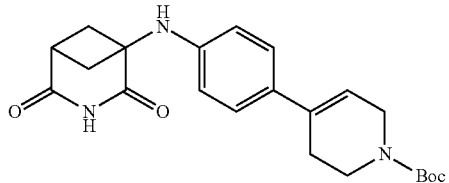 [SMILES: CC(C)(C)OC(=O)N1CC=C(c2ccc(NC34CC(C3)C(=O)NC4=O)cc2)CC1]

Sodium carbonate (1.98 g, 18.7 mmol) was added to a stirred solution of 5-(4-iodoanilino)-3-azabicyclo[3.1.1]heptane-2,4-dione (2.9 g, 8.48 mmol) and tert-butyl 4-(4,4,5,5-tetramethyl-1,3,2-dioxaborolan-2-yl)-3,6-dihydro-2H-pyridine-1-carboxylate (5.24 g, 17.0 mmol) in DMF (32 mL) and water (8 mL) and the reaction was degassed with argon. Pd(dppf)Cl$_2$ (692 mg, 848 µmol) was added under inert atmosphere. The resulting mixture was heated at 80° C. for 16 h. The reaction mixture was diluted with ethyl acetate and filtered through a short pad of celite. The filtrate was washed with water, brine, dried over anhydrous sodium sulphate, filtered and concentrated under reduced pressure. The residue was purified by column chromatography (5-10% ethyl acetate-hexane) to yield tert-butyl 4-[4-[(2,4-dioxo-3-azabicyclo[3.1.1]heptan-5-yl)amino]phenyl]-3,6-dihydro-2H-pyridine-1-carboxylate (1.91 g, 4.81 mmol, 57% yield). LCMS ES+398 (M+H$^+$)

Step-5: Preparation of 4-[4-(2,4-Dioxo-3-aza-bicyclo[3.1.1]hept-1-ylamino)-phenyl]-piperidine-1-carboxylic acid tert-butyl ester

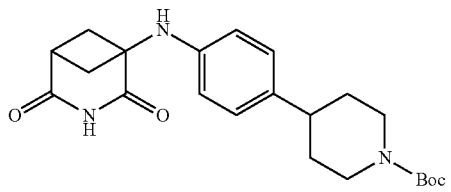 [SMILES: CC(C)(C)OC(=O)N1CCC(c2ccc(NC34CC(C3)C(=O)NC4=O)cc2)CC1]

10% Pd—C (50% wet, 1 g) was added to a degassed solution of tert-butyl 4-[4-[(2,4-dioxo-3-azabicyclo[3.1.1]heptan-5-yl)amino]phenyl]-3,6-dihydro-2H-pyridine-1-carboxylate (1.91 g, 4.81 mmol) in ethanol (20 mL). The resulting mixture was stirred at ambient temperature under a hydrogen balloon atmosphere for 3 h. After completion (confirmed by LCMS), the reaction mixture was filtered through a short pad of celite, washed with ethyl acetate and concentrated under reduced pressure. The residue was purified by silica gel chromatography (60-70% ethyl acetate-hexane) to yield tert-butyl 4-[4-[(2,4-dioxo-3-azabicyclo[3.1.1]heptan-5-yl)amino]phenyl]piperidine-1-carboxylate (1.4 g, 3.50 mmol, 73% yield) LCMS ES+400 (M+H$^+$)

Step-6: Preparation of 5-(4-Piperidin-4-yl-phenylamino)-3-aza-bicyclo [3.1.1] heptane-2,4-dione hydrochloride

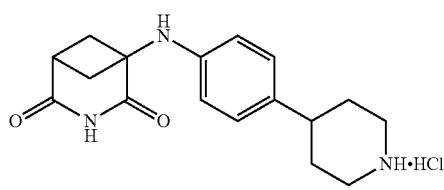

Dioxane HCl (4M, 15 mL, 60 mmol) was added to tert-butyl 4-[4-[(2,4-dioxo-3-azabicyclo[3.1.1]heptan-5-yl)amino]phenyl]piperidine-1-carboxylate (1.4 g, 3.50 mmol) at 10° C. The resulting mixture was warmed to ambient temperature and stirred for 5 h. The reaction mixture was concentrated under reduced pressure, triturated with ether and lyophilized to yield 5-[4-(4-piperidyl)anilino]-3-azabicyclo[3.1.1]heptane-2,4-dione hydrochloride (1.08 g, 3.34 mmol, 95% yield) as an off white solid. LCMS ES+300 (M+H$^+$), $^1$H-NMR (400 MHz, DMSO-D6) δ 10.72 (s, 1H), 8.95 (br s, 1H), 8.81-8.79 (m, 1H), 6.90 (d, J=8.2 Hz, 2H), 6.44 (d, J=8.16 Hz, 2H), 3.32-3.29 (m, 2H), 2.95-2.91 (m, 3H), 2.73-2.62 (m, 3H), 2.49 (br m, 2H), 1.85-1.72 (m, 4H).

Synthesis of 3-[3-(difluoromethyl)-4-(4-piperidyl)anilino]piperidine-2,6-dione hydrochloride

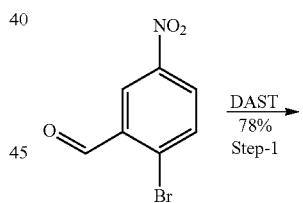

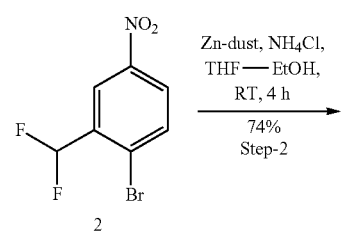

561
-continued

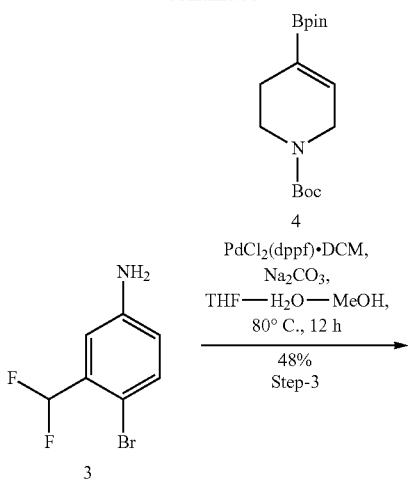

562
-continued

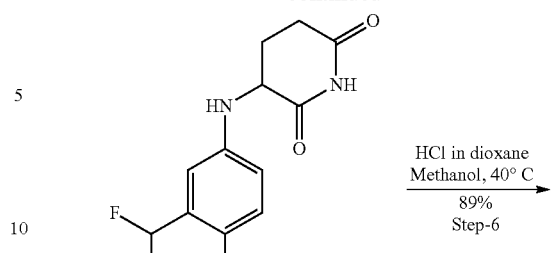

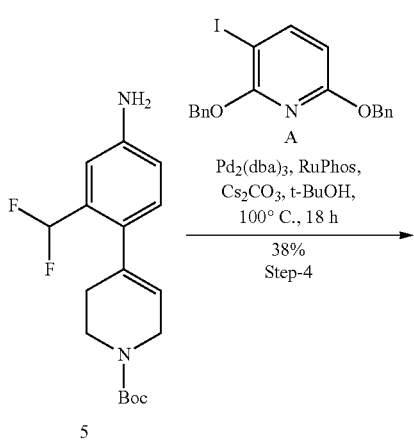

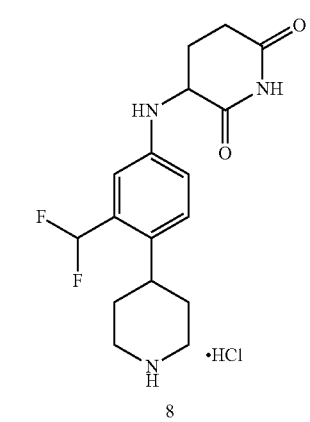

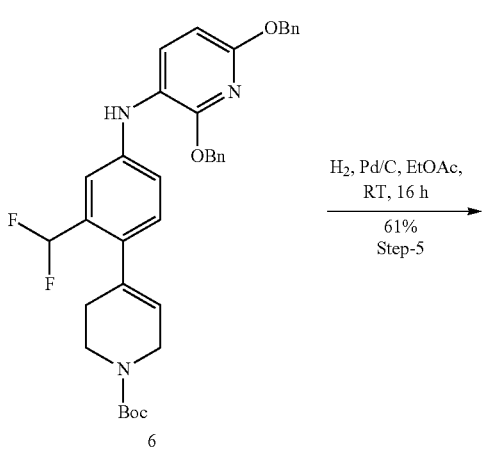

Step-1: Synthesis of
1-Bromo-2-difluoromethyl-4-nitro-benzene

DAST (24.13 mL, 182.60 mmol) was added to a stirred solution of 2-bromo-5-nitro-benzaldehyde (7 g, 30.4 mmol) in dichloromethane (350 mL) at 0° C. and the resulting reaction mixture was stirred at ambient temperature for 16 h. After completion, the reaction mixture was basified with 10% NaHCO₃ solution and extracted with dichloromethane. The combined organic extracts were washed with water, brine, dried over sodium sulphate, filtered and concentrated under reduced pressure. The residue was purified by column chromatography (10% ethyl acetate/hexane) to afford 1-bromo-2-(difluoromethyl)-4-nitro-benzene (6 g, 23.8 mmol, 78% yield).

Step-2: Synthesis of 4-Bromo-3-difluoromethyl-phenylamine

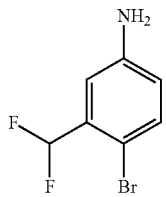 [SMILES: Nc1ccc(Br)c(C(F)F)c1]

Ammonium chloride (12.7 g, 238 mmol) and zinc (15.6 g, 238 mmol) were added to a stirred solution of 1-bromo-2-(difluoromethyl)-4-nitro-benzene (6.0 g, 23.8 mmol) in THF (70 mL) and ethanol (70 mL) at ambient temperature. The resulting mixture was stirred at ambient temperature for 4 h. After completion, reaction mixture was filtered through a short pad of celite and washed with ethanol. The filtrate was concentrated under reduced pressure and the residue purified by column chromatography (40% ethyl acetate-hexane) to afford 4-bromo-3-(difluoromethyl) aniline (3.95 g, 17.8 mmol, 75% yield). LC MS: ES+221 (M+H$^+$).

Step-3: Synthesis of 4-(4-Amino-2-difluoromethyl-phenyl)-3,6-dihydro-2H-pyridine-1-carboxylic acid tert-butyl ester

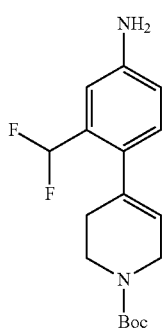 [SMILES: CC(C)(C)OC(=O)N1CC=C(c2ccc(N)cc2C(F)F)CC1]

Sodium carbonate (3.06 g, 28.82 mmol) was added to a stirred solution of 4-bromo-3-(difluoromethyl)aniline (3.2 g, 14.4 mmol) and tert-butyl 4-methyl-3,6-dihydro-2H-pyridine-1-carboxylate (3.08 g, 15.9 mmol) in THF (20 mL), methanol (10 mL) and water (10 mL) and the mixture was thoroughly purged with argon. PdCl$_2$(dppf).dichloromethane (2.35 g, 2.88 mmol) was added under inert atmosphere. Resulting mixture was heated at 80° C. for 12 h. After completion, the reaction mixture was diluted with ethyl acetate, filtered through a short pad of celite and washed with ethyl acetate. The combined organic part was washed with water, brine, dried over anhydrous sodium sulphate, filtered and concentrated under reduced pressure. The residue was purified by column chromatography (20% ethyl acetate-hexane) to afford tert-butyl 4-[4-amino-2-(difluoromethyl)phenyl]-3,6-dihydro-2H-pyridine-1-carboxylate (2.24 g, 6.91 mmol, 48% yield). LC MS: ES+325 (M+H$^+$).

Step-4: Synthesis of 4-[4-(2,6-Bis-benzyloxy-pyridin-3-ylamino)-2-difluoromethyl-phenyl]-3,6-dihydro-2H pyridine-1-carboxylic acid tert-butyl ester

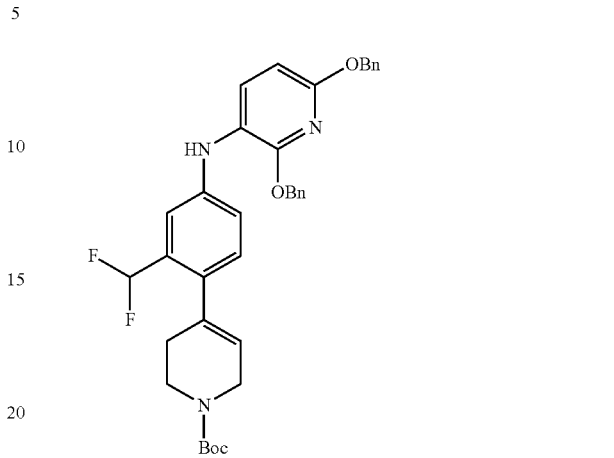

Cesium carbonate (5.12 g, 15.72 mmol) was added to a stirred solution of tert-butyl 4-[4-amino-2-(difluoromethyl)phenyl]-3,6-dihydro-2H-pyridine-1-carboxylate (1.7 g, 5.24 mmol) and 2,6-dibenzyloxy-3-iodo-pyridine (2.41 g, 5.77 mmol) in tert Butanol (40 mL). The resulting mixture was degassed with argon and Pd$_2$(dba)$_3$ (96 mg, 1.05 mmol), Ruphos (978 mg, 2.10 mmol) were added under inert atmosphere. The resulting mixture was heated at 100° C. for 18 h. After completion, the reaction mixture was diluted with ethyl acetate, filtered through a short pad of celite and washed with ethyl acetate. The filtrate was washed with water, brine, dried over anhydrous sodium sulphate, filtered and concentrated under reduced pressure. The residue was purified by column chromatography (25% ethyl acetate-hexane) to afford tert-butyl 4-[4-[(2,6-dibenzyloxy-3-pyridyl)amino]-2-(difluoromethyl)phenyl]-3,6-dihydro-2H-pyridine-1-carboxylate (1.23 g, 2.00 mmol, 38% yield). LC MS: ES+614 (M+H$^+$).

Step-5: Synthesis of 4-[2-Difluoromethyl-4-(2,6-dioxo-piperidin-3-ylamino)-phenyl]-piperidine-1-carboxylic acid tert-butyl ester

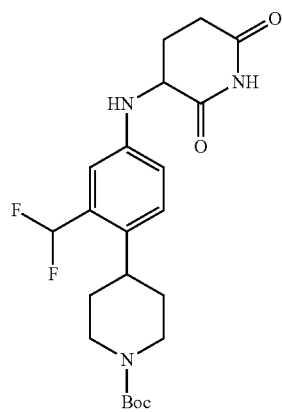 [SMILES: CC(C)(C)OC(=O)N1CCC(c2ccc(NC3CCC(=O)NC3=O)cc2C(F)F)CC1]

10% Pd—C (50% wet, 2 g) was added to a degassed solution of tert-butyl 4-[4-[(2,6-dibenzyloxy-3-pyridyl)

amino]-2-(difluoromethyl)phenyl]-3,6-dihydro-2H-pyridine-1-carboxylate (2 g, 3.26 mmol) in ethyl acetate (15 mL). The resulting mixture was stirred at ambient temperature under a hydrogen balloon atmosphere for 16 h. After completion, the reaction mixture was filtered through a short pad of celite, washed with ethyl acetate and concentrated under reduced pressure. The residue was purified by silica gel chromatography (60% ethyl acetate in hexane) to afford tert-butyl 4-[2-(difluoromethyl)-4-[(2,6-dioxo-3-piperidyl)amino]phenyl]piperidine-1-carboxylate (880 mg, 1.99 mmol, 61% yield) as a light blue solid. LC MS: ES+438 (M+H$^+$). $^1$H NMR (400 MHz, DMSO-d6) δ 10.77 (s, 1H), 7.26-6.98 (m, 2H), 6.81 (s, 1H), 6.77 (d, J=8.8 Hz, 1H), 6.03 (d, J=7.8 Hz, 1H), 4.34 (bs, 1H), 4.06-4.03 (m, 2H), 2.90-2.70 (m, 4H), 2.60-2.56 (m, 1H), 2.09-2.06 (m, 1H), 1.91-1.87 (m, 1H), 1.61-1.59 (m, 2H), 1.51-1.46 (m, 2H), 1.41 (s, 9H).

Step 6: Synthesis of 3-[3-(difluoromethyl)-4-(4-piperidyl)anilino]piperidine-2,6-dione hydrochloride

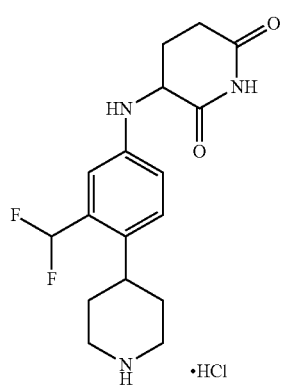 [SMILES: O=C1CCC(Nc2ccc(C3CCNCC3)c(C(F)F)c2)C(=O)N1 ; Cl]

tert-Butyl 4-[2-(difluoromethyl)-4-[(2,6-dioxo-3-piperidyl)amino]phenyl]piperidine-1-carboxylate (191 mg, 436.59 μmol) was dissolved in a methanol (3 mL) and hydrogen chloride solution (4.0 M in dioxane, 1.09 mL) was added. The reaction mixture was heated at 40° C. for 4 h, and the reaction was complete. The volatiles were evaporated under reduce pressure. The material was submitted to high vacuum, frozen to −78° C. and thawed to afford 3-[3-(difluoromethyl)-4-(4-piperidyl)anilino]piperidine-2,6-dione hydrochloride (145 mg, 388 μmol, 89% yield) as a dense off-white solid. LCMS (ESI+): Rt=0.954 min., MS (ESI+): 338.3 (M+H$^+$).

Synthesis of 5-[(2,6-dioxo-3-piperidyl)amino]-2-(4-piperidyl)benzonitrile hydrochloride

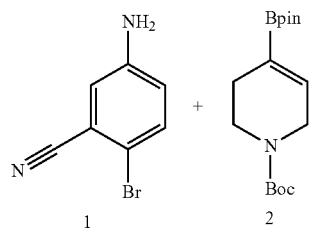

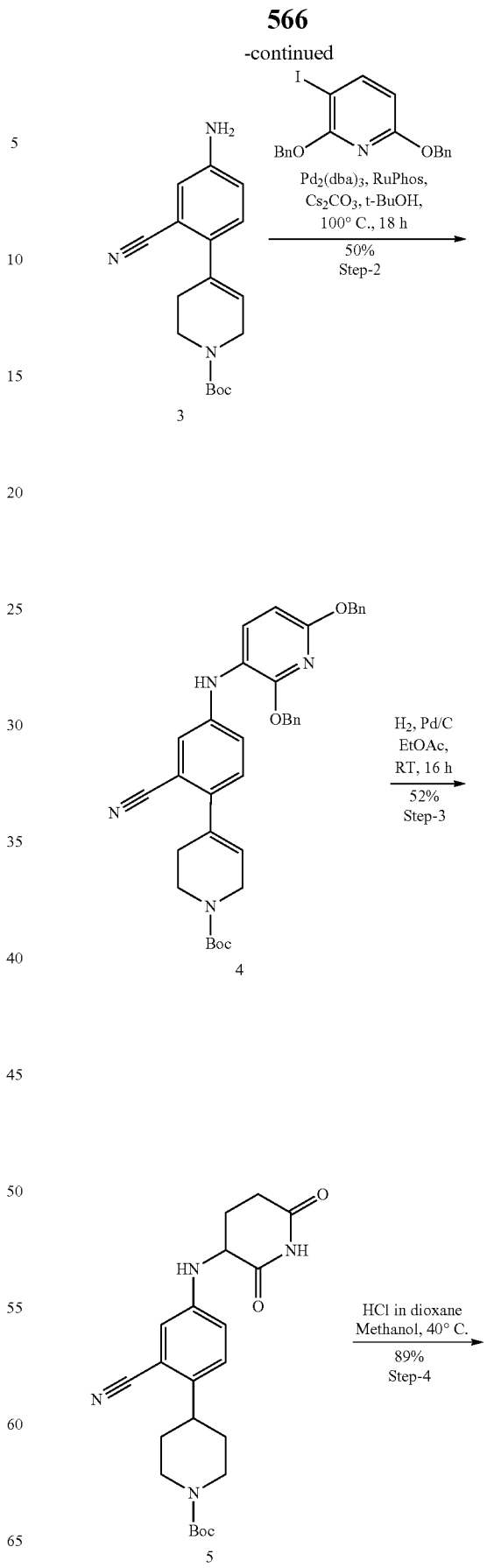

-continued

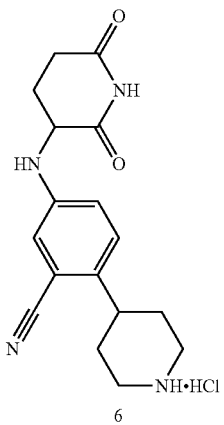

6

Step-1: Synthesis of 4-(4-Amino-2-cyano-phenyl)-3,6-dihydro-2H-pyridine-1-carboxylic acid tert-butyl ester

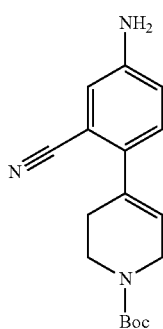 [SMILES: CC(C)(C)OC(=O)N1CC=C(c2ccc(N)cc2C#N)CC1]

To a stirred solution of 5-amino-2-bromo-benzonitrile (5 g, 25.38 mmol) and tert-butyl 4-(4,4,5,5-tetramethyl-1,3,2-dioxaborolan-2-yl)-3,6-dihydro-2H-pyridine-1-carboxylate (11.77 g, 38.06 mmol) in DMF (60 mL) was added cesium fluoride (7.71 g, 50.75 mmol, 1.87 mL) and the reaction mixture was degassed with argon. PdCl$_2$(dppf).dichloromethane (4.14 g, 5.08 mmol) was added under inert atmosphere. Resulting mixture was heated at 90° C. for 16 h. After completion, reaction mixture was diluted with ethyl acetate, filtered through a short pad of celite and washed with ethyl acetate. Combined organic part was washed with water, brine, dried over anhydrous sodium sulphate, filtered and concentrated under reduced pressure. Crude mass was purified by column chromatography (20% ethyl acetate-hexane) to afford tert-butyl 4-(4-amino-2-cyano-phenyl)-3,6-dihydro-2H-pyridine-1-carboxylate (4.3 g, 14.36 mmol, 56.60% yield). LC MS: ES+300 (M+H).

Step-2: Synthesis of 4-[4-(2,6-Bis-benzyloxy-pyridin-3-ylamino)-2-cyano-phenyl]-3,6-dihydro-2H-pyridine-1-carboxylic acid tert-butyl ester

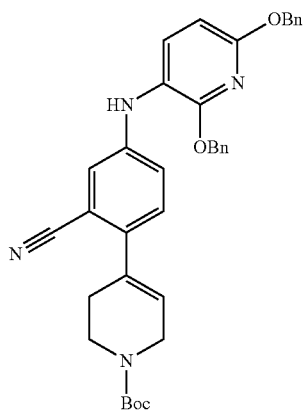 [SMILES: CC(C)(C)OC(=O)N1CC=C(c2ccc(Nc3ccc(OCc4ccccc4)nc3OCc3ccccc3)cc2C#N)CC1]

To a stirred solution of tert-butyl 4-(4-amino-2-cyano-phenyl)-3,6-dihydro-2H-pyridine-1-carboxylate (3 g, 10.02 mmol) and 2,6-dibenzyloxy-3-iodo-pyridine (4.60 g, 11.02 mmol) in t-BuOH (50 mL), cesium carbonate (9.80 g, 30.06 mmol) was added. Resulting mixture was degassed with argon and Pd$_2$(dba)$_3$ (458.83 mg, 501.06 µmol), RuPhos (467.62 mg, 1.00 mmol) were added under inert atmosphere. Resulting mixture was heated at 100° C. for 18 h. The reaction mixture was diluted with ethyl acetate, filtered through a short pad of celite and washed with ethyl acetate. Combined organic part was washed with water, brine, dried over anhydrous sodium sulphate, filtered and concentrated under reduced pressure. Crude mass was purified by column chromatography (25% ethyl acetate-hexane) to afford tert-butyl 4-[2-cyano-4-[(2,6-dibenzyloxy-3-pyridyl)amino]phenyl]-3,6-dihydro-2H-pyridine-1-carboxylate (3 g, 5.10 mmol, 50.85% yield) LC MS: ES+589 (M+H).

Step-3: Synthesis of 4-[2-Cyano-4-(2,6-dioxo-piperidin-3-ylamino)-phenyl]-piperidine-1-carboxylic acid tert-butyl ester

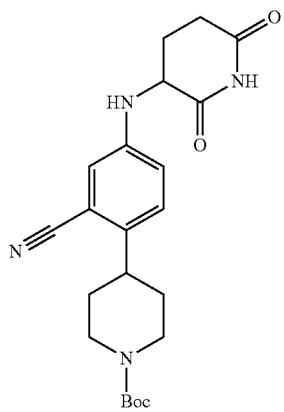 [SMILES: CC(C)(C)OC(=O)N1CCC(c2ccc(NC3CCC(=O)NC3=O)cc2C#N)CC1]

To a degassed solution of tert-butyl 4-[2-cyano-4-[(2,6-dibenzyloxy-3-pyridyl)amino]phenyl]-3,6-dihydro-2H-pyridine-1-carboxylate (3 g, 5.10 mmol) in ethyl acetate (60 mL), 10% Pd—C (50% wet, 3 g) was added. Resulting mixture was stirred at ambient temperature under hydrogen at balloon pressure for 16 h. The reaction mixture was filtered through a short pad of celite, washed with ethyl acetate and concentrated under reduced pressure. The crude mass was purified by silica gel column chromatography (60% ethyl acetate in hexane) to afford tert-butyl 4-[2-cyano-4-[(2,6-dioxo-3-piperidyl)amino]phenyl]piperidine-1-carboxylate (1.1 g, 2.65 mmol, 52.07% yield) as pale green solid. LCMS: ES+413 (M+H). $^1$H NMR (400 MHz, DMSO-d6) δ 10.81 (s, 1H), 7.20 (d, J=8.5 Hz, 1H), 6.96 (t, J=8.7 Hz, 2H), 6.26 (d, J=7.9 Hz, 1H), 4.43-4.37 (m, 1H), 4.09-4.06 (m, 2H), 2.87-2.69 (m, 4H), 2.60-2.55 (m, 1H), 2.10-2.06 (m, 1H), 1.92-1.87 (m, 1H), 1.70-1.67 (m, 2H), 1.57-1.46 (m, 2H), 1.41 (s, 9H).

Step-4

Synthesis of 5-[(2,6-dioxo-3-piperidyl)amino]-2-(4-piperidyl)benzonitrile hydrochloride

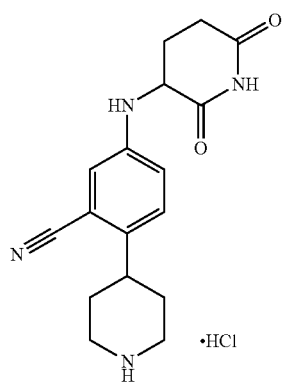 [SMILES: N#Cc1cc(NC2CCC(=O)NC2=O)ccc1C1CCNCC1 ; Cl]

Tert-butyl 4-[2-cyano-4-[(2,6-dioxo-3-piperidyl)amino]phenyl]piperidine-1-carboxylate (120 mg, 290.92 μmol) was dissolved in methanol mixture (3 mL) mL) and Hydrogen chloride solution 4.0M in dioxane (4 M, 727.31 μL) was added. The reaction mixture was heated at 40° C. for 4 hours, and the reaction was complete. The volatiles were evaporated under reduce pressure. The material was submitted to high vacuum, frozen to −78° C. and thawed to afford 5-[(2,6-dioxo-3-piperidyl)amino]-2-(4-piperidyl)benzonitrile hydrochloride (107 mg, 277.51 μmol, 95% yield) as a dense solid. LCMS (ESI+): 313.2 (M+H)

Synthesis of 3-[3-methyl-4-(4-piperidyl)anilino]piperidine-2,6-dione hydrochloride

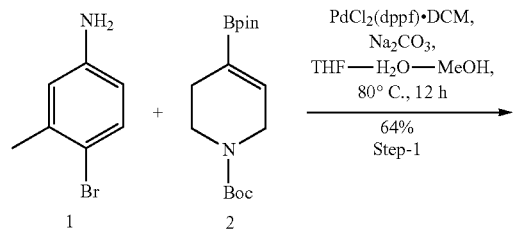

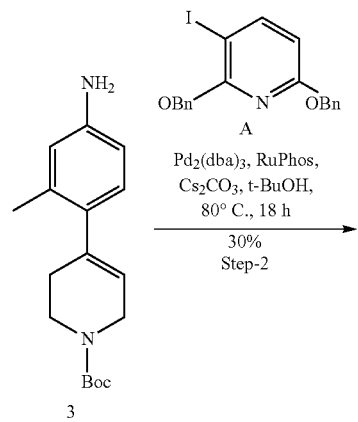

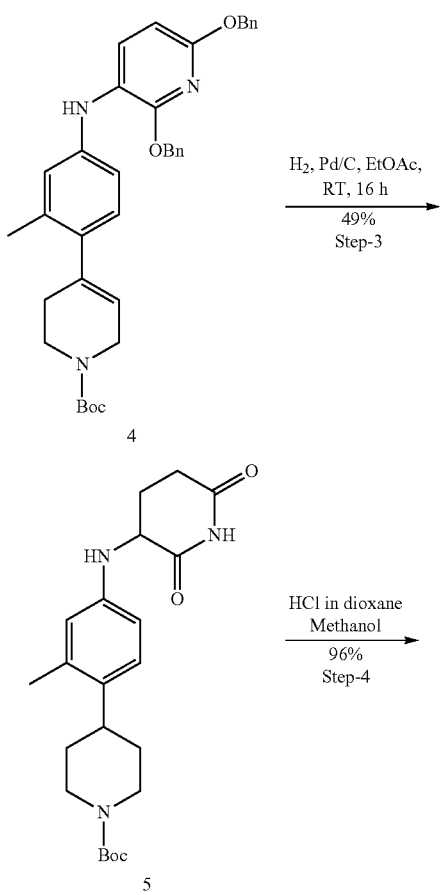

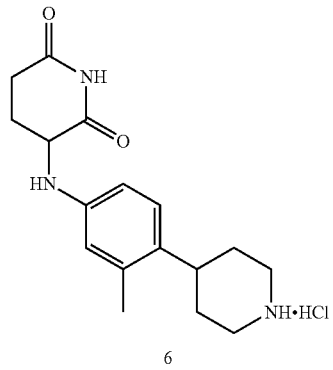

Step-1: Synthesis of 4-(4-Amino-2-methyl-phenyl)-3,6-dihydro-2H-pyridine-1-carboxylic acid tert-butyl ester

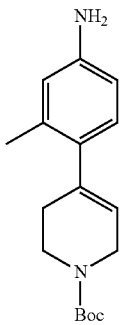 [SMILES: Cc1cc(N)ccc1C1=CCN(C(=O)OC(C)(C)C)CC1]

To a stirred solution of 4-bromo-3-methyl-aniline (5 g, 26.87 mmol) and tert-butyl 4-(4,4,5,5-tetramethyl-1,3,2-dioxaborolan-2-yl)-3,6-dihydro-2H-pyridine-1-carboxylate (9.14 g, 29.56 mmol) in THF (60 mL), water (12 mL) and methanol (24 mL) was added sodium carbonate (6.27 g, 59.12 mmol) and thoroughly purged with argon. PdCl2 (dppf).CH$_2$Cl$_2$ (438.94 mg, 537.49 µmol) was added under inert atmosphere. Resulting mixture was heated at 80° C. for 12 h. Reaction mixture was diluted with ethyl acetate, filtered through a short pad of celite and washed with ethyl acetate. Combined organic part was washed with water, brine, dried over anhydrous sodium sulphate, filtered and concentrated under reduced pressure. Crude mass was purified by column chromatography (15% ethyl acetate-hexane) to afford tert-butyl 4-(4-amino-2-methyl-phenyl)-3,6-dihydro-2H-pyridine-1-carboxylate (5 g, 17.34 mmol, 64.51% yield) as a dense solid. LC MS: ES+289 (M+H).

Step-2: Synthesis of 4-[4-(2,6-Bis-benzyloxy-pyridin-3-ylamino)-2-methyl-phenyl]-3,6-dihydro-2H-pyridine-1-carboxylic acid tert-butyl ester

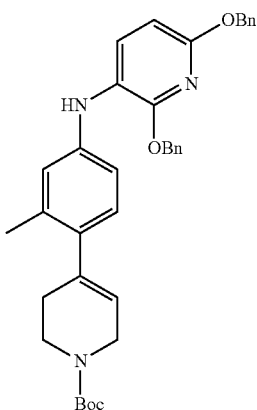 [SMILES: Cc1cc(Nc2ccc(OCc3ccccc3)nc2OCc2ccccc2)ccc1C1=CCN(C(=O)OC(C)(C)C)CC1]

To a stirred solution of tert-butyl 4-(4-amino-2-methyl-phenyl)-3,6-dihydro-2H-pyridine-1-carboxylate (5 g, 17.34 mmol) and 2,6-dibenzyloxy-3-iodo-pyridine (7.96 g, 19.07 mmol) in t-BuOH (80 mL) cesium carbonate (16.95 g, 52.01 mmol) was added. Resulting mixture was degassed with argon and Pd$_2$(dba)$_3$ (793.83 mg, 866.90 µmol), RuPhos (809.04 mg, 1.73 mmol) were added under inert atmosphere. Resulting mixture was heated at 100° C. for 18 h. Reaction mixture was diluted with ethyl acetate, filtered through a short pad of celite and washed with ethyl acetate. Combined organic part was washed with water, brine, dried over anhydrous sodium sulphate, filtered and concentrated under reduced pressure. Crude mass was purified by column chromatography (25% ethyl acetate-hexane) to afford tert-butyl 4-[4-[(2,6-dibenzyloxy-3-pyridyl)amino]-2-methyl-phenyl]-3,6-dihydro-2H-pyridine-1-carboxylate (3 g, 5.19 mmol, 29.95% yield) LCMS (ESI+): 578 (M+H$^+$).

Step-3: Synthesis of 4-[4-(2,6-Dioxo-piperidin-3-ylamino)-2-methyl-phenyl]-piperidine-1-carboxylic acid tert-butyl ester

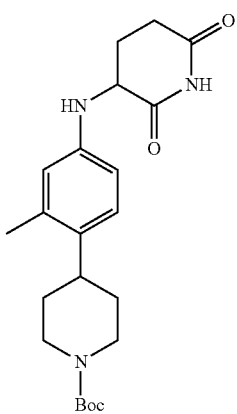 [SMILES: Cc1cc(NC2CCC(=O)NC2=O)ccc1C1CCN(C(=O)OC(C)(C)C)CC1]

To a degassed solution of tert-butyl 4-[4-[(2,6-dibenzyloxy-3-pyridyl)amino]-2-methyl-phenyl]-3,6-dihydro-2H-pyridine-1-carboxylate (3 g, 5.19 mmol) in ethyl acetate (60 mL), 10% Pd—C (50% wet, 3 g) was added. Resulting mixture was stirred at ambient temperature under hydrogen atmosphere at balloon pressure for 16 h. After completion, the reaction mixture was filtered through a short pad of celite, washed with ethyl acetate and concentrated under reduced pressure. The crude residue was purified by silica gel column chromatography (60% ethyl acetate in hexane) to afford tert-butyl 4-[4-[(2,6-dioxo-3-piperidyl)amino]-2-methyl-phenyl]piperidine-1-carboxylate (1020 mg, 2.53 mmol, 48.78% yield) as pale blue solid. LC MS: ES+402 (M+H).

Step 4: Synthesis of 3-[3-methyl-4-(4-piperidyl)anilino]piperidine-2,6-dione hydrochloride

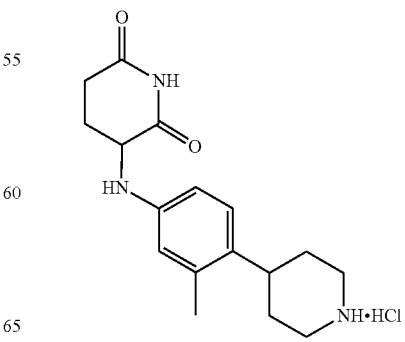

Tert-butyl 4-[4-[(2,6-dioxo-3-piperidyl)amino]-2-methylphenyl]piperidine-1-carboxylate (180 mg, 448.32 µmol) was dissolved in methanol (3 mL) and Hydrogen chloride solution 4.0M in dioxane (4 M, 1.12 mL) was added. The reaction mixture was heated at 40° C. for 4 hours, and the reaction was complete. The volatiles were evaporated under reduce pressure. The material was submitted to high vacuum, frozen to −78° C. and thawed to afford 3-[3-methyl-4-(4-piperidyl)anilino]piperidine-2,6-dione hydrochloride (145 mg, 429.19 µmol, 95.73% yield) as a dense solid. LCMS (ESI+): 302.3 (M+H).

Synthesis of 4-[3-(2,4-dioxohexahydropyrimidin-1-yl)-1-methyl-indazol-6-yl]-3,3-difluoro-piperidine hydrochloride Step 1: Synthesis of tert-butyl 3,3-difluoro-4-(trifluoromethylsulfonyloxy)-2,6-dihydropyridine-1-carboxylate

N,N-diethylethanamine (3.23 g, 31.9 mmol, 4.44 mL, followed by trifluoromethylsulfonic anhydride (4.50 g, 15.9 mmol, 2.68 mL) were added drop-wise to a stirred solution of tert-butyl 3,3-difluoro-4-oxo-piperidine-1-carboxylate (2.5 g, 10.6 mmol) in dichloromethane (25 mL) at 0° C. The reaction was stirred at ambient temperature for 16 h. Then, the reaction was quenched with aqueous NaHCO₃, and extracted with dichloromethane, washed with brine, dried over Na₂SO₄, and concentrated. The residue was purified by silica gel chromatography (100% hexanes to 4:1 hexanes:ethyl acetate) to yield tert-butyl 3,3-difluoro-4-(trifluoromethylsulfonyloxy)-2,6-dihydropyridine-1-carboxylate (1.2 g, 2.29 mmol, 21% yield). ¹H NMR (400 MHz, Methanol-d4) δ 6.59 (s, 1H), 4.29 (q, J=4.3 Hz, 2H), 4.04 (t, J=11.0 Hz, 2H), 1.51 (s, 9H).

Step 2: 1-[1-methyl-6-(4,4,5,5-tetramethyl-1,3,2-dioxaborolan-2-yl)indazol-3-yl]hexahydropyrimidine-2,4-dione

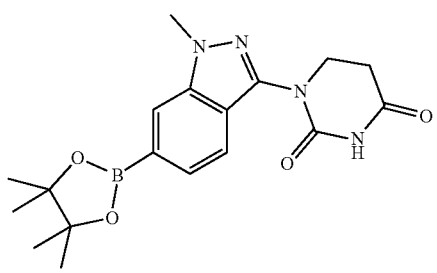 [SMILES: Cn1nc(N2CCC(=O)NC2=O)c2ccc(B3OC(C)(C)C(C)(C)O3)cc21]

Potassium acetate (911 mg, 9.28 mmol) and Pd(dppf)Cl₂ (113 mg, 155 µmol) were added to a solution of 1-(6-bromo-1-methyl-indazol-3-yl)hexahydropyrimidine-2,4-dione (1.0 g, 3.09 mmol) and bis(pinacolato)diboron (1.18 g, 4.64 mmol) in dioxane (15 mL). The mixture was stirred at 85° C. under a nitrogen atmosphere for 16 h. The mixture was cooled to ambient temperature and filtered through a pad of silica gel. The filter cake was washed with ethyl acetate and the filtrate was concentrated under reduced pressure. The residue was purified by silica gel chromatography (100% hexanes to 100% ethyl acetate) to yield 1-[1-methyl-6-(4,4,5,5-tetramethyl-1,3,2-dioxaborolan-2-yl)indazol-3-yl]hexahydropyrimidine-2,4-dione (1.1 g, 2.97 mmol, 96% yield). LCMS (ESI+): 371 (M+H).

Step 3: tert-Butyl 4-(3-(2,4-dioxotetrahydropyrimidin-1(2H)-yl)-1-methyl-1H-indazol-6-yl)-3,3-difluoro-3,6-dihydropyridine-1(2H)-carboxylate

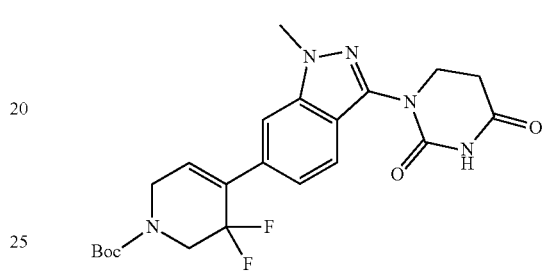

Sodium carbonate (485 mg, 4.57 mmol) was added to a solution of 1-[1-methyl-6-(4,4,5,5-tetramethyl-1,3,2-dioxaborolan-2-yl)indazol-3-yl]hexahydropyrimidine-2,4-dione (677 mg, 1.83 mmol) and tert-butyl 3,3-difluoro-4-(trifluoromethylsulfonyloxy)-2,6-dihydropyridine-1-carboxylate (560 mg, 1.52 mmol) in dioxane (10 mL) and water (2.5 mL) and the solvent was sparged with N₂ gas for 10 min. 1,1′-Bis(Diphenylphosphino)ferrocenepalladium (II) dichloride (111 mg, 152 µmol) was added and the reaction mixture was stirred at 55° C. for 2 h. Then, the reaction mixture was cooled and diluted with water/ethyl acetate. After extraction, organic layer was washed with brine, dried over Na₂SO₄, and concentrated. The residue was purified by silica gel chromatography (100% hexanes to 100% ethyl acetate) to give tert-butyl 4-[3-(2,4-dioxohexahydropyrimidin-1-yl)-1-methyl-indazol-6-yl]-3,3-difluoro-2,6-dihydropyridine-1-carboxylate (480 mg, 1.04 mmol, 68% yield). LCMS (ESI+): 462.2 (M+H)

Step 4: tert-butyl 4-[3-(2,4-dioxohexahydropyrimidin-1-yl)-1-methyl-indazol-6-yl]-3,3-difluoro-piperidine-1-carboxylate

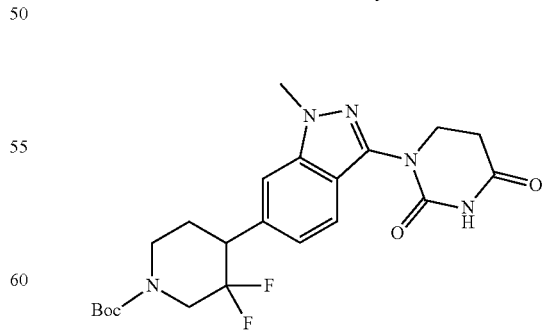

Palladium, 10% on carbon (Type 487, dry, 331 mg, 311 µmol) was added to a solution of tert-butyl 4-[3-(2,4-dioxohexahydropyrimidin-1-yl)-1-methyl-indazol-6-yl]-3,3-difluoro-2,6-dihydropyridine-1-carboxylate (478 mg, 1.04 mmol) in methanol (10.3 mL) and the mixture was stirred at ambient temperature under a hydrogen balloon atmosphere. After 24 h, the hydrogen balloon was removed and the mixture was diluted with dichloromethane (20 mL) and the slurry was stirred for additional 24 h. Then, the mixture was filtered through a pad of celite, washed using a solution of dichloromethane/methanol (3:1), and concentrated to afford tert-butyl 4-[3-(2,4-dioxohexahydropyrimidin-1-yl)-1-methyl-indazol-6-yl]-3,3-difluoro-piperidine-1-carboxylate (450 mg, 94% yield). LCMS (ESI+): 408.2 (M-tert-butyl+H).

Step 5: 4-[3-(2,4-dioxohexahydropyrimidin-1-yl)-1-methyl-indazol-6-yl]-3,3-difluoro-piperidine hydrochloride

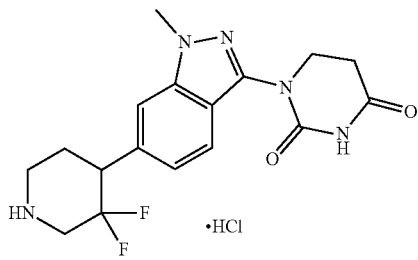 [SMILES: Cn1nc(N2CCC(=O)NC2=O)c2ccc(C3CCNCC3(F)F)cc21 ; Cl]

4-[3-(2,4-dioxohexahydropyrimidin-1-yl)-1-methyl-indazol-6-yl]-3,3-difluoro-piperidine hydrochloride was obtained in quantitative yield from tert-butyl 4-[3-(2,4-dioxohexahydropyrimidin-1-yl)-1-methyl-indazol-6-yl]-3,3-difluoro-piperidine-1-carboxylate using General method B for the removal of the tert-butoxycarbonyl group. LCMS (ESI+): 354.2 (M+H)

Synthesis of tert-butyl 3,3-difluoro-4-(4-nitrophenyl)piperidine-1-carboxylate, isomer 1 and tert-butyl 3,3-difluoro-4-(4-nitrophenyl)piperidine-1-carboxylate, isomer 2

Step 1: Synthesis of tert-butyl 4-(4-nitrophenyl)-3-oxo-piperidine-1-carboxylate

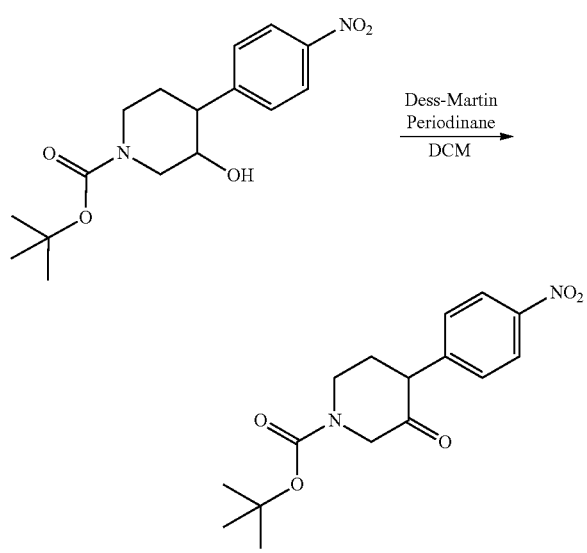

tert-Butyl 3-hydroxy-4-(4-nitrophenyl)piperidine-1-carboxylate (19.5 g, 60.5 mmol) (CAS #1232788-17-8) was dissolved in dichloromethane (200 mL) and cooled to 0° C. Dess-Martin Periodinane (38.5 g, 90.7 mmol) was added portion-wise. Internal temperature increased from 0 to 2.2° C. during the initial addition. The reaction solution was stirred at that temperature for 2 h and stirring was continued while the temperature gradually climbed up to ambient temperature. After 17 h, the reaction solution became a slurry due to some solvent evaporation. Dichloromethane (100 mL) was added, followed by Dess-Martin Periodinane (8.3 g, 19.6 mmol) at 16° C. and the reaction was stirred for 17 h. The reaction solution was cooled back down to 4° C. Saturated NaHCO₃ solution (250 mL) was carefully added, followed by sodium thiosulfate pentahydrate (13.8 g, 48.4 mmol) dissolved in 175 mL of water. The mixture was diluted with dichloromethane (150 mL). The resulting precipitate was removed by filtration and the cake was washed with dichloromethane (75 mL×3). The filtrate was separated into layers and the organic layer was dried over $Na_2SO_4$, filtered and concentrated to afford tert-butyl 4-(4-nitrophenyl)-3-oxo-piperidine-1-carboxylate (19.4 g, 60.5 mmol, quantitative yield). LCMS (ESI+): 354.1 (M+Na)/221.0 (M-Boc+H).

Step 2: Synthesis of tert-butyl 3,3-difluoro-4-(4-nitrophenyl)piperidine-1-carboxylate

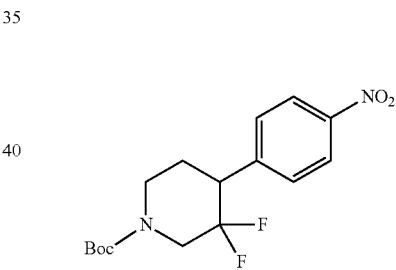

tert-Butyl 4-(4-nitrophenyl)-3-oxo-piperidine-1-carboxylate (3.78 g, 11.8 mmol) was dissolved in dichloromethane (40 mL) and the solution was cooled to 0° C. DAST (3.80 g, 23.6 mmol, 3.12 mL) was added slowly via a syringe. The reaction mixture was warmed slowly to room temperature while it was stirred overnight. The reaction solution was cooled to −1.3° C. and saturated aqueous NaHCO₃ (100 mL) was added carefully via an addition funnel (exothermic). Internal temperature was maintained below 18° C. during the addition. The reaction mixture was diluted with ethyl acetate (80 mL) and warmed up to ambient temperature. The layers were separated and the aqueous layer was washed with ethyl acetate (80 mL). The combined organics were washed with aqueous 18% NaCl solution and concentrated. The residue was purified by silica gel chromatography (gradient: 10-30% ethyl acetate in hexanes to afford tert-butyl 3,3-difluoro-4-(4-nitrophenyl)piperidine-1-carboxylate (2.50 g, 62% yield) LCMS (ESI+): 280.2 (M-tert-Butyl+H)/243.1 (M-Boc+H).

Step 3: Chiral separation to obtain tert-butyl 3,3-difluoro-4-(4-nitrophenyl)piperidine-1-carboxylate, isomer 1 and tert-butyl 3,3-difluoro-4-(4-nitrophenyl)piperidine-1-carboxylate, isomer 2

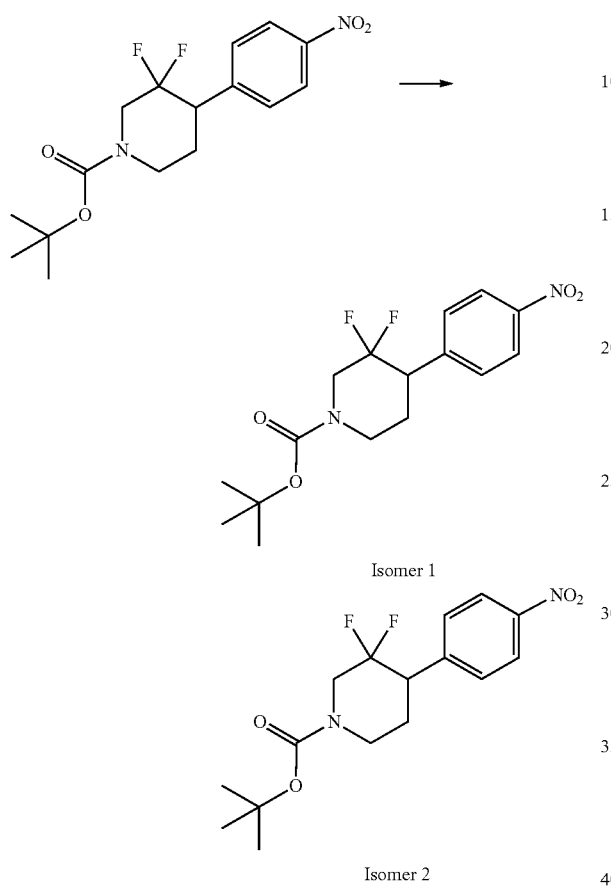

Isomer 1

Isomer 2

Racemic tert-butyl 3,3-difluoro-4-(4-nitrophenyl)piperidine-1-carboxylate (2.49 g) was subjected to a Chiral SFC separation, under the following conditions:
Column: ChiralPak IC-H 21×250 mm
Mobile Phase: 10% 2-propanol in carbon dioxide.
Flow rate: 70 mL/min
Detection: 220 nm UV
Pressure: 100 bar The first eluting set of fractions was evaporated under reduced pressure to afford tert-butyl 3,3-difluoro-4-(4-nitrophenyl)piperidine-1-carboxylate, isomer 1 (800 mg, 32% yield, Rt=1.74 min, >99% enantiomeric excess) LCMS: 280.2 (M-tBu+H)/243.1 (M-Boc+H).

The second eluting set of fractions was evaporated under reduced pressure to afford tert-butyl 3,3-difluoro-4-(4-nitrophenyl)piperidine-1-carboxylate, isomer 2 (800 mg, 32% yield, Rt=2.31 min., 99.6% enantiomeric excess). LCMS 280.2 (M-tert-Butyl+H)/243.1 (M-Boc+H).

The enantiomeric excess of the purified enantiomers was determined using the following analytical SFC method.
Column: ChiralPak IC-H 4.6×100 mm
Mobile phase: 10% iso-propanol in carbon dioxide
Flow rate: 4 mL/min
Pressure: 100 bar

Synthesis of 3-[4-[3,3-difluoro-4-piperidyl]anilino]piperidine-2,6-dione dihydrochloride, isomer 1

Step 1: tert-butyl-4-(4-aminophenyl)-3,3-difluoro-piperidine-1-carboxylate, isomer 1

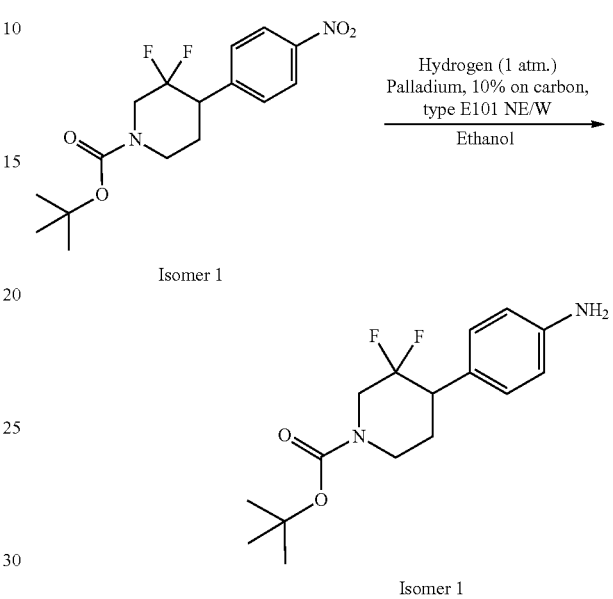

Isomer 1

Isomer 1 tert-Butyl 3,3-difluoro-4-(4-nitrophenyl)piperidine-1-carboxylate, isomer 1 (0.8 g, 2.34 mmol) was dissolved in ethanol (12 mL) and the solution was degassed with nitrogen. Palladium, 10% on carbon, type E101 NE/W (125 mg, 1.17 mmol) was then added. After degassing again with nitrogen couple, the reaction mixture was stirred under a hydrogen balloon atmosphere for 16 h. The reaction mixture was filtered through a pad of celite, washed with ethyl acetate (12 mL×3) and the filtrate was concentrated to yield tert-butyl-4-(4-aminophenyl)-3,3-difluoro-piperidine-1-carboxylate, isomer 1 (722 mg, 98% yield). LCMS (ESI+): 257 (M-tBu+H)

Step 2: tert-butyl (4S)-4-[4-[(2,6-dioxo-3-piperidyl)amino]phenyl]-3,3-difluoro-piperidine-1-carboxylate, isomer 1

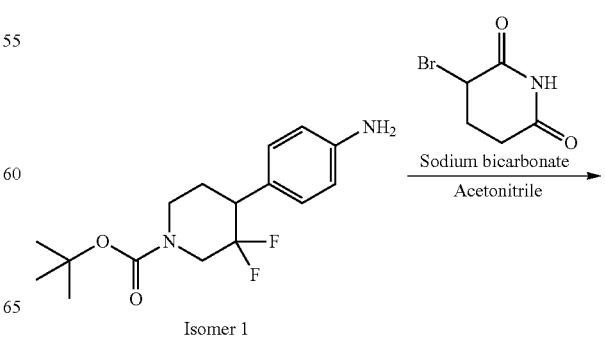

Isomer 1

-continued

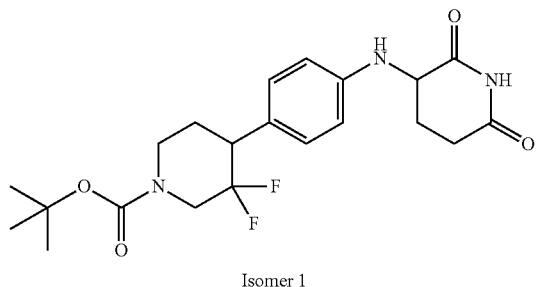

Isomer 1

Acetonitrile (3.5 mL) was added to tert-Butyl 4-(4-aminophenyl)-3,3-difluoro-piperidine-1-carboxylate, isomer 1 (520 mg, 1.66 mmol), 3-bromopiperidine-2,6-dione (478 mg, 2.49 mmol) and NaHCO$_3$ (418 mg, 4.98 mmol) in a vial. The reaction mixture was heated to 70° C. for 45 h. 3-bromopiperidine-2,6-dione (92 mg, 0.28 equiv) and NaHCO$_3$ (110 mg, 0.78 equiv) were added and heating was continued for a further 72 h, at which point, the reaction was cooled to ambient temperature and water (18 mL) was slowly added. The mixture was stirred for 4 h, then the precipitate was collected by filtration, washing with water (10 mL×3), then with 9:1 hexane:ethyl acetate (5 mL×3). The filter cake was dried under vacuum to afford tert-butyl 4-[4-[(2,6-dioxo-3-piperidyl)amino]phenyl]-3,3-difluoro-piperidine-1-carboxylate, isomer 1 (577 mg, 78% yield) as a green solid. LCMS (ESI+): 446 (M+Na)

Step 3: 3-[4-[3,3-difluoro-4-piperidyl]anilino]piperidine-2,6-dione dihydrochloride, isomer 1

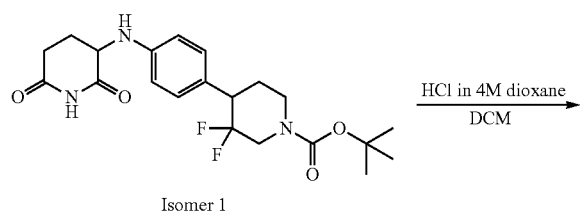

Isomer 1

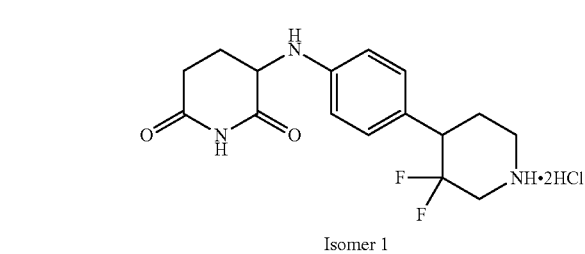

Isomer 1

Tert-butyl 4-[4-[(2,6-dioxo-3-piperidyl)amino]phenyl]-3,3-difluoro-piperidine-1-carboxylate, isomer 1 (300 mg, 709 μmol), was dissolved in dichloromethane (3.4 mL), and hydrogen chloride (4M in 1,4-dioxane, 850 μL, 3.4 mmol) was added under stirring. After 1 hour, the reaction mixture was concentrated to afford 3-[4-[3,3-difluoro-4-piperidyl]anilino]piperidine-2,6-dione dihydrochloride, isomer 1 in quantitative yield. LCMS (ESI+): 324 (M+H).

Synthesis of 3-[4-[3,3-difluoro-4-piperidyl]anilino]piperidine-2,6-dione dihydrochloride, isomer 2

Step 1: Synthesis of tert-butyl-4-(4-aminophenyl)-3,3-difluoro-piperidine-1-carboxylate, isomer 2

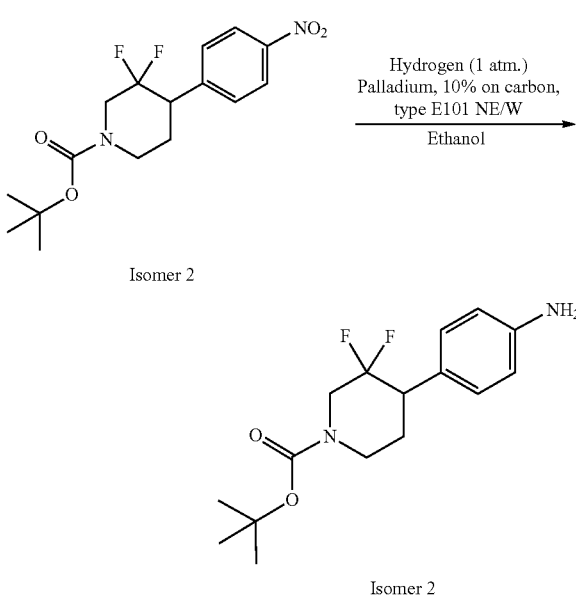

Isomer 2

Tert-butyl 3,3-difluoro-4-(4-nitrophenyl)piperidine-1-carboxylate, isomer 2 (800 mg, 2.34 mmol) was dissolved in Ethanol (12 mL). The solution was evacuated and backfilled with nitrogen couple times. Palladium, 10% on carbon, type E101 NE/W (124.35 mg, 1.17 mmol) was then added. After evacuated and backfilled with nitrogen couple more times, the reaction mixture was subjected to hydrogenation (H2 balloon) at ambient temperature for 16 hours. The reaction mixture was filtered through a pad of Celite. The celite cake was washed with ethyl acetate (12 mL×3). The filtrate was concentrated in vacuo and further dried under vacuum to yield a semi-solid (oily) upon standing; tert-butyl-4-(4-aminophenyl)-3,3-difluoro-piperidine-1-carboxylate, isomer 2 (724 mg, 94% yield). LCMS (ESI+): 257.1 (M-tBu+H)

Step 2: Synthesis of 4-[4-[(2,6-dioxo-3-piperidyl)amino]phenyl]-3,3-difluoro-piperidine-1-carboxylate, isomer 2

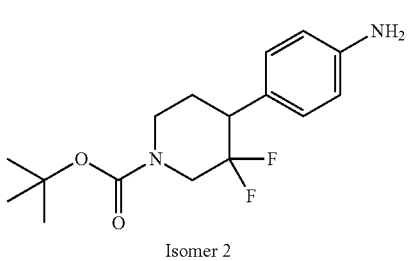

Isomer 2           +

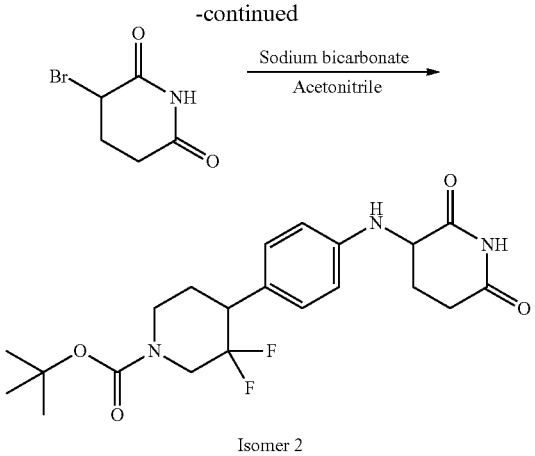

Isomer 2

To a vial was added tert-butyl 4-(4-aminophenyl)-3,3-difluoro-piperidine-1-carboxylate, isomer 2 (721.54 mg, 2.31 mmol), 3-bromopiperidine-2,6-dione (665.32 mg, 3.47 mmol), and Sodium bicarbonate (582.19 mg, 6.93 mmol, 269.53 µL). Added Acetonitrile (5 mL). Reaction mixture was warmed to 70° C. (block temperature) overnight. After 48 hours, added additional amount of 3-bromopiperidine-2,6-dione (129 mg, 0.28 equiv), NaHCO$_3$ (129 mg, 0.66 equiv). After another 72 hours, cooled to ambient temperature. Water (25 mL) was added slowly. Stirred at ambient temperature for couple hours. Reaction mixture was filtered to collect solid. Washed with water (12 mL×3), 9:1 hexane:ethyl acetate (5 mL×2), and dried under vacuum to afford tert-butyl 4-[4-[(2,6-dioxo-3-piperidyl)amino]phenyl]-3,3-difluoro-piperidine-1-carboxylate, isomer 2 (838 mg, 81.4% yield) as a green solid. LCMS (ESI+): 446.4 (M+Na)

Step 3: Synthesis of 3-[4-[3,3-difluoro-4-piperidyl]anilino]piperidine-2,6-dione dihydrochloride, isomer 2

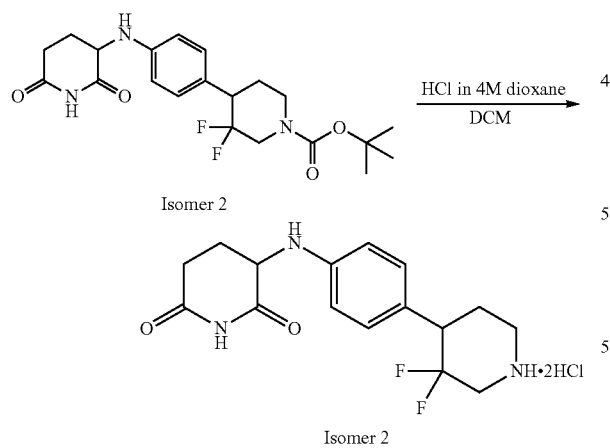

Isomer 2

Tert-butyl 4-[4-[(2,6-dioxo-3-piperidyl)amino]phenyl]-3,3-difluoro-piperidine-1-carboxylate, isomer 2 (300 mg, 708.5 µmol), was dissolved in Dichloromethane (3.4 mL), and hydrogen chloride (4M in 1,4-dioxane, 850 µL, 3.4 mmol) was added under stirring. After 1 hour, the reaction mixture was evaporated to dryness under reduced pressure to afford 3-[4-[3,3-difluoro-4-piperidyl]anilino]piperidine-2,6-dione dihydrochloride, isomer 2 in quantitative yield. LCMS (ESI+): 324.1 (M+H) Synthesis of 2-[1-[4-[(2,6-dioxo-3-piperidyl)amino]-2-(trifluoromethyl)phenyl]-4-hydroxy-4-piperidyl]acetic acid Step 1: tert-butyl 2-[4-hydroxy-1-[4-nitro-2-(trifluoromethyl)phenyl]-4-piperidyl]acetate

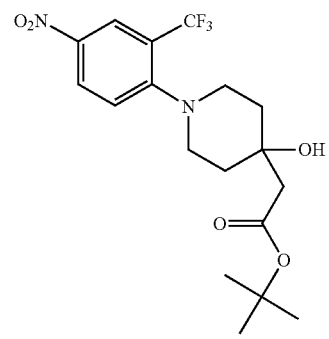 [SMILES: CC(C)(C)OC(=O)CC1(O)CCN(c2ccc(N)cc2C(F)(F)F)CC1]

Lithium diisopropylamide (0.7 M in THF, 54 mL, 37.82 mmol) was added dropwise over a period of 10 min to a stirred solution of tert-butyl acetate (1.76 g, 15.1 mmol, 2.04 mL) in dry THF (40 ml) at −78° C. The reaction mixture was stirred for 1 h. 1-[4-nitro-2-(trifluoromethyl)phenyl]piperidin-4-one (4.36 g, 15.1 mmol) dissolved in THF (20 ml) was added slowly. The reaction was stirred for 1 h at −78° C. The reaction was quenched with aqueous ammonium chloride solution at −78° C. and the mixture was warmed to ambient temperature and extracted with ethyl acetate. The organic layer was washed with brine and concentrated to afford a residue which was used without further purification. LCMS (ESI−): m/z 403.1 [M−H$^+$].

Step 2: tert-butyl 2-[1-[4-amino-2-(trifluoromethyl)phenyl]-4-hydroxy-4-piperidyl]acetate

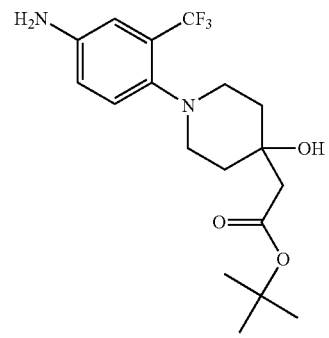

A stirred solution of tert-butyl 2-[4-hydroxy-1-[4-nitro-2-(trifluoromethyl)phenyl]-4-piperidyl]acetate (2 g, 4.95 mmol) in a ethyl acetate (40 mL) was purged with nitrogen for 5 min. Pd/C, 10% on dry basis (1.05 g, 9.89 mmol) was added to the reaction mixture. The reaction mixture was placed under an hydrogen atmosphere (balloon). The reaction mixture was stirred for 4 h. The reaction mixture was filtered through a celite bed by flushing with a dichloromethane:ethyl acetate mixture (1:1, 500 mL). The filtrate was concentrated under reduced pressure to afford brownish solid was dissolved in dichloromethane (20 mL) and dry packed on silica under reduced pressure. The compound was purified by silica gel (230-400 mesh) column chromatography using a ethyl acetate:petroleum ether. The pure fractions were combined and concentrated under reduced pressure to afford pure reddish-brown solid tert-butyl 2-[1-[4-amino-2-(trifluoromethyl)phenyl]-4-hydroxy-4-piperidyl]acetate (1.1 g, 1.96 mmol, 40% yield). LCMS (m/z: 375.2 (M+H$^+$)).

Step 3: tert-butyl 2-[1-[4-[(2,6-dioxo-3-piperidyl)amino]-2-(trifluoromethyl)phenyl]-4-hydroxy-4-piperidyl]acetate

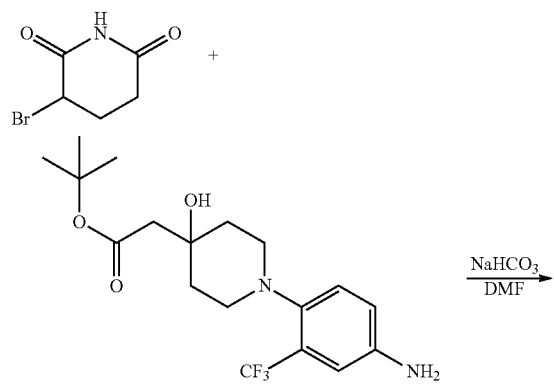

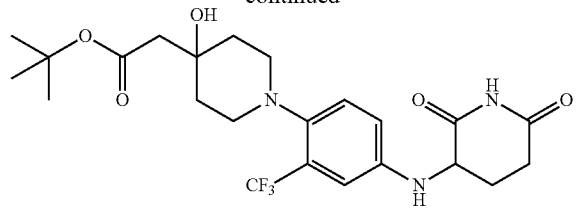

To a stirred solution of tert-butyl 2-[1-[4-amino-2-(trifluoromethyl)phenyl]-4-hydroxy-4-piperidyl]acetate (1.1 g, 2.94 mmol) and 3-bromopiperidine-2,6-dione (846.21 mg, 4.41 mmol) in DMF (10 mL) was added sodium bicarbonate (740.45 mg, 8.81 mmol) at room temperature, after 10 min the temperature of the reaction was raised to 60° C. and continued the reaction about 12 hr. The reaction mixture was diluted with ice-cold water (20 mL) and extracted by ethyl acetate (2*100 mL), washed with brine (10 mL), dried over anhydrous Na2SO4, filtered and concentrated under reduced pressure. The crude product was purified using silica gel chromatography using a 10% to 100% Ethyl acetate in Petroleum ether eluent gradient. The pure fractions were combined and concentrated under reduced pressure to afford tert-butyl 2-[1-[4-[(2,6-dioxo-3-piperidyl)amino]-2-(trifluoromethyl)phenyl]-4-hydroxy-4-piperidyl]acetate (300 mg, 468.45 μmol, 16% yield) as a brownish-green solid. LCMS (ESI+) m/z: 486.2 (M+H$^+$).

Step 4: Synthesis of 2-[1-[4-[(2,6-dioxo-3-piperidyl)amino]-2-(trifluoromethyl)phenyl]-4-hydroxy-4-piperidyl]acetic acid

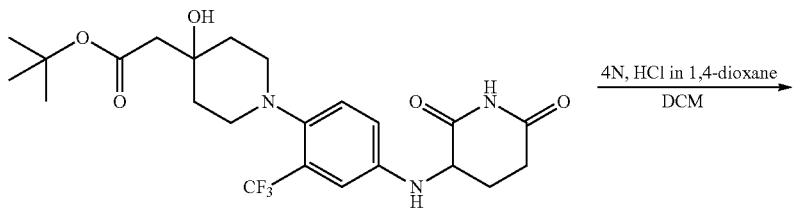

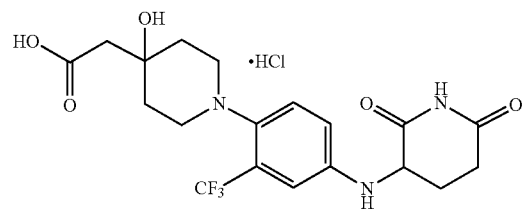

To a stirred solution of tert-butyl 2-[1-[4-[(2,6-dioxo-3-piperidyl)amino]-2-(trifluoromethyl)phenyl]-4-hydroxy-4-piperidyl]acetate (620 mg, 1.28 mmol) in dichloromethane (3 mL) was added hydrogen chloride (4M in 1,4-dioxane, 0.32 mL, 6.39 mmol) dropwise at 0° C. under nitrogen atmosphere, it was stirred for 6 h at room temperature. The reaction mixture was distilled under vacuum and triturated with diethyl ether, decanted the diethyl ether then dried to afford 2-[1-[4-[(2,6-dioxo-3-piperidyl)amino]-2-(trifluoromethyl)phenyl]-4-hydroxy-4-piperidyl]acetic acid (345 mg, 661 μmol, 52% yield) as a green colored solid. LCMS (m/z: 430.1 (M+H)) General procedure C for the alkylation of intermediates with tert-butyl 2-bromoacetate:

Synthesis of tert-butyl 2-[4-[4-[(2,6-dioxo-3-piperidyl)amino]phenyl]-1-piperidyl]acetate

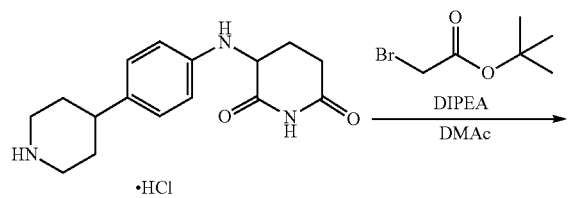

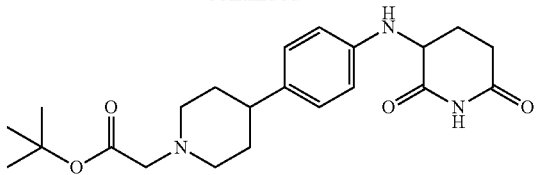

3-[4-(4-piperidyl)anilino]piperidine-2,6-dione hydrochloride (1 g, 3.09 mmol) was dissolved in N,N-dimethyl acetamide (15 mL) and N,N-diisopropyl ethyl amine (1.60 g, 12.4 mmol, 2.15 mL) was added. The mixture was cooled to 0° C., and tert-butyl 2-bromoacetate (663 mg, 3.40 mmol, 498 μL) was added. The mixture was stirred at 0° C. for 4 h. The reaction was diluted with ethyl acetate and washed with saturated sodium bicarbonate and brine. The organic layer was concentrated and purified by silica gel chromatography (0-10% Methanol in dichloromethane) to yield tert-butyl 2-[4-[4-[(2,6-dioxo-3-piperidyl)amino]phenyl]-1-piperidyl]acetate (0.84 g, 2.09 mmol, 680 yield) as a white solid. LCMS (ESI+): 402.2 (M+H$^+$)

The following compounds were synthesized using General procedure C, as that used for the synthesis of tert-butyl 2-[4-[4-[(2,6-dioxo-3-piperidyl)amino]phenyl]-1-piperidyl]acetate from 3-[4-(4-piperidyl)anilino]piperidine-2,6-dione hydrochloride.

| Starting material | Product | LCMS (ESI+) m/z | % Yield |
|---|---|---|---|
| 3-((6-(piperidin-4-yl)pyridin-3-yl)amino)piperidine-2,6-dione hydrochloride | tert-butyl 2-(4-(5-((2,6-dioxopiperidin-3-yl)amino)pyridin-2-yl)piperidin-1-yl)acetate | 347.2 [M − tBu + 1] | 73% |
| 3-((3-fluoro-4-(piperidin-4-yl)phenyl)amino)piperidine-2,6-dione hydrochloride | tert-butyl 2-(4-(4-((2,6-dioxopiperidin-3-yl)amino)-2-fluorophenyl)piperidin-1-yl)acetate | 420.2 (M + 1) | 72% |
| 3-((2-fluoro-4-(piperidin-4-yl)phenyl)amino)piperidine-2,6-dione hydrochloride | tert-butyl 2-(4-(4-((2,6-dioxopiperidin-3-yl)amino)-3-fluorophenyl)piperidin-1-yl)acetate | 420.2 (M + 1) | 65% |

-continued

| Starting material | Product | LCMS (ESI+) m/z | % Yield |
|---|---|---|---|
| 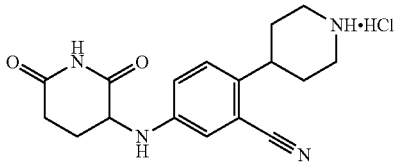 5-((2,6-dioxopiperidin-3-yl)amino)-2-(piperidin-4-yl)benzonitrile hydrochloride | 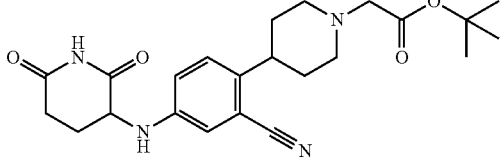 tert-butyl 2-(4-(2-cyano-4-((2,6-dioxopiperidin-3-yl)amino)phenyl)piperidin-1-yl)acetate | 427 (M + H) | 82% |
| 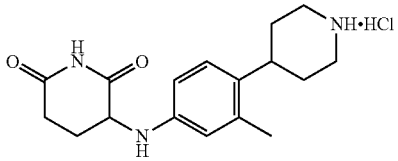 3-((3-methyl-4-(piperidin-4-yl)phenyl)amino)piperidine-2,6-dione hydrochloride | 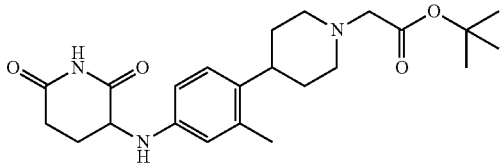 [SMILES: Cc1cc(NC2CCC(=O)NC2=O)ccc1C1CCN(CC(=O)OC(C)(C)C)CC1] tert-butyl 2-(4-(4-((2,6-dioxopiperidin-3-yl)amino)-2-methylphenyl)piperidin-1-yl)acetate | 416.3 (M + H) | 75% |
| 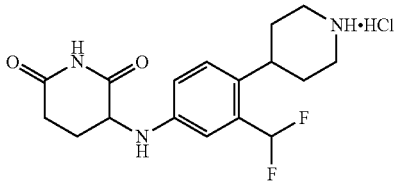 3-((3-(difluoromethyl)-4-(piperidin-4-yl)phenyl)amino)piperidine-2,6-dione hydrochloride | 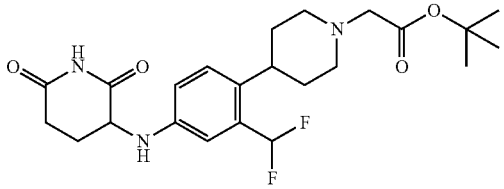 [SMILES: CC(C)(C)OC(=O)CN1CCC(c2ccc(NC3CCC(=O)NC3=O)cc2C(F)F)CC1] tert-butyl 2-(4-(2-(difluoromethyl)-4-((2,6-dioxopiperidin-3-yl)amino)phenyl)piperidin-1-yl)acetate | 452.2 (M + H) | 68% |
| 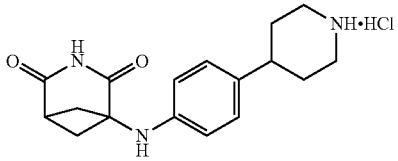 1-((4-(piperidin-4-yl)phenyl)amino)-3-azabicyclo[3.1.1]heptane-2,4-dione hydrochloride | 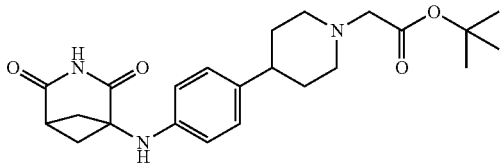 [SMILES: CC(C)(C)OC(=O)CN1CCC(c2ccc(NC34CC(C3)C(=O)NC4=O)cc2)CC1] tert-Butyl 2-(4-(4-((2,4-dioxo-3-azabicyclo[3.1.1]heptan-1-yl)amino)phenyl)piperidin-1-yl)acetate | 414.51 [M + H] | 57% |
| 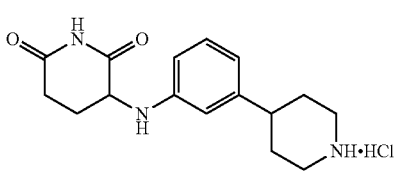 3-((3-(piperidin-4-yl)phenyl)amino)piperidine-2,6-dione hydrochloride | 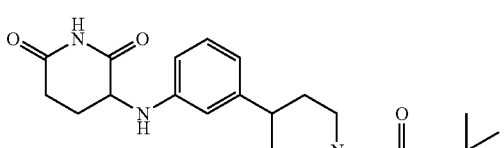 tert-butyl 2-(4-(3-((2,6-dioxopiperidin-3-yl)amino)phenyl)piperidin-1-yl)acetate | 402.1 [M + H] | 24% |

-continued

| Starting material | Product | LCMS (ESI+) m/z | % Yield |
|---|---|---|---|
| 1-(1-methyl-6-(piperidin-4-yl)-1H-indazol-3-yl)dihydropyrimidine-2,4(1H,3H)-dione hydrochloride | tert-butyl 2-(4-(3-(2,4-dioxotetrahydropyrimidin-1(2H)-yl)-1-methyl-1H-indazol-6-yl)piperidin-1-yl)acetate | 442.3 (M + H) | 75% |
| 1-(6-(3,3-difluoropiperidin-4-yl)-1-methyl-1H-indazol-3-yl)dihydropyrimidine-2,4(1H,3H)-dione hydrochloride | tert butyl 2-(4-(3-(2,4-dioxotetrahydropyrimidin-1(2H)-yl)-1-methyl-1H-indazol-6-yl)-3,3-difluoropiperidin-1-yl)acetate | 478.5 (M + H) | 47% |
| (S)-3-((3-fluoro-4-(piperidin-4-yl)phenyl)amino)piperidine-2,6-dione hydrochloride | tert-butyl (S)-2-(4-(4-((2,6-dioxopiperidin-3-yl)amino)-2-fluorophenyl)piperidin-1-yl)acetate | 420.0 (M + H) | 68% |
| | | 420.2 (M + H) | 86.1% |

-continued

| Starting material | Product | LCMS (ESI+) m/z | % Yield |
|---|---|---|---|
| (R)-3-((3-fluoro-4-(piperidin-4-yl)phenyl)amino)piperidine-2,6-dione hydrochloride | tert-butyl (R)-2-(4-(4-((2,6-dioxopiperidin-3-yl)amino)-2-fluorophenyl)piperidin-1-yl)acetate | 438.2 (M + H) | 84% |
| 3-[4-[3,3-difluoro-4-piperidyl]anilino]piperidine-2,6-dione dihydrochloride, isomer 1 | tert-butyl 2-(4-(4-((2,6-dioxopiperidin-3-yl)amino)phenyl)-3,3-difluoropiperidin-1-yl)acetate, isomer 1 | 438.2 (M + H) | 87% |
| 3-[4-[3,3-difluoro-4-piperidyl]anilino]piperidine-2,6-dione dihydrochloride, isomer 2 | tert-butyl 2-(4-(4-((2,6-dioxopiperidin-3-yl)amino)phenyl)-3,3-difluoropiperidin-1-yl)acetate, isomer 2 | | |

General Procedure D for the Tert-Butyl Ester Cleavage of Intermediates: 2-[4-[4-[(2,6-dioxo-3-piperidyl)amino]phenyl]-1-piperidyl]acetic acid, trifluoroacetic acid salt

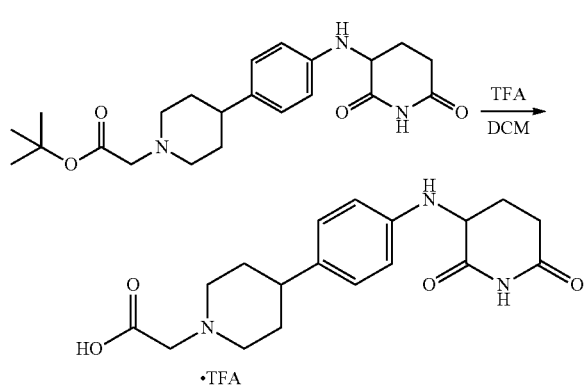

tert-Butyl 2-[4-[4-[(2,6-dioxo-3-piperidyl)amino]phenyl]-1-piperidyl]acetate was dissolved in dichloromethane (5 mL) and TFA (1.61 mL, 20.9 mmol) was added. The reaction mixture was heated at 40° C. for 4 h, and the reaction was complete. The volatiles were evaporated under reduce pressure. The material was frozen to −78° C., submitted to high vacuum, and thawed to afford a dense solid. The solid was re-dissolved in methanol:dicloromethane (1:4), MTBE was added dropwise, until a precipitate formed. The suspension was submitted to sonication, and the solid was filtered under suction. The green solid was collected by filtration to afford 2-[4-[4-[(2,6-dioxo-3-piperidyl)amino]phenyl]-1-piperidyl]acetic acid, trifluoroacetic acid salt (0.95 g, 2.07 mmol, 97% yield). LCMS (ESI+): 346.4 (M+H⁺) The following intermediates were synthesized from the appropriate starting materials using general procedure D for 2-[4-[4-[(2,6-dioxo-3-piperidyl)amino]phenyl]-1-piperidyl]acetic acid, trifluoroacetic acid salt synthesis.

| Starting material | Product | Yield | LCMS ESI+ m/z |
|---|---|---|---|
| 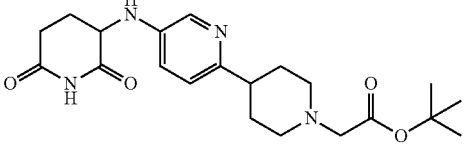<br>tert-butyl 2-(4-(5-((2,6-dioxopiperidin-3-yl)amino)pyridin-2-yl)piperidin-1-yl)acetate | 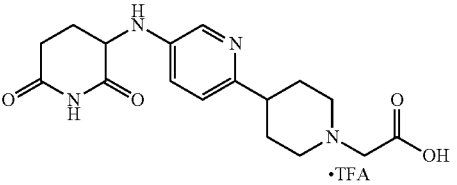 [SMILES: O=C(O)CN1CCC(c2ccc(NC3CCC(=O)NC3=O)cn2)CC1]<br>2-(4-(5-((2,6-dioxopiperidin-3-yl)amino)pyridin-2-yl)piperidin-1-yl)acetic acid | 72% | 347.2 (M + H) |
| 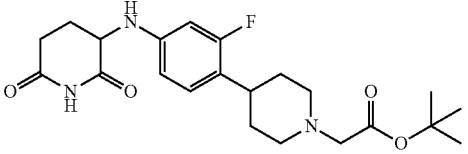 [SMILES: CC(C)(C)OC(=O)CN1CCC(c2ccc(NC3CCC(=O)NC3=O)cc2F)CC1]<br>tert-butyl 2-(4-(4-((2,6-dioxopiperidin-3-yl)amino)-2-fluorophenyl)piperidin-1-yl)acetate | 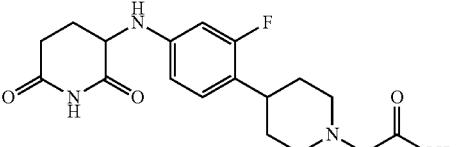<br>2-(4-(5-((2,6-dioxopiperidin-3-yl)amino)pyridin-2-yl)piperidin-1-yl)acetic acid | >98% | 364.2 (M + H) |
| 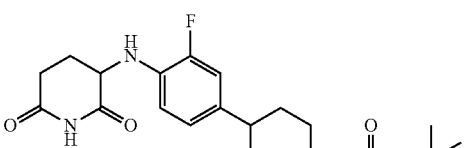<br>tert-butyl 2-(4-(4-((2,6-dioxopiperidin-3-yl)amino)-3-fluorophenyl)piperidin-1-yl)acetate | 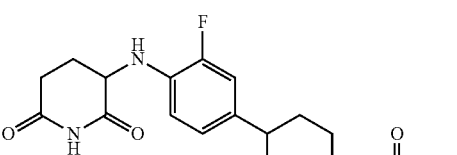<br>2-(4-(4-((2,6-dioxopiperidin-3-yl)amino)-3-fluorophenyl)piperidin-1-yl)acetic acid | >98% | 364.5 (M + H) |
| 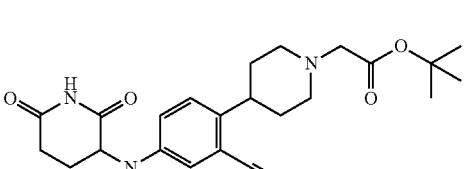<br>tert-butyl 2-(4-(2-cyano-4-((2,6-dioxopiperidin-3-yl)amino)phenyl)piperidin-1-yl)acetate | 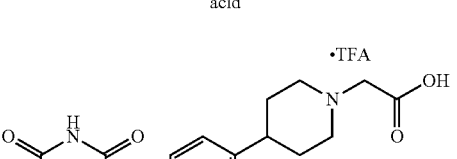<br>2-(4-(2-cyano-4-((2,6-dioxopiperidin-3-yl)amino)phenyl)piperidin-1-yl)acetic acid | >98% | 371.2 (M + H) |
| 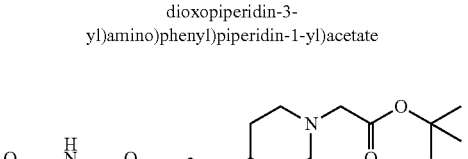<br>tert-butyl 2-(4-(4-((2,6-dioxopiperidin-3-yl)amino)-2-methylphenyl)piperidin-1-yl)acetate | 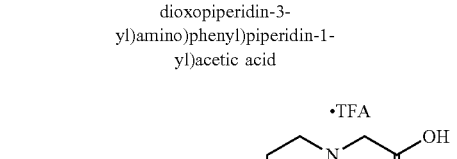<br>2-(4-(4-((2,6-dioxopiperidin-3-yl)amino)-2-methylphenyl)piperidin-1-yl)acetic acid | 86% | 360.3 (M + H) |

-continued

| Starting material | Product | Yield | LCMS ESI+ m/z |
|---|---|---|---|
| 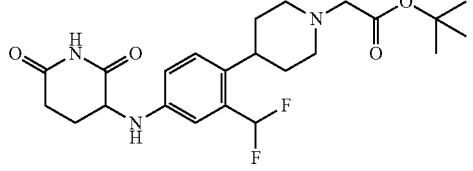<br>tert-butyl 2-(4-(2-(difluoromethyl)-4-((2,6-dioxopiperidin-3-yl)amino)phenyl)piperidin-1-yl)acetate | 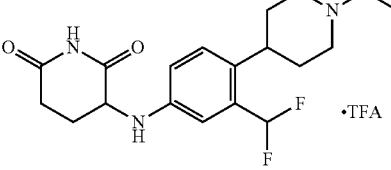<br>2-(4-(2-(difluoromethyl)-4-((2,6-dioxopiperidin-3-yl)amino)phenyl)piperidin-1-yl)acetic acid | 94% | 369.2 (M + H) |
| 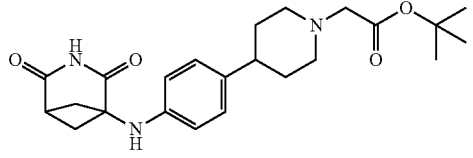 [SMILES: CC(C)(C)OC(=O)CN1CCC(c2ccc(NC34CC(C3)C(=O)NC4=O)cc2)CC1]<br>tert-butyl 2-(4-(4-((2,4-dioxo-3-azabicyclo[3.1.1]heptan-1-yl)amino)phenyl)piperidin-1-yl)acetate | 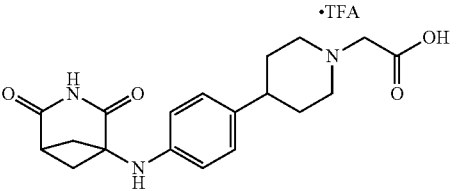 [SMILES: O=C(O)CN1CCC(c2ccc(NC34CC(C3)C(=O)NC4=O)cc2)CC1]<br>2-(4-(4-((2,4-dioxo-3-azabicyclo[3.1.1]heptan-1-yl)amino)phenyl)piperidin-1-yl)acetic acid | 73% | 358.1 (M + H) |
| 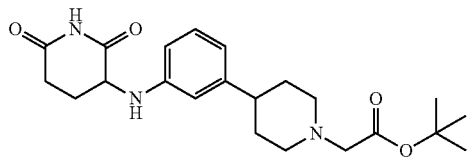 [SMILES: CC(C)(C)OC(=O)CN1CCC(c2cccc(NC3CCC(=O)NC3=O)c2)CC1]<br>tert-butyl 2-(4-(3-((2,6-dioxopiperidin-3-yl)amino)phenyl)piperidin-1-yl)acetate | 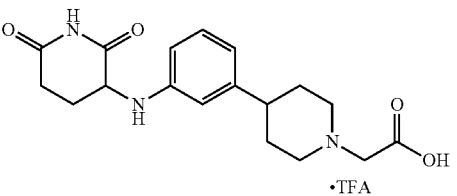 [SMILES: O=C(O)CN1CCC(c2cccc(NC3CCC(=O)NC3=O)c2)CC1]<br>2-(4-(3-((2,6-dioxopiperidin-3-yl)amino)phenyl)piperidin-1-yl)acetic acid | 91% | 346.7 (M + H) |
| 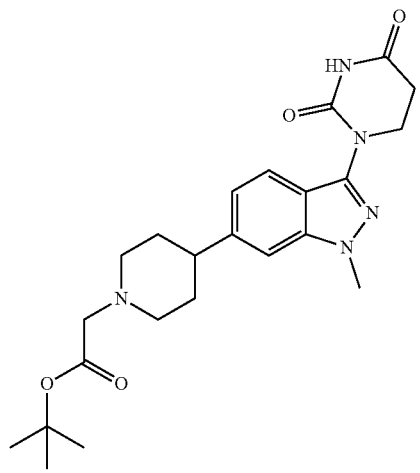 [SMILES: Cn1nc(N2CCC(=O)NC2=O)c2ccc(C3CCN(CC(=O)OC(C)(C)C)CC3)cc21]<br>tert-butyl 2-(4-(3-(2,4-dioxotetrahydropyrimidin-1(2H)-yl)-1-methyl-1H-indazol-6-yl)piperidin-1-yl)acetate | 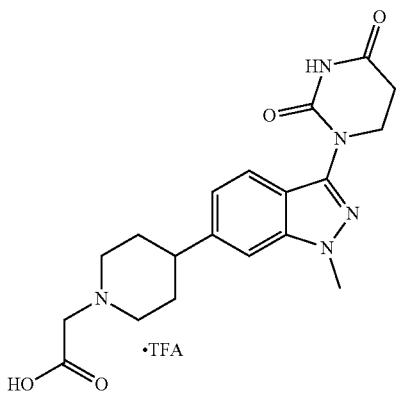 [SMILES: Cn1nc(N2CCC(=O)NC2=O)c2ccc(C3CCN(CC(=O)O)CC3)cc21]<br>2-(4-(3-(2,4-dioxotetrahydropyrimidin-1(2H)-yl)-1-methyl-1H-indazol-6-yl)piperidin-1-yl)acetic acid | 82% | 386.1 (M + H) |

| Starting material | Product | Yield | LCMS ESI+ m/z |
|---|---|---|---|
| tert-butyl (S)-2-(4-(4-((2,6-dioxopiperidin-3-yl)amino)-2-fluorophenyl)piperidin-1-yl)acetate | (S)-2-(4-(4-((2,6-dioxopiperidin-3-yl)amino)-2-fluorophenyl)piperidin-1-yl)acetic acid ·TFA | 93% | 364.1 [M + 1] |
| tert-butyl (R)-2-(4-(4-((2,6-dioxopiperidin-3-yl)amino)-2-fluorophenyl)piperidin-1-yl)acetate | (R)-2-(4-(4-((2,6-dioxopiperidin-3-yl)amino)-2-fluorophenyl)piperidin-1-yl)acetic acid ·TFA | 79% | 364.1 [M + 1] |

The enantiomeric excess for intermediate (S)-2-(4-(4-((2,6-dioxopiperidin-3-yl)amino)-2-fluorophenyl)piperidin-1-yl)acetic acid was measured at >99.900 ee (Rt=2.11 min.) using the following SFC method:

Column: Lux A1

Eluent: 50% Isopropanol with 0.5% isopropyl amine in $CO_2$ (isochratic)

Pressure: 100 bar

Temperature: 35° C.

Run time: 7 min

The enantiomeric excess for intermediate (R)-2-(4-(4-((2,6-dioxopiperidin-3-yl)amino)-2-fluorophenyl)piperidin-1-yl)acetic acid was measured at 98% ee (Rt=3.93 min.) using the following SFC method:

Column: Lux A1

Eluent: 50% Isopropanol with 0.5% isopropyl amine in $CO_2$ (isochratic)

Pressure: 100 bar

Temperature: 35° C.

Run time: 7 min

General Procedure E: Synthesis of 2-[4-[4-[(2,6-dioxo-3-piperidyl)amino]phenyl]-1-piperidyl]acetic acid hydrochloride

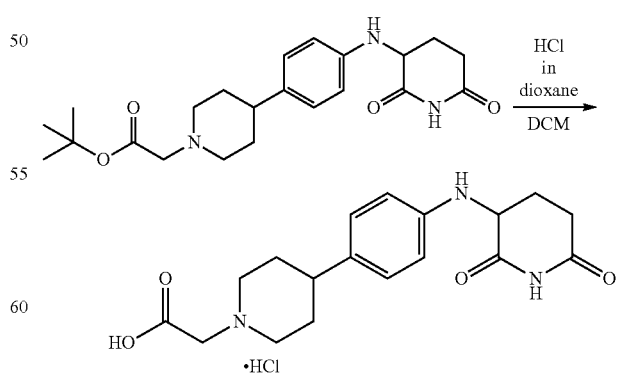

tert-Butyl 2-[4-[4-[(2,6-dioxo-3-piperidyl)amino]phenyl]-1-piperidyl]acetate (228 mg, 568 μmol) was dissolved in dichloromethane (2 mL) and 4M hydrochloric acid in 1,4

Dioxane (8 mmol, 2 mL) was added. The resulting mixture was stirred at room temperature for 4 h. The reaction mixture was concentrated under reduced pressure and the residue was triturated with diethyl ether and then filtered to afford 2-[4-[4-[(2,6-dioxo-3-piperidyl)amino]phenyl]-1-piperidyl] acetic acid hydrochloride (210 mg, 428 μmol) as grey solid. LCMS m/z: 345 (M+H$^+$).

The following intermediates were synthesized from the appropriate starting materials using the above General procedure E for 2-[4-[4-[(2,6-dioxo-3-piperidyl)amino]phenyl]-1-piperidyl]acetic acid hydrochloride synthesis

| Starting material | Intermediate | Yield | LCMS (ESI+) m/z |
|---|---|---|---|
| tert-butyl 2-(4-(3-(2,4-dioxotetrahydropyrimidin-1(2H)-yl)-1-methyl-1H-indazol-6-yl)-3,3-difluoropiperidin-1-yl)acetate | 2-(4-(3-(2,4-dioxotetrahydropyrimidin-1(2H)-yl)-1-methyl-1H-indazol-6-yl)-3,3-difluoropiperidin-1-yl)acetic acid hydrochloride | 90% | |
| Isomer 1<br>tert-butyl 2-(4-(4-((2,6-dioxopiperidin-3-yl)amino)phenyl)-3,3-difluoropiperidin-1-yl)acetate, isomer 1 | Isomer 1<br>2-(4-(4-((2,6-dioxopiperidin-3-yl)amino)phenyl)-3,3-difluoropiperidin-1-yl)acetic acid hydrochloride | >98% | 382.2 (M + H) |
| Isomer 2<br>tert-butyl 2-(4-(4-((2,6-dioxopiperidin-3-yl)amino)phenyl)-3,3-difluoropiperidin-1-yl)acetate, isomer 2 | Isomer 2<br>2-(4-(4-((2,6-dioxopiperidin-3-yl)amino)phenyl)-3,3-difluoropiperidin-1-yl)acetic acid hydrochloride | >98% | 382.2 (M + H) |

Synthesis of intermediate: Ethyl 2-amino-2-(6,7-dihydro-5H-pyrrolo[1,2-c]imidazol-1-yl)acetate dihydrochloride

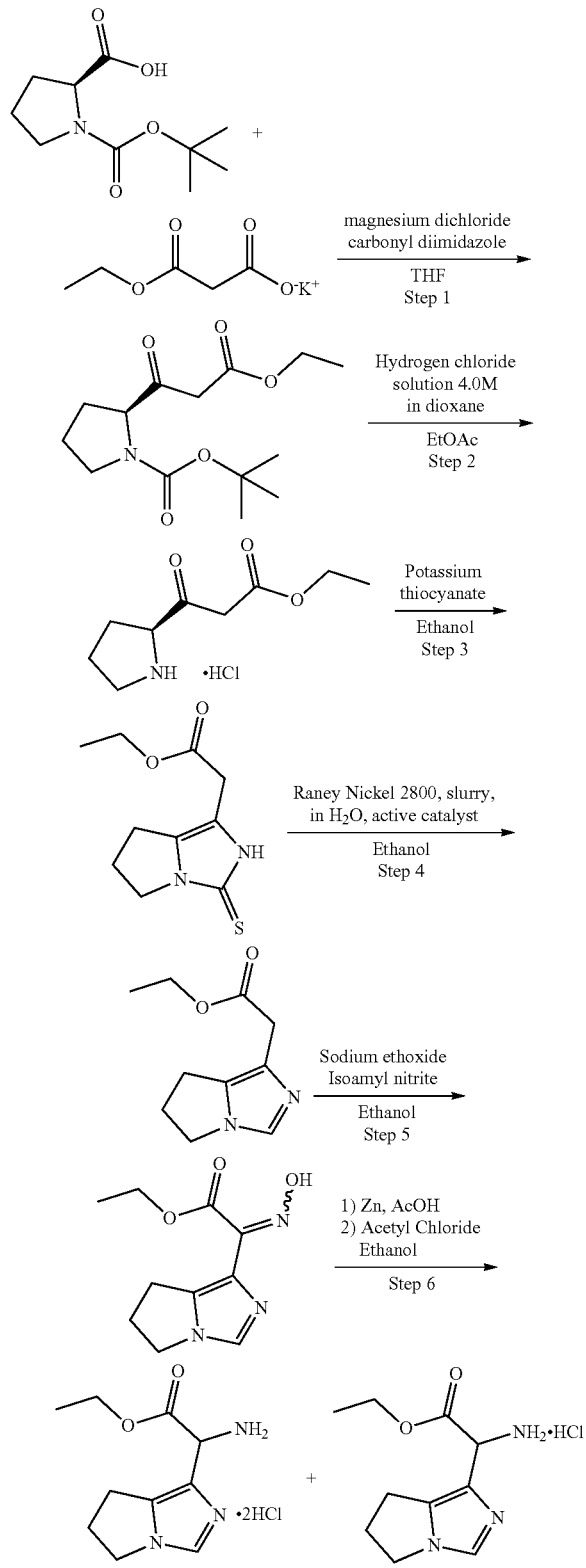

Step 1: tert-butyl (S)-2-(3-ethoxy-3-oxopropanoyl)pyrrolidine-1-carboxylate

Potassium ethyl malonate (85.8 g, 504 mmol) was added to a stirred solution of magnesium chloride (31.0 g, 325 mmol) in THF (1400 mL) under argon atmosphere and the reaction mixture was heated at 50° C. for 6 h. In a separate flask, (2S)-1-tert-butoxycarbonylpyrrolidine-2-carboxylic acid (70.0 g, 325 mmol) was dissolved in THF (1400 mL), cooled at 0° C. and carbonyl diimidazole (81.7 g, 504 mmol) was added portion-wise over a period of 20 minutes. The reaction mixture was warmed to room temperature and stirred for another 2 h. The heated reaction mixture was cooled to room temperature and the activated ester solution was added drop-wise over a period of 20 min and the reaction mixture was stirred for 20 h. After completion of the reaction, the solvent was removed by distillation under reduced pressure to obtain thick white semisolid. This residue was dissolved in half saturated potassium bisulphate solution and extracted twice with ethyl acetate. The combined organic layers were washed with saturated NaHCO$_3$ solution, dried over sodium sulphate, filtered and concentrated to afford a crude light brown clear oil. This oil was purified by silica gel chromatography (10% Ethyl acetate: Pet ether) to afford tert-butyl (S)-2-(3-ethoxy-3-oxopropanoyl)pyrrolidine-1-carboxylate (76 g, 213 mmol, 66% yield) as a colorless clear oil. LCMS: (ESI−) (m/z: 284.0 [M−1]).

Step 2: ethyl 3-oxo-3-[(2S)-pyrrolidin-2-yl]propanoate hydrochloride tert-Butyl (2S)-2-(3-ethoxy-3-oxo-propanoyl)pyrrolidine-1-carboxylate (67.4 g, 236 mmol) was dissolved in ethyl acetate (70 mL) in a 2 L RBF. Hydrogen chloride (4 M in dioxane, 207 mL) was added. The reaction was stirred at rt overnight, then concentrated. The residual oil was stirred with MTBE (200 mL) overnight. The MTBE supernatant was decanted, the MTBE supernatant was discarded and the residue was concentrated under reduced pressure to give ethyl 3-oxo-3-[(2S)-pyrrolidin-2-yl]propanoate hydrochloride (52.4 g, 228 mmol, 97%) as a brown oil. LCMS (m/z: 186.1 [M+H$^+$])

Step 3: ethyl 2-(3-thioxo-2,5,6,7-tetrahydropyrrolo[1,2-c]imidazol-1-yl)acetate Potassium thiocyanate (23.3 g, 240 mmol, 12.3 mL) was added to a solution of ethyl 3-oxo-3-[(2S)-pyrrolidin-2-yl]propanoate hydrochloride (50.6 g, 228.26 mmol) in ethanol (250 mL). The heterogeneous mixture was stirred at 80° C. for 2 h, then was cooled and concentrated. The residue was dissolved in ethyl acetate (500 mL) and water (500 mL). Saturated aqueous NaHCO$_3$ (500 mL) was added to the mixture and extracted with ethyl acetate (3×500 mL). The combined organic layers were concentrated then mixed with 500 mL MTBE and stirred at rt overnight. The precipitate formed was collected by filtration to yield ethyl 2-(3-thioxo-2,5,6,7-tetrahydropyrrolo[1,2-c]imidazol-1-yl)acetate (47.1 g, 208 mmol, 91% yield) as a yellow solid. LCMS (m/z: 227.1 [M+H])

Step 4: Ethyl 2-(6,7-dihydro-5H-pyrrolo[1,2-c]imidazol-1-yl)-2-oxo-acetate

To a 3-neck 2 L RBF was charged Raney Nickel® 2800, slurry, in H$_2$O, active catalyst (51.00 g, 595.27 mmol) and rinsed with EtOH (100 mL). The ethanol layer was discarded. A slurry of ethyl 2-(3-thioxo-2,5,6,7-tetrahydropyrrolo[1,2-c]imidazol-1-yl)acetate (51 g, 225.37 mmol) in EtOH (400 mL) was added. The mixture was refluxed at 80° C. for 2 h. The reaction mixture was cooled and filtered through a pad of Celite and washed with EtOH. The filtrate was concentrated to yield ethyl 2-(6,7-dihydro-5H-pyrrolo[1,2-c]imidazol-1-yl)-2-oxo-acetate as a brown oil (45.6 g, 235 mmol, quantitative yield). LCMS (ESI+): m/z: 194.9 [M+1]

Step 5: Ethyl (2Z)-2-(6,7-dihydro-5H-pyrrolo[1,2-c]imidazol-1-yl)-2-hydroxyimino-acetate To a solution of ethyl 2-(6,7-dihydro-5H-pyrrolo[1,2-c]imidazol-1-yl)acetate (20 g, 102.97 mmol) in Ethanol (100 mL) was added dropwise Sodium ethoxide, 21% w/w in ethanol (21.02 g, 308.91 mmol, 24.22 mL) at 0° C. The reaction mixture was stirred for 30 minutes. The reaction mixture was cooled to 0° C., followed by the drop wise addition of Isoamyl nitrite (41 mL, 309 mmol) at this temperature and after 3 hr, additional Isoamyl nitrite (27 mL, 206 mmol) was added to the reaction mixture. The reaction mixture was allowed slowly to reach room temperature and stirred under nitrogen atmosphere. The reaction mixture was diluted with ethanol (80 ml). The reaction mixture was neutralized by dropwise addition of 4M Hydrochloric acid in Methanol at 0° C., until a pH of 6 was obtained, using pH paper. The mixture turned to a light yellow color suspension. The solid was filtered under suction, washed with ethanol (twice) and the filtrate were concentrated under reduced pressure. The crude material was diluted with water and extracted twice with dichloromethane and the combined organic layers were concentrated to afford ethyl 2-(6,7-dihydro-5H-pyrrolo[1,2-c]imidazol-1-yl)-2-hydroxyimino-acetate (17.2 g, 67.16 mmol, 65.22% yield) as a brown gum, which was used in the next step without further purification. LCMS (ESI+) m/z 224.0 (M+H).

Step 6: ethyl 2-amino-2-(6,7-dihydro-5H-pyrrolo[1,2-c]imidazol-1-yl)acetate hydrochloride and ethyl 2-amino-2-(6,7-dihydro-5H-pyrrolo[1,2-c]imidazol-1-yl)acetate dihydrochloride Ethyl 2-(6,7-dihydro-5H-pyrrolo[1,2-c]imidazol-1-yl)-2-hydroxyimino-acetate (30.40 g, 136.18 mmol) was dissolved in AcOH (300 mL) in a 2 L 3-neck RBF with mechanic stir under nitrogen. Zinc (26.72 g, 408.55 mmol, 3.74 mL) was added. The reaction mixture was heated at 50° C. overnight. The reaction mixture was filtered through Celite and washed with additional AcOH. The solvent was removed under reduced pressure to afford a brown crude residue. In a separate reaction vessel, Ethanol (125 mL) was cooled to 0° C. in a 3-neck 500 mL RBF. Acetyl chloride (28.14 g, 358.43 mmol, 21.81 mL) was added dropwise while keeping the internal temperature below 10° C. The solution was stirred for 15 minutes. The crude residue was added the solution. The reaction was stirred at room temperature for 16 hours. Then the mixture was heated at 50° C. for 24 hours. The reaction mixture was concentrated under reduced pressure. The crude was dissolved in 150 mL acetonitrile and 150 mL $H_2O$ was added. White precipitate formed and the mixture was filtered. The filter cake to afford ethyl 2-amino-2-(6,7-dihydro-5H-pyrrolo[1,2-c]imidazol-1-yl)acetate hydrochloride (2.77 g, 11.3 mmol, 8.3% yield) as a white solid. $^1$H NMR (400 MHz, DMSO-$d_6$) δ 8.54 (s, 3H), 7.65 (s, 1H), 5.16 (s, 1H), 4.57-4.10 (m, 2H), 4.01 (t, J=7.3 Hz, 2H), 2.75 (h, J=8.4 Hz, 2H), 2.55 (q, J=7.1 Hz, 2H), 1.20 (t, J=7.1 Hz, 3H). LCMS (ESI+): m/z 210.1 [M+H]. The mother liquor was concentrated and azeotroped with IPA (3×) to yield ethyl 2-amino-2-(6,7-dihydro-5H-pyrrolo[1,2-c]imidazol-1-yl)acetate dihydrochloride form of the desired product (32.7 g, 116.4 mmol, 86% yield) as a brown solid. LCMS (ESI+): m/z 210.1 [M+H]. $^1$H NMR (400 MHz, DMSO-$d_6$) δ 8.93 (s, 4H), 8.56 (s, 1H), 5.46 (s, 1H), 4.45-4.05 (m, 5H), 3.06-2.69 (m, 3H), 2.58 (q, J=7.3 Hz, 2H), 1.23 (t, J=7.1 Hz, 4H).

Synthesis of Intermediate: Ethyl 2-(6,7-dihydro-5H-pyrrolo[1,2-c]imidazol-1-yl)-2-(4-fluoro-6-iodo-1-oxo-isoindolin-2-yl)acetate

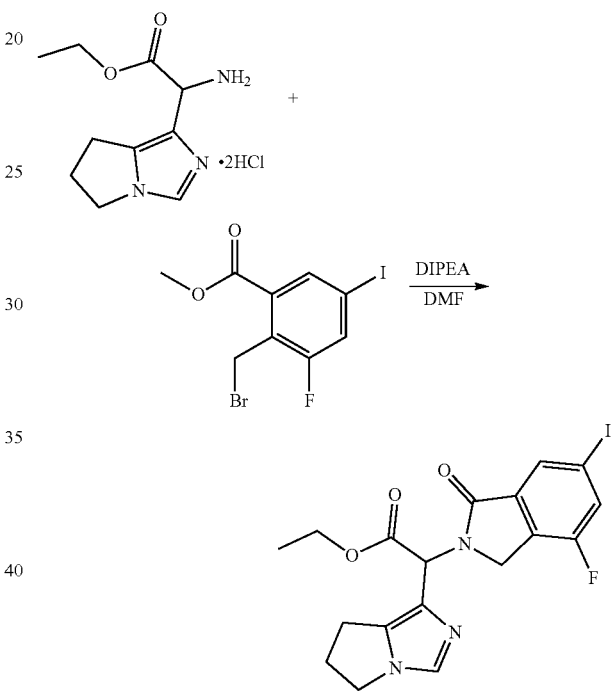

Ethyl 2-amino-2-(6,7-dihydro-5H-pyrrolo[1,2-c]imidazol-1-yl)acetate dihydrochloride (4.02 g, 12.62 mmol) was dissolved in DMF (36 mL). Methyl 2-(bromomethyl)-3-fluoro-5-iodo-benzoate (3.81 g, 10.22 mmol) was added, followed by N-ethyl-N-isopropyl-propan-2-amine (6.52 g, 50.47 mmol, 8.79 mL). The reaction mixture was stirred at rt for 16 hours. The reaction mixture was stirred at 45° C. The reaction mixture was diluted with ethyl acetate and washed with saturated aqueous sodium bicarbonate and brine. The organic layer was dried with sodium sulfate and concentrated to afford a brown oil, which was purified by flash column chromatography on silica gel (0-10% methanol in dichloromethane) to yield ethyl 2-(6,7-dihydro-5H-pyrrolo[1,2-c]imidazol-1-yl)-2-(4-fluoro-6-iodo-1-oxo-isoindolin-2-yl)acetate (2.03 g, 4.33 mmol, 34.29% yield) as a yellow solid. LCMS (ESI+): 470.2 (M+H), $^1$H NMR (400 MHz, DMSO-$d_6$) δ 8.04-7.82 (m, 2H), 7.56 (s, 1H), 5.85 (s, 1H), 4.60 (d, J=18.0 Hz, 1H), 4.31-4.06 (m, 3H), 3.98 (q, J=6.9 Hz, 2H), 2.92-2.71 (m, 1H), 2.69-2.53 (m, 3H), 1.18 (t, J=7.1 Hz, 3H).

605

Synthesis of Intermediate: Ethyl 2-(6-bromo-4-fluoro-1-oxo-isoindolin-2-yl)-2-(6,7-dihydro-5H-pyrrolo[1,2-c]imidazol-1-yl)acetate

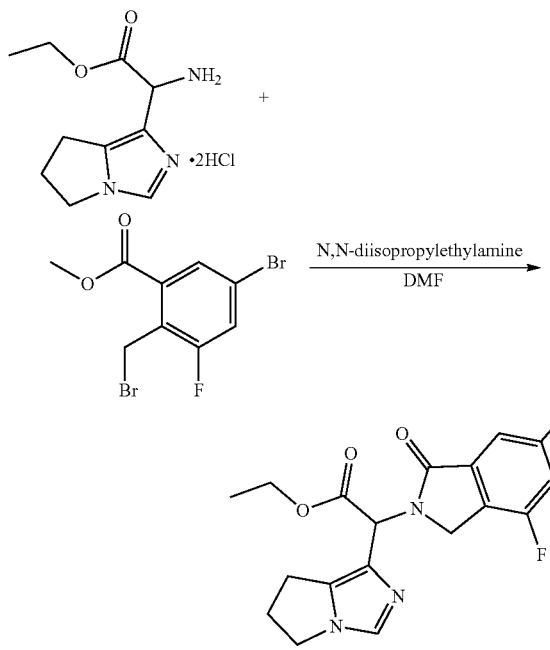

Ethyl 2-amino-2-(6,7-dihydro-5H-pyrrolo[1,2-c]imidazol-1-yl)acetate dihydrochloride (6.2 g, 21.97 mmol)) was dissolved in DMF (55 mL). Methyl 5-bromo-2-(bromomethyl)-3-fluoro-benzoate (5.73 g, 17.58 mmol) was added, followed by N-ethyl-N-isopropyl-propan-2-amine (11.36 g, 87.89 mmol, 15.31 mL). Reaction mixture was stirred at rt overnight. The reaction mixture was diluted with ethyl acetate and washed with saturated sodium bicarbonate and brine (2×). The organic layer was dried and concentrated to give a brown oil, which was purified by flash column chromatography on silica gel (0-10% methanol in dichloromethane) to provide ethyl 2-(6-bromo-4-fluoro-1-oxo-isoindolin-2-yl)-2-(6,7-dihydro-5H-pyrrolo[1,2-c]imidazol-1-yl)acetate (3.2 g, 7.58 mmol, 34.49% yield) as a yellow solid. LCMS (ESI+): 422.0/424.0 (M+H, Br pattern)

Example 1

Synthesis of 5-[2-[7-Fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]ethynyl]-N-[1-[2-[4-[4-[[(3RS)-2,6-dioxo-3-piperidyl]amino]phenyl]-1-piperidyl]acetyl]-4-piperidyl]pyridine-2-carboxamide, Compound 1

Step 1: tert-Butyl 4-[4-[[(3RS)-2,6-dioxo-3-piperidyl]amino]phenyl]piperidine-1-carboxylate

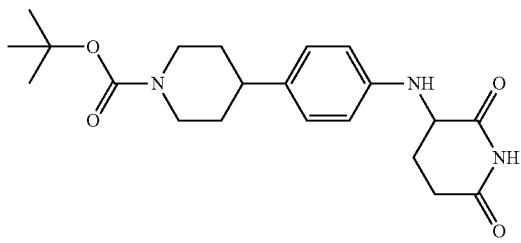 [SMILES: CC(C)(C)OC(=O)N1CCC(c2ccc(NC3CCC(=O)NC3=O)cc2)CC1]

606 tert-Butyl 4-(4-aminophenyl)piperidine-1-carboxylate (CAS 170011-57-1) (798 mg, 2.89 mmol) was dissolved in 10 ml of acetonitrile. Sodium bicarbonate (485 mg, 5.77 mmol, 2 equiv.) was added followed by 3-bromopiperidine-2,6-dione (CAS 62595-74-8) (610 mg, 3.18 mmol, 1.1 equiv.). The reaction mixture was stirred at 90° C. for 16 hours. The reaction mixture was cooled to room temperature, adsorbed on Isolute® and purified by flash chromatography on a silica gel column eluting with an ethyl acetate: heptane 30:70 to 100:0 gradient. The desired tert-butyl 4-[4-[[(3RS)-2,6-dioxo-3-piperidyl]amino]phenyl]piperidine-1-carboxylate (850 mg, 76% yield) was obtained as an off-white solid, MS: m/e=359.4 (([M-tBu+H]$^+$).

Step 2: (3RS)-3-[4-(4-Piperidyl)anilino]piperidine-2,6-dione hydrochloride

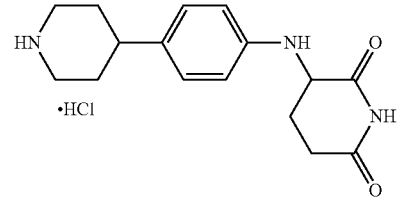 [SMILES: O=C1CCC(Nc2ccc(C3CCNCC3)cc2)C(=O)N1 ; Cl]

tert-Butyl 4-[4-[[(3RS)-2,6-dioxo-3-piperidyl]amino]phenyl]piperidine-1-carboxylate (850 mg, 2.19 mmol) and HCl (4 Min dioxane) (5.48 ml, 21.9 mmol, 10 equiv.) were combined with 10 ml of methanol at 0-5° C. in an ice bath. The reaction mixture was stirred at room temperature for 18 hours. The reaction mixture was concentrated to dryness and used without further purification. The desired (3RS)-3-[4-(4-piperidyl)anilino]piperidine-2,6-dione hydrochloride (818 mg, quantitative, purity=87%) was obtained as an off-white solid, MS: m/e=286.1 ([M+H]$^+$).

Step 3: tert-Butyl 2-[4-[4-[[(3RS)-2,6-dioxo-3-piperidyl]amino]phenyl]-1-piperidyl]acetate

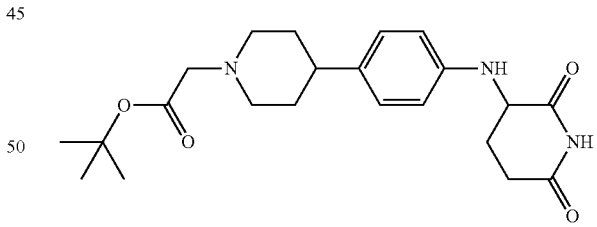

A mixture of (3RS)-3-[4-(4-piperidyl)anilino]piperidine-2,6-dione hydrochloride (200 mg, 0.618 mmol), tert-butyl 2-bromoacetate (CAS 5292-43-3) (157 mg, 0.119 ml, 0.803 mmol, 1.3 equiv.) and Hunig's base (399 mg, 0.539 ml, 3.09 mmol, 5 equiv.) in 4.0 ml of N,N-Dimethylformamide was stirred at room temperature for 2 hours. The reaction mixture was extracted with ethyl acetate and water. The aqueous layer was backextracted with ethyl acetate. The organic layers were combined, dried over sodium sulfate, filtered and concentrated to dryness. The crude product was purified by flash chromatography on a silica gel column eluting with an ethyl acetate:heptane 50:50 to 100:0 gradient. The desired tert-butyl 2-[4-[4-[[(3RS)-2,6-dioxo-3-piperidyl]amino]

phenyl]-1-piperidyl]acetate (164 mg, 66% yield) was obtained as a white solid, MS: m/e=402.2 ([M+H]⁺).

Step 4: 2-[4-[4-[[(3RS)-2,6-Dioxo-3-piperidyl]amino]phenyl]-1-piperidyl]acetic acid trifluoroacetate

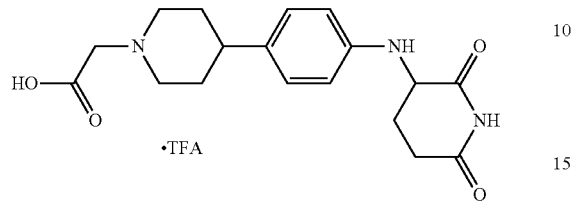

tert-Butyl 2-[4-[4-[[(3RS)-2,6-dioxo-3-piperidyl]amino]phenyl]-1-piperidyl]acetate (164 mg, 0.408 mmol) was combined with 3.0 ml of dichloromethane. Trifluoroacetic acid (1.48 g, 1 ml, 13 mmol, 31.8 equiv.) was added at 0-5° C. The reaction mixture was stirred at room temperature for 6 hours. The reaction mixture was concentrated in vacuo, dried under high vacuum and used without further purification. The desired 2-[4-[4-[[(3RS)-2,6-dioxo-3-piperidyl]amino]phenyl]-1-piperidyl]acetic acid trifluoroacetate (quantitative yield) was obtained as a light blue foam, MS: m/e=346.2 ([M+H]⁺).

Synthesis of Intermediate: tert-butyl 4-[[5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]pyridine-2-carbonyl]amino]piperidine-1-carboxylate

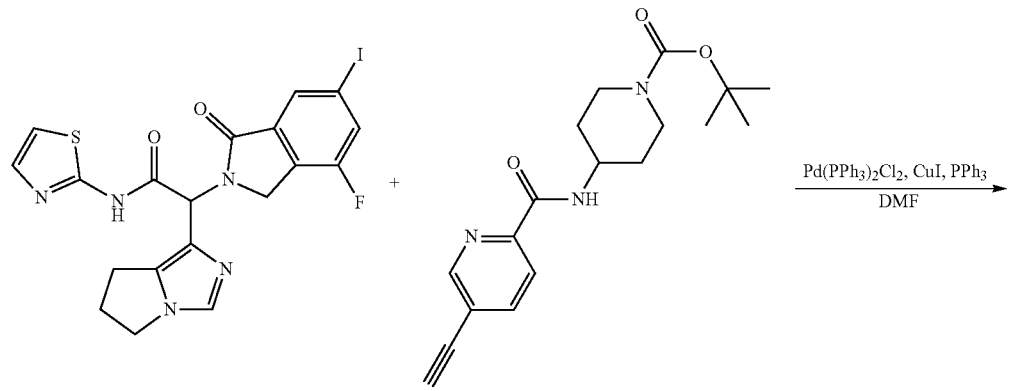

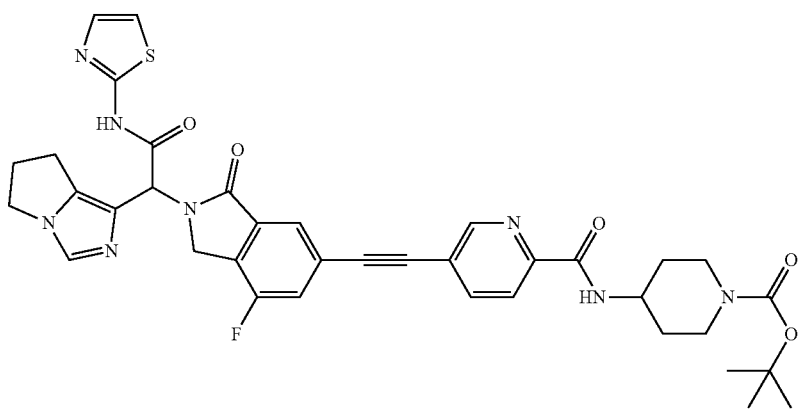

To a solution of 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (250 mg, 477.72 μmol) and tert-butyl 4-[(5-ethynylpyridine-2-carbonyl)amino]piperidine-1-carboxylate (188.83 mg, 573.26 μmol) in DMF (5 mL) was added N,N-Diisopropylethylamine (370.45 mg, 2.87 mmol, 499.26 μL) and the mixture was degassed with nitrogen for 15 min. Bis(Triphenylphosphine)palladium (II) chloride (16.77 mg, 23.89 μmol), Copper (I) iodide (4.55 mg, 23.89 μmol), Triphenylphosphine (12.53 mg, 47.77 μmol) were added. The reaction mixture was further degassed with nitrogen gas for 5 min and heated at 80° C. under microwave irradiation for 2 h. Water was added to the reaction mixture and the reaction mixture was extracted with 10% methanol in dichloromethane (3×50 ml). The organic layer was washed with brine (20 ml), dried with $Na_2SO_4$, filtered and concentrated under reduced pressure. The crude was purified by flash column chromatography 0 to 3% methanol in ethyl acetate to provide tert-butyl 4-[[5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]pyridine-2-carbonyl]amino]piperidine-1-carboxylate (280 mg, 376.86 μmol, 78.89% yield) as a light yellow solid. LCMS (ESI+): 725.3 [M+H$^+$].

Synthesis of Intermediate: 5-[2-[7-Fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]ethynyl]-N-(4-piperidyl)pyridine-2-carboxamide

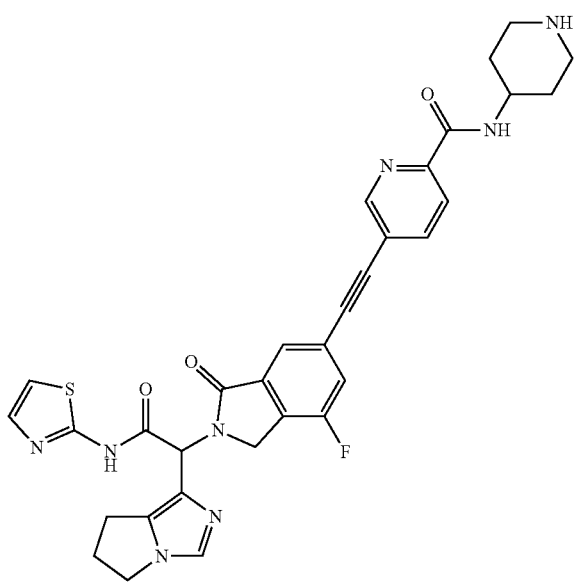 [SMILES: O=C(NC1CCNCC1)c1ccc(C#Cc2cc(F)c3c(c2)C(=O)N(C(C(=O)Nc2nccs2)c2ncn4c2CCC4)C3)cn1]

tert-Butyl 4-[[5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]pyridine-2-carbonyl]amino]piperidine-1-carboxylate (360 mg, 0.497 mmol) was dissolved in 3.0 ml of dichloromethane and 1.5 ml of methanol. HCl (4 M in dioxane) (1.24 ml, 4.97 mmol, 10 equiv.) was added at room temperature and the reaction mixture was stirred at room temperature for 6 hours. The reaction mixture was extracted with saturated NaHCO$_3$-solution and three times with a mixture of dichloromethane:methanol (9:1). The organic layers were combined, dried over sodium sulfate, filtered and concentrated to dryness. The crude product was used without further purification. The desired 5-[2-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]ethynyl]-N-(4-piperidyl)pyridine-2-carboxamide (300 mg, 97% yield) was obtained as a light brown solid, MS: m/e=625.4 ([M+H]$^+$).

Synthesis of 5-[2-[7-Fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]ethynyl]-N-[1-[2-[4-[4-[[(3RS)-2,6-dioxo-3-piperidyl]amino]phenyl]-1-piperidyl]acetyl]-4-piperidyl]pyridine-2-carboxamide

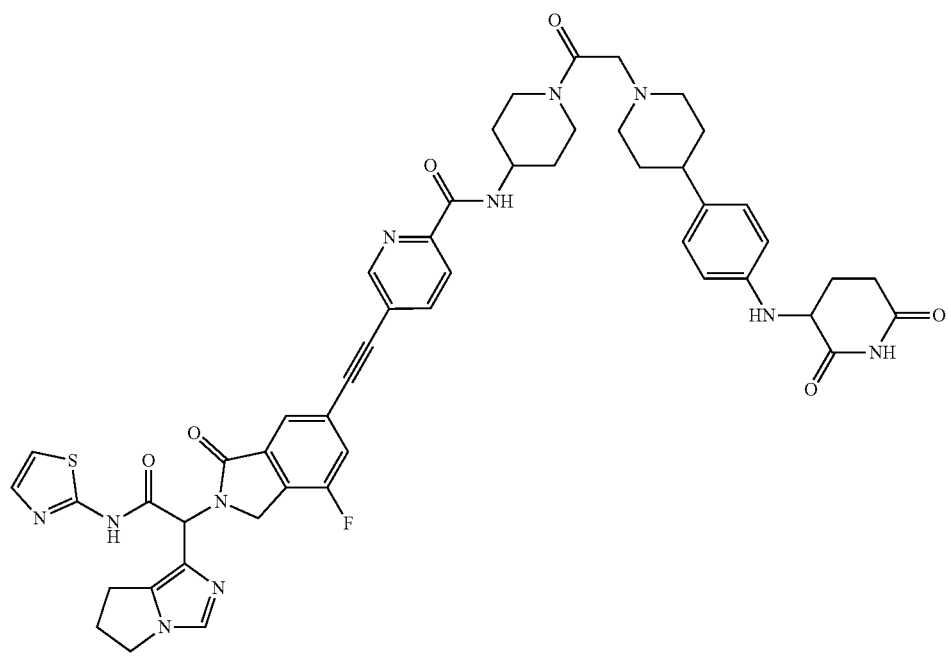 [SMILES: O=C1CCC(Nc2ccc(C3CCN(CC(=O)N4CCC(NC(=O)c5ccc(C#Cc6cc(F)c7c(c6)C(=O)N(C(C(=O)Nc6nccs6)c6ncn8c6CCC8)C7)cn5)CC4)CC3)cc2)C(=O)N1]

2-[4-[4-[[(3RS)-2,6-Dioxo-3-piperidyl]amino]phenyl]-1-piperidyl]acetic acid trifluoroacetate (61.3 mg, 0.080 mmol, 1 equiv.) and 5-[2-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]ethynyl]-N-(4-piperidyl)pyridine-2-carboxamide (50 mg, 0.080 mmol) were dissolved in 1.0 ml of N,N-dimethylformamide. Hunig's base (155 mg, 0.210 ml, 1.2 mmol, 15 equiv.) was added followed by TBTU (30.8 mg, 0.096 mmol, 1.2 equiv.). The reaction mixture was stirred at room temperature for 2 hours. The reaction mixture was extracted with saturated NaHCO$_3$-solution and three times with a mixture of dichloromethane:methanol (9:1). The organic layers were washed with water. The organic layers were combined, dried over sodium sulfate, filtered and concentrated to dryness. The crude product was purified by flash chromatography on a silica gel column eluting with a dichloromethane:methanol 100:0 to 90:10 gradient to obtain the desired Compound 1 (28 mg, 37% yield) as an off-white solid, MS: m/e=952.6 ([M+H]$^+$).

Example 2

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[(2,6-dioxo-3-piperidyl)amino]phenyl]acetyl]-4-piperidyl]pyridine-2-carboxamide, Compound 2

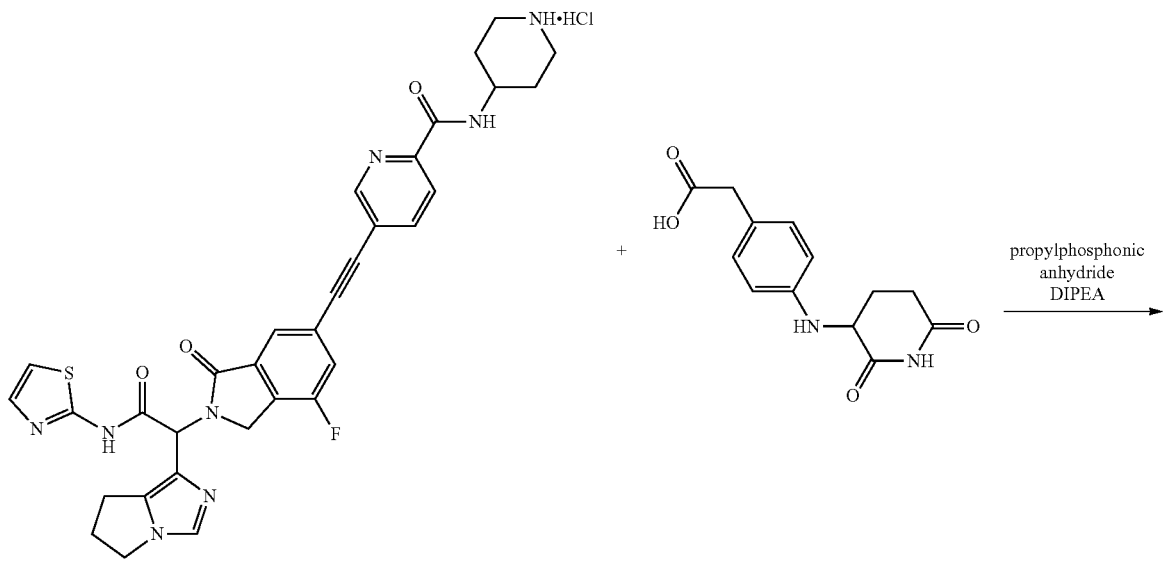

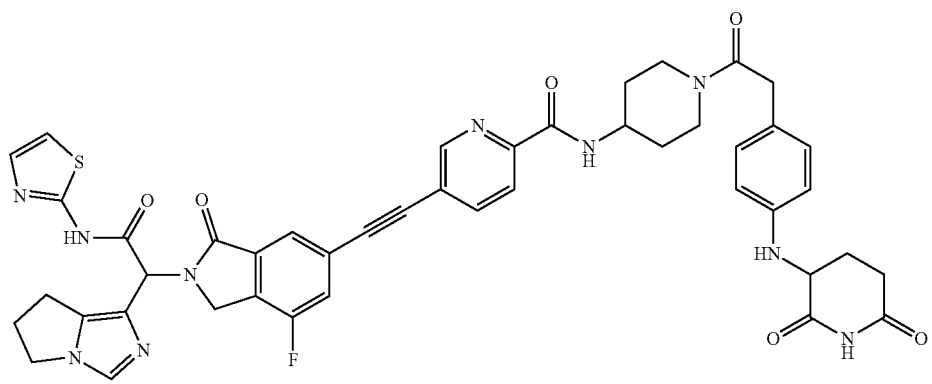

To the stirred solution of 5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-(4-piperidyl)pyridine-2-carboxamide hydrochloride (40 mg, 60.50 μmol) and 2-[4-[(2,6-dioxo-3-piperidyl)amino]phenyl]acetic acid (19.04 mg, 72.60 μmol) in DMF (1 mL) was cooled to 0° C. Propylphosphonic anhydride solution (50 wt. % in ethyl acetate) (48.13 mg, 151.25 μmol) was added to the reaction mixture followed by N,N-Diisopropylethylamine (46.92 mg, 363.01 μmol, 63.23 μL) at 0° C. The reaction mixture stirred at rt for 2 h. The reaction mixture poured to ice water (2 ml), and extracted with ethyl acetate (2*10 ml). The organic layer washed with brine solution (10 ml), dried with Na$_2$SO$_4$ and concentrated under reduced pressure The crude was purified by preparative HPLC (0-100% 0.1% NH$_4$OAc in water and Acetonitrile) to get Compound 2 (20 mg, 22.76 μmol, 37.62% yield) as an off-white solid. LCMS m/z 869.2 (M+H). $^1$H-NMR (400 MHz, DMSO-d6): δ 12.55 (s, 1H), 10.79 (s, 1H), 8.86 (dd, J=2.0, 0.8 Hz, 1H), 8.76 (d, J=8.4 Hz, 1H), 8.21 (dd, J=8.2, 2.4 Hz, 1H), 8.09 (t, J=8.4 Hz, 1H), 7.84-7.79 (m, 2H), 7.61 (s, 1H), 7.48 (s, 1H), 7.26 (bs, 1H), 6.97 (d, J=8.40 Hz, 2H), 6.64 (d, J=8.80 Hz, 2H), 6.13 (s, 1H), 5.75 (d, J=7.60 Hz, 1H), 4.89 (d, J=16.8 Hz, 1H), 4.45-4.35 (m, 1H), 4.31-4.26 (m, 2H), 4.05-3.98 (m, 4H), 3.56-3.55 (m, 2H), 3.15-3.08 (m, 1H), 2.78-2.71 (m, 2H), 2.68-2.60 (m, 2H), 2.57-2.55 (m, 3H), 2.11-2.10 (m, 1H), 1.91-1.90 (m, 1H), 1.78-1.75 (m, 2H), 1.53-1.45 (m, 2H).

Example 3

Synthesis of 5-[2-[7-Fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]ethynyl]-N-[1-[2-[4-[4-[[(3RS)-2,6-dioxo-3-piperidyl]oxy]phenyl]piperazin-1-yl]acetyl]-4-piperidyl]pyridine-2-carboxamide, Compound 3

Step 1: tert-Butyl 4-[4-[[(3RS)-2,6-dioxo-3-piperidyl]oxy]phenyl]piperazine-1-carboxylate

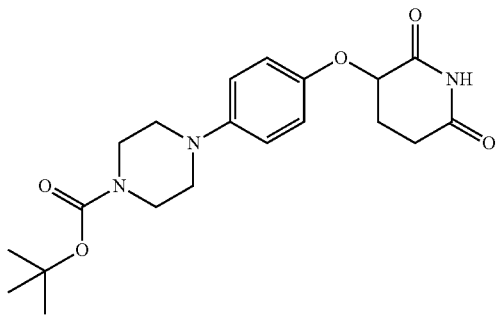 [SMILES: CC(C)(C)OC(=O)N1CCN(c2ccc(OC3CCC(=O)NC3=O)cc2)CC1]

tert-Butyl 4-(4-hydroxyphenyl)piperazine-1-carboxylate (CAS 158985-25-2) (500 mg, 1.8 mmol) was dissolved in 8.0 ml of N,N-Dimethylformamide and cooled to 0-5° C. Sodium hydride (60% dispersion in mineral oil) (180 mg, 4.49 mmol, 2.5 equiv.) was added portionwise. The reaction mixture was stirred at 0-5° C. for 30 min. 3-Bromopiperidine-2,6-dione (CAS 62595-74-8) (517 mg, 2.69 mmol, 1.5 equiv.) was added and the reaction mixture was stirred at 0-5° C. for 1 hour. The reaction mixture was quenched by adding crushed ice and extracted with ethyl acetate. The organic layer was washed with water and brine. The organic layers were combined, dried over sodium sulfate, filtered and concentrated to dryness to afford the desired tert-butyl 4-[4-[[(3RS)-2,6-dioxo-3-piperidyl]oxy]phenyl]piperazine-1-carboxylate (634 mg, 91% yield) as a white solid, MS: m/e=390.1 ([M+H]$^+$).

Step 2: (3RS)-3-(4-Piperazin-1-ylphenoxy)piperidine-2,6-dione hydrochloride

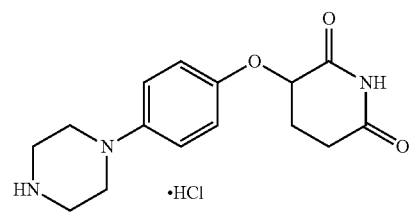 [SMILES: O=C1CCC(Oc2ccc(N3CCNCC3)cc2)C(=O)N1 ; Cl]

tert-Butyl 4-[4-[[(3RS)-2,6-dioxo-3-piperidyl]oxy]phenyl]piperazine-1-carboxylate (634 mg, 1.63 mmol) was dissolved in 5.0 ml of dichloromethane and 2.5 ml of methanol. HCl (4 M in dioxane) (4.07 ml, 16.3 mmol, 10 equiv.) was added and the reaction mixture was stirred at room temperature for 1 hour. The reaction mixture was concentrated to dryness and used without further purification. The desired (3RS)-3-(4-piperazin-1-ylphenoxy)piperidine-2,6-dione hydrochloride (720 mg, 88% yield, purity=65%) was obtained as an off-white solid, MS: m/e=290.2 ([M+H]$^+$).

Step 3: tert-Butyl 2-[4-[4-[[(3RS)-2,6-dioxo-3-piperidyl]oxy]phenyl]piperazin-1-yl]acetate

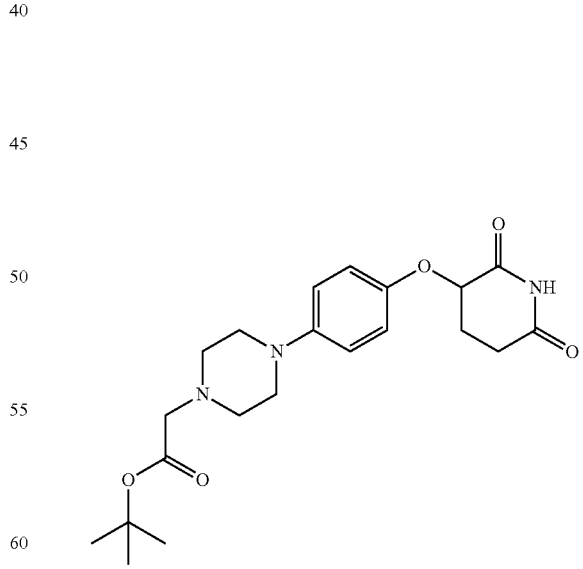

The title compound was obtained as a colorless solid, MS: m/e=404.3 ([M+H]$^+$), using chemistry similar to that described in Example 1, step 3 starting from (3RS)-3-(4-piperazin-1-ylphenoxy)piperidine-2,6-dione hydrochloride and tert-butyl 2-bromoacetate (CAS 5292-43-3).

Step 4: 5-[2-[7-Fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]ethynyl]-N-[1-[2-[4-[4-[[(3RS)-2,6-dioxo-3-piperidyl]oxy]phenyl]piperazin-1-yl]acetyl]-4-piperidyl]pyridine-2-carboxamide

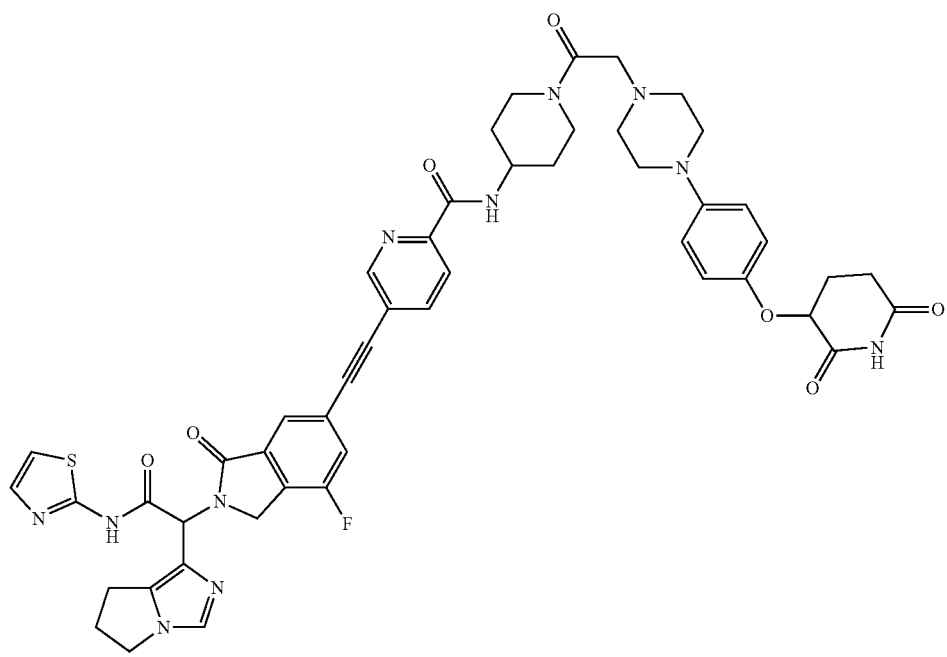 [SMILES: O=C1CCC(Oc2ccc(N3CCN(CC(=O)N4CCC(NC(=O)c5ccc(C#Cc6cc(F)c7c(c6)C(=O)N(C(C(=O)Nc6nccs6)c6ncn8c6CCC8)C7)cn5)CC4)CC3)cc2)C(=O)N1]

tert-Butyl 2-[4-[4-[[(3RS)-2,6-dioxo-3-piperidyl]oxy]phenyl]piperazin-1-yl]acetate (48.4 mg, 0.120 mmol, 1.5 equiv.) was dissolved in 1.0 ml of dichloromethane and trifluoroacetic acid (183 mg, 0.123 ml, 1.6 mmol, 20 equiv.) was added. The reaction mixture was stirred at room temperature for 2 hours. Trifluoroacetic acid (183 mg, 0.123 ml, 1.6 mmol, 20 equiv.) was added and the reaction mixture was stirred at room temperature for 16 hours. The reaction mixture was concentrated to dryness. The residue and 5-[2-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]ethynyl]-N-(4-piperidyl)pyridine-2-carboxamide (Example 1, step 5) (50 mg, 0.080 mmol) were dissolved in 1.0 ml of N,N-Dimethylformamide. Hunig's base (155 mg, 0.210 ml, 1.2 mmol, 15 equiv.) was added followed by TBTU (30.8 mg, 0.096 mmol, 1.2 equiv.). The reaction mixture was stirred at room temperature for 2 hours. The reaction mixture was extracted with saturated NaHCO$_3$-solution and three times with a mixture of dichloromethane:methanol (9:1). The organic layers were washed with water. The organic layers were combined, dried over sodium sulfate, filtered and concentrated to dryness. The crude product was purified by flash chromatography on a silica gel column eluting with a dichloromethane:methanol 100:0 to 90:10 gradient to obtain the desired Compound 3 (31 mg, 41% yield) as an off-white solid, MS: m/e=954.7 ([M+H]$^+$).

Example 4

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[4-[[(3S)-2,6-dioxo-3-piperidyl]amino]-2-fluoro-phenyl]-1-piperidyl]acetyl]-4-piperidyl]pyridine-2-carboxamide, Compound 4

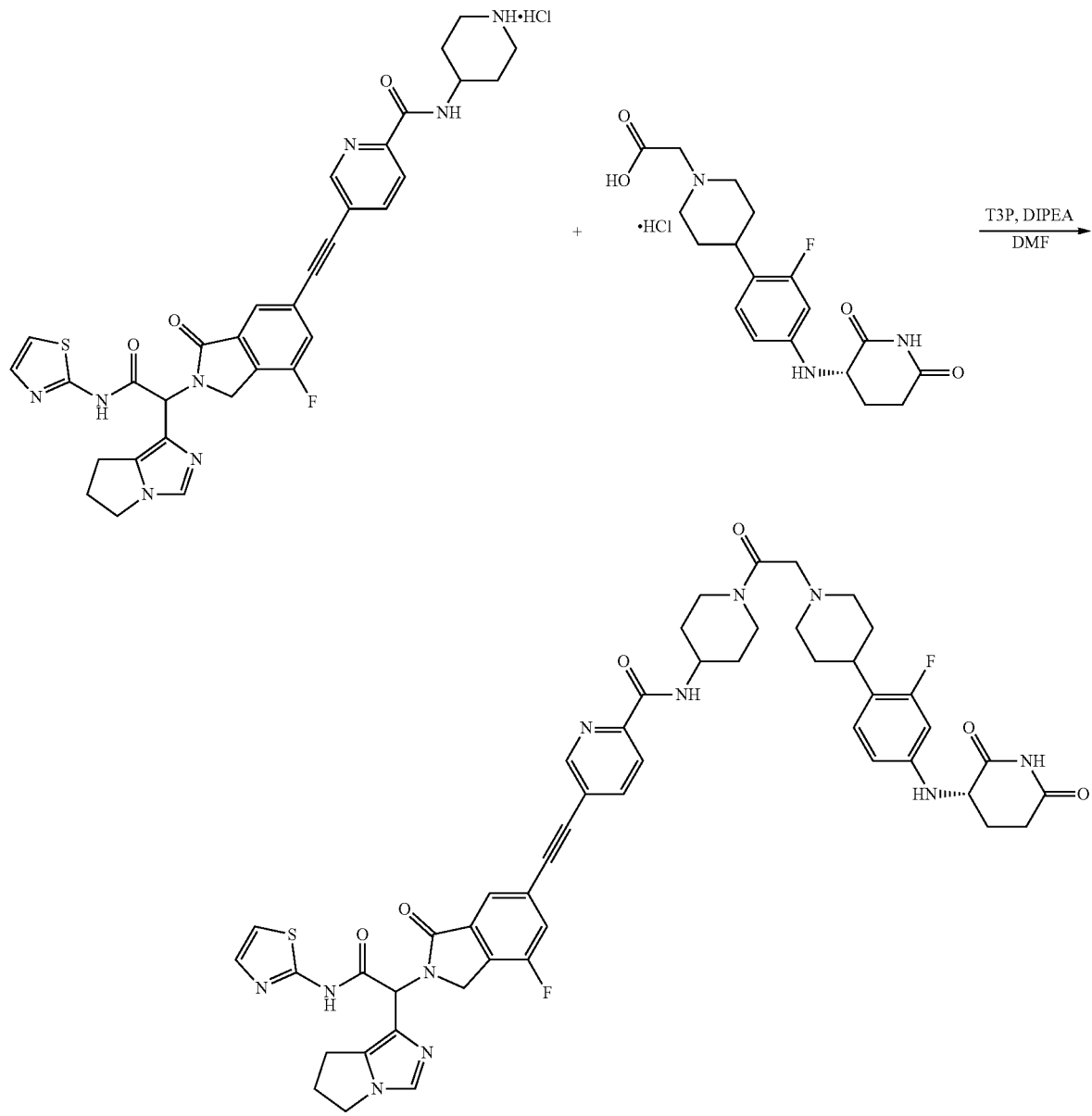

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-(4-piperidyl)pyridine-2-carboxamide hydrochloride (120 mg, 181.50 μmol) and 2-[4-[4-[[(3S)-2,6-dioxo-3-piperidyl]amino]-2-fluoro-phenyl]-1-piperidyl] acetic acid hydrochloride (87.09 mg, 217.80 μmol) were mixed in DMF (2 mL). N,N-Diisopropylethylamine (140.75 mg, 1.09 mmol, 189.69 μL) was added to the reaction mixture at 0° C. Propyl phosphonic anhydride solution (50 wt. % in ethyl acetate) (144.38 mg, 453.76 μmol) was added to the reaction mixture at 0° C. The reaction mixture stirred at rt for 2 h. The reaction mixture poured to ice water (5 ml), solid compound precipitated. The solid compound was filtered and dried. The crude solid was purified by preparative HPLC (Column: X-Bridge $C_8$ (50×4.6 mm, 3.5 m) (Mobile Phase A: 10 mM Ammonium acetate in milli-q water and Mobile phase B: Acetonitrile, Flow rate: 1.0 ml/min). The pure fraction was frozen and lyophilized to afford Compound 4 (55 mg, 55.68 μmol, 31% yield) as an off white solid. LCMS (ESI+): 970.2 [M+H]. 1H-NMR (400 MHz, DMSO-d6): δ 12.55 (s, 1H), 10.79 (s, 1H), 8.88-8.83 (m, 2H), 8.23-8.21 (m, 1H), 8.12-8.10 (m, 1H), 7.82-7.79 (m, 2H), 7.61 (s, 1H), 7.49 (d, J=3.20 Hz, 1H), 7.26-7.25 (m, 1H), 7.02-6.97 (m, 1H), 6.97-6.42 (m, 2H), 6.13 (s, 1H), 6.01 (d, J=7.60 Hz, 1H), 4.85-4.99 (m, 1H), 4.46-4.28 (m, 3H), 4.26-4.01 (m, 2H), 3.99-3.98 (m, 2H), 3.33-3.27 (m, 1H), 3.05-3.02 (m, 2H), 2.93-2.91 (m, 2H), 2.77-2.71 (m, 2H), 2.68-2.67 (m, 2H), 2.59-2.53 (m, 2H), 2.53-2.51 (m, 4H), 2.10-2.07 (m, 3H), 1.91-1.85 (m, 3H), 1.71-1.59 (m, 4H).
Example 5
2-(6,7-dihydro-5H-pyrrolo[1,2-c]imidazol-1-yl)-2-[6-[4-[4-[2-[4-[4-[(2,6-dioxo-3-piperidyl)amino]phenyl]-1-piperidyl]acetyl]piperazin-1-yl]phenyl]-4-fluoro-1-oxo-isoindolin-2-yl]-N-thiazol-2-yl-acetamide, Compound 5
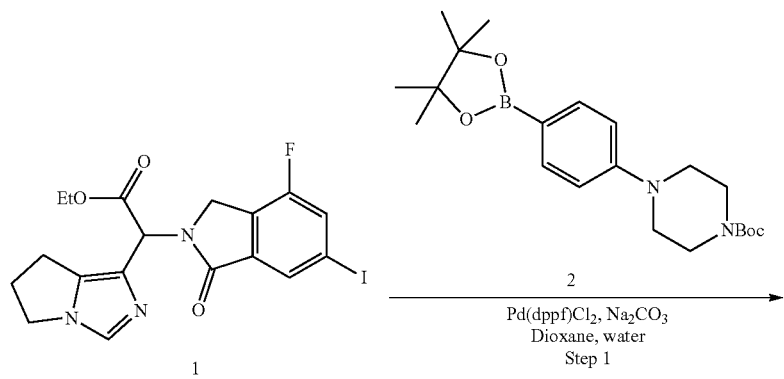
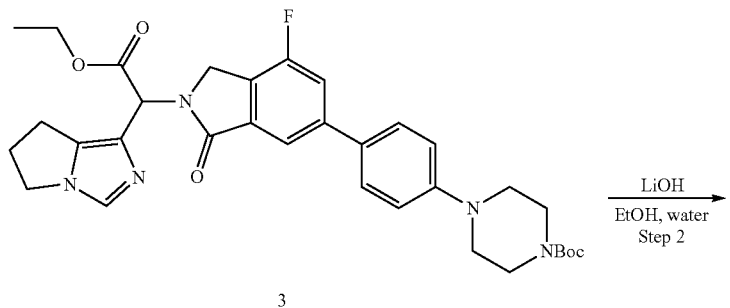
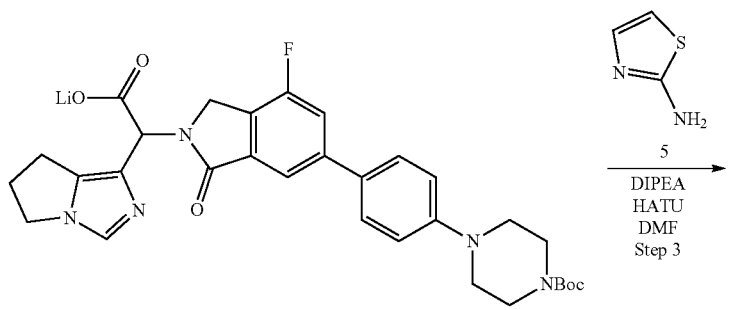

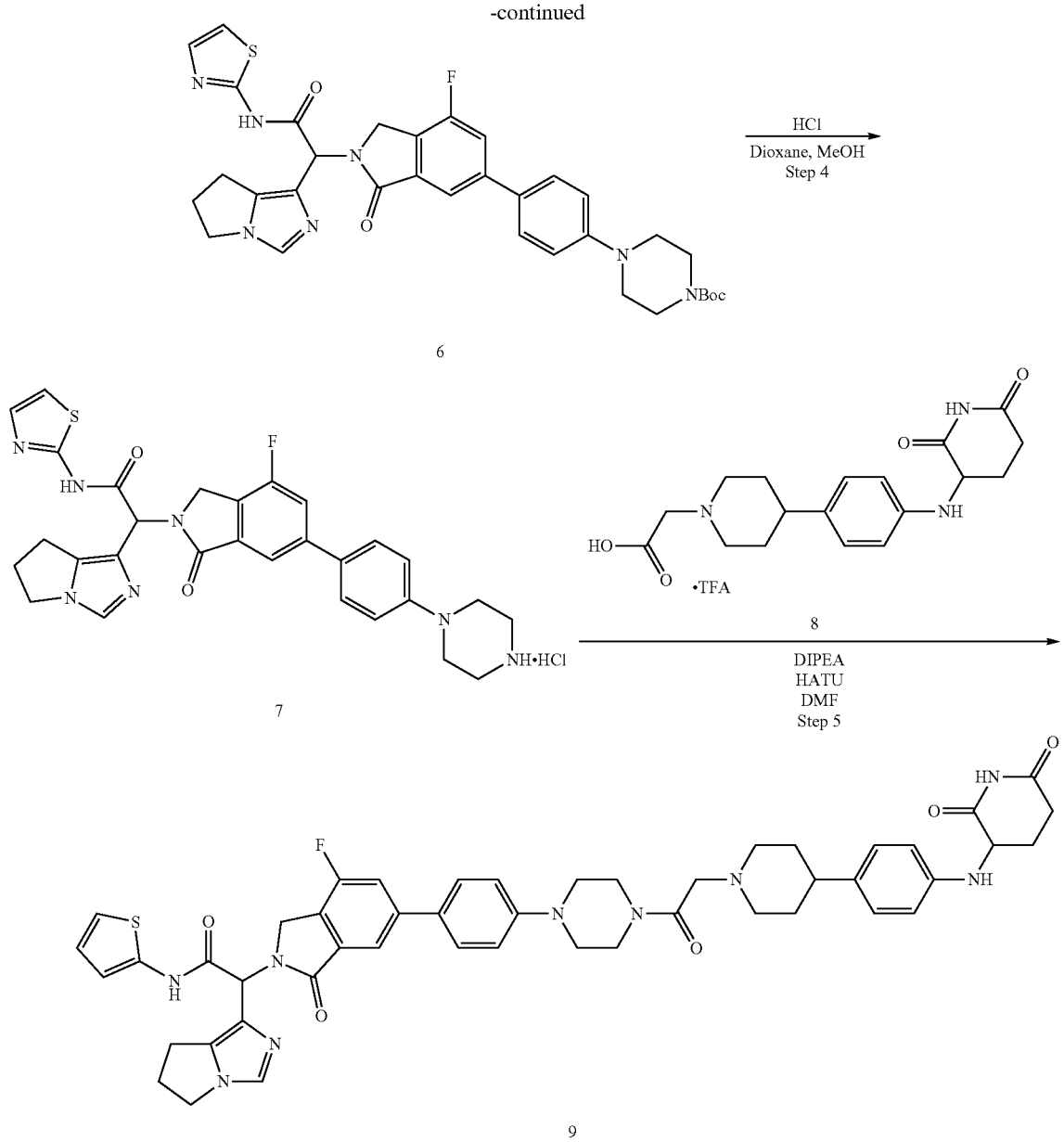

Step 1: tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]piperazine-1-carboxylate In a 100-mL round bottom flask, ethyl 2-(6-bromo-4-fluoro-1-oxo-isoindolin-2-yl)-2-(6,7-dihydro-5H-pyrrolo[1,2-c]imidazol-1-yl)acetate (2.25 g, 5.33 mmol) and tert-butyl 4-[4-(4,4,5,5-tetramethyl-1,3,2-dioxaborolan-2-yl)phenyl]piperazine-1-carboxylate (2.79 g, 7.19 mmol) were dissolved in dioxane (36 mL) and 1,1'-Bis(Diphenylphosphino)ferrocenepalladium (II) dichloride (217.58 mg, 266.43 μmol) and tBuXPhos (336.37 mg, 532.86 μmol) were added, followed by Sodium carbonate (1.24 g, 11.72 mmol, 491.11 μL) dissolved in water (9 mL). The mixture was degassed with nitrogen. The reaction was capped with a septum, fitted with a nitrogen inlet and heated at 80° C. on a heating block for 3 h. The reaction mixture was cooled to room temperature, the mixture was diluted with ethyl acetate, and the organic layer was separated from the aqueous layer as well as the solid precipitate. The mixture was concentrated under reduced pressure. The crude residue purified by flash column chromatography on silica gel (40 g column, 0-10% Methanol in ethyl acetate) to give tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]piperazine-1-carboxylate (2.70 g, 4.25 mmol, 79.74% yield) as a pale orange foam. LCMS (ESI+): 604.8 (M+H)/504.7 (M-Boc+H)

Step 2: lithium 2-(6-(4-(1-(tert-butoxycarbonyl)piperidin-4-yl)phenyl)-4-fluoro-1-oxoisoindolin-2-yl)-2-(6,7-dihydro-5H-pyrrolo[1,2-c]imidazol-1-yl)acetate tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]piperazine-1-carboxylate (2700 mg, 4.47 mmol) was dissolved in Ethanol (20 mL). Lithium hydroxide (1 M aqueous solution, 4.47 mL) was added at 0° C. The reaction mixture was warmed and stirred for 4 hours at 20° C. The reaction mixture was concentrated in vacuo, suspended in benzene, evaporated, then submitted to high vacuum to afford lithium [2-[6-[4-(4-tert-butoxycarbonylpiperazin-1-yl)phenyl]-4-fluoro-1-oxo-isoindolin-2-yl]-2-(6,7-dihydro-5H-pyrrolo[1,2-c]imidazol-1-yl)acetyl]oxylithium (2.51 g, 4.32 mmol, 96.50% yield) as a light brown solid. LCMS (ESI+): 576.7 (M+H)/476.6 (M-Boc+H)

Step 3: tert-butyl 4-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenyl)piperidine-1-carboxylate Lithium [2-[6-[4-(4-tert-butoxycarbonylpiperazin-1-yl)phenyl]-4-fluoro-1-oxo-isoindolin-2-yl]-2-(6,7-dihydro-5H-pyrrolo[1,2-c]imidazol-1-yl)acetyl]oxylithium (410 mg, 705.00 μmol) and thiazol-2-amine (75.54 mg, 754.35 μmol) were mixed in DMF; the reaction mixture was cooled to 0° C. N,N-Diisopropylethylamine (455.58 mg, 3.52 mmol, 613.99 μL) was added to the reaction mixture, and HATU (321.67 mg, 846.00 μmol) was added, and the reaction mixture was stirred for 4 hours. A saturated NaHCO3-solution was added, and the mixture was extracted two times ethyl acetate. The organic layers were washed with brine, dried over Na2SO4, filtered and concentrated in vacuo. The crude material was purified by flash chromatography on silica gel (24 g, 0-10% methanol in dichloromethane). Fractions containing product were combined and concentrated to afford tert-butyl 4-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenyl)piperidine-1-carboxylate (195 mg, 297 μmol, 66.3% yield) as an orange viscous oil.

Step 4: 2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide; hydrochloride tert-Butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]piperazine-1-carboxylate (350 mg, 532.11 μmol) was dissolved in methanol and Hydrogen chloride solution (4.0M in dioxane, 1 mL, 4 mmol) was added. The reaction mixture was heated at 40° C. for 4 hours, and the reaction was complete. The volatiles were evaporated under reduce pressure. The material was submitted to high vacuum, frozen to −78° C. and thawed to afford a dense amber solid to afford 2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide; hydrochloride (316 mg, 478.71 μmol, 89.96% yield) as an yellow solid. LCMS (ESI+): 558.3 (M+H)/279.9 (M+2H/2)

Step 5: 2-(6,7-dihydro-5H-pyrrolo[1,2-c]imidazol-1-yl)-2-[6-[4-[4-[2-[4-[4-[(2,6-dioxo-3-piperidyl)amino]phenyl]-1-piperidyl]acetyl]piperazin-1-yl]phenyl]-4-fluoro-1-oxo-isoindolin-2-yl]-N-thiazol-2-yl-acetamide 2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide hydrochloride (100 mg, 168.32 μmol) and 2-[4-[4-[(2,6-dioxo-3-piperidyl)amino]phenyl]-1-piperidyl]acetic acid, trifluoroacetic acid salt (81.20 mg, 176.74 μmol) were mixed in DMF, the reaction mixture was cooled to 0° C. N,N-Diisopropylethylamine (108.77 mg, 841.61 μmol, 146.59 μL) was added to the reaction mixture, and HATU (76.80 mg, 201.99 μmol) was added, and the reaction mixture was stirred for 4 hours while warming to room temperature. The reaction mixture was acidified with 4-5 drops of TFA, and injected directly on a C18 column (50 g C18) for low pressure liquid chromatography purification (5% to 100% ACN (+0.1% TFA) in water (+0.1% TFA) over 12 minutes). The pure fractions were neutralized with saturated aqueous sodium bicarbonate (ca. 60 mL), and extracted twice with a isopropanol:chloroform (1:4) mixture. The organic layer was evaporated under reduced pressure to afford a solid. The solid was dissolved in dichloromethane and injected on a 24 g silica gel column flushed with 100% dichloromethane and purified using a 0% to 20% methanol in dichloromethane gradient over 20 minutes. The pure fractions were evaporated under reduced pressure. The crude residue was dissolved in dichloromethane, transferred to a 8 mL vial, and evaporated under reduced pressure. 1 mL water+1 mL acetonitrile were added, and the mixture was thoroughly sonicated, vortexed and sonicated again. The suspension was frozen at −78° C. and lyophilized to afford Compound 5 (45 mg, 49.83 μmol, 29.60% yield). LCMS (ESI+): 885.9 (M+H), LCMS (ESI−): 883.5 (M−H).

Example 6

2-(6,7-dihydro-5H-pyrrolo[1,2-c]imidazol-1-yl)-2-[6-[4-[4-[2-[4-[4-[[(3S)-2,6-dioxo-3-piperidyl]amino]phenyl]-1-piperidyl]acetyl]piperazin-1-yl]phenyl]-4-fluoro-1-oxo-isoindolin-2-yl]-N-thiazol-2-yl-acetamide, Compound 6

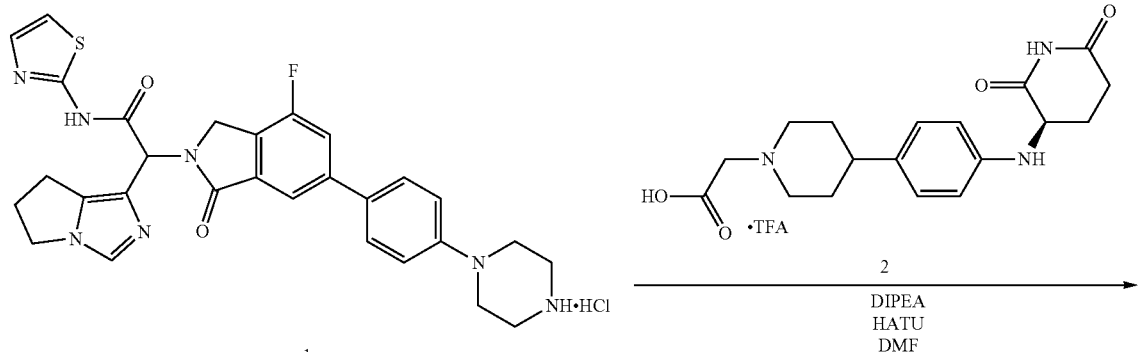

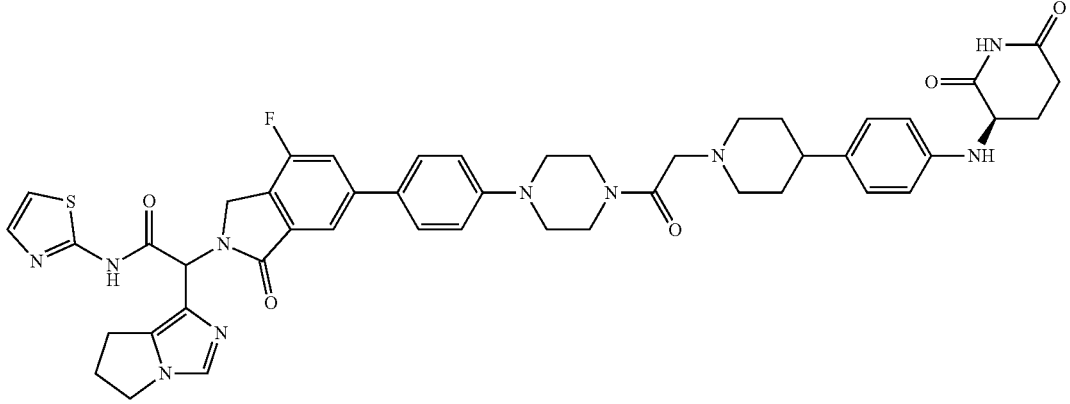

2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide; hydrochloride (100 mg, 168.32 μmol) and 2-[4-[4-[[(3R)-2,6-dioxo-3-piperidyl]amino]phenyl]-1-piperidyl]acetic acid, trifluoroacetic acid salt (81.20 mg, 176.74 μmol) were mixed in DMF, the reaction mixture was cooled to 0° C. N,N-Diisopropylethylamine (108.77 mg, 841.61 μmol, 146.59 μL) was added to the reaction mixture, and HATU (76.80 mg, 201.99 μmol) was added, and the reaction mixture was stirred for 4 hours. The reaction mixture was acidified with 4-5 drops of TFA, and injected directly on a RP C18 column (50 g C18) for purification using a 5% to 100% acetonitrile (+0.1% TFA) in water (+0.1% TFA) eluent gradient. The pure fractions were neutralized with aqueous aqueous NaHCO₃ (ca. 60 mL), extracted with a isopropanol:chloroform mixture (1:4). The organic layer was evaporated under reduced pressure to afford a solid. The solid was dissolved in dichloromethane, an injected on a 24 g silica gel column flushed with 100% dichloromethane and purified using a 0% to 20% methanol in dichloromethane gradient over 20 minutes. Desired product comes out late. The pure fractions were evaporated under reduced pressure. The crude residue was dissolved in dichloromethane, transferred to a 8 mL vial, and evaporated under reduced pressure. The compound was suspended in an acetonitrile:water mixture and the mixture was thoroughly sonicated, vortexed and sonicated again. The suspension was frozen at −78° C. and lyophilized to afford Compound 6 (44 mg, 49.47 μmol, 29.39% yield) LCMS: Rt=1.155 min., MS (ESI+): 885.6 (M+H), MS (ESI−): 883.5 (M−H). ¹H NMR (400 MHz, DMSO-d6) δ 12.51 (s, 1H), 10.75 (s, 1H), 7.78 (d, J=1.3 Hz, 1H), 7.74 (dd, J=10.6, 1.4 Hz, 1H), 7.69 (d, J=8.9 Hz, 2H), 7.60 (s, 1H), 7.48 (d, J=3.6 Hz, 1H), 7.25 (d, J=3.5 Hz, 1H), 7.08 (d, J=9.0 Hz, 2H), 6.95 (d, J=8.5 Hz, 2H), 6.60 (d, J=8.5 Hz, 2H), 6.15 (s, 1H), 5.63 (d, J=7.5 Hz, 1H), 4.80 (d, J=17.7 Hz, 1H), 4.37-4.09 (m, 2H), 4.09-3.86 (m, 2H), 3.76 (s, 2H), 3.62 (s, 2H), 3.25 (d, J=37.3 Hz, 5H), 2.92 (d, J=10.7 Hz, 2H), 2.83-2.62 (m, 2H), 2.62-2.51 (m, 2H), 2.47 (d, J=6.0 Hz, 1H), 2.39-2.23 (m, 2H), 2.10 (d, J=6.7 Hz, 2H), 1.85 (qd, J=12.6, 5.1 Hz, 1H), 1.70 (d, J=12.3 Hz, 2H), 1.57 (q, J=11.9 Hz, 2H). 47 protons found/49 expected (solvent, water obscuration)

Example 7

2-(6,7-dihydro-5H-pyrrolo[1,2-c]imidazol-1-yl)-2-[6-[4-[4-[2-[4-[4-[[(3R)-2,6-dioxo-3-piperidyl]amino]phenyl]-1-piperidyl]acetyl]piperazin-1-yl]phenyl]-4-fluoro-1-oxo-isoindolin-2-yl]-N-thiazol-2-yl-acetamide, Compound 7

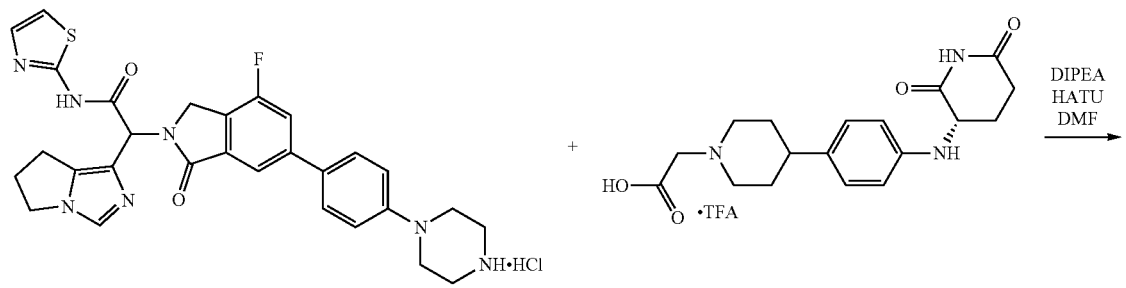

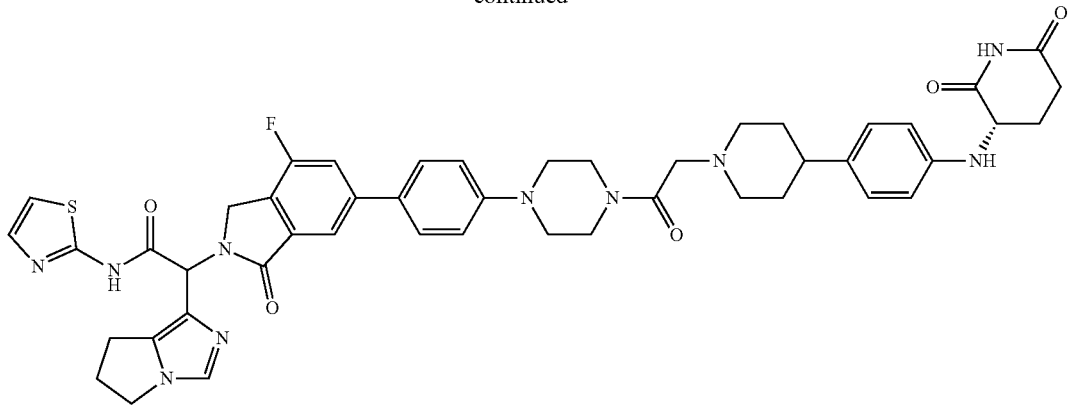

2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide hydrochloride (100 mg, 168.32 µmol) and 2-[4-[4-[[(3S)-2,6-dioxo-3-piperidyl]amino]phenyl]-1-piperidyl]acetic acid trifluoroacetic acid (81.20 mg, 176.74 µmol) were mixed in DMF, the reaction mixture was cooled to 0° C. N,N-Diisopropylethylamine (108.77 mg, 841.61 µmol, 146.59 µL) was added to the reaction mixture, and HATU (76.80 mg, 201.99 µmol) was added, and the reaction mixture was stirred for 4 hours. The reaction mixture was acidified with 4-5 drops of TFA, and injected directly on a RP C18 column (50 g C18) for purification using a 5% to 100% acetonitrile (+0.1% TFA) in water (+0.1% TFA) eluent gradient. The pure fractions were neutralized with aqueous $NaHCO_3$ (ca. 60 mLs), extracted with 1:4 isopropanol:chloroform mixture. The organic layer was evaporated under reduced pressure to afford a solid. The solid was dissolved in dichloromethane, an injected on a 24 g silica gel column flushed with 100% dichloromethane, and purified using a 0% to 20% methanol in dichloromethane gradient over 20 minutes. Desired product comes out late. The pure fractions were evaporated under reduced pressure. The crude residue was dissolved in dichloromethane, transferred to a 8 mL vial, and evaporated under reduced pressure. The compound was suspended in an acetonitrile:water mixture, and the mixture was thoroughly sonicated and vortexed. The suspension was frozen at −78° C. and lyophilized to afford Compound 7 (22.8 mg, 25.50 µmol, 15.15% yield). LCMS (ESI+): 885.9 (M+H)/443.8 (M+2H/2), MS (ESI−): 883.5 (M−H). $^1$H NMR (400 MHz, DMSO-d6) δ 12.51 (s, 1H), 10.75 (s, 1H), 7.78 (d, J=1.3 Hz, 1H), 7.74 (dd, J=10.6, 1.4 Hz, 1H), 7.71-7.63 (m, 2H), 7.60 (s, 1H), 7.48 (d, J=3.6 Hz, 1H), 7.25 (d, J=3.6 Hz, 1H), 7.08 (d, J=8.9 Hz, 2H), 7.01-6.82 (m, 2H), 6.72-6.49 (m, 2H), 6.15 (s, 1H), 5.63 (d, J=7.4 Hz, 1H), 4.80 (d, J=17.7 Hz, 1H), 4.37-4.15 (m, 2H), 4.05-3.88 (m, 2H), 3.76 (s, 2H), 3.62 (s, 2H), 3.25 (d, J=37.1 Hz, 4H), 2.92 (d, J=10.7 Hz, 2H), 2.82-2.65 (m, 2H), 2.56 (dq, J=17.5, 4.2 Hz, 1H), 2.47-2.39 (m, 1H), 2.39-2.22 (m, 1H), 2.08 (d, J=7.4 Hz, 3H), 1.98-1.75 (m, 1H), 1.70 (d, J=12.1 Hz, 2H), 1.57 (q, J=12.1 Hz, 2H).

Example 8

(2RS)-2-(6,7-Dihydro-5H-pyrrolo[1,2-c]imidazol-1-yl)-2-[4-fluoro-1-oxo-6-[4-[4-[4-oxo-4-[4-[[(3RS)-2,6-dioxo-3-piperidyl]amino]phenyl]-1-piperidyl]butyl]piperazin-1-yl]phenyl]isoindolin-2-yl]-N-thiazol-2-yl-acetamide, Compound 8

Step 1: tert-Butyl 4-[4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazin-1-yl]butanoate

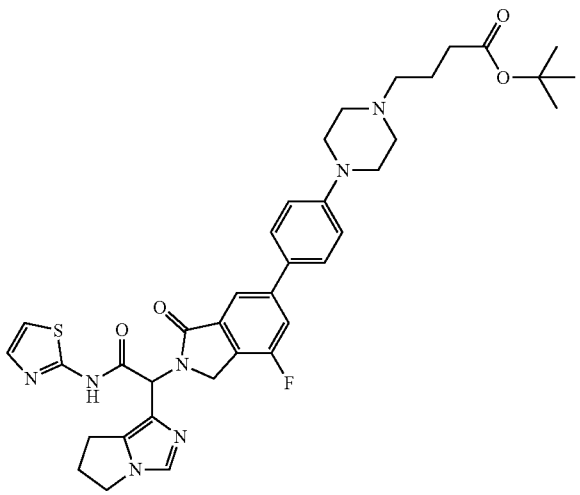 [SMILES: CC(C)(C)OC(=O)CCCN1CCN(c2ccc(-c3cc(F)c4c(c3)C(=O)N(C(C(=O)Nc3nccs3)c3ncn5c3CCC5)C4)cc2)CC1]

(2RS)-2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide (Example 5, step 9) (60 mg, 0.108 mmol) and Hunig's base (69.5 mg, 0.094 ml, 0.538 mmol, 5 equiv.) were dissolved in 1.0 ml of N,N-Dimethylformamide. tert-Butyl 4-bromobutanoate (CAS 110661-91-1) (38.4 mg, 0.028 ml, 0.172 mmol, 1.6 equiv.) was added and the reaction mixture was stirred at 60° C. for 20 hours. The reaction mixture was extracted with saturated $NaHCO_3$-solution and two times with ethyl acetate. The organic layers were washed with water and brine. The organic layers were combined, dried over sodium sulfate, filtered and concentrated to dryness. The crude product was purified by flash chromatography on a silica gel column eluting with a dichloromethane:methanol 100:0 to 90:10 gradient to obtain the desired tert-butyl 4-[4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazin-1-yl]butanoate (30 mg, 40% yield) as a light yellow oil, MS: m/e=700.6 ([M+H]⁺).

Step 2: (2RS)-2-(6,7-Dihydro-5H-pyrrolo[1,2-c]imidazol-1-yl)-2-[4-fluoro-1-oxo-6-[4-[4-[4-oxo-4-[4-[4-[[(3RS)-2,6-dioxo-3-piperidyl]amino]phenyl]-1-piperidyl]butyl]piperazin-1-yl]phenyl]isoindolin-2-yl]-N-thiazol-2-yl-acetamide

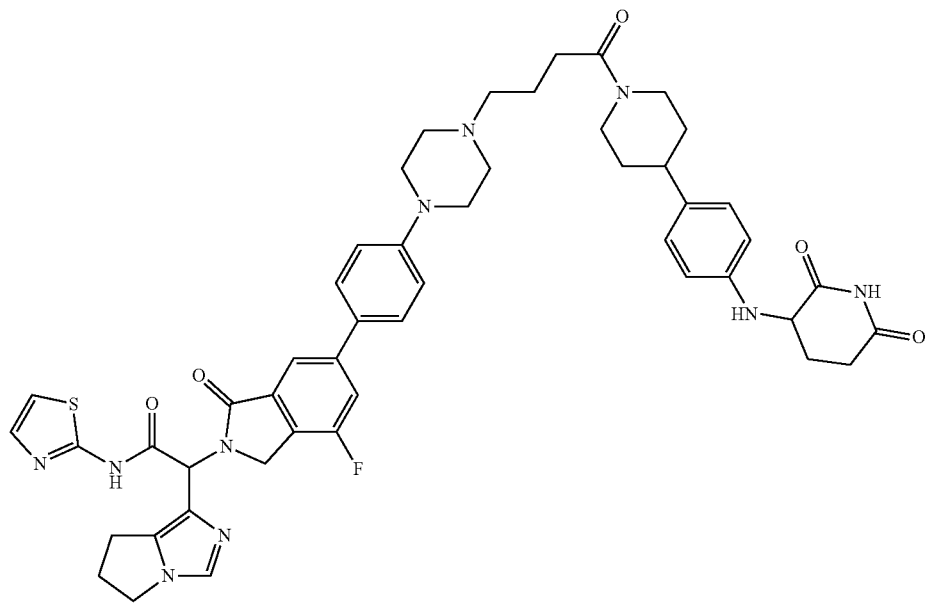 [SMILES: O=C1CCC(Nc2ccc(C3CCN(C(=O)CCCN4CCN(c5ccc(-c6cc(F)c7c(c6)C(=O)N(C(C(=O)Nc6nccs6)c6ncn8c6CCC8)C7)cc5)CC4)CC3)cc2)C(=O)N1]

The title compound, Compound 8, was obtained as an off-white solid, MS: m/e=913.7 ([M+H]⁺) using chemistry similar to that described in Example 4, step 4 starting from tert-butyl 4-[4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazin-1-yl]butanoate (Example 6, step 1) and (3RS)-3-[4-(4-piperidyl)anilino]piperidine-2,6-dione hydrochloride (Example 1, step 2).

Example 9

(2RS)-2-(6,7-Dihydro-5H-pyrrolo[1,2-c]imidazol-1-yl)-2-[4-fluoro-1-oxo-6-[4-[4-[2-[4-[4-[[(3RS)-2,6-dioxo-3-piperidyl]amino]phenyl]cyclohexyl]acetyl]piperazin-1-yl]phenyl]isoindolin-2-yl]-N-thiazol-2-yl-acetamide, Compound 9

Step 1: Methyl 2-[4-(4-nitrophenyl)cyclohexylidene]acetate

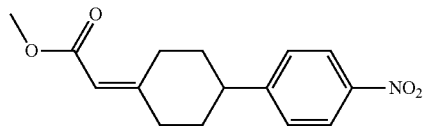 [SMILES: COC(=O)C=C1CCC(c2ccc([N+](=O)[O-])cc2)CC1]

4-(4-Nitrophenyl)cyclohexan-1-one (CAS 124500-60-3) (2.00 g, 9.12 mmol) was suspended in 15 ml of THF and cooled to 0-5° C. Sodium hydride (60% dispersion in mineral oil) (365 mg, 9.12 mmol, 1 equiv.) was added in four portions and the reaction mixture was stirred at room temperature for 2.5 hours (suspension A). In a second flask, sodium hydride (60% dispersion in mineral oil) (620 mg, 15.5 mmol, 1.7 equiv.) was suspended in 10 ml of THF and cooled to 0-5° C. Trimethyl phosphonoacetate (1.99 g, 10.9 mmol, 1.2 equiv.) dissolved in 15 ml of THF was added at 0-5° C. and the reaction mixture was stirred at room temperature for 5 hours (suspension B). Suspension A (with 20 ml of THF) was added dropwise to suspension B and the reaction mixture was stirred at room temperature for 1.5 hours. The reaction mixture was quenched with water and extracted with ethyl acetate. The aqueous layer was backextracted with ethyl acetate. The organic layers were washed with brine. The organic layers were combined, dried over sodium sulfate, filtered and concentrated on Isolute® to dryness. The crude product was purified by flash chromatography on a silica gel column eluting with an ethyl acetate:heptane 0:100 to 20:80 gradient to obtain the desired methyl 2-[4-(4-nitrophenyl)cyclohexylidene]acetate (1.822 g, 73% yield) as a white solid, MS: m/e=276.2 ([M+H]⁺).

Step 2: Methyl 2-[4-(4-aminophenyl)cyclohexyl]acetate

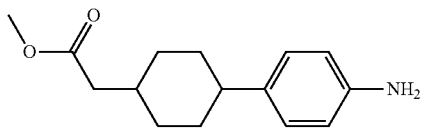 [SMILES: COC(=O)CC1CCC(c2ccc(N)cc2)CC1]

Methyl 2-(4-(4-nitrophenyl)cyclohexylidene)acetate (Example 8, step 1) (900 mg, 3.27 mmol) was dissolved in 10 ml of ethyl acetate. The flask was twice alternating evacuated and backfilled with argon. Palladium on carbon (10% Pd) (80 mg, 0.08 mmol, 0.023 equiv., 10%) was added. The flask was evacuated, flushed with argon, evacuated and flushed with hydrogen. The reaction mixture was stirred under hydrogen atmosphere (balloon) at room temperature for 4 hours. The reaction mixture was filtered and the filtrate was concentrated to dryness. The desired methyl 2-[4-(4-aminophenyl)cyclohexyl]acetate (741 mg, 92% yield) was obtained as a light red solid, MS: m/e=248.3 ([M+H]$^+$).

Step 3: Methyl 2-[4-[4-[[(3RS)-2,6-dioxo-3-piperidyl]amino]phenyl]cyclohexyl]acetate

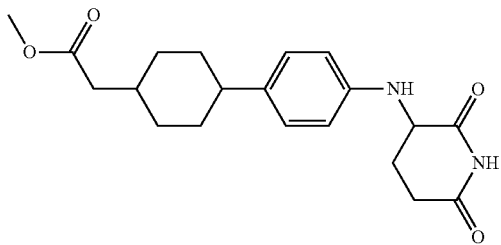 [SMILES: COC(=O)CC1CCC(c2ccc(NC3CCC(=O)NC3=O)cc2)CC1]

Methyl 2-[4-(4-aminophenyl)cyclohexyl]acetate (Example 8, step 2) (370 mg, 1.5 mmol) was dissolved in 6.2 ml of acetonitrile. Sodium bicarbonate (503 mg, 5.98 mmol, 4 equiv.) was added followed by 3-bromopiperidine-2,6-dione (CAS 62595-74-8) (316 mg, 1.65 mmol, 1.1 equiv.). The reaction mixture was stirred at 85° C. for 16 hours. The reaction mixture was cooled to room temperature, adsorbed on Isolute® and purified by flash chromatography on a silica gel column eluting with an ethyl acetate:heptane 0:100 to 50:50 gradient. The desired methyl 2-[4-[4-[[(3RS)-2,6-dioxo-3-piperidyl]amino]phenyl]cyclohexyl]acetate (355 mg, 66% yield) was obtained as a light blue solid, MS: m/e=359.4 ([M+H]$^+$).

Step 4: 2-[4-[4-[[(3RS)-2,6-Dioxo-3-piperidyl]amino]phenyl]cyclohexyl]acetic acid

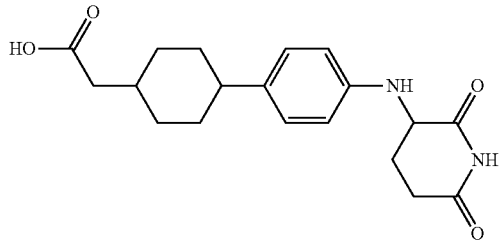 [SMILES: O=C(O)CC1CCC(c2ccc(NC3CCC(=O)NC3=O)cc2)CC1]

Methyl 2-[4-[4-[[(3RS)-2,6-dioxo-3-piperidyl]amino]phenyl]cyclohexyl]acetate (Example 8, step 3) (352 mg, 0.98 mmol) was dissolved in phosphoric acid (5.71 g, 3.4 ml, 49.5 mmol, 50.5 equiv.) and the reaction mixture was stirred at 90° C. for 4 hours. The reaction mixture was cooled to 0-5° C. and 10 ml of water was added. The reaction mixture was stirred for 1 hour. The reaction mixture was carefully added to a cold saturated NaHCO$_3$-solution (15 ml). Then, saturated Na$_2$CO$_3$-solution (5 ml) was added dropwise at 0-5° C. The reaction mixture was extracted with ethyl acetate. The aqueous layer was backextracted with ethyl acetate. The organic layers were washed with water and brine. The organic layers were combined, dried over sodium sulfate, filtered and concentrated on Isolute® to dryness. The crude product was purified by flash chromatography on a silica gel column eluting with an ethyl acetate:heptane 0:100 to 65:35 gradient to obtain the desired 2-[4-[4-[[(3RS)-2,6-dioxo-3-piperidyl]amino]phenyl]cyclohexyl]acetic acid (151 mg, 40% yield, purity=90%) as a light blue solid, MS: m/e=345.3 ([M+H]$^+$).

Step 5: (2RS)-2-(6,7-Dihydro-5H-pyrrolo[1,2-c]imidazol-1-yl)-2-[4-fluoro-1-oxo-6-[4-[4-[2-[4-[4-[[(3RS)-2,6-dioxo-3-piperidyl]amino]phenyl]cyclohexyl]acetyl]piperazin-1-yl]phenyl]isoindolin-2-yl]-N-thiazol-2-yl-acetamide

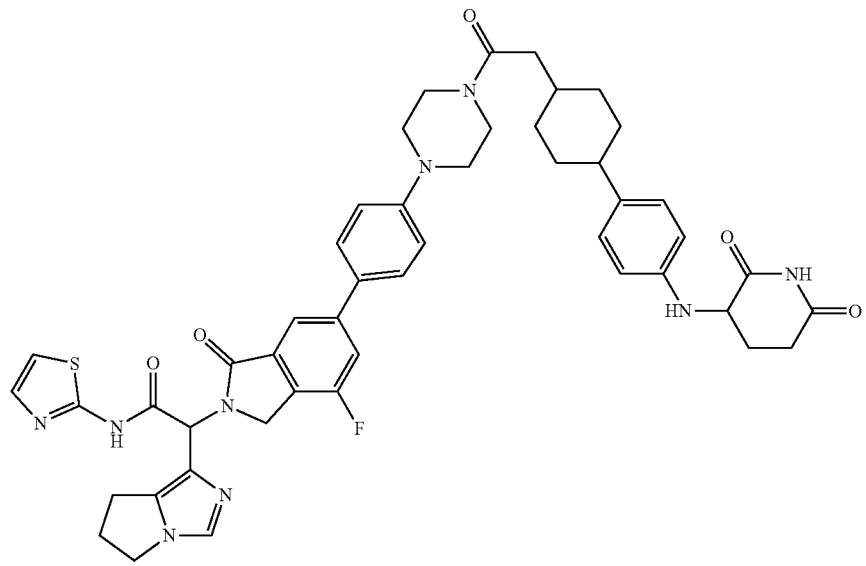 [SMILES: O=C1CCC(Nc2ccc(C3CCC(CC(=O)N4CCN(c5ccc(-c6cc(F)c7c(c6)C(=O)N(C(C(=O)Nc6nccs6)c6ncn8c6CCC8)C7)cc5)CC4)CC3)cc2)C(=O)N1]

The title compound, Compound 9, was obtained as a white foam, MS: m/e=884.7 ([M+H]⁺), using chemistry similar to that described in Example 1, step 5 starting from (2RS)-2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide (Example 5, step 3) and 2-[4-[4-[[(3RS)-2,6-dioxo-3-piperidyl]amino]phenyl]cyclohexyl]acetic acid (Example 8, step 4).

Example 10

2-(6,7-dihydro-5H-pyrrolo[1,2-c]imidazol-1-yl)-2-(6-(4-(4-(2-(4-(4-((2,6-dioxopiperidin-3-yl)amino)phenyl)piperidin-1-yl)-2-oxoethyl)piperazin-1-yl)phenyl)-4-fluoro-1-oxoisoindolin-2-yl)-N-(thiazol-2-yl)acetamide, Compound 10

Step 1: Ethyl 2-(6,7-dihydro-5H-pyrrolo[1,2-c]imidazol-1-yl)-2-oxo-acetate

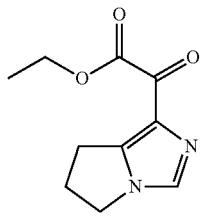

To a solution of ethyl 2-(6,7-dihydro-5H-pyrrolo[1,2-c]imidazol-1-yl)acetate (CAS 869113-97-3) (20.0 g, 102.97 mmol) dissolved in 200 ml of 1,4-dioxane was added selenium dioxide (22.85 g, 205.94 mmol, 2 equiv.). The reaction mixture was stirred for 5 hours at 80° C. The reaction mixture was concentrated under vacuum to give a residue. The crude product was purified by flash chromatography on a silica gel column eluting with petroleum ether:ethyl acetate 2:1 to ethyl acetate:ethanol 10:1 gradient to obtain the desired ethyl 2-(6,7-dihydro-5H-pyrrolo[1,2-c]imidazol-1-yl)-2-oxo-acetate (quantitative yield) as a light brown oil, MS: m/e=209.1 ([M+H]⁺).

Step 2: Ethyl 2-(6,7-dihydro-5H-pyrrolo[1,2-c]imidazol-1-yl)-2-hydroxyimino-acetate

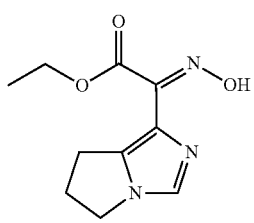 [SMILES: CCOC(=O)/C(=N/O)c1ncn2c1CCC2]

To a solution of ethyl 2-(6,7-dihydro-5H-pyrrolo[1,2-c]imidazol-1-yl)-2-oxo-acetate (17.5 g, 84.05 mmol) dissolved in 145 ml of ethanol was added hydroxylamine hydrochloride (6.42 g, 92.45 mmol, 1.1 equiv.) and sodium acetate (13.79 g, 168.1 mmol, 2 equiv.) at room temperature. The reaction mixture was stirred at 80° C. for 3.5 hours. The reaction mixture was concentrated and extracted with water and five times with a mixture of ethanol/THF/ethyl acetate 1:1:8. The organic layers were concentrated to dryness. The desired ethyl 2-(6,7-dihydro-5H-pyrrolo[1,2-c]imidazol-1-yl)-2-hydroxyimino-acetate (15 g, 80% yield) was obtained as a yellow solid, MS: m/e=224.1 ([M+H]⁺) and used directly in the next step.

Step 3: Ethyl (2RS)-2-amino-2-(6,7-dihydro-5H-pyrrolo[1,2-c]imidazol-1-yl)acetate

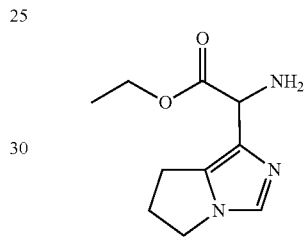

To a solution of ethyl 2-(6,7-dihydro-5H-pyrrolo[1,2-c]imidazol-1-yl)-2-hydroxyimino-acetate (15.0 g, 67.2 mmol) dissolved in 225 ml of ethanol and 120 ml of THF was added Pd/C (30.0 g, 67.2 mmol, 1 eq, 10%) at room temperature. The mixture was hydrogenated with H₂ at 45° C. for 24 hours. The reaction mixture was filtered and the filtrate was concentrated under vacuum. The desired ethyl (2RS)-2-amino-2-(6,7-dihydro-5H-pyrrolo[1,2-c]imidazol-1-yl)acetate (quantitative yield) was obtained as a brown oil, MS: m/e=210.1 ([M+H]⁺) and used directly in the next step.

Step 4: Ethyl (2RS)-2-amino-2-(6,7-dihydro-5H-pyrrolo[1,2-c]imidazol-1-yl)acetate

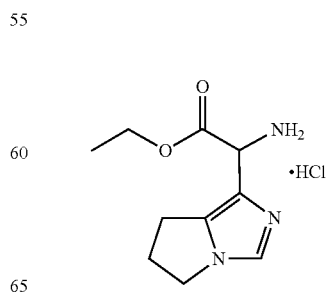

A solution of ethyl (2RS)-2-amino-2-(6,7-dihydro-5H-pyrrolo[1,2-c]imidazol-1-yl)acetate (15.0 g, 82.79 mmol) in HCl/EtOH (300 ml, 1200 mmol, 14.5 equiv., 2.5 mol/L) was stirred at 25° C. for 36 hours. The reaction mixture was concentrated under vacuum below 25° C. to give a residue as brown oil. 150 ml of acetonitrile were added to the residue and the precipitated yellow solid was collected and dried under vacuum below 25° C. to give the desired ethyl (2RS)-2-amino-2-(6,7-dihydro-5H-pyrrolo[1,2-c]imidazol-1-yl)acetate hydrochloride (quantitative yield) as yellow solid, MS: m/e=210.1 ([M+H]$^+$).

Step 5: Methyl 5-bromo-2-(bromomethyl)-3-fluoro-benzoate

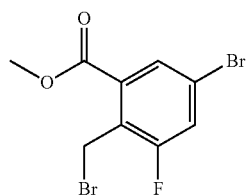

Methyl 5-bromo-3-fluoro-2-methylbenzoate (CAS 2090424-20-5) (5.91 g, 23.9 mmol) was dissolved in 100 ml trifluorotoluene and N-bromosuccinimide (4.26 g, 23.9 mmol, 1 equiv.) and AIBN (393 mg, 2.39 mmol, 0.1 equiv.) were added at room temperature. The mixture was stirred at 110° C. for 3 hours. The reaction mixture was cooled, extracted with water and two times with ethyl acetate. The organic layers were dried over sodium sulfate and concentrated to dryness. The crude product was purified by flash chromatography on a silica gel column eluting with an ethyl acetate:heptane 0:100 to 50:50 gradient to obtain the desired methyl 5-bromo-2-(bromomethyl)-3-fluoro-benzoate (7.29 g, 94% yield) as a light yellow liquid, MS: m/e=326.8 ([M+H]$^+$).

Step 6: Ethyl (2RS)-2-(6-bromo-4-fluoro-1-oxo-isoindolin-2-yl)-2-(6,7-dihydro-5H-pyrrolo[1,2-c]imidazol-1-yl)acetate

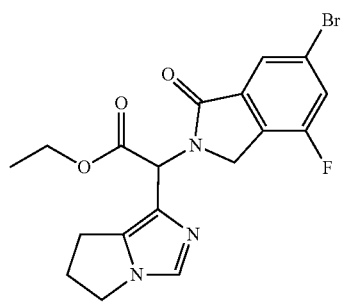 [SMILES: CCOC(=O)C(c1ncn2c1CCC2)N1Cc2c(F)cc(Br)cc2C1=O]

Ethyl (2RS)-2-amino-2-(6,7-dihydro-5H-pyrrolo[1,2-c]imidazol-1-yl)acetate hydrochloride (4.15 g, 16.9 mmol, 1 equiv.) was dissolved in 35 ml of N,N-Dimethylformamide. Methyl 5-bromo-2-(bromomethyl)-3-fluoro-benzoate (5.0 g, 15.3 mmol) and triethylamine (10.7 ml, 76.7 mmol, 5 equiv.) were added at room temperature. The mixture was stirred at 80° C. for 16 hours. The reaction mixture was extracted with water and two times with ethyl acetate. The organic layers were extracted with brine, dried over sodium sulfate and concentrated to dryness. The crude product was purified by flash chromatography on a silica gel column eluting with a dichloromethane:methanol 100:0 to 90:10 gradient to obtain the desired ethyl (2RS)-2-(6-bromo-4-fluoro-1-oxo-isoindolin-2-yl)-2-(6,7-dihydro-5H-pyrrolo[1,2-c]imidazol-1-yl)acetate (2.6 g, 40% yield) as a yellow solid, MS: m/e=422.1/424.1 ([M+H]$^+$).

Step 7: tert-Butyl 4-[4-[7-fluoro-3-oxo-2-[(1RS)-1-(6,7-dihydro-5H-pyrrolo[1,2-c]imidazol-1-yl)-2-ethoxy-2-oxo-ethyl]isoindolin-5-yl]phenyl]piperazine-1-carboxylate

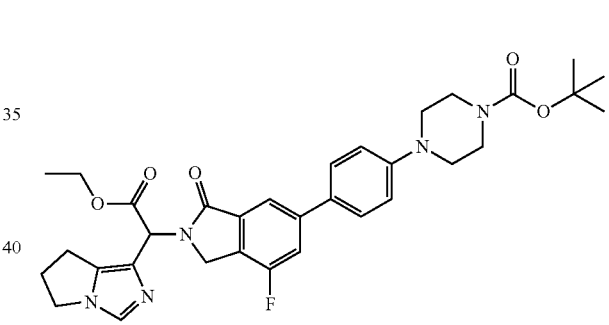

Ethyl (2RS)-2-(6-bromo-4-fluoro-1-oxo-isoindolin-2-yl)-2-(6,7-dihydro-5H-pyrrolo[1,2-c]imidazol-1-yl)acetate (56 mg, 0.133 mmol) and (4-(4-(tert-butoxycarbonyl)piperazin-1-yl)phenyl)boronic acid (CAS 457613-78-4) (41 mg, 0.133 mmol, 1.0 equiv.) were dissolved in 1.0 ml of 1,2-dimethoxyethane and 2M aq. Na$_2$CO$_3$-solution (0.199 ml, 0.398 mmol, 3.0 equiv.). Tetrakis(triphenylphosphine)palladium (0) (15 mg, 0.0133 mmol, 0.1 equiv.) was added and the reaction mixture was stirred at 80° C. for 4 hours. The reaction mixture was cooled to room temperature and then extracted with ethyl acetate and saturated NaHCO$_3$-solution. The aqueous layer was back-extracted with ethyl acetate. The organic layers were washed with water and brine. The organic layers were combined, dried over sodium sulfate, filtered and concentrated to dryness. The crude product was purified by flash chromatography on a silica gel column eluting with an ethyl acetate:heptane 5:95 to 100:0 gradient. The desired tert-butyl 4-[4-[7-fluoro-3-oxo-2-[(1RS)-1-(6,7-dihydro-5H-pyrrolo[1,2-c]imidazol-1-yl)-2-ethoxy-2-oxo-ethyl]isoindolin-5-yl]phenyl]piperazine-1-carboxylate (48 mg, 60% yield) was obtained as a light brown oil, MS: m/e=604.4 ([M+H]$^+$).

Step 8: tert-Butyl 4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazine-1-carboxylate

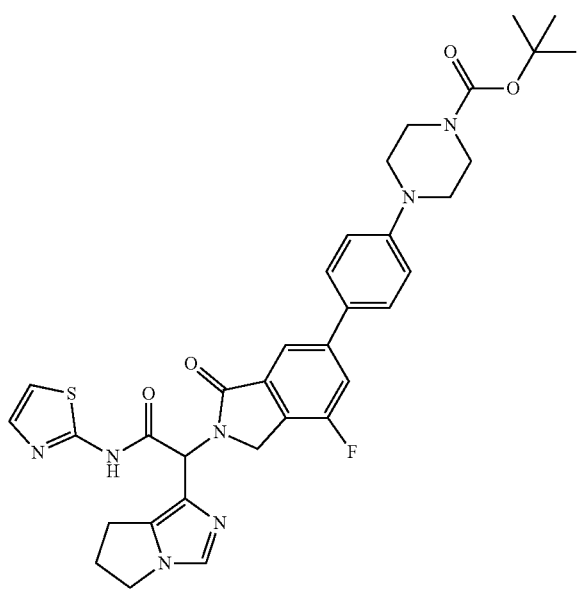 [SMILES: CC(C)(C)OC(=O)N1CCN(c2ccc(-c3cc(F)c4c(c3)C(=O)N(C(C(=O)Nc3nccs3)c3ncn5c3CCC5)C4)cc2)CC1]

tert-Butyl 4-[4-[7-fluoro-3-oxo-2-[(1RS)-1-(6,7-dihydro-5H-pyrrolo[1,2-c]imidazol-1-yl)-2-ethoxy-2-oxo-ethyl]isoindolin-5-yl]phenyl]piperazine-1-carboxylate (48 mg, 0.0795 mmol) was combined with 11 ml of ethanol to give a light yellow solution. LiOH (1M in water) (0.0954 ml, 0.0954 mmol, 1.2 equiv.) was added. The reaction mixture was stirred at room temperature for 2 hours. The reaction mixture was concentrated in vacuo. The residue was taken up in ethanol and concentrated in vacuo and then dissolved in 7.0 ml of N,N-Dimethylformamide. Thiazol-2-amine (9.55 mg, 0.0954 mmol, 1.2 equiv.) and Hunig's base (0.0694 ml, 0.398 mmol, 5 equiv.) were added followed by HATU (36.3 mg, 0.0954 mmol, 1.2 equiv.). The mixture was stirred at room temperature for 1 hour. The reaction mixture was extracted with ethyl acetate and saturated NaHCO$_3$-solution. The aqueous layer was back-extracted with ethyl acetate. The organic layers were washed with water and brine. The organic layers were combined, dried over sodium sulfate, filtered and concentrated to dryness. The crude product was purified by flash chromatography on a silica gel column eluting with a dichloromethane:methanol 100:0 to 90:10 gradient to obtain the desired tert-butyl 4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazine-1-carboxylate (22 mg, 42% yield) as a yellow oil, MS: m/e=658.3 ([M+H]$^+$).

Step 9: (2RS)-2-(6,7-Dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide

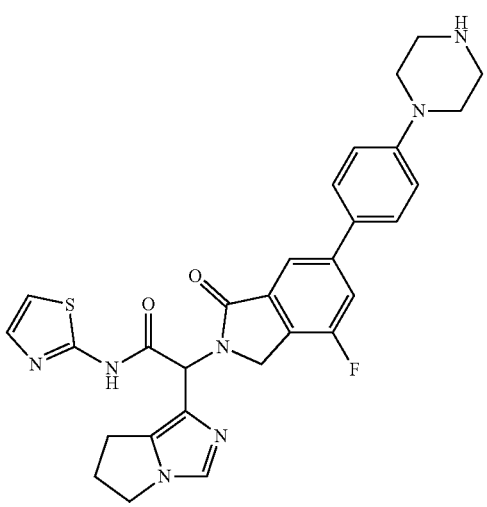 [SMILES: O=C(Nc1nccs1)C(c1ncn2c1CCC2)N1Cc2c(F)cc(-c3ccc(N4CCNCC4)cc3)cc2C1=O]

tert-Butyl 4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazine-1-carboxylate (26 mg, 0.0395 mmol) was dissolved in 0.5 ml of dichloromethane and 0.25 ml of methanol. HCl (4 M in dioxane) (0.099 ml, 0.395 mmol, 10 equiv.) was added at room temperature and the reaction mixture was stirred at room temperature for 16 hours. The reaction mixture was extracted with saturated NaHCO$_3$-solution and twice with dichloromethane. The organic layers were combined, dried over sodium sulfate, filtered and concentrated to dryness. The desired (2RS)-2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide (22 mg, 99.8% yield) was obtained as a light yellow oil, MS: m/e=558.2 ([M+H]$^+$).

Step 10: tert-Butyl 2-[4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazin-1-yl]acetate

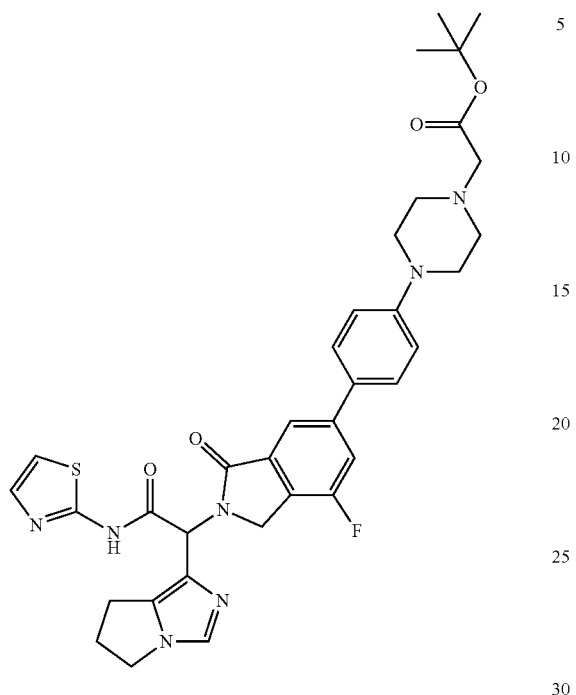

The title compound was obtained as a yellow oil, using chemistry similar to that described in Example 1, step 3 starting from (2RS)-2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide and tert-butyl 2-bromoacetate (CAS 5292-43-3).

Step 11: (2RS)-2-(6,7-Dihydro-5H-pyrrolo[1,2-c]imidazol-1-yl)-2-[4-fluoro-1-oxo-6-[4-[4-[2-oxo-2-[4-[4-[[(3RS)-2,6-dioxo-3-piperidyl]amino]phenyl]-1-piperidyl]ethyl]piperazin-1-yl]phenyl]isoindolin-2-yl]-N-thiazol-2-yl-acetamide

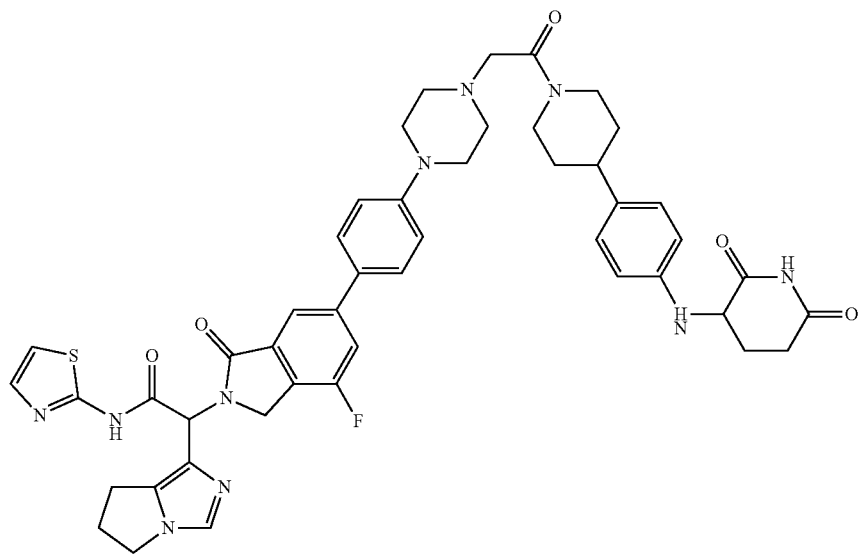 [SMILES: O=C1CCC(Nc2ccc(C3CCN(C(=O)CN4CCN(c5ccc(-c6cc(F)c7c(c6)C(=O)N(C(C(=O)Nc6nccs6)c6ncn8c6CCC8)C7)cc5)CC4)CC3)cc2)C(=O)N1]

The title compound, Compound 10, was obtained as an off-white solid, MS: m/e=885.6 ([M+H]+) using chemistry similar to that described in Example 3, step 4 starting from tert-butyl 2-[4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazin-1-yl]acetate and (3RS)-3-[4-(4-piperidyl)anilino]piperidine-2,6-dione hydrochloride (Example 1, step 2).

Example 11

Synthesis of 2-(6,7-dihydro-5H-pyrrolo[1,2-c]imidazol-1-yl)-2-[6-[4-[4-[2-[4-[5-[(2,6-dioxo-3-piperidyl)amino]-2-pyridyl]-1-piperidyl]acetyl]piperazin-1-yl]phenyl]-4-fluoro-1-oxo-isoindolin-2-yl]-N-thiazol-2-yl-acetamide, Compound 11

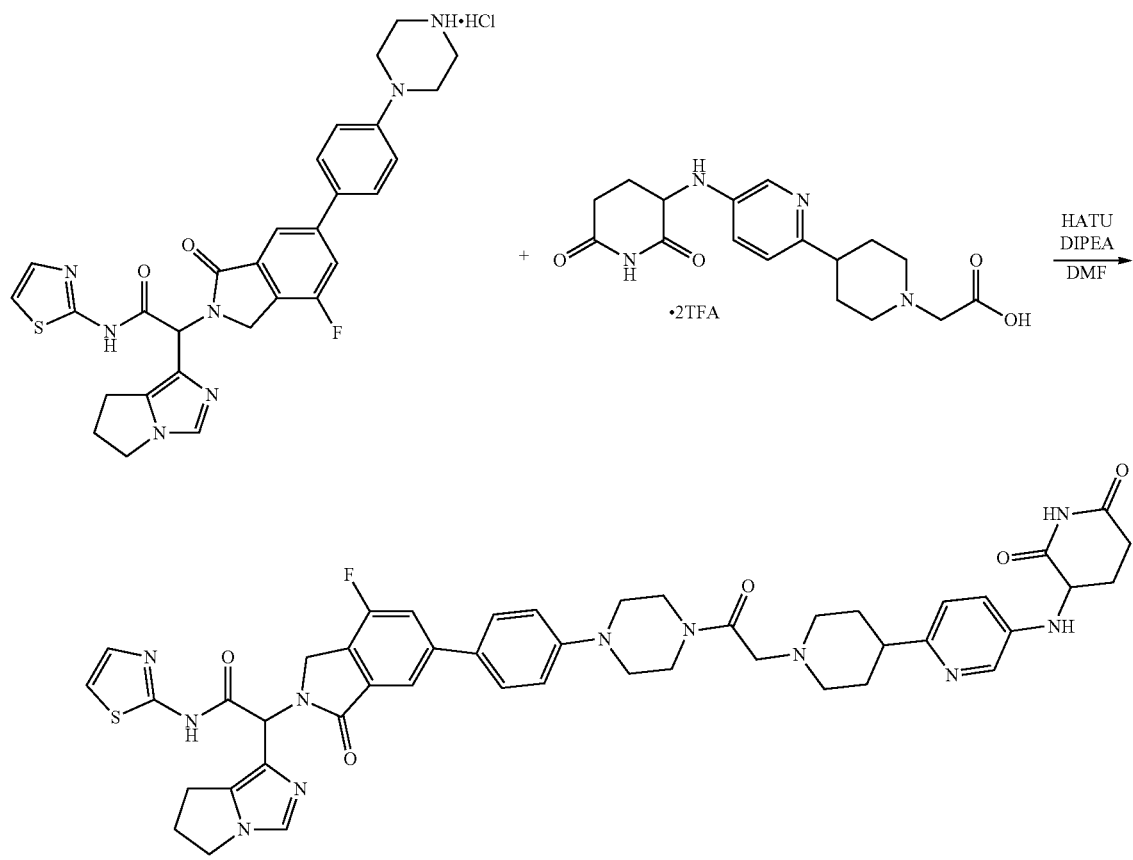

2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide; hydrochloride (75 mg, 126.24 μmol) and 2-[4-[5-[(2,6-dioxo-3-piperidyl)amino]-2-pyridyl]-1-piperidyl]acetic acid bis(trifluoroacetic acid) salt (79.77 mg, 138.87 μmol) were mixed in DMF, the reaction mixture was cooled to 0° C. N,N-Diisopropylethylamine (81.58 mg, 631.21 μmol, 109.94 μL) was added to the reaction mixture, and HATU (62.40 mg, 164.11 μmol) was added, and the reaction mixture was stirred for 4 hours while warming to room temperature. The reaction mixture was acidified with 4-5 drops of TFA and injected directly on a RP C18 column (50 g C18) for purification using a 5% to 100% acetonitrile (+0.1% TFA) in water (+0.1% TFA) eluent gradient. The pure fractions were neutralized with aqueous NaHCO3 (60 mL), extracted with a isopropanol:chloroform mixture (1:4). The organic layer was evaporated under reduced pressure to afford a solid. The solid was dissolved in dichloromethane, an injected on a 24 g silica gel column flushed with 100% dichloromethane and purified using a 0% to 20% methanol in dichloromethane gradient over 20 minutes. The pure fractions were evaporated under reduced pressure. The crude residue in dichloromethane was transferred to an 8 mL vial, and evaporated under reduced pressure. The compound was suspended in an acetonitrile:water mixture, and the mixture was thoroughly sonicated, vortexed and sonicated again. The suspension was frozen and lyophilized to afford Compound 11 (35 mg, 39.11 μmol, 30.98% yield). LCMS (ESI+): 886.6 (M+H). ¹H NMR (400 MHz, DMSO-d$_6$) δ 12.52 (s, 1H), 10.78 (s, 1H), 7.97 (t, J=1.8 Hz, 1H), 7.78 (d, J=1.3 Hz, 1H), 7.76 (s, 1H), 7.72-7.65 (m, 2H), 7.61 (s, 1H), 7.49 (d, J=3.6 Hz, 1H), 7.26 (d, J=3.5 Hz, 1H), 7.08 (d, J=8.8 Hz, 2H), 6.97 (d, J=1.8 Hz, 2H), 6.16 (s, 1H), 5.92 (d, J=7.8 Hz, 1H), 4.81 (d, J=17.7 Hz, 1H), 4.33 (ddd, J=12.2, 7.8, 4.9 Hz, 1H), 4.23 (d, J=17.7 Hz, 1H), 4.11-3.85 (m, 2H), 3.70 (d, J=58.2 Hz, 4H), 3.21 (s, 4H), 2.93 (d, J=10.7 Hz, 2H), 2.85-2.65 (m, 2H), 2.67-2.52 (m, 1H), 2.49 (m, 2H), 2.12 (m, 2H), 1.90 (qd, J=12.3, 4.7 Hz, 1H), 1.84-1.48 (m, 4H).

Example 12

Synthesis of 2-(6,7-dihydro-5H-pyrrolo[1,2-c]imidazol-1-yl)-2-[6-[4-[4-[2-[4-[4-[(2,6-dioxo-3-piperidyl)amino]-2-fluoro-phenyl]-1-piperidyl]acetyl]piperazin-1-yl]phenyl]-4-fluoro-1-oxo-isoindolin-2-yl]-N-thiazol-2-yl-acetamide, Compound 12

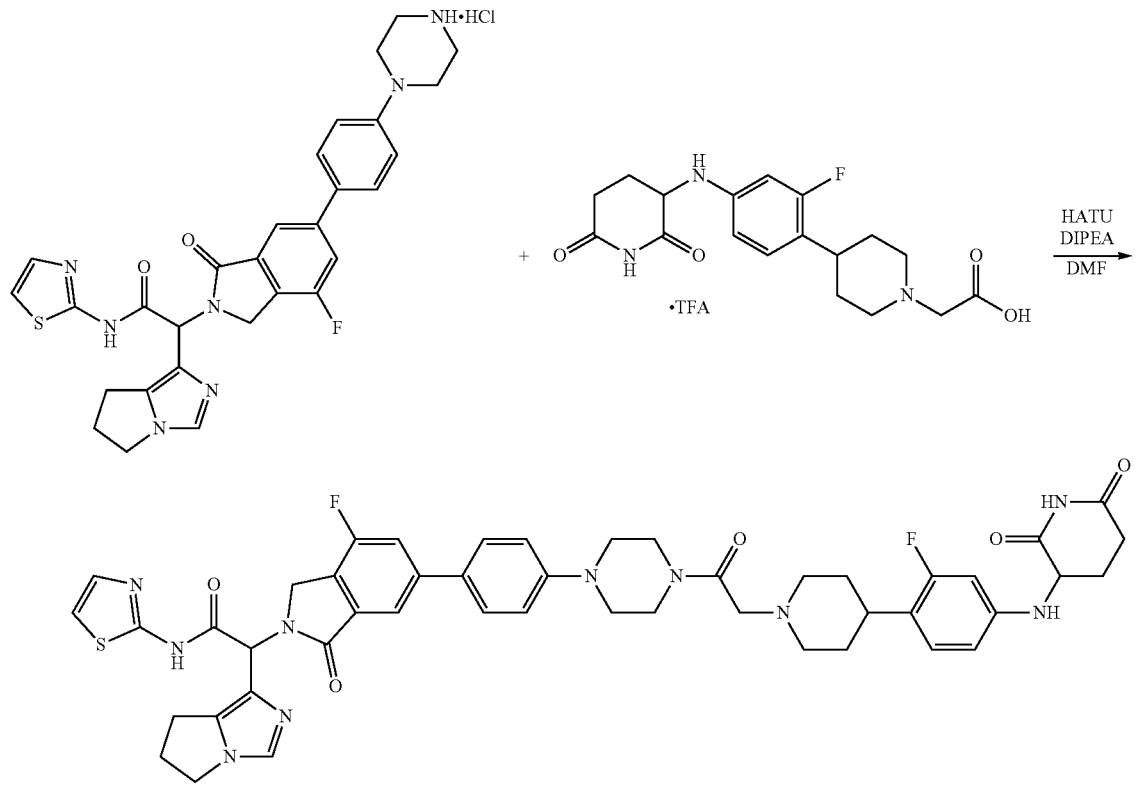

2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide; hydrochloride (51.85 mg, 87.28 µmol) and 2-[4-[4-[(2,6-dioxo-3-piperidyl)amino]-2-fluoro-phenyl]-1-piperidyl]acetic acid, trifluoroacetic acid salt (50 mg, 104.73 µmol) were mixed in DMF, the reaction mixture was cooled to 0° C. N,N-Diisopropylethylamine (56.40 mg, 436.39 µmol, 76.01 µL) was added to the reaction mixture, and HATU (43.14 mg, 113.46 µmol) was added, and the reaction mixture was stirred for 4 hours while warming to room temperature. The reaction mixture was acidified with 4-5 drops of TFA, and injected directly on a RP C18 column (50 g C18) for purification using a 5% to 100% acetonitrile (+0.1% TFA) in water (+0.1% TFA) eluent gradient. The pure fractions were neutralized with saturated aqueous sodium bicarbonate (60 mL), extracted with 1:4 isopropanol:chloroform mixture. The organic layer was evaporated under reduced pressure to afford a solid. The solid was dissolved in dichloromethane, an injected on a 24 g silica gel column flushed with 100% dichloromethane, and purified using a 0% to 20% methanol in dichloromethane gradient over 20 minutes. The pure fractions were evaporated under reduced pressure. The crude residue was dissolved in dichloromethane, transferred to a 8 mL vial, and evaporated under reduced pressure. 1 mL water+1 mL acetonitrile were added, and the mixture was thoroughly sonicated, vortexed and sonicated again. The suspension was frozen and lyophilized to afford Compound 12 (20 mg, 21.48 µmol, 24.62% yield). LCMS (ESI+): 903.7 (M+H). ¹H NMR (400 MHz, DMSO-d$_6$) δ 12.51 (s, 1H), 10.77 (s, 1H), 7.93-7.63 (m, 4H), 7.60 (s, 1H), 7.48 (d, J=3.6 Hz, 1H), 7.36 (s, 1H), 7.25 (d, J=3.6 Hz, 1H), 7.14-7.02 (m, 2H), 6.98 (t, J=8.8 Hz, 1H), 6.58-

6.32 (m, 2H), 6.15 (s, 1H), 5.99 (d, J=7.7 Hz, 1H), 4.80 (d, J=17.7 Hz, 1H), 4.30 (td, J=7.5, 3.9 Hz, 1H), 4.22 (d, J=17.7 Hz, 1H), 3.98 (m, 2H), 3.85-3.45 (m, 4H), 3.25 (d, J=34.8 Hz, 6H), 2.93 (d, J=10.7 Hz, 2H), 2.83-2.65 (m, 2H), 2.64-2.51 (m, 2H), 2.47 (m, 1H), 2.18-1.97 (m, 3H), 1.95-1.76 (m, 1H), 1.66 (m, 4H).

Example 13

Synthesis of 2-(6,7-dihydro-5H-pyrrolo[1,2-c]imidazol-1-yl)-2-[6-[4-[4-[2-[4-[4-[(2,6-dioxo-3-piperidyl)amino]-3-fluoro-phenyl]-1-piperidyl]acetyl]piperazin-1-yl]phenyl]-4-fluoro-1-oxo-isoindolin-2-yl]-N-thiazol-2-yl-acetamide, Compound 13

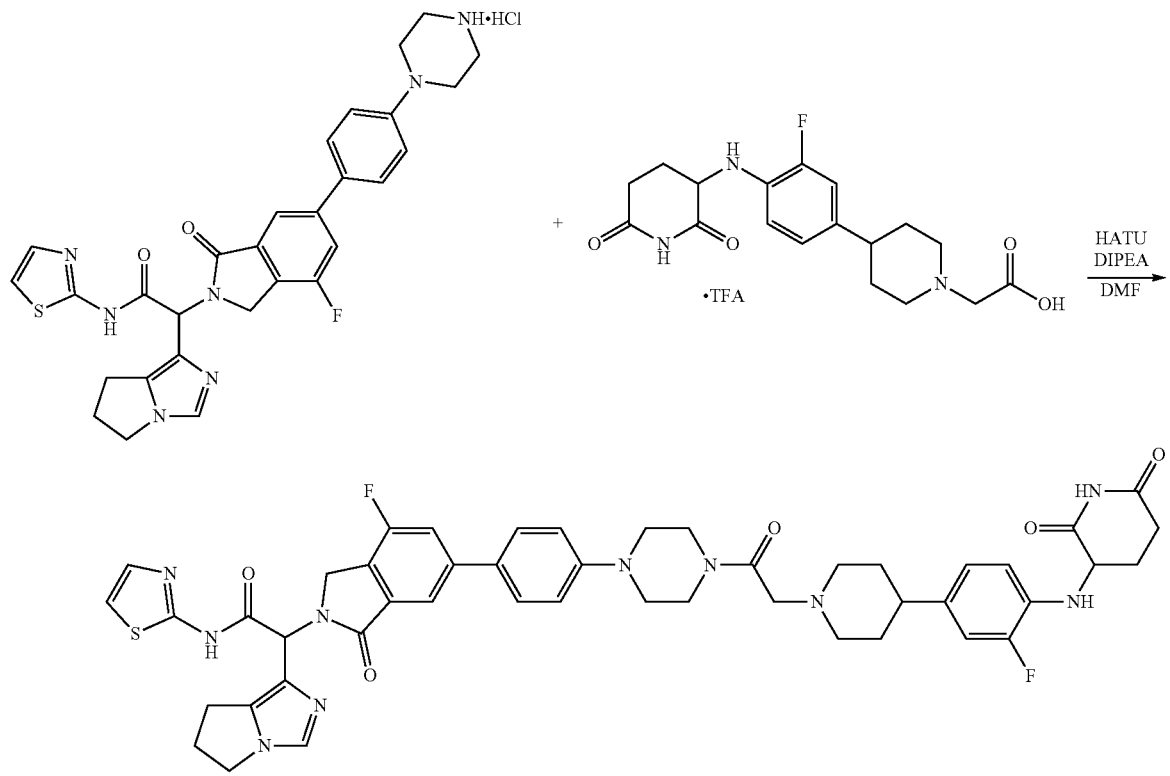

2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide; hydrochloride (48.5 mg, 81.64 µmol) and 2-[4-[4-[(2,6-dioxo-3-piperidyl)amino]-3-fluoro-phenyl]-1-piperidyl]acetic acid, trifluoroacetic acid salt (46.77 mg, 97.96 µmol) were mixed in DMF, the reaction mixture was cooled to 0° C. N,N-Diisopropylethylamine (52.75 mg, 408.18 µmol, 71.10 µL) was added to the reaction mixture, and HATU (40.35 mg, 106.13 µmol) was added, and the reaction mixture was stirred for 4 hours while warming to room temperature. The reaction mixture was acidified with 4-5 drops of TFA, and injected directly on a RP C18 column (50 g C18) for purification (5% to 100% acetonitrile+0.1% TFA in water+0.1% TFA over 12 minutes). The pure fractions were neutralized with aqueous NaHCO₃ (60 mL), extracted with a isopropanol:chloroform mixture (1:4). The organic layer was evaporated under reduced pressure to afford a solid. The solid was dissolved in dichloromethane, an injected on a 24 g silica gel column flushed with 100% dichloromethane, and purified using a 0% to 20% methanol in dichloromethane gradient over 20 minutes. The pure fractions were evaporated under reduced pressure. The crude residue was dissolved in dichloromethane, transferred to a 8 mL vial, and evaporated under reduced pressure. The compound was dissolved in a water: acetonitrile mixture (1 mL:1 mL) were added, and the mixture was thoroughly sonicated, vortexed and sonicated again. The suspension was frozen and lyophilized to afford Compound 13 (15.5 mg, 16.65 µmol, 20.40% yield). LCMS (ESI+): 903.6 (M+H), ¹H NMR (400 MHz, DMSO-d₆) δ 12.52 (s, 1H), 10.80 (s, 1H), 7.78 (d, J=1.3 Hz, 1H), 7.74 (dd, J=10.6, 1.4 Hz, 1H), 7.69 (d, J=8.8 Hz, 2H), 7.61 (s, 1H), 7.49 (d, J=3.6 Hz, 1H), 7.37 (s, 2H), 7.26 (d, J=3.6 Hz, 1H), 7.08 (d, J=8.9 Hz, 2H), 6.94 (dd, J=13.3, 1.9 Hz, 1H), 6.84 (dd, J=8.4, 1.9 Hz, 1H), 6.75 (t, J=8.9 Hz, 1H), 6.15 (s, 1H), 5.38 (dd, J=7.9, 2.4 Hz, 1H), 4.80 (d, J=17.7 Hz, 1H), 4.35 (ddd, J=12.6, 7.9, 5.2 Hz, 1H), 4.23 (d, J=17.7 Hz, 1H), 4.10-3.88 (m, 2H), 3.69 (d, J=54.2 Hz, 4H), 3.26 (d, J=31.5

Hz, 6H), 2.93 (d, J=10.7 Hz, 2H), 2.83-2.69 (m, 1H), 2.63-2.52 (m, 1H), 2.50-2.25 (m, 2H), 2.25-1.88 (m, 4H), 1.73 (d, J=12.1 Hz, 2H), 1.58 (q, J=12.1 Hz, 2H).

General Procedure A1 for the Coupling of 2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide hydrochloride with acids

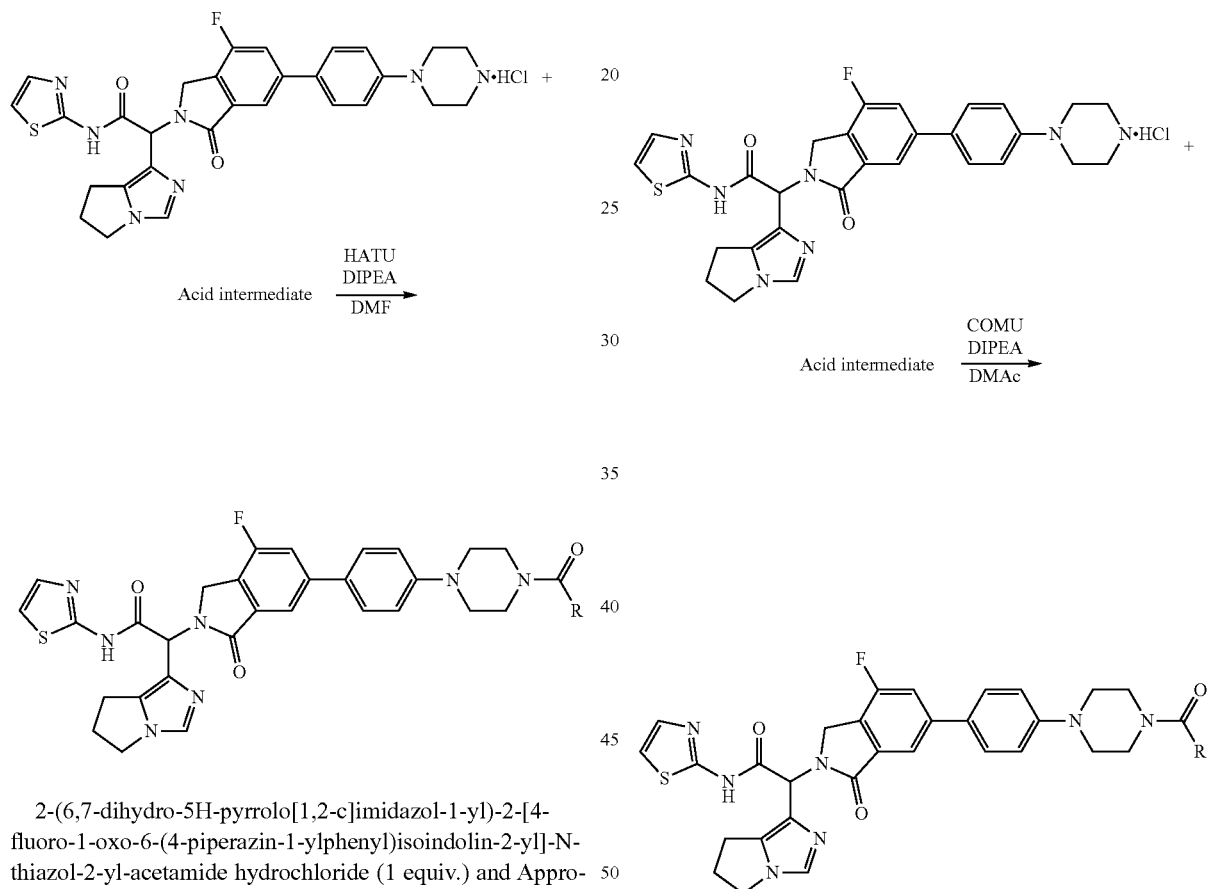

2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide hydrochloride (1 equiv.) and Appropriate Acid intermediate (1.2 equiv.) were mixed in DMF (0.2 M), the reaction mixture was cooled to 0° C. N,N-Diisopropylethylamine (5 equiv.) was added to the reaction mixture, and HATU (1.3 equiv.) was added, and the reaction mixture was stirred for 4 hours while warming to room temperature. The reaction mixture was acidified with 4-5 drops of TFA, and injected directly on a RP C18 column (50 g C18) for purification using a 5% to 100% acetonitrile (+0.1% TFA) in water (+0.1% TFA) eluent gradient. The pure fractions were neutralized with aqueous aqueous NaHCO₃, extracted with an isopropanol:chloroform (1:4) mixture. The organic layer was evaporated under reduced pressure to afford a solid. The solid was dissolved in dichloromethane, and injected on a 24 g silica gel column flushed with 100% dichloromethane and purified using a 0% to 20% methanol in dichloromethane gradient over 20 minutes. The pure fractions were evaporated under reduced pressure. The crude residue was dissolved in dichloromethane, transferred to a 8 mL vial, and evaporated under reduced pressure. The compound was suspended in an acetonitrile:water mixture and the mixture was thoroughly sonicated and vortexed. The suspension was frozen and lyophilized to afford the title compound.

General Procedure B1 for the Coupling of 2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide hydrochloride with acids To a solution of 2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide (1 equiv.) and Appropriate Acid intermediate (1.2 equiv.) in DMAc (0.2 M) was added N,N-Diisopropylethylamine (34.77 mg, 268.99 μmol, 46.85 μL) and (1-Cyano-2-ethoxy-2-oxoethylideaminooxy)dimethylamino-morpholino-carbenium hexafluorophosphate (57.60 mg, 134.50 μmol) at 0° C. the reaction mixture was stirred for 3 hours. The volatiles were evaporated under reduced pressure and the crude was purified by prep HPLC under the following conditions: Column: Agilent preparative C18 (50*21.2 mm, 5 μm). Eluent mixture: 10 mM Ammonium acetate in water:Acetonitrile. Pure fractions were lyophilized to afford the title compound.

Example 14

2-[6-[4-[4-[2-[4-[2-cyano-4-[(2,6-dioxo-3-piperidyl)amino]phenyl]-1-piperidyl]acetyl]piperazin-1-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, Compound 14

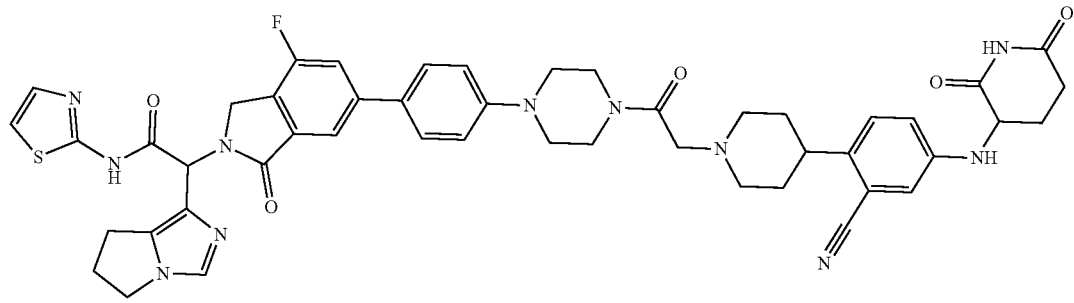 [SMILES: N#Cc1cc(NC2CCC(=O)NC2=O)ccc1C1CCN(CC(=O)N2CCN(c3ccc(-c4cc(F)c5c(c4)C(=O)N(C(C(=O)Nc4nccs4)c4ncn6c4CCC6)C5)cc3)CC2)CC1]

General Procedure A1

LCMS (ESI+): 910.5 (M+H)

$^1$H NMR (400 MHz, DMSO-d$_6$) δ 12.52 (s, 1H), 10.79 (s, 1H), 7.78 (d, J=1.3 Hz, 1H), 7.74 (dd, J=10.6, 1.4 Hz, 1H), 7.68 (d, J=8.6 Hz, 2H), 7.60 (s, 1H), 7.48 (d, J=3.6 Hz, 1H), 7.36 (s, 1H), 7.25 (d, J=3.6 Hz, 1H), 7.20 (d, J=8.4 Hz, 1H), 7.08 (d, J=8.9 Hz, 2H), 6.96 (d, J=8.2 Hz, 2H), 6.23 (d, J=7.9 Hz, 1H), 6.15 (s, 1H), 4.80 (d, J=17.7 Hz, 1H), 4.39 (ddd, J=12.3, 7.9, 4.9 Hz, 1H), 4.22 (d, J=17.7 Hz, 1H), 3.98 (ddd, J=10.2, 8.0, 4.8 Hz, 2H), 3.74 (s, 2H), 3.61 (d, J=6.1 Hz, 2H), 3.27 (dd, J=32.1, 12.0 Hz, 3H), 2.97 (d, J=10.7 Hz, 2H), 2.85-2.52 (m, 3H), 2.30-1.96 (m, 3H), 1.89 (dt, J=12.3, 6.1 Hz, 1H), 1.69 (s, 4H).

50% Yield.

Example 15

2-[6-[4-[4-[2-[4-[2-(difluoromethyl)-4-[(2,6-dioxo-3-piperidyl)amino]phenyl]-1-piperidyl]acetyl]piperazin-1-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, Compound 15

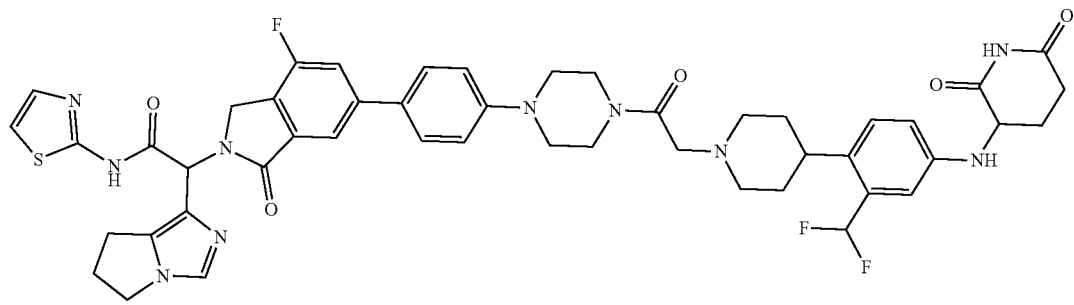 [SMILES: O=C1CCC(Nc2ccc(C3CCN(CC(=O)N4CCN(c5ccc(-c6cc(F)c7c(c6)C(=O)N(C(C(=O)Nc6nccs6)c6ncn8c6CCC8)C7)cc5)CC4)CC3)c(C(F)F)c2)C(=O)N1]

General Procedure A1

LCMS (ESI+): 935.7 (M+H)

$^1$H NMR (400 MHz, DMSO-d$_6$) δ 12.52 (s, 1H), 10.76 (s, 1H), 7.79 (d, J=1.3 Hz, 1H), 7.75 (dd, J=10.6, 1.4 Hz, 1H), 7.72-7.65 (m, 2H), 7.61 (s, 1H), 7.49 (d, J=3.6 Hz, 1H), 7.37 (s, 2H), 7.26 (d, J=3.6 Hz, 1H), 7.15 (d, J=8.5 Hz, 1H), 7.12-7.01 (m, 2H), 6.87-6.68 (m, 2H), 6.16 (s, 1H), 6.00 (d, J=7.8 Hz, 1H), 4.81 (d, J=17.7 Hz, 1H), 4.33 (ddd, J=12.2, 7.8, 4.9 Hz, 1H), 4.23 (d, J=17.7 Hz, 1H), 4.15-3.90 (m, 2H), 3.77 (s, 2H), 3.63 (s, 2H), 3.23 (s, 3H), 2.93 (d, J=10.7 Hz, 2H), 2.75 (dtt, J=19.2, 12.6, 6.4 Hz, 2H), 2.63-2.52 (m, 3H), 2.47 (m, 1H), 2.25-1.98 (m, 3H), 1.90 (tt, J=12.0, 6.1 Hz, 1H), 1.65 (d, J=21.2 Hz, 4H).

26% Yield.

Example 16

2-(6,7-dihydro-5H-pyrrolo[1,2-c]imidazol-1-yl)-2-(6-(4-(4-(2-(4-(3-((2,6-dioxopiperidin-3-yl)amino)phenyl)piperidin-1-yl)acetyl)piperazin-1-yl)phenyl)-4-fluoro-1-oxoisoindolin-2-yl)-N-(thiazol-2-yl)acetamide, Compound 16

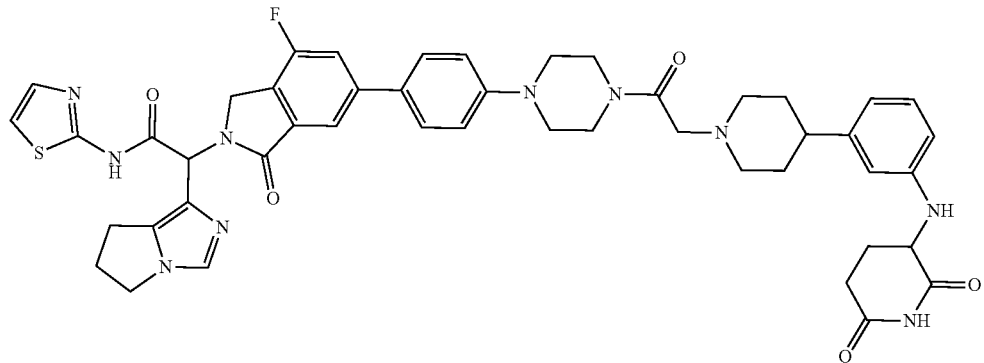 [SMILES: O=C1CCC(Nc2cccc(C3CCN(CC(=O)N4CCN(c5ccc(-c6cc(F)c7c(c6)C(=O)N(C(C(=O)Nc6nccs6)c6ncn8c6CCC8)C7)cc5)CC4)CC3)c2)C(=O)N1]

General Procedure A1

LCMS (ESI+) 885.2 (M+H)

$^1$H NMR (400 MHz, DMSO-$d_6$) δ 12.52 (s, 1H), 10.76 (s, 1H), 7.89-7.65 (m, 4H), 7.61 (s, 1H), 7.49 (d, J=3.5 Hz, 1H), 7.37 (s, 3H), 7.26 (d, J=3.5 Hz, 1H), 7.08 (d, J=8.7 Hz, 2H), 6.99 (t, J=7.8 Hz, 1H), 6.57 (t, J=1.9 Hz, 1H), 6.54-6.38 (m, 2H), 6.16 (s, 1H), 5.73 (d, J=7.6 Hz, 1H), 4.81 (d, J=17.7 Hz, 1H), 4.32 (ddd, J=11.9, 7.5, 4.8 Hz, 1H), 4.23 (d, J=17.7 Hz, 1H), 4.09-3.87 (m, 2H), 3.77 (d, J=5.7 Hz, 2H), 3.62 (d, J=5.5 Hz, 2H), 3.33-3.25 (m, 7H), 3.22 (d, J=7.4 Hz, 4H), 2.95 (d, J=10.7 Hz, 2H), 2.88-2.68 (m, 2H), 2.58 (m, 1H), 2.47 (d, J=5.7 Hz, 1H), 2.44-2.28 (m, 1H), 2.10 (m, 3H), 1.86 (m, 1H), 1.80-1.53 (m, 4H).

15% Yield.

Example 17

2-(6,7-dihydro-5H-pyrrolo[1,2-c]imidazol-1-yl)-2-(6-(4-(4-(2-(4-(3-(2,4-dioxotetrahydropyrimidin-1(2H)-yl)-1-methyl-1H-indazol-6-yl)piperidin-1-yl)acetyl)piperazin-1-yl)phenyl)-4-fluoro-1-oxoisoindolin-2-yl)-N-(thiazol-2-yl)acetamide, Compound 17

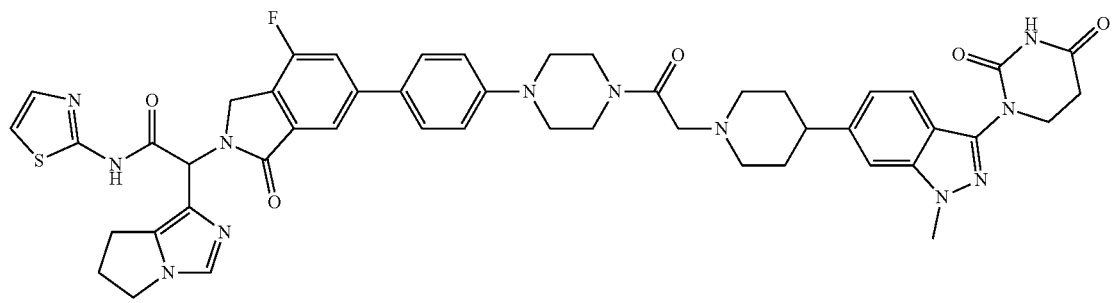 [SMILES: Cn1nc(N2CCC(=O)NC2=O)c2ccc(C3CCN(CC(=O)N4CCN(c5ccc(-c6cc(F)c7c(c6)C(=O)N(C(C(=O)Nc6nccs6)c6ncn8c6CCC8)C7)cc5)CC4)CC3)cc21]

General Procedure A1

LCMS (ESI+) 925.4 (M+H)

$^1$H NMR (400 MHz, DMSO-d6) δ 12.51 (s, 1H), 10.52 (s, 1H), 7.82-7.64 (m, 4H), 7.61 (s, 1H), 7.55 (d, J=8.4 Hz, 1H), 7.48 (d, J=3.6 Hz, 1H), 7.43 (s, 1H), 7.36 (s, 1H), 7.25 (d, J=3.6 Hz, 1H), 7.06 (dd, J=18.9, 8.5 Hz, 3H), 6.15 (s, 1H), 4.80 (d, J=17.8 Hz, 1H), 4.22 (d, J=17.7 Hz, 1H), 4.00 (s, 4H), 3.90 (t, J=6.7 Hz, 2H), 3.77 (s, 2H), 3.63 (s, 2H), 3.27-3.12 (m, 4H), 2.99 (s, 2H), 2.74 (t, J=6.9 Hz, 3H), 2.17 (s, 2H), 1.80 (d, J=20.6 Hz, 4H).

25% Yield.

Example 18

2-(6,7-dihydro-5H-pyrrolo[1,2-c]imidazol-1-yl)-2-(6-(4-(4-(2-(1-(4-((2,6-dioxopiperidin-3-yl)amino)-2-(trifluoromethyl)phenyl)-4-hydroxypiperidin-4-yl)acetyl)piperazin-1-yl)phenyl)-4-fluoro-1-oxoisoindolin-2-yl)-N-(thiazol-2-yl)acetamide, Compound 18

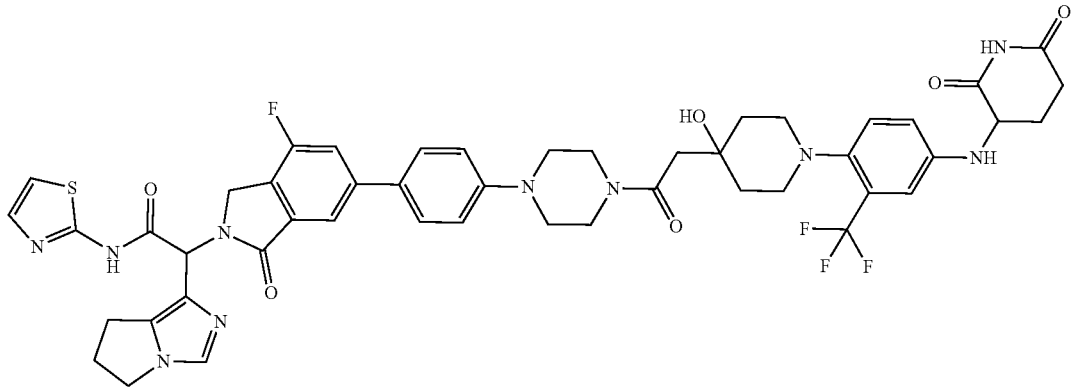 [SMILES: O=C1CCC(Nc2ccc(N3CCC(O)(CC(=O)N4CCN(c5ccc(-c6cc(F)c7c(c6)C(=O)N(C(C(=O)Nc6nccs6)c6ncn8c6CCC8)C7)cc5)CC4)CC3)c(C(F)(F)F)c2)C(=O)N1]

General Procedure B1

LCMS (ESI+) 969.3 (M+H)

$^1$H-NMR (400 MHz, DMSO-d6): δ 12.48 (s, 1H), 10.79 (s, 1H), 7.78-7.69 (m, 4H), 7.57 (s, 1H), 7.39 (bs, 1H), 7.32 (d, J=9.20 Hz, 1H), 7.07 (d, J=8.80 Hz, 3H), 6.92-6.88 (m, 2H), 6.16 (d, J=8.00 Hz, 1H), 6.05 (bs, 1H), 4.93-4.90 (m, 2H), 4.41-4.35 (m, 1H), 4.21 (d, J=17.60 Hz, 2H), 4.00-3.97 (m, 2H), 3.71 (bd, J=26.00 Hz, 3H), 3.25-3.19 (m, 3H), 3.05-2.89 (m, 2H), 2.79-2.70 (m, 3H), 2.68-2.67 (m, 5H), 2.10-2.07 (m, 1H), 2.06-1.92 (m, 1H), 1.26-1.15 (m, 6H).

12% Yield.

Example 19

Synthesis of 2-(6,7-dihydro-5H-pyrrolo[1,2-c]imidazol-1-yl)-2-(6-(4-(4-(2-(4-(4-((2,6-dioxopiperidin-3-yl)amino)phenyl)piperidin-1-yl)acetyl)piperazin-1-yl)phenyl)-4-fluoro-1-oxoisoindolin-2-yl)-N-(pyridin-2-yl)acetamide, Compound 19

Step 1: 2-[6-[4-(4-tert-butoxycarbonylpiperazin-1-yl)phenyl]-4-fluoro-1-oxo-isoindolin-2-yl]-2-(6,7-dihydro-5H-pyrrolo[1,2-c]imidazol-1-yl)acetic acid

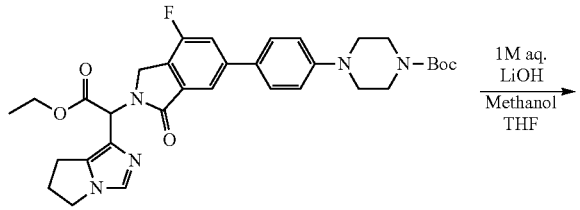

-continued

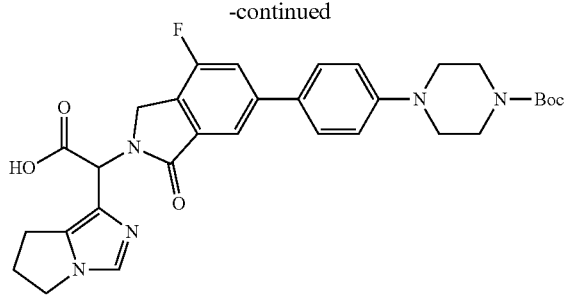

To a solution of tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]piperazine-1-carboxylate (Example 5, step 2) (1.1 g, 1.82 mmol) in THF (6 mL) and Methanol (6 mL) was added 1M Lithium hydroxide monohydrate, 98% (76.46 mg, 1.82 mmol) Water (6 mL) at 0° C. Reaction mixture was stirred at room temperature for 3 hr. Reaction mixture was concentrated to get crude which was dissolved in 5 mL water and acidified by using potassium hydrogen sulfate salt (pH 1-2). The aqueous layer was extracted with ethyl acetate. The combined organic layer washed with brine solution, dried over Na$_2$SO$_4$ and concentrated to afford 2-[6-[4-(4-tert-butoxycarbonylpiperazin-1-yl)phenyl]-4-fluoro-1-oxo-isoindolin-2-yl]-2-(6,7-dihydro-5H-pyrrolo[1,2-c]imidazol-1-yl)acetic acid (700 mg, 942.2 µmol, 50.7% yield). LCMS (ESI+): m/z 576.1 (M+H$^+$)

Step 2: tert-butyl 4-[4-[2-[1-(6,7-dihydro-5H-pyrrolo[1,2-c]imidazol-1-yl)-2-oxo-2-(2-pyridylamino)ethyl]-7-fluoro-3-oxo-isoindolin-5-yl]phenyl]piperazine-1-carboxylate

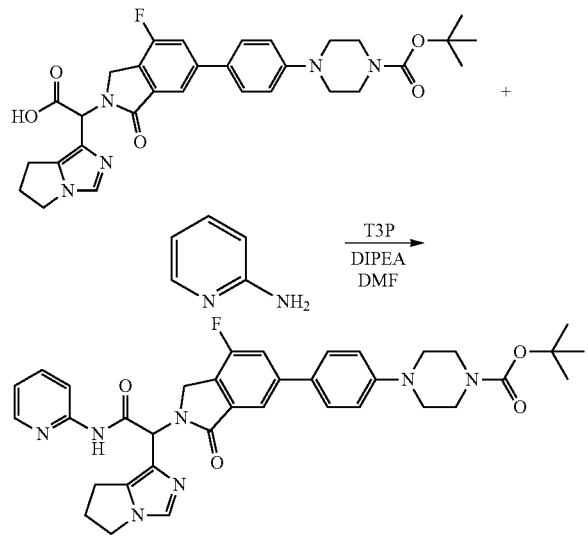

To a solution of 2-[6-[4-(4-tert-butoxycarbonylpiperazin-1-yl)phenyl]-4-fluoro-1-oxo-isoindolin-2-yl]-2-(6,7-dihydro-5H-pyrrolo[1,2-c]imidazol-1-yl)acetic acid (250 mg, 434.31 µmol) in DMF (3 mL) was added and N,N-diisopropyl ethyl amine (378.23 µL, 280.65 mg, 2.17 mmol) and propylphosphonic anhydride, 50% solution in ethyl acetate (276.38 mg, 868.61 µmol) at 0° C. After 15 min, pyridin-2-amine (40.87 mg, 434.31 µmol) was added and reaction mixture heated at 60° C. for 16 hr. The reaction mixture was concentrated and diluted with dichloromethane and washed with water and brine, organic layer dried over Na2SO4, filtered and concentrated in vacuo. The crude product was purified by flash column chromatography, eluting with 3% methanol/dichloromethane. The appropriate fractions were combined and evaporated in vacuo to afford tert-butyl 4-[4-[2-[1-(6,7-dihydro-5H-pyrrolo[1,2-c]imidazol-1-yl)-2-oxo-2-(2-pyridylamino)ethyl]-7-fluoro-3-oxo-isoindolin-5-yl]phenyl]piperazine-1-carboxylate (105 mg, 161 µmol, 37% yield) LCMS m/z 652.3 (M+H$^+$).

Step 3: 2-(6,7-dihydro-5H-pyrrolo[1,2-c]imidazol-1-yl)-2-[4-fluoro-1-oxo-6-(4-piperazin-1-ylphenyl)isoindolin-2-yl]-N-(2-pyridyl)acetamide hydrochloride

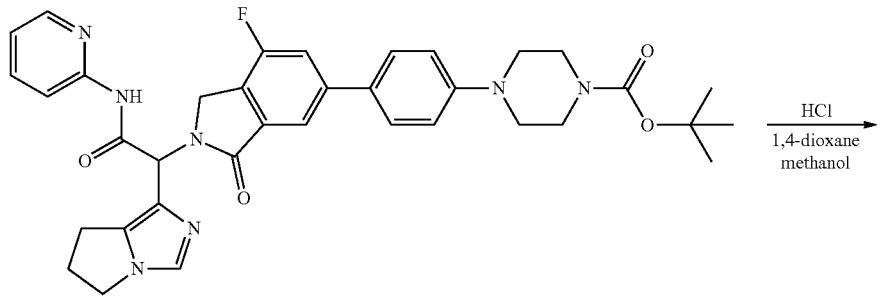

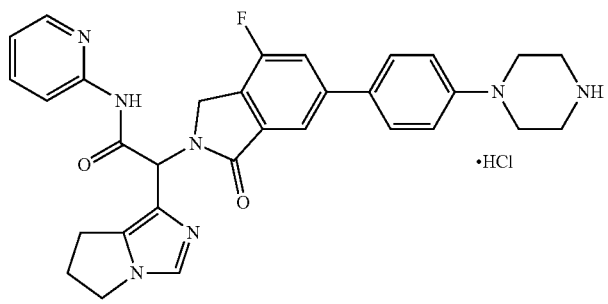

2-(6,7-dihydro-5H-pyrrolo[1,2-c]imidazol-1-yl)-2-[4-fluoro-1-oxo-6-(4-piperazin-1-ylphenyl)isoindolin-2-yl]-N-(2-pyridyl)acetamide hydrochloride was obtained in 83% yield from tert-butyl 4-[4-[2-[1-(6,7-dihydro-5H-pyrrolo[1,2-c]imidazol-1-yl)-2-oxo-2-(2-pyridylamino)ethyl]-7-fluoro-3-oxo-isoindolin-5-yl]phenyl]piperazine-1-carboxylate using the same procedure as (Example 5, step 4). LCMS (ESI+): 552.3 (M+H).

Step 4: 2-(6,7-dihydro-5H-pyrrolo[1,2-c]imidazol-1-yl)-2-(6-(4-(4-(2-(4-(4-((2,6-dioxopiperidin-3-yl)amino)phenyl)piperidin-1-yl)acetyl)piperazin-1-yl)phenyl)-4-fluoro-1-oxoisoindolin-2-yl)-N-(pyridin-2-yl)acetamide

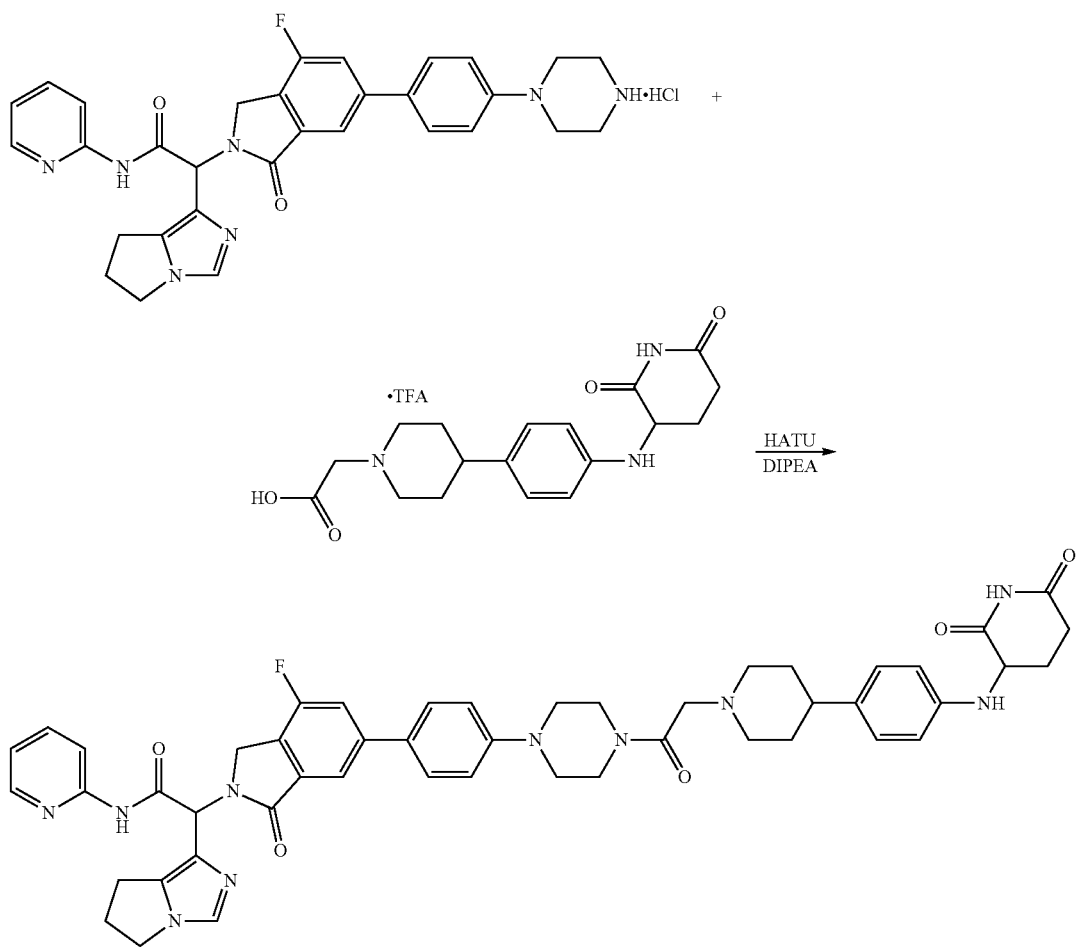

To a solution of 2-[4-[4-[(2,6-dioxo-3-piperidyl)amino]phenyl]-1-piperidyl]acetic acid (61.38 mg, 177.70 µmol) in DMAc (1 mL) was added N,N-diisopropyl ethyl amine (104.39 mg, 807.72 µmol, 140.69 µL) and COMU (83.02 mg, 193.85 µmol) at 0° C. After 15 min, 2-(6,7-dihydro-5H-pyrrolo[1,2-c]imidazol-1-yl)-2-[4-fluoro-1-oxo-6-(4-piperazin-1-ylphenyl)isoindolin-2-yl]-N-(2-pyridyl)acetamide (95 mg, 161.54 µmol) was added. The reaction mixture was stirred for 2 h. The reaction mixture was quenched with ice cold water and solid was precipitated. The crude was purified by reverse phase chromatography using C-18 (30 g) column (0-100% of 0.1% NH₄OAc in water and Acetonitrile). Fractions were lyophilized to afford desired product Compound 19 (14 mg, 14.81 µmol, 9.2% yield) as white solid. LCMS (ESI+): 879.3 (M+H); $^1$H-NMR (400 MHz, DMSO-d6): 10.82 (s, 1H), 10.69 (s, 1H), 8.26-8.25 (m, 1H), 8.00 (d, J=8.1 Hz, 1H), 7.75-7.71 (m, 2H), 7.69-7.58 (m, 3H), 7.54 (s, 1H), 7.07-7.00 (m, 3H), 6.88 (d, J=8.4 Hz, 2H), 6.53 (d, J=8.5 Hz, 2H), 6.13 (s, 1H), 5.58 (d, J=7.5 Hz, 1H), 4.73 (d, J=17.7 Hz, 1H), 4.20-4.15 (m, 2H), 3.96-3.90 (m, 2H), 3.69-3.65 (m, 2H), 3.59-3.55 (m, 2H), 3.27-3.20 (m, 2H), 3.13-3.05 (m, 5H), 2.89-2.84 (m, 2H), 2.72-2.69 (m, 2H), 2.25-2.20 (m, 4H), 2.02-2.00 (m, 2H), 1.85-1.83 (m, 1H), 1.80-1.80 (m, 1H), 1.69-1.61 (m, 2H), 1.58-1.49 (m, 2H).

Example 20

Synthesis of 2-(6,7-dihydro-5H-pyrrolo[1,2-c]imidazol-1-yl)-2-[6-[4-[4-[2-[4-[4-[(2,6-dioxo-3-piperidyl)amino]-2-fluoro-phenyl]-1-piperidyl]acetyl]piperazin-1-yl]phenyl]-4-fluoro-1-oxo-isoindolin-2-yl]-N-(2-pyridyl)acetamide, Compound 20

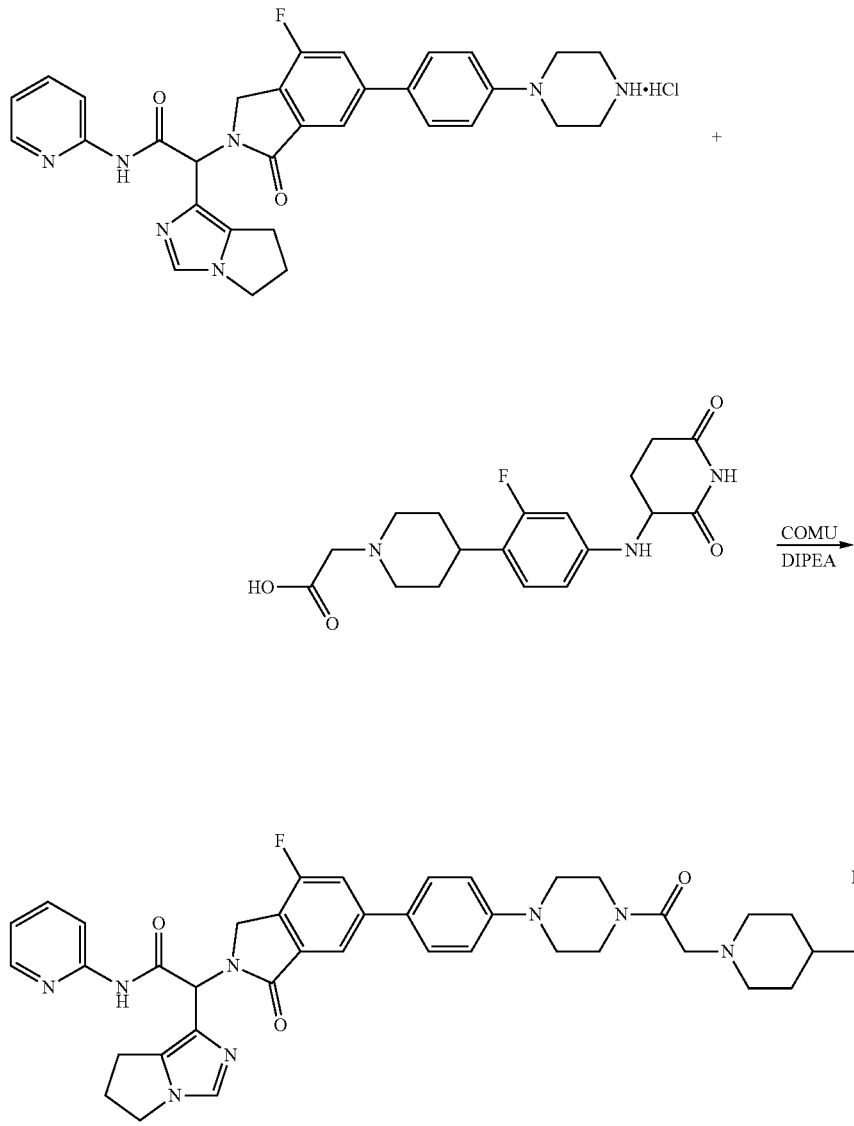

To a solution of 2-[4-[4-[(2,6-dioxo-3-piperidyl)amino]-2-fluoro-phenyl]-1-piperidyl]acetic acid (27.19 mg, 74.82 μmol) in DMAc (1 mL) was added N,N-diisopropyl ethyl amine (43.95 mg, 340.09 μmol, 59.24 μL) and COMU (37.29 mg, 87.06 μmol) at 0° C. After 15 min 2-(6,7-dihydro-5H-pyrrolo[1,2-c]imidazol-1-yl)-2-[4-fluoro-1-oxo-6-(4-piperazin-1-ylphenyl)isoindolin-2-yl]-N-(2-pyridyl)acetamide (40 mg, 68.02 μmol) was added and the reaction was stirred for 2 h. Water (2 mL) was added to the reaction mixture upon which precipitation occurs. The solid precipitate was collected by filtration and dissolved in dichloromethane, then the solution was concentrated. The crude was purified by reverse phase C-18 chromatography (0-100% of 0.1% NH$_4$OAc in water and Acetonitrile). Fractions were lyophilized to get afford desired product as white solid Compound 20 (2.5 mg, 2.70 μmol, 4% yield) as an off-white solid. LCMS (ESI+): 897.3 (M+H$^+$), $^1$H-NMR (400 MHz, DMSO-d6): 10.82 (s, 1H), 10.71 (s, 1H), 8.26-8.25 (m, 1H), 8.00 (d, J=8.2 Hz, 1H), 7.75-7.61 (m, 6H), 7.54 (s, 1H), 7.07-7.00 (m, 3H), 6.91 (t, J=8.4 Hz, 1H), 6.38-6.35 (m, 2H), 6.13 (s, 1H), 5.93 (d, J=7.7 Hz, 1H), 4.73 (d, J=17.6 Hz, 1H), 4.24-4.20 (m, 1H), 4.15 (d, J=17.6 Hz, 1H), 4.01-3.87 (m, 3H), 3.71-3.69 (m, 2H), 3.02-3.55 (m, 2H), 3.27-3.18 (m, 2H), 3.18-3.10 (m, 4H), 2.86 (d, J=10.4 Hz, 1H), 2.74-2.70 (m, 2H), 2.69-2.61 (m, 4H), 2.13-2.03 (m, 3H), 1.84-1.81 (m, 1H), 1.69-1.58 (m, 4H).

Example 21
Synthesis of 2-(6,7-dihydro-5H-pyrrolo[1,2-c]imidazol-1-yl)-2-(6-(4-(1-(2-(4-(4-((2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide, Compound 21
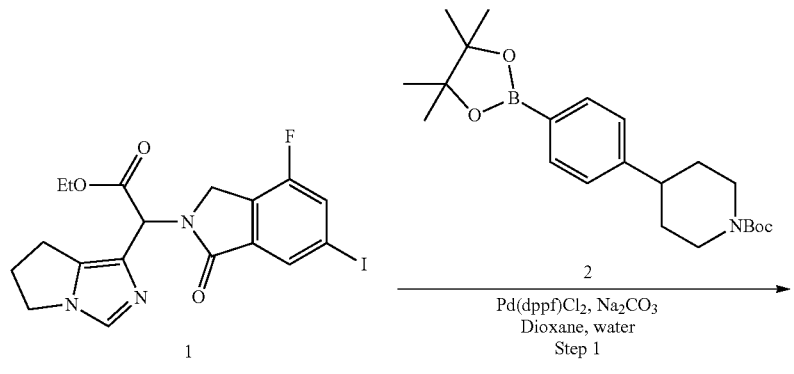
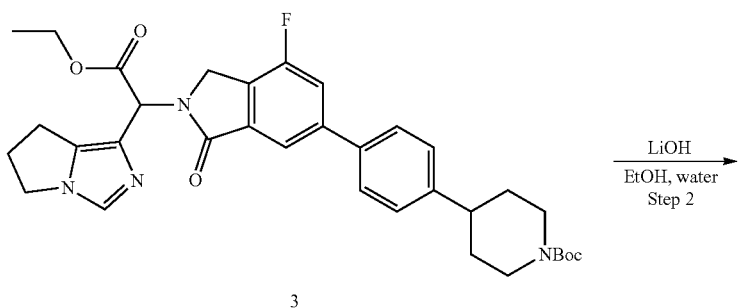
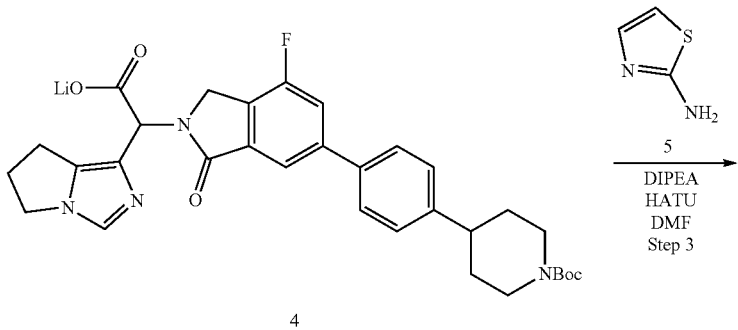
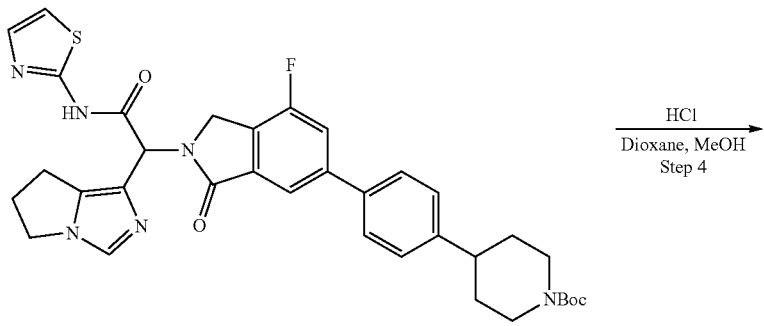

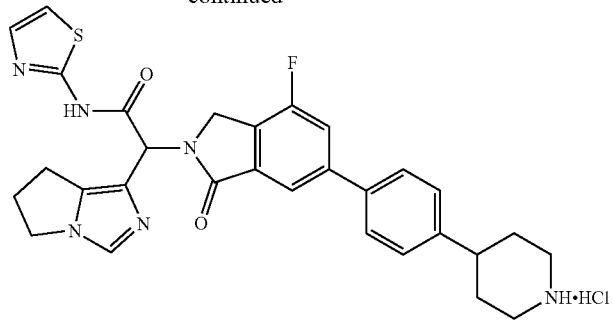

7

Step 1: Tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]piperidine-1-carboxylate In a 100-mL round bottom flask, ethyl 2-(6,7-dihydro-5H-pyrrolo[1,2-c]imidazol-1-yl)-2-(4-fluoro-6-iodo-1-oxo-isoindolin-2-yl)acetate (0.48 g, 1.02 mmol) and tert-butyl 4-[4-(4,4,5,5-tetramethyl-1,3,2-dioxaborolan-2-yl)phenyl]piperidine-1-carboxylate (534.86 mg, 1.38 mmol) were dissolved in dioxane (8.11 mL) and Pd(dppf)Cl$_2$·CH$_2$Cl$_2$ (41.77 mg, 51.15 μmol) and tBuXPhos (64.57 mg, 102.29 μmol) were added, followed by Sodium carbonate (238.52 mg, 2.25 mmol) dissolved in Water (2.03 mL) Water (2.03 mL). The mixture was degassed with nitrogen. The reaction was capped with a septum, with a nitrogen inlet and heated at 80° C. on a heating block for 3 h. The mixture was diluted with ethyl acetate, and the organic layer was separated from the aqueous layer as well as the solid precipitate. The crude residue purified by flash column chromatography on silica gel (0-10% Methanol in ethyl acetate) to give tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]piperidine-1-carboxylate (0.364 g, 603.95 μmol, 59.04% yield) as a pale orange foam. LCMS: Rt=1.473 min., MS (ESI+): 603.8 (M+H)/503.7 (M-Boc+H).

Step 2: [2-[6-[4-(1-tert-butoxycarbonyl-4-piperidyl)phenyl]-4-fluoro-1-oxo-isoindolin-2-yl]-2-(6,7-dihydro-5H-pyrrolo[1,2-c]imidazol-1-yl)acetyl]oxylithium

[2-[6-[4-(1-tert-butoxycarbonyl-4-piperidyl)phenyl]-4-fluoro-1-oxo-isoindolin-2-yl]-2-(6,7-dihydro-5H-pyrrolo[1,2-c]imidazol-1-yl)acetyl]oxylithium was obtained in quantitative yield from tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]piperidine-1-carboxylate using a similar procedure to that used for Example 5, step 2 LCMS (ESI+): 575.4 (M+H)

Step 3: tert-butyl 4-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenyl)piperidine-1-carboxylate tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]piperidine-1-carboxylate was obtained in 66% yield from 2-[6-[4-(1-tert-butoxycarbonyl-4-piperidyl)phenyl]-4-fluoro-1-oxo-isoindolin-2-yl]-2-(6,7-dihydro-5H-pyrrolo[1,2-c]imidazol-1-yl)acetic acid using a procedure similar to the one used for Example 5, step 3. LCMS (ESI+): 657.2 (M+H$^+$)

Step 4: 2-(6,7-dihydro-5H-pyrrolo[1,2-c]imidazol-1-yl)-2-[4-fluoro-1-oxo-6-[4-(4-piperidyl)phenyl]isoindolin-2-yl]-N-thiazol-2-yl-acetamide hydrochloride 2-(6,7-dihydro-5H-pyrrolo[1,2-c]imidazol-1-yl)-2-[4-fluoro-1-oxo-6-[4-(4-piperidyl)phenyl]isoindolin-2-yl]-N-thiazol-2-yl-acetamide hydrochloride was obtained from tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]piperidine-1-carboxylate using a procedure similar to the one used for Example 5, Step 4

General Procedure for Coupling of Acids to 2-(6,7-dihydro-5H-pyrrolo[1,2-c]imidazol-1-yl)-2-(4-fluoro-1-oxo-6-(4-(piperidin-4-yl)phenyl)isoindolin-2-yl)-N-(thiazol-2-yl)acetamide

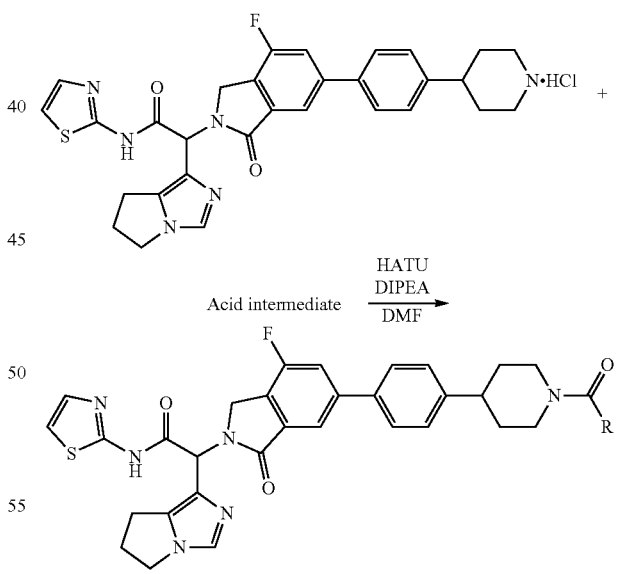

2-(6,7-dihydro-5H-pyrrolo[1,2-c]imidazol-1-yl)-2-(4-fluoro-1-oxo-6-(4-(piperidin-4-yl)phenyl)isoindolin-2-yl)-N-(thiazol-2-yl)acetamide (1 equiv.) and Appropriate Acid intermediate (1.2 equiv.) were mixed in DMF and the reaction mixture was cooled to 0° C. N,N-Diisopropylethylamine (5 equiv.) was added to the reaction mixture, and HATU (1.3 equiv.) was added, and the reaction mixture was stirred for 4 hours while warming to room temperature. The reaction mixture was acidified with 4-5 drops of TFA, and injected directly on a C18 column (50 g C18) for purification (5% to 100% acetonitrile (+0.1% TFA) in water (+0.1% TFA) over 12 minutes). The pure fractions were neutralized with aqueous NaHCO$_3$ (ca. 60 mL), extracted with 1:4 isopropanol:chloroform (1:1) mixture. The organic layer was evaporated under reduced pressure to afford a solid. The solid was dissolved in dichloromethane, and injected on a 24 g silica gel column flushed with 100% dichloromethane, and purified using a 0% to 20% methanol in dichloromethane gradient over 20 minutes. The pure fractions were evaporated under reduced pressure. The crude residue was dissolved in dichloromethane, transferred to a 8 mL vial, and evaporated under reduced pressure. Water (1 mL) and acetonitrile (1 mL) were added, and the mixture was thoroughly sonicated, vortexed and sonicated again. The suspension was frozen and lyophilized to afford the title compound.

Example 21

2-(6,7-dihydro-5H-pyrrolo[1,2-c]imidazol-1-yl)-2-(6-(4-(1-(2-(4-(4-((2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide, Compound 21

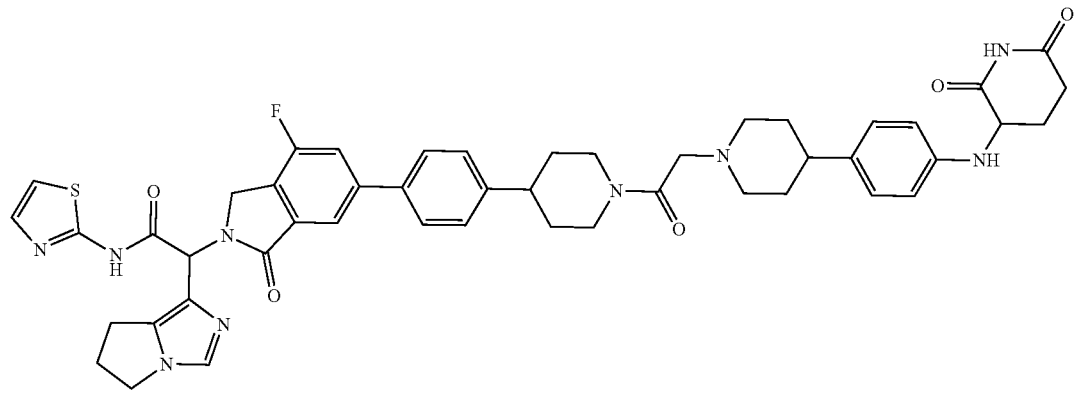 [SMILES: O=C1CCC(Nc2ccc(C3CCN(CC(=O)N4CCC(c5ccc(-c6cc(F)c7c(c6)C(=O)N(C(C(=O)Nc6nccs6)c6ncn8c6CCC8)C7)cc5)CC4)CC3)cc2)C(=O)N1]

Made using the general procedure for the coupling of acids to 2-(6,7-dihydro-5H-pyrrolo[1,2-c]imidazol-1-yl)-2-(4-fluoro-1-oxo-6-(4-(piperidin-4-yl)phenyl)isoindolin-2-yl)-N-(thiazol-2-yl)acetamide.

LCMS (ESI+) 884.6 (M+H)

$^1$H NMR (400 MHz, DMSO-d$_6$) δ 12.52 (s, 1H), 10.76 (s, 1H), 7.94-7.78 (m, 2H), 7.77-7.68 (m, 2H), 7.61 (s, 1H), 7.49 (d, J=3.6 Hz, 1H), 7.45-7.31 (m, 2H), 7.26 (d, J=3.6 Hz, 1H), 7.06-6.84 (m, 2H), 6.72-6.50 (m, 2H), 6.16 (s, 1H), 5.64 (d, J=7.4 Hz, 1H), 4.83 (d, J=17.8 Hz, 1H), 4.54 (d, J=12.5 Hz, 1H), 4.29-4.13 (m, 3H), 4.10-3.86 (m, 2H), 3.28 (s, 1H), 3.22-3.02 (m, 2H), 3.02-2.53 (m, 6H), 2.50-2.43 (m, 1H), 2.33 (ddd, J=11.8, 9.6, 5.9 Hz, 1H), 2.19-1.99 (m, 3H), 1.94-1.34 (m, 9H).

24.5% Yield

Example 22

2-(6,7-dihydro-5H-pyrrolo[1,2-c]imidazol-1-yl)-2-(6-(4-(1-(2-(4-(4-(((S)-2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide, Compound 22

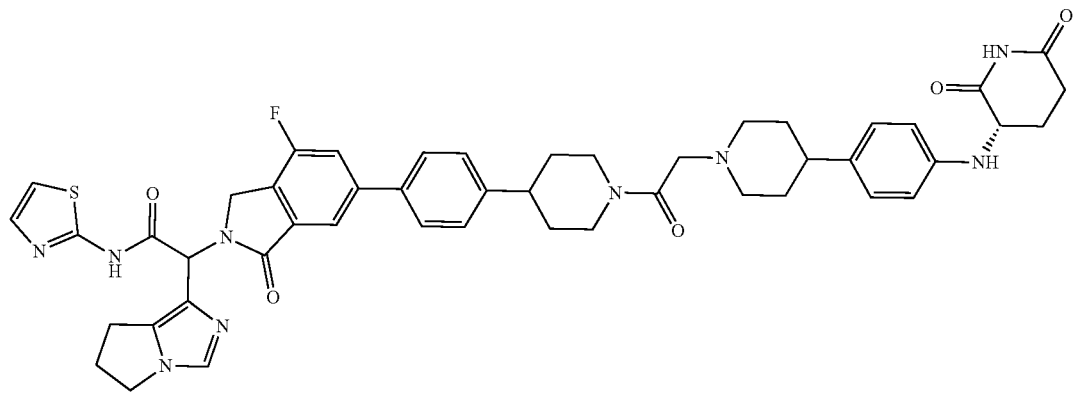 [SMILES: O=C1CC[C@H](Nc2ccc(C3CCN(CC(=O)N4CCC(c5ccc(-c6cc(F)c7c(c6)C(=O)N(C(C(=O)Nc6nccs6)c6ncn8c6CCC8)C7)cc5)CC4)CC3)cc2)C(=O)N1]

Made using the general procedure for the coupling of acids to 2-(6,7-dihydro-5H-pyrrolo[1,2-c]imidazol-1-yl)-2-(4-fluoro-1-oxo-6-(4-(piperidin-4-yl)phenyl)isoindolin-2-yl)-N-(thiazol-2-yl)acetamide.

LCMS (ESI+) 884.6 (M+H)

$^1$H NMR (400 MHz, DMSO-$d_6$) δ 12.52 (s, 1H), 10.76 (s, 1H), 7.86-7.77 (m, 2H), 7.77-7.71 (m, 2H), 7.61 (s, 1H), 7.49 (d, J=3.6 Hz, 1H), 7.40-7.34 (m, 2H), 7.26 (d, J=3.6 Hz, 1H), 6.98-6.92 (m, 2H), 6.65-6.57 (m, 2H), 6.16 (s, 1H), 5.65 (d, J=7.5 Hz, 1H), 4.83 (d, J=17.8 Hz, 1H), 4.54 (d, J=12.6 Hz, 1H), 4.31-4.20 (m, 3H), 4.05-3.93 (m, 3H), 3.28 (s, 1H), 3.09 (m, 2H), 3.01-2.56 (m, 8H), 2.42-2.28 (m, 1H), 2.09 (m, 3H), 2.00-1.35 (m, 8H).

15.5% Yield

Example 23

2-(6,7-dihydro-5H-pyrrolo[1,2-c]imidazol-1-yl)-2-(6-(4-(1-(2-(4-(4-(((R)-2,6-dioxopiperidin-3-yl)amino)phenyl)piperidin-1-yl)acetyl)piperidin-4-yl)phenyl)-4-fluoro-1-oxoisoindolin-2-yl)-N-(thiazol-2-yl)acetamide, Compound 23

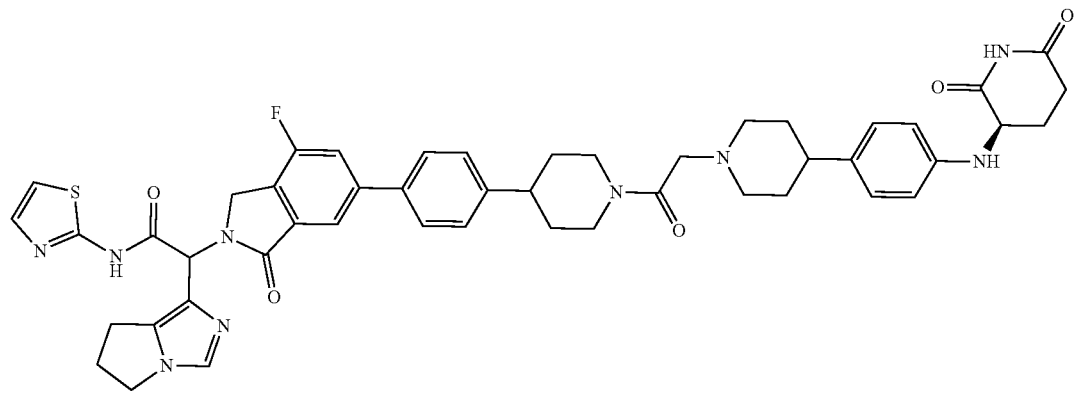 [SMILES: O=C1CC[C@@H](Nc2ccc(C3CCN(CC(=O)N4CCC(c5ccc(-c6cc(F)c7c(c6)C(=O)N(C(C(=O)Nc6nccs6)c6ncn8c6CCC8)C7)cc5)CC4)CC3)cc2)C(=O)N1]

Made using the general procedure for the coupling of acids to 2-(6,7-dihydro-5H-pyrrolo[1,2-c]imidazol-1-yl)-2-(4-fluoro-1-oxo-6-(4-(piperidin-4-yl)phenyl)isoindolin-2-yl)-N-(thiazol-2-yl)acetamide.

LCMS (ESI+) 884.5 (M+H)

$^1$H NMR (400 MHz, DMSO-$d_6$) δ 12.52 (s, 1H), 10.76 (s, 1H), 7.86-7.77 (m, 2H), 7.77-7.71 (m, 2H), 7.61 (s, 1H), 7.49 (d, J=3.6 Hz, 1H), 7.40-7.34 (m, 2H), 7.26 (d, J=3.6 Hz, 1H), 6.98-6.92 (m, 2H), 6.65-6.57 (m, 2H), 6.16 (s, 1H), 5.65 (d, J=7.5 Hz, 1H), 4.83 (d, J=17.8 Hz, 1H), 4.54 (d, J=12.6 Hz, 1H), 4.31-4.20 (m, 3H), 4.05-3.93 (m, 3H), 3.28 (s, 1H), 3.09 (m, 2H), 3.01-2.56 (m, 8H), 2.42-2.28 (m, 1H), 2.09 (m, 3H), 2.00-1.35 (m, 8H).

26.6% Yield

Example 24

2-(6,7-dihydro-5H-pyrrolo[1,2-c]imidazol-1-yl)-2-(6-(4-(1-(2-(4-(4-(((R)-2,6-dioxopiperidin-3-yl)amino)-2-fluorophenyl)piperidin-1-yl)acetyl)piperidin-4-yl)phenyl)-4-fluoro-1-oxoisoindolin-2-yl)-N-(thiazol-2-yl)acetamide, Compound 24

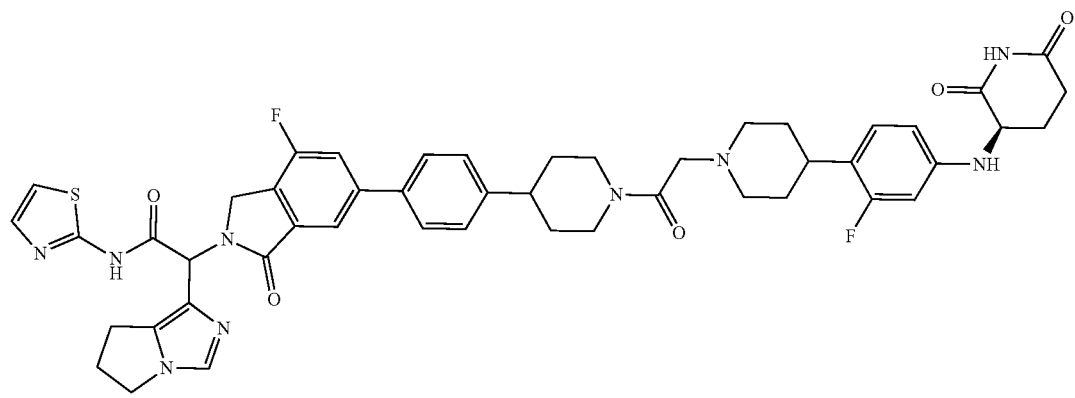 [SMILES: O=C1CC[C@@H](Nc2ccc(C3CCN(CC(=O)N4CCC(c5ccc(-c6cc(F)c7c(c6)C(=O)N(C(C(=O)Nc6nccs6)c6ncn8c6CCC8)C7)cc5)CC4)CC3)c(F)c2)C(=O)N1]

Made using the general procedure for the coupling of acids to 2-(6,7-dihydro-5H-pyrrolo[1,2-c]imidazol-1-yl)-2-(4-fluoro-1-oxo-6-(4-(piperidin-4-yl)phenyl)isoindolin-2-yl)-N-(thiazol-2-yl)acetamide.

LCMS (ESI+) 902.1 (M+H)

$^1$H-NMR (400 MHz, DMSO-d6): δ 12.51 (s, 1H), 10.79 (s, 1H), δ 7.81 (d, J=13.7 Hz, 2H), 7.74 (d, J=8.1 Hz, 2H), 7.61 (s, 1H), 7.48 (d, J=3.5 Hz, 1H), 7.37 (d, J=8.2 Hz, 2H), 7.25 (d, J=3.1 Hz, 1H), 6.97 (t, J=8.3 Hz, 1H), 6.45 (s, 1H), 6.42 (d, J=4.8 Hz, 1H), 6.14 (s, 1H), 6.01 (d, J=8.0 Hz, 1H), 4.83 (d, J=17.6 Hz, 1H), 4.55-4.52 (m, 1H), 4.32-4.22 (m, 3H), 4.00-3.94 (m, 2H), 3.31-2.25 (m, 1H), 3.11-3.07 (m, 2H), 2.94-2.77 (m, 3H), 2.75-2.68 (m, 2H), 2.65-2.60 (m, 3H), 2.09-2.07 (m, 4H), 1.90-1.85 (m, 4H), 1.75-1.66 (m, 5H), 1.56-1.41 (m, 1H).

12% Yield

Example 25

2-(6-(4-(1-(2-(4-(2-cyano-4-((2,6-dioxopiperidin-3-yl)amino)phenyl)piperidin-1-yl)acetyl)piperidin-4-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide, Compound 25

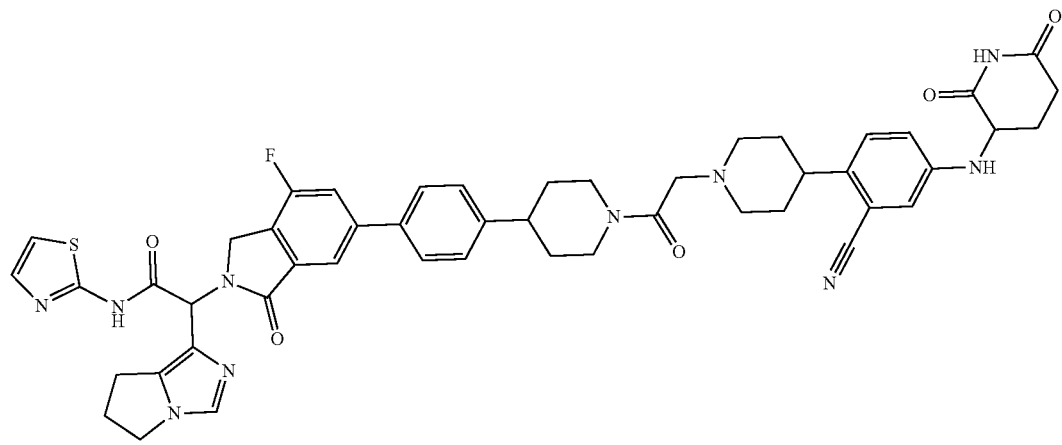 [SMILES: N#Cc1cc(NC2CCC(=O)NC2=O)ccc1C1CCN(CC(=O)N2CCC(c3ccc(-c4cc(F)c5c(c4)C(=O)N(C(C(=O)Nc4nccs4)c4ncn6c4CCC6)C5)cc3)CC2)CC1]

Made using the general procedure for the coupling of acids to 2-(6,7-dihydro-5H-pyrrolo[1,2-c]imidazol-1-yl)-2-(4-fluoro-1-oxo-6-(4-(piperidin-4-yl)phenyl)isoindolin-2-yl)-N-(thiazol-2-yl)acetamide.

LCMS (ESI+) 909.4 (M+H)

¹H NMR (400 MHz, DMSO-d₆) δ 12.52 (s, 1H), 10.80 (s, 1H), 7.92-7.77 (m, 2H), 7.75 (d, J=8.1 Hz, 2H), 7.61 (s, 1H), 7.49 (d, J=3.5 Hz, 1H), 7.38 (d, J=8.2 Hz, 2H), 7.26 (d, J=3.6 Hz, 1H), 7.19 (d, J=8.5 Hz, 1H), 7.04-6.83 (m, 2H), 6.24 (d, J=7.9 Hz, 1H), 6.16 (s, 1H), 4.83 (d, J=17.8 Hz, 1H), 4.55 (d, J=12.5 Hz, 1H), 4.40 (ddd, J=12.3, 7.8, 4.9 Hz, 1H), 4.25 (d, J=17.7 Hz, 2H), 4.05-3.85 (m, 2H), 3.22-3.05 (m, 3H), 3.04-2.93 (m, 2H), 2.93-2.52 (m, 9H), 2.27-1.99 (m, 3H), 1.98-1.80 (m, 3H), 1.70 (s, 5H), 1.49 (q, J=12.3 Hz, 1H).

18.6% Yield

Example 26

Synthesis of 2-(6,7-dihydro-5H-pyrrolo[1,2-c]imidazol-1-yl)-2-[6-[4-[1-[2-[4-[(2,6-dioxo-3-piperidyl)amino]phenyl]-1-piperidyl]-2-oxo-ethyl]-4-piperidyl]phenyl]-4-fluoro-1-oxo-isoindolin-2-yl]-N-thiazol-2-yl-acetamide, Compound 26

Step 1: (2RS)-2-(6,7-Dihydro-5H-pyrrolo[1,2-c]imidazol-1-yl)-2-[4-fluoro-1-oxo-6-[4-(4-piperidyl)phenyl]isoindolin-2-yl]-N-thiazol-2-yl-acetamide

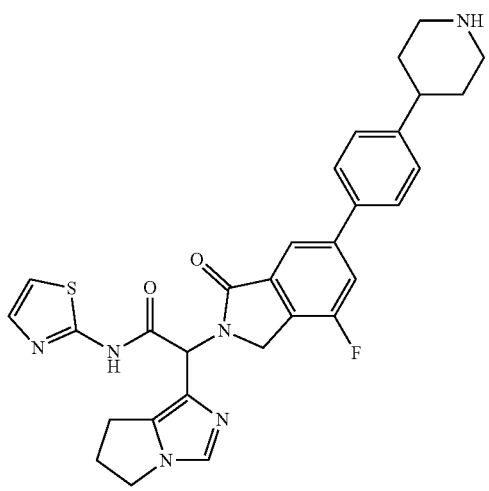 [SMILES: O=C(Nc1nccs1)C(c1ncn2c1CCC2)N1Cc2c(F)cc(-c3ccc(C4CCNCC4)cc3)cc2C1=O]

To a solution of tert-butyl 4-[4-[2-[(1RS)-1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]piperidine-1-carboxylate (Example 21, step 3) (189 mg, 288 μmol) in a mixture of dichloromethane (1.5 ml) and methanol (750 μl was added dropwise HCl in Dioxane 4M (719 μl, 2.88 mmol, Eq: 10). The reaction mixture was stirred at room temperature for 1 hour. The solvents were evaporated and the residue was dissolved in dichloromethane and washed with saturated NaHCO₃-solution. The aqueous layer was extracted a second time with dichloromethane. The combined organic layers were washed with water, dried over Na₂SO₄, filtered and concentrated to afford (2RS)-2-(6,7-dihydro-5H-pyrrolo[1,2-c]imidazol-1-yl)-2-[4-fluoro-1-oxo-6-[4-(4-piperidyl)phenyl]isoindolin-2-yl]-N-thiazol-2-yl-acetamide (180 mg, 291 μmol, 101% yield) as an orange solid. MS: m/e=557.5 ([M+H]⁺).

Step 2: tert-Butyl 2-[4-[4-[2-[(1RS)-1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-1-piperidyl]acetate

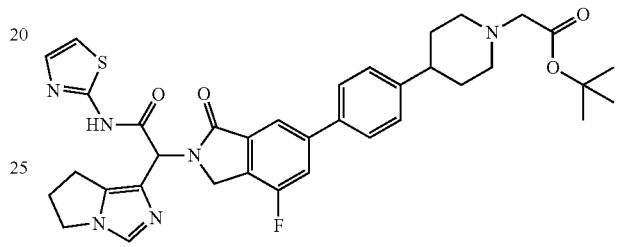

The title compound was obtained as a yellow oil, using chemistry similar to that described in Example 1, step 3 starting from (2RS)-2-(6,7-dihydro-5H-pyrrolo[1,2-c]imidazol-1-yl)-2-[4-fluoro-1-oxo-6-[4-(4-piperidyl)phenyl]isoindolin-2-yl]-N-thiazol-2-yl-acetamide (Example 11, step 1) and tert-butyl 2-bromoacetate (CAS 5292-43-3). MS: m/e=671.4 ([M+H]⁺).

Step 3: 2-[4-[4-[2-[(1RS)-1-(6,7-Dihydro-5H-pyrrolo[1,2-c]imidazol-1-yl)-2-oxo-2-(thiazol-2-ylamino)ethyl]-7-fluoro-3-oxo-isoindolin-5-yl]phenyl]-1-piperidyl]acetic acid 2,2,2-trifluoroacetic acid salt

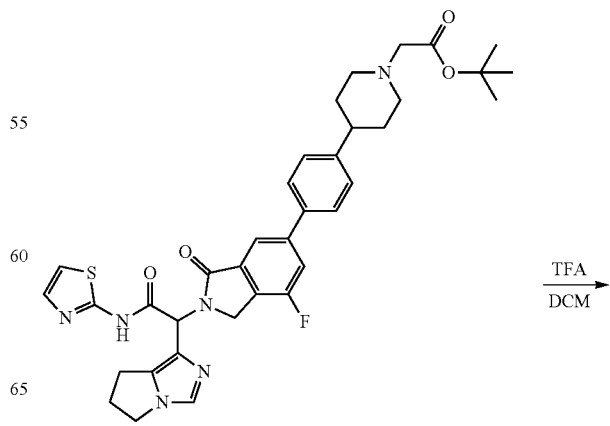

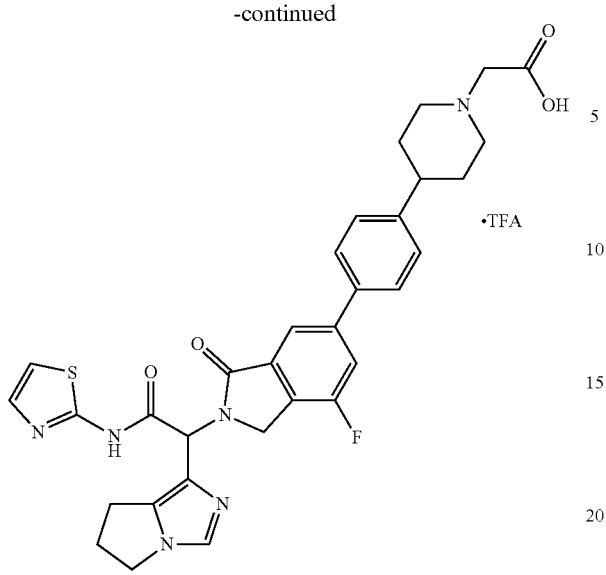

To a stirred solution of tert-butyl 2-(4-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenyl)piperidin-1-yl)acetate (10 mg, 14.9 μmol, Eq: 1) in dichloromethane (0.1 ml) was added TFA (34 mg, 23 μl, 298 μmol, Eq: 20). The reaction mixture was stirred at room temperature for 16 hr. The reaction mixture was concentrated in vacuo to 2-[4-[4-[2-[(1S)-1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-1-piperidyl]acetic acid (15 mg, 20.6 μmol, 138% yield) as an off-white solid. MS: m/e=613.5 ([M+H]⁺).

Step 4: (2RS)-2-(6,7-Dihydro-5H-pyrrolo[1,2-c]imidazol-1-yl)-2-[6-[4-[1-[2-[4-[4-[(2,6-dioxo-3-piperidyl)amino]phenyl]-1-piperidyl]-2-oxo-ethyl]-4-piperidyl]phenyl]-4-fluoro-1-oxo-isoindolin-2-yl]-N-thiazol-2-yl-acetamide

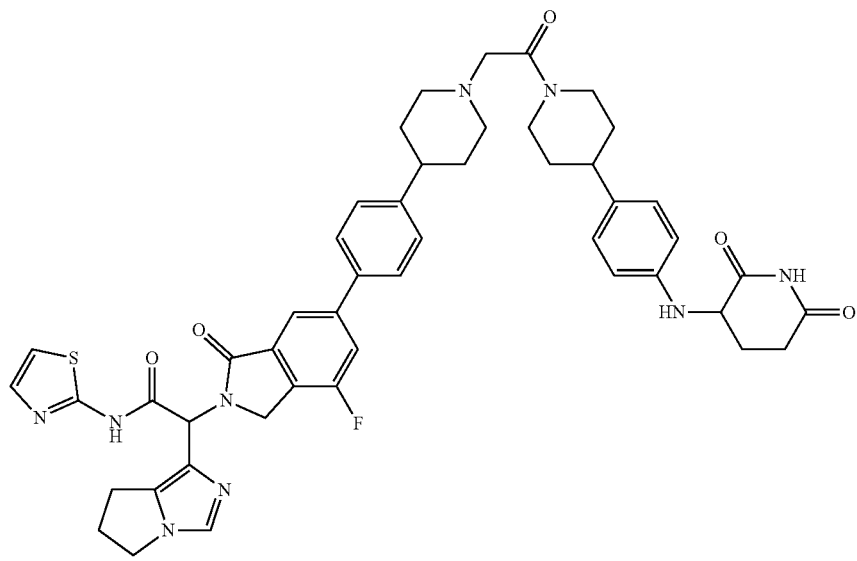 [SMILES: O=C1CCC(Nc2ccc(C3CCN(C(=O)CN4CCC(c5ccc(-c6cc(F)c7c(c6)C(=O)N(C(C(=O)Nc6nccs6)c6ncn8c6CCC8)C7)cc5)CC4)CC3)cc2)C(=O)N1]

The title compound, Compound 26, was obtained as a white gum, MS: m/e=884.7 ([M+H]⁺), using chemistry similar to that described in Example 4, step 4 starting from 2-[4-[4-[2-[(1RS)-1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-1-piperidyl]acetic acid 2,2,2-trifluoroacetic acid salt (Example 11, step 3) and (3RS)-3-[4-(4-piperidyl)anilino]piperidine-2,6-dione hydrochloride (Example 1, step 2).

Example 27

2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]acetyl]piperazin-1-yl]-3-pyridyl]-4-fluoro-1-oxo-isoindolin-2-yl]-N-thiazol-2-yl-acetamide, Compound 27

Step 1: tert-butyl 4-[5-[2-[1-(6,7-dihydro-5H-pyrrolo[1,2-c]imidazol-1-yl)-2-ethoxy-2-oxo-ethyl]-7-fluoro-3-oxo-isoindolin-5-yl]-2-pyridyl]piperazine-1-carboxylate

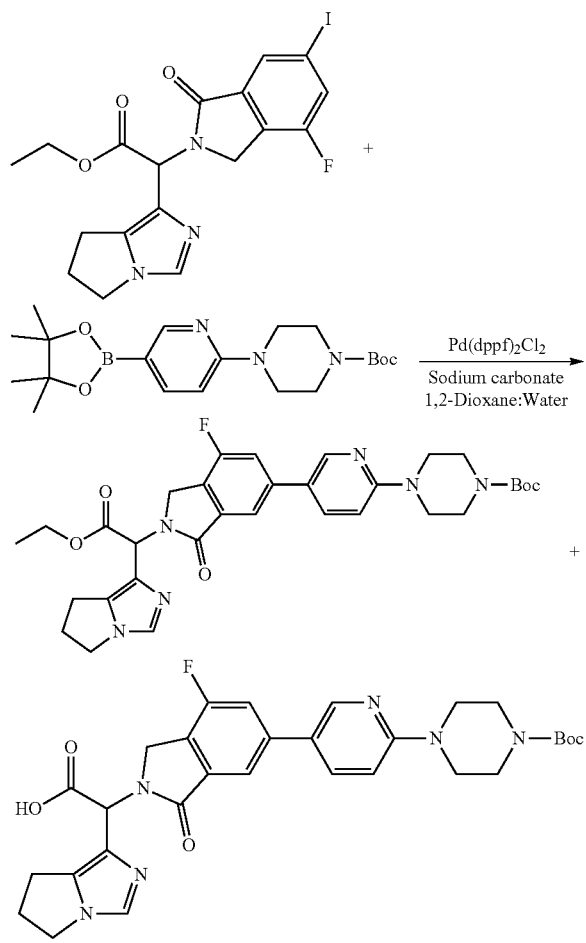

A solution of ethyl 2-(6,7-dihydro-5H-pyrrolo[1,2-c]imidazol-1-yl)-2-(4-fluoro-6-iodo-1-oxo-isoindolin-2-yl)acetate (1.5 g, 3.20 mmol) and tert-butyl 4-[5-(4,4,5,5-tetramethyl-1,3,2-dioxaborolan-2-yl)-2-pyridyl]piperazine-1-carboxylate (1.87 g, 4.79 mmol) in 1,4-Dioxane (20 mL) and Water (2 mL) was degassed with nitrogen for 15 min. Sodium carbonate (677.61 mg, 6.39 mmol) and [1,1'-Bis(diphenylphosphino)ferrocene]dichloropalladium(II), complex with dichloromethane (87.02 mg, 106.55 μmol) was added to the reaction mixture and purged with nitrogen gas for 5 mins then heated at 80° C. for 2 h under inert atmosphere. The reaction mixture was diluted with ethyl acetate and filtered through celite. The filtrate was washed with ice water (5 ml) and extracted using ethyl acetate (3×15 mL). The organic layer was washed with brine (15 ml), dried with Na₂SO₄ and concentrated under reduced pressure to afford a mixture of tert-butyl 4-[5-[2-[1-(6,7-dihydro-5H-pyrrolo[1,2-c]imidazol-1-yl)-2-ethoxy-2-oxo-ethyl]-7-fluoro-3-oxo-isoindolin-5-yl]-2-pyridyl]piperazine-1-carboxylate and 2-[6-[6-(4-tert-butoxycarbonylpiperazin-1-yl)-3-pyridyl]-4-fluoro-1-oxo-isoindolin-2-yl]-2-(6,7-dihydro-5H-pyrrolo[1,2-c]imidazol-1-yl)acetic acid (2.2 g, 1.83 mmol, 57.14% yield), which was used in next step without further purification. LCMS (ESI+): m/z 605.3 (M+H⁺) and ester hydrolyzed product mass LCMS (ESI+): m/z 577.3 (M+H)

Step 2: 2-[6-[6-(4-tert-butoxycarbonylpiperazin-1-yl)-3-pyridyl]-4-fluoro-1-oxo-isoindolin-2-yl]-2-(6,7-dihydro-5H-pyrrolo[1,2-c]imidazol-1-yl)acetic acid

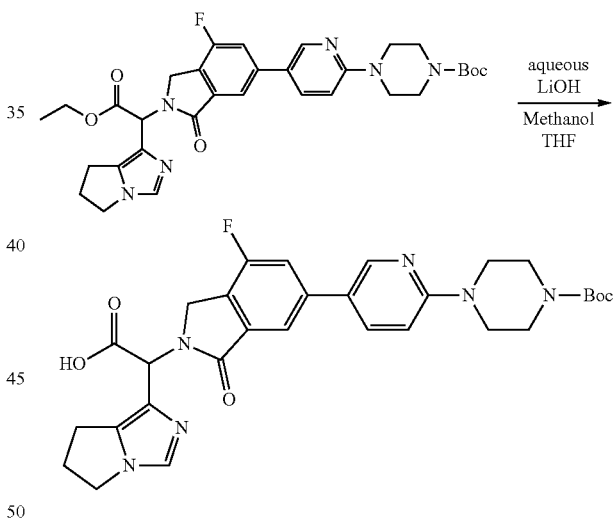

1M Lithium hydroxide monohydrate, 98% (152.68 mg, 3.64 mmol) dissolved in Water (20 mL) was added to a solution of tert-butyl 4-[5-[2-[1-(6,7-dihydro-5H-pyrrolo[1,2-c]imidazol-1-yl)-2-ethoxy-2-oxo-ethyl]-7-fluoro-3-oxo-isoindolin-5-yl]-2-pyridyl]piperazine-1-carboxylate (2.2 g, 3.64 mmol) dissolved in THF (20 mL) and Methanol (20 mL) at 0° C. The reaction mixture was stirred at room temperature for 3 h. The reaction mixture was concentrated then the residue was dissolved in 50 mL water and acidified by using KHSO4 salt (pH 1-2). The solid precipitate was filtered and dried under vacuum to afford desired product 2-[6-[6-(4-tert-butoxycarbonylpiperazin-1-yl)-3-pyridyl]-4-fluoro-1-oxo-isoindolin-2-yl]-2-(6,7-dihydro-5H-pyrrolo[1,2-c]imidazol-1-yl)acetic acid (800 mg, 1.31 mmol, 36.12% yield).

LCMS (ESI+): [m/z: 577.0 (M+H⁺)]

Step 3: tert-butyl 4-[5-[2-[1-(6,7-dihydro-5H-pyr-rolo[1,2-c]imidazol-1-yl)-2-oxo-2-(thiazol-2-ylamino)ethyl]-7-fluoro-3-oxo-isoindolin-5-yl]-2-pyridyl]piperazine-1-carboxylate

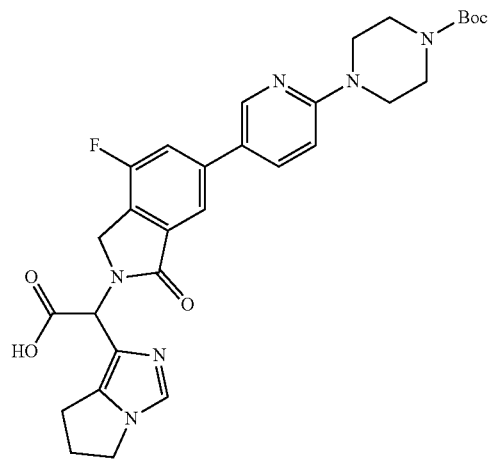

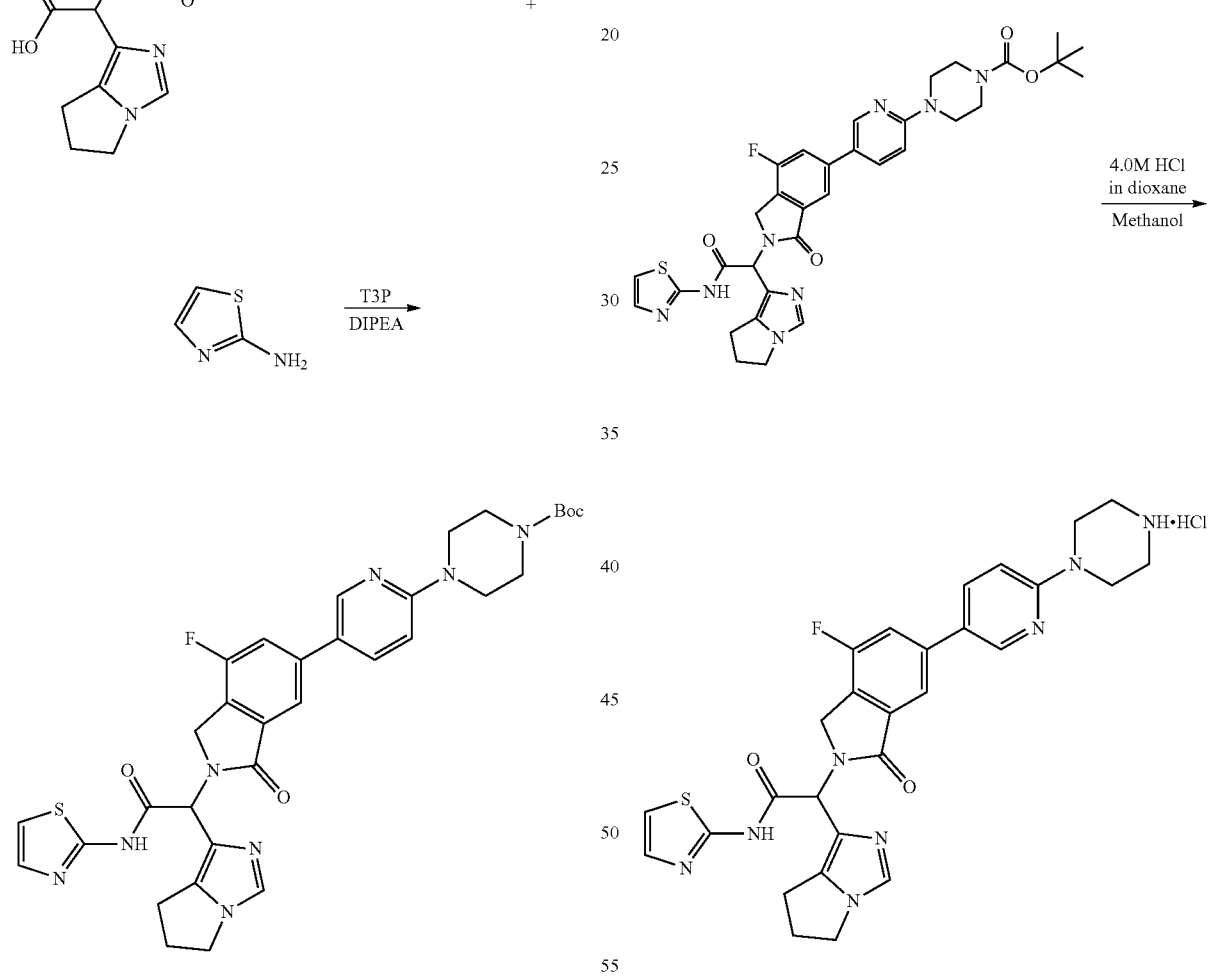

To a solution of 2-[6-[6-(4-tert-butoxycarbonylpiperazin-1-yl)-3-pyridyl]-4-fluoro-1-oxo-isoindolin-2-yl]-2-(6,7-dihydro-5H-pyrrolo[1,2-c]imidazol-1-yl)acetic acid (700 mg, 1.21 mmol) in DMF (10 mL) was added N,N-diisopropyl-ethylamine (627.59 mg, 4.86 mmol, 845.81 µL) and propylphosphonic anhydride (T3P), 50% solution in ethyl acetate (772.36 mg, 2.43 mmol) at 0° C. The reaction mixture was stirred for 15 minutes. Thiazol-2-amine (145.88 mg, 1.46 mmol) was added under a nitrogen atmosphere. The reaction mixture stirred at room temperature for 16 h. The reaction mixture poured to ice water (35 ml), and the mixture was extracted with ethyl acetate (2×50 ml). The organic layer was washed with brine (45 ml), dried with Na2SO4 and concentrated under reduced pressure. The crude residue was purified by silica column chromatography using a methanol:dichloromethane eluent mixture and collected fractions were concentrated to yield tert-butyl 4-[5-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-2-pyridyl]piperazine-1-carboxylate (490 mg, 641.93 µmol, 52.88% yield). LCMS (ESI+): (m/z: 659.2 [M+H])

Step 4: 2-(6,7-dihydro-5H-pyrrolo[1,2-c]imidazol-1-yl)-2-[4-fluoro-1-oxo-6-(6-piperazin-1-yl-3-pyridyl)isoindolin-2-yl]-N-thiazol-2-yl-acetamide hydrochloride Hydrogen chloride solution 4.0 M in dioxane (1.46 mmol, 66.42 µL) was added to a solution of tert-butyl 4-[5-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-2-pyridyl]piperazine-1-carboxylate (480 mg, 728.66 µmol) in Methanol (5 mL) at 0° C. After 2 hours, the reaction mixture was concentrated to get crude product 2-(6,7-dihydro-5H-pyrrolo[1,2-c]imidazol-1-yl)-2-[4-fluoro-1-oxo-6-(6-piperazin-1-yl-3-pyridyl)isoindolin-2-yl]-N-thiazol-2-yl-acetamide (440 mg, 692.06 µmol, 94.98% yield) as a hydrochloride salt. LCMS (m/z: 558.9 [M+1])

Step 5: 2-(6,7-dihydro-5H-pyrrolo[1,2-c]imidazol-1-yl)-2-(6-(6-(4-(2-(4-(4-(((S)-2,6-dioxopiperidin-3-yl)amino)-2-fluorophenyl)piperidin-1-yl)acetyl)piperazin-1-yl)pyridin-3-yl)-4-fluoro-1-oxoisoindolin-2-yl)-N-(thiazol-2-yl)acetamide

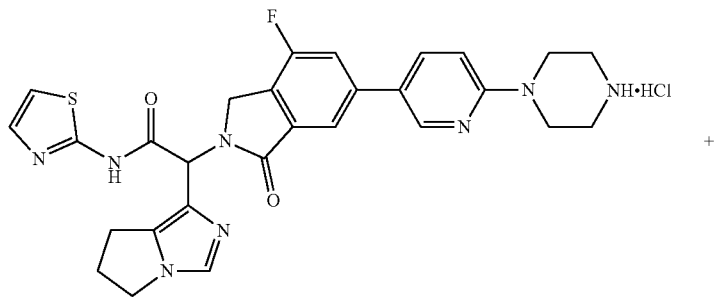

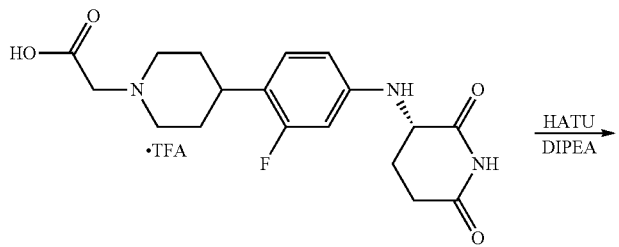

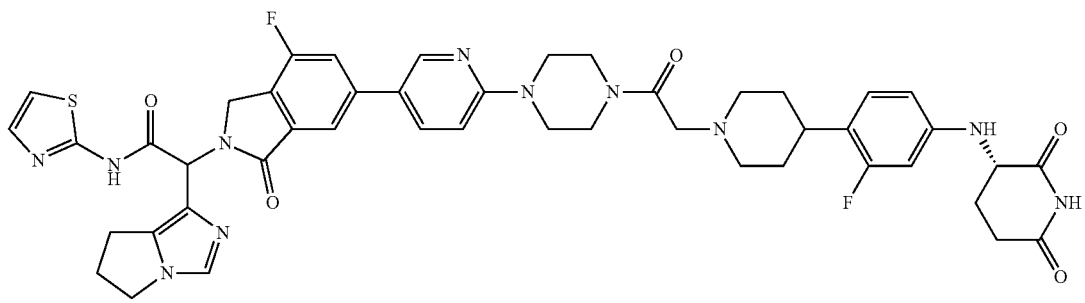

A stirred solution of 2-(6,7-dihydro-5H-pyrrolo[1,2-c]imidazol-1-yl)-2-[4-fluoro-1-oxo-6-(6-piperazin-1-yl-3-pyridyl)isoindolin-2-yl]-N-thiazol-2-yl-acetamide hydrochloride (50 mg, 84.02 μmol) and 2-[4-[4-[[(3 S)-2,6-dioxo-3-piperidyl]amino]-2-fluoro-phenyl]-1-piperidyl]acetic acid, trifluoroacetic acid salt (36.64 mg, 76.74 μmol) in DMF (1 mL) was cooled to 0° C. COMU (46.78 mg, 109.23 μmol) was added to the reaction mixture followed by N,N-Diisopropylethylamine (65.15 mg, 504.13 μmol, 87.81 μL) at 0° C. The reaction mixture stirred at rt for 5 h. The reaction mixture was concentrated under reduced pressure. The crude was purified by reverse phase C-18 chromatography (0-100% of 0.1% NH4OAc in water and Acetonitrile) to afford Compound 27 (18.2 mg, 19.3 μmol, 12% yield). LCMS (ESI+) (m/z: 904.8 [M+1]), $^1$H-NMR (400 MHz, DMSO-d6): δ 12.53 (s, 1H), 10.78 (s, 1H), 8.60 (d, J=2.0 Hz, 1H), 8.04 (dd, J=8.8, 2.4 Hz, 1H), 7.81 (d, J=11.2 Hz, 2H), 7.62 (s, 1H), 7.49 (d, J=3.6 Hz, 1H), 7.26 (d, J=3.2 Hz, 1H), 7.02-6.97 (m, 2H), 6.53-6.45 (m, 2H), 6.16 (s, 1H), 6.00 (d, J=7.6 Hz, 1H), 4.82 (d, J=17.6 Hz, 1H), 4.30-4.28 (m, 1H), 4.24 (d, J=17.6 Hz, 1H), 4.02-3.97 (m, 2H), 3.75-3.67 (m, 4H), 3.59 (s, 4H), 3.23 (s, 2H), 2.94 (d, J=9.2 Hz, 2H), 2.77-2.68 (m, 2H), 2.59-2.58 (m, 4H), 2.10-2.07 (m, 4H), 1.92-1.84 (m, 1H), 1.66 (s, 4H).

Example 28

Synthesis of 2-(6,7-dihydro-5H-pyrrolo[1,2-c]imidazol-1-yl)-2-[6-[1-[1-[2-[4-[4-[[(3S)-2,6-dioxo-3-piperidyl]amino]phenyl]-1-piperidyl]acetyl]-4-piperidyl]pyrazol-4-yl]-4-fluoro-1-oxo-isoindolin-2-yl]-N-thiazol-2-yl-acetamide, Compound 28

Step 1: tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]pyrazol-1-yl]piperidine-1-carboxylate

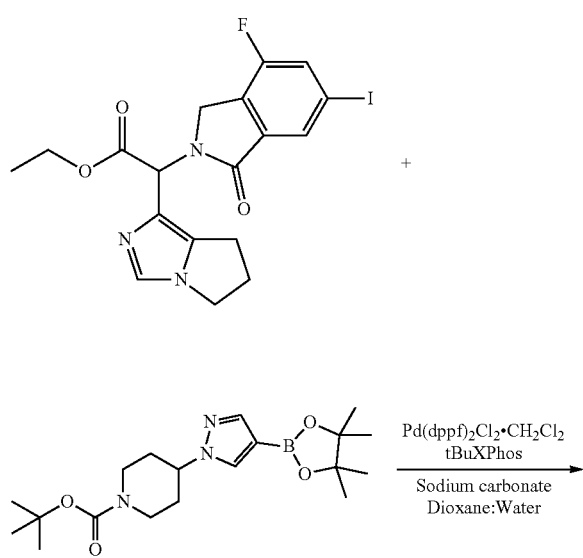

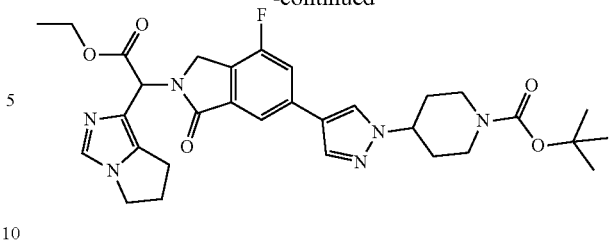

In a 100-mL round bottom flask, ethyl 2-(6,7-dihydro-5H-pyrrolo[1,2-c]imidazol-1-yl)-2-(4-fluoro-6-iodo-1-oxo-isoindolin-2-yl)acetate (530 mg, 1.13 mmol) and tert-butyl 4-[4-(4,4,5,5-tetramethyl-1,3,2-dioxaborolan-2-yl)pyrazol-1-yl]piperidine-1-carboxylate (575.28 mg, 1.52 mmol) were dissolved in dioxane (6.4 mL), 1,1'-Bis(Diphenylphosphino)ferrocenepalladium (II) dichloride, dichloromethane complex (46.12 mg, 56.47 μmol) and tBuXPhos (71.30 mg, 112.95 μmol) were added, followed by Sodium carbonate (263.37 mg, 2.48 mmol) dissolved in Water (1.6 mL). The mixture was degassed with nitrogen. The reaction was capped with a septum, with a nitrogen inlet, and heated at 80° C. for 2 hr. The mixture was diluted with ethyl acetate, and the organic layer was separated from the aqueous layer. The crude residue was purified by flash column chromatography on silica gel (0-10% Methanol in ethyl acetate) to give tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]pyrazol-1-yl]piperidine-1-carboxylate (550 mg, 0.928 mmol, 82% yield) as an off-white foam. LCMS (ESI+): 593.8 (M+H).

Step 2: [2-[6-[1-(1-tert-butoxycarbonyl-4-piperidyl)pyrazol-4-yl]-4-fluoro-1-oxo-isoindolin-2-yl]-2-(6,7-dihydro-5H-pyrrolo[1,2-c]imidazol-1-yl)acetyl]oxy-lithium

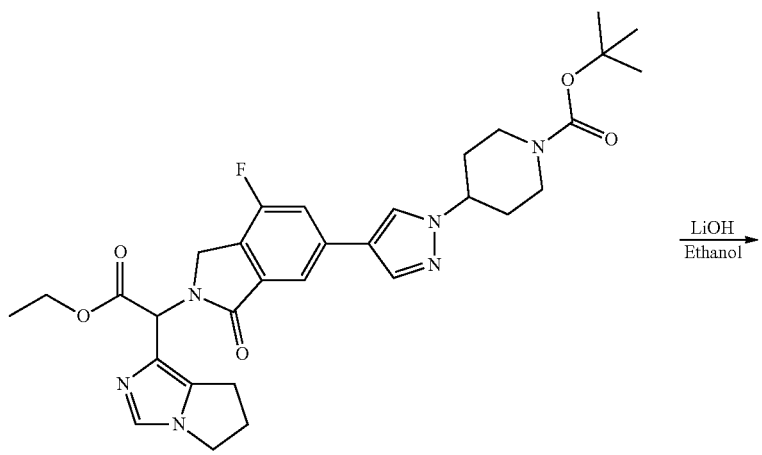

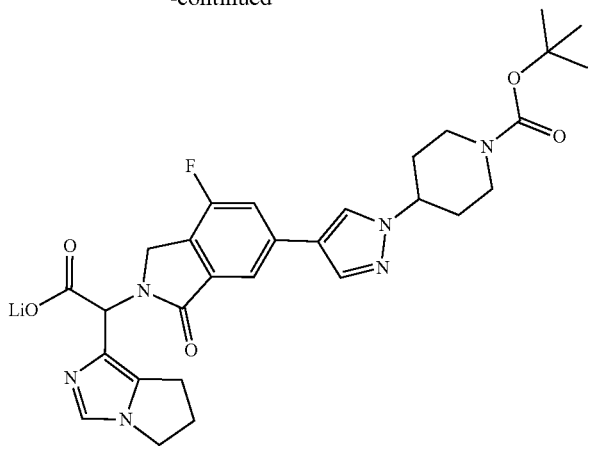

To a solution of tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]pyrazol-1-yl]piperidine-1-carboxylate (550 mg, 928.02 μmol) in Ethanol (4 mL) was added Lithium hydroxide (1 M aqueous solution, 1.02 mL) and stirred at ambient temperature overnight. The reaction mixture was warmed to 30° C. and stirred for 3 hours. The volatiles were evaporated under reduced pressure to afford [2-[6-[1-(1-tert-butoxycarbonyl-4-piperidyl)pyrazol-4-yl]-4-fluoro-1-oxo-isoindolin-2-yl]-2-(6,7-dihydro-5H-pyrrolo[1,2-c]imidazol-1-yl)acetyl]oxylithium (529.47 mg, 928.02 μmol, quantitative yield) as an off-white solid. LCMS (ESI+): 565.8 (M+H).

Step 3: tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]pyrazol-1-yl]piperidine-1-carboxylate

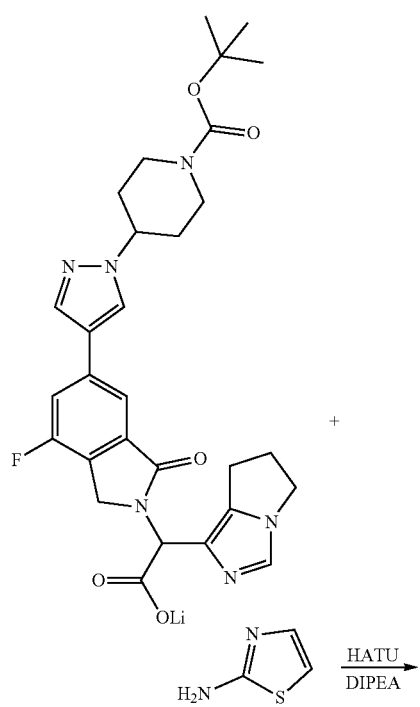

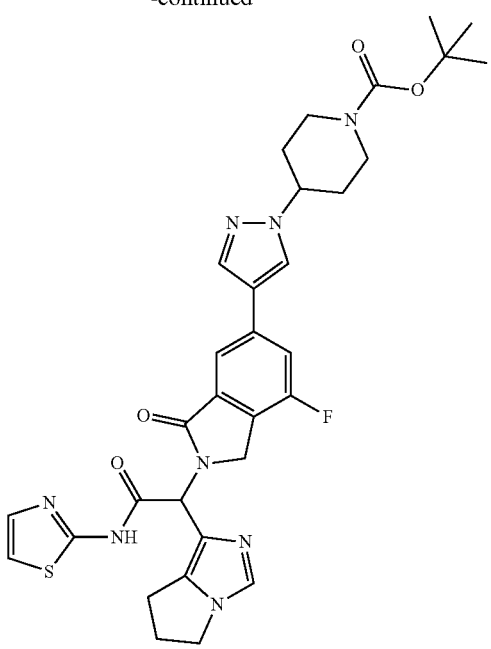

[2-[6-[1-(1-tert-butoxycarbonyl-4-piperidyl)pyrazol-4-yl]-4-fluoro-1-oxo-isoindolin-2-yl]-2-(6,7-dihydro-5H-pyrrolo[1,2-c]imidazol-1-yl)acetyl]oxylithium (529.47 mg, 928.02 μmol) and thiazol-2-amine (97.58 mg, 974.42 μmol) were mixed in DMF (5 mL), the reaction mixture was cooled to 0° C. N,N-Diisopropylethylamine (479.75 mg, 3.71 mmol, 646.56 μL) was added to the reaction mixture, and HATU (458.72 mg, 1.21 mmol) was added, and the reaction mixture was stirred for 30 min at 0° C. Saturated aqueous sodium bicarbonate was added to the reaction mixture, and the reaction was extracted ethyl acetate (×2). The organic layers were extracted with water and brine, dried over Na₂SO₄, filtered and concentrated in vacuo. The crude material was purified by flash chromatography on silica gel (24 g, 0-10% methanol in dichloromethane). Fractions containing product were combined and concentrated to afford tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]pyrazol-1-yl]piperidine-1-carboxylate (520 mg, 804.04 μmol, 86.64% yield) as an off-white solid. LCMS (ESI+): 647.7 (M+H).

Step 4: 2-(6,7-dihydro-5H-pyrrolo[1,2-c]imidazol-1-yl)-2-[4-fluoro-1-oxo-6-[1-(4-piperidyl)pyrazol-4-yl]isoindolin-2-yl]-N-thiazol-2-yl-acetamide

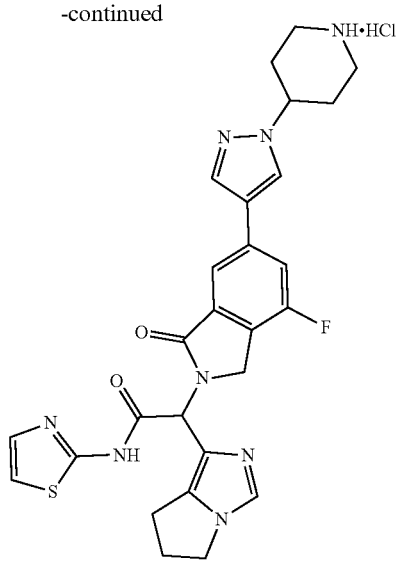

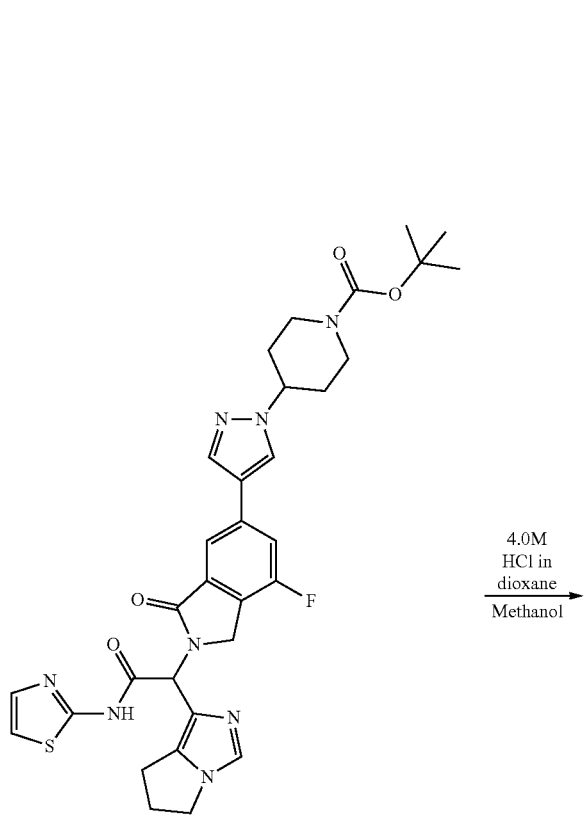

4.0M HCl in dioxane / Methanol → tert-Butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]pyrazol-1-yl]piperidine-1-carboxylate (515 mg, 796.31 μmol) was dissolved in a 1,4-dioxane:methanol mixture and Hydrogen chloride solution (4.0 M in dioxane, 1.4 mL, 5.6 mmol) was added. The reaction mixture was heated at 40° C. for 4 hours. The volatiles were evaporated under reduce pressure. The material was submitted to high vacuum, frozen to −78° C. and thawed to afford 2-(6,7-dihydro-5H-pyrrolo[1,2-c]imidazol-1-yl)-2-[4-fluoro-1-oxo-6-[1-(4-piperidyl)pyrazol-4-yl]isoindolin-2-yl]-N-thiazol-2-yl-acetamide (415 mg, 90.1% yield) as an off-white solid. LCMS (ESI+): 547.3 (M+H).

Step 5: 2-(6,7-dihydro-5H-pyrrolo[1,2-c]imidazol-1-yl)-2-[6-[1-[1-[2-[4-[[(3S)-2,6-dioxo-3-piperidyl]amino]phenyl]-1-piperidyl]acetyl]-4-piperidyl]pyrazol-4-yl]-4-fluoro-1-oxo-isoindolin-2-yl]-N-thiazol-2-yl-acetamide

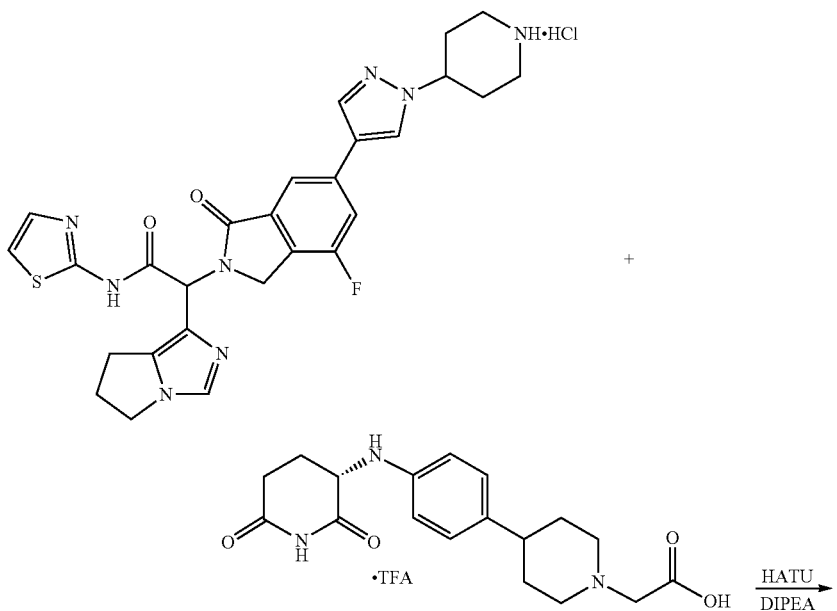

-continued

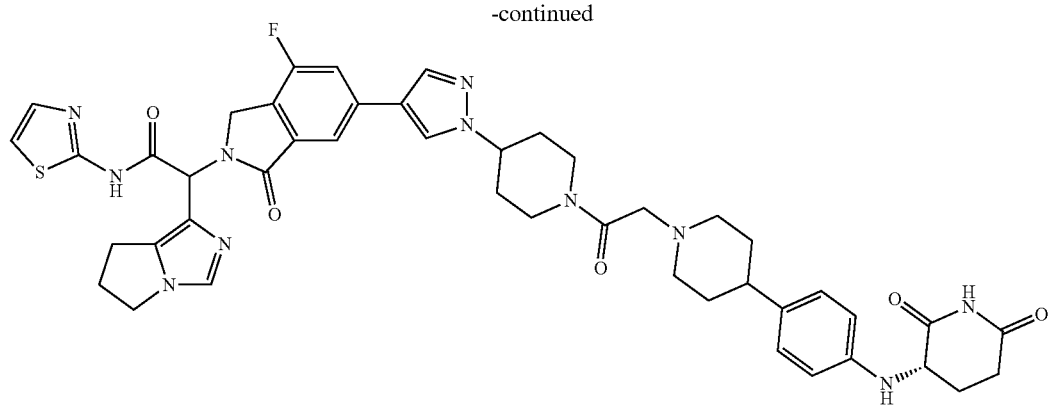

2-(6,7-dihydro-5H-pyrrolo[1,2-c]imidazol-1-yl)-2-[4-fluoro-1-oxo-6-[1-(4-piperidyl)pyrazol-4-yl]isoindolin-2-yl]-N-thiazol-2-yl-acetamide hydrochloride (55.4 mg, 95.01 μmol) and 2-[4-[4-[[(3S)-2,6-dioxo-3-piperidyl]amino]phenyl]-1-piperidyl]acetic acid, trifluoroacetic acid salt (56.75 mg, 123.52 μmol) were mixed in DMF, the reaction mixture was cooled to 0° C. N,N-Diisopropylethylamine (61.40 mg, 475.06 μmol, 82.75 μL) was added to the reaction mixture, and HATU (46.96 mg, 123.52 μmol) was added, and the reaction mixture was stirred for 1 h in an ice bath. The reaction mixture was acidified with 4-5 drops of TFA, and injected directly on a RP C18 column (50 g C18) for purification using a using a 5% to 100% acetonitrile (+0.1% TFA) in water (+0.1% TFA) eluent gradient. The pure fractions were neutralized with aqueous NaHCO₃ (ca. 60 mL), extracted twice with 1:4 isopropanol:chloroform mixture. The organic layer was dried over Na₂SO₄, filtered, and evaporated under reduced pressure to afford a solid. The solid was dissolved in dichloromethane, an injected on a 24 g Highly Spherical silica gel column flushed with 100% dichloromethane and purified using a 0% to 30% methanol in dichloromethane gradient over 20 minutes. The pure fractions were evaporated under reduced pressure. The crude residue was dissolved in dichloromethane, transferred to an 8 mL vial, and evaporated under reduced pressure. 1 mL water+1 mL acetonitrile were added, and the mixture was thoroughly sonicated, vortexed and sonicated again. The suspension was frozen and lyophilized to afford Compound 28 (31.3 mg, 35.45 μmol, 37.32% yield) as a white solid. LCMS (ESI+): 874.6 (M+H), ¹H NMR (400 MHz, DMSO-d6) δ 12.52 (s, 1H), 10.76 (s, 1H), 8.53 (s, 1H), 8.10 (s, 1H), 7.84 (d, J=1.3 Hz, 1H), 7.75 (dd, J=10.4, 1.3 Hz, 1H), 7.61 (s, 1H), 7.49 (d, J=3.6 Hz, 1H), 7.26 (d, J=3.6 Hz, 1H), 6.95 (d, J=8.2 Hz, 2H), 6.61 (d, J=8.1 Hz, 2H), 6.15 (s, 1H), 5.64 (d, J=7.3 Hz, 1H), 4.78 (d, J=17.7 Hz, 1H), 4.45 (d, J=12.2 Hz, 2H), 4.31-4.14 (m, 3H), 4.00 (td, J=10.6, 5.7 Hz, 2H), 3.28-3.17 (m, 2H), 3.17-3.06 (m, 1H), 2.93 (s, 2H), 2.88-2.66 (m, 4H), 2.62-2.41 (m, 3H), 2.39-2.28 (m, 2H), 2.22-2.04 (m, 4H), 2.04-1.77 (m, 3H), 1.77-1.66 (m, 2H), 1.66-1.50 (m, 2H).

Example 29

Synthesis of 2-(6,7-dihydro-5H-pyrrolo[1,2-c]imidazol-1-yl)-2-[6-[4-[1-[2-[4-[4-[[(3S)-2,6-dioxo-3-piperidyl]amino]phenyl]-1-piperidyl]acetyl]-4-piperidyl]pyrazol-1-yl]-4-fluoro-1-oxo-isoindolin-2-yl]-N-thiazol-2-yl-acetamide, Compound 29

Step 1: tert-butyl 4-[1-[2-[1-(6,7-dihydro-5H-pyrrolo[1,2-c]imidazol-1-yl)-2-ethoxy-2-oxo-ethyl]-7-fluoro-3-oxo-isoindolin-5-yl]pyrazol-4-yl]piperidine-1-carboxylate

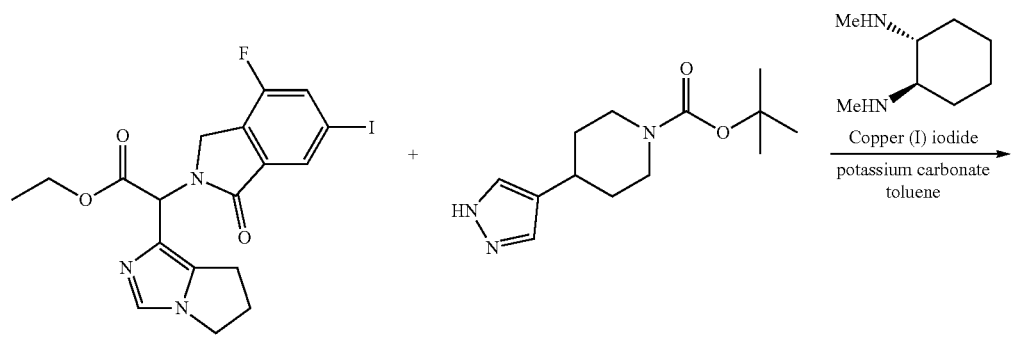

-continued

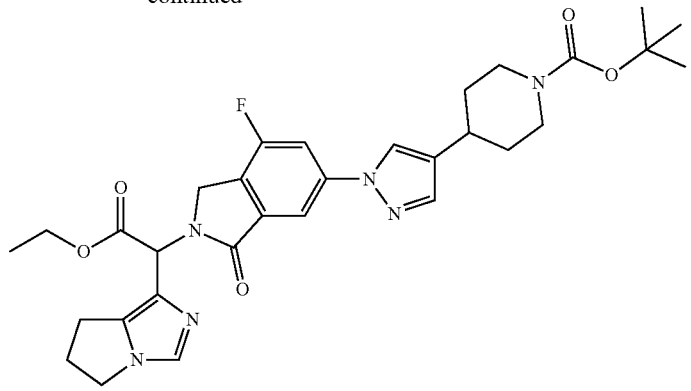

A solution of ethyl 2-(6,7-dihydro-5H-pyrrolo[1,2-c]imidazol-1-yl)-2-(4-fluoro-6-iodo-1-oxo-isoindolin-2-yl)acetate (205 mg, 436.87 μmol) and tert-butyl 4-(1H-pyrazol-4-yl)piperidine-1-carboxylate (CAS #278798-15-5) (109.80 mg, 436.87 μmol) in toluene (2.2 mL) was sparged with $N_2$ for 10 min. Then, trans-N,N'-Dimethylcyclohexane-1,2-diamine (12.43 mg, 87.37 μmol, 13.78 μL), potassium carbonate (120.76 mg, 873.74 μmol, 52.73 μL), and copper (I) iodide (8.32 mg, 43.69 μmol, 1.48 μL) were added sequentially and the mixture was stirred at 100° C. for 16 h. The reaction mixture was cooled down to ambient temperature and filtered through a pad of silica gel, washed with EA, and concentrated. The crude mixture was isolated by silica gel chromatography (100% dichloromethane to dichloromethane:methanol=4:1) to give tert-butyl 4-[1-[2-[1-(6,7-dihydro-5H-pyrrolo[1,2-c]imidazol-1-yl)-2-ethoxy-2-oxo-ethyl]-7-fluoro-3-oxo-isoindolin-5-yl]pyrazol-4-yl]piperidine-1-carboxylate (185 mg, 312.15 μmol, 71.45% yield) as a tan solid. LCMS (ESI+): 593.8 (M+H).

Step 2: [2-[6-[4-(1-tert-butoxycarbonyl-4-piperidyl)pyrazol-1-yl]-4-fluoro-1-oxo-isoindolin-2-yl]-2-(6,7-dihydro-5H-pyrrolo[1,2-c]imidazol-1-yl)acetyl]

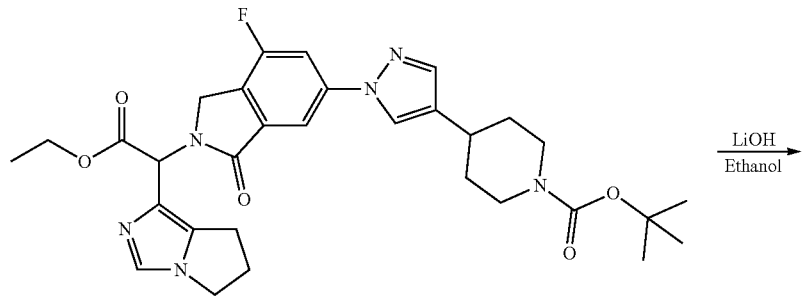

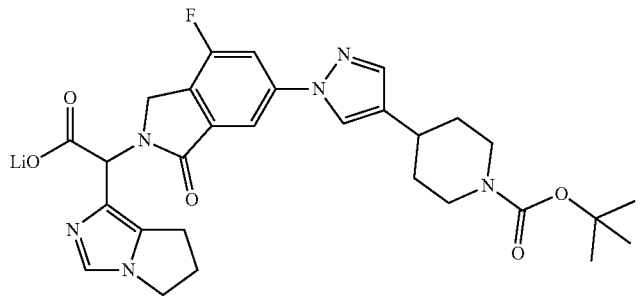

To a solution of tert-butyl 4-[1-[2-[1-(6,7-dihydro-5H-pyrrolo[1,2-c]imidazol-1-yl)-2-ethoxy-2-oxo-ethyl]-7-fluoro-3-oxo-isoindolin-5-yl]pyrazol-4-yl]piperidine-1-carboxylate (245 mg, 413.39 μmol) in Ethanol (1.6 mL) was added Lithium hydroxide (1 M aqueous solution, 475.40 μL) and the mixture was stirred at 20° C. overnight. The reaction was evaporated to dryness under reduced pressure to afford [2-[6-[4-(1-tert-butoxycarbonyl-4-piperidyl)pyrazol-1-yl]-4-fluoro-1-oxo-isoindolin-2-yl]-2-(6,7-dihydro-5H-pyrrolo[1,2-c]imidazol-1-yl)acetyl]oxylithium (236 mg, 413 μmol, quantitative yield) as a brown solid. LCMS (ESI+): 565.8 (M+H).

Step 3: tert-butyl 4-[1-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]pyrazol-4-yl]piperidine-1-carboxylate

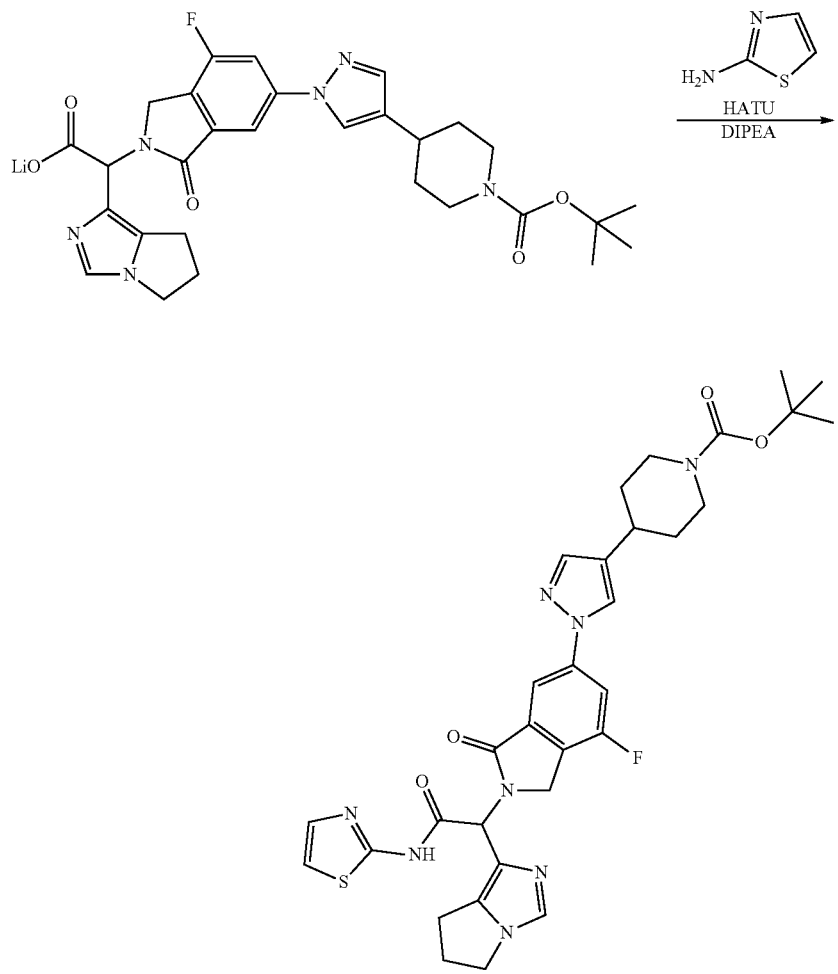

[2-[6-[4-(1-tert-butoxycarbonyl-4-piperidyl)pyrazol-1-yl]-4-fluoro-1-oxo-isoindolin-2-yl]-2-(6,7-dihydro-5H-pyrrolo[1,2-c]imidazol-1-yl)acetyl]oxylithium (235.85 mg, 413.38 μmol) and thiazol-2-amine (43.47 mg, 434.05 μmol) were mixed in DMF, the reaction mixture was cooled to 0° C. N,N-Diisopropylethylamine (213.71 mg, 1.65 mmol, 288.02 μL) was added to the reaction mixture, and HATU (204.34 mg, 537.39 μmol) was added, and the reaction mixture was stirred for 30 min at 0° C. The reaction mixture was diluted with aqueous NaHCO₃-solution and extracted with ethyl acetate. The organic layers were washed with water and brine, dried over Na₂SO₄, filtered and concentrated in vacuo. The crude material was purified by silica gel chromatography (24 g, 0-10% methanol in dichloromethane). Fractions containing product were combined and concentrated to afford tert-butyl 4-[1-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]pyrazol-4-yl]piperidine-1-carboxylate (88 mg, 136.07 μmol, 32.92% yield) as an off-white solid. LCMS (ESI+): 647.7 (M+H)

Step 4: 2-(6,7-dihydro-5H-pyrrolo[1,2-c]imidazol-1-yl)-2-[4-fluoro-1-oxo-6-[4-(4-piperidyl)pyrazol-1-yl]isoindolin-2-yl]-N-thiazol-2-yl-acetamide Hydrochloride

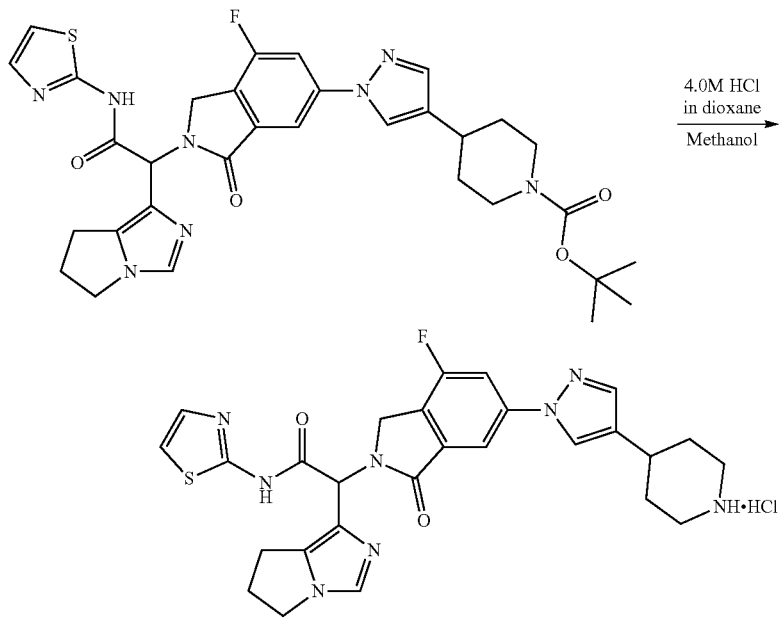

tert-Butyl 4-[1-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]pyrazol-4-yl]piperidine-1-carboxylate (88.00 mg, 136.07 µmol) was dissolved in a 1,4-dioxane:methanol mixture and Hydrogen chloride solution 4.0M in dioxane (4 M, 239.22 µL) was added. The reaction mixture was heated at 40° C. for 4 hours, and the reaction was complete. The volatiles were evaporated under reduce pressure. The material was submitted to high vacuum, frozen to −78° C. and thawed to afford a dense off-white solid; 2-(6,7-dihydro-5H-pyrrolo[1,2-c]imidazol-1-yl)-2-[4-fluoro-1-oxo-6-[4-(4-piperidyl)pyrazol-1-yl]isoindolin-2-yl]-N-thiazol-2-yl-acetamide Hydrochloride (67 mg, quantitative yield) as an off-white solid. LCMS (ESI+): 547.3 (M+H).

Step 5: 2-(6,7-dihydro-5H-pyrrolo[1,2-c]imidazol-1-yl)-2-[6-[4-[1-[2-[4-[4-[[(3S)-2,6-dioxo-3-piperidyl]amino]phenyl]-1-piperidyl]acetyl]-4-piperidyl]pyrazol-1-yl]-4-fluoro-1-oxo-isoindolin-2-yl]-N-thiazol-2-yl-acetamide

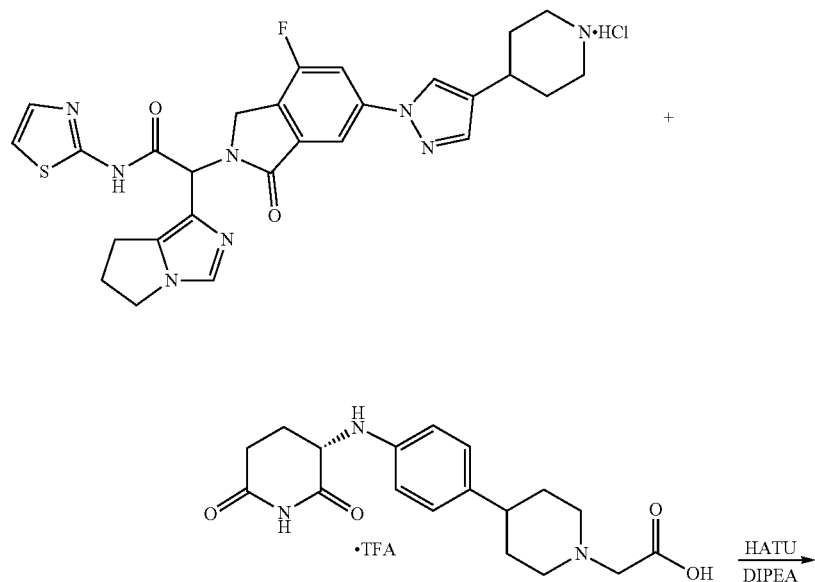

-continued

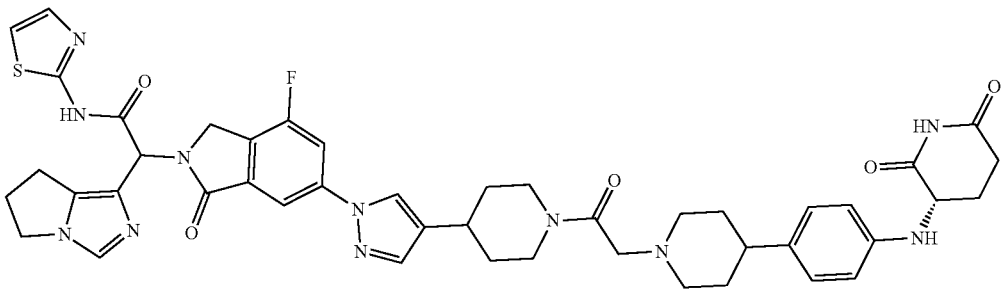

2-(6,7-Dihydro-5H-pyrrolo[1,2-c]imidazol-1-yl)-2-[4-fluoro-1-oxo-6-[4-(4-piperidyl)pyrazol-1-yl]isoindolin-2-yl]-N-thiazol-2-yl-acetamide; hydrochloride (44.00 mg, 75.46 μmol) and 2-[4-[4-[[(3S)-2,6-dioxo-3-piperidyl]amino]phenyl]-1-piperidyl]acetic acid, trifluoroacetic acid salt (45.07 mg, 98.10 μmol) were mixed in DMF, the reaction mixture was cooled to 0° C. N,N-Diisopropylethylamine (48.76 mg, 377.31 μmol, 65.72 μL) was added to the reaction mixture, and HATU (37.30 mg, 98.10 μmol) was added, and the reaction mixture was stirred for 1 h in ice bath. The reaction mixture was acidified with 4-5 drops of TFA, and injected directly on a RP C18 column (50 g C18) for purification (5% to 100% acetonitrile (+0.1% TFA) in water (+0.1% TFA) over 12 minutes). The pure fractions were neutralized with aqueous aqueous NaHCO$_3$ (ca. 60 mL), extracted twice with a 1:4 isopropanol:chloroform mixture. The organic layer was dried over Na$_2$SO$_4$, filtered, and evaporated under reduced pressure to afford a solid. The solid was dissolved in dichloromethane, an injected on a 24 g silica gel column flushed with 100% dichloromethane and purified using a 0% to 20% methanol in dichloromethane gradient over 20 minutes. The pure fractions were evaporated under reduced pressure. The crude residue was dissolved in dichloromethane, transferred to an 8 mL vial, and evaporated under reduced pressure. 1 mL water+1 mL acetonitrile were added, and the mixture was thoroughly sonicated, vortexed and sonicated again. The suspension was frozen and lyophilized to afford Compound 29 (28 mg, 31.72 μmol, 42.03% yield) as an off-white solid. LCMS (ESI+): 874.8 (M+H); 1H NMR (400 MHz, DMSO-d6) δ 12.53 (s, 1H), 10.76 (s, 1H), 8.62 (s, 1H), 8.05 (d, J=1.8 Hz, 1H), 7.98 (dd, J=10.4, 1.8 Hz, 1H), 7.75 (s, 1H), 7.61 (s, 1H), 7.49 (d, J=3.6 Hz, 1H), 7.26 (d, J=3.6 Hz, 1H), 6.95 (d, J=8.5 Hz, 2H), 6.60 (d, J=8.5 Hz, 2H), 6.16 (s, 1H), 5.63 (d, J=7.4 Hz, 1H), 4.82 (d, J=17.8 Hz, 1H), 4.39 (d, J=12.7 Hz, 1H), 4.30-4.12 (m, 3H), 4.06-3.93 (m, 2H), 3.28-3.07 (m, 3H), 2.92 (s, 2H), 2.89-2.67 (m, 4H), 2.63-2.42 (m, 3H), 2.39-2.28 (m, 2H), 2.17-1.93 (m, 5H), 1.85 (qd, J=12.2, 4.7 Hz, 1H), 1.71 (d, J=12.1 Hz, 2H), 1.66-1.50 (m, 3H), 1.44 (dd, J=24.0, 12.2 Hz, 1H).

Example 30

Synthesis of 2-(6,7-dihydro-5H-pyrrolo[1,2-c]imidazol-1-yl)-2-(6-(1-(1-(2-(4-(4-(((S)-2,6-dioxopiperidin-3-yl)amino)phenyl)piperidin-1-yl)acetyl)piperidin-4-yl)-1H-1,2,3-triazol-4-yl)-4-fluoro-1-oxoisoindolin-2-yl)-N-(thiazol-2-yl)acetamide, Compound 30

Step 1: [2-(6,7-dihydro-5H-pyrrolo[1,2-c]imidazol-1-yl)-2-(4-fluoro-6-iodo-1-oxo-isoindolin-2-yl)acetyl]oxylithium

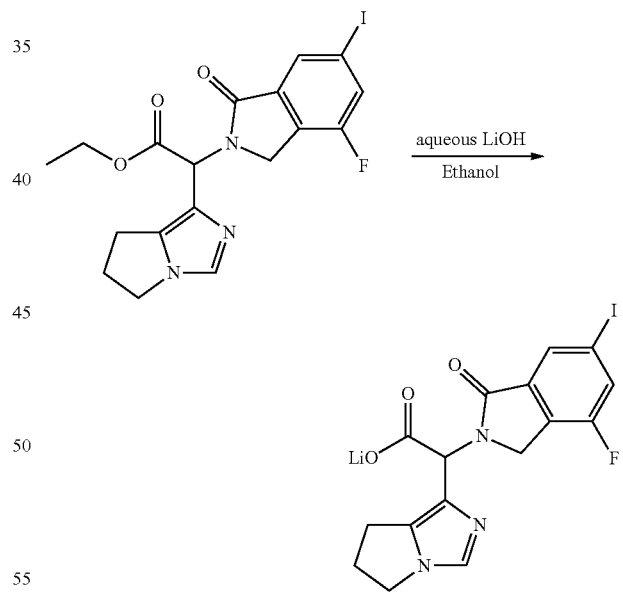

To a solution of ethyl 2-(6,7-dihydro-5H-pyrrolo[1,2-c]imidazol-1-yl)-2-(4-fluoro-6-iodo-1-oxo-isoindolin-2-yl)acetate (1 g, 2.13 mmol) in Ethanol (9 mL) was added Lithium hydroxide (1 M aqueous solution, 2.34 mL, 2.34 mmol) and the mixture was stirred at ambient temperature overnight. The reaction mixture was evaporated to dryness to afford [2-(6,7-dihydro-5H-pyrrolo[1,2-c]imidazol-1-yl)-2-(4-fluoro-6-iodo-1-oxo-isoindolin-2-yl)acetyl]oxylithium (952 mg, 2.13 mmol, quantitative yield) as a tan solid. LCMS (ESI+): 442.1 (M+H)

Step 2: 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide

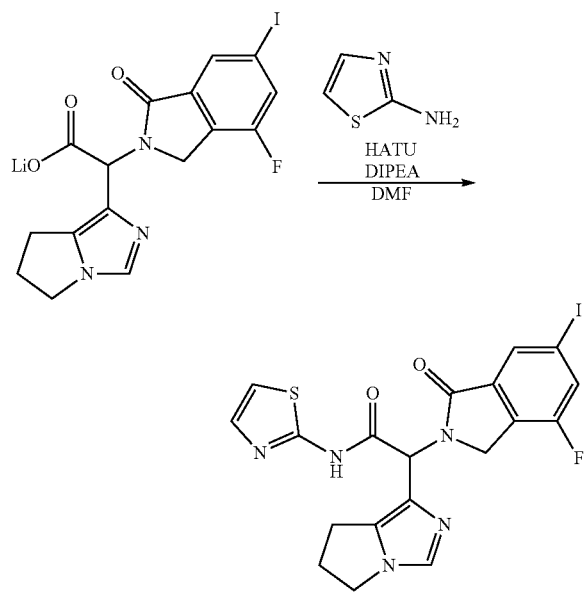

[2-(6,7-Dihydro-5H-pyrrolo[1,2-c]imidazol-1-yl)-2-(4-fluoro-6-iodo-1-oxo-isoindolin-2-yl)acetyl]oxylithium (952.38 mg, 2.13 mmol) and thiazol-2-amine (223.97 mg, 2.24 mmol) were mixed in DMF, the reaction mixture was cooled to 0° C. N,N-Diisopropylethylamine (1.10 g, 8.52 mmol, 1.48 mL) was added to the reaction mixture, and HATU (1.05 g, 2.77 mmol) was added, and the reaction mixture was stirred for 30 min at 0° C. The reaction mixture was diluted with aqueous NaHCO$_3$-solution and extracted two times with ethyl acetate. The combined organic layers were washed with water and brine, dried over Na$_2$SO$_4$, filtered and concentrated in vacuo. The crude material was purified by flash chromatography on silica gel (24 g, 0-10% methanol in dichloromethane). Fractions containing product were combined and concentrated to afford 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (1.2 g, 2.29 mmol, quantitative yield) as a tan solid. LCMS (ESI+): 524.5 (M+H).

Step 3: 2-(6,7-dihydro-5H-pyrrolo[1,2-c]imidazol-1-yl)-2-[4-fluoro-1-oxo-6-(2-trimethylsilylethynyl)isoindolin-2-yl]-N-thiazol-2-yl-acetamide

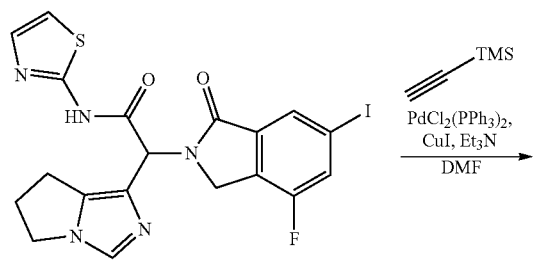

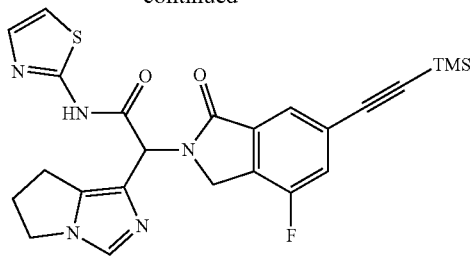

Ethynyl(trimethyl)silane (469.21 mg, 4.78 mmol, 675.13 µL) was added to a solution of 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (500 mg, 955.44 µmol) in DMF (3.5 mL). Triethylamine (290.04 mg, 2.87 mmol, 399.51 µL) was added. The reaction mixture was degassed with nitrogen for 10 min and PdCl$_2$(PPh$_3$)$_2$ (67.06 mg, 95.54 µmol) and copper (I) iodide (18.20 mg, 95.54 µmol, 3.24 µL) were added to the reaction mixture and heated to 60° C. After 30 min, the reaction mixture was diluted with water and extracted with ethyl acetate. The combined organic layers were washed with brine, dried over sodium sulphate, filtered and evaporated under reduced pressure. The crude residue was purified by silica gel column chromatography (100% dichloromethane to 10:1 dichloromethane:methanol) to yield 2-(6,7-dihydro-5H-pyrrolo[1,2-c]imidazol-1-yl)-2-[4-fluoro-1-oxo-6-(2-trimethylsilylethynyl)isoindolin-2-yl]-N-thiazol-2-yl-acetamide (270 mg, 546.97 µmol, 57% yield). LCMS (ESI+): 494.7 (M+H)

Step 4: 2-(6,7-dihydro-5H-pyrrolo[1,2-c]imidazol-1-yl)-2-(6-ethynyl-4-fluoro-1-oxo-isoindolin-2-yl)-N-thiazol-2-yl-acetamide

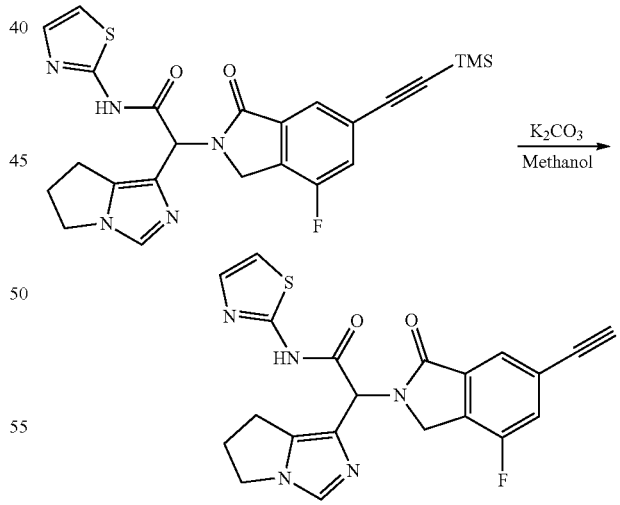

Potassium carbonate (90.04 mg, 651.50 µmol) was added to a solution of 2-(6,7-dihydro-5H-pyrrolo[1,2-c]imidazol-1-yl)-2-[4-fluoro-1-oxo-6-(2-trimethylsilylethynyl)isoindolin-2-yl]-N-thiazol-2-yl-acetamide (268 mg, 542.92 µmol) in Methanol (5.4 mL) at ambient temperature. The mixture was stirred at ambient temperature for 40 min. The reaction mixture was filtered through a pad of silica gel, washing with dichloromethane/methanol (4:1). The filtrate was concentrated in vacuo, then purified by silica gel column chromatography (100% dichloromethane to 10:1 dichloromethane/methanol=10:1) to yield 2-(6,7-dihydro-5H-pyrrolo[1,2-c]imidazol-1-yl)-2-(6-ethynyl-4-fluoro-1-oxo-isoindolin-2-yl)-N-thiazol-2-yl-acetamide (215 mg, 510.15 μmol, 94% yield).

Step 5: tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]triazol-1-yl]piperidine-1-carboxylate

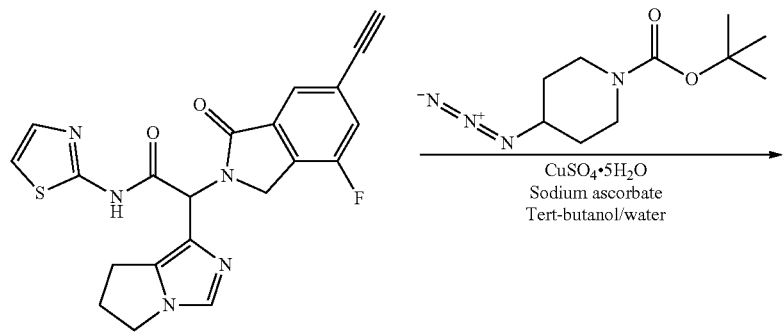

Copper (II) sulfate pentahydrate (651.69 ug, 2.61 μmol) and sodium ascorbate (1.29 mg, 6.53 μmol) were added to a solution of 2-(6,7-dihydro-5H-pyrrolo[1,2-c]imidazol-1-yl)-2-(6-ethynyl-4-fluoro-1-oxo-isoindolin-2-yl)-N-thiazol-2-yl-acetamide (55 mg, 130.50 μmol) and (1-tert-butoxycarbonyl-4-piperidyl)-diazonio-azanide (35.44 mg, 156.60 μmol) in water (0.3 mL) and tert-butanol (0.3 mL). The reaction mixture was stirred at ambient temperature for 18 h. The mixture was diluted with water/EA and the separated organic layer was washed with brine. The combined organic layer was dried over sodium sulfate, filtered, concentrated in vacuo, and the crude mixture was purified by silica gel column chromatography (100% dichloromethane to 5:1 dichloromethane:methanol) to give tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]triazol-1-yl]piperidine-1-carboxylate (57 mg, 88.00 μmol, 67% yield).

Step 6: 2-(6,7-dihydro-5H-pyrrolo[1,2-c]imidazol-1-yl)-2-[4-fluoro-1-oxo-6-[1-(4-piperidyl)triazol-4-yl]isoindolin-2-yl]-N-thiazol-2-yl-acetamide hydrochloride

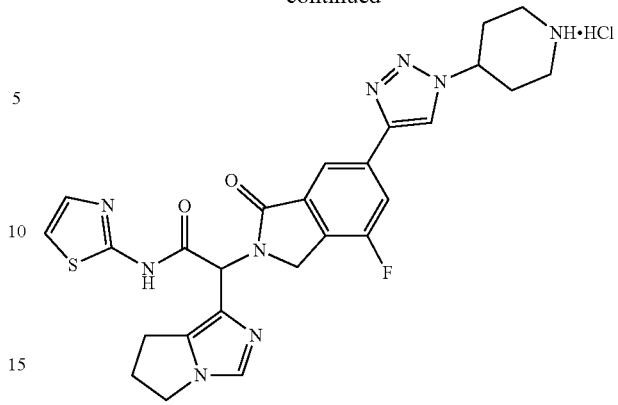

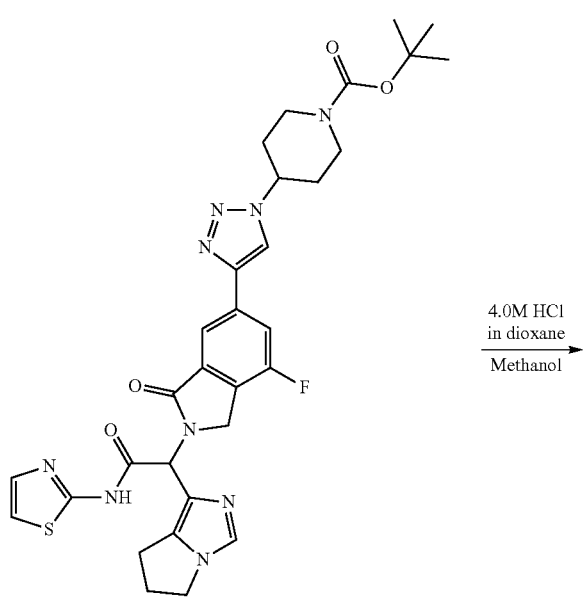

4.0M HCl in dioxane
Methanol

Tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]triazol-1-yl]piperidine-1-carboxylate (56 mg, 86.46 µmol) was dissolved in a 1,4-dioxane:methanol mixture and Hydrogen chloride solution (4.0M in dioxane, 0.15 mL, 0.6 mmol) was added. The reaction mixture was heated at 40° C. for 4 hours, and the reaction was complete. The volatiles were evaporated under reduce pressure. The material was submitted to high vacuum, frozen to −78° C. and thawed to afford 2-(6,7-dihydro-5H-pyrrolo[1,2-c]imidazol-1-yl)-2-[4-fluoro-1-oxo-6-[1-(4-piperidyl)triazol-4-yl]isoindolin-2-yl]-N-thiazol-2-yl-acetamide hydrochloride (50 mg, 86.4 µmol, quantitative yield), as a dense off-white solid that was used as was in next step. LCMS (ESI+): 548.3 (M+H).

Step 7: 2-(6,7-dihydro-5H-pyrrolo[1,2-c]imidazol-1-yl)-2-(6-(1-(1-(2-(4-(4-(((S)-2,6-dioxopiperidin-3-yl)amino)phenyl)piperidin-1-yl)acetyl)piperidin-4-yl)-1H-1,2,3-triazol-4-yl)-4-fluoro-1-oxoisoindolin-2-yl)-N-(thiazol-2-yl)acetamide

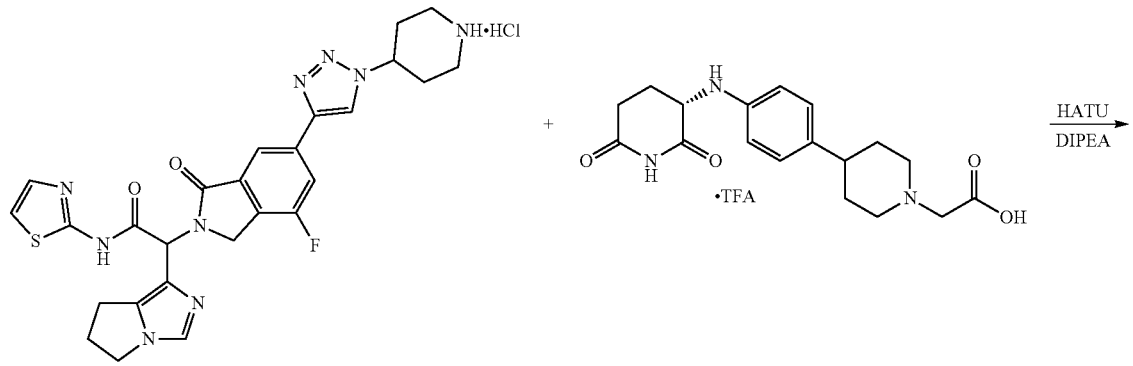

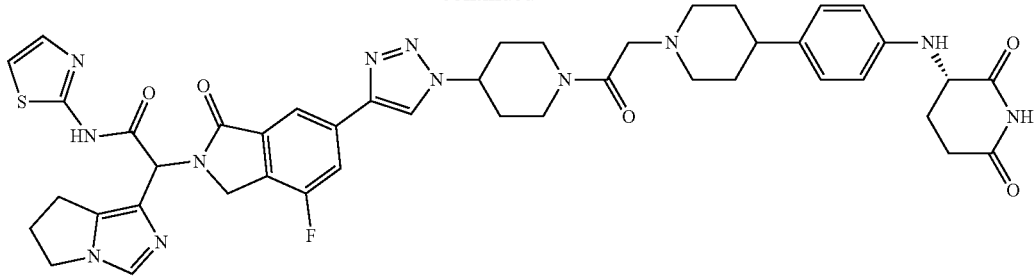

Compound 30 was synthesized from 5H-pyrrolo[1,2-c]imidazol-1-yl)-2-[4-fluoro-1-oxo-6-[1-(4-piperidyl)triazol-4-yl]isoindolin-2-yl]-N-thiazol-2-yl-acetamide hydrochloride in 23.4% yield using the method used for 2-(6,7-dihydro-5H-pyrrolo[1,2-c]imidazol-1-yl)-2-[6-[4-[1-[2-[4-[4-[[(3S)-2,6-dioxo-3-piperidyl]amino]phenyl]-1-piperidyl]acetyl]-4-piperidyl]pyrazol-1-yl]-4-fluoro-1-oxo-isoindolin-2-yl]-N-thiazol-2-yl-acetamide (Example 29, step 5). LCMS (ESI+): 875.6 (M+H), 1H NMR (400 MHz, DMSO-d6) δ 12.54 (s, 1H), 10.76 (s, 1H), 8.97 (s, 1H), 8.08 (d, J=1.2 Hz, 1H), 7.95 (dd, J=10.0, 1.2 Hz, 1H), 7.61 (s, 1H), 7.49 (d, J=3.5 Hz, 1H), 7.26 (d, J=3.6 Hz, 1H), 6.95 (d, J=8.3 Hz, 2H), 6.60 (d, J=8.3 Hz, 2H), 6.16 (s, 1H), 5.63 (d, J=7.4 Hz, 1H), 4.93-4.79 (m, 2H), 4.46 (d, J=12.9 Hz, 1H), 4.33-4.20 (m, 3H), 3.99 (ddt, J=17.3, 10.9, 6.1 Hz, 2H), 3.31-3.22 (m, 1H), 3.14 (d, J=12.5 Hz, 1H), 3.01-2.82 (m, 3H), 2.83-2.66 (m, 2H), 2.63-2.44 (m, 5H), 2.40-2.30 (m, 1H), 2.22 (q, J=13.0, 10.9 Hz, 2H), 2.16-1.94 (m, 4H), 1.94-1.78 (m, 2H), 1.77-1.66 (m, 2H), 1.67-1.53 (m, 2H).

Example 31

2-(6,7-dihydro-5H-pyrrolo[1,2-c]imidazol-1-yl)-2-[6-[4-[[1-[2-[4-[4-[(2,6-dioxo-3-piperidyl)amino]phenyl]-1-piperidyl]acetyl]-4-piperidyl]oxy]phenyl]-4-fluoro-1-oxo-isoindolin-2-yl]-N-thiazol-2-yl-acetamide, Compound 31

Step 1: tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenoxy]piperidine-1-carboxylate

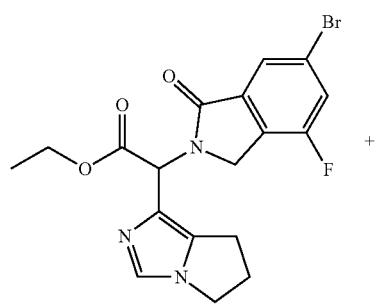

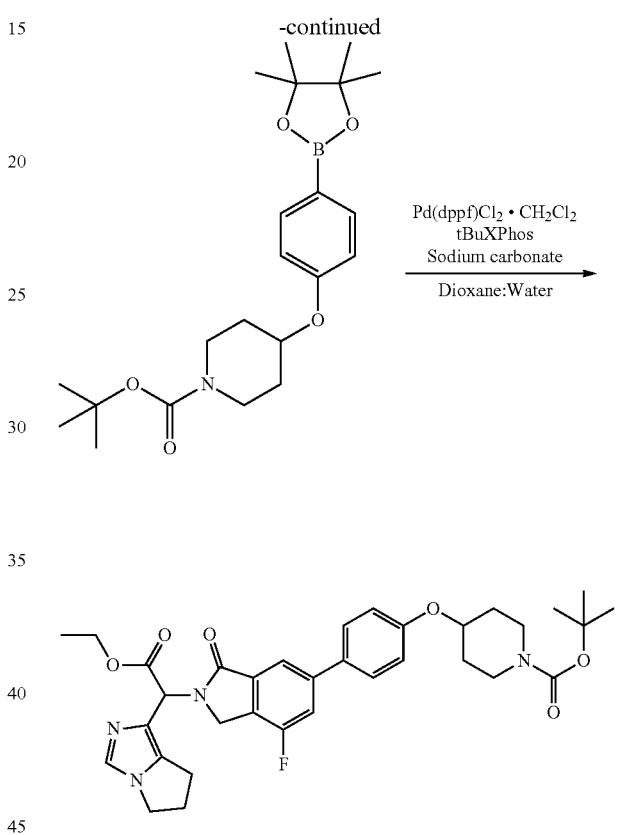

In a 100-mL round bottom flask, ethyl 2-(6-bromo-4-fluoro-1-oxo-isoindolin-2-yl)-2-(6,7-dihydro-5H-pyrrolo[1,2-c]imidazol-1-yl)acetate (3.1 g, 7.34 mmol) and tert-butyl 4-[4-(4,4,5,5-tetramethyl-1,3,2-dioxaborolan-2-yl)phenoxy]piperidine-1-carboxylate (4.00 g, 9.91 mmol) were dissolved in dioxane (44 mL) and Pd(dppf)Cl$_2$·CH$_2$Cl$_2$ (299.77 mg, 367.08 μmol) and tBuXPhos (463.44 mg, 734.17 μmol) were added, followed by Sodium carbonate (1.71 g, 16.15 mmol) dissolved in Water (11 mL). The mixture was degassed with nitrogen. The reaction was capped with a septum, fitted with a nitrogen inlet, and heated at 80° C. on a heating block for 5 h. The mixture was diluted with ethyl acetate, and the organic layer was separated from the aqueous layer as well as the solid precipitate. The crude residue purified by flash column chromatography on silica gel (0-10% Methanol in ethyl acetate) to give tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenoxy]piperidine-1-carboxylate (3.6 g, 5.82 mmol, 79.26% yield) as a pale orange foam. LCMS: 619.4 (M+H)

711

Step 2: [2-[6-[4-[(1-tert-butoxycarbonyl-4-piperidyl)oxy]phenyl]-4-fluoro-1-oxo-isoindolin-2-yl]-2-(6,7-dihydro-5H-pyrrolo[1,2-c]imidazol-1-yl)acetyl]

712

Step 3: tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]piperidine-1-carboxylate

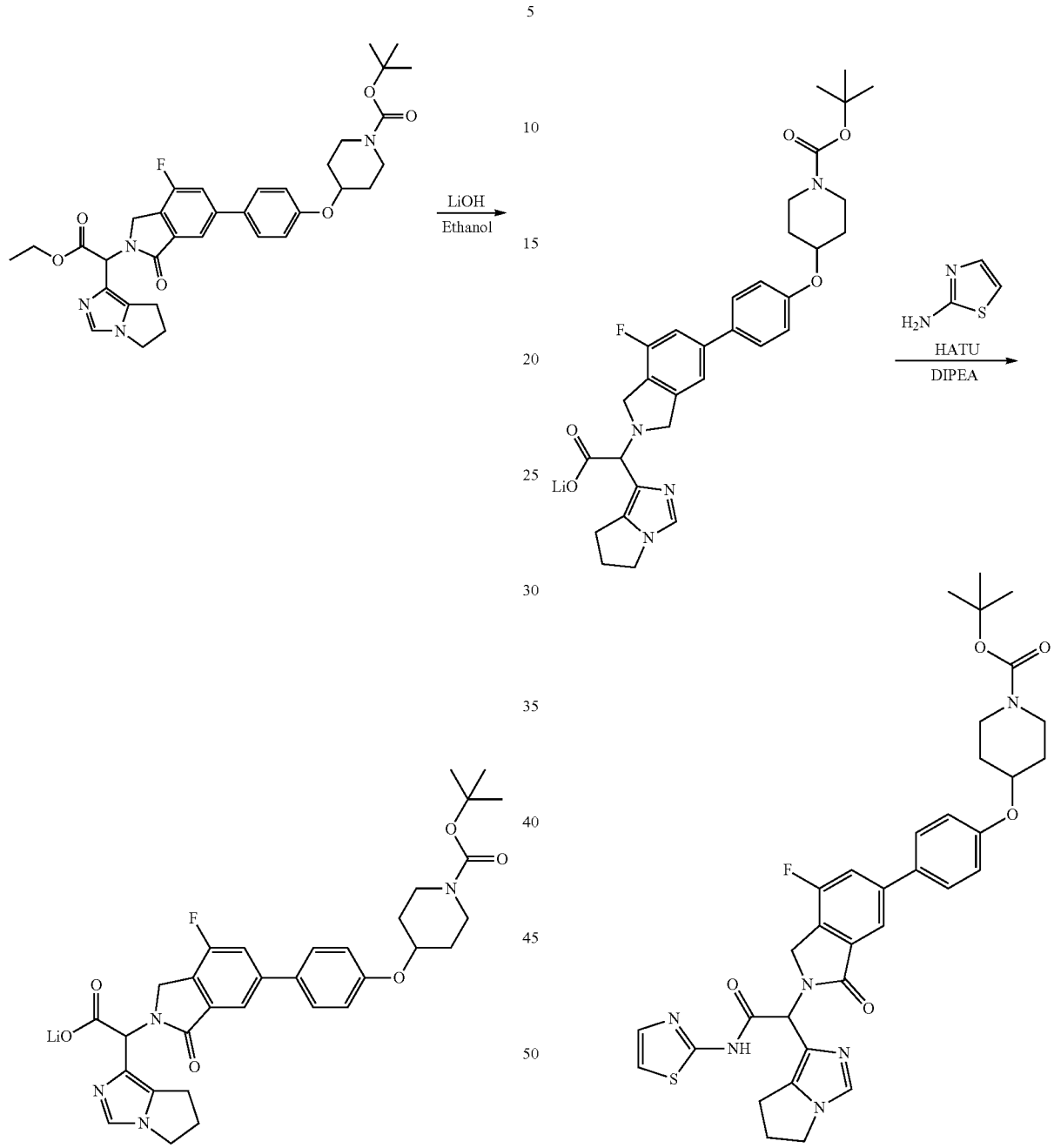

Lithium hydroxide (1 M, 5.82 mL) was added to a solution of tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenoxy]piperidine-1-carboxylate (3.6 g, 5.82 mmol) in Ethanol (25 ml). The reaction mixture was heated to 40° C. for 16 h. The reaction mixture was concentrated in vacuo, suspended in benzene and evaporated The residue was submitted to high vacuum to afford [2-[6-[4-[(1-tert-butoxycarbonyl-4-piperidyl)oxy]phenyl]-4-fluoro-1-oxo-isoindolin-2-yl]-2-(6,7-dihydro-5H-pyrrolo[1,2-c]imidazol-1-yl)acetyl]oxylithium (3.47 g, quantitative yield). LCMS (ESI+): 590.9 (M+H)

[2-[6-[4-[(1-tert-butoxycarbonyl-4-piperidyl)oxy]phenyl]-4-fluoro-1-oxo-isoindolin-2-yl]-2-(6,7-dihydro-5H-pyrrolo[1,2-c]imidazol-1-yl)acetyl]oxylithium (3.47 g, 5.82 mmol) and thiazol-2-amine (640.73 mg, 6.40 mmol) were mixed in DMF and the reaction mixture was cooled to 0° C. N,N-Diisopropylethylamine (3.01 g, 23.27 mmol, 4.05 mL) was added to the reaction mixture, and HATU (2.88 g, 7.56 mmol) was added, and the reaction mixture was stirred for 30 min at 0° C. Saturated aqueous sodium bicarbonate was added to the reaction mixture. The reaction mixture was extracted with ethyl acetate (2×). The organic layers were washed with water, brine, dried over $Na_2SO_4$, filtered and concentrated under reduced pressure. The crude material was purified by flash chromatography on silica gel (24 g, 0-10% methanol in dichloromethane) to afford tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]piperidine-1-carboxylate (3 g, 4.46 mmol, 77% yield). LCMS (ESI+): 673.2 (M+H)

Step 4: 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride

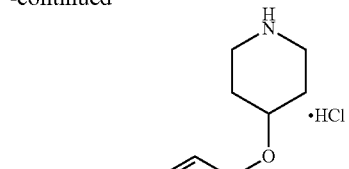

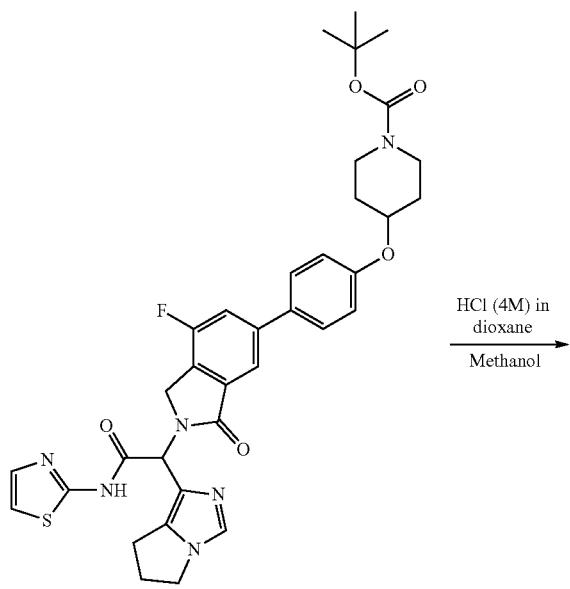

tert-Butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]piperidine-1-carboxylate (3 g, 4.46 mmol) was dissolved in 1,4-dioxane (10 mL) and methanol (10 mL). A hydrogen chloride solution (4.0M in 1,4-dioxane, 8 mL, 32 mmol) was added. The reaction mixture was heated at 40° C. for 4 hours. The volatiles were evaporated under reduced pressure. The material was submitted to high vacuum, frozen to −78° C. and thawed to afford 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride (3.2 g, 5.25 mmol, quantitative yield) as a dense solid.

Step 5: 2-(6,7-dihydro-5H-pyrrolo[1,2-c]imidazol-1-yl)-2-[6-[4-[[1-[2-[4-[4-[(2,6-dioxo-3-piperidyl)amino]phenyl]-1-piperidyl]acetyl]-4-piperidyl]oxy]phenyl]-4-fluoro-1-oxo-isoindolin-2-yl]-N-thiazol-2-yl-acetamide

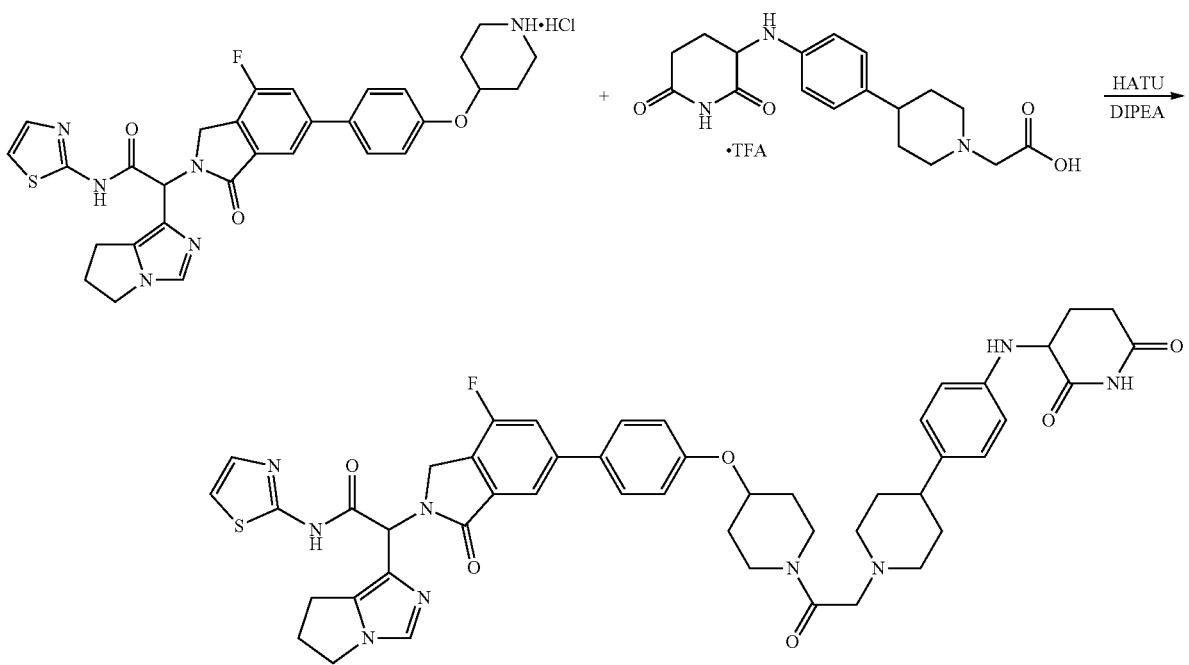

2-(6,7-Dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride (100 mg, 164.17 µmol) and 2-[4-[4-[(2,6-dioxo-3-piperidyl)amino]phenyl]-1-piperidyl]acetic acid trifluoroacetic acid salt (98.05 mg, 213.43 µmol) were mixed in DMF, the reaction mixture was cooled to 0° C. N,N-Diisopropylethylamine (106.09 mg, 820.87 µmol, 142.98 µL) was added to the reaction mixture, and HATU (81.15 mg, 213.43 µmol) was added, and the reaction mixture was stirred for 1 h in an ice bath. The reaction mixture was acidified with 4-5 drops of TFA, and injected directly on a RP C18 column (50 g C18) for purification using a 5% to 100% acetonitrile (+0.1% TFA) in water (+0.1% TFA) eluent gradient. The pure fractions were neutralized with aqueous NaHCO₃ (ca. 60 mL), extracted twice with a isopropanol:chloroform mixture (1; 4). The organic layer was dried over sodium sulfate, filtered, and evaporated under reduced pressure to afford a solid. The solid was dissolved in dichloromethane, injected on a 24 g silica gel column flushed with 100% dichloromethane, and purified using a 0% to 20% methanol in dichloromethane gradient over 20 minutes. The pure fractions were evaporated under reduced pressure. The crude residue was dissolved in dichloromethane, transferred to an 8 mL vial, and evaporated under reduced pressure. Water (1 mL) and acetonitrile (1 mL) were added, and the mixture was thoroughly sonicated, vortexed and sonicated again. The suspension was frozen and lyophilized to afford Compound 31 (62 mg, 68.20 µmol, 41% yield) as an off-white solid. LCMS (ESI+): 900.7 (M+H), 1H NMR (400 MHz, DMSO-d6) δ 12.53 (s, 1H), 10.76 (s, 1H), 7.82-7.74 (m, 3H), 7.76-7.71 (m, 1H), 7.61 (s, 1H), 7.49 (d, J=3.6 Hz, 1H), 7.26 (d, J=3.6 Hz, 1H), 7.15-7.08 (m, 2H), 7.00-6.93 (m, 2H), 6.66-6.59 (m, 2H), 6.16 (s, 1H), 5.65 (d, J=7.5 Hz, 1H), 4.82 (d, J=17.7 Hz, 1H), 4.74 (dq, J=8.1, 3.9 Hz, 1H), 4.32-4.20 (m, 2H), 3.99 (dddd, J=11.2, 8.2, 6.3, 3.1 Hz, 2H), 3.89 (d, J=12.0 Hz, 2H), 3.45 (t, J=10.2 Hz, 1H), 3.31-3.10 (m, 3H), 2.91 (d, J=10.7 Hz, 2H), 2.75 (ddt, J=23.3, 11.9, 5.7 Hz, 2H), 2.63-2.44 (m, 4H), 2.40-2.28 (m, 1H), 2.16-2.00 (m, 4H), 2.00-1.89 (m, 1H), 1.86 (qd, J=12.2, 4.8 Hz, 1H), 1.77-1.64 (m, 3H), 1.57 (q, J=12.2 Hz, 3H).

Example 32

Synthesis of 2-(6,7-dihydro-5H-pyrrolo[1,2-c]imidazol-1-yl)-2-[6-[4-[[1-[2-[4-[4-[[(3S)-2,6-dioxo-3-piperidyl]amino]phenyl]-1-piperidyl]acetyl]-4-piperidyl]oxy]phenyl]-4-fluoro-1-oxo-isoindolin-2-yl]-N-thiazol-2-yl-acetamide, Compound 32

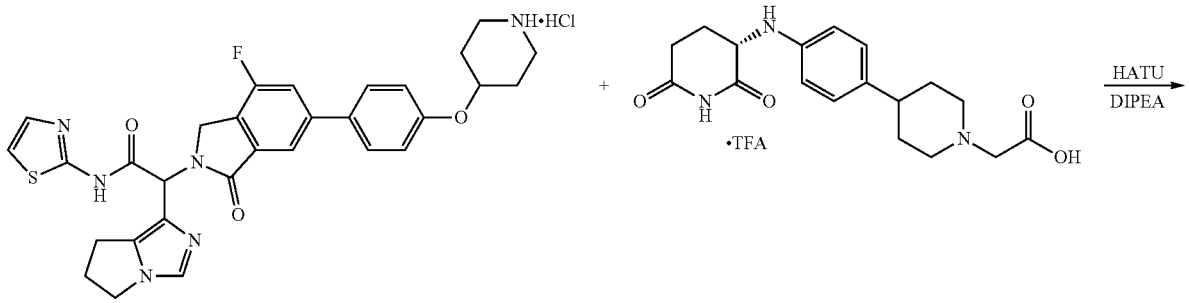

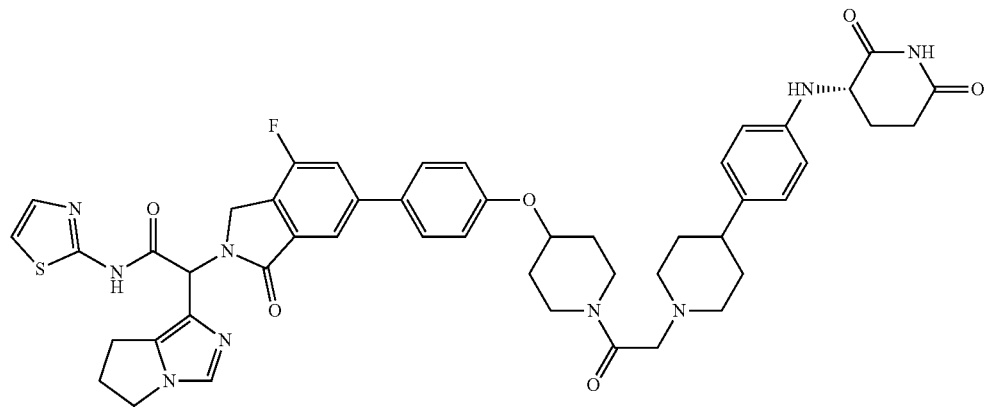

Compound 32 was prepared in 47% yield using the same procedure as 2-(6,7-dihydro-5H-pyrrolo[1,2-c]imidazol-1-yl)-2-[6-[4-[[1-[2-[4-[4-[[2,6-dioxo-3-piperidyl]amino]phenyl]-1-piperidyl]acetyl]-4-piperidyl]oxy]phenyl]-4-fluoro-1-oxo-isoindolin-2-yl]-N-thiazol-2-yl-acetamide, using 2-[4-[4-[[(3S)-2,6-dioxo-3-piperidyl]amino]phenyl]-1-piperidyl]acetic acid trifluoroacetic acid salt instead of 2-[4-[4-[[2,6-dioxo-3-piperidyl]amino]phenyl]-1-piperidyl]acetic acid trifluoroacetic acid salt. LCMS (ESI+): 900.3 (M+H), 1H NMR (400 MHz, DMSO-d6) δ 12.52 (s, 1H), 10.76 (s, 1H), 7.82-7.72 (m, 4H), 7.61 (s, 1H), 7.49 (d, J=3.6 Hz, 1H), 7.26 (d, J=3.6 Hz, 1H), 7.12 (d, J=8.5 Hz, 2H), 6.96 (d, J=8.2 Hz, 2H), 6.62 (d, J=8.2 Hz, 2H), 6.16 (s, 1H), 5.65 (d, J=7.5 Hz, 1H), 4.82 (d, J=17.7 Hz, 1H), 4.77-4.68 (m, 1H), 4.32-4.19 (m, 2H), 4.08-3.95 (s, 2H), 3.95-3.83 (m, 2H), 3.52-3.08 (m, 4H), 2.92 (m, 2H), 2.83-2.67 (m, 2H), 2.64-2.42 (m, 4H), 2.40-2.28 (m, 1H), 2.18-2.02 (m, 4H), 1.99-1.79 (m, 2H), 1.79-1.65 (m, 3H), 1.63-1.50 (m, 3H).

Example 33

Synthesis of 2-(6,7-dihydro-5H-pyrrolo[1,2-c]imidazol-1-yl)-2-[6-[4-[[1-[2-[4-[4-[[(3R)-2,6-dioxo-3-piperidyl]amino]phenyl]-1-piperidyl]acetyl]-4-piperidyl]oxy]phenyl]-4-fluoro-1-oxo-isoindolin-2-yl]-N-thiazol-2-yl-acetamide, Compound 33

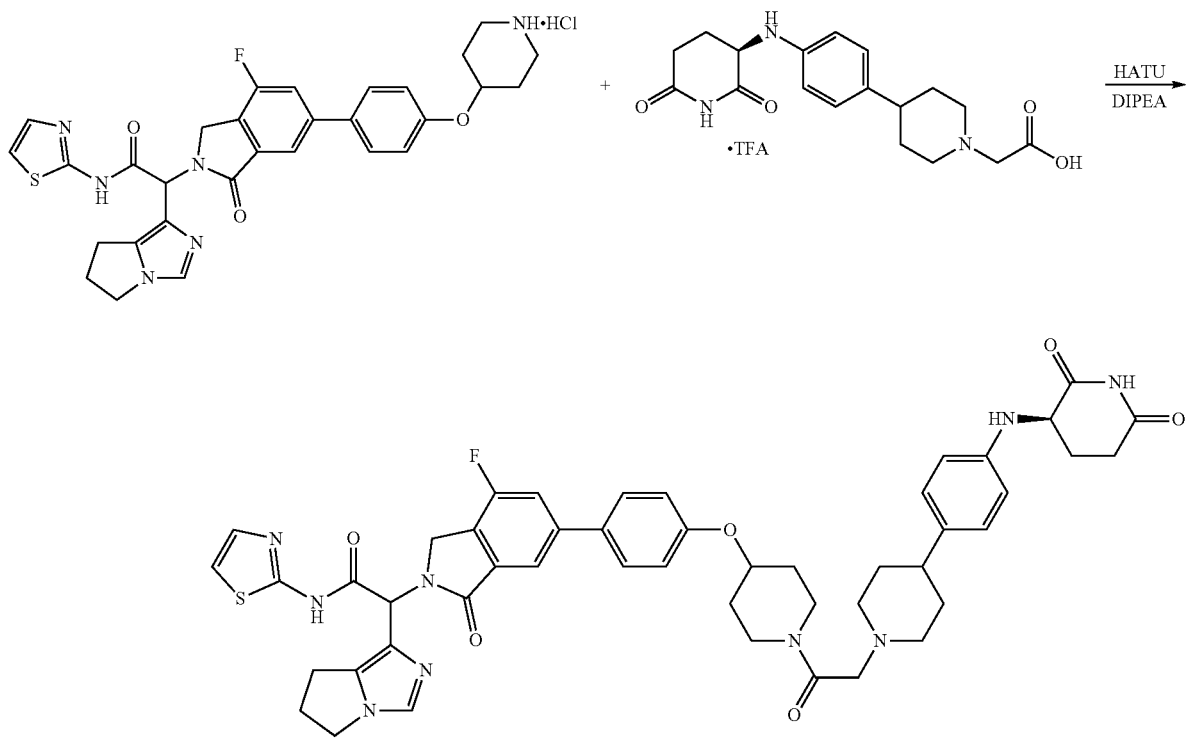

Compound 33 was prepared in 36% yield using the same procedure as 2-(6,7-dihydro-5H-pyrrolo[1,2-c]imidazol-1-yl)-2-[6-[4-[[1-[2-[4-[4-[[2,6-dioxo-3-piperidyl]amino]phenyl]-1-piperidyl]acetyl]-4-piperidyl]oxy]phenyl]-4-fluoro-1-oxo-isoindolin-2-yl]-N-thiazol-2-yl-acetamide, using 2-[4-[4-[[(3R)-2,6-dioxo-3-piperidyl]amino]phenyl]-1-piperidyl]acetic acid trifluoroacetic acid salt instead of 2-[4-[4-[[2,6-dioxo-3-piperidyl]amino]phenyl]-1-piperidyl]acetic acid trifluoroacetic acid salt. (54 mg, 59.40 μmol, 36.18% yield). LCMS (ESI+): 900.6 (M+H), ¹H NMR (400 MHz, DMSO-d6) δ 12.52 (s, 1H), 10.76 (s, 1H), 7.82-7.73 (m, 4H), 7.61 (s, 1H), 7.49 (d, J=3.5 Hz, 1H), 7.26 (d, J=3.6 Hz, 1H), 7.15-7.09 (m, 2H), 6.96 (d, J=8.2 Hz, 2H), 6.62 (d, J=8.2 Hz, 2H), 6.16 (s, 1H), 5.65 (d, J=7.5 Hz, 1H), 4.82 (d, J=17.8 Hz, 1H), 4.74 (m, 1H), 4.32-4.21 (m, 2H), 4.06-3.95 (m, 2H), 3.89 (m, 2H), 3.46 (m, 1H), 3.33-3.10 (m, 3H), 2.91 (d, J=10.5 Hz, 2H), 2.82-2.66 (m, 3H), 2.62-2.42 (m, 3H), 2.33 (dd, J=3.8, 1.9 Hz, 1H), 2.17-2.01 (m, 4H), 1.88 (ddd, J=20.1, 15.0, 9.8 Hz, 2H), 1.77-1.64 (m, 3H), 1.64-1.49 (m, 3H).

General Method A for Amide Coupling of 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride to Acid Intermediates The compounds were synthesized from 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride using the method used in for the synthesis Example 31, Step 5.

General Method B for Amide Coupling of 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride to Acid Intermediates To a solution of 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride (1 equiv.) and acid intermediate (1.1 equiv.) in DMF (0.1 M) was added N,N-diisopropylethylamine (5 equiv.) followed by HATU (1.3 equiv.) at ambient temperature. The reaction was further stirred at ambient temperature for 16 h. The reaction mixture was quenched with ice cold water and extracted with 10% methanol in dichloromethane (50 ml). Concentrated organic layer under reduced pressure afforded crude. Purified crude on Reverse phase column eluting compound in 40-50% acetonitrile in Water (with 0.1% TFA phase modifier). Pure fractions were lyophilized to afford a solid, which was further purified by Prep HPLC. Purification method: Column: Zorbax Extend C18 (50×4.6 mm) 5 m, Mobile Phase A: 10 mM Ammonium acetate in water, Mobile Phase B: Acetonitrile. The pure fractions were frozen and lyophilized to afford the title compound.

Example 34

Synthesis of 2-(6,7-dihydro-5H-pyrrolo[1,2-c]imidazol-1-yl)-2-(6-(4-((1-(2-(4-(4-((2,6-dioxopiperidin-3-yl)amino)-3-fluorophenyl)piperidin-1-yl)acetyl)piperidin-4-yl)oxy)phenyl)-4-fluoro-1-oxoisoindolin-2-yl)-N-(thiazol-2-yl)acetamide, Compound 34

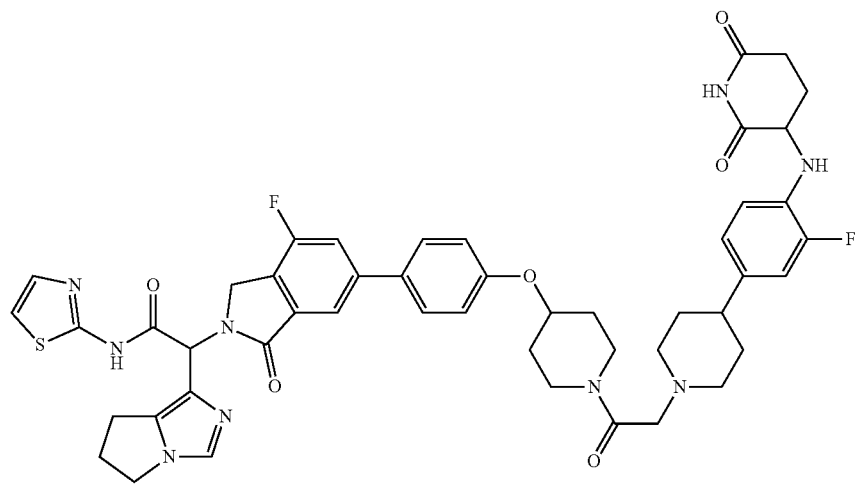 [SMILES: O=C1CCC(Nc2ccc(C3CCN(CC(=O)N4CCC(Oc5ccc(-c6cc(F)c7c(c6)C(=O)N(C(C(=O)Nc6nccs6)c6ncn8c6CCC8)C7)cc5)CC4)CC3)cc2F)C(=O)N1]

Synthesized according to General Method A for Amide Coupling of 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride to Acid Intermediates in 52% Yield.

LCMS (ESI+) 918.7 (M+H)

$^1$H NMR (400 MHz, DMSO-d6) δ 12.52 (s, 1H), 10.78 (s, 1H), 7.82-7.70 (m, 4H), 7.61 (s, 1H), 7.49 (d, J=3.6 Hz, 1H), 7.26 (d, J=3.6 Hz, 1H), 7.15-7.09 (m, 2H), 6.99 (t, J=8.8 Hz, 1H), 6.49-6.40 (m, 2H), 6.16 (s, 1H), 6.00 (d, J=7.8 Hz, 1H), 4.82 (d, J=17.7 Hz, 1H), 4.73 (t, J=3.7 Hz, 1H), 4.31 (td, J=7.4, 3.8 Hz, 1H), 4.24 (d, J=17.8 Hz, 1H), 4.06-3.95 (m, 2H), 3.89 (m, 2H), 3.51-3.40 (m, 1H), 3.30-3.08 (m, 3H), 2.92 (d, J=10.7 Hz, 2H), 2.83-2.66 (m, 2H), 2.62-2.41 (m, 3H), 2.15-2.02 (m, 5H), 1.88-1.79 (m, 1H), 1.87 (qd, J=12.3, 4.6 Hz, 3H), 1.74-1.59 (m, 6H), 1.59-1.47 (m, 1H).

Example 35

Synthesis of 2-(6,7-dihydro-5H-pyrrolo[1,2-c]imidazol-1-yl)-2-(6-(4-((1-(2-(4-(4-((2,6-dioxopiperidin-3-yl)amino)-2-fluorophenyl)piperidin-1-yl)acetyl)piperidin-4-yl)oxy)phenyl)-4-fluoro-1-oxoisoindolin-2-yl)-N-(thiazol-2-yl)acetamide, Compound 35

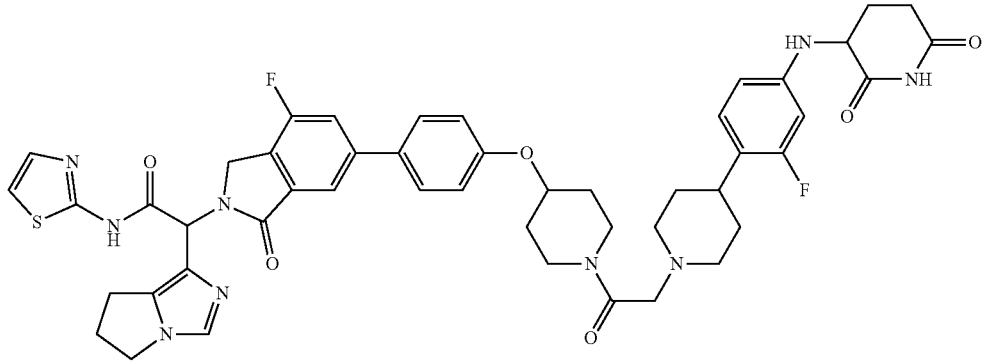 [SMILES: O=C1CCC(Nc2ccc(C3CCN(CC(=O)N4CCC(Oc5ccc(-c6cc(F)c7c(c6)C(=O)N(C(C(=O)Nc6nccs6)c6ncn8c6CCC8)C7)cc5)CC4)CC3)c(F)c2)C(=O)N1]

Synthesized according to General Method A for Amide Coupling of 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride to Acid Intermediates in 52% Yield.

LCMS (ESI+) 918.7 (M+H)

$^1$H NMR (400 MHz, DMSO-d6) δ 12.52 (s, 1H), 10.78 (s, 1H), 7.82-7.70 (m, 4H), 7.61 (s, 1H), 7.49 (d, J=3.6 Hz, 1H), 7.26 (d, J=3.6 Hz, 1H), 7.15-7.09 (m, 2H), 6.99 (t, J=8.8 Hz, 1H), 6.49-6.40 (m, 2H), 6.16 (s, 1H), 6.00 (d, J=7.8 Hz, 1H), 4.82 (d, J=17.7 Hz, 1H), 4.73 (t, J=3.7 Hz, 1H), 4.31 (td, J=7.4, 3.8 Hz, 1H), 4.24 (d, J=17.8 Hz, 1H), 4.06-3.95 (m, 2H), 3.89 (m, 2H), 3.51-3.40 (m, 1H), 3.30-3.08 (m, 3H), 2.92 (d, J=10.7 Hz, 2H), 2.83-2.66 (m, 2H), 2.62-2.41 (m, 3H), 2.15-2.02 (m, 5H), 1.88-1.79 (m, 1H), 1.87 (qd, J=12.3, 4.6 Hz, 3H), 1.74-1.59 (m, 6H), 1.59-1.47 (m, 1H).

Example 36

Synthesis of 2-(6,7-dihydro-5H-pyrrolo[1,2-c]imidazol-1-yl)-2-(6-(4-((1-(2-(4-(5-((2,6-dioxopiperidin-3-yl)amino)pyridin-2-yl)piperidin-1-yl)acetyl)piperidin-4-yl)oxy)phenyl)-4-fluoro-1-oxoisoindolin-2-yl)-N-(thiazol-2-yl)acetamide, Compound 36

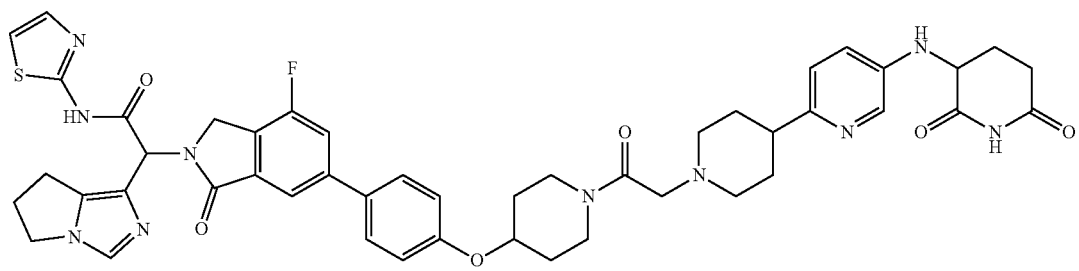 [SMILES: O=C1CCC(Nc2ccc(C3CCN(CC(=O)N4CCC(Oc5ccc(-c6cc(F)c7c(c6)C(=O)N(C(C(=O)Nc6nccs6)c6ncn8c6CCC8)C7)cc5)CC4)CC3)nc2)C(=O)N1]

Synthesized according to General Method A for Amide Coupling of 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride to Acid Intermediates in 30% Yield.

LCMS (ESI+) 901.5 (M+H)

$^1$H NMR (400 MHz, DMSO-d6) δ 12.52 (s, 1H), 10.79 (s, 1H), 7.98 (t, J=1.8 Hz, 1H), 7.82-7.72 (m, 4H), 7.61 (s, 1H), 7.49 (d, J=3.6 Hz, 1H), 7.26 (d, J=3.6 Hz, 1H), 7.15-7.09 (m, 2H), 6.98 (d, J=1.8 Hz, 2H), 6.16 (s, 1H), 5.93 (d, J=7.8 Hz, 1H), 4.82 (d, J=17.7 Hz, 1H), 4.78-4.69 (m, 1H), 4.34 (ddd, J=12.2, 7.8, 4.9 Hz, 1H), 4.24 (d, J=17.7 Hz, 1H), 4.06-3.84 (m, 4H), 3.45 (t, J=10.0 Hz, 1H), 3.31-3.07 (m, 2H), 2.91 (d, J=10.7 Hz, 2H), 2.83-2.67 (m, 2H), 2.64-2.42 (m, 6H), 2.17-2.01 (m, 4H), 2.00-1.83 (m, 2H), 1.82-1.60 (m, 5H), 1.60-1.47 (m, 1H).

Example 37

Synthesis of 2-(6-(4-((1-(2-(4-(2-cyano-4-((2,6-dioxopiperidin-3-yl)amino)phenyl)piperidin-1-yl)acetyl)piperidin-4-yl)oxy)phenyl)-4-fluoro-1-oxoisoindolin-2-yl)-2-(6,7-dihydro-5H-pyrrolo[1,2-c]imidazol-1-yl)-N-(thiazol-2-yl)acetamide, Compound 37

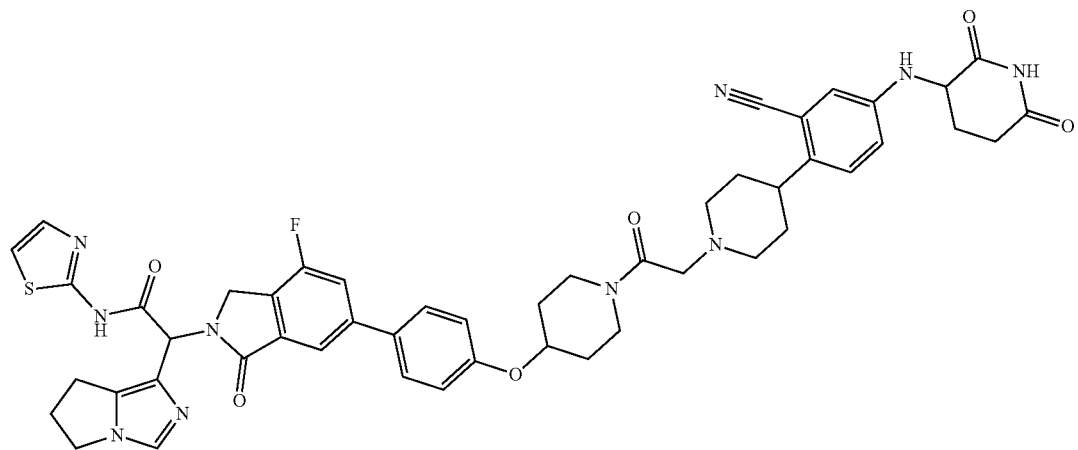 [SMILES: N#Cc1cc(NC2CCC(=O)NC2=O)ccc1C1CCN(CC(=O)N2CCC(Oc3ccc(-c4cc(F)c5c(c4)C(=O)N(C(C(=O)Nc4nccs4)c4ncn6c4CCC6)C5)cc3)CC2)CC1]

Synthesized according to General Method A for Amide Coupling of 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride to Acid Intermediates in 46% Yield.

LCMS (ESI+) 925.5 (M+H)

$^1$H NMR (400 MHz, DMSO-d6) δ 12.52 (s, 1H), 10.80 (s, 1H), 7.82-7.71 (m, 4H), 7.62 (s, 1H), 7.49 (d, J=3.6 Hz, 1H), 7.26 (d, J=3.6 Hz, 1H), 7.21 (d, J=8.7 Hz, 1H), 7.15-7.09 (m, 2H), 6.97 (d, J=7.6 Hz, 2H), 6.25 (d, J=7.9 Hz, 1H), 6.16 (s, 1H), 4.82 (d, J=17.7 Hz, 1H), 4.78-4.70 (m, 1H), 4.40 (ddd, J=12.3, 7.9, 4.9 Hz, 1H), 4.24 (d, J=17.7 Hz, 1H), 4.00 (ddt, J=10.5, 7.5, 4.6 Hz, 2H), 3.93-3.83 (m, 2H), 3.46 (t, J=10.4 Hz, 1H), 3.30-3.13 (m, 3H), 2.96 (d, J=10.2 Hz, 2H), 2.83-2.64 (m, 3H), 2.64-2.45 (m, 3H), 2.20-2.02 (m, 4H), 2.02-1.83 (m, 2H), 1.70 (s, 5H), 1.55 (d, J=8.8 Hz, 1H).

Example 38

Synthesis of 2-(6,7-dihydro-5H-pyrrolo[1,2-c]imidazol-1-yl)-2-(6-(4-((1-(2-(4-(4-((2,4-dioxo-3-azabicyclo[3.1.1]heptan-1-yl)amino)phenyl)piperidin-1-yl)acetyl)piperidin-4-yl)oxy)phenyl)-4-fluoro-1-oxoisoindolin-2-yl)-N-(thiazol-2-yl)acetamide, Compound 38

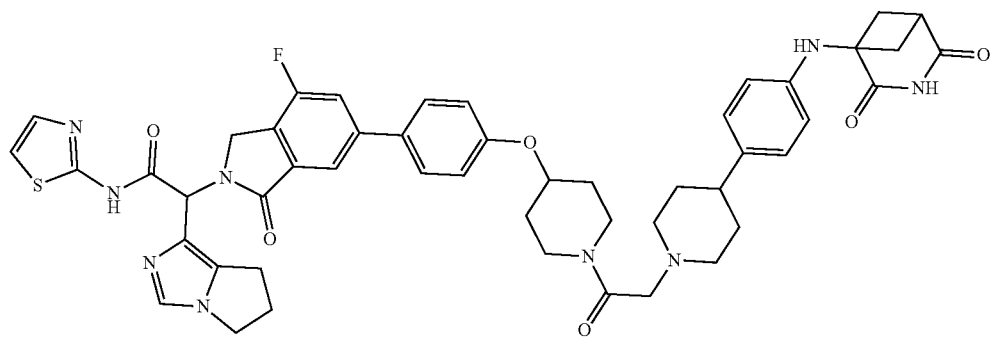 [SMILES: O=C1NC(=O)C2(Nc3ccc(C4CCN(CC(=O)N5CCC(Oc6ccc(-c7cc(F)c8c(c7)C(=O)N(C(C(=O)Nc7nccs7)c7ncn9c7CCC9)C8)cc6)CC5)CC4)cc3)CC1C2]

Synthesized according to General Method B for Amide Coupling of 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride to Acid Intermediates in 4.47% Yield.

LCMS (ESI+) 912.2 (M+H)

$^1$H-NMR (400 MHz, DMSO-d6): δ 12.53 (s, 1H), 10.71 (s, 1H), 7.78 (dd, J=1.2, 12.4 Hz, 4H), 7.62 (s, 1H), 7.49 (d, J=3.6 Hz, 1H), 7.27 (d, J=3.6 Hz, 1H), 7.12 (d, J=8.8 Hz, 2H), 6.92 (d, J=8.4 Hz, 2H), 6.40 (d, J=8.4 Hz, 2H), 6.15 (s, 1H), 6.08 (s, 1H), 4.82 (d, J=17.6 Hz, 1H), 4.77-4.68 (m, 1H), 4.24 (d, J=17.6 Hz, 1H), 4.05-3.98 (m, 2H), 3.97-3.88 (m, 2H), 3.28-3.27 (m, 3H), 2.97-2.81 (m, 4H), 2.80-2.71 (m, 3H), 2.15-2.01 (m, 4H), 1.95-1.88 (m, 2H), 1.75-1.61 (m, 4H), 1.61-1.49 (m, 4H).

Example 39

Synthesis of 2-(6,7-dihydro-5H-pyrrolo[1,2-c]imidazol-1-yl)-2-(6-(4-((1-(2-(4-(4-(((S)-2,6-dioxopiperidin-3-yl)amino)-2-fluorophenyl)piperidin-1-yl)acetyl)piperidin-4-yl)oxy)phenyl)-4-fluoro-1-oxoisoindolin-2-yl)-N-(thiazol-2-yl)acetamide, Compound 39

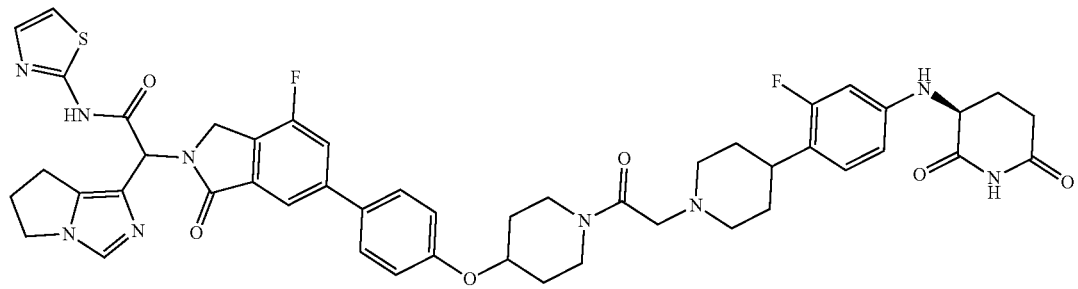 [SMILES: O=C1CC[C@H](Nc2ccc(C3CCN(CC(=O)N4CCC(Oc5ccc(-c6cc(F)c7c(c6)C(=O)N(C(C(=O)Nc6nccs6)c6ncn8c6CCC8)C7)cc5)CC4)CC3)c(F)c2)C(=O)N1]

Synthesized according to General Method B for Amide Coupling of 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide hydrochloride to Acid Intermediates in 39% Yield.

LCMS (ESI+) 919.0 (M+H)

$^1$H-NMR (400 MHz, DMSO-d6): 12.56 (s, 1H), 10.79 (s, 1H), 7.80-7.73 (m, 4H), 7.62 (s, 1H), 7.49 (d, J=3.6 Hz, 1H), 7.27 (d, J=3.6 Hz, 1H), 7.12 (d, J=8.8 Hz, 2H), 6.99 (d, J=9.2 Hz, 1H), 6.47-6.43 (m, 2H), 6.16 (s, 1H), 6.02 (d, J=7.6 Hz, 1H), 4.84-4.74 (m, 2H), 4.31-4.22 (m, 2H), 4.03-3.97 (m, 4H), 3.48-3.41 (m, 1H), 3.34-3.12 (m, 3H), 2.92-2.88 (m, 2H), 2.78-2.67 (m, 2H), 2.61-2.54 (m, 3H), 2.11-2.06 (m, 4H), 1.92-1.86 (m, 3H), 1.76-1.51 (m, 7H).

Example 40

Synthesis of 2-(6,7-dihydro-5H-pyrrolo[1,2-c]imidazol-1-yl)-2-[6-[4-[[1-[2-[4-[4-[(2,6-dioxo-3-piperidyl)amino]phenyl]-1-piperidyl]-2-oxo-acetyl]-4-piperidyl]oxy]phenyl]-4-fluoro-1-oxo-isoindolin-2-yl]-N-thiazol-2-yl-acetamide, Compound 40

Step 1: Ethyl 2-[4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]-1-piperidyl]-2-oxo-acetate

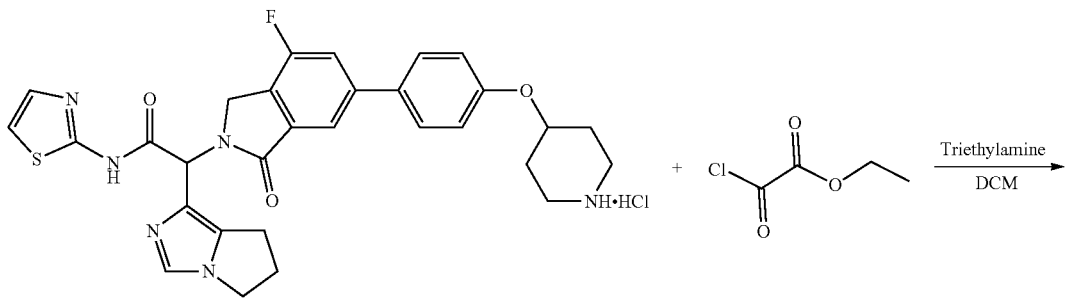

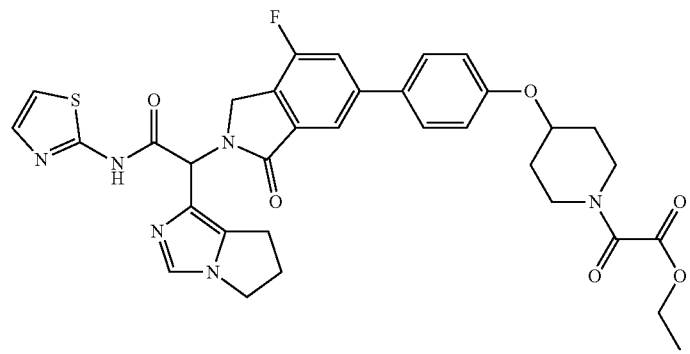

729

To a stirred solution of 2-(6,7-dihydro-5H-pyrrolo[1,2-c]imidazole-1-yl)-2-[4-fluoro-1-oxo-6-[4-(4-piperidyloxy)phenyl]isoindolin-2-yl]-N-thiazol-2-yl-acetamide; hydrochloride (58 mg, 95.22 μmol) in dichloromethane (1 mL) was added Triethylamine (24.09 mg, 238.05 μmol, 33.18 μL) and ethyl 2-chloro-2-oxo-acetate (14.30 mg, 104.74 μmol, 11.72 μL) and the mixture was stirred at ambient temperature. After completion, the reaction mixture was diluted with chloroform/isopropanol (4:1) and NaHCO$_3$ (aqueous). The separated organic layer was washed with brine, dried over Na$_2$SO$_4$, and concentrated. The mixture was purified by silica gel column chromatography using a 0% to 20% methanol in dichloromethane eluent gradient to yield ethyl 2-[4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]-1-piperidyl]-2-oxo-acetate (37 mg, 55.00 μmol, 58% yield). LCMS (ESI+): 673.2 (M+H).

Step 2: 2-[4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]-1-piperidyl]-2-oxo-acetic acid lithium salt

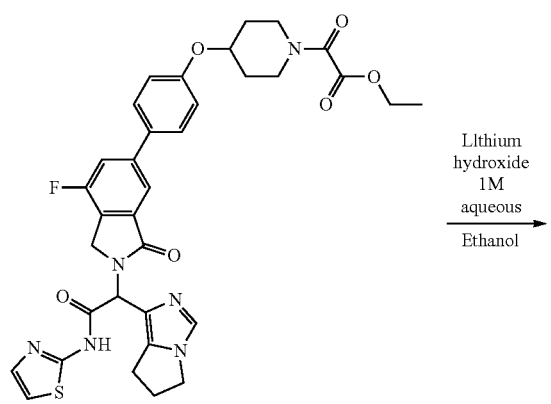

Lithium hydroxide 1M aqueous
Ethanol

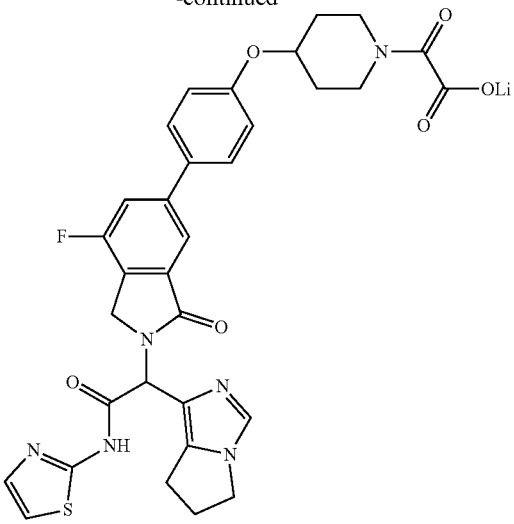

To a solution of ethyl 2-[4-[4-[2-[1-(6,7-dihydro-5H-pyrrolo[1,2-c]imidazol-1-yl)-2-oxo-2-(2-thienylamino)ethyl]-7-fluoro-3-oxo-isoindolin-5-yl]phenoxy]-1-piperidyl]-2-oxo-acetate (37 mg, 55.08 μmol) in Ethanol (0.5 mL) was added Lithium hydroxide (1 M aqueous solution, 61 μmol, 61 μL) and the mixture was stirred at ambient temperature for 2 hours. The reaction mixture was evaporated to dryness under reduced pressure to afford 2-[4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]-1-piperidyl]-2-oxo-acetic acid lithium salt (35.9 mg, 55.08 μmol, quantitative yield). LCMS (ESI+): 645.2 (M+H).

Step 3: 2-(6,7-dihydro-5H-pyrrolo[1,2-c]imidazol-1-yl)-2-[6-[4-[[1-[2-[4-[4-[(2,6-dioxo-3-piperidyl)amino]phenyl]-1-piperidyl]-2-oxo-acetyl]-4-piperidyl]oxy]phenyl]-4-fluoro-1-oxo-isoindolin-2-yl]-N-thiazol-2-yl-acetamide

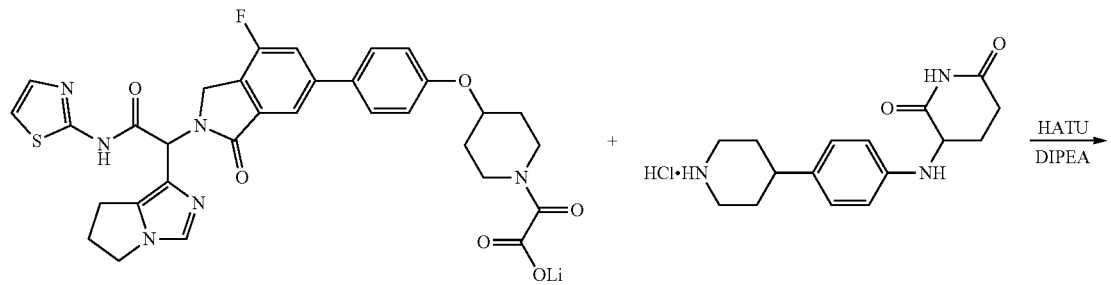

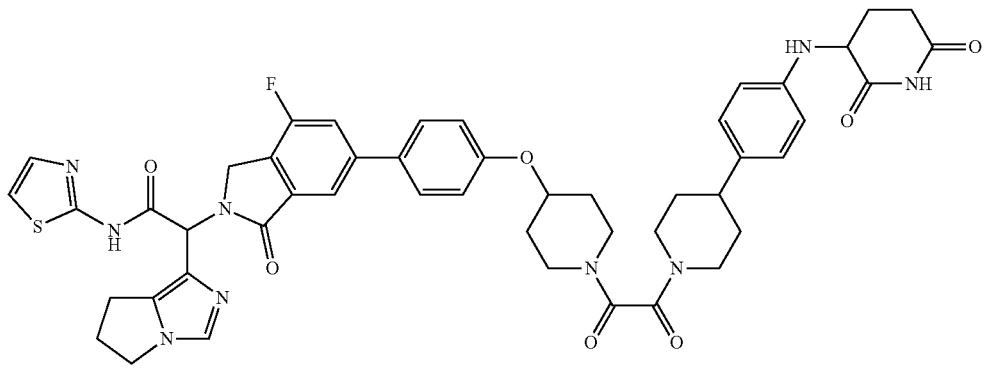

2-[4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]-1-piperidyl]-2-oxo-acetic acid lithium salt (35.9 mg, 55.08 μmol) and 3-[4-(4-piperidyl)anilino]piperidine-2,6-dione; hydrochloride (21.40 mg, 66.09 μmol) were mixed in DMF (0.5 mL) and the reaction mixture was cooled to 0° C. N,N-Diisopropylethylamine (35.59 mg, 275.39 μmol, 47.97 μL) was added to the reaction mixture, and HATU (27.23 mg, 71.60 μmol) was added, and the reaction mixture was stirred for 1 h at 0° C. The reaction mixture was acidified with 4-5 drops of TFA, and injected directly on a RP C18 column (50 g C18) for purification (5% to 100% ACETONITRILE (+0.1% TFA) in water (+0.1% TFA) over 12 minutes). The pure fractions were neutralized with aqueous NaHCO₃ (ca. 60 mL), extracted twice with isopropanol:chloroform mixture (1:4). The organic layer was dried over Na₂SO₄, filtered, and evaporated under reduced pressure. The residue was purified by silica gel column chromatography (0% to 20% methanol in dichloromethane). The desired fractions were evaporated under reduced pressure, then dissolved in dichloromethane, transferred to an 8 mL vial, and evaporated under reduced pressure. Water (1 mL) and (1 mL) acetonitrile were added, and the mixture was thoroughly sonicated, vortexed and sonicated again. The suspension was frozen and lyophilized to afford Compound 40 (25.7 mg, 27.84 μmol, 50% yield). LCMS (ESI+): 914.3 (M+H), ¹H NMR (400 MHz, DMSO-d6) δ 12.57 (s, 1H), 10.82 (d, J=2.9 Hz, 1H), 7.86 (s, 1H), 7.85-7.77 (m, 3H), 7.67 (s, 1H), 7.55 (d, J=3.6 Hz, 1H), 7.32 (d, J=3.6 Hz, 1H), 7.18 (d, J=8.4 Hz, 2H), 7.03 (d, J=8.1 Hz, 2H), 6.68 (dd, J=8.7, 2.9 Hz, 2H), 6.22 (s, 1H), 5.75 (dd, J=7.5, 3.6 Hz, 1H), 4.94-4.79 (m, 2H), 4.48 (d, J=12.6 Hz, 1H), 4.37-4.25 (m, 2H), 4.13-3.99 (m, 2H), 3.99-3.84 (m, 1H), 3.64 (t, J=14.8 Hz, 2H), 3.57-3.34 (m, 3H), 3.28 (t, J=13.3 Hz, 1H), 2.92-2.68 (m, 4H), 2.68-2.57 (m, 3H), 2.21-2.01 (m, 3H), 1.99-1.81 (m, 3H), 1.81-1.65 (m, 2H), 1.53 (dd, J=15.6, 7.9 Hz, 2H).

Example 41

Synthesis of 2-(6,7-dihydro-5H-pyrrolo[1,2-c]imidazol-1-yl)-2-[6-[4-[(3R)-1-[2-[4-[4-[[(3S)-2,6-dioxo-3-piperidyl]amino]phenyl]-1-piperidyl]acetyl]pyrrolidin-3-yl]oxyphenyl]-4-fluoro-1-oxo-isoindolin-2-yl]-N-thiazol-2-yl-acetamide, Compound 41

Step 1: tert-butyl 4-(4-(2-(1-(6,7-dihydro-5H-pyrrolo[1,2-c]imidazol-1-yl)-2-ethoxy-2-oxoethyl)-7-fluoro-3-oxoisoindolin-5-yl)phenoxy)piperidine-1-carboxylate

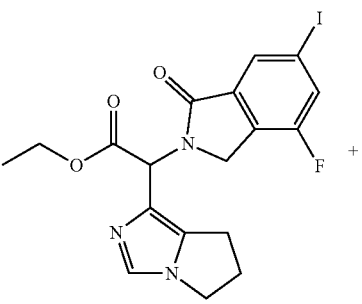 +

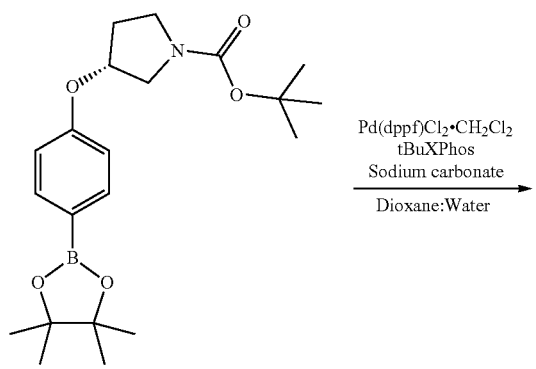

Pd(dppf)Cl₂·CH₂Cl₂
tBuXPhos
Sodium carbonate
⎯⎯⎯⎯⎯⎯⎯⎯→
Dioxane:Water

733
-continued

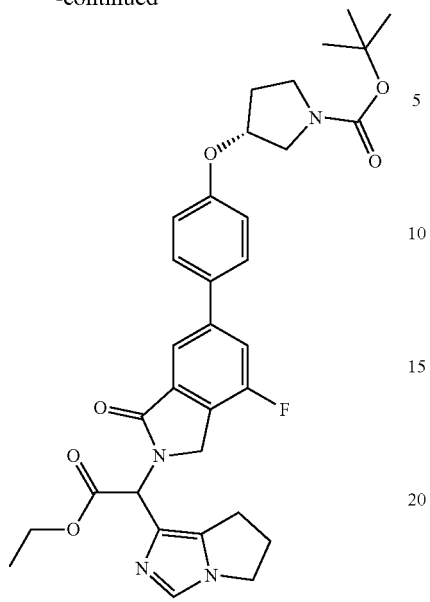

tert-Butyl (3R)-3-(4-(2-(1-(6,7-dihydro-5H-pyrrolo[1,2-c]imidazol-1-yl)-2-ethoxy-2-oxoethyl)-7-fluoro-3-oxoisoindolin-5-yl)phenoxy)pyrrolidine-1-carboxylate was prepared from ethyl 2-(6,7-dihydro-5H-pyrrolo[1,2-c]imidazol-1-yl)-2-(4-fluoro-6-iodo-1-oxoisoindolin-2-yl)acetate and tert-butyl (R)-3-(4-(4,4,5,5-tetramethyl-1,3,2-dioxaborolan-2-yl)phenoxy)pyrrolidine-1-carboxylate (Cas #1383793-73-4) in 43% yield using the procedure used in Example 31, step 1. LCMS (ESI+): 605.3 (M+H)

Step 2: 2-[6-[4-[(3R)-1-tert-butoxycarbonylpyrrolidin-3-yl]oxyphenyl]-4-fluoro-1-oxo-isoindolin-2-yl]-2-(6,7-dihydro-5H-pyrrolo[1,2-c]imidazol-1-yl)acetic acid 734
-continued To a solution of tert-butyl (3R)-3-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenoxy]pyrrolidine-1-carboxylate (600 mg, 992.28 μmol) in THF (3 mL) and Methanol (3 mL) and Water (3 mL) was added Lithium hydroxide monohydrate (41.64 mg, 992.28 μmol) at 0° C. The reaction mixture was stirred at room temperature for 3 h, then the reaction mixture was concentrated. The crude residue was dissolved in 5 ml water and acidified by using $KHSO_4$ salt (pH 1-2). The solution was filtered to get solid compound 2-[6-[4-[(3R)-1-tert-butoxycarbonylpyrrolidin-3-yl]oxyphenyl]-4-fluoro-1-oxo-isoindolin-2-yl]-2-(6,7-dihydro-5H-pyrrolo[1,2-c]imidazol-1-yl)acetic acid (450 mg, 522 μmol, 53% yield). LCMS (ESI+): 577.0 (M+H).

Step 3: (3R)-3-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]pyrrolidine-1-carboxylate

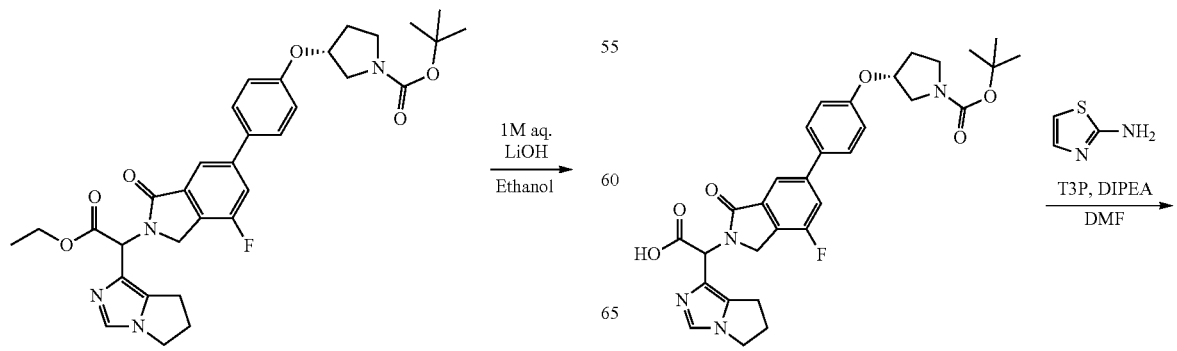

735

-continued

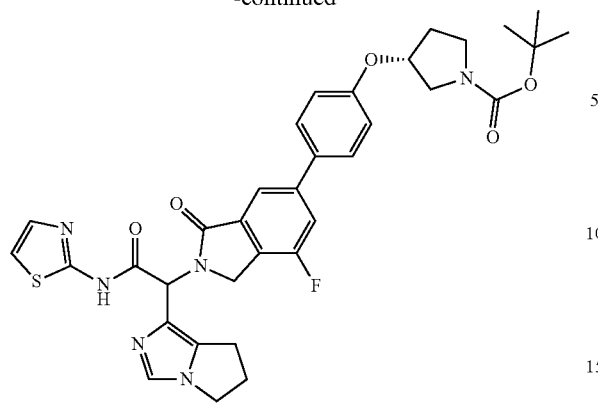

To a solution of 2-[6-[4-[(3R)-1-tert-butoxycarbonylpyrrolidin-3-yl]oxyphenyl]-4-fluoro-1-oxo-isoindolin-2-yl]-2-(6,7-dihydro-5H-pyrrolo[1,2-c]imidazol-1-yl)acetic acid (200 mg, 346.85 µmol) in DMF (2 mL) was added N,N-diisopropyl ethyl amine (224.14 mg, 1.73 mmol, 302.08 µL) and propylphosphonic anhydride, 50% solution in ethyl acetate (220.72 mg, 693.70 µmol) at 0° C. After 15 min, thiazol-2-amine (34.73 mg, 346.85 µmol) was added and the mixture was stirred at 50° C. for 16 hours. Water was added to the reaction mixture to afford precipitation. The precipitate was collected by filtration, then was dissolved in dichloromethane and the solution was concentrated. The crude product was purified by flash column chromatography, product eluted in 3% methanol/dichloromethane. The appropriate fractions were combined and concentrated to give tert-butyl (3R)-3-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]pyrrolidine-1-carboxylate (110 mg, 111.9 µmol, 32% yield). LMCS (ESI+): 659.2 (M+H).

Step 4: 2-(6,7-dihydro-5H-pyrrolo[1,2-c]imidazol-1-yl)-2-[4-fluoro-1-oxo-6-[4-[(3R)-pyrrolidin-3-yl]oxyphenyl]isoindolin-2-yl]-N-thiazol-2-yl-acetamide hydrochloride

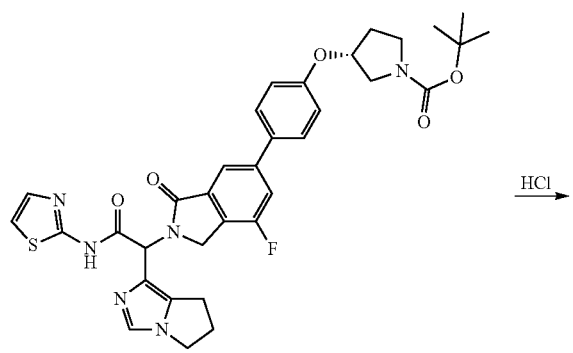

HCl →

736

-continued

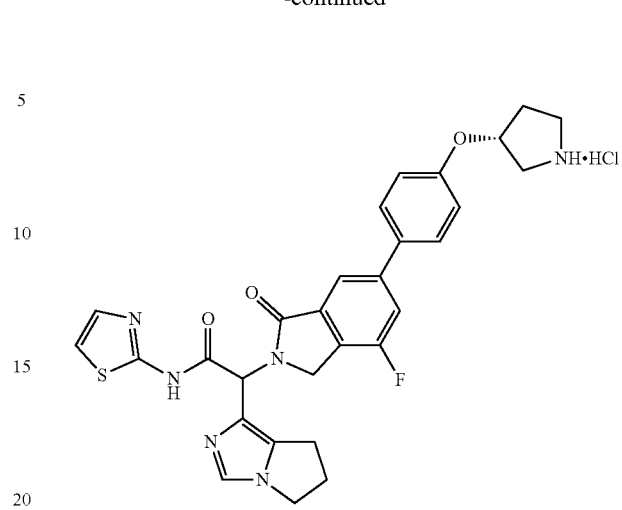

To a solution of tert-butyl (3R)-3-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenoxy]pyrrolidine-1-carboxylate (150 mg, 227.71 µmol) in dichloromethane (1.5 mL) was added Hydrogen chloride solution (4.0M in dioxane, 426 µL, 1.71 mmol) at 0° C. After 2 h the reaction mixture was concentrated under reduced pressure and the solid residue was washed with diethyl ether to afford 2-(6,7-dihydro-5H-pyrrolo[1,2-c]imidazol-1-yl)-2-[4-fluoro-1-oxo-6-[4-[(3R)-pyrrolidin-3-yl]oxyphenyl]isoindolin-2-yl]-N-thiazol-2-yl-acetamide hydrochloride (140 mg, 174.1 µmol, 76.5% yield). LCMS m/z 559.2 (M+H)

Step 5: 2-(6,7-dihydro-5H-pyrrolo[1,2-c]imidazol-1-yl)-2-[6-[4-[(3R)-1-[2-[4-[4-[[(3S)-2,6-dioxo-3-piperidyl]amino]phenyl]-1-piperidyl]acetyl]pyrrolidin-3-yl]oxyphenyl]-4-fluoro-1-oxo-isoindolin-2-yl]-N-thiazol-2-yl-acetamide

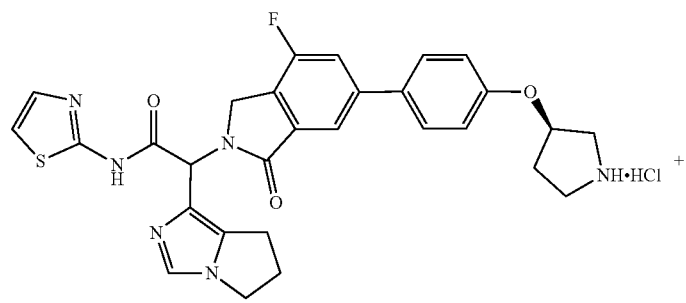

+

-continued

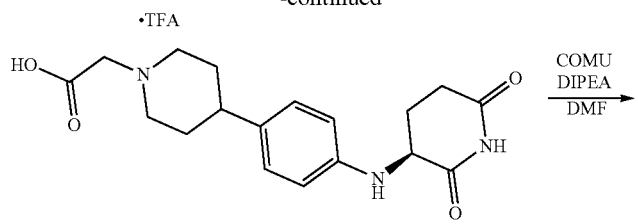

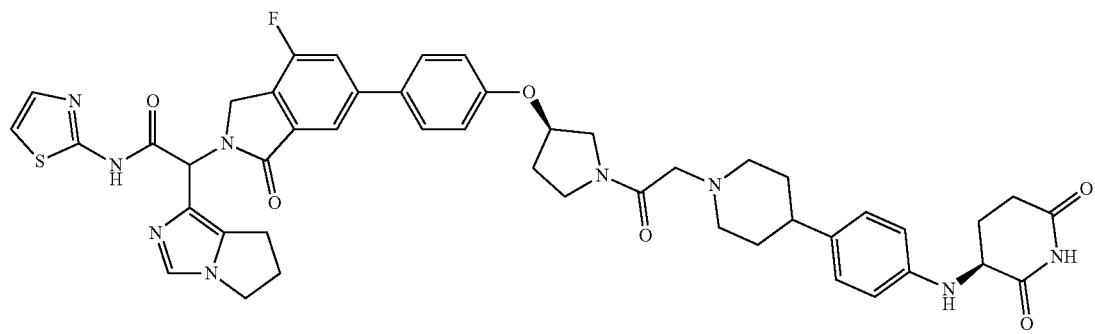

To a solution of 2-[4-[4-[[(3S)-2,6-dioxo-3-piperidyl]amino]phenyl]-1-piperidyl]acetic acid (63.84 mg, 138.97 µmol) in DMF (1 mL) was added N,N-diisopropyl ethyl amine (119.45 mg, 924.24 µmol, 160.99 µL) and COMU (118.75 mg, 277.27 µmol) at 0° C. After 15 min, 2-(6,7-dihydro-5H-pyrrolo[1,2-c]imidazol-1-yl)-2-[4-fluoro-1-oxo-6-[4-[(3R)-pyrrolidin-3-yl]oxyphenyl]isoindolin-2-yl]-N-thiazol-2-yl-acetamide hydrochloride (110 mg, 184.85 µmol) was added. After stirring for 1 hour, 5 ml of water added to the reaction mixture and a solid precipitate was formed. The solid was collected by filtration, then dissolved in dichloromethane and the solution was concentrated. The crude was purified by reverse phase C-18 chromatography (0-100% of 0.1% ammonium acetate in water and Acetonitrile). Fractions were lyophilized to get afford Compound 41 as a white solid. LCMS (ESI+): 887.0 (M+H), 1H-NMR (400 MHz, DMSO-d6): 12.53 (s, 1H), 10.77 (s, 1H), 7.80-7.77 (m, 4H), 7.64 (s, 1H), 7.55 (s, 1H), 7.26 (s, 1H), 7.11-7.02 (m, 2H), 6.97-6.95 (m, 1H), 6.91-6.87 (m, 1H), 6.62 (d, J=8.4 Hz, 1H), 6.56 (s, 1H), 6.15 (s, 1H), 5.72-5.65 (m, 1H), 5.23-5.13 (m, 1H), 4.82 (d, J=17.6 Hz, 1H), 4.44-4.24 (m, 2H), 4.04-3.92 (m, 2H), 3.90-3.61 (m, 3H), 3.61-3.45 (m, 2H), 3.61-3.45 (m, 4H), 3.11-2.88 (m, 2H), 2.90-2.85 (m, 1H), 2.71-2.67 (m, 2H), 2.65-2.58 (m, 2H), 2.12-2.42 (m, 4H), 1.85-1.78 (m, 1H), 1.72-1.64 (m, 2H)

Example 42

Synthesis of 2-(6,7-dihydro-5H-pyrrolo[1,2-c]imidazol-1-yl)-2-[6-[4-[(3S)-1-[2-[4-[4-[[(3S)-2,6-dioxo-3-piperidyl]amino]phenyl]-1-piperidyl]acetyl]pyrrolidin-3-yl]oxyphenyl]-4-fluoro-1-oxo-isoindolin-2-yl]-N-thiazol-2-yl-acetamide, Compound 42

Step 1: tert-butyl (3S)-3-(4-(2-(1-(6,7-dihydro-5H-pyrrolo[1,2-c]imidazol-1-yl)-2-ethoxy-2-oxoethyl)-7-fluoro-3-oxoisoindolin-5-yl)phenoxy)pyrrolidine-1-carboxylate

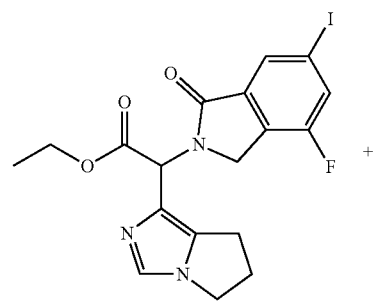

739

-continued

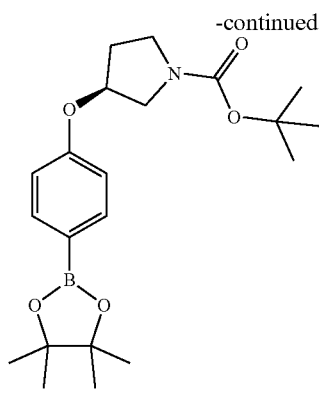

Pd(dppf)Cl₂•CH₂Cl₂
tBuXPhos
Sodium carbonate
───────────────
Dioxane:Water

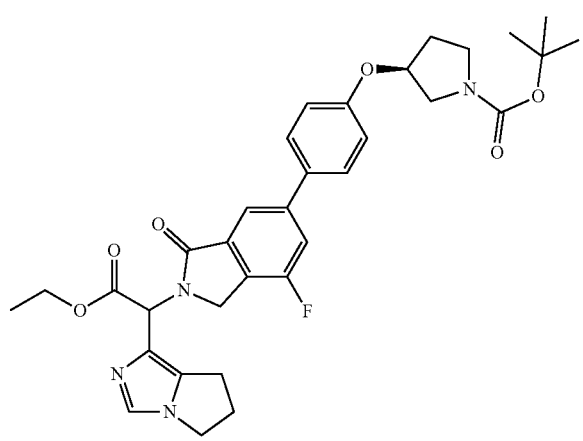

tert-butyl (3S)-3-(4-(2-(1-(6,7-dihydro-5H-pyrrolo[1,2-c]imidazol-1-yl)-2-ethoxy-2-oxoethyl)-7-fluoro-3-oxoisoindolin-5-yl)phenoxy)pyrrolidine-1-carboxylate was prepared in 68.5% yield from ethyl 2-(6,7-dihydro-5H-pyrrolo[1,2-c]imidazol-1-yl)-2-(4-fluoro-6-iodo-1-oxoisoindolin-2-yl)acetate and tert-butyl (S)-3-(4-(4,4,5,5-tetramethyl-1,3,2-dioxaborolan-2-yl)phenoxy)pyrrolidine-1-carboxylate (CAS #1383793-75-6) in 43% yield using the procedure used in Example 31, step 1. LCMS (ESI+): 605.3 (M+H)

Step 2: 2-(6-(4-(((S)-1-(tert-butoxycarbonyl)pyrrolidin-3-yl)oxy)phenyl)-4-fluoro-1-oxoisoindolin-2-yl)-2-(6,7-dihydro-5H-pyrrolo[1,2-c]imidazol-1-yl)acetic acid

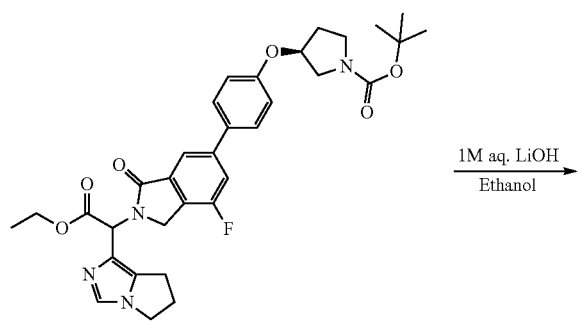

1M aq. LiOH
─────────
Ethanol

740

-continued

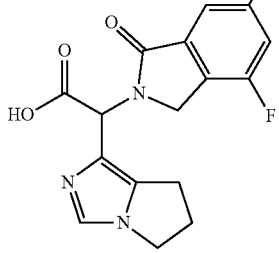

2-(6-(4-(((S)-1-(tert-butoxycarbonyl)pyrrolidin-3-yl)oxy)phenyl)-4-fluoro-1-oxoisoindolin-2-yl)-2-(6,7-dihydro-5H-pyrrolo[1,2-c]imidazol-1-yl)acetic acid was prepared in 84% yield from tert-butyl (3S)-3-(4-(2-(1-(6,7-dihydro-5H-pyrrolo[1,2-c]imidazol-1-yl)-2-ethoxy-2-oxoethyl)-7-fluoro-3-oxoisoindolin-5-yl)phenoxy)pyrrolidine-1-carboxylate using the same procedure as Example 41, step 2. LCMS (ESI+): 576.8 (M+H)

Step 3: tert-Butyl (3S)-3-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenoxy)pyrrolidine-1-carboxylate

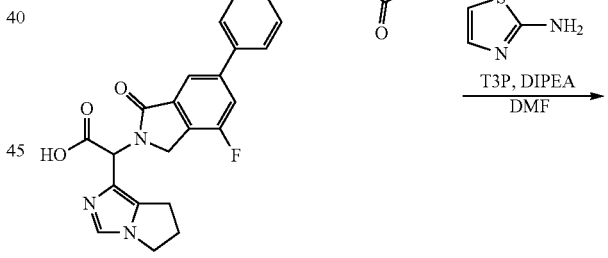

T3P, DIPEA
─────────
DMF

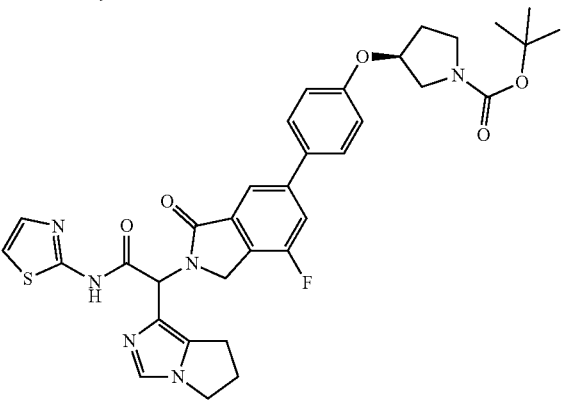

tert-Butyl (3S)-3-(4-(2-(1-(6,7-dihydro-5H-pyrrolo[1,2-c]imidazol-1-yl)-2-oxo-2-(thiazol-2-ylamino)ethyl)-7-

741 fluoro-3-oxoisoindolin-5-yl)phenoxy)pyrrolidine-1-carboxylate was synthesized in 44% yield from 2-(6-(4-(((S)-1-(tert-butoxycarbonyl)pyrrolidin-3-yl)oxy)phenyl)-4-fluoro-1-oxoisoindolin-2-yl)-2-(6,7-dihydro-5H-pyrrolo[1,2-c]imidazol-1-yl)acetic acid using the same procedure as Example 41, step 3. LCMS (ESI+): 659.2 (M+H)

Step 4: 2-(6,7-dihydro-5H-pyrrolo[1,2-c]imidazol-1-yl)-2-(4-fluoro-1-oxo-6-(4-(((S)-pyrrolidin-3-yl)oxy)phenyl)isoindolin-2-yl)-N-(thiazol-2-yl)acetamide hydrochloride

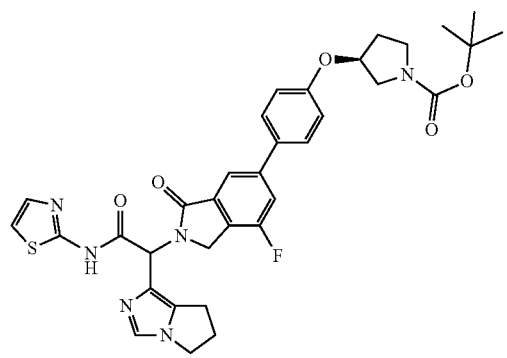

HCl →

-continued

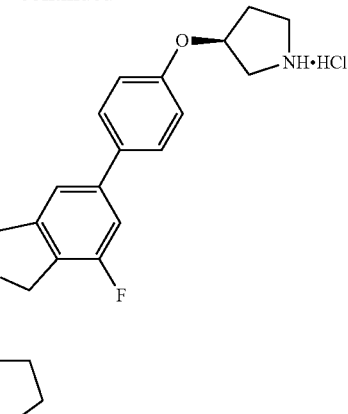

2-(6,7-dihydro-5H-pyrrolo[1,2-c]imidazol-1-yl)-2-(4-fluoro-1-oxo-6-(4-(((S)-pyrrolidin-3-yl)oxy)phenyl)isoindolin-2-yl)-N-(thiazol-2-yl)acetamide hydrochloride was prepared in 94.56% yield from tert-butyl (3S)-3-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenoxy)pyrrolidine-1-carboxylate using the same procedure as Example 41, step 4. LCMS (ESI+): 558.8 (M+H).

Step 5: 2-(6,7-dihydro-5H-pyrrolo[1,2-c]imidazol-1-yl)-2-[6-[4-[(3S)-1-[2-[4-[4-[[(3S)-2,6-dioxo-3-piperidyl]amino]phenyl]-1-piperidyl]acetyl]pyrrolidin-3-yl]oxyphenyl]-4-fluoro-1-oxo-isoindolin-2-yl]-N-thiazol-2-yl-acetamide

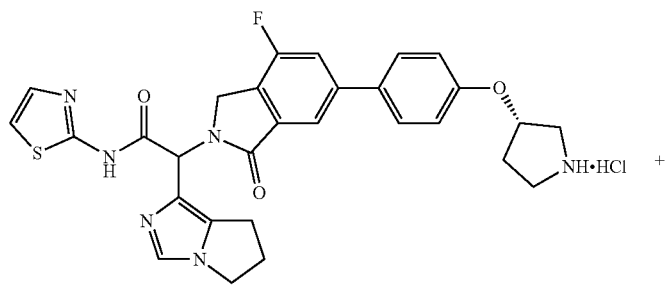

+

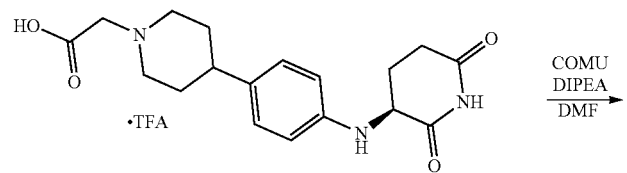

COMU
DIPEA
DMF →

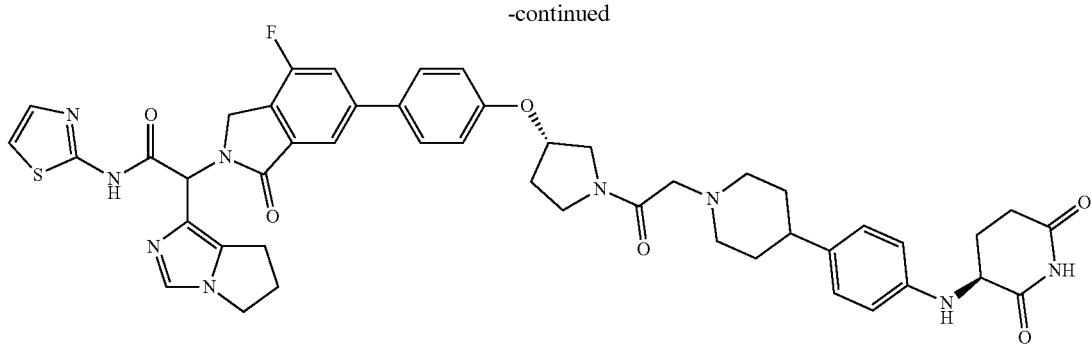

Compound 42 was prepared as a white solid in 15.2% yield from 2-(6,7-dihydro-5H-pyrrolo[1,2-c]imidazol-1-yl)-2-(4-fluoro-1-oxo-6-(4-(((S)-pyrrolidin-3-yl)oxy)phenyl)isoindolin-2-yl)-N-(thiazol-2-yl)acetamide hydrochloride using the same procedure as Example 41, step 5. LCMS (ESI+): 886.2 (M+H), 1H-NMR (400 MHz, DMSO-d6) 12.53 (s, 1H), 10.77 (s, 1H), 7.81-7.75 (m, 4H), 7.61 (s, 1H), 7.49 (s, 1H), 7.26 (s, 1H), 7.11-7.07 (m, 2H), 6.97 (s, 1H), 6.91 (s, 1H), 6.62 (d, J=8.4 Hz, 1H), 6.59 (s, 1H), 6.16 (s, 1H), 5.72-5.65 (m, 1H), 5.26-5.16 (m, 1H), 4.82 (d, J=17.6 Hz, 1H), 4.24 (d, J=18.0 Hz, 2H), 4.04-3.99 (m, 2H), 3.98-3.97 (m, 1H), 3.72-3.61 (m, 2H), 3.61-3.45 (m, 6H), 2.78-2.71 (m, 5H), 2.12-2.05 (m, 5H), 1.92-1.84 (m, 2H), 1.69-1.64 (m, 4H)

Example 43

Synthesis of (2RS)-2-[6-[4-[4-[2-[4-[4-[[(3RS)-2,6-Dioxo-3-piperidyl]amino]phenyl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide, Compound 43

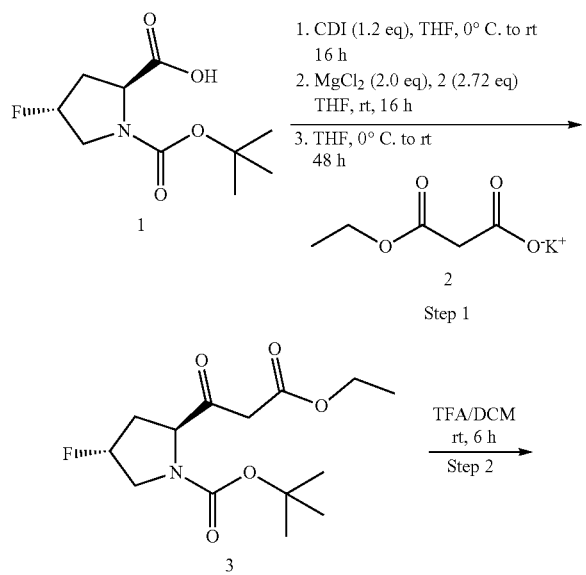

Step 1: Tert-butyl (2S,4R)-2-(3-ethoxy-3-oxopropanoyl)-4-fluoropyrrolidine-1-carboxylate Tert-butyl (2S,4R)-2-(3-ethoxy-3-oxopropanoyl)-4-fluoropyrrolidine-1-carboxylate was obtained in quantitative yield using a procedure similar to that used for Intermediate Ethyl 2-amino-2-(6,7-dihydro-5H-pyrrolo[1,2-c]imidazol-1-yl)acetate dihydrochloride, Step 1, using (2S,4R)-1-(tert-butoxycarbonyl)-4-fluoropyrrolidine-2-carboxylic acid (CAS #203866-14-2) instead of tert-butyl (2S,4R)-2-(3-ethoxy-3-oxopropanoyl)-pyrrolidine-1-carboxylate. LCMS (ESI+): 304.1 (M+H)

Step 2: Ethyl 3-((2S,4R)-4-fluoropyrrolidin-2-yl)-3-oxopropanoate, trifluoroacetic acid salt Tert-butyl (2S,4R)-2-(3-ethoxy-3-oxopropanoyl)-4-fluoropyrrolidine-1-carboxylate (11 grams, 36 mmol) was dissolved in dichloromethane (150 mL) and trifluoroacetic acid (50 mL) was added. The reaction mixture was stirred for 2 hours at 22° C., and the volatiles were evaporated to afford ethyl 3-((2S,4R)-4-fluoropyrrolidin-2-yl)-3-oxopropanoate, trifluoroacetic acid salt (7.36 g, 36 mmol, quantitative yield). LCMS (ESI+): 204.1 (M+H).

Step 3: Ethyl (R)-2-(6-fluoro-3-thioxo-2,5,6,7-tetrahydro-3H-pyrrolo[1,2-c]imidazol-1-yl)acetate Ethyl (R)-2-(6-fluoro-3-thioxo-2,5,6,7-tetrahydro-3H-pyrrolo[1,2-c]imidazol-1-yl)acetate was obtained in 88% yield from ethyl 3-((2S,4R)-4-fluoropyrrolidin-2-yl)-3-oxopropanoate, trifluoroacetic acid salt using a procedure similar to that used for Intermediate Ethyl 2-amino-2-(6,7-dihydro-5H-pyrrolo[1,2-c]imidazol-1-yl)acetate dihydrochloride, Step 3. LCMS (ESI+): 245.1 (M+H)

Step 4: Ethyl (R)-2-(6-fluoro-6,7-dihydro-5H-pyrrolo[1,2-c]imidazol-1-yl)acetate Ethyl (R)-2-(6-fluoro-6,7-dihydro-5H-pyrrolo[1,2-c]imidazol-1-yl)acetate was obtained in 47% yield from using a procedure similar to that used for the synthesis of Intermediate Ethyl 2-amino-2-(6,7-dihydro-5H-pyrrolo[1,2-c]imidazol-1-yl)acetate dihydrochloride, Step 4.

LCMS (ESI+) m/z=213 [M+H$^+$], $^1$H-NMR (400 MHz, CDCl$_3$): 7.51 (br. s, 1H), 5.79 (d, J=51 Hz, 1H), 4.30-4.09 (m, 4H), 3.59 (br, s, 2H), 3.25-3.02 (m, 2H), 1.28 (t, J=6.7 Hz, 3H).

Step 5: ethyl 2-[(6R)-6-fluoro-6,7-dihydro-5H-pyrrolo[1,2-c]imidazol-1-yl]-2-hydroxyimino-acetate

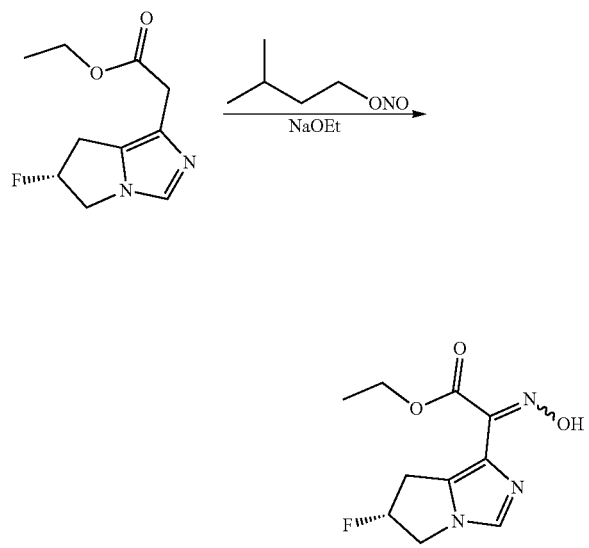

Ethyl 2-[(6R)-6-fluoro-6,7-dihydro-5H-pyrrolo[1,2-c]imidazol-1-yl]-2-hydroxyimino-acetate was obtained in 77.5% yield from ethyl (R)-2-(6-fluoro-6,7-dihydro-5H-pyrrolo[1,2-c]imidazol-1-yl)acetate using a procedure similar to that used for Intermediate Ethyl 2-amino-2-(6,7-dihydro-5H-pyrrolo[1,2-c]imidazol-1-yl)acetate dihydrochloride, Step 5.

LCMS (ESI+): 242.1 (M+H$^+$)

Step 6: ethyl 2-amino-2-[(6R)-6-fluoro-6,7-dihydro-5H-pyrrolo[1,2-c]imidazol-1-yl]acetate

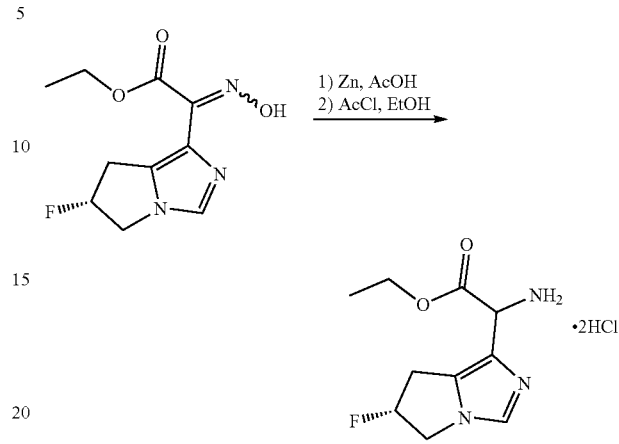

Ethyl 2-amino-2-[(6R)-6-fluoro-6,7-dihydro-5H-pyrrolo[1,2-c]imidazol-1-yl]acetate dihydrochloride was obtained in 29% yield from ethyl 2-[(6R)-6-fluoro-6,7-dihydro-5H-pyrrolo[1,2-c]imidazol-1-yl]-2-hydroxyimino-acetate using a procedure similar as the one used for Intermediate Ethyl 2-amino-2-(6,7-dihydro-5H-pyrrolo[1,2-c]imidazol-1-yl)acetate dihydrochloride, Step 6. LCMS (ESI+): 228.1 (M+H).

Step 7: 2-[(6R)-6-fluoro-6,7-dihydro-5H-pyrrolo[1,2-c]imidazol-1-yl]-2-(4-fluoro-6-iodo-1-oxo-isoindolin-2-yl)acetate

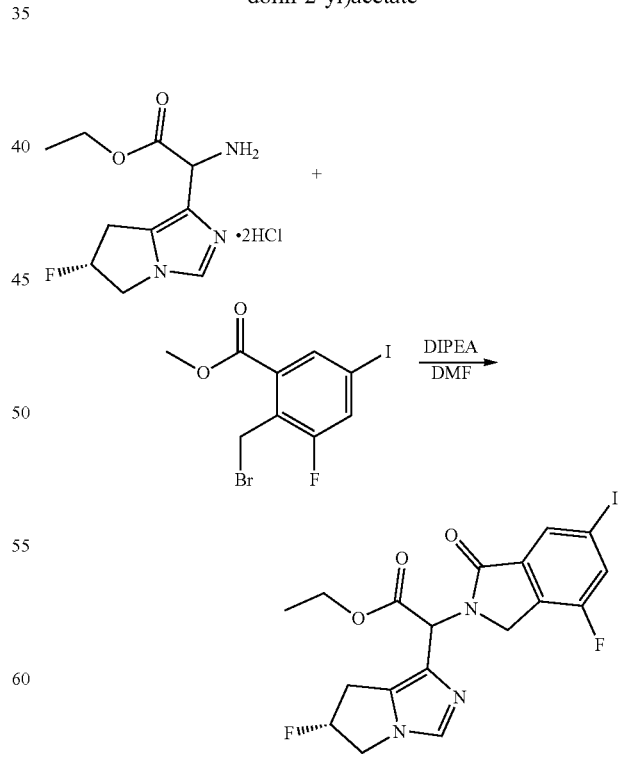

Ethyl 2-amino-2-[(6R)-6-fluoro-6,7-dihydro-5H-pyrrolo[1,2-c]imidazol-1-yl]acetate; dihydrochloride (3.9 g, 4.02 mmol) was dissolved in DMF (10 mL). Methyl 2-(bromomethyl)-3-fluoro-5-iodo-benzoate (1.20 g, 3.22 mmol) was added, followed by N-ethyl-N-isopropyl-propan-2-amine (2.08 g, 16.08 mmol, 2.80 mL). The reaction mixture was stirred at rt for 30 min. The reaction mixture was heated at 80° C. for 4 h. The reaction mixture was partitioned between ethyl acetate and sodium bicarbonate (aqueous, aqueous). The organic layer was isolated and washed with brine, dried with sodium sulfate, filtered and evaporated under reduced pressure. The crude residue was purified by silica gel chromatography (40 g column, 0% to 25% methanol in ethyl acetate). Pure fractions were evaporated to afford ethyl 2-[(6R)-6-fluoro-6,7-dihydro-5H-pyrrolo[1,2-c]imidazol-1-yl]-2-(4-fluoro-6-iodo-1-oxo-isoindolin-2-yl)acetate (951 mg, 1.95 mmol, 48.55% yield). LCMS: 1.253 min., MS (ESI+): 488 (M+H)

Step 8: tert-butyl 4-[4-[2-[2-ethoxy-1-[(6R)-6-fluoro-6,7-dihydro-5H-pyrrolo[1,2-c]imidazol-1-yl]-2-oxo-ethyl]-7-fluoro-3-oxo-isoindolin-5-yl]phenyl]piperazine-1-carboxylate Ethyl 2-[(6R)-6-fluoro-6,7-dihydro-5H-pyrrolo[1,2-c]imidazol-1-yl]-2-(4-fluoro-6-iodo-1-oxo-isoindolin-2-yl)acetate (951 mg, 1.95 mmol) and tert-butyl 4-[4-(4,4,5,5-tetramethyl-1,3,2-dioxaborolan-2-yl)phenyl]piperazine-1-carboxylate (833.70 mg, 2.15 mmol) were mixed in water (2.5 mL) and 1,4-dioxane (7.5 mL). Pd(dppf)Cl$_2$ (99.97 mg, 136.63 μmol) and Potassium carbonate (269.75 mg, 1.95 mmol, 117.80 μL) were added, and the reaction mixture was degassed with nitrogen under sonication for 15 minutes. The reaction mixture was heated at 80° C. for 4 hours. The reaction mixture was partitioned between ethyl acetate and sodium bicarbonate (aqueous, aqueous). The organic layer was washed with brine, dried with sodium sulfate, filtered and evaporated under reduced pressure. The crude residue was purified by silica gel chromatography (40 g column, 0% to 20% methanol in ethyl acetate). Pure fractions were evaporated to afford tert-butyl 4-[4-[2-[2-ethoxy-1-[(6R)-6-fluoro-6,7-dihydro-5H-pyrrolo[1,2-c]imidazol-1-yl]-2-oxo-ethyl]-7-fluoro-3-oxo-isoindolin-5-yl]phenyl]piperazine-1-carboxylate (436 mg, 701.33 μmol, 35.93% yield). LCMS (ESI+): 622.2 (M+H)/522 (M-Boc+H)

Step 9: [2-[6-[4-(4-tert-butoxycarbonylpiperazin-1-yl)phenyl]-4-fluoro-1-oxo-isoindolin-2-yl]-2-[(6R)-6-fluoro-6,7-dihydro-5H-pyrrolo[1,2-c]imidazol-1-yl]acetyl]oxylithium

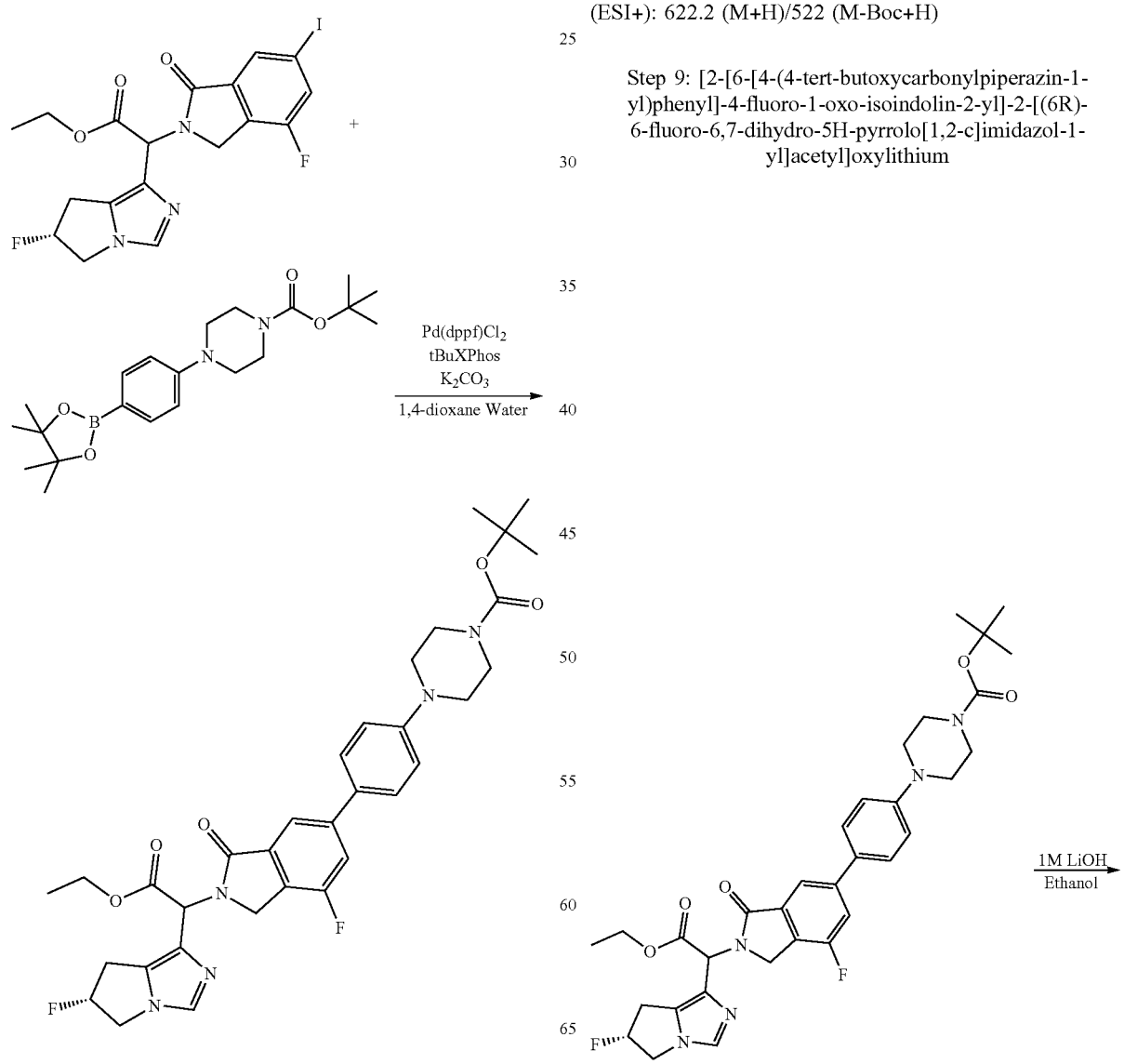

749
-continued

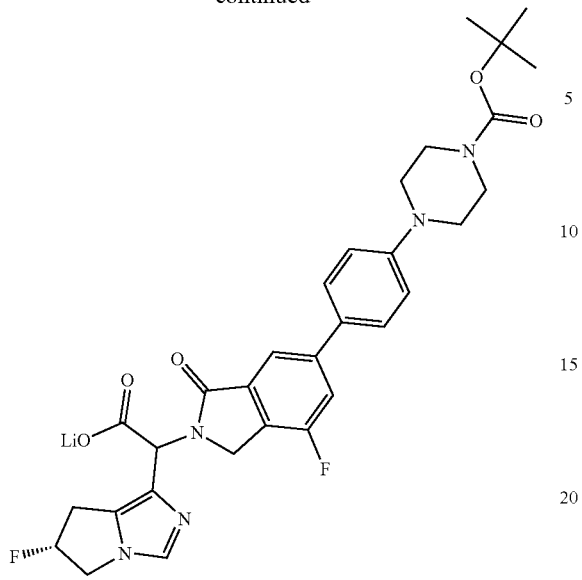

Tert-butyl 4-[4-[2-[2-ethoxy-1-[(6R)-6-fluoro-6,7-dihydro-5H-pyrrolo[1,2-c]imidazol-1-yl]-2-oxo-ethyl]-7-fluoro-3-oxo-isoindolin-5-yl]phenyl]piperazine-1-carboxylate (435 mg, 699.73 μmol) was dissolved in ethanol (5 mL), cooled to 0° C. and lithium hydroxide, 1M (1 M, 699.73 μL) was added. The reaction mixture was stirred for 3 hours. The crude residue was dissolved in dichloromethane with 0.5 mL of benzene and evaporated under reduced pressure, then submitted to high vacuum to afford [2-[6-[4-(4-tert-butoxycarbonylpiperazin-1-yl)phenyl]-4-fluoro-1-oxo-isoindolin-2-yl]-2-[(6R)-6-fluoro-6,7-dihydro-5H-pyrrolo[1,2-c]imidazol-1-yl]acetyl]oxylithium (410 mg, 683.84 μmol, 97.73% yield). LCMS (ESI+): 594.2 (M+H, free acid).

Step 10: tert-butyl 4-[4-[7-fluoro-2-[1-[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]phenyl]piperazine-1-carboxylate 750
-continued

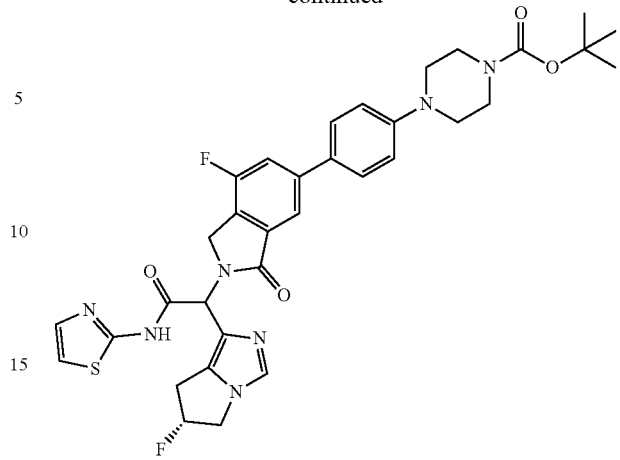

[2-[6-[4-(4-tert-butoxycarbonylpiperazin-1-yl)phenyl]-4-fluoro-1-oxo-isoindolin-2-yl]-2-[(6R)-6-fluoro-6,7-dihydro-5H-pyrrolo[1,2-c]imidazol-1-yl]acetyl]oxylithium (410 mg, 683.84 μmol) and thiazol-2-amine (82.18 mg, 820.61 μmol) were mixed in DMF and cooled to 0° C. N,N-diisopropylethylamine (265.15 mg, 2.05 mmol, 357.34 μL) was added to the reaction mixture, and HATU (312.02 mg, 820.61 μmol) was added, and the reaction mixture was stirred for 4 hours. The reaction mixture was partitioned between ethyl acetate and sodium bicarbonate (aqueous, aqueous). The organic layer was washed with brine, dried with sodium sulfate, filtered and evaporated under reduced pressure. The crude residue was purified by silica gel chromatography (24 g column, 0% to 20% methanol in dichloromethane). Pure fractions were evaporated to afford tert-butyl 4-[4-[7-fluoro-2-[1-[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]phenyl]piperazine-1-carboxylate (315 mg, 419.54 μmol, 61.35% yield). LCMS (ESI+): 676.2 (M+H).

Step 11: 2-[(6R)-6-fluoro-6,7-dihydro-5H-pyrrolo[1,2-c]imidazol-1-yl]-2-[4-fluoro-1-oxo-6-(4-piperazin-1-ylphenyl)isoindolin-2-yl]-N-thiazol-2-yl-acetamide; hydrochloride Step 11: (2RS)-2-[(6R)-6-Fluoro-6,7-dihydro-5H-pyrrolo[1,2-c]imidazol-1-yl]-2-[4-fluoro-1-oxo-6-(4-piperazin-1-ylphenyl)isoindolin-2-yl]-N-thiazol-2-yl-acetamide hydrochloride salt

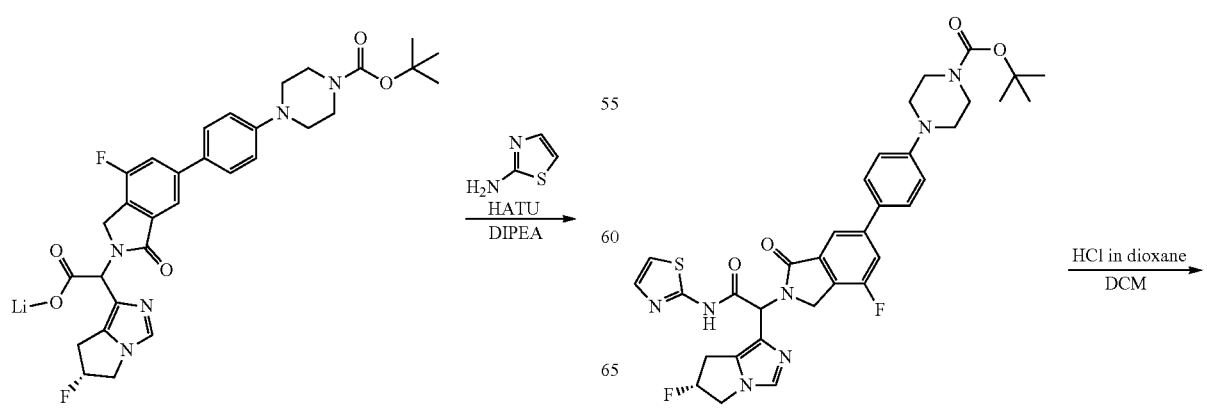

751
-continued

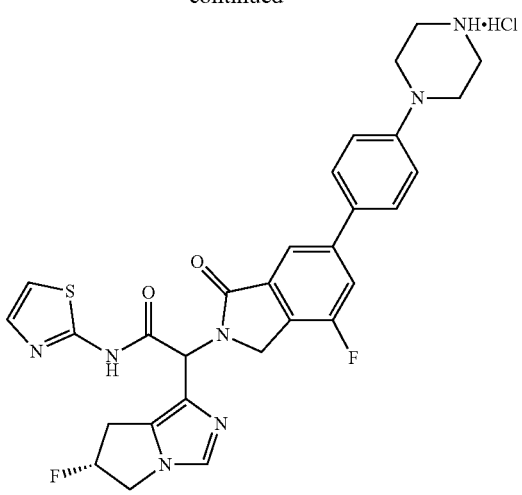

To a solution of tert-butyl 4-[4-[7-fluoro-2-[(1RS)-1-[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]phenyl]piperazine-1-carboxylate (25 mg, 37 μmol) in dichloromethane (0.5 ml) was added HCl 4M in dioxane (46.2 μl, 185 μmol, Eq: 5). The reaction mixture was stirred at room temperature for 3 hours. The reaction mixture was concentrated to dryness to afford crude (2RS)-2-[(6R)-6-fluoro-6,7-dihydro-5H-pyrrolo[1,2-c]imidazol-1-yl]-2-[4-fluoro-1-oxo-6-(4-piperazin-1-ylphenyl)isoindolin-2-yl]-N-thiazol-2-yl-acetamide hydrochloride salt (22.6 mg, 36.9 μmol, 99.7%) as an off-white solid. MS: m/e=576.4 ([M+H]⁺).

Step 12: 2-(4-(4-((2,6-Dioxopiperidin-3-yl)amino)phenyl)piperidin-1-yl)acetic acid hydrochloride

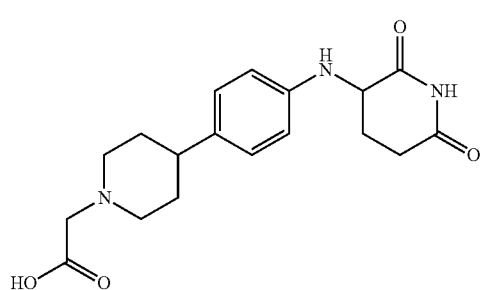 [SMILES: O=C(O)CN1CCC(c2ccc(NC3CCC(=O)NC3=O)cc2)CC1]

752

To a solution of tert-butyl 2-(4-(4-((2,6-dioxopiperidin-3-yl)amino)phenyl)piperidin-1-yl)acetate (543 mg, 1.35 mmol, Eq: 1) in ethyl acetate (8 ml) was added 4 M hydrogen chloride solution in 1,4-dioxane (6.3 g, 6 ml, 24 mmol, Eq: 17.7) at room temperature and stirring was continued over the weekend. The product was collected by filtration, washed with ethyl acetate and dried over high vacuo to afford 2-(4-(4-((2,6-dioxopiperidin-3-yl)amino)phenyl)piperidin-1-yl)acetic acid hydrochloride (537 mg, 1.27 mmol, 93.6% yield) as light red solid. MS: m/e=346.2 ([M+H]⁺).

Step 13: (2RS)-2-[6-[4-[4-[2-[4-[4-[[(3RS)-2,6-Dioxo-3-piperidyl]amino]phenyl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide

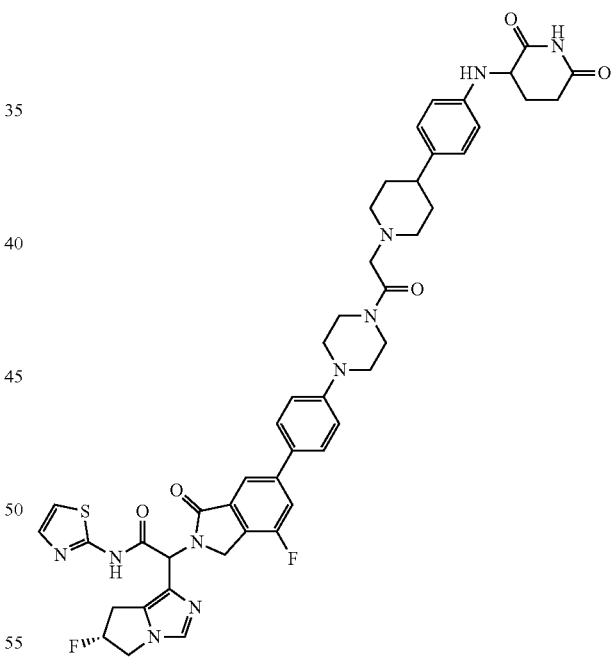

The title compound, Compound 43, was obtained as a light yellow solid, MS: m/e=903.7 ([M+H]⁺), using chemistry similar to that described in Example 1, step 6 starting from (2RS)-2-[(6R)-6-fluoro-6,7-dihydro-5H-pyrrolo[1,2-c]imidazol-1-yl]-2-[4-fluoro-1-oxo-6-(4-piperazin-1-ylphenyl)isoindolin-2-yl]-N-thiazol-2-yl-acetamide hydrochloride salt (Example 10, step 1) and 2-(4-(4-((2,6-dioxopiperidin-3-yl)amino)phenyl)piperidin-1-yl)acetic acid hydrochloride (Example 10, step 2).

Example 44
Synthesis of 2-[6-[4-[4-[2-[4-[4-[[(3S)-2,6-dioxo-3-piperidyl]amino]-2-fluoro-phenyl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide, Compound 44
Step 1: 2-[(6R)-6-fluoro-6,7-dihydro-5H-pyrrolo[1,2-c]imidazol-1-yl]-2-[4-fluoro-1-oxo-6-(4-piperazin-1-ylphenyl)isoindolin-2-yl]-N-thiazol-2-yl-acetamide hydrochloride
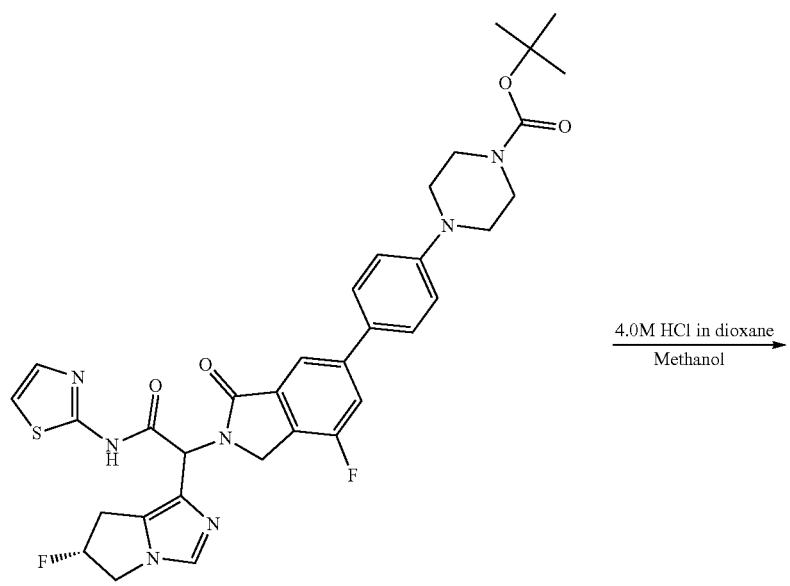
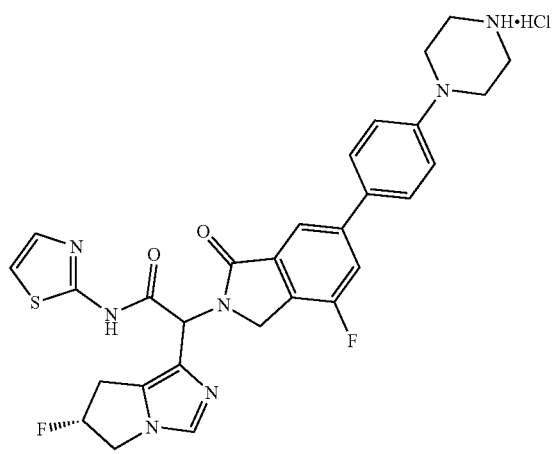

tert-Butyl 4-[4-[7-fluoro-2-[1-[[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]phenyl]piperazine-1-carboxylate (315 mg, 466.15 µmol) was dissolved in Methanol (3 mL) and Hydrogen chloride solution 4.0 M in dioxane (4 M, 5.6 mmol, 1.40 mL) was added. The reaction mixture was heated at 40° C. for 4 hours, and the reaction was complete. The volatiles were evaporated under reduce pressure. The material was submitted to high vacuum, frozen to −78° C. and thawed to afford 2-[(6R)-6-fluoro-6,7-dihydro-5H-pyrrolo[1,2-c]imidazol-1-yl]-2-[4-fluoro-1-oxo-6-(4-piperazin-1-ylphenyl)isoindolin-2-yl]-N-thiazol-2-yl-acetamide hydrochloride (237 mg, 387.20 µmol, 83.06% yield). LCMS (ESI+): 576.2 (M+H)

Step 2: 2-[6-[4-[4-[2-[4-[4-[[(3S)-2,6-dioxo-3-piperidyl]amino]-2-fluoro-phenyl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide

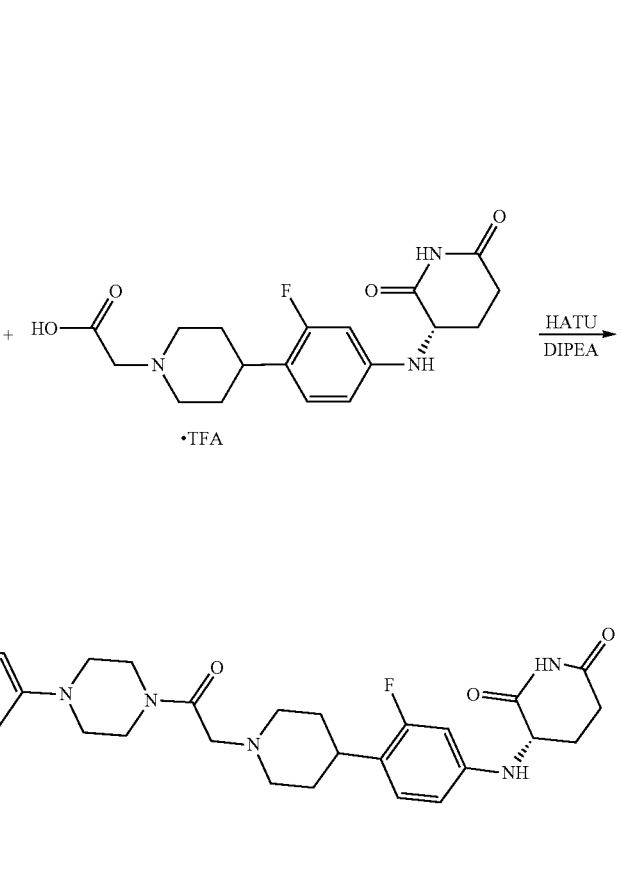

2-[(6R)-6-Fluoro-6,7-dihydro-5H-pyrrolo[1,2-c]imidazol-1-yl]-2-[4-fluoro-1-oxo-6-(4-piperazin-1-ylphenyl)isoindolin-2-yl]-N-thiazol-2-yl-acetamide; hydrochloride (63 mg, 102.93 µmol) and 2-[4-[4-[[(3S)-2,6-dioxo-3-piperidyl]amino]-2-fluoro-phenyl]-1-piperidyl]acetic acid, trifluoroacetic acid (51.59 mg, 108.07 µmol) were mixed in DMAc (0.6 mL) and cooled to 0° C. N,N-diisopropylethylamine (66.51 mg, 514.63 µmol, 89.64 µL) was added to the reaction mixture, and HATU (50.88 mg, 133.80 µmol) was added, and the reaction mixture was stirred while warming for 4 hours. The mixture was injected on a 50 g C18 column, and purified using a 0% to 100% Acetonitrile in water+0.1% TFA water elution gradient. The desired fractions were pooled and partitioned between ethyl acetate and sodium bicarbonate (aqueous, aqueous). The organic layer was washed with brine, dried with sodium sulfate, filtered and evaporated under reduced pressure. The residue was purified by silica gel chromatography (24 g column, 0% to 20% methanol in ethyl acetate). Pure fractions were evaporated; the solid material was dissolved in acetonitrile:water (1:1), frozen and lyophilized to afford Compound 44 (22 mg, 23.41 µmol, 22.74% yield). LCMS (ESI+): 921.2 (M+H). $^1$H NMR (400 MHz, DMSO-$d_6$) δ 12.56 (d, J=6.7 Hz, 1H), 10.77 (s, 1H), 7.89-7.72 (m, 2H), 7.68 (d, J=4.8 Hz, 2H), 7.49 (dd, J=3.6, 2.0 Hz, 1H), 7.26 (dd, J=3.6, 1.8 Hz, 1H), 7.08 (d, J=8.5 Hz, 2H), 6.98 (t, J=8.8 Hz, 1H), 6.56-6.31 (m, 2H), 6.17 (d, J=5.1 Hz, 1H), 5.99 (d, J=7.7 Hz, 1H), 5.82 (d, J=51.1 Hz, 1H), 4.82 (dd, J=17.6, 6.0 Hz, 1H), 4.45-4.16 (m, 4H), 4.08 (q, J=5.3 Hz, 1H), 3.75 (s, 2H), 3.62 (s, 2H), 3.26-3.18 (m, 2H), 3.19-3.09 (m, 3H), 3.01-2.83 (m, 2H), 2.82-2.52 (m, 2H), 2.26-2.01 (m, 4H), 1.85 (qd, J=12.1, 4.6 Hz, 1H), 1.65 (m, 4H).

Example 45

Synthesis of 2-[6-[4-[4-[2-[4-[3-(2,4-dioxohexahydropyrimidin-1-yl)-1-methyl-indazol-6-yl]-1-piperidyl]acetyl]piperazin-1-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide, Compound 45

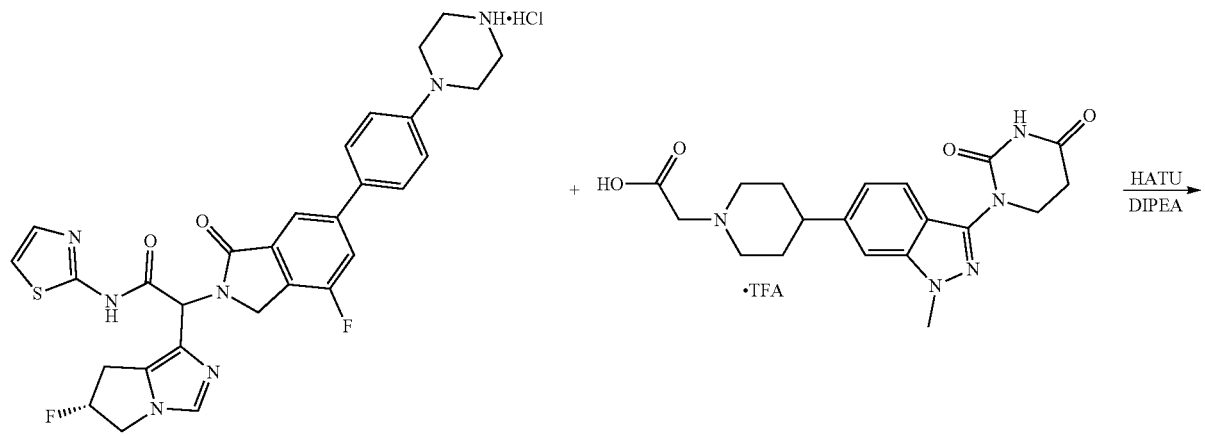

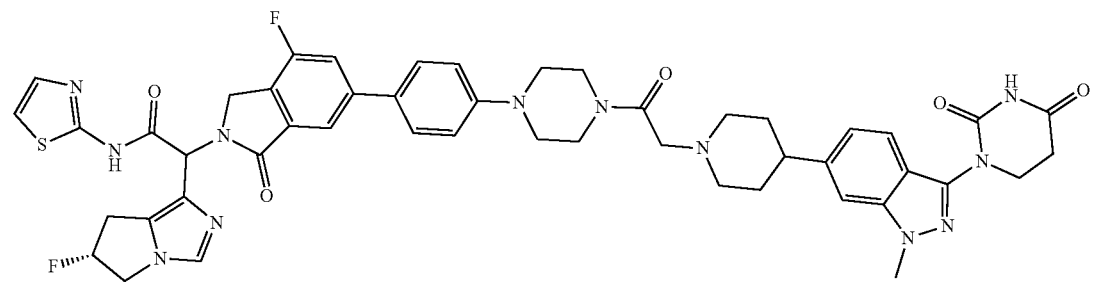

2-[(6R)-6-Fluoro-6,7-dihydro-5H-pyrrolo[1,2-c]imidazol-1-yl]-2-[4-fluoro-1-oxo-6-(4-piperazin-1-ylphenyl)isoindolin-2-yl]-N-thiazol-2-yl-acetamide hydrochloride (120 mg, 196.05 μmol) and 2-[4-[3-(2,4-dioxohexahydropyrimidin-1-yl)-1-methyl-3a,7a-dihydroindazol-6-yl]-1-piperidyl]acetic acid, trifluoroacetic acid salt (83.10 mg, 196.05 μmol) were mixed in DMF (1.2 mL). The reaction mixture was cooled to 0° C. N,N-diisopropylethylamine (170.74 μL, 980.24 μmol) was added to the reaction mixture, and HATU (96.91 mg, 254.86 μmol) was added. The reaction mixture was stirred while warming for 4 h. The mixture was injected on a 50 g C18 column and purified using a 0% to 100% acetonitrile (+0.1% TFA) in water (+0.1% TFA) elution gradient. The desired fractions were pooled and partitioned between ethyl acetate and aqueous saturated sodium bicarbonate. The organic layer was washed with brine, dried with sodium sulfate, filtered and evaporated under reduced pressure. The crude residue was purified by silica gel chromatography (24 g column, 0% to 20% methanol in ethyl acetate). The pure fractions were evaporated to afford Compound 45 (49 mg, 50.92 μmol, 25.97% yield). LCMS (ESI+): 943.3 (M+H$^+$), LCMS (ESI−): 941.1 (M−H), $^1$H NMR (400 MHz, DMSO-d$_6$) δ 12.55 (s, 1H), 10.53 (s, 1H), 7.99-7.61 (m, 5H), 7.56 (d, J=8.5 Hz, 1H), 7.51-7.45 (m, 1H), 7.44 (s, 1H), 7.22 (s, 1H), 7.09 (d, J=8.8 Hz, 2H), 7.04 (dd, J=8.6, 1.3 Hz, 1H), 6.15 (s, 1H), 5.95-5.66 (m, 1H), 4.86 (d, J=17.6 Hz, 1H), 4.47-4.07 (m, 3H), 3.97 (s, 3H), 3.90 (t, J=6.7 Hz, 2H), 3.78 (s, 2H), 3.64 (s, 2H), 3.29-3.08 (m, 4H), 3.13-2.84 (m, 3H), 2.75 (t, J=6.7 Hz, 2H), 2.72-2.55 (m, 1H), 2.18 (t, J=10.9 Hz, 2H), 1.97-1.55 (m, 4H).

Example 46

Synthesis of 2-(6,7-dihydro-5H-pyrrolo[1,2-c]imidazol-1-yl)-2-(6-(4-(2-(2-(4-(4-(((S)-2,6-dioxopiperidin-3-yl)amino)-2-fluorophenyl)piperidin-1-yl)acetyl)-2,7-diazaspiro[3.5]nonan-7-yl)phenyl)-4-fluoro-1-oxoisoindolin-2-yl)-N-(thiazol-2-yl)acetamide, Compound 46

Step 1: tert-butyl 7-(4-bromophenyl)-2,7-diazaspiro[3.5]nonane-2-carboxylate

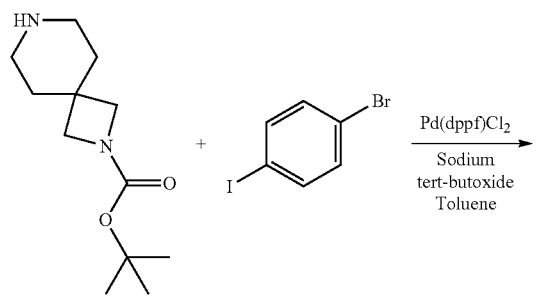

Step 2: tert-butyl 7-[4-(4,4,5,5-tetramethyl-1,3,2-dioxaborolan-2-yl)phenyl]-2,7-diazaspiro[3.5]nonane-2-carboxylate

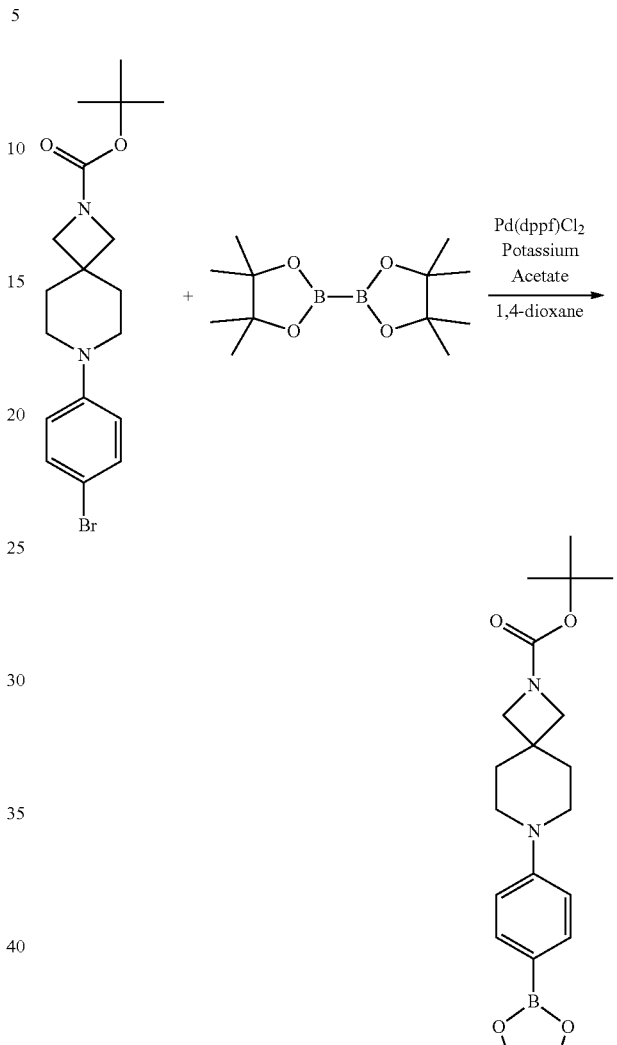

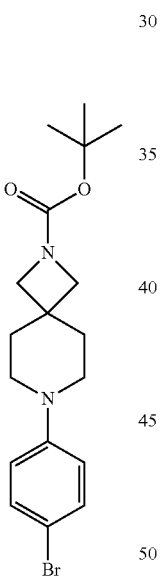

1-Bromo-4-iodo-benzene (1.25 g, 4.40 mmol) and tert-butyl 2,7-diazaspiro[3.5]nonane-2-carboxylate (453 mg, 2.00 mmol) were mixed in toluene (10 mL). Sodium tert-butoxide (423.19 mg, 4.40 mmol) and 1,1'-Bis(Diphenylphosphino)ferrocenepalladium (II) dichloride (146.46 mg, 200.16 μmol) were added, and the reaction mixture was degassed with nitrogen. The reaction mixture was heated at 65° C. for 60 hours. The reaction mixture was dry packed on silica gel, and the product was purified using a 0% to 100% ethyl acetate:hexanes gradient. Pure fractions were evaporated to afford tert-butyl 7-(4-bromophenyl)-2,7-diazaspiro[3.5]nonane-2-carboxylate (452 mg, 1.19 mmol, 59.22% yield) as a white solid. LCMS (ESI+): 381.1/383.1 (M+H, Bromine pattern).

In a round bottom flask, tert-butyl 7-(4-bromophenyl)-2,7-diazaspiro[3.5]nonane-2-carboxylate (452.00 mg, 1.19 mmol) and 4,4,5,5-tetramethyl-2-(4,4,5,5-tetramethyl-1,3,2-dioxaborolan-2-yl)-1,3,2-dioxaborolane (391.32 mg, 1.54 mmol) were mixed in 1,4-dioxane (6 mL). The reaction mixture was degassed with a stream of nitrogen, and Potassium Acetate (349.01 mg, 3.56 mmol, 222.30 μL) and 1,1'-Bis(Diphenylphosphino)ferrocenepalladium (II) dichloride (48.40 mg, 59.27 μmol) were added. The reaction mixture was placed under a nitrogen atmosphere and heated under stirring for 16 hours at 80° C. The reaction mixture was cooled, evaporated under reduced pressure, and the crude residue was purified by silica gel column chromatography (5% to 50% ethyl acetate in hexanes eluent gradient). Desired fractions were evaporated to afford tert-butyl 7-[4-(4,4,5,5-tetramethyl-1,3,2-dioxaborolan-2-yl)phenyl]-2,7-diazaspiro[3.5]nonane-2-carboxylate (321 mg, 749.35 μmol, 63.22% yield) as a white solid. LCMS (ESI+): 428.4/429.4/430.4 (M+H, Br pattern).

Step 3: tert-butyl 7-(4-(2-(1-(6,7-dihydro-5H-pyrrolo[1,2-c]imidazol-1-yl)-2-ethoxy-2-oxoethyl)-7-fluoro-3-oxoisoindolin-5-yl)phenyl)-2,7-diazaspiro[3.5]nonane-2-carboxylate
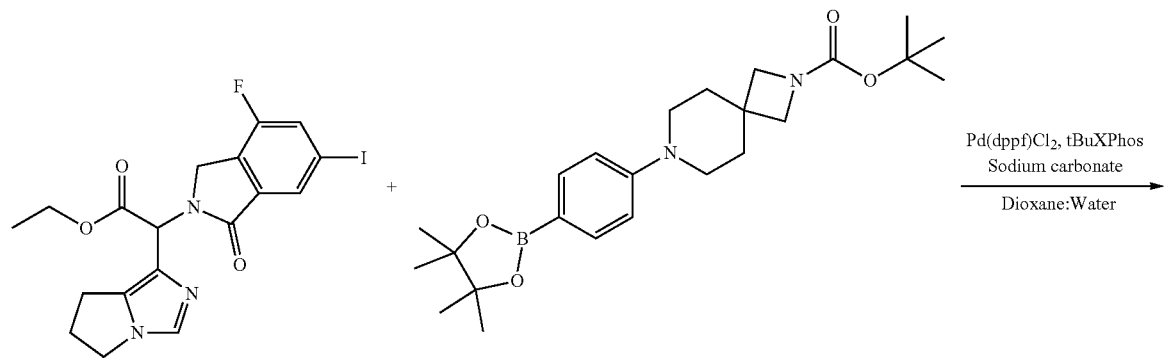
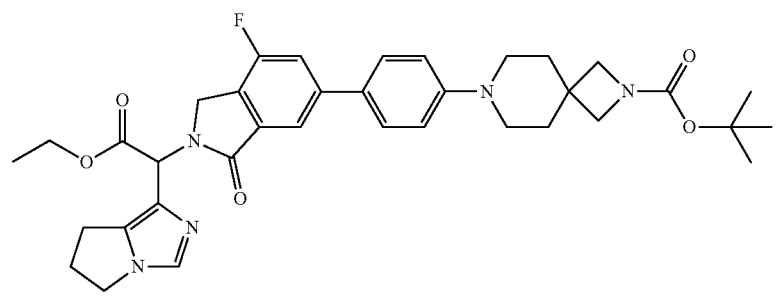

763 tert-Butyl 7-(4-(2-(1-(6,7-dihydro-5H-pyrrolo[1,2-c]imidazol-1-yl)-2-ethoxy-2-oxoethyl)-7-fluoro-3-oxoisoindolin-5-yl)phenyl)-2,7-diazaspiro[3.5]nonane-2-carboxylate was obtained from ethyl 2-(6,7-dihydro-5H-pyrrolo[1,2-c]imidazol-1-yl)-2-(4-fluoro-6-iodo-1-oxoisoindolin-2-yl)acetate using a procedure similar to Example 5, step 1, using tert-butyl 7-[4-(4,4,5,5-tetramethyl-1,3,2-dioxaborolan-2-yl)phenyl]-2,7-diazaspiro[3.5]nonane-2-carboxylate instead of tert-butyl 4-[4-(4,4,5,5-tetramethyl-1,3,2-dioxaborolan-2-yl)phenyl]piperazine-1-carboxylate. LCMS (ESI+): 644.2 (M+H⁺)

Step 4: Lithium 2-(6-(4-(2-(tert-butoxycarbonyl)-2,7-diazaspiro[3.5]nonan-7-yl)phenyl)-4-fluoro-1-oxoisoindolin-2-yl)-2-(6,7-dihydro-5H-pyrrolo[1,2-c]imidazol-1-yl)acetate

764

(6,7-dihydro-5H-pyrrolo[1,2-c]imidazol-1-yl)acetate was obtained from tert-butyl 7-(4-(2-(1-(6,7-dihydro-5H-pyrrolo[1,2-c]imidazol-1-yl)-2-ethoxy-2-oxoethyl)-7-fluoro-3-oxoisoindolin-5-yl)phenyl)-2,7-diazaspiro[3.5]nonane-2-carboxylate using a procedure similar to Example 5, Step 2. LCMS (ESI+): 616.2 (M+H).

Step 5: tert-butyl 7-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenyl)-2,7-diazaspiro[3.5]nonane-2-carboxylate

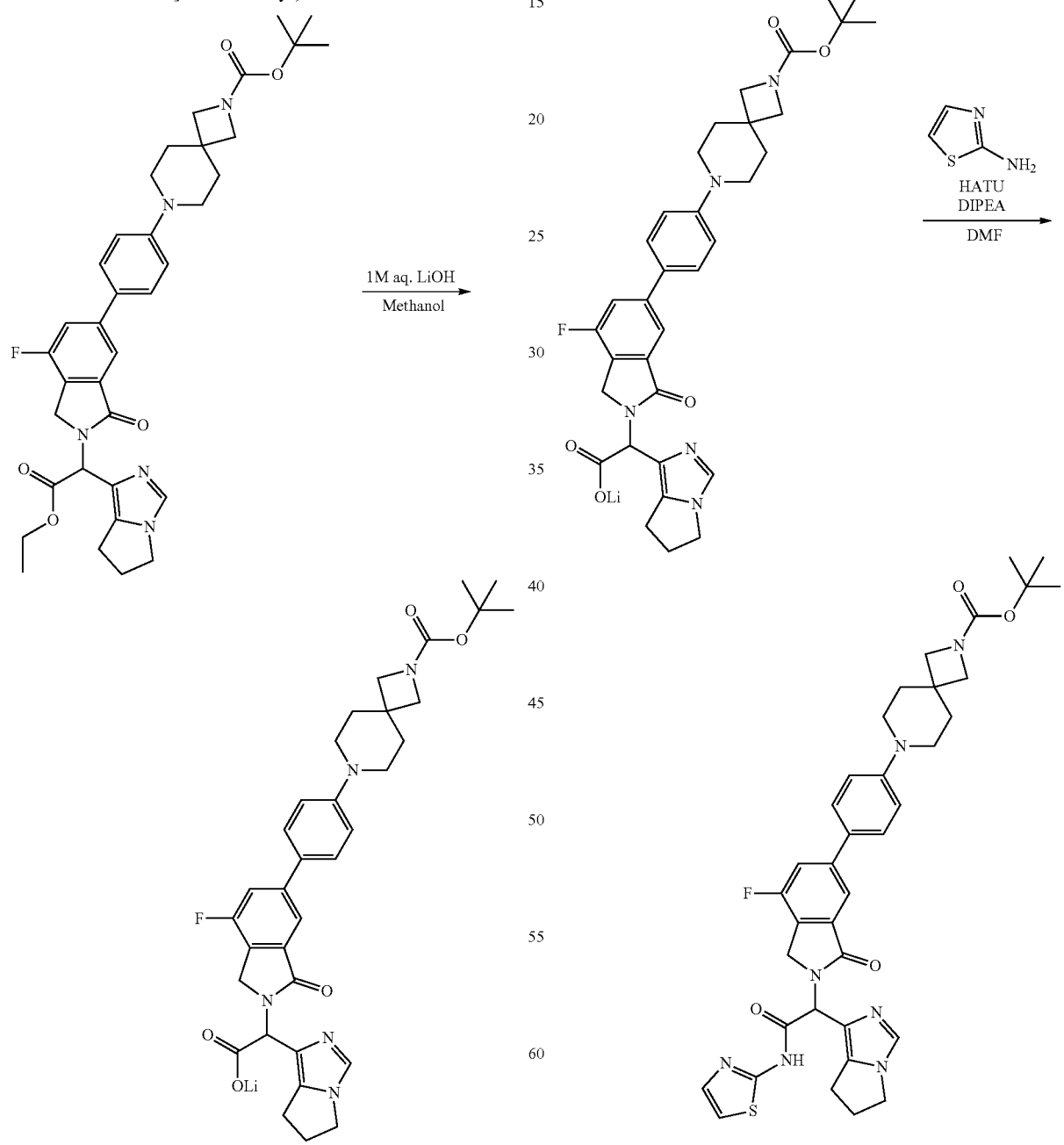

Lithium 2-(6-(4-(2-(tert-butoxycarbonyl)-2,7-diazaspiro[3.5]nonan-7-yl)phenyl)-4-fluoro-1-oxoisoindolin-2-yl)-2- tert-Butyl 7-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenyl)-2,7-diazaspiro[3.5]nonane-2-

765 carboxylate was obtained from lithium 2-(6-(4-(2-(tert-butoxycarbonyl)-2,7-diazaspiro[3.5]nonan-7-yl)phenyl)-4-fluoro-1-oxoisoindolin-2-yl)-2-(6,7-dihydro-5H-pyrrolo[1,2-c]imidazol-1-yl)acetate using a procedure similar to Example 5, Step 3. LCMS (ESI+): 698.3 (M+H).

Step 6: 2-(6-(4-(2,7-diazaspiro[3.5]nonan-7-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide hydrochloride

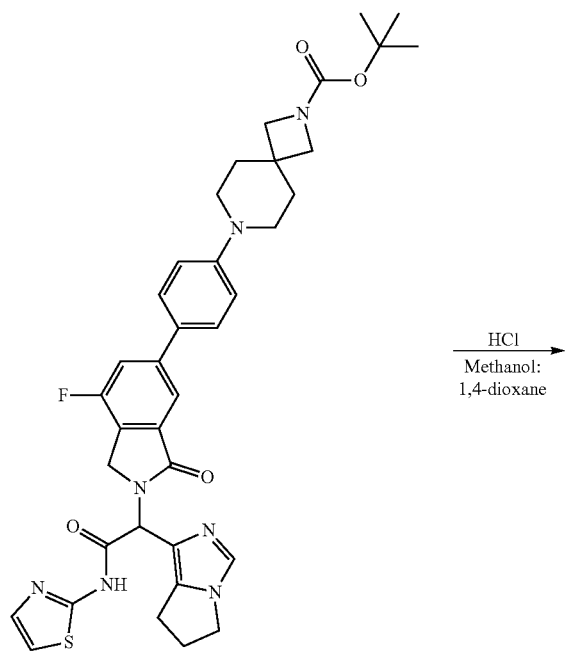

766

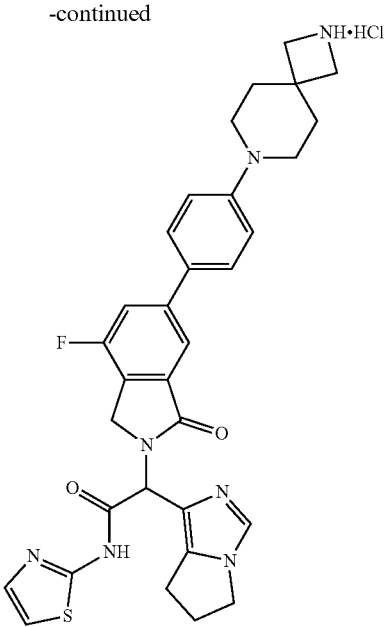

2-(6-(4-(2,7-Diazaspiro[3.5]nonan-7-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide hydrochloride was obtained using a procedure similar to the one used for Example 5, step 4. LCMS (ESI+): 598.2 (M+H$^+$)

Step 7: 2-(6,7-dihydro-5H-pyrrolo[1,2-c]imidazol-1-yl)-2-(6-(4-(2-(2-(4-(4-(((S)-2,6-dioxopiperidin-3-yl)amino)-2-fluorophenyl)piperidin-1-yl)acetyl)-2,7-diazaspiro[3.5]nonan-7-yl)phenyl)-4-fluoro-1-oxoisoindolin-2-yl)-N-(thiazol-2-yl)acetamide

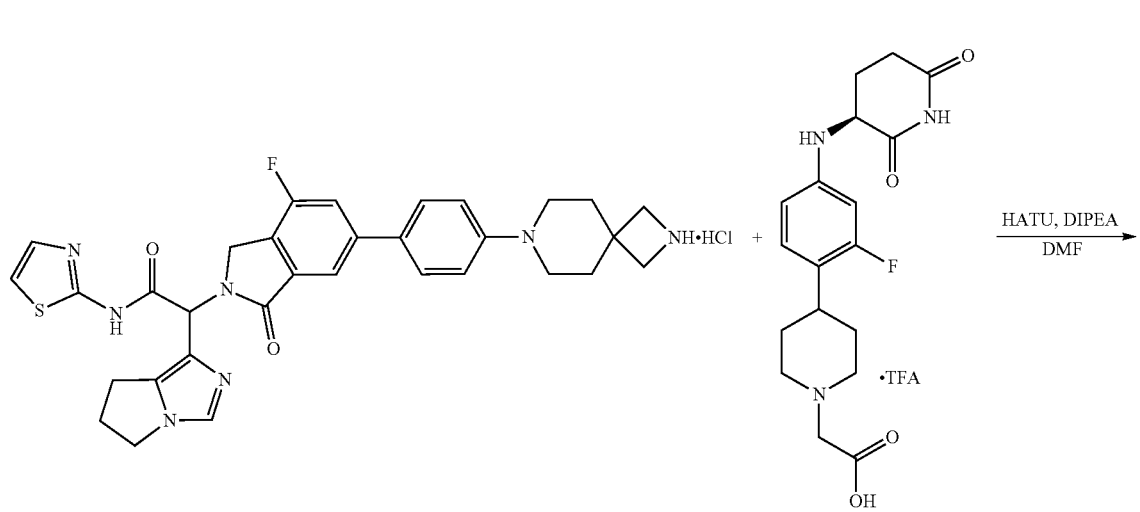

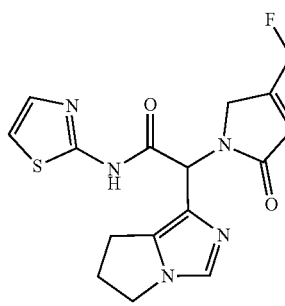

2-[6-[4-(2,7-Diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide hydrochloride (0.117 g, 184.49 μmol) and 2-[4-[4-[[(3S)-2,6-dioxo-3-piperidyl]amino]-2-fluoro-phenyl]-1-piperidyl]acetic acid (77.10 mg, 212.17 μmol) were mixed in DMF (2 mL) and cooled to 0° C. N,N-Diisopropylethylamine (119.22 mg, 922.47 μmol, 160.67 μL) was added to the reaction mixture, and HATU (98.21 mg, 258.29 μmol) was added, and the reaction mixture was stirred for 4 hours. The mixture was injected on a 50 g C18 column and purified using a 0% to 100% Acetonitrile (+0.1% TFA) in water (+0.1% TFA) elution gradient. The pure fractions were pooled and partitioned between ethyl acetate and sodium bicarbonate (aqueous, aqueous). The organic layer was washed with brine, dried with sodium sulfate, filtered and evaporated under reduced pressure. The crude residue was purified by silica gel chromatography (24 g column, 0% to 20% methanol in ethyl acetate). Pure fractions were evaporated; the solid material was dissolved in acetonitrile:water (1:1), frozen and lyophilized to afford Compound 46 (36 mg, 21% yield). LCMS (ESI+): 943.2 (M+H), $^1$H NMR (400 MHz, DMSO-d$_6$) δ 12.52 (s, 1H), 10.78 (s, 1H), 7.77 (s, 1H), 7.73 (dd, J=10.7, 1.4 Hz, 1H), 7.66 (d, J=8.6 Hz, 2H), 7.61 (s, 1H), 7.49 (d, J=3.5 Hz, 1H), 7.26 (d, J=3.6 Hz, 1H), 7.06 (d, J=8.7 Hz, 2H), 7.00 (t, J=8.8 Hz, 1H), 6.54-6.32 (m, 2H), 6.16 (s, 1H), 6.00 (d, J=7.7 Hz, 1H), 4.81 (d, J=17.7 Hz, 1H), 4.42-4.27 (m, 1H), 4.23 (d, J=17.7 Hz, 1H), 3.98 (s, 3H), 3.63 (s, 2H), 3.25 (s, 5H), 3.01 (s, 2H), 2.92 (d, J=10.8 Hz, 2H), 2.84-2.62 (m, 2H), 2.63-2.53 (m, 2H), 2.09 (d, J=11.6 Hz, 4H), 1.95-1.72 (m, 5H), 1.72-1.50 (m, 4H).

Example 47

Synthesis of 2-(6,7-dihydro-5H-pyrrolo[1,2-c]imidazol-1-yl)-2-[6-[4-[2-[2-[4-[4-[(2,6-dioxo-3-piperidyl)amino]phenyl]-1-piperidyl]acetyl]-2,6-diazaspiro[3.3]heptan-6-yl]phenyl]-4-fluoro-1-oxo-isoindolin-2-yl]-N-thiazol-2-yl-acetamide, Compound 47

Step 1: tert-butyl 6-(4-bromophenyl)-2,6-diazaspiro[3.3]heptane-2-carboxylate

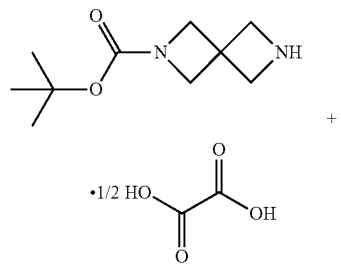

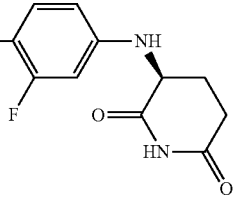

1-Bromo-4-iodo-benzene (9.06 g, 32.01 mmol) and tert-butyl 2,6-diazaspiro[3.3]heptane-2-carboxylate hemioxalate (6.49 g, 13.34 mmol) were suspended in toluene (48 mL), and the reaction mixture was degassed with a nitrogen stream. Sodium tert-butoxide (12.82 g, 133.39 mmol) was added, and the reaction mixture was sonicated, under a nitrogen atmosphere, until the solids were mostly dissolved and the solution was homogeneous. 1,1'-Bis(Diphenylphosphino)ferrocenepalladium (II) dichloride (1.95 g, 2.67 mmol) was added, and the reaction mixture was heated under nitrogen at 90° C. for 16 hours. The solution was filtered through celite, washing with ethyl acetate and the filtrate was evaporated under reduced pressure. The crude residue was purified by silica gel chromatography using a 0% to 50% Ethyl acetate in hexanes eluent gradient to afford tert-butyl 6-(4-bromophenyl)-2,6-diazaspiro[3.3]heptane-2-carboxylate (6.25 g, 17.69 mmol, 66.32% yield). LCMS (ESI+): 353/355 (M+H, Br pattern), $^1$H-NMR (400 MHz, CDCl$_3$): 7.31 (d, J=8.4 Hz, 2H), 6.34 (d, J=8.4 Hz, 2H), 4.11 (s, 4H), 3.96 (s, 4H), 1.47 (s, 9H).

Step 2: tert-butyl 6-[4-(4,4,5,5-tetramethyl-1,3,2-dioxaborolan-2-yl)phenyl]-2,6-diazaspiro[3.3]heptane-2-carboxylate

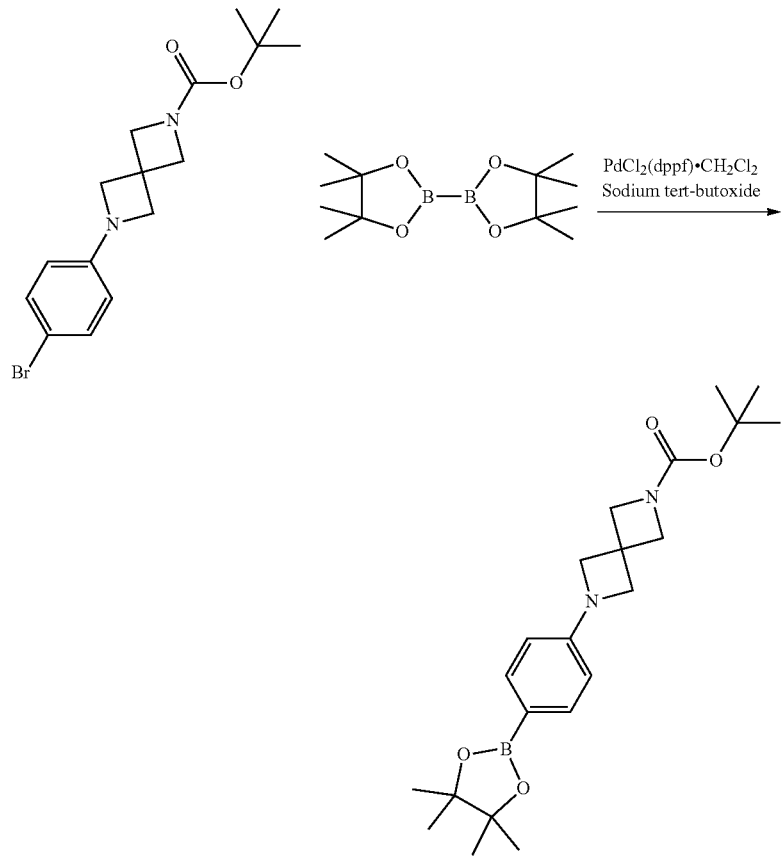

To a solution of tert-butyl 6-(4-bromophenyl)-2,6-diazaspiro[3.3]heptane-2-carboxylate (6.2 g, 17.55 mmol), 4,4,5,5-tetramethyl-2-(4,4,5,5-tetramethyl-1,3,2-dioxaborolan-2-yl)-1,3,2-dioxaborolane (5.79 g, 22.82 mmol), and Potassium Acetate (5.17 g, 52.65 mmol, 3.29 mL) in 1,4-dioxane (48 mL) was added 1,1'-Bis(Diphenylphosphino)ferrocenepalladium (II) dichloride dichloromethane (716.65 mg, 877.56 μmol) and the mixture was stirred at 80° C. for 16 hours. The mixture was cooled and filtered through a pad of celite, then was concentrated under reduced pressure. The crude residue was purified by silica gel chromatography (0% to 50% Ethyl acetate in hexanes) to give tert-butyl 6-[4-(4,5,5-tetramethyl-1,3,2-dioxaborolan-2-yl)phenyl]-2,6-diazaspiro[3.3]heptane-2-carboxylate (6.32 g, 15.79 mmol, 89.95% yield). LCMS (ESI+): MS (ESI+): 400.3/401.3/402.3 (M+H, Boron pattern); 1H NMR (400 MHz, DMSO-d6) δ 7.48 (d, J=8.3 Hz, 2H), 6.38 (d, J=8.3 Hz, 2H), 4.03 (s, 4H), 3.96 (s, 4H), 1.39 (s, 9H), 1.26 (s, 12H).

Step 3: tert-butyl 6-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]-2,6-diazaspiro[3.3]heptane-2-carboxylate

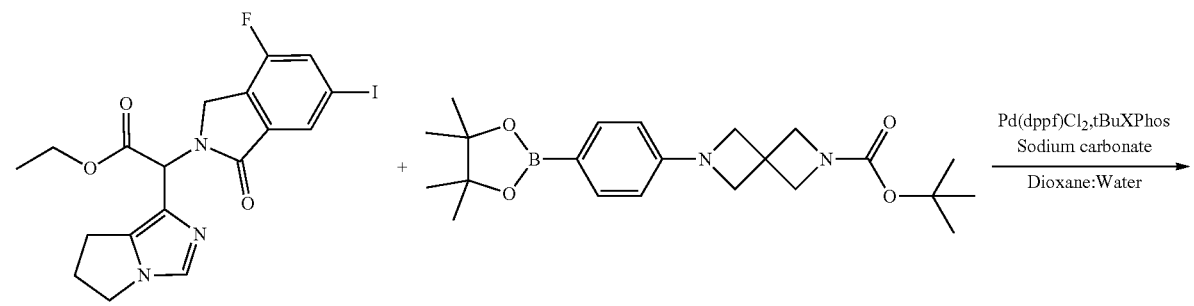

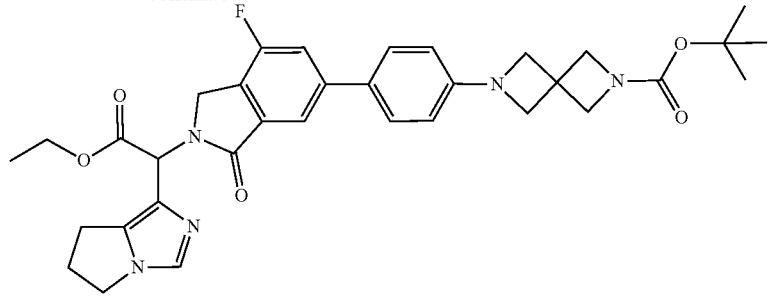

Ethyl 2-(6,7-dihydro-5H-pyrrolo[1,2-c]imidazol-1-yl)-2-(4-fluoro-6-iodo-1-oxo-isoindolin-2-yl)acetate (1.57 g, 3.35 mmol) and tert-butyl 6-[4-(4,4,5,5-tetramethyl-1,3,2-dioxaborolan-2-yl)phenyl]-2,6-diazaspiro[3.3]heptane-2-carboxylate (1.74 g, 4.35 mmol) were dissolved in dioxane (10 mL) and tBuXPhos (422.40 mg, 669.16 µmol) was added, followed by Sodium carbonate (780.16 mg, 7.36 mmol) dissolved in Water (2.5 mL). The mixture was degassed with argon and 1,1'-Bis(Diphenylphosphino)ferrocenepalladium (II) dichloride (293.69 mg, 401.49 µmol) was added. The reaction was sealed and heated at 80° C. on a heating block for 4 hours. The mixture was concentrated and purified by flash column chromatography on silica gel (0-100% ethyl acetate in hexane) to give tert-butyl 6-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]-2,6-diazaspiro[3.3]heptane-2-carboxylate (1.8 g, 2.92 mmol, 87.38% yield) as a yellow oil. LCMS (ESI+): 616.2 (M+H)

Step 4: [2-[6-[4-(2-tert-butoxycarbonyl-2,6-diazaspiro[3.3]heptan-6-yl)phenyl]-4-fluoro-1-oxo-isoindolin-2-yl]-2-(6,7-dihydro-5H-pyrrolo[1,2-c]imidazol-1-yl)acetyl]oxylithium

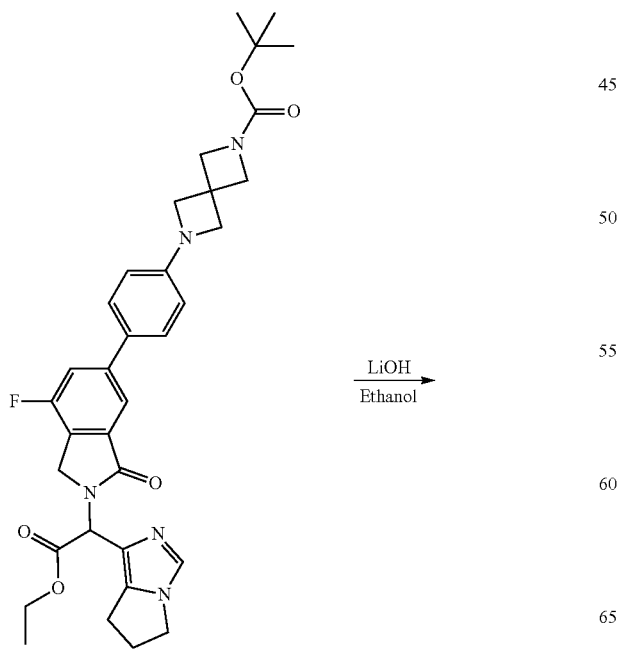

LiOH / Ethanol

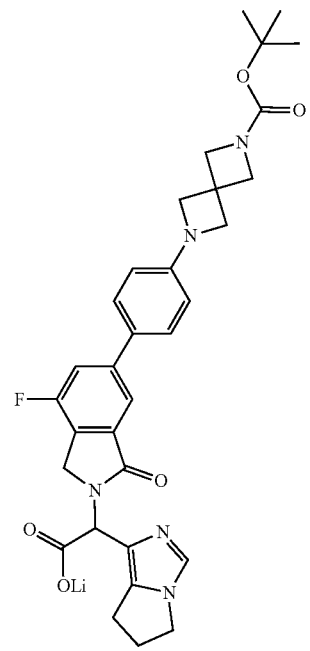

[2-[6-[4-(2-tert-butoxycarbonyl-2,6-diazaspiro[3.3]heptan-6-yl)phenyl]-4-fluoro-1-oxo-isoindolin-2-yl]-2-(6,7-dihydro-5H-pyrrolo[1,2-c]imidazol-1-yl)acetyl]oxylithium was prepared in quantitative yield in a way similar to Example 5, step 2). LCMS (ESI+): 588.3 (M+H)

Step 5: tert-butyl 6-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,6-diazaspiro[3.3]heptane-2-carboxylate

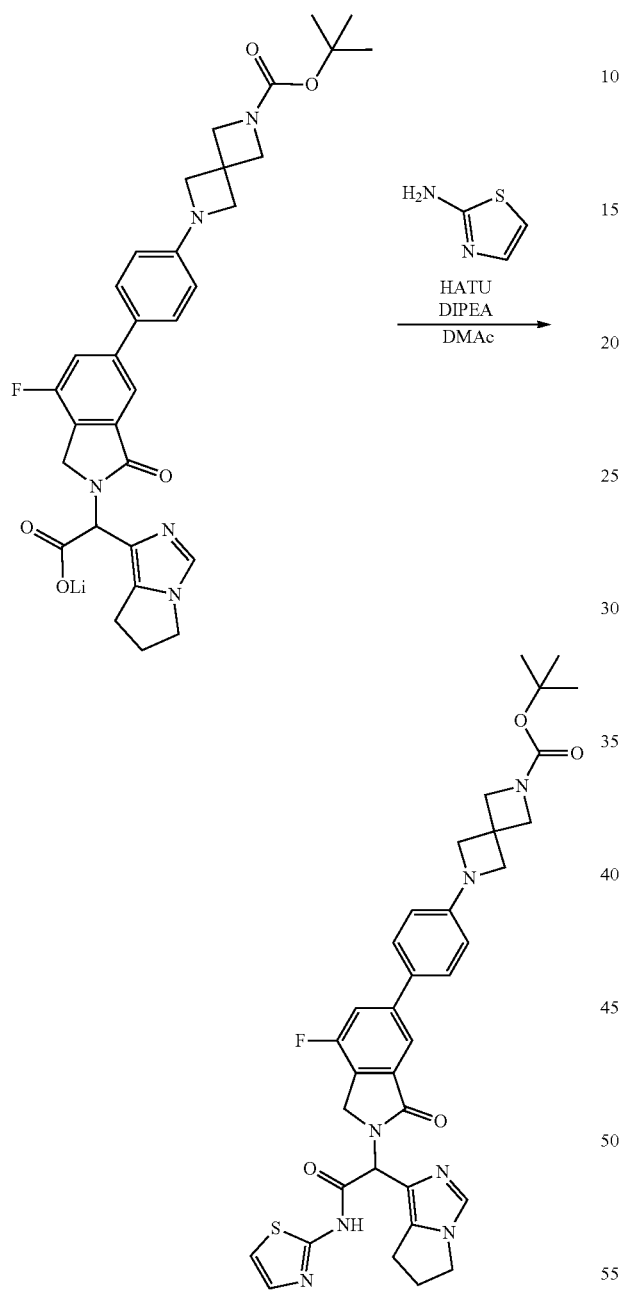

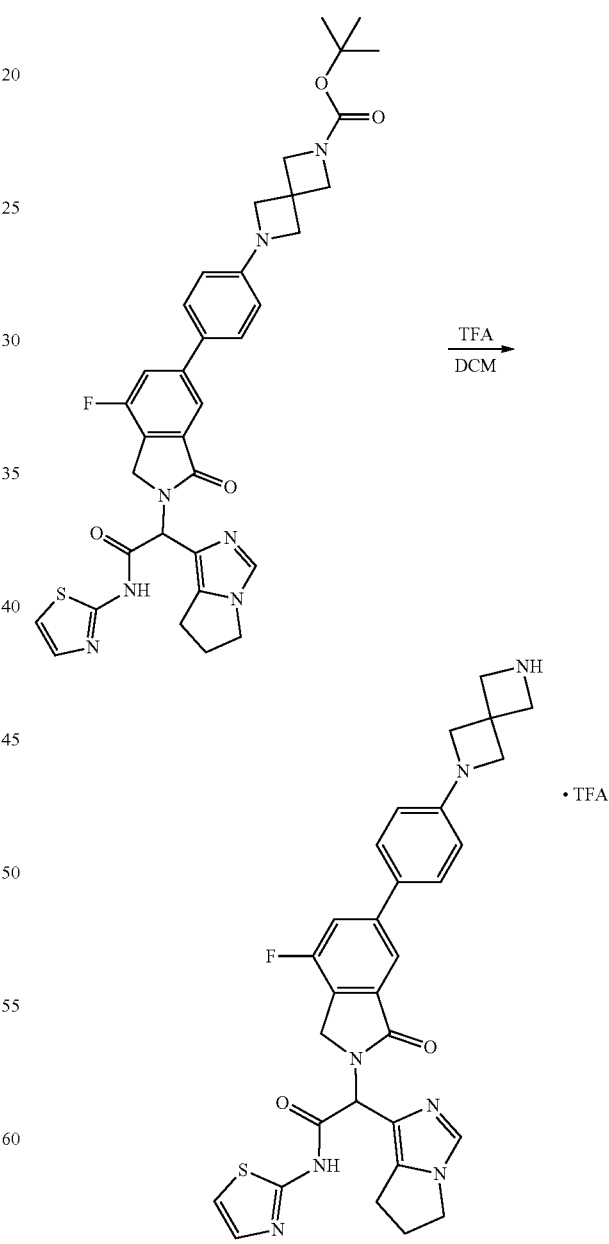

Thiazol-2-amine (106.29 mg, 1.06 mmol) and [2-[6-[4-(2-tert-butoxycarbonyl-2,6-diazaspiro[3.3]heptan-6-yl)phenyl]-4-fluoro-1-oxo-isoindolin-2-yl]-2-(6,7-dihydro-5H-pyrrolo[1,2-c]imidazol-1-yl)acetyl]oxylithium (600 mg, 1.01 mmol) were mixed in DMAc (5 mL) and cooled to 0° C. N,N-Diisopropylethylamine (522.56 mg, 4.04 mmol, 704.26 µL) was added to the reaction mixture, and HATU (499.65 mg, 1.31 mmol) was added, and the reaction mixture was stirred for 30 min at 0° C. The reaction mixture was warmed to 20° C. and stirred for 2 hours. The reaction mixture was diluted with saturated aqueous NaHCO₃ and extracted with ethyl acetate. The organic layers were washed with water and brine, dried over Na₂SO₄, filtered and concentrated in vacuo. The crude material was purified by silica gel chromatography (0-20% methanol in dichloromethane) to afford tert-butyl 6-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,6-diazaspiro[3.3]heptane-2-carboxylate (630 mg, 940.63 µmol, 93.06% yield). LCMS (ESI+): 670.3 (M+H).

Step 6: 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt tert-Butyl 6-[4-[2-[1-(6,7-dihydro-5H-pyrrolo[1,2-c]imidazol-1-yl)-2-oxo-2-(thiazol-2-ylamino)ethyl]-7-fluoro-3- oxo-isoindolin-5-yl]phenyl]-2,6-diazaspiro[3.3]heptane-2-carboxylate (86 mg, 128.40 μmol) was dissolved in dichloromethane (2 mL) and Trifluoroacetic acid (585.64 mg, 5.14 mmol, 395.70 μL) was added. The reaction mixture was stirred for 2 h. The reaction mixture was added dropwise under stirring to MTBE (10 mL). The precipitate was allowed to settle, and the supernatant was decanted and discarded. The resulting solid was submitted to high vacuum to afford 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (107 mg, 134.14 μmol, quantitative yield). LCMS (ESI+): 564.2 (M+H)

Step 7: 2-(6,7-dihydro-5H-pyrrolo[1,2-c]imidazol-1-yl)-2-[6-[4-[2-[2-[4-[4-[(2,6-dioxo-3-piperidyl)amino]phenyl]-1-piperidyl]acetyl]-2,6-diazaspiro[3.3]heptan-6-yl]phenyl]-4-fluoro-1-oxo-isoindolin-2-yl]-N-thiazol-2-yl-acetamide

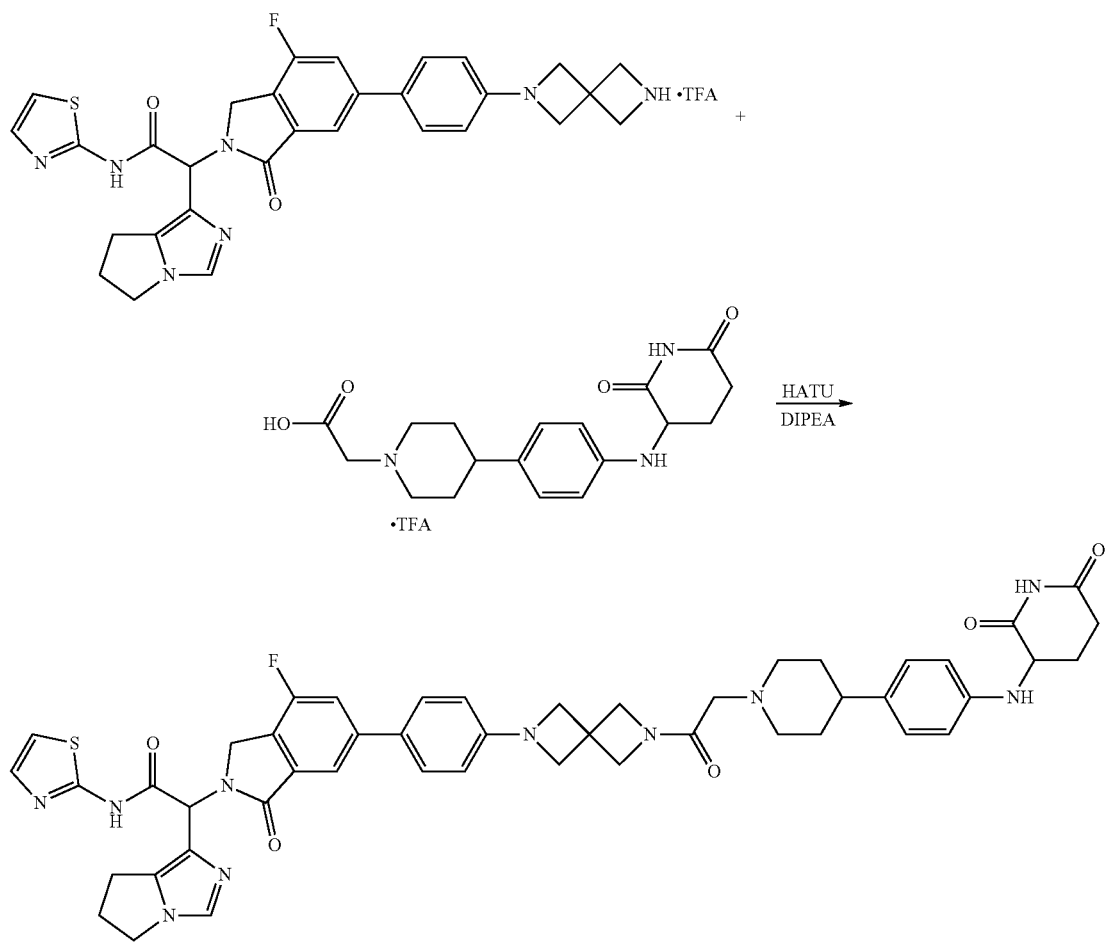

2-[6-[4-(2,6-Diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (113 mg, 165.28 μmol) and 2-[4-[4-[(2,6-dioxo-3-piperidyl)amino]phenyl]-1-piperidyl]acetic acid, trifluoroacetic acid (91.12 mg, 198.34 μmol) were mixed in DMF and cooled to 0° C. N,N-Diisopropylethylamine (106.81 mg, 826.42 μmol, 143.94 μL) was added to the reaction mixture, and HATU (81.70 mg, 214.87 μmol) was added, and the reaction mixture was stirred for 1 h at 0° C. The reaction mixture was acidified with 4-5 drops of TFA, and injected directly on a RP C18 column (50 g C18) for purification (5% to 100% acetonitrile (+0.1% TFA) in water (+0.1% TFA) over 12 minutes). The desired fractions were neutralized with aqueous NaHCO₃ (ca. 60 mL) and extracted with 1:4 isopropanol:chloroform mixture. The organic layer was dried over Na₂SO₄, filtered, and evaporated under reduced pressure to afford a solid. The solid was dissolved in dichloromethane, and purified by silica gel chromatography (0% to 20% methanol in dichloromethane). The desired fractions were evaporated under reduced pressure, then dissolved in dichloromethane, transferred to a 8 mL vial, and evaporated under reduced pressure. 4 mL water+4 mL acetonitrile were added, and the mixture was thoroughly sonicated, vortexed and sonicated again. The suspension was frozen and lyophilized to afford Compound 47 (56 mg, 59.31 μmol, 35.88% yield). LCMS (ESI+): 897.4 (M+H), LCMS (ESI−): 895.3 (M−H), $^1$H NMR (400 MHz, DMSO-$d_6$) δ 12.44 (s, 1H), 10.69 (s, 1H), 7.67 (s, 1H), 7.63 (d, J=10.7 Hz, 2H), 7.57 (d, J=8.5 Hz, 2H), 7.54 (s, 1H), 7.42 (d, J=3.5 Hz, 1H), 7.19 (d, J=3.6 Hz, 1H), 6.90 (d, J=8.2 Hz, 2H), 6.54 (d, J=8.3 Hz, 2H), 6.47 (d, J=8.3 Hz, 2H), 6.08 (s, 1H), 5.57 (d, J=7.4 Hz, 1H), 4.73 (d, J=17.7 Hz, 1H), 4.36 (s, 2H), 4.30-4.07 (m, 2H), 4.01 (s, 2H), 3.96 (s, 6H), 3.91 (m, 1H), 2.92 (s, 2H), 2.82 (m, 2H), 2.76-2.58 (m, 2H), 2.56-2.46 (m, 1H), 2.01 (m, 3H), 1.80 (m, 1H), 1.55 (m, 4H).

Example 48

Synthesis of 2-(6,7-dihydro-5H-pyrrolo[1,2-c]imidazol-1-yl)-2-[6-[4-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]phenyl]-4-fluoro-1-oxo-isoindolin-2-yl]-N-thiazol-2-yl-acetamide, Compound 48

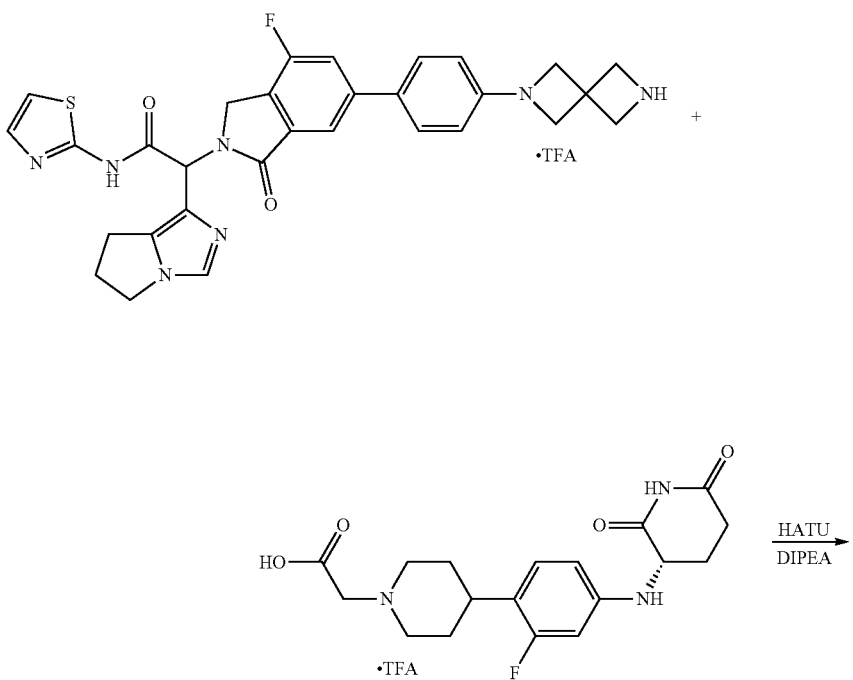

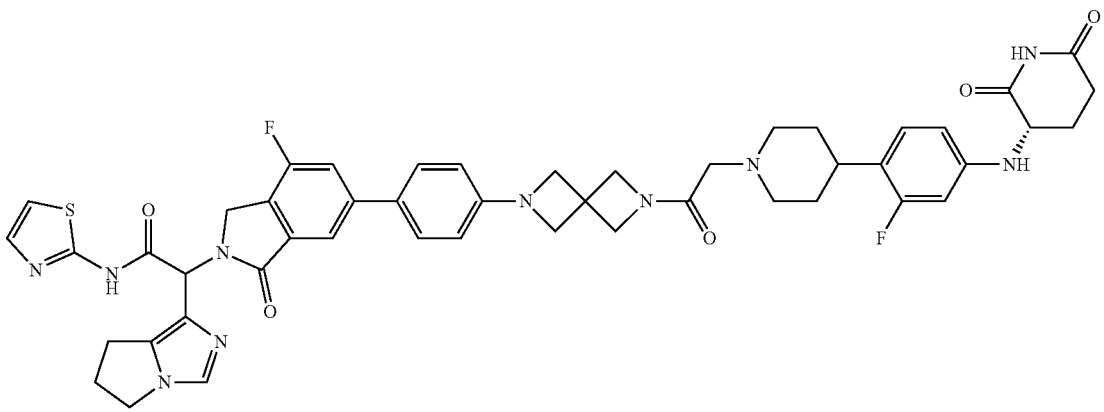

2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide trifluoroacetic acid (40 mg, 58.51 µmol) and 2-[4-[4-[[(3S)-2,6-dioxo-3-piperidyl]amino]-2-fluoro-phenyl]-1-piperidyl]acetic acid trifluoroacetic acid (33.52 mg, 70.21 µmol) were mixed in DMF and cooled to 0° C. N,N-Diisopropylethylamine (37.81 mg, 292.54 µmol, 50.95 µL) was added to the reaction mixture, and HATU (28.92 mg, 76.06 µmol) was added, and the reaction mixture was stirred for 1 h at 0° C. The reaction mixture was acidified with 4-5 drops of TFA, and injected directly on a RP C18 column (50 g C18) for purification (5% to 100% can (+0.1% TFA) in water (+0.1% TFA) over 12 minutes). The desired fractions were neutralized with aqueous NaHCO₃ (ca. 60 mL), extracted twice with a 1:4 isopropanol:chloroform mixture. The organic layer was dried over Na₂SO₄, filtered, and evaporated under d reduced pressure to afford a solid. The solid was dissolved in dichloromethane, and purified by silica gel chromatography (0% to 20% methanol in dichloromethane). The desired fractions were evaporated under reduced pressure, then dissolved in dichloromethane, transferred to a 8 mL vial, and evaporated under reduced pressure. Water (1 mL) and acetonitrile (1 mL) were added, and the mixture was thoroughly sonicated, vortexed and sonicated again. The suspension was frozen and lyophilized to afford Compound 48 (27.9 mg, 30.19 µmol, 51.59% yield). LCMS (ESI+): 915.3 (M+H), ¹H NMR (400 MHz, DMSO-d₆) δ 12.51 (s, 1H), 10.77 (s, 1H), 7.74 (d, J=1.3 Hz, 1H), 7.70 (dd, J=10.7, 1.4 Hz, 1H), 7.64 (d, J=8.5 Hz, 2H), 7.60 (s, 1H), 7.48 (d, J=3.5 Hz, 1H), 7.25 (d, J=3.6 Hz, 1H), 7.01 (t, J=8.8 Hz, 1H), 6.54 (d, J=8.4 Hz, 2H), 6.50-6.34 (m, 2H), 6.15 (s, 1H), 5.99 (d, J=7.7 Hz, 1H), 4.79 (d, J=17.7 Hz, 1H), 4.43 (s, 2H), 4.30 (ddd, J=12.1, 7.7, 4.8 Hz, 1H), 4.21 (d, J=17.6 Hz, 1H), 4.08 (s, 2H), 4.02 (s, 3H), 4.01-3.87 (m, 2H), 3.16-2.83 (m, 4H), 2.83-2.64 (m, 2H), 2.64-2.52 (m, 1H), 2.49-2.38 (m, 1H), 2.22-1.97 (m, 3H), 1.86 (qd, J=12.0, 4.5 Hz, 1H), 1.65 (s, 4H).

Example 49

Synthesis of 2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-1-piperidyl]acetyl]-2,6-diazaspiro[3.3]heptan-6-yl]phenyl]-4-fluoro-1-oxo-isoindolin-2-yl]-N-thiazol-2-yl-acetamide, Compound 49

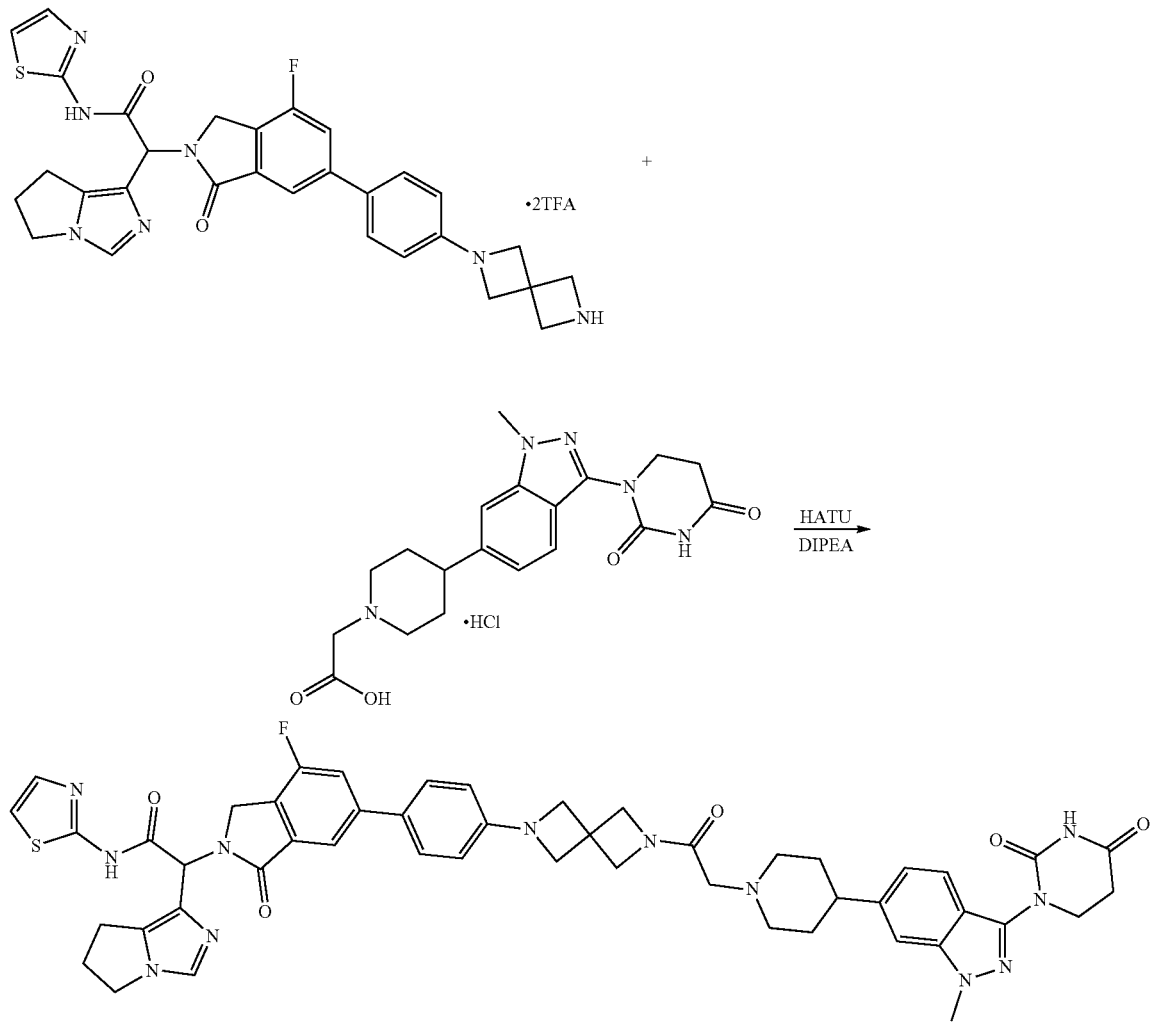

2-[4-[3-(2,4-Dioxohexahydropyrimidin-1-yl)-1-methyl-indazol-6-yl]-1-piperidyl]acetic acid hydrochloride (52.89 mg, 125.36 µmol) was dissolved in DMF (0.5 mL) and cooled to 0° C. N,N-diisopropylethylamine (40.50 mg, 313.40 µmol, 54.59 µL) was added to the reaction mixture. HATU (35.75 mg, 94.02 µmol) was added and the reaction mixture was stirred at 35° C. for 10 minutes. The solution was cooled to 0° C. and 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide bis trifluoroacetic acid salt (50 mg, 62.68 µmol, 062) was added. The reaction mixture was warmed to room temperature and stirred for 2 hours. The mixture was injected on a 50 g C18 column, and purified using a 0% to 100% Acetonitrile in water+0.1% TFA water elution gradient. Desired fractions were pooled and partitioned between ethyl acetate and sodium bicarbonate (aqueous, aqueous). The organic layer was washed with brine, dried with sodium sulfate, filtered and evaporated under reduced pressure. The crude residue was purified by silica gel chromatography (0% to 20% methanol in dichloromethane). Desired fractions were evaporated to afford Compound 49 (35 mg, 37.35 µmol, 59.59% yield). LCMS (ESI+): 937.2 (M+H), LCMS (ESI−): 935.2 (M−H), $^1$H NMR (400 MHz, DMSO-d6) δ 12.45 (s, 1H), 10.46 (s, 1H), 7.67 (s, 1H), 7.63 (d, J=11.0 Hz, 1H), 7.57 (d, J=8.6 Hz, 2H), 7.54 (s, 1H), 7.49 (d, J=8.5 Hz, 1H), 7.42 (d, J=3.6 Hz, 1H), 7.38 (s, 1H), 7.19 (d, J=3.5 Hz, 1H), 6.99 (d, J=8.5 Hz, 1H), 6.48 (d, J=8.5 Hz, 2H), 6.08 (s, 1H), 4.72 (d, J=17.7 Hz, 1H), 4.39 (s, 2H), 4.15 (d, J=17.6 Hz, 1H), 4.02 (s, 2H), 3.97 (s, 3H), 3.97-3.91 (m, 1H), 3.90 (s, 3H), 3.84 (t, J=6.7 Hz, 2H), 3.03-2.79 (m, 4H), 2.68 (t, J=6.6 Hz, 3H), 2.60-2.45 (m, 1H), 2.38-2.25 (m, 1H), 2.19-2.02 (m, 2H), 1.99-1.85 (m, 1H), 1.73 (s, 5H).

Example 50

Synthesis of 2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, Compound 50

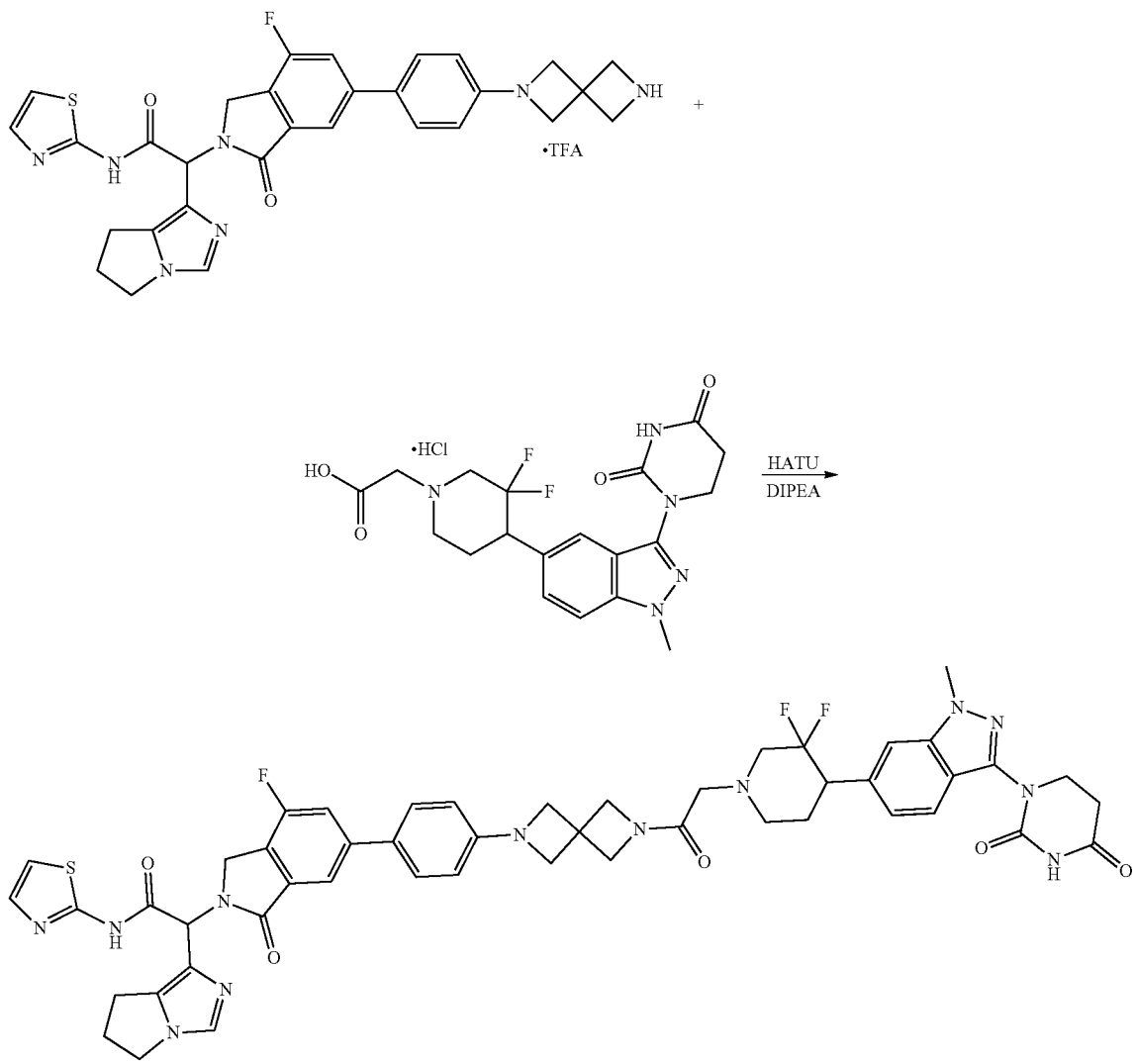

N,N-Diisopropylethylamine (47.26 mg, 365.67 µmol, 63.69 µL) was added to a solution for 2-[4-[3-(2,4-dioxo-hexahydropyrimidin-1-yl)-1-methyl-indazol-5-yl]-3,3-difluoro-1-piperidyl]acetic acid hydrochloride (43.53 mg, 95.07 µmol) in DMF (0.8 mL) at 0° C. HATU (30.59 mg, 80.45 µmol) was added at 0° C. and the mixture was stirred at ambient temperature for 10 min. Then, 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide trifluoroacetic acid salt (50 mg, 73.13 µmol) dissolved in DMF (0.4 mL) was added. The Reaction mixture was stirred for 30 minutes. The mixture was injected on a 50 g C18 column, and purified using a 0% to 100% Acetonitrile in water+0.1% TFA water elution gradient. Desired fractions were pooled and partitioned between ethyl acetate and sodium bicarbonate (aqueous, aqueous). The organic layer was washed with brine, dried with sodium sulfate, filtered and evaporated under reduced pressure. The crude residue was purified by silica gel chromatography (0% to 20% methanol in dichloromethane). Pure fractions were evaporated to afford Compound 50 (30.3 mg, 29 µmol, 41% yield) as an off-white solid. LCMS (ESI+): 973.2 (M+H), 1H NMR (400 MHz, DMSO-d6) δ 12.44 (s, 1H), 10.48 (s, 1H), 7.67 (d, J=1.4 Hz, 1H), 7.63 (dd, J=10.6, 1.4 Hz, 1H), 7.58 (d, J=8.6 Hz, 2H), 7.54-7.48 (m, 3H), 7.41 (d, J=3.5 Hz, 1H), 7.19 (d, J=3.6 Hz, 1H), 7.03 (d, J=8.5 Hz, 1H), 6.51-6.46 (m, 2H), 6.08 (s, 1H), 4.72 (d, J=17.7 Hz, 1H), 4.37 (s, 2H), 4.15 (d, J=17.7 Hz, 1H), 4.06-3.94 (m, 6H), 3.96-3.88 (m, 5H), 3.85 (t, J=6.7 Hz, 2H), 3.19-3.07 (m, 4H), 2.92 (d, J=10.8 Hz, 1H), 2.76-2.65 (m, 3H), 2.65-2.55 (m, 1H), 2.51-2.44 (m, 1H), 2.43-2.33 (m, 3H), 2.20 (dd, J=27.1, 14.4 Hz, 1H), 1.77 (m, 1H).

Example 51

Synthesis of 2-(6,7-dihydro-5H-pyrrolo[1,2-c]imidazol-1-yl)-2-(6-(4-(6-(2-(4-(4-((2,6-dioxopiperidin-3-yl)amino)phenyl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide, Isomer 1, Compound 51

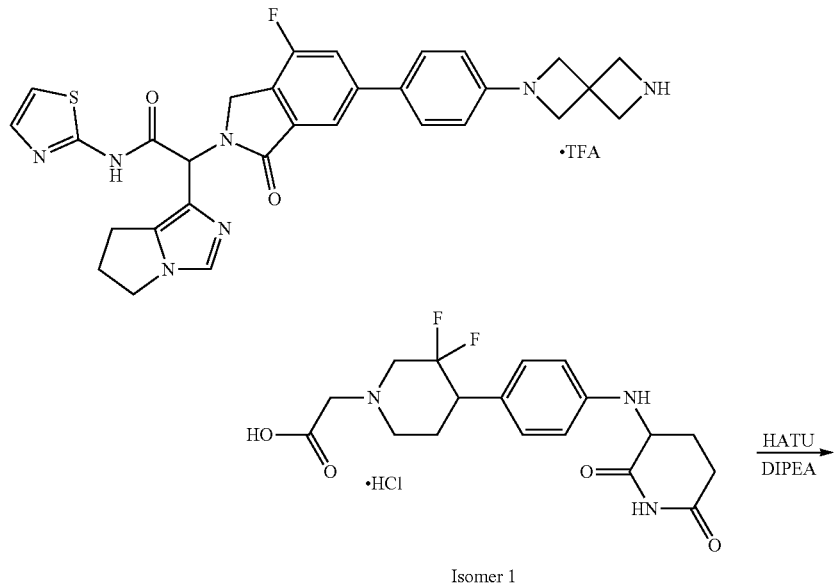

Isomer 1

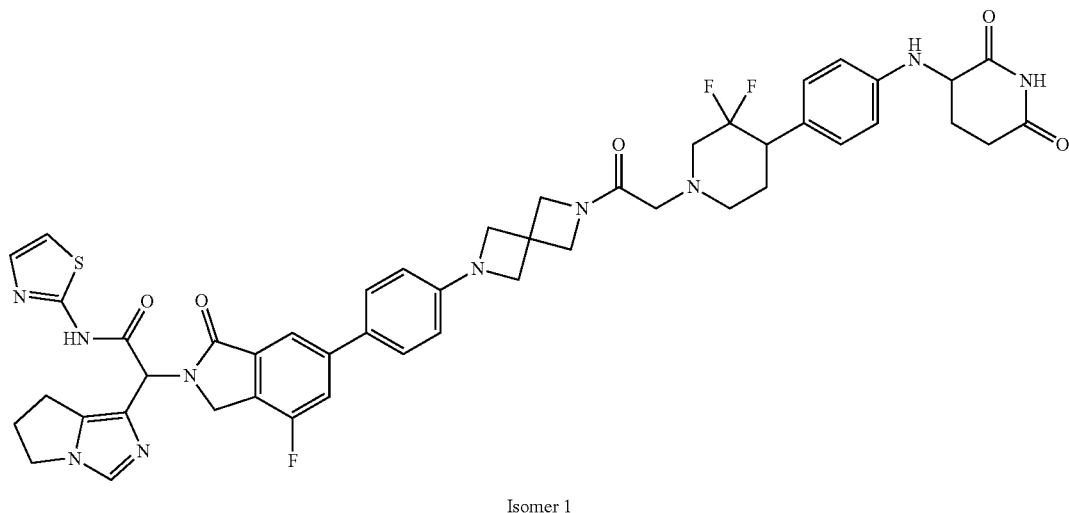

Isomer 1

N,N-Diisopropylethylamine (56.71 mg, 438.81 µmol, 76.43 µL) was added to a solution of 2-[4-[4-[(2,6-dioxo-3-piperidyl)amino]phenyl]-3,3-difluoro-1-piperidyl]acetic acid hydrochloride isomer 1 (47.67 mg, 114.09 µmol) (47.67 mg, 114.09 µmol) in DMF (0.8 mL). HATU (36.71 mg, 96.54 µmol) was added at 0° C. and the mixture was stirred at ambient temperature for 10 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide trifluoroacetic acid salt (60 mg, 87.76 µmol) dissolved in DMF (0.4 ml) was added. The reaction mixture was stirred for 2 hours. The mixture was injected on a 50 g C18 column, and purified using a 0% to 100% Acetonitrile in water+0.1% TFA water elution gradient. Desired fractions were pooled and partitioned between ethyl acetate and sodium bicarbonate (aqueous, aqueous). The organic layer was washed with brine, dried with sodium sulfate, filtered and evaporated under reduced pressure. The crude residue was purified by silica gel chromatography (24 g column, 0% to 20% methanol in ethyl acetate). Desired fractions were evaporated and the solid was dissolved in an acetonitrile:water mixture (1:1, 2 mL). The solution was frozen and lyophilized to afford Compound 51 (19.2 mg, 20.37 µmol, 23.2%). LCMS (ESI+): 933.3 (M+H), 1H NMR (400 MHz, DMSO-d6) δ 12.52 (s, 1H), 10.78 (s, 1H), 7.75 (d, J=1.4 Hz, 1H), 7.71 (dd, J=10.7, 1.4 Hz, 1H), 7.68-7.62 (m, 2H), 7.61 (s, 1H), 7.49 (d, J=3.6 Hz, 1H), 7.26 (d, J=3.5 Hz, 1H), 7.02 (d, J=8.2 Hz, 2H), 6.64 (d, J=8.6 Hz, 2H), 6.55 (d, J=8.6 Hz, 2H), 6.15 (s, 1H), 5.81 (d, J=7.5 Hz, 1H), 4.80 (d, J=17.7 Hz, 1H), 4.42 (s, 2H), 4.30 (ddd, J=12.0, 7.5, 4.8 Hz, 1H), 4.22 (d, J=17.7 Hz, 1H), 4.10 (s, 2H), 4.07-3.93 (m, 6H), 3.21-3.08 (m, 3H), 2.97-2.87 (m, 2H), 2.88-2.67 (m, 3H), 2.67-2.44 (m, 4H), 2.42-2.30 (m, 1H), 2.16-1.97 (m, 2H), 1.89 (tt, J=12.1, 6.2 Hz, 1H), 1.71 (d, J=13.1 Hz, 1H).

Example 52

Synthesis of 2-(6,7-dihydro-5H-pyrrolo[1,2-c]imidazol-1-yl)-2-(6-(4-(6-(2-(4-(4-((2,6-dioxopiperidin-3-yl)amino)phenyl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide, Isomer 2, Compound 52

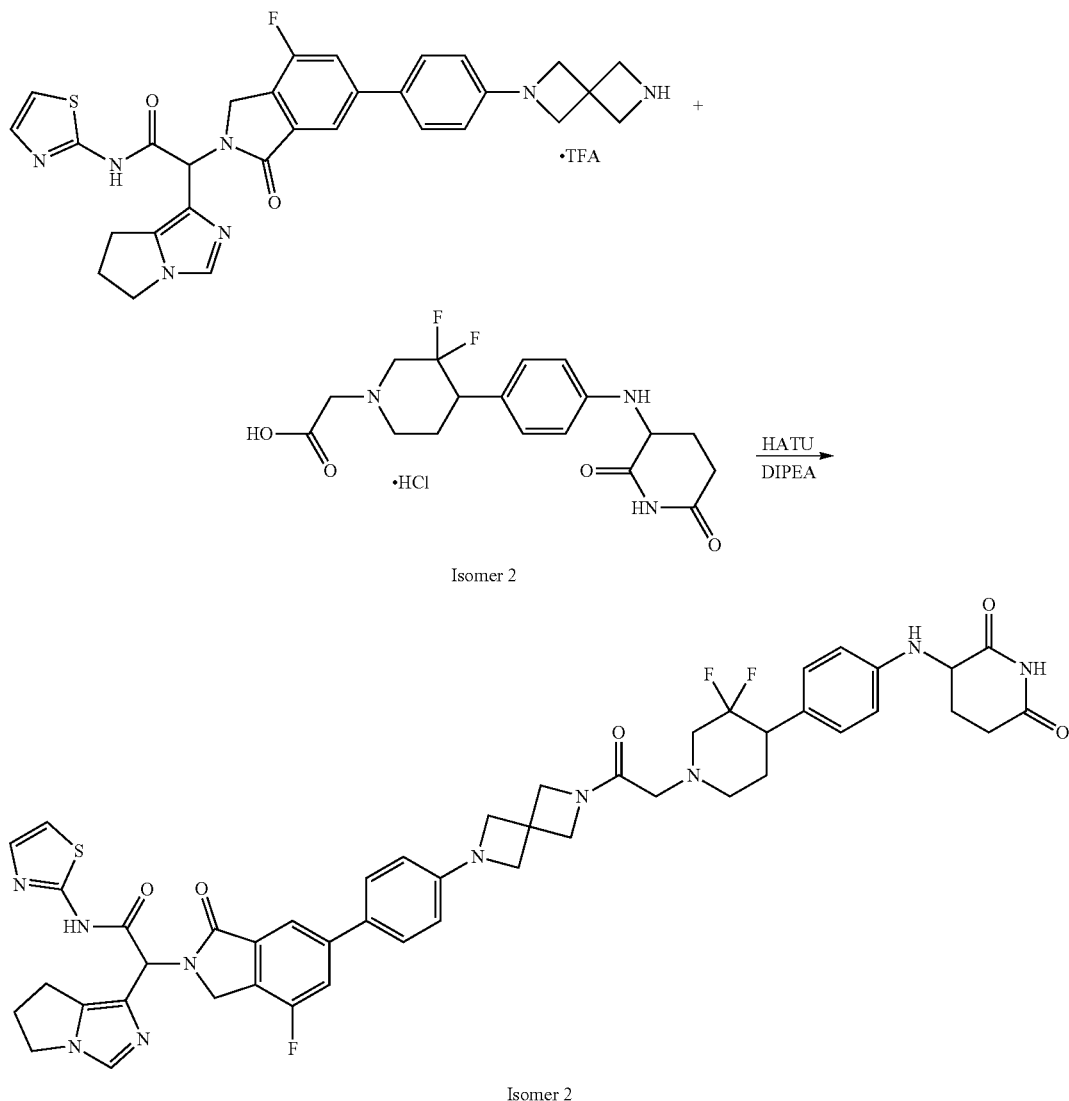

Compound 52 was synthesized in 19.5% using the same procedure as 2-(6,7-dihydro-5H-pyrrolo[1,2-c]imidazol-1-yl)-2-(6-(4-(6-(2-(4-(4-((2,6-dioxopiperidin-3-yl)amino)phenyl)-3,3-difluoropiperidin-1-yl)acetyl)-2,6-diazaspiro[3.3]heptan-2-yl)phenyl)-4-fluoro-1-oxoisoindolin-2-yl)-N-(thiazol-2-yl)acetamide, Isomer 1 (Example 51), using 2-[4-[4-[(2,6-dioxo-3-piperidyl)amino]phenyl]-3,3-difluoro-1-piperidyl]acetic acid hydrochloride, isomer 2 instead of 2-[4-[4-[(2,6-dioxo-3-piperidyl)amino]phenyl]-3,3-difluoro-1-piperidyl]acetic acid hydrochloride isomer 1. LCMS (ESI+): 933.4 (M+H), $^1$H NMR (400 MHz, DMSO-d6) δ 12.52 (s, 1H), 10.78 (s, 1H), 7.75 (d, J=1.3 Hz, 1H), 7.71 (dd, J=10.7, 1.4 Hz, 1H), 7.65 (d, J=8.7 Hz, 2H), 7.61 (s, 1H), 7.49 (d, J=3.5 Hz, 1H), 7.26 (d, J=3.6 Hz, 1H), 7.02 (d, J=8.2 Hz, 2H), 6.64 (d, J=8.4 Hz, 2H), 6.55 (d, J=8.7 Hz, 2H), 6.15 (s, 1H), 5.80 (d, J=7.5 Hz, 1H), 4.80 (d, J=17.7 Hz, 1H), 4.42 (s, 2H), 4.30 (ddd, J=12.0, 7.6, 4.9 Hz, 1H), 4.22 (d, J=17.7 Hz, 1H), 4.10 (s, 2H), 4.07-3.93 (m, 6H), 3.23-3.07 (m, 3H), 2.97-2.87 (m, 2H), 2.88-2.67 (m, 3H), 2.67-2.44 (m, 4H), 2.43-2.31 (m, 1H), 2.16-1.97 (m, 2H), 1.88 (qd, J=12.2, 4.8 Hz, 1H), 1.71 (d, J=13.3 Hz, 1H).

Example 53

Synthesis of 2-(6,7-dihydro-5H-pyrrolo[1,2-c]imidazol-1-yl)-2-[6-[4-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]phenyl]-4-fluoro-1-oxo-isoindolin-2-yl]-N-(2-pyridyl)acetamide, Compound 53

Step 1: tert-butyl 6-[4-[2-[1-(6,7-dihydro-5H-pyrrolo[1,2-c]imidazol-1-yl)-2-oxo-2-(2-pyridylamino)ethyl]-7-fluoro-3-oxo-isoindolin-5-yl]phenyl]-2,6-diazaspiro[3.3]heptane-2-carboxylate

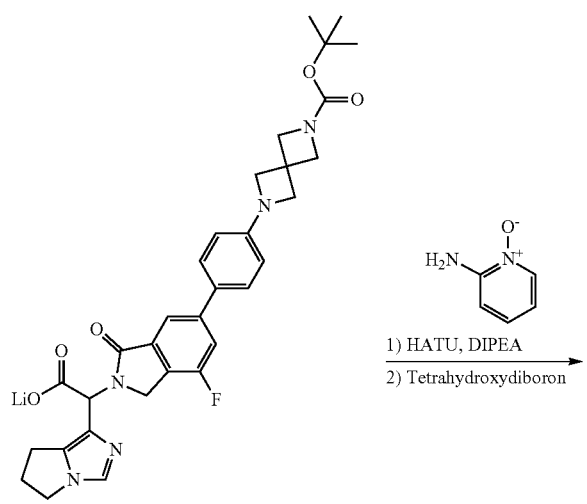

1) HATU, DIPEA
2) Tetrahydroxydiboron

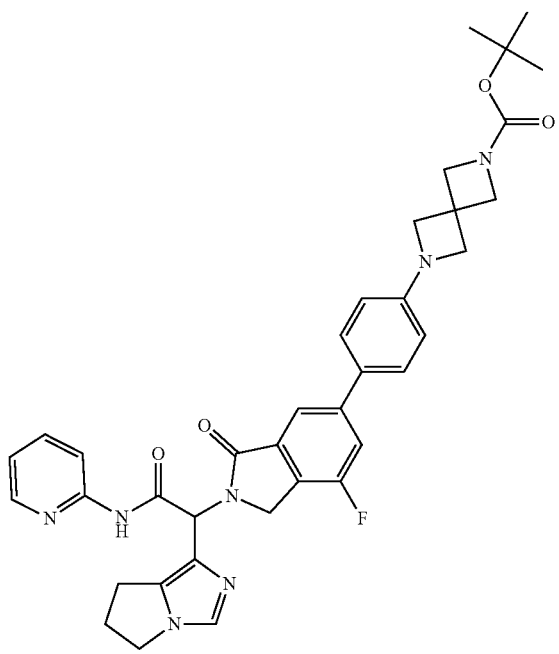

To a solution of 1-oxidopyridin-1-ium-2-amine (43.67 mg, 396.58 µmol) and [2-[6-[4-(2-tert-butoxycarbonyl-2,6-diazaspiro[3.3]heptan-6-yl)phenyl]-4-fluoro-1-oxo-isoindolin-2-yl]-2-(6,7-dihydro-5H-pyrrolo[1,2-c]imidazol-1-yl)acetyl]oxylithium (214 mg, 360.53 µmol) in DMF (3 mL) was added N,N-Diisopropylethylamine (186.38 mg, 1.44 mmol, 251.18 µL) and HATU (178.21 mg, 468.69 µmol) at ambient temperature. After 15 minutes, tetrahydroxydiboron (96.96 mg, 1.08 mmol) was added and stirred for 30 minutes. The reaction mixture was diluted with a water:brine mixture (1:1), extracted with Ethyl Acetate, washed with brine, dried over Na$_2$SO$_4$, and concentrated. The crude residue was purified by silica gel column chromatography (24 grams, 0% to 20% Methanol in dichloromethane) to afford tert-butyl 6-[4-[2-[1-(6,7-dihydro-5H-pyrrolo[1,2-c]imidazol-1-yl)-2-oxo-2-(2-pyridylamino)ethyl]-7-fluoro-3-oxo-isoindolin-5-yl]phenyl]-2,6-diazaspiro[3.3]heptane-2-carboxylate (175 mg, 263.66 µmol, 73.13% yield) as a yellow solid. LCMS (ESI+): 664.3 (M+H)/608.3 (M-tBu+H)

Step 2: 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-(2-pyridyl)acetamide, bis-trifluoroacetic acid salt

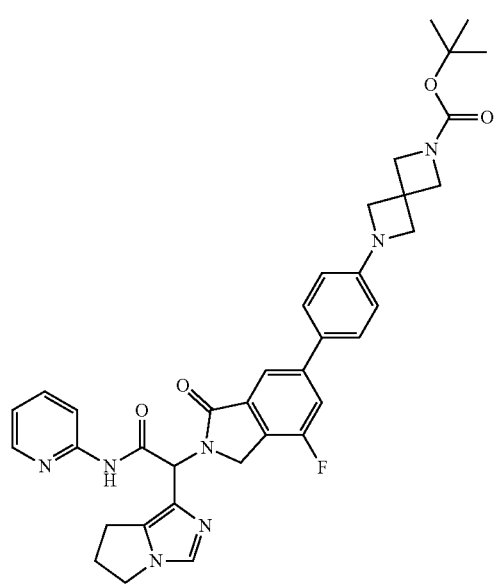

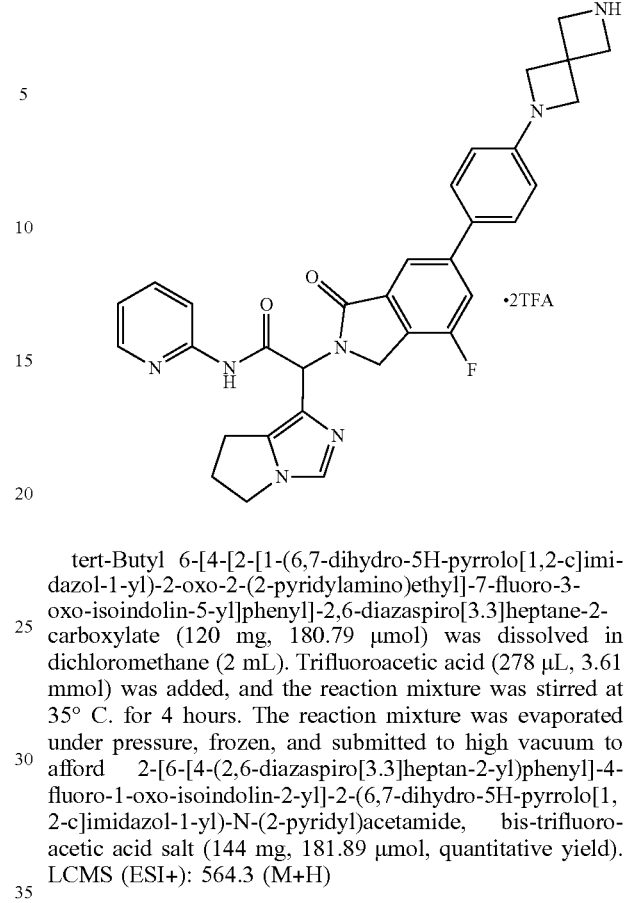

tert-Butyl 6-[4-[2-[1-(6,7-dihydro-5H-pyrrolo[1,2-c]imidazol-1-yl)-2-oxo-2-(2-pyridylamino)ethyl]-7-fluoro-3-oxo-isoindolin-5-yl]phenyl]-2,6-diazaspiro[3.3]heptane-2-carboxylate (120 mg, 180.79 μmol) was dissolved in dichloromethane (2 mL). Trifluoroacetic acid (278 μL, 3.61 mmol) was added, and the reaction mixture was stirred at 35° C. for 4 hours. The reaction mixture was evaporated under pressure, frozen, and submitted to high vacuum to afford 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-(2-pyridyl)acetamide, bis-trifluoroacetic acid salt (144 mg, 181.89 μmol, quantitative yield). LCMS (ESI+): 564.3 (M+H)

Step 3: 2-(6,7-dihydro-5H-pyrrolo[1,2-c]imidazol-1-yl)-2-[6-[4-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]phenyl]-4-fluoro-1-oxo-isoindolin-2-yl]-N-(2-pyridyl)acetamide

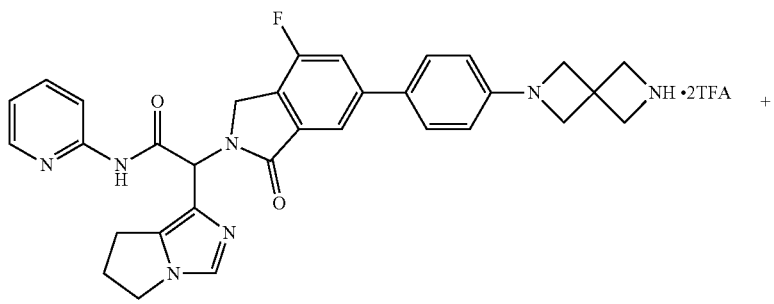

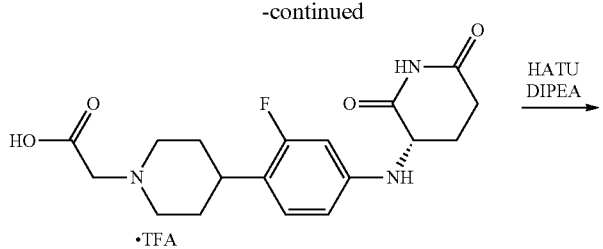

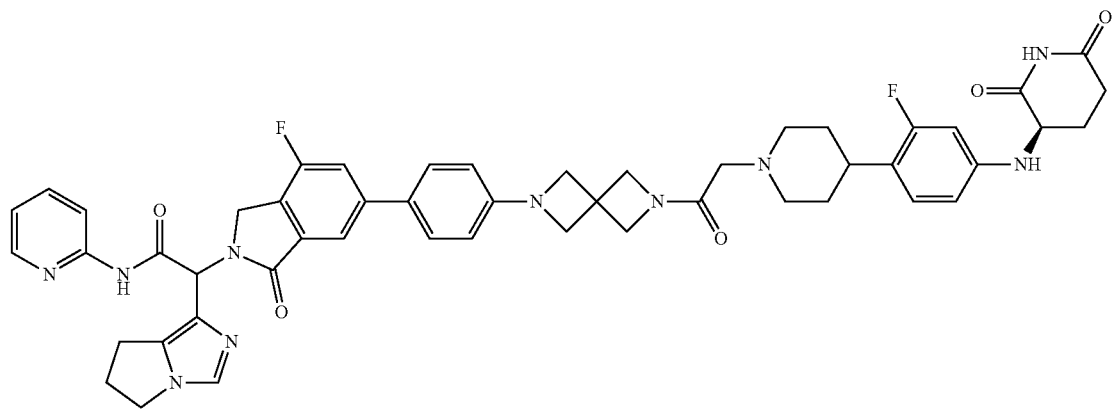

2-[6-[4-(2,6-Diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-(2-pyridyl)acetamide bis-trifluoroacetic acid salt (111 mg, 163.80 μmol) and 2-[4-[4-[[(3 S)-2,6-di oxo-3-piperidyl]amino]-2-fluoro-phenyl]-1-piperidyl]acetic acid trifluoroacetic acid salt (93.84 mg, 196.56 μmol) were mixed in DMF and cooled to 0° C. N,N-Diisopropyl ethyl amine (105.85 mg, 819.01 μmol, 142.65 μL) was added to the reaction mixture, and HATU (80.97 mg, 212.94 μmol) was added, and the reaction mixture was stirred for 1 h at 0° C. The reaction mixture was acidified with 4-5 drops of TFA, and injected directly on a RP C18 column (50 g C18) for purification using a 5% to 100% acetonitrile (+0.1% TFA) in water (+0.1% TFA) eluent gradient. The desired fractions were neutralized with aqueous NaHCO₃ (ca. 60 mL) and extracted with 1:4 isopropanol:chloroform. The organic layer was dried over Na₂SO₄, filtered, and evaporated under reduced pressure to afford a solid. The solid was dissolved in dichloromethane, and purified by silica gel chromatography (0% to 20% methanol in dichloromethane). The desired fractions were evaporated under reduced pressure. The crude residue was dissolved in dichloromethane, transferred to a 8 mL vial, and evaporated under reduced pressure. Water (1 mL) and acetonitrile (1 mL) were added, and the mixture was thoroughly sonicated, vortexed and sonicated again. The suspension was frozen and lyophilized to afford Compound 53 (4 mg, 4.18 μmol, 2.55% yield, 95% purity). LCMS (ESI+): 909.4 (M+H), $^1$H NMR (400 MHz, DMSO-$d_6$) δ 10.81 (s, 1H), 10.71 (s, 2H), 8.37-8.09 (m, 1H), 8.00 (d, J=8.4 Hz, 1H), 7.89-7.31 (m, 7H), 7.05 (dd, J=7.3, 4.8 Hz, 1H), 6.92 (q, J=11.4, 10.2 Hz, 1H), 6.48 (d, J=8.3 Hz, 2H), 6.43-6.21 (m, 2H), 6.12 (s, 1H), 5.94 (d, J=7.6 Hz, 1H), 4.72 (d, J=17.7 Hz, 1H), 4.35 (s, 2H), 4.23 (dt, J=12.2, 6.8 Hz, 1H), 4.14 (d, J=17.7 Hz, 1H), 4.03 (s, 2H), 3.96 (s, 4H), 3.95-3.77 (m, 1H), 3.11-2.46 (m, 4H), 2.20-1.87 (m, 2H), 1.88-1.24 (m, 7H).

Example 54

Synthesis of 2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-1-piperidyl]acetyl]-2,6-diazaspiro[3.3]heptan-6-yl]phenyl]-4-fluoro-1-oxo-isoindolin-2-yl]-N-(2-pyridyl)acetamide, Compound 54

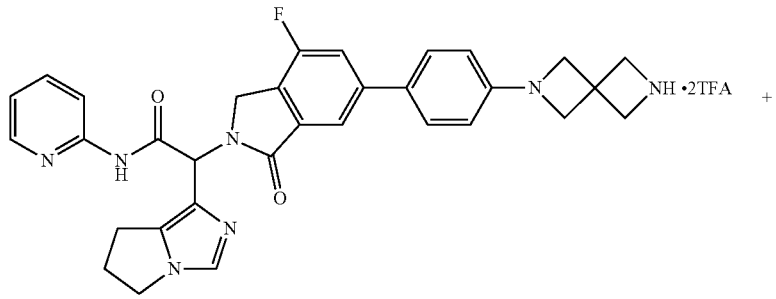

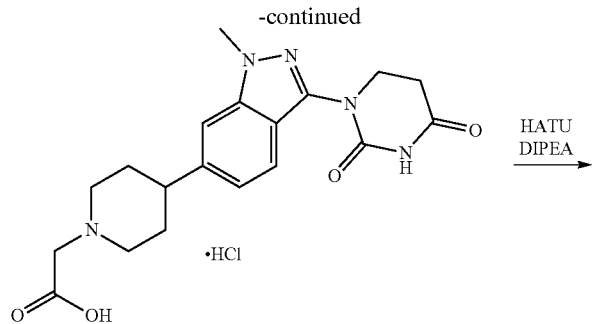

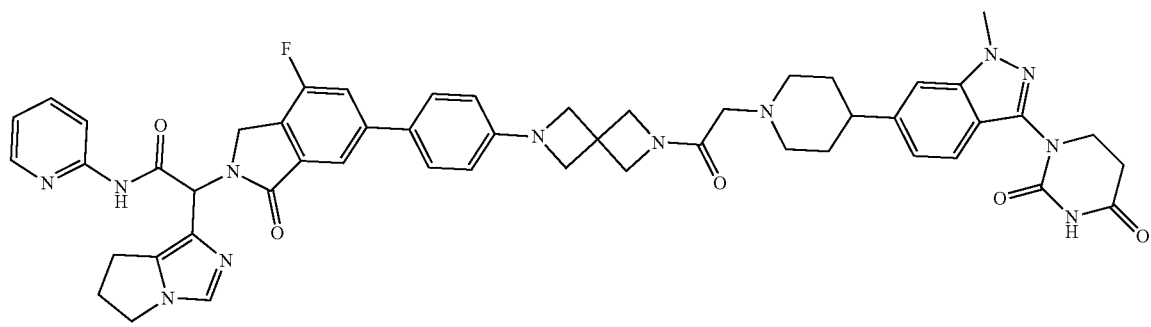

2-[4-[3-(2,4-Dioxohexahydropyrimidin-1-yl)-1-methyl-indazol-6-yl]-1-piperidyl]acetic acid hydrochloride (28.61 mg, 67.87 μmol) were mixed in DMF, the reaction mixture was cooled to 0° C. N,N-diisopropylethylamine (22.04 mg, 170.53 μmol, 29.70 μL) was added to the reaction mixture, and HATU (19.45 mg, 51.16 μmol) was added, and the reaction mixture was stirred at 35° C. for 10 minutes. The reaction mixture was cooled to 0° C. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-(2-pyridyl)acetamide, bis trifluoroacetic acid salt (27 mg, 34.11 μmol) was added in one portion, and the reaction mixture was stirred for 2 hours while warming to 20° C. The mixture was injected on a 50 g C18 column and purified using a 0% to 100% Acetonitrile in water+0.1% TFA water elution gradient. Desired fractions were neutralized with sodium bicarbonate (aqueous, aqueous), and the aqueous mixture was extracted twice with an isopropanol:chloroform mixture (1:4). The organic layer was washed with brine, dried with sodium sulfate, filtered and evaporated under reduced pressure. The residue was purified by silica gel chromatography (0% to 20% methanol in dichloromethane) to afford Compound 54 (16 mg, 16.33 μmol, 47.87% yield). LCMS (ESI+): 931.3 (M+H), LCMS (ESI−): 929.3 (M−H), $^1$H NMR (400 MHz, DMSO-d$_6$) δ 10.88 (s, 1H), 10.53 (s, 1H), 8.32 (ddd, J=4.9, 1.9, 0.9 Hz, 1H), 8.07 (d, J=8.4 Hz, 1H), 7.87-7.75 (m, 1H), 7.74 (d, J=1.4 Hz, 1H), 7.69 (dd, J=10.6, 1.4 Hz, 1H), 7.67-7.61 (m, 2H), 7.60 (s, 1H), 7.56 (d, J=8.4 Hz, 1H), 7.45 (s, 1H), 7.12 (ddd, J=7.4, 4.9, 1.0 Hz, 1H), 7.05 (dd, J=8.6, 1.3 Hz, 1H), 6.68-6.36 (m, 2H), 6.19 (s, 1H), 4.79 (d, J=17.7 Hz, 1H), 4.45 (s, 2H), 4.21 (d, J=17.7 Hz, 1H), 4.09 (s, 2H), 4.04 (s, 3H), 4.01 (s, 1H), 3.97 (s, 3H), 3.90 (t, J=6.7 Hz, 2H), 3.18-2.87 (m, 4H), 2.87-2.70 (m, 3H), 2.70-2.57 (m, 1H), 2.59-2.50 (m, 5H), 2.31-2.08 (m, 2H), 1.92-1.60 (m, 4H).

Example 55

Synthesis of 2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-(2-pyridyl)acetamide, Compound 55

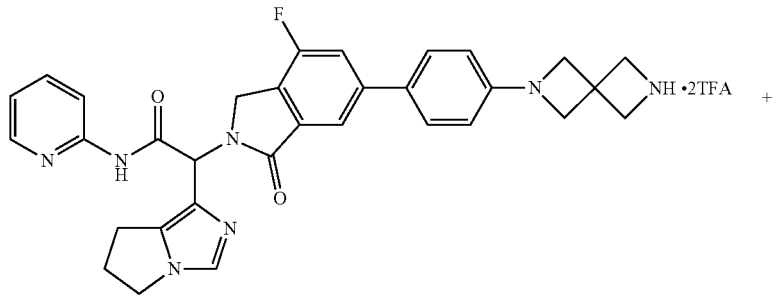

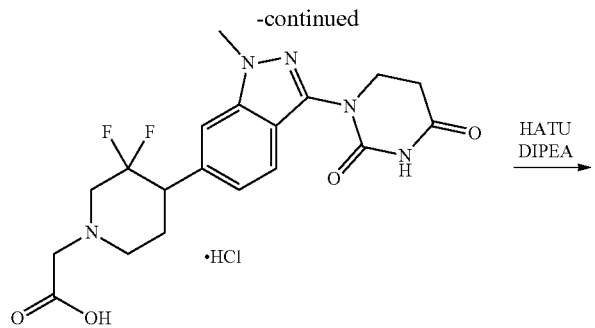

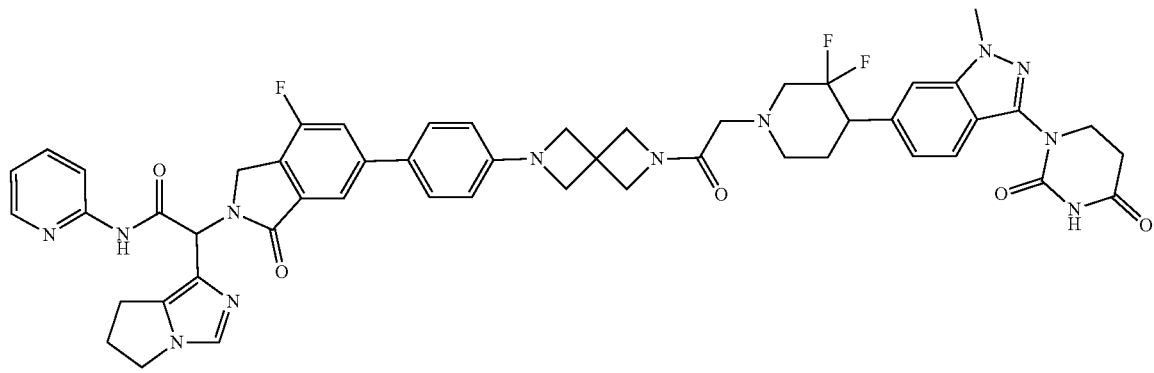

N,N-diisopropylethylamine (53.06 mg, 410.55 µmol, 71.51 µL) was added to 2-[4-[3-(2,4-Dioxohexahydropyrimidin-1-yl)-1-methyl-indazol-6-yl]-3,3-difluoro-1-piperidyl]acetic acid hydrochloride (45.11 mg, 98.53 µmol) (55.64 mg, 82.11 µmol) in DMF (0.5 mL). HATU (34.34 mg, 90.32 µmol) was added at 0° C. and stirred at ambient temperature for 10 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-(2-pyridyl)acetamide; trifluoroacetic acid salt in DMF (0.4 ml) was added. The reaction mixture was stirred for 2 hours while warming to 20° C. The mixture was injected on a 50 g C18 column and purified using a 0% to 100% Acetonitrile in water+0.1% TFA water elution gradient. Desired fractions were neutralized with sodium bicarbonate (aqueous, aqueous), and the aqueous mixture was extracted twice with a 1:4 isopropanol: chloroform mixture. The organic layer was washed with brine, dried with sodium sulfate, filtered and evaporated under reduced pressure. The residue was purified by silica gel chromatography (0% to 20% methanol in ethyl acetate) to afford Compound 55 (47.3 mg, 48.42 µmol, 58.98% yield). LCMS (ESI+): 967.3 (M+H), 1H NMR (400 MHz, DMSO-d6) δ 10.96 (s, 1H), 10.61 (s, 1H), 8.38 (dd, J=5.3, 1.9 Hz, 1H), 8.13 (d, J=8.4 Hz, 1H), 7.86 (ddd, J=8.8, 7.3, 2.0 Hz, 1H), 7.81 (d, J=1.3 Hz, 1H), 7.76 (dd, J=10.7, 1.4 Hz, 1H), 7.73-7.68 (m, 2H), 7.66 (d, J=8.5 Hz, 1H), 7.62 (s, 1H), 7.21-7.14 (m, 2H), 6.64-6.59 (m, 2H), 6.26 (s, 1H), 4.86 (d, J=17.7 Hz, 1H), 4.51 (s, 2H), 4.28 (d, J=17.7 Hz, 1H), 4.17 (s, 2H), 4.10 (d, J=5.9 Hz, 4H), 4.08-4.02 (m, 4H), 3.98 (t, J=6.7 Hz, 2H), 3.33-3.21 (m, 4H), 3.06 (d, J=10.9 Hz, 1H), 2.91-2.79 (m, 3H), 2.78-2.68 (m, 1H), 2.64-2.46 (m, 2H), 2.41-2.27 (m, 1H), 1.91 (d, J=12.5 Hz, 1H).

Example 56

Synthesis of 2-(6,7-dihydro-5H-pyrrolo[1,2-c]imidazol-1-yl)-2-[6-[4-[[4-[2-[4-[4-[(2,6-dioxo-3-piperidyl)amino]phenyl]-1-piperidyl]acetyl]piperazin-1-yl]methyl]phenyl]-4-fluoro-1-oxo-isoindolin-2-yl]-N-thiazol-2-yl-acetamide, Compound 56

Step 1: tert-butyl 4-[[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]methyl]piperazine-1-carboxylate

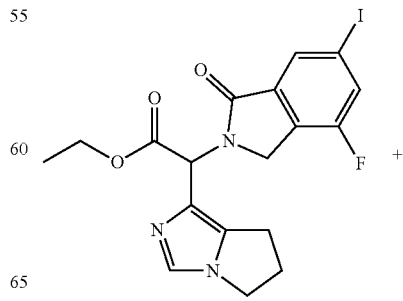

-continued

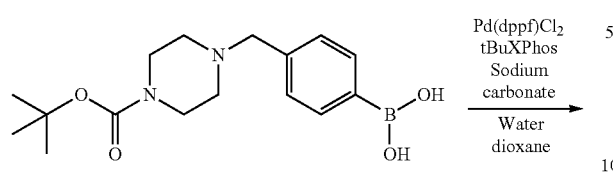

Step 2: [2-[6-[4-[(4-tert-butoxycarbonylpiperazin-1-yl)methyl]phenyl]-4-fluoro-1-oxo-isoindolin-2-yl]-2-(6,7-dihydro-5H-pyrrolo[1,2-c]imidazol-1-yl)acetyl]oxylithium

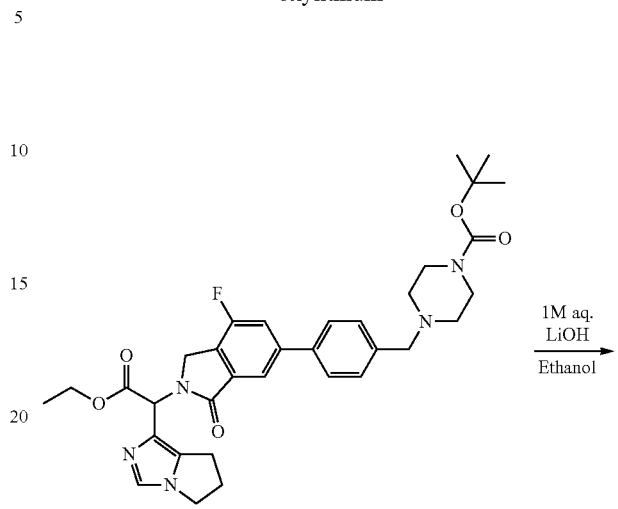

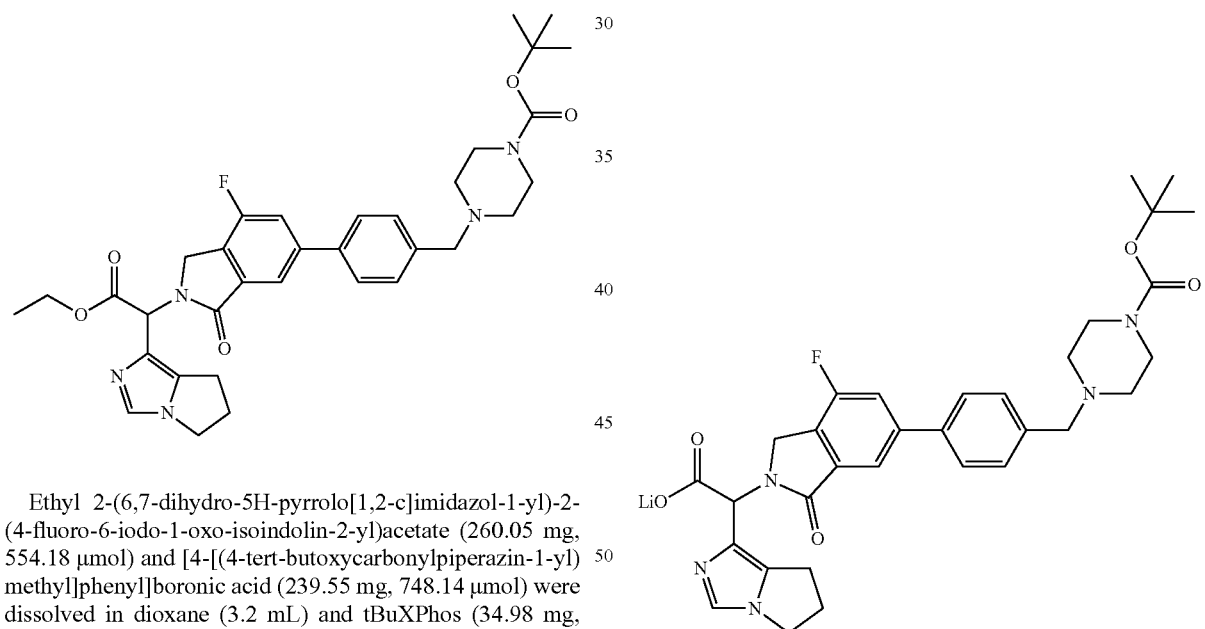

Ethyl 2-(6,7-dihydro-5H-pyrrolo[1,2-c]imidazol-1-yl)-2-(4-fluoro-6-iodo-1-oxo-isoindolin-2-yl)acetate (260.05 mg, 554.18 μmol) and [4-[(4-tert-butoxycarbonylpiperazin-1-yl)methyl]phenyl]boronic acid (239.55 mg, 748.14 μmol) were dissolved in dioxane (3.2 mL) and tBuXPhos (34.98 mg, 55.42 μmol) was added, followed by sodium carbonate (139 mg, 1.31 mmol) dissolved in water (0.8 mL). The mixture was degassed with argon and 1,1'-Bis(Diphenylphosphino)ferrocenepalladium (II) dichloride (22.30 mg, 30.48 μmol) was added. The reaction was sealed and heated at 80° C. on a heating block for 2 h. The mixture was concentrated and purified by flash column chromatography on silica gel (0-100% ethyl acetate in hexane). The desired fractions were concentrated and re-purified by silica gel chromatography (0% to 20% methanol in ethyl acetate) to afford tert-butyl 4-[[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]methyl]piperazine-1-carboxylate (243 mg, 393.39 μmol, 70.99% yield). LCMS (ESI+): 618.5 (M+H$^+$).

tert-Butyl 4-[[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]methyl]piperazine-1-carboxylate (243 mg, 393.39 μmol) was dissolved in Ethanol (3 mL), cooled to 0° C. and an aqueous lithium hydroxide solution (1 M, 393.39 μL) was added. The reaction mixture was stirred for 3 hours. dichloromethane and 0.5 mL of benzene were added and the mixture was concentrated to afford [2-[6-[4-[(4-tert-butoxycarbonylpiperazin-1-yl)methyl]phenyl]-4-fluoro-1-oxo-isoindolin-2-yl]-2-(6,7-dihydro-5H-pyrrolo[1,2-c]imidazol-1-yl)acetyl]oxylithium (215 mg, 360.99 μmol, 91.76% yield). LCMS (ESI+): 590.4 (M+H$^+$).

Step 3: tert-butyl 4-[[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperazine-1-carboxylate

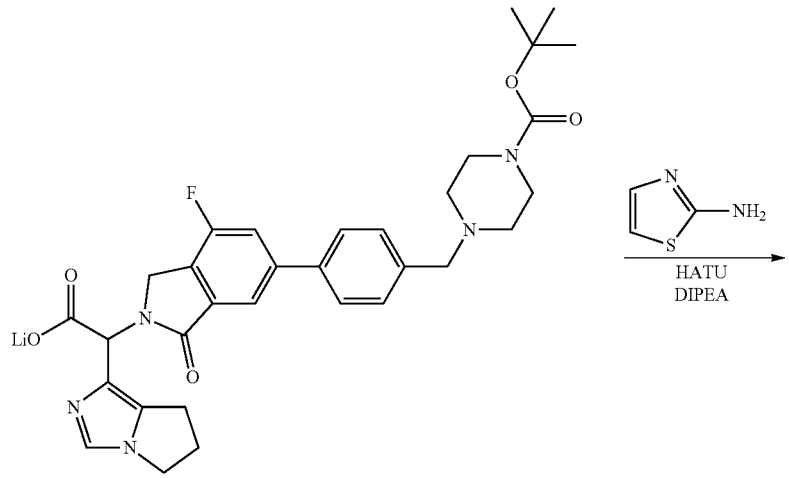

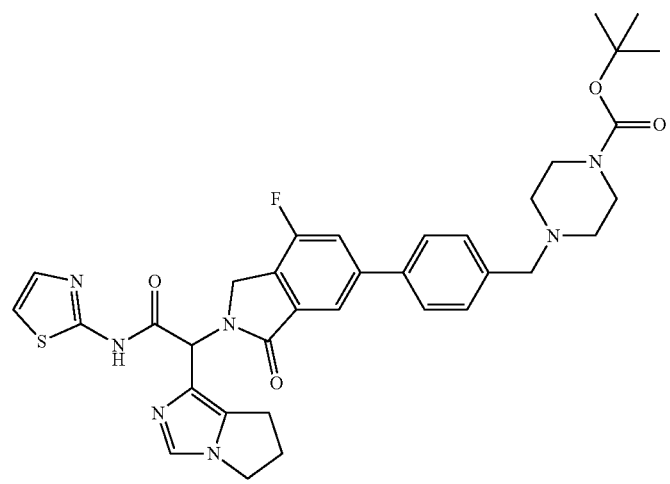

[2-[6-[4-[(4-tert-Butoxycarbonylpiperazin-1-yl)methyl]phenyl]-4-fluoro-1-oxo-isoindolin-2-yl]-2-(6,7-dihydro-5H-pyrrolo[1,2-c]imidazol-1-yl)acetyl]oxylithium (260 mg, 440.94 μmol) and thiazol-2-amine (44.16 mg, 440.94 μmol) were mixed in DMF and cooled to 0° C. N,N-diisopropylethylamine (142.47 mg, 1.10 mmol, 192.01 μL) and HATU (201.19 mg, 529.12 μmol) were added and the reaction mixture was stirred for 3 hours. The reaction mixture was partitioned between ethyl acetate and sodium bicarbonate (aqueous, aqueous). The organic layer was washed with brine, dried with sodium sulfate, filtered and evaporated under reduced pressure. The residue was purified by silica gel chromatography (0% to 20% methanol in dichloromethane) to afford tert-butyl 4-[[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperazine-1-carboxylate (211 mg, 314.09 μmol, 71.23% yield). LCMS (ESI+): 672.2 (M+H$^+$).

801

Step 4: 2-(6,7-dihydro-5H-pyrrolo[1,2-c]imidazol-1-yl)-2-[4-fluoro-1-oxo-6-[4-(piperazin-1-ylmethyl)phenyl]isoindolin-2-yl]-N-thiazol-2-yl-acetamide dihydrochloride

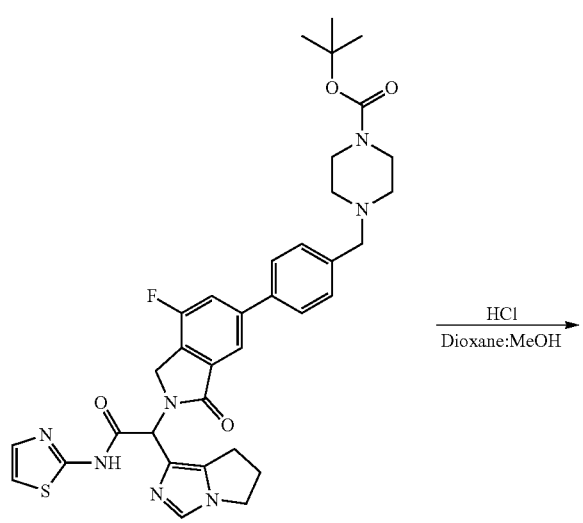

802

-continued

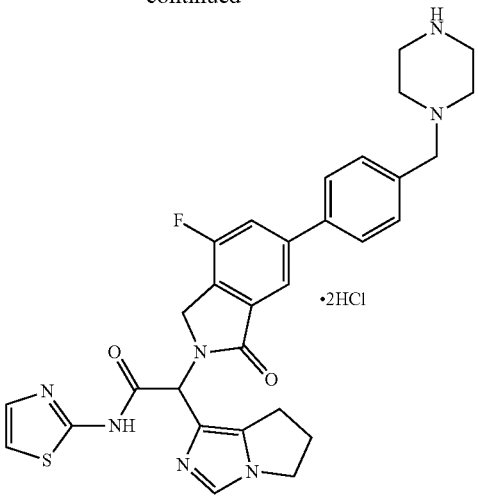

2-(6,7-Dihydro-5H-pyrrolo[1,2-c]imidazol-1-yl)-2-[4-fluoro-1-oxo-6-[4-(piperazin-1-ylmethyl)phenyl]isoindolin-2-yl]-N-thiazol-2-yl-acetamide dihydrochloride was prepared in quantitative yield from tert-butyl 4-[[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperazine-1-carboxylate using the same procedure as Example 5, step 2. LCMS (ESI+): 572.1 (M+H)

Step 5: 2-(6,7-dihydro-5H-pyrrolo[1,2-c]imidazol-1-yl)-2-[6-[4-[[4-[2-[4-[4-[(2,6-dioxo-3-piperidyl)amino]phenyl]-1-piperidyl]acetyl]piperazin-1-yl]methyl]phenyl]-4-fluoro-1-oxo-isoindolin-2-yl]-N-thiazol-2-yl-acetamide

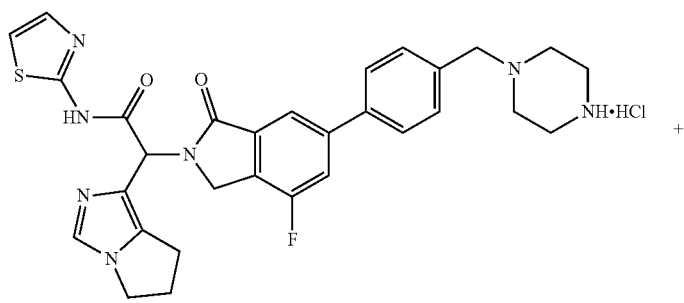

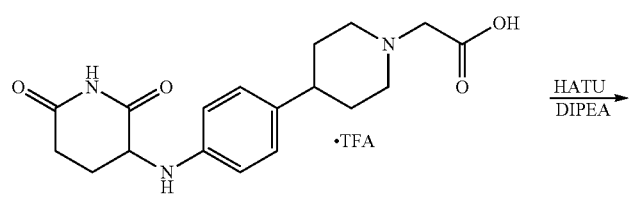

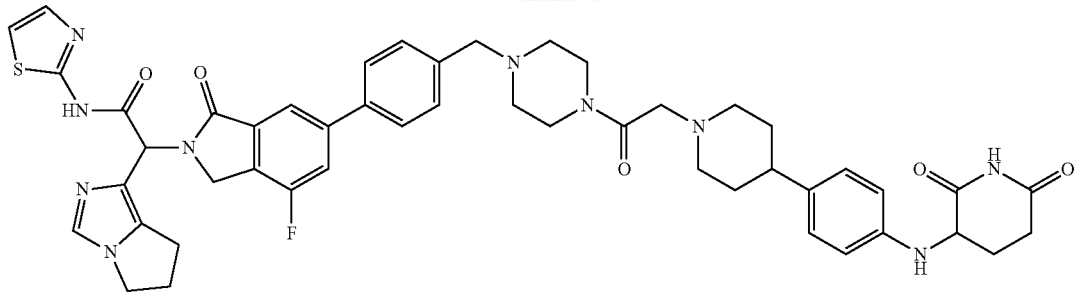

2-(6,7-Dihydro-5H-pyrrolo[1,2-c]imidazol-1-yl)-2-[4-fluoro-1-oxo-6-[4-(piperazin-1-ylmethyl)phenyl]isoindolin-2-yl]-N-thiazol-2-yl-acetamide dihydrochloride (60 mg, 93.08 μmol, 022) and 2-[4-[4-[(2,6-dioxo-3-piperidyl)amino]phenyl]-1-piperidyl]acetic acid, trifluoroacetic acid (42.76 mg, 93.08 μmol) were mixed in DMF, the reaction mixture was cooled to 0° C. N,N-Diisopropylethylamine (60.15 mg, 465.41 μmol, 81.06 μL) was added to the reaction mixture, and HATU (46.01 mg, 121.01 μmol) was added, and the reaction mixture was stirred for 4 hours while warming to room temperature. The reaction mixture was acidified with 4-5 drops of TFA, and injected directly on a RP C18 column (50 g C18) for purification using a 5% to 100% acetonitrile (+0.1% TFA) in water (+0.1% TFA) eluent gradient. The pure fractions were neutralized with aqueous NaHCO₃ (ca. 60 mL), extracted with 1:4 isopropanol:chloroform mixture. The organic layer was evaporated under reduced pressure to afford a solid. The solid was purified by silica gel chromatography (0% to 20% methanol in dichloromethane). The desired fractions were evaporated under reduced pressure. The residue was dissolved in dichloromethane, transferred to a 8 mL vial, and evaporated under reduced pressure. Water (1 mL) and acetonitrile (1 mL) were added, and the mixture was thoroughly sonicated, vortexed and sonicated again. The suspension was frozen and lyophilized to afford Compound 56 (10.5 mg, 11.21 μmol, 12.05% yield, 96% purity). LCMS (ESI+): 899.4 (M+H), $^1$H NMR (400 MHz, DMSO-d6) δ 12.53 (s, 1H), 10.76 (s, 1H), 7.98-7.70 (m, 4H), 7.61 (s, 1H), 7.49 (d, J=3.5 Hz, 1H), 7.45 (d, J=8.1 Hz, 2H), 7.37 (s, 2H), 7.26 (d, J=3.6 Hz, 1H), 6.95 (d, J=8.4 Hz, 2H), 6.61 (d, J=8.4 Hz, 2H), 6.16 (s, 1H), 5.64 (d, J=7.5 Hz, 1H), 4.84 (d, J=17.8 Hz, 1H), 4.41-4.16 (m, 2H), 4.15-3.87 (m, 3H), 3.74-3.52 (m, 4H), 3.47 (s, 2H), 3.14 (s, 2H), 2.88 (d, J=10.6 Hz, 2H), 2.84-2.64 (m, 2H), 2.63-2.53 (m, 1H), 2.48-2.19 (m, 4H), 2.22-1.94 (m, 3H), 1.95-1.77 (m, 1H), 1.77-1.63 (m, 2H), 1.63-1.42 (m, 1H).

Example 57

Synthesis of 2-(6,7-dihydro-5H-pyrrolo[1,2-c]imidazol-1-yl)-2-[6-[4-[[4-[2-[4-[4-[(2,6-dioxo-3-piperidyl)amino]-2-fluoro-phenyl]-1-piperidyl]acetyl]piperazin-1-yl]methyl]phenyl]-4-fluoro-1-oxo-isoindolin-2-yl]-N-thiazol-2-yl-acetamide, Compound 57

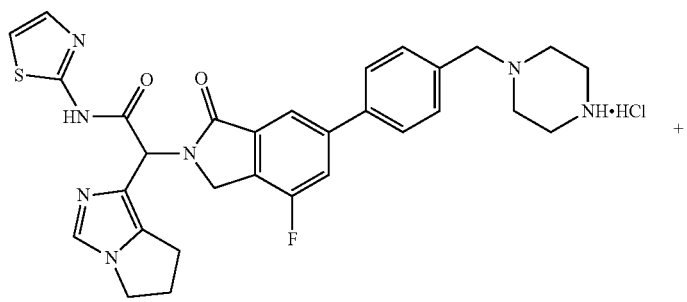

+

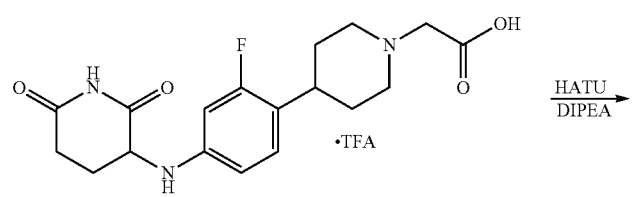

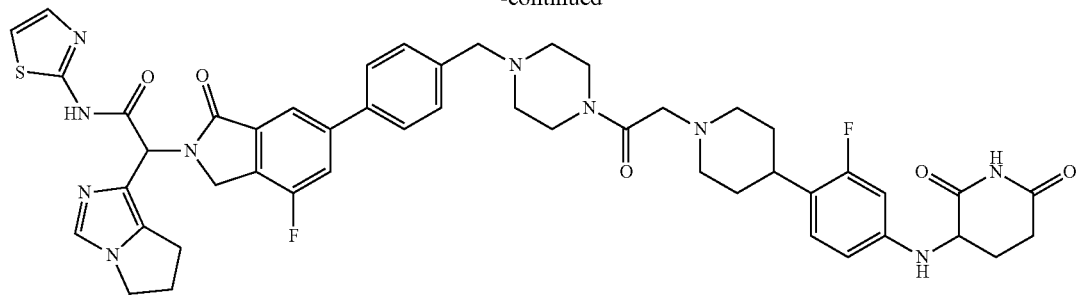

Compound 57 was prepared in 23% yield using the same procedure as Example 56, step 5 (2-(6,7-dihydro-5H-pyrrolo[1,2-c]imidazol-1-yl)-2-[6-[4-[[4-[2-[4-[4-[(2,6-dioxo-3-piperidyl)amino]phenyl]-1-piperidyl]acetyl]piperazin-1-yl]methyl]phenyl]-4-fluoro-1-oxo-isoindolin-2-yl]-N-thiazol-2-yl-acetamide), using 2-[4-[4-[(2,6-dioxo-3-piperidyl)amino]-2-fluoro-phenyl]-1-piperidyl]acetic acid, trifluoracetic acid salt instead of 2-[4-[4-[(2,6-dioxo-3-piperidyl)amino]phenyl]-1-piperidyl]acetic acid, trifluoracetic acid salt. LCMS (ESI+): 917.2 (M+H), $^1$H NMR (400 MHz, DMSO-d6) δ 10.67 (s, 1H), 7.77 (s, 1H), 7.70-7.61 (m, 3H), 7.59 (s, 1H), 7.44 (d, J=3.5 Hz, 1H), 7.39 (d, J=8.0 Hz, 2H), 7.33 (s, 2H), 7.19 (d, J=3.6 Hz, 1H), 6.91 (t, J=8.7 Hz, 1H), 6.48-6.27 (m, 2H), 6.09 (s, 1H), 5.80 (dd, J=7.9, 3.6 Hz, 1H), 4.74 (d, J=17.9 Hz, 1H), 4.27-4.15 (m, 2H), 3.60-3.31 (m, 6H), 3.12 (s, 2H), 2.89-2.63 (m, 4H), 2.63-2.53 (m, 1H), 2.48-2.22 (m, 7H), 2.07 (m, 3H), 1.95-1.74 (m, 1H), 1.65-1.40 (m, 4H).

Example 58

Synthesis of 2-(6,7-dihydro-5H-pyrrolo[1,2-c]imidazol-1-yl)-2-[6-[4-[[4-[2-[4-[4-[[(3S)-2,6-dioxo-3-piperidyl]amino]-2-fluoro-phenyl]-1-piperidyl]acetyl]piperazin-1-yl]methyl]phenyl]-4-fluoro-1-oxo-isoindolin-2-yl]-N-thiazol-2-yl-acetamide, Compound 58

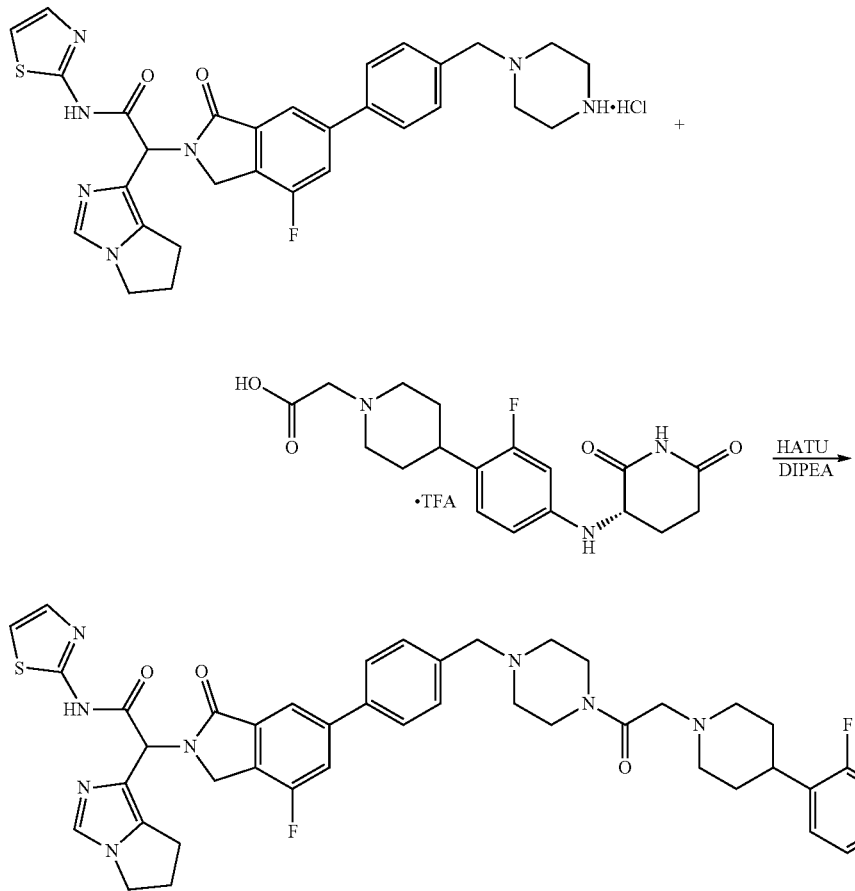

2-(6,7-Dihydro-5H-pyrrolo[1,2-c]imidazol-1-yl)-2-[4-fluoro-1-oxo-6-[4-(piperazin-1-ylmethyl)phenyl]isoindolin-2-yl]-N-thiazol-2-yl-acetamide; dihydrochloride (48 mg, 74.47 μmol) and 2-[4-[4-[[(3S)-2,6-dioxo-3-piperidyl]amino]-2-fluoro-phenyl]-1-piperidyl]acetic acid, trifluoroacetic acid salt (42.66 mg, 89.36 μmol) were mixed in DMF (0.5 mL), the reaction mixture was cooled to 0° C. N,N-Diisopropylethylamine (57.74 mg, 446.80 μmol, 77.82 μL) was added to the reaction mixture, and HATU (36.81 mg, 96.81 μmol) was added, and the reaction mixture was stirred for 1 h at 0° C. The reaction mixture was acidified with 4-5 drops of TFA, and injected directly on a RP C18 column (50 g C18) for purification (5% to 100% acetonitrile (+0.1% TFA) in water (+0.1% TFA) over 12 minutes). The pure fractions were neutralized with aqueous NaHCO₃ (ca. 60 mL), extracted twice with 1:4 isopropanol:chloroform mixture. The organic layer was dried over Na₂SO₄, filtered, and evaporated under reduced pressure to afford a solid. The solid was purified by silica gel chromatography (0% to 20% methanol in dichloromethane). The desired fractions were evaporated under reduced pressure. The residue was dissolved in dichloromethane, transferred to a 8 mL vial, and evaporated under reduced pressure. 1 mL water+1 mL acetonitrile were added, and the mixture was thoroughly sonicated, vortexed and sonicated again. The suspension was frozen and lyophilized to afford Compound 58 (19.2 mg, 20.73 μmol, 27.84% yield). LCMS (ESI+): 917.2 (M+H), 1H NMR (400 MHz, DMSO-d6) δ 12.53 (s, 1H), 10.78 (s, 1H), 7.84 (s, 1H), 7.81 (d, J=10.4 Hz, 1H), 7.77 (d, J=7.9 Hz, 2H), 7.62 (s, 1H), 7.49 (d, J=3.6 Hz, 1H), 7.45 (d, J=7.9 Hz, 2H), 7.26 (d, J=3.6 Hz, 1H), 6.98 (t, J=8.7 Hz, 1H), 6.50-6.40 (m, 2H), 6.16 (s, 1H), 5.99 (d, J=7.7 Hz, 1H), 4.84 (d, J=17.8 Hz, 1H), 4.37-4.21 (m, 2H), 4.00 (td, J=14.1, 11.6, 6.5 Hz, 2H), 3.58 (d, J=13.2 Hz, 5H), 3.47 (s, 3H), 3.14 (s, 2H), 2.88 (d, J=10.9 Hz, 3H), 2.83-2.41 (m, 4H), 2.34 (s, 3H), 2.16-1.99 (m, 4H), 1.87 (ddd, J=25.0, 12.1, 4.1 Hz, 1H), 1.72-1.51 (m, 4H).

Example 59

Synthesis of 2-(6,7-dihydro-5H-pyrrolo[1,2-c]imidazol-1-yl)-2-[6-[4-[[4-[2-[4-[[(3S)-2,6-dioxo-3-piperidyl]amino]-2-fluoro-phenyl]-1-piperidyl]-2-oxo-ethyl]piperazin-1-yl]methyl]phenyl]-4-fluoro-1-oxo-isoindolin-2-yl]-N-thiazol-2-yl-acetamide, Compound 59

Step 1: tert-butyl 2-[4-[[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperazin-1-yl]acetate

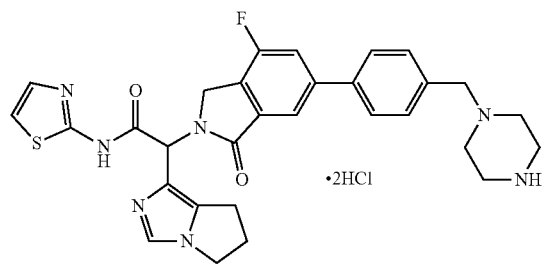

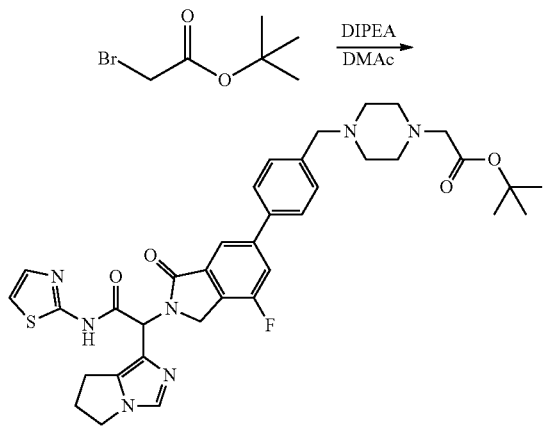

To a stirred solution of 2-(6,7-dihydro-5H-pyrrolo[1,2-c]imidazol-1-yl)-2-[4-fluoro-1-oxo-6-[4-(piperazin-1-ylmethyl)phenyl]isoindolin-2-yl]-N-thiazol-2-yl-acetamide dihydrochloride (109.5 mg, 160.78 μmol) in DMAc (1 mL) was added N,N-diisopropylethylamine (72.73 mg, 562.73 μmol, 98.02 μL) and tert-butyl 2-bromoacetate (34.50 mg, 176.86 μmol, 25.94 μL). The reaction mixture was stirred at ambient temperature. After completion, the reaction mixture was diluted with chloroform/isopropanol (4:1) and aqueous sodium bicarbonate was added. The organic layers were separated, washed with brine, dried over Na₂SO₄, filtered and concentrated under reduced pressure. The mixture was purified by silica gel column chromatography (dichloromethane:methanol) to give tert-butyl 2-[4-[[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperazin-1-yl]acetate (64 mg, 93.32 μmol, 58% yield). LCMS (ESI+): 686.3 (M+H)

Step 2: 2-[4-[[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperazin-1-yl]acetic acid, bis-trifluoroacetic acid salt

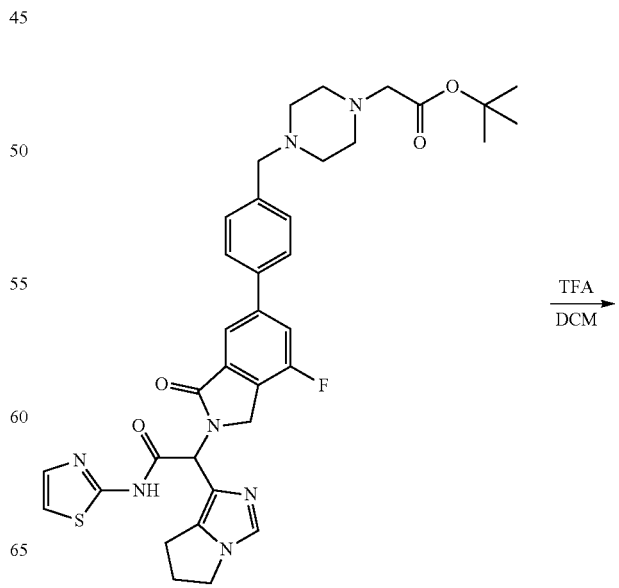

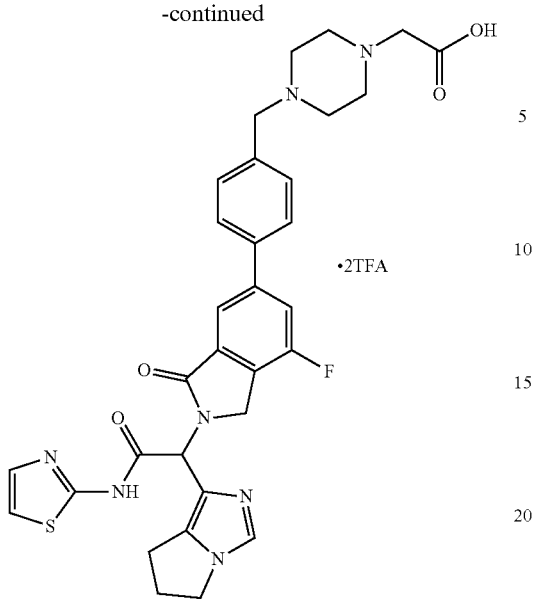

2-[4-[[4-[2-[1-(6,7-Dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperazin-1-yl]acetic acid, bis-trifluoroacetic acid salt was obtained from tert-butyl 2-[4-[[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperazin-1-yl]acetate in quantitative yield using the procedure for Example 10 step 3. LCMS (ESI+): 630.3 (M+H)

Step 3: N2-(6,7-dihydro-5H-pyrrolo[1,2-c]imidazol-1-yl)-2-[6-[4-[[4-[2-[4-[4-[[(3S)-2,6-dioxo-3-piperidyl]amino]-2-fluoro-phenyl]-1-piperidyl]-2-oxo-ethyl]piperazin-1-yl]methyl]phenyl]-4-fluoro-1-oxo-isoindolin-2-yl]-N-thiazol-2-yl-acetamide

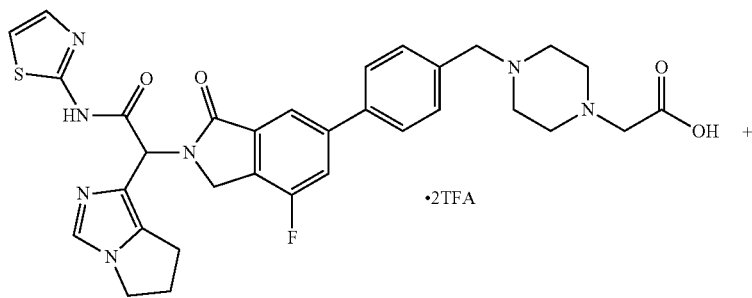

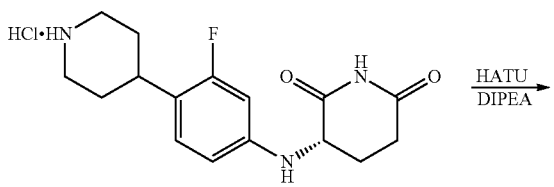

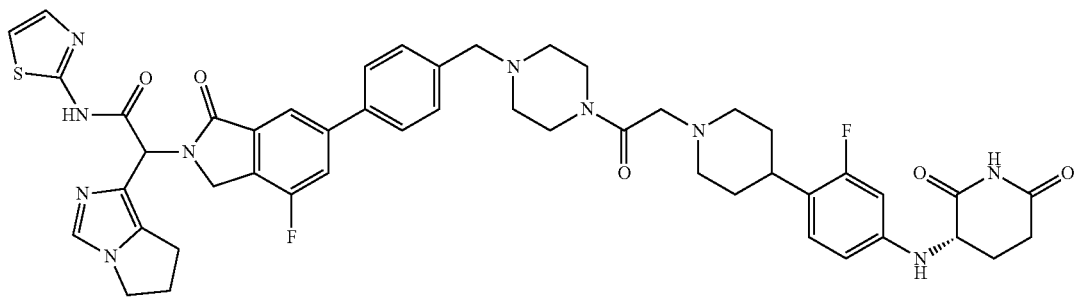

2-[4-[[4-[2-[1-(6,7-Dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperazin-1-yl]acetic acid, trifluoroacetic acid salt (78.79 mg, 91.86 μmol) and (3S)-3-[3-fluoro-4-(4-piperidyl)anilino]piperidine-2,6-dione; hydrochloride (37.68 mg, 110.23 μmol) were mixed in DMF and cooled to 0° C. N,N-Diisopropylethylamine (83.10 mg, 643.00 μmol, 112.00 μL) was added to the reaction mixture, and HATU (45.40 mg, 119.41 μmol) was added, and the reaction mixture was stirred for 1 h at 0° C. The reaction mixture was acidified with 4-5 drops of TFA and injected directly on a RP C18 column (50 g C18) for purification (5% to 100% acetonitrile in water+0.1% TFA over 12 minutes). The desired fractions were neutralized with aqueous NaHCO₃ (ca. 60 mL), extracted with 1:4 isopropanol:chloroform mixture X2. The organic layer was dried over Na₂SO₄, filtered, and evaporated under reduced pressure to afford a solid. The solid was purified by silica gel column chromatography (0% to 20% methanol in dichloromethane). The desired fractions were evaporated under reduced pressure. The residue was dissolved in dichloromethane, transferred to a 8 mL vial, and evaporated under reduced pressure. 1 mL water+1 mL acetonitrile were added, and the mixture was thoroughly sonicated, vortexed and sonicated again. The suspension was frozen and lyophilized to afford Compound 59 (45 mg, 48.58 μmol, 52.89% yield). LCMS (ESI+): 917.3 (M+H), ¹H-NMR (400 MHz, DMSO-d6) δ 12.52 (s, 1H), 10.79 (s, 1H), 7.85-7.79 (m, 2H), 7.76 (d, J=7.9 Hz, 2H), 7.61 (s, 1H), 7.49 (d, J=3.6 Hz, 1H), 7.42 (d, J=7.9 Hz, 2H), 7.26 (d, J=3.6 Hz, 1H), 6.95 (t, J=8.7 Hz, 1H), 6.48 (s, 1H), 6.45 (d, J=6.3 Hz, 1H), 6.16 (s, 1H), 6.03 (d, J=7.7 Hz, 1H), 4.83 (d, J=17.8 Hz, 1H), 4.48 (d, J=12.9 Hz, 1H), 4.37-4.20 (m, 2H), 4.16 (d, J=12.7 Hz, 1H), 4.07-3.93 (m, 2H), 3.59-3.46 (m, 3H), 3.44-3.23 (m, 2H), 3.13-2.98 (m, 2H), 2.88 (t, J=10.8 Hz, 2H), 2.82-2.36 (m, 10H), 2.14-2.03 (m, 2H), 1.93-1.81 (m, 1H), 1.77-1.57 (m, 4H), 1.42 (m, 1H).

Example 60

Synthesis of 2-(6,7-dihydro-5H-pyrrolo[1,2-c]imidazol-1-yl)-2-[6-[4-[[1-[2-[4-[4-[[(3S)-2,6-dioxo-3-piperidyl]amino]-2-fluoro-phenyl]-1-piperidyl]acetyl]-4-piperidyl]methyl]phenyl]-4-fluoro-1-oxo-isoindolin-2-yl]-N-thiazol-2-yl-acetamide, Compound 60

Step 1: tert-butyl 4-[[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]methyl]piperidine-1-carboxylate

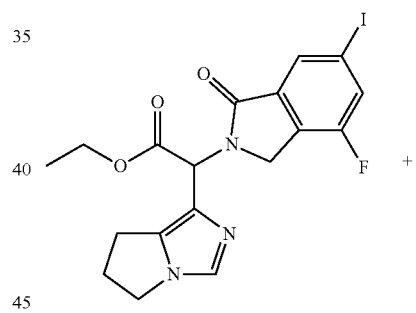

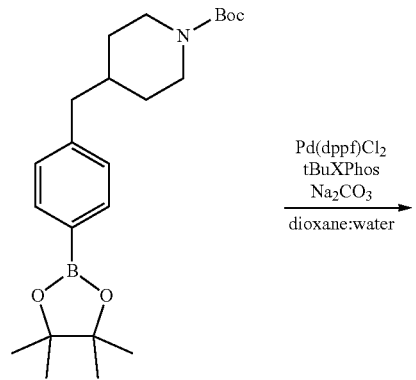

813
-continued

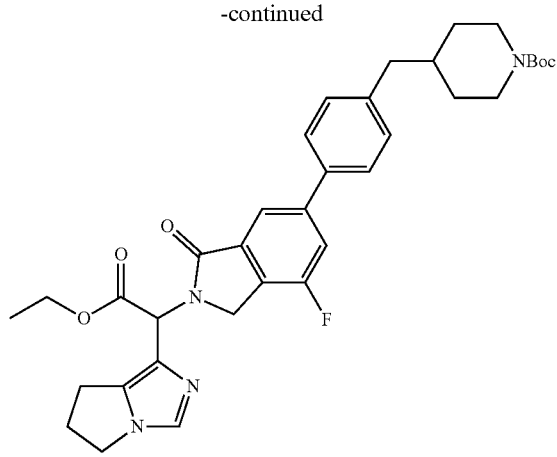

Ethyl 2-(6,7-dihydro-5H-pyrrolo[1,2-c]imidazol-1-yl)-2-(4-fluoro-6-iodo-1-oxo-isoindolin-2-yl)acetate (400 mg, 852.43 μmol) and tert-butyl 4-[[4-(4,4,5,5-tetramethyl-1,3,2-dioxaborolan-2-yl)phenyl]methyl]piperidine-1-carboxylate (461.86 mg, 1.15 mmol) were dissolved in dioxane (4.8 mL) and tBuXPhos (53.81 mg, 85.24 μmol) was added, followed by Sodium carbonate (198.77 mg, 1.88 mmol, 78.56 μL) dissolved in Water (1.2 mL). The mixture was degassed with argon and Pd(dppf)Cl$_2$ (31.18 mg, 42.62 μmol) was added. The reaction was sealed and heated at 80° C. on a heating block for 2 h. The mixture was concentrated and purified by silica gel chromatography on (0-100% ethyl acetate in hexane). The desired fractions were concentrated and re-purified by silica gel chromatography (0-20% methanol in ethyl acetate) to give tert-butyl 4-[[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]methyl]piperidine-1-carboxylate (380 mg, 616.16 μmol, 72.28% yield). LCMS (ESI+): 617.3 (M+H)

Step 2: [2-[6-[4-[(1-tert-butoxycarbonyl-4-piperidyl)methyl]phenyl]-4-fluoro-1-oxo-isoindolin-2-yl]-2-(6,7-dihydro-5H-pyrrolo[1,2-c]imidazol-1-yl)acetyl]oxylithium

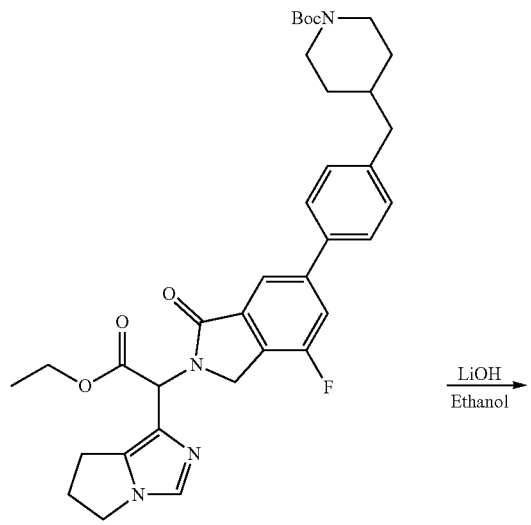

814
-continued

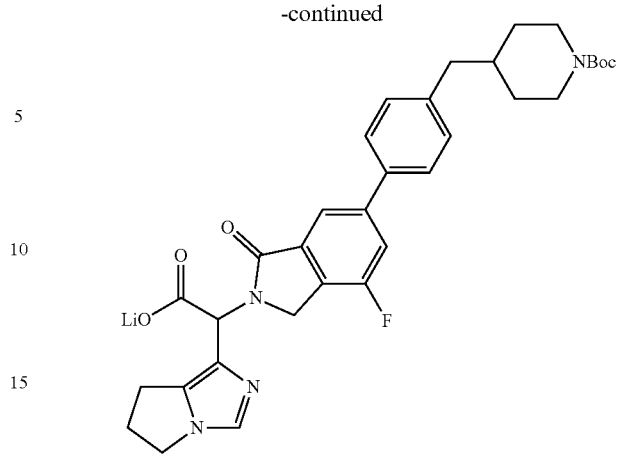

To a solution of tert-butyl 4-[[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]methyl]piperidine-1-carboxylate (380 mg, 616.16 μmol) in Ethanol (2.8 mL) was added Lithium hydroxide (1 M aqueous solution, 678 μmol, 678 μL) and stirred at ambient temperature. The reaction mixture was evaporated to dryness to afford [2-[6-[4-[(1-tert-butoxycarbonyl-4-piperidyl)methyl]phenyl]-4-fluoro-1-oxo-isoindolin-2-yl]-2-(6,7-dihydro-5H-pyrrolo[1,2-c]imidazol-1-yl)acetyl]oxylithium (366 mg, 616 μmol) as a yellow solid in quantitative yield. LCMS (ESI+): 589.2 (M+H)

Step 3: tert-butyl 4-[[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperidine-1-carboxylate

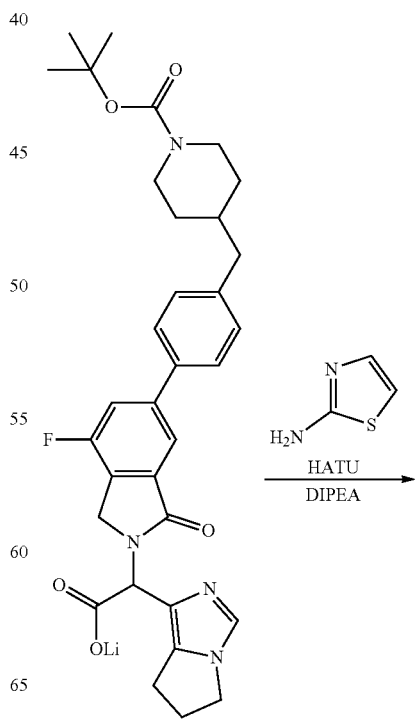

815
-continued

[2-[6-[4-[(1-tert-butoxycarbonyl-4-piperidyl)methyl]phenyl]-4-fluoro-1-oxo-isoindolin-2-yl]-2-(6,7-dihydro-5H-pyrrolo[1,2-c]imidazol-1-yl)acetyl]oxylithium (366.37 mg, 616.16 μmol) and thiazol-2-amine (64.79 mg, 646.97 μmol) were mixed in DMF, the reaction mixture was cooled to 0° C. N,N-Diisopropylethylamine (318.53 mg, 2.46 mmol, 429.29 μL) was added to the reaction mixture, and HATU (304.57 mg, 801.01 μmol) was added, and the reaction mixture was stirred for 30 min at 0° C. The reaction mixture was quenched with saturated NaHCO₃-solution and extracted with ethyl acetate. The organic layers were washed with water and brine, dried over Na₂SO₄, filtered and concentrated. The residue was purified by silica gel chromatography (0-10% methanol in dichloromethane) to afford tert-butyl 4-[[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperidine-1-carboxylate (250 mg, 372.69 μmol, 60.49% yield) LCMS (ESI+): 671.2 (M+H).

816

Step 4: 2-(6,7-dihydro-5H-pyrrolo[1,2-c]imidazol-1-yl)-2-[4-fluoro-1-oxo-6-[4-(4-piperidylmethyl)phenyl]isoindolin-2-yl]-N-thiazol-2-yl-acetamide hydrochloride

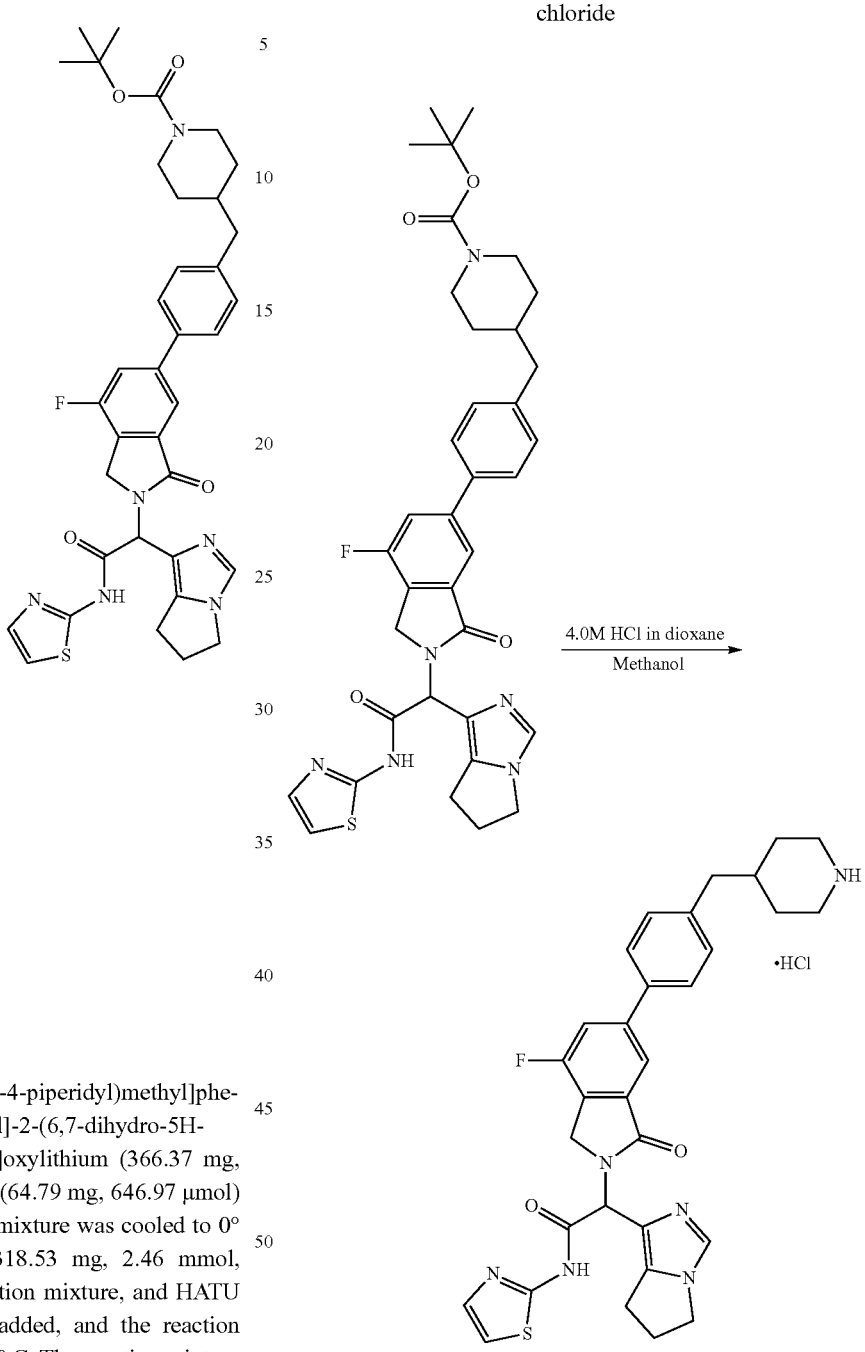

tert-Butyl 4-[[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]methyl]piperidine-1-carboxylate (250 mg, 372.69 μmol) was dissolved in methanol (3 mL) and Hydrogen chloride solution (4.0M in dioxane, 652.67 μL, 2.62 mmol) was added. The reaction mixture was heated at 40° C. for 4 hours. The volatiles were evaporated under reduce pressure. The material was submitted to high vacuum, frozen to −78° C. and thawed to afford a dense solid. The crude material was purified by ISCO column (dichloromethane:methanol=100:0→50:50) to give 2-(6,7-dihydro-5H-pyrrolo[1,2-c]imidazol-1-yl)-2-[4-fluoro-1- oxo-6-[4-(4-piperidylmethyl)phenyl]isoindolin-2-yl]-N-thiazol-2-yl-acetamide hydrochloride (157 mg, 258.59 μmol, 69.38% yield). LCMS (ESI+): 571.2 (M+H)

Step 5: 2-(6,7-dihydro-5H-pyrrolo[1,2-c]imidazol-1-yl)-2-[6-[4-[[1-[2-[4-[4-[[(3S)-2,6-dioxo-3-piperidyl]amino]-2-fluoro-phenyl]-1-piperidyl]acetyl]-4-piperidyl]methyl]phenyl]-4-fluoro-1-oxo-isoindolin-2-yl]-N-thiazol-2-yl-acetamide

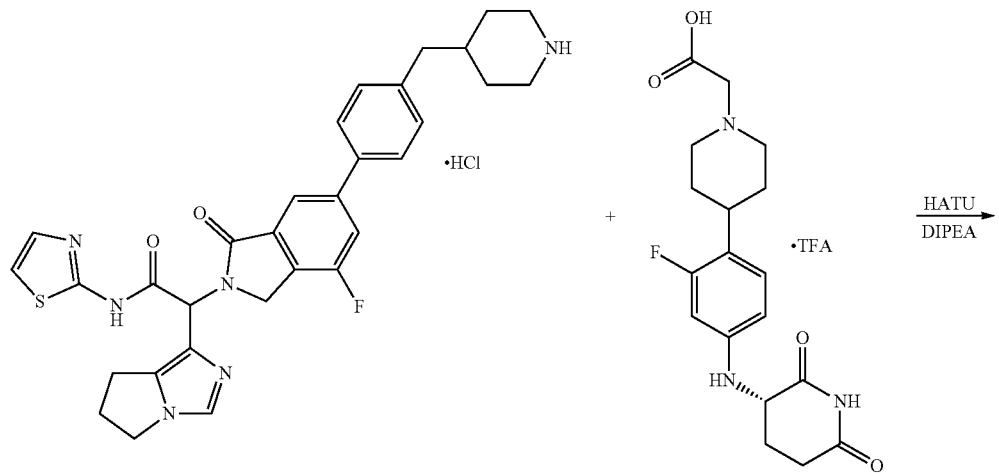

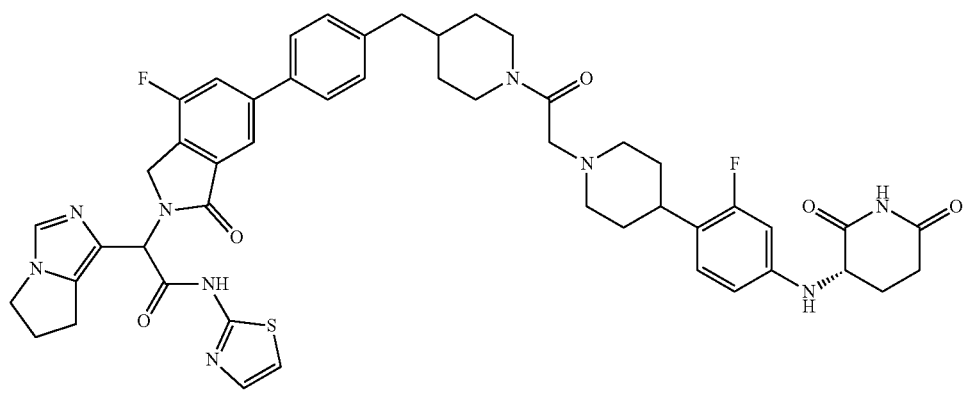

2-(6,7-dihydro-5H-pyrrolo[1,2-c]imidazol-1-yl)-2-[4-fluoro-1-oxo-6-[4-(4-piperidylmethyl)phenyl]isoindolin-2-yl]-N-thiazol-2-yl-acetamide; hydrochloride (47 mg, 77.41 μmol) and 2-[4-[4-[[(3S)-2,6-dioxo-3-piperidyl]amino]-2-fluoro-phenyl]-1-piperidyl]acetic acid, trifluoroacetic acid salt (44.35 mg, 92.89 μmol) were mixed in DMF and cooled to 0° C. N,N-Diisopropylethylamine (50.02 mg, 387.06 μmol, 67.42 μL) was added to the reaction mixture, and HATU (38.26 mg, 100.64 μmol) was added, and the reaction mixture was stirred for 1 h at 0° C. The reaction mixture was acidified with 4-5 drops of TFA and injected directly on a C18 column (50 g C18) for purification (5% to 100% acetonitrile in water+0.1% TFA). The desired fractions were neutralized with aqueous NaHCO₃ (ca. 60 mL), extracted twice with a 1:4 isopropanol:chloroform mixture. The organic layer was dried over Na2SO4, filtered, and evaporated under reduced pressure to afford a solid. The solid was purified by silica gel chromatography (0% to 20% methanol in dichloromethane). The desired fractions were evaporated under reduced pressure. The crude residue was dissolved in dichloromethane, transferred to an 8 mL vial, and evaporated under reduced pressure. water (1 mL) and acetonitrile (1 mL) were added, and the mixture was thoroughly sonicated, vortexed and sonicated again. The suspension was frozen and lyophilized to afford Compound 60 (44.9 mg, 48.52 μmol, 62.68% yield). LCMS (ESI+): 916.3 (M+H), $^1$H NMR (400 MHz, DMSO-d6) δ 12.52 (s, 1H), 10.78 (s, 1H), 7.82 (s, 1H), 7.78 (d, J=10.4 Hz, 1H), 7.72 (d, J=7.9 Hz, 2H), 7.61 (s, 1H), 7.49 (d, J=3.6 Hz, 1H), 7.32 (d, J=8.0 Hz, 2H), 7.26 (d, J=3.6 Hz, 1H), 6.98 (t, J=8.6 Hz, 1H), 6.50-6.40 (m, 2H), 6.16 (s, 1H), 5.99 (d, J=7.8 Hz, 1H), 4.83 (d, J=17.8 Hz, 1H), 4.36-4.29 (m, 2H), 4.25 (d, J=17.8 Hz, 1H), 4.12-3.93 (m, 3H), 3.21 (d, J=13.1 Hz, 1H), 3.10-2.84 (m, 4H), 2.82-2.66 (m, 3H), 2.65-2.54 (m, 6H), 2.07 (d, J=10.7 Hz, 3H), 1.94-1.78 (m, 2H), 1.75-1.54 (m, 6H), 1.30-1.13 (m, 2H), 1.02 (m, 1H).

Example 61

Synthesis of (2RS)-2-[4,7-Dichloro-6-[4-[4-[2-[4-[4-[[(3RS)-2,6-dioxo-3-piperidyl]amino]phenyl]-1-piperidyl]acetyl]piperazin-1-yl]phenyl]indazol-2-yl]-2-(6,7-dihydro-5H-pyrrolo[1,2-c]imidazol-1-yl)-N-thiazol-2-yl-acetamide, Compound 61

Step 1: 4-Bromo-3,6-dichloro-2-fluorobenzaldehyde

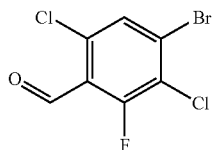

A solution of 1-bromo-2,5-dichloro-3-fluorobenzene (CAS 202865-57-4) (9.414 g, 38.6 mmol) in tetrahydrofuran (70 ml) was cooled in a dry ice/acetone bath. LDA, 2 mol/l in THF (21.2 ml, 42.5 mmol, Eq: 1.1) was added and the mixture was stirred at −75° C. for 20 min. N,N-dimethylformamide (2.82 g, 2.99 ml, 38.6 mmol, Eq: 1) was added dropwise and stirred for 1 hour. A solution of acetic acid in diethylether (1:1, 10 ml) was added. The mixture was allowed to warm to room temperature. Water was added and the mixture was extracted with ethylacetate. The organic layers were washed with water, dried (MgSO$_4$), filtered and concentrated in vacuo to give crude 4-bromo-3,6-dichloro-2-fluorobenzaldehyde (11.3 g, 41.6 mmol, >100%) as a light yellow solid. The compound was used for the next step without further purification.

Step 2: 6-Bromo-4,7-dichloro-1H-indazole

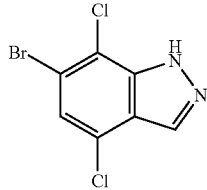 [SMILES: Clc1cc(Br)c(Cl)c2[nH]ncc12]

To a solution of 4-bromo-3,6-dichloro-2-fluorobenzaldehyde (Example 61, step 1) (10.5 g, 38.6 mmol) in Dioxane (50 ml) was added hydrazine hydrate (CAS 10217-52-4) (3.86 g, 3.78 ml, 77.2 mmol, Eq: 2.0). The mixture was stirred at room temperature for 3 days. Hydrazine hydrate (3.86 g, 3.78 ml, 77.2 mmol, Eq: 2.0) was added and the mixture was warmed to 70° C. for 7 hours. After cooling to room temperature water was added and the precipitated solid was collected by filtration. To the solid was added a small amount of acetonitrile and stirred for 2 hours. The solid was collected by filtration, washed with a small amount of acetonitrile and dried to give 6-bromo-4,7-dichloro-1H-indazole (7.84 g, 29.5 mmol, 76.4%) as an off-white solid. MS: m/e=267.0 ([M+H]$^+$).

Step 3: Ethyl 2-(6-bromo-4,7-dichloro-2H-indazol-2-yl)acetate

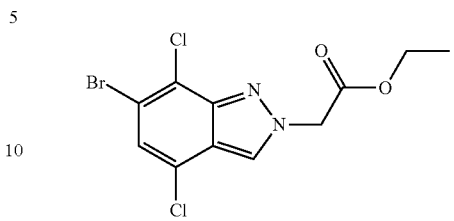

A mixture of 6-bromo-4,7-dichloro-1H-indazole (Example 61, step 2) (7.84 g, 29.5 mmol) and ethyl 2-bromoacetate (CAS 105-36-2) (9.85 g, 6.53 ml, 59 mmol, Eq: 2) in N,N-dimethylacetamide (11.5 ml) was heated to 100° C. for 25 hours. After cooling to room temperature, ice is added and the precipitated solid is collected by filtration and washed with water. The crude was dissolved in boiling ethanol. After cooling the solid was filtered, washed with ethanol and dried to afford ethyl 2-(6-bromo-4,7-dichloro-2H-indazol-2-yl)acetate (7.511 g, 21.3 mmol, 70.9%) MS: m/e=267.0 ([M+H]$^+$).

Step 4: tert-Butyl (2S)-2-[(2RS)-2-(6-bromo-4,7-chloro-indazol-2-yl)-3-ethoxy-3-oxo-propanoyl]pyrrolidine-1-carboxylate

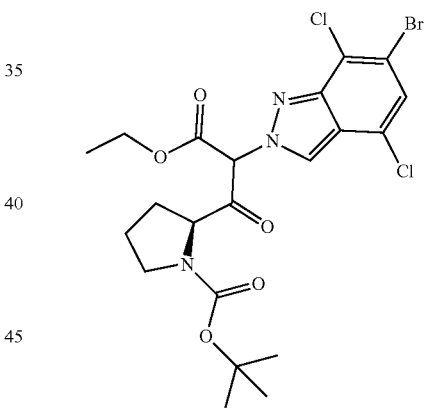

A solution of (tert-butoxycarbonyl)-L-proline (CAS 15761-39-4) (4.93 g, 22.9 mmol, Eq: 1.55) in Tetrahydrofuran (25 ml) was cooled in an ice bath. Carbonyldiimidazole (3.71 g, 22.9 mmol, Eq: 1.55) was added. The cooling bath was removed and the mixture was stirred for 3 h to give solution A. A solution of ethyl 2-(6-bromo-4,7-dichloro-2H-indazol-2-yl)acetate (Example 61, step 3) (5.2 g, 14.8 mmol, Eq: 1) in Tetrahydrofuran (7.5 ml) was cooled to −75° C. LDA, 2 mol/l in THF (11.4 ml, 22.9 mmol, Eq: 1.55) was added dropwise within 5 min. The mixture was stirred for 30 min at −75° C. Solution A was added dropwise within 5 min. The mixture was allowed to warm to room temperature in the cooling bath overnight. After addition of saturated aqueous NH$_4$Cl-solution, the mixture was extracted twice with ethylacetate. The organic layers were washed with water, combined, dried over sodium sulphate and concentrated to dryness to give tert-butyl (2S)-2-[(2RS)-2-(6-bromo-4,7-chloro-indazol-2-yl)-3-ethoxy-3-oxo-propanoyl]pyrrolidine-1-carboxylate (10.06 g>100%) which was used for the next step without further purification. MS: m/e=550.2 ([M+H]⁺).

Step 5: Ethyl (2RS)-2-(6-bromo-4,7-dichloro-indazol-2-yl)-2-(3-thioxo-2,5,6,7-tetrahydropyrrolo[1,2-c]imidazol-1-yl)acetate

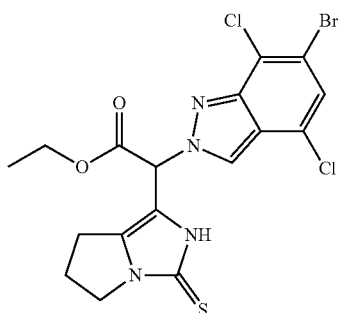 [SMILES: CCOC(=O)C(c1[nH]c(=S)n2c1CCC2)n1cc2c(Cl)cc(Br)c(Cl)c2n1]

A solution of tert-butyl (2S)-2-[(2RS)-2-(6-bromo-6,7-chloro-indazol-2-yl)-3-ethoxy-3-oxo-propanoyl]pyrrolidine-1-carboxylate (Example 61, step 4) (10 g, 18.2 mmol) in HCl, 4M in dioxane (31.9 ml) was stirred for 1 hour at room temperature. The mixture was concentrated to dryness. The residue was dissolved in ethanol (87.5 ml), potassium thiocyanate (2.35 g, 24.2 mmol, Eq: 1.33) and HCl, 0.5 M in ethanol (36.4 ml, 18.2 mmol, Eq: 1) were added and stirred for 36 hours. Water was added and the mixture was extracted with ethylacetate. The organic layers were washed with brine, dried over MgSO₄, filtered, concentrated and dried to give ethyl (2RS)-2-(6-bromo-4,7-dichloro-indazol-2-yl)-2-(3-thioxo-2,5,6,7-tetrahydropyrrolo[1,2-c]imidazol-1-yl)acetate (8.534 g, 17.4 mmol, 95.6%) which was used for the next step without further purification. MS: m/e=491.1 ([M+H]⁺).

Step 6: Ethyl (2RS)-2-(6-bromo-4,7-dichloro-indazol-2-yl)-2-(6,7-dihydro-5H-pyrrolo[1,2-c]imidazol-1-yl)acetate

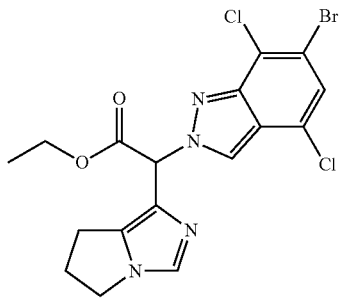 [SMILES: CCOC(=O)C(c1ncn2c1CCC2)n1cc2c(Cl)cc(Br)c(Cl)c2n1]

A solution of ethyl (2RS)-2-(6-bromo-4,7-dichloro-indazol-2-yl)-2-(3-thioxo-2,5,6,7-tetrahydropyrrolo[1,2-c]imidazol-1-yl)acetate (Example 61, step 5) (8.53 g, 17.4 mmol) in AcOH (32.2 ml) at 40° C. After cooling to room temperature, hydrogen peroxide 35% (6.76 g, 6.09 ml, 69.6 mmol, Eq: 4) was added dropwise. The reaction mixture was stirred for 1 hour at room temperature. The excess of hydrogen peroxide was destroyed by addition of saturated sodium sulfit solution. After addition of some water (just enough to dissolve all salts) and ethylacetate the mixture was brought to pH 9 by careful addition of solid sodium carbonate. The mixture was extracted with ethylacetate. The organic layers were washed with water, dried over sodium sulphate and concentrated. The crude product was purified by chromatography (SiO₂, 0-100% ethylacetate in heptane) to give ethyl (2RS)-2-(6-bromo-4,7-dichloro-indazol-2-yl)-2-(6,7-dihydro-5H-pyrrolo[1,2-c]imidazol-1-yl)acetate (3.21 g, 6.67 mmol, 40.3%) as a light yellow solid. MS: m/e=457.1 ([M+H]⁺).

Step 7: tert-Butyl 4-[4-[4,7-dichloro-2-[(1RS)-1-(6,7-dihydro-5H-pyrrolo[1,2-c]imidazol-1-yl)-2-ethoxy-2-oxo-ethyl]indazol-6-yl]phenyl]piperazine-1-carboxylate

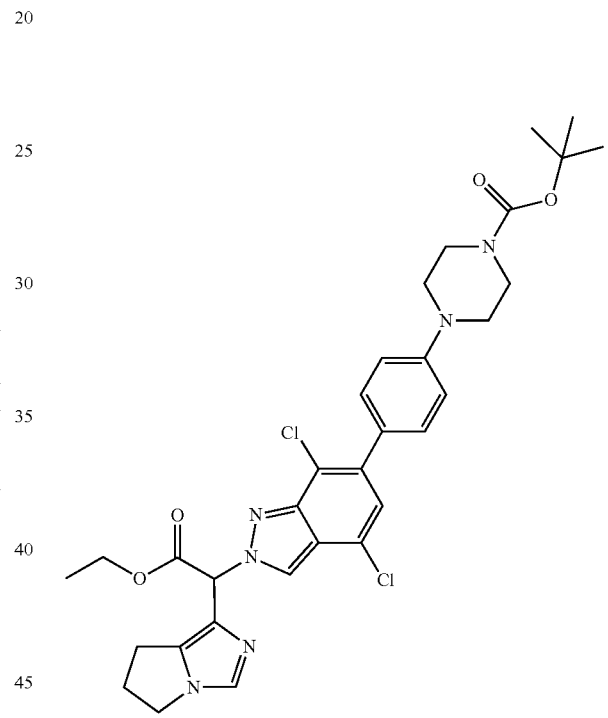

(2RS)-2-(6-Bromo-4,7-dichloro-indazol-2-yl)-2-(6,7-dihydro-5H-pyrrolo[1,2-c]imidazol-1-yl)acetate (Example 61, step 6) (200 mg, 437 µmol) and (4-(4-(tert-butoxycarbonyl)piperazin-1-yl)phenyl)boronic acid (CAS 457613-78-4) (401 mg, 1.31 mmol, Eq: 3) were mixed with toluene (5.3 ml), degassed by bubbling argon through the mixture under ultra sonic treatment. [1,1'-Bis(diphenylphosphino)ferrocene]dichloropalladium(II) (31.9 mg, 43.7 µmol, Eq: 0.1) was added and the mixture was stirred for 40 min at 115° C. in a sealed tube. The mixture was cooled to room temperature, diluted with ethylacetate, washed with half concentrated sodium carbonate solution, dried over sodium sulphate and concentrated. The crude material was purified by flash chromatography (SiO₂, 0% to 100% ethylacetate:methanol 3:2 in ethylacetate) to give tert-butyl 4-[4-[4,7-dichloro-2-[(1RS)-1-(6,7-dihydro-5H-pyrrolo[1,2-c]imidazol-1-yl)-2-ethoxy-2-oxo-ethyl]indazol-6-yl]phenyl]piperazine-1-carboxylate (191.5 mg, 29.9 mmol, 63.1%) as a light brown solid. MS: m/e=639.5 ([M+H]⁺).

823

Step 8: tert-Butyl 4-[4-[4,7-dichloro-2-[(1RS)-1-(6,7-dihydro-5H-pyrrolo[1,2-c]imidazol-1-yl)-2-oxo-2-(thiazol-2-ylamino)ethyl]indazol-6-yl]phenyl]piperazine-1-carboxylate

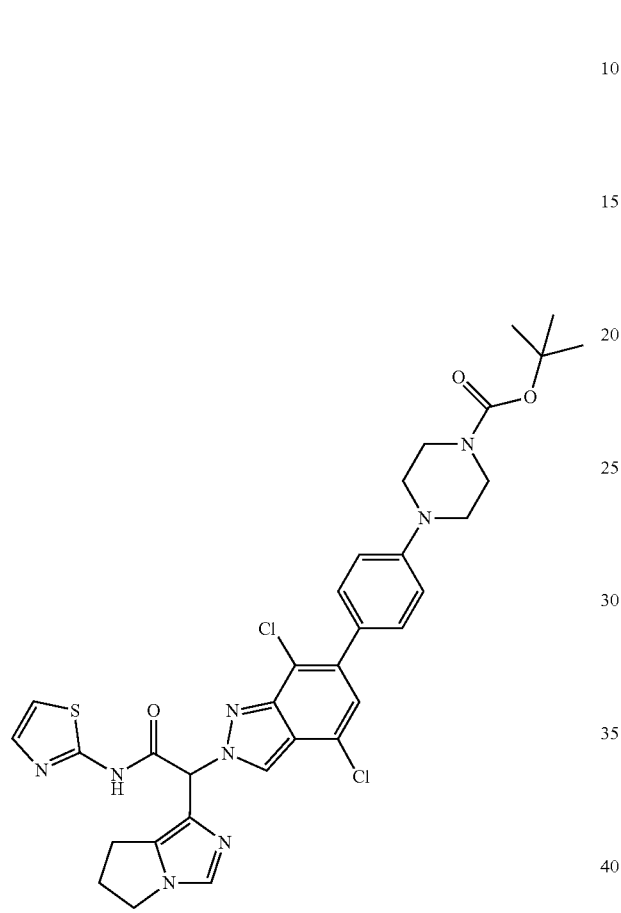

tert-Butyl 4-[4-[4,7-dichloro-2-[(1RS)-1-(6,7-dihydro-5H-pyrrolo[1,2-c]imidazol-1-yl)-2-ethoxy-2-oxo-ethyl]indazol-6-yl]phenyl]piperazine-1-carboxylate (Example 61, step 7) (190 mg, 0.297 mmol) was dissolved in 3 ml of THF. LiOH (1M in water) (0.45 ml, 0.446 mmol, 1.5 equiv.) was added. The reaction mixture was stirred at room temperature for 30 minutes. The reaction mixture was concentrated in vacuo. The residue was dissolved in 3 ml of N,N-dimethylformamide. Thiazol-2-amine (36 mg, 0.356 mmol, 1.2 equiv.) and Hunig's base (0.156 ml, 0.89 mmol, 3 equiv.) were added followed by HATU (136 mg, 0.356 mmol, 1.2 equiv.). The mixture was stirred at room temperature for 2 hours. The reaction mixture was extracted with ethyl acetate and water. The aqueous layer was back-extracted with ethyl acetate. The organic layers were washed with water and brine. The organic layers were combined, dried over sodium sulfate, filtered and concentrated to dryness. The crude product was purified by flash chromatography on a silica gel column eluting with an ethyl acetate:methanol 100:0 to 70:30 gradient to obtain the desired product (94 mg, 44% yield) as a light brown solid, MS: m/e=691.5 ([M+H]$^+$).

824

Step 9: (2RS)-2-[4,7-Dichloro-6-(4-piperazin-1-ylphenyl)indazol-2-yl]-2-(6,7-dihydro-5H-pyrrolo[1,2-c]imidazol-1-yl)-N-thiazol-2-yl-acetamide hydrochloride salt

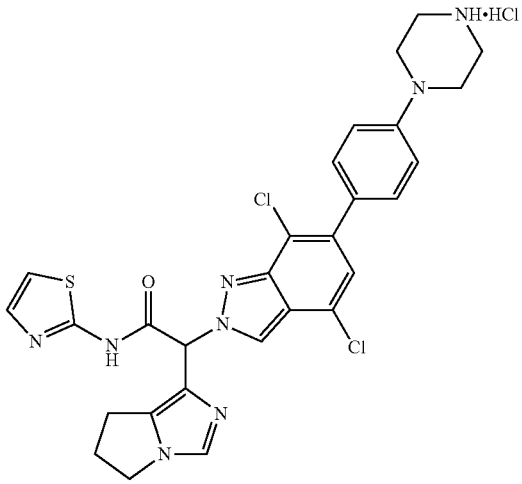

tert-Butyl 4-[4-[4,7-dichloro-2-[(1RS)-1-(6,7-dihydro-5H-pyrrolo[1,2-c]imidazol-1-yl)-2-oxo-2-(thiazol-2-ylamino)ethyl]indazol-6-yl]phenyl]piperazine-1-carboxylate (Example 61, step 9) (92 mg, 0.133 mmol) and HCl (4 M in dioxane) (1.7 ml, 6.63 mmol, 50 equiv.) were combined with 3 ml of dichloromethane and 1.8 ml of methanol. The reaction mixture was stirred at room temperature for 1 hour. The reaction mixture was concentrated to dryness and used without further purification. The desired product (93 mg, quantitative) was obtained as a light yellow solid, MS: m/e=591.4 ([M+H]$^+$).

Step 10: tert-Butyl 4-[4-[[(3RS)-2,6-dioxo-3-piperidyl]amino]phenyl]piperidine-1-carboxylate

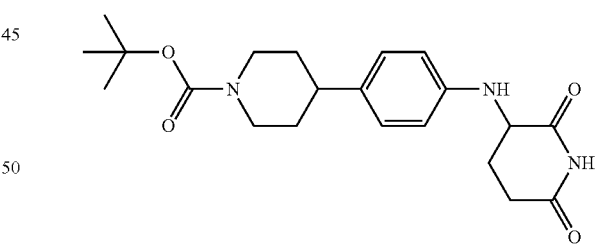

tert-Butyl 4-(4-aminophenyl)piperidine-1-carboxylate (CAS 170011-57-1) (798 mg, 2.89 mmol) was dissolved in 10 ml of acetonitrile. Sodium bicarbonate (485 mg, 5.77 mmol, 2 equiv.) was added followed by 3-bromopiperidine-2,6-dione (CAS 62595-74-8) (610 mg, 3.18 mmol, 1.1 equiv.). The reaction mixture was stirred at 90° C. for 16 hours. The reaction mixture was cooled to room temperature, adsorbed on Isolute® and purified by flash chromatography on a silica gel column eluting with an ethyl acetate:heptane 30:70 to 100:0 gradient. The desired tert-butyl 4-[4-[[(3RS)-2,6-dioxo-3-piperidyl]amino]phenyl]piperidine-1-carboxylate (850 mg, 76% yield) was obtained as an off-white solid, MS: m/e=359.4 (([M-tBu+H]$^+$).

Step 11: (3RS)-3-[4-(4-Piperidyl)anilino]piperidine-2,6-dione hydrochloride

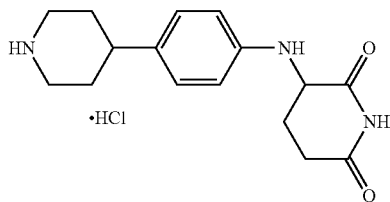 [SMILES: O=C1CCC(Nc2ccc(C3CCNCC3)cc2)C(=O)N1 ; Cl]

tert-Butyl 4-[4-[[(3RS)-2,6-dioxo-3-piperidyl]amino]phenyl]piperidine-1-carboxylate (Example 61, step 10) (850 mg, 2.19 mmol) and HCl (4 M in dioxane) (5.48 ml, 21.9 mmol, 10 equiv.) were combined with 10 ml of methanol at 0-5° C. in an ice bath. The reaction mixture was stirred at room temperature for 18 hours. The reaction mixture was concentrated to dryness and used without further purification. The desired (3RS)-3-[4-(4-piperidyl)anilino]piperidine-2,6-dione hydrochloride (818 mg, quantitative, purity=87%) was obtained as an off-white solid, MS: m/e=286.1 ([M+H]$^+$).

Step 12: tert-Butyl 2-[4-[4-[[(3RS)-2,6-dioxo-3-piperidyl]amino]phenyl]-1-piperidyl]acetate

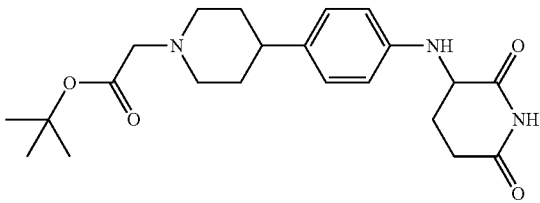 [SMILES: CC(C)(C)OC(=O)CN1CCC(c2ccc(NC3CCC(=O)NC3=O)cc2)CC1]

A mixture of (3RS)-3-[4-(4-piperidyl)anilino]piperidine-2,6-dione hydrochloride (Example 61, step 11) (200 mg, 0.618 mmol), tert-butyl 2-bromoacetate (CAS 5292-43-3) (157 mg, 0.119 ml, 0.803 mmol, 1.3 equiv.) and Hunig's base (399 mg, 0.539 ml, 3.09 mmol, equiv.) in 4.0 ml of N,N-Dimethylformamide was stirred at room temperature for 2 hours. The reaction mixture was extracted with ethyl acetate and water. The aqueous layer was backextracted with ethyl acetate. The organic layers were combined, dried over sodium sulfate, filtered and concentrated to dryness. The crude product was purified by flash chromatography on a silica gel column eluting with an ethyl acetate:heptane 50:50 to 100:0 gradient. The desired tert-butyl 2-[4-[4-[[(3RS)-2,6-dioxo-3-piperidyl]amino]phenyl]-1-piperidyl]acetate (164 mg, 66% yield) was obtained as a white solid, MS: m/e=402.2 ([M+H]$^+$).

Step 13: 2-[4-[4-[[(3RS)-2,6-Dioxo-3-piperidyl]amino]phenyl]-1-piperidyl]acetic acid hydrochloride salt

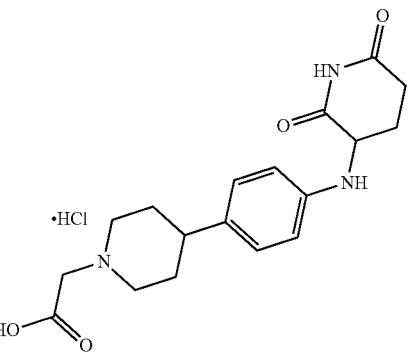

To a solution of tert-Butyl 2-[4-[4-[[(3RS)-2,6-dioxo-3-piperidyl]amino]phenyl]-1-piperidyl]acetate (Example 61, step 12) (543 mg, 1.35 mmol, Eq: 1) in ethyl acetate (8 ml) was added 4 M hydrogen chloride solution in 1,4-dioxane (6.3 g, 6 ml, 24 mmol, Eq: 17.7) at room temperature and stirring was continued over the weekend. The product was collected by filtration, washed with ethyl acetate and dried under vacuo. The desired 2-[4-[4-[[(3RS)-2,6-Dioxo-3-piperidyl]amino]phenyl]-1-piperidyl]acetic acid (537 mg, 1.27 mmol, 93.6% yield) was obtained as light red solid. MS: m/e=346.2 ([M+H]$^+$).

Step 14: (2RS)-2-[4,7-Dichloro-6-[4-[4-[2-[4-[4-[[(3RS)-2,6-dioxo-3-piperidyl]amino]phenyl]-1-piperidyl]acetyl]piperazin-1-yl]phenyl]indazol-2-yl]-2-(6,7-dihydro-5H-pyrrolo[1,2-c]imidazol-1-yl)-N-thiazol-2-yl-acetamide

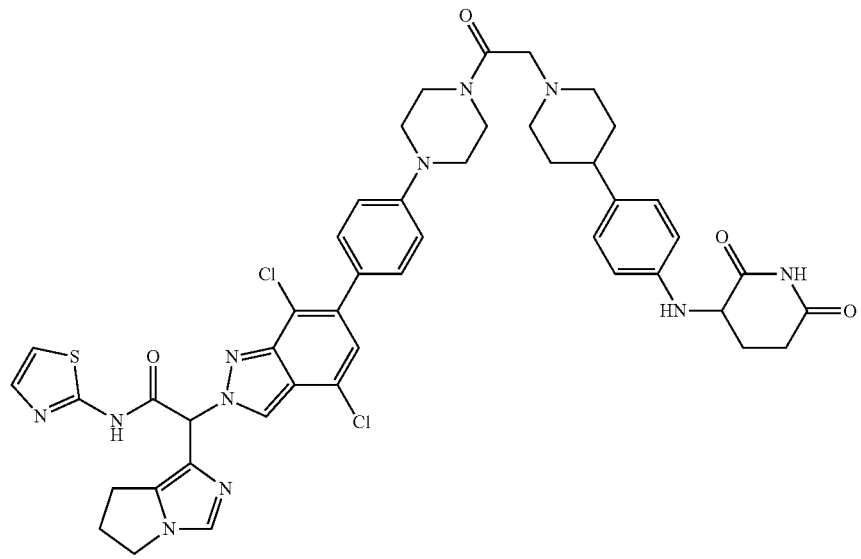 [SMILES: O=C1CCC(Nc2ccc(C3CCN(CC(=O)N4CCN(c5ccc(-c6cc(Cl)c7cn(C(C(=O)Nc8nccs8)c8ncn9c8CCC9)nc7c6Cl)cc5)CC4)CC3)cc2)C(=O)N1]

(2RS)-2-[4,7-Dichloro-6-(4-piperazin-1-ylphenyl)inda-zol-2-yl]-2-(6,7-dihydro-5H-pyrrolo[1,2-c]imidazol-1-yl)-N-thiazol-2-yl-acetamide hydrochloride salt (Example 61, step 9) (50 mg, 0.08 mmol) and 2-[4-[4-[[(3RS)-2,6-dioxo-3-piperidyl]amino]phenyl]-1-piperidyl]acetic acid hydrochloride salt (Example 61, step 13) (30 mg, 0.08 mmol, 1.0 equiv.) were dissolved in 0.5 ml of N,N-dimethylformamide. Hunig's base (0.07 ml, 0.4 mmol, 5 equiv.) was added followed by HATU (45 mg, 0.12 mmol, 1.5 equiv.). The reaction mixture was stirred at room temperature for 2 hours. The reaction mixture was extracted with saturated NaHCO₃-solution and three times with a mixture of dichloromethane:methanol (9:1). The organic layers were washed with water. The organic layers were combined, dried over sodium sulfate, filtered and concentrated to dryness. The crude product was purified by flash chromatography on a silica gel column eluting with a dichloromethane:methanol 100:0 to 80:20 gradient to obtain Compound 61 (17 mg, 23% yield) as an off-white solid, MS: m/e=920.5 ([M+H]⁺).

Example 62

Synthesis of (2RS)-2-(6,7-Dihydro-5H-pyrrolo[1,2-c]imidazol-1-yl)-2-[7-fluoro-6-[6-[4-[4-oxo-4-[1-oxo-2-[(3RS)-2,6-dioxo-3-piperidyl]isoindolin-4-yl]oxy-1-piperidyl]butyl]piperazin-1-yl]-3-pyridyl]indazol-2-yl]-N-thiazol-2-yl-acetamide, Compound 62

Step 1: Ethyl 2-(6-bromo-7-fluoro-2H-indazol-2-yl)acetate

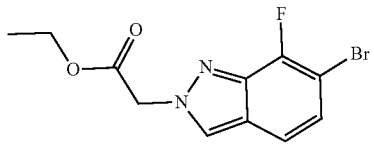 [SMILES: CCOC(=O)Cn1cc2ccc(Br)c(F)c2n1]

The title compound was obtained as a light yellow solid, MS: m/e=302.9 (M+H⁺), using chemistry similar to that described in Example 1, step 3 starting from 6-bromo-7-fluoro-1H-indazole.

Step 2: tert-Butyl (2S)-2-[(2RS)-2-(6-bromo-7-fluoro-indazol-2-yl)-3-ethoxy-3-oxo-propanoyl]pyrrolidine-1-carboxylate

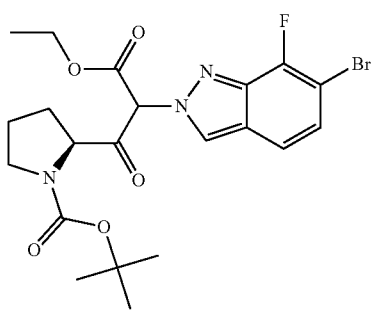 [SMILES: CCOC(=O)C(C(=O)[C@@H]1CCCN1C(=O)OC(C)(C)C)n1cc2ccc(Br)c(F)c2n1]

The title compound was obtained as a light yellow solid, MS: m/e=498.2/500.2 ([M+H]⁺) Br isotopes, using chemistry similar to that described in Example 61, step 4 starting from ethyl 2-(6-bromo-7-fluoro-2H-indazol-2-yl)acetate (Example 62, step 1).

Step 3: Ethyl (2RS)-2-(6-bromo-7-fluoro-indazol-2-yl)-2-(3-thioxo-2,5,6,7-tetrahydropyrrolo[1,2-c]imidazol-1-yl)acetate

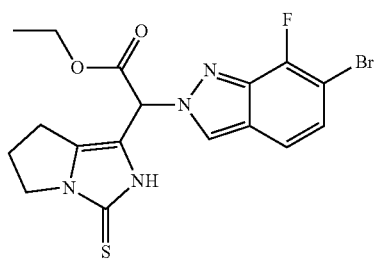 [SMILES: CCOC(=O)C(c1[nH]c(=S)n2c1CCC2)n1cc2ccc(Br)c(F)c2n1]

The title compound was obtained as a light yellow solid, MS: m/e=439.2/441.2 ([M+H]⁺ bromo isotopes) using chemistry similar to that described in Example 62, step 5 starting from tert-butyl (2S)-2-[(2RS)-2-(6-bromo-7-fluoro-indazol-2-yl)-3-ethoxy-3-oxo-propanoyl]pyrrolidine-1-carboxylate (Example 62, step 2).

Step 4: Ethyl (2RS)-2-(6-bromo-7-fluoro-indazol-2-yl)-2-(6,7-dihydro-5H-pyrrolo[1,2-c]imidazol-1-yl)acetate

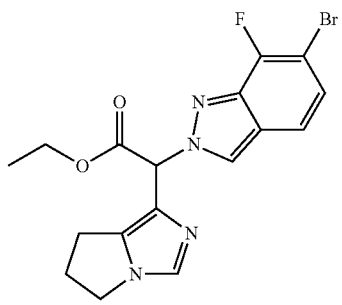 [SMILES: CCOC(=O)C(c1ncn2c1CCC2)n1cc2ccc(Br)c(F)c2n1]

The title compound was obtained as a light brown amorphous solid, MS: m/e=407.2/409.2 ([M+H]⁺) Bromo isotopes using chemistry similar to that described in Example 62, step 6 starting from (2RS)-2-(6-bromo-7-fluoro-indazol-2-yl)-2-(3-thioxo-2,5,6,7-tetrahydropyrrolo[1,2-c]imidazol-1-yl)acetate (Example 62, step 3).

Step 5: tert-Butyl 4-[5-[7-fluoro-2-[(1RS)-1-(6,7-dihydro-5H-pyrrolo[1,2-c]imidazol-1-yl)-2-ethoxy-2-oxo-ethyl]indazol-6-yl]-2-pyridyl]piperazine-1-carboxylate

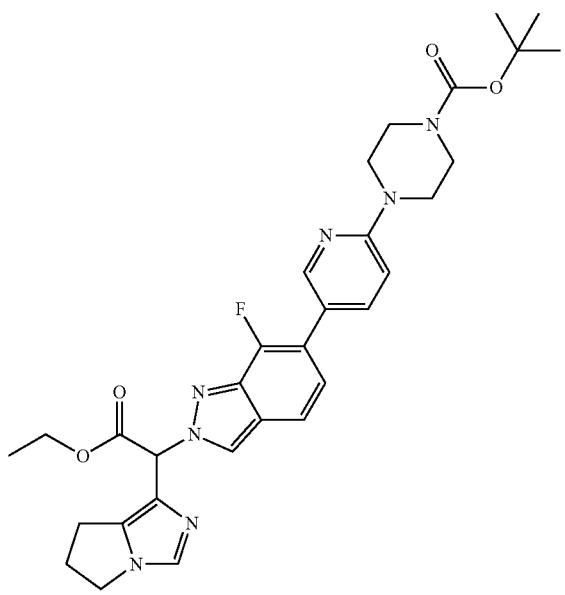 [SMILES: CCOC(=O)C(c1ncn2c1CCC2)n1cc2ccc(-c3ccc(N4CCN(C(=O)OC(C)(C)C)CC4)nc3)c(F)c2n1]

The title compound was obtained as a light brown amorphous solid, MS: m/e=590.5 ([M+H]$^+$) using chemistry similar to that described in Example 62, step 7 starting from ethyl (2RS)-2-(6-bromo-7-fluoro-indazol-2-yl)-2-(6,7-dihydro-5H-pyrrolo[1,2-c]imidazol-1-yl)acetate (Example 62, step 4).

Step 6: tert-Butyl 4-[5-[7-fluoro-2-[(1RS)-1-(6,7-dihydro-5H-pyrrolo[1,2-c]imidazol-1-yl)-2-oxo-2-(thiazol-2-ylamino)ethyl]indazol-6-yl]-2-pyridyl]piperazine-1-carboxylate

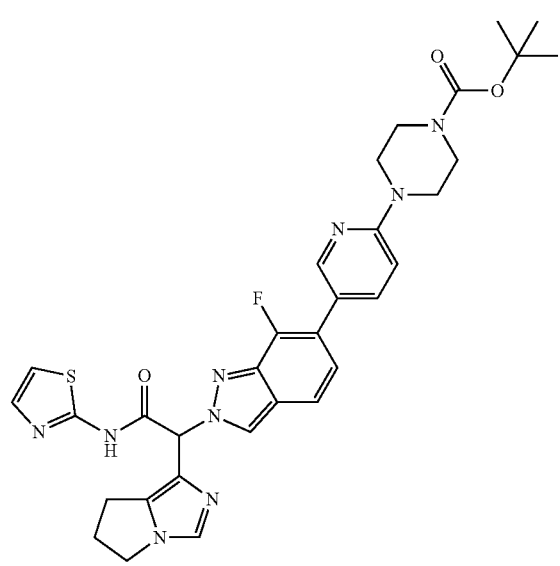 [SMILES: CC(C)(C)OC(=O)N1CCN(c2ccc(-c3ccc4cn(C(C(=O)Nc5nccs5)c5ncn6c5CCC6)nc4c3F)cn2)CC1]

The title compound was obtained as a light brown solid, MS: m/e=644.4 ([M+H]$^+$), using chemistry similar to that described in Example 62, step 8 starting from tert-butyl 4-[5-[7-fluoro-2-[(1RS)-1-(6,7-dihydro-5H-pyrrolo[1,2-c]imidazol-1-yl)-2-ethoxy-2-oxo-ethyl]indazol-6-yl]-2-pyridyl]piperazine-1-carboxylate (Example 62, step 5) and thiazol-2-amine.

Step 7: (2RS)-2-(6,7-Dihydro-5H-pyrrolo[1,2-c]imidazol-1-yl)-2-[7-fluoro-6-(6-piperazin-1-yl-3-pyridyl)indazol-2-yl]-N-thiazol-2-yl-acetamide

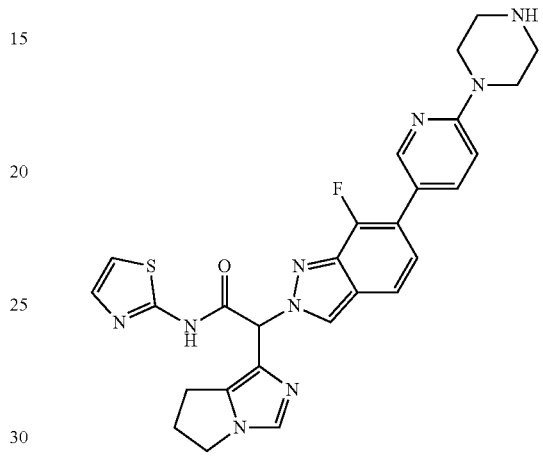

The title compound was obtained as a light brown solid, MS: m/e=544.4 ([M+H]$^+$), using chemistry similar to that described in Example 62, step 9 starting from tert-butyl 4-[5-[7-fluoro-2-[(1RS)-1-(6,7-dihydro-5H-pyrrolo[1,2-c]imidazol-1-yl)-2-oxo-2-(thiazol-2-ylamino)ethyl]indazol-6-yl]-2-pyridyl]piperazine-1-carboxylate (Example 62, step 6).

Step 8: tert-Butyl 4-[4-[5-[7-fluoro-2-[(1RS)-1-(6,7-dihydro-5H-pyrrolo[1,2-c]imidazol-1-yl)-2-oxo-2-(thiazol-2-ylamino)ethyl]indazol-6-yl]-2-pyridyl]piperazin-1-yl]butanoate

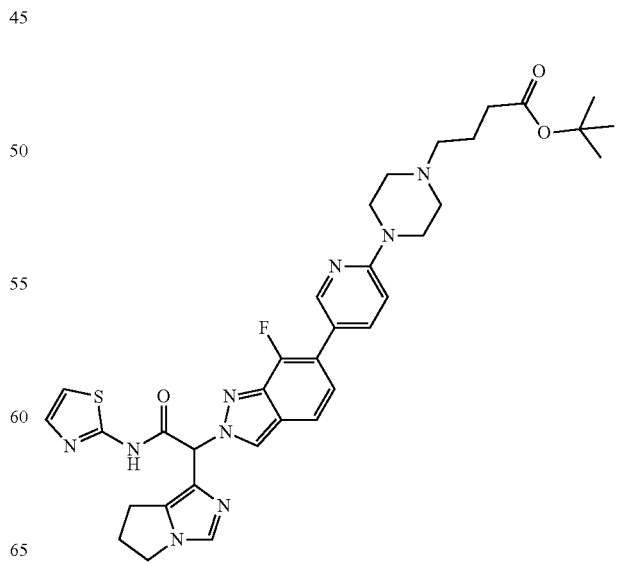

(2RS)-2-(6,7-Dihydro-5H-pyrrolo[1,2-c]imidazol-1-yl)-2-[7-fluoro-6-(6-piperazin-1-yl-3-pyridyl)indazol-2-yl]-N-thiazol-2-yl-acetamide (Example 62, step 7) (50 mg, 0.092 mmol) and Hunig's base (0.080 ml, 0.046 mmol, 5 equiv.) were dissolved in 1.0 ml of N,N-dimethylformamide. tert-Butyl 4-bromobutanoate (CAS 110661-91-1) (33 mg, 0.024 ml, 0.147 mmol, 1.6 equiv.) was added and the reaction mixture was stirred at 60° C. for 7 hours. The reaction mixture was extracted with water and two times with ethyl acetate. The organic layers were washed with water and brine. The organic layers were combined, dried over sodium sulfate, filtered and concentrated to dryness. The crude product was purified by flash chromatography on a silica gel column eluting with a dichloromethane:methanol 100:0 to 95:5 gradient to obtain the desired product (43 mg, 68% yield) as a light brown oil.

Step 9: (2RS)-2-(6,7-Dihydro-5H-pyrrolo[1,2-c]imidazol-1-yl)-2-[7-fluoro-6-[6-[4-[4-oxo-4-[4-[1-oxo-2-[(3RS)-2,6-dioxo-3-piperidyl]isoindolin-4-yl]oxy-1-piperidyl]butyl]piperazin-1-yl]-3-pyridyl]indazol-2-yl]-N-thiazol-2-yl-acetamide

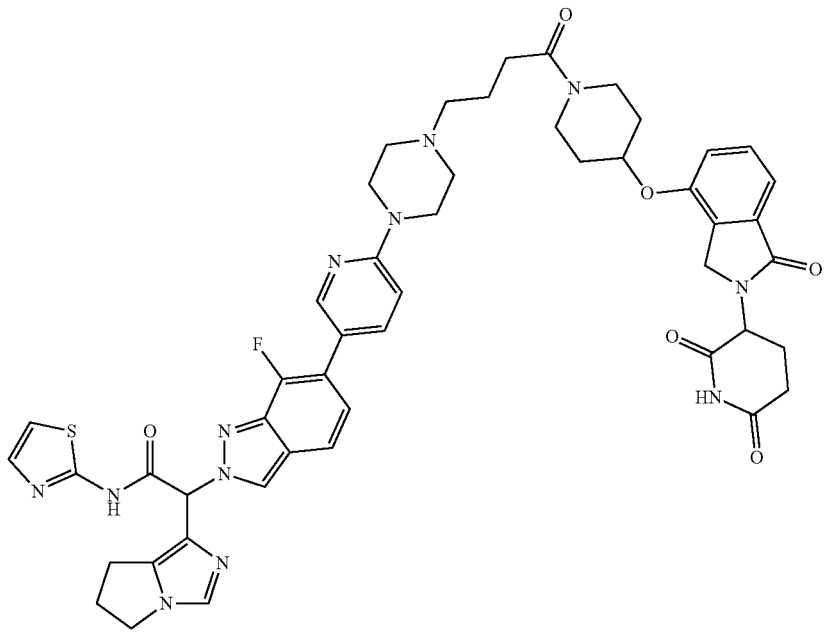 [SMILES: O=C1CCC(N2Cc3c(OC4CCN(C(=O)CCCN5CCN(c6ccc(-c7ccc8cn(C(C(=O)Nc9nccs9)c9ncn%10c9CCC%10)nc8c7F)cn6)CC5)CC4)cccc3C2=O)C(=O)N1]

tert-Butyl 4-[4-[5-[7-fluoro-2-[(1RS)-1-(6,7-dihydro-5H-pyrrolo[1,2-c]imidazol-1-yl)-2-oxo-2-(thiazol-2-ylamino)ethyl]indazol-6-yl]-2-pyridyl]piperazin-1-yl]butanoate (Example 62, step 8) (43 mg, 0.062 mmol) was dissolved in 0.3 ml of dichloromethane and trifluoroacetic acid (148 mg, 0.10 ml, 1.3 mmol, 20 equiv.) was added. The reaction mixture was stirred at room temperature for 90 minutes. The reaction mixture was concentrated to dryness. The residue and (3RS)-3-[1-oxo-4-(4-piperidyloxy)isoindolin-2-yl]piperidine-2,6-dione hydrochloride (CAS 1061605-57-9) (25 mg, 0.065 mmol, 1 equiv.) were dissolved in 0.6 ml of N,N-dimethylformamide. Hunig's base (0.11 ml, 0.62 mmol, 10 equiv.) was added followed by TBTU (22 mg, 0.069 mmol, 1.1 equiv.). The reaction mixture was stirred at room temperature for 2 hours. The reaction mixture was extracted with water and three times with a mixture of dichloromethane:methanol (9:1). The organic layers were washed with water. The organic layers were combined, dried over sodium sulfate, filtered and concentrated to dryness. The crude product was purified by flash chromatography on an amino-silica gel column eluting with a dichloromethane:methanol 100:0 to 95:5 gradient to obtain Compound 62 (30 mg, 50% yield) as an off-white foam, MS: m/e=955.6 ([M+H]$^+$).

Example 63

Synthesis of (2RS)-2-(6,7-Dihydro-5H-pyrrolo[1,2-c]imidazol-1-yl)-2-[7-fluoro-6-[6-[4-[2-[4-[4-[[(3RS)-2,6-dioxo-3-piperidyl]amino]phenyl]-1-piperidyl]acetyl]piperazin-1-yl]-3-pyridyl]indazol-2-yl]-N-thiazol-2-yl-acetamide

Step 1: tert-Butyl 4-[4-[[(3RS)-2,6-dioxo-3-piperidyl]amino]phenyl]piperidine-1-carboxylate

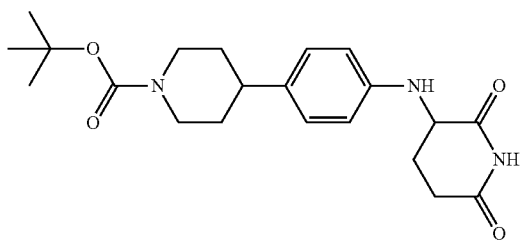 [SMILES: CC(C)(C)OC(=O)N1CCC(c2ccc(NC3CCC(=O)NC3=O)cc2)CC1]

tert-Butyl 4-(4-aminophenyl)piperidine-1-carboxylate (CAS 170011-57-1) (798 mg, 2.89 mmol) was dissolved in 10 ml of acetonitrile. Sodium bicarbonate (485 mg, 5.77 mmol, 2 equiv.) was added followed by 3-bromopiperidine-2,6-dione (CAS 62595-74-8) (610 mg, 3.18 mmol, 1.1 equiv.). The reaction mixture was stirred at 90° C. for 16 hours. The reaction mixture was cooled to room temperature, adsorbed on Isolute® and purified by flash chromatography on a silica gel column eluting with an ethyl acetate: heptane 30:70 to 100:0 gradient. The desired tert-butyl 4-[4-[[(3RS)-2,6-dioxo-3-piperidyl]amino]phenyl]piperidine-1-carboxylate (850 mg, 76% yield) was obtained as an off-white solid, MS: m/e=359.4 (([M-tBu+H]$^+$).

Step 2: (3RS)-3-[4-(4-Piperidyl)anilino]piperidine-2,6-dione hydrochloride

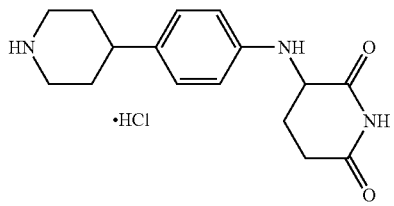 [SMILES: O=C1CCC(Nc2ccc(C3CCNCC3)cc2)C(=O)N1 ; Cl]

tert-Butyl 4-[4-[[(3RS)-2,6-dioxo-3-piperidyl]amino]phenyl]piperidine-1-carboxylate (Example 63, step 1) (850 mg, 2.19 mmol) and HCl (4 M in dioxane) (5.48 ml, 21.9 mmol, 10 equiv.) were combined with 10 ml of methanol at 0-5° C. in an ice bath. The reaction mixture was stirred at room temperature for 18 hours. The reaction mixture was concentrated to dryness and used without further purification. The desired (3RS)-3-[4-(4-piperidyl)anilino]piperidine-2,6-dione hydrochloride (818 mg, quantitative, purity=87%) was obtained as an off-white solid, MS: m/e=286.1 ([M+H]$^+$).

Step 3: tert-Butyl 2-[4-[4-[[(3RS)-2,6-dioxo-3-piperidyl]amino]phenyl]-1-piperidyl]acetate

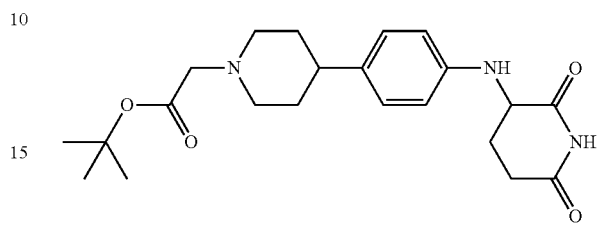

A mixture of (3RS)-3-[4-(4-piperidyl)anilino]piperidine-2,6-dione hydrochloride (Example 63, step 2) (200 mg, 0.618 mmol), tert-butyl 2-bromoacetate (CAS 5292-43-3) (157 mg, 0.119 ml, 0.803 mmol, 1.3 equiv.) and Hunig's base (399 mg, 0.539 ml, 3.09 mmol, 5 equiv.) in 4.0 ml of N,N-Dimethylformamide was stirred at room temperature for 2 hours. The reaction mixture was extracted with ethyl acetate and water. The aqueous layer was backextracted with ethyl acetate. The organic layers were combined, dried over sodium sulfate, filtered and concentrated to dryness. The crude product was purified by flash chromatography on a silica gel column eluting with an ethyl acetate:heptane 50:50 to 100:0 gradient. The desired tert-butyl 2-[4-[4-[[(3RS)-2,6-dioxo-3-piperidyl]amino]phenyl]-1-piperidyl]acetate (164 mg, 66% yield) was obtained as a white solid, MS: m/e=402.2 ([M+H]$^+$).

Step 4: [2-[4-[4-[(3RS)-2,6-Dioxo-3-piperidyl]amino]phenyl]-1-piperidyl]acetic acid hydrochloride

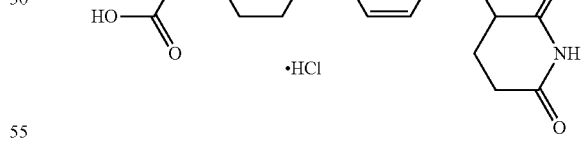

To a solution of tert-butyl 2-[4-[4-[[(3RS)-2,6-dioxo-3-piperidyl]amino]phenyl]-1-piperidyl]acetate (Example 63, step 3) (543 mg, 1.35 mmol) in 8.0 ml of ethyl acetate was added HCl (4 M in dioxane) (6.3 g, 6 ml, 24 mmol, 17.7 equiv.) at room temperature and stirring was continued for 72 hours. The product was collected by filtration, washed with ethyl acetate and dried under high vacuum. The desired 2-[4-[4-[(3RS)-2,6-dioxo-3-piperidyl]amino]phenyl]-1-piperidyl]acetic acid hydrochloride (quantitative yield) was obtained as light red solid, MS: m/e=346.2 ([M+H]$^+$).

Step 5: (2RS)-2-(6,7-Dihydro-5H-pyrrolo[1,2-c]imidazol-1-yl)-2-[7-fluoro-6-[6-[4-[2-[4-[4-[[(3RS)-2,6-dioxo-3-piperidyl]amino]phenyl]-1-piperidyl]acetyl]piperazin-1-yl]-3-pyridyl]indazol-2-yl]-N-thiazol-2-yl-acetamide

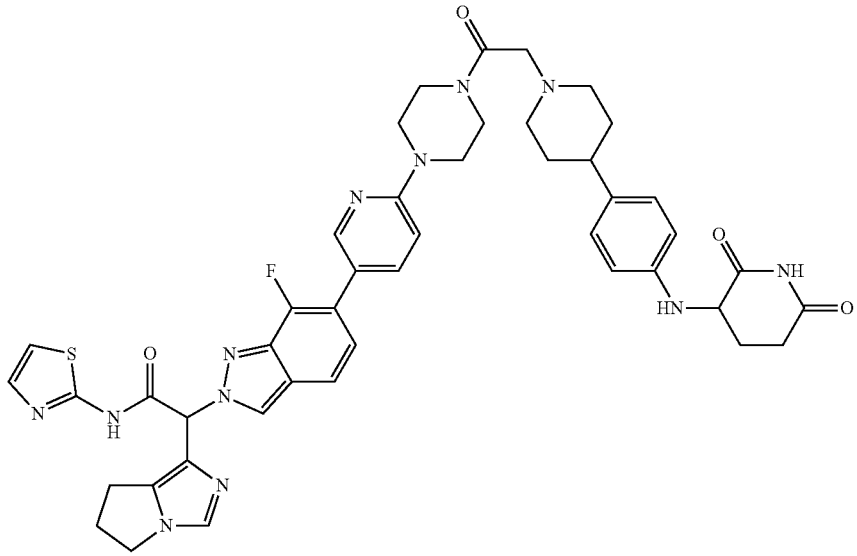 [SMILES: O=C1CCC(Nc2ccc(C3CCN(CC(=O)N4CCN(c5ccc(-c6ccc7cn(C(C(=O)Nc8nccs8)c8ncn9c8CCC9)nc7c6F)cn5)CC4)CC3)cc2)C(=O)N1]

The title compound, Compound 63, was obtained as a light grey solid, MS: m/e=871.7 ([M+H]$^+$), using chemistry similar to that described in Example 1, step 14 starting from (2RS)-2-(6,7-dihydro-5H-pyrrolo[1,2-c]imidazol-1-yl)-2-[7-fluoro-6-(6-piperazin-1-yl-3-pyridyl)indazol-2-yl]-N-thiazol-2-yl-acetamide (Example 62, step 7) and 2-[4-[4-[[(3RS)-2,6-dioxo-3-piperidyl]amino]phenyl]-1-piperidyl]acetic acid hydrochloride (Example 63, step 4).

Example 64

Synthesis of 2-(6,7-dihydro-5H-pyrrolo[1,2-c]imidazol-1-yl)-2-[6-[6-[4-[2-[4-[4-[(2,6-dioxo-3-piperidyl)amino]-2-fluoro-phenyl]-1-piperidyl]acetyl]piperazin-1-yl]-3-pyridyl]-4-fluoro-indazol-2-yl]-N-thiazol-2-yl-acetamide, Compound 64

Step 1: ethyl 2-(6-bromo-4-fluoro-indazol-2-yl)acetate 6-bromo-4-fluoro-1H-indazole (15.0 g, 69.76 mmol) and ethyl 2-bromoacetate (46.60 g, 279.04 mmol, 30.86 mL) in N,N-dimethylformamide (170 mL) were stirred at 100° C. for 35 h. The reaction mixture was cooled to ambient temperature and poured onto crushed ice. The mixture was extracted with ethyl acetate (300 mL×3). The combined organic layers were washed with 10% Sodium bicarbonate solution, brine, concentrated under reduced pressure and the residue was purified by silica gel chromatography (10-30% Ethyl acetate:Petroleum Ether) to afford ethyl 2-(6-bromo-4-fluoro-indazol-2-yl)acetate (11 g, 30.69 mmol, 44% yield) as an off white solid. LCMS (ESI+) m/z: 303.0 [M+H], $^1$H-NMR (DMSO-d6) δ 8.66 (s, 1H0, 7.77 (s, 1H), 7.08 (d, J=9.9 Hz, 1H), 5.44 (s, 2H), 4.18 (q, J=6.6 Hz, 2H), 1.22 (t, J=6.9 Hz, 3H).

Step 2: tert-butyl 2-[2-(6-bromo-4-fluoro-indazol-2-yl)-3-ethoxy-3-oxo-propanoyl]pyrrolidine-1-carboxylate

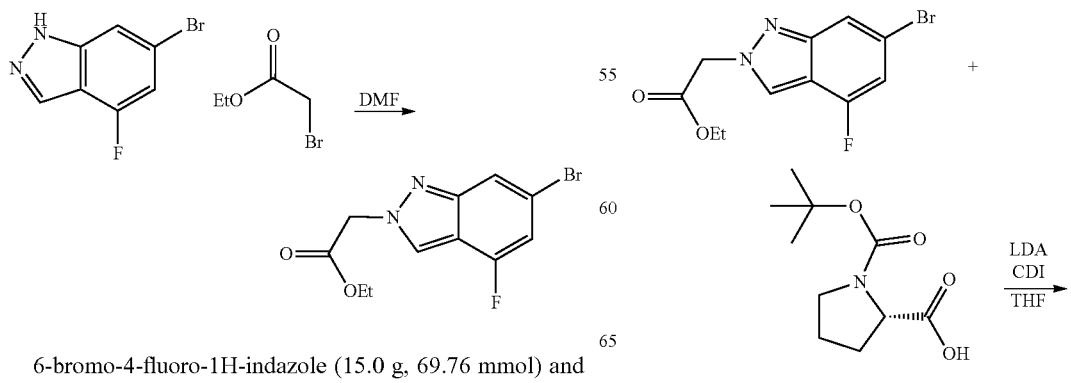

-continued

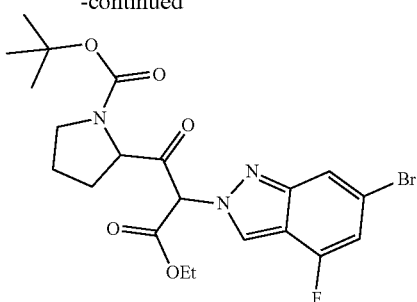

Ethyl 2-(6-bromo-4-fluoro-indazol-2-yl)acetate (10 g, 33.21 mmol) was dissolved in tetrahydrofuran (100 mL) and the solution was cooled to −78° C. Lithium diisopropylamide (0.7 M in tetrahydrofuran, 142 mL, 99.63 mmol) was added to the reaction mixture, upon which a yellow coloured precipitate was observed. The reaction mixture was stirred for 1 hour in −78° C. In a separate vessel, N-(tert-Butoxycarbonyl)-L-proline was dissolved in tetrahydrofuran (100 mL) and 1,1'-Carbonyldiimidazole (8.08 g, 49.82 mmol) was added under stirring. The reaction mixture was stirred for 1 hour. The N-(tert-Butoxycarbonyl)-L-proline/1,1'-Carbonyldiimidazole reaction mixture was slowly added to the 250 mL round bottom flask containing ethyl 2-(6-bromo-4-fluoro-indazol-2-yl)acetate and lithium diisopropylamide. The reaction mixture was stirred for 1 hour at −78° C., warmed to room temperature and stirred for 30 h at room temperature. A saturated ammonium chloride solution was added to the reaction mixture, and the organic layer was separated. Aqueous layer was extracted twice with ethyl acetate (250 mL×2). The combined organic layers were dried over sodium sulfate, concentrated under reduced pressure and the residue was purified by silica gel chromatography (0 to 100% ethyl acetate in petroleum ether) to afford tert-butyl 2-[2-(6-bromo-4-fluoro-indazol-2-yl)-3-ethoxy-3-oxo-propanoyl]pyrrolidine-1-carboxylate (8 g, 14.45 mmol, 44% yield) as a white solid. LCMS (ESI+): m/z 498.0/500.0 [M+H, Br pattern]

Step 3: Ethyl 2-(6-bromo-4-fluoro-indazol-2-yl)-3-oxo-3-pyrrolidin-2-yl-propanoate

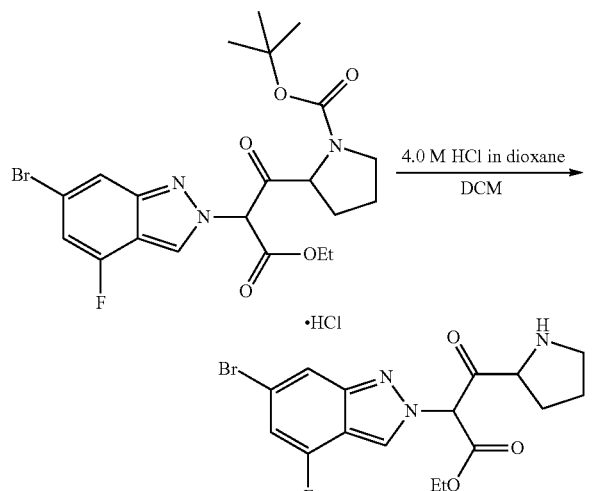

tert-Butyl 2-[2-(6-bromo-4-fluoro-indazol-2-yl)-3-ethoxy-3-oxo-propanoyl]pyrrolidine-1-carboxylate (16 g, 32.11 mmol) was dissolved in dichloromethane (160 mL) and the solution was cooled to 0° C. HCl (4.0 M in dioxane, 32.1 mL, 128.43 mmol) was added dropwise at 0° C. The reaction mixture was stirred at room temperature for 9 hours. The reaction mixture was evaporated to dryness to yield ethyl 2-(6-bromo-4-fluoro-indazol-2-yl)-3-oxo-3-pyrrolidin-2-yl-propanoate hydrochloride (13.5 g, 23.29 mmol, 72.55% yield) as a yellow colored solid. LCMS (ESI+): 398.0/400.1 (M+H, Br pattern).

Step 4: Ethyl 2-(6-bromo-4-fluoro-indazol-2-yl)-2-(3-thioxo-2,5,6,7-tetrahydropyrrolo[1,2-c]imidazol-1-yl)acetate

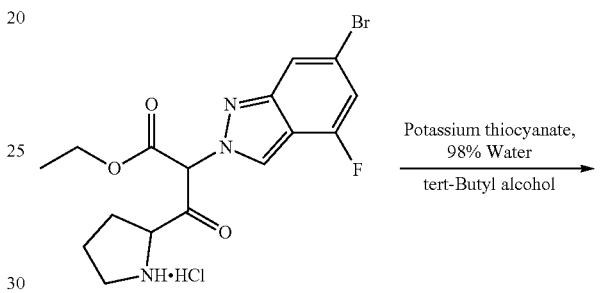

Potassium thiocyanate (2.47 g, 25.43 mmol, 1.31 mL) was added to a stirred solution of ethyl 2-(6-bromo-4-fluoro-indazol-2-yl)-3-oxo-3-[pyrrolidin-2-yl]propanoate (6.75 g, 16.95 mmol) in Water (75 mL) and tert-butyl alcohol (24.5 mL) under a nitrogen atmosphere. The reaction mixture was heated to 90° C. for 8 hours. The reaction mixture was cooled to room temperature and extracted with 10% methanol in dichloromethane solution. The organic layer was dried over anhydrous sodium sulfate and concentrated. The residue was purified by silica gel chromatography (0 to 100% ethyl acetate in petroleum ether) to afford ethyl 2-(6-bromo-4-fluoro-indazol-2-yl)-2-(3-thioxo-2,5,6,7-tetrahydropyrrolo[1,2-c]imidazol-1-yl)acetate (2.9 g, 6.40 mmol, 38% yield) as a yellow colored solid. LCMS (ESI+) M/z: 439.0/441.0 [M+H, Br pattern], $^1$H-NMR (400 MHz, DMSO-d6) δ 12.11 (s, 1H), 8.69 (s, 1H), 7.81 (s, 1H), 7.11 (d, J=9.6 Hz, 1H), 6.65 (s, 1H), 4.31-4.19 (m, 2H), 3.81-3.69 (m, 2H), 2.62-2.80 (m, 2H), 2.49-2.39 (m, 2H), 1.20 (t, J=6.8 Hz, 3H).

Step 5: ethyl 2-(6-bromo-4-fluoro-indazol-2-yl)-2-(6,7-dihydro-5H-pyrrolo[1,2-c]imidazol-1-yl)acetate

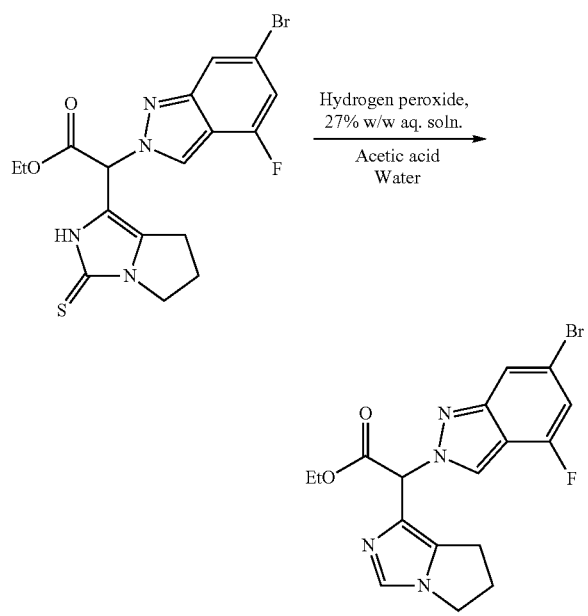

Ethyl 2-(6-bromo-4-fluoro-indazol-2-yl)-2-(3-thioxo-2,5,6,7-tetrahydropyrrolo[1,2-c]imidazol-1-yl)acetate (5.9 g, 13.43 mmol) was dissolved in Acetic acid (56 mL) and Water (19 mL). The solution was cooled to −10° C. Under a nitrogen atmosphere, Hydrogen peroxide (27% w/w aq. soln., stabilized, 1.37 g, 40.29 mmol, 1.25 mL) was added dropwise. The reaction was stirred at −10° C. for 100 minutes. A saturated sodium bicarbonate solution was added to the reaction mixture. The reaction mixture was extracted with ethyl acetate. The organic layer was washed with brine, dried over anhydrous sodium sulfate, filtered and concentrated to afford ethyl 2-(6-bromo-4-fluoro-indazol-2-yl)-2-(6,7-dihydro-5H-pyrrolo[1,2-c]imidazol-1-yl)acetate (4.1 g, 7.65 mmol, 69% yield) as a brown colored gum.

LCMS (ESI+) M/z: 407 [M+H])

Step 6: 2-[6-[6-(4-tert-butoxycarbonylpiperazin-1-yl)-3-pyridyl]-4-fluoro-indazol-2-yl]-2-(6,7-dihydro-5H-pyrrolo[1,2-c]imidazol-1-yl)acetic acid

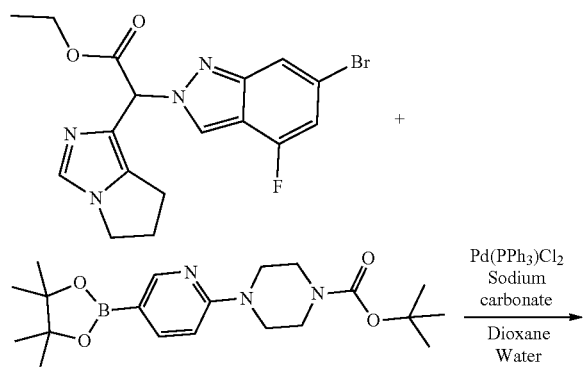

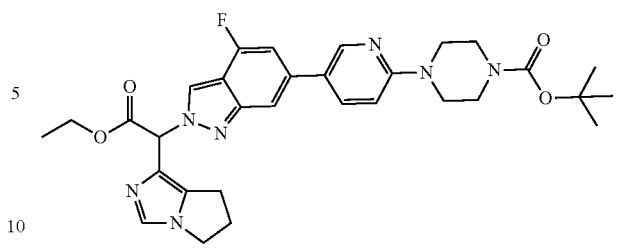

In a 100-mL sealed tube, ethyl 2-(6-bromo-4-fluoro-indazol-2-yl)-2-(6,7-dihydro-5H-pyrrolo[1,2-c]imidazol-1-yl)acetate (2.2 g, 5.40 mmol) and tert-butyl 4-[5-(4,4,5,5-tetramethyl-1,3,2-dioxaborolan-2-yl)-2-pyridyl]piperazine-1-carboxylate (2.52 g, 6.48 mmol) were dissolved in Dioxane (32 mL) and Water (8 mL). Sodium carbonate (1.15 g, 10.80 mmol, 452.64 µL) was added and the reaction mixture was purged with nitrogen for 5 min. Dichlorobis(triphenylphosphine)palladium(II) (379.29 mg, 540.23 µmol) was added under nitrogen atmosphere and the tube was sealed. The reaction was stirred at 90° C. in a heating block for 16 h. The reaction mixture was filtered over celite and washed with ethyl acetate. The organic layer was separated, washed with brine and concentrated. The residue was purified by silica gel chromatography (1% to 5% methanol in dichloromethane) to afford tert-butyl 4-[5-[2-[1-(6,7-dihydro-5H-pyrrolo[1,2-c]imidazol-1-yl)-2-ethoxy-2-oxo-ethyl]-4-fluoro-indazol-6-yl]-2-pyridyl]piperazine-1-carboxylate (1.1 g, 1.36 mmol, 25.2% yield) as an off-white solid. LCMS m/z: 590.0 [M+H]

Step 7: 2-[6-[6-(4-tert-butoxycarbonylpiperazin-1-yl)-3-pyridyl]-4-fluoro-indazol-2-yl]-2-(6,7-dihydro-5H-pyrrolo[1,2-c]imidazol-1-yl)acetic acid

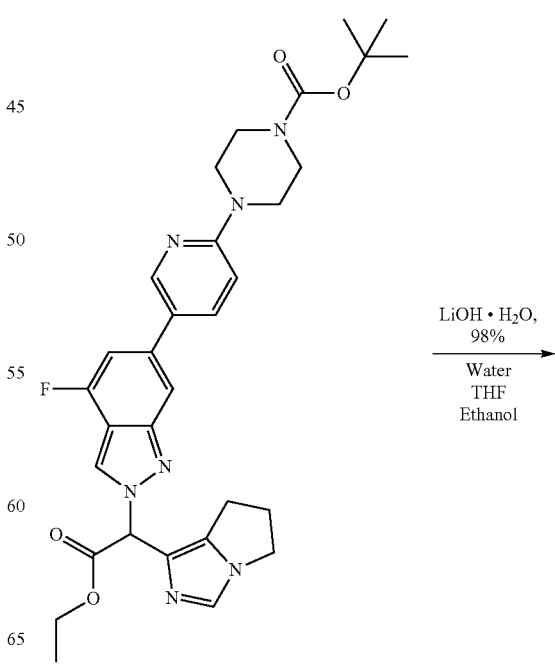

841
-continued

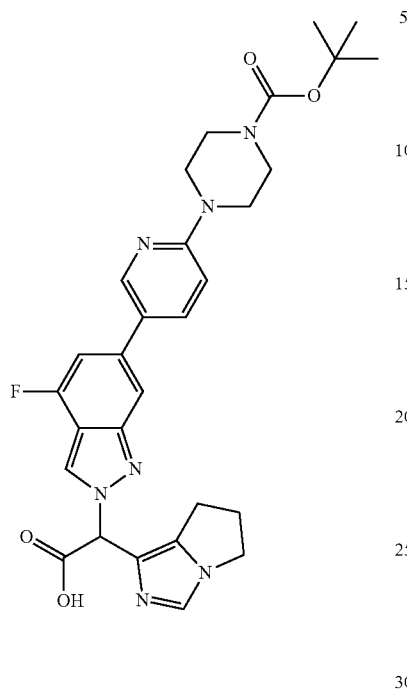

tert-Butyl 4-[5-[2-[1-(6,7-dihydro-5H-pyrrolo[1,2-c]imidazol-1-yl)-2-ethoxy-2-oxo-ethyl]-4-fluoro-indazol-6-yl]-2-pyridyl]piperazine-1-carboxylate (1.1 g, 1.87 mmol) was dissolved in ethanol (8 mL) tetrahydrofuran (8 mL), and water (8 mL). Lithium hydroxide monohydrate, 98% (156.56 mg, 3.73 mmol) was added at ambient temperature and the reaction mixture was further stirred at ambient temperature for 5 h. The reaction mixture was adjusted to pH 5-6 with an aqueous potassium bisulfate solution and the mixture was extracted with 10% methanol-dichloromethane (100 ml×2). The organic layer was concentrated under reduced pressure. The resulting solid was stirred in ether, the ether layer was decanted and discarded, and the solid residue was dried under vacuum to afford compound 2-[6-[6-(4-tert-butoxycarbonylpiperazin-1-yl)-3-pyridyl]-4-fluoro-indazol-2-yl]-2-(6,7-dihydro-5H-pyrrolo[1,2-c]imidazol-1-yl)acetic acid (0.75 g, 1.07 mmol, 57% yield) as pale yellow solid. LCMS (ESI+): 561.9 (M+H).

842

Step 8: tert-butyl 4-[5-[2-[1-(6,7-dihydro-5H-pyrrolo[1,2-c]imidazol-1-yl)-2-oxo-2-(thiazol-2-ylamino)ethyl]-4-fluoro-indazol-6-yl]-2-pyridyl]piperazine-1-carboxylate

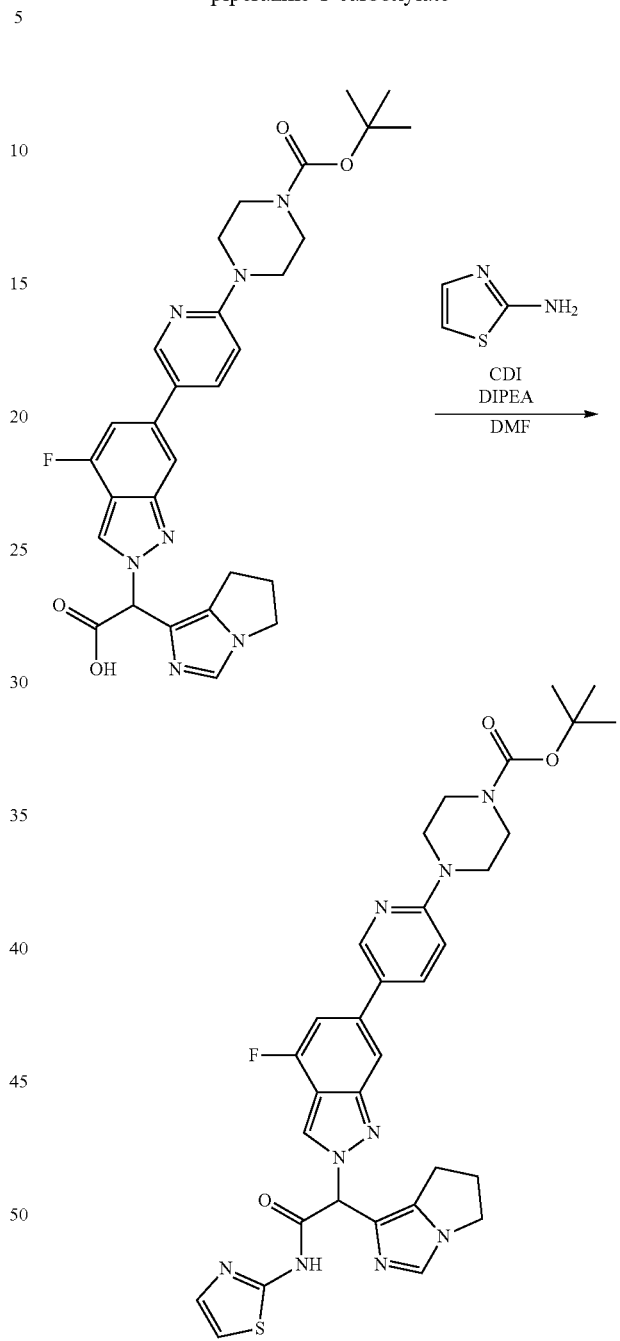

To a stirred solution of 2-[6-[6-(4-tert-butoxycarbonylpiperazin-1-yl)-3-pyridyl]-4-fluoro-indazol-2-yl]-2-(6,7-dihydro-5H-pyrrolo[1,2-c]imidazol-1-yl)acetic acid (0.2 g, 356.12 µmol) in N,N-dimethylformamide (7 mL) was added Carbonyldiimidazole (115.49 mg, 712.24 µmol) at RT and the mixture was stirred for 2 h. Thiazol-2-amine (46.36 mg, 462.96 µmol) was added and the reaction mixture was stirred at ambient temperature for 16 h. The reaction mixture was further stirred at 50° C. for 3 h. The reaction mixture was quenched with water and extracted 10% methanol in dichloromethane. The organic layer was concentrated under reduced pressure and the residue purified by silica gel chromatography (3% to 8% methanol in dichloromethane) to afford tert-butyl 4-[5-[2-[1-(6,7-dihydro-5H-pyrrolo[1,2-c]imidazol-1-yl)-2-oxo-2-(thiazol-2-ylamino)ethyl]-4-fluoro-indazol-6-yl]-2-pyridyl]piperazine-1-carboxylate (0.16 g, 245 µmol, 69% yield). LCMS (ESI+) m/z: 644.2 (M+H).

Step 9: 2-(6,7-dihydro-5H-pyrrolo[1,2-c]imidazol-1-yl)-2-[4-fluoro-6-(6-piperazin-1-yl-3-pyridyl)indazol-2-yl]-N-thiazol-2-yl-acetamide

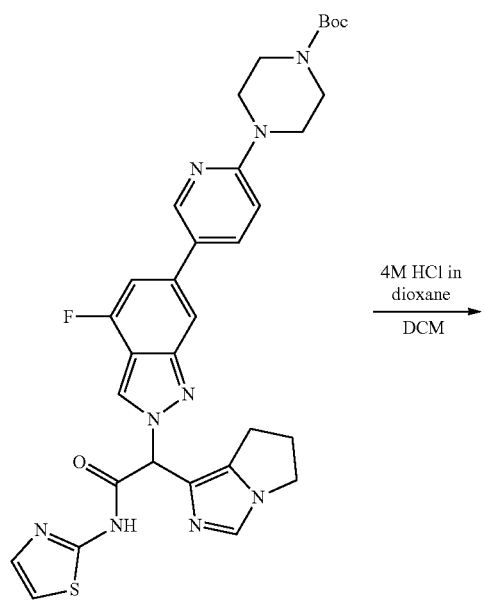

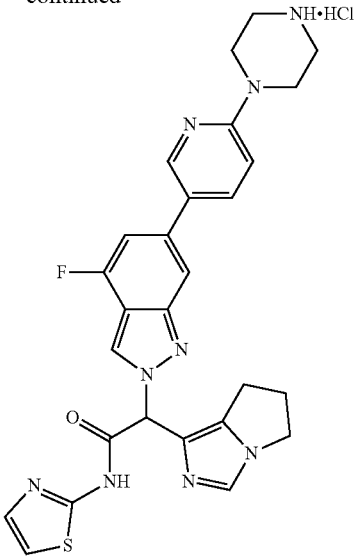

Hydrogen Chloride (4M in 1,4-dioxane, 0.5 mL, 2.0 mmol) was added to a stirred solution of tert-butyl 4-[5-[2-[1-(6,7-dihydro-5H-pyrrolo[1,2-c]imidazol-1-yl)-2-oxo-2-(thiazol-2-ylamino)ethyl]-4-fluoro-indazol-6-yl]-2-pyridyl]piperazine-1-carboxylate (0.15 g, 233.02 µmol) in dichloromethane (8 mL) at 0° C. After addition the reaction mixture temperature was raised slowly to Room Temperature and stirred further for 5 h. The reaction mixture was concentrated under reduced pressure. Diethyl ether (15 mL) was added to the solid residue and the mixture was stirred for 15 min. The ether layer was decanted and discarded. The solid was dried under vacuum to afford 2-(6,7-dihydro-5H-pyrrolo[1,2-c]imidazol-1-yl)-2-[4-fluoro-6-(6-piperazin-1-yl-3-pyridyl)indazol-2-yl]-N-thiazol-2-yl-acetamide (0.13 g, 221.9 µmol, 95.2% yield) as a brown solid. LCMS (ESI+): m/z 544.2 (M+H).

Step 10: 2-(6,7-dihydro-5H-pyrrolo[1,2-c]imidazol-1-yl)-2-[6-[6-[4-[2-[4-[4-[(2,6-dioxo-3-piperidyl)amino]-2-fluoro-phenyl]-1-piperidyl]acetyl]piperazin-1-yl]-3-pyridyl]-4-fluoro-indazol-2-yl]-N-thiazol-2-yl-acetamide

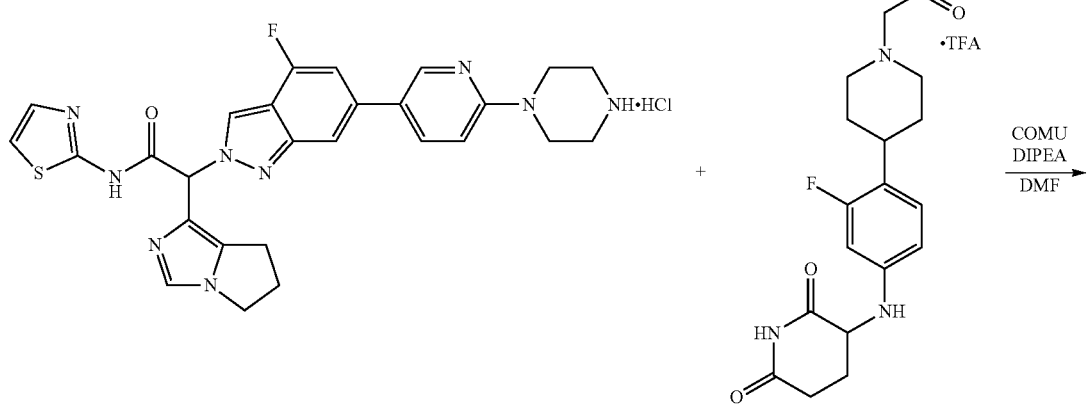

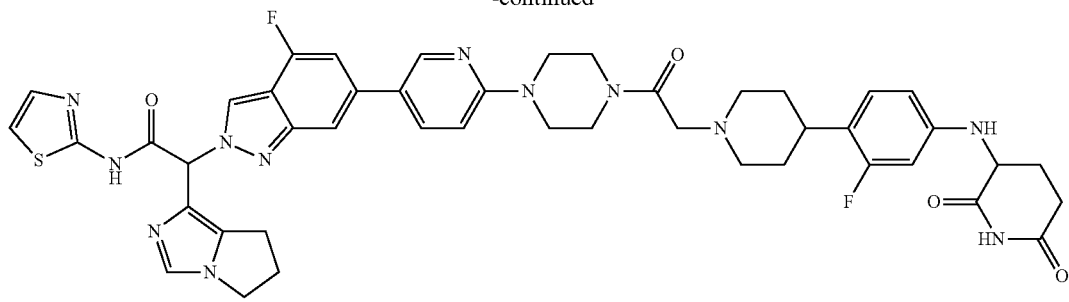

N,N-diisopropylethylamine (189.17 µL, 140.37 mg, 1.09 mmol) was added to a stirred solution of 2-(6,7-dihydro-5H-pyrrolo[1,2-c]imidazol-1-yl)-2-[4-fluoro-6-(6-piperazin-1-yl-3-pyridyl)indazol-2-yl]-N-thiazol-2-yl-acetamide hydrochloride (90 mg, 155.15 µmol) and 2-[4-[4-[(2,6-dioxo-3-piperidyl)amino]-2-fluoro-phenyl]-1-piperidyl]acetic acid hydrochloride (56.38 mg, 141.00 µmol) in N,N-dimethylformamide (1.5 mL) at 0° C. The mixture was stirred for 10 min. COMU was added (99.67 mg, 232.73 µmol), and reaction mixture was stirred for a further 2 h. The reaction mixture was concentrated and the residue was purified by reverse phase silica gel chromatography (C18, 0:100 to 100:0 Acetonitrile: 0.1% Ammonium acetate in water). The desired fractions were pooled, frozen and lyophilized. The residue was further purified by Preparative HPLC. (Purification method: Column: X-Bridge C8 (50×4.6 mm), 3.5 m; Mobile Phase A: 10 mM Ammonium acetate in milli-q water; Mobile phase B: Acetonitrile) to afford Compound 64 (26 mg, 29.04 µmol, 19% yield) as an off white solid. LCMS (m/z: 889.2, [M+H]), $^1$H-NMR (400 MHz, DMSO-d6) δ 13.01-12.66 (br. S, 1H), 10.79 (s, 1H), 8.57 (d, J=2.6 Hz, 1H), 8.28 (s, 1H), 7.99 (dd, J=8.9, 2.6 Hz, 1H), 7.69 (d, J=6.1 Hz, 2H), 7.50 (d, J=3.7 Hz, 1H), 7.39-7.09 (m, 2H), 6.99 (t, J=8.6 Hz, 2H), 6.68 (s, 1H), 6.61-6.26 (m, 2H), 6.00 (d, J=7.8 Hz, 1H), 4.30 (dt, J=11.8, 6.2 Hz, 1H), 4.14-3.90 (m, 2H), 3.68 (d, J=30.0 Hz, 5H), 3.58 (s, 4H), 3.22 (s, 2H), 2.94 (d, J=10.7 Hz, 2H), 2.89-2.65 (m, 1H), 2.58 (m, 4H), 2.09 (d, J=8.8 Hz, 2H), 1.91-1.80 (m, 1H), 1.66 (s, 5H).

Example 65

Synthesis of 2-(6,7-dihydro-5H-pyrrolo[1,2-c]imidazol-1-yl)-2-[6-[6-[4-[2-[4-[4-[(2,6-dioxo-3-piperidyl)amino]phenyl]-1-piperidyl]acetyl]piperazin-1-yl]-3-pyridyl]-4-fluoro-indazol-2-yl]-N-thiazol-2-yl-acetamide, Compound 65

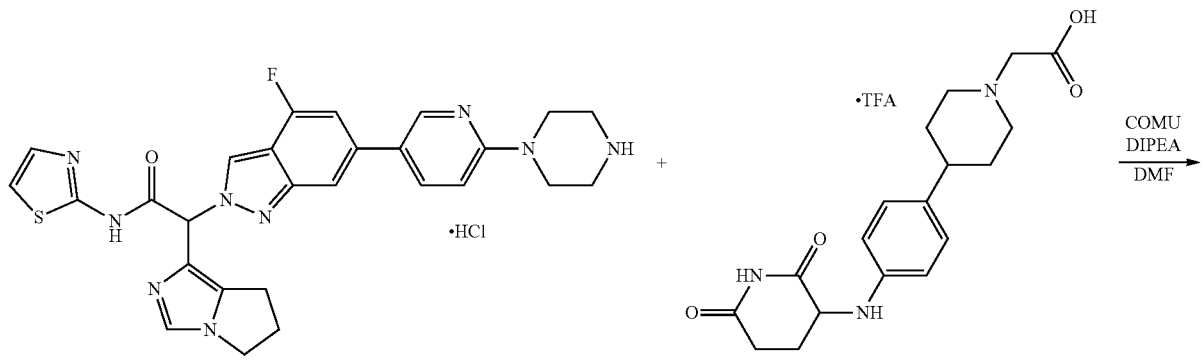

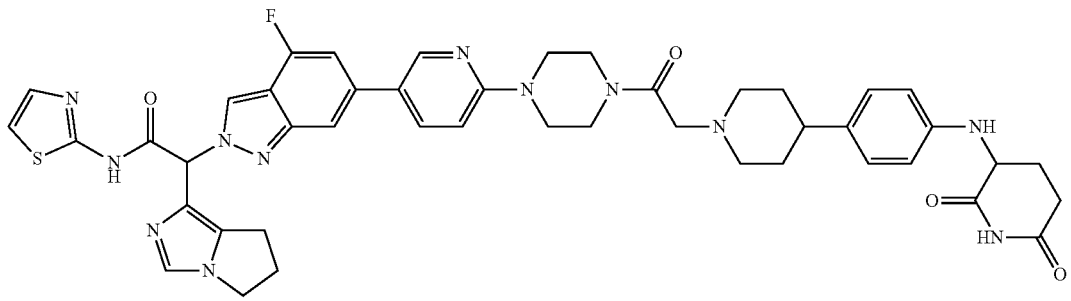

N,N-diisopropylethylamine (151.51 mg, 1.17 mmol, 204.19 µL) was added to a stirred solution of 2-(6,7-dihydro-5H-pyrrolo[1,2-c]imidazol-1-yl)-2-[4-fluoro-6-(6-piperazin-1-yl-3-pyridyl)indazol-2-yl]-N-thiazol-2-yl-acetamide hydrochloride (0.085 g, 146.53 µmol) and 2-[4-[4-[(2,6-dioxo-3-piperidyl)amino]phenyl]-1-piperidyl]acetic acid trifluoroacetic acid (50.61 mg, 110.16 µmol) in N,N-dimethylformamide (3 mL) at 0° C. The mixture was stirred for 15 min. COMU was added (94.12 mg, 219.80 µmol) and the temperature was slowly raised to RT and stirred for 3 h. The reaction mixture was concentrated and the residue was purified on a Reverse phase column (C18), eluting with a 10 to 50% acetonitrile (0.1% TFA) in water (0.1% TFA) gradient. The desired fractions were lyophilized to afford the a dry solid. A 10% sodium bicarbonate solution was added, and the aqueous layer was extracted with ethyl acetate (×2). The organic layers were combined, concentrated and lyophilized to afford Compound 65 (10 mg, 9.84 µmol, 6.7% yield) as an off white solid. LCMS m/z: 871.1 [M+H], $^1$H NMR (400 MHz, DMSO-$d_6$) δ 12.83 (s, 1H), 10.78 (s, 1H), 8.58 (d, J=2.6 Hz, 1H), 8.29 (d, J=0.9 Hz, 1H), 8.00 (dd, J=8.9, 2.6 Hz, 1H), 7.70 (d, J=3.7 Hz, 2H), 7.52 (d, J=3.6 Hz, 1H), 7.29 (d, J=3.6 Hz, 1H), 7.20 (dd, J=12.2, 1.1 Hz, 1H), 6.98 (dd, J=11.7, 8.6 Hz, 3H), 6.71 (s, 1H), 6.61 (d, J=8.1 Hz, 2H), 5.67 (d, J=7.2 Hz, 1H), 4.27 (dt, J=11.9, 6.7 Hz, 1H), 4.13-3.91 (m, 2H), 3.62 (q, J=31.7, 26.3 Hz, 9H), 3.22 (s, 2H), 2.95 (s, 1H), 2.85-2.69 (m, 1H), 2.64-2.55 (m, 2H), 2.52 (s, 4H), 2.20-2.01 (m, 2H), 1.95-1.79 (m, 1H), 1.78-1.47 (m, 3H).

Example 66

Synthesis of 2-(6,7-dihydro-5H-pyrrolo[1,2-c]imidazol-1-yl)-2-[6-[6-[4-[2-[4-[5-[(2,6-dioxo-3-piperidyl)amino]-2-pyridyl]-1-piperidyl]acetyl]piperazin-1-yl]-3-pyridyl]-4-fluoro-indazol-2-yl]-N-thiazol-2-yl-acetamide, Compound 66

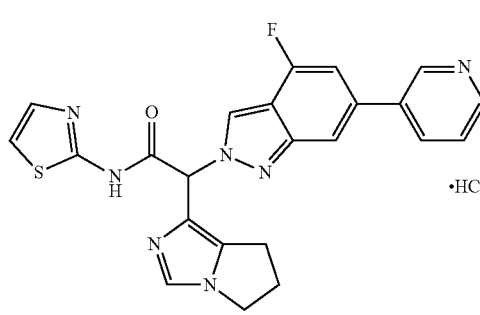
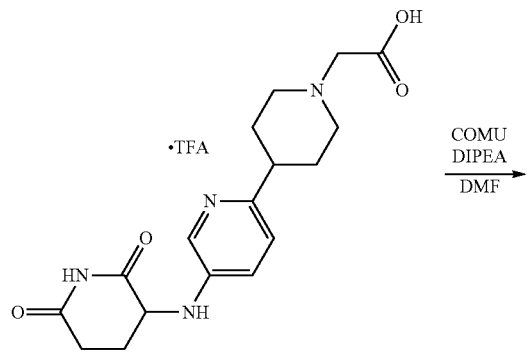
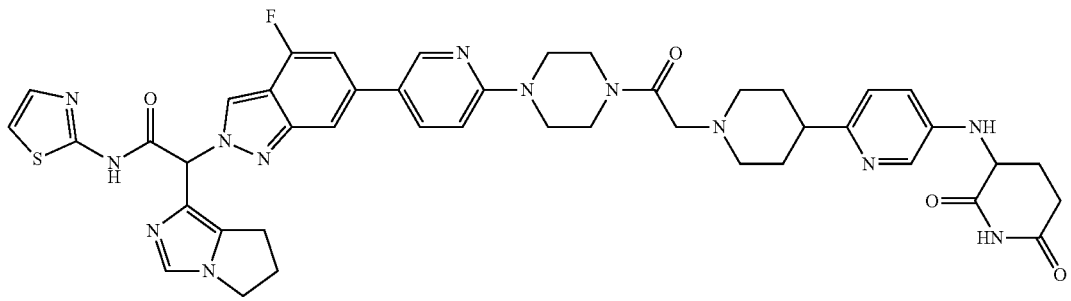

N,N-diisopropylethylamine (151.51 mg, 1.17 mmol, 204.19 μL) was added to a stirred solution of 2-(6,7-dihydro-5H-pyrrolo[1,2-c]imidazol-1-yl)-2-[4-fluoro-6-(6-piperazin-1-yl-3-pyridyl)indazol-2-yl]-N-thiazol-2-yl-acetamide hydrochloride (0.085 g, 146.53 μmol) and 2-[4-[5-[(2,6-dioxo-3-piperidyl)amino]-2-pyridyl]-1-piperidyl]acetic acid, trifluoroacetic acid salt (50.76 mg, 110.24 μmol) in N,N-dimethylformamide (3 mL) at 0° C. The reaction mixture was stirred for 15 min. COMU (94.12 mg, 219.80 μmol) was then added and the temperature was slowly raised to RT. The reaction mixture was stirred for 3 h. The reaction mixture was concentrated under reduced pressure. The crude residue was purified on reverse phase column (C18), eluting with a 10 to 50% acetonitrile (0.1% TFA) in water (0.1% TFA) gradient. The desired fractions were lyophilized. The residue was further purified by preparative HPLC (Purification method: Column: XBRIDGE C8 (4.6×50 mm), 3.5 m; Mobile Phase A: 10 mM Ammonium acetate in water; Mobile phase B: Acetonitrile) to afford Compound 66 (15.5 mg, 16.85 μmol, 11.50% yield) as an off white solid. LCMS (ESI+): m/z 872.1 [M+H]; $^1$H NMR (400 MHz, DMSO-$d_6$) δ 12.85 (br. s, 1H), 10.80 (s, 1H), 8.57 (d, J=2.6 Hz, 1H), 8.28 (s, 1H), 8.08-7.84 (m, 2H), 7.69 (d, J=4.8 Hz, 2H), 7.50 (d, J=3.6 Hz, 1H), 7.42-7.08 (m, 2H), 7.05-6.79 (m, 3H), 6.69 (s, 1H), 5.93 (d, J=7.8 Hz, 1H), 4.33 (dt, J=12.5, 6.0 Hz, 1H), 4.14-3.92 (m, 2H), 3.85-3.44 (m, 8H), 3.21 (s, 2H), 2.93 (d, J=10.7 Hz, 2H), 2.87-2.52 (m, 2H), 2.50-2.40 (m, 4H), 2.17-2.00 (m, 3H), 2.00-1.38 (m, 5H).

Example 67

Synthesis of 2-(6,7-dihydro-5H-pyrrolo[1,2-c]imidazol-1-yl)-2-[6-[6-[4-[2-[4-[3-(2,4-dioxohexahydropyrimidin-1-yl)-1-methyl-indazol-6-yl]-1-piperidyl]acetyl]piperazin-1-yl]-3-pyridyl]-4-fluoro-indazol-2-yl]-N-thiazol-2-yl-acetamide, Compound 67

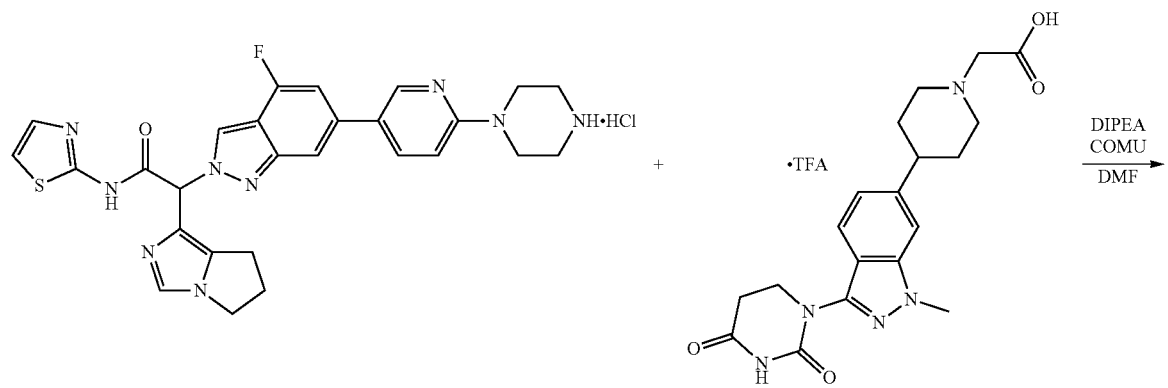

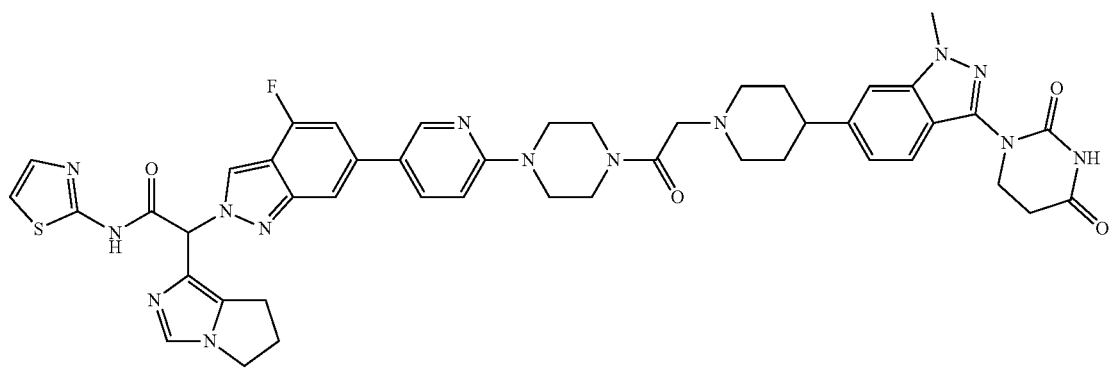

N,N-diisopropylethylamine (133.68 mg, 1.03 mmol, 180.16 μL) was added to a stirred solution of 2-(6,7-dihydro-5H-pyrrolo[1,2-c]imidazol-1-yl)-2-[4-fluoro-6-(6-piperazin-1-yl-3-pyridyl)indazol-2-yl]-N-thiazol-2-yl-acetamide hydrochloride (0.075 g, 129.29 μmol) and 2-[4-[3-(2,4-dioxohexahydropyrimidin-1-yl)-1-methyl-indazol-6-yl]-1-piperidyl]acetic acid, trifluoroacetic acid salt (71.03 mg, 142.22 μmol) in N,N-dimethylformamide (3 mL) at 0° C. The reaction mixture was stirred for 5 min. COMU (83.06 mg, 193.94 μmol) was added at 0° C. and the reaction was further stirred for 2 h. The reaction mixture was concentrated and the residue was purified by reverse phase silica gel chromatography (C18, 1:1 0.1% Ammonium acetate in water:Acetonitrile). The desired fractions were lyophilized to afford Compound 67 (38.4 mg, 41.11 μmol, 32% yield) as an off white solid. LCMS (ESI−): m/z 909.3 [M−H]. 1H NMR (400 MHz, DMSO-$d_6$) δ 12.82 (s, 1H), 10.54 (s, 1H), 8.57 (d, J=2.6 Hz, 1H), 8.29 (d, J=0.9 Hz, 1H), 8.00 (dd, J=9.0, 2.6 Hz, 1H), 7.70 (d, J=3.8 Hz, 2H), 7.61-7.47 (m, 2H), 7.44 (s, 1H), 7.29 (d, J=3.5 Hz, 1H), 7.20 (dd, J=12.2, 1.1 Hz, 1H), 7.13-7.02 (m, 1H), 6.99 (d, J=8.9 Hz, 1H), 6.71 (s, 1H), 4.09-3.98 (m, 2H), 3.97 (s, 3H), 3.91 (t, J=6.6 Hz, 2H), 3.71 (d, J=29.0 Hz, 4H), 3.60 (s, 5H), 3.26 (s, 3H), 3.01 (d, J=10.6 Hz, 2H), 2.89-2.71 (m, 3H), 2.67-2.53 (m, 2H), 2.27-2.12 (m, 2H), 1.89-1.68 (m, 4H).

Example 68

Synthesis of 2-(6,7-dihydro-5H-pyrrolo[1,2-c]imidazol-1-yl)-2-(6-(6-(4-(2-(4-(4-(((S)-2,6-dioxopiperidin-3-yl)amino)-2-fluorophenyl)piperidin-1-yl)acetyl)piperazin-1-yl)pyridin-3-yl)-4-fluoro-2H-indazol-2-yl)-N-(thiazol-2-yl)acetamide, Compound 68

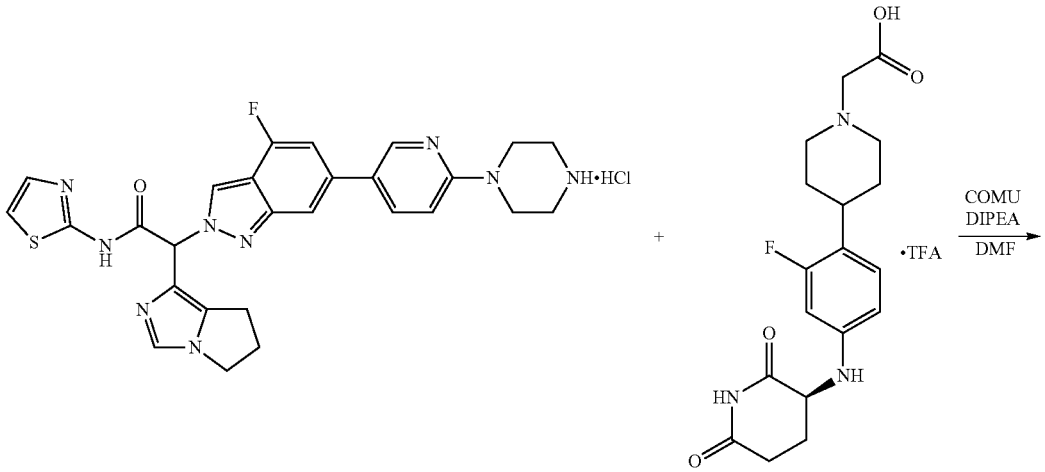

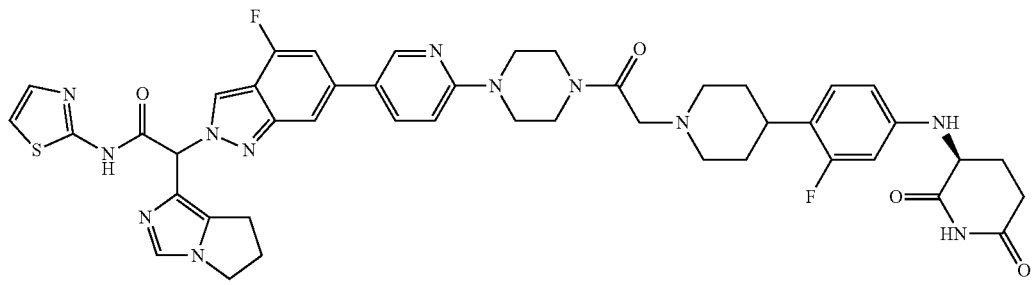

Compound 68 was synthesized in 35% yield from 2-(6,7-dihydro-5H-pyrrolo[1,2-c]imidazol-1-yl)-2-[4-fluoro-6-(6-piperazin-1-yl-3-pyridyl)indazol-2-yl]-N-thiazol-2-yl-acetamide hydrochloride using a procedure similar to that used for Example 64, step 10, using (S)-2-(4-(4-((2,6-dioxopiperidin-3-yl)amino)-2-fluorophenyl)piperidin-1-yl) acetic acid instead of 2-(4-(4-((2,6-dioxopiperidin-3-yl)amino)-2-fluorophenyl)piperidin-1-yl)acetic acid. LCMS (ESI+): 889.3 (M+H), $^1$H NMR (400 MHz, DMSO-$d_6$) δ 12.80 (s, 1H), 10.79 (s, 1H), 8.57 (d, J=2.6 Hz, 1H), 8.28 (d, J=0.9 Hz, 1H), 7.99 (dd, J=9.0, 2.6 Hz, 1H), 7.80-7.57 (m, 2H), 7.51 (d, J=3.6 Hz, 1H), 7.27 (s, 1H), 7.20 (dd, J=12.1, 1.1 Hz, 1H), 7.00 (t, J=8.6 Hz, 2H), 6.70 (s, 1H), 6.55-6.25 (m, 2H), 6.00 (d, J=7.7 Hz, 1H), 4.30 (ddd, J=12.3, 7.7, 4.8 Hz, 1H), 4.13-3.90 (m, 2H), 3.69 (d, J=30.1 Hz, 4H), 3.58 (s, 4H), 3.22 (s, 2H), 2.94 (d, J=10.7 Hz, 2H), 2.90-2.52 (m, 3H), 2.21-1.96 (m, 4H), 1.91-1.76 (m, 1H), 1.66 (s, 4H).

Example 69

2-(6,7-dihydro-5H-pyrrolo[1,2-c]imidazol-1-yl)-2-[6-[6-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]-3-pyridyl]-7-fluoro-indazol-2-yl]-N-thiazol-2-yl-acetamide, Compound 69

Step 1: Synthesis of tert-butyl 6-(5-(2-(1-(6,7-dihydro-5H-pyrrolo[1,2-c]imidazol-1-yl)-2-ethoxy-2-oxoethyl)-7-fluoro-2H-indazol-6-yl)pyridin-2-yl)-2,6-diazaspiro[3.3]heptane-2-carboxylate

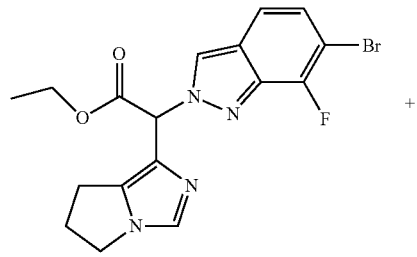

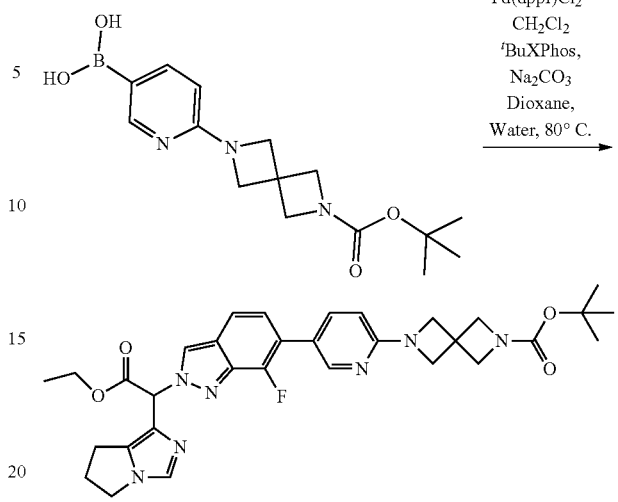

In a 50-mL sealed tube, ethyl 2-(6-bromo-7-fluoro-indazol-2-yl)-2-(6,7-dihydro-5H-pyrrolo[1,2-c]imidazol-1-yl) acetate (Example 2, step 4, 0.83 g, 2.04 mmol) and [6-(2-tert-butoxycarbonyl-2,6-diazaspiro[3.3]heptan-6-yl)-3-pyridyl]boronic acid (780.59 mg, 2.45 mmol) in 1,4-dioxane (8 mL) was added Sodium carbonate (540.05 mg, 5.10 mmol, 213.46 L) in Water (2 ml). The reaction mixture was degassed with nitrogen for 10 minutes. [1,1'-Bis(diphenylphosphino)ferrocene]dichloropalladium(II), complex with dichloromethane (166.43 mg, 203.81 µmol) and 2-di-tert-butylphosphino-2',4',6'-triisopropylbiphenyl (86.55 mg, 203.81 µmol) was added under nitrogen atmosphere and the mixture was further degassed with nitrogen for 5 minutes. The tube was sealed and was stirred at 80° C. in a heating block for 5 h. The reaction mixture was filtered over celite and washed with ethyl acetate. was separated from the aqueous layer. The organic layer was dried over sodium sulfate, filtered, and concentrated under reduced pressure. The crude residue purified by flash column chromatography on silica gel (0-10% Methanol in Dichloromethane) to give tert-butyl 6-[5-[2-[1-(6,7-dihydro-5H-pyrrolo[1,2-c]imidazol-1-yl)-2-ethoxy-2-oxo-ethyl]-7-fluoro-indazol-6-yl]-2-pyridyl]-2,6-diazaspiro[3.3]-heptane-2-carboxylate (0.43 g, 630.35 µmol, 30.93% yield) as a brown solid. LCMS (ESI+) m/z: 602.3 [M+H]$^+$ Step 2: Synthesis of lithium 2-(6-(6-(6-(tert-butoxycarbonyl)-2,6-diazaspiro[3.3]heptan-2-yl)pyridin-3-yl)-7-fluoro-2H-indazol-2-yl)-2-(6,7-dihydro-5H-pyrrolo[1,2-c]imidazol-1-yl)acetate

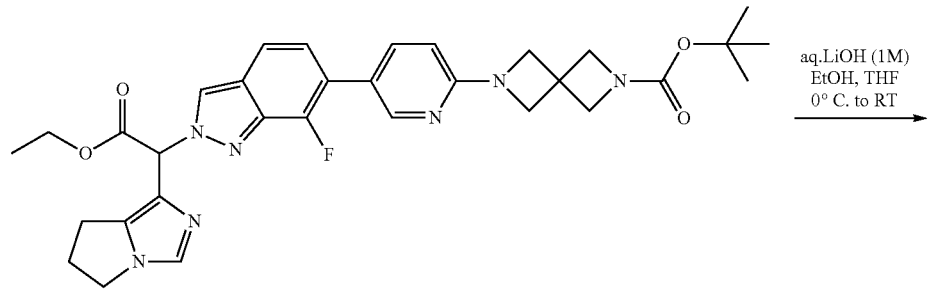

-continued

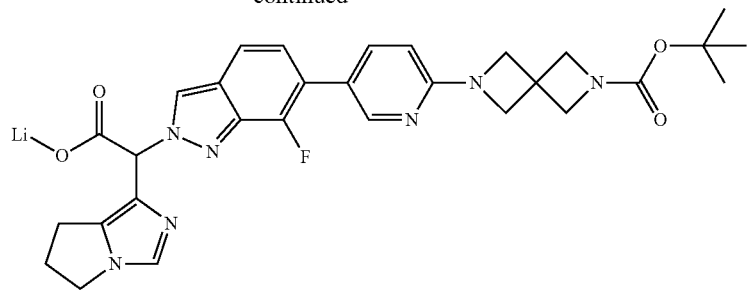

To a stirred solution of tert-butyl 6-[5-[2-[1-(6,7-dihydro-5H-pyrrolo[1,2-c]imidazol-1-yl)-2-ethoxy-2-oxo-ethyl]-7-fluoro-indazol-6-yl]-2-pyridyl]-2,6-diazaspiro[3.3]heptane-2-carboxylate (0.42 g, 698.06 µmol) in ethanol (3 mL) and tetrahydrofuran (3 mL) was added lithium hydroxide (1M aqueous, 0.9 mL, 907.47 µmol) at ambient temperature and the reaction mixture was stirred for 3 h. The mixture was concentrated under reduced pressure to afford solid, which was further triturated with diethyl ether, decanted and dried to get lithium 2-(6-(6-(6-(tert-butoxycarbonyl)-2,6-diazaspiro[3.3]heptan-2-yl)pyridin-3-yl)-7-fluoro-2H-indazol-2-yl)-2-(6,7-dihydro-5H-pyrrolo[1,2-c]imidazol-1-yl)acetate (0.38 g, 529.13 µmol, 93.9% yield) as a brown solid. LCMS (ESI+) m/z: 574.3 [M+H]$^+$ Step 3: tert-butyl 6-(5-(2-(1-(6,7-dihydro-5H-pyrrolo[1,2-c]imidazol-1-yl)-2-oxo-2-(thiazol-2-ylamino)ethyl)-7-fluoro-2H-indazol-6-yl)pyridin-2-yl)-2,6-diazaspiro[3.3]heptane-2-carboxylate

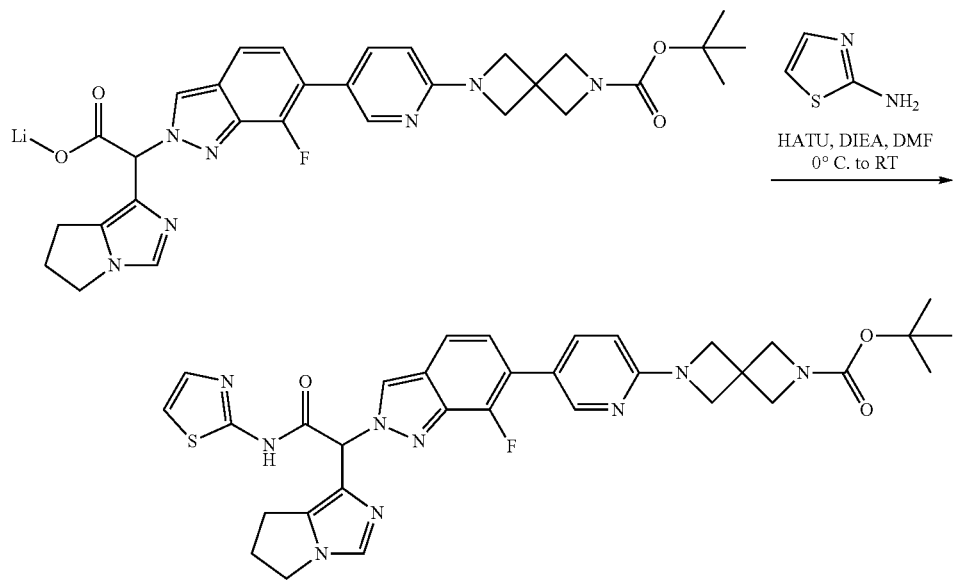

To a stirred solution of [2-[6-[6-(2-tert-butoxycarbonyl-2,6-diazaspiro[3.3]heptan-6-yl)-3-pyridyl]-7-fluoro-indazol-2-yl]-2-(6,7-dihydro-5H-pyrrolo[1,2-c]imidazol-1-yl)acetyl]oxylithium (0.37 g, 638.43 µmol) in N,N-dimethylformamide (8 mL) was added N,N-Diisopropylethylamine (495.07 mg, 3.83 mmol, 667.21 µL) at 0° C. 1-[Bis(dimethylamino)methylene]-1H-1,2,3-triazolo[4,5-b]pyridinium 3-oxid hexafluoro-phosphate (364.12 mg, 957.64 µmol) was added at the same temperature. Thiazol-2-amine (95.90 mg, 957.64 µmol) was added and the reaction mixture was stirred at room temperature for 16 h. The reaction mixture was added ice cold water and obtained solid was filtered, washed with water, and dried by an air stream. The crude solid residue was purified by flash chromatography using silica (0-8% Methanol in Dichloromethane) to afford tert-butyl 6-[5-[2-[1-(6,7-dihydro-5H- pyrrolo[1,2-c]imidazol-1-yl)-2-oxo-2-(thiazol-2-ylamino) ethyl]-7-fluoro-indazol-6-yl]-2-pyridyl]-2,6-diazaspiro[3.3] heptane-2-carboxylate (0.23 g, 323.74 mol, 50.71% yield) as a brown solid. LCMS (ESI+) m/z: 656.3 [M+H]⁺.

Step 4: Synthesis of 2-(6-(6-(2,6-diazaspiro[3.3] heptan-2-yl)pyridin-3-yl)-7-fluoro-2H-indazol-2-yl)-2-(6,7-dihydro-5H-pyrrolo[1,2-c]imidazol-1-yl)-N-(thiazol-2-yl)acetamide, trifluoroacetic acid

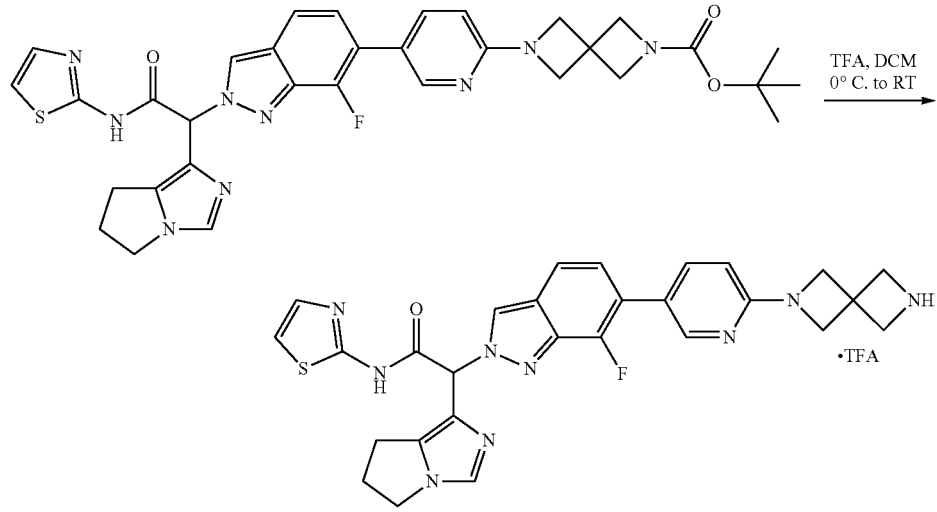

To a stirred solution of tert-butyl 6-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-2,6-diazaspiro[3.3]heptane-2-carboxylate (0.12 g, 183.00 μmol) in dichloromethane (10 mL) was added trifluoroacetic acid (83.46 mg, 731.99 μmol, 56.39 μL) dissolved in dichloromethane (2 mL) at 0° C. dropwise. The temperature of the reaction mixture was slowly raised to ambient temperature and stirred for 4 h. The reaction mixture was concentrated under reduced pressure, triturated at −40° C. with diethyl ether, decanted to afford 2-[6-[6-(2,6-diazaspiro[3.3]heptan-2-yl)-3-pyridyl]-7-fluoro-indazol-2-yl]-2-(6,7-dihydro-5H-pyrrolo[1,2-c]imidazol-1-yl)-N-thiazol-2-yl-acetamide, trifluoroacetic acid salt as a brown solid. LCMS (ESI+) m/z: 556.2 [M+H]⁺.

Step 5: 2-(6,7-dihydro-5H-pyrrolo[1,2-c]imidazol-1-yl)-2-(6-(6-(6-(2-(4-(4-(((S)-2,6-dioxopiperidin-3-yl)amino)-2-fluorophenyl)piperidin-1-yl)acetyl)-2,6-diazaspiro[3.3]heptan-2-yl)pyridin-3-yl)-7-fluoro-2H-indazol-2-yl)-N-(thiazol-2-yl)acetamide

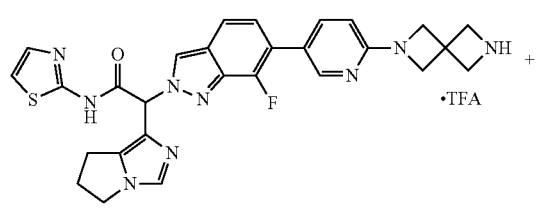

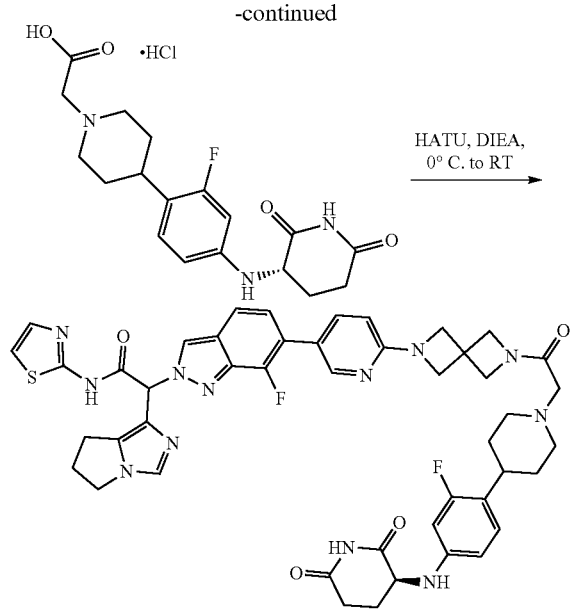

To a stirred solution of 2-[4-[4-[[(3S)-2,6-dioxo-3-piperidyl]amino]-2-fluoro-phenyl]-1-piperidyl]acetic acid; hydrochloride (48.84 mg, 122.14 μmol) in N,N-dimethylformamide (4 mL) at 0° C. was added N,N-Diisopropylethylamine (138.96 mg, 1.08 mmol, 187.28 μL). 1-[Bis(dimethylamino)methylene]-1H-1,2,3-triazolo[4,5-b]pyridinium 3-oxid hexafluorophosphate (76.65 mg, 201.60 mol) was added at the same temperature. 2-[6-[6-(2,6-diazaspiro[3.3] heptan-2-yl)-3-pyridyl]-7-fluoro-indazol-2-yl]-2-(6,7-dihydro-5H-pyrrolo[1,2-c]imidazol-1-yl)-N-thiazol-2-yl-acetamide, trifluoroacetic acid salt (0.09 g, 134.40 mol) was added and the reaction mixture was stirred for 2 h while warming to room temperature. The crude mixture was directly injected on a C18 column (50 g) for purification eluting (0% to 60% acetonitrile in water+0.1% ammonium acetate over 15 minutes, then steep gradient to 100% acetonitrile). The pure fractions were frozen and lyophilized to afford Compound 69 (60 mg, 64.82 µmol, 48.23% yield) as an off white solid. LCMS (ESI+) m/z: 899.3 [M−H]+. 1H-NMR (400 MHz, DMSO-d6: δ 12.81 (s, 1H), 10.79 (s, 1H), 8.33 (t, J=Hz, 2H), 7.79 (d, J=10.00 Hz, 1H), 7.69 (s, 1H), 7.59 (d, J=8.80 Hz, 1H), 7.52 (d, J=3.60 Hz, 1H), 7.28 (d, J=3.60 Hz, 1H), 7.12 (dd, J=8.60, 6.80 Hz, 1H), 7.02 (t, J=8.40 Hz, 1H), 6.72 (s, 1H), 6.53 (d, J=8.80 Hz, 1H), 6.48 (m, 2H), 6.01 (d, J=7.60 Hz, 1H), 4.45 (s, 2H), 4.31-4.30 (m, 1H), 4.16-04.14 (m, 4H), 4.09 (s, 2H), 4.02 (m, 2H), 3.00 (s, 2H), 2.92-2.89 (m, 2H), 2.68☐2.84 (m, 2H), 2.52☐2.60 (m, 4H), 2.07☐2.10 (m, 3H), 1.88 (m, 1H), 1.69☐1.65 (m, 4H).

Example 70

2-(6,7-dihydro-5H-pyrrolo[1,2-c]imidazol-1-yl)-2-[6-[6-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]-3-pyridyl]-7-fluoro-indazol-2-yl]-N-thiazol-2-yl-acetamide, Compound 70

Step 1: Tert-butyl 3,3-difluoro-4-(trifluoromethylsulfonyloxy)-2,6-dihydropyridine-1-carboxylate

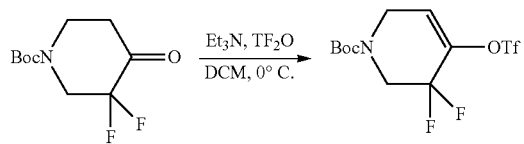

Triethylamine (3.23 g, 31.9 mmol, 4.44 mL) was added to a stirred solution of tert-butyl 3,3-difluoro-4-oxo-piperidine-1-carboxylate (2.5 g, 10.6 mmol) in dichloromethane (25 mL) at 0° C. Trifluoromethylsulfonic anhydride (4.50 g, 15.9 mmol, 2.68 mL) was added dropwise to the reaction mixture. The reaction was stirred at ambient temperature for 16 h. Then, the reaction was quenched with aqueous sodium bicarbonate, and extracted with dichloromethane, washed with brine, dried over sodium sulfate, and concentrated under reduced pressure. The residue was purified by silica gel chromatography (100% hexanes to 4:1 hexanes:ethyl acetate) to yield tert-butyl 3,3-difluoro-4-(trifluoromethylsulfonyloxy)-2,6-dihydropyridine-1-carboxylate (1.2 g, 2.29 mmol, 21% yield). 1H NMR (400 MHz, Methanol-d4) δ 6.59 (s, 1H), 4.29 (q, J=4.3 Hz, 2H), 4.04 (t, J=11.0 Hz, 2H), 1.51 (s, 9H).

Step 2: 1-[1-methyl-6-(4,4,5,5-tetramethyl-1,3,2-dioxaborolan-2-yl)indazol-3-yl]hexahydropyrimidine-2,4-dione

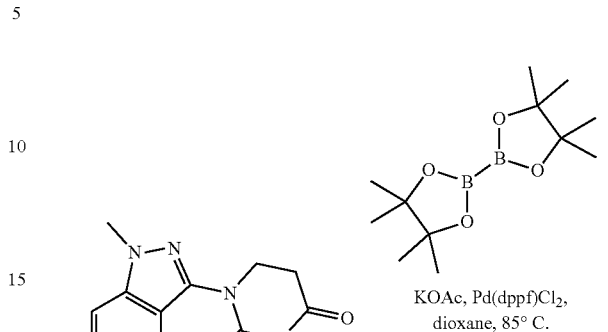

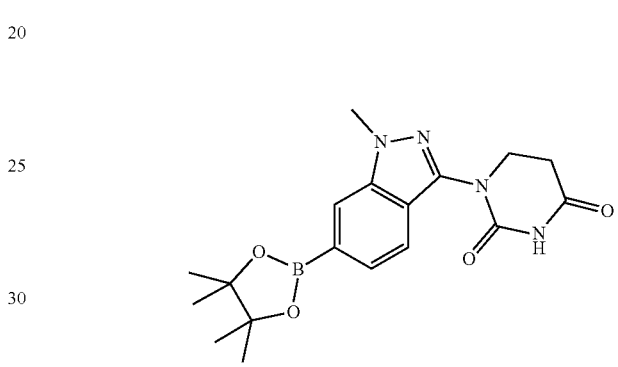

Potassium acetate (911 mg, 9.28 mmol) and Pd(dppf)Cl2 (113 mg, 155 µmol) were added to a solution of 1-(6-bromo-1-methyl-indazol-3-yl)hexahydropyrimidine-2,4-dione (1.0 g, 3.09 mmol) and bis(pinacolato)diboron (1.18 g, 4.64 mmol) in 1,4-dioxane (15 mL). The mixture was stirred at 85° C. under a nitrogen atmosphere for 16 h. The mixture was cooled to ambient temperature and filtered through a pad of silica gel. The filter cake was washed with ethyl acetate and the filtrate was concentrated under reduced pressure. The residue was purified by silica gel chromatography (100% hexanes to 100% ethyl acetate) to yield 1-[1-methyl-6-(4,4,5,5-tetramethyl-1,3,2-dioxaborolan-2-yl)indazol-3-yl]hexahydropyrimidine-2,4-dione (1.1 g, 2.97 mmol, 96% yield). LCMS (ESI+): 371 (M+H).

Step 3: tert-Butyl 4-(3-(2,4-dioxotetrahydropyrimidin-1(2H)-yl)-1-methyl-1H-indazol-6-yl)-3,3-difluoro-3,6-dihydropyridine-1(2H)-carboxylate

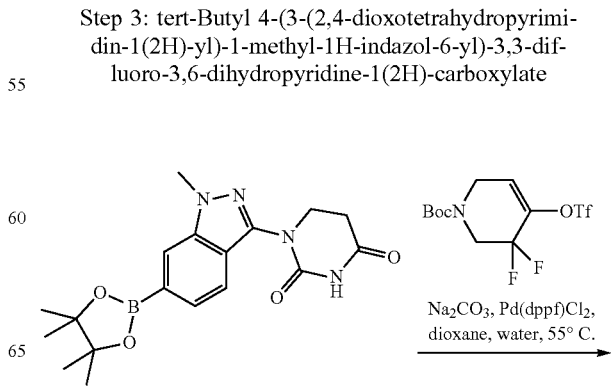

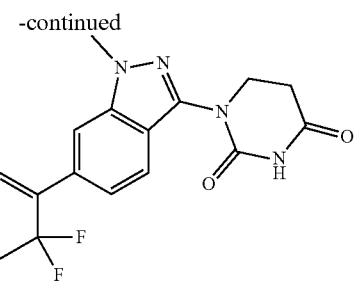

Sodium carbonate (485 mg, 4.57 mmol) was added to a solution of 1-[1-methyl-6-(4,4,5,5-tetramethyl-1,3,2-dioxaborolan-2-yl)indazol-3-yl]hexahydropyrimidine-2,4-dione (677 mg, 1.83 mmol) and tert-butyl 3,3-difluoro-4-(trifluoromethylsulfonyloxy)-2,6-dihydropyridine-1-carboxylate (560 mg, 1.52 mmol) in 1,4-dioxane (10 mL) and water (2.5 mL) and the solvent was sparged with $N_2$ gas for 10 minute. 1,1'-Bis(Diphenylphosphino)ferrocenepalladium (II) dichloride (111 mg, 152 μmol) was added and the reaction mixture was stirred at 55° C. for 2 h. The reaction mixture was cooled and diluted with water/ethyl acetate. After extraction, organic layer was washed with brine, dried over sodium sulfate, and concentrated. The residue was purified by silica gel chromatography (100% hexanes to 100% ethyl acetate) to give tert-butyl 4-[3-(2,4-dioxohexahydropyrimidin-1-yl)-1-methyl-indazol-6-yl]-3,3-difluoro-2,6-dihydropyridine-1-carboxylate (480 mg, 1.04 mmol, 68% yield). LCMS (ESI+): 462.2 (M+H)

Step 4: tert-butyl 4-[3-(2,4-dioxohexahydropyrimidin-1-yl)-1-methyl-indazol-6-yl]-3,3-difluoro-piperidine-1-carboxylate

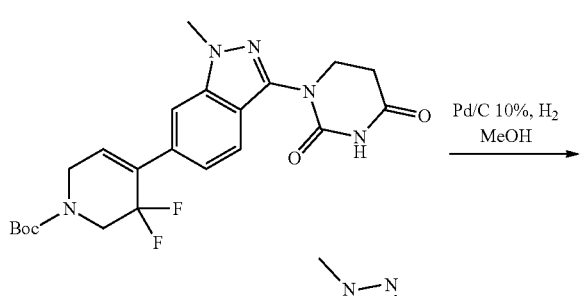

Palladium, 10% on carbon (Type 487, dry) (331 mg, 311 μmol) was added to a solution of tert-butyl 4-[3-(2,4-dioxohexahydropyrimidin-1-yl)-1-methyl-indazol-6-yl]-3,3-difluoro-2,6-dihydropyridine-1-carboxylate (478 mg, 1.04 mmol) in methanol (10.3 mL) and the mixture was stirred at ambient temperature under a hydrogen balloon atmosphere for 24 h. The hydrogen balloon was removed, and the mixture was diluted with dichloromethane (20 mL) and the slurry was stirred for additional 24 h. Then, the mixture was filtered through a pad of celite, washed using a solution of dichloromethane/methanol (3:1), and concentrated to afford tert-butyl 4-[3-(2,4-dioxohexahydropyrimidin-1-yl)-1-methyl-indazol-6-yl]-3,3-difluoro-piperidine-1-carboxylate (450 mg, 94% yield). LCMS (ESI+): 408.2 (M-tert-butyl+H).

Step 5: 4-[3-(2,4-dioxohexahydropyrimidin-1-yl)-1-methyl-indazol-6-yl]-3,3-difluoro-piperidine hydrochloride

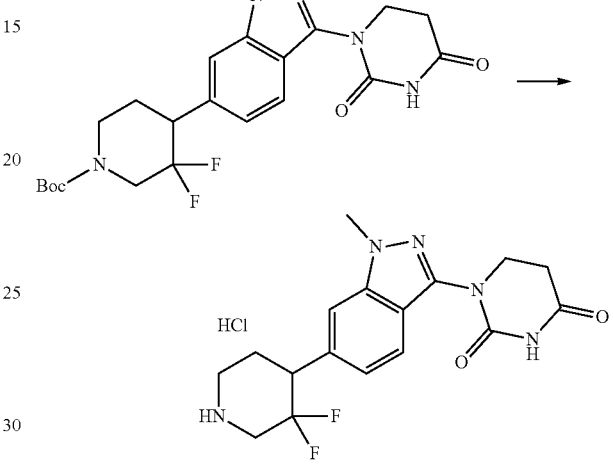

4-[3-(2,4-dioxohexahydropyrimidin-1-yl)-1-methyl-indazol-6-yl]-3,3-difluoro-piperidine hydrochloride was obtained in quantitative yield from tert-butyl 4-[3-(2,4-dioxohexahydropyrimidin-1-yl)-1-methyl-indazol-6-yl]-3,3-difluoro-piperidine-1-carboxylate using General method B for the removal of the tert-butoxycarbonyl group. LCMS (ESI+): 354.2 (M+H)

Step 6: tert-butyl 2-(4-(3-(2,4-dioxotetrahydropyrimidin-1(2H)-yl)-1-methyl-1H-indazol-6-yl)-3,3-difluoropiperidin-1-yl)acetate

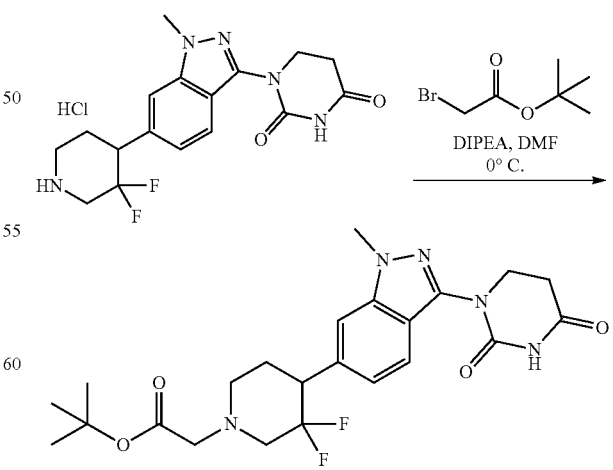

1-(6-(3,3-difluoropiperidin-4-yl)-1-methyl-1H-indazol-3-yl)dihydropyrimidine-2,4(1H,3H)-dione hydrochloride (1.75 g, 4.38 mmol) was dissolved in N,N-dimethylformamide (15 mL) and N,N-diisopropylethylamine (3.43 mL, 2.55 g, 19.7 mmol) was added. The mixture was cooled to 0° C., and tert-butyl 2-bromoacetate (770 µL, 1.02 g, 5.25 mmol) was added. The mixture was stirred at 0° C. for 4 h. The reaction was diluted with ethyl acetate and washed with saturated sodium bicarbonate and brine. The organic layer was concentrated and purified by silica gel chromatography (0-10% Methanol in dichloromethane) to yield tert-butyl 2-(4-(3-(2,4-dioxotetrahydropyrimidin-1(2H)-yl)-1-methyl-1H-indazol-6-yl)-3,3-difluoropiperidin-1-yl)acetate (1.90 g, 3.97 mmol, 90.6%) as a white solid. LCMS (ESI+): 478.3 (M+H)$^+$ Step 7: 2-(4-(3-(2,4-dioxotetrahydropyrimidin-1(2H)-yl)-1-methyl-1H-indazol-6-yl)-3,3-difluoropiperidin-1-yl)acetic acid, trifluoroacetic acid salt

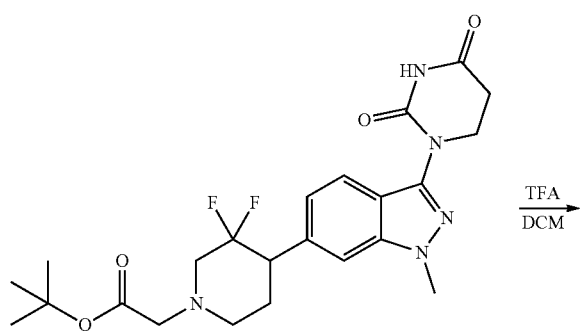

TFA
DCM

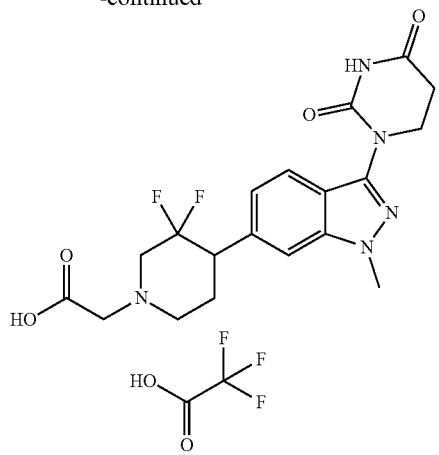

To the stirred solution of tert-butyl 2-[4-[3-(2,4-dioxohexahydropyrimidin-1-yl)-1-methyl-indazol-6-yl]-3,3-difluoro-1-piperidyl]acetate (100 mg, 209.42 µmol) in dichloromethane (5 mL) was added trifluoroacetic acid (1.48 g, 1.0 mL, 12.98 mmol) dropwise at 0° C. The reaction mixture stirred at ambient temperature for 3 h. The reaction mixture was concentrated under reduced pressure to give 2-[4-[3-(2,4-dioxohexahydropyrimidin-1-yl)-1-methyl-indazol-6-yl]-3,3-difluoro-1-piperidyl]acetic acid, trifluoroacetic acid salt (90 mg, 155.00 mol, 74.01% yield) as an off-white solid. LCMS (ESI+): 422.2 (M+H)$^+$ Step 8: 2-(6,7-dihydro-5H-pyrrolo[1,2-c]imidazol-1-yl)-2-[6-[6-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]-3-pyridyl]-7-fluoro-indazol-2-yl]-N-thiazol-2-yl-acetamide

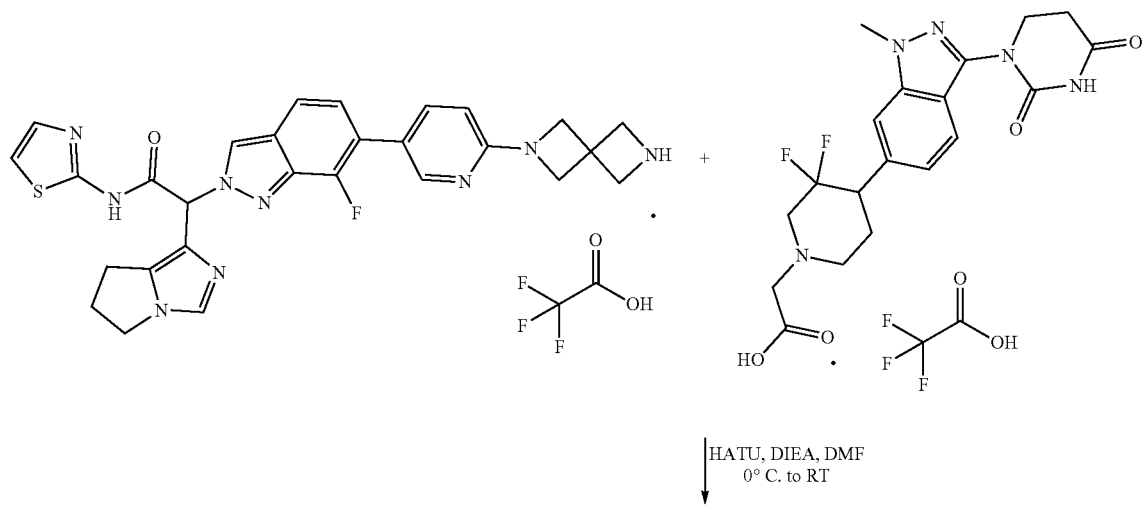

HATU, DIEA, DMF
0° C. to RT

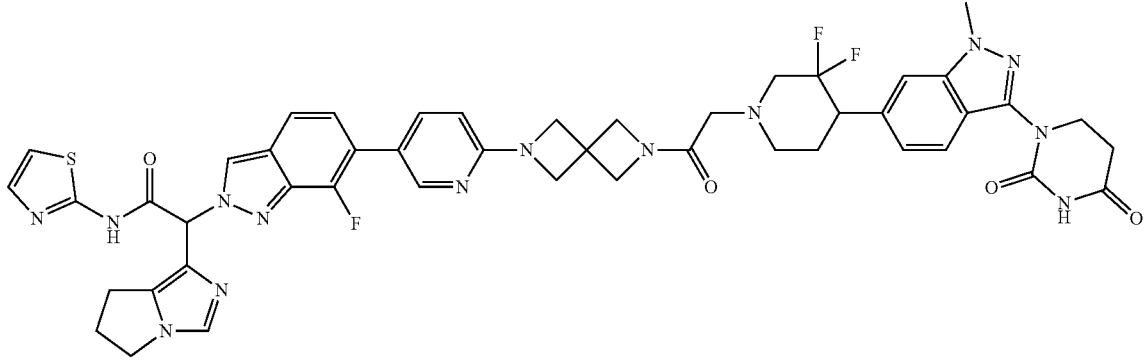

To a stirred solution of 2-[4-[3-(2,4-dioxohexahydropyrimidin-1-yl)-1-methyl-indazol-6-yl]-3,3-difluoro-1-piperidyl]acetic acid, trifluoroacetic acid salt (48.45 mg, 90.50 μmol) in N,N-dimethylformamide (5 mL) at 0° C. was added N,N-Diisopropylethylamine (108.08 mg, 836.26 μmol, 145.66 μL). 1-[Bis(dimethylamino)methylene]-1H-1,2,3-triazolo[4,5-b] pyridinium 3-oxid hexafluorophosphate (39.75 mg, 104.53 μmol) was added at the same temperature. 2-[6-[6-(2,6-diazaspiro[3.3]heptan-2-yl)-3-pyridyl]-7-fluoro-indazol-2-yl]-2-(6,7-dihydro-5H-pyrrolo[1,2-c]imidazol-1-yl)-N-thiazol-2-yl-acetamide, trifluoroacetic acid salt (Example 9, step 4, 70 mg, 104.53 μmol) was added and the reaction mixture was stirred for 2 h while warming to room temperature. The crude mixture was directly injected on a C18 column (50 g) for purification while eluting (0% to 60% of acetonitrile in water+0.1% ammonium acetate over 30 minutes, then steep gradient to 1000% acetonitrile). The pure fractions were frozen and lyophilized to afford Compound 70 (41 mg, 42.08 mol, 40.25% yield) as an off white solid. LCMS (ESI+) m/z: 959.3 [M+H]⁺. 1H-NMR (400 MHz, DMSO-d6: δ 12.85 (s, 1H), 10.58 (s, 1H), 8.34 (dd, J=9.60, 2.80 Hz, 2H), 7.80 (d, J=9.60 Hz, 1H), 7.69 (s, 1H), 7.61 (s, 1H), 7.58 (d, J=6.00 Hz, 2H), 7.52☐7.51 (m, 1H), 7.29 (bs, 1H), 7.14☐7.09 (m, 2H), 6.72 (bs, 1H), 6.55 (d, J=8.80 Hz, 1H), 4.45 (s, 2H), 4.16☐4.12 (m, 6H), 4.04☐4.02 (m, 2H), 4.00 (s, 3H), 3.93 (t, J=6.80 Hz, 2H), 3.26☐3.23 (m, 4H), 3.01☐2.98 (m, 1H), 2.84☐2.83 (m, 1H), 2.76 (t, J ☐☐☐☐☐Hz, 2H), 2.52☐2.51 (m, 2H), 2.50☐2.40 (m, 2H), 2.33☐2.30 (m, 1H), 1.89☐1.81 (m, 1H) (A proton signal could not be observed due to water obscuration).

Example 71

2-(6,7-dihydro-5H-pyrrolo[1,2-c]imidazol-1-yl)-2-[6-[6-[2-[2-[1-[4-[(2,6-dioxo-3-piperidyl)amino]-3-fluoro-phenyl]-4-hydroxy-4-piperidyl]acetyl]-2,6-diazaspiro[3.3]heptan-6-yl]-3-pyridyl]-7-fluoro-indazol-2-yl]-N-thiazol-2-yl-acetamide, Compound 71

Step 1: 1-(3-fluoro-4-nitrophenyl)piperidin-4-one

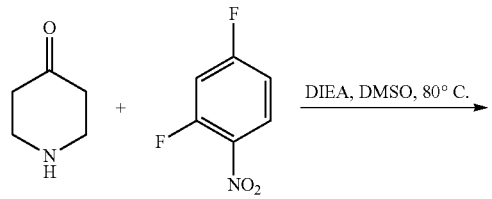

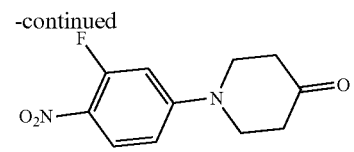

To a stirred solution of piperidin-4-one (13 g, 131.14 mmol), 2,4-difluoro-1-nitro-benzene (20.86 g, 131.14 mmol, 14.39 mL) in N,N-dimethylformamide (80 mL) was added N,N-Diisopropylethylamine (67.80 g, 524.56 mmol, 91.37 mL). The reaction mixture was stirred at 110° C. in a heating block for 16 h. The reaction mixture was diluted with ethyl acetate (500 mL), washed with cold water (150 mL). The organic layer was washed with brine solution (150 mL), dried over sodium sulphate and concentrated under reduced pressure to get crude. The residue was purified by column chromatography on silica gel eluted with 40% ethyl acetate in pet ether to afford 1-(3-fluoro-4-nitrophenyl) piperidin-4-one (9.0 g, 36.65 mmol, 27.95% yield) as brown solid. LCMS (ESI+) m/z: 239.1 [M+H]⁺.

Step 2: tert-butyl 2-[1-(3-fluoro-4-nitrophenyl)-4-hydroxy-4-piperidyl] acetate

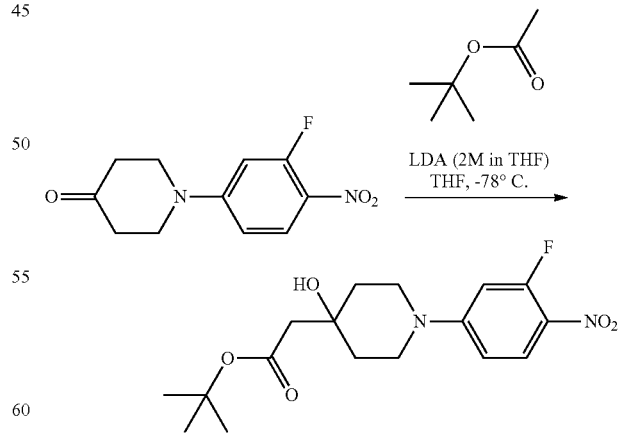

A round bottomed flask was charged with tert-butyl acetate (4.39 g, 37.78 mmol, 5.09 mL) in tetrahydrofuran (150 mL) and the solution was cooled to −78° C. Lithium diisopropylamide (2M solution in tetrahydrofuran, 75.56 mmol, 38 mL) was added dropwise over 15 minutes. The solution was stirred for 1 h at −78° C. 1-(3-fluoro-4-nitrophenyl) piperidin-4-one (9.00 g, 37.78 mmol) in tetrahydrofuran (50 ml) was added to the reaction mixture at −78° C. and stirred at same reaction temperature for 2 h. The reaction mixture was slowly warmed to −40° C. The reaction mixture was quenched with ammonium chloride solution and extracted with ethyl acetate (600 mL). Organic layers were washed with brine (150 mL), dried over anhydrous sodium sulfate and concentrated under reduced pressure to get crude product. The crude residue was purified using silica gel column chromatography, eluting with 0-50% ethyl acetate in petroleum ether, to afford tert-butyl 2-[1-(3-fluoro-4-nitro-phenyl)-4-hydroxy-4-piperidyl]acetate (11.91 g, 29.56 mmol, 77.28% yield) as brown solid. LCMS (ESI+) m/z: 355.1 [M+H]⁺.

Step 3: tert-butyl 2-[1-(4-amino-3-fluoro-phenyl)-4-hydroxy-4-piperidyl]acetate

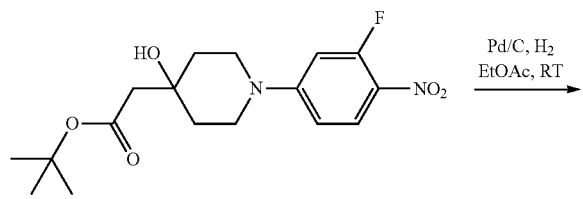

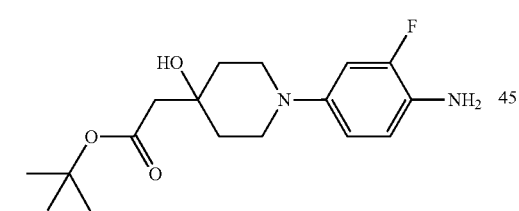

A round bottomed flask was charged with tert-butyl 2-[1-(3-fluoro-4-nitro-phenyl)-4-hydroxy-4-piperidyl]acetate (11.91 g, 33.62 mmol) in water (4 mL), ethanol (20 mL) were added Fe powder (9.39 g, 168.11 mmol, 1.19 mL), ammonium chloride (5.40 g, 100.87 mmol, 3.53 mL) and stirred at 70° C. for 4 h. After completion of the reaction, the reaction mixture was filtered through celite and washed with ethyl acetate (200 mL). The filtrate was washed with water (80 mL), sodium bicarbonate solution (60 mL) and brine (60 mL). The organic layer was dried over sodium sulphate and concentrated under reduced pressure to get crude. The residue was purified by column chromatography on silica gel eluted with 70% ethyl acetate in pet ether to afford tert-butyl 2-[1-(4-amino-3-fluoro-phenyl)-4-hydroxy-4-piperidyl]acetate (8.5 g, 24.63 mmol, 73.26% yield) as brownish solid. LCMS (ESI+) m/z: 325.2 [M+H]⁺.

Step 4: tert-butyl 2-[1-[4-[(2,6-dioxo-3-piperidyl)amino]-3-fluoro-phenyl]-4-hydroxy-4-piperidyl]acetate

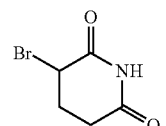

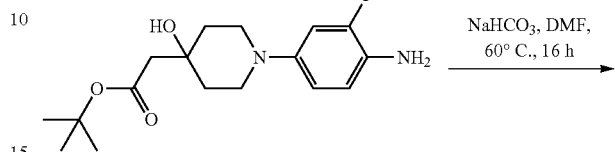

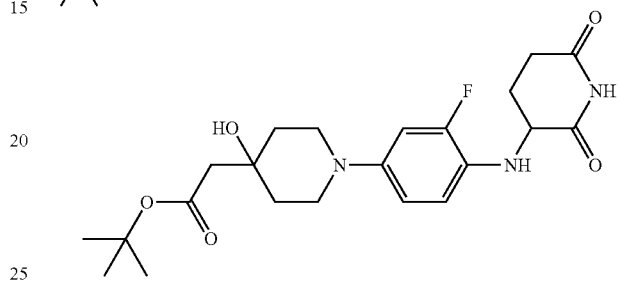

In a sealed tube, solution of tert-butyl 2-[1-(4-amino-3-fluoro-phenyl)-4-hydroxy-4-piperidyl]acetate (4.50 g, 13.87 mmol) in N,N-dimethylformamide (50 mL) was added Sodium bicarbonate (4.08 g, 48.55 mmol, 1.89 mL) and 3-bromopiperidine-2,6-dione (6.66 g, 34.68 mmol). The reaction tube was sealed and heated in a heating block at 70° C. for 16 h. Reaction mixture was cooled to room temperature, quenched with ice cooled water, extracted using ethyl acetate (200 ml) and washed with brine solution (50 ml). Organic layers were collected and concentrated under reduced pressure to afford crude residue. The crude product was purified using flash silica gel chromatography eluting with 0 to 70% ethyl acetate in petroleum ether to afford tert-butyl 2-[1-[4-[(2,6-dioxo-3-piperidyl)amino]-3-fluoro-phenyl]-4-hydroxy-4-piperidyl]acetate (5 g, 10.22 mmol, 73.66% yield) as a green solid. LCMS (ESI+) m/z: 436.3 [M+H]⁺

Step 5: 2-(1-(4-((2,6-dioxopiperidin-3-yl) amino)-3-fluorophenyl)-4 hydroxypiperidin-4-yl) acetic acid; hydrochloride

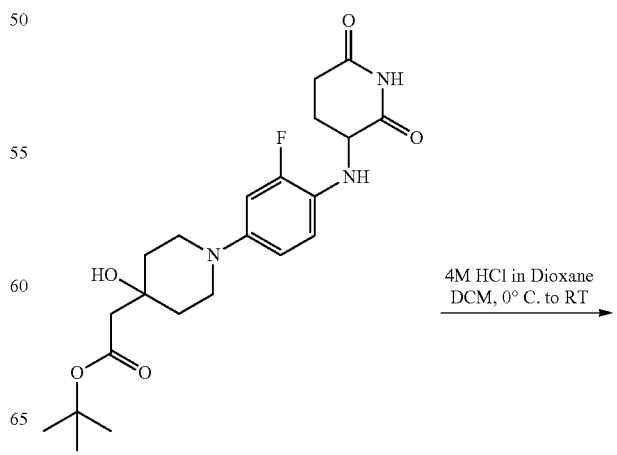

869
-continued

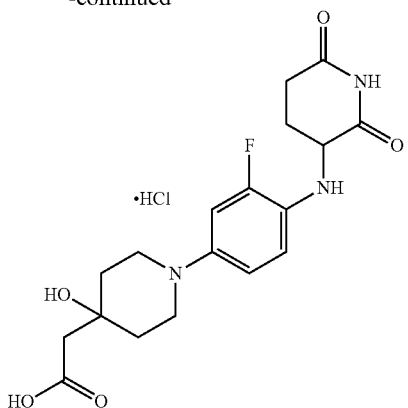

870

To a stirred solution of tert-butyl 2-[1-[4-[(2,6-dioxo-3-piperidyl)amino]-3-fluoro-phenyl]-4-hydroxy-4-piperidyl]acetate (300 mg, 688.88 µmol) in dichloromethane (10 mL) at 0° C. under nitrogen added hydrogen chloride (4M in 1,4-dioxane, 1.38 mL, 201.15 mg, 5.51 mmol). The reaction mixture was concentrated under reduced pressure to afford solid residue. Solid residue was stirred in diethyl ether for 10 minute, decanted and dried to afford 2-(1-(4-((2,6-dioxopiperidin-3-yl) amino)-3-fluorophenyl)-4 hydroxypiperidin-4-yl) acetic acid; hydrochloride (250.0 mg, 581.95 µmol, 84.48% yield). LCMS (ESI+) m/z: 380.1 [M+H]+

Step 6: 2-(6,7-dihydro-5H-pyrrolo[1,2-c]imidazol-1-yl)-2-[6-[6-[2-[2-[1-[4-[(2,6-dioxo-3-piperidyl)amino]-3-fluoro-phenyl]-4-hydroxy-4-piperidyl]acetyl]-2,6-diazaspiro[3.3]heptan-6-yl]-3-pyridyl]-7-fluoro-indazol-2-yl]-N-thiazol-2-yl-acetamide

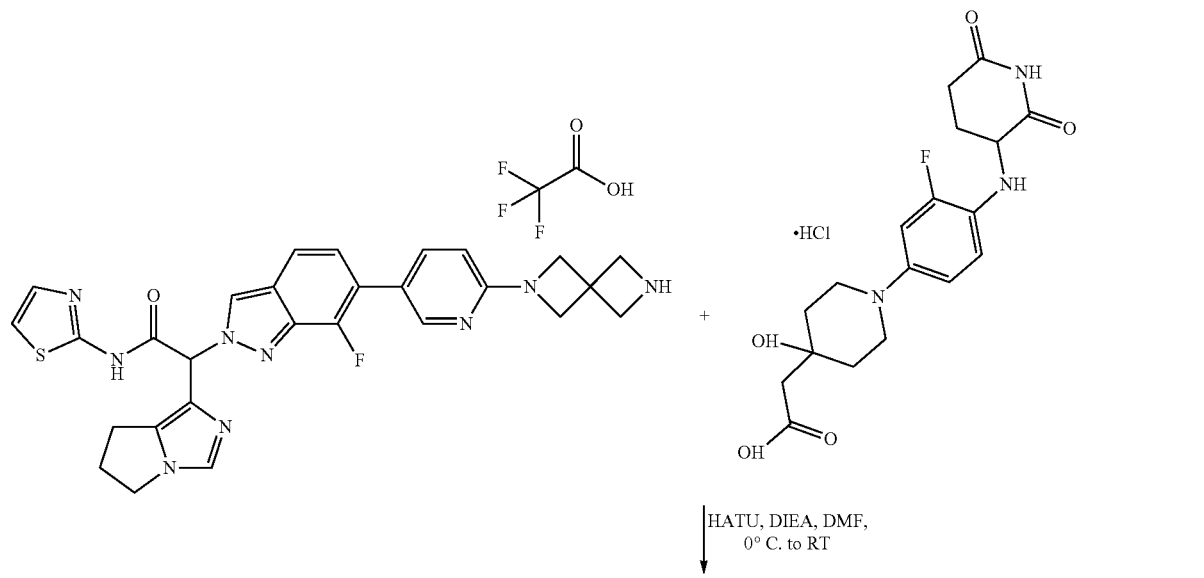

HATU, DIEA, DMF,
0° C. to RT

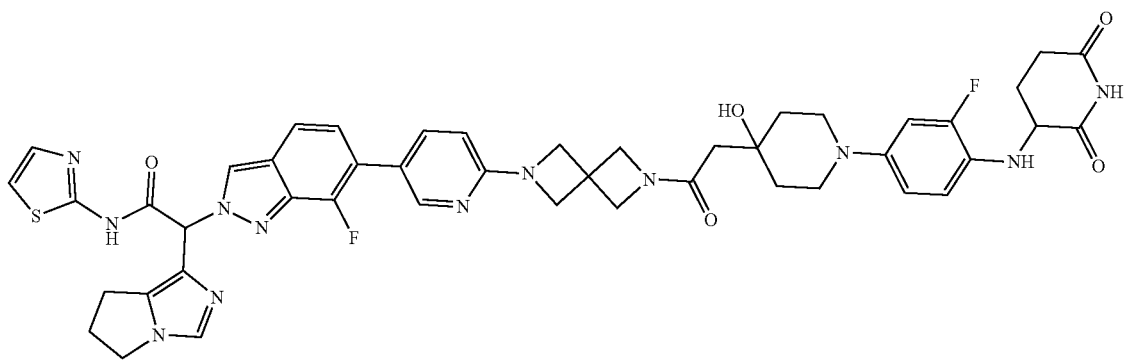

To a stirred solution of 2-[1-[4-[(2,6-dioxo-3-piperidyl)amino]-3-fluoro-phenyl]-4-hydroxy-4-piperidyl]acetic acid hydrochloride (43.47 mg, 104.53 μmol) in N,N-dimethylformamide (4 mL) at 0° C. was added N,N-diisopropylethylamine (108.08 mg, 836.26 μmol, 145.66 μL). 1-[Bis(dimethylamino)methylene]-1H-1,2,3-triazolo[4,5-b]pyridinium 3-oxide hexafluoro-phosphate (59.62 mg, 156.80 μmol) was added at the same temperature. 2-[6-[6-(2,6-diazaspiro[3.3]heptan-2-yl)-3-pyridyl]-7-fluoro-indazol-2-yl]-2-(6,7-dihydro-5H-pyrrolo[1,2-c]imidazol-1-yl)-N-thiazol-2-yl-acetamide, trifluoroacetic acid salt (Example 9, step 4, 0.07 g, 104.53 μmol) was added and the reaction mixture was stirred for 2 h while warming to room temperature. The crude mixture was directly injected on a C18 column (50 g) for purification, eluting with 0% to 60% acetonitrile in water (+0.1% ammonium acetate) over 30 minutes, then steep gradient to 100% acetonitrile. The pure fractions were frozen and lyophilized to afford product Compound 71 (45 mg, 48.19 μmol, 46.10% yield) as an off white solid. LCMS (ESI+) m/z: 917.3 [M+H]⁺; 1H-NMR (400 MHz, DMSO-d6: δ 12.80 (s, 1H), 10.81 (s, 1H), 8.33☐8.32 (m, 2H), 7.79 (d, J=9.20 Hz, 2H), 7.69 (s, 1H), 7.59 (d, J=8.80 Hz, 1H), 7.52 (d, J=3.60 Hz, 1H), 7.29 (d, J=3.60 Hz, 1H), 7.12 (dd, J=1.60, Hz, 1H), 6.74-6.73 (m, 3H), 6.59 (d, J=2.00 Hz, 1H), 6.54 (d, J=8.80 Hz, 1H), 5.04 (d, J=6.00 Hz, 1H), 4.78 (s, 1H), 4.38 (s, 2H), 4.31-4.26 (m, 1H), 4.15 (s, 4H), 4.09 (s, 2H), 4.04☐4.02 (m, 2H), 3.18☐3.15 (m, 2H), 2.95☐2.93 (m, 2H), 2.84☐2.76 (m, 2H), 2.52☐2.51 (m, 2H), 2.22 (s, 2H), 2.09☐2.08 (m, 1H), 1.98-1.97 (m, 1H), 1.75☐1.73 (m, 2H), 1.64☐1.61 (m, 2H) (water obscuration).

Example 72

2-(6,7-dihydro-5H-pyrrolo[1,2-c]imidazol-1-yl)-2-[6-[6-[4-[2-[4-[3-(2,4-dioxohexahydropyrimidin-1-yl)-1-methyl-indazol-6-yl]-3,3-difluoro-1-piperidyl]acetyl]piperazin-1-yl]-3-pyridyl]-4-fluoro-indazol-2-yl]-N-thiazol-2-yl-acetamide, Compound 72

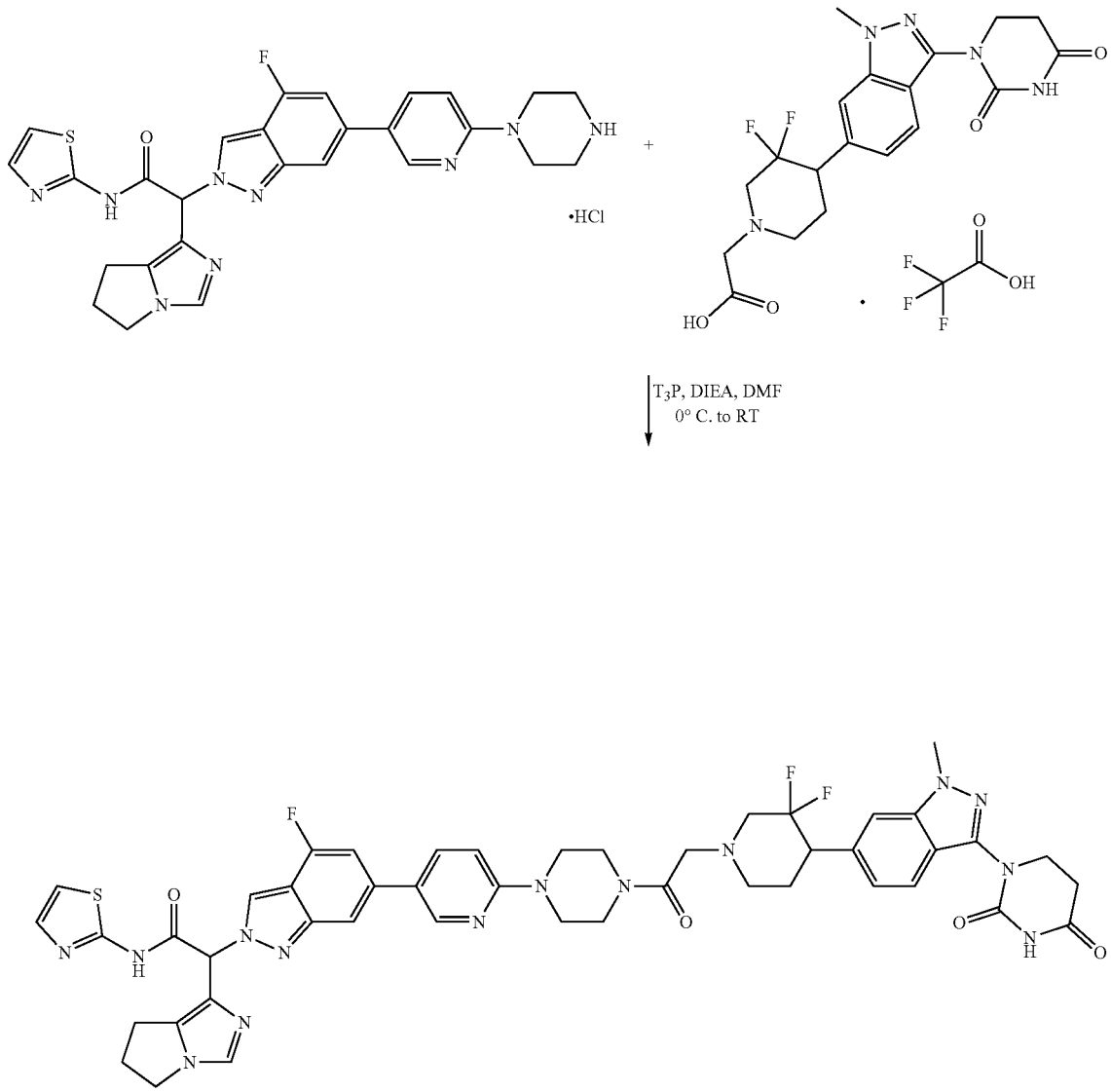

To a stirred solution of 2-[4-[3-(2,4-dioxohexahydropyrimidin-1-yl)-1-methyl-indazol-6-yl]-3,3-difluoro-1-piperidyl]acetic acid, trifluoroacetic acid salt (71.07 mg, 132.74 µmol) in N,N-dimethylformamide (5 mL) at 0° C. was added N,N-diisopropylethylamine (124.77 mg, 965.39 mol, 168.15 µL). Propylphosphonic anhydride solution (50 wt. % in ethyl acetate) (57.59 mg, 181.01 µmol) was added to the reaction mixture and stirred for 15 minutes. 2-(6,7-dihydro-5H-pyrrolo[1,2-c]imidazol-1-yl)-2-[4-fluoro-6-(6-piperazin-1-yl-3-pyridyl)indazol-2-yl]-N-thiazol-2-yl-acetamide hydrochloride (Example 4, step 9, 0.07 g, 120.67 µmol) was added and the reaction mixture was stirred for 5 h while warming to room temperature. The crude mixture was purified by C18 column (50 g) for purification (0% to 60% acetonitrile in water (with 0.1% ammonium acetate) over 45 minutes, then steep gradient to 100% acetonitrile). The pure fractions were frozen and lyophilized to afford product Compound 72 (49 mg, 50.45 µmol, 41.81% yield) as an off white solid. LCMS (ESI+) m/z: 947.3 [M+H]+. 1H-NMR (400 MHz, DMSO-d6): δ 12.85 (s, 1H), 10.57 (s, 1H), 8.58 (d, J=2.80 Hz, 1H), 8.28 (s, 1H), 8.00 (dd, J 15=9.00, 2.80 Hz, 1H), 7.69 (d, J=8.40 Hz, 2H), 7.60 (d, J=8.40 Hz, 1H), 7.55 (s, 1H), 7.50 (s, 1H), 7.27 (bs, 1H), 7.20 (d, J=12.40 Hz, 1H), 7.10 (d, J=8.80 Hz, 1H), 7.00 (d, J=8.80 Hz, 1H), 6.71 (bs, 1H), 4.01 (m, 2H), 3.99 (s, 3H), 3.92 (t, J=6.80 Hz, 2H), 3.69 (s, 4H), 3.61 (s, 4H), 3.47-3.44 (m, 2H), 3.29☐3.26 (m, 2H), 3.05-3.02 (m, 1H), 2.83 (m, 1H), 2.76 (t, J=6.80 Hz, 3H), 2.56-2.56 (m, 3H), 2.29 (m, 1H), 1.43 (m, 1H) (A proton signal was not observed due to water obscuration).

Example 73

2-(6,7-dihydro-5H-pyrrolo[1,2-c]imidazol-1-yl)-2-[6-[6-[6-[2-[4-[3-(2,4-dioxohexahydropyrimidin-1-yl)-1-methyl-indazol-6-yl]-3,3-difluoro-1-piperidyl]-2-oxo-ethyl]-2,6-diazaspiro[3.3]heptan-2-yl]-3-pyridyl]-7-fluoro-indazol-2-yl]-N-thiazol-2-yl-acetamide, Compound 73

Step 1: Synthesis of tert-butyl 6-[5-[2-[1-(6,7-dihydro-5H-pyrrolo[1,2-c]imidazol-1-yl)-2-ethoxy-2-oxo-ethyl]-7-fluoro-indazol-6-yl]-2-pyridyl]-2,6-diazaspiro[3.3]heptane-2-carboxylate

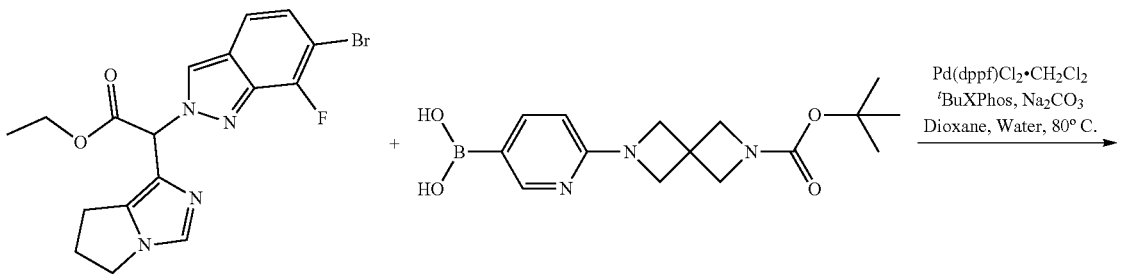

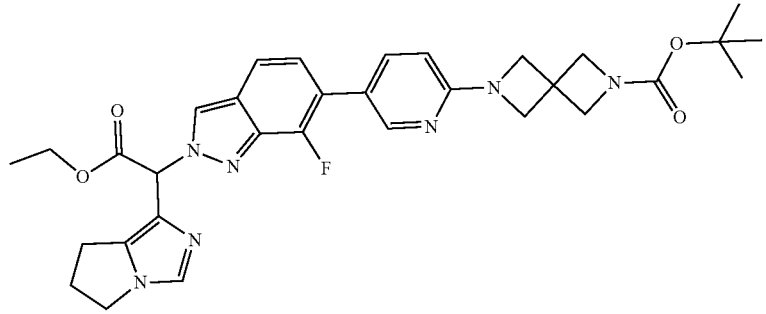

In a 50-mL sealed tube, ethyl 2-(6-bromo-7-fluoro-indazol-2-yl)-2-(6,7-dihydro-5H-pyrrolo[1,2-c]imidazol-1-yl)acetate (Example 2, step 4, 1.1 g, 2.70 mmol) and [6-(2-tert-butoxycarbonyl-2,6-diazaspiro[3.3]heptan-6-yl)-3-pyridyl]boronic acid (1.03 g, 3.24 mmol) in 1,4-dioxane (40 mL) was added Sodium carbonate (715.73 mg, 6.75 mmol, 282.90 µL) in water (10 ml). The reaction mixture was degassed with nitrogen for 10 mins. [1,1'-Bis(diphenylphosphino)ferrocene]-dichloropalladium(II), complex with dichloromethane (220.57 mg, 270.11 µmol) and 2-Di-tert-butylphosphino-2',4',6'-triisopropylbiphenyl (114.70 mg, 270.11 µmol) was added under nitrogen atmosphere and the mixture was further degassed with Nitrogen for 5 minutes. The tube was sealed and was stirred at 80° C. in a heating block for 5 h. The reaction mixture was filtered over celite and washed with 10% methanol in dichloromethane. The organic layer was separated, washed with brine and concentrated. The residue was purified by silica gel chromatography (0-10% methanol in dichloromethane) to afford tert-butyl 6-[5-[2-[1-(6,7-dihydro-5H-pyrrolo[1,2-c]imidazol-1-yl)-2-ethoxy-2-oxo-ethyl]-7-fluoro-indazol-6-yl]-2-pyridyl]-2,6-diazaspiro[3.3]-heptane-2-carboxylate (650 mg, 985.26 µmol, 36.48% yield) as a brown solid. LCMS (ESI+) m/z: 602.3 [M+H]+.

Step 2: Lithium 2-(6-(6-(6-(tert-butoxycarbonyl)-2,6-diazaspiro[3.3]heptan-2-yl)pyridin-3-yl)-7-fluoro-2H-indazol-2-yl)-2-(6,7-dihydro-5H-pyrrolo[1,2-c]imidazol-1-yl)acetate

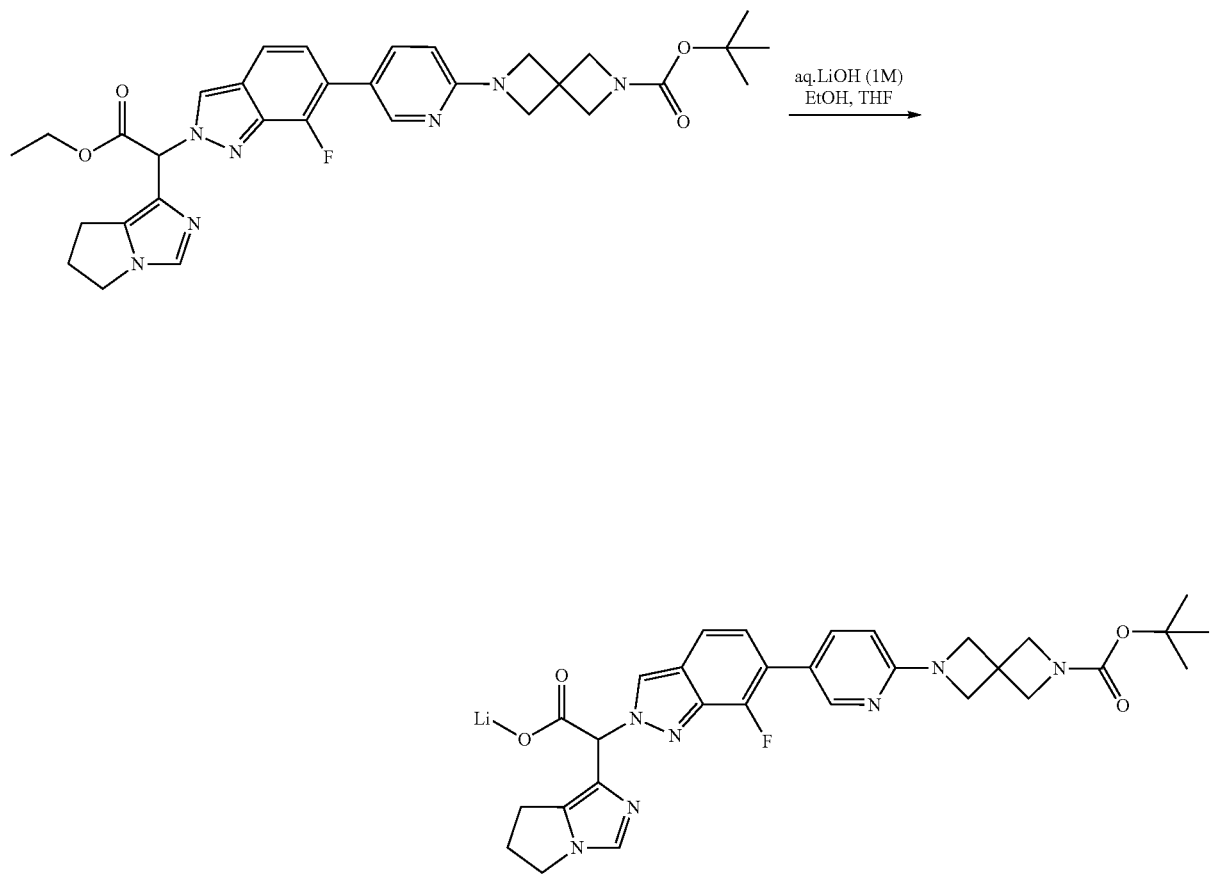

To a stirred solution of tert-butyl 6-[5-[2-[1-(6,7-dihydro-5H-pyrrolo[1,2-c]imidazol-1-yl)-2-ethoxy-2-oxo-ethyl]-7-fluoro-indazol-6-yl]-2-pyridyl]-2,6-diazaspiro[3.3]heptane-2-carboxylate (0.65 g, 1.08 mmol) in Ethanol (3 mL) and tetrahydrofuran (3 mL) was added LiOH (1M) (49.86 mg, 1.19 mmol) at ambient temperature and was further stirred for 3 h. The reaction mixture was concentrated under reduced pressure to afford solid, which was further triturated with diethyl ether, decanted and dried to get lithium 2-(6-(6-(6-(tert-butoxycarbonyl)-2,6-diazaspiro[3.3]heptan-2-yl)pyridin-3-yl)-7-fluoro-2H-indazol-2-yl)-2-(6,7-dihydro-5H-pyrrolo[1,2-c]imidazol-1-yl)acetate (600 mg, 852.04 µmol, 78.87%) as a brown solid. LCMS (ESI+) m/z: 574.2 [M+H]⁺.

Step 3: Synthesis of tert-butyl 6-(5-(2-(1-(6,7-dihydro-5H-pyrrolo[1,2-c]imidazol-1-yl)-2-oxo-2-(thiazol-2-ylamino)ethyl)-7-fluoro-2H-indazol-6-yl)pyridin-2-yl)-2,6-diazaspiro[3.3]heptane-2-carboxylate

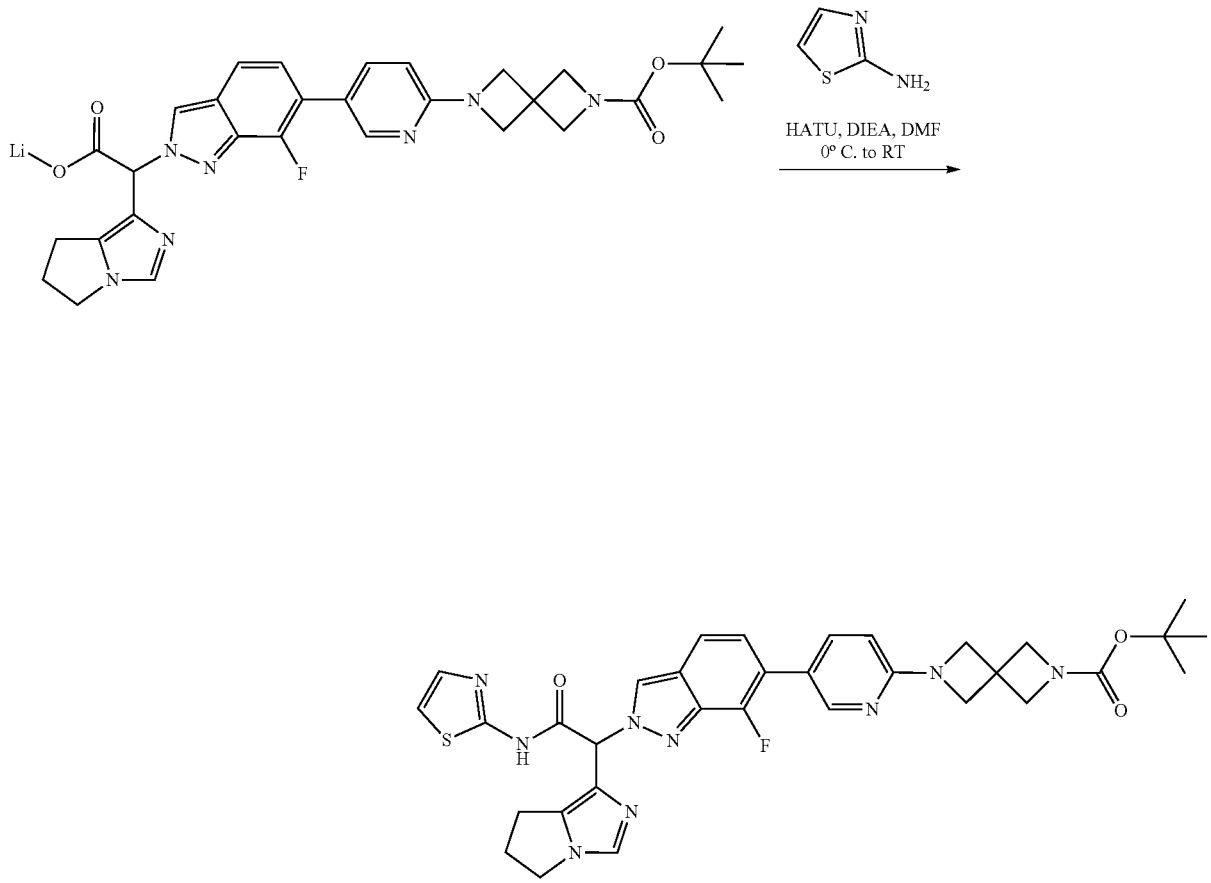

To a stirred solution of [2-[6-[6-(2-tert-butoxycarbonyl-2,6-diazaspiro[3.3]heptan-6-yl)-3-pyridyl]-7-fluoro-indazol-2-yl]-2-(6,7-dihydro-5H-pyrrolo[1,2-c]imidazol-1-yl)acetyl]oxylithium (0.35 g, 603.92 µmol) in N,N-dimethylformamide (8 mL) was added N,N-Diisopropylethylamine (390.25 mg, 3.02 mmol, 525.95 µL) at 0° C. 1-[Bis(dimethylamino)methylene]-1H-1,2,3-triazolo[4,5-b]pyridinium 3-oxid hexafluoro-phosphate (364.12 mg, 957.64 µmol) was added at the same temperature. After 10 minute, thiazol-2-amine (60.48 mg, 603.92 µmol) was added and the reaction mixture was stirred at room temperature for 16 h. The reaction mixture was added ice cold water and obtained solid was filtered, washed with water, and dried. This crude solid residue was purified by silica gel chromatography (3-8% of Methanol in Dichloromethane) to afford tert-butyl 6-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-2,6-diazaspiro[3.3]heptane-2-carboxylate (230 mg, 310.76 µmol, 51.46% yield) as brown solid. LCMS (ESI+) m/z: 656.3 [M+H]⁺.

Step 4: Synthesis of 2-(6-(6-(2,6-diazaspiro[3.3] heptan-2-yl)pyridin-3-yl)-7-fluoro-2H-indazol-2-yl)-2-(6,7-dihydro-5H-pyrrolo[1,2-c]imidazol-1-yl)-N-(thiazol-2-yl)acetamide, trifluoroacetic acid salt

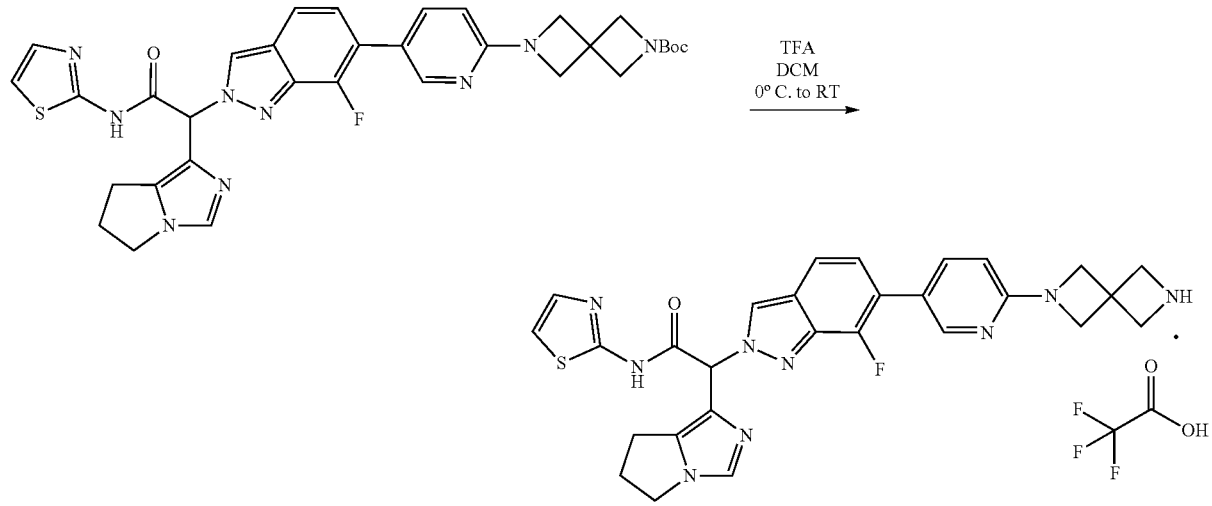

To a stirred solution of tert-butyl 6-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-2,6-diazaspiro[3.3]heptane-2-carboxylate (0.20 g, 305.00 μmol) in dichloromethane (8 mL) was added trifluoro acetic acid (278.21 mg, 2.44 mmol, 187.98 μL) dissolved in 2 ml of dichloromethane at 0° C. dropwise. The temperature of the reaction mixture was brought to ambient temperature and stirred for 4 h. The reaction mixture was concentrated under reduced pressure, triturated at −40° C. with diethyl ether, and decanted to afford 2-(6-(6-(2,6-diazaspiro[3.3]heptan-2-yl) pyridin-3-yl)-7-fluoro-2H-indazol-2-yl)-2-(6,7-dihydro-5H-pyrrolo[1,2-c]imidazol-1-yl)-N-(thiazol-2-yl)acetamide, trifluoroacetic acid salt (190 mg, 258.19 μmol, 84.65% yield) as a brown solid. LCMS (ESI+) m/z: 554.2 [M−H]+.

Step 5: Synthesis of 2-[2-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-2,6-diazaspiro[3.3]heptan-6-yl]acetic acid

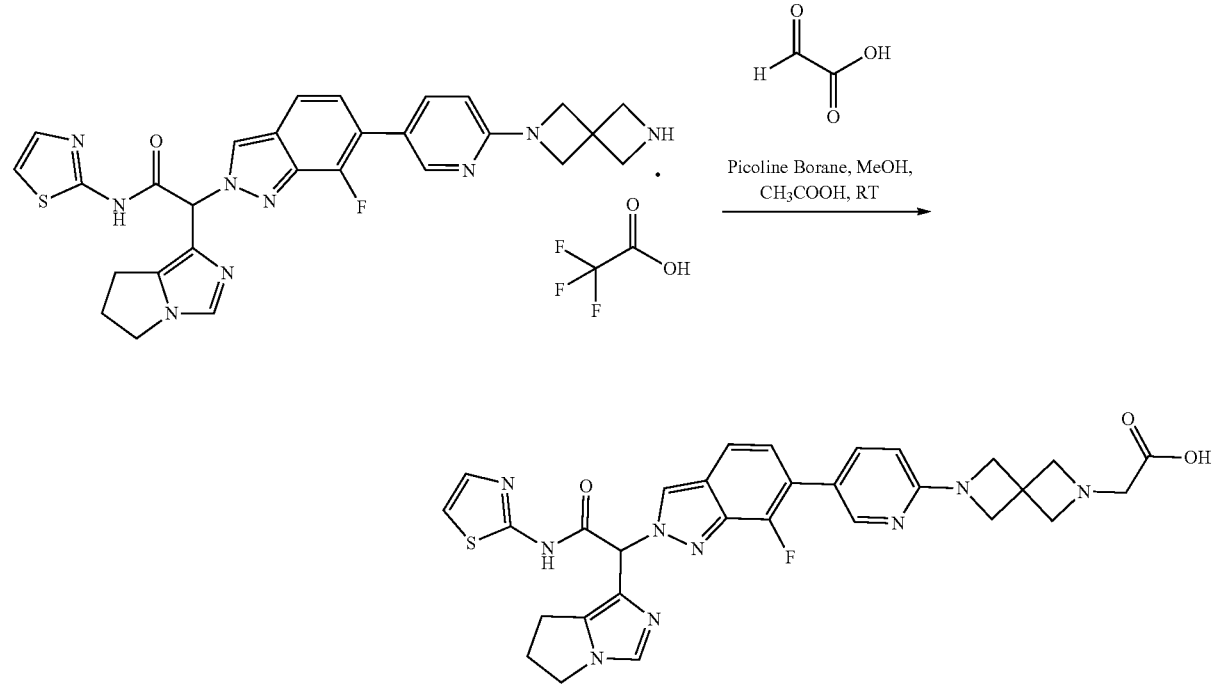

2-[6-[6-(2,6-diazaspiro[3.3]heptan-2-yl)-3-pyridyl]-7-fluoro-indazol-2-yl]-2-(6,7-dihydro-5H-pyrrolo[1,2-c]imidazol-1-yl)-N-thiazol-2-yl-acetamide, trifluoroacetic acid salt (0.1 g, 149.33 μmol) and glyoxylic acid (16.58 mg, 224.00 μmol, 12.38 μL) in methanol (4 mL) was added catalytic amount of acetic acid and stirred at ambient temperature for 4 h. Picoline borane (23.28 mg, 224.00 μmol) was added and continued further stirring for 16 h at room temperature. The reaction mixture was concentrated and purified over C18 reverse phase column eluting with (0% to 60% acetonitrile in water+0.1% ammonium acetate over 30 minutes, then steep gradient to 100% acetonitrile). The pure fractions were frozen and lyophilized to afford product 2-[2-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-2,6-diazaspiro[3.3]heptan-6-yl]acetic acid (50 mg, 74.72 μmol, 50.03% yield) as a white solid. LCMS (ESI+) m/z: 614.2 [M+H]+.

Step 6: Synthesis of 2-(6,7-dihydro-5H-pyrrolo[1,2-c]imidazol-1-yl)-2-[6-[6-[6-[2-[4-[3-(2,4-dioxohexahydropyrimidin-1-yl)-1-methyl-indazol-6-yl]-3,3-difluoro-1-piperidyl]-2-oxo-ethyl]-2,6-diazaspiro[3.3]heptan-2-yl]-3-pyridyl]-7-fluoro-indazol-2-yl]-N-thiazol-2-yl-acetamide

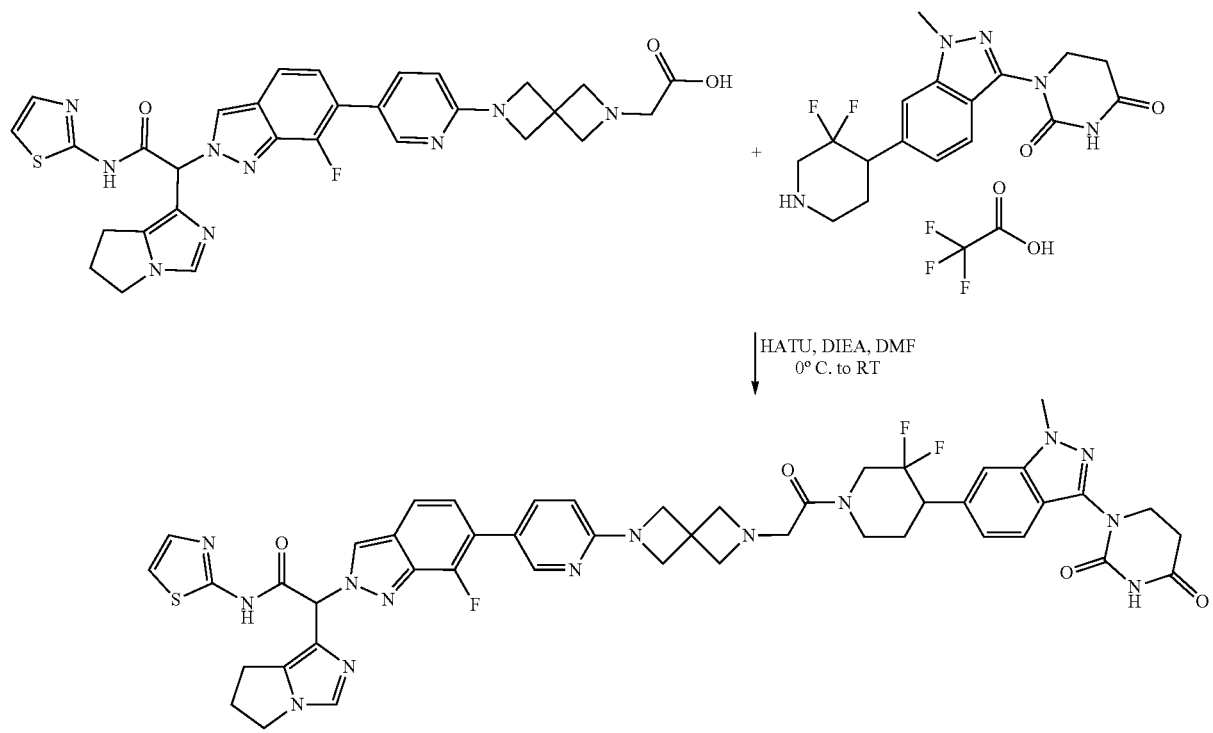

To a stirred solution of 2-[2-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-2,6-diazaspiro[3.3]heptan-6-yl]acetic acid (0.04 g, 65.18 μmol) in N,N-dimethylformamide (4 mL) at 0° C. was added N,N-Diisopropylethylamine (42.12 mg, 325.91 μmol, 56.77 μL). Propylphosphonic anhydride solution (50 wt. % in ethyl acetate) (31.11 mg, 29.1 μL, 97.77 μmol) was added at the same temperature. 1-[6-(3,3-difluoro-4-piperidyl)-1-methyl-indazol-3-yl]hexahydropyrimidine-2,4-dione, trifluoroacetic acid salt (34.23 mg, 71.70 μmol) was added to the reaction mixture while maintaining 0° C., and the reaction mixture was stirred for 16 h while warming to room temperature. The crude mixture was directly injected in C18 column (50 g) for purification while eluting with (0% to 60% acetonitrile in water+0.1% ammonium acetate over 30 minutes, then steep gradient to 100% acetonitrile). The pure fractions were frozen and lyophilized to afford product Compound 73 (24 mg, 23.65 μmol, 36.28% yield) as an off white solid. LCMS (ESI+) m/z: 960.2 [M+H]+. 1H-NMR (400 MHz, DMSO-d6): δ 12.81 (s, 1H), 10.58 (s, 1H), 8.32 (d, J=2.80 Hz, 2H), 7.78 (d, J=8.40 Hz, 1H), 7.70 (s, 1H), 7.63-7.56 (m, 4H), 7.52 (d, J=3.60 Hz, 1H), 7.29 (d, J=3.20 Hz, 1H), 7.14-7.07 (m, 2H), 6.72 (s, 1H), 6.54 (d, J=3.60 Hz, 1H), 4.79-4.49 (m, 1H), 4.12-3.98 (m, 10H), 3.93 (t, J=6.40 Hz, 2H), 3.65-3.51 (m, 5H), 2.96-2.79 (m, 1H), 2.77 (t, J=6.40 Hz, 2H), 2.09-1.81 (m, 1H), 1.24 (s, 2H), 1.19-1.06 (m, 1H) (Proton signals were not observed due to water obscuration).

Example 74

2-(6,7-dihydro-5H-pyrrolo[1,2-c]imidazol-1-yl)-2-[6-[6-[2-[2-[1-[4-[(2,6-dioxo-3-piperidyl)amino]-2-fluoro-phenyl]-4-hydroxy-4-piperidyl]acetyl]-2,6-diazaspiro[3.3]heptan-6-yl]-3-pyridyl]-7-fluoro-indazol-2-yl]-N-thiazol-2-yl-acetamide, Compound 74

Step 1: 1-(2-fluoro-4-nitro-phenyl)piperidin-4-one

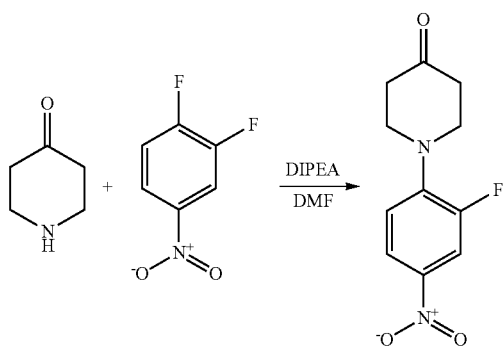

To a solution of piperidin-4-one (15.0 g, 151.31 mmol), 1,2-difluoro-4-nitro-benzene (24.07 g, 151.31 mmol, 16.72 mL) in N,N-dimethylformamide (30 mL) was added N,N-diisopropylethylamine (78.22 g, 605.26 mmol, 105.42 mL) and heated at 110° C. for 14 h. The reaction mixture was diluted with ethyl acetate (500 mL) and washed with cold water (150 mL). The organic layer was washed with a brine solution (150 mL), dried over sodium sulfate and concentrated under reduced pressure. The residue was purified by column chromatography on silica gel (40% ethyl acetate in petroleum ether) to afford 1-(2-fluoro-4-nitro-phenyl)piperidin-4-one (21 g, 77.93 mmol, 51.50% yield) as a brown solid. LCMS, m/z: 238.9 [M+H]$^+$ Step 2: Synthesis of tert-butyl 2-[1-(4-amino-2-fluoro-phenyl)-4-hydroxy-4-piperidyl]acetate

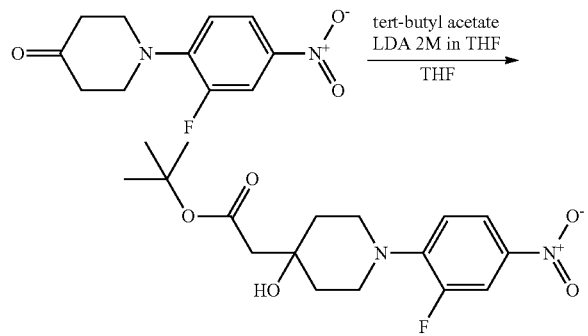

Lithium diisopropylamide (2 M, 12.59 mL) was added dropwise to a stirred solution of tert-butyl acetate (1.76 g, 15.11 mmol, 2.03 mL) in tetrahydrofuran (25 mL) at −78° C. The reaction mixture was stirred at −78° C. for 45 minutes. 1-(2-fluoro-4-nitro-phenyl)piperidin-4-one (3 g, 12.59 mmol) dissolved in tetrahydrofuran (15 mL) was added to it at −78° C. The reaction mixture was stirred at −78° C. for 2 h. The reaction mixture was quenched with saturated ammonium chloride solution and the mixture was extracted with ethyl acetate. The organic layer was dried over sodium sulfate and concentrated under reduced pressure. The residue was purified by silica gel (100-200 mesh) column chromatography (eluent: 30% to 40% Ethyl acetate in Petroleum ether) to afford tert-butyl 2-[1-(2-fluoro-4-nitro-phenyl)-4-hydroxy-4-piperidyl]acetate (2.7 g, 7.01 mmol, 55.66% yield) as light yellow sticky solid. LCMS: 355.1 (M+H)+

Step 3: tert-butyl 2-[1-(4-amino-2-fluoro-phenyl)-4-hydroxy-4-piperidyl]acetate

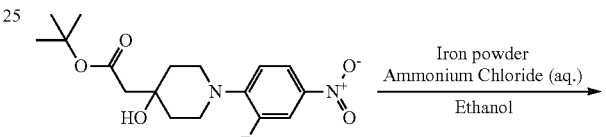

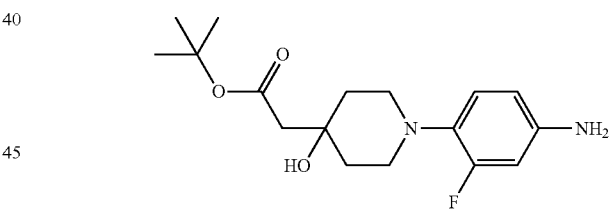

To a solution of tert-butyl 2-[1-(2-fluoro-4-nitro-phenyl)-4-hydroxy-4-piperidyl]acetate (1.5 g, 4.23 mmol) in Ethanol (10 mL) and water (2 mL) were added iron powder (1.18 g, 21.16 mmol, 150.37 μL) and ammonium chloride (679.26 mg, 12.70 mmol, 443.96 μL). The reaction was stirred at 70° C. for 4 h. The reaction mixture was filtered through celite and the filter cake was washed with ethyl acetate (60 mL). The filtrate was washed with water (20 mL), aqueous sodium bicarbonate (20 mL) and brine (20 mL). The organic layer was dried over sodium sulfate and concentrated under reduced pressure to get crude, which was purified by column chromatography on silica gel eluted with 70% ethyl acetate in petroleum ether to afford tert-butyl 2-[1-(4-amino-2-fluoro-phenyl)-4-hydroxy-4-piperidyl]acetate (1.2 g, 3.44 mmol, 81.28% yield) as a brown sticky solid. LCMS m/z: 325.1 [M+H], $^1$HNMR (DMSO-d6) 8.02-7.89 (m, 2H), 7.23-7.05 (m, 1H), 4.69 (s, 1H), 3.55-3.43 (m, 2H), 3.22-3.19 (m, 2H), 2.36 (s, 2H), 1.88-1.64 (m, 3H), 1.41 (s, 9H).

885

Step 4: tert-butyl 2-[1-[4-[(2,6-dioxo-3-piperidyl)amino]-2-fluoro-phenyl]-4-hydroxy-4-piperidyl]acetate

886

Step 5: 2-[1-[4-[(2,6-dioxo-3-piperidyl)amino]-2-fluoro-phenyl]-4-hydroxy-4-piperidyl]acetic acid hydrochloride

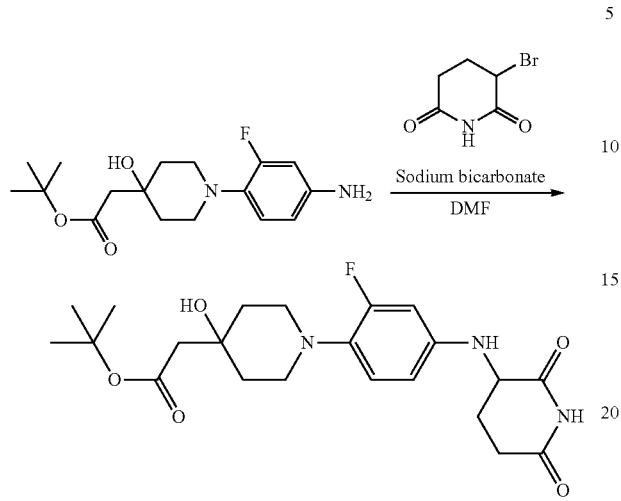
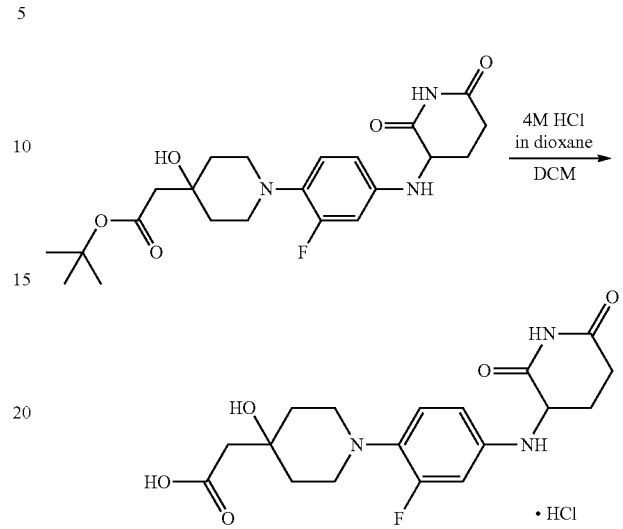

To a stirred solution of tert-butyl 2-[1-(4-amino-2-fluoro-phenyl)-4-hydroxy-4-piperidyl]acetate (1 g, 3.08 mmol) in N,N-dimethylformamide (10 mL) were added sodium bicarbonate (517.94 mg, 6.17 mmol, 239.79 µL) under nitrogen atmosphere in 25 ml seal tube. The vial was sealed and heated at 60° C. overnight. The reaction mixture was filtered through celite bed, washed 2 times with ethyl acetate and filtrate was concentrated under reduced pressure at 35° C. The crude residue was purified over silica column (100-200 mesh) eluting the compound in 65-70% ethyl acetate in petroleum ether. Pure fractions were evaporated under reduced pressure to afford the desired compound tert-butyl 2-[1-[4-[(2,6-dioxo-3-piperidyl)amino]-2-fluoro-phenyl]-4-hydroxy-4-piperidyl]acetate (760 mg, 1.67 mmol, 54.11% yield) as an off white solid. LCMS m/z: 436.0 [M+H], $^1$H-NMR (DMSO-d6): 10.79 (s, 1H), 6.87-6.80 (m, 1H), 6.52 (dd, J=13.6 Hz, 3.6 Hz, 1H), 6.41 (dd, J=3.7 Hz, 1.6 Hz, 1H), 4.89 (d, J=3.6 Hz, 1H), 4.45 (s, 1H), 4.30-4.19 (m, 1H), 2.90-2.80 (m, 4H), 2.78-2.51 (m, 3H), 2.49-2.41 (m, 1H), 2.13-2.01 (m, 2H), 1.95-1.63 (m, 4H), 1.42 (s, 9H).

To the stirred solution of tert-butyl 2-[1-[4-[(2,6-dioxo-3-piperidyl)amino]-2-fluoro-phenyl]-4-hydroxy-4-piperidyl]acetate (1.0 g, 2.30 mmol) in dichloromethane (10 mL) was added hydrogen chloride (4M in 1,4-dioxane, 8.00 g, 219.41 mmol, 10 mL) dropwise at 0° C. The reaction mixture stirred at 25° C. for 3 h. The reaction mixture was concentrated under reduced pressure to give 2-[1-[4-[(2,6-dioxo-3-piperidyl)amino]-2-fluoro-phenyl]-4-hydroxy-4-piperidyl]acetic acid hydrochloride (900 mg, 2.16 mmol, 93.89% yield) as an off-white solid. LCMS m/z 380.2 (M+H)$^+$.

Step 6: 2-(6,7-dihydro-5H-pyrrolo[1,2-c]imidazol-1-yl)-2-[6-[6-[2-[2-[1-[4-[(2,6-dioxo-3-piperidyl)amino]-2-fluoro-phenyl]-4-hydroxy-4-piperidyl]acetyl]-2,6-diazaspiro[3.3]heptan-6-yl]-3-pyridyl]-7-fluoro-indazol-2-yl]-N-thiazol-2-yl-acetamide

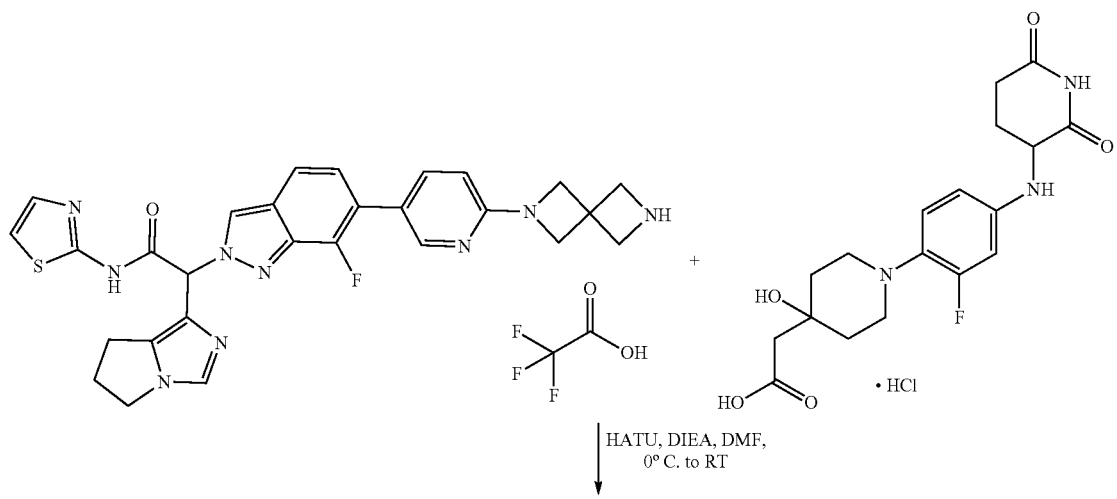

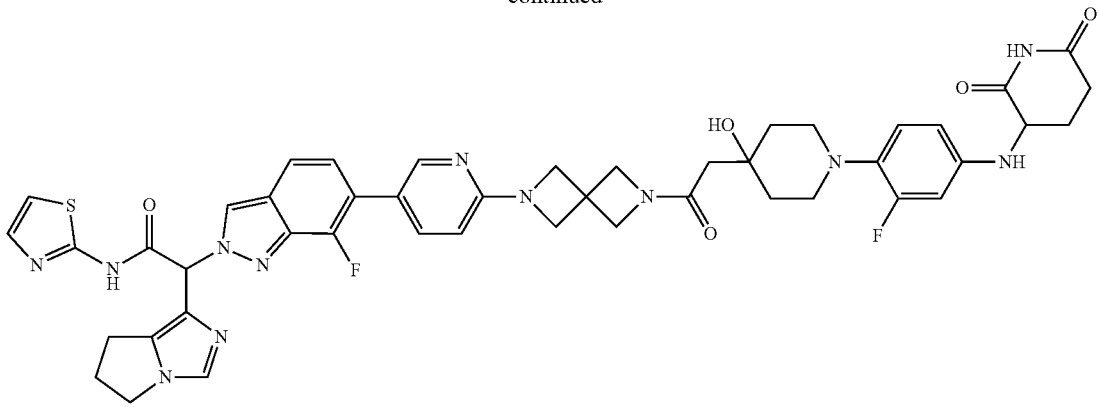

To a mixture of 2-[6-[6-(2,6-diazaspiro[3.3]heptan-2-yl)-3-pyridyl]-7-fluoro-indazol-2-yl]-2-(6,7-dihydro-5H-pyrrolo[1,2-c]imidazol-1-yl)-N-thiazol-2-yl-acetamide, trifluoroacetic acid salt (100 mg, 149.33 μmol) and 2-[1-[4-[(2,6-dioxo-3-piperidyl)amino]-2-fluoro-phenyl]-4-hydroxy-4-piperidyl]acetic acid hydrochloride (56.65 mg, 136.24 μmol) in N,N-dimethylformamide (2 mL) were added N,N-Diisopropylethylamine (57.90 mg, 447.99 μmol, 78.03 μL) at 0° C. 1-[Bis(dimethylamino)methylene]-1H-1,2,3-triazolo[4,5-b]pyridinium 3-oxid hexafluoro-phosphate (85.17 mg, 224.00 μmol) was added and the reaction mixture was stirred for 2 h at room temperature. The reaction mixture was directly injected on C18 column (50 g) for purification while eluting with (0% to 55% acetonitrile in water (+0.1% ammonium acetate) over 30 minutes, then steep gradient to 100% acetonitrile). The pure fractions were frozen and lyophilized to get Compound 74 (37.01 mg, 37.12 μmol, 24.86% yield) as grey colour solid. LCMS (ESI+) m/z: 915.3 [M−H]⁺. 1H-NMR (400 MHz, DMSO-d6): δ 12.81 (s, 1H), 10.79 (s, 1H), 8.33 (d, J=4.80 Hz, 2H), 7.80 (d, J=4.80 Hz, 1H), 7.69 (s, 1H), 7.59 (d, J=8.80 Hz, 1H), 7.52 (d, J=3.60 Hz, 1H), 7.30 (s, 1H), 7.12 (d, J=1.60 Hz, 1H), 6.52☐6.41 (m, 3H), 5.78 (d, J=7.6 Hz, 1H), 4.77 (s, 1H), 4.40 (s, 2H), 4.29☐4.20 (m, 1H), 4.09 (bs, 4H), 4.02 (d, J=7.6 Hz, 2H), 4.00 (bs, 2H), 2.90☐2.56 (m, 12H), 2.33 (s, 2H), 2.12-2.01 (m, 1H), 1.90-1.71 (m, 3H), 1.69-1.56 (m, 1H) (Water obscuration).

Example 75

2-(6,7-dihydro-5H-pyrrolo[1,2-c]imidazol-1-yl)-2-[6-[6-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]-3-pyridyl]-4-fluoro-indazol-2-yl]-N-thiazol-2-yl-acetamide, Compound 75

Step 1: tert-butyl 2-[1-[4-[[(3S)-2,6-dioxo-3-piperidyl]amino]-2-fluoro-phenyl]-4-hydroxy-4-piperidyl]acetate

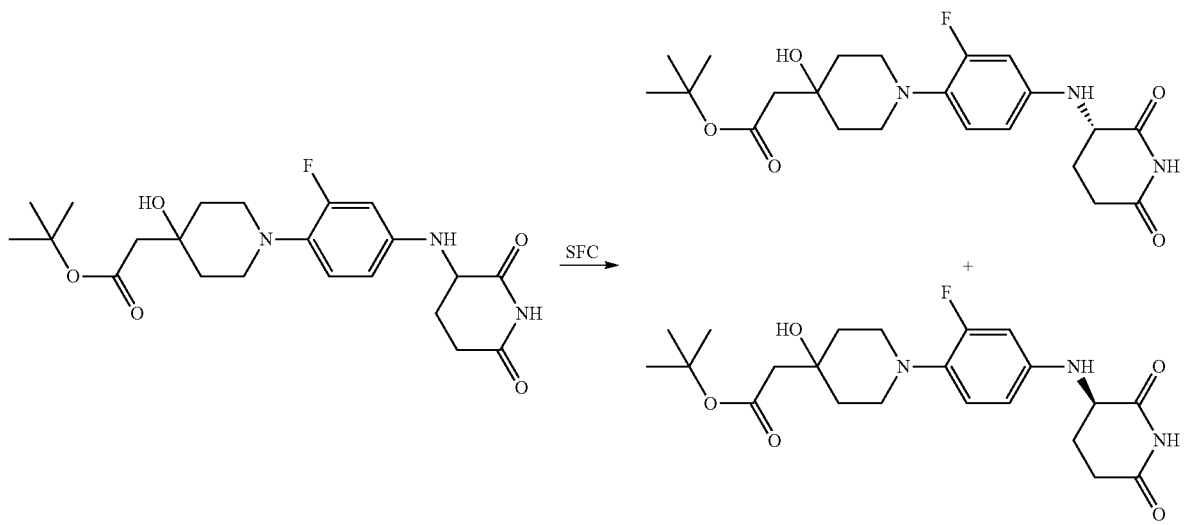

The racemic mixture tert-butyl 2-[1-[4-[(2,6-dioxo-3-piperidyl)amino]-2-fluoro-phenyl]-4-hydroxy-4-piperidyl]acetate (2 g, 4.59 mmol) was resolved by chiral SFC. 2.0 g of tert-butyl 2-[1-[4-[(2,6-dioxo-3-piperidyl)amino]-2-fluoro-phenyl]-4-hydroxy-4-piperidyl]acetate was dissolved in 22.0 ml of acetonitrile. SFC separation conditions: Column: LUX A1 [250×10 mm, 5-micron particle size]; Mobile phase: CO$_2$: Isopropanol (45:55); Flow rate: 12 g/min; Cycle time: 11.0 minute; Back pressure: 100 bar UV collection, wavelength: 254 nm; Volume: 0.4 ml per injection The first eluting set of fractions was evaporated under pressure to afford tert-butyl 2-[1-[4-[[(3S)-2,6-dioxo-3-piperidyl]amino]-2-fluoro-phenyl]-4-hydroxy-4-piperidyl]acetate (850 mg, 1.84 mmol, 40.04% yield) as an off white solid. LCMS m/z: 436.0 [M+H], LCMS (ESI+) m/z: 436.2 [M+H]$^+$. 1H-NMR (400 MHz, DMSO-d6): δ 10.77 (s, 1H), 6.83 (t, J=12.00 Hz, 1H), 6.49 (d, J=20.00 Hz, 1H), 6.41 (d, J=12.00 Hz, 1H), 5.77 (d, J=7.60 Hz, 1H), 4.44 (s, 1H), 4.29-4.12 (m, 1H), 2.91-2.79 (m, 5H), 2.74-2.70 (m, 1H), 2.34 (s, 2H), 2.16-2.02 (m, 1H), 1.89-1.69 (m, 3H), 1.65 (d, J=16.80 Hz, 2H), 1.42 (s, 9H), 99.18% ee by chiral SFC (Rt=2.33 minute), Specific optical rotation: −46.2° [α]$^{20}_D$ The second eluting set of fractions was evaporated under pressure to afford tert-butyl 2-[1-[4-[[(3R)-2,6-dioxo-3-piperidyl]amino]-2-fluoro-phenyl]-4-hydroxy-4-piperidyl]acetate (530 mg, 1.17 mmol, 25.52% yield) as an off white solid. LCMS (ESI+) m/z: 436.0 [M+H]$^+$. 1H-NMR (400 MHz, DMSO-d6): δ 10.78 (s, 1H), 6.84 (t, J=13.20 Hz, 1H), 6.49 (d, J=20.00 Hz, 1H), 6.41 (d, J=12.40 Hz, 1H), 5.77 (d, J=10.40 Hz, 1H), 4.44 (s, 1H), 4.27-4.22 (m, 1H), 2.92-2.77 (m, 5H), 2.73-2.63 (m, 1H), 2.34 (s, 2H), 2.18-2.03 (m, 1H), 1.87-1.73 (m, 3H), 1.64 (d, J=18.00 Hz, 2H), 1.48 (s, 9H), 99.13% ee by chiral SFC (Rt=4.92 minute), Specific optical rotation: +46.8° [α]$^{20}_D$ Step 2: 2-[1-[4-[[(3S)-2,6-dioxo-3-piperidyl]amino]-2-fluoro-phenyl]-4-hydroxy-4-piperidyl]acetic acid hydrochloride

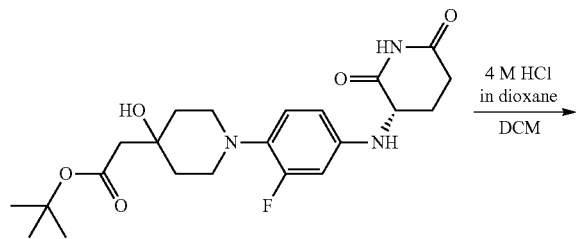

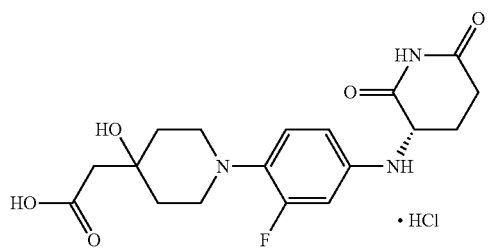

To a stirred solution of tert-butyl 2-[1-[4-[[(3S)-2,6-dioxo-3-piperidyl]amino]-2-fluoro-phenyl]-4-hydroxy-4-piperidyl]acetate (600 mg, 1.38 mmol) in dichloromethane (15 mL) at 0° C. was added hydrogen chloride (4M solution in 1,4-dioxane, 1.72 mL, 6.89 mmol) dropwise. The reaction mixture was stirred at room temperature for 6 h. The volatiles were removed by rotary evaporation under reduced pressure. The residue was triturated twice with diethyl ether (2×10 ml). The solid residue was dried under vacuum to afford 2-[1-[4-[[(3S)-2,6-dioxo-3-piperidyl]amino]-2-fluoro-phenyl]-4-hydroxy-4-piperidyl]acetic acid hydrochloride (610 mg, 1.09 mmol, 78.96% yield) as a grey solid. LCMS (ESI+) m/z: 380.0 [M+H]$^+$, $^1$H-NMR (400 MHz, DMSO-d6): δ 12.03 (bs, 1H), 10.86 (s, 1H), 7.63 (s, 1H), 6.70 (d, J=15.20 Hz, 1H), 6.58 (dd, J=11.40, 6.80 Hz, 1H), 4.43 (dd, J=11.60, 4.40 Hz, 1H), 3.88-3.65 (m, 5H), 3.41-3.36 (m, 2H), 2.74-2.68 (m, 1H), 2.59-2.54 (m, 1H), 2.46 (s, 2H), 2.33 (bs, 2H), 2.10-2.08 (m, 1H), 1.94-1.88 (m, 2H).

Step 3: 2-(6,7-dihydro-5H-pyrrolo[1,2-c]imidazol-1-yl)-2-[6-[6-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]-3-pyridyl]-4-fluoro-indazol-2-yl]-N-thiazol-2-yl-acetamide

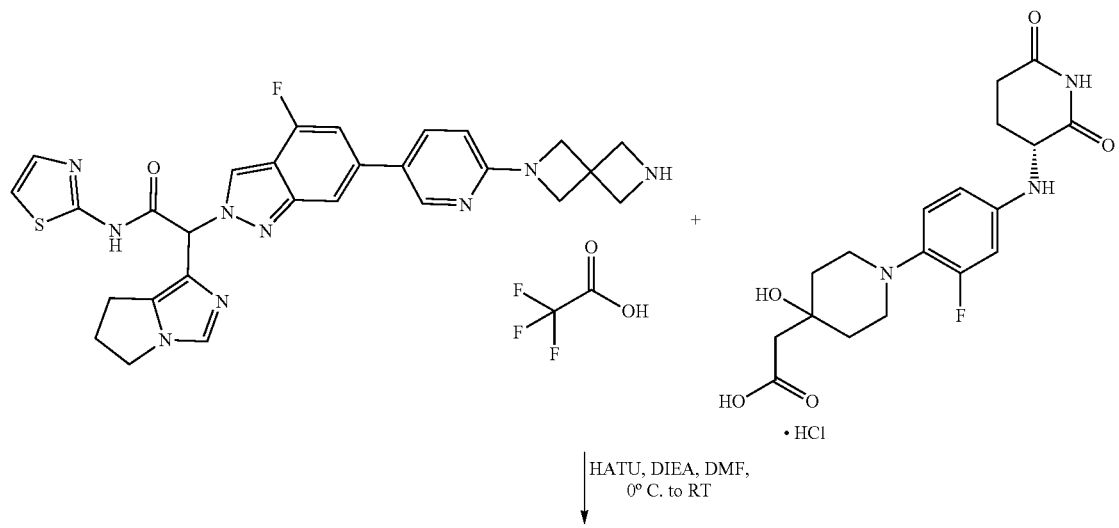

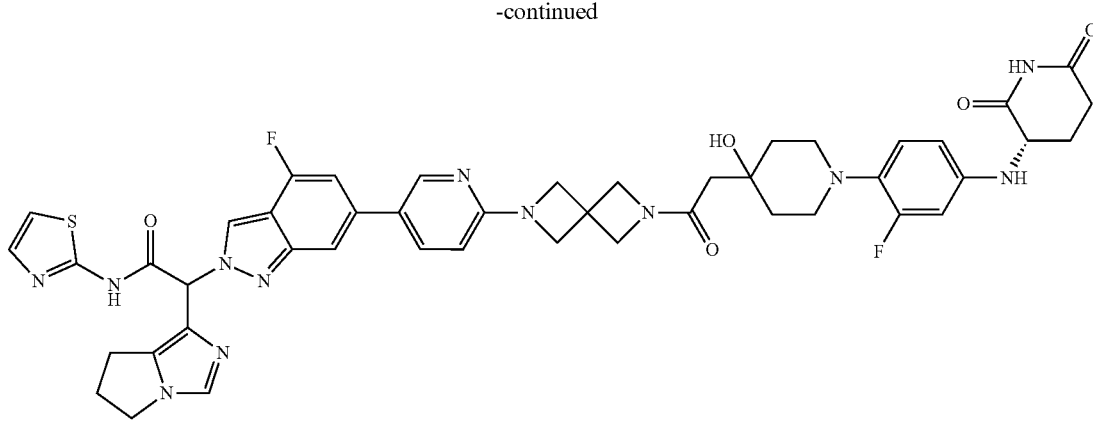

To a stirred solution of 2-[1-[4-[[(3S)-2,6-dioxo-3-piperidyl]amino]-2-fluoro-phenyl]-4-hydroxy-4-piperidyl]acetic acid hydrochloride (29.34 mg, 70.56 μmol) in N,N-dimethylformamide (3 mL) was added N,N-Diisopropylethylamine (69.48 mg, 537.59 μmol, 93.64 μL) at 0° C. 1-[Bis(dimethylamino)methylene]-1H-1,2,3-triazolo[4,5-b]pyridinium 3-oxid hexafluoro-phosphate (38.33 mg, 100.80 μmol) was added at the same temperature. 2-[6-[6-(2,6-diazaspiro[3.3]heptan-2-yl)-3-pyridyl]-4-fluoro-indazol-2-yl]-2-(6,7-dihydro-5H-pyrrolo[1,2-c]imidazol-1-yl)-N-thiazol-2-yl-acetamide, trifluoroacetic acid salt (45 mg, 67.20 mol) was added, and the reaction mixture was stirred for 5 h while warming to room temperature. The reaction mixture was directly injected on a C18 column (120 g) for purification (0% to 60% acetonitrile in water (+0.1% ammonium acetate) over 45 minutes, then steep gradient to 100% acetonitrile). The pure fractions were frozen and lyophilized to afford product Compound 75 (38 mg, 40.98 μmol, 60.99% yield) as off white solid. LCMS (ESI+) m/z: 917.3 [M+H]+. $^1$H-NMR (400 MHz, DMSO-d6): δ 12.83 (s, 1H), 10.79 (s, 1H), 8.51 (d, J=2.40 Hz, 1H), 8.28 (s, 1H), 7.95 (dd, J=8.80, 2.40 Hz, 1H), 7.68 (d, J=11.20 Hz, 1H), 7.51 (d, J=3.60 Hz, 1H), 7.29 (s, 1H), 7.16 (d, J=12.00 Hz, 1H), 6.85 (t, J=9.60 Hz, 1H), 6.70 (s, 1H), 6.50 (d, J=9.20 Hz, 2H), 6.45 (d, J=Hz, 1H), 5.79 (d, J=7.60 Hz, 1H), 4.77 (s, 1H), 4.39 (s, 1H), 4.29–4.21 (m, 1H), 4.14 (s, 4H), 4.12 (s, 2H), 4.09 (m, 2H), 2.85 (m, 7H), 2.51 (m, 2H), 2.22 (s, 2H), 2.09 (m, 1H), 1.87 (m, 1H), 1.80 (m, 2H), 1.62 (br d, J=12.8 Hz, 2H).

Example 76

2-(6,7-dihydro-5H-pyrrolo[1,2-c]imidazol-1-yl)-2-[6-[4-[2-[2-[(4R)-4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-indazol-2-yl]-N-thiazol-2-yl-acetamide, Compound 76

Step 1: 1-[6-[(4R)-3,3-difluoro-4-piperidyl]-1-methyl-indazol-3-yl]hexahydropyrimidine-2,4-dione and 1-[6-[(4S)-3,3-difluoro-4-piperidyl]-1-methyl-indazol-3-yl]hexahydropyrimidine-2,4-dione by chiral SFC separation

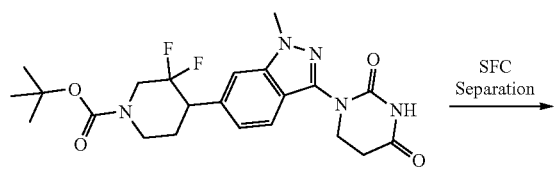

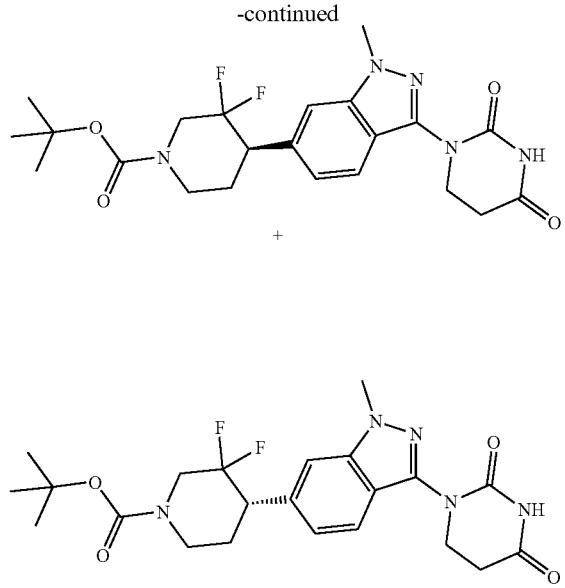

Racemic tert-butyl 4-(3-(2,4-dioxotetrahydropyrimidin-1(2H)-yl)-1-methyl-1H-indazol-6-yl)-3,3-difluoropiperidine-1-carboxylate (5.06 g, 1 g/50 mL ethanol:dichloromethane (50%:50%)) was resolved using SFC separation under the following conditions: Column: ChiralCel OD-H 21×250 mm; Mobile Phase: 20% 2-Propanol in CO2; Flow Rate: 70 mL/min; Detection: 220 nm; Sample: 1 mL/Injection The first eluting set of fractions was collected and evaporated to afford 1-[6-[(4R)-3,3-difluoro-4-piperidyl]-1-methyl-indazol-3-yl]hexahydropyrimidine-2,4-dione (2.21 g, 43% yield, 100% ee) using the following analytical conditions. SFC retention time: 3.18 minute (25% isopropanol in supercritical CO2, OD-H 4.6×100 mm, 40° C. 4 ml/min, 100 psi, 5 μL (Ethanol) injection), LCMS: 464 (M+H)

The second eluting set of fractions was collected and evaporated to afford 1-[6-[(4S)-3,3-difluoro-4-piperidyl]-1-methyl-indazol-3-yl]hexahydropyrimidine-2,4-dione (2.21 g, 43% yield, 100% ee) using the following analytical conditions. SFC Retention time: 4.07 minute (25% isopropanol in supercritical CO2, OD-H 4.6×100 mm, 40° C. 4 ml/min, 100 psi, 5 μL (Ethanol) injection), LCMS: 464 (M+H)

Step 2: 1-[6-[(4R)-3,3-difluoro-4-piperidyl]-1-methyl-indazol-3-yl]hexahydropyrimidine-2,4-dione

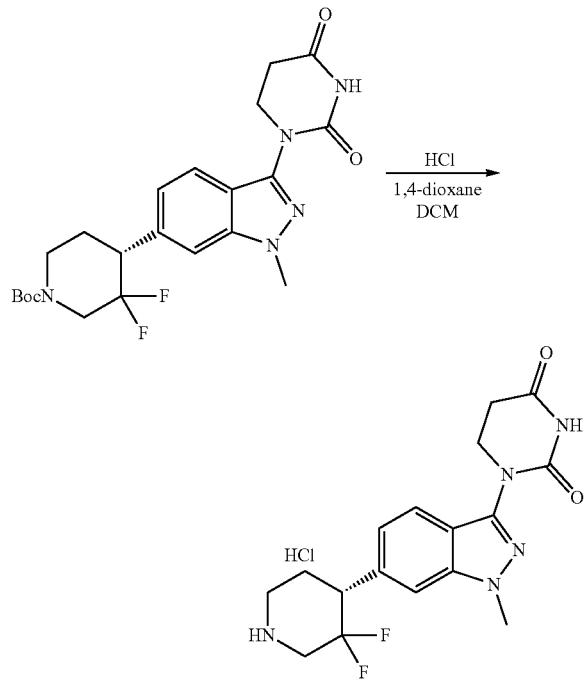

tert-butyl (4R)-4-[3-(2,4-dioxohexahydropyrimidin-1-yl)-1-methyl-indazol-6-yl]-3,3-difluoro-piperidine-1-carboxylate (325 mg, 701.22 µmol) was dissolved in a 1,4-dioxane:methanol mixture (1:1, 3 mL) and hydrogen chloride solution (4.0 M in 1,4-dioxane, 3.51 mL, 14 mmol) was added. The reaction mixture was heated at 40° C. for 4 h. The volatiles were evaporated under reduce pressure. The solid residue was submitted to high vacuum to afford 1-[6-[(4R)-3,3-difluoro-4-piperidyl]-1-methyl-indazol-3-yl]hexahydropyrimidine-2,4-dione (280 mg, 665.30 µmol, 94.88% yield). LCMS (ESI+): 364.1 (M+H)

Step 3: tert-butyl 2-[(4R)-4-[3-(2,4-dioxohexahydropyrimidin-1-yl)-1-methyl-indazol-6-yl]-3,3-difluoro-1-piperidyl]acetate

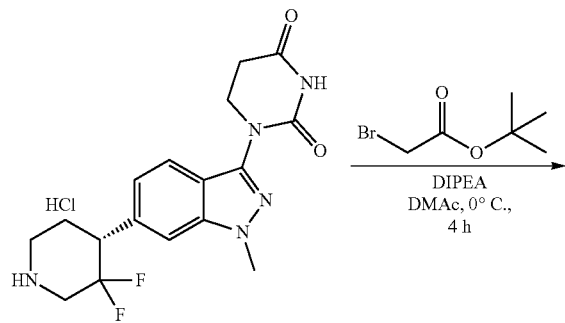

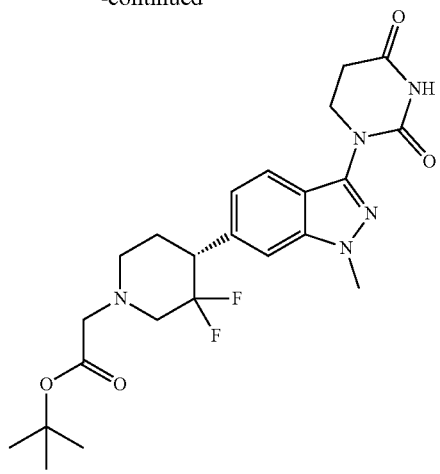

1-[6-[(4R)-3,3-difluoro-4-piperidyl]-1-methyl-indazol-3-yl]hexahydropyrimidine-2,4-dione hydrochloride (285 mg, 784.34 µmol) and N,N-diisopropylethylamine (304.11 mg, 2.35 mmol, 409.85 µL) mixed in DMAc (0.5 mL). The reaction mixture was cooled to 0° C. tert-butyl 2-bromoacetate (168.29 mg, 862.78 µmol, 126.53 µL) was added to the reaction mixture, and the mixture was warmed to 23° C. while stirring for 4 h. The reaction mixture was partitioned between ethyl acetate and sodium bicarbonate (aqueous, saturated). The organic layer was washed with brine, dried with sodium sulfate, filtered, and evaporated under reduced pressure. The crude residue was purified by silica gel chromatography (24 g column, 0% to 10% methanol in dichloromethane). Pure fractions were evaporated under reduced pressure to afford tert-butyl 2-[(4R)-4-[3-(2,4-dioxohexahydropyrimidin-1-yl)-1-methyl-indazol-6-yl]-3,3-difluoro-1-piperidyl]acetate (330 mg, 656.54 µmol, 83.71% yield). LCMS (ESI+): 478.2 (M+H)/422.2 (M-tBu+H)

Step 4: 2-[(4R)-4-[3-(2,4-dioxohexahydropyrimidin-1-yl)-1-methyl-indazol-6-yl]-3,3-difluoro-1-piperidyl]acetic acid, trifluoroacetic acid salt

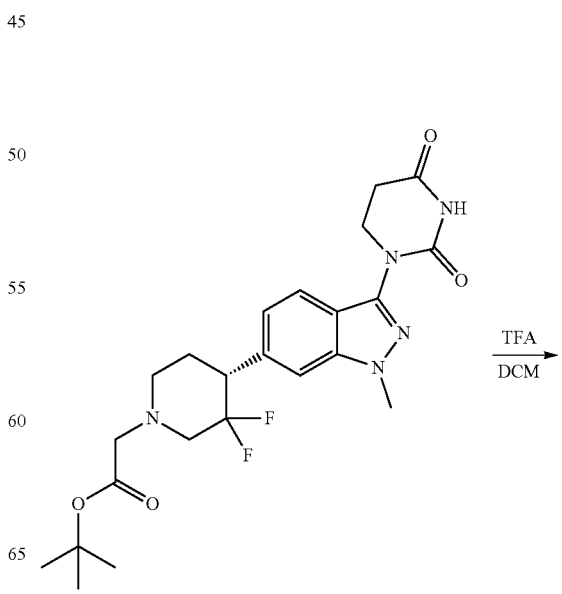

-continued

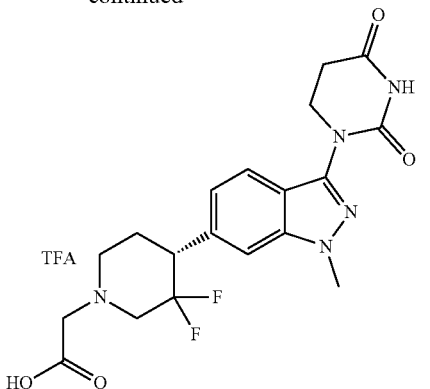

tert-butyl 2-[(4R)-4-[3-(2,4-dioxohexahydropyrimidin-1-yl)-1-methyl-indazol-6-yl]-3,3-difluoro-1-piperidyl]acetate (330 mg, 691.09 μmol) was dissolved in a dichloromethane (2 mLs) and trifluoroacetic acid (1.42 g, 12.44 mmol, 958.39 μL) was added. The reaction mixture was heated at 40° C. for 4 h. The reaction mixture was cooled, added to methyl tert-butyl ether (20 mLs) under stirring at 0-5° C. The resulting suspension was stirred for 2 minutes. The suspension was transferred to a vial for centrifugation, and the suspension was centrifugated at 2400 rpm for 5 minutes. The supernatant solvent was decanted and discarded. methyl tert-butyl ether (20 mLs) was added the solid and the resulting suspension was stirred for 2 minutes. The suspension was transferred to a vial for centrifugation, and the suspension was centrifugated at 2400 rpm for 5 minutes. The supernatant solvent was decanted and discarded. The volatiles were evaporated in vacuo, and the compound was subjected to high vacuum for 1 h to afford 2-[(4R)-4-[3-(2,4-dioxohexahydropyrimidin-1-yl)-1-methyl-indazol-6-yl]-3,3-difluoro-1-piperidyl]acetic acid, trifluoroacetic acid salt (150 mg, 274.55 μmol, 39.73% yield). LCMS (ESI+): 422.2 (M+H)

Step 5: 2-[6-[4-(2-tert-butoxycarbonyl-2,6-diazaspiro[3.3]heptan-6-yl)phenyl]-4-fluoro-indazol-2-yl]-2-(6,7-dihydro-5H-pyrrolo[1,2-c]imidazol-1-yl) acetic acid

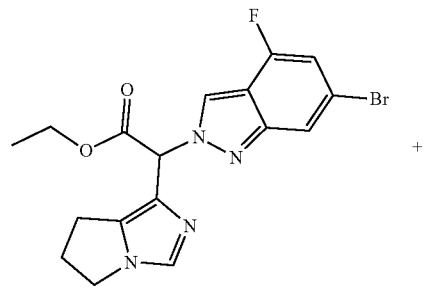

+

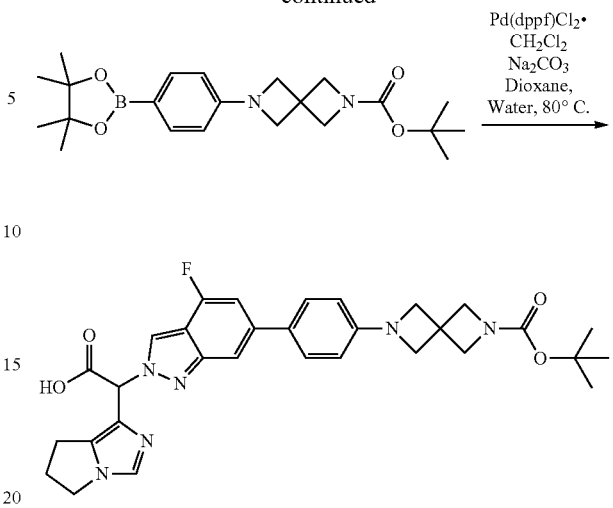

To a solution of ethyl 2-(6-bromo-4-fluoro-indazol-2-yl)-2-(6,7-dihydro-5H-pyrrolo[1,2-c]imidazol-1-yl)acetate (Example 4, step 5, 1.5 g, 3.68 mmol) and tert-butyl 6-[4-(4,4,5,5-tetramethyl-1,3,2-dioxaborolan-2-yl)phenyl]-2,6-diazaspiro[3.3]heptane-2-carboxylate (1.92 g, 4.79 mmol) in 1,4-Dioxane (21 mL) was added Sodium carbonate (1.17 g, 11.05 mmol, 462.92 μL) in water (9 mL) The reaction mixture was degassed with nitrogen for 15 minutes. [1,1'-Bis(diphenylphosphino)ferrocene]dichloropalladium(II), complex with dichloromethane (87.02 mg, 106.55 μmol) was added and further degassed with nitrogen gas for 5 minutes. The reaction mixture was heated a in heating block at 80° C. under nitrogen for 16 h. The reaction mixture was concentrated under reduced presser. The crude was diluted with water (50 ml) and washed with ethyl acetate (50 ml). The aqueous layer was acidified to pH 5-6 with 5% aqueous potassium hydrogen sulfate solution and extracted three times with dichloromethane (3×50 mL). The organic layer was washed with brine (75 ml), dried over sodium sulphate and concentrated under reduced pressure to get 2-[6-[4-(2-tert-butoxycarbonyl-2,6-diazaspiro[3.3]heptan-6-yl)phenyl]-4-fluoro-indazol-2-yl]-2-(6,7-dihydro-5H-pyrrolo[1,2-c]imidazol-1-yl)acetic acid (2.0 g, 2.51 mmol, 68.07% yield) as a dark brown solid. LCMS (ESI+) m/z: 573.2 (M+H)$^+$ and m/z: 529.2 (M-CO$_2$+H)$^+$.

Step 6: tert-butyl 6-[4-[2-[1-(6,7-dihydro-5H-pyrrolo[1,2-c]imidazol-1-yl)-2-oxo-2-(thiazol-2-ylamino)ethyl]-4-fluoro-indazol-6-yl]phenyl]-2,6-diazaspiro[3.3]heptane-2-carboxylate

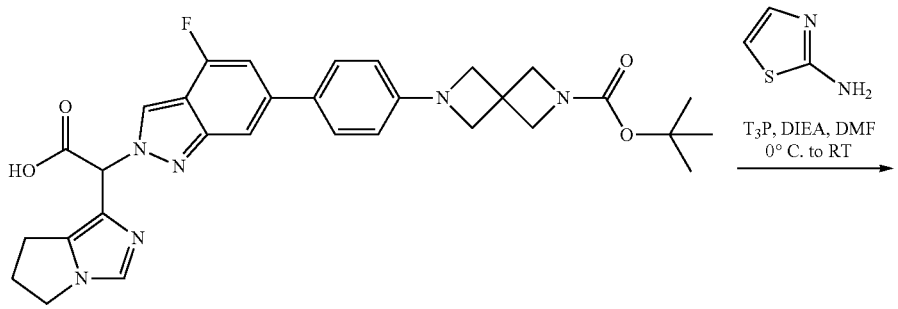

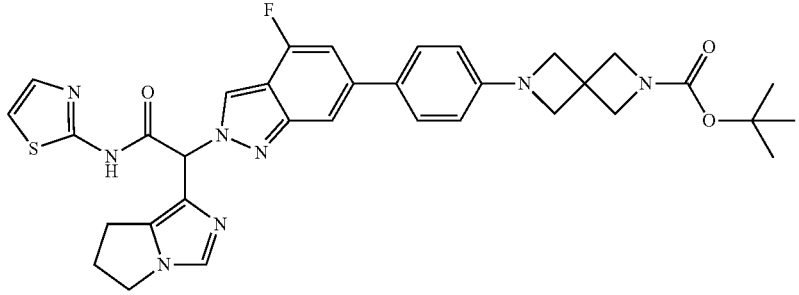

To the stirred solution of 2-[6-[4-(2-tert-butoxycarbonyl-2,6-diazaspiro[3.3]heptan-6-yl)phenyl]-4-fluoro-indazol-2-yl]-2-(6,7-dihydro-5H-pyrrolo[1,2-c]imidazol-1-yl)acetic acid (2.0 g, 2.51 mmol) and thiazol-2-amine (326.39 mg, 3.26 mmol) in N,N-dimethylformamide (20 mL) was added N,N-diisopropylethylamine (1.94 g, 15.04 mmol, 2.62 mL) at 0° C. Propylphosphonic anhydride solution (50% in ethyl acetate) (39.89 mg, 6.27 mmol, 37.28 L) was added at 0° C. and the reaction mixture was stirred at rt for 5 h. The reaction mixture poured to ice water (150 ml) and the solid was filtered, washed with water, and dried. The residue was purified by flash column chromatography on silica gel (0-10% Methanol in dichloromethane) to get tert-butyl 6-[4-[2-[1-(6,7-dihydro-5H-pyrrolo[1,2-c]imidazol-1-yl)-2-oxo-2-(thiazol-2-ylamino)ethyl]-4-fluoro-indazol-6-yl]phenyl]-2,6-diazaspiro[3.3]heptane-2-carboxylate (720 mg, 981.22 μmol, 39.14% yield) as a brown solid. LCMS (ESI+) m/z: 655.2 (M+H)+.

Step 7: 2-[6-[4-(2,6-diazaspiro[3.3]heptan-2-yl)phenyl]-4-fluoro-indazol-2-yl]-2-(6,7-dihydro-5H-pyrrolo[1,2-c]imidazol-1-yl)-N-thiazol-2-yl-acetamide, trifluoroacetic acid salt

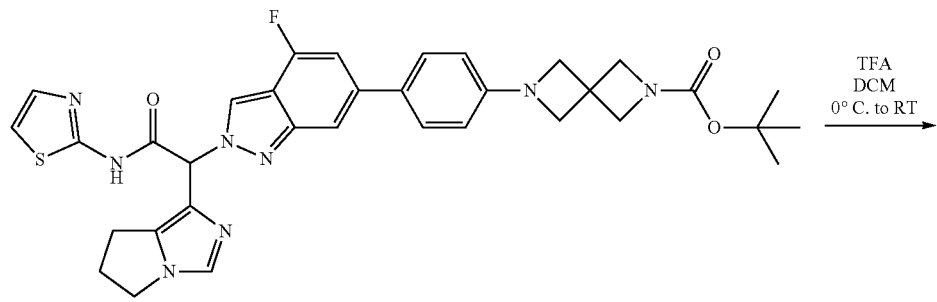

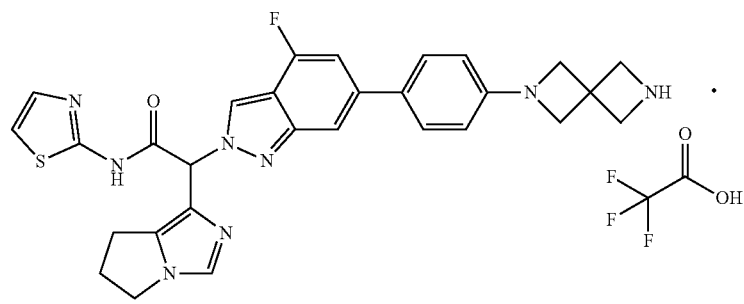

To the stirred solution of tert-butyl 6-[4-[2-[1-(6,7-dihydro-5H-pyrrolo[1,2-c]imidazol-1-yl)-2-oxo-2-(thiazol-2-ylamino)ethyl]-4-fluoro-indazol-6-yl]phenyl]-2,6-diazaspiro[3.3]heptane-2-carboxylate (700 mg, 1.07 mmol) in dichloromethane (10 mL) was added trifluoroacetic acid (10.36 g, 90.86 mmol, 7 mL) dropwise at 0° C. The reaction mixture was stirred at ambient temperature for 3 h. The reaction mixture was concentrated under reduced pressure The solid obtained was triturated with diethyl ether (2×25 ml), decanted and dried under reduced pressure to get 2-[6-[4-(2,6-diazaspiro[3.3]heptan-2-yl)phenyl]-4-fluoro-indazol-2-yl]-2-(6,7-dihydro-5H-pyrrolo[1,2-c]imidazol-1-yl)-N-thiazol-2-yl-acetamide, trifluoroacetic acid salt (820 mg, 931.56 μmol, 87.13% yield) as an off-white solid. LCMS (ESI+) m/z: 555.2 [M+H]$^+$.

Step 8: 2-(6,7-dihydro-5H-pyrrolo[1,2-c]imidazol-1-yl)-2-[6-[4-[2-[2-[(4R)-4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-indazol-2-yl]-N-thiazol-2-yl-acetamide

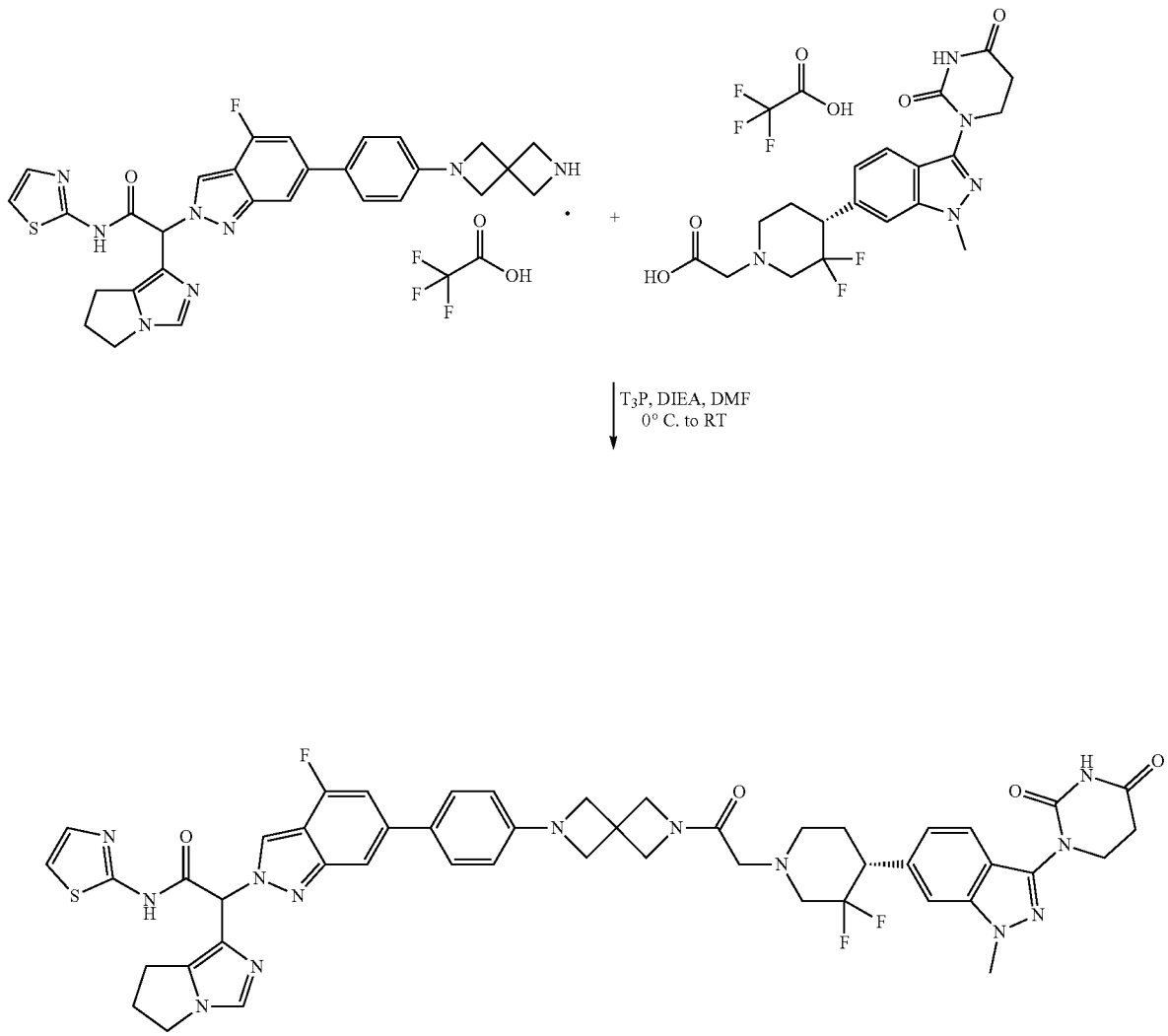

2-[6-[4-(2,6-diazaspiro[3.3]heptan-2-yl)phenyl]-4-fluoro-indazol-2-yl]-2-(6,7-dihydro-5H-pyrrolo[1,2-c]imidazol-1-yl)-N-thiazol-2-yl-acetamide, trifluoroacetic acid salt (150 mg, 224.33 μmol) and 2-[(4R)-4-[3-(2,4-dioxo-hexahydropyrimidin-1-yl)-1-methyl-indazol-6-yl]-3,3-difluoro-1-piperidyl]acetic acid, trifluoroacetic acid salt (132.12 mg, 246.76 μmol) were mixed in N,N-dimethylformamide (2 mL) and the reaction mixture was cooled to 0° C. N,N-Diisopropylethylamine (173.96 mg, 1.35 mmol, 234.44 μL) was added to the reaction mixture at the same temperature. Propylphosphonic anhydride solution (50 wt. % in ethyl acetate) (178.44 mg, 560.82 μmol) was added at the same temperature and stirred for 2 h while warming to room temperature. The reaction mixture was directly injected on a C-18 column (100 g) for purification (0-45% of acetonitrile in water (+0.1% ammonium acetate) over 30 minutes, then steep gradient to 100% acetonitrile). The pure fractions were combined and lyophilized to get Compound 76 (78 mg, 79.69 μmol, 35.52% yield) as an off-white solid. LCMS (ESI+) m/z: 958.8 (M+H)$^+$. $^1$H-NMR (400 MHz, DMSO-d6): δ 12.82 (s, 1H), 10.58 (s, 1H), 8.26 (s, 1H), 7.69 (s, 1H), 7.62–7.57 (m, 5H), 7.52 (d, J=3.60 Hz, 1H), 7.30 (d, J=3.20 Hz, 1H), 7.14–7.09 (m, 2H), 6.70 (s, 1H), 6.55 (d, J=8.80 Hz, 2H), 4.45 (s, 2H), 4.11 (s, 3H), 4.04–4.00 (m, 10H), 3.94–3.91 (m, 2H), 3.28–3.17 (m, 4H), 3.01–2.99 (m, 1H), 2.86–2.64 (m, 6H), 2.34–2.26 (m, 1H), 1.86–1.83 (m, 1H).

Example 77

2-(6,7-dihydro-5H-pyrrolo[1,2-c]imidazol-1-yl)-2-[6-[4-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]phenyl]-4-fluoro-indazol-2-yl]-N-thiazol-2-yl-acetamide, Compound 77

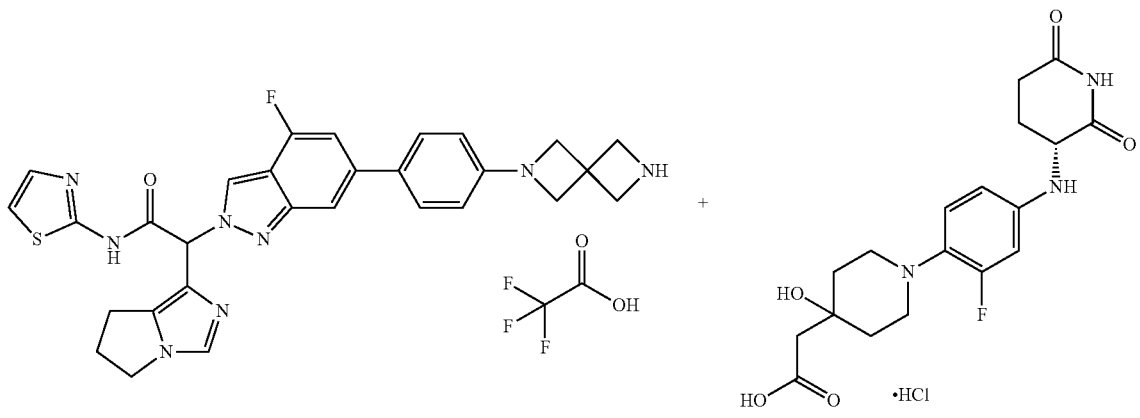

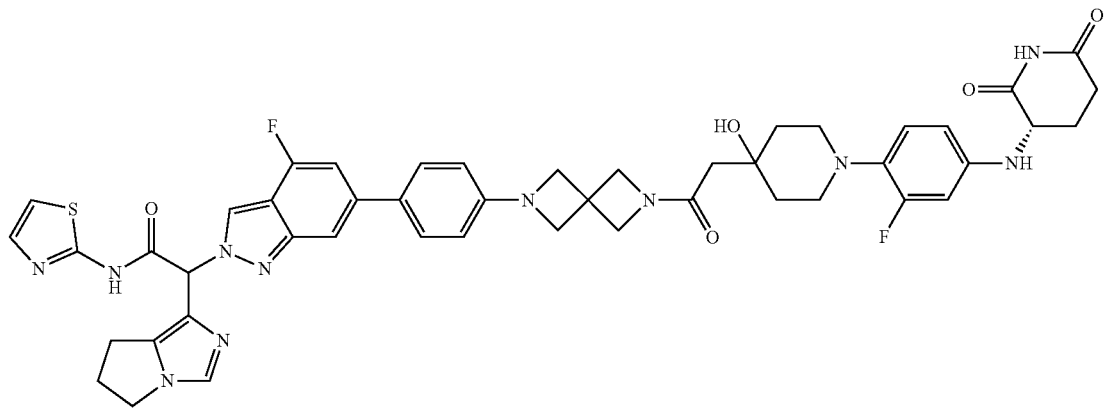

2-[6-[4-(2,6-diazaspiro[3.3]heptan-2-yl)phenyl]-4-fluoro-indazol-2-yl]-2-(6,7-dihydro-5H-pyrrolo[1,2-c]imidazol-1-yl)-N-thiazol-2-yl-acetamide, trifluoroacetic acid salt (Example 16, step 7, 300 mg, 448.66 μmol) and 2-[1-[4-[[(3S)-2,6-dioxo-3-piperidyl]amino]-2-fluoro-phenyl]-4-hydroxy-4-piperidyl]acetic acid hydrochloride (223.88 mg, 538.39 μmol) were mixed in N,N-dimethylformamide (2.5 mL). The reaction mixture was cooled to 0° C. and N,N-diisopropylethylamine (347.91 mg, 2.69 mmol, 468.89 μL) was added. HATU (221.77 mg, 583.25 μmol) was added, and stirred for 2 h while warming to room temperature. The reaction mixture was directly injected on a C-18 column (100 g) for purification (0-45% of acetonitrile in water+0.1% ammonium acetate over 30 minutes, then steep gradient to 100% acetonitrile). The pure fractions were combined and lyophilized to get Compound 77 (102 mg, 108.41 μmol, 24.16% yield) as an off white solid. LCMS (ESI+) m/z: 916.8 [M+H]+, 1H-NMR (400 MHz, DMSO-d6): δ 12.81 (s, 1H), 10.78 (s, 1H), 8.25 (s, 1H), 7.68 (s, 1H), 7.60 (d, J=8.40 Hz, 3H), 7.49 (d, J=2.80 Hz, 1H), 7.28-7.21 (m, 1H), 7.11 (d, J=12.40 Hz, 1H), 6.86 (t, J=9.60 Hz, 1H), 6.68☐6.62 (m, 1H), 6.55☐6.48 (m, 3H), 6.43 ☐6.41 (m, 1H), 5.78 (d, J=7.60 Hz, 1H), 4.77 (s, 1H), 4.41☐4.37 (m, 2H), 4.27☐4.24 (m, 1H), 4.09☐4.01 (m, 8H), 2.92-2.83 (m, 5H), 2.80☐2.70 (m, 1H), 2.61☐2.52 (m, 4H), 2.34☐2.33 (m, 2H), 2.12☐2.08 (m, 1H), 1.90☐1.84 (m, 1H), 1.80☐1.74 (m, 2H), 1.63 (s, 2H).

Example 78

2-(6,7-dihydro-5H-pyrrolo[1,2-c]imidazol-1-yl)-2-[6-[4-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]phenyl]-7-fluoro-indazol-2-yl]-N-thiazol-2-yl-acetamide, Compound 78

Step 1: 2-[6-[4-(2-tert-butoxycarbonyl-2,6-diazaspiro[3.3]heptan-6-yl)phenyl]-7-fluoro-indazol-2-yl]-2-(6,7-dihydro-5H-pyrrolo[1,2-c]imidazol-1-yl) acetic acid

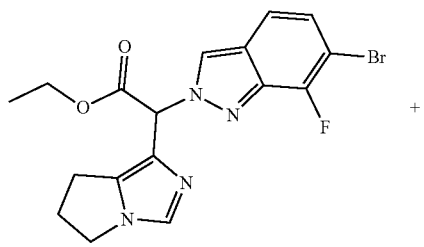

+

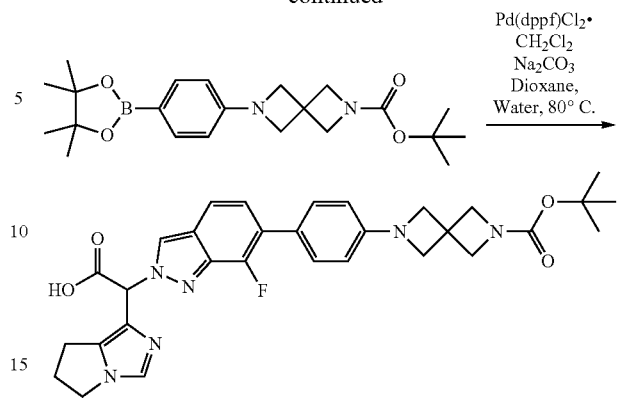

To a solution of ethyl 2-(6-bromo-7-fluoro-indazol-2-yl)-2-(6,7-dihydro-5H-pyrrolo[1,2-c]imidazol-1-yl)acetate (Example 2, step 4, 1 g, 2.46 mmol) and tert-butyl 6-[4-(4,4,5,5-tetramethyl-1,3,2-dioxaborolan-2-yl)phenyl]-2,6-diazaspiro[3.3]heptane-2-carboxylate (1.18 g, 2.95 mmol) in 1,4-dioxane (15 mL) was added sodium carbonate (780.79 mg, 7.37 mmol, 308.61 μL) in Water (2 mL). The mixture was degassed with nitrogen for 15 minutes. [1,1'-Bis(diphenylphosphino)ferrocene]dichloropalladium(II), complex with dichloromethane (400.75 mg, 491.12 μmol) was added to the reaction mixture and further degassed with nitrogen for 15 minutes and heated at 90° C. under nitrogen for 16 h. The reaction mixture was concentrated under reduced pressure. The reaction mixture was concentrated under reduced presser. The crude was diluted with water (50 ml) and washed with ethyl acetate (50 ml). The aqueous layer was acidified to pH 5-6 with 5% aqueous potassium hydrogen sulfate solution and extracted three times using dichloromethane (100 mL). The organic layer was washed with brine solution (75 ml), dried over sodium sulphate and concentrated under reduced pressure to get desired product 2-[6-[4-(2-tert-butoxycarbonyl-2,6-diazaspiro[3.3]heptan-6-yl)phenyl]-7-fluoro-indazol-2-yl]-2-(6,7-dihydro-5H-pyrrolo[1,2-c]imidazol-1-yl)acetic acid (1.7 g, 2.21 mmol, 90.07% yield) as dark brown solid. LCMS (ESI+) m/z: 573.2 [M+H]+.

Step 2: tert-butyl 6-[4-[2-[1-(6,7-dihydro-5H-pyrrolo[1,2-c]imidazol-1-yl)-2-oxo-2-(thiazol-2-ylamino)ethyl]-7-fluoro-indazol-6-yl]phenyl]-2,6-diazaspiro[3.3]heptane-2-carboxylate

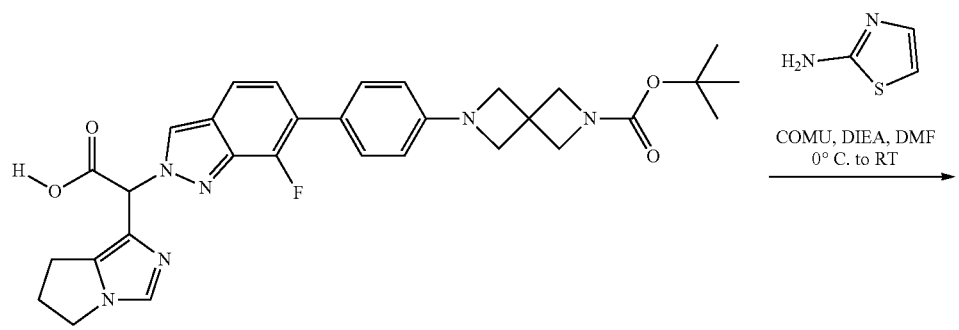

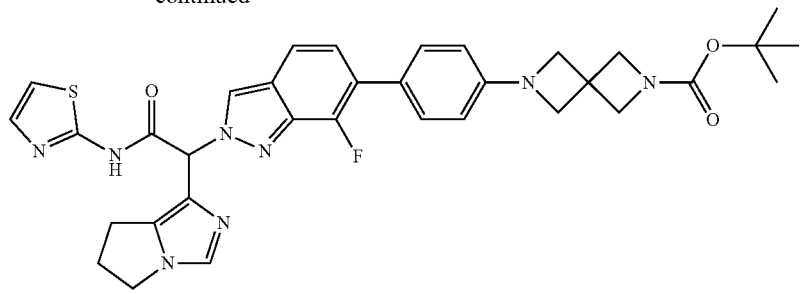

To a stirred solution of 2-[6-[4-(2-tert-butoxycarbonyl-2,6-diazaspiro[3.3]heptan-6-yl)phenyl]-7-fluoro-indazol-2-yl]-2-(6,7-dihydro-5H-pyrrolo[1,2-c]imidazol-1-yl)acetic acid (1.6 g, 2.79 mmol) in N,N-dimethylformamide (16 mL) at 0° C. were added N,N-Diisopropylethylamine (1.08 g, 8.38 mmol, 1.46 mL). (1-Cyano-2-ethoxy-2-oxoethylidenaminooxy)dimethylamino-morpholino-carbenium hexafluorophosphate (1.79 g, 4.19 mmol) was added at the same temperature. Thiazol-2-amine (419.71 mg, 4.19 mmol) was added, and the reaction mixture was stirred for 4 h while warming to room temperature. The reaction mixture was added with ice cold water and extracted with 10% methanol in dichloromethane. The organic layer was washed with brine, dried over sodium sulfate and concentrated under reduced pressure. The crude residue was purified by flash column chromatography using silica (5-8% methanol in dichloromethane) to get tert-butyl 6-[4-[2-[1-(6,7-dihydro-5H-pyrrolo[1,2-c]imidazol-1-yl)-2-oxo-2-(thiazol-2-ylamino)ethyl]-7-fluoro-indazol-6-yl]phenyl]-2,6-diazaspiro[3.3]heptane-2-carboxylate (1.25 g, 1.39 mmol, 49.71% yield) as a brown solid. LCMS (ESI+) m/z: 655.2 [M+H]⁺

Step 3: 2-[6-[4-(2,6-diazaspiro[3.3]heptan-2-yl)phenyl]-7-fluoro-indazol-2-yl]-2-(6,7-dihydro-5H-pyrrolo[1,2-c]imidazol-1-yl)-N-thiazol-2-yl-acetamide, trifluoroacetic acid

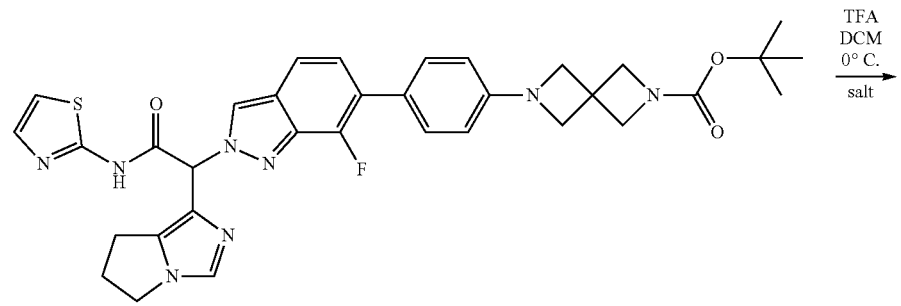

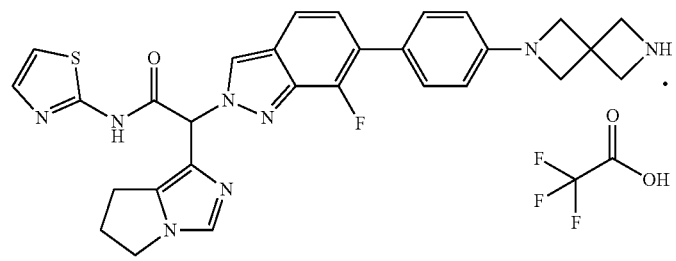

907

To a stirred solution of tert-butyl 6-[4-[2-[1-(6,7-dihydro-5H-pyrrolo[1,2-c]imidazol-1-yl)-2-oxo-2-(thiazol-2-ylamino)ethyl]-7-fluoro-indazol-6-yl]phenyl]-2,6-diazaspiro[3.3]heptane-2-carboxylate (400.00 mg, 610.92 μmol) in dichloromethane (6 mL) at 0° C. was added drop-wise trifluoroacetic acid (1.74 g, 15.27 mmol, 1.18 mL). The reaction mixture was stirred at 0° C. for 4 h. The reaction mixture was concentrated under reduced pressure, the residue was triturated with diethyl ether (2×50 ml), decanted and dried to afford 2-[6-[4-(2,6-diazaspiro[3.3]heptan-2-yl)phenyl]-7-fluoro-indazol-2-yl]-2-(6,7-dihydro-5H-pyrrolo[1,2-c]imidazol-1-yl)-N-thiazol-2-yl-acetamide, trifluoroacetic acid salt (410 mg, 373.23 μmol, 61.09% yield) as a brown solid. LCMS (ESI+) m/z: 555.2 [M+H]⁺

Step 4: 2-(6,7-dihydro-5H-pyrrolo[1,2-c]imidazol-1-yl)-2-[6-[4-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]phenyl]-7-fluoro-indazol-2-yl]-N-thiazol-2-yl-acetamide

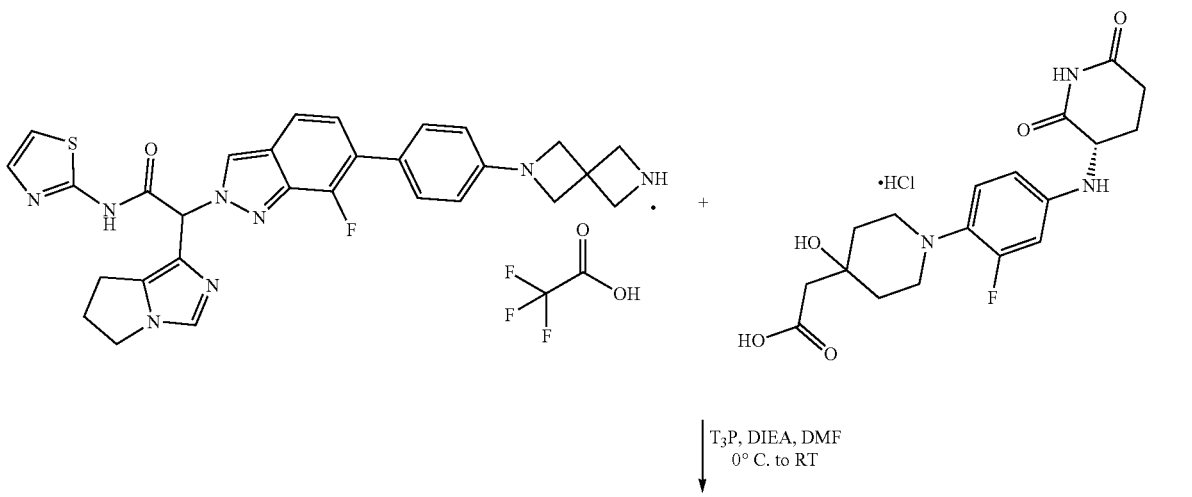

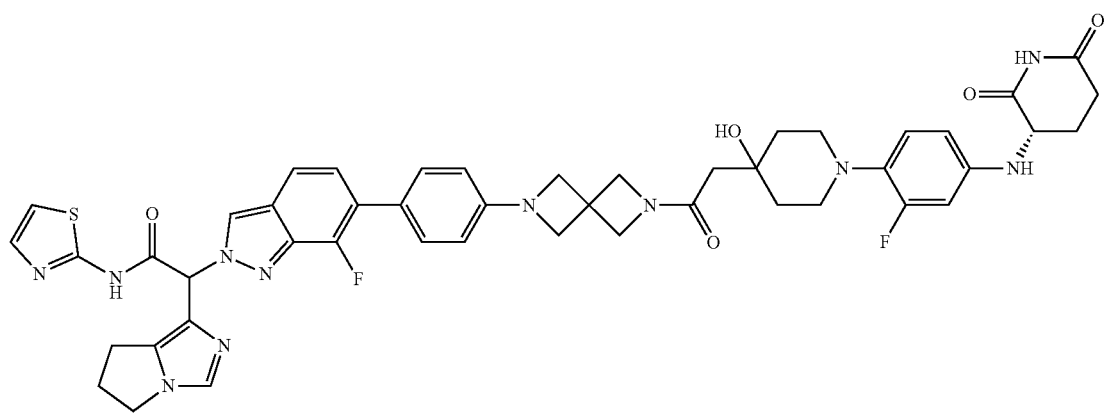

2-[6-[4-(2,6-diazaspiro[3.3]heptan-2-yl)phenyl]-7-fluoro-indazol-2-yl]-2-(6,7-dihydro-5H-pyrrolo[1,2-c]imidazol-1-yl)-N-thiazol-2-yl-acetamide, trifluoroacetic acid salt (200 mg, 299.10 µmol) and 2-[1-[4-[[(3 S)-2,6-dioxo-3-piperidyl]amino]-2-fluoro-phenyl]-4-hydroxy-4-piperidyl]acetic acid hydrochloride (99.50 mg, 239.28 µmol) were mixed in in N,N-dimethylformamide (2 mL). The mixture was cooled to 0° C. and N, N-Diisopropylethylamine (193.29 mg, 1.50 mmol, 260.49 µL) was added. Propylphosphonic anhydride (50 wt. % in ethyl acetate) (114.20 mg, 358.93 µmol) was added at the same temperature. The reaction mixture stirred at ambient temperature for 1 h. The reaction mixture was directly injected on a C-18 column (100 g) for purification (0-50% acetonitrile in water+0.1% ammonium acetate over 30 minutes, then steep gradient to 100% acetonitrile). The pure fractions were combined and lyophilized to get Compound 78 (28.21 mg, 30.64 µmol, 10.24% yield) as an off-white solid. LCMS (ESI+): 915.8 [M+H]; $^1$H-NMR (400 MHz, DMSO-d6): δ 12.81 (s, 1H), 10.79 (s, 1H), 8.29 (s, 1H), 7.68 (s, 1H), 7.55 (d, J=8.80 Hz, 1H), 7.50 (s, 1H), 7.45 (d, J=7.60 Hz, 2H), 7.26 (s, 1H), 7.10 (t, J=8.00 Hz, 1H), 6.86 (t, J=9.60 Hz, 1H), 6.69 (s, 1H), 6.57 (dd, J=8.40, Hz, 3H), 6.51 (d, J=15.20 Hz, 1H), 5.78 (d, J=7.20 Hz, 1H), 4.77 (s, 1H), 4.39 (s, 2H), 4.29-4.21 (m, 1H), 4.02-4.09 (m, 8H), 2.92-2.84 (m, 5H), 2.23 (s, 3H), 2.13-2.05 (m, 2H), 1.89-1.71 (m, 4H), 1.63 (d, J=11.20 Hz, 2H) (Water obscuration).

Example 79

2-(6,7-dihydro-5H-pyrrolo[1,2-c]imidazol-1-yl)-2-[6-[4-[7-[2-[1-[4-[[(3S)-2,6-dioxo-3-piperidyl]amino]-2-fluoro-phenyl]-4-hydroxy-4-piperidyl]acetyl]-2,7-diazaspiro[3.5]nonan-2-yl]phenyl]-4-fluoro-indazol-2-yl]-N-thiazol-2-yl-acetamide, Compound 79

Step 1: [2-(6-bromo-4-fluoro-indazol-2-yl)-2-(6,7-dihydro-5H-pyrrolo[1,2-c]imidazol-1-yl)acetyl]oxylithium

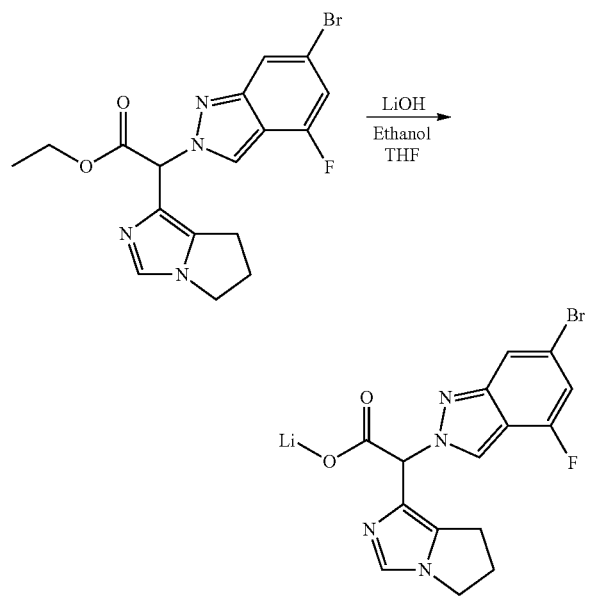

To a stirred solution of ethyl 2-(6-bromo-4-fluoro-indazol-2-yl)-2-(6,7-dihydro-5H-pyrrolo[1,2-c]imidazol-1-yl)acetate (Example 4, step 5, 1.4 g, 3.44 mmol) in tetrahydrofuran (10 mL) and ethanol (10 mL) was added lithium hydroxide (1M solution aqueous, 4.13 mL, 4.13 mmol) at 0° C. and stirred at room temperature for 2 h. The reaction mixture was dried under reduced pressure. Toluene was added to the residue, and the volatiles were evaporated under reduced pressure (2×20 mL). The obtained crude residue was triturated by diethyl ether (2×25 ml), and dried completely under reduced pressure afford 2-(6-bromo-4-fluoro-indazol-2-yl)-2-(6,7-dihydro-5H-pyrrolo[1,2-c]imidazol-1-yl)acetyl]oxylithium (1.1 g, 2.77 mmol, 80.59% yield) as a pale brown solid, which was proceed for next step without making salt free. LCMS m/z: 379.1/381.1 [M+1], Br pattern Step 2: 2-(6-bromo-4-fluoro-indazol-2-yl)-2-(6,7-dihydro-5H-pyrrolo[1,2-c]imidazol-1-yl)-N-thiazol-2-yl-acetamide

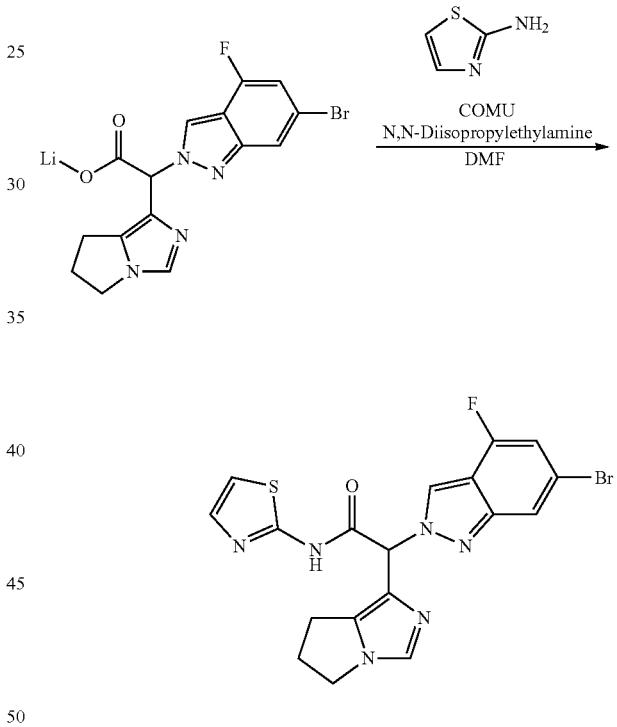

To a stirred solution of [2-(6-bromo-4-fluoro-indazol-2-yl)-2-(6,7-dihydro-5H-pyrrolo[1,2-c]imidazol-1-yl)acetyl]oxylithium (1.1 g, 2.86 mmol) and 2-amino thiazole (429.05 mg, 4.28 mmol) in N,N-dimethylformamide (12 mL) was added N,N-Diisopropylethylamine (1.11 g, 8.57 mmol, 1.49 mL) at 0° C. and 1-Cyano-2-ethoxy-2-oxoethylidenaminooxy)dimethylamino-morpholino-carbenium hexafluorophosphate (1.59 g, 3.71 mmol) was added at the same temperature. The reaction mixture stirred at room temperature for 1 h. The reaction was concentrated under high vacuum to remove N,N-diisopropylethylamine and ice cold water was added. The resulting precipitate was stirred for 10 minutes, filtered, and dried under high vacuum to afford product 2-(6-bromo-4-fluoro-indazol-2-yl)-2-(6,7-dihydro-5H-pyrrolo[1,2-c]imidazol-1-yl)-N-thiazol-2-yl-acetamide (950 mg, 1.69 mmol, 59.12% yield) as a pale brown solid. LCMS (m/z: 460.0/462.0 (M+H), Bromide Pattern)

Step 3: tert-butyl 2-[4-[2-[1-(6,7-dihydro-5H-pyrrolo[1,2-c]imidazol-1-yl)-2-oxo-2-(thiazol-2-ylamino)ethyl]-4-fluoro-indazol-6-yl]phenyl]-2,7-diazaspiro[3.5]nonane-7-carboxylate

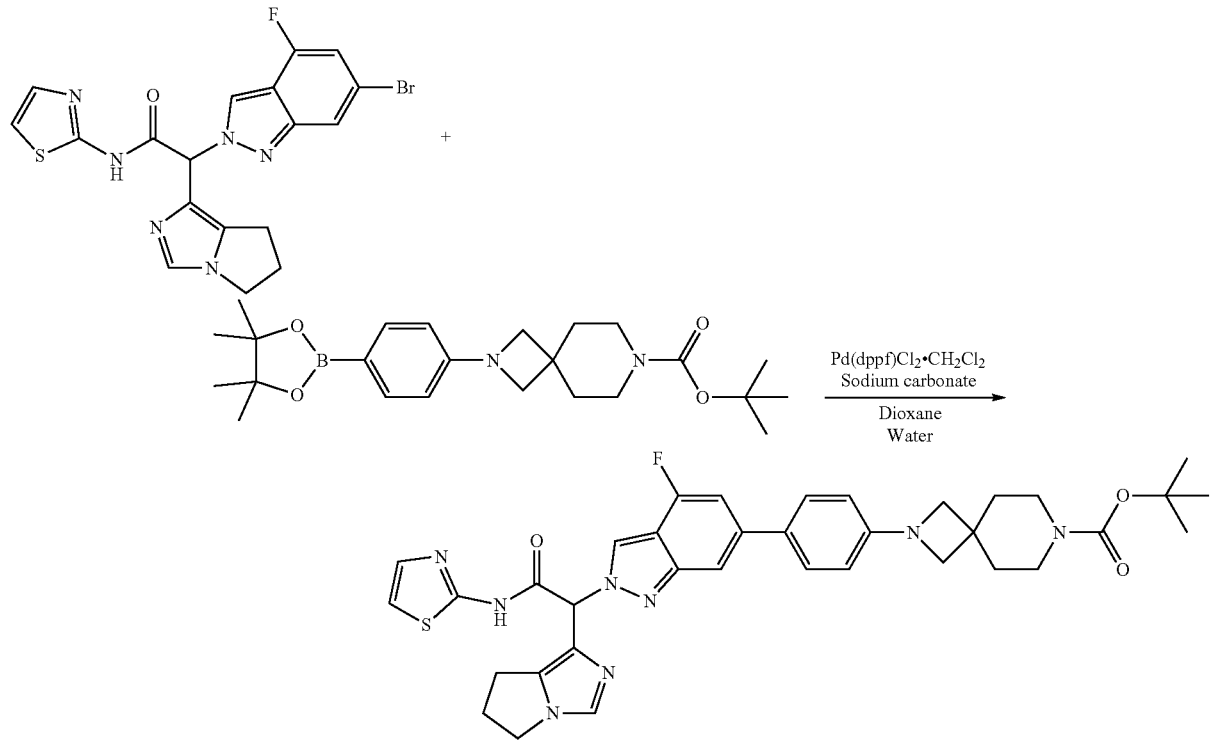

To a stirred solution of 2-(6-bromo-4-fluoro-indazol-2-yl)-2-(6,7-dihydro-5H-pyrrolo[1,2-c]imidazol-1-yl)-N-thiazol-2-yl-acetamide (0.5 g, 1.08 mmol) and tert-butyl 2-[4-(4,4,5,5-tetramethyl-1,3,2-dioxaborolan-2-yl)phenyl]-2,7-diazaspiro[3.5]nonane-7-carboxylate (557.16 mg, 1.30 mmol) in 1,4-dioxane (15 mL) and Water (3 mL) was added sodium carbonate (344.63 mg, 3.25 mmol, 136.22 µL). The reaction mixture was degassed under nitrogen for 25 minutes. The [1,1'-Bis(diphenylphosphino)ferrocene]dichloropalladium(II), complex with dichloromethane (177.03 mg, 216.77 µmol) was added into reaction mixture and continue degassed for 10 minute. The reaction mixture was heated at 90° C. under nitrogen for 18 h. The reaction mixture was cooled to ambient temperature and filtered on celite. The celite was washed with 10% methanol in dichloromethane (100 ml). The filtrate was concentrated under reduced pressure. The compound was purified by silica gel column chromatography (0% to 10% methanol in dichloromethane). The pure fractions were evaporated under reduced pressure to afford tert-butyl 2-[4-[2-[1-(6,7-dihydro-5H-pyrrolo[1,2-c]imidazol-1-yl)-2-oxo-2-(thiazol-2-ylamino)ethyl]-4-fluoro-indazol-6-yl]phenyl]-2,7-diazaspiro[3.5]nonane-7-carboxylate (255 mg, 155.21 µmol, 14.32% yield) as a light brown color solid. LCMS (m/z: 683.2 [M+1])

Step 4: 2-[6-[4-(2,7-diazaspiro[3.5]nonan-2-yl)phenyl]-4-fluoro-indazol-2-yl]-2-(6,7-dihydro-5H-pyrrolo[1,2-c]imidazol-1-yl)-N-thiazol-2-yl-acetamide

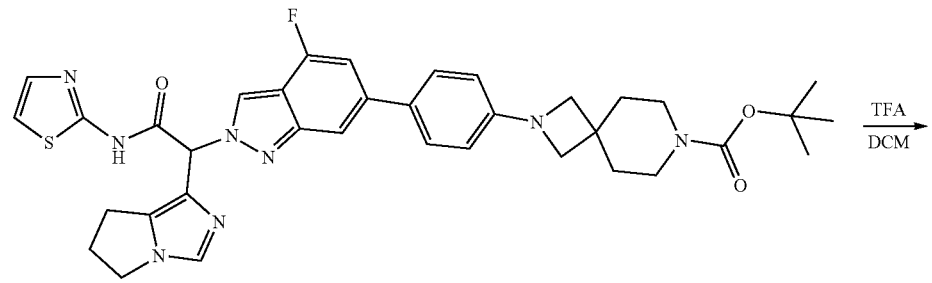

913 914

-continued

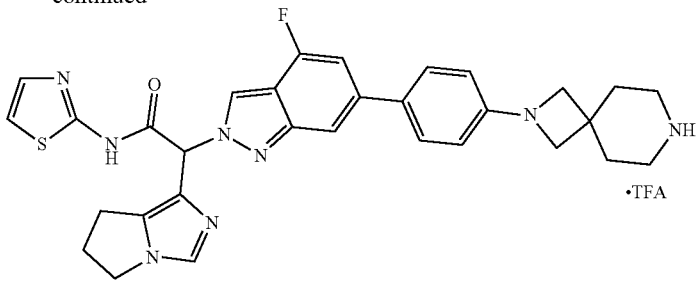

To a stirred solution of tert-butyl 2-[4-[2-[1-(6,7-dihydro-5H-pyrrolo[1,2-c]imidazol-1-yl)-2-oxo-2-(thiazol-2-ylamino)ethyl]-4-fluoro-indazol-6-yl]phenyl]-2,7-diazaspiro[3.5]nonane-7-carboxylate (300 mg, 439.36 µmol) in dichloromethane (3 mL) at 0° C. was added dropwise trifluoroacetic acid (250.49 mg, 2.20 mmol, 169.25 µL). After addition allow reaction to stirred at room temperature for 4 h. The reaction mixture was evaporated to dryness under reduced pressure. The obtained residue was triturated by diethyl ether (2×30 ml). The solid was dried under vacuum afford 2-[6-[4-(2,7-diazaspiro[3.5]nonan-2-yl)phenyl]-4-fluoro-indazol-2-yl]-2-(6,7-dihydro-5H-pyrrolo[1,2-c]imidazol-1-yl)-N-thiazol-2-yl-acetamide, trifluoroacetic acid salt (305 mg, 278.68 µmol, 63.43% yield) as an off white solid compound. LCMS (m/z: 583.2, [M+1])

Step 5: 2-(6,7-dihydro-5H-pyrrolo[1,2-c]imidazol-1-yl)-2-[6-[4-[7-[2-[1-[4-[[(3S)-2,6-dioxo-3-piperidyl]amino]-2-fluoro-phenyl]-4-hydroxy-4-piperidyl]acetyl]-2,7-diazaspiro[3.5]nonan-2-yl]phenyl]-4-fluoro-indazol-2-yl]-N-thiazol-2-yl-acetamide

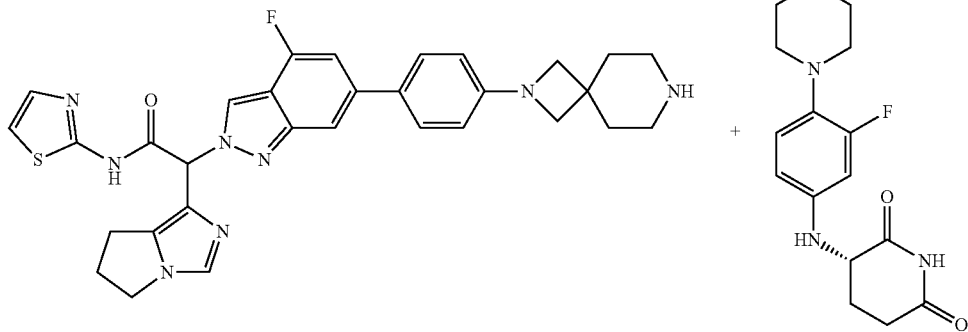

COMU
DIPEA
DMF

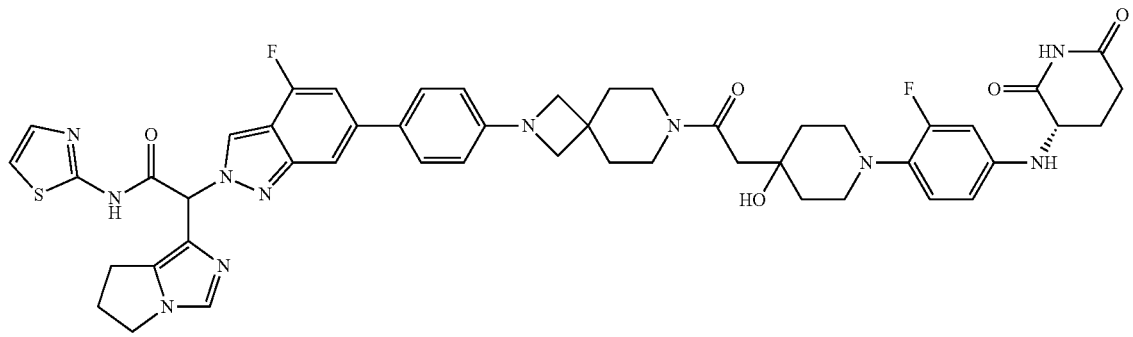

To a stirred solution of 2-[6-[4-(2,7-diazaspiro[3.5]nonan-2-yl)phenyl]-4-fluoro-indazol-2-yl]-2-(6,7-dihydro-5H-pyrrolo[1,2-c]imidazol-1-yl)-N-thiazol-2-yl-acetamide, trifluoroacetic acid salt (252.22 mg, 362.02 μmol) and 2-[1-[4-[[(3S)-2,6-dioxo-3-piperidyl]amino]-2-fluoro-phenyl]-4-hydroxy-4-piperidyl]acetic acid hydrochloride (150 mg, 360.71 μmol) in N,N-dimethylformamide (4 mL) was added N-ethyl-N-isopropyl-propan-2-amine (233.09 mg, 1.80 mmol, 314.14 μL) at 0° C. and COMU (185.38 mg, 432.86 μmol) was added at the same temperature and the reaction mixture stirred at ambient temperature for 2 h. The reaction mixture was directly injected on a C-18 column (100 g) for purification (0-55% of acetonitrile in water (with 0.1% of ammonium acetate) over 30 minutes, then steep gradient to 100% acetonitrile). The pure fractions were combined and lyophilized to get Compound 79 (51.84 mg, 52.99 μmol, 14.69% yield) as a gray solid. LCMS m/z: 943.8 (M+H), $^1$H-NMR (400 MHz, DMSO-d6): δ 12.82 (s, 1H), 10.79 (s, 1H), 8.25 (s, 1H), 7.69-7.51 (m, 5H), 7.29 (d, J=3.2 Hz, 1H), 7.11 (d, J=12.4 Hz, 1H), 6.89-6.81 (m, 1H), 6.70 (s, 1H), 6.53-6.40 (m, 4H), 5.78 (d, J=7.6 Hz, 1H), 4.94 (s, 1H), 4.29-4.19 (m, 1H), 4.07-4.00 (m, 2H), 3.70-3.52 (m, 4H), 3.39-3.31 (m, 4H), 2.93-2.51 (m, 6H), 1.87-1.63 (m, 10H) (solvent and water obscuration).

Intermediates

Intermediates Z1 and Z2

Preparation of tert-Butyl (4R)-4-[3-(2,4-dioxohexahydropyrimidin-1-yl)-1-methyl-indazol-6-yl]-3,3-difluoro-piperidine-1-carboxylate and tert-Butyl (4S)-4-[3-(2,4-dioxohexahydropyrimidin-1-yl)-1-methyl-indazol-6-yl]-3,3-difluoro-piperidine-1-carboxylate by chiral SFC separation

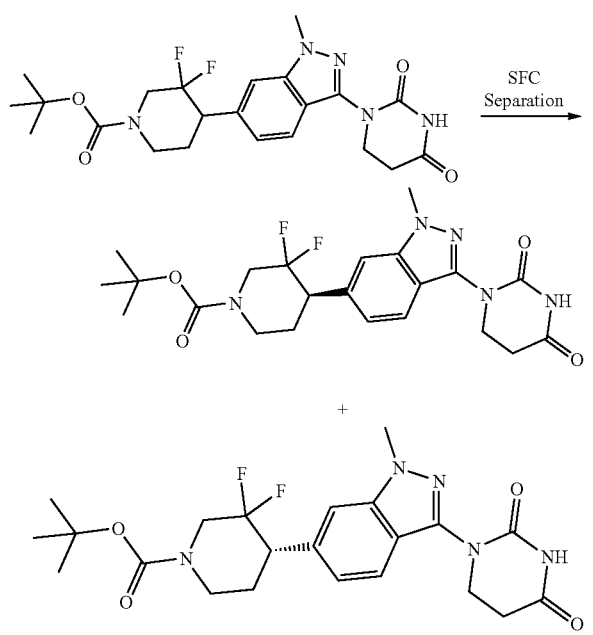

Racemic tert-butyl 4-(3-(2,4-dioxotetrahydropyrimidin-1(2H)-yl)-1-methyl-1H-indazol-6-yl)-3,3-difluoropiperidine-1-carboxylate was resolved using SFC separation under the following conditions:

Sample Weight: 5.06 g
Column: ChiralCel OD-H 21×250 mm
Mobile Phase: 20% 2-Propanol in CO2
Flow Rate: 70 mL/min
Sample: Every 1 g sample was dissolved in 25 mL Ethanol and 25 mL Dichloromethane
Injection: 1 mL
Detection: 220 nm The first eluting set of fractions was collected and evaporated to afford tert-Butyl (4R)-4-[3-(2,4-dioxohexahydropyrimidin-1-yl)-1-methyl-indazol-6-yl]-3,3-difluoro-piperidine-1-carboxylate (2.21 g, 43% yield, 100% ee) using the following analytical conditions. SFC retention time: 3.18 min (25% iso-propanol in supercritical $CO_2$, OD-H 4.6×100 mm, 40° C. 4 mL/min, 100 psi, 5 μL (Ethanol) injection), LCMS: 464 (M+H)

The second eluting set of fractions was collected and evaporated to afford tert-Butyl (4S)-4-[3-(2,4-dioxohexahydropyrimidin-1-yl)-1-methyl-indazol-6-yl]-3,3-difluoro-piperidine-1-carboxylate (2.21 g, 43% yield, 100% ee) using the following analytical conditions. Retention time: 4.07 min (25% iso-propanol in supercritical $CO_2$, OD-H 4.6×100 mm, 40° C. 4 mL/min, 100 psi, 5 μL (Ethanol) injection), LCMS: 464 (M+H)

Intermediate Y: Synthesis of 1-(5-fluoro-6-iodo-1-methyl-1H-indazol-3-yl)dihydropyrimidine-2,4(1H,3H)-dione

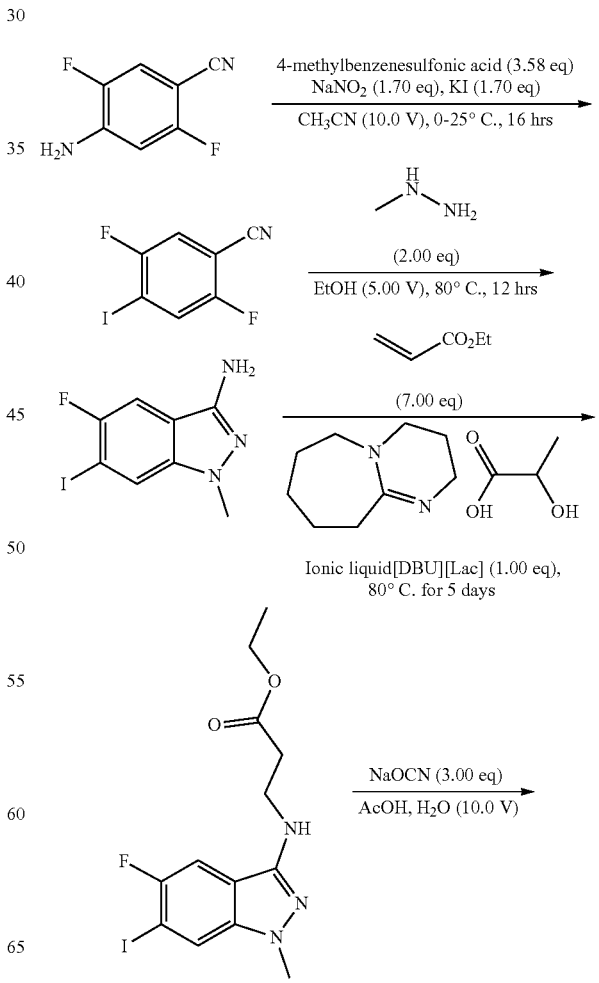

917
-continued

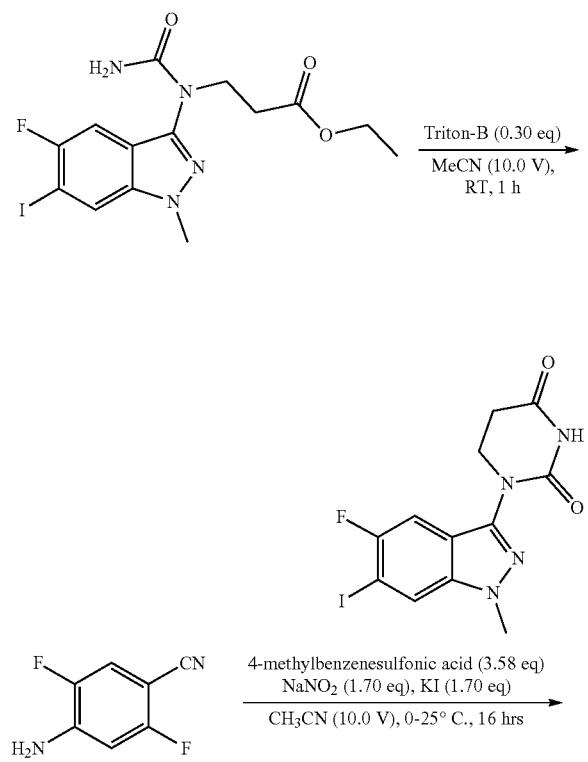

918
-continued

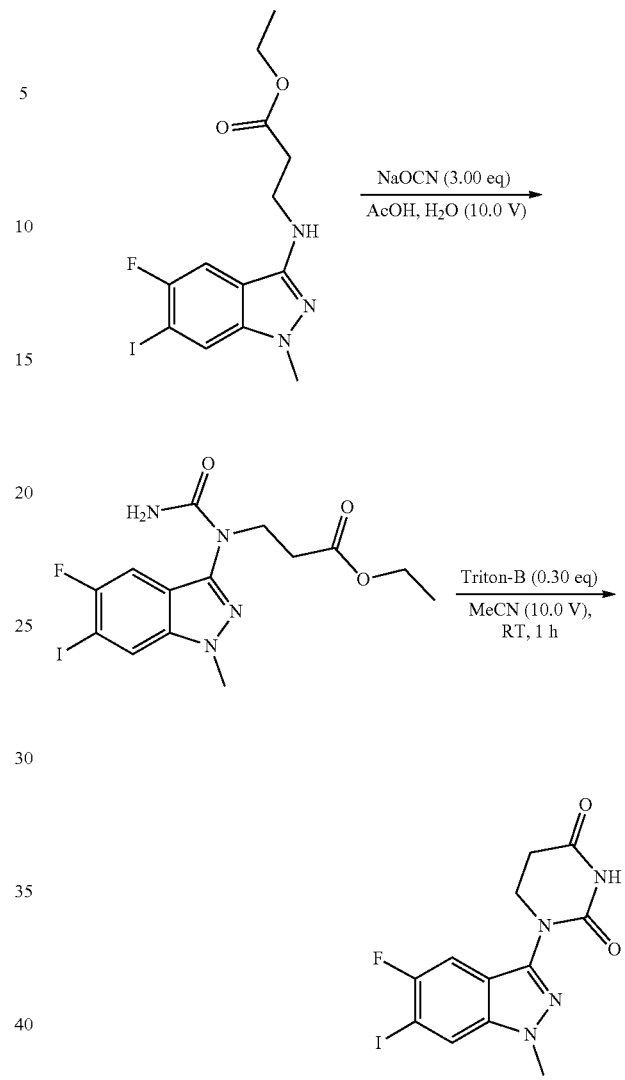

Step 1: 2,5-difluoro-4-iodobenzonitrile

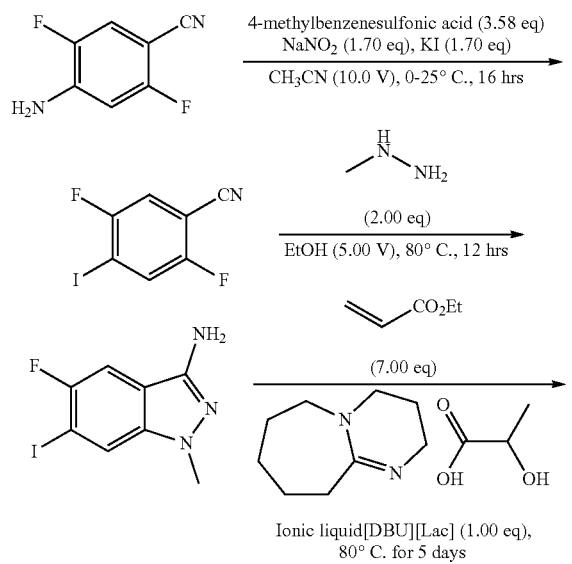

A mixture of compound 4-amino-2,5-difluorobenzonitrile (52.0 g, 0.33 mol), 4-methylbenzenesulfonic acid (208 g, 1.21 mol) in acetonitrile (1.06 L) was stirred for 4 h at 15° C. Sodium nitrite (39.6 g, 0.57 mol) and potassium iodide (95.2 g, 0.57 mol) were added into reactor at 0° C. Then the mixture was stirred for 12 h at 15° C. The mixture was quenched with aqueous sodium hydrogen sulfite (200 mL, 3.85× by volume). The aqueous phase was extracted with ethyl acetate (500 mL, 9.61× by volume). The combined organic phase was washed with brine (200 mL, 3.85× by volume), dried with anhydrous Sodium sulfate, filtered, and concentrated in vacuum. 2,5-difluoro-4-iodobenzonitrile (40 g, 47.7% yield). $^1$H NMR: 400 MHz, CDCl$_3$. δ 7.39 (s, 1H), 7.12-7.00 (m, 1H).

Step 2: Synthesis of 1-(5-fluoro-6-iodo-1-methyl-1H-indazol-3-yl)dihydropyrimidine-2,4(1H,3H)-dione

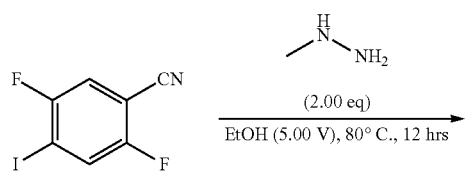

A mixture of 2,5-difluoro-4-iodobenzonitrile (60.0 g, 0.22 mol) and compound methyl hydrazine (59.6 mL, 0.45 mol) in ethanol (600 mL) was degassed and purged with N₂ for 3 times at 15° C., and the mixture was stirred at 80° C. for 16 h under N₂ atmosphere. The reaction mixture was concentrated in vacuum under reduced pressure. The residue yellow solid was triturated with ethanol (120 mL) at 15° C. for 5 h and filtered to give compound 5-fluoro-6-iodo-1-methyl-1H-indazol-3-amine (54.5 g, 82.7% yield) as a white solid. LCMS (ESI+): 292.1 (M+H).

Step 3: ethyl 3-((5-fluoro-6-iodo-1-methyl-1H-indazol-3-yl)amino)propanoate

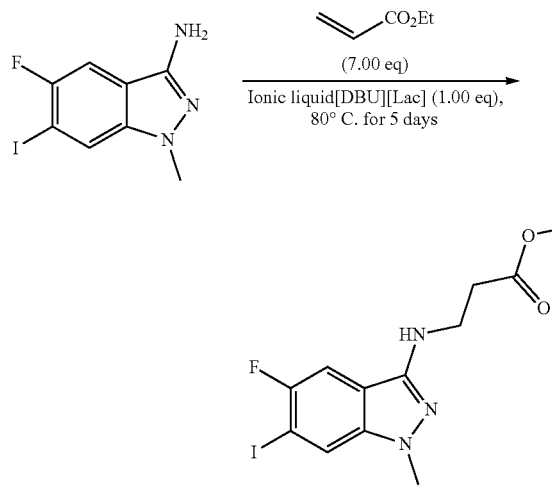

A mixture of compound 5-fluoro-6-iodo-1-methyl-1H-indazol-3-amine (54.5 g, 220 mmol), compound ethyl acrylate (142 mL, 1.31 mol) and [DBU]·[Lac] (26.4 g, 180 mmol) was degassed and purged with N₂ for 3 times, the resulting mixture was stirred at 80° C. for 120 h under N₂ atmosphere. The residue was diluted with dichloromethane (500 mL) and water (500 mL), the organic layers were washed with brine (300 mL) dried over sodium sulfate, filtered and filtrate concentrated under reduced pressure to give a residue. The residue was purified by column chromatography (silica, petroleum ether/ethyl acetate=50/1 to 1/1). Ethyl 3-((5-fluoro-6-iodo-1-methyl-1H-indazol-3-yl)amino)propanoate (35 g, 89.2 mmol, 47.7% yield) was obtained as a yellow solid. LCMS (ESI+): 392.0 (M+H).

Step 4: ethyl 3-(1-(5-fluoro-6-iodo-1-methyl-1H-indazol-3-yl)ureido)propanoate

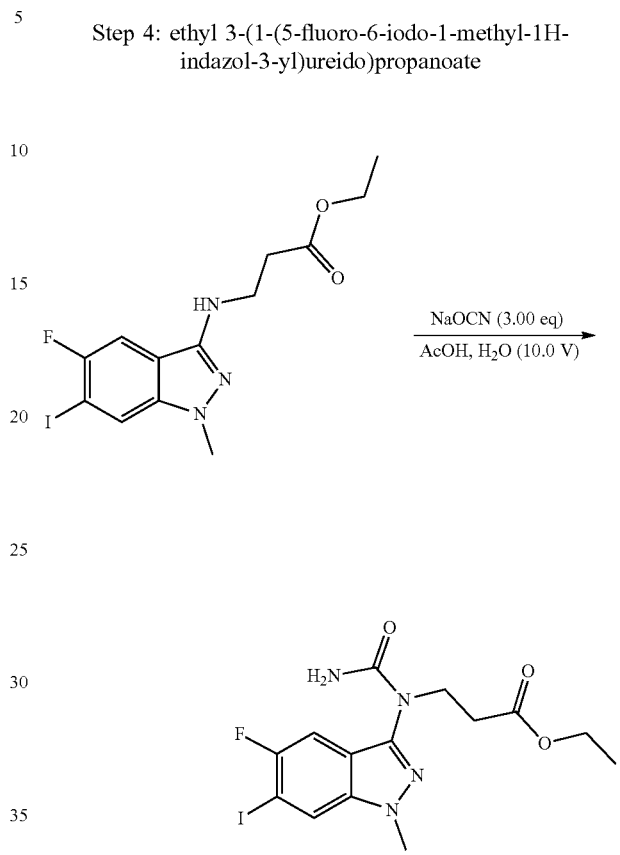

A mixture of ethyl 3-((5-fluoro-6-iodo-1-methyl-1H-indazol-3-yl)amino)propanoate (50.0 g, 0.39 mol, 1.00 eq), sodium cyanate (24.9 g, 0.38 mol, 3.00 eq) in acetic acid (225 mL) and water (75.0 mL) was stirred at 15° C. for 3 h. The aqueous phase was extracted with ethyl acetate (150 mL, 3× by volume). The combined organic phase was washed with saturated aqueous sodium bicarbonate solution (150 mL, 3.00× by volume), dried with anhydrous sodium sulfate, filtered, and concentrated in vacuum to give ethyl 3-(1-(5-fluoro-6-iodo-1-methyl-1H-indazol-3-yl)ureido) propanoate (32.0 g, 56.6% yield) as a white solid. LCMS (ESI+): 417.1 (M+H).

Step 5: 1-(5-fluoro-6-iodo-1-methyl-1H-indazol-3-yl)dihydropyrimidine-2,4(1H,3H)-dione

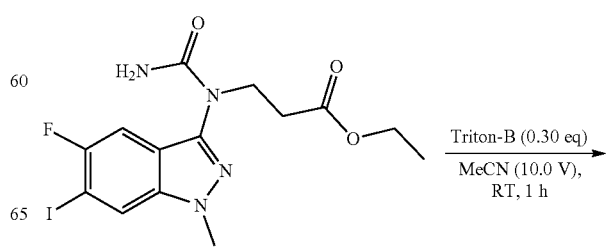

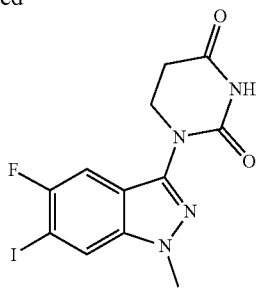

A mixture of ethyl 3-(1-(5-fluoro-6-iodo-1-methyl-1H-indazol-3-yl)ureido)propanoate (32.0 g, 73.0 mmol, 1.00 eq) and Triton B (22.0 mmol, 4.02 mL, 0.30 eq) in acetonitrile (320 mL) was stirred at 15° C. for 3 h. The reaction mixture was filtered to give cake and the cake was concentrated under reduced pressure to give 1-(5-fluoro-6-iodo-1-methyl-1H-indazol-3-yl)dihydropyrimidine-2,4(1H,3H)-dione (24.0 g, 83.9% yield) as an off-white solid. LCMS (ESI+): 389.0 (M+H), $^1$H-NMR (400 MHz, DMSO-d6): δ 10.56 (s, 1H), 8.27-8.01 (m, 1H), 7.51-7.45 (m, 1H), 3.97 (s, 3H), 3.95-3.90 (m, 2H), 2.79-2.73 (m, 2H)

Example 80

2-(6,7-dihydro-5H-pyrrolo[1,2-c]imidazol-1-yl)-2-[6-[4-[(1R,4R)-2-[2-[4-[4-[[(3S)-2,6-dioxo-3-piperidyl]amino]-2-fluoro-phenyl]-1-piperidyl]acetyl]-2,5-diazabicyclo[2.2.1]heptan-5-yl]phenyl]-4-fluoro-1-oxo-isoindolin-2-yl]-N-thiazol-2-yl-acetamide, Compound 80

Step 1: tert-Butyl (1R,4R)-5-(4-bromophenyl)-2,5-diazabicyclo[2.2.1]heptane-2-carboxylate

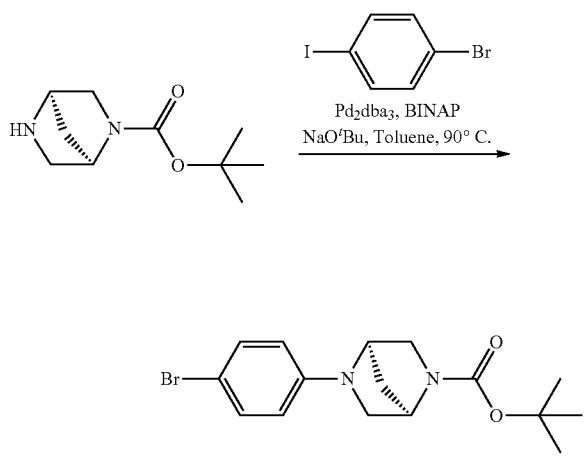

Into a 100 mL sealed tube containing a well-stirred solution of tert-butyl (1R,4R)-2,5-diazabicyclo[2.2.1]heptane-2-carboxylate (1.00 g, 5.04 mmol) and 1-bromo-4-iodo-benzene (3.57 g, 12.61 mmol) in anhydrous toluene (20 mL) was added Sodium tert-butoxide (1.45 g, 15.13 mmol) at ambient temperature under nitrogen atmosphere and the resulting mixture was degassed by bubbling nitrogen gas for 10 minutes. Tris(dibenzylideneacetone)dipalladium (0) (230.94 mg, 252.19 μmol), rac-BINAP (314.07 mg, 504.38 μmol) were added to the reaction mixture and further degassed with nitrogen gas for 5 minutes. The reaction mixture was heated in a heating block at 90° C. for 16 h. The reaction mixture was diluted with ethyl acetate and filtered through celite. The filtrate was washed with ice cold water (100 mL) and extracted using ethyl acetate (3×150 mL). The organic layer was further washed with brine solution (150 mL), dried over sodium sulphate and concentrated under reduced pressure. The crude residue obtained was purified by column chromatography using silica (0-20% ethyl acetate in Pet Ether) to get tert-butyl (1R,4R)-5-(4-bromophenyl)-2,5-diazabicyclo[2.2.1]heptane-2-carboxylate (1.45 g, 3.79 mmol, 75.11% yield) as an off white solid. LCMS (ESI+) m/z: 353.1 [M+H]$^+$.

Step 2: tert-Butyl (1R,4R)-5-[4-(4,4,5,5-tetramethyl-1,3,2-dioxaborolan-2-yl)phenyl]-2,5-diazabicyclo[2.2.1]heptane-2-carboxylate

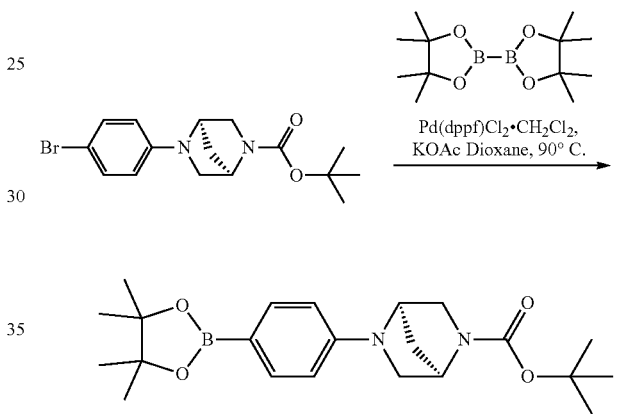

Into a 100 mL double-necked round-bottomed flask containing a well-stirred solution of tert-butyl (1R,4R)-5-(4-bromophenyl)-2,5-diazabicyclo[2.2.1]heptane-2-carboxylate (1.45 g, 4.10 mmol) and 4,4,5,5-tetramethyl-2-(4,4,5,5-tetramethyl-1,3,2-dioxaborolan-2-yl)-1,3,2-oxaborolane (1.04 g, 4.10 mmol) in anhydrous 1,4-dioxane (20 mL) was added potassium acetate (1.21 g, 12.31 mmol) at ambient temperature under nitrogen atmosphere and the resulting mixture was degassed by bubbling nitrogen gas for 10 minutes. [1,1'-Bis(diphenylphosphino)ferrocene] dichloropalladium(II), complex with dichloromethane (87.02 mg, 106.55 μmol) were added to the reaction mixture and further degassed with nitrogen gas for 5 minutes. The reaction mixture was heated to 90° C. for 16 h under inert atmosphere. The reaction mixture was diluted with ethyl acetate and filtered through celite. The filtrate was washed with ice cold water (50 mL) and extracted using ethyl acetate (3×100 mL). The combined organic layers were further washed with brine solution (100 mL), dried over sodium sulfate and concentrated under reduced pressure. The crude was purified by column chromatography using silica gel (0-10% ethyl acetate in Pet ether) to get tert-butyl (1R,4R)-5-[4-(4,4,5,5-tetramethyl-1,3,2-dioxaborolan-2-yl)phenyl]-2,5-diazabicyclo[2.2.1]heptane-2-carboxylate (720 mg, 1.43 mmol, 34.72% yield) as an off white solid. LCMS (ESI+) m/z: 401.2 [M+H]$^+$.

Step 3: tert-Butyl (1R,4R)-5-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,5-diazabicyclo[2.2.1]heptane-2-carboxylate

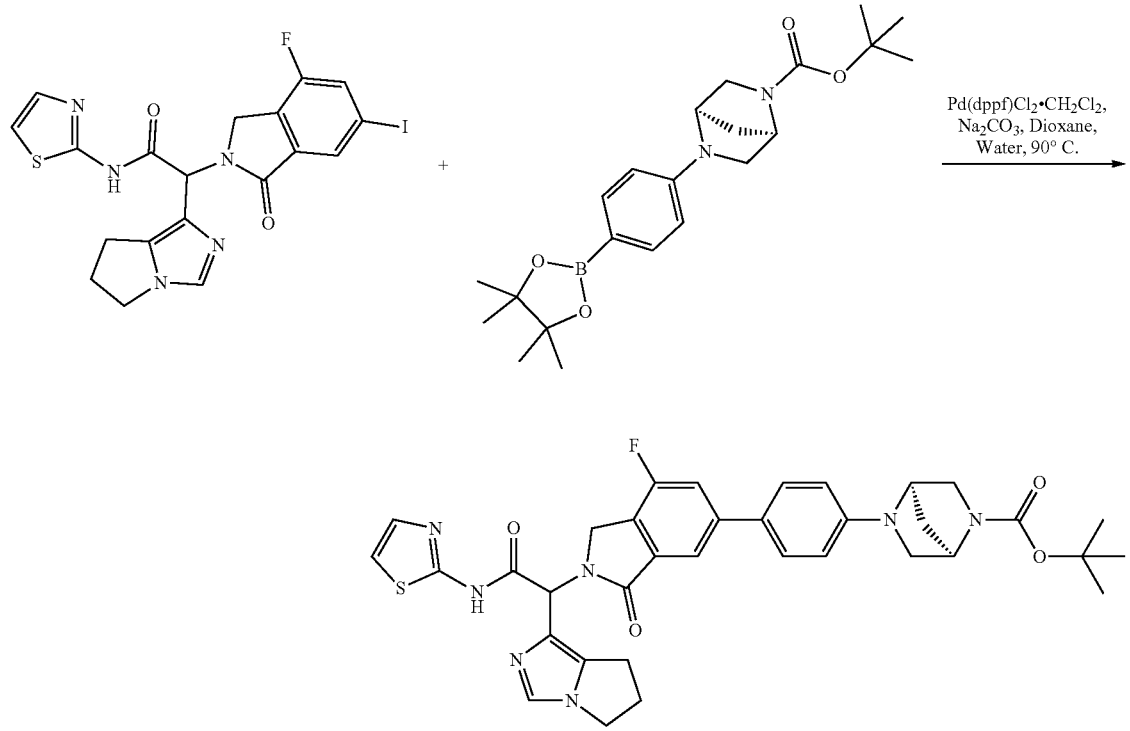

In a 100 mL double-necked round-bottomed flask containing a well-stirred solution of 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (800 mg, 1.53 mmol) and tert-butyl (1R,4R)-5-[4-(4,4,5,5-tetramethyl-1,3,2-dioxaborolan-2-yl)phenyl]-2,5-diazabicyclo[2.2.1]heptane-2-carboxylate (795.55 mg, 1.99 mmol) in anhydrous 1,4-dioxane (15 mL) was added sodium carbonate (405.07 mg, 3.82 mmol, 160.11 µL) in water (3 mL) at ambient temperature under nitrogen atmosphere. The resulting mixture was degassed by bubbling nitrogen gas for 10 minutes. [1,1'-Bis(diphenylphosphino)ferrocene] dichloropalladium (II), complex with dichloromethane (87.02 mg, 106.55 µmol) was added to it and further degassed with nitrogen gas for 5 minutes. The reaction mixture was heated at 80° C. in a heating block for 16 h under inert atmosphere. The reaction mixture was diluted with ethyl acetate and filtered through celite. The filtrate was washed with ice cold water (50 mL) and extracted using ethyl acetate (3×100 mL). The organic layer was washed with brine solution (100 mL), dried over sodium sulfate, and concentrated under reduced pressure. The crude was purified by column chromatography using silica (0-3% methanol in dichloromethane) to get tert-butyl (1R,4R)-5-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,5-diazabicyclo[2.2.1]heptane-2-carboxylate (420 mg, 570.28 µmol, 37.30% yield) as an off-white solid. LCMS (ESI+) m/z: 670.0 [M+H]+.

Step 4: 2-[6-[4-[(1R,4R)-2,5-diazabicyclo[2.2.1]heptan-2-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

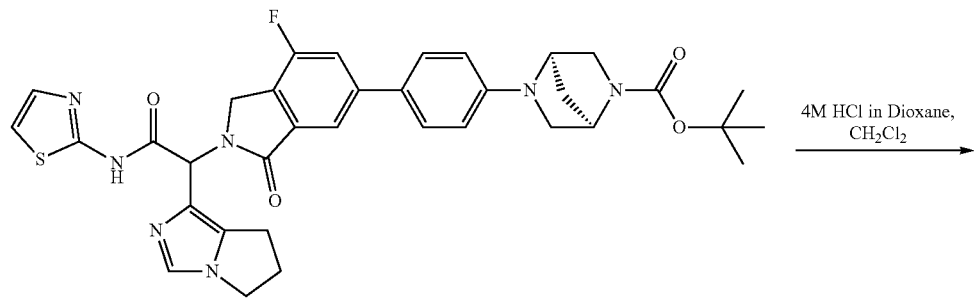

-continued

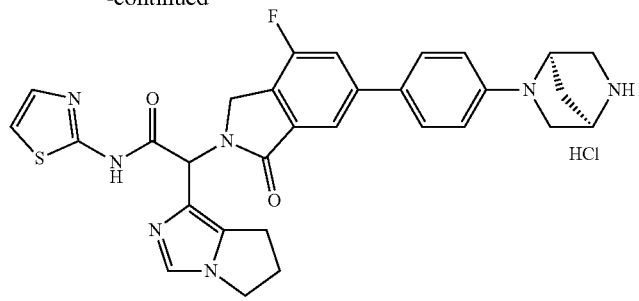

In to a 50 mL single-neck round bottom flask containing a well-stirred solution of tert-butyl (1R,4R)-5-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,5-diazabicyclo[2.2.1]heptane-2-carboxylate (420 mg, 627.08 μmol) in anhydrous dichloromethane (5 mL) was added Hydrogen chloride solution (4.0M in 1,4-dioxane, 228.64 mg, 6.27 mmol, 285.80 μL) dropwise at 0° C. under nitrogen atmosphere. The resulting reaction mixture was stirred at ambient temperature for 2 h. Solvent was removed from the reaction mixture under reduced pressure. The residue was triturated with diethyl ether to get 2-[6-[4-[(1R,4R)-2,5-diazabicyclo[2.2.1]heptan-2-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide (370 mg, 598.33 μmol, 95.41% yield) as an off white solid. LCMS (ESI+) m/z: 570.0 [M+H]$^+$.

Step 5: 2-(6,7-dihydro-5H-pyrrolo[1,2-c]imidazol-1-yl)-2-[6-[4-[(1R,4R)-2-[2-[4-[4-[[(3S)-2,6-dioxo-3-piperidyl]amino]-2-fluoro-phenyl]-1-piperidyl]acetyl]-2,5-diazabicyclo[2.2.1]heptan-5-yl]phenyl]-4-fluoro-1-oxo-isoindolin-2-yl]-N-thiazol-2-yl-acetamide

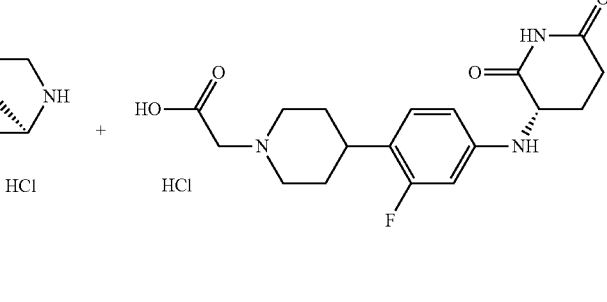

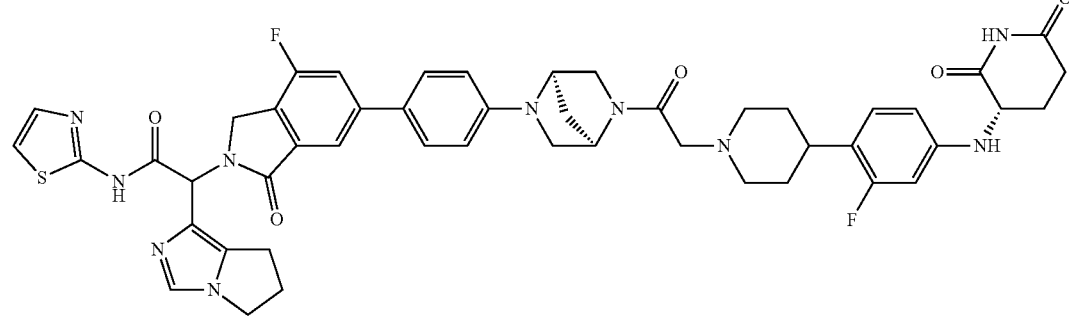

Into a 10 mL single-necked round-bottomed flask containing a well-stirred solution of 2-[6-[4-[(1R,4R)-2,5-diazabicyclo[2.2.1]heptan-2-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide; hydrochloride (100 mg, 164.99 μmol) and 2-[4-[4-[[(3S)-2,6-dioxo-3-piperidyl]amino]-2-fluoro-phenyl]-1-piperidyl]acetic acid hydrochloride (79.16 mg, 197.98 μmol) in anhydrous N,N-dimethylformamide (2 mL) under nitrogen atmosphere was added anhydrous N,N-diisopropylethylamine (127.94 mg, 989.92 μmol, 172.42 μL) at 0° C. Propylphosphonic anhydride solution (>50 wt. % in ethyl acetate, 131.24 mg, 412.46 μmol) was added at the same temperature and the reaction mixture was further stirred for 1 h while warming to room temperature. The reaction mixture was poured into ice cold water (10 mL), and the solid precipitated was filtered. The solid was washed with water and dried. The crude was purified using Prep HPLC (Purification method: Column: X-Bridge C$_8$ (50×4.6 mm), 3.5 micron; (Mobile Phase A: 10 mM Ammonium acetate in milli-q water; Mobile phase B: acetonitrile); Flow rate: 15 mL\min. The pure fractions were combined and lyophilized to get Compound 80 (67 mg, 73.17 μmol, 44.35% yield) as an off-white solid. LCMS (ESI+) m/z: 916.4 [M+H]$^+$. 1H-NMR (400 MHz, DMSO-d6): δ 12.49 (s, 1H), 10.75 (s, 1H), 7.75-7.72 (m, 1H), 7.72-7.68 (m, 3H), 7.60 (s, 1H), 7.47 (bs, 1H), 7.23 (bs, 1H), 7.03 (t, J=8.80 Hz, 1H), 6.73 (t, J=8.40 Hz, 2H), 6.47 (t, J=14.40 Hz, 1H), 6.36 (d, J=13.60 Hz, 1H), 6.20-6.13 (m, 2H), 6.02 (d, J=7.60 Hz, 1H), 5.84 (d, J=6.80 Hz, 1H), 4.92-4.79 (m, 2H), 4.66 (d, J=27.60 Hz, 1H), 4.38-4.29 (m, 1H), 4.23-4.19 (m, 1H), 4.00-3.98 (m, 2H), 3.89-3.68 (m, 1H), 3.65-3.54 (m, 1H), 3.37-3.33 (m, 1H), 3.30-3.21 (m, 2H), 3.04-3.00 (m, 2H), 2.83-2.72 (m, 3H), 2.68-2.51 (m, 1H), 2.34-2.11 (m, 3H), 2.11-1.87 (m, 4H), 1.68-1.66 (m, 2H), 1.59-1.25 (m, 2H). [48H Expected, 47H observed (water obscuration)].

Example 81

2-(6,7-dihydro-5H-pyrrolo[1,2-c]imidazol-1-yl)-2-[6-[4-[[1-[2-[4-[4-[(2,6-dioxo-3-piperidyl)amino]phenyl]phenyl]acetyl]-4-piperidyl]oxy]phenyl]-4-fluoro-1-oxo-isoindolin-2-yl]-N-thiazol-2-yl-acetamide, Compound 81

Step 1: Benzyl 2-[4-[4-[(2,6-dioxo-3-piperidyl)amino]phenyl]phenyl]acetate

To a stirred solution of benzyl 2-[4-(4-aminophenyl)phenyl]acetate (CAS #70957-50-5, 1.6 g, 5.04 mmol) in N,N-dimethylformamide (15 mL) was added sodium bicarbonate (2.54 g, 30.25 mmol, 1.18 mL) at 25° C. followed by the addition of 3-bromopiperidine-2,6-dione (3.87 g, 20.17 mmol). The reaction mixture was heated at 70° C. for 12 h. The reaction mixture was concentrated under reduced pressure. The crude was purified by column chromatography using an Isolera instrument. The product eluted in 60% ethyl acetate/petroleum ether to get the benzyl 2-[4-[4-[(2,6-dioxo-3-piperidyl)amino]phenyl]phenyl]acetate (1.5 g, 2.69 mmol, 53.33% yield). LCMS m/z 429.1 (M+H$^+$).

Step 2: 2-[4-[4-[(2,6-dioxo-3-piperidyl)amino]phenyl]phenyl]acetic acid

929

-continued

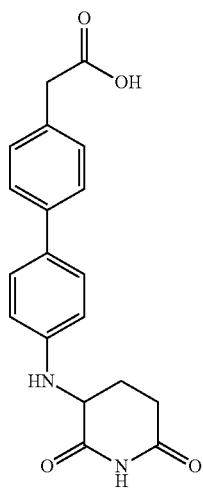

To a stirred solution of benzyl 2-[4-[4-[(2,6-dioxo-3-piperidyl)amino]phenyl]phenyl]acetate (1.5 g, 3.50 mmol) in tetrahydrofuran (100 mL) and Methanol (50 mL) was added Palladium, 10% on carbon, Type 487, dry (372.55 mg, 3.50 mmol) at room temperature. The reaction mixture was degassed and stirred at room temperature under hydrogen balloon pressure for 2 h. The reaction mixture was filtered through the celite bed and washed with methanol. The filtrate was concentrated under reduced pressure. The solid was washed with diethyl ether to afford 2-[4-[4-[(2,6-dioxo-3-piperidyl)amino]phenyl]phenyl]acetic acid (600 mg, 1.48 mmol, 42.30% yield). LCMS m/z 339.1 (M+H$^+$).

Step 3: 2-(6,7-dihydro-5H-pyrrolo[1,2-c]imidazol-1-yl)-2-[6-[4-[[1-[2-[4-[4-[(2,6-dioxo-3-piperidyl)amino]phenyl]phenyl]acetyl]-4-piperidyl]oxy]phenyl]-4-fluoro-1-oxo-isoindolin-2-yl]-N-thiazol-2-yl-acetamide

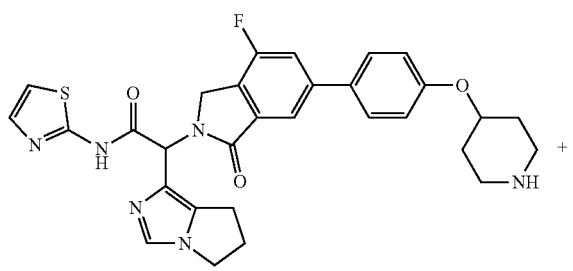

930

-continued

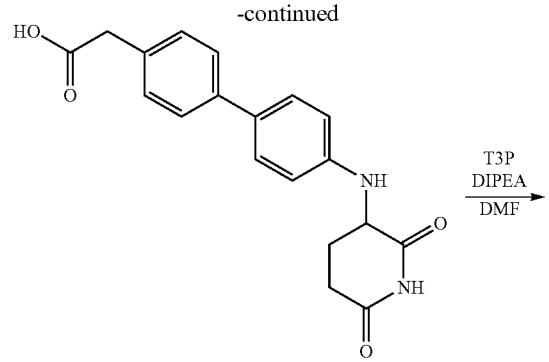

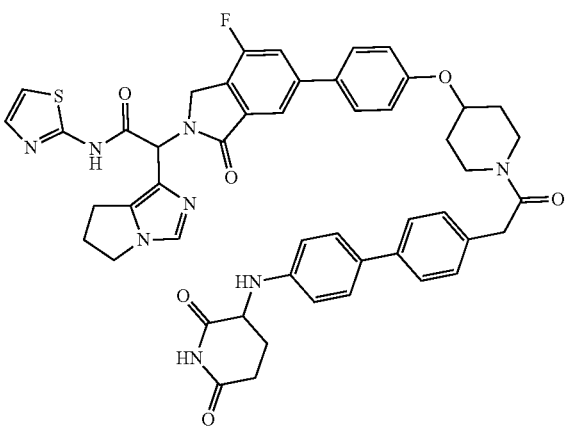

To a solution of 2-(6,7-dihydro-5H-pyrrolo[1,2-c]imidazol-1-yl)-2-[4-fluoro-1-oxo-6-[4-(4-piperidyloxy)phenyl]isoindolin-2-yl]-N-thiazol-2-yl-acetamide (0.1 g, 164.17 µmol, 021) in N,N-dimethylformamide (2 mL) was added 2-[4-[4-[(2,6-dioxo-3-piperidyl)amino]phenyl]phenyl]acetic acid (66.66 mg, 197.01 µmol) and Propylphosphonic anhydride solution (50 wt. % in ethyl acetate) (104.47 mg, 328.35 µmol) and stirred for 5 min at 0° C. N,N-diisopropylethylamine (63.65 mg, 492.52 µmol, 85.79 µL) was added and the mixture was stirred at 0° C. for 2 h. Solvent was removed under reduced pressure. The residue was purified by preparative HPLC (column AGILENT C18 using 55% water with 0.1% ammonium acetate in acetonitrile as an eluent). Collected fractions were lyophilized to get the desired product Compound 81 (15.63 mg, 17.00 µmol, 10.36% yield) as an off white solid. LCMS m/z: 893.3 (M+H), $^1$H-NMR (400 MHz, DMSO-d6): δ 12.48 (s, 1H), 10.82 (s, 1H), 7.78-7.71 (m, 4H), 7.58 (s, 1H), 7.52 (d, J=8.40 Hz, 2H), 7.43 (d, J=8.80 Hz, 3H), 7.26 (d, J=8.40 Hz, 2H), 7.08 (d, J=8.80 Hz, 2H), 6.76 (d, J=8.80 Hz, 2H), 6.04-6.02 (m, 2H), 4.90-4.86 (m, 1H), 4.70-4.67 (m, 1H), 4.43-4.37 (m, 1H), 4.24-4.20 (m, 1H), 4.02-3.92 (m, 3H), 3.90.1-3.75 (m, 3H), 2.78-2.76 (m, 1H), 2.75-2.73 (m, 1H), 2.69-2.61 (m, 2H), 2.59-2.51 (m, 4H), 2.34-2.33 (m, 1H), 1.95-1.76 (m, 3H), 1.54-1.51 (m, 2H).

Example 82

2-(6,7-dihydro-5H-pyrrolo[1,2-c]imidazol-1-yl)-2-[6-[4-[(1R,4R)-2-[2-[4-[3-(2,4-dioxohexahydropyrimidin-1-yl)-1-methyl-indazol-6-yl]-1-piperidyl]acetyl]-2,5-diazabicyclo[2.2.1]heptan-5-yl]phenyl]-4-fluoro-1-oxo-isoindolin-2-yl]-N-thiazol-2-yl-acetamide Compound 82

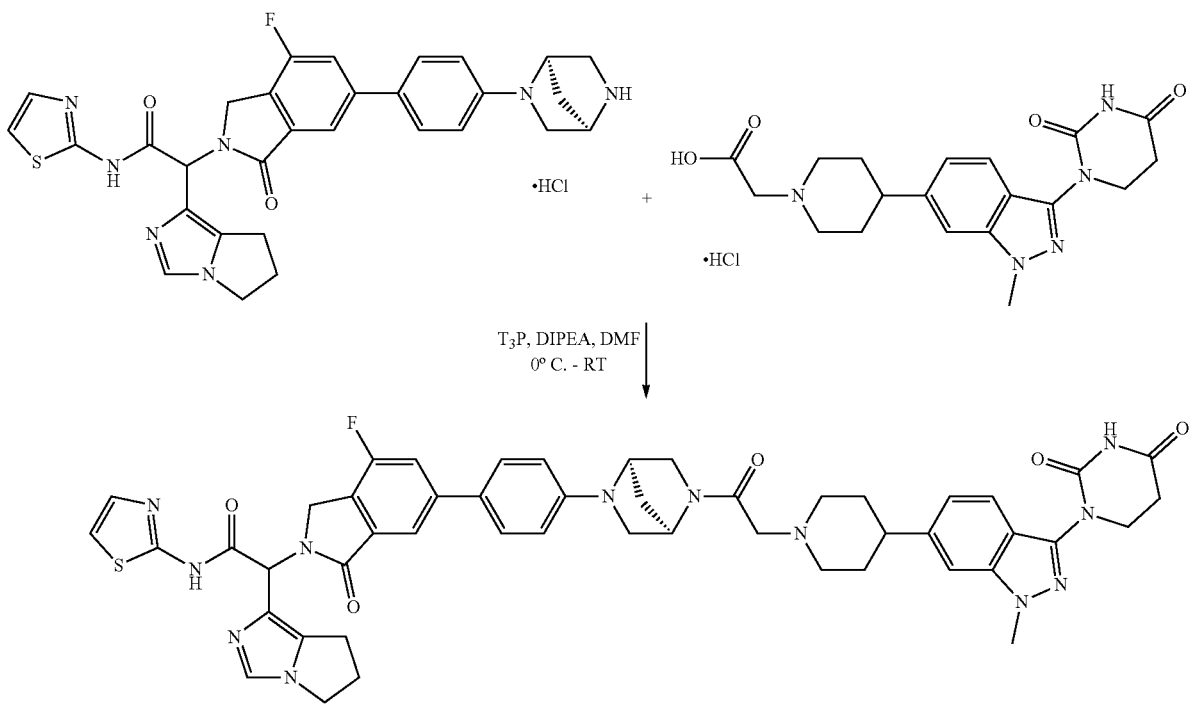 [SMILES: O=C(Nc1nccs1)C(c1ncn2c1CCC2)N1Cc2c(F)cc(-c3ccc(N4C[C@H]5C[C@@H]4CN5)cc3)cc2C1=O ; Cl ; Cn1nc(N2CCC(=O)NC2=O)c2ccc(C3CCN(CC(=O)O)CC3)cc21 ; Cl ; Cn1nc(N2CCC(=O)NC2=O)c2ccc(C3CCN(CC(=O)N4C[C@H]5C[C@@H]4CN5c4ccc(-c5cc(F)c6c(c5)C(=O)N(C(C(=O)Nc5nccs5)c5ncn7c5CCC7)C6)cc4)CC3)cc21]

Into a 10 mL single-necked round-bottomed flask containing a well-stirred solution of 2-[6-[4-[(1R,4R)-2,5-diazabicyclo[2.2.1]heptan-2-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide; hydrochloride (100 mg, 164.99 μmol) and 2-[4-[3-(2,4-dioxohexahydropyrimidin-1-yl)-1-methyl-indazol-6-yl]-1-piperidyl]acetic acid; hydrochloride (83.52 mg, 197.98 μmol) in anhydrous N,N-dimethylformamide (1 mL) under nitrogen atmosphere was added anhydrous N,N-diisopropylethylamine (127.94 mg, 989.92 μmol, 172.43 μL) at 0° C. Propylphosphonic anhydride solution ≥50 wt. % in ethyl acetate (131.24 mg, 412.46 μmol) was added at the same temperature and the reaction mixture was further stirred for 1 h while warming to room temperature. The reaction mixture was poured onto ice cold water (10 mL), and the solid was filtered. The solid was washed with water and dried. The crude was purified using Prep HPLC (Purification method: Column: X-Bridge C8 (50×4.6) mm, 3.5 micron; (Mobile Phase A: 10 mM Ammonium acetate in water; Mobile phase B: acetonitrile); Flow rate: 15 mL/min. The pure fractions were combined and lyophilized to get Compound 82 (30 mg, 31.07 μmol, 18.83% yield) as an off-white solid. LCMS (ESI+) m/z: 937.3 [M+H]$^+$. 1H-NMR (400 MHz, DMSO-d6): δ 12.49 (s, 1H), 10.55 (s, 1H), 7.74-7.70 (m, 1H), 7.65 (d, J=8.40 Hz, 1H), 7.61 (d, J=6.00 Hz, 1H), 7.60-7.58 (m, 1H), 7.49-7.45 (m, 1H), 7.46 (s, 1H), 7.38 (d, J=8.40 Hz, 1H), 7.30 (s, 1H), 7.26 (d, J=3.60 Hz, 1H), 7.08 (d, J=8.00 Hz, 1H), 6.87 (d, J=8.40 Hz, 1H), 6.74 (t, J=8.40 Hz, 1H), 6.14 (d, J=4.80 Hz, 1H), 4.93 (s, 1H), 4.81-4.71 (m, 2H), 4.63 (bs, 1H), 4.20 (dd, J=17.80, 4.40 Hz, 1H), 3.99-3.87 (m, 7H), 3.81-3.58 (m, 2H), 3.41-3.33 (m, 1H), 3.28-3.24 (m, 2H), 3.22-2.89 (m, 4H), 2.78-2.72 (m, 3H), 2.68-2.57 (m, 1H), 2.45-2.34 (m, 1H), 2.25-2.05 (m, 3H), 1.97-1.91 (m, 2H), 1.41-1.83 (m, 4H).

Example 83

2-(6,7-dihydro-5H-pyrrolo[1,2-c]imidazol-1-yl)-2-[6-[4-[4-[2-[1-[4-[(2,6-dioxo-3-piperidyl)amino]-2-fluoro-phenyl]-4-hydroxy-4-piperidyl]acetyl]piperazin-1-yl]phenyl]-4-fluoro-1-oxo-isoindolin-2-yl]-N-thiazol-2-yl-acetamide, Compound 83

Step 1: 1-(2-fluoro-4-nitro-phenyl)piperidin-4-one

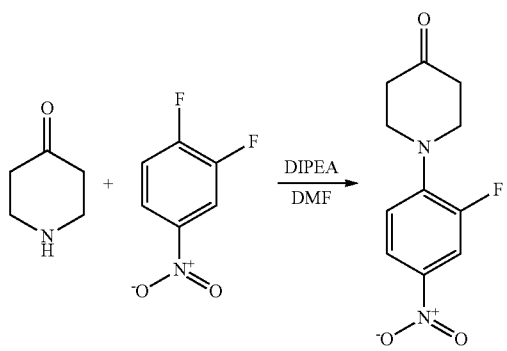

To a solution of piperidin-4-one (15.0 g, 151.31 mmol), 1,2-difluoro-4-nitro-benzene (24.07 g, 151.31 mmol, 16.72 mL) in N,N-dimethylformamide (30 mL) was added N,N-diisopropylethylamine (78.22 g, 605.26 mmol, 105.42 mL) and heated at 110° C. for 14 h. The reaction mixture was diluted with ethyl acetate (500 mL) and washed with cold water (150 mL). The organic layer was washed with a brine solution (150 mL), dried over sodium sulfate and concentrated under reduced pressure. The residue was purified by column chromatography on silica gel (40% ethyl acetate in petroleum ether) to afford 1-(2-fluoro-4-nitro-phenyl)piperidin-4-one (21 g, 77.93 mmol, 51.50% yield) as brown solid. LCMS, m/z: 238.9 [M+H]$^+$

Step 2: Synthesis of tert-butyl 2-[1-(4-amino-2-fluoro-phenyl)-4-hydroxy-4-piperidyl]acetate

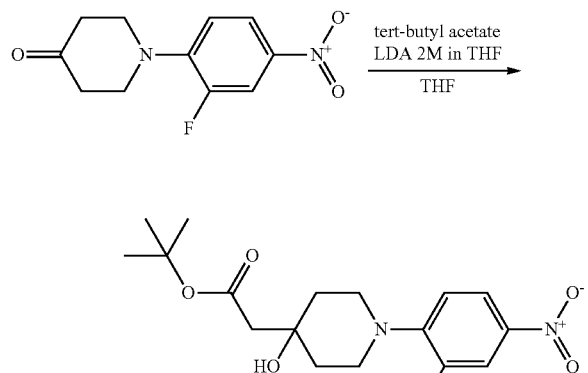

To a stirred solution of tert-butyl acetate (1.76 g, 15.11 mmol, 2.03 mL) in tetrahydrofuran (25 mL) was added dropwise lithium diisopropylamide (2 M in tetrahydrofuran, 12.59 mL) at −78° C. The reaction mixture was stirred at −78° C. for 45 minutes. 1-(2-fluoro-4-nitro-phenyl)piperidin-4-one (3 g, 12.59 mmol) dissolved in tetrahydrofuran (15 mL) was added at −78° C. The reaction mixture was stirred at −78° C. for 2 h. The reaction mixture was quenched with saturated ammonium chloride solution and the mixture was extracted with ethyl acetate. The organic layer was dried over sodium sulfate and concentrated under reduced pressure. The residue was purified by silica gel (100-200 mesh) column chromatography (eluent. 30% to 40% ethyl acetate in petroleum ether) to afford tert-butyl 2-[1-(2-fluoro-4-nitro-phenyl)-4-hydroxy-4-piperidyl]acetate (2.7 g, 7.01 mmol, 55.66% yield) as light yellow sticky solid. LCMS (355.1 (M+H)$^+$)

Step 3: tert-Butyl 2-[1-(4-amino-2-fluoro-phenyl)-4-hydroxy-4-piperidyl]acetate

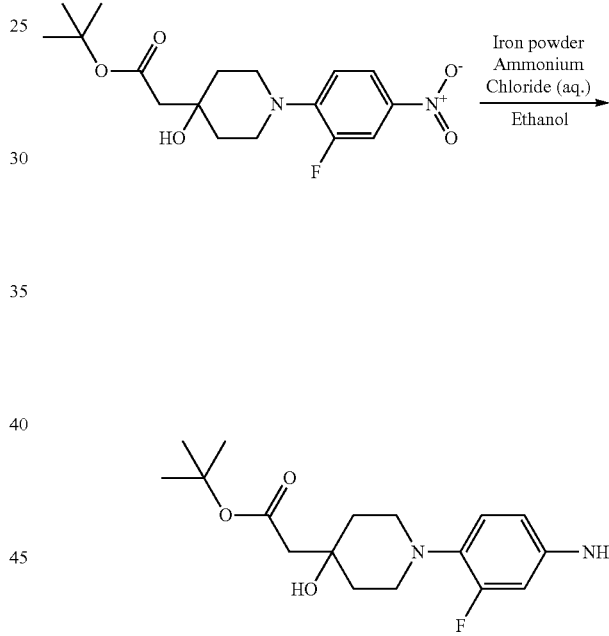

To a solution of tert-butyl 2-[1-(2-fluoro-4-nitro-phenyl)-4-hydroxy-4-piperidyl]acetate (1.5 g, 4.23 mmol) in Ethanol (10 mL) and water (2 mL) were added iron powder (1.18 g, 21.16 mmol, 150.37 µL) and ammonium chloride (679.26 mg, 12.70 mmol, 443.96 µL). The reaction was stirred at 70° C. for 4 h. The reaction mixture was filtered through celite and the filter cake was washed with ethyl acetate (60 mL). The filtrate was washed with water (20 mL), aqueous sodium bicarbonate (20 mL) and brine (20 mL). The organic layer was dried over sodium sulfate and concentrated under reduced pressure to yield a residue, which was purified by column chromatography on silica gel, eluting with 70% ethyl acetate in petroleum ether to afford tert-butyl 2-[1-(4-amino-2-fluoro-phenyl)-4-hydroxy-4-piperidyl]acetate (1.2 g, 3.44 mmol, 81.28% yield) as brown sticky solid. LCMS m/z: 325.1 [M+H], $^1$HNMR (DMSO-d6) 8.02-7.89 (m, 2H), 7.23-7.05 (m, 1H), 4.69 (s, 1H), 3.55-3.43 (m, 2H), 3.22-3.19 (m, 2H), 2.36 (s, 2H), 1.88-1.64 (m, 3H), 1.41 (s, 9H).

Step 4: tert-Butyl 2-[1-[4-[(2,6-dioxo-3-piperidyl)amino]-2-fluoro-phenyl]-4-hydroxy-4-piperidyl]acetate

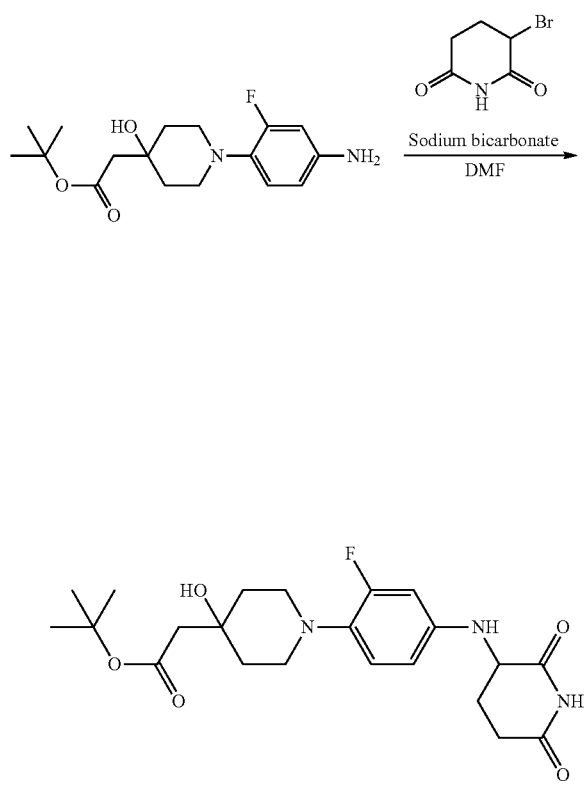

To a stirred solution of tert-butyl 2-[1-(4-amino-2-fluoro-phenyl)-4-hydroxy-4-piperidyl]acetate (1 g, 3.08 mmol) in N,N-dimethylformamide (10 mL) were added sodium bicarbonate (517.94 mg, 6.17 mmol, 239.79 µL) under nitrogen atmosphere in a 25 mL sealed tube. The vial was sealed and heated at 60° C. overnight. The reaction mixture was filtered through celite bed, washed 2 times with ethyl acetate and filtrate was concentrated under reduced pressure at 35° C. The crude residue was purified over silica column (100-200 mesh) eluting with 65-70% ethyl acetate:petroleum ether to afford tert-butyl 2-[1-[4-[(2,6-dioxo-3-piperidyl)amino]-2-fluoro-phenyl]-4-hydroxy-4-piperidyl]acetate (760 mg, 1.67 mmol, 54.11% yield) as an off white solid. LCMS m/z: 436.0 [M+H]. $^1$H-NMR (DMSO-d6): 10.79 (s, 1H), 6.87-6.80 (m, 1H), 6.52 (dd, J=13.6 Hz, 3.6 Hz, 1H), 6.41 (dd, J=3.7 Hz, 1.6 Hz, 1H), 4.89 (d, J=3.6 Hz, 1H), 4.45 (s, 1H), 4.30-4.19 (m, 1H), 2.90-2.80 (m, 4H), 2.78-2.51 (m, 3H), 2.49-2.41 (m, 1H), 2.13-2.01 (m, 2H), 1.95-1.63 (m, 4H), 1.42 (s, 9H).

Step 5: 2-[1-[4-[(2,6-dioxo-3-piperidyl)amino]-2-fluoro-phenyl]-4-hydroxy-4-piperidyl]acetic acid hydrochloride

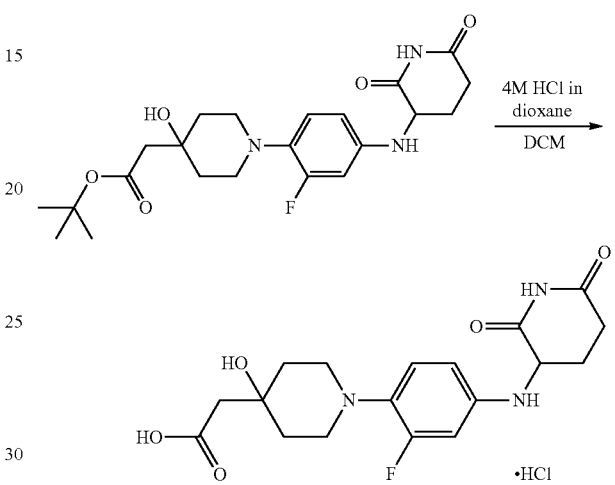

To a stirred solution of tert-butyl 2-[1-[4-[(2,6-dioxo-3-piperidyl)amino]-2-fluoro-phenyl]-4-hydroxy-4-piperidyl]acetate (1.0 g, 2.30 mmol) in dichloromethane (10 mL) was added hydrogen chloride (4M in 1,4-dioxane, 400 mmol, 10 mL) dropwise at 0° C. The reaction mixture stirred at 25° C. for 3 h. The reaction mixture was concentrated under reduced pressure to give 2-[1-[4-[(2,6-dioxo-3-piperidyl)amino]-2-fluoro-phenyl]-4-hydroxy-4-piperidyl]acetic acid hydrochloride (900 mg, 2.16 mmol, 93.89% yield) as an off-white solid. LCMS m/z 380.2 (M+H)$^+$.

Step 6: 2-(6,7-dihydro-5H-pyrrolo[1,2-c]imidazol-1-yl)-2-[6-[4-[4-[2-[1-[4-[(2,6-dioxo-3-piperidyl)amino]-2-fluoro-phenyl]-4-hydroxy-4-piperidyl]acetyl]piperazin-1-yl]phenyl]-4-fluoro-1-oxo-isoindolin-2-yl]-N-thiazol-2-yl-acetamide

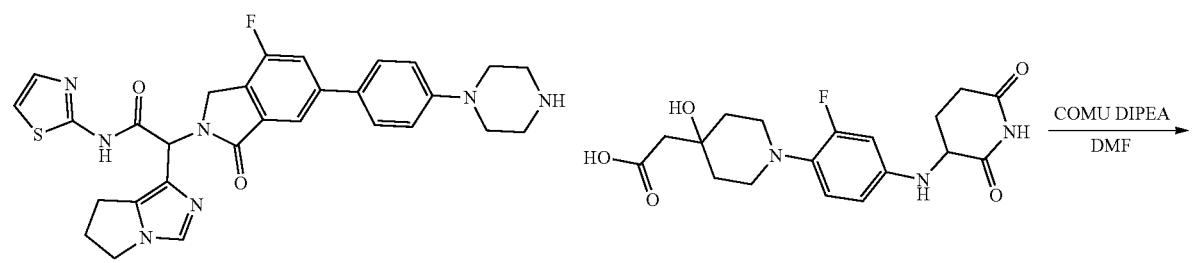

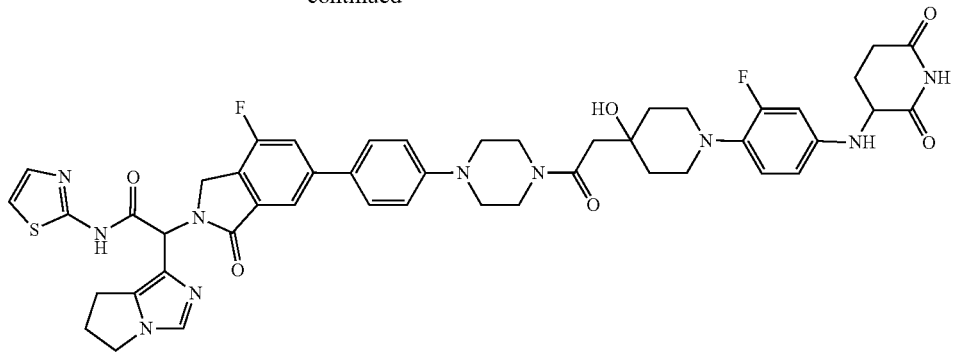

To a stirred solution of 2-[1-[4-[(2,6-dioxo-3-piperidyl)amino]-2-fluoro-phenyl]-4-hydroxy-4-piperidyl]acetic acid hydrochloride (115.49 mg, 277.73 μmol) in N,N-dimethylformamide (1.5 mL) in a round bottom flask was added N,N-diisopropylethylamine (195.79 mg, 1.51 mmol, 263.87 μL) dropwise at 0° C. Reaction mixture was stirred for 5 minutes. 1-[(1-(Cyano-2-ethoxy-2-oxoethylideneaminooxy)-dimethylamino-morpholino)] uronium hexafluorophosphate (324.39 mg, 757.45 μmol) was added, and the reaction mixture was stirred for 5 minutes. 2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide hydrochloride (150 mg, 252.48 μmol) was added. The reaction was continued about 40 min at 0° C. Cold water was added to the reaction mixture, solid was precipitated, collected by filtration, washed with water and dried under suction. The precipitate was purified by preparative HPLC. Purification conditions: Column: Agilent C18 (50*21.2 mm), 5 micron particle size. Mobile Phase: 10 mM ammonium acetate in water:acetonitrile. The collected pure fraction were lyophilized to afford Compound 83 as a pale yellow solid (47 mg, 51.00 μmol, 20.20% yield). LCMS (m/z: 917.3 (M−1)) $^1$H-NMR (400 MHz, DMSO-d6): δ 12.53 (s, 1H), 10.78 (s, 1H), 7.79-7.69 (m, 4H), 7.62 (s, 1H), 7.49 (d, J=3.60 Hz, 1H), 7.27 (d, J=3.60 Hz, 1H), 7.07 (d, J=8.80 Hz, 2H), 6.86 (t, J=9.60 Hz, 1H), 6.50 (dd, J=2.40, 14.80 Hz, 1H), 6.42 (dd, J=6.00, Hz, 1H), 6.16 (s, 1H), 5.78 (d, J=7.60 Hz, 1H), 4.83 (t, J=17.60 Hz, 2H), 4.25-4.21 (m, 2H), 4.02-3.96 (m, 2H), 3.73-3.68 (m, 4H), 3.44-3.34 (m, 2H), 3.44-3.23 (m, 5H), 2.91-2.84 (m, 4H), 2.78-2.67 (m, 2H), 2.58-2.52 (m, 3H), 2.13-2.02 (m, 1H), 1.89-1.65 (m, 5H).

Example 84

2-(6,7-dihydro-5H-pyrrolo[1,2-c]imidazol-1-yl)-2-[6-[4-[4-[2-[4-[4-[[(3S)-2,6-dioxo-3-piperidyl]amino]-2-fluoro-phenyl]-1-piperidyl]acetyl]-1,4-diazepan-1-yl]phenyl]-4-fluoro-1-oxo-isoindolin-2-yl]-N-thiazol-2-yl-acetamide, Compound 84

Step 1: tert-Butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-1,4-diazepane-1-carboxylate

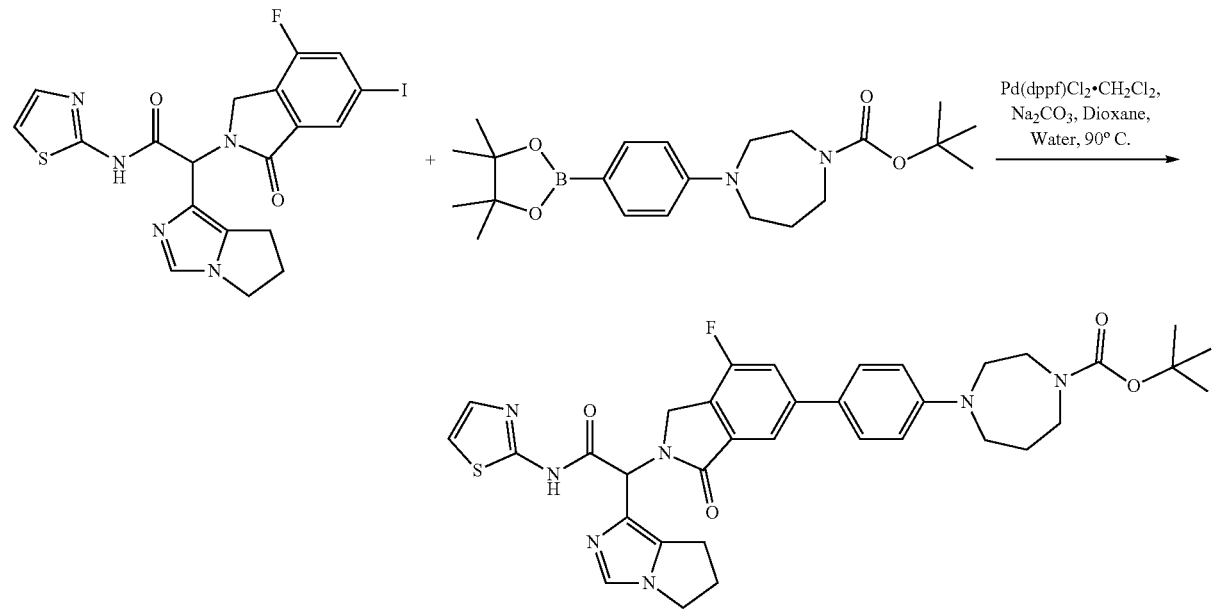

In a 100 mL single-neck round bottom flask containing a well-stirred solution of 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (800 mg, 1.53 mmol) and tert-butyl 4-[4-(4,4,5,5-tetramethyl-1,3,2-dioxaborolan-2-yl)phenyl]-1,4-diazepane-1-carboxylate (CAS #1042917-51-0, 799.56 mg, 1.99 mmol) in anhydrous 1,4-dioxane (10 mL) was added Sodium carbonate (486.08 mg, 4.59 mmol, 192.13 µL) in water (2 mL) and the resulting mixture was degassed with bubbling nitrogen for 15 minutes. [1,1'-Bis(diphenylphosphino)ferrocene] dichloropalladium (II), complex with dichloromethane (87.02 mg, 106.55 µmol) was added to the reaction mixture and further degassed with nitrogen gas for 5 minutes and heated in a heating block at 80° C. under nitrogen atmosphere for 16 h. The reaction mixture was diluted with ethyl acetate and filtered through celite. The filtrate was washed with ice cold water (50 mL) and extracted using ethyl acetate (3×75 mL). The organic layer was washed with brine solution (50 mL), dried over sodium sulphate and concentrated under reduced pressure. The crude was purified by column chromatography using silica (0-5% methanol in dichloromethane) to get tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-1,4-diazepane-1-carboxylate (520 mg, 561.83 µmol, 36.75% yield) as a brown solid. LCMS (ESI+) m/z: 672.3 [M+H]$^+$.

Step 2: 2-[6-[4-(1,4-diazepan-1-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide

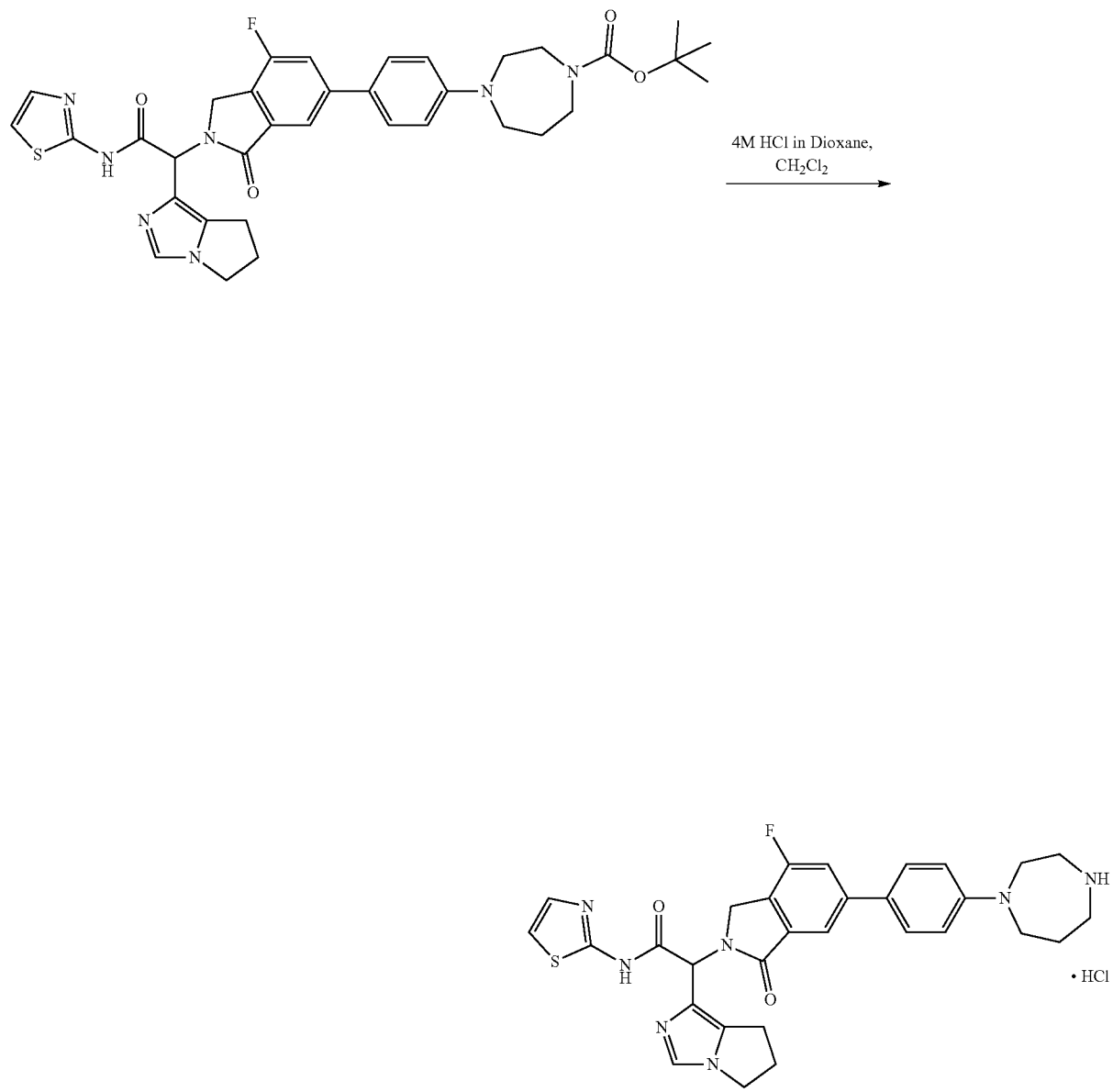

In to a 50 mL single-neck round bottom flask containing a well-stirred solution of tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-1,4-diazepane-1-carboxylate (520 mg, 774.06 µmol) in anhydrous dichloromethane (5 mL) was added Hydrogen chloride solution (4.0 M in 1,4-dioxane, 282.22 mg, 7.74 mmol, 352.78 µL) dropwise at 0° C. The reaction mixture was stirred at ambient temperature for 2 h. The reaction mixture was concentrated under reduced pressure, triturated with diethyl ether, decanted and dried to give 2-[6-[4-(1,4-diazepan-1-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide (480 mg, 684.78 µmol, 88.47% yield) as an light yellow solid. LCMS (ESI+) m/z: 572.2 [M+H]$^+$.

Step 3: 2-(6,7-dihydro-5H-pyrrolo[1,2-c]imidazol-1-yl)-2-[6-[4-[4-[2-[4-[4-[[(3S)-2,6-dioxo-3-piperidyl]amino]-2-fluoro-phenyl]-1-piperidyl]acetyl]-1,4-diazepan-1-yl]phenyl]-4-fluoro-1-oxo-isoindolin-2-yl]-N-thiazol-2-yl-acetamide

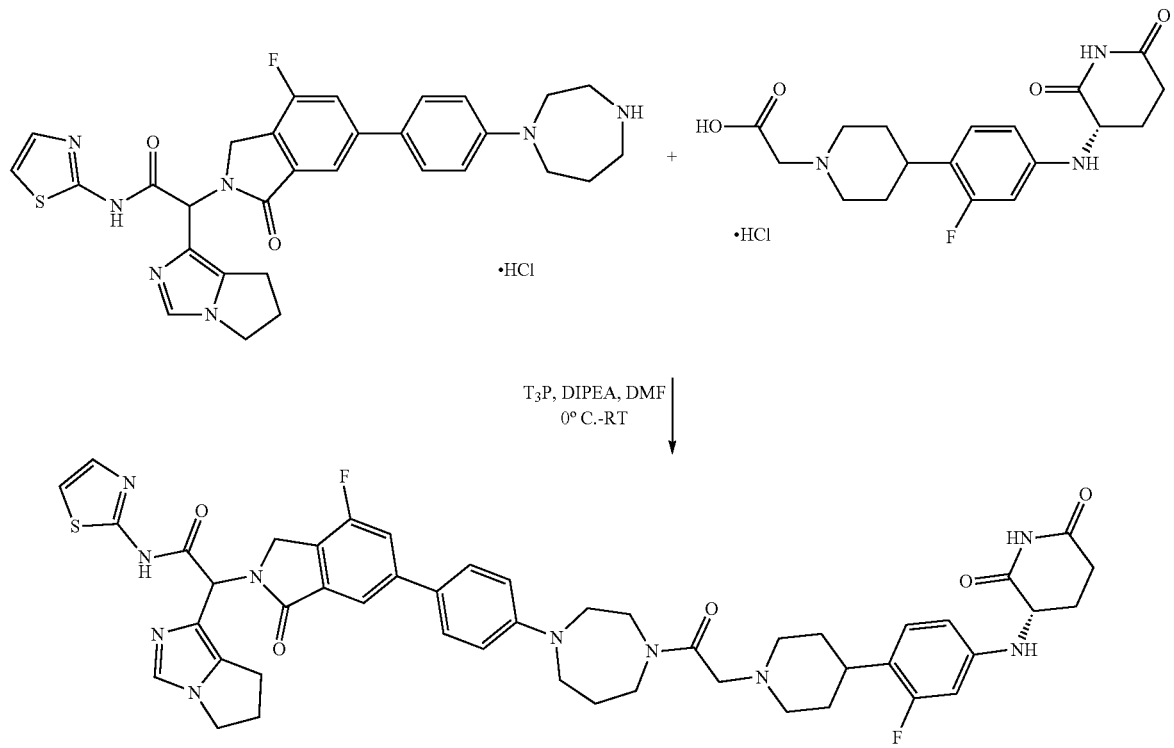

In a 10 mL single-necked round-bottomed flask containing a well-stirred solution of 2-[6-[4-(1,4-diazepan-1-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide hydrochloride (100 mg, 164.44 µmol) and 2-[4-[4-[[(3S)-2,6-dioxo-3-piperidyl]amino]-2-fluoro-phenyl]-1-piperidyl]acetic acid hydrochloride (78.90 mg, 197.33 µmol) in anhydrous N,N-dimethylformamide (2 mL) under nitrogen atmosphere was added N,N-diisopropylethylamine (21.25 mg, 164.44 µmol, 28.64 µL) at 0° C.

Propylphosphonic anhydride solution (50 wt. % in ethyl acetate) (52.32 mg, 164.44 µmol) was added at the same temperature. The reaction mixture was further stirred while warming to room temperature for 0.5 h. The reaction mixture was poured into ice cold water (10 mL), and the solid precipitated was filtered. The solid was washed with water and dried. The crude was purified using Prep HPLC (Purification method: Column: X-Bridge C8 (50×4.6) mm, 3.5 micron; (Mobile Phase A: 10 mM ammonium acetate in milli-q water; Mobile phase B: acetonitrile); Flow rate: 15 mL\min. The pure fractions were combined and lyophilized to Compound 84 (50 mg, 54.39 µmol, 33.07% yield) as an off-white solid. LCMS (ESI+) m/z: 917.3 [M+H]$^+$. 1H-NMR (400 MHz, DMSO-d6): δ 12.49 (s, 1H), 10.80 (s, 1H), 7.74-7.70 (m, 1H), 7.66 (d, J=5.60 Hz, 1H), 7.62 (d, J=11.20 Hz, 1H), 7.57 (s, 1H), 7.40 (s, 1H), 7.10 (bs, 1H), 6.96-6.83 (m, 3H), 6.46-6.42 (m, 2H), 6.06 (s, 1H), 6.00 (t, J=4.00 Hz, 1H), 4.90-4.86 (m, 1H), 4.30-4.29 (m, 1H), 4.19 (dd, J=17.40, 4.80 Hz, 1H), 4.00-3.96 (m, 2H), 3.83-3.75 (m, 1H), 3.71-3.68 (m, 2H), 3.67-3.67 (m, 1H), 3.62-3.57 (m, 2H), 3.52-3.22 (m, 1H), 3.33-3.28 (m, 2H), 3.12 (s, 1H), 3.07 (s, 1H), 2.87-2.85 (m, 1H), 2.81-2.79 (m, 1H), 2.73-2.69 (m, 2H), 2.59-2.54 (m, 1H), 2.08-1.99 (m, 4H), 2.22-1.84 (m, 2H), 1.81 (s, 2H), 1.61-1.54 (m, 4H). [48H Observed/50H Expected (water obscuration)].
Example 85
2-(6,7-dihydro-5H-pyrrolo[1,2-c]imidazol-1-yl)-2-[6-[4-[1-[2-[4-[3-(2,4-dioxohexahydropyrimidin-1-yl)-1-methyl-indazol-6-yl]-1-piperidyl]-2-oxo-ethyl]-4-piperidyl]phenyl]-4-fluoro-1-oxo-isoindolin-2-yl]-N-thiazol-2-yl-acetamide, Compound 85
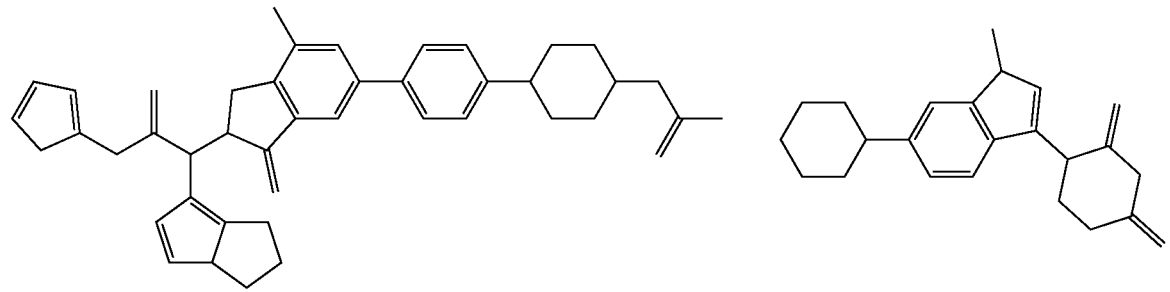
COMU
N,N-Diisopropylethylamine
DMF
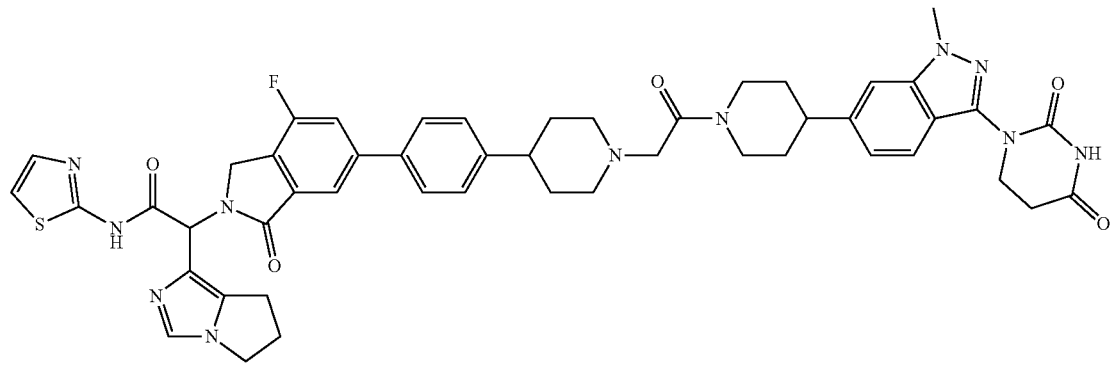

To a solution of 2-[4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-1-piperidyl]acetic acid hydrochloride (130 mg, 199.65 μmol) in N,N-dimethylformamide (1.5 mL), N,N-diisopropylethylamine (129.01 mg, 998.23 μmol, 173.87 μL) and 1-[(1-(cyano-2-ethoxy-2-oxoethylideneaminooxy)-dimethylamino-morpholino)]uronium hexafluorophosphate (171.01 mg, 399.30 μmol) were added at 0° C. The reaction mixture was stirred for 15 minutes. 1-[1-methyl-6-(4-piperidyl)indazol-3-yl]hexahydropyrimidine-2,4-dione hydrochloride (72.64 mg, 199.65 μmol) was added. The reaction mixture was stirred for 1 h. The reaction mixture was concentrated under reduced pressure. The residue was purified by reverse phase chromatography (C18 column, 0-100% of 0.1% ammonium acetate in water and acetonitrile). The fractions containing compound were frozen and lyophilized. The residue purified by reverse phase prep HPLC using Column: Zorbax Extend C18(50× 4.6 mm) 5 m, Mobile Phase A: 10 mM ammonium acetate in water, Mobile Phase B: acetonitrile. Pure fractions were lyophilized to get Compound 85 (4.81 mg, 5.07 μmol, 2.54% yield) as a white solid which was submitted for analysis. LCMS (ESI+): 924.3 (M+H); 1H-NMR (400 MHz, DMSO-d6): 12.50 (s, 1H), 10.55 (d, J=10.0 Hz, 1H), 7.81 (d, J=5.6 Hz, 2H), 7.73 (d, J=8.0 Hz, 2H), 7.63 (s, 1H), 7.59 (d, J=8.40 Hz, 1H), 7.49 (d, J=3.6 Hz, 1H), 7.45 (s, 1H), 7.37 (d, J=8.4 Hz, 2H), 7.26 (d, J=3.2 Hz, 1H), 7.05 (d, J=8.4 Hz, 1H), 6.15 (s, 1H), 4.83 (d, J=17.6 Hz, 1H), 4.61-4.53 (m, 1H), 4.27-4.22 (m, 2H), 4.01-3.91 (m, 7H), 3.34-3.17 (m, 3H), 3.00-2.97 (m, 5H), 2.78-2.75 (m, 4H), 2.33-2.17 (m, 3H), 1.91-1.70 (m, 9H).

Example 86

2-(6,7-dihydro-5H-pyrrolo[1,2-c]imidazol-1-yl)-2-[6-[4-[4-[2-[4-[4-[(2,6-dioxo-3-piperidyl)amino]-2-fluoro-phenyl]-1-piperidyl]-2-oxo-ethyl]-1-piperidyl]phenyl]-4-fluoro-1-oxo-isoindolin-2-yl]-N-thiazol-2-yl-acetamide, Compound 86

Step 1: methyl 2-(1-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenyl)piperidin-4-yl)acetate

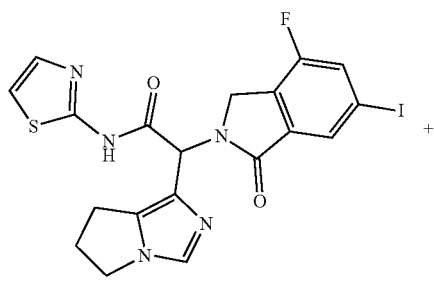
+
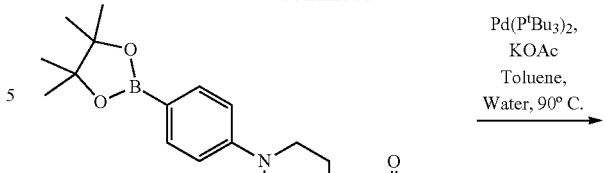

Into a 100 mL sealed tube containing a well-stirred solution of 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (400 mg, 764.35 μmol) and methyl 2-[1-[4-(4,4,5,5-tetramethyl-1,3,2-dioxaborolan-2-yl)phenyl]-4-piperidyl]acetate (411.91 mg, 1.15 mmol) in anhydrous toluene (5 mL) and water (1.5 mL) was added potassium acetate (225.04 mg, 2.29 mmol, 143.34 μL) at the ambient temperature under nitrogen atmosphere. The resulting mixture was degassed with $N_2$ for 10 minutes. Bis(tri-tert-butylphosphine) palladium (0) (78.12 mg, 152.87 μmol) was added and the reaction mixture was stirred at 95° C. for 64 h. The reaction mixture was diluted with ethyl acetate and filtered through celite. The filtrate was evaporated under reduced pressure. The crude residue was triturated with diethyl ether to afford methyl 2-[1-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-4-piperidyl]acetate (205 mg, 295 μmol, 42.7% yield). LCMS (ESI+) m/z: 629.2 [M+H]+.

Step 2: 2-[1-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-4-piperidyl]acetic acid

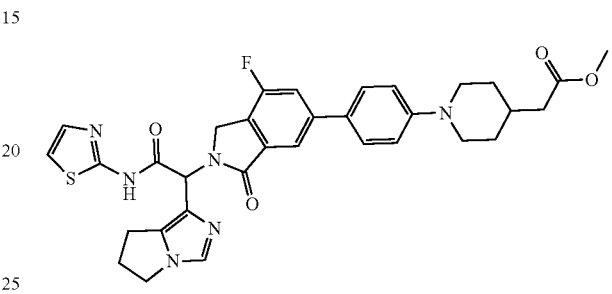

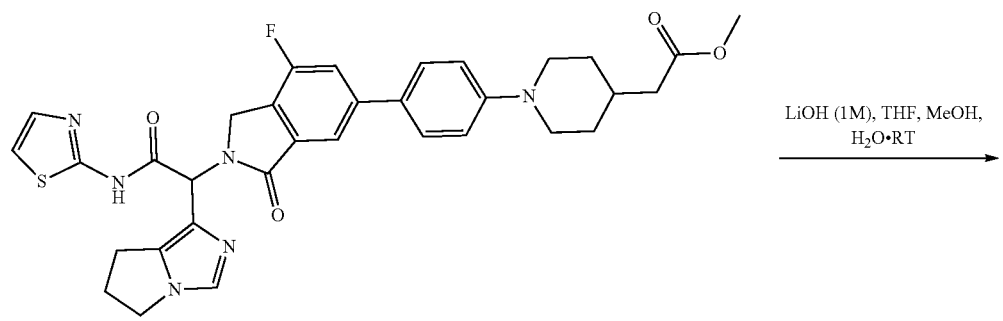

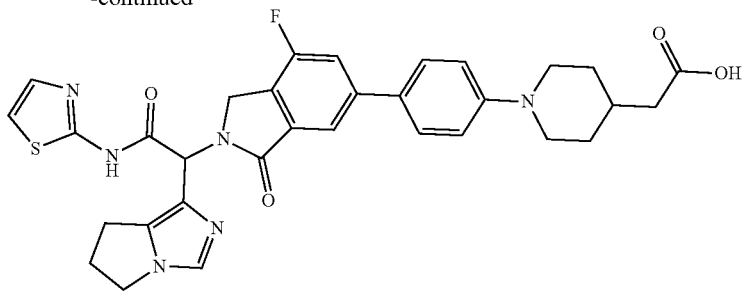

To a solution of methyl 2-[1-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-4-piperidyl]acetate (200 mg, 318.11 μmol) in tetrahydrofuran (2 mL) and methanol (2 mL) and water (2 mL) was added a lithium hydroxide (1M aqueous solution, 318 μL, 318.11 μmol) at 0° C. Reaction mixture was stirred for 3 hr at room temperature. Reaction mixture was concentrated to get crude, which was further dissolved in 5 mL of water and acidified using aqueous sodium bisulfate (pH 5-6). The solid precipitated was filtered to get 2-[1-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-4-piperidyl]acetic acid (150 mg, 244.03 μmol, 39.9% yield). LCMS (ESI+) m/z: 615.2 [M+H]+.

Step 3: 2-(6,7-dihydro-5H-pyrrolo[1,2-c]imidazol-1-yl)-2-[6-[4-[4-[2-[4-[4-[(2,6-dioxo-3-piperidyl)amino]-2-fluoro-phenyl]-1-piperidyl]-2-oxo-ethyl]-1-piperidyl]phenyl]-4-fluoro-1-oxo-isoindolin-2-yl]-N-thiazol-2-yl-acetamide

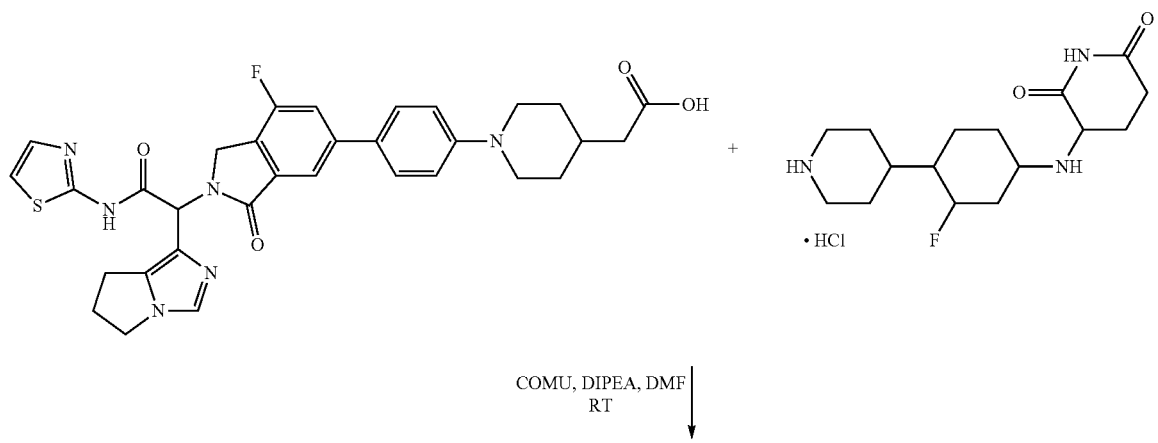

COMU, DIPEA, DMF
RT

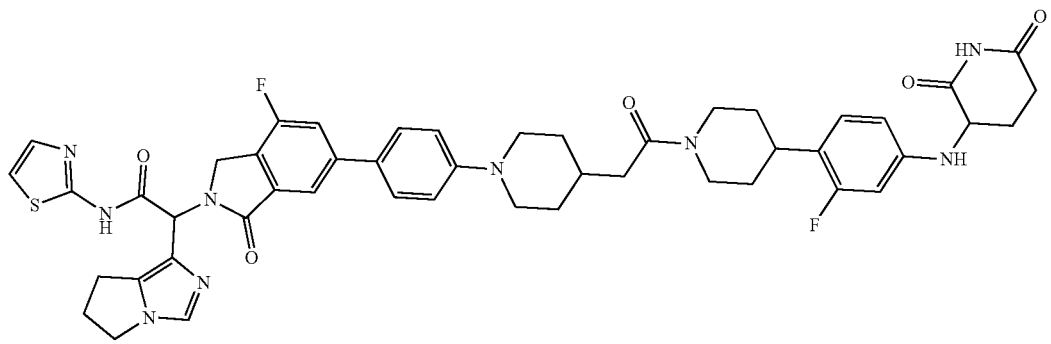

To a solution of 2-[1-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-4-piperidyl]acetic acid (150 mg, 244.03 μmol) in N,N-dimethylformamide (2 mL) was added N, Ndiisopropylethylamine (157.69 mg, 1.22 mmol, 212.52 μL) and 1-[(1-(cyano-2-ethoxy-2-oxo-ethylideneaminooxy)-dimethylamino-morpholino)] uronium hexafluorophosphate (209.02 mg, 488.05 μmol) at 0° C. 3-[3-fluoro-4-(4-piperidyl) anilino] piperidine-2,6-dione hydrochloride (74.51 mg, 218.00 μmol) was added and stirred for 1 h. The crude was purified by reverse phase chromatography (C18 column, 0-100% of 0.1% Formic acid in water and acetonitrile). Collected fraction were lyophilized. The residue was purified by reverse phase preparative HPLC using Column: Zorbax Extend C18 (50×4.6 mm), 5 m, (Mobile Phase A: 10 mM ammonium acetate in milli-q water; Mobile phase B: acetonitrile). The pure fractions were frozen and lyophilized to get Compound 86 (4.57 mg, 5.04 μmol, 2.06% yield) as a white solid. LCMS (ESI+) m/z: 902.3 [M+H]$^+$. 1H-NMR (400 MHz, DMSO-d6): δ 12.61 (s, 1H), 10.80 (s, 1H), 7.76 (s, 1H), 7.73 (d, J=10.80 Hz, 1H), 7.65 (d, J=8.80 Hz, 2H), 7.61 (s, 1H), 7.48 (s, 1H), 7.25 (s, 1H), 7.02 (d, J=6.40 Hz, 2H), 6.97 (d, J=8.80 Hz, 1H), 6.47 (s, 1H), 6.44 (d, J=4.00 Hz, 1H), 6.14 (s, 1H), 6.04 (d, J=8.00 Hz, 1H), 4.81 (d, J=17.20 Hz, 1H), 4.60 (d, J=8.40 Hz, 1H), 4.32 (m, 1H), 4.33 (d, J=16.00 Hz, 1H), 4.20-3.99 (m, 3H), 3.81 (d, J=12.00 Hz, 2H), 3.11 (t, J=13.20 Hz, 1H), 2.87 (t, J=10.40 Hz, 1H), 2.79-2.71 (m, 4H), 2.68-2.61 (m, 3H), 2.33 (d, J=6.80 Hz, 2H), 2.09-2.07 (m, 1H), 1.92-1.90 (m, 2H), 1.88-1.71 (m, 5H), 1.68-1.32 (m, 2H), 1.31-1.24 (m, 3H).

Example 87

2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)pyridin-3-yl)-4-fluoro-1-oxoisoindolin-2-yl)-N-(thiazol-2-yl)acetamide, Compound 87

Step 1: tert-Butyl 6-(5-bromo-2-pyridyl)-2,6-diazaspiro[3.3]heptane-2-carboxylate

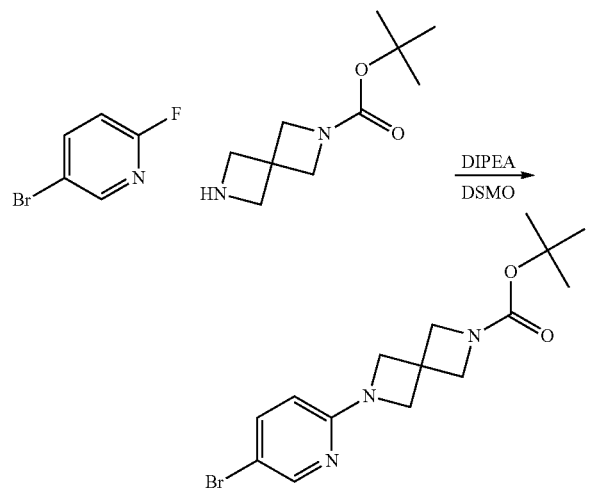

To a stirred solution of tert-butyl 2,6-diazaspiro[3.3]heptane-2-carboxylate (1.69 g, 8.52 mmol) in dimethylsulfoxide (10 mL) were added N,N-diisopropylethylamine (5.51 g, 42.62 mmol, 7.42 mL) and 5-bromo-2-fluoropyridine (1.5 g, 8.52 mmol, 877.19 μL). The reaction mixture was heated at 90° C. for 4 h. The reaction mixture was cooled to room temperature and quenched in crushed ice. Solid precipitated and it was filtered and dried to afford tert-butyl 6-(5-bromo-2-pyridyl)-2,6-diazaspiro[3.3]heptane-2-carboxylate (1.5 g, 4.14 mmol, 48.57% yield) as a white solid. LCMS (m/z: 356.1 [M+1]).

Step 2: [6-(2-tert-Butoxycarbonyl-2,6-diazaspiro[3.3]heptan-6-yl)-3-pyridyl]boronic acid

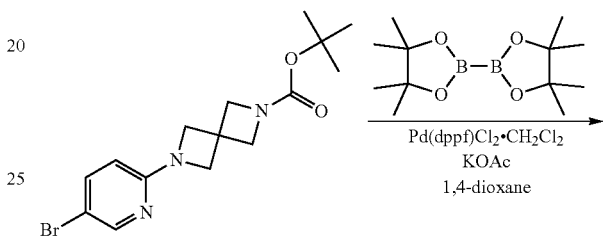

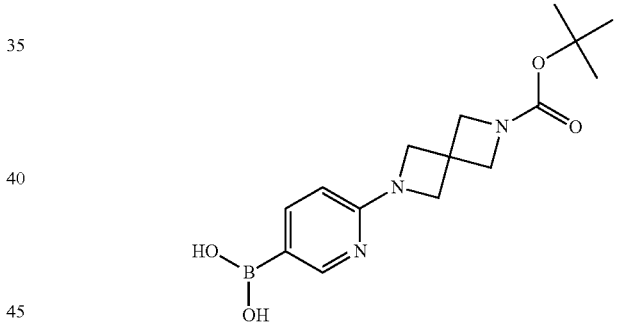

In a sealed tube to a stirred solution of tert-butyl 6-(5-bromo-2-pyridyl)-2,6-diazaspiro[3.3]heptane-2-carboxylate (650 mg, 1.83 mmol) in 1,4-dioxane (7 mL) was added 4,4,5,5-tetramethyl-2-(4,4,5,5-tetramethyl-1,3,2-dioxaborolan-2-yl)-1,3,2-dioxaborolane (698.93 mg, 2.75 mmol) followed by potassium acetate (360.16 mg, 3.67 mmol, 229.40 μL) added to the reaction mixture. The reaction mixture was degassed with nitrogen for 20 mins, followed by Pd(dppf)$_2$Cl$_2$·CH$_2$Cl$_2$ (449.52 mg, 550.47 μmol) added to the reaction mixture and degassed with nitrogen for 10 mins. The reaction mixture was heated at 90° C. on a heating block for 16 h. The reaction mixture was cooled to ambient temperature, the mixture was filtered through a pad of celite and washed with ethyl acetate. The filtrate was evaporated under reduced pressure afford [6-(2-tert-butoxycarbonyl-2,6-diazaspiro[3.3]heptan-6-yl)-3-pyridyl]boronic acid (810 mg, 1.14 mmol, 62.17% yield) which was submitted for analysis. LCMS data (m/z: 320.2 [M+1]).

Step 3: tert-Butyl 6-[5-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-2-pyridyl]-2,6-diazaspiro[3.3]heptane-2-carboxylate

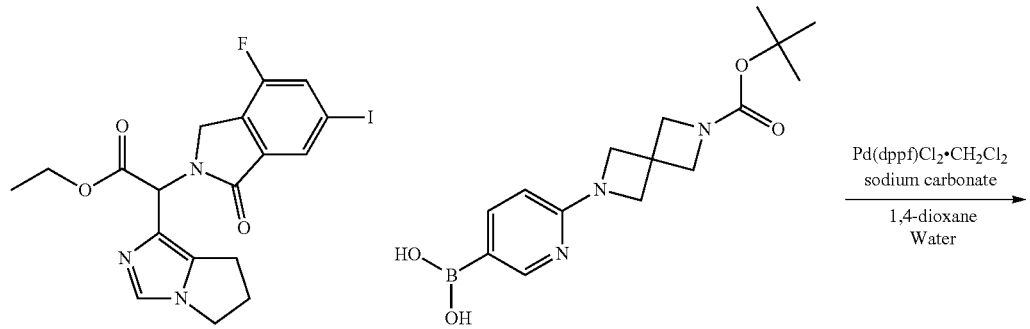

A solution of 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (350 mg, 668.80 μmol) and [6-(2-tert-butoxycarbonyl-2,6-diazaspiro[3.3]heptan-6-yl)-3-pyridyl] boronic acid (298.84 mg, 936.33 μmol) in 1,4-dioxane (8 mL) and water (2 mL) was degassed with nitrogen for 15 minutes. Sodium carbonate (212.66 mg, 2.01 mmol, 84.06 μL) and [1,1'-Bis(diphenylphosphino)ferrocene]dichloropalladium(II), complex with dichloromethane (87.02 mg, 106.55 μmol) were added to the reaction mixture and purged with nitrogen gas for 5 mins. The reaction mixture was heated at 80° C. under nitrogen for 16 h. The reaction mixture poured to ice water and the solid was filtered and the solid washed with water and dried. The crude was purified by silica gel column chromatography (0-7% Dichloromethane and Methanol) to get tert-butyl 6-[5-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-2-pyridyl]-2,6-diazaspiro[3.3]heptane-2-carboxylate (160 mg, 224.60 μmol, 34% yield) as a brown solid. LCMS m/z 671.3 (M+H)⁺.

Step 4: [2-[6-[6-(2-tert-butoxycarbonyl-2,6-diazaspiro[3.3]heptan-6-yl)-3-pyridyl]-4-fluoro-1-oxo-isoindolin-2-yl]-2-(6,7-dihydro-5H-pyrrolo[1,2-c]imidazol-1-yl)acetyl]oxylithium

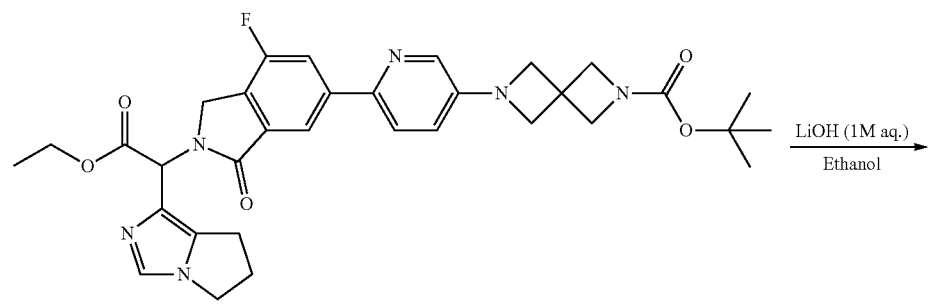

-continued

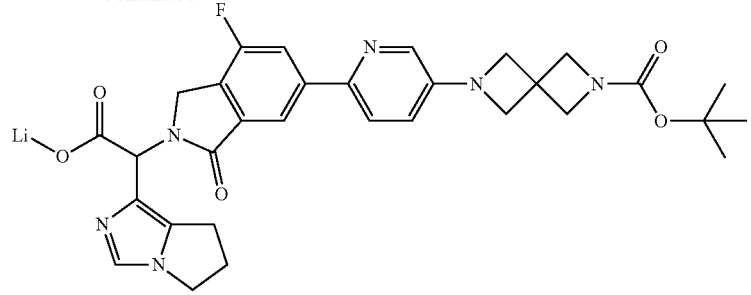

To a solution of tert-butyl 6-[5-[2-[1-(6,7-dihydro-5H-pyrrolo[1,2-c]imidazol-1-yl)-2-ethoxy-2-oxo-ethyl]-7-fluoro-3-oxo-isoindolin-5-yl]-2-pyridyl]-2,6-diazaspiro[3.3]heptane-2-carboxylate (440 mg, 713.50 μmol) in ethanol (3.2 mL) was added a lithium hydroxide aqueous solution (1 M, 784.85 μL) and stirred at 22° C. for 1 h. The volatiles were evaporated under reduced pressure to afford [2-[6-[6-(2-tert-butoxycarbonyl-2,6-diazaspiro[3.3]heptan-6-yl)-3-pyridyl]-4-fluoro-1-oxo-isoindolin-2-yl]-2-(6,7-dihydro-5H-pyrrolo[1,2-c]imidazol-1-yl)acetyl]oxylithium (420 mg, 698 μmol, 98% yield) LCMS. 598.2 (M+H)

Step 5: Synthesis of tert-butyl 6-(6-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)pyridin-3-yl)-2,6-diazaspiro[3.3]heptane-2-carboxylate

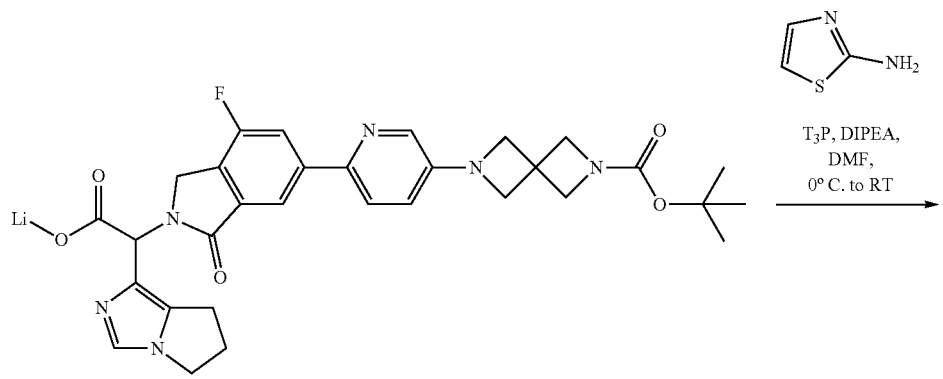

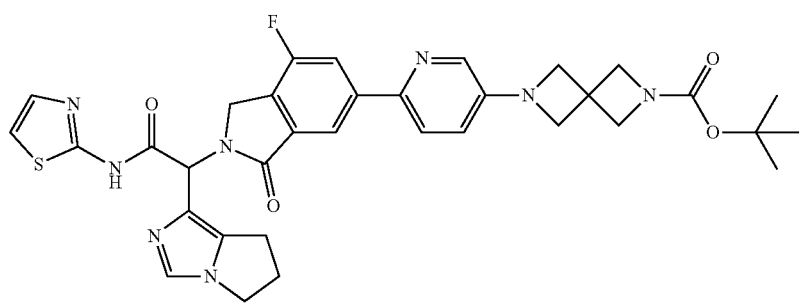

Into a 50 mL single-necked round-bottomed flask containing a well-stirred solution of [2-[6-[6-(2-tert-butoxycarbonyl-2,6-diazaspiro[3.3]heptan-6-yl)-3-pyridyl]-4-fluoro-1-oxo-isoindolin-2-yl]-2-(6,7-dihydro-5H-pyrrolo[1,2-c]imidazol-1-yl)acetyl]oxylithium (400.00 mg, 672.77 μmol) and 2-thiazole amine (87.58 mg, 874.59 μmol) in N,N-dimethylformamide (2.5 mL) was added N,N-diisopropylethylamine (542.95 mg, 672.77 μmol, 117.18 μL) under nitrogen atmosphere at 0° C. Propylphosphonic anhydride solution (50 wt. % in ethyl acetate) (521 μL, 874.59 μmol) was added at 0° C. and the resulting reaction mixture was stirred at room temperature for 4 h. The reaction mixture was added ice cold water and solid precipitated was filtered and dried under reduced pressure to afford tert-butyl 6-[5-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-2-pyridyl]-2,6-diazaspiro[3.3]heptane-2-carboxylate (290 mg, 380.47 μmol, 56.55% yield) as an off-white solid. LCMS (ESI+) m/z: 671.3 [M+H]+.

Step 6: Synthesis of 2-(6-(6-(2,6-diazaspiro[3.3]heptan-2-yl)pyridin-3-yl)-4-fluoro-1-oxoisoindolin-2-yl)-2-(6,7-dihydro-5H-pyrrolo[1,2-c]imidazol-1-yl)-N-(thiazol-2-yl)acetamide

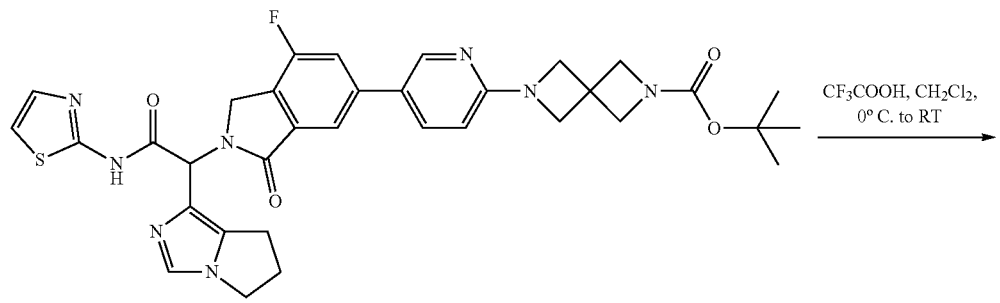

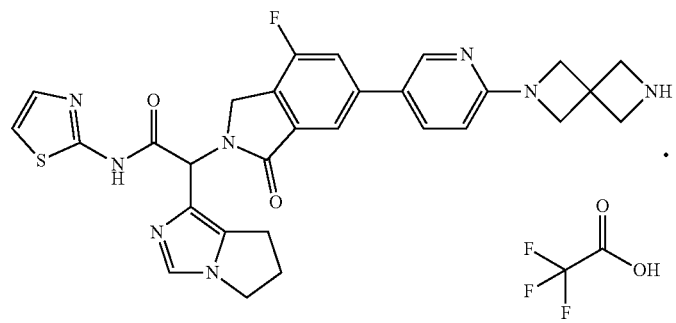

Into a 25 mL single-necked round-bottomed flask containing a well-stirred solution of tert-butyl 6-[5-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-2-pyridyl]-2,6-diazaspiro[3.3]heptane-2-carboxylate (280.00 mg, 417.44 μmol) in dichloromethane (3.0 mL) was added trifluoroacetic acid (475.97 mg, 4.17 mmol, 321.60 μL) at 0° C. The mixture was stirred at ambient temperature for 3 h. The reaction mixture was concentrated under reduced pressure to afford crude, co-distilled with dichloromethane, triturated with diethyl ether and decanted to afford 2-[6-[6-(2,6-diazaspiro[3.3]heptan-2-yl)-3-pyridyl]-4-fluoro-1-oxo-isoindolin-2-yl]-2-(6,7-dihydro-5H-pyrrolo[1,2-c]imidazol-1-yl)-N-thiazol-2-yl-acetamide (270 mg, 345.06 μmol, 82.66% yield) as an off white solid. LCMS (ESI+) m/z: 571.2 [M+H]+.

Step 7: Synthesis of 2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)pyridin-3-yl)-4-fluoro-1-oxoisoindolin-2-yl)-N-(thiazol-2-yl)acetamide

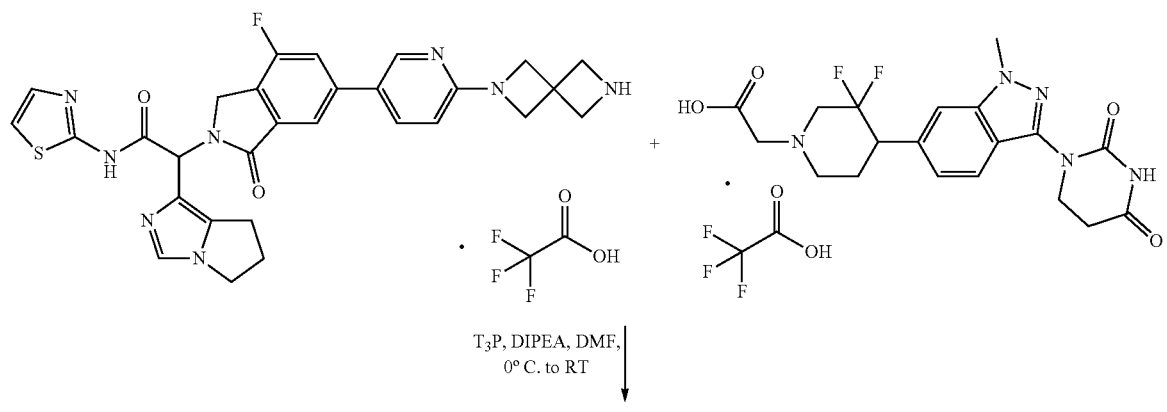

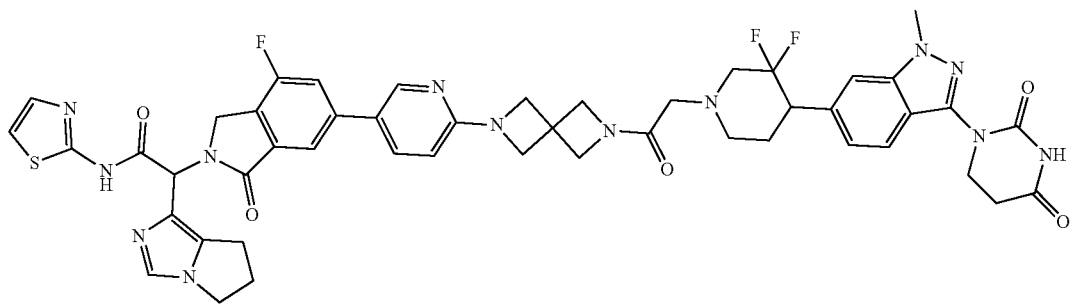

Into a 10 mL single-necked round-bottomed flask containing a well-stirred solution of 2-[6-[6-(2,6-diazaspiro[3.3]heptan-2-yl)-3-pyridyl]-4-fluoro-1-oxo-isoindolin-2-yl]-2-(6,7-dihydro-5H-pyrrolo[1,2-c]imidazol-1-yl)-N-thiazol-2-yl-acetamide; 2,2,2-trifluoroacetic acid (120 mg, 175.27 μmol), and 2-[4-[3-(2,4-dioxohexahydropyrimidin-1-yl)-1-methyl-indazol-6-yl]-3,3-difluoro-1-piperidyl]acetic acid; 2,2,2-trifluoroacetic acid (80.25 mg, 175.27 μmol) in N,N-dimethylformamide (4 mL) was added N, N-diisopropylethylamine (113.26 mg, 876.34 μmol, 152.64 μL) at 0° C. Propylphosphonic anhydride solution (50 wt. % in ethyl acetate) (139.42 mg, 438.17 μmol) was added to the reaction mixture at the same temperature and stirred while warming to room temperature for 1 h. The crude mixture was directly injected on a C18 column (100 g) for purification while eluting (0%-50% of acetonitrile in water+0.1% ammonium acetate over 30 minutes, followed by a steep gradient to 100% acetonitrile). The pure fraction was frozen and lyophilized to afford Compound 87 (48 mg, 48.95 μmol, 27.93% yield) as an off-white solid. LCMS (ESI+) m/z: 975.3[M+H]$^+$. 1H-NMR (400 MHz, DMSO-d6): δ 12.53 (s, 1H), 10.58 (s, 1H), 8.54 (d, J=2.40 Hz, 1H), 8.00 (dd, J=8.60, 2.40 Hz, 1H), 7.80 (s, 1H), 7.77 (s, 1H), 7.62 (s, 1H), 7.60 (d, J=8.80 Hz, 1H), 7.57 (s, 1H), 7.49 (d, J=3.60 Hz, 1H), 7.27 (d, J=3.60 Hz, 1H), 7.10 (d, J=8.40 Hz, 1H), 6.52 (d, J=8.40 Hz, 1H), 6.15 (s, 1H), 4.81 (d, J=18.00 Hz, 1H), 4.45 (s, 2H), 4.25-4.15 (m, 6H), 4.12 (s, 2H), 4.02-4.00 (m, 5H), 3.93 (t, J=6.80 Hz, 3H), 3.21 (d, J=8.40 Hz, 4H), 3.01-2.98 (m, 1H), 2.78 (t, J=6.40 Hz, 4H), 2.51-2.50 (m, 2H), 2.35-2.30 (m, 1H), 1.89-1.80 (m, 1H).

Example 88

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[4-[3-(2,4-dioxohexahydropyrimidin-1-yl)-1-methyl-indazol-6-yl]-3,3-difluoro-1-piperidyl]acetyl]-4-piperidyl]pyridine-2-carboxamide, Compound 88

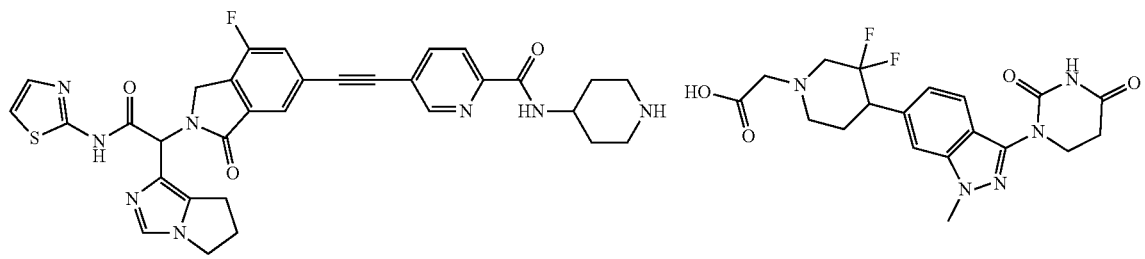

T3P
DIPEA
DMF

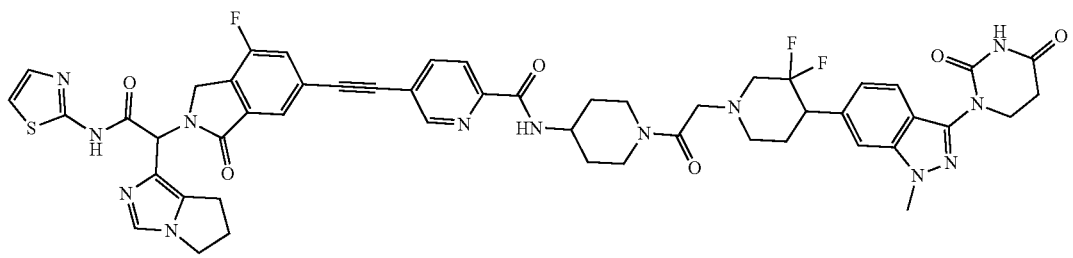

To the stirred solution of 5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-(4-piperidyl)pyridine-2-carboxamide hydrochloride (100 mg, 151.25 μmol) and 2-[4-[3-(2,4-dioxohexahydropyrimidin-1-yl)-1-methyl-indazol-6-yl]-3,3-difluoro-1-piperidyl]acetic acid, trifluoroacetic acid salt (80.98 mg, 151.25 μmol) in N,N-dimethylformamide (2 mL) was cooled to 0° C. N,N-diisopropylethylamine (117.29 mg, 907.51 μmol, 158.07 μL) was added to the reaction mixture followed by propanephosphonic acid anhydride (50% in N,N-dimethylformamide) (96.25 mg, 302.50 μmol) at 0° C. The reaction mixture stirred at ambient temperature for 1 h. The reaction mixture was directly injected on a C18 column (100 g) for purification (0-50%, water (0.1% ammonium acetate) in Acetonitrile over 30 minutes, followed by steep gradient to 100% acetonitrile). The pure fractions were combined and lyophilized to get Compound 88 (93 mg, 89.01 μmol, 58.85% yield) as Off-white solid. LCMS m/z 1028.3 (M+H)$^+$. 1H-NMR (400 MHz, DMSO-d6): δ 10.58 (s, 1H), 8.84 (dd, J=8.40, 30.00 Hz, 2H), 8.24-8.22 (m, 1H), 8.13-8.10 (m, 1H), 7.85-7.80 (m, 2H), 7.61-7.49 (m, 4H), 7.27 (d, J=3.60 Hz, 1H), 7.10 (d, J=8.40 Hz, 1H), 6.14 (s, 1H), 4.86 (d, J=18.00 Hz, 1H), 4.40-4.38 (m, 1H), 4.28 (d, J=18.40 Hz, 1H), 4.10-4.07 (m, 2H), 3.98-3.91 (m, 7H), 3.47 (d, J=13.20 Hz, 2H), 3.28-3.12 (m, 3H), 3.02-2.99 (m, 1H), 2.78-2.73 (m, 4H), 2.68-2.65 (m, 2H), 2.51-2.50 (m, 2H), 2.36-2.18 (m, 1H), 1.92-1.45 (m, 6H).

Example 89

2-(6,7-dihydro-5H-pyrrolo[1,2-c]imidazol-1-yl)-2-[6-[4-[2-[2-[1-[4-[(2,6-dioxo-3-piperidyl)amino]-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, Compound 89

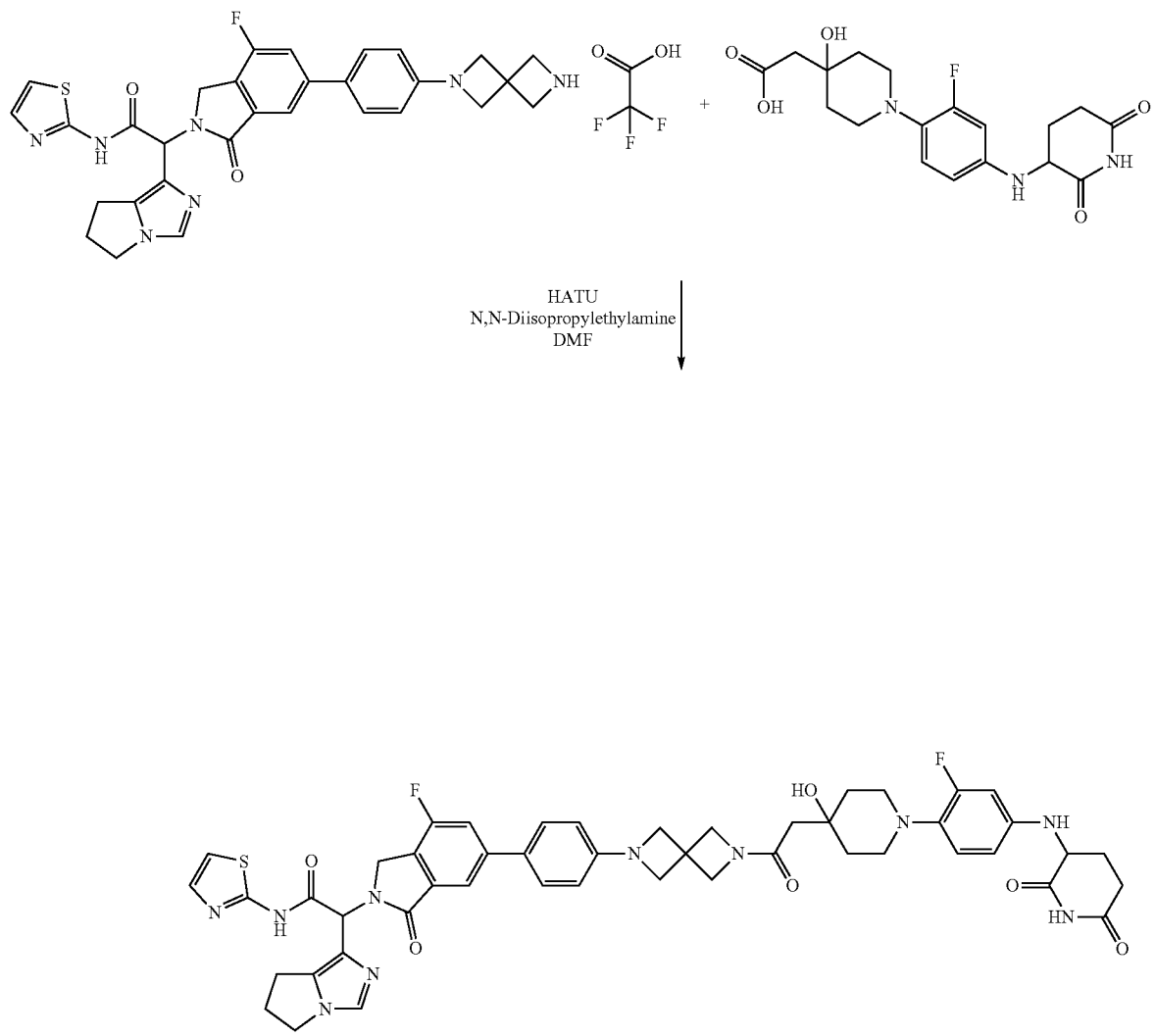

To a stirred solution of 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide trifluoroacetic acid (100 mg, 146.27 μmol) and 2-[1-[4-[(2,6-dioxo-3-piperidyl)amino]-2-fluoro-phenyl]-4-hydroxy-4-piperidyl]acetic acid hydrochloride (60.82 mg, 146.27 μmol) in N,N-dimethylformamide (1.0 mL) at 0° C. was added N,N-diisopropylethylamine (94.52 mg, 731.34 μmol, 127.39 μL) followed by 1-[bis(dimethylamino)methylene]-1H-1,2,3-triazolo[4,5-b]pyridinium 3-oxide hexafluorophosphate (66.74 mg, 175.52 μmol) and stirred at room temperature for 1 h. The reaction mixture was directly injected on a C18 column (100 g) for purification (0-50% of acetonitrile+0.1% ammonium acetate in water over 30 minutes, followed by a steep gradient to 100% acetonitrile). The pure fractions were collected, frozen and lyophilized to afford Compound 89 (21 mg, 22.24 μmol, 15.21% yield) as a white solid. LCMS m/Z: 931.3[M+H], $^1$H-NMR (400 MHz, DMSO-d6): δ 12.53 (s, 1H), 10.78 (s, 1H), 7.75 (s, 1H), 7.71 (d, J=11.20 Hz, 1H), 7.65 (d, J=8.40 Hz, 2H), 7.61 (s, 1H), 7.49 (d, J=3.60 Hz, 1H), 7.27 (d, J=3.20 Hz, 1H), 6.86 (t, J=9.60 Hz, 1H), 6.55 (d, J=8.80 Hz, 1H), 6.50 (dd, J=2.40, 14.8 Hz, 1H), 6.42 (d, J=8.40 Hz, 2H), 6.15 (s, 1H), 5.78 (d, J=7.60 Hz, 1H), 4.80 (d, J=17.60 Hz, 1H), 4.76 (s, 1H), 4.39 (s, 2H), 4.27-4.24 (m, 2H), 4.20-4.01 (m, 9H), 2.90-2.60 (m, 8H), 2.59 (d, J=4.00 Hz, 1H), 2.23 (s, 2H), 2.10-2.08 (m, 1H), 1.80-1.74 (m, 3H), 1.63-1.59 (m, 2H). A proton signal could not be observed due to water obscuration.

Example 90
2-(6,7-dihydro-5H-pyrrolo[1,2-c]imidazol-1-yl)-2-
[6-[4-[2-[2-[1-[5-[(2,6-dioxo-3-piperidyl)amino]-3-
fluoro-2-pyridyl]-4-hydroxy-4-piperidyl]acetyl]-2,6-
diazaspiro[3.3]heptan-6-yl]phenyl]-4-fluoro-1-oxo-
isoindolin-2-yl]-N-thiazol-2-yl-acetamide,
Compound 90
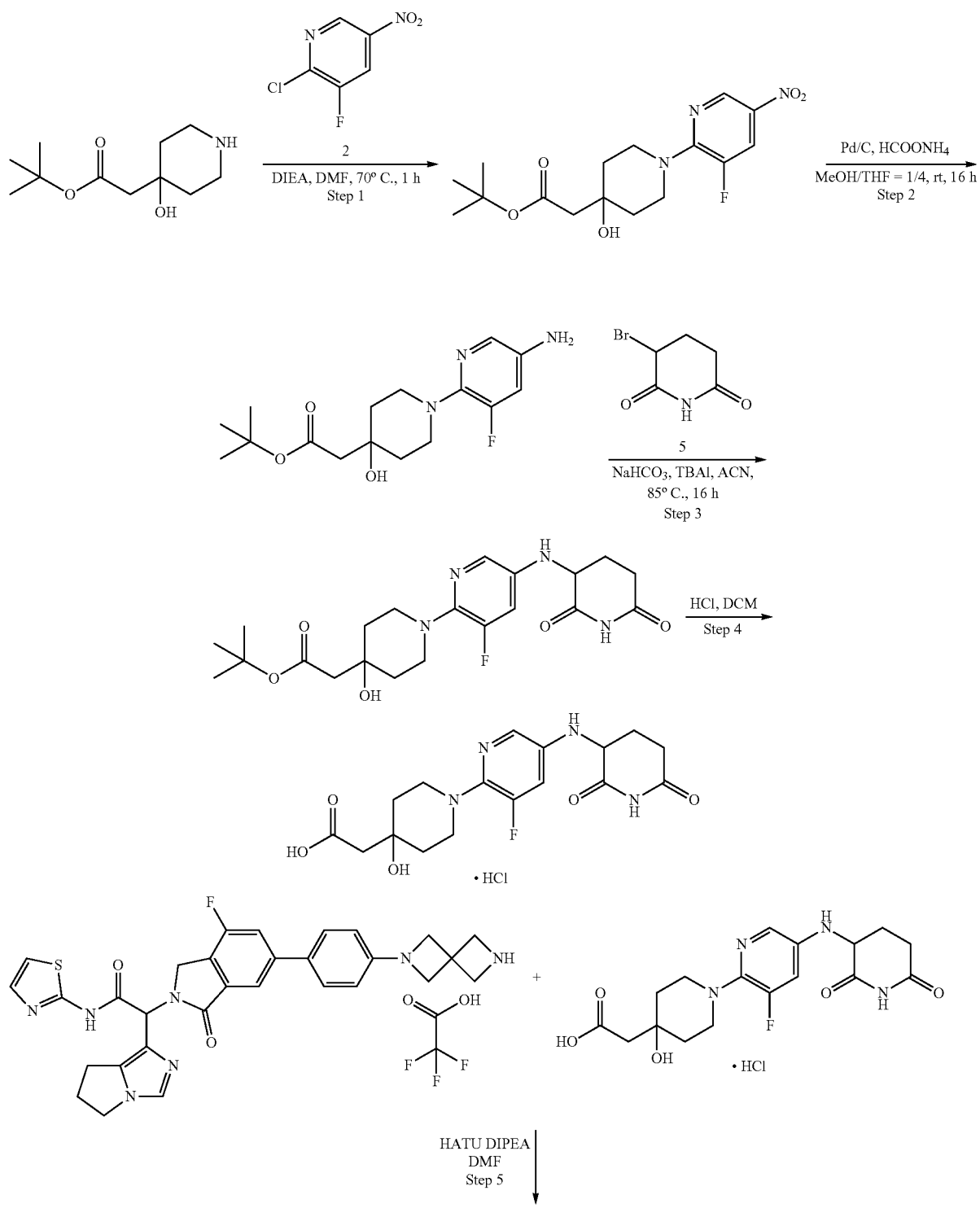

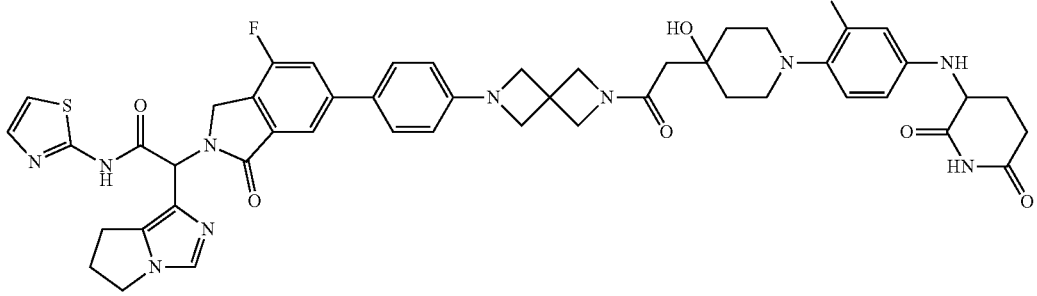

Step 1: tert-butyl 2-[1-(3-fluoro-5-nitro-2-pyridyl)-4-hydroxy-4-piperidyl]acetate To a solution of 2-chloro-3-fluoro-5-nitro-pyridine (2 g, 11.33 mmol) and N-ethyl-N-isopropylpropan-2-amine (2.20 g, 16.99 mmol, 2.96 mL) in N,N-dimethylformamide (10 mL) was added tert-butyl 2-(4-hydroxy-4-piperidyl) acetate (2.68 g, 12.46 mmol). The mixture was stirred at 70° C. for 1 h. After being cooled to room temperature, the mixture was poured into water (20 mL). The mixture was stirred at 25° C. for 10 min. A large quantity of yellow precipitate was formed. The mixture was filtered, the filter cake was washed with water (10 mL) and dried under vacuum to give tert-butyl 2-[1-(3-fluoro-5-nitro-2-pyridyl)-4-hydroxy-4-piperidyl] acetate (4.3 g, 10.89 mmol, 96% yield) as a yellow solid. $^1$H NMR (400 MHz, CHLOROFORM-d) δ=8.84 (dd, J=1.2, 2.4 Hz, 1H), 7.91 (d, J=2.4 Hz, 1H), 7.94 (d, J=2.4 Hz, 1H), 4.37 (d, J=13.2 Hz, 2H), 3.94 (s, 1H), 3.58-3.46 (m, 2H), 2.95 (s, 1H), 2.88 (s, 1H), 2.40 (s, 2H), 1.85-1.77 (m, 2H), 1.68-1.57 (m, 2H), 1.47 (s, 9H).

Step 2: tert-butyl 2-[1-(5-amino-3-fluoro-2-pyridyl)-4-hydroxy-4-piperidyl] acetate To a solution of tert-butyl 2-[1-(3-fluoro-5-nitro-2-pyridyl)-4-hydroxy-4-piperidyl]acetate (4.3 g, 12.10 mmol) and palladium 10% on charcoal (430 mg, 354.04 μmol) in methanol (8 mL) and tetrahydrofuran (32 mL) was added ammonium formate (3.83 g, 60.69 mmol) at 0° C. The mixture was stirred at 25° C. for 16 h. The reaction mixture was filtered through a pad of Celite and the filtrate was concentrated under reduced pressure. The residue was diluted with ethyl acetate (20 mL) and saturated aqueous sodium bicarbonate solution (20 mL). The mixture was separated, and the aqueous layer was extracted with ethyl acetate (3×20 mL). Combined extracts were washed with brine (40 mL), dried over sodium sulfate, filtered, and concentrated under reduced pressure to give tert-butyl 2-[1-(5-amino-3-fluoro-2-pyridyl)-4-hydroxy-4-piperidyl]acetate (2 g, 6.15 mmol, 51% yield, 67% purity) as a black solid. LCMS (ESI): m/z 326.2 [M+H]$^+$

Step 3: tert-butyl 2-[1-[5-[(2,6-dioxo-3-piperidyl)amino]-3-fluoro-2-pyridyl]-4-hydroxy-4-piperidyl] acetate To a solution of tert-butyl 2-[1-(5-amino-3-fluoro-2-pyridyl)-4-hydroxy-4-piperidyl]acetate (1.55 g, 4.76 mmol) and 3-bromopiperidine-2,6-dione (1.83 g, 9.53 mmol) in acetonitrile (16 mL) were added sodium bicarbonate (1.20 g, 14.30 mmol, 556.14 μL) and tetrabutylammonium iodide (176 mg, 476.49 μmol). The mixture was stirred at 85° C. for 16 h. The mixture was concentrated under reduced pressure. The crude product was purified by column chromatography on silica gel (petroleum ether/ethyl acetate=5/1 to 0/1) to give tert-butyl 2-[1-[5-[(2,6-dioxo-3-piperidyl)amino]-3-fluoro-2-pyridyl]-4-hydroxy-4-piperidyl]acetate (1.42 g, 3.19 mmol, 67% yield) as a deep brown solid. LCMS (ESI): m/z 437.3 [M+H]$^+$

Step 4: 2-[1-[5-[(2,6-dioxo-3-piperidyl)amino]-3-fluoro-2-pyridyl]-4-hydroxy-4-piperidyl]acetic acid To stirred solution of tert-butyl 2-[1-[5-[(2,6-dioxo-3-piperidyl)amino]-3-fluoro-2-pyridyl]-4-hydroxy-4-piperidyl]acetate (9 g, 20.62 mmol) in 1,4-dioxane (10 mL) was added Hydrogen chloride solution (4.0 M in 1,4-dioxane, 90 mL, 360 mmol) at room temperature. The reaction was stirred for 16 h at room temperature. The solvent removed by concentration under reduced pressure and the residue was triturated with diethyl ether (100 mL) for 0.5 h. After drying of material afford 2-[1-[5-[(2,6-dioxo-3-piperidyl)amino]-3-fluoro-2-pyridyl]-4-hydroxy-4-piperidyl]acetic acid hydrochloride (8.0 g, 17.93 mmol, 86.94% yield) as a pale blue solid. LCMS m/z=381.0 [M+H]$^+$

Step 5: 2-(6,7-dihydro-5H-pyrrolo[1,2-c]imidazol-1-yl)-2-[6-[4-[2-[2-[1-[5-[(2,6-dioxo-3-piperidyl)amino]-3-fluoro-2-pyridyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide To a solution of 2-[1-[5-[(2,6-dioxo-3-piperidyl)amino]-3-fluoro-2-pyridyl]-4-hydroxy-4-piperidyl]acetic acid (47.62 mg, 125.19 μmol) in N,N-dimethylformamide (0.6 mL) was added N,N-diisopropylethylamine (49.78 mg, 385.20 μmol, 67.09 μL). 1-[Bis(dimethylamino)methylene]-1H-1,2,3-triazolo[4,5-b]pyridinium 3-oxide hexafluorophosphate (40.28 mg, 105.93 μmol) was added and stirred at ambient temperature for 15 minutes. The solids had mostly dissolved after stirring for 15 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide trifluoroacetic acid salt (65.84 mg, 96.30 μmol) in N,N-dimethylformamide (0.3 mL) was added at 0° C. and warmed up to 25° C. The reaction mixture was acidified with 4-5 drops of trifluoroacetic acid, and injected directly on a C18 column (50 g C18) for low pressure liquid chromatography purification (5% to 100% acetonitrile (+0.1% trifluoroacetic acid) in water (+0.1% trifluoroacetic acid) over 12 minutes). The pure fractions were neutralized with saturated aqueous sodium bicarbonate (ca. 60 mL), and extracted twice with a isopropanol:chloroform (1:4) mixture. The organic layer was evaporated under reduced pressure to afford a solid. The solid was dissolved in dichloromethane and injected on a 24 g silica gel column flushed with 100% dichloromethane and purified using a 0% to 20% methanol in dichloromethane gradient over 20 minutes. The pure fractions were evaporated under reduced pressure. The crude residue was dissolved in dichloromethane, transferred to a 8 mL vial, and evaporated under reduced pressure. Water (1 mL) and acetonitrile (1 mL) were added, and the mixture was thoroughly sonicated, vortexed and sonicated again. The suspension was frozen at −78° C. and lyophilized to afford Compound 90 (38.9 mg, 41.32 μmol, 42.91% yield). LCMS (ESI+): 932.3 (M+H). $^1$H NMR (400 MHz, DMSO-d6) δ 12.44 (s, 1H), 10.73 (s, 1H), 7.67 (d, J=1.3 Hz, 1H), 7.63 (dd, J=10.7, 1.4 Hz, 1H), 7.60-7.54 (m, 2H), 7.53 (s, 2H), 7.49 (dd, J=2.5, 1.0 Hz, 1H), 7.41 (d, J=3.5 Hz, 1H), 7.18 (s, 1H), 6.91 (dd, J=14.8, 2.4 Hz, 1H), 6.47 (d, J=8.7 Hz, 2H), 6.07 (s, 1H), 5.81 (d, J=7.8 Hz, 1H), 4.76-4.69 (m, 2H), 4.30 (s, 2H), 4.21 (ddd, J=12.1, 7.7, 4.8 Hz, 1H), 4.14 (d, J=17.6 Hz, 1H), 4.03-3.83 (m, 8H), 3.16 (d, J=12.2 Hz, 2H), 2.99 (t, J=11.3 Hz, 2H), 2.74-2.57 (m, 2H), 2.55-2.45 (m, 3H), 2.14 (s, 2H), 2.08-1.98 (m, 1H), 1.81 (qd, J=12.3, 4.7 Hz, 1H), 1.66 (t, J=10.5 Hz, 2H), 1.54 (d, J=12.6 Hz, 2H).

Example 91

2-(6,7-dihydro-5H-pyrrolo[1,2-c]imidazol-1-yl)-2-[6-[4-[4-[2-[4-[3-(2,4-dioxohexahydropyrimidin-1-yl)-1-methyl-indazol-6-yl]-3,3-difluoro-1-piperidyl]acetyl]-1,4-diazepan-1-yl]phenyl]-4-fluoro-1-oxo-isoindolin-2-yl]-N-thiazol-2-yl-acetamide, Compound 91

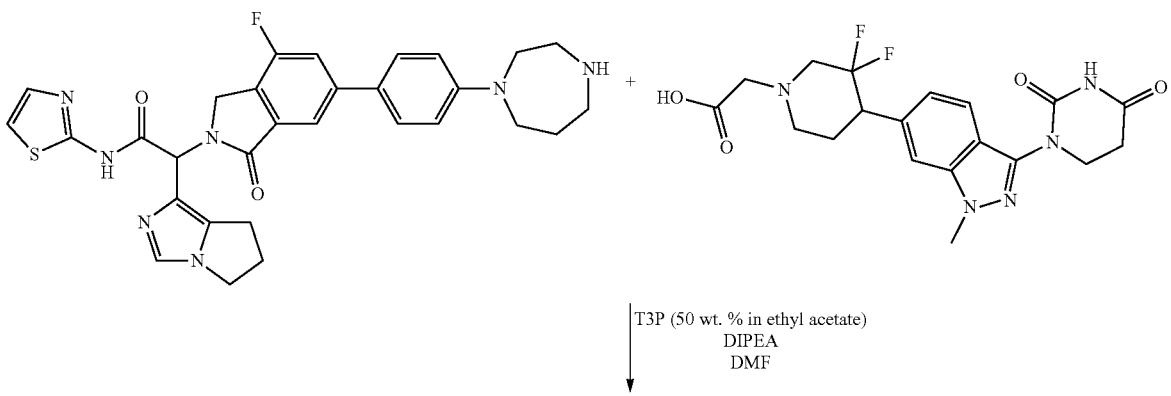

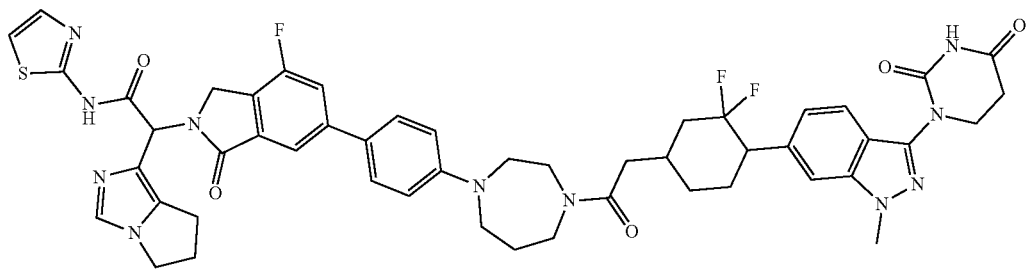

969

To the stirred solution of 2-[6-[4-(1,4-diazepan-1-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide hydrochloride (120 mg, 197.33 µmoll) and 2-[4-[3-(2,4-dioxohexahydropyrimidin-1-yl)-1-methyl-indazol-6-yl]-3,3-difluoro-1-piperidyl]acetic acid, trifluoroacetic acid salt (84.52 mg, 157.86 µmol) in N,N-dimethylformamide (2 mL) was cooled to 0° C. N,N-diisopropylethylamine (153.02 mg, 1.18 mmol, 206.22 µL) was added to the reaction mixture followed by propylphosphonic anhydride solution (50 wt. % in ethyl acetate) (125.57 mg, 394.65 µmol) at 0° C. The reaction mixture stirred at ambient temperature for 1 h. The reaction mixture was directly injected on a C18 column (100 g) for purification (0-50% 0.1% ammonium acetate in water and acetonitrile over 30 minutes, followed by a steep gradient to 100% acetonitrile). The pure fractions were combined and lyophilized to get Compound 91 (95 mg, 96.45 µmol, 48.88% yield) as brown solid. LCMS m/z 975.3 (M+H)$^+$. 1H-NMR (400 MHz, DMSO-d6): δ 12.53 (s, 1H), 10.58 (s, 1H), 8.62-7.57 (m, 6H), 7.49 (d, J=3.60 Hz, 2H), 7.26 (d, J=3.60 Hz, 1H), 7.05 (t, J=8.80 Hz, 1H), 6.88 (q, J=9.20 Hz, 2H), 6.14 (d, J=4.80 Hz, 1H), 4.81-4.75 (m, 1H), 4.23-4.19 (m, 1H), 3.99-3.90 (m, 7H), 3.68-3.44 (m, 6H), 3.28-3.11 (m, 4H), 2.76 (t, J=6.80 Hz, 3H), 2.67-2.55 (m, 2H), 2.48-2.32 (m, 3H), 2.23-2.11 (m, 1H), 2.08-1.96 (m, 1H), 1.92-1.68 (m, 3H).

Example 92

2-(6,7-dihydro-5H-pyrrolo[1,2-c]imidazol-1-yl)-2-[6-[4-[4-[2-[4-[3-(2,4-dioxohexahydropyrimidin-1-yl)-1-methyl-indazol-6-yl]piperazin-1-yl]acetyl]piperazin-1-yl]phenyl]-4-fluoro-1-oxo-isoindolin-2-yl]-N-thiazol-2-yl-acetamide, Compound 92

Step 1: tert-Butyl 4-[3-(2,4-dioxohexahydropyrimidin-1-yl)-1-methyl-indazol-6-yl]piperazine-1-carboxylate

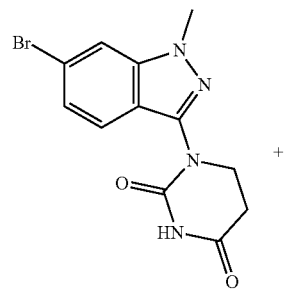

+

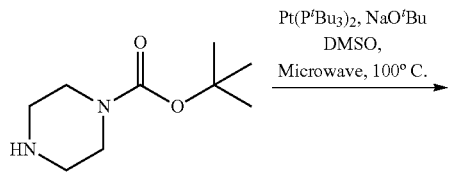

Pt(P$^t$Bu$_3$)$_2$, NaO$^t$Bu
DMSO,
Microwave, 100° C.

970

-continued

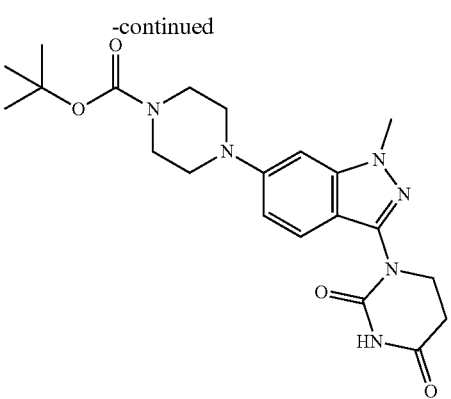

Into a 10 mL microwave vial containing a well-stirred solution of 1-(6-bromo-1-methyl-indazol-3-yl)hexahydropyrimidine-2,4-dione (300 mg, 928.38 µmol) and tert-butyl piperazine-1-carboxylate (238 mg, 1.28 mmol) in DMSO (4 mL) was degassed with nitrogen for 10 min. Sodium tert-butoxide (245.60 mg, 2.56 mmol) and bis(tri-tert-butylphosphine)palladium(0) (21.77 mg, 42.59 µmol) was added to the reaction mixture and further degassed with nitrogen for 5 min. The reaction vial was heated at 100° C. for 0.5 h under Microwave irradiation. Water (20 mL) was added to the reaction mixture. The reaction mixture was extracted with ethyl acetate (3×50 mL). The organic layers were washed with brine (50 mL), dried over sodium sulphate, filtered and concentrated under reduced pressure. The residue was purified by flash column chromatography using silica gel and the desired product was eluted with 80% ethyl acetate in Pet-ether to get tert-butyl 4-[3-(2,4-dioxohexahydropyrimidin-1-yl)-1-methyl-indazol-6-yl]piperazine-1-carboxylate (250 mg, 415.48 µmol, 48.77% yield). LCMS (ESI+) m/z: 429.2 [M+H]$^+$.

Step 2: 1-(1-methyl-6-piperazin-1-yl-indazol-3-yl)hexahydropyrimidine-2,4-dione

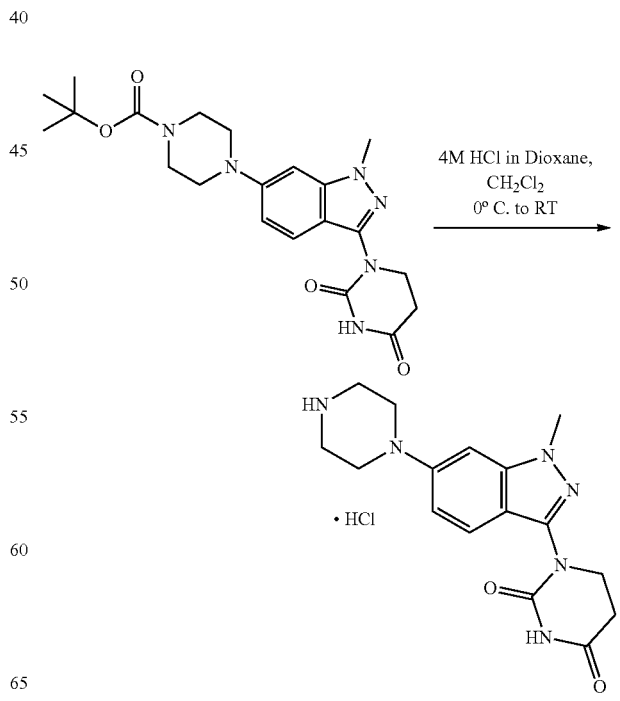

Into a 25 mL single-necked round-bottomed flask containing a well-stirred solution of tert-butyl 4-[3-(2,4-dioxohexahydropyrimidin-1-yl)-1-methyl-indazol-6-yl]piperazine-1-carboxylate (0.25 g, 583.45 μmol) in dichloromethane (5 mL) was added hydrogen chloride solution (4.0 M in 1,4-dioxane, 2.92 mmol, 730 μL) at 0° C. The suspension was stirred for 3 h at room temperature. The reaction mixture was concentrated under reduced pressure, triturated with diethyl ether, and decanted to get 1-(1-methyl-6-piperazin-1-yl-indazol-3-yl)hexahydropyrimidine-2,4-dione, hydrochloride (0.187 g, 183.60 μmol, 31.47% yield). LCMS (ESI+) m/z: 329.1 [M+H]⁺.

Step 3: tert-butyl 2-[4-[3-(2,4-dioxohexahydropyrimidin-1-yl)-1-methyl-indazol-6-yl]piperazin-1-yl]acetate

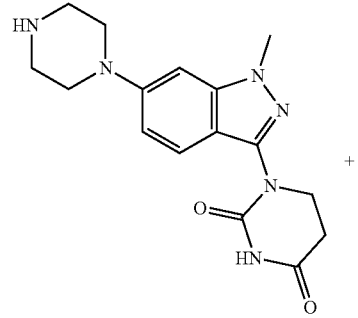

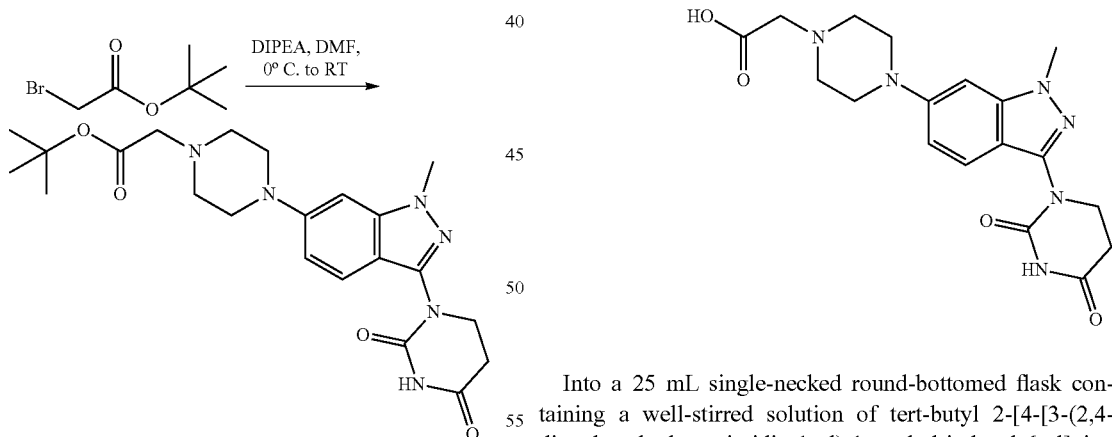

Into a 25 mL single-necked round-bottomed flask containing a well-stirred solution of 1-(1-methyl-6-piperazin-1-yl-indazol-3-yl)hexahydropyrimidine-2,4-dione; hydrochloride (0.187 g, 512.57 μmol) in N,N-dimethylformamide (3 mL) was added N,N-diisopropylethylamine (331.23 mg, 2.56 mmol, 446.40 μL) under nitrogen atmosphere at 0° C. tert-Butyl 2-bromoacetate (109.98 mg, 563.83 μmol, 82.69 μL) was added and the reaction mixture was stirred at ambient temperature for 4 h. The reaction mixture was quenched with ice cold water and extracted using Ethyl acetate (2×50 mL). The organic layer was washed using brine solution (25 mL), dried over sodium sulphate and concentrated in vacuo to get crude. The crude residue was purified flash column chromatography using silica gel and the desired product was eluted with 0 to 70% ethyl acetate in petroleum ether to get tert-butyl 2-[4-[3-(2,4-dioxohexahydropyrimidin-1-yl)-1-methyl-indazol-6-yl]piperazin-1-yl]acetate (0.135 g, 271.82 μmol, 53.03% yield) as an off-white solid. LCMS (ESI+) m/z: 443.2 [M+H]⁺.

Step 4: 2-[4-[3-(2,4-dioxohexahydropyrimidin-1-yl)-1-methyl-indazol-6-yl]piperazin-1-yl]acetic acid

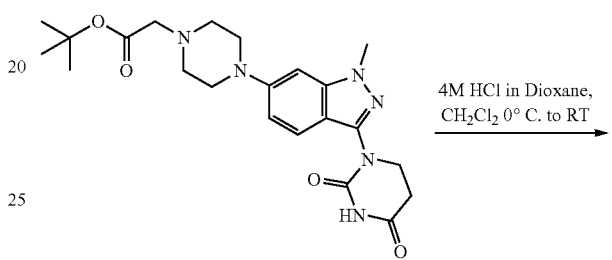

Into a 25 mL single-necked round-bottomed flask containing a well-stirred solution of tert-butyl 2-[4-[3-(2,4-dioxohexahydropyrimidin-1-yl)-1-methyl-indazol-6-yl]piperazin-1-yl]acetate (0.135 g, 305.08 μmol) in dichloromethane (4 mL) was added hydrogen chloride solution (4.0M in 1,4-dioxane, 0.38 mL, 1.53 mmol) at 0° C. The suspension was stirred at ambient temperature for 4 h. The reaction mixture was concentrated under reduced pressure, triturated with diethyl ether, and decanted to get 2-[4-[3-(2,4-dioxohexahydropyrimidin-1-yl)-1-methyl-indazol-6-yl]piperazin-1-yl]acetic acid hydrochloride (0.112 g, 214.38 μmol, 70.27% yield) as a brown solid. LCMS (ESI+) m/z: 387.1 [M+H]⁺.

Step 5: 2-(6,7-dihydro-5H-pyrrolo[1,2-c]imidazol-1-yl)-2-[6-[4-[4-[2-[4-[3-(2,4-dioxohexahydropyrimidin-1-yl)-1-methyl-indazol-6-yl]piperazin-1-yl]acetyl]piperazin-1-yl]phenyl]-4-fluoro-1-oxo-isoindolin-2-yl]-N-thiazol-2-yl-acetamide

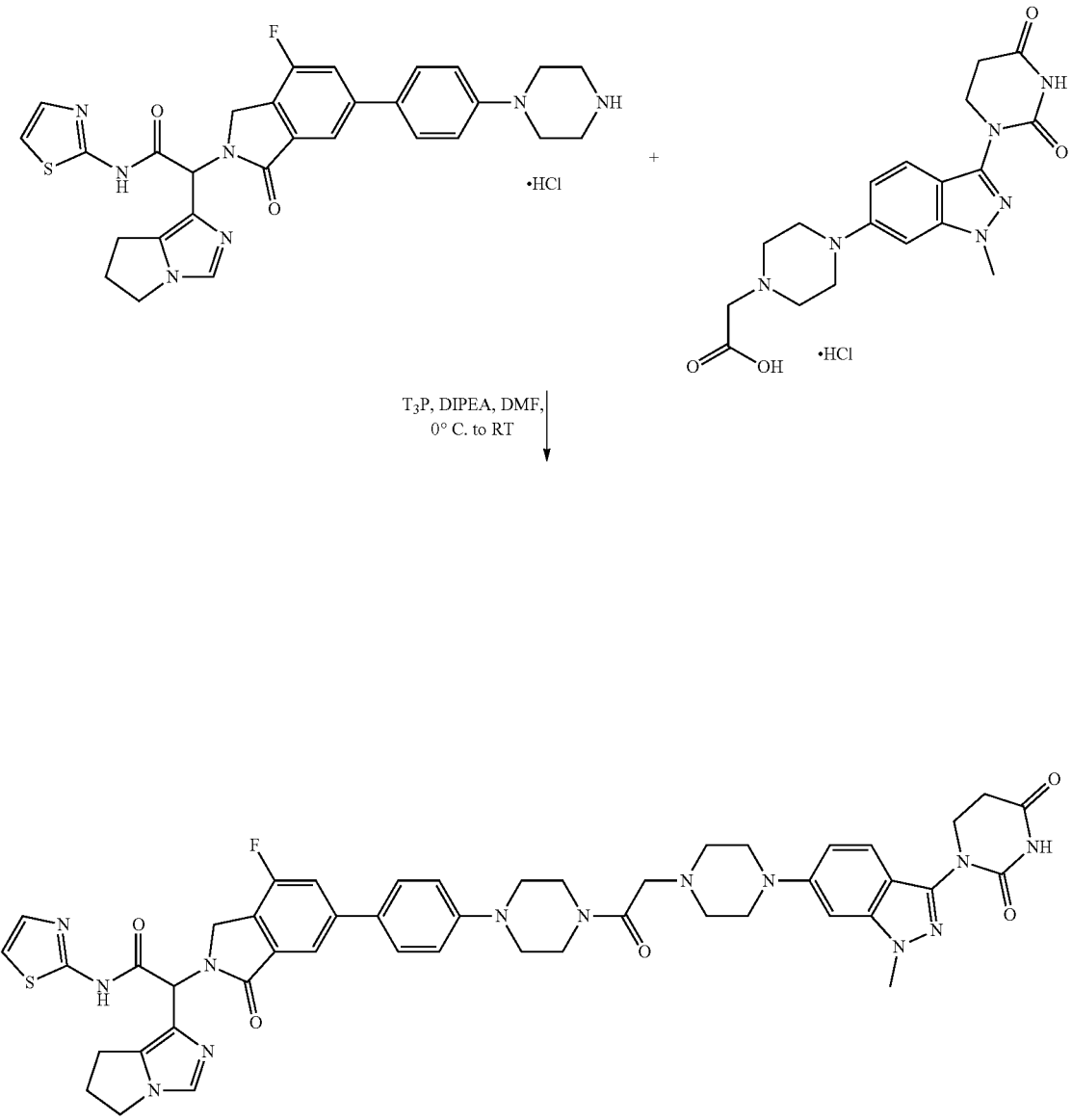

In a 10 mL single-necked round-bottomed flask containing a well-stirred solution of 2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide hydrochloride (120 mg, 201.99 μmol) and 2-[4-[3-(2,4-dioxohexahydropyrimidin-1-yl)-1-methyl-indazol-6-yl]piperazin-1-yl]acetic acid hydrochloride (111.04 mg, 262.58 μmol) in N,N-dimethylformamide (2 mL) was added N,N-diisopropylethylamine (130.53 mg, 1.01 mmol, 175.91 μL) under nitrogen atmosphere at 0° C. Propylphosphonic anhydride solution (50 wt. % in ethyl acetate; 128.54 mg, 403.97 μmol) was added at the same temperature and allowed to stirred at room temperature for 2 h. The crude mixture was directly injected on a C18 column (100 g) for purification while eluting (0%-55% of acetonitrile in water (+0.1% ammonium acetate) over 30 minutes, then steep gradient to 100% acetonitrile). The pure fraction was frozen and lyophilized to afford Compound 92 (50 mg, 53.89 μmol, 26.68% yield) as an off-white solid. LCMS m/z: 924.3 (M−H). $^1$H-NMR (400 MHz, DMSO-d6): δ 12.48 (s, 1H), 10.51 (s, 1H), 7.78-7.73 (m, 4H), 7.68-7.61 (m, 1H), 7.70 (s, 1H), 7.68 (s, 1H), 7.49-7.50 (m, 1H), 7.46 (d, J=8.80 Hz, 1H), 7.26 (d, J=3.60 Hz, 2H), 7.08 (s, 1H), 6.94 (s, 1H), 4.80 (d, J=17.60 Hz, 1H), 4.22 (d, J=17.60 Hz, 1H), 4.03-3.98 (m, 4H), 3.96 (s, 3H), 3.89 (d, J=5.20 Hz, 2H), 3.71 (d, J=50.40 Hz, 2H), 3.34-3.31 (m, 4H), 3.31-3.24 (m, 6H), 2.75-2.74 (m, 3H), 2.53-2.67 (m, 4H), 2.53-2.50 (m, 3H).

Example 93
2-(6,7-dihydro-5H-pyrrolo[1,2-c]imidazol-1-yl)-2-[6-[4-[2-[2-[(4R)-4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, Compound 93
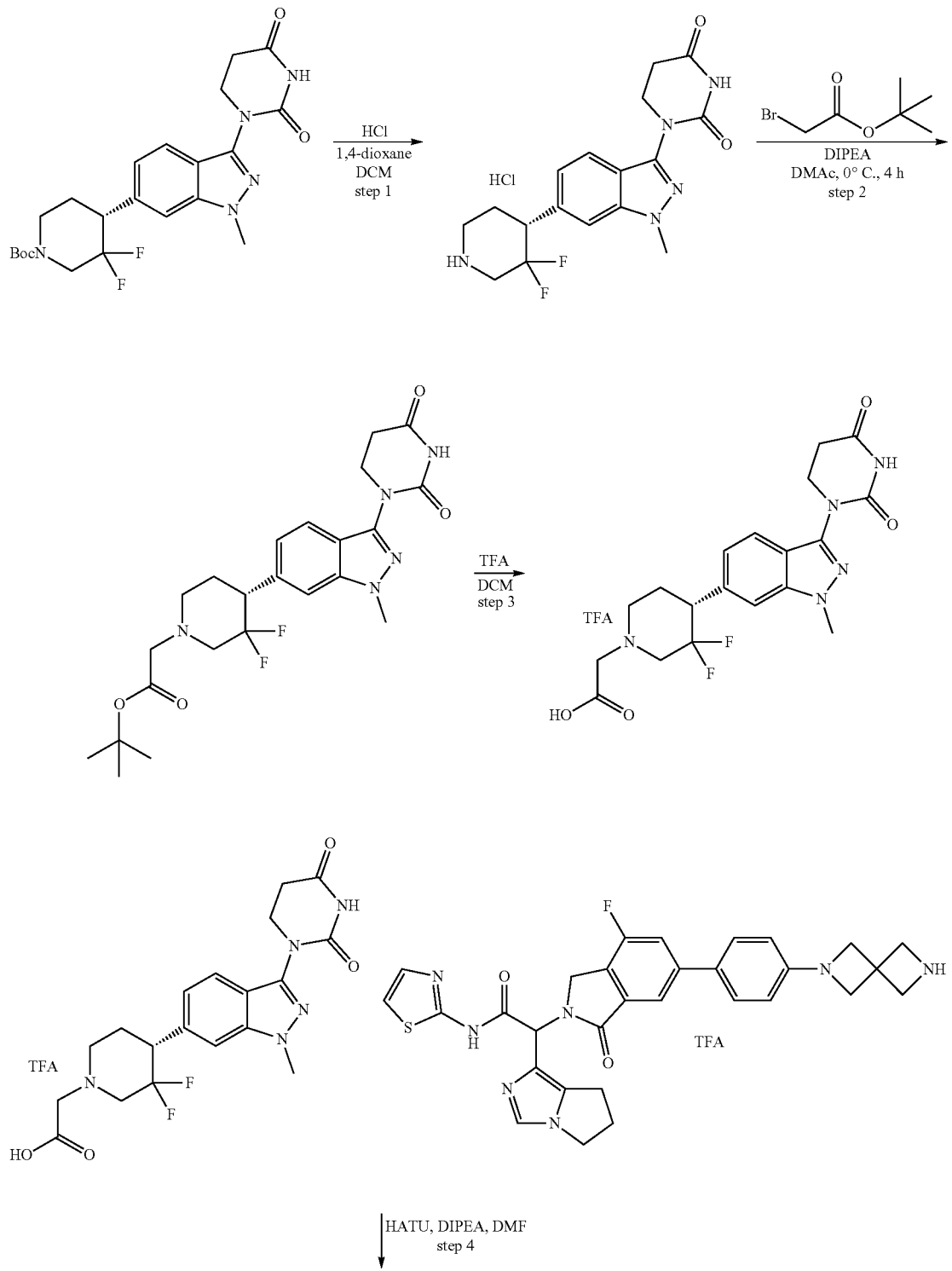

-continued

Step 1: 1-[6-[(4R)-3,3-difluoro-4-piperidyl]-1-methyl-indazol-3-yl]hexahydropyrimidine-2,4-dione hydrochloride tert-Butyl (4R)-4-[3-(2,4-dioxohexahydropyrimidin-1-yl)-1-methyl-indazol-6-yl]-3,3-difluoro-piperidine-1-carboxylate (Intermediate Z1, 325 mg, 701.22 µmol) was dissolved in a 1,4-dioxane:methanol mixture (1:1, 3 mL) and hydrogen chloride solution (4.0 M in 1,4-dioxane, 3.51 mL, 14 mmol) was added. The reaction mixture was heated at 40° C. for 4 h. The volatiles were evaporated under reduce pressure. The solid residue was submitted to high vacuum to afford 1-[6-[(4R)-3,3-difluoro-4-piperidyl]-1-methyl-indazol-3-yl]hexahydropyrimidine-2,4-dione hydrochloride (280 mg, 665.30 µmol, 94.88% yield). LCMS (ESI+): 364.1 (M+H)

Step 2: tert-Butyl 2-[(4R)-4-[3-(2,4-dioxohexahydropyrimidin-1-yl)-1-methyl-indazol-6-yl]-3,3-difluoro-1-piperidyl]acetate 1-[6-[(4R)-3,3-difluoro-4-piperidyl]-1-methyl-indazol-3-yl]hexahydropyrimidine-2,4-dione hydrochloride (285 mg, 784.34 µmol) and N,N-diisopropylethylamine (304.11 mg, 2.35 mmol, 409.85 µL) mixed in DMAc (0.5 mL). The reaction mixture was cooled to 0° C. tert-Butyl 2-bromoacetate (168.29 mg, 862.78 µmol, 126.53 µL) was added to the reaction mixture, and the mixture was warmed to 23° C. while stirring for 4 h. The reaction mixture was partitioned between ethyl acetate and sodium bicarbonate (aq., sat.). The organic layer was washed with brine, dried with sodium sulfate, filtered, and evaporated under reduced pressure. The crude residue was purified by silica gel chromatography (24 g column, 0% to 10% methanol in dichloromethane). Pure fractions were evaporated under reduced pressure to afford tert-butyl 2-[(4R)-4-[3-(2,4-dioxohexahydropyrimidin-1-yl)-1-methyl-indazol-6-yl]-3,3-difluoro-1-piperidyl]acetate (330 mg, 656.54 µmol, 83.71% yield). LCMS (ESI+): 478.2 (M+H)/422.2 (M-t-Bu+H)

Step 3: 2-[(4R)-4-[3-(2,4-dioxohexahydropyrimidin-1-yl)-1-methyl-indazol-6-yl]-3,3-difluoro-1-piperidyl]acetic acid, trifluoroacetic acid salt tert-Butyl 2-[(4R)-4-[3-(2,4-dioxohexahydropyrimidin-1-yl)-1-methyl-indazol-6-yl]-3,3-difluoro-1-piperidyl]acetate (330 mg, 691.09 µmol) was dissolved in dichloromethane (2 mL) and Trifluoroacetic acid (1.42 g, 12.44 mmol, 958.39 µL) was added. The reaction mixture was heated at 40° C. for 4 h. The reaction mixture was cooled, added to methyl tert-butyl ether (20 mLs) under stirring at 0-5° C. The resulting suspension was stirred for 2 minutes. The suspension was transferred to a vial for centrifugation, and the suspension was centrifugated at 2400 rpm for 5 minutes. The supernatant solvent was decanted and discarded. methyl tert-butyl ether (20 mLs) was added the solid and the resulting suspension was stirred for 2 minutes. The suspension was transferred to a vial for centrifugation, and the suspension was centrifugated at 2400 rpm for 5 minutes. The supernatant solvent was decanted and discarded. The volatiles were evaporated in vacuo, and the solid was subjected to high vacuum for 1 h to afford 2-[(4R)-4-[3-(2,4-dioxohexahydropyrimidin-1-yl)-1-methyl-indazol-6-yl]-3,3-difluoro-1-piperidyl]acetic acid, trifluoroacetic acid salt (150 mg, 274.55 µmol, 39.73% yield). LCMS (ESI+): 422.2 (M+H)

Step 4: 2-(6,7-dihydro-5H-pyrrolo[1,2-c]imidazol-1-yl)-2-[6-[4-[2-[2-[(4R)-4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (240 mg, 351.04 µmol) and 2-[(4R)-4-[3-(2,4-dioxohexahydropyrimidin-1-yl)-1-methyl-indazol-6-yl]-3,3-difluoro-1-piperidyl]acetic acid, trifluoroacetic acid salt (147.93 mg, 351.04 µmol) were mixed in N,N-dimethylformamide, the reaction mixture was cooled to 0° C. N,N-diisopropylethylamine (272.22 mg, 2.11 mmol, 366.87 µL) was added to the reaction mixture, and 1-[bis(dimethylamino)methylene]-1H-1,2,3-triazolo[4,5-b]pyridinium 3-oxide hexafluorophosphate (133.48 mg, 351.04 µmol) was added, and the reaction mixture was cooled at 4° C. for 16 h. Water (300 µL) was added to the reaction mixture and stirred for 2 h. The mixture was injected on a 100 g C18 column, and purified using a 0% to 100% acetonitrile in water (+0.1% trifluoroacetic acid) elution gradient. The pure fractions were pooled and partitioned between 20:80 iPrOH:chloroform and sodium bicarbonate (aq., sat.). The organic layer was washed with brine, dried with sodium sulfate, filtered, and evaporated under reduced pressure. The residue was purified by silica gel chromatography (24 g column, 0% to 20% methanol in dichloromethane). Pure fractions were evaporated under reduced pressure. The solid was dissolved in 70:30 acetonitrile:water, sonicated to solubilize, frozen and lyophilized to afford Compound 93 (150 mg, 151.07

μmol, 43.04% yield). LCMS (ESI+): 973.2 (M+H), $^1$H-NMR (400 MHz, DMSO-d6) δ 12.45 (s, 1H), 10.50 (s, 1H), 7.67 (d, J=1.3 Hz, 1H), 7.64 (dd, J=10.7, 1.4 Hz, 1H), 7.58 (d, J=8.5 Hz, 2H), 7.55-7.45 (m, 3H), 7.40 (d, J=3.5 Hz, 1H), 7.16 (s, 1H), 7.03 (d, J=8.5 Hz, 1H), 6.48 (d, J=8.5 Hz, 2H), 6.06 (s, 1H), 4.75 (d, J=17.7 Hz, 1H), 4.37 (s, 2H), 4.14 (d, J=17.7 Hz, 1H), 4.07-3.94 (m, 7H), 3.92 (s, 4H), 3.85 (t, J=6.7 Hz, 2H), 3.16 (qd, J=14.9, 14.3, 7.1 Hz, 5H), 2.92 (d, J=10.8 Hz, 1H), 2.69 (t, J=6.8 Hz, 3H), 2.65-2.45 (m, 2H), 2.41-2.30 (m, 1H), 2.28-2.11 (m, 1H), 1.84-1.72 (m, 1H).

Example 94

2-(6,7-dihydro-5H-pyrrolo[1,2-c]imidazol-1-yl)-2-[6-[4-[2-[2-[(4S)-4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, Compound 94

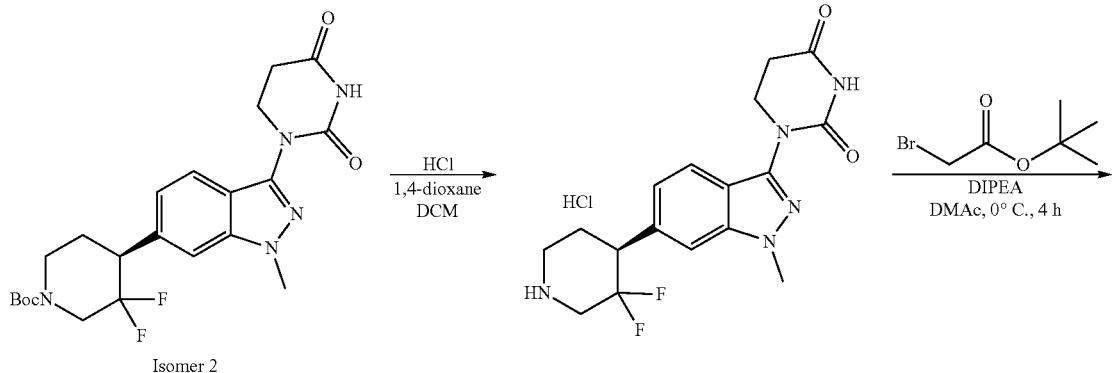

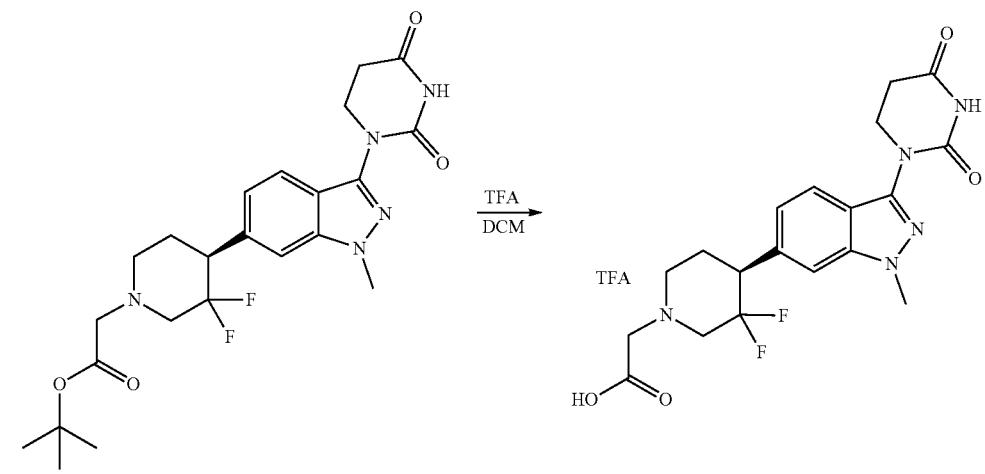

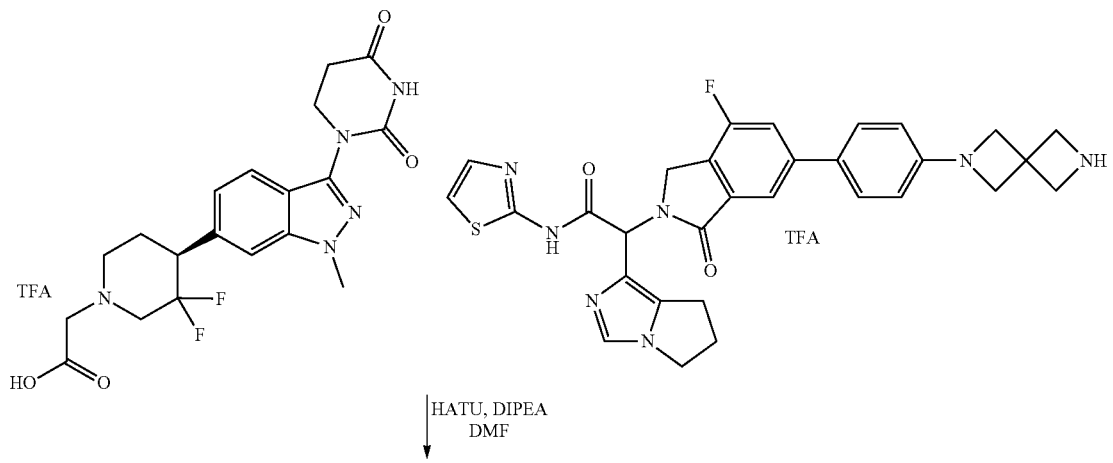

-continued

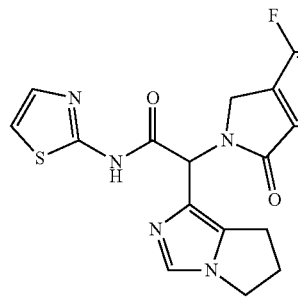 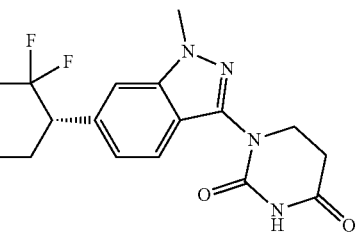

Step 1: 1-[6-[(4S)-3,3-difluoro-4-piperidyl]-1-methyl-indazol-3-yl]hexahydropyrimidine-2,4-dione tert-Butyl (4S)-4-[3-(2,4-dioxohexahydropyrimidin-1-yl)-1-methyl-indazol-6-yl]-3,3-difluoro-piperidine-1-carboxylate (Intermediate Z2, 261.00 mg, 563.14 μmol) was dissolved in dichloromethane (2 mL) and hydrogen chloride solution (4.0 M in 1,4-dioxane, 0.28 mL, 11.26 mmol) was added. The reaction mixture was heated at 40° C. for 24 h. The volatiles were evaporated under reduce pressure. The material was submitted to high vacuum to afford 1-[6-[(4S)-3,3-difluoro-4-piperidyl]-1-methyl-indazol-3-yl]hexahydropyrimidine-2,4-dione hydrochloride (225 mg, 545.87 μmol, 96.93% yield) as a dense white solid. LCMS (ESI+): 364.2 (M+Na).

Step 2: tert-Butyl 2-[(4S)-4-[3-(2,4-dioxohexahydropyrimidin-1-yl)-1-methyl-indazol-6-yl]-3,3-difluoro-1-piperidyl]acetate 1-[6-[(4S)-3,3-difluoro-4-piperidyl]-1-methyl-indazol-3-yl]hexahydropyrimidine-2,4-dione hydrochloride (227.20 mg, 625.28 μmol) was dissolved in DMAc (3.5 mL) at 0° C. N,N-diisopropylethylamine (404.05 mg, 3.13 mmol, 544.55 μL) was added, and the reaction mixture was cooled to 0° C. tert-butyl 2-bromoacetate (121.96 mg, 625.28 μmol, 91.70 μL) was added. The reaction temperature was increased to 35° C. The reaction mixture was partitioned between ethyl acetate and sodium bicarbonate (aq., sat.). The organic layer was washed with brine, dried with sodium sulfate, filtered, and evaporated under reduced pressure. The crude residue was purified by silica gel chromatography (24 g column, 0% to 20% methanol in ethyl acetate). Pure fractions were evaporated under reduced pressure to afford tert-butyl 2-[(4S)-4-[3-(2,4-dioxohexahydropyrimidin-1-yl)-1-methyl-indazol-6-yl]-3,3-difluoro-1-piperidyl]acetate (298 mg, 605.36 μmol, 96.81% yield). LCMS (ESI+): 478.2 (M+H)/422.2 (M-tBu+H)

Step 3: 2-[(4S)-4-[3-(2,4-dioxohexahydropyrimidin-1-yl)-1-methyl-indazol-6-yl]-3,3-difluoro-1-piperidyl]acetic acid, trifluoroacetic acid salt tert-Butyl 2-[(4S)-4-[3-(2,4-dioxohexahydropyrimidin-1-yl)-1-methyl-indazol-6-yl]-3,3-difluoro-1-piperidyl]acetate (286.50 mg, 600 μmol) was dissolved in dichloromethane (3 mL). Trifluoroacetic acid (752.55 mg, 6.60 mmol, 508.48 μL) was added, and the reaction mixture was stirred at 35° C. for 4 h. The reaction mixture was added to methyl tert-butyl ether (20 mLs) under stirring at 0-5° C. The resulting suspension was stirred for 2 minutes. The suspension was transferred to a vial for centrifugation, and the suspension was centrifuged at 1600 rpm for 3 minutes. The supernatant solvent was decanted and discarded. Methyl tert-butyl ether (20 mL) was added the solid and the resulting suspension was stirred for 2 minutes. The suspension was transferred to a vial for centrifugation, and the suspension was centrifuged at 1600 rpm for 3 minutes. The supernatant solvent was decanted and discarded. The volatiles were evaporated in vacuo, and the solid was subjected to high vacuum for 1 h to afford 2-[(4S)-4-[3-(2,4-dioxohexahydropyrimidin-1-yl)-1-methyl-indazol-6-yl]-3,3-difluoro-1-piperidyl]acetic acid, trifluoroacetic acid salt (320 mg, 567.78 μmol, 94.63% yield). LCMS: Rt=0.951 min., MS (ESI+): 422.3 (M+H)

Step 4: 2-(6,7-dihydro-5H-pyrrolo[1,2-c]imidazol-1-yl)-2-[6-[4-[2-[2-[(4S)-4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (354.03 mg, 517.83 μmol) and 2-[(4S)-4-[3-(2,4-dioxohexahydropyrimidin-1-yl)-1-methyl-indazol-6-yl]-3,3-difluoro-1-piperidyl]acetic acid, trifluoroacetic acid salt (218.21 mg, 517.83 μmol) were mixed in N,N-dimethylformamide (7 mL), the reaction mixture was cooled to 0° C. N,N-diisopropylethylamine (468.47 mg, 3.62 mmol, 631.36 μL) was added to the reaction mixture, and 1-[bis(dimethylamino)methylene]-1H-1,2,3-triazolo[4,5-b]pyridinium 3-oxide hexafluorophosphate (236.27 mg, 621.40 μmol) was added, and the reaction mixture was stirred for 2 h. Water (1 mL) and methanol (0.5 mL) were added to the reaction mixture. Stirred 30 minutes. The mixture was injected on a 50 g C18 column and purified using a 0% to 100% acetonitrile in water (+0.1% trifluoroacetic acid) elution gradient. The pure fractions were pooled and partitioned between ethyl acetate and sodium bicarbonate (aq., sat.). The organic layer was washed with brine, dried with sodium sulfate, filtered, and evaporated under reduced pressure. The crude residue was purified by silica gel chromatography (40 g column, 0% to 20% methanol in dichloromethane). Pure fractions were evaporated. Solid dissolved in acetonitrile: water mixture. Frozen and lyophilized to afford Compound 94 (125 mg, 127.82 μmol, 24.68% yield). LCMS: (ESI+): 973.3 (M+H)/482.5 (M+2H/2); MS (ESI-): 971.0 (M-H).

¹H NMR (400 MHz, DMSO-d₆) δ 12.53 (s, 1H), 10.57 (s, 1H), 7.74 (d, J=1.3 Hz, 1H), 7.70 (dd, J=10.7, 1.4 Hz, 1H), 7.64 (d, J=8.4 Hz, 2H), 7.62-7.51 (m, 3H), 7.48 (d, J=3.5 Hz, 1H), 7.25 (d, J=3.5 Hz, 1H), 7.10 (d, J=8.5 Hz, 1H), 6.55 (d, J=8.4 Hz, 2H), 6.15 (s, 1H), 4.80 (d, J=17.6 Hz, 1H), 4.43 (s, 2H), 4.22 (d, J=17.6 Hz, 1H), 4.10 (s, 2H), 4.03 (d, J=6.0 Hz, 4H), 3.99 (s, 3H), 3.92 (t, J=6.7 Hz, 2H), 3.29-3.11 (m, 3H), 2.99 (d, J=10.7 Hz, 1H), 2.87-2.53 (m, 4H), 2.48-2.35 (m, 2H), 2.34-2.16 (m, 1H), 1.99-1.59 (m, 1H) (solvent obscuration observed).

Example 95

2-(6,7-dihydro-5H-pyrrolo[1,2-c]imidazol-1-yl)-2-[6-[6-[2-[2-[4-[4-[[(3S)-2,6-dioxo-3-piperidyl]amino]-2-fluoro-phenyl]-1-piperidyl]acetyl]-2,6-diazaspiro[3.3]heptan-6-yl]-3-pyridyl]-4-fluoro-1-oxo-isoindolin-2-yl]-N-thiazol-2-yl-acetamide, Compound 95

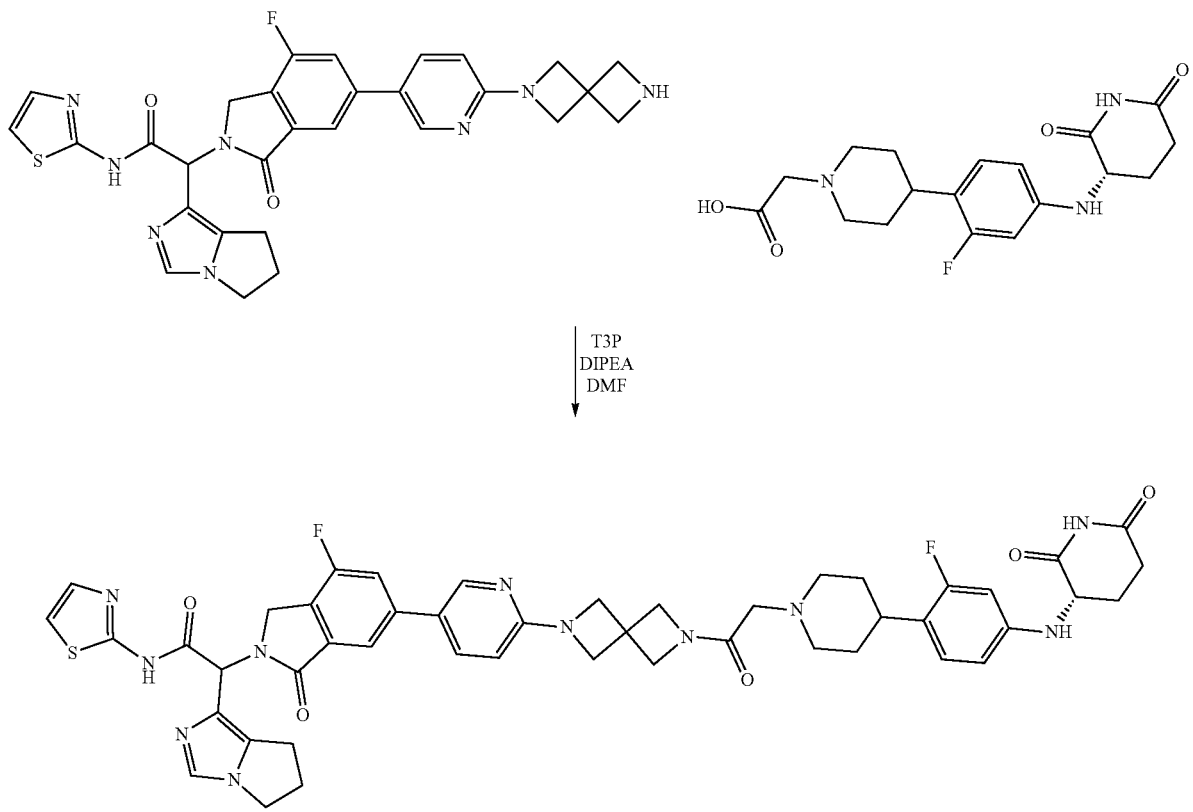 [SMILES: O=C(Nc1nccs1)C(c1ncn2c1CCC2)N1Cc2c(F)cc(-c3ccc(N4CC5(CNC5)C4)nc3)cc2C1=O ; O=C(O)CN1CCC(c2ccc(N[C@H]3CCC(=O)NC3=O)cc2F)CC1 ; O=C1CC[C@H](Nc2ccc(C3CCN(CC(=O)N4CC5(C4)CN(c4ccc(-c6cc(F)c7c(c6)C(=O)N(C(C(=O)Nc6nccs6)c6ncn8c6CCC8)C7)cn4)C5)CC3)c(F)c2)C(=O)N1]

To a stirred solution of 2-[6-[6-(2,6-diazaspiro[3.3]heptan-2-yl)-3-pyridyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (160 mg, 233.69 μmol) and 2-[4-[4-[[(3S)-2,6-dioxo-3-piperidyl]amino]-2-fluoro-phenyl]-1-piperidyl]acetic acid (112.13 mg, 280.43 μmol, 021) in N,N-dimethylformamide (1.5 mL) at 0° C. was added N,N-diisopropylethylamine (151.02 mg, 1.17 mmol, 203.52 μL) followed by propanephosphonic acid anhydride (185.89 mg, 584.23 μmol). The reaction mixture was stirred at room temperature for 1 h. The compound was purified by reverse phase column preparative HPLC (Column: C18 Gold column, Mobile Phase: acetonitrile in 10 mM ammonium acetate in water). The pure fractions were collected, frozen and lyophilized to afford Compound 95 (50 mg, 54.23 μmol, 23.21% yield) as an off-white solid compound. LCMS m/Z: 916.3, [M+1], ¹H-NMR (400 MHz, DMSO-d6): δ 12.53 (s, 1H), 10.80 (s, 1H), 8.54 (d, J=2.40 Hz, 1H), 8.00 (d, J=2.40 Hz, 1H), 7.79 (s, 1H), 7.76 (s, 1H), 7.62 (s, 1H), 7.49 (d, J=3.60 Hz, 1H), 7.27 (d, J=3.60 Hz, 1H), 7.01 (t, J=8.80 Hz, 1H), 6.52-6.46 (m, 3H), 6.15 (s, 1H), 6.05 (d, J=Hz, 1H), 4.81 (d, J=17.60 Hz, 1H), 4.44 (s, 2H), 4.31 (m, 1H), 4.23 (d, J=17.60 Hz, 2H), 4.17 (s, 4H), 4.15 (s, 2H), 4.10-3.98 (m, 2H), 3.00 (d, J=Hz, 3H), 2.77-2.67 (m, 2H), 2.60-2.57 (m, 2H), 2.11-2.06 (m, 3H), 1.92-1.66 (m, 5H), (Proton signal missing due to solvent and water obscuration).

Example 96

5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-[1-[2-[1-[4-[(2,6-dioxo-3-piperidyl)amino]-2-fluoro-phenyl]-4-hydroxy-4-piperidyl]acetyl]-4-piperidyl]pyridine-2-carboxamide, Compound 96

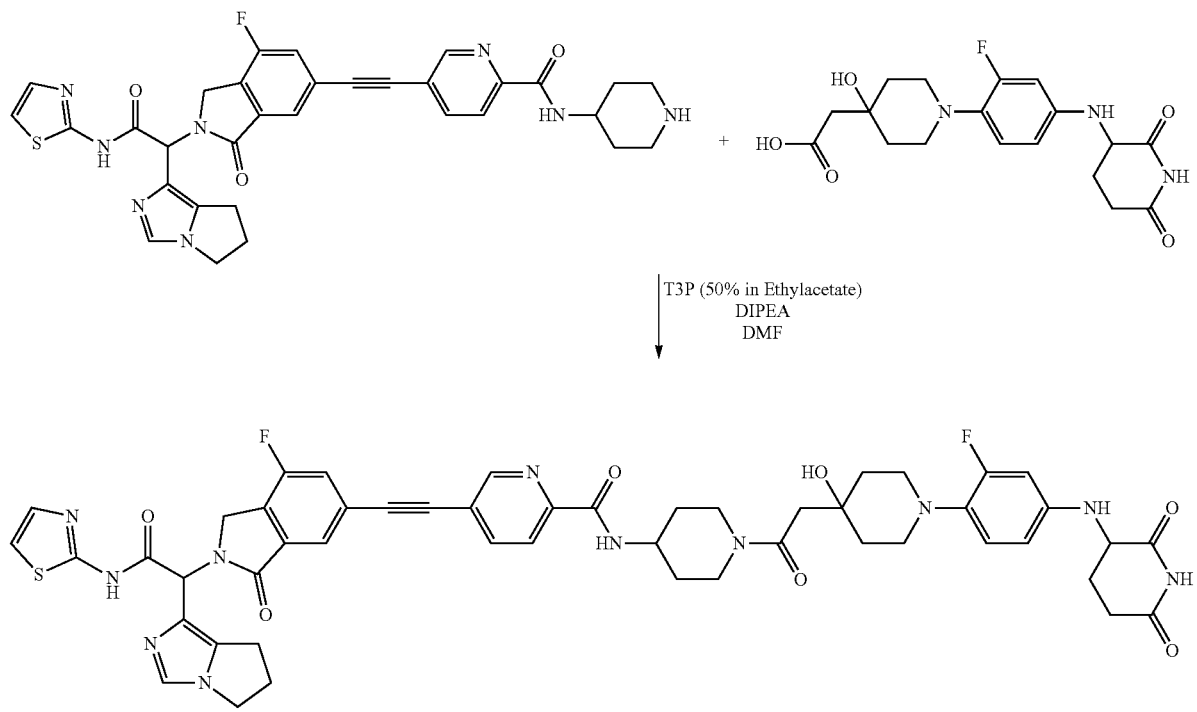 [SMILES: O=C(NC1CCNCC1)c1ccc(C#Cc2cc(F)c3c(c2)C(=O)N(C(C(=O)Nc2nccs2)c2ncn4c2CCC4)C3)cn1 ; O=C(O)CC1(O)CCN(c2ccc(NC3CCC(=O)NC3=O)cc2F)CC1 ; O=C1CCC(Nc2ccc(N3CCC(O)(CC(=O)N4CCC(NC(=O)c5ccc(C#Cc6cc(F)c7c(c6)C(=O)N(C(C(=O)Nc6nccs6)c6ncn8c6CCC8)C7)cn5)CC4)CC3)c(F)c2)C(=O)N1]

To a stirred solution of 5-[2-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]ethynyl]-N-(4-piperidyl)pyridine-2-carboxamide hydrochloride (170 mg, 257.13 µmol) and 2-[1-[4-[(2,6-dioxo-3-piperidyl)amino]-2-fluoro-phenyl]-4-hydroxy-4-piperidyl]acetic acid hydrochloride (106.93 mg, 257.13 µmol) in N,N-dimethylformamide (3 mL) at 0° C. was added N,N-diisopropylethylamine (199.39 mg, 1.54 mmol, 268.72 µL) followed by propanephosphonic acid anhydride (50% in Ethyl acetate) (163.63 mg, 514.26 µmol) at 0° C. The reaction mixture stirred at ambient temperature for 1 h. The reaction mixture was directly injected on a C18 column (100 g) for purification (Gradient mixture: 0-50% 0.1% ammonium acetate in water in acetonitrile over 30 minutes, followed by a steep gradient to 100% acetonitrile). The pure fractions were combined and frozen and lyophilized to get Compound 96 (125.5 mg, 126.93 µmol) as an off-white solid. LCMS (ESI−) m/z: 984.3 [M−H]; $^1$H-NMR (400 MHz, DMSO-d6): δ 12.55 (s, 1H), 10.79 (s, 1H), 8.87 (dd, J=2.00, 0.8 Hz, 1H), 8.81 (d, J=8.0 Hz, 1H), 8.22 (dd, J=8.0, 2.0 Hz, 1H), 8.10 (d, J=8.0 Hz, 1H), 7.84 (s, 1H), 7.81 (d, J=9.2 Hz, 1H), 7.61 (s, 1H), 7.49 (d, J=3.6 Hz, 1H), 7.26 (s, 1H), 6.86 (t, J=9.6 Hz, 1H), 6.50 (dd, J=15.20, 2.4 Hz, 1H), 6.48-6.43 (m, 1H), 6.13 (s, 1H), 5.80-5.78 (m, 1H), 4.97 (s, 1H), 4.87 (d, J=18.8 Hz, 1H), 4.30-4.26 (m, 2H), 4.10-3.99 (m, 4H), 3.15-3.19 (m, 1H), 2.91-2.87 (m, 4H), 2.77-2.67 (m, 3H), 2.59-2.50 (m, 2H), 2.25-2.08 (m, 1H), 1.87-1.63 (m, 10H).

Example 97

2-(6,7-dihydro-5H-pyrrolo[1,2-c]imidazol-1-yl)-2-[6-[4-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, Compound 97

Step 1: tert-Butyl 2-[1-[4-[[(3S)-2,6-dioxo-3-piperidyl]amino]-2-fluoro-phenyl]-4-hydroxy-4-piperidyl]acetate

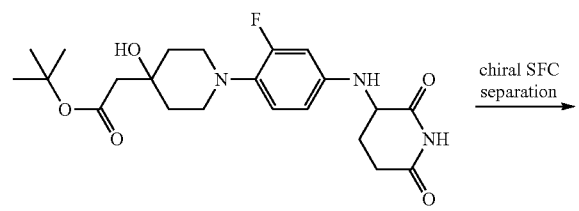

chiral SFC separation

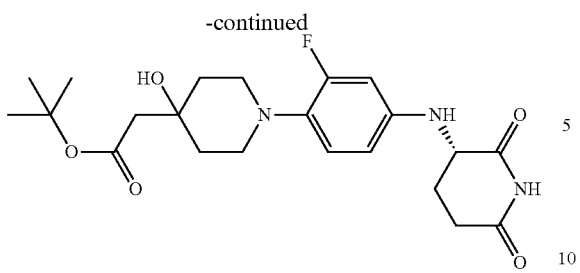

+

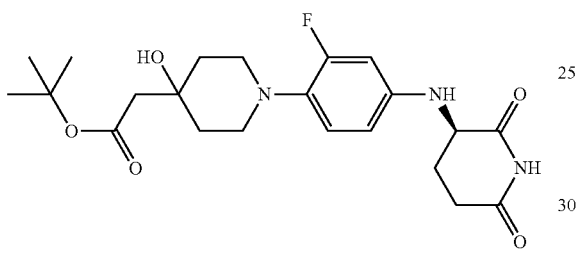

The racemic mixture tert-butyl 2-[1-[4-[(2,6-dioxo-3-piperidyl)amino]-2-fluoro-phenyl]-4-hydroxy-4-piperidyl]acetate (Example 70, step 3, 2 g, 4.59 mmol) was resolved by chiral SFC. 2.0 g of sample was dissolved in 22.0 mL of acetonitrile.

SFC separation conditions: Column: LUX A1 [250*10 mm, 5-micron particle size]; Mobile phase: $CO_2$: Isopropanol (45:55); Flow rate: 12 g/min; Cycle time: 11.0 min; Back pressure: 100 bar UV collection, wavelength: 254 nm; Volume: 0.4 mL per injection The first eluting set of fractions was evaporated under pressure to afford tert-butyl 2-[1-[4-[[(3S)-2,6-dioxo-3-piperidyl]amino]-2-fluoro-phenyl]-4-hydroxy-4-piperidyl]acetate (850 mg, 1.84 mmol, 40.04% yield) as an off white solid. LCMS m/z: 436.0 [M+H], LCMS (ESI+) m/z: 436.2 [M+H]$^+$. 1H-NMR (400 MHz, DMSO-d6): δ 10.77 (s, 1H), 6.83 (t, J=12.00 Hz, 1H), 6.49 (d, J=20.00 Hz, 1H), 6.41 (d, J=12.00 Hz, 1H), 5.77 (d, J=7.60 Hz, 1H), 4.44 (s, 1H), 4.29-4.12 (m, 1H), 2.91-2.79 (m, 5H), 2.74-2.70 (m, 1H), 2.34 (s, 2H), 2.16-2.02 (m, 1H), 1.89-1.69 (m, 3H), 1.65 (d, J=16.80 Hz, 2H), 1.42 (s, 9H), 99.18% ee by chiral SFC (Rt=2.33 min), Specific optical rotation: −46.2° [α]$^{20}_D$ The second eluting set of fractions was evaporated under pressure to afford tert-butyl 2-[1-[4-[[(3R)-2,6-dioxo-3-piperidyl]amino]-2-fluoro-phenyl]-4-hydroxy-4-piperidyl]acetate (530 mg, 1.17 mmol, 25.52% yield) as an off white solid. LCMS m/z: 436.0 [M+H], LCMS (ESI+) m/z: 436.0 [M+H]$^+$. 1H-NMR (400 MHz, DMSO-d6): δ 10.78 (s, 1H), 6.84 (t, J=13.20 Hz, 1H), 6.49 (d, J=20.00 Hz, 1H), 6.41 (d, J=12.40 Hz, 1H), 5.77 (d, J=10.40 Hz, 1H), 4.44 (s, 1H), 4.27-4.22 (m, 1H), 2.92-2.77 (m, 5H), 2.73-2.63 (m, 1H), 2.34 (s, 2H), 2.18-2.03 (m, 1H), 1.87-1.73 (m, 3H), 1.64 (d, J=18.00 Hz, 2H), 1.48 (s, 9H), 99.13% ee by chiral SFC (Rt 10=4.92 min), Specific optical rotation: +46.8° [α]$^{20}_D$ Step 2: 2-[1-[4-[[(3S)-2,6-dioxo-3-piperidyl]amino]-2-fluoro-phenyl]-4-hydroxy-4-piperidyl]acetic acid hydrochloride

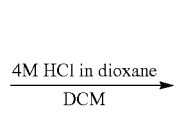

To a stirred solution of tert-butyl 2-[1-[4-[[(3S)-2,6-dioxo-3-piperidyl]amino]-2-fluoro-phenyl]-4-hydroxy-4-piperidyl]acetate (600 mg, 1.38 mmol) in dichloromethane (15 mL) at 0° C. was added hydrogen chloride (4M solution in 1,4-dioxane, 1.72 mL, 6.89 mmol) dropwise. The reaction mixture was stirred at room temperature for 6 h. The volatiles were removed by rotary evaporation. The residue was triturated twice with diethyl ether (2×10 mL). The solid residue was dried under rotary vacuum to afford 2-[1-[4-[[(3S)-2,6-dioxo-3-piperidyl]amino]-2-fluoro-phenyl]-4-hydroxy-4-piperidyl]acetic acid hydrochloride (610 mg, 1.09 mmol, 78.96% yield) as a grey solid. LCMS (ESI+) m/z: 380.0 [M+H]$^+$, $^1$H-NMR (400 MHz, DMSO-d6): δ 12.03 (bs, 1H), 10.86 (s, 1H), 7.63 (s, 1H), 6.70 (d, J=15.20 Hz, 1H), 6.58 (dd, J=11.40, 6.80 Hz, 1H), 4.43 (dd, J=11.60, 4.40 Hz, 1H), 3.88-3.65 (m, 5H), 3.41-3.36 (m, 2H), 2.74-2.68 (m, 1H), 2.59-2.54 (m, 1H), 2.46 (s, 2H), 2.33 (bs, 2H), 2.10-2.08 (m, 1H), 1.94-1.88 (m, 2H).

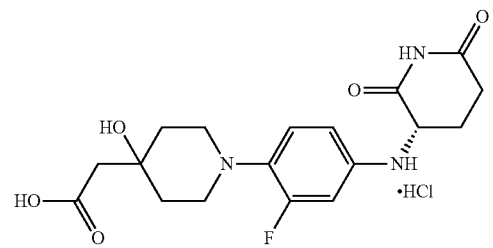

Step 3: 2-(6,7-dihydro-5H-pyrrolo[1,2-c]imidazol-1-yl)-2-[6-[4-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide

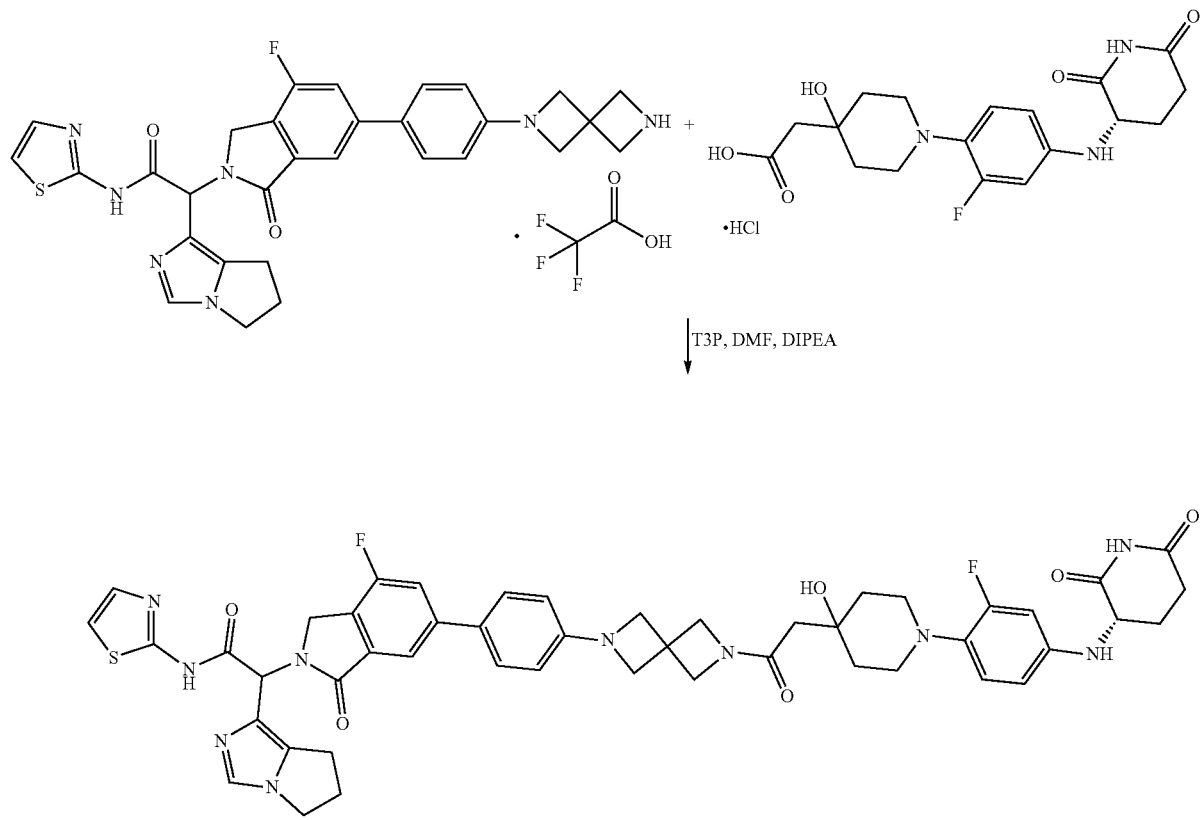

2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (270 mg, 394.92 µmol) and 2-[1-[4-[[(3S)-2,6-dioxo-3-piperidyl]amino]-2-fluoro-phenyl]-4-hydroxy-4-piperidyl]acetic acid hydrochloride (197.07 mg, 473.91 µmol) were mixed in N,N-dimethylformamide (5 mL). N,N-diisopropylethylamine (357.29 mg, 2.76 mmol, 481.52 µL) was added to the reaction mixture at 0° C. Propylphosphonic anhydride solution (50 wt. % in ethyl acetate, 176 µL, 188.49 mg, 592.39 µmol) was added to the reaction mixture at 0° C. The reaction mixture was stirred at ambient temperature for 2 h. The crude mixture was purified by reverse phase chromatography (C18 column (100 g); 0% to 50% in acetonitrile in water (0.1% ammonium acetate) over 30 minutes, then steep gradient to 100% acetonitrile). The pure fraction was frozen and lyophilized to afford Compound 97 (143.5 mg, 150.39 µmol, 38.08% yield) as an off white solid compound. LCMS (ESI+): 931.3 [M+H], 1H-NMR (400 MHz, DMSO-$d_6$) δ=12.60-12.33 (s, 1H), 10.79 (br s, 1H), 7.77-7.59 (m, 5H), 7.49 (d, J=3.6 Hz, 1H), 7.26 (d, J=3.6 Hz, 1H), 6.85 (t, J=9.2 Hz, 1H), 6.59-6.47 (m, 3H), 6.42 (br d, J=8.8 Hz, 1H), 6.15 (s, 1H), 5.78 (br d, J=7.6 Hz, 1H), 4.84-4.74 (m, 2H), 4.39 (s, 2H), 4.29-4.17 (m, 2H), 4.12-3.93 (m, 8H), 2.93-2.66 (m, 6H), 2.62-2.54 (m, 2H), 2.47 (br d, J=5.6 Hz, 2H), 2.22 (s, 2H), 2.09 (td, J=4.4, 8.0 Hz, 1H), 1.90-1.71 (m, 3H), 1.68-1.57 (m, 2H)

Example 98

2-(6,7-dihydro-5H-pyrrolo[1,2-c]imidazol-1-yl)-2-[6-[4-[2-[2-[1-[4-[[(3R)-2,6-dioxo-3-piperidyl]-amino]-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, Compound 98

Step 1: 2-[1-[4-[[(3R)-2,6-dioxo-3-piperidyl]amino]-2-fluoro-phenyl]-4-hydroxy-4-piperidyl] acetic acid

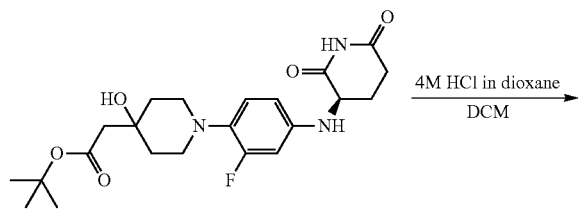

-continued

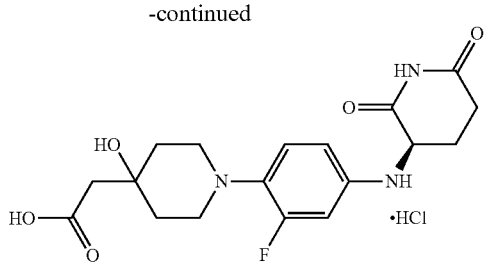

To a stirred solution of tert-butyl 2-[1-[4-[[(3R)-2,6-dioxo-3-piperidyl]amino]-2-fluoro-phenyl]-4-hydroxy-4-piperidyl]acetate (530 mg, 1.22 mmol) in dichloromethane (10 mL) at 0° C. was added hydrogen chloride (4M in 1,4-dioxane, 1.52 mL, 6.09 mmol) dropwise. After addition allow reaction to stirred at room temperature for 6 h. Volatiles were removed by rotary evaporation. The obtained residue was triturated with Diethyl ether (2×10 mL) two times. The solid residue was dried under rotary vacuum to afford 2-[1-[4-[[(3R)-2,6-dioxo-3-piperidyl]amino]-2-fluoro-phenyl]-4-hydroxy-4-piperidyl]acetic acid (470 mg, 928.08 μmol, 76.26% yield) as a bluish gray solid. LCMS (ESI+) m/z: 380.0 [M+H]$^+$. $^1$H-NMR (400 MHz, DMSO-d6): δ 12.01 (bs, 1H), 10.86 (s, 1H), 7.64 (s, 1H), 6.70 (d, J=15.60 Hz, 1H), 6.58 (d, J=8.80 Hz, 1H), 4.43 (dd, J=12.00, 4.40 Hz, 2H), 3.79-3.61 (m, 2H), 3.41-3.38 (m, 2H), 2.74-2.68 (m, 1H), 2.61-2.53 (m, 1H), 2.46 (s, 3H), 2.30-2.19 (m, 2H), 2.09-2.06 (m, 1H), 1.94-1.88 (m, 3H).

Step 2: 2-(6,7-dihydro-5H-pyrrolo[1,2-c]imidazol-1-yl)-2-[6-[4-[2-[2-[1-[4-[[(3R)-2,6-dioxo-3-piperidyl]amino]-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide

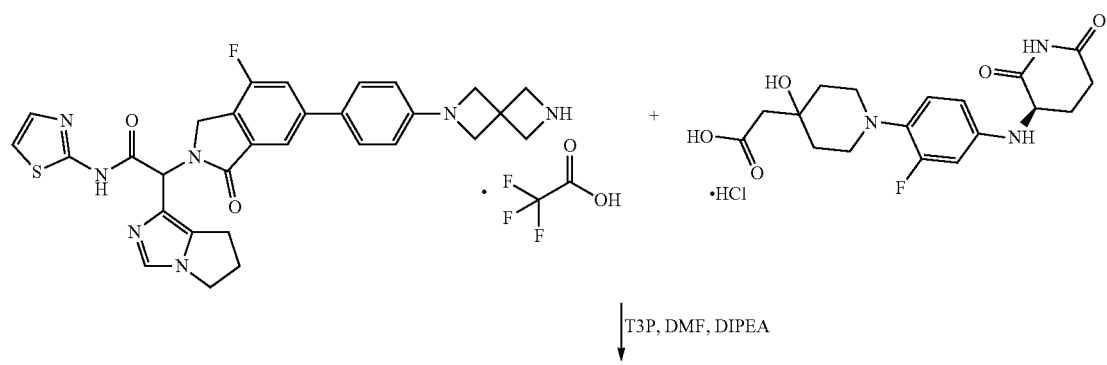

T3P, DMF, DIPEA

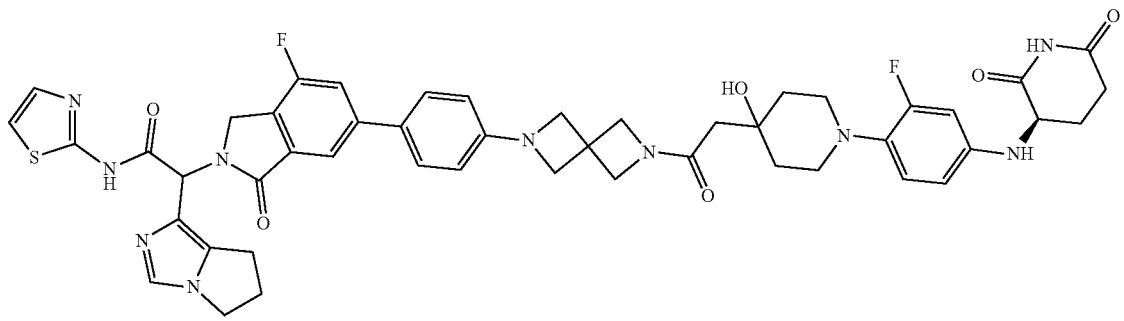

2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, 2,2,2-trifluoroacetic acid (220 mg, 321.79 µmol), and 2-[1-[4-[[(3R)-2,6-dioxo-3-piperidyl]amino]-2-fluoro-phenyl]-4-hydroxy-4-piperidyl]acetic acid; hydrochloride (160.58 mg, 386.15 µmol) were mixed in N,N-dimethylformamide (4 mL). N,N-diisopropylethylamine (207.95 mg, 1.61 mmol, 280.25 µL) was added to the reaction mixture at 0° C. Propyl phosphonic anhydride solution (50 wt. % in ethyl acetate, 204.77 mg, 643.58 µmol) was added to the reaction mixture at 0° C. The reaction mixture was stirred at ambient temperature for 2 h. The crude mixture was directly injected on a C18 column (100 g) for purification while eluting (0% to 50% of acetonitrile+0.1% ammonium acetate in water over 30 minutes, then steep gradient to 100% acetonitrile). The pure fraction was frozen and lyophilized to afford Compound 98 (88.39 mg, 93.64 µmol, 29.10% yield) as an off-white solid compound. LCMS (ESI+): 931.3 [M+H]. $^1$H-NMR (400 MHz, DMSO-d6): $^1$H-NMR (400 MHz, DMSO-d6): δ 12.58 (s, 1H), 10.78 (s, 1H), 7.75-7.70 (m, 2H), 7.65 (d, J=8.80 Hz, 2H), 7.61 (s, 1H), 7.49 (d, J=3.60 Hz, 1H), 7.26 (d, J=3.60 Hz, 1H), 6.86 (t, J=9.60 Hz, 1H), 6.55 (d, J=8.40 Hz, 2H), 6.50 (dd, J=2.40, 14.80 Hz, 1H), 6.42 (dd, J=2.40, 8.80 Hz, 1H), 6.15 (s, 1H), 5.78 (d, J=7.60 Hz, 1H), 4.82-4.76 (m, 2H), 4.39 (bs, 2H), 4.26-4.20 (m, 2H), 4.09 (bs, 2H), 4.05-3.96 (m, 6H), 2.90-2.82 (m, 4H), 2.77-2.68 (m, 3H), 2.23 (bs, 2H), 2.14-2.01 (m, 1H), 1.92-1.81 (m, 1H), 1.80-1.72 (m, 3H), 1.67-1.56 (m, 2H). (Proton signals were not observed due to water obscuration)

Example 99

2-(6,7-dihydro-5H-pyrrolo[1,2-c]imidazol-1-yl)-2-[6-[4-[2-[2-[1-[4-[(2,6-dioxo-3-piperidyl)amino]-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-N-(2-pyridyl)acetamide, Compound 99

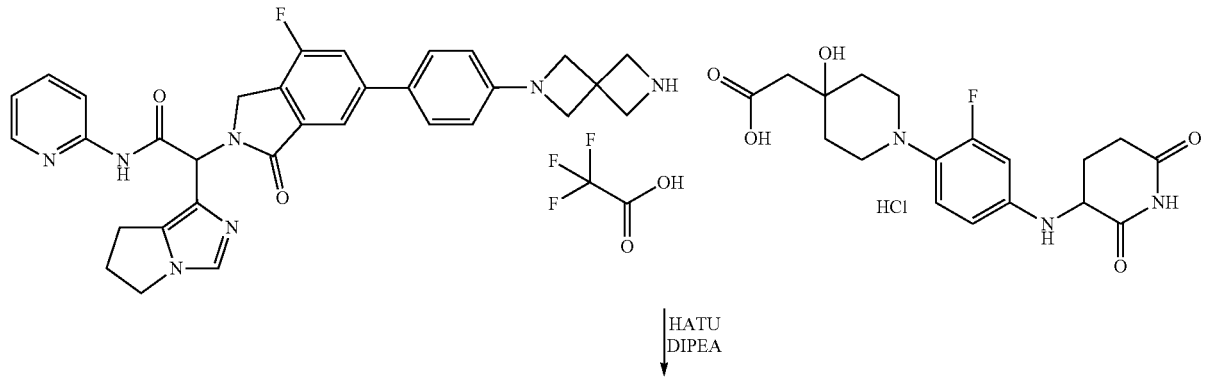

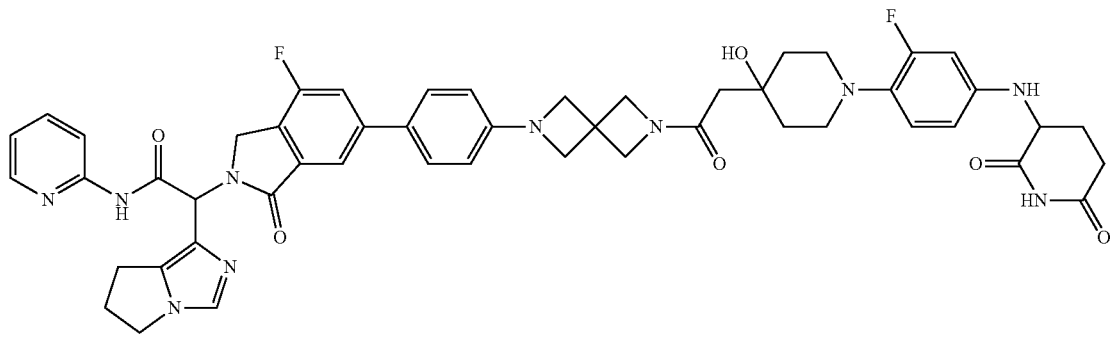

2-[1-[4-[(2,6-dioxo-3-piperidyl)amino]-2-fluoro-phenyl]-4-hydroxy-4-piperidyl]acetic acid hydrochloride (110 mg, 264.52 µmol) and 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-(2-pyridyl)acetamide, trifluoroacetic acid salt (179.25 mg, 264.52 µmol) were mixed in N,N-dimethylformamide, the reaction mixture was cooled to 0° C. N,N-diisopropylethylamine (170.93 mg, 1.32 mmol, 230.37 µL) was added to the reaction mixture, and 1-[bis(dimethylamino)methylene]-1H-1,2,3-triazolo[4,5-b]pyridinium 3-oxide hexafluorophosphate (110.64 mg, 290.98 µmol) was added, and the reaction mixture was stirred for 4 h. The mixture was injected on a 50 g C18 column and purified using a 0% to 100% acetonitrile in water (+0.1% trifluoroacetic acid) water elution gradient. The pure fractions were pooled, partitioned between ethyl acetate and sodium bicarbonate (aq., sat.). The organic layer was washed with brine, dried with sodium sulfate, filtered, and evaporated under reduced pressure. The residue was purified by silica gel chromatography (24 g column, 0% to 20% methanol in ethyl acetate). Pure fractions were evaporated under reduced pressure to afford Compound 99 (80 mg, 83.89 µmol, 31.71% yield). LCMS (ESI+). 925.3 (M+H)/463.4 (M+2H). $^1$H NMR (400 MHz, DMSO-$d_6$) δ 10.83 (s, 1H), 10.71 (s, 1H), 8.25 (ddd, J=4.9, 2.0, 0.9 Hz, 1H), 8.00 (d, J=8.4 Hz, 1H), 7.72 (ddd, J=8.7, 7.4, 2.0 Hz, 1H), 7.67 (s, 1H), 7.62 (d, J=10.7 Hz, 1H), 7.60-7.42 (m, 3H), 7.05 (ddd, J=7.4, 4.9, 1.1 Hz, 1H), 6.78 (dd, J=10.0, 8.7 Hz, 1H), 6.47 (d, J=8.5 Hz, 2H), 6.43 (dd, J=15.1, 2.6 Hz, 1H), 6.34 (dd, J=8.7, 2.6 Hz, 1H), 6.13 (s, 1H), 5.70 (d, J=7.6 Hz, 1H), 4.72 (d, J=17.7 Hz, 1H), 4.69 (s, 1H), 4.31 (s, 2H), 4.23-4.09 (m, 2H), 4.01 (s, 2H), 3.99-3.84 (m, 6H), 2.96-2.57 (m, 4H), 2.57-2.45 (m, 2H), 2.15 (s, 2H), 2.08-1.91 (m, 1H), 1.92-1.64 (m, 3H), 1.55 (d, J=12.4 Hz, 2H).

Example 100

2-(6,7-dihydro-5H-pyrrolo[1,2-c]imidazol-1-yl)-2-[6-[4-[6-[2-[4-[[(3S)-2,6-dioxo-3-piperidyl]amino]-2-fluoro-phenyl]-1-piperidyl]-2-oxo-ethyl]-2-azaspiro[3.3]heptan-2-yl]phenyl]-4-fluoro-1-oxo-isoindolin-2-yl]-N-thiazol-2-yl-acetamide, Compound 100

Step 1: ethyl 2-[2-[4-(4,4,5,5-tetramethyl-1,3,2-dioxaborolan-2-yl)phenyl]-2-azaspiro[3.3]heptan-6-yl]acetate

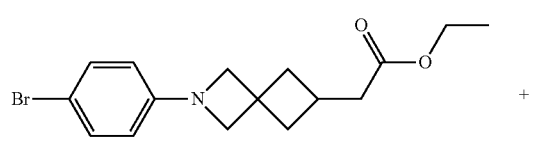

-continued

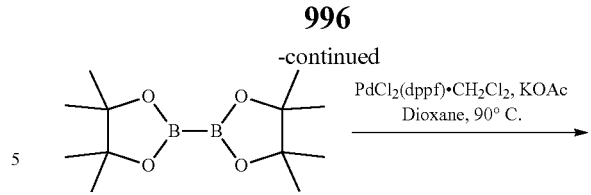

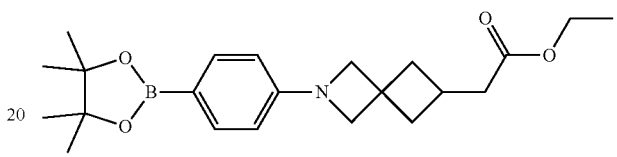

In a 100 mL sealed-tube containing a well-stirred solution of ethyl 2-[2-(4-bromophenyl)-2-azaspiro[3.3]heptan-6-yl]acetate (2.2 g, 6.50 mmol) and 4,4,5,5-tetramethyl-2-(4,4,5,5-tetramethyl-1,3,2-dioxaborolan-2-yl)-1,3,2-dioxaborolane (2.48 g, 9.76 mmol) in 1,4-dioxane (25 mL) was added potassium Acetate (1.92 g, 19.51 mmol, 1.22 mL) and the resulting mixture was degassed with nitrogen for 15 minutes. Subsequently, [1,1'-Bis(diphenylphosphino)ferrocene]dichloropalladium (II), complex with dichloromethane (531.17 mg, 650.43 µmol) was added to the reaction mixture and further degassed with nitrogen gas for 5 minutes and heated at 90° C. for 16 h. The reaction mixture was diluted with ethyl acetate and filtered through celite. The filtrate was washed with ice cold water and extracted using ethyl acetate (3×75 mL). The organic layer was further washed with brine solution, dried over sodium sulfate and concentrated under reduced pressure to get crude. The resulting crude residue was purified by column chromatography using silica (100-200 mesh) with 0-6% ethyl acetate in petroleum ether to get ethyl 2-[2-[4-(4,4,5,5-tetramethyl-1,3,2-dioxaborolan-2-yl)phenyl]-2-azaspiro[3.3]heptan-6-yl]acetate (1.8 g, 3.83 mmol, 58.90% yield). LCMS (ESI+) m/z: 386.2 [M+H]$^+$.

Step 2: ethyl 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptan-6-yl]acetate

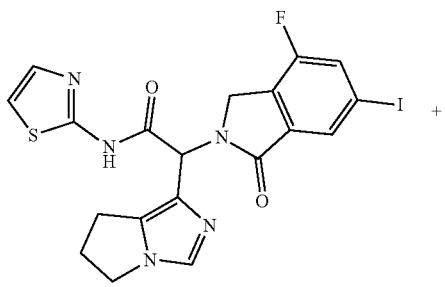

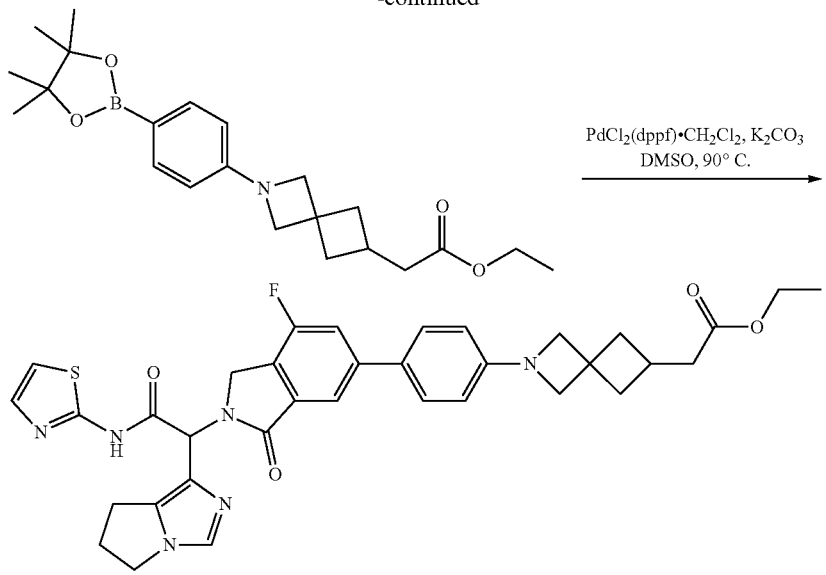

In a 100 mL Two-necked round-bottomed flask containing a well-stirred solution of 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (450 mg, 859.89 μmol) and ethyl 2-[2-[4-(4,4,5,5-tetramethyl-1,3,2-dioxaborolan-2-yl)phenyl]-2-azaspiro[3.3]heptan-6-yl]acetate (397.58 mg, 1.03 mmol) in DMSO (5 mL) was added Potassium carbonate, anhydrous, 99% (297.11 mg, 2.15 mmol, 129.74 μL) in Water (0.5 mL) and the resulting mixture was degassed with bubbling nitrogen for 10 min. Subsequently, [1,1'-Bis(diphenylphosphino)ferrocene]dichloropalladium(II), complex with dichloromethane (70.22 mg, 85.99 μmol) was added to the reaction mixture and further degassed with nitrogen for 5 minutes and heated at 90° C. in a heating block for 16 h under nitrogen atmosphere. The reaction mixture was diluted with ethyl acetate and filtered through celite. The filtrate was washed with ice cold water and the aqueous layer was extracted with ethyl acetate (2×100 mL). The organic layers were washed with brine, dried over sodium sulfate and concentrated under reduced pressure to get 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptan-6-yl]acetate (380 mg, 249.56 μmol, 29.02% yield). LCMS(ESI+) m/z: 655.3 [M+H]⁺.

Step 3: 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptan-6-yl]acetic acid

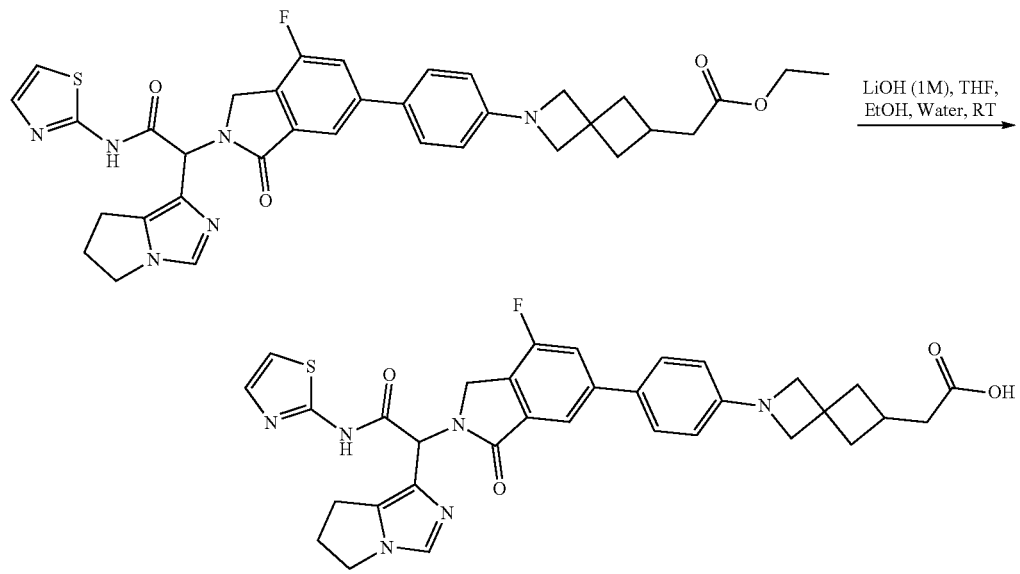

Into a 50 mL Single-necked round-bottomed flask containing a well-stirred solution of ethyl 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptan-6-yl]acetate (375 mg, 572.74 mol) in tetrahydrofuran (2 mL) and Methanol (2 mL) and Water (2 mL) was added 1M LiOH (13.72 mg, 572.74 μmol) at 0° C. Reaction mixture was stirred at room temperature for 3 hr. The reaction mixture was concentrated under reduced pressure, and the crude residue was purified using reverse phase chromatography (30 g HP Redisep Gold C18) column for purification while eluting (0-60% of acetonitrile in water+ 0.1% ammonium acetate over 30 minutes, then steep gradient to 100% acetonitrile). The pure fractions were collected and concentrated under reduced pressure to get 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptan-6-yl]acetic acid (82 mg, 113.83 μmol, 19.88% yield). LCMS (ESI+) m/z: 627.2 (M+H)$^+$.

Step 4: 2-(6,7-dihydro-5H-pyrrolo[1,2-c]imidazol-1-yl)-2-[6-[4-[6-[2-[4-[4-[[(3S)-2,6-dioxo-3-piperidyl]amino]-2-fluoro-phenyl]-1-piperidyl]-2-oxo-ethyl]-2-azaspiro[3.3]heptan-2-yl]phenyl]-4-fluoro-1-oxo-isoindolin-2-yl]-N-thiazol-2-yl-acetamide

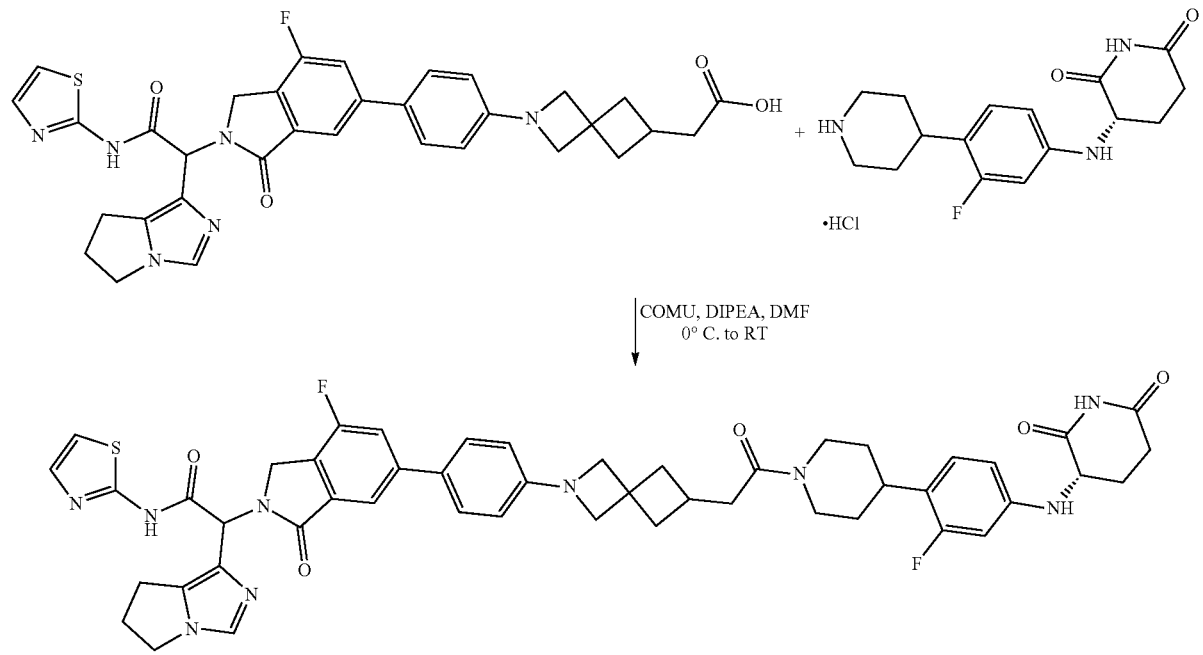 [SMILES: O=C(O)CC1CC2(C1)CN(c1ccc(-c3cc(F)c4c(c3)C(=O)N(C(C(=O)Nc3nccs3)c3ncn5c3CCC5)C4)cc1)C2 ; Cl ; O=C1CC[C@H](Nc2ccc(C3CCNCC3)c(F)c2)C(=O)N1 ; O=C1CC[C@H](Nc2ccc(C3CCN(C(=O)CC4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1]

Into a 10 mL single-necked round-bottomed flask containing a well-stirred solution of 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptan-6-yl]acetic acid (80.00 mg, 127.65 μmol) and (3S)-3-[3-fluoro-4-(4-piperidyl)anilino]piperidine-2,6-dione; hydrochloride (46.77 mg, 136.84 μmol) were mixed in N,N-dimethylformamide (1 mL) under nitrogen atmosphere and the resulting mixture was added N,N-diisopropylethylamine (82.49 mg, 638.26 mol, 111.17 μL) at 0° C. Subsequently, (1-Cyano-2-ethoxy-2-oxoethylidenaminooxy)dimethylamino-morpholino-carbenium hexafluorophosphate (109.34 mg, 255.31 μmol) was added and the reaction mixture was stirred for 1 h while warming to room temperature. The crude was directly injected in reverse phase C18 chromatography (0-55% of acetonitrile in water+ 0.1% ammonium acetate over 30 minutes, then steep gradient to 100% acetonitrile). The pure fractions were frozen and lyophilized to get Compound 100 (44.6 mg, 47.30 μmol, 37.1% yield) as an off-white solid. LCMS (ESI+) m/z: 914.0 [M+H]$^+$. LCMS (ESI−): 912.2 (M−H); 1H-NMR (400 MHz, DMSO-d6): δ 12.52 (s, 1H), 10.80 (s, 1H), 7.73 (s, 1H), 7.70 (d, J=10.80 Hz, 1H), 7.68 (s, 1H), 7.62 (d, J=3.60 Hz, 2H), 7.47 (s, 1H), 7.23 (s, 1H), 6.98 (t, J=8.80 Hz, 1H), 6.51 (s, 1H), 6.48 (d, J=6.40 Hz, 2H), 6.44 (d, J=2.00 Hz, 1H), 6.13 (s, 1H), 6.04 (d, J=7.60 Hz, 1H), 4.80 (d, J=5.60 Hz, 1H), 4.50 (d, J=4.00 Hz, 1H), 4.38-4.32 (m, 1H), 4.21 (d, J=17.60 Hz, 1H), 4.02-3.97 (m, 3H), 3.91 (s, 2H), 3.78 (s, 2H), 3.09 (t, J=8.80 Hz, 1H), 2.91-2.87 (m, 1H), 2.77-2.71 (m, 2H), 2.68 (s, 1H), 2.60-2.55 (m, 4H), 2.46 (m, 2H), 2.36-2.34 (m, 2H), 2.15-2.08 (m, 1H), 1.92-1.89 (m, 3H), 1.72-1.65 (m, 2H), 1.51-1.50 (m, 1H).
Example 101
2-(6,7-dihydro-5H-pyrrolo[1,2-c]imidazol-1-yl)-2-[6-[4-[2-[2-[1-[4-[(2,6-dioxo-3-piperidyl)amino]-2,6-difluoro-phenyl]-4-piperidyl]acetyl]-2,6-diazaspiro[3.3]heptan-6-yl]phen-yl]-4-fluoro-1-oxo-isoindolin-2-yl]-N-thiazol-2-yl-acetamide, Compound 101
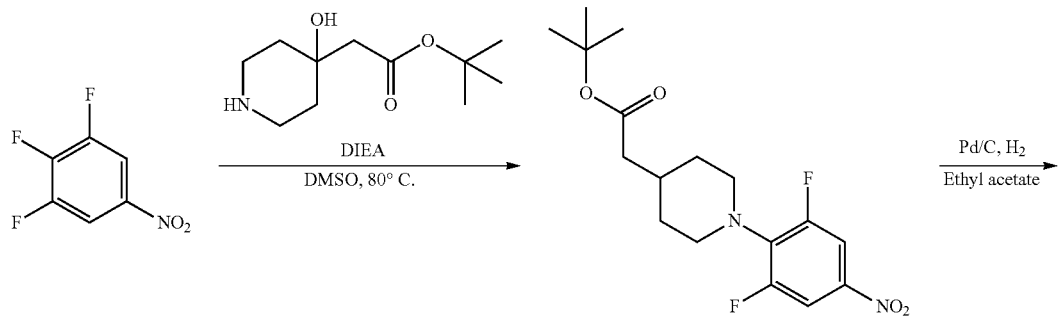
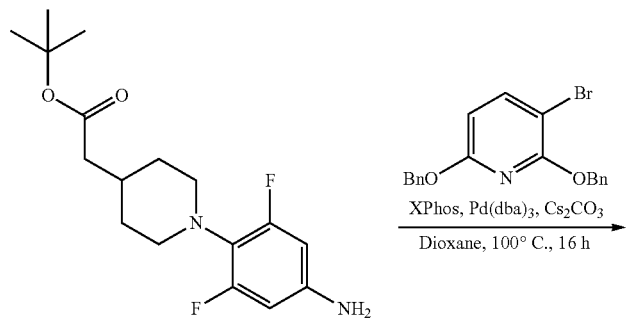
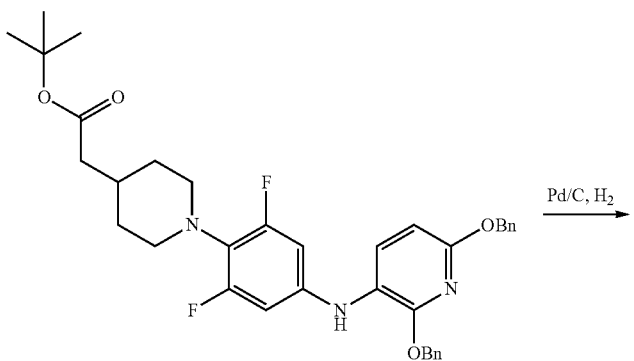

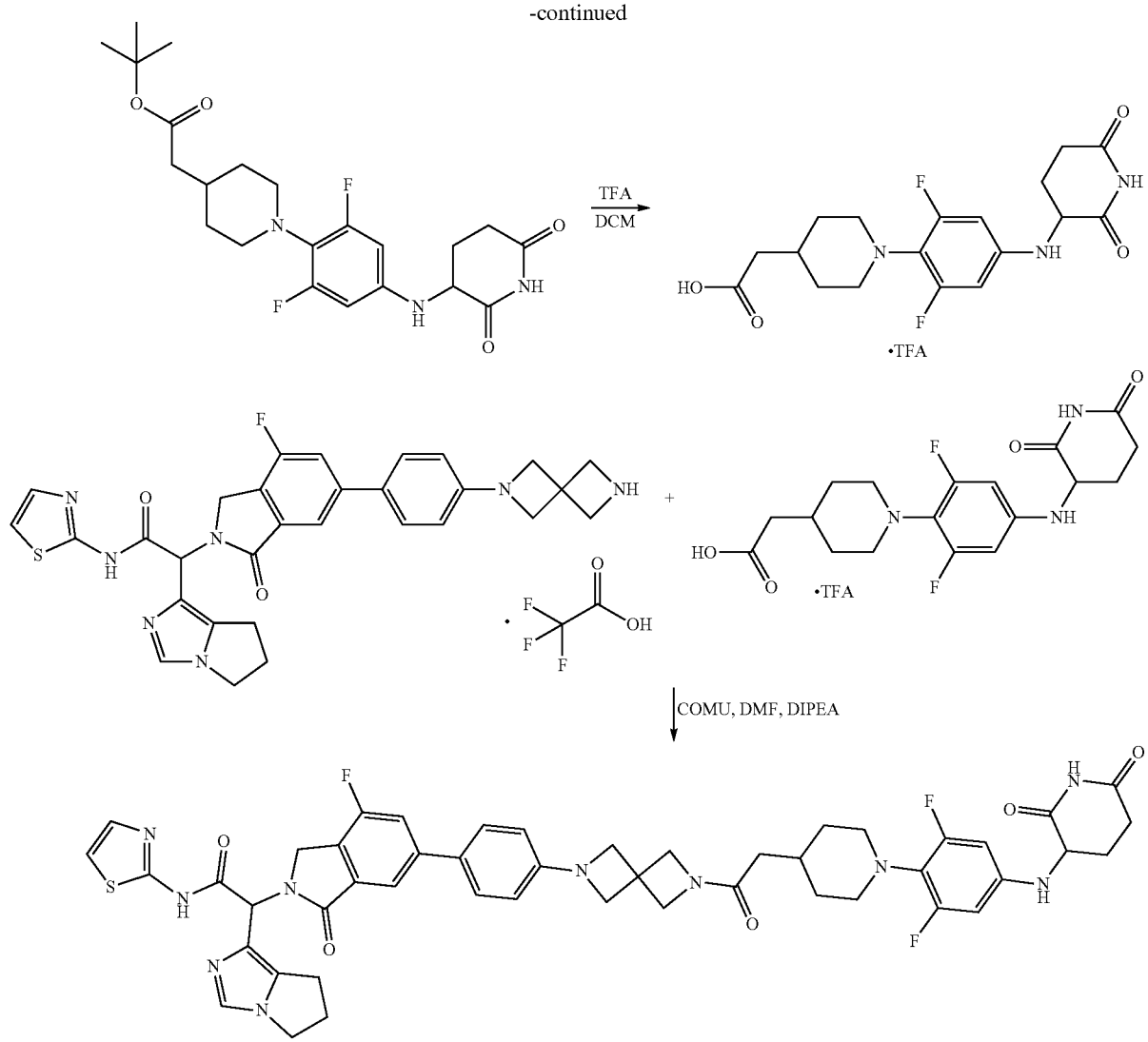

Step 1: Methyl 2-[1-(2,6-difluoro-4-nitro-phenyl)-4-piperidyl]acetate

To a stirred solution of methyl 2-(4-piperidyl)acetate (1.7 g, 10.81 mmol) in DMSO (20 mL) in a round bottom flask was added N,N-diisopropyl ethyl amine (6.99 g, 54.07 mmol, 9.42 mL) dropwise, was added 1,2,3-trifluoro-5-nitro-benzene (2.30 g, 12.98 mmol) slowly after 5 minutes, the temperature of the reaction was raised to 80° C. and continued the reaction for 3 h. The reaction mixture was diluted with ice-cold water. The solid precipitate was filtered and the solid was washed with water, the solid was dried to get methyl 2-[1-(2,6-difluoro-4-nitro-phenyl)-4-piperidyl]acetate (1.5 g, 4.49 mmol, 41.49% yield) as a yellow colored product. LCMS m/z 315.1 (M+H$^+$)

Step 2: Methyl 2-[1-(4-amino-2,6-difluoro-phenyl)-4-piperidyl]acetate

A stirred solution of methyl 2-[1-(2,6-difluoro-4-nitro-phenyl)-4-piperidyl]acetate (1.5 g, 4.77 mmol) in Ethyl acetate (15 mL) was purged with nitrogen for 5 minutes and was added Palladium, 10% on carbon, Type 487, dry (558.71 mg, 5.25 mmol) the reaction mixture was hydrogenated at bladder pressure. the reaction was stirred for 5 h at room temperature. The reaction mixture was diluted with ethyl acetate and filtered through celite. the filtrate was concentrated under reduced pressure to afford light brown solid was triturated with pentane and dried under vacuum to afford methyl 2-[1-(4-amino-2,6-difluoro-phenyl)-4-piperidyl]acetate (1.2 g, 4.01 mmol, 84.02% yield). LCMS m/z 285.1 (M+H$^+$).

Step 3: methyl 2-[1-[4-[(2,6-dibenzyloxy-3-pyridyl)amino]-2,6-difluoro-phenyl]-4-piperidyl]acetate To a solution of methyl 2-[1-(4-amino-2,6-difluoro-phenyl)-4-piperidyl]acetate (800 mg, 2.81 mmol) and 2,6-dibenzyloxy-3-bromo-pyridine (1.25 g, 3.38 mmol) in 1,4-dioxane (8 mL) was degassed with nitrogen for 10 mints. Cesium carbonate (2.75 g, 8.44 mmol) and 4,5-Bis(diphenylphosphino)-9,9-dimethylxanthene (162.82 mg, 281.39 μmol) as well as Tris(Dibenzylideneacetone)dipalladium (0) (128.84 mg, 140.70 μmol) was added to the reaction mixture and purged with nitrogen gas for 5 minutes. The reaction mixture was heated at 100° C. for 16 h under inert atmosphere. The reaction mixture was diluted with ethyl acetate and filtered through celite. The filtrate washed with ethyl acetate and concentrated under reduced pressure to get crude. The crude was purified by (230-400) silica gel chromatography using a 10% ethyl acetate in petroleum ether mixture as an eluent. The pure fractions were collected and evaporated under reduced pressure to afford methyl 2-[1-[4-[(2,6-dibenzyloxy-3-pyridyl)amino]-2,6-difluoro-phenyl]-4-piperidyl]acetate (570 mg, 944 μmol, 33.5% yield). LCMS m/z 574.3 (M+H$^+$)

Step 4: methyl 2-[1-[4-[(2,6-dioxo-3-piperidyl) amino]-2,6-difluoro-phenyl]-4-piperidyl]acetate A stirred solution of methyl 2-[1-[4-[(2,6-dibenzyloxy-3-pyridyl)amino]-2,6-difluoro-phenyl]-4-piperidyl]acetate (500 mg, 871.64 μmol) in 1,4-dioxane (5 mL) was purged with nitrogen for 5 min and was added palladium hydroxide on carbon 10% (183.61 mg, 1.31 mmol) the reaction mixture was hydrogenated at bladder pressure. The reaction was stirred for 16 hr at room temperature. The reaction mixture diluted with ethyl acetate and filtered through celite. The filtrate was concentrated under reduced pressure to afford methyl 2-[1-[4-[(2,6-dioxo-3-piperidyl)amino]-2,6-difluoro-phenyl]-4-piperidyl]acetate (330 mg, 742.79 μmol, 85.22% yield). LCMS m/z 396.0 (M+H$^+$)

Step 5: 2-[1-[4-[(2,6-dioxo-3-piperidyl)amino]-2,6-difluoro-phenyl]-4-piperidyl]acetic acid To a stirred solution of methyl 2-[1-[4-[(2,6-dioxo-3-piperidyl)amino]-2,6-difluoro-phenyl]-4-piperidyl]acetate (320 mg, 809.31 μmol) in hydrochloric acid (6N) (809.31 μmol, 7 mL) was added at 0° C. and reaction mixture was stirred for 16 h. 1,4-dioxane was added to the reaction mixture. The volatiles were evaporated under reduced pressure. The crude was purified by reverse phase chromatography (C18 column, 0-100% of 0.1% ammonium acetate in water and acetonitrile). Fractions were concentrated to afford 2-[1-[4-[(2,6-dioxo-3-piperidyl)amino]-2,6-difluoro-phenyl]-4-piperidyl]acetic acid (210 mg, 490 μmol, 60.5% yield). LCMS: 382.1 (M+H$^+$)

Step 6: 2-(6,7-dihydro-5H-pyrrolo[1,2-c]imidazol-1-yl)-2-[6-[4-[2-[2-[1-[4-[(2,6-dioxo-3-piperidyl) amino]-2,6-difluoro-phenyl]-4-piperidyl]acetyl]-2,6-diazaspiro[3.3]heptan-6-yl]phen-yl]-4-fluoro-1-oxo-isoindolin-2-yl]-N-thiazol-2-yl-acetamide To a solution of 2-[1-[4-[(2,6-dioxo-3-piperidyl)amino]-2,6-difluoro-phenyl]-4-piperidyl]acetic acid (170 mg, 445.76 μmol) in N,N-dimethylformamide (2 mL) was added N, N-diisopropylethylamine (288.05 mg, 2.23 mmol, 388.21 μL) at 0° C. 1-[(1-(Cyano-2-ethoxy-2-oxoethylideneaminooxy)-dimethylamino-morpholino)] uronium hexafluorophosphate (380.93 mg, 891.52 μmol) was added to the mixture while maintaining 0° C. After 10 minutes, 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, 2,2,2-trifluoroacetic acid (243.80 mg, 356.61 μmol), was added to the reaction mixture at 0° C. The reaction mixture was stirred at ambient temperature for 1 h. The crude mixture was directly injected on a C18 column (100 g) for purification while eluting (0% to 50% of acetonitrile+0.1% ammonium acetate in water over 30 minutes, then steep gradient to 100% acetonitrile). The pure fraction was frozen and lyophilized to afford Compound 101 (27 mg, 28.07 μmol, 6.30% yield) as an off-white solid compound. LCMS (ESI+): 933.4 [M+H]. 1H-NMR (400 MHz, DMSO-d6): δ 12.55 (s, 1H), 10.82 (s, 1H), 7.75-7.64 (m, 5H), 7.49 (d, J=2.80 Hz, 1H), 7.27 (d, J=3.20 Hz, 1H), 6.54 (d, J=8.00 Hz, 2H), 6.32 (d, J=12.00 Hz, 2H), 6.24 (d, J=7.20 Hz, 1H), 6.16 (s, 1H), 4.80 (d, J=17.60 Hz, 1H), 4.33-4.21 (m, 4H), 4.13-4.02 (m, 8H), 2.92 (bs, 4H), 2.78-2.68 (m, 2H), 2.65-2.57 (m, 2H), 2.12-1.90 (m, 3H), 1.92-1.65 (m, 5H), 1.29 (s, 2H) (Some proton signals were not observed due to water obscuration).

Example 102

2-(6,7-dihydro-5H-pyrrolo[1,2-c]imidazol-1-yl)-2-(6-(4-(6-(2-(4-(3-(2,4-dioxotetra-hydropyrimidin-1 (2H)-yl)-1-methyl-1H-indazol-6-yl)-3,3-difluoropiperidin-1-yl)-2-oxoethyl)-2-azaspiro[3.3]heptan-2-yl) phenyl)-4-fluoro-1-oxoisoindolin-2-yl)-N-(thiazol-2-yl)acetamide, Compound 102

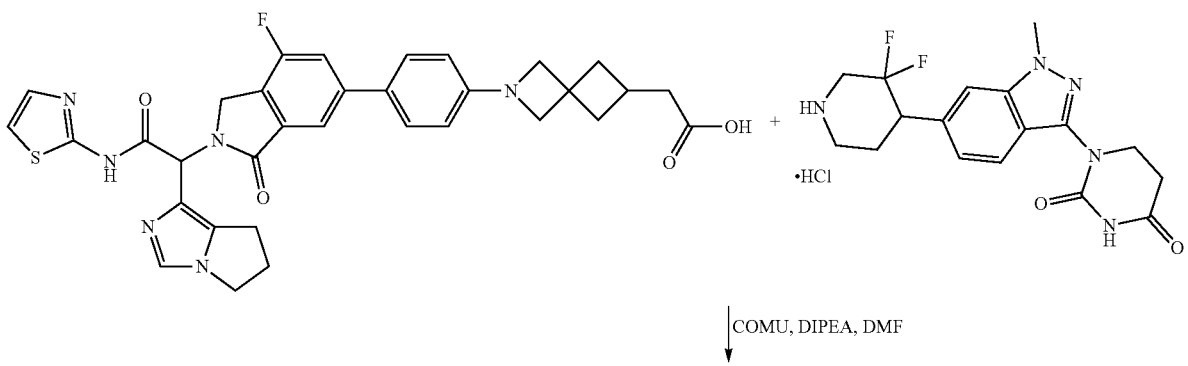

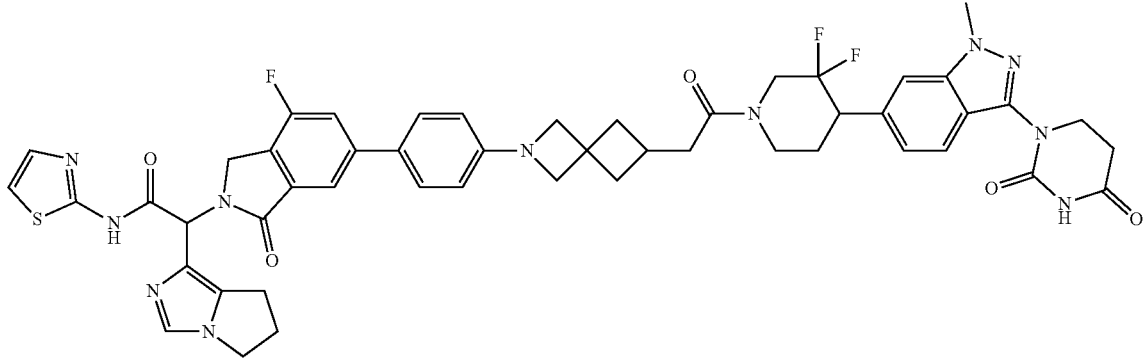

2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptan-6-yl]acetic acid (160 mg, 255.31 μmol) and 1-[6-(3,3-difluoro-4-piperidyl)-1-methyl-indazol-3-yl]hexahydropyrimidine-2,4-dione hydrochloride (91.87 mg, 229.78 μmol) were mixed in N,N-dimethylformamide (1.5 mL). N,N-diisopropylethyl amine (164.98 mg, 1.28 mmol, 222.35 μL) was added to the reaction mixture at 0° C. 1-[Bis(dimethylamino)methylene]-1H-1,2,3-triazolo[4,5-b]pyridinium 3-oxide hexafluorophosphate (194.15 mg, 510.61 μmol) was added at the same temperature. The reaction mixture was stirred at ambient temperature for 1 h. The crude mixture was directly injected on a C18 column (60 g) for purification while eluting (0% to 50% of acetonitrile+0.1% ammonium acetate in water over 30 minutes, then steep gradient to 100% acetonitrile). The pure fraction was frozen and lyophilized to afford Compound 102 (61 mg, 62.21 μmol, 24.37% yield) as an off-white solid compound. LCMS (ESI+): 972.3, [M+H]);

1H-NMR (400 MHz, DMSO-d6): δ 12.53 (s, 1H), 10.58 (s, 1H), 7.74 (s, 1H), 7.70 (d, J=10.80 Hz, 1H), 7.63-7.59 (m, 4H), 7.56 (d, J=6.40 Hz, 1H), 7.49 (d, J=3.20 Hz, 1H), 7.26 (d, J=3.20 Hz, 1H), 7.09-7.06 (m, 1H), 6.52-6.49 (m, 2H), 6.15 (s, 1H), 4.82-4.78 (m, 2H), 4.62-4.53 (m, 1H), 4.37-4.26 (m, 1H), 4.21 (d, J=17.60 Hz, 1H), 4.13-3.87 (m, 10H), 3.79 (d, J=7.20 Hz, 2H), 3.62-3.54 (m, 2H), 3.09 (dd, J=13.20, 32.60 Hz, 1H), 2.85-2.77 (m, 4H), 2.68-2.60 (m, 3H), 2.46-2.34 (m, 2H), 2.30-2.10 (m, 1H), 1.94-1.90 (m, 3H).

Example 103

2-(6,7-dihydro-5H-pyrrolo[1,2-c]imidazol-1-yl)-2-[6-[4-[2-[2-[1-[4-[(2,6-dioxo-3-piperidyl)-amino]-2,6-difluoro-phenyl]-4-hydroxy-4-piperidyl]acetyl]-2,6-diazaspiro[3.3]hept-an-6-yl]-phenyl]-4-fluoro-1-oxo-isoindolin-2-yl]-N-thiazol-2-yl-acetamide, Compound 103

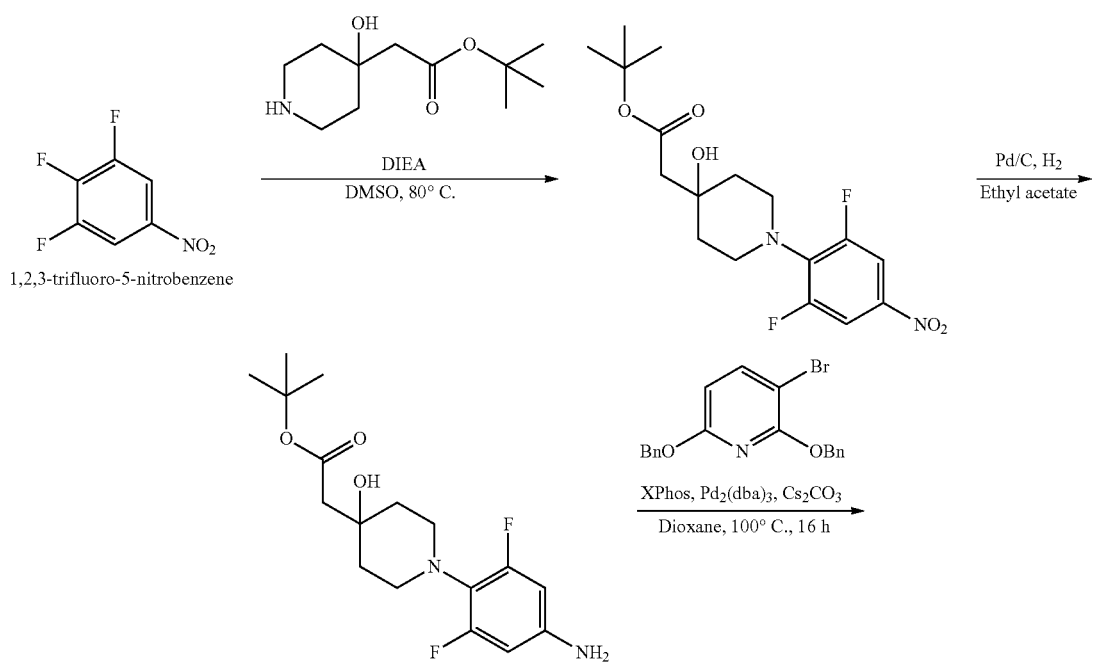

-continued
1009
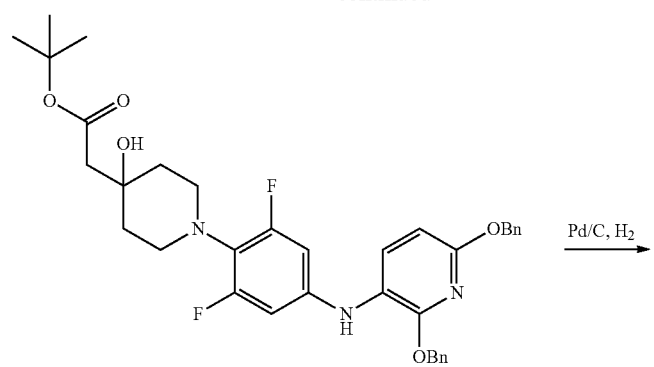
1010
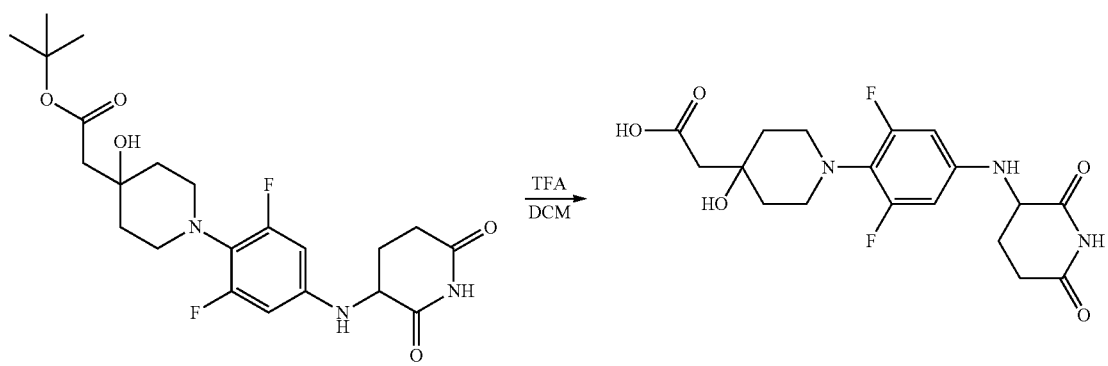
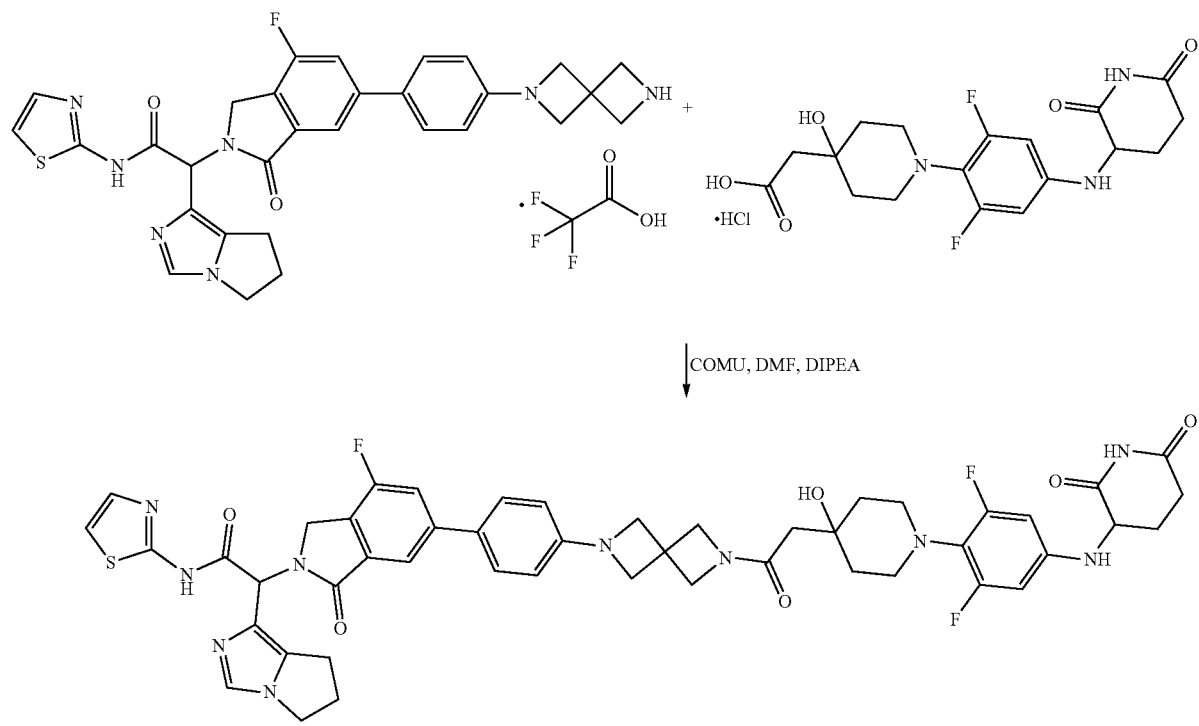

Step 1: tert-Butyl 2-[1-(2,6-difluoro-4-nitro-phenyl)-4-hydroxy-4-piperidyl]acetate To a solution of tert-butyl 2-(4-hydroxy-4-piperidyl)acetate (6.69 g, 31.06 mmol) and 1,2,3-trifluoro-5-nitrobenzene (5 g, 28.24 mmol) in DMSO (50 mL) was added N,N-diisopropylethylamine (10.95 g, 84.71 mmol, 14.75 mL). The mixture was stirred at 80° C. for 1 h. The mixture was poured into water (200 mL). The precipitated solid was collected by filtering and dried under high vacuum without purification to afford tert-butyl 2-[1-(2,6-difluoro-4-nitro-phenyl)-4-hydroxy-4-piperidyl]acetate (10.5 g, 24.81 mmol, 87.88% yield) as a yellow oil. $^1$H NMR (400 MHz, DMSO-d6) δ=7.95 (d, J=10.4 Hz, 2H), 4.66 (s, 1H), 3.47-3.39 (m, 2H), 3.25 (d, J=12.8 Hz, 2H), 2.37 (s, 2H), 1.82-1.72 (m, 2H), 1.69-1.62 (m, 2H), 1.41-1.40 (s, 9H).

Step 2: tert-Butyl 2-(1-(4-amino-2,6-difluorophenyl)-4-hydroxypiperidin-4-yl) acetate To a solution of tert-butyl 2-[1-(2,6-difluoro-4-nitro-phenyl)-4-hydroxy-4-piperidyl]acetate (10 g, 26.86 mmol) in ethyl acetate (100 mL) was added palladium, 10% on charcoal (6.00 g, 4.94 mmol) under $N_2$ atmosphere. The suspension was degassed and purged with $H_2$ for 3 times. The mixture was stirred under $H_2$ (15 Psi) at 25° C. for 6 h. The reaction mixture was filtered, the filtrate was concentrated in vacuum to give tert-butyl 2-(1-(4-amino-2,6-difluorophenyl)-4-hydroxypiperidin-4-yl) acetate (9.1 g, 25.24 mmol, 94.02% yield) as yellow oil. $^1$H NMR (400 MHz, DMSO-d6) δ=6.16-6.06 (m, 2H), 5.38 (s, 2H), 4.40 (s, 1H), 3.17 (d, J=5.2 Hz, 2H), 2.70-2.62 (m, 2H), 2.32 (s, 2H), 1.74-1.65 (m, 2H), 1.58 (br d, J=12.4 Hz, 2H), 1.41 (s, 9H).

Step 3: tert-Butyl 2-(1-(4-((2,6-bis(benzyloxy)pyridin-3-yl)amino)-2,6-difluorophenyl)-4-hydroxypiperidin-4-yl)acetate A stirred solution of tert-butyl 2-[1-(4-amino-2,6-difluoro-phenyl)-4-hydroxy-4-piperidyl]acetate (8.7 g, 25.41 mmol), 2,6-dibenzyloxy-3-bromo-pyridine (12.47 g, 33.68 mmol) and $CS_2CO_3$ (27.41 g, 76.23 mmol) in 1,4-dioxane (360 mL), the reaction mixture was degassed with nitrogen for 15 minutes. Xphos (1.34 g, 2.54 mmol) and $Pd_2(dba)_3$ (2.57 g, 2.54 mmol) were added and the mixture was degassed with nitrogen for 5 minutes. The reaction mixture was heated to 100° C. for 16 h. The reaction mixture was concentrated, diluted with water. The mixture was extracted with ethyl acetate (200 mL×3). The combined organic phase was washed with brine (200×2 mL), dried with anhydrous sodium sulfate, filtered, and concentrated in vacuum to give a residue. The residue was purified by silica gel chromatography (Petroleum ether/Ethyl acetate=5:1) to afford tert-butyl 2-[1-[4-[(2,6-dibenzyloxy-3-pyridyl)amino]-2,6-difluoro-phenyl]-4-hydroxy-4-piperidyl]acetate (12.75 g, 19.17 mmol, 75.5% yield) as a yellow oil. LCMS (ESI): m/z 632.2 [M+H]$^+$, $^1$H NMR (400 MHz, DMSO-d6) δ=7.61 (s, 1H), 7.54 (d, J=8.4 Hz, 1H), 7.43-7.27 (m, 10H), 6.44 (d, J=8.4 Hz, 1H), 6.28-6.21 (m, 2H), 5.38 (s, 2H), 5.30 (s, 2H), 4.44 (s, 1H), 3.23 (t, J=10.4 Hz, 2H), 2.76-2.68 (m, 2H), 2.33 (s, 2H), 1.77-1.67 (m, 2H), 1.64-1.57 (m, 2H), 1.41 (s, 9H).

Step 4: tert-Butyl 2-(1-(4-((2,6-dioxopiperidin-3-yl)amino)-2,6-difluorophenyl)-4-hydroxypiperidin-4-yl)acetate To a solution of tert-butyl 2-[1-[4-[(2,6-dibenzyloxy-3-pyridyl)amino]-2,6-difluoro-phenyl]-4-hydroxy-4-piperidyl]acetate (12.75 g, 20.18 mmol) in 1,4-dioxane (850 mL) was added Pd/C (8.29 g, 68.24 mmol) under $N_2$ atmosphere. The suspension was degassed and purged with $H_2$ for 3 times. The mixture was stirred under $H_2$ (15 Psi) at 25° C. for 16 h. The reaction mixture was filtered, the mother solution concentrated in vacuum to afford tert-butyl 2-(1-(4-((2,6-dioxopiperidin-3-yl)amino)-2,6-difluorophenyl)-4-hydroxypiperidin-4-yl)acetate (8.5 g, 16.49 mmol, 81.72% yield). LCMS (ESI): m/z 454.1 [M+H]$^+$, $^1$H NMR (400 MHz, DMSO-d6) δ=10.80 (s, 1H), 6.30 (d, J=12.0 Hz, 2H), 6.20 (d, J=8.0 Hz, 1H), 4.44-4.39 (m, 1H), 4.35-4.26 (m, 1H), 3.26-3.19 (m, 2H), 2.74-2.66 (m, 1H), 2.71-2.65 (m, 1H), 2.61-2.56 (m, 1H), 2.33 (s, 2H), 2.11-2.01 (m, 1H), 1.90-1.79 (m, 1H), 1.75-1.66 (m, 2H), 1.63-1.56 (m, 2H), 1.41 (s, 9H)

Step 5: 2-[1-[4-[(2,6-dioxo-3-piperidyl)amino]-2,6-difluoro-phenyl]-4-hydroxy-4-piperidyl]acetic acid hydrochloride To a stirred solution of tert-butyl 2-[1-[4-[(2,6-dioxo-3-piperidyl)amino]-2,6-difluoro-phenyl]-4-hydroxy-4-piperidyl]acetate (200 mg, 441.04 μmol) in dichloromethane (2 mL) was cooled at 0° C. and added hydrogen chloride (4M in 1,4-dioxane, 1.1 mL, 4.41 mmol) drop wise into reaction mixture. After addition allow the reaction mixture stirred at room temperature for 16 h. The reaction mixture was evaporated under reduced pressure. The obtained solid was washed by diethyl ether (30 mL) to afford crude solid 2-[1-[4-[(2,6-dioxo-3-piperidyl)amino]-2,6-difluoro-phenyl]-4-hydroxy-4-piperidyl]acetic acid hydrochloride (182 mg, 394.97 μmol, 89.56% yield). This crude compound was carried forward next step without purification. LCMS m/z: 398.1 [M+1]

Step 6: 2-(6,7-dihydro-5H-pyrrolo[1,2-c]imidazol-1-yl)-2-[6-[4-[2-[2-[1-[4-[(2,6-dioxo-3-piper-idyl)amino]-2,6-difluoro-phenyl]-4-hydroxy-4-piperidyl]acetyl]-2,6-diazaspiro[3.3]heptan-6-yl]-phenyl]-4-fluoro-1-oxo-isoindolin-2-yl]-N-thiazol-2-yl-acetamide To a solution of 2-[1-[4-[(2,6-dioxo-3-piperidyl)amino]-2,6-difluoro-phenyl]-4-piperidyl]acetic acid hydrochloride (98.81 mg, 227.76 μmol) in N,N-dimethylformamide (2 mL) was added N,N-diisopropylethylamine (128.55 mg, 994.63 μmol, 173.25 μL) at 0° C. 1-[(1-(Cyano-2-ethoxy-2-oxoethylideneaminooxy)-dimethylamino-morpholino)] uronium hexafluorophosphate (159.74 mg, 372.98 μmol) was added to the reaction mixture at 0° C. After 10 minutes, 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (170 mg, 248.66 μmol), was added to the reaction mixture at the same temperature. The reaction mixture was stirred at ambient temperature for 2 h. The crude mixture was directly injected on a C18 column (60 g) for purification while eluting (0% to 70% of acetonitrile in water (+0.1% ammonium acetate) over 30 minutes, then steep gradient to 100% acetonitrile). The pure fraction was frozen and lyophilized to afford Compound 103 (25.05 mg, 25.48 μmol, 10.25% yield) as an off white solid compound. LCMS (ESI+): 949.3 [M+H]. $^1$H-NMR (400 MHz, DMSO-d6): δ 12.53 (s, 1H), 10.82 (s, 1H), 7.75 (s, 1H), 7.71 (d, J=10.80 Hz, 1H), 7.65 (d, J=8.40 Hz, 2H), 7.61 (s, 1H), 7.49 (d, J=3.60 Hz, 1H), 7.27 (d, J=3.60 Hz, 1H), 6.55 (d, J=8.80 Hz, 2H), 6.32 (d, J=12.40 Hz, 2H), 6.32 (d, J=12.40 Hz, 1H), 6.15 (s, 1H), 4.80 (d, J=17.60 Hz, 1H), 4.75 (s, 1H), 4.39 (s, 2H), 4.38-4.27 (m, 1H), 4.22 (d, J=17.60 Hz, 1H), 4.09 (s, 2H), 4.03-3.96 (m, 7H), 3.30-3.21 (m, 3H), 2.78-2.67 (m, 5H), 2.22 (s, 2H), 2.12-2.02 (m, 1H), 1.89-1.79 (m, 1H), 1.71-1.69 (m, 2H), 1.59-1.56 (m, 2H).

Example 104

2-[6-[4-[2-[2-[1-[2-(difluoromethyl)-4-[(2,6-dioxo-3-piperidyl)amino]phenyl]-4xy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, Compound 104

Step 1: 1-[2-(difluoromethyl)-4-nitro-phenyl]piperidin-4-one

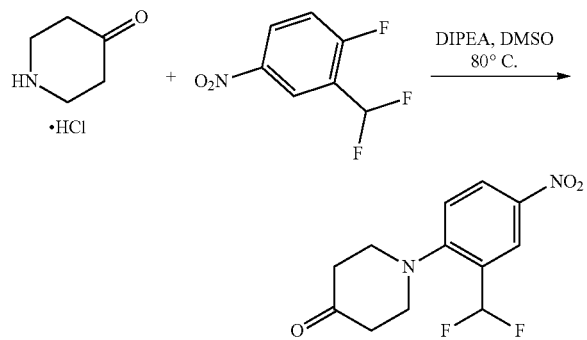

Into a 250 mL sealed tube containing a well-stirred solution of piperidin-4-one hydrochloride (3 g, 22.13 mmol) and 2-(difluoromethyl)-1-fluoro-4-nitro-benzene (4.23 g, 22.13 mmol) in DMSO (30 mL) were added N, N-Diisopropylethylamine (11.44 g, 88.50 mmol, 15.41 mL) under nitrogen atmosphere. The resulting mixture was heated in a heating block at 80° C. for 5 h. The reaction mixture was poured into ice cold water and solid was precipitated and filtered and dried under vacuum to get 1-[2-(difluoromethyl)-4-nitro-phenyl]piperidin-4-one (4.7 g, 16.32 mmol, 73.74% yield) as a yellow colour solid. LCMS (ESI): 269.0 [M−H].

Step 2: tert-Butyl 2-[1-[2-(difluoromethyl)-4-nitro-phenyl]-4-hydroxy-4 piperidyl]acetate

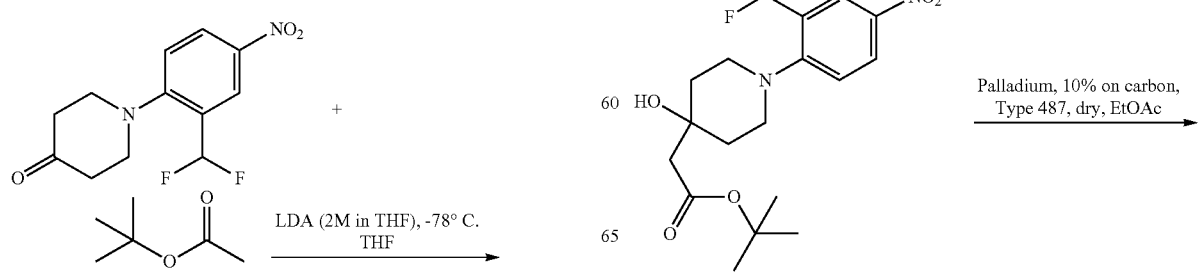

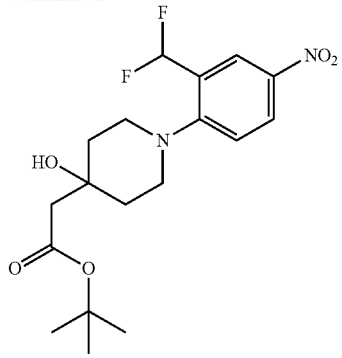

Into a 100 mL single-necked round-bottomed flask containing a well-stirred solution of tert-butyl acetate (2.42 g, 20.87 mmol, 2.81 mL) in tetrahydrofuran (30 mL) under nitrogen atmosphere at −78° C. was added Lithium diisopropylamide solution 2M in tetrahydrofuran (2.79 g, 26.09 mmol, 13 mL) dropwise over a period of 10 min. The resulting suspension was further stirred at −78° C. for 1 hr. Then solution of freshly prepared 1-[2-(difluoromethyl)-4-nitro-phenyl] piperidin-4-one (4.7 g, 17.39 mmol) in tetrahydrofuran (20 mL) was added dropwise to the reaction mixture while maintaining −78° C. and continued stirring for 3 h. The reaction mixture was brought room temperature and quenched with saturated ammonium chloride solution. Organic layer was separated, and the aqueous layer was extracted with ethyl acetate (2×100 mL). Combined organic layer was washed with brine (100 mL), concentrated under reduced pressure. The crude residue was purified by column chromatography using silica (0-40% ethyl acetate in Pet Ether to get tert-butyl 2-[1-[2-(difluoromethyl)-4-nitro-phenyl]-4-hydroxy-4-piperidyl] acetate (4.55 g, 11.26 mmol, 64.73% yield). LCMS (ESI+) m/z: 387.2 [M+H]$^+$.

Step 3: tert-Butyl 2-[1-[4-amino-2-(difluoromethyl) phenyl]-4-hydroxy-4-piperidyl]acetate -continued

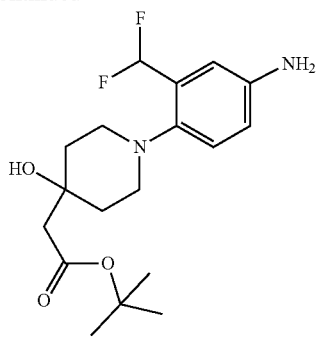

Into a 250 mL single-necked round-bottomed flask containing a well-stirred solution of tert-butyl 2-[1-[2-(difluoromethyl)-4-nitro-phenyl]-4-hydroxy-4-piperidyl]acetate (4.1 g, 10.61 mmol) in Ethyl acetate (40 mL) was added Palladium, 10% on carbon, dry (1.58 g, 14.86 mmol) and at ambient temperature under nitrogen atmosphere. The resulting suspension was stirred at ambient temperature under hydrogen atmosphere (bladder) for 6 h. The reaction mixture was filtered through a pad of Celite and Celite bed was washed with ethyl acetate (100 mL). The filtrate was concentrated under reduced pressure to yield tert-butyl 2-[1-[4-amino-2-(difluoromethyl) phenyl]-4-hydroxy-4-piperidyl]acetate (3.5 g, 9.40 mmol, 88.60% yield). LCMS (ESI+): 357.2 [M+H]+.

Step 4: Synthesis of tert-butyl 2-[1-[2-(difluoromethyl)-4-[(2,6-dioxo-3-piperidyl)amino]phenyl]-4-hydroxy-4-piperidyl]acetate

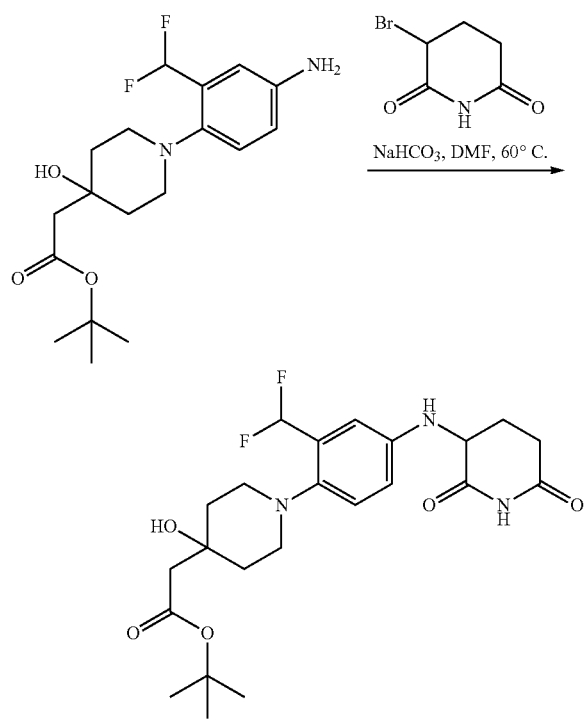

Into a 100 mL sealed tube containing a well-stirred solution of tert-butyl 2-[1-[4-amino-2-(difluoromethyl)phenyl]-4-hydroxy-4-piperidyl]acetate (3.4 g, 9.54 mmol) and 3-bromopiperidine-2,6-dione (2.75 g, 14.31 mmol in N,N-dimethylformamide (35 mL)) under nitrogen atmosphere were added sodium bicarbonate (1.60 g, 19.08 mmol, 742.03 µL) at room temperature. The resulting suspension was heated at 60° C. for 16 h. The reaction mixture was treated with water (30 mL) and the product extracted with ethyl acetate (2×100 mL). The organic layer was dried (anhydrous sodium sulfate), filtered and the filtrate was concentrated under reduced pressure to get a crude residue. The crude product was purified by flash silica-gel (230-400 mesh; 100 g SNAP) column with 60% ethyl acetate/petroleum ether to afford tert-butyl 2-[1-[2-(difluoromethyl)-4-[(2,6-dioxo-3-piperidyl)amino]phenyl]-4-hydroxy-4-piperidyl]acetate (3.3 g, 6.78 mmol, 71.10% yield). LCMS (ESI+) m/z: 468.2 [M+H]+.

Step 5: Synthesis of 2-[I-[2-(difluoromethyl)-4-[(2,6-dioxo-3-piperidyl)amino]phenyl]-4-hydroxy-4-piperidyl]acetic acid

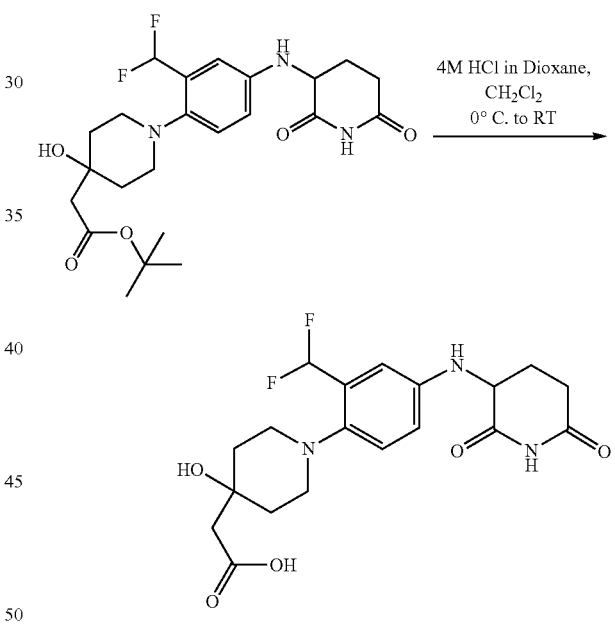

Into a 100 mL single-necked round-bottomed flask containing a well-stirred solution of tert-butyl 2-[1-[2-(difluoromethyl)-4-[(2,6-dioxo-3-piperidyl)amino]phenyl]-4-hydroxy-4-piperidyl]acetate (3.2 g, 6.84 mmol) in anhydrous dichloromethane (30 mL) was added hydrogen chloride (4 M 1,4-dioxane, 8.6 mL, 34.22 mmol) at 0° C. under nitrogen atmosphere. The resulting mixture was stirred at ambient temperature for 8 h under nitrogen atmosphere. The solvent was removed from the reaction mixture under reduced pressure to get a crude mass. The crude product was triturated with Et2O (30 mL) to get 2-[1-[2-(difluoromethyl)-4-[(2,6-dioxo-3-piperidyl)amino]phenyl]-4-hydroxy-4-piperidyl]acetic acid hydrochloride (3.11 g, 6.61 mmol, 96.58% yield) as an off white solid. LCMS (ESI+) m/z: 412.0 [M+H]+.

Step 6: 2-[6-[4-[2-[2-[1-[2-(difluoromethyl)-4-[(2,6-dioxo-3-piperidyl)amino]phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

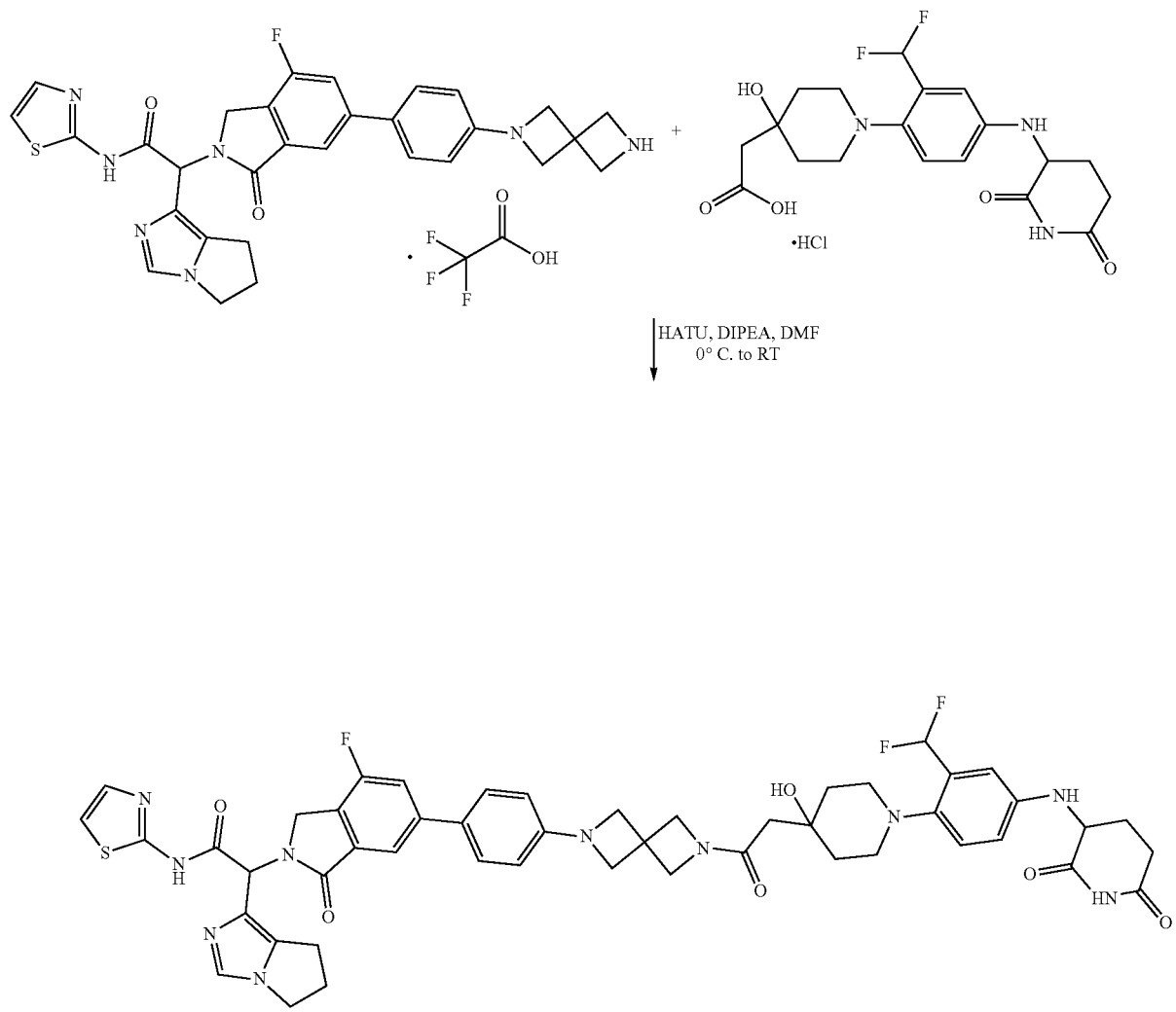

Into a 10 mL single-necked round-bottomed flask containing a well-stirred solution of 2-[1-[2-(difluoromethyl)-4-[(2,6-dioxo-3-piperidyl)amino]phenyl]-4-hydroxy-4-piperidyl]acetic acid hydrochloride (79.26 mg, 176.98 μmol) in N,N-dimethylformamide (1 mL) was added N,N-diisopropylethylamine (62.38 mg, 482.69 μmol, 84.08 μL) under nitrogen atmosphere at 0° C. Subsequently, 1-[bis(dimethylamino)methylene]-1H-1,2,3-triazolo[4,5-b]pyridinium 3-oxide hexafluorophosphate (73.41 mg, 193.07 μmol) was added at the same temperature. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide; 2,2,2-trifluoroacetic acid (110 mg, 160.90 μmol) was added to the reaction mixture. The reaction mixture was stirred at room temperature for 2 h. The crude reaction mass was directly injected in a reverse phase column. C18 Gold column (100 g) for purification while eluting (0%-50% of acetonitrile in water+0.1% ammonium acetate over 30 minutes, then steep gradient to 100% acetonitrile). The pure fraction was frozen and lyophilized to afford Compound 104 (51.14 mg, 52.34 μmol, 32.53% yield) as an off-white solid compound. LCMS (ESI+): 963.3 [M+H]$^+$. 1H-NMR (400 MHz, DMSO-d6): δ 12.55 (s, 1H), 10.78 (s, 1H), 7.72 (t, J=10.80 Hz, 2H), 7.64 (t, J=11.60 Hz, 3H), 7.49 (d, J=3.60 Hz, 1H), 7.25 (d, J=11.60 Hz, 1H), 7.13 (t, J=16.00 Hz, 2H), 6.82 (t, J=8.80 Hz, 2H), 6.55 (d, J=8.80 Hz, 2H), 6.15 (s, 1H), 5.98 (d, J=8.00 Hz, 1H), 4.81 (t, J=−9.20 Hz, 2H), 4.78-4.35 (m, 3H), 4.22 (d, J=17.60 Hz, 1H), 4.19 (s, 2H), 4.09-3.98 (m, 6H), 2.94 (t, J=9.60 Hz, 2H), 2.76-2.68 (m, 2H), 2.67 (d, J=1.60 Hz, 3H), 2.24 (s, 2H), 2.08 (d, J=2.80 Hz, 2H), 1.81 (t, J=5.20 Hz, 1H), 1.75-1.65 (m, 2H), 1.62 (d, J=4.00 Hz, 2H) (Two proton signals could not be observed due to water obscuration).

Example 105

2-(6,7-dihydro-5H-pyrrolo[1,2-c]imidazol-1-yl)-2-[6-[1-[1-[2-[4-[3-(2,4-dioxohexahydropyrimidin-1-yl)-1-methyl-indazol-6-yl]-3,3-difluoro-1-piperidyl]acetyl]-4-piperidyl]pyrazol-4-yl]-4-fluoro-1-oxo-isoindolin-2-yl]-N-thiazol-2-yl-acetamide, Compound 105

Step 1: 2-(6,7-dihydro-5H-pyrrolo[1,2-c]imidazol-1-yl)-2-[6-[1-[1-[2-[4-[3-(2,4-dioxohexahydropyrimidin-1-yl)-1-methyl-indazol-6-yl]-3,3-difluoro-1-piperidyl]acetyl]-4-piperidyl]pyrazol-4-yl]-4-fluoro-1-oxo-isoindolin-2-yl]-N-thiazol-2-yl-acetamide

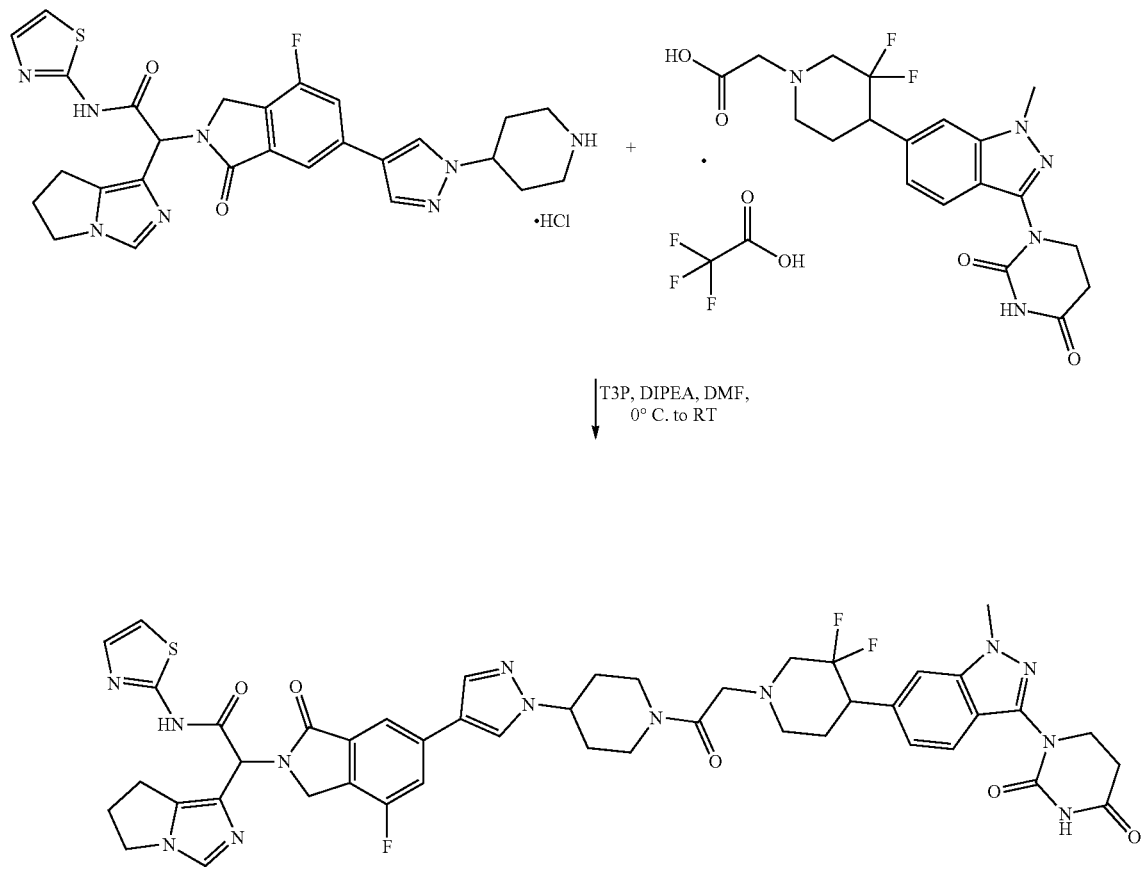

Into a 10 mL single-necked round-bottomed flask containing a well-stirred solution of 2-[4-[3-(2,4-dioxohexahydropyrimidin-1-yl)-1-methyl-indazol-6-yl]-3,3-difluoro-1-piperidyl]acetic acid; 2,2,2-trifluoroacetic acid (127.20 mg, 301.86 μmol) in N,N-dimethylformamide (2 mL) was added N,N-diisopropylethylamine (177.33 mg, 1.37 mmol, 238.98 μL) under nitrogen atmosphere at 0° C. Propylphosphonic anhydride solution (50 wt. % in ethyl acetate) (174.53 mg, 548.83 μmol) was added while maintaining 0° C. After 10 minutes, 2-(6,7-dihydro-5H-pyrrolo[1,2-c]imidazol-1-yl)-2-[4-fluoro-1-oxo-6-[1-(4-piperidyl)pyrazol-4-yl]isoindolin-2-yl]-N-thiazol-2-yl-acetamide hydrochloride (Example 28, step 4, 150 mg, 274.41 μmol) was added and the resulting mixture was stirred for 1 h under nitrogen atmosphere at ambient temperature. The reaction mixture was directly injected in a reverse phase C18 chromatography (100 g) while eluting (0-45% acetonitrile in water+0.1% ammonium acetate over 30 minutes, then steep gradient to 100% acetonitrile). The pure Fractions were frozen and lyophilized to get Compound 105 (47.3 mg, 48.81 μmol, 17.79% yield) as an off-white solid. LCMS (ESI+) m/z: 950.3 [M+H]$^+$. 1H-NMR (400 MHz, DMSO-d6): δ 12.50 (s, 1H), 10.58 (s, 1H), 8.54 (d, J=11.60 Hz, 1H), 8.11 (d, J=9.20 Hz, 1H), 7.85 (d, J=7.60 Hz, 1H), 7.75 (t, J=10.40 Hz, 1H), 7.60 (s, 1H), 7.58 (s, 1H), 7.54 (d, J=7.20 Hz, 1H), 7.42 (s, 1H), 7.09 (d, J=4.80 Hz, 2H), 6.08 (s, 1H), 4.89 (s, 1H), 4.46 (d, J=11.20 Hz, 2H), 4.18 (d, J=17.60 Hz, 2H), 3.99 (d, J=6.40 Hz, 3H), 3.93 (t, J=6.40 Hz, 4H), 3.49 (d, J=20.40 Hz, 2H), 3.49-3.44 (m, 3H), 3.02 (s, 1H), 2.86-2.68 (m, 4H), 2.46 (m, 4H), 2.34-2.33 (m, 1H), 2.29-2.10 (m, 2H), 2.08-1.95 (m, 1H), 1.88-1.82 (m, 3H).

Example 106

2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3,3-difluoro-1-piperidyl]acetyl]-2,7-diazaspiro[3.5]nonan-7-yl]phenyl]-4-fluoro-1-oxo-isoindolin-2-yl]-N-thiazol-2-yl-acetamide, Compound 106

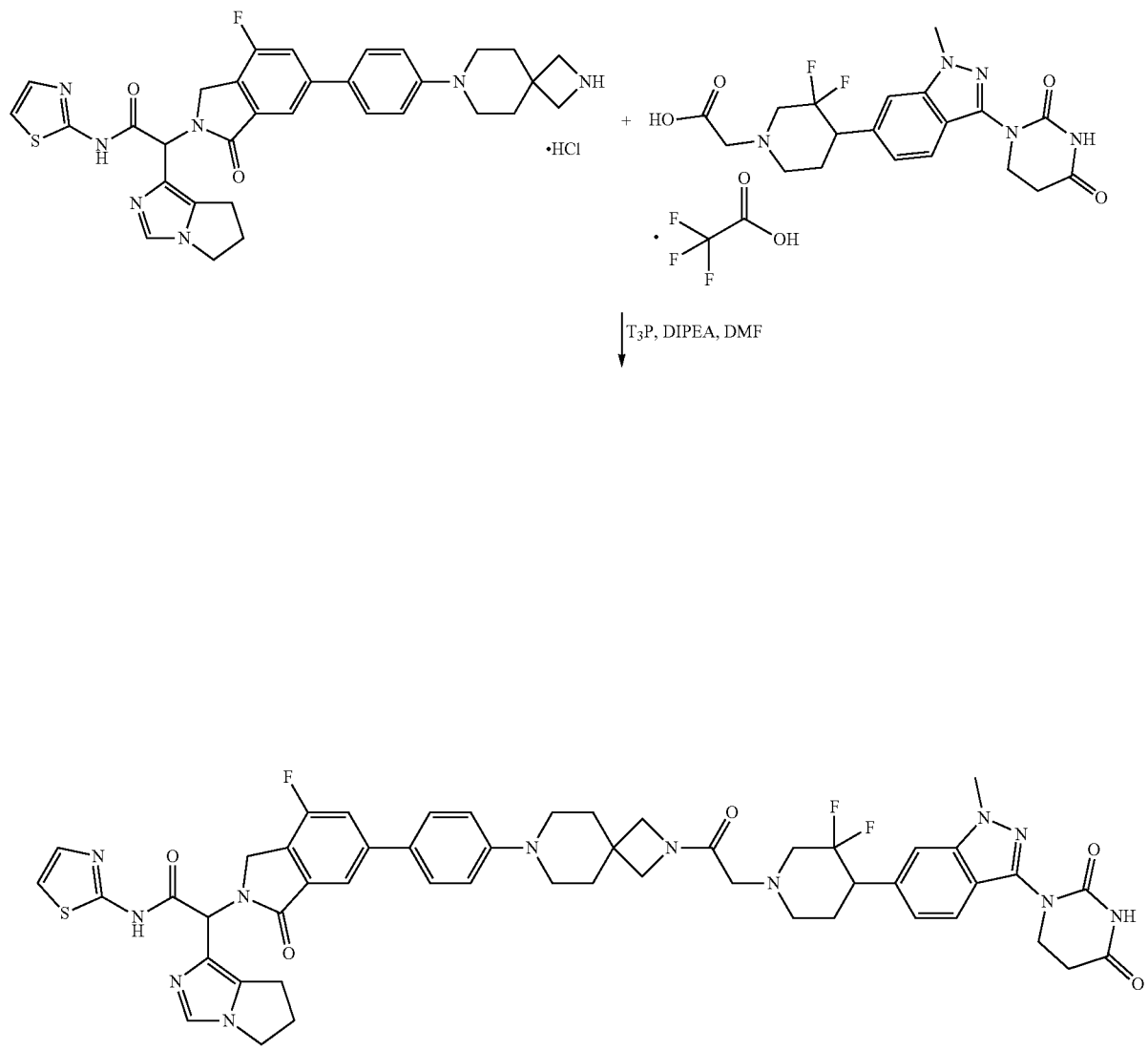

2-[6-[4-(2,7-diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide hydrochloride (Example 46, step 6, 100 mg, 157.69 μmol) and 2-[4-[3-(2,4-dioxohexahydropyrimidin-1-yl)-1-methyl-indazol-6-yl]-3,3-difluoro-1-piperidyl]acetic acid, trifluoroacetic acid salt (86.64 mg, 189.23 mol) were mixed in N,N-dimethylformamide (2 mL). N, N-diisopropylethylamine (203.80 mg, 1.58 mmol, 274.66 μL) was added to the reaction mixture at 0° C. Propylphosphonic anhydride solution (50 wt. % in ethyl acetate) (100.35 mg, 315.38 μmol) was added to the reaction mixture at 0° C. The reaction mixture was stirred at room temperature for 1 h. The crude mixture was directly injected on a C18 column (100 g) for purification while eluting (0% to 45% of acetonitrile+0.1% ammonium acetate in water over 30 minutes, then steep gradient to 100% acetonitrile). The pure fraction was frozen and lyophilized to afford Compound 106 (56 mg, 54.95 μmol, 34.85% yield) as an off white solid. LCMS (ESI+): 1001.4 [M+H]. 1H-NMR (400 MHz, DMSO-d6): δ 12.49 (s, 1H), 10.57 (s, 1H), 7.77-7.73 (m, 3H), 7.68-7.59 (m, 4H), 7.56-7.49 (m, 1H), 7.25 (bs, 1H), 7.11-7.06 (m, 3H), 6.15 (s, 1H), 4.84-4.79 (m, 1H), 4.25-4.20 (m, 1H), 4.00-3.79 (m, 10H), 3.66 (bs, 2H), 3.34-3.23 (m, 9H), 3.10-2.90 (m, 1H), 2.76-2.56 (m, 6H), 1.90-1.82 (m, 6H).

Example 107

2-(6,7-dihydro-5H-pyrrolo[1,2-c]imidazol-1-yl)-2-[6-[4-[2-[2-[1-[4-[(2,6-dioxo-3-piperidyl)amino]-2-fluoro-phenyl]-4-hydroxy-4-piperidyl]acetyl]-2,7-diazaspiro[3.5]nonan-7-yl]phen-yl]-4-fluoro-1-oxo-isoindolin-2-yl]-N-thiazol-2-yl-acetamide, Compound 107

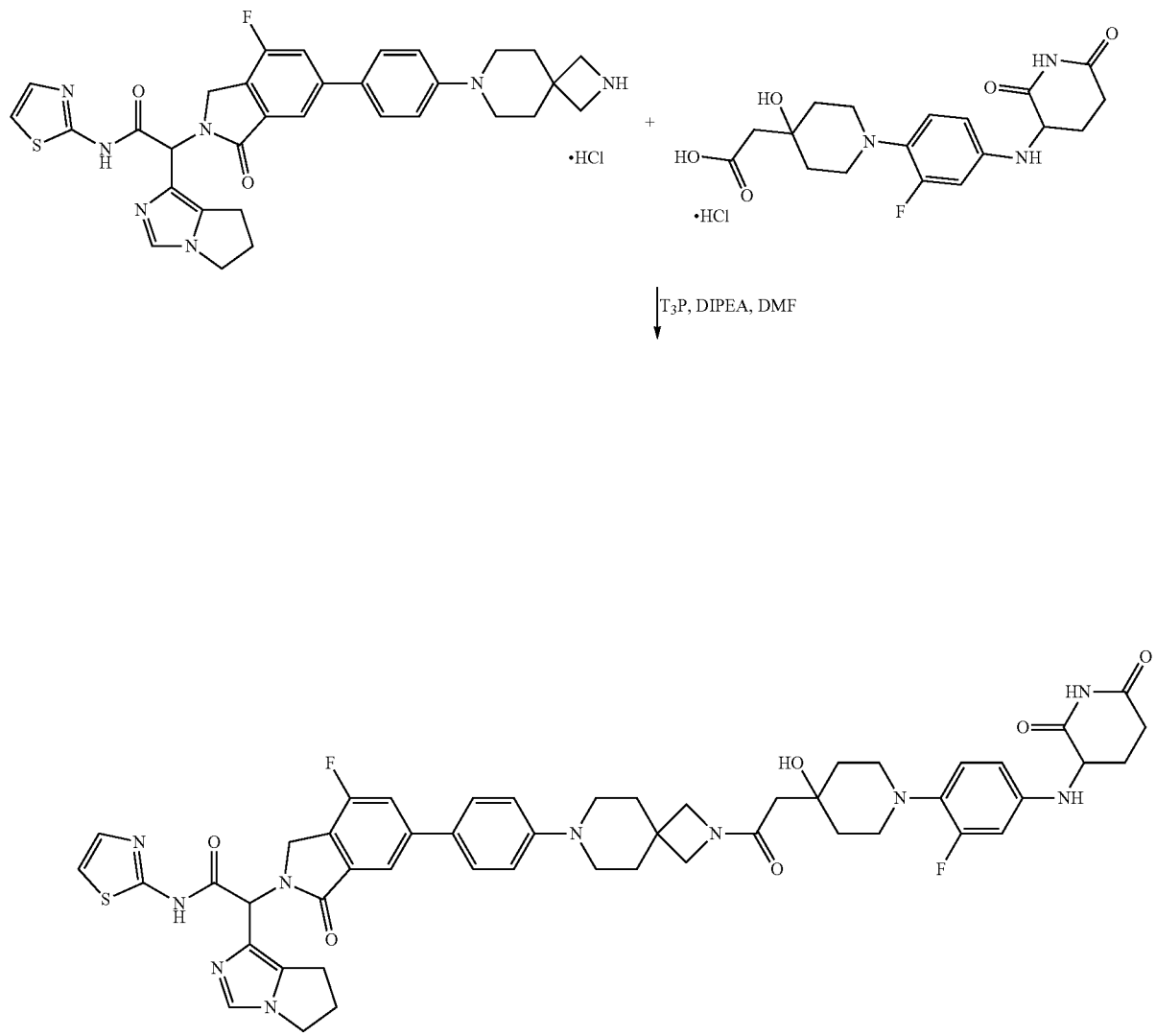

2-[6-[4-(2,7-diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide hydrochloride (150 mg, 236.53 μmol), and 2-[1-[4-[(2,6-dioxo-3-piperidyl)amino]-2-fluoro-phenyl]-4-hydroxy-4-piperidyl]acetic acid hydrochloride (118.03 mg, 283.84 μmol), were mixed in N,N-dimethylformamide (3 mL). N, N-diisopropylethylamine (305.70 mg, 2.37 mmol, 411.99 μL) was added to the reaction mixture at 0° C. 1-[Bis(dimethylamino)methylene]-1H-1,2,3-triazolo[4,5-b]pyridinium 3-oxide hexafluorophosphate (116.92 mg, 307.49 μmol) was added to the reaction mixture at 0° C. The reaction mixture was stirred at room temperature for 1 h. The crude mixture was directly injected on a C18 column (100 g) for purification while eluting (0% to 45% of acetonitrile+0.1% ammonium acetate in water over 30 minutes, then steep gradient to 100% acetonitrile). The pure fraction was frozen and lyophilized to afford Compound 107 (58 mg, 60.02 μmol, 25.38% yield) as an off-white solid. LCMS (ESI+): 958.3. 1H-NMR (400 MHz, DMSO-d6): δ 12.35 (s, 1H), 10.79 (s, 1H), 7.76 (s, 1H), 7.73 (d, J=10.40 Hz, 1H), 7.66 (d, J=8.40 Hz, 2H), 7.60 (s, 1H), 7.46 (bs, 1H), 7.20 (bs, 1H), 7.06 (d, J=8.40 Hz, 2H), 6.86 (t, J=9.20 Hz, 1H), 6.50 (d, J=15.20 Hz, 1H), 6.42 (d, J=8.80 Hz, 1H), 6.12 (s, 1H), 5.78 (d, J=7.20 Hz, 1H), 4.86-4.78 (m, 2H), 4.24-4.19 (m, 2H), 4.00-3.94 (m, 5H), 3.63 (bs, 2H), 3.33-3.25 (m, 5H), 2.93-2.85 (m, 4H), 2.75-2.68 (m, 2H), 2.24 (bs, 3H), 2.15-2.08 (m, 1H), 1.87-1.77 (m, 8H), 1.65-1.62 (m, 2H).

Example 108

N-[1-[2-[1-[4-[[(3R)-2,6-dioxo-3-piperidyl]amino]-2-fluoro-phenyl]-4-hydroxy-4-piperidyl]acetyl]-4-piperidyl]-5-[2-[7-fluoro-2-[1-[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]ethynyl]pyridine-2-carboxamide, Compound 108

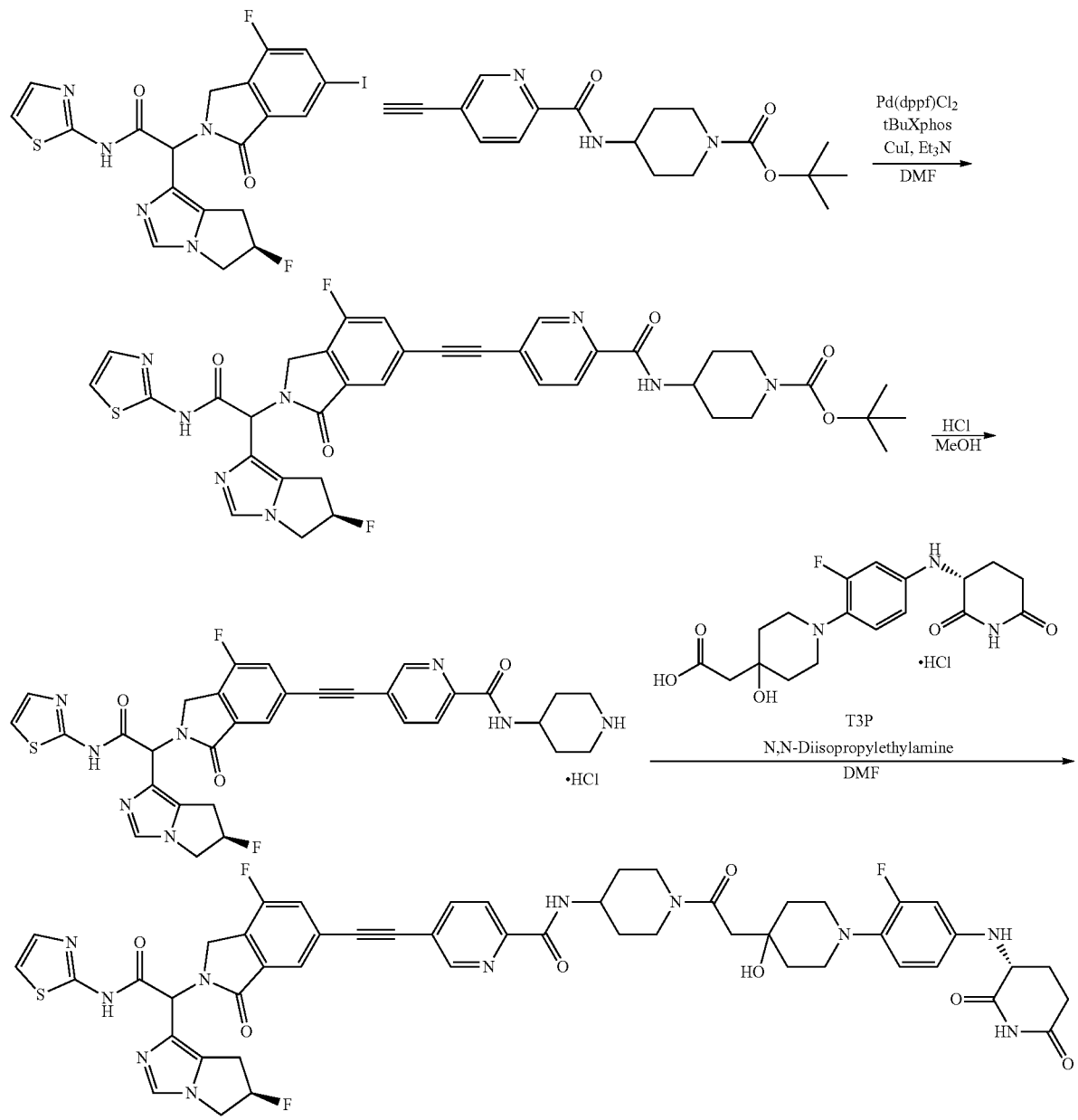

Step 1: tert-Butyl 4-[[5-[2-[7-fluoro-2-[1-[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]ethynyl]pyridine-2-carbonyl]amino]piperidine-1-carboxylate To a stirred solution of 2-[(6R)-6-fluoro-6,7-dihydro-5H-pyrrolo[1,2-c]imidazol-1-yl]-2-(4-fluoro-6-iodo-1-oxo-isoindolin-2-yl)-N-thiazol-2-yl-acetamide (360 mg, 665.05 μmol) and tert-butyl 4-[(5-ethynylpyridine-2-carbonyl)amino]piperidine-1-carboxylate (262.88 mg, 798.06 μmol) in N,N-dimethylformamide (4 mL) was added triethylamine (336.48 mg, 3.33 mmol, 463.47 μL), the reaction mixture was purged with nitrogen for 10 min. Copper (I) iodide (1.76 mg, 9.24 μmol) followed by tert-butyl Xphos (56.48 mg, 133.01 μmol), Pd(dppf)Cl₂ (48.66 mg, 66.51 μmol) was added and the reaction mixture was stirred for 2 h at 90° C. under microwave heating. The reaction mixture was filtered through celite bed and washed with dichloromethane and methanol. The filtrate was concentrated under reduced pressure. The crude residue was purified by isolera column chromatography, desired product was eluted afford tert-butyl 4-[[5-[2-[7-fluoro-2-[1-[(6R)-6-fluoro-6,7-dihydro-5H-pyrrolo[1,2-c]imidazol-1-yl]-2-oxo-2-(thiazol-2-ylamino) ethyl]-3-oxo-isoindolin-5-yl]ethynyl]pyridine-2-carbonyl] amino]piperidine-1-carboxylate (233 mg, 279.18 µmol, 42% yield). LCMS (ESI+): 743.2 (M+H).

Step 2: 5-[2-[7-fluoro-2-[1-[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]ethynyl]-N-(4-piperidyl)pyridine-2-carboxamide hydrochloride To a stirred solution of tert-butyl 4-[[5-[2-[7-fluoro-2-[1-[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]ethynyl]pyridine-2-carbonyl]amino]piperidine-1-carboxylate (230 mg, 309.64 µmol) in dichloromethane (4 mL) was added 4M hydrochloric acid in 1,4-dioxane (11.29 mg, 309.64 µmol, 0.8 mL) dropwise at 0° C., it was stirred at room temperature for 2 h. The reaction mixture was concentrated under reduced pressure, dried under high vacuum to get the crude product as 5-[2-[7-fluoro-2-[1-[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]ethynyl]-N-(4-piperidyl)pyridine-2-carboxamide hydrochloride (204 mg, 291.37 µmol, 94.10% yield). LCMS m/z 643.1 (M+H)

Step 3: N-[1-[2-[1-[4-[[(3R)-2,6-dioxo-3-piperidyl] amino]-2-fluoro-phenyl]-4-hydroxy-4-piperidyl] acetyl]-4-piperidyl]-5-[2-[7-fluoro-2-[1-[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]ethynyl]pyridine-2-carboxamide To a solution of 5-[2-[7-fluoro-2-[1-[(6R)-6-fluoro-6,7-dihydro-5H-pyrrolo[1,2-c]imidazol-1-yl]-2-oxo-2-(thiazol-2-ylamino)ethyl]-3-oxo-isoindolin-5-yl]ethynyl]-N-(4-piperidyl)pyridine-2-carboxamide hydrochloride (150 mg, 220.87 µmol) in N,N-dimethylformamide (2 mL) was added N,N-diisopropylethylamine (142.73 mg, 1.10 mmol, 192.36 µL) followed by Propylphosphonic anhydride solution (50 wt. % in ethyl acetate) (140.55 mg, 441.74 µmol) at 0° C., after 15 min. 2-[1-[4-[[(3R)-2,6-dioxo-3-piperidyl]amino]-2-fluoro-phenyl]-4-hydroxy-4-piperidyl]acetic acid hydrochloride (100.55 mg, 241.80 µmol, 021) was added and stirred for 1 hr at room temperature. The reaction mixture was directly injected on a C18 column (100 g) for purification (0-50% 0.1% ammonium acetate in water and acetonitrile over 30 minutes, then steep gradient to 100% acetonitrile). The pure fractions were combined, frozen and lyophilized to get Compound 108 (70.02 mg, 69.04 µmol, 31.26% yield) as an off-white solid. LCMS (ESI+): 1005.3 (M+H+); 1H-NMR (400 MHz, DMSO-d6): 10.79 (s, 1H), 8.87 (s, 1H), 8.81 (d, J=7.60 Hz, 1H), 8.23 (d, J=1.60 Hz, 1H), 8.10 (d, J=8.40 Hz, 1H), 7.81 (t, J=9.20 Hz, 2H), 7.66 (d, J=3.20 Hz, 1H), 7.41 (s, 1H), 7.13 (s, 1H), 6.86 (t, J=9.60 Hz, 1H), 6.52 (d, J=2.40 Hz, 1H), 6.42 (d, J=6.80 Hz, 1H), 6.08 (s, 1H), 5.87-5.74 (m, 2H), 4.98 (s, 2H), 4.47 (d, J=8.80 Hz, 1H), 4.27 (d, J=13.20 Hz, 4H), 4.08 (d, J=10.80 Hz, 2H), 3.17 (t, J=12.00 Hz, 2H), 3.00-2.88 (m, 5H), 2.77-2.64 (m, 2H), 2.10-2.07 (m, 1H), 1.89-1.72 (m, 12H).

Example 109

2-(6,7-dihydro-5H-pyrrolo[1,2-c]imidazol-1-yl)-2-[6-[4-[2-[2-[1-[3-(2,4-dioxohexahydropyrimidin-1-yl)-1-methyl-indazol-6-yl]-4-hydroxy-4-piperidyl] acetyl]-2,6-diazaspiro[3.3]heptan-6-yl]phenyl]-4-fluoro-1-oxo-isoindolin-2-yl]-N-thiazol-2-yl-acetamide, Compound 109

Step 1: 1-[6-(1,4-dioxa-8-azaspiro[4.5]decan-8-yl)-1-methyl-indazol-3-yl]hexahydropyrimidine-2,4-dione

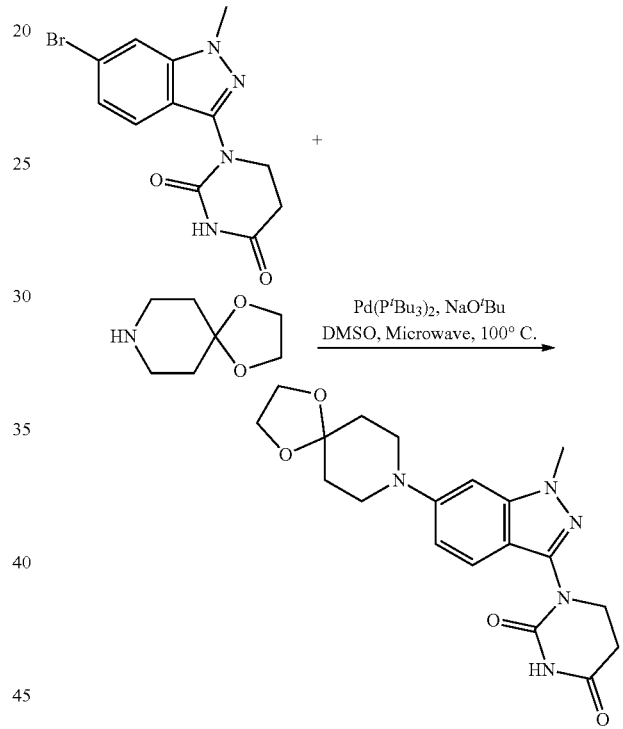

Into a 50 mL sealed-tube containing a well-stirred solution of 1-(6-bromo-1-methyl-indazol-3-yl)hexahydropyrimidine-2,4-dione (1 g, 3.09 mmol) and 1,4-dioxa-8-azaspiro[4.5]decane (443.09 mg, 3.09 mmol, 395.62 µL) in DMSO (10 mL) was added sodium tert-butoxide (356.87 mg, 3.71 mmol) under nitrogen atmosphere and the resulting mixture was degassed with nitrogen for 10 minutes. Subsequently, Bis(tri-tert-butylphosphine)palladium(0) (316.31 mg, 618.94 µmol) was added and the reaction mixture was degassed with nitrogen for 5 minutes. The reaction vial was heated at 100° C. for 16 h. The reaction mixture was added with water (30 mL) and the mixture was extracted using ethyl acetate (3×75 mL). The organic layer was washed with brine solution (50 mL), dried over sodium sulphate and concentrated under reduced pressure to get crude. The crude residue was purified by flash column chromatography using silica gel and the desired product was eluted with (0-100%) ethyl acetate in Pet-ether to get 1-[6-(1,4-dioxa-8-azaspiro [4.5]decan-8-yl)-1-methyl-indazol-3-yl]hexahydropyrimidine-2,4-dione (610 mg, 902.14 μmol, 29.15% yield). LCMS (ESI+) m/z: 386.1 [M+H]+.

Step 2: 1-[1-methyl-6-(4-oxo-1-piperidyl)indazol-3-yl]hexahydropyrimidine-2,4-dione

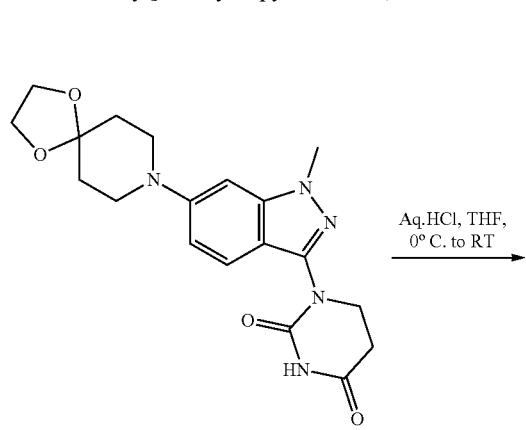

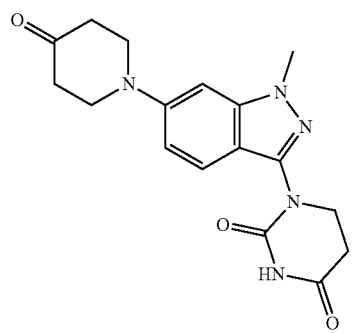

Into a 50 mL single-necked round-bottomed flask containing a well-stirred solution of 1-[6-(1,4-dioxa-8-azaspiro[4.5]decan-8-yl)-1-methyl-indazol-3-yl]hexahydropyrimidine-2,4-dione (600 mg, 1.56 mmol) in tetrahydrofuran (6 mL) was added Hydrochloric acid, 36% w/w aq. soln. (2.40 g, 65.82 mmol, 3 mL) at 0° C. The reaction mixture stirred at room temperature for 16 h. Reaction mixture was basified with saturated aqueous sodium bicarbonate solution and compound was extracted using 5% Methanol in Dichloromethane. The combined organic layers were dried over anhydrous sodium sulphate and concentrated under reduced pressure. The crude residue was purified by column chromatography using silica with 0 to 100% Ethyl acetate in petroleum ether to get 1-[1-methyl-6-(4-oxo-1-piperidyl)indazol-3-yl]hexahydropyrimidine-2,4-dione (305 mg, 589.69 mol, 37.88% yield). LCMS (ESI+) m/z: 342.1 [M+H]+.

Step 3: tert-butyl 2-[1-[3-(2,4-dioxohexahydropyrimidin-1-yl)-1-methyl-indazol-6-yl]-4-hydroxy-4-piperidyl]acetate

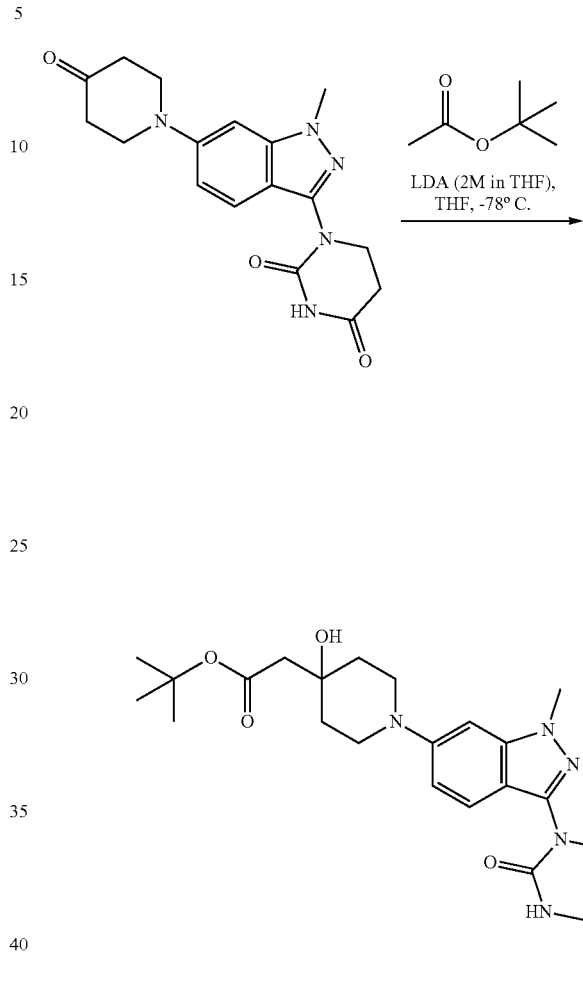

Into a 50 mL double-necked round-bottomed flask containing a well-stirred solution of tert-butyl acetate (245.00 mg, 2.11 mmol, 283.89 μL) in anhydrous tetrahydrofuran (5 mL) under nitrogen atmosphere was added Lithium diisopropylamide (2M) (225.94 mg, 2.11 mmol) at −78° C. and the resulting solution was stirred for 1 h at −78° C. In another 50 mL single-necked round-bottomed flask containing a well-stirred solution 1-[1-methyl-6-(4-oxo-1-piperidyl)indazol-3-yl]hexahydropyrimidine-2,4-dione (180 mg, 527.30 μmol) in anhydrous tetrahydrofuran (5 mL) under nitrogen was added into the above solution at −78° C. The Reaction temperature was slowly raised to room temperature stirred for 16 h. The reaction mixture was quenched with saturated Ammonium chloride solution and the product was extracted using Ethyl acetate (3×50 mL). Organic phases were combined and washed with brine solution (50 mL). Combined organic phases were dried (anhydrous sodium sulfate), filtered and the filtrate was concentrated under reduced pressure to get a crude residue, which was purified by flash silica gel (230-400 mesh) column with 0-100% ethyl acetate/petroleum ether to afford tert-butyl 2-[1-[3-(2,4-dioxohexahydropyrimidin-1-yl)-1-methyl-indazol-6-yl]-4-hydroxy-4-piperidyl]acetate (60 mg, 91.80 μmol, 17.41% yield) and taken for next step. LCMS (ESI+) m/z: 458.2 [M+H]+.

1031

Step 4: 2-[1-[3-(2,4-dioxohexahydropyrimidin-1-yl)-1-methyl-indazol-6-yl]-4-hydroxy-4-piperidyl] acetic acid

1032

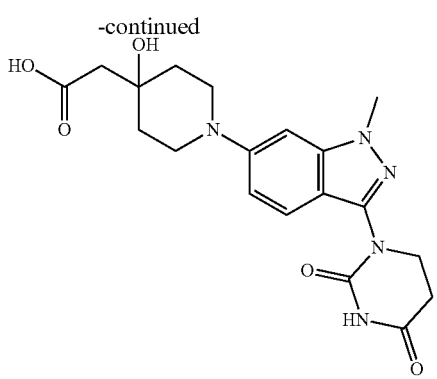

Into a 25 mL single-necked round-bottomed flask containing a well-stirred solution of tert-butyl 2-[1-[3-(2,4-dioxohexahydropyrimidin-1-yl)-1-methyl-indazol-6-yl]-4-hydroxy-4-piperidyl]acetate (60 mg, 131.14 μmol) in anhydrous dichloromethane (0.7 mL) was added hydrogen chloride (4M solution in 1,4-dioxane, 229 μL, 33.47 mg, 917.99 μmol) at 0° C. under nitrogen atmosphere. The resulting mixture was stirred at ambient temperature for 3 h under nitrogen atmosphere. The solvent was removed from the reaction mixture under reduced pressure. The crude product was triturated with Et$_2$O (10 mL) to get 2-[1-[3-(2,4-dioxohexahydropyrimidin-1-yl)-1-methyl-indazol-6-yl]-4-hydroxy-4-piperidyl]acetic acid; hydrochloride (60 mg, 104.14 μmol, 79.41% yield). LCMS (ESI+) m/z: 402.1 [M+H]$^+$.

Step 5: 2-(6,7-dihydro-5H-pyrrolo[1,2-c]imidazol-1-yl)-2-[6-[4-[2-[2-[1-[3-(2,4-dioxohexahydropyrimidin-1-yl)-1-methyl-indazol-6-yl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide

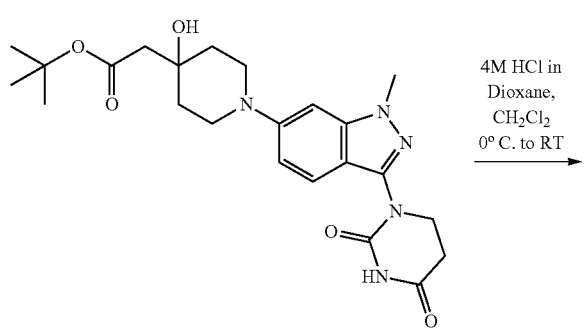

4M HCl in Dioxane, CH$_2$Cl$_2$
0° C. to RT

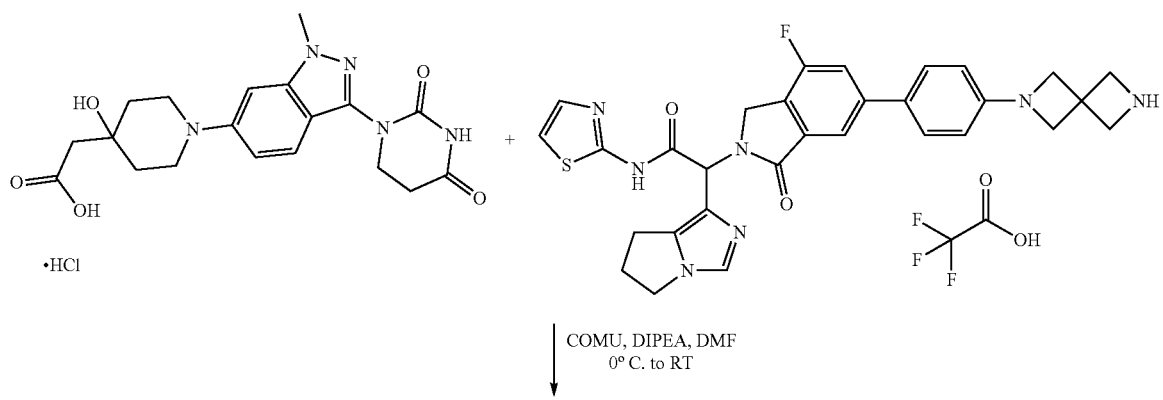

COMU, DIPEA, DMF
0° C. to RT

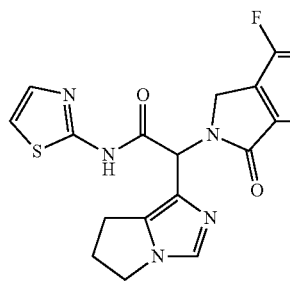

Into a 10 mL single-necked round-bottomed flask containing a well-stirred solution of 2-[1-[3-(2,4-dioxohexahydropyrimidin-1-yl)-1-methyl-indazol-6-yl]-4-hydroxy-4-piperidyl]acetic acid; hydrochloride (60 mg, 137.02 μmol) in N,N-dimethylformamide (0.6 mL) was added N,N-diisopropylethylamine (88.55 mg, 685.12 μmol, 119.33 μL) under nitrogen atmosphere at 0° C. Subsequently, (1-Cyano-2-ethoxy-2-oxoethylidenaminooxy)dimethylamino-morpholino-carbenium hexafluorophosphate (117.37 mg, 274.05 μmol) was added at the same temperature. After 15 minutes, 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide; 2,2,2-trifluoroacetic acid (74.94 mg, 109.62 μmol) was added to the reaction mixture and the resulting solution was stirred for 1 h at ambient temperature. The reaction mixture was directly purified by reverse phase C-18 chromatography (100 g) eluting with (0-55% of acetonitrile in water+0.1% ammonium acetate over 30 minutes, then steep gradient to 100% acetonitrile). The pure fractions were frozen and lyophilized to get Compound 109 (20 mg, 19.97 μmol, 14.58% yield) as an off-white solid. LCMS (ESI+) m/z: 953.3 [M+H]+. 1H-NMR (400 MHz, DMSO-d6): δ 12.53 (s, 1H), 10.52 (s, 1H), 7.74 (s, 1H), 7.72 (d, J=4.40 Hz, 1H), 7.66 (d, J=8.80 Hz, 1H), 7.61 (s, 2H), 7.49 (d, J=3.20 Hz, 1H), 7.43 (d, J=9.20 Hz, 1H), 7.26 (d, J=3.20 Hz, 1H), 6.91 (d, J=1.60 Hz, 1H), 6.83 (s, 1H), 6.55 (d, J=8.40 Hz, 2H), 6.15 (s, 1H), 4.87 (s, 1H), 4.80 (d, J=17.60 Hz, 1H), 4.38 (s, 2H), 4.22 (d, J=9.60 Hz, 1H), 4.19 (s, 2H), 4.08-4.02 (m, 6H), 3.99-3.91 (m, 6H), 3.52 (d, J=4.80 Hz, 2H), 3.24 (t, J=10.40 Hz, 2H), 2.77-2.72 (m, 3H), 2.24 (s, 2H), 1.77-1.75 (m, 2H), 1.68-1.65 (m, 2H), 1.38-1.20 (m, 2H)

Example 110

2-(6,7-dihydro-5H-pyrrolo[1,2-c]imidazol-1-yl)-2-[6-[6-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]-3-pyridyl]-4-fluoro-1-oxo-isoindolin-2-yl]-N-thiazol-2-yl-acetamide, Compound 110

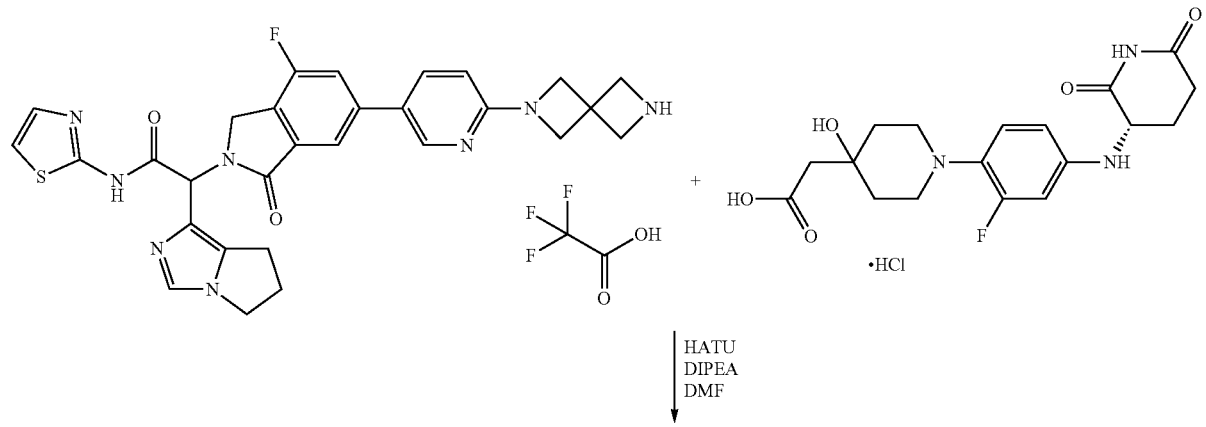

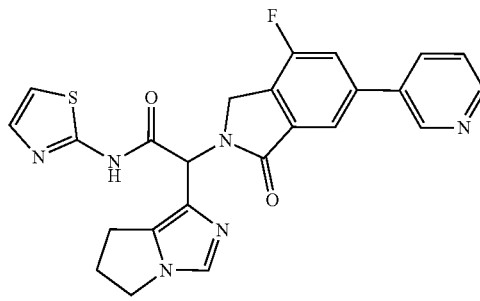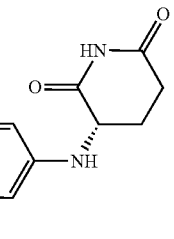

To a stirred solution of 2-[1-[4-[[(3S)-2,6-dioxo-3-piperidyl]amino]-2-fluoro-phenyl]-4-hydroxy-4-piperidyl]acetic acid (53.45 mg, 128.53 μmol, 021) in N,N-dimethylformamide (4 mL) at 0° C. was added N,N-diisopropylethylamine (120.81 mg, 934.77 μmol, 162.82 L) followed by 1-[bis(dimethylamino)methylene]-1H-1,2,3-triazolo[4,5-b]pyridinium 3-oxide hexafluorophosphate (66.64 mg, 175.27 μmol). After 5 min, 2-[6-[6-(2,6-diazaspiro[3.3]heptan-2-yl)-3-pyridyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid (80 mg, 116.85 mol) was added while maintaining 0° C., and the reaction mixture was stirred for 5 h while warming to room temperature. The reaction mixture was concentrated under reduced pressure at lower temperature, crude mixture was purified by C18 column (100 g) for purification (0% to 60% acetonitrile in water+0.1 ammonium acetate over 45 minutes, then steep gradient to 100% acetonitrile). The pure fractions were frozen and lyophilized to afford product Compound 110 (39 mg, 40.57 μmol, 34.72% yield) as an off white solid. LCMS (m/z: 932.3 [M+1]), $^1$H-NMR (400 MHz, DMSO-d6): 10.79 (s, 1H), 8.54 (d, J=2.00 Hz, 1H), 8.00 (dd, J=6.00, Hz, 1H), 7.79 (s, 1H), 7.78 (d, J=10.80 Hz, 1H), 7.61 (s, 1H), 7.48 (s, 1H), 7.26 (bs, 1H), 6.87 (t, J=9.20 Hz, 1H), 6.50 (m, 2H), 6.41 (dd, J=6.80, Hz, 1H), 6.14 (s, 1H), 5.79 (d, J=7.60 Hz, 1H), 4.80 (m, 1H), 4.77 (s, 1H), 4.39 (s, 2H), 4.25 (m, 2H), 4.20 (s, 3H), 4.09 (s, 2H), 3.98 (m, 2H), 2.86 (m, 4H), 2.77 (m, 2H), 2.59 (m, 2H), 2.22 (s, 2H), 2.10 (m, 1H), 1.76 (m, 1H), 1.73 (m, 2H), 1.63 (m, 2H).

Example 111

2-(6,7-dihydro-5H-pyrrolo[1,2-c]imidazol-1-yl)-2-[6-[6-[2-[2-[1-[4-[[(3R)-2,6-dioxo-3-piperidyl]amino]-2-fluoro-phenyl]-4-hydroxy-4-piperidyl]acetyl]-2,6-diazaspiro[3.3]heptan-6-yl]-3-pyridyl]-4-fluoro-1-oxo-isoindolin-2-yl]-N-thiazol-2-yl-acetamide, Compound 111

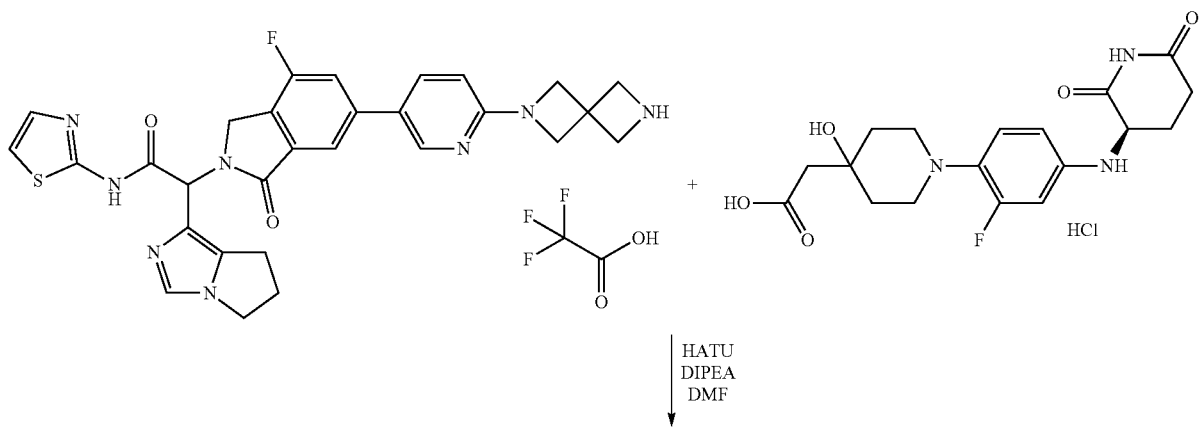

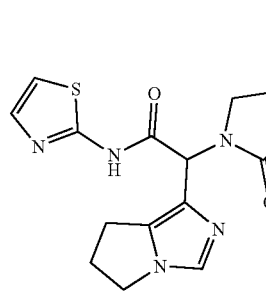

To a solution of 2-[1-[4-[[(3R)-2,6-dioxo-3-piperidyl]amino]-2-fluoro-phenyl]-4-hydroxy-4-piperidyl]acetic acid (62.10 mg, 149.33 μmol, 021) in N,N-dimethylformamide (2 mL). Added N,N-diisopropylethylamine (57.90 mg, 447.99 μmol, 78.03 μL) and 1-[bis(dimethylamino)methylene]-1H-1,2,3-triazolo[4,5-b]pyridinium 3-oxide hexafluorophosphate (85.17 mg, 224.0 μmol) at 0° C. and stir for 15 min followed by the addition of 2-[6-[6-(2,6-diazaspiro[3.3]heptan-2-yl)-3-pyridyl]-4-fluoro-1-oxo-isoindolin-2-yl]-2-(6,7-dihydro-5H-pyrrolo[1,2-c]imidazol-1-yl)-N-thiazol-2-yl-acetamide (85.21 mg, 149.33 μmol). After 2 h, the solvent was evaporated the solvent and crude product submitted for the analysis. The compound was purified by reverse phase column chromatography (C18 column (50 g), 5% to 75% acetonitrile in water (0.1% ammonium acetate) as a eluent). Water (10 mL) and acetonitrile (5 mL) were added to the purified fractions, and the mixture was thoroughly sonicated and vortexed. The suspension was frozen and lyophilized to afford Compound 111 (48 mg, 51.19 μmol, 34.28% yield) as an off-white solid. LCMS m/z: 932.3 (M+H). $^1$H-NMR (400 MHz, DMSO-$d_6$): δ10.79 (d, J=Hz, 1H), 8.54 (d, J=2270.40 Hz, 1H), 8.00 (dd, J=2.40, 8.80 Hz, 1H), 7.79 (s, 1H), 7.78 (dd, J=10.40, Hz, 2H), 7.61 (s, 1H), 7.50-7.49 (m, 1H), 7.27-7.26 (m, 1H), 6.88-6.83 (m, 1H), 6.52-6.48 (m, 2H), 6.43-6.40 (m, 1H), 6.15 (s, 1H), 5.80-5.78 (m, 1H), 4.83-4.77 (m, 2H), 4.39 (s, 2H), 4.25 (s, 2H), 4.21 (m, 4H), 4.16-4.02 (m, 2H), 4.01-3.99 (m, 2H), 2.78-2.82 (m, 4H), 2.71-2.67 (m, 2H), 2.60-2.51 (m, 3H), 2.34-2.22 (m, 2H), 2.22-1.91 (m, 1H), 1.76-1.61 (m, 5H).

Example 112

2-(6,7-dihydro-5H-pyrrolo[1,2-c]imidazol-1-yl)-2-[6-[4-[2-[2-[4-[5-[(2,6-dioxo-3-piperidyl)amino]-3-fluoro-2-pyridyl]-1-piperidyl]acetyl]-2,6-diazaspiro[3.3]heptan-6-yl]phenyl]-4-fluoro-1-oxo-isoindolin-2-yl]-N-thiazol-2-yl-acetamide, Compound 112

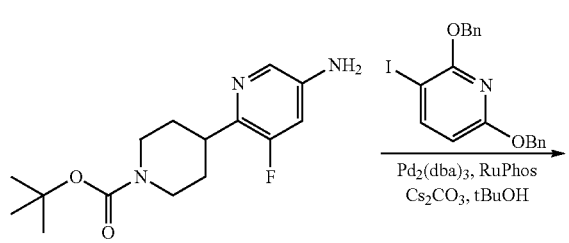

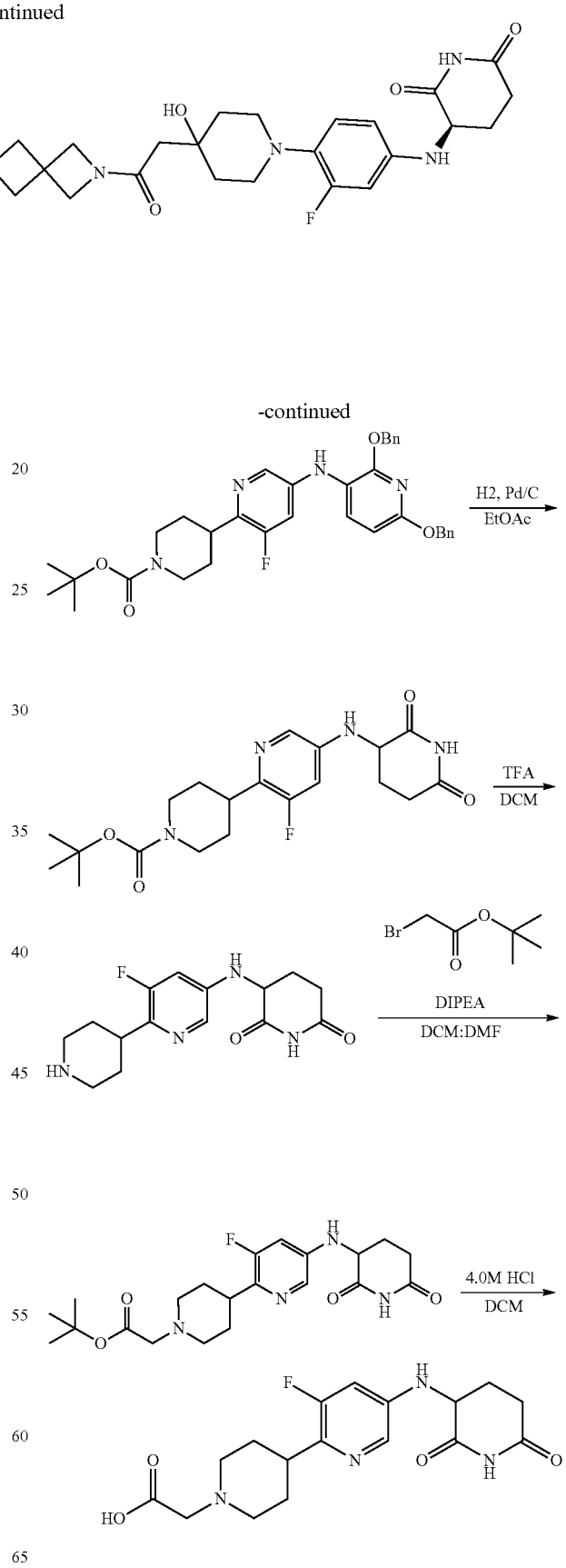

Step 1: tert-Butyl 4-[5-[(2,6-dibenzyloxy-3-pyridyl)amino]-3-fluoro-2-pyridyl]piperidine-1-carboxylate To a stirred solution of 2,6-dibenzyloxy-3-iodo-pyridine (3.73 g, 8.94 mmol) and tert-butyl 4-(5-amino-3-fluoro-2-pyridyl)piperidine-1-carboxylate (CAS #2351275-60-8, 2.4 g, 8.13 mmol) in tert-butanol (25 mL). Tris(Dibenzylideneacetone)dipalladium (0) (744.11 mg, 812.59 µmol) was added. Resulting mixture was degassed with argon and cesium carbonate (2.65 g, 8.13 mmol) and RuPhos (379.18 mg, 812.59 µmol) were added under inert atmosphere. Resulting mixture was heated at 100° C. for 18 h. The reaction mixture was diluted with ethyl acetate, filtered through a short pad of celite and washed with ethyl acetate. Combined organic part was washed with water and brine, dried over anhydrous sodium sulfate, filtered, and concentrated under reduced pressure. The residue was purified by column chromatography (25% ethyl acetate-hexane) to afford tert-butyl 4-[5-[(2,6-dibenzyloxy-3-pyridyl)amino]-3-fluoro-2-pyridyl]piperidine-1-carboxylate (2.6 g, 4.45 mmol, 54.72% yield). LCMS (ESI+): 585.2 (M+H)

Step 2: 3-[[6-[1-(1-tert-butoxyethyl)-4-piperidyl]-5-fluoro-3-pyridyl]amino]piperidine-2,6-dione To a degassed solution of tert-butyl 4-[5-[(2,6-dibenzyloxy-3-pyridyl)amino]-3-fluoro-2-pyridyl]piperidine-1-carboxylate (2.5 g, 4.23 mmol) in ethyl acetate (20 mL), Palladium, 10% on carbon, Type 487, dry (450.38 mg, 4.23 mmol) was added. Resulting mixture was stirred at room temperature under hydrogen balloon pressure for 16 h. The reaction mixture was filtered through a short pad of celite, washed with ethyl acetate and concentrated under reduced pressure. Crude mass was purified by combiflash chromatography (60% ethyl acetate in hexanes) to afford 3-[[6-[1-(1-tert-butoxyethyl)-4-piperidyl]-5-fluoro-3-pyridyl]amino]piperidine-2,6-dione (900 mg, 2.21 mmol, 52.32% yield). LCMS (ESI+): 407.0 (M+H).

Step 3: 3-[[5-fluoro-6-(4-piperidyl)-3-pyridyl]amino]piperidine-2,6-dione

To a stirred solution of 3-[[6-[1-(1-tert-butoxyethyl)-4-piperidyl]-5-fluoro-3-pyridyl]amino]piperidine-2,6-dione (900 mg, 2.21 mmol) in dichloromethane (15 mL), trifluoroacetic acid (2.52 g, 22.14 mmol, 1.71 mL) was added dropwise at 0° C. Resulting mixture was warmed to room temperature and stirred for 5 h. The reaction mixture was concentrated under reduced pressure, the solid residue was triturated with ether and submitted to high vacuum to afford 3-[[5-fluoro-6-(4-piperidyl)-3-pyridyl]amino]piperidine-2,6-dione (690 mg, 1.59 mmol, 71.72% yield) as blue solid. LCMS (ESI+): 307.0 (M+H).

Step 4: tert-butyl 2-[4-[5-[(2,6-dioxo-3-piperidyl)amino]-3-fluoro-2-pyridyl]-1-piperidyl]acetate To a stirred solution of 3-[[5-fluoro-6-(4-piperidyl)-3-pyridyl]amino]piperidine-2,6-dione, trifluoroacetic acid salt (150 mg, 356.84 µmol) in N,N-dimethylformamide (3 mL) at 0° C. was added N,N-diisopropylethylamine (310.77 µL, 230.59 mg, 1.78 mmol) and tert-butyl 2-bromoacetate (54.95 µL, 73.08 mg, 374.68 µmol) was added in to the reaction mixture dropwise. The reaction mixture was stirred for 16 h in room temperature. The mixture was added ice cold water (10 mL) and extracted using ethyl acetate (2×20 mL). The combined organic layer was dried over sodium sulfate, filtered, and concentrated under reduced pressure to afford crude mixture. The crude mixture was purified using flash silica gel column chromatography eluting in 5% methanol in dichloromethane to afford tert-butyl 2-[4-[5-[(2,6-dioxo-3-piperidyl)amino]-3-fluoro-2-pyridyl]-1-piperidyl]acetate (80 mg, 171.50 µmol, 48.06% yield). LCMS m/z: 421.0 [M+H]

Step 5: 2-[4-[5-[(2,6-dioxo-3-piperidyl)amino]-3-fluoro-2-pyridyl]-1-piperidyl]acetic acid hydrochloride tert-Butyl 2-[4-[5-[(2,6-dioxo-3-piperidyl)amino]-3-fluoro-2-pyridyl]-1-piperidyl]acetate (80 mg, 190.26 µmol) was dissolved in dichloromethane (2 mL) and added Hydrogen chloride (4.0 M in 1,4-dioxane, 238 µL, 951.30 µmol) dropwise at 0° C. and stirred the reaction mixture for 6 h. The reaction mixture was concentrated and co-distilled with 10 mL of dichloromethane under reduced pressure. The solid was triturated with diethyl ether to give 2-[4-[5-[(2,6-dioxo-3-piperidyl)amino]-3-fluoro-2-pyridyl]-1-piperidyl]acetic acid hydrochloride (70 mg, 155.43 mol, 81.69% yield) as an off white solid. LCMS: m/z 365 (M+H$^+$)

Step 6: 2-(6,7-dihydro-5H-pyrrolo[1,2-c]imidazol-1-yl)-2-[6-[4-[2-[2-[4-[5-[(2,6-dioxo-3-piperidyl)amino]-3-fluoro-2-pyridyl]-1-piperidyl]acetyl]-2,6-diazaspiro[3.3]heptan-6-yl]phenyl]-4-fluoro-1-oxo-isoindolin-2-yl]-N-thiazol-2-yl-acetamide To a solution of 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (80 mg, 117.01 µmol) 2-[4-[5-[(2,6-dioxo-3-piperidyl)amino]-3-fluoro-2-pyridyl]-1-piperidyl] acetic acid (51.17 mg, 140.44 µmol) in N,N-dimethylformamide (1 mL) was added N,N-diisopropylethylamine (75.61 mg, 585.07 µmol, 101.91 µL) at 0° C. followed by the addition of 1-[(1-(cyano-2-ethoxy-2-oxoethylideneaminooxy)-dimethylamino-morpholino)] uronium hexafluorophosphate (100.23 mg, 234.03 µmol). The reaction mixture was stirred for 1 h at room temperature. The crude reaction mixture was directly injected and purified by reverse phase C18 chromatography (0.1% ammonium acetate in water and acetonitrile). The pure fractions were lyophilized to afford required product Compound 112 (28 mg, 29.53 µmol, 25.24% yield) off white solid which was submitted for analysis. LCMS at m/z 916.4 (M+H$^+$). $^1$H-NMR (400 MHz, DMSO-d6): δ 12.54 (s, 1H), 10.85 (s, 1H), 7.86 (s, 1H), 7.74 (s, 1H), 7.71 (d, J=10.80 Hz, 1H), 7.65 (d, J=8.80 Hz, 2H), 7.60 (s, 1H), 7.47 (s, 1H), 7.24 (s, 1H), 6.88 (dd, J=13.20, 2.40 Hz, 1H), 6.54 (d, J=8.40 Hz, 1H), 6.34 (d, J=8.40 Hz, 1H), 6.12 (s, 1H), 4.83-4.77 (m, 1H), 4.44 (s, 2H), 4.39-4.35 (m, 1H), 4.21 (d, J=17.20 Hz, 1H), 4.09 (s, 2H), 4.03 (s, 4H), 4.00-3.98 (m, 2H), 3.00 (s, 2H), 2.90 (d, J=10.80 Hz, 2H), 2.79-2.69 (m, 3H), 2.56-2.53 (m, 3H), 2.13-2.08 (m, 3H), 1.98-1.76 (m, 5H), 1.63 (d, J=11.20 Hz, 2H).

Example 113

2-(6,7-dihydro-5H-pyrrolo[1,2-c]imidazol-1-yl)-2-[6-[4-[7-[2-[4-[3-(2,4-dioxohexahydropyrimidin-1-yl)-1-methyl-indazol-6-yl]-3,3-difluoro-1-piperidyl]acetyl]-2,7-diazaspiro[3.4]octan-2-yl]phenyl]-4-fluoro-1-oxo-isoindolin-2-yl]-N-thiazol-2-yl-acetamide, Compound 113

Step 1: tert-Butyl 2-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenyl)-2,6-diazaspiro[3.4]octane-6-carboxylate

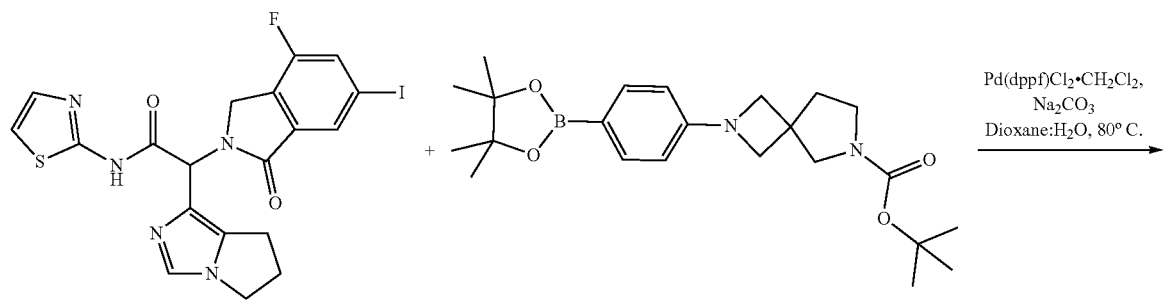

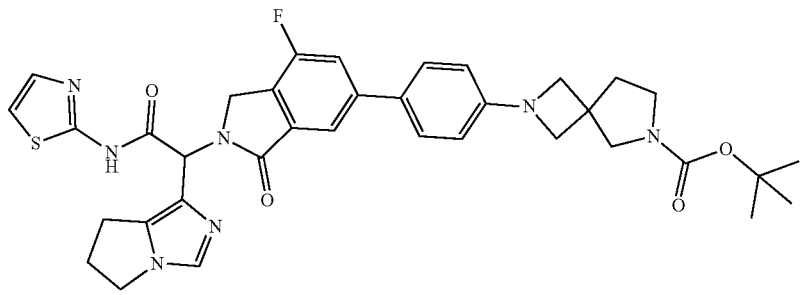

Into a 100 mL double-necked round-bottomed flask containing a well-stirred solution of 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (800 mg, 1.53 mmol) and tert-butyl 2-[4-(4,4,5,5-tetramethyl-1,3,2-dioxaborolan-2-yl)phenyl]-2,7-diazaspiro[3.4]octane-7-carboxylate (760.09 mg, 1.83 mmol) in anhydrous 1,4-dioxane (15 mL) was added Sodium carbonate (486.08 mg, 4.59 mmol, 192.12 µL) in Water (3.5 mL) under nitrogen atmosphere. The resulting mixture was degassed with nitrogen for 15 minutes. Subsequently, [1,1' Bis(diphenylphosphino) ferrocene] dichloropalladium (II), complex with dichloromethane (124.77 mg, 152.87 µmol) was added and further degassed for 10 minutes, and the reaction mixture was heated at 80° C. for 16 h. The reaction mixture was diluted with dichloromethane and filtered through celite, and the filtrate was concentrated under reduced pressure to get crude. The crude residue was purified by flash column chromatography using silica gel (100-200 mesh) eluting with 3% methanol in dichloromethane to get tert-butyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.4]octane-7-carboxylate (410 mg, 355.44 µmol, 23.25% yield) as a light brown solid. LCMS(ESI+) m/z: 684.3 [M+H]+.

Step 2: 2-(6-(4-(2,6-diazaspiro[3.4]octan-2-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide

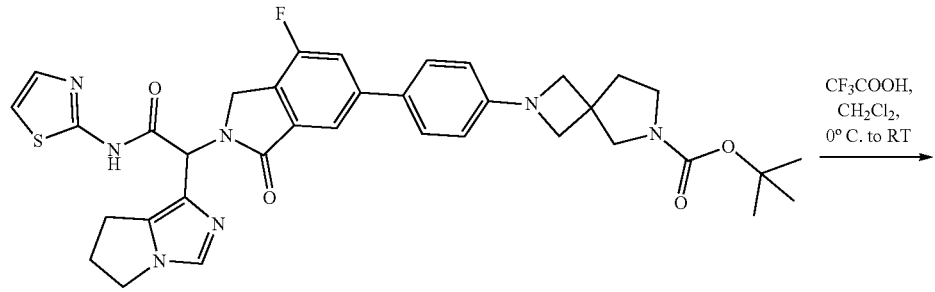

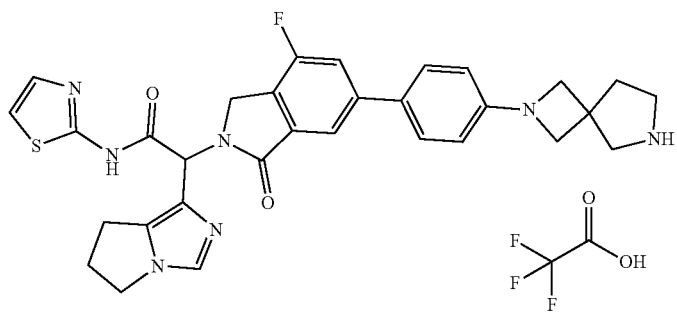

Into a 100 mL single-necked round-bottomed flask containing a well-stirred solution of tert-butyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.4]octane-7-carboxylate (120 mg, 175.5 μmol) in anhydrous dichloromethane (2.0 mL) was added trifluoroacetic acid (200.1 mg, 1.75 mmol, 135 μL) dropwise at 0° C. The reaction mixture was stirred for 4 h at ambient temperature under nitrogen atmosphere. The solvent was removed under reduced pressure. The residue was co-distilled with dichloromethane and triturated with Et₂O (50 mL) to afford 2-[6-[4-(2,7-diazaspiro[3.4]octan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt as an off white solid. LCMS(ESI+) m/z: 584.2 [M+H]⁺.

Step 3: 2-(6,7-dihydro-5H-pyrrolo[1,2-c]imidazol-1-yl)-2-(6-(4-(6-(2-(4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.4]octan-2-yl)phenyl)-4-fluoro-1-oxoisoindolin-2-yl)-N-(thiazol-2-yl)acetamide

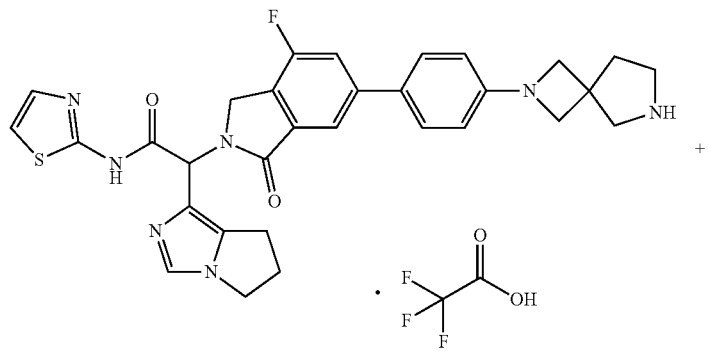

-continued

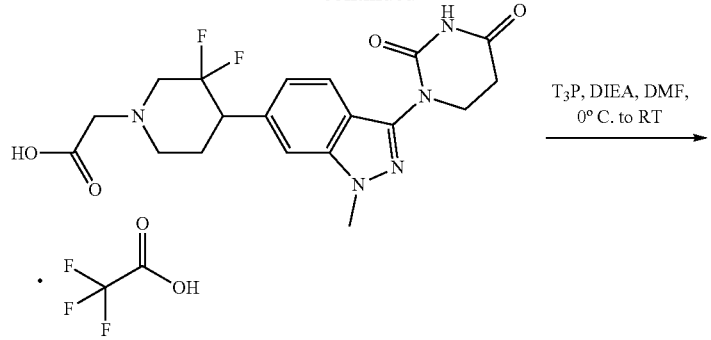

T₃P, DIEA, DMF,
0° C. to RT
→

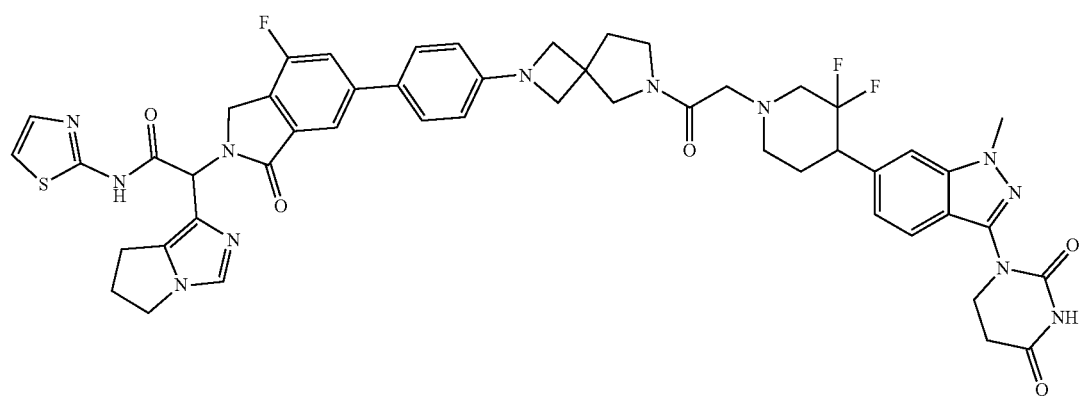

Into a 10 mL single-necked round-bottomed flask containing a well-stirred solution of 2-[6-[4-(2,7-diazaspiro[3.4]octan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide trifluoroacetic acid salt (150 mg, 214.99 μmol) and 2-[4-[3-(2,4-dioxohexahydropyrimidin-1-yl)-1-methyl-indazol-6-yl]-3,3-difluoro-1-piperidyl]acetic acid, trifluoroacetic acid salt (115.11 mg, 214.99 μmol) in N,N-dimethylformamide (1.5 mL) was added N,N-diisopropylethylamine (138.93 mg, 1.07 mmol, 187.24 μL) under nitrogen atmosphere at 0° C. Subsequently, Propane phosphonic acid anhydride (136.81 mg, 429.98 μmol) was added to the reaction mixture at 0° C. and stirred for 1 h at ambient temperature under nitrogen atmosphere. The crude mixture was directly injected on a C18 column (100 g) for purification while eluting (0% to 50% of acetonitrile+0.1% ammonium acetate in water over 30 minutes, then steep gradient to 100% acetonitrile). The pure fraction was frozen and lyophilized to afford Compound 113 (34.1 mg, 33.61 μmol, 19.1% yield over 2 steps) as an off-white solid. LCMS (ESI+) m/z: 988.4 [M+H]⁺. 1H-NMR (400 MHz, DMSO-d6): δ 12.52 (s, 1H), 10.58 (s, 1H), 7.75 (s, 1H), 7.72 (d, J=10.80 Hz, 1H), 7.67 (d, J=3.20 Hz, 1H), 7.65 (d, J=3.60 Hz, 1H), 7.61 (s, 1H), 7.58 (d, J=4.80 Hz, 2H), 7.55 (s, 1H), 7.49 (d, J=3.60 Hz, 1H), 7.26 (d, J=3.20 Hz, 1H), 7.10-7.08 (m, 1H), 6.56 (t, J 20=7.20 Hz, 2H), 6.15 (s, 1H), 4.80 (d, J=17.60 Hz, 1H), 4.22 (d, J=17.60 Hz, 1H), 3.99 (d, J=7.60 Hz, 5H), 3.92-3.87 (m, 2H), 3.85-3.80 (m, 4H), 3.77 (s, 1H), 3.60-3.57 (m, 2H), 3.43-3.39 (m, 2H), 3.27-3.20 (m, 2H), 3.03 (br d, J=10.00 Hz, 1H), 2.85-2.70 (s, 5H), 2.33-2.21 (m, 2H), 2.09 (t, J=5.60 Hz, 1H), 1.85 (d, J=11.60 Hz, 1H) (A number of proton signals could not be observed due to water obscuration).

Example 114

2-(6,7-dihydro-5H-pyrrolo[1,2-c]imidazol-1-yl)-2-[6-[4-[7-[2-[1-[4-[(2,6-dioxo-3-piperidyl)amino]-2-fluoro-phenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide,
Compound 114

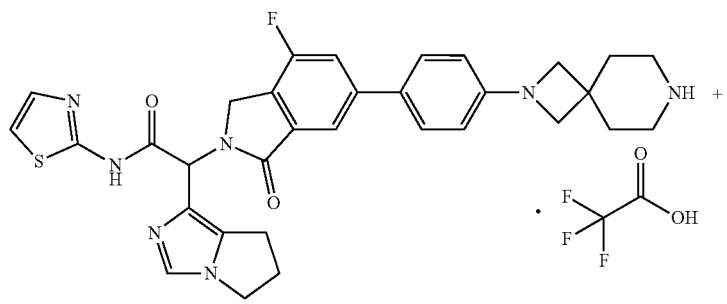

-continued

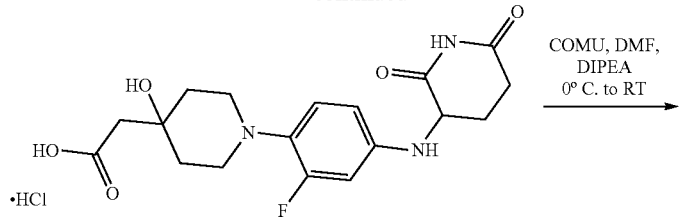

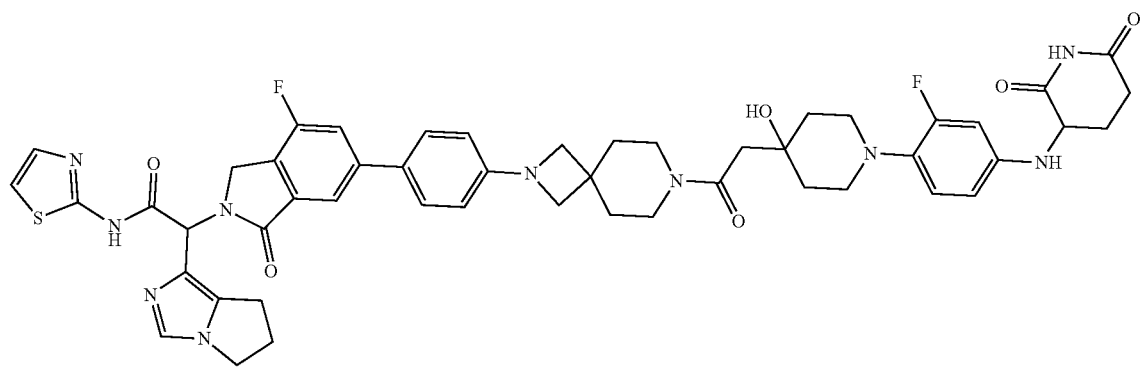

2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide; 2,2,2-trifluoro-acetic acid (150 mg, 210.75 μmol), and 2-[1-[4-[(2,6-dioxo-3-piperidyl)amino]-2-fluoro-phenyl]-4-hydroxy-4-piperidyl]acetic acid; hydrochloride (103.99 mg, 210.75 μmol), were mixed in N,N-dimethylformamide (1.5 mL). N,N-diisopropylethylamine (136.19 mg, 1.05 mmol, 183.55 μL) was added to the reaction mixture at 0° C. 1-[Bis(dimethylamino)methylene]-1H-1,2,3-triazolo[4,5-b]pyridinium 3-oxid hexafluorophosphate (160.27 mg, 421.51 μmol) was added to the reaction mixture at 0° C. The reaction mixture was stirred at room temperature for 1 h. The crude mixture was directly injected on a C18 column (100 g) for purification while eluting (0% to 50% of acetonitrile+0.1% ammonium acetate in water over 30 minutes, then steep gradient to 100% acetonitrile). The pure fraction was frozen and lyophilized to afford Compound 114 (20 mg, 20.54 μmol, 9.75% yield) as an off-white solid. LCMS (ESI+): 959.4 [M+H]. 1H-NMR (400 MHz, DMSO-d6): δ 12.53 (s, 1H), 10.79 (s, 1H), 7.74 (s, 1H), 7.71 (d, J=10.80 Hz, 1H), 7.64 (d, J=8.80 Hz, 2H), 7.61 (s, 1H), 7.49 (d, J=3.60 Hz, 1H), 7.27 (d, J=3.60 Hz, 1H), 6.86 (t, J=9.60 Hz, 1H), 6.53 (d, J=8.40 Hz, 2H), 6.48 (d, J=2.40 Hz, 1H), 6.42 (dd, J=2.00, 8.80 Hz, 1H), 6.15 (s, 1H), 5.79 (d, J=7.60 Hz, 1H), 4.94 (s, 1H), 4.80 (d, J=17.60 Hz, 1H), 4.26-4.19 (m, 2H), 4.02-3.99 (m, 2H), 3.69-3.65 (m, 4H), 3.52 (s, 4H), 2.90-2.83 (m, 4H), 2.75-2.71 (m, 2H), 2.59 (t, J=4.00 Hz, 1H), 2.11-2.08 (m, 1H), 1.86-1.63 (m, 9H), [Expected 52H, Observed 47H (water obscuration)].

Example 115

2-(6,7-dihydro-5H-pyrrolo[1,2-c]imidazol-1-yl)-2-[6-[4-[7-[2-[1-[4-[(2,6-dioxo-3-piperidyl)amino]-2-fluoro-phenyl]-4-hydroxy-4-piperidyl]acetyl]-2,7-diazaspiro[3.4]octan-2-yl]phenyl]-4-fluoro-1-oxo-isoindolin-2-yl]-N-thiazol-2-yl-acetamide, Compound 115

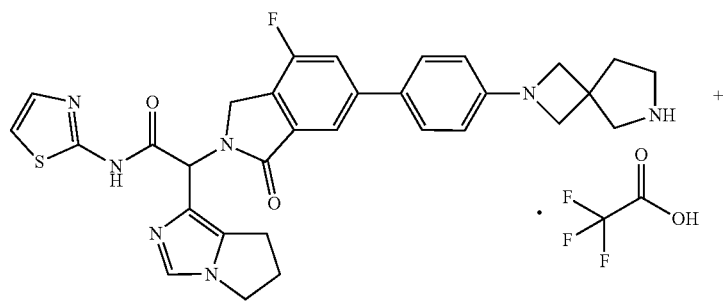

-continued

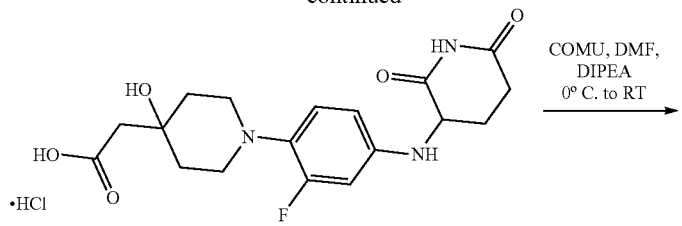

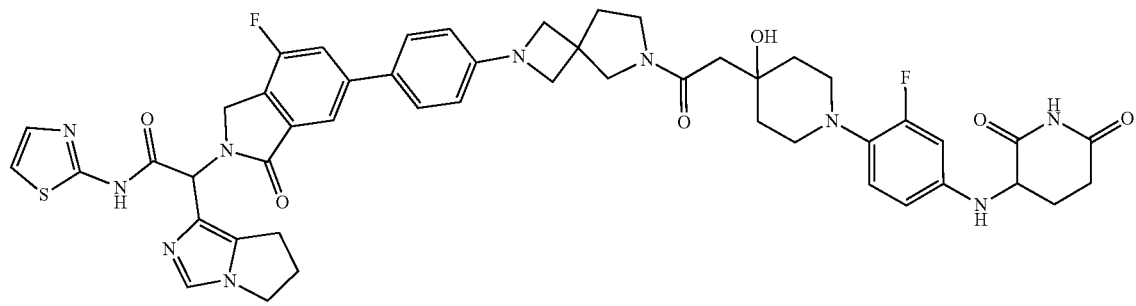

2-[6-[4-(2,7-diazaspiro[3.4]octan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide; 2,2,2-trifluoroacetic acid (120 mg, 171.99 µmol), and 2-[1-[4-[(2,6-dioxo-3-piperidyl)amino]-2-fluoro-phenyl]-4-hydroxy-4-piperidyl]acetic acid; hydrochloride (78.67 mg, 159.45 µmol), were mixed in N,N-dimethylformamide (1.5 mL). N,N-diisopropylethylamine (136.19 mg, 1.05 mmol, 183.55 µL) was added to the reaction mixture at 0° C. 1-Cyano-2-ethoxy-2-oxoethylidenaminooxy) dimethylamino-morpholino-carbenium hexafluorophosphate (95.29 mg, 223.59 µmol) was added to the reaction mixture at 0° C. The reaction mixture was stirred at room temperature for 1 h. The crude mixture was directly injected on a C18 column (100 g) for purification while eluting (0% to 50% of acetonitrile in water (+0.1% ammonium acetate) over 30 minutes, then steep gradient to 100% acetonitrile). The pure fraction was frozen and lyophilized to afford Compound 115 (62.5 mg, 65.58 µmol, 38.13% yield) as an off-white solid. LCMS (ESI−): 943.4 [M−H]. $^1$H-NMR (400 MHz, DMSO-d6): δ 12.52 (s, 1H), 10.78 (s, 1H), 7.75 (s, 1H), 7.73 (s, 1H), 7.71 (s, 1H), 7.70 (d, J=Hz, 1H), 7.66 (d, J=2.40 Hz, 1H), 7.64 (d, J=2.40 Hz, 1H), 7.61 (s, 1H), 7.49 (d, J=3.60 Hz, 1H), 7.26 (d, J=3.60 Hz, 1H), 6.89-6.83 (m, 1H), 6.52 (t, J=2.40 Hz, 1H), 6.48 (d, J=2.80 Hz, 1H), 6.42 (d, J=8.40 Hz, 1H), 6.15 (s, 1H), 5.77 (d, J=7.60 Hz, 1H), 4.95 (d, J=8.80 Hz, 1H), 4.80 (d, J=17.60 Hz, 2H), 4.20 (s, 1H), 4.01-3.98 (m, 3H), 3.87-3.82 (m, 4H), 3.78 (s, 1H), 3.60-3.57 (m, 2H), 3.42 (t, J=6.80 Hz, 1H), 2.91-2.86 (m, 4H), 2.74-2.67 (m, 2H), 2.59 (s, 2H), 2.45 (s, 3H), 2.20 (t, J=Hz, 1H), 2.11-2.09 (m, 2H), 1.76-1.65 (m, 4H) Water obscuration.

Example 116

2-[6-[4-[2-[2-[4-[3-(2,4-dioxohexahydropyrimidin-1-yl)-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide, Compound 116

Step 1: 6-(4-(2-(2-ethoxy-1-((R)-6-fluoro-6,7-dihydro-5H-pyrrolo[1,2-c]imidazol-1-yl)-2-oxoethyl)-7-fluoro-3-oxoisoindolin-5-yl)phenyl)-2,6-diazaspiro[3.3]heptane-2-carboxylate

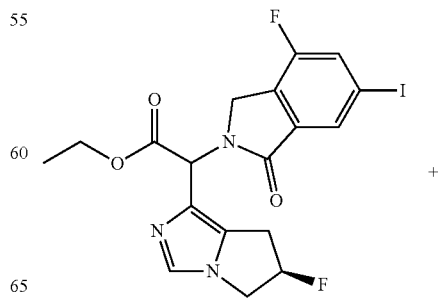

-continued

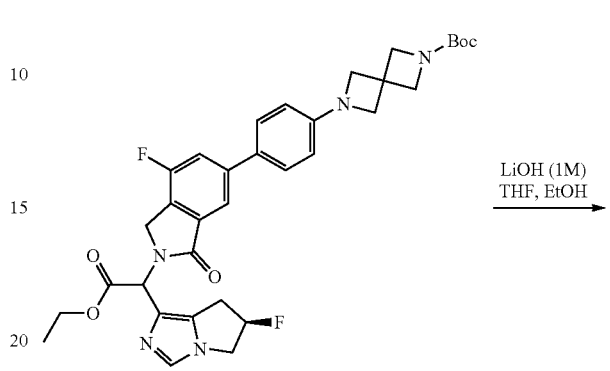

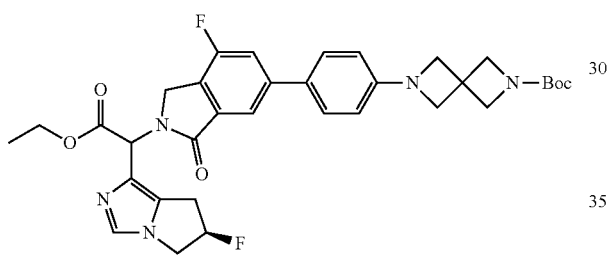

To a stirred solution of ethyl 2-[(6R)-6-fluoro-6,7-dihydro-5H-pyrrolo[1,2-c]imidazol-1-yl]-2-(4-fluoro-6-iodo-1-oxo-isoindolin-2-yl)acetate (1.0 g, 2.05 mmol) and tert-butyl 6-[4-(4,4,5,5-tetramethyl-1,3,2-dioxaborolan-2-yl)phenyl]-2,6-diazaspiro[3.3]heptane-2-carboxylate (985.93 mg, 2.46 mmol) in 1,4-dioxane (10 mL) and sodium carbonate (652.60 mg, 6.16 mmol, 257.94 µL) in water (1 mL) was added. The reaction mixture was degassed with nitrogen for 10 min. [1,1'-Bis(diphenylphosphino)ferrocene] dichloropalladium (II), complex with dichloromethane (167.61 mg, 205.24 µmol)) was added into reaction mixture and further degassed for 5 min. The reaction mixture was heated at 80° C. under nitrogen for 16 h. The reaction mixture was filtered through celite, washed using ethyl acetate (2×50 mL), and the organic layer was separated, dried with sodium sulfate and concentrated under reduced pressure to get crude, which was purified by using 230-400 silica-gel with gradient (0-10% methanol in dichloromethane) to get tert-butyl 6-(4-(2-(2-ethoxy-1-((R)-6-fluoro-6,7-dihydro-5H-pyrrolo[1,2-c]imidazol-1-yl)-2-oxoe-thyl)-7-fluoro-3-oxoi-soindolin-5-yl)phenyl)-2,6-diazaspiro[3.3]heptane-2-carboxylate (380 mg, 16.95%% yield) as a dark brown solid, LCMS (ESI+): 634.3 [M+H].

Step 2: [2-[6-[4-(2-tert-butoxycarbonyl-2,6-diazaspiro[3.3]heptan-6-yl)phenyl]-4-fluoro-1-oxo-isoindolin-2-yl]-2-[(6R)-6-fluoro-6,7-dihydro-5H-pyrrolo[1,2-c]imidazol-1-yl]acetyl]oxylithium

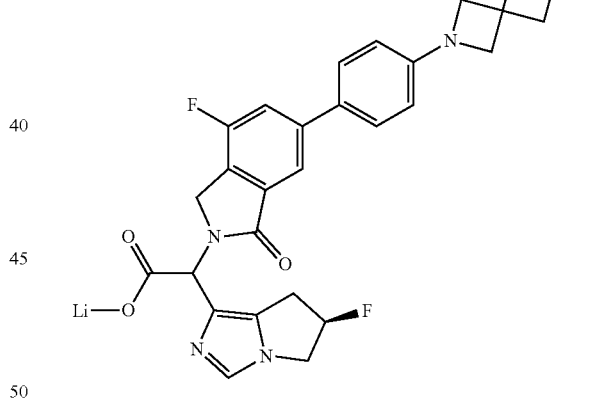

To a stirred solution of tert-butyl 6-[4-[2-[2-ethoxy-1-[(6R)-6-fluoro-6,7-dihydro-5H-pyrrolo[1,2-c]imidazol-1-yl]-2-oxo-ethyl]-7-fluoro-3-oxo-isoindolin-5-yl]phenyl]-2,6-diazaspiro[3.3]heptane-2-carboxylate (380 mg, 599.67 µmol) in tetrahydrofuran (2 mL) and ethanol (2 mL) was added 1M LiOH (14.36 mg, 599.67 µmol) at 0° C. Reaction mixture was stirred at room temperature for 3 h. The reaction mixture was concentrated under reduced to get crude which was further triturated with diethyl ether, solvent was decanted to afford [2-[6-[4-(2-tert-butoxycarbonyl-2,6-diazaspiro[3.3]heptan-6-yl)phenyl]-4-fluoro-1-oxo-isoindolin-2-yl]-2-[(6R)-6-fluoro-6,7-dihydro-5H-pyrrolo[1,2-c]imidazol-1-yl]acetyl]oxylithium (350 mg, 55.35% yield) brown solid. LCMS (ESI+): 606.2 [M+H].

Step 3: tert-Butyl 6-(4-(7-fluoro-2-(1-((R)-6-fluoro-6,7-dihydro-5H-pyrrolo[1,2-c]imidazol-1-yl)-2-oxo-2-(thiazol-2-ylamino)ethyl)-3-oxoisoindolin-5-yl)phenyl)-2,6-diazaspiro[3.3]heptane-2-carboxylate

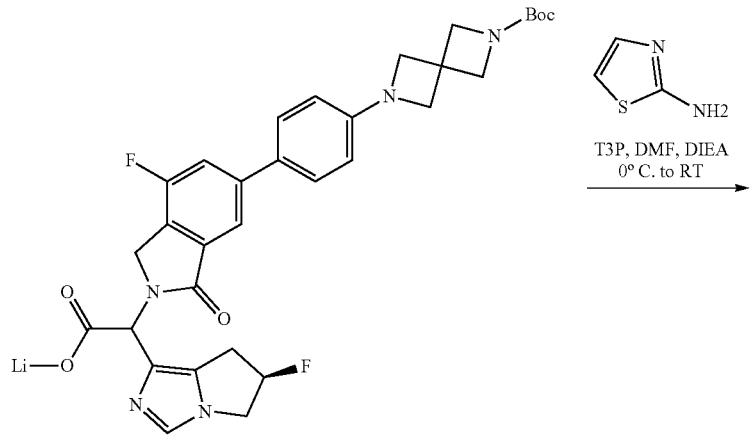

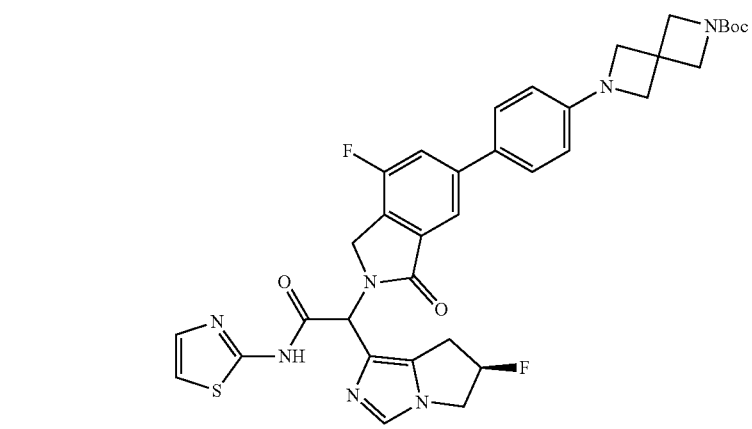

To a stirred solution of [2-[6-[4-(2-tert-butoxycarbonyl-2,6-diazaspiro[3.3]heptan-6-yl)phenyl]-4-fluoro-1-oxo-isoindolin-2-yl]-2-[(6R)-6-fluoro-6,7-dihydro-5H-pyrrolo[1,2-c]imidazol-1-yl]acetyl]oxylithium (350 mg, 572.30 µmol) and thiazol-2-amine (171.94 mg, 1.72 mmol) in N,N-dimethylformamide (4 mL) was added N,N-diisopropylethylamine (369.82 mg, 2.86 mmol, 498.41 µL) and Propyl phosphonic anhydride solution (50 wt. % in ethyl acetate, 364.19 mg, 1.14 mmol) at 0° C. The reaction mixture was stirred at room temperature for 4 h. The reaction mixture was diluted with saturated aqueous sodium bicarbonate-solution and extracted using ethyl acetate [3×25 mL] and combined organic layers washed with brine, dried over sodium sulfate, and concentrated under reduced pressure. The crude material was purified by flash column chromatography on silica gel (230-400) with (0-10% of methanol in dichloromethane) to afford tert-butyl 6-(4-(7-fluoro-2-(1-((R)-6-fluoro-6,7-dihydro-5H-pyrrolo[1,2-c]imidazol-1-yl)-2-oxo-2-(thiazol-2-ylamino)ethyl)-3-oxoisoindolin-5-yl)phenyl)-2,6-diazaspiro[3.3]heptane-2-carboxylate (160 mg, 25.61% yield) as a brown solid, LCMS (ESI+): 688.3 [M+H]).

Step 4: Synthesis of 2-(6-(4-(2,6-diazaspiro[3.3]heptan-2-yl)phenyl)-4-fluoro-1-oxoisoindolin-2-yl)-2-((R)-6-fluoro-6,7-dihydro-5H-pyrrolo[1,2-c]imidazol-1-yl)-N-(thiazol-2-yl)acetamide

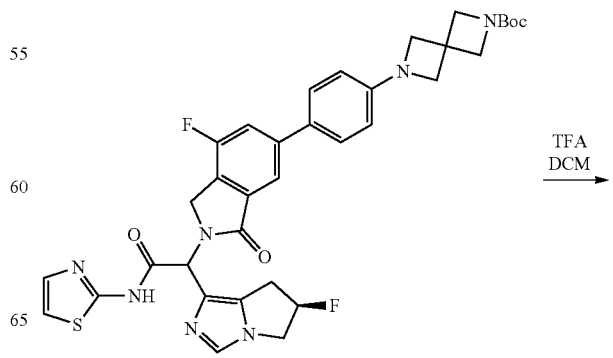

1055
-continued

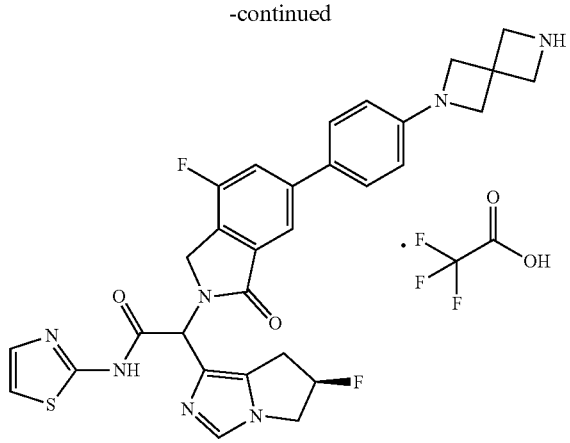

To a stirred solution of tert-butyl 6-[4-[7-fluoro-2-[1-[(6R)-6-fluoro-6,7-dihydro-5H-pyrrolo[1,2-c]imidazol-1-

1056 yl]-2-oxo-2-(thiazol-2-ylamino)ethyl]-3-oxo-isoindolin-5-yl]phenyl]-2,6-diazaspiro-[3.3]heptane-2-carboxylate (82 mg, 119.23 µmol) in dichloromethane (2 mL) was added drop wise trifluoroacetic acid (95.16 mg, 834.60 µmol, 64.30 µL) at 0° C. and stirred the reaction mixture at room temperature for 6 h. The reaction mixture was concentrated under reduced pressure and further codistilled with dichloromethane (2×5 mL), and triturated with diethyl ether (5 mL) to obtain 2-(6-(4-(2,6-diazaspiro[3.3]heptan-2-yl)phenyl)-4-fluoro-1-oxoisoindolin-2-yl)-2-((R)-6-fluoro-6,7-dihydro-5H-pyrrolo[1,2-c]imidazol-1-yl)-N-(thiazol-2-yl)acetamide (80 mg, 77.46% yield) as brown solid. LCMS (ESI+): 588.1 [M+H].

Step 5: 2-(6-(4-(6-(2-(4-(3-(2,4-dioxotetrahydropyrimidin-1(2H)-yl)-1-methyl-1H-indazol-6-yl)-3,3-difluoropiperidin-1-yl)acetyl)-2,6-diazaspiro[3.3]heptan-2-yl)phenyl)-4-fluoro-1-oxoisoindolin-2-yl)-2-((R)-6-fluoro-6,7-dihydro-5H-pyrrolo[1,2-c]imidazol-1-yl)-N-(thiazol-2-yl)acetamide

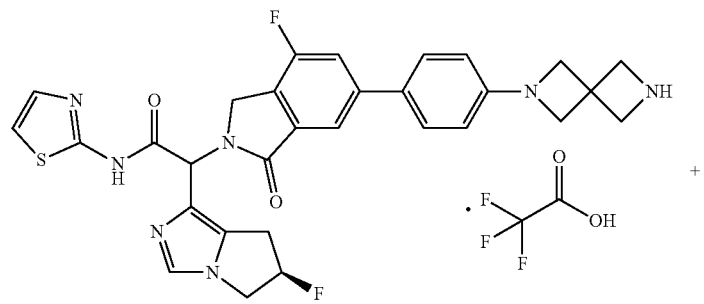

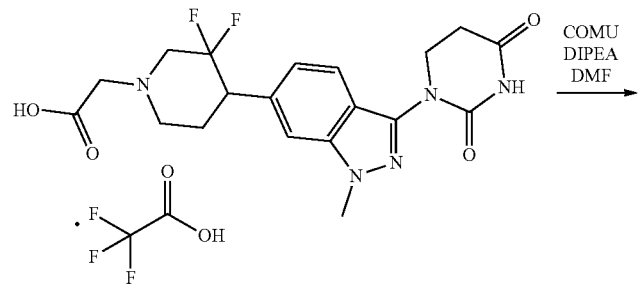

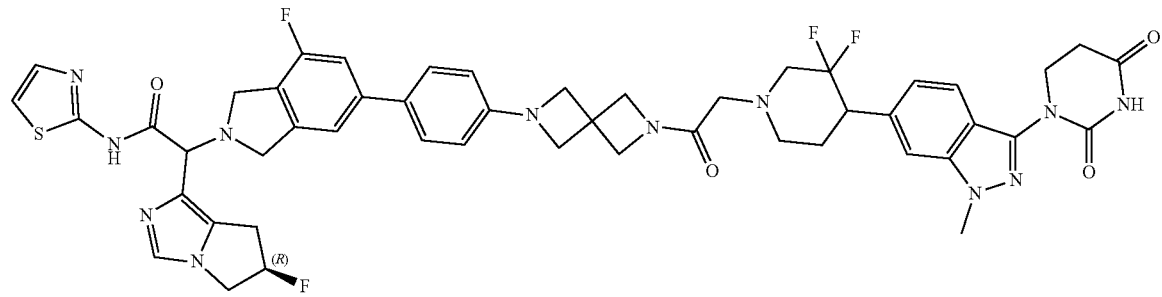

To a stirred solution of 2-[6-[4-(2,6-diazaspiro[3.3]heptan-2-yl)phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide, trifluoroacetic acid salt (70 mg, 99.76 μmol) and 2-[4-[3-(2,4-dioxohexahydropyrimidin-1-yl)-1-methyl-indazol-6-yl]-3,3-difluoro-1-piperidyl]acetic acid, trifluoroacetic acid salt (53.41 mg, 99.76 μmol) in N,N-dimethylformamide (0.7 mL) was added N,N-diisopropylethylamine (64.47 mg, 498.81 μmol, 86.88 μL) at 0° C. followed by the addition of 1-[(1-(cyano-2-ethoxy-2-oxo-ethylideneaminooxy)-dimethylamino-morpholino)] uronium hexafluorophosphate (85.45 mg, 199.53 μmol) at the same temperature. The reaction mixture was stirred for 1 h at room temperature. The crude mixture was directly injected on a C18 column (60 g) for purification while eluting (0% to 50% of acetonitrile+0.1% ammonium acetate in water over 30 minutes, then steep gradient to 100% acetonitrile). The pure fraction was frozen and lyophilized to afford Compound 116 (12 mg, 11.74 μmol, 11.77% yield) as an off-white solid. LCMS (ESI+): 991.2 [M+H]; 1H-NMR (400 MHz, DMSO-d6): δ 12.57 (s, 1H), 10.58 (s, 1H), 7.75-7.73 (m, 2H), 7.69 (t, J=4.80 Hz, 1H), 7.65 (d, J=8.80 Hz, 2H), 7.60 (d, J=8.40 Hz, 1H), 7.57 (s, 1H), 7.48 (d, J=1.60 Hz, 1H), 7.25 (s, 1H), 7.10 (d, J=8.80 Hz, 1H), 6.56 (d, J=8.80 Hz, 2H), 6.15 (s, 1H), 5.84 (d, J=54.80 Hz, 1H), 4.91-4.75 (m, 1H), 4.45 (s, 2H), 4.36-4.16 (m, 3H), 4.11 (s, 2H), 4.04 (d, J=6.00 Hz, 4H), 4.00 (s, 3H), 3.93 (t, J=6.40 Hz, 2H), 3.28-3.17 (m, 4H), 3.03-2.98 (m, 2H), 2.76 (t, J=6.80 Hz, 3H), 2.69-2.59 (m, 1H), 2.50-2.39 (m, 1H), 2.31-2.19 (m, 1H).

Example 117

2-[6-[4-[2-[2-[1-[2-chloro-4-[(2,6-dioxo-3-piperidyl)amino]phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, Compound 117

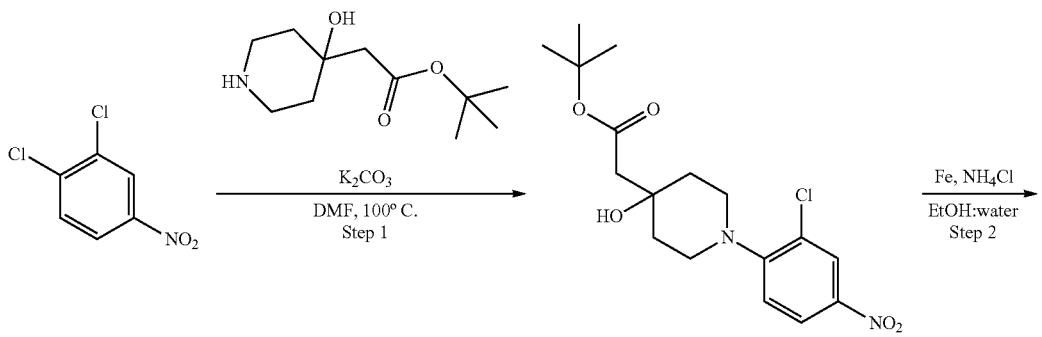

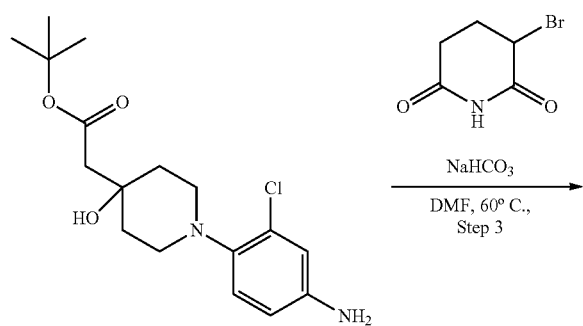

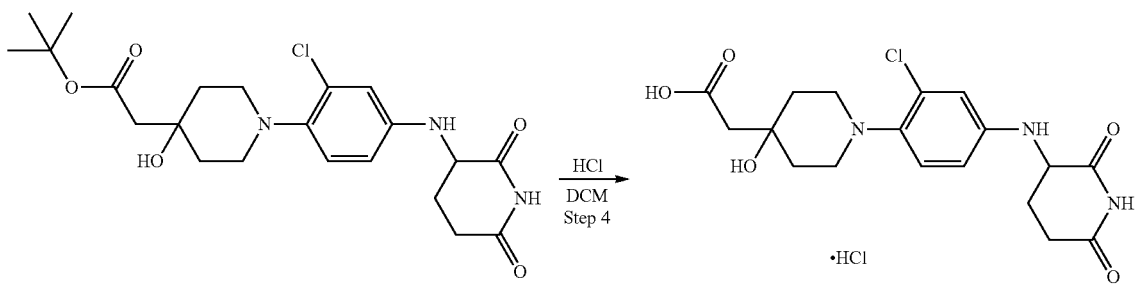

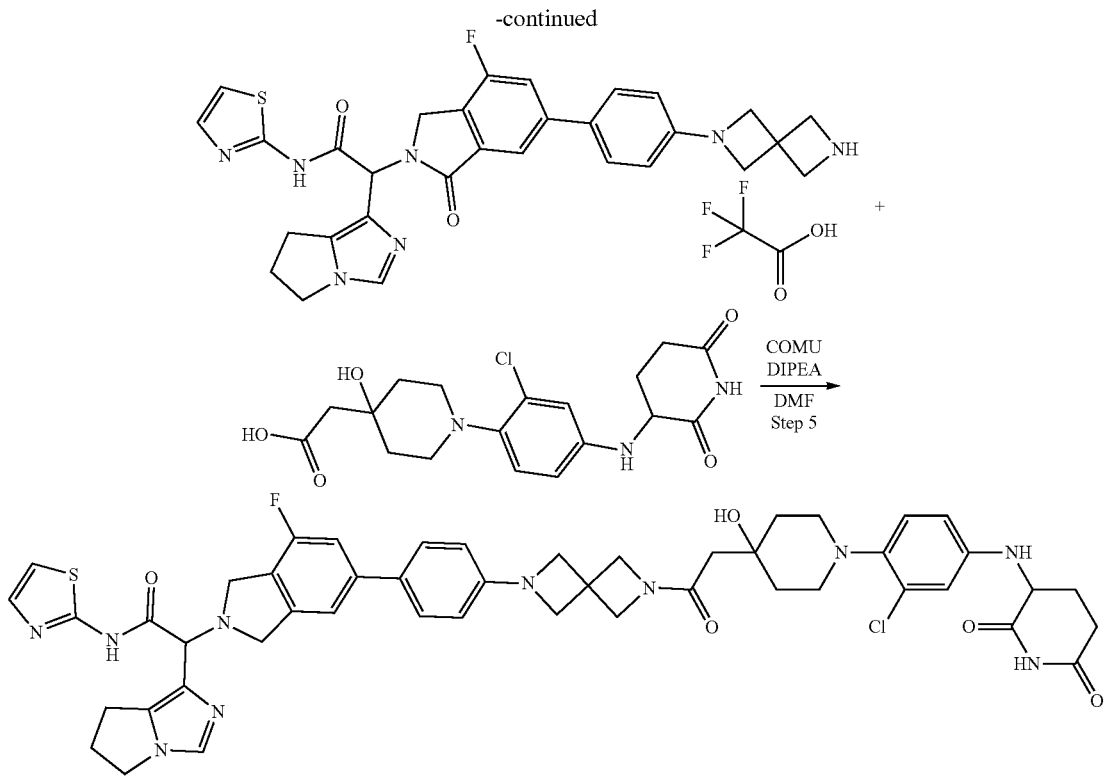

Step 1: tert-Butyl 2-(1-(2-chloro-4-nitrophenyl)-4-hydroxypiperidin-4-yl)acetate To a solution of 1,2-dichloro-4-nitro-benzene (5 g, 26.04 mmol) and 1,2-dichloro-4-nitro-benzene (5 g, 26.04 mmol) in DMSO (50 mL) was added $K_2CO_3$ (10.8 g, 78.13 mmol). The mixture was stirred at 110° C. for 1 h. The mixture was poured into water (200 mL), the mixture was extracted with ethyl acetate (100 mL×3). The combined organic phase was washed with brine (100 mL×2), dried with anhydrous sodium sulfate, filtered and concentrated in vacuum to afford tert-butyl 2-[1-(2-chloro-4-nitro-phenyl)-4-hydroxy-4-piperidyl]acetate (9.6 g, 22.52 mmol, 86.5% yield) as a yellow oil. $^1$H NMR (400 MHz, DMSO-$d_6$) δ=8.20 (d, J=2.4 Hz, 1H), 8.12 (dd, J=2.4, J=8.8, 9.0 Hz, 1H), 7.28 (d, J=8.8 Hz, 1H), 4.65 (s, 1H), 3.29 (br d, J=12.4 Hz, 2H), 3.17-3.09 (m, 2H), 2.39 (s, 2H), 1.88-1.79 (m, 2H), 1.75-1.68 (m, 2H), 1.42-1.41 (m, 9H)

Step 2: tert-Butyl 2-(1-(4-amino-2-chlorophenyl)-4-hydroxypiperidin-4-yl) acetate A mixture of tert-butyl 2-[1-(2-chloro-4-nitro-phenyl)-4-hydroxy-4-piperidyl] acetate (9.4 g, 25.35 mmol) in ethanol (190 mL) and water (38 mL) was added ammonium chloride (4.07 g, 76.05 mmol, 2.66 mL). The reaction mixture was stirred at 90° C. for 16 h. The reaction mixture was filtered to remove Iron powder, concentrated to remove solvent. The mixture was poured into water (400 mL). The mixture was extracted with ethyl acetate (200 mL×3). The combined organic phase was washed with brine (200 mL×2), dried with anhydrous sodium sulfate, filtered, and concentrated in vacuum to give tert-butyl 2-[1-(4-amino-2-chloro-phenyl)-4-hydroxy-4-piperidyl]acetate (8.6 g, 22.83 mmol, 85.53% yield).

Step 3: tert-Butyl 2-(1-(2-chloro-4-((2,6-dioxopiperidin-3-yl)amino)phenyl)-4-hydroxypiperidin-4-yl) acetate To a stirred solution of tert-butyl 2-[1-(4-amino-2-chlorophenyl)-4-hydroxy-4-piperidyl]acetate (6.4 g, 18.78 mmol) in acetonitrile (100 mL) was added TBAI (13 g, 9.39 mmol), sodium bicarbonate (4.41 g, 56.33 mmol), after 5 min of stirring was added 3-bromopiperidine-2,6-dione (3.61 g, 18.78 mmol), after 10 min, the temperature of the reaction was raised to 90° C. and continued the reaction about 72 h. The reaction mixture was concentrated under reduced pressure to remove solvent. The residue was diluted with water (400 mL) and extracted with ethyl acetate (150 mL×3). The combined organic layers were washed with brine (20 mL×2), dried over anhydrous sodium sulfate, filtered and concentrated under reduced pressure. The residue was purified by silica gel chromatography (Petroleum ether/Ethyl acetate=1:1) to afford tert-butyl 2-[1-[2-chloro-4-[(2,6-dioxo-3-piperidyl)amino]phenyl]-4-hydroxy-4-piperidyl]acetate (3.4 g, 7.23 mmol, 49.25% yield) as a blue solid. LCMS (ESI+): 452.1 (M+H), $^1$H NMR (400 MHz, CHLOROFORM-d) δ=8.05 (br s, 1H), 7.02 (d, J=8.8 Hz, 1H), 6.73 (d, J=2.8 Hz, 1H), 6.57 (dd, J=2.8, 8.8 Hz, 1H), 4.60 (d, J=3.6 Hz, 1H), 4.01 (td, J=4.2, 12.4 Hz, 1H), 3.76 (s, 1H), 3.09-2.95 (m, 4H), 2.94-2.83 (m, 1H), 2.81-2.67 (m, 1H), 2.61-2.50 (m, 1H), 2.45 (s, 2H), 1.90 (dq, J=4.8, 13.2 Hz, 1H), 1.83-1.77 (m, 4H), 1.49 (s, 9H).

Step 4: 2-[1-[2-chloro-4-[(2,6-dioxo-3-piperidyl)amino]phenyl]-4-hydroxy-4-piperidyl]acetic acid hydrochloride To a solution of tert-butyl 2-[1-[2-chloro-4-[(2,6-dioxo-3-piperidyl)amino]phenyl]-4-hydroxy-4-piperidyl]acetate (3.4 g, 7.52 mmol) in dichloromethane (50 mL) was added concentrated hydrochloric acid (12 M, 6.27 mL) at 0° C. The mixture was stirred at 20° C. for 1 hr. The reaction mixture was concentrated under vacuum. Toluene (50 mL) was added to the residue, and the volatiles were removed under reduced pressure. Toluene and tetrahydrofuran (50 mL: 50 mL) were added, and the volatiles were removed under reduced pressure. The residue was diluted with ethyl acetate (100 mL), the mixture was stirred at 15° C. for 12 h, filtered and the filter cake was collected to afford 2-[1-[2-chloro-4-[(2,6-dioxo-3-piperidyl)amino]phenyl]-4-hydroxy-4-piperidyl]acetic acid hydrochloride (2.9 g, 6.14 mmol, 81.59% yield) was obtained as a gray solid. LCMS (ESI+): 396.0 (M+H), $^1$H NMR (400 MHz, DEUTERIUM OXIDE) δ=7.52-7.45 (m, 1H), 6.91-6.87 (m, 1H), 6.79-6.72 (m, 1H), 4.40 (dd, J=5.2, 12.4 Hz, 1H), 3.89-3.76 (m, 2H), 3.60 (br d, J=12.4 Hz, 2H), 2.84-2.67 (m, 2H), 2.63 (s, 2H), 2.27-1.96 (m, 6H).

Step 5: 2-[6-[4-[2-[2-[1-[2-chloro-4-[(2,6-dioxo-3-piperidyl)amino]phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide To a solution of 2-[1-[2-chloro-4-[(2,6-dioxo-3-piperidyl)amino]phenyl]-4-hydroxy-4-piperidyl]acetic acid hydrochloride (102.44 mg, 236.95 μmol) in N,N-dimethylformamide (3 mL) was added N,N-diisopropylethylamine (127.60 mg, 987.31 μmol, 171.97 μL) followed by 1-[(1-(cyano-2-ethoxy-2-oxoethylideneaminooxy)-dimethylamino-morpholino)] uronium hexafluorophosphate (169.11 mg, 394.92 μmol) at 0° C., stirred for 15 minutes. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (135 mg, 197.46 μmol) was added to the reaction mixture and stirred for 2 h at room temperature. The reaction mixture was directly injected on a C18 column (100 g) for purification (0-50% acetonitrile in water+0.1% ammonium acetate, over 30 minutes, then steep gradient to 100% acetonitrile). The pure fractions were combined, frozen and lyophilized to get Compound 117 (32.5 mg, 32.90 μmol, 16.66% yield) as an off-white solid. LCMS (ESI+): 947.3 (M+H⁺); $^1$H-NMR (400 MHz, DMSO-d6): 12.53 (bs, 1H), 10.79 (s, 1H), 7.74 (s, 1H), 7.71 (d, J=10.80 Hz, 1H), 7.65 (d, J=8.40 Hz, 2H), 7.60 (s, 1H), 7.46 (bs, 1H), 7.21 (bs, 1H), 6.97 (d, J=8.40 Hz, 1H), 6.75 (d, J=2.40 Hz, 1H), 6.60 (dd, J=2.40, 8.80 Hz, 2H), 6.55 (d, J=8.80 Hz, 1H), 6.12 (s, 1H), 5.84 (d, J=8.00 Hz, 1H), 4.89-4.78 (m, 2H), 4.39 (s, 2H), 4.29-4.25 (m, 1H), 4.21 (d, J=17.60 Hz, 1H), 4.09 (s, 2H), 4.03-3.96 (m, 6H), 2.87 (t, J=10.00 Hz, 2H), 2.81-2.69 (m, 4H), 2.58 (t, J=10.40 Hz, 1H), 2.24 (s, 2H), 2.11-2.08 (m, 1H), 1.89-1.70 (m, 4H), 1.64 (d, J=12.40 Hz, 2H).

Example 118

2-(6,7-dihydro-5H-pyrrolo[1,2-c]imidazol-1-yl)-2-(6-(6-(6-(2-(4-(3-(2,4-dioxotetrahydropyrimidin-1(2H)-yl)-1-methyl-1H-indazol-6-yl)-3,3-difluoropiperidin-1-yl)-2-oxoethyl)-2,6-diazaspiro[3.3]heptan-2-yl)pyridin-3-yl)-4-fluoro-1-oxoisoindolin-2-yl)-N-(thiazol-2-yl)acetamide, Compound 118

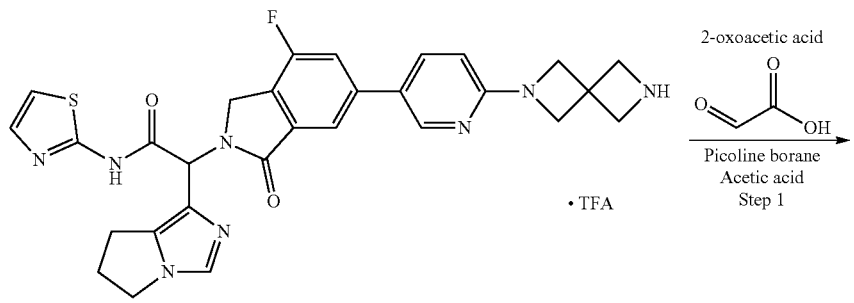

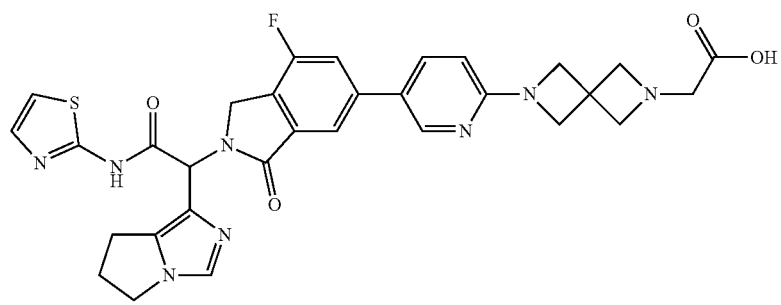

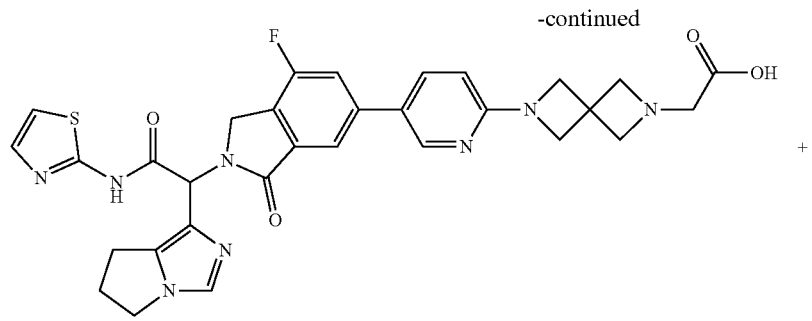

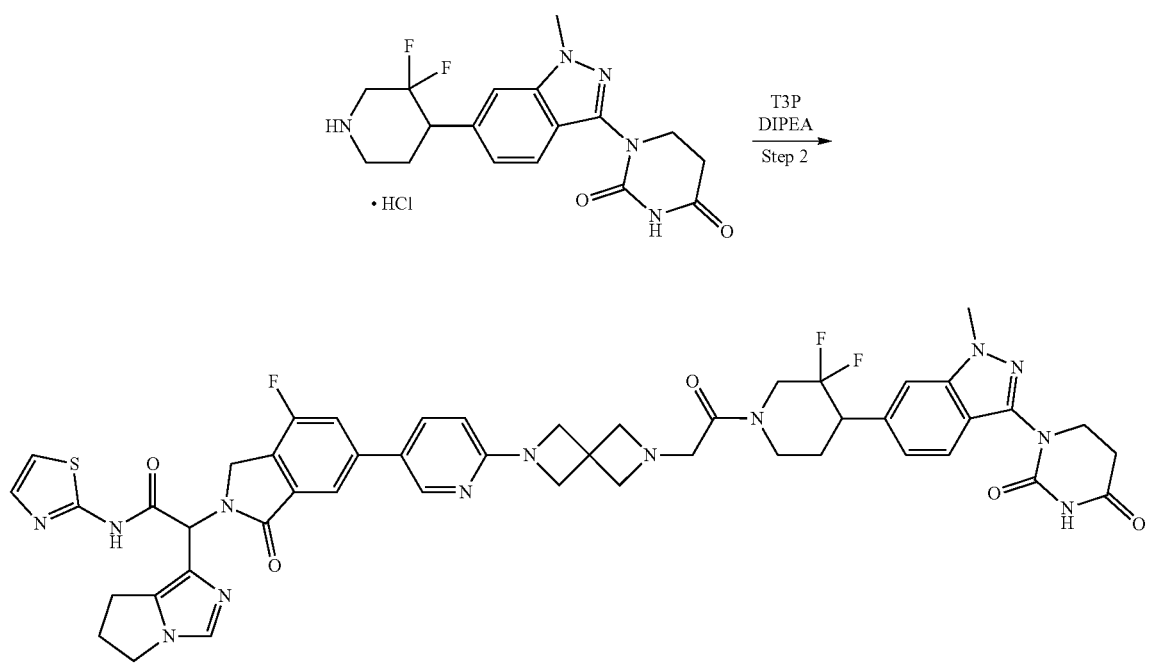

Step 1: 2-[2-[5-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-2-pyridyl]-2,6-diazaspiro[3.3]heptan-6-yl]acetic acid To a solution of 2-[6-[6-(2,6-diazaspiro[3.3]heptan-2-yl)-3-pyridyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid (140 mg, 204.48 umol) and 2-oxoacetic acid (37.64 mg, 408.96 umol, 28.09 uL) in Methanol (5 mL) was added acetic acid (613.95 ug, 10.22 umol, 0.58 uL) and stirred at room temperature. After 2 h Picoline borane (43.74 mg, 408.96 umol) was added to the reaction mixture. The reaction mixture was concentrated and purified by reverse phase chromatography (100 g C-18 column, 0-45% acetonitrile in water with 0.1% ammonium acetate, then steep gradient to 100% acetonitrile). The pure fractions were combined and lyophilized to get 2-[2-[5-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-2-pyridyl]-2,6-diazaspiro[3.3]heptan-6-yl]acetic acid (80 mg, 120.07 umol, 58.72% yield) as an off-white solid. LCMS m/z 629.2 (M+H)+.

Step 2: 2-(6,7-dihydro-5H-pyrrolo[1,2-c]imidazol-1-yl)-2-[6-[6-[6-[2-[4-[3-(2,4-dioxohexahydropyrimidin-1-yl)-1-methyl-indazol-6-yl]-3,3-difluoro-1-piperidyl]-2-oxo-ethyl]-2,6-diazaspiro[3.3]heptan-2-yl]-3-pyridyl]-4-fluoro-1-oxo-isoindolin-2-yl]-N-thiazol-2-yl-acetamide To the stirred solution of 2-[2-[5-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-2-pyridyl]-2,6-diazaspiro[3.3]heptan-6-yl]acetic acid (65 mg, 103.39 umol) and 1-[6-(3,3-difluoro-4-piperidyl)-1-methyl-indazol-3-yl]hexahydropyrimidine-2,4-dione (49.61 mg, 124.07 umol) DMF (1 mL) was cooled to 0° C. N,N-Diisopropylethylamine (80.18 mg, 620.35 umol, 108.05 uL) was added to the reaction mixture followed by Propylphosphonic anhydride solution (50 wt. % in ethyl acetate) (49.35 mg, 155.09 umol) at 0° C. The reaction mixture stirred at room temperature for 1 h. The reaction mixture was directly injected on a C-18 column (100 g) for purification (0-45% acetonitrile in water with 0.1% ammonium acetate over 30 minutes, then steep gradient to 100% acetonitrile). The pure fractions were combined and lyophilized to get Compound 118 (18 mg, 18.02 umol, 17.43% yield) as an off white solid. LCMS m/z 974.3 (M+H)+. 1H-NMR (400 MHz, DMSO-d6): δ 12.49 (s, 1H), 10.57 (s, 1H), 8.52 (s, 1H), 7.98 (d, J=8.80 Hz, 1H), 7.79-7.75 (m, 2H), 7.63-7.52 (m, 3H), 7.48 (d, J=3.60 Hz, 1H), 7.25 (d, J=3.20 Hz, 1H), 7.09-7.07 (m, 1H), 6.50 (d, J=8.80 Hz, 1H), 6.15 (s, 1H), 4.82 (d, J=17.20 Hz, 1H), 4.50-4.79 (m, 1H), 4.23 (d, J=17.60 Hz, 1H), 4.10-4.08 (m, 4H), 4.02-3.73 (m, 9H), 3.45-3.43 (m, 7H), 3.30-3.18 (m, 2H), 2.78-2.75 (m, 5H).
Example 119
2-(6,7-dihydro-5H-pyrrolo[1,2-c]imidazol-1-yl)-2-(6-(4-(6-(2-(1-(4-(((S)-2,6-dioxopiperidin-3-yl)amino)-2,6-difluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide, isomer 1, Compound 119
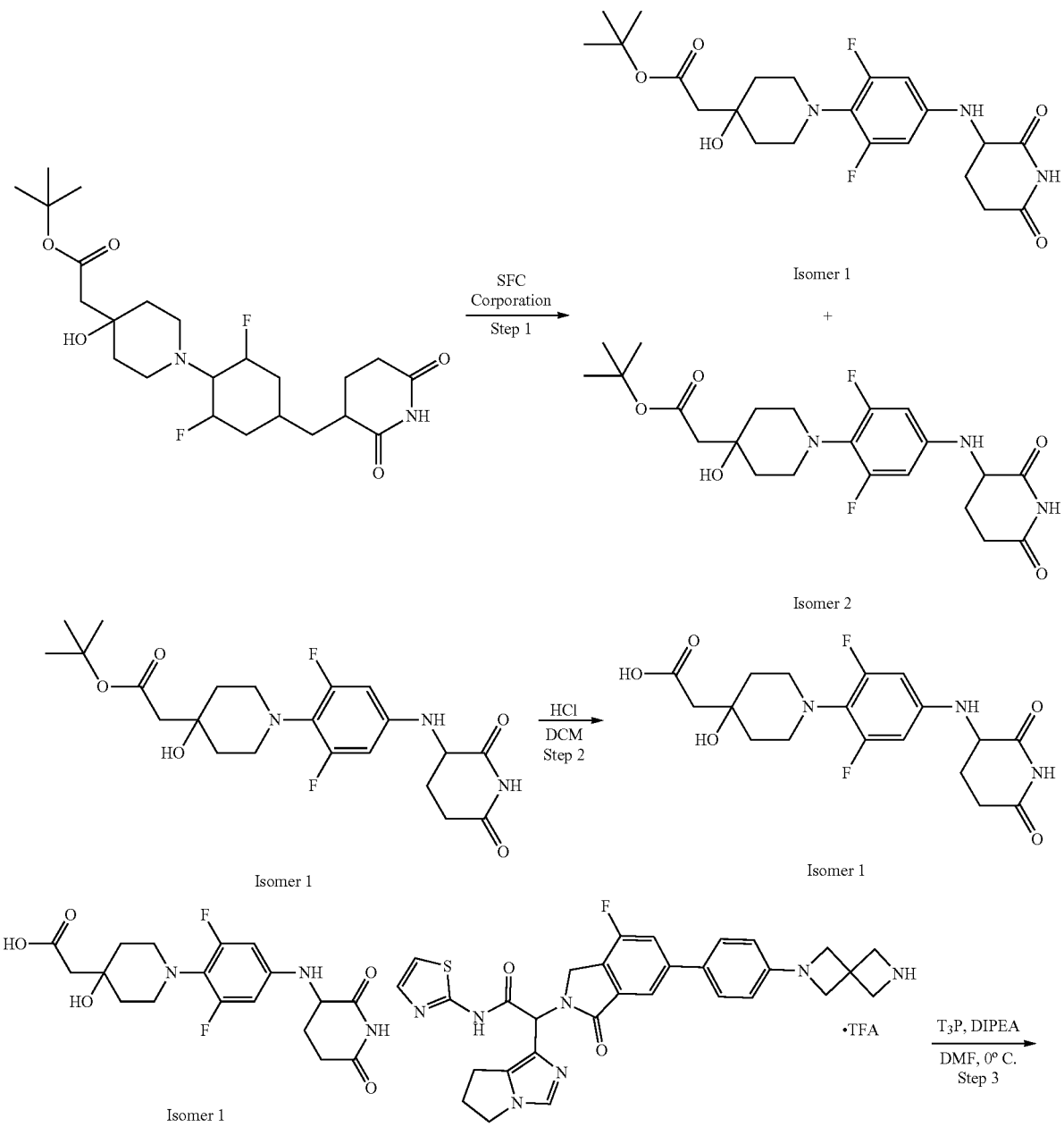

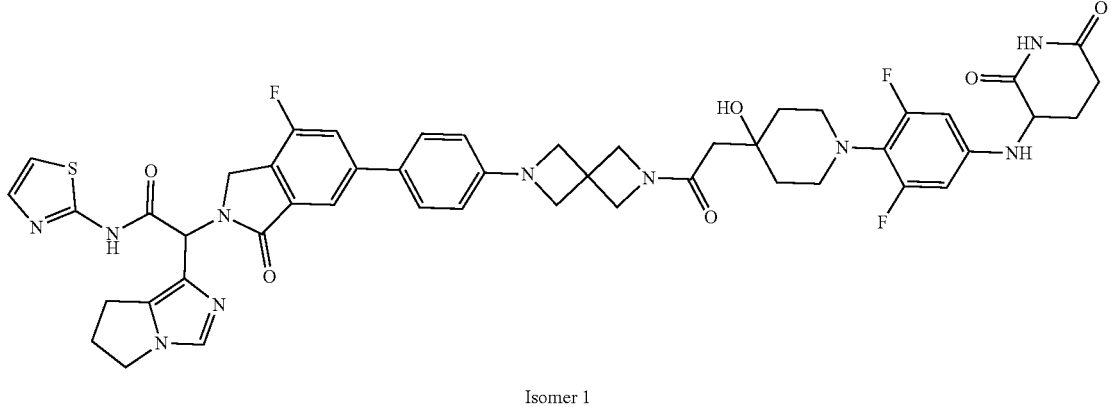

Isomer 1

Step 1: tert-Butyl 2-(1-(4-((2,6-dioxopiperidin-3-yl)amino)-2,6-difluorophenyl)-4-hydroxypiperidin-4-yl)acetate, isomer 1 and tert-butyl 2-(1-(4-((2,6-dioxopiperidin-3-yl)amino)-2,6-difluorophenyl)-4-hydroxypiperidin-4-yl)acetate, isomer 2

Racemic tert-Butyl 2-(1-(4-((2,6-dioxopiperidin-3-yl)amino)-2,6-difluorophenyl)-4-hydroxypiperidin-4-yl)acetate (5 g) was separated by preparative SFC separation. Column: Regis (S,S)-Whelk-O1 column, 250×50 mm I.D., 10 um particle size; Gradient elution: 40% Phase B, 60% Phase A; Flow rate: 200 g/min; Detector: PDA; Column Temp: 35° C.; Back Pressure: 100 bar.

Analytical SFC conditions: Column: (S,S) Whelk-O1 100×4.6 mm I.D., 3.5 um; Gradient elution: 40% EtOH (0.05% diethylamine) in $CO_2$; Flow rate: 3 mL/min; Detector: PDA; Column Temp: 35° C.; Back Pressure: 100 bar.

First eluting fractions were evaporated to afford tert-butyl 2-(1-(4-((2,6-dioxopiperidin-3-yl)amino)-2,6-difluorophenyl)-4-hydroxypiperidin-4-yl)acetate, Isomer 1 (2.5 g, 50% yield). SFC analytical Rt=1.175 min $^1$H NMR (400 MHz, DMSO-d6) δ=10.80 (s, 1H), 6.30 (d, J=12.0 Hz, 2H), 6.20 (d, J=8.0 Hz, 1H), 4.42 (s, 1H), 4.34-4.26 (m, 1H), 3.22 (br t, J=10.4 Hz, 2H), 2.73-2.66 (m, 3H), 2.58 (t, J=3.6 Hz, 1H), 2.33 (s, 2H), 2.11-2.02 (m, 1H), 1.85 (dd, J=4.4, 12.4 Hz, 1H), 1.76-1.66 (m, 2H), 1.63-1.55 (m, 2H), 1.41 (s, 9H).

Second eluting fractions were evaporated to afford tert-butyl 2-(1-(4-((2,6-dioxopiperidin-3-yl)amino)-2,6-difluorophenyl)-4-hydroxypiperidin-4-yl)acetate, isomer 2 (2.45 g, 49% yield). SFC analytical Rt=1.393 min. $^1$HNMR (400 MHz, DMSO-d6) δ=10.80 (s, 1H), 6.30 (d, J=12.4 Hz, 2H), 6.20 (d, J=8.0 Hz, 1H), 4.42 (s, 1H), 4.34-4.26 (m, 1H), 3.22 (br t, J=10.4 Hz, 2H), 2.70 (br dd, J=6.8, 11.2 Hz, 3H), 2.58 (br t, J=3.6 Hz, 1H), 2.33 (s, 2H), 2.11-2.02 (m, 1H), 1.85 (br dd, J=4.4, 12.4 Hz, 1H), 1.74-1.66 (m, 2H), 1.62-1.56 (m, 2H), 1.41 (s, 9H)

Step 2: 2-(1-(4-((2,6-dioxopiperidin-3-yl)amino)-2,6-difluorophenyl)-4-hydroxypiperidin-4-yl)acetic acid, isomer 1

To a solution of tert-butyl 2-[1-[4-[[2,6-dioxo-3-piperidyl]amino]-2,6-difluoro-phenyl]-4-hydroxy-4-piperidyl]acetate, isomer 1 (500 mg, 1.10 mmol) in dichloromethane (7.5 mL) was added hydrochloric acid (12 M, 1 mL, 12 mmol). The mixture was stirred at 25° C. for 1 h. The reaction mixture was concentrated. The residue was diluted with ethyl acetate (15 V), the mixture was stirred at 25° C. for 12 h, filtered and collected the filtered cake to afford 2-[1-[4-[[2,6-dioxo-3-piperidyl]amino]-2,6-difluoro-phenyl]-4-hydroxy-4-piperidyl]acetic acid hydrochloride, isomer 1 (400 mg, 0.830 mmol, 75% yield).

Step 3: 2-(6,7-dihydro-5H-pyrrolo[1,2-c]imidazol-1-yl)-2-(6-(4-(6-(2-(1-(4-((2,6-dioxopiperidin-3-yl)amino)-2,6-difluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide, isomer 1

To a solution of 2-[1-[2-chloro-4-[[2,6-dioxo-3-piperidyl]amino]phenyl]-4-hydroxy-4-piperidyl]acetic acid trifluoroacetic acid hydrochloride, isomer 1 (80 mg, 185.06 μmol) and propylphosphonic anhydride solution (50 wt. % in ethyl acetate) (176.65 mg, 277.59 μmol) in N,N-dimethylformamide (1.2 mL) was added N,N-diisopropylethylamine (167.42 mg, 1.30 mmol, 225.64 μL). The mixture was stirred at 0° C. for 20 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (89.61 mg, 131.06 μmol) was added, the mixture was stirred at 0° C. for 1 h. Propylphosphonic anhydride solution (50 wt. % in ethyl acetate) (105.99 mg, 166.55 μmol) was added to the mixture. The mixture was stirred at 0° C. for 1 h. The reaction mixture was dissolved with acetonitrile (2 mL). The reaction mixture was purified by prep-HPLC (Column: Waters Xbridge C18 150*50 mm*10 um phase: [water-acetonitrile]; B %: 28%-58%, 11 min) to afford Compound 119 (73.73 mg, 74.58 μmol, 21.57% yield) as a white solid. LCMS (ESI): m/z 947.5 [M+H]+H NMR (400 MHz, DMSO-d$_6$) δ=12.62-11.74 (m, 1H), 11.15-10.40 (m, 1H), 7.73 (s, 1H), 7.72-7.67 (m, 1H), 7.64 (br d, J=8.8 Hz, 2H), 7.59 (s, 1H), 7.45 (br d, J=3.6 Hz, 1H), 7.20 (br s, 1H), 6.96 (d, J=8.8 Hz, 1H), 6.75 (d, J=2.4 Hz, 1H), 6.67-6.48 (m, 3H), 6.11 (s, 1H), 5.83 (d, J=8.0 Hz, 1H), 4.90-4.74 (m, 2H), 4.38 (s, 2H), 4.33-4.16 (m, 2H), 4.08 (s, 1H), 3.92 (br s, 6H), 2.92-2.84 (m, 2H), 2.82-2.70 (m, 4H), 2.58 (br d, J=4.4 Hz, 1H), 2.48-2.42 (m, 1H), 2.23 (s, 2H), 2.12-2.02 (m, 1H), 1.92-1.82 (m, 1H), 1.80-1.71 (m, 2H), 1.63 (br d, J=12.4 Hz, 2H)

Example 120
2-(6-(4-(6-(2-(1-(2-chloro-4-((2,6-dioxopiperidin-3-yl)amino)phenyl)-4-hydroxypiperidin-4-yl)acetyl)-2,6-diazaspiro[3.3]heptan-2-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide, isomer 1, Compound 120
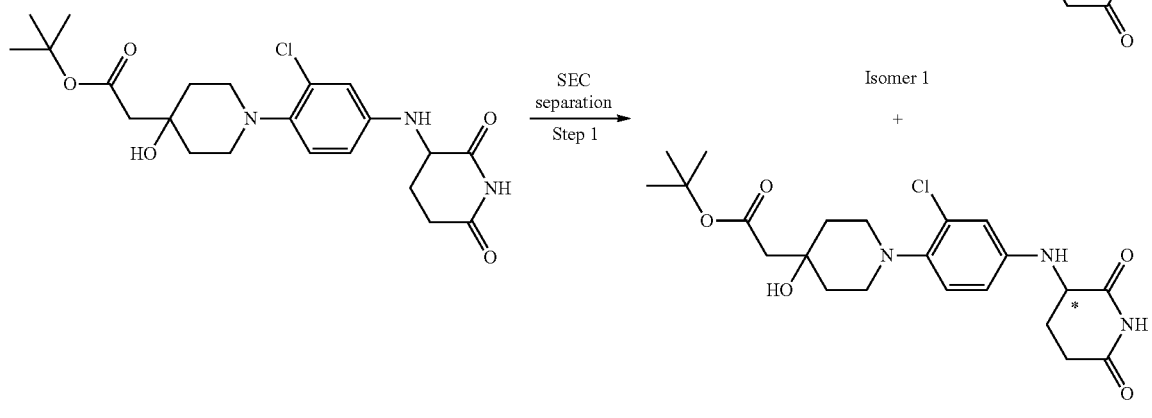
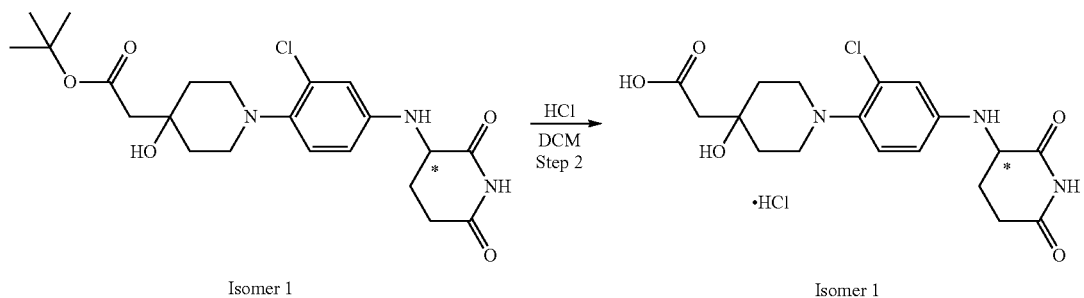
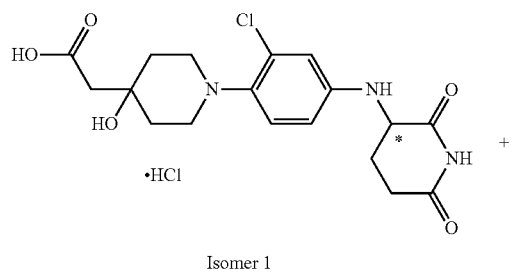

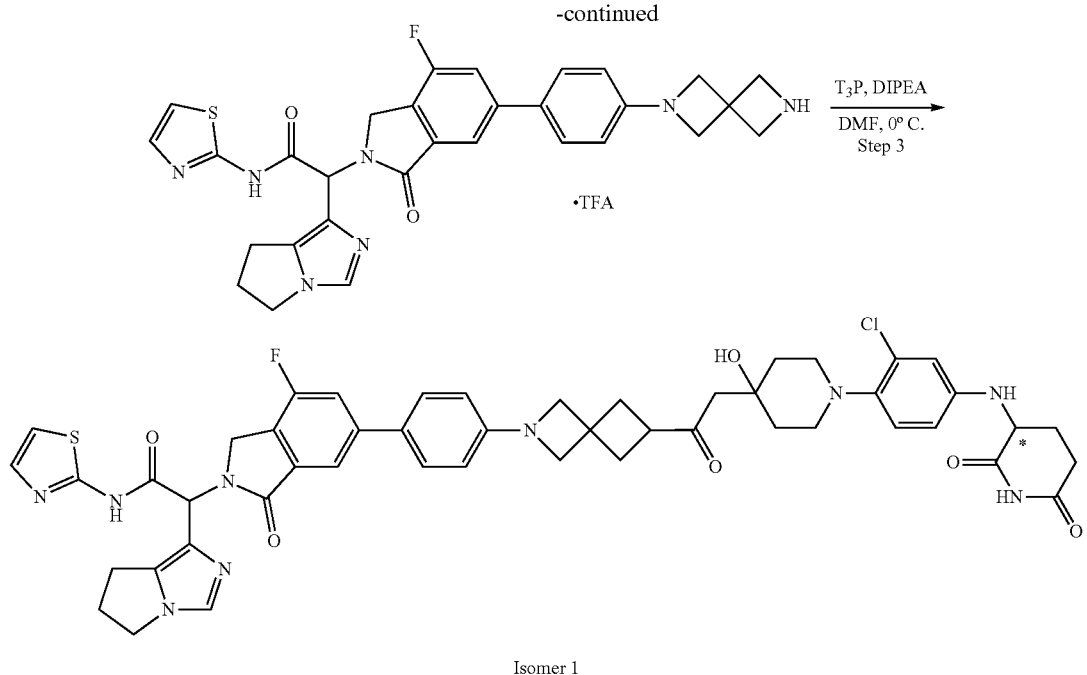

Isomer 1

Step 1: tert-Butyl 2-(1-(2-chloro-4-((2,6-dioxopiperidin-3-yl)amino)phenyl)-4-hydroxypiperidin-4-yl) acetate, isomer 1 and tert-butyl 2-(1-(2-chloro-4-((2,6-dioxopiperidin-3-yl)amino)phenyl)-4-hydroxypiperidin-4-yl)acetate, isomer 2

Racemic tert-Butyl 2-(1-(2-chloro-4-((2,6-dioxopiperidin-3-yl)amino)phenyl)-4-hydroxypiperidin-4-yl)acetate (4.5 g, 9.96 mmol) was separated by preparative SFC separation (Column: Regis-(S,S) Whelk-O1 column, 250× 50 mm I.D., 10 um particle size; Mobile phase: Phase A for Supercritical CO2, and Phase B for EtOH; Gradient elution: 40% Phase B, 60% Phase A; Flow rate: 200 g/min; Detector: PDA; Column Temp: 35° C.; Back Pressure: 100 bar to keep the CO2 in Supercritical flow) to afford two sets of fractions based on elution order. The first eluting set of fractions was evaporated under pressure to afford tert-butyl 2-(1-(2-chloro-4-((2,6-dioxopiperidin-3-yl)amino)phenyl)-4-hydroxypiperidin-4-yl)acetate, isomer 1 (2.1 g, 4.55 mmol, 45.7% yield). $^1$H-NMR (400 MHz, DMSO-d6) δ=10.76 (s, 1H), 6.95 (d, J=8.8 Hz, 1H), 6.74 (d, J=2.4 Hz, 1H), 6.59 (dd, J=2.4, 8.8 Hz, 1H), 5.82 (d, J=7.6 Hz, 1H), 4.45 (s, 1H), 4.32-4.24 (m, 1H), 2.92-2.83 (m, 2H), 2.81-2.75 (m, 2H), 2.74-2.68 (m, 1H), 2.59 (t, J=4.0 Hz, 1H), 2.35 (s, 2H), 2.11-2.03 (m, 1H), 1.85 (br dd, J=4.3, 12.5 Hz, 1H), 1.82-1.73 (m, 2H), 1.69-1.60 (m, 2H), 1.42 (s, 9H), SFC (Column: (S,S) Whelk-O1 100×4.6 mm I.D., 3.5 um, Mobile phase: 40% EtOH (0.05% diethylamine) in CO$_2$, Flow rate: 3 mL/min; Detector: PDA, Column Temp: 35° C.; Back Pressure: 100 bar): Rt=1.910 min, 100% ee.

The second eluting set of fractions was evaporated under pressure to afford tert-butyl 2-(1-(2-chloro-4-((2,6-dioxopiperidin-3-yl)amino)phenyl)-4-hydroxypiperidin-4-yl)acetate, isomer 2 (2.04 g, 4.42 mmol, 44.4% yield). $^1$H-NMR (400 MHz, DMSO-d6) δ=10.76 (s, 1H), 6.95 (d, J=8.8 Hz, 1H), 6.74 (d, J=2.7 Hz, 1H), 6.59 (dd, J=2.7, 8.8 Hz, 1H), 5.82 (d, J=7.8 Hz, 1H), 4.45 (s, 1H), 4.32-4.24 (m, 1H), 2.91-2.83 (m, 2H), 2.81-2.76 (m, 2H), 2.73-2.66 (m, 1H), 2.59 (br t, J=3.9 Hz, 1H), 2.35 (s, 2H), 2.11-2.03 (m, 1H), 1.85 (br dd, J=4.2, 12.3 Hz, 1H), 1.82-1.74 (m, 2H), 1.68-1.61 (m, 2H), 1.41 (s, 9H), SFC (Column: (S,S) Whelk-O1 100×4.6 mm I.D., 3.5 um, Mobile phase: 40% EtOH (0.05% diethylamine) in CO$_2$, Flow rate: 3 mL/min; Detector: PDA, Column Temp: 35° C.; Back Pressure: 100 bar): Rt=2.616 min, 100% ee.

Step 2: 2-(1-(2-chloro-4-((2,6-dioxopiperidin-3-yl) amino)phenyl)-4-hydroxypiperidin-4-yl)acetic acid, isomer 1

To a solution of tert-butyl 2-[1-[2-chloro-4-[[2,6-dioxo-3-piperidyl]amino] phenyl]-4-hydroxy-4-piperidyl]acetate, isomer 1 (300 mg, 663.80 μmol) in dichloromethane (4.5 mL) was added hydrochloride acid (12 M, 0.6 mL, 7.2 mmol). The mixture was stirred at 25° C. for 1 h. The reaction mixture was concentrated, the residue was diluted with ethyl acetate (15 V), the mixture was stirred at 25° C. for 12 h. The solid was collected by filtration to afford 2-[1-[2-chloro-4-[[2,6-dioxo-3-piperidyl]amino]phenyl]-4-hydroxy-4-piperidyl]acetic acid hydrochloride, isomer 1 (280 mg, 550.5 μmol, 82.9% yield). LCMS (ESI+): 396.0 (M+H), $^1$H NMR (400 MHz, deuterium oxide) δ=7.55 (br d, J=9.2 Hz, 1H), 6.96 (d, J=2.4 Hz, 1H), 6.82 (br dd, J=2.4, 9.0 Hz, 1H), 4.48 (br dd, J=5.2, 12.4 Hz, 1H), 3.95-3.83 (m, 2H), 3.72-3.65 (m, 2H), 2.90-2.78 (m, 1H), 2.81 (br d, J=5.2 Hz, 1H), 2.69 (s, 2H), 2.35-2.24 (m, 3H), 2.22-2.14 (m, 2H), 2.11-2.03 (m, 1H).

Step 3: 2-(6-(4-(6-(2-(1-(2-chloro-4-((2,6-dioxopiperidin-3-yl)amino)phenyl)-4-hydroxypiperidin-4-yl) acetyl)-2,6-diazaspiro[3.3]heptan-2-yl)phenyl)-4-fluoro-1-oxoisoindolin-2-yl)-2-(6,7-dihydro-5H-pyrrolo[1,2-c]imidazol-1-yl)-N-(thiazol-2-yl) acetamide, isomer 1

To a solution of 2-[1-[2-chloro-4-[[2,6-dioxo-3-piperidyl]amino]phenyl]-4-hydroxy-4-piperidyl]acetic acid hydrochloride (80 mg, 185.06 µmol) and propylphosphonic anhydride solution (50 wt. % in ethyl acetate) (176.65 mg, 277.59 µmol) in N,N-dimethylformamide (1.2 mL) was added N,N-diisopropylethylamine (167.42 mg, 1.30 mmol, 225.64 µl). The mixture was stirred at 0° C. for 20 min, then 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (89.61 mg, 131.06 µmol) was added, the mixture was stirred at 0° C. for 1 h. Propylphosphonic anhydride solution (50 wt. % in ethyl acetate) (105.99 mg, 166.55 µmol) was added to the mixture and stirred at 0° C. for 1 h. The reaction mixture was dissolved with acetonitrile (2 mL). The reaction mixture was purified by prep-HPLC (Column: Waters Xbridge C18 150*50 mm, 10 m phase, Mobile phase: 28% to 58% acetonitrile in water, 11 min) to afford Compound 120 (39.27 mg, 39.79 µmol, 21.50% yield) as a white solid. LCMS (ESI+): m/z 947.5 [M+H]+, $^1$H NMR (400 MHz, DMSO-$d_6$) δ=12.62-11.74 (m, 1H), 11.15-10.40 (m, 1H), 7.73 (s, 1H), 7.72-7.67 (m, 1H), 7.64 (br d, J=8.8 Hz, 2H), 7.59 (s, 1H), 7.45 (br d, J=3.6 Hz, 1H), 7.20 (br s, 1H), 6.96 (d, J=8.8 Hz, 1H), 6.75 (d, J=2.4 Hz, 1H), 6.67-6.48 (m, 3H), 6.11 (s, 1H), 5.83 (d, J=8.0 Hz, 1H), 4.90-4.74 (m, 2H), 4.38 (s, 2H), 4.33-4.16 (m, 2H), 4.08 (s, 1H), 3.92 (br s, 6H), 2.92-2.84 (m, 2H), 2.82-2.70 (m, 4H), 2.58 (br d, J=4.4 Hz, 1H), 2.48-2.42 (m, 1H), 2.23 (s, 2H), 2.12-2.02 (m, 1H), 1.92-1.82 (m, 1H), 1.80-1.71 (m, 2H), 1.63 (br d, J=12.4 Hz, 2H).

Example 121

2-(6,7-dihydro-5H-pyrrolo[1,2-c]imidazol-1-yl)-2-[6-[4-[7-[2-[1-[4-[[(3S)-2,6-dioxo-3-piperidyl]amino]-2-fluoro-phenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide, Compound 121

Step 1: Synthesis of tert-butyl 2-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]-2,7-diazaspiro[3.5]nonane-7-carboxylate

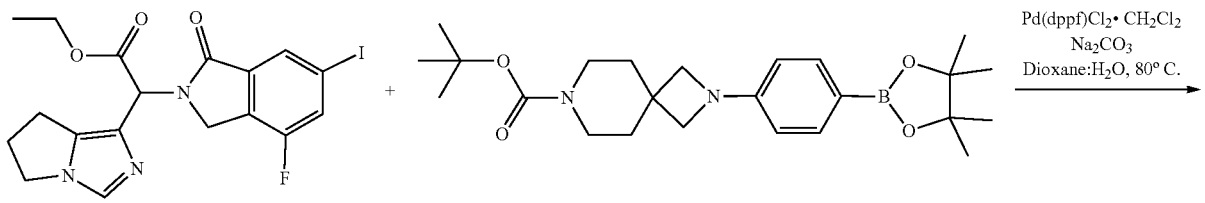

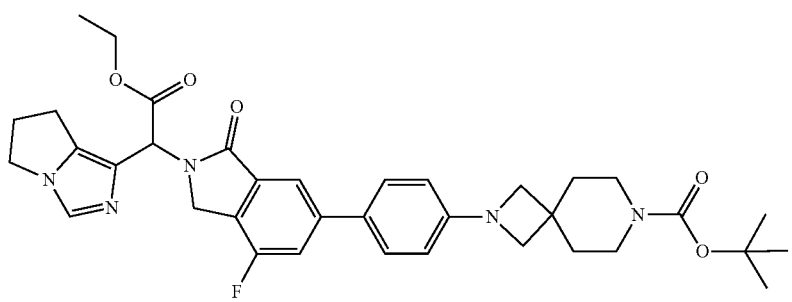

To a solution of ethyl 2-(6,7-dihydro-5H-pyrrolo[1,2-c]imidazol-1-yl)-2-(4-fluoro-6-iodo-1-oxo-isoindolin-2-yl)acetate (800 mg, 1.70 mmol) and tert-butyl 2-[4-(4,4,5,5-tetramethyl-1,3,2-dioxaborolan-2-yl)phenyl]-2,7-diazaspiro[3.5]nonane-7-carboxylate (730.31 mg, 1.70 mmol) in Dioxane (30 mL) was added Sodium carbonate (451.74 mg, 4.26 mmol, 178.55 µL) in Water (3 mL). The reaction mixture was degassed with nitrogen for 15 min, [1,1' Bis(diphenylphosphino) ferrocene] dichloropalladium (II), complex with dichloromethane (139.22 mg, 170.49 µmol) was added and further degassed for 10 minutes, and was heated at 80° C. for 16 h. Reaction mixture was diluted with dichloromethane and filtered through celite, and the filtrate was concentrated under reduced pressure and purified using flash silica gel (100-200 mesh) column chromatography eluting with 3% Methanol in dichloromethane to afford tert-butyl 2-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]-2,7-diazaspiro[3.5]nonane-7-carboxylate (790 mg, 1.12 mmol, 65.86% yield) as a light brown solid. LCMS(ESI+): 644.3 (M+H).

Step 2: Synthesis of 2-[6-[4-(7-tert-butoxycarbonyl-2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)acetyl]oxylithium

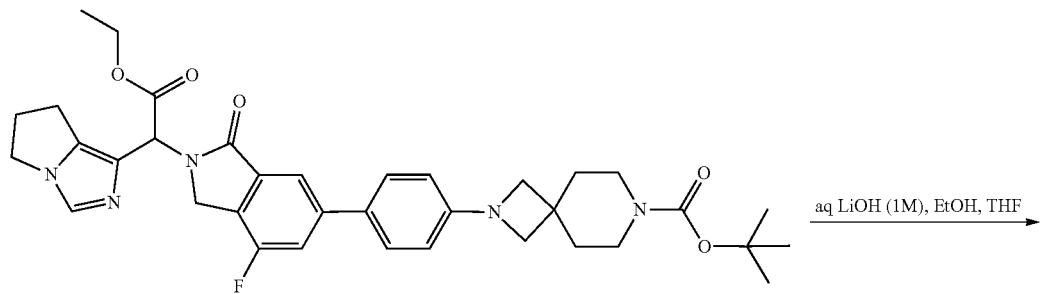

aq LiOH (1M), EtOH, THF

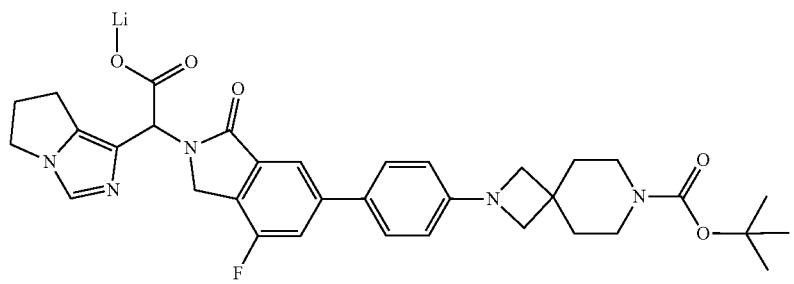

To a stirred solution of tert-butyl 2-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]-2,7-diazaspiro[3.5]nonane-7-carboxylate (790 mg, 1.22 mmol) in EtOH (3 mL) and tetrahydrofuran (3 mL) was added aq. LiOH (1M, 1.22 mL) at 0° C. and the reaction mixture was further stirred for 4 h at 25° C. The reaction mixture was concentrated under reduced pressure to afford product as lithium salt which was triturated with diethyl ether, decanted and dried to get 2-[6-[4-(7-tert-butoxycarbonyl-2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)acetyl]oxylithium (750 mg, 1.10 mmol, 88.78% yield) as an off white solid. LCMS (ESI+): 616.3 [M+H].

Step 3: Synthesis of tert-butyl 6-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,6-diazaspiro[3.3]heptane-2-carboxylate

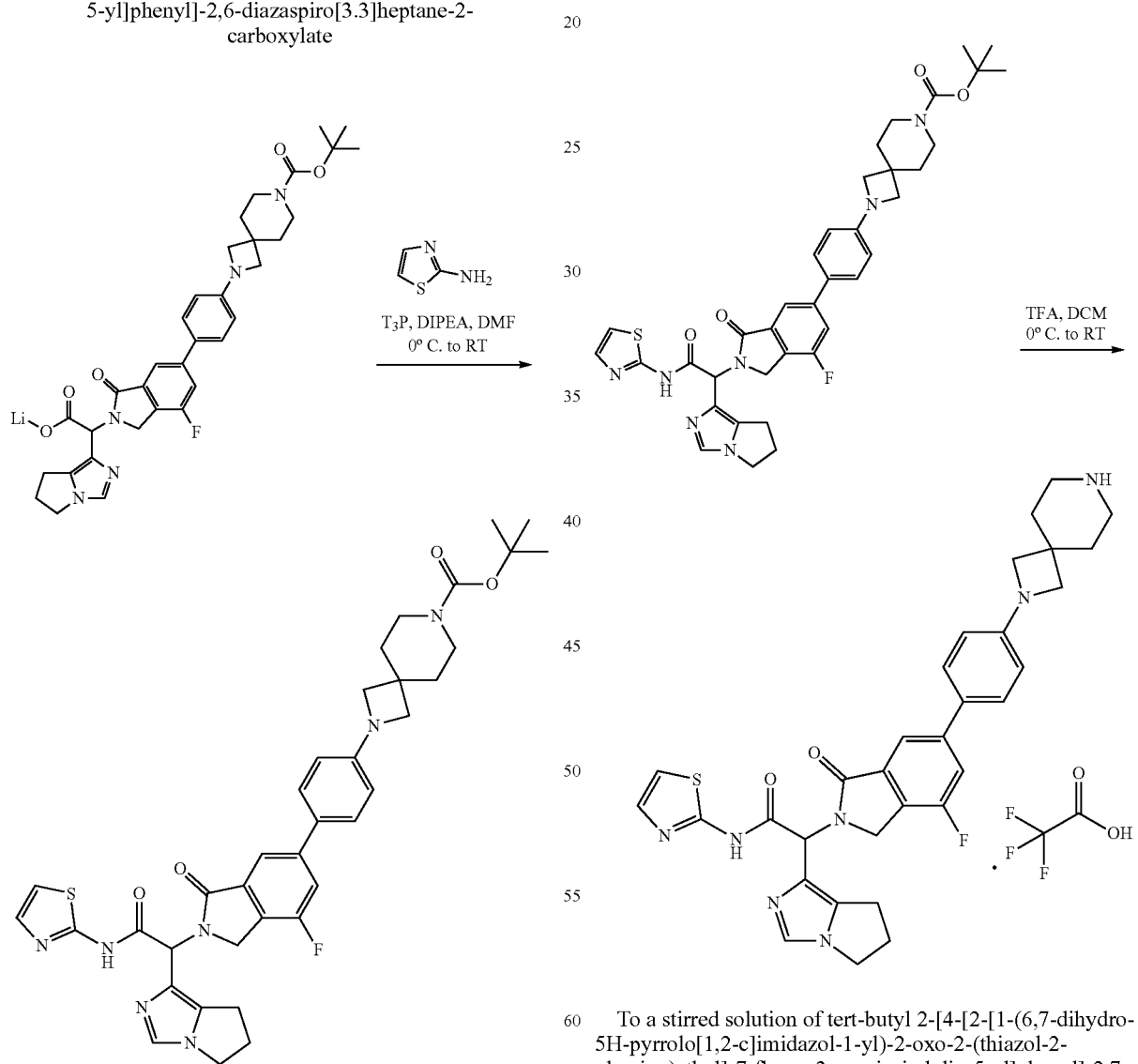

To a stirred solution of 2-[6-[4-(7-tert-butoxycarbonyl-2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)acetyl]oxylithium (750 mg, 1.20 mmol) and thiazol-2-amine (180.97 mg, 1.80 mmol) in N,N-dimethylformamide (5 mL) was added N, N-diisopropylethylamine (465.26 mg, 3.60 mmol, 627.03 µL) at 0° C. 2,4,6-Tripropyl-1,3,5,2,4,6-trioxatriphosphorinane-2,4,6-trioxide solution (763.63 mg, 2.4 mmol) was added at 0° C. and stirred at room temperature for 4 h. The reaction mixture was added ice cold water and solid precipitated was filtered and dried on reduced pressure to afford tert-butyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonane-7-carboxylate (500 mg, 709.35 µmol, 55.12% yield) as an off white solid. LCMS(ESI+): 698.3 [M+H].

Step 4: Synthesis of 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide To a stirred solution of tert-butyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonane-7-carboxylate (500 mg, 716.52 µmol) in dichloromethane (5.0 mL) at 0° C. was added trifluoroacetic acid (1.23 g, 10.75 mmol, 828.04 µL) drop wise at 0° C. and stirred for 4 h at room temperature. Solvent was removed under reduced pressure to afford crude, codistilled with dichloromethane, triturated with diethyl ether and decanted to afford 2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide; 2,2,2-trifluoroacetic acid (520 mg, 699.35 μmol, 97.60% yield) as an off white solid. LCMS(ESI+): 598.3 (M+H).

Step 5: 2-(6,7-dihydro-5H-pyrrolo[1,2-c]imidazol-1-yl)-2-[6-[4-[7-[2-[1-[4-[[(3S)-2,6-dioxo-3-piperidyl]amino]-2-fluoro-phenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide

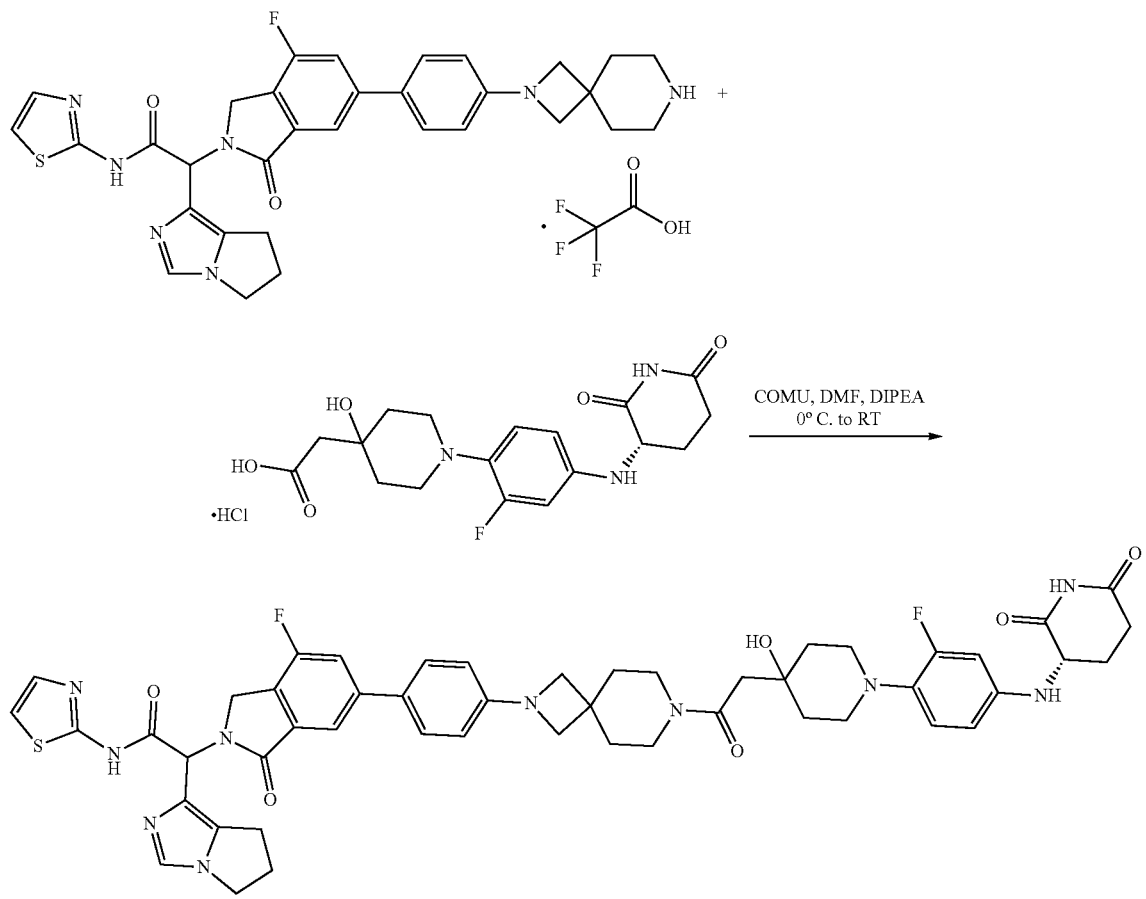

2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide; 2,2,2-trifluoroacetic acid (250 mg, 351.26 μmol), and 2-[1-[4-[[(3S)-2,6-dioxo-3-piperidyl]amino]-2-fluoro-phenyl]-4-hydroxy-4-piperidyl]acetic acid hydrochloride (175.28 mg, 421.51 μmol were mixed in N,N-dimethylformamide (5 mL). N,N-diisopropylethylamine (226.99 mg, 1.76 mmol, 305.91 μL) was added to the reaction mixture at 0° C. 1-Cyano-2-ethoxy-2-oxoethylidenaminooxy)dimethylamino-morpholino-carbenium hexafluorophosphate (180.52 mg, 421.51 μmol) was added to the reaction mixture at 0° C. The reaction mixture was stirred at room temperature for 1 h. The crude mixture was directly injected on a C18 column (100 g) for purification while eluting (0% to 50% of acetonitrile in 0.1% ammonium acetate in water over 30 minutes, then steep gradient to 100% acetonitrile). The pure fraction was frozen and lyophilized to afford Compound 121 (140 mg, 143.52 μmol, 40.86% yield) as an off-white solid. LCMS (ESI+): 959.3[M+H]. 1H-NMR (400 MHz, DMSO-d6): δ 12.53 (s, 1H), 10.79 (s, 1H), 7.74 (s, 1H), 7.71 (d, J=10.80 Hz, 1H), 7.64 (d, J=8.80 Hz, 2H), 7.61 (s, 1H), 7.49 (d, J=3.60 Hz, 1H), 7.27 (d, J=3.60 Hz, 1H), 6.86 (t, J=9.60 Hz, 1H), 6.53 (d, J=8.40 Hz, 2H), 6.48 (d, J=2.40 Hz, 1H), 6.42 (d, J=8.80 Hz, 2H), 6.15 (s, 1H), 5.79 (d, J=7.60 Hz, 1H), 4.94 (s, 1H), 4.80 (d, J=17.60 Hz, 1H), 4.26-4.23 (m, 1H), 4.21 (d, J=17.60 Hz, 1H), 4.02-3.98 (m, 2H), 3.69-3.65 (m, 4H), 3.52-3.48 (m, 4H), 2.90-2.83 (m, 4H), 2.82-2.71 (m, 2H), 2.59 (d, J=3.60 Hz, 1H), 2.10-2.07 (m, 1H), 1.89-1.61 (m, 10H), (proton signals obscured by water and solvent signals).

Example 122

2-(6,7-dihydro-5H-pyrrolo[1,2-c]imidazol-1-yl)-2-[6-[4-[7-[2-[(4R)-4-[3-(2,4-dioxohexahydropyrimidin-1-yl)-1-methyl-indazol-6-yl]-3,3-difluoro-1-piperidyl]acetyl]-2,7-diazaspiro[3.5]nonan-2-yl]phenyl]-4-fluoro-1-oxo-isoindolin-2-yl]-N-thiazol-2-yl-acetamide, Compound 122

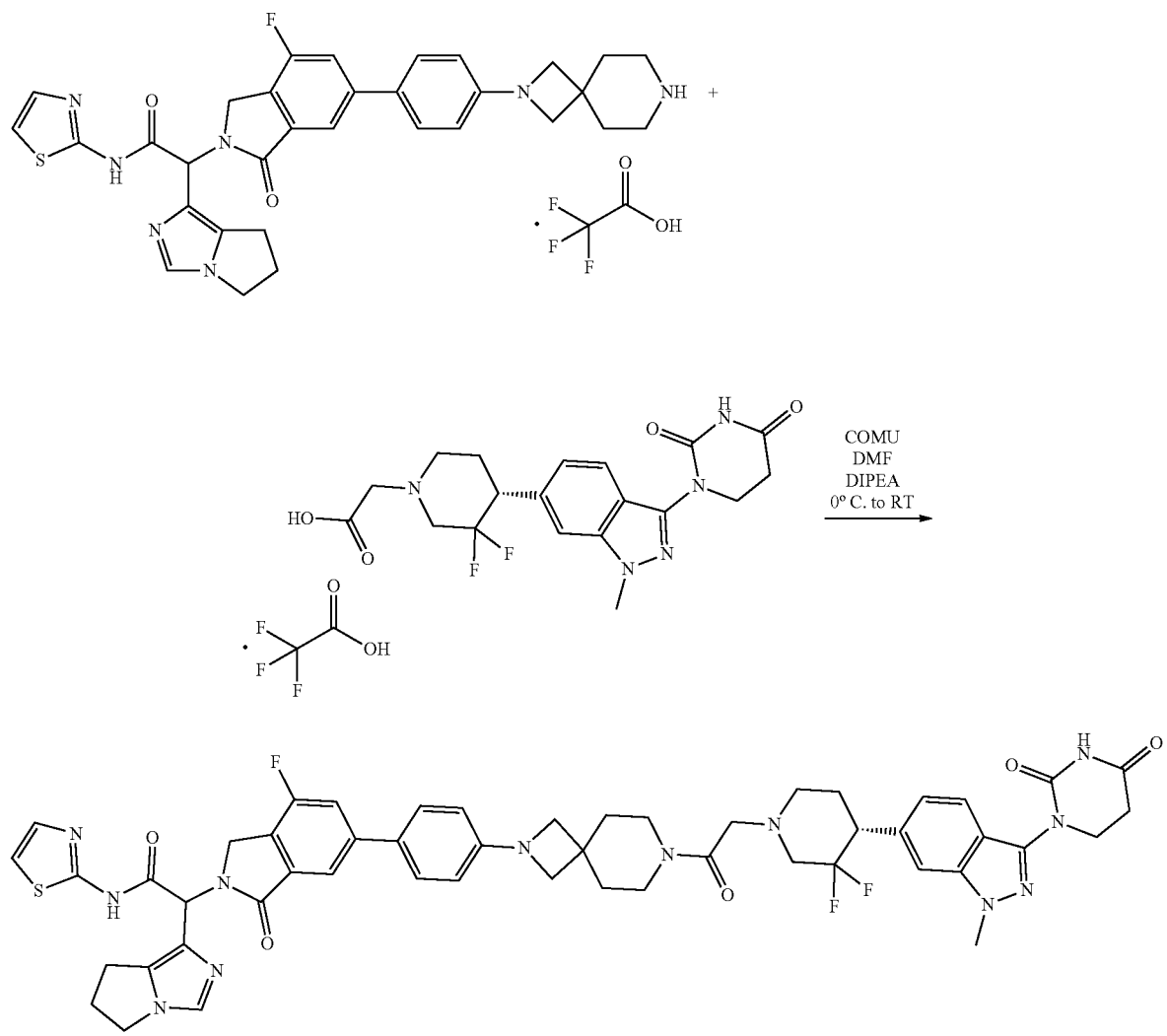

2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide; 2,2,2-trifluoroacetic acid (150 mg, 210.75 µmol), and 2-[(4R)-4-[3-(2,4-dioxohexahydropyrimidin-1-yl)-1-methyl-indazol-6-yl]-3,3-difluoro-1-piperidyl]acetic acid, trifluoroacetic acid salt (96.50 mg, 210.75 µmol) were mixed in N,N-dimethylformamide (1.5 mL). N,N-diisopropylethylamine (136.19 mg, 1.05 mmol, 183.55 µL) was added to the reaction mixture at 0° C. 1-Cyano-2-ethoxy-2-oxoethylidenaminooxy)dimethylamino-morpholino-carbenium hexafluorophosphate (107.89 mg, 252.91 µmol) was added to the reaction mixture at 0° C. The reaction mixture was stirred at room temperature for 1 h. The crude mixture was directly injected on a C18 column (100 g) for purification while eluting (0% to 50% of acetonitrile in 0.1% ammonium acetate in water over 30 minutes, then steep gradient to 100% acetonitrile). The pure fraction was frozen and lyophilized to afford Compound 122 (99.5 mg, 99.12 µmol, 47.03% yield) as a white solid. LCMS (ESI+): 959.3[M+H]. 1H-NMR (400 MHz, DMSO-d6): δ 12.53 (s, 1H), 10.58 (s, 1H), 7.75 (s, 1H), 7.71 (d, J=10.80 Hz, 1H), 7.65 (d, J=8.40 Hz, 2H), 7.61 (s, 1H), 7.59 (s, 1H), 7.55 (s, 1H), 7.49 (d, J=3.60 Hz, 1H), 7.27 (d, J=3.20 Hz, 1H), 7.10 (d, J=8.40 Hz, 1H), 6.54 (d, J=8.80 Hz, 2H), 6.15 (s, 1H), 4.80 (d, J=17.60 Hz, 1H), 4.21 (d, J=17.60 Hz, 1H), 4.00 (s, 3H), 3.93 (t, J=6.80 Hz, 4H), 3.72-3.68 (m, 4H), 3.52-3.44 (m, 5H), 3.39 (s, 2H), 3.22-3.18 (m, 2H), 3.00 (d, J=9.60 Hz, 1H), 2.78-2.70 (m, 5H), 2.50 (s, 2H), 2.33-2.23 (m, 1H), 1.90-1.84 (m, 3H), 1.75-1.73 (m, 2H).

Example 123
2-(6,7-dihydro-5H-pyrrolo[1,2-c]imidazol-1-yl)-2-[6-[4-[2-[2-[4-[3-(2,4-dioxohexahydropyrimidin-1-yl)-5-fluoro-1-methyl-indazol-6-yl]piperazin-1-yl]acetyl]-2,6-diazaspiro[3.3]heptan-6-yl]phenyl]-4-fluoro-1-oxo-isoindolin-2-yl]-N-thiazol-2-yl-acetamide, Compound 123
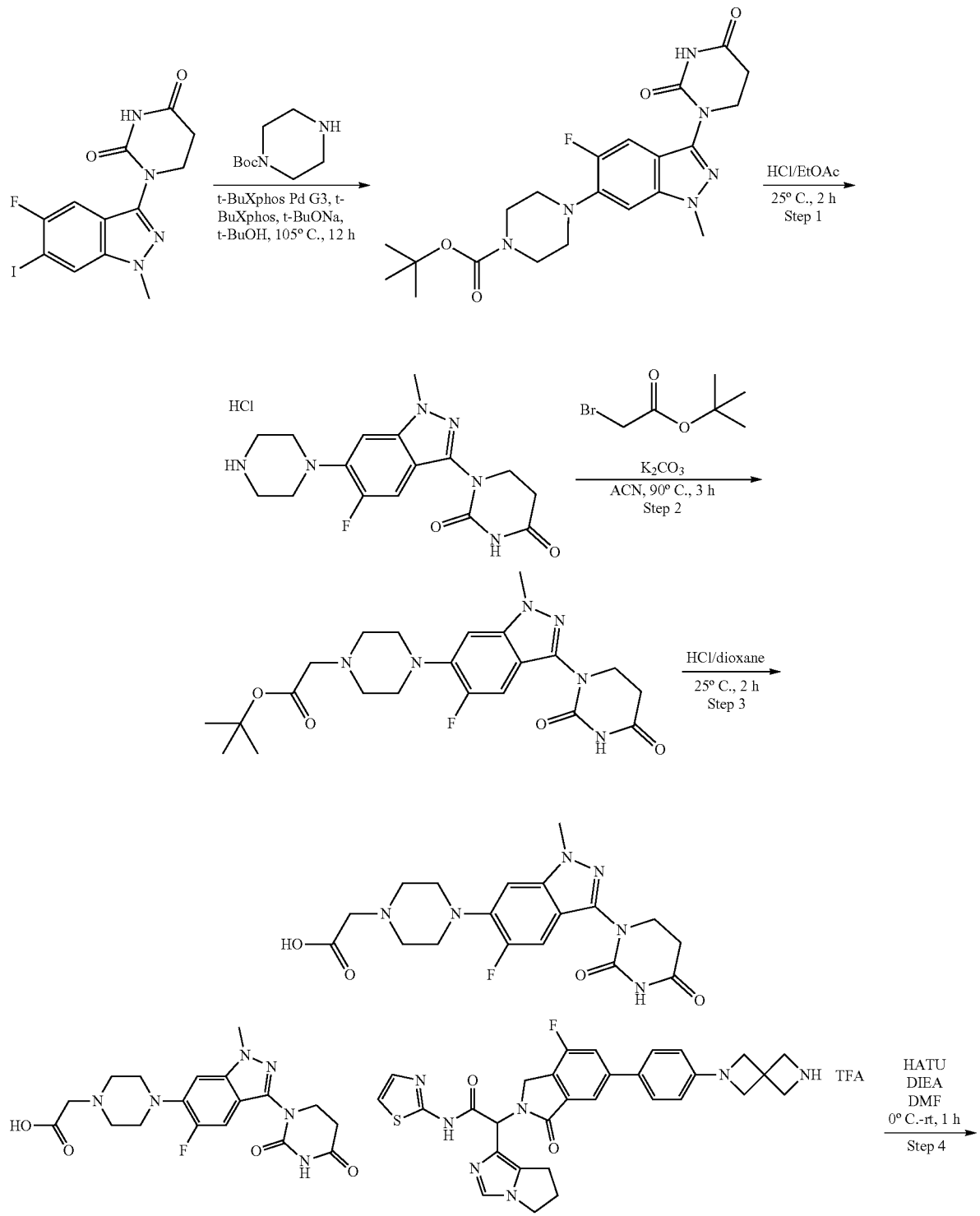

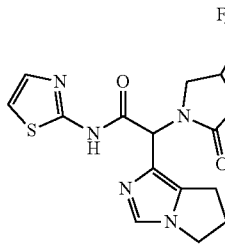

Step 1: tert-Butyl 4-(3-(2,4-dioxotetrahydropyrimidin-1(2H)-yl)-5-fluoro-1-methyl-1H-indazol-6-yl)piperazine-1-carboxylate To a solution of 1-(5-fluoro-6-iodo-1-methyl-1H-indazol-3-yl)dihydropyrimidine-2,4(1H,3H)-dione (2.5 g, 6.44 mmol) in t-BuOH (50 mL) was added tert-butyl piperazine-1-carboxylate (2.40 g, 12.8 mmol), t-BuONa (1.86 g, 19.3 mmol), tBuXphos (2.74 g, 6.44 mmol) and tBuBrettPhos Pd G3 (2.56 g, 3.22 mmol), the reaction mixture was stirred at 100° C. for 12 h. The reaction mixture was diluted with water (50 mL), extracted with ethyl acetate (50 mL×3). The combined organic layers were washed by brine (50 mL), dried over sodium sulfate, filtered, concentrated under reduced pressure to give a residue, which was purified by flash silica gel chromatography (ISCO®; 5 g SepaFlash® Silica Flash Column, Eluent of 0% to 20% ethyl acetate/petroleum ether gradient, TLC:ethyl acetate/petroleum ether=2/1, $R_f$=0.2) to afford tert-butyl 4-(3-(2,4-dioxotetrahydropyrimidin-1(2H)-yl)-5-fluoro-1-methyl-1H-indazol-6-yl)piperazine-1-carboxylate (944 mg, 30.3% yield) as yellow solid. LCMS (ESI+): 447.2 (M+H); $^1$H NMR (400 MHz, CDCl3) δ 7.63 (s, 1H), 7.35 (d, J=12.3 Hz, 1H), 6.69 (d, J=6.6 Hz, 1H), 4.08 (t, J=6.7 Hz, 2H), 3.99-3.87 (m, 3H), 3.70-3.60 (m, 4H), 3.14-3.01 (m, 4H), 2.87 (t, J=6.7 Hz, 2H), 1.49 (s, 9H).

Step 2: 1-(5-fluoro-1-methyl-6-piperazin-1-yl-indazol-3-yl)hexahydropyrimidine-2,4-dione A mixture of tert-butyl 4-[3-(2,4-dioxohexahydropyrimidin-1-yl)-5-fluoro-1-methyl-indazol-6-yl]piperazine-1-carboxylate (490 mg, 1.10 mmol) in hydrogen chloride (4 M in ethyl acetate, 4.90 mL) was stirred at 25° C. for 2 h. The mixture was concentrated under reduced pressure to give 1-(5-fluoro-1-methyl-6-piperazin-1-yl-indazol-3-yl)hexahydropyrimidine-2,4-dione hydrochloride (400 mg, 971.74 μmol, 89% yield) as a brown solid. LCMS (ESI): m/z 347.3 [M+H]$^+$

Step 3: tert-Butyl 2-[4-[3-(2,4-dioxohexahydropyrimidin-1-yl)-5-fluoro-1-methyl-indazol-6-yl]piperazin-1-yl]acetate To a suspension of 1-(5-fluoro-1-methyl-6-piperazin-1-yl-indazol-3-yl)hexahydropyrimidine-2,4-dione hydrochloride (200 mg, 522.44 μmol) in acetonitrile (5 mL) were added tert-butyl 2-bromoacetate (123 mg, 630.59 μmol, 92.48 μL) and potassium carbonate (181 mg, 1.31 mmol, 79.04 μL). The mixture was heated to 90° C. and stirred at 90° C. for 3 h. The mixture was concentrated under reduced pressure. The crude product was purified by reversed phase column (FA conditions) to give tert-butyl 2-[4-[3-(2,4-dioxohexahydropyrimidin-1-yl)-5-fluoro-1-methyl-indazol-6-yl]piperazin-1-yl]acetate (110 mg, 214.98 μmol, 41% yield) as a yellow solid. LCMS (ESI): m/z 461.3 [M+H]$^+$

Step 4: 2-[4-[3-(2,4-dioxohexahydropyrimidin-1-yl)-5-fluoro-1-methyl-indazol-6-yl]piperazin-1-yl]acetic acid A mixture of tert-butyl 2-[4-[3-(2,4-dioxohexahydropyrimidin-1-yl)-5-fluoro-1-methyl-indazol-6-yl]piperazin-1-yl]acetate (110 mg, 238.87 μmol) in hydrogen chloride (4 M in 1,4-dioxane, 5 mL, 20 mmol) was stirred at 25° C. for 2 h. The mixture was concentrated under reduced pressure. The crude product was purified by reversed phase column (using hydrochloride acid as a phase modifier) to give 2-[4-[3-(2,4-dioxohexahydropyrimidin-1-yl)-5-fluoro-1-methyl-indazol-6-yl]piperazin-1-yl]acetic acid hydrochloride (100 mg, 208.69 μmol, 87% yield) as a light yellow solid. LCMS (ESI): m/z 405.3 [M+H]$^+$

Step 5: 2-(6,7-dihydro-5H-pyrrolo[1,2-c]imidazol-1-yl)-2-[6-[4-[2-[2-[4-[3-(2,4-dioxohexahydropyrimidin-1-yl)-5-fluoro-1-methyl-indazol-6-yl]piperazin-1-yl]acetyl]-2,6-diazaspiro[3.3]heptan-6-yl]phenyl]-4-fluoro-1-oxo-isoindolin-2-yl]-N-thiazol-2-yl-acetamide To a solution of 2-[4-[3-(2,4-dioxohexahydropyrimidin-1-yl)-5-fluoro-1-methyl-indazol-6-yl]piperazin-1-yl]acetic acid hydrochloride (66 mg, 149.71 μmol) in N,N-dimethylformamide (0.4 mL) were added 1-[bis(dimethylamino)methylene]-1H-1,2,3-triazolo[4,5-b]pyridinium 3-oxide hexafluorophosphate (56 mg, 147.28 μmol) and N,N-diisopropylethylamine (133 mg, 1.03 mmol, 179.25 μL) at 0° C. The mixture was stirred at 0° C. for 0.5 h. Then 2-[6-[4-(2,6-diazaspiro[3.3]heptan-2-yl)phenyl]-4-fluoro-1-oxo-isoindolin-2-yl]-2-(6,7-dihydro-5H-pyrrolo [1,2-c]imidazol-1-yl)-N-thiazol-2-yl-acetamide, trifluoroacetic acid salt (80 mg, 117.01 μmol) was added to the mixture. The resulting mixture was stirred at 25° C. for 0.5 h. The mixture was filtered. The filtrate was purified by Prep-HPLC (flow: 30 mL/min; gradient: from 22%-52% acetonitrile in water over 8 min; column: Phenomenex Gemini-NX C18 75×30 mm×3 μm) and lyophilized to give Compound 123 (36.43 mg, 37.72 μmol, 26% yield) as a gray solid. LCMS (ESI): m/z 956.8 [M+H]$^+$, $^1$H-NMR (400 MHz, DMSO-d6) δ=12.50 (s, 1H), 10.54 (s, 1H), 7.73 (s, 1H), 7.70 (d, J=10.8 Hz, 1H), 7.64 (d, J=8.8 Hz, 2H), 7.59 (s, 1H), 7.46 (d, J=3.2 Hz, 1H), 7.36 (d, J=12.8 Hz, 1H), 7.21 (s, 1H), 7.12 (d, J=7.2 Hz, 1H), 6.54 (d, J=8.8 Hz, 2H), 6.12 (s, 1H), 4.82 (d, J=18.0 Hz, 1H), 4.50-4.42 (m, 2H), 4.20 (d, J=17.6 Hz, 1H), 4.12-4.07 (m, 2H), 4.06-3.92 (m, 7H), 3.89 (t, J=6.8 Hz, 2H), 3.20-2.96 (m, 6H), 2.80-2.69 (m, 3H), 2.68-2.60 (m, 4H), 2.57-2.51 (m, 2H), 2.47-2.42 (m, 1H).
Example 124
2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3-fluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1, Compound 124
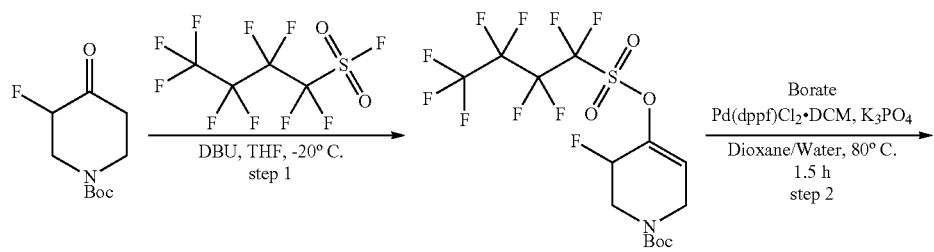
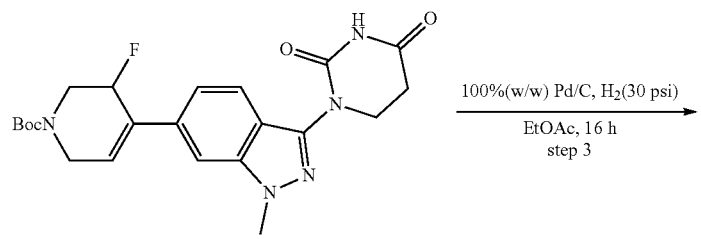
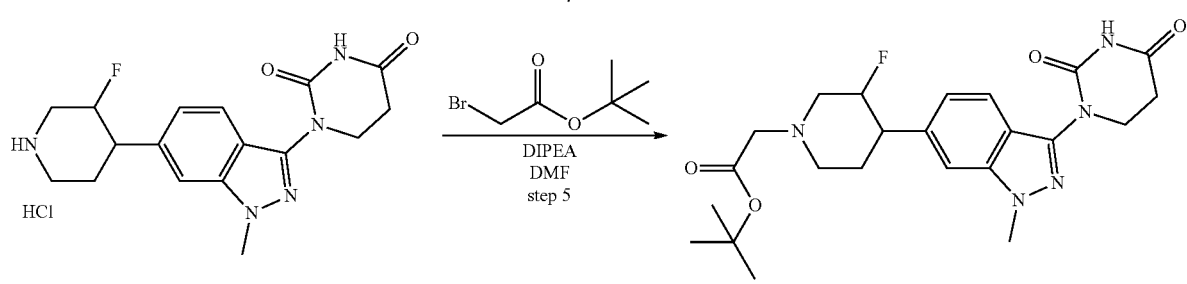

-continued
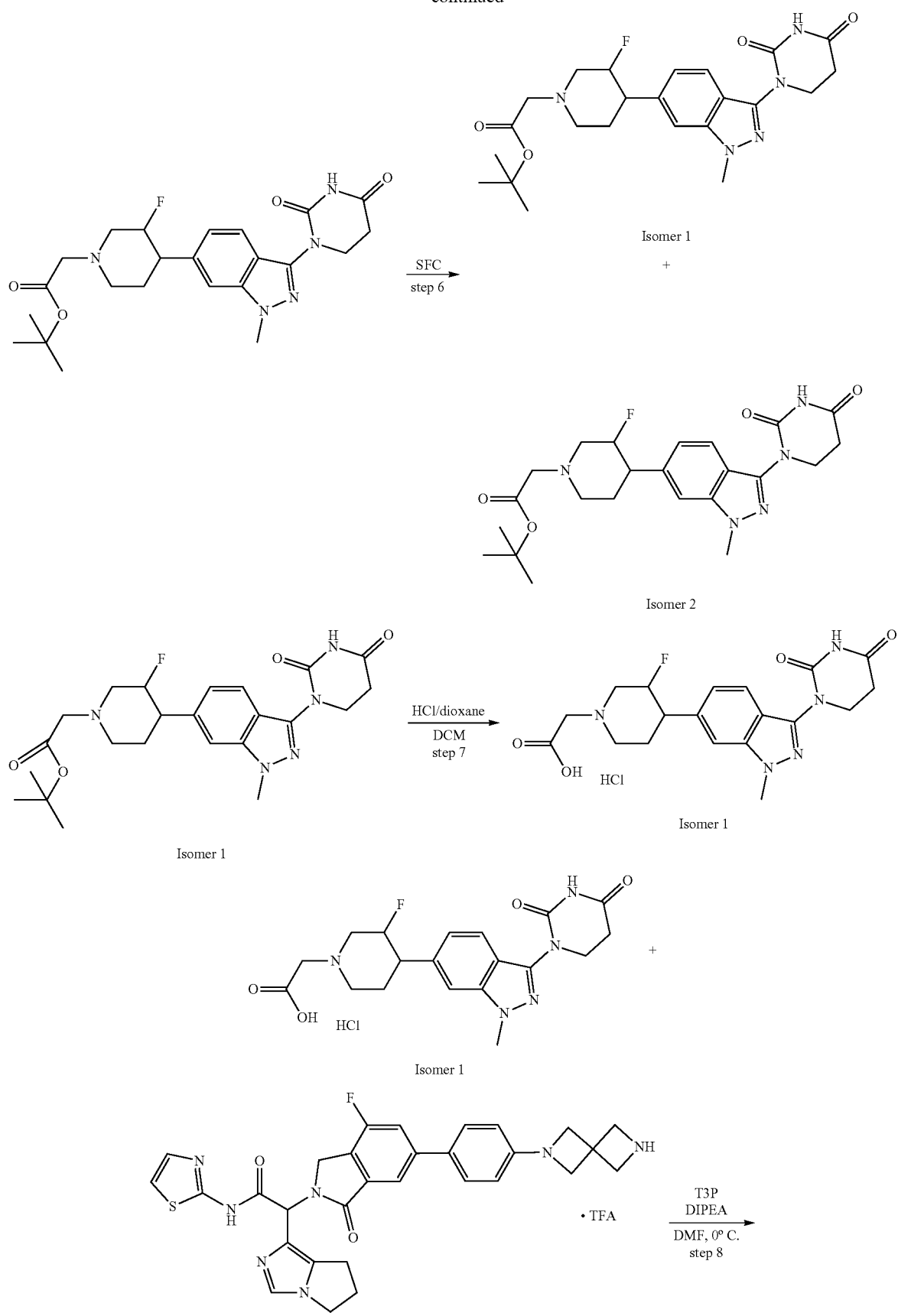

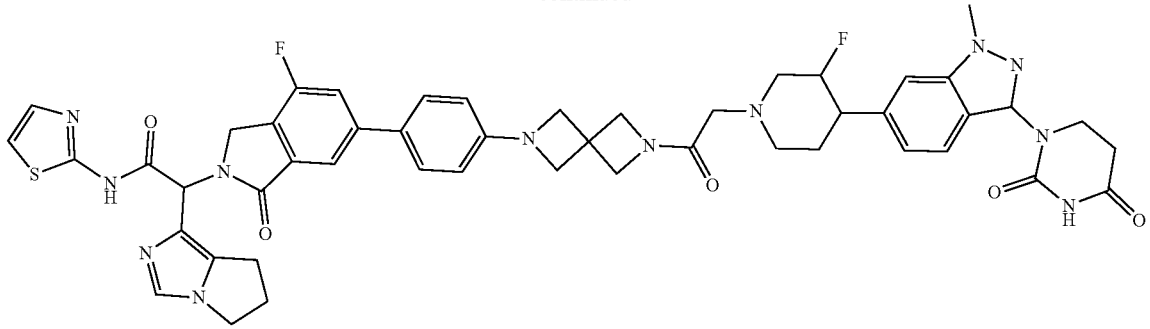

Isomer 1

Step 1: tert-Butyl 3-fluoro-4-(1,1,2,2,3,3,4,4,4-non-afluorobutylsulfonyloxy)-3,6-dihydro-2H-pyridine-1-carboxylate To a solution of tert-butyl 3-fluoro-4-oxo-piperidine-1-carboxylate (20.5 g, 94.37 mmol) and DBU (43.10 g, 283.10 mmol, 42.67 mL) in tetrahydrofuran (800 mL) was added a solution of 1,1,2,2,3,3,4,4,4-nonafluorobutane-1-sulfonyl fluoride (85.52 g, 283.10 mmol, 49.72 mL) in tetrahydrofuran (800 mL) dropwise at 0° C. The mixture was warmed to 20° C. and stirred for 1 h. The mixture was poured into water (1.5 L). The aqueous phase was extracted with ethyl acetate (1 L×2). The combined organic phase was washed with brine (2.5 L), dried with anhydrous sodium sulfate, filtered and concentrated in vacuum. The residue was purified by flash silica gel chromatography (ISCO®; 330 g SepaFlash® Silica Flash Column, Eluent of 0-20% ethyl acetate/petroleum ether gradient @ 100 mL/min) to give tert-butyl 3-fluoro-4-(1,1,2,2,3,3,4,4,4-nonafluorobutylsulfonyloxy)-3,6-dihydro-2H-pyridine-1-carboxylate (41.8 g, 83.71 mmol, 88.71% yield) was obtained as a white solid. $^1$H NMR (400 MHz, $CDCl_3$-d) 6 ppm 6.20 (br s, 1H), 5.02 (br d, J=10.40 Hz, 1H), 4.30-4.74 (m, 2H), 3.81 (br s, 1H), 3.29-3.45 (m, 1H), 1.49 (s, 9H)

Step 2: tert-Butyl 4-[3-(2,4-dioxohexahydropyrimidin-1-yl)-1-methyl-indazol-6-yl]-3-fluoro-3,6-dihydro-2H-pyridine-1-carboxylate To a mixture of tert-butyl 3-fluoro-4-(1,1,2,2,3,3,4,4,4-nonafluorobutylsulfonyloxy)-3,6-dihydro-2H-pyridine-1-carboxylate (28.32 g, 56.72 mmol), 1-[1-methyl-6-(4,4,5,5-tetramethyl-1,3,2-dioxaborolan-2-yl)indazol-3-yl]hexahydropyrimidine-2,4-dione (7 g, 18.91 mmol) and $K_3PO_4$ (8.03 g, 37.82 mmol) in 1,4-dioxane (100 mL) and water (10 mL) was added $Pd(dppf)Cl_2·CH_2Cl_2$ (1.38 g, 1.89 mmol) under $N_2$. The mixture was stirred at 80° C. for 1.5 h. The mixture was poured into water (500 mL). The aqueous phase was extracted with ethyl acetate (200 mL×2). The combined organic phase was washed with brine (400 mL), dried with anhydrous sodium sulfate, filtered and concentrated in vacuum. The residue was purified by silica gel chromatography (Petroleum ether/Ethyl acetate=1/1 to 0/1) to afford tert-butyl 4-[3-(2,4-dioxohexahydropyrimidin-1-yl)-1-methyl-indazol-6-yl]-3-fluoro-3,6-dihydro-2H-pyridine-1-carboxylate (7 g, 15.63 mmol, 82.65% yield) as yellow solid.

Step 3: tert-Butyl 4-[3-(2,4-dioxohexahydropyrimidin-1-yl)-1-methyl-indazol-6-yl]-3-fluoro-piperidine-1-carboxylate To a solution of tert-butyl 4-[3-(2,4-dioxohexahydropyrimidin-1-yl)-1-methyl-indazol-6-yl]-3-fluoro-3,6-dihydro-2H-pyridine-1-carboxylate (3 g, 6.76 mmol) in ethyl acetate (45 mL) was added Palladium, 10% on carbon, dry (3.00 g, 28.19 mmol) under $N_2$. The suspension was degassed under vacuum and purged with $H_2$ three times. The mixture was stirred under $H_2$ (30 psi) at 30° C. for 16 h. The mixture was filtered and concentrated in vacuum. The residue was purified by prep-HPLC (column: Phenomenex Synergi Max-RP 250*50 mm*10 m; mobile phase: [water (0.225% formic acid)-acetonitrile]; B %: 35%-65%, 18 min) to give tert-butyl 4-[3-(2,4-dioxohexahydropyrimidin-1-yl)-1-methyl-indazol-6-yl]-3-fluoro-piperidine-1-carboxylate (1.2 g, 2.42 mmol, 35.84% yield) as a yellow solid.

Step 4: 1-[6-(3-fluoro-4-piperidyl)-1-methyl-indazol-3-yl]hexahydropyrimidine-2,4-dione To the mixture of tert-butyl 4-[3-(2,4-dioxohexahydropyrimidin-1-yl)-1-methyl-indazol-6-yl]-3-fluoro-piperidine-1-carboxylate (1 g, 2.24 mmol) in dichloromethane (5 mL) was added hydrogen chloride solution (4 M in 1,4-dioxane, 5 mL, 20 mmol). The mixture was stirred at 25° C. for 2 h. The reaction mixture was concentrated under reduced pressure to give 1-[6-(3-fluoro-4-piperidyl)-1-methyl-indazol-3-yl]hexahydropyrimidine-2,4-dione hydrochloride (0.9 g, 2.05 mmol, 91.35% yield) as a white solid. LCMS (ES+): 346.4 [M+H]$^+$

Step 5: tert-Butyl 2-[4-[3-(2,4-dioxohexahydropyrimidin-1-yl)-1-methyl-indazol-6-yl]-3-fluoro-1-piperidyl]acetate To a solution of 1-[6-(3-fluoro-4-piperidyl)-1-methyl-indazol-3-yl]hexahydropyrimidine-2,4-dione hydrochloride (0.9 g, 2.27 mmol) and N,N-diisopropylethylamine (1.17 g, 9.07 mmol, 1.58 mL) in N,N-dimethylformamide (9 mL) was added tert-butyl 2-bromoacetate (442.21 mg, 2.27 mmol, 332.49 μL) at 0° C. dropwise addition. After addition, the mixture was stirred at this temperature for 2 h. The reaction mixture was diluted with water (300 mL) and extracted with ethyl acetate (300 mL×2). The combined organic layers were washed with brine (100 mL), dried over sodium sulfate, filtered and concentrated under reduced pressure to give tert-butyl 2-[4-[3-(2,4-dioxohexahydropyrimidin-1-yl)-1-methyl-indazol-6-yl]-3-fluoro-1-piperidyl]
acetate (0.9 g, 1.94 mmol, 85.53% yield) as a white solid.
LCMS (ES+): 460.3 [M+H]⁺

Step 6: tert-Butyl 2-[4-[3-(2,4-dioxohexahydropy-
rimidin-1-yl)-1-methyl-indazol-6-yl]-3-fluoro-1-
piperidyl]acetate, isomer 1 and tert-butyl 2-[(3S,
4R)-4-[3-(2,4-dioxohexahydropyrimidin-1-yl)-1-
methyl-indazol-6-yl]-3-fluoro-1-piperidyl]acetate,
isomer 2

Racemic tert-butyl 2-[4-[3-(2,4-dioxohexahydropyrimi-
din-1-yl)-1-methyl-indazol-6-yl]-3-fluoro-1-piperidyl]ac-
etate (900 mg, 1.96 mmol) was separated by prep-SFC
(Sample preparation: Dissolved sample into ethanol:dichlo-
romethane (4:1) (90 mL). Instrument: Thar 80 SFC; Mobile
Phase: 35% methanol (+0.1% ammonia) in Supercritical
CO₂; Flow Rate: 60 g/min; Cycle Time: 5.4 min; total time:
120 min; Single injection volume: 4.0 mL; Back Pressure:
100 bar to keep the CO₂ in Supercritical flow) to afford two
sets of fractions.
The first eluting fractions were evaporated under reduced
pressure to afford tert-butyl 2-[4-[3-(2,4-dioxohexahydropy-
rimidin-1-yl)-1-methyl-indazol-6-yl]-3-fluoro-1-piperidyl]
acetate, isomer 1 (260 mg, 503.58 µmol, 25.71% yield) as a
white solid. SFC (Column: Chiral OJ-3 50×4.6 mm, 3 m
particle size, Mobile phase: 5% to 40% EtOH (+0.05%
diethethylamine) in CO₂, Flow rate: 3 mL/min, Tempera-
ture: 35° C., Pressure: 100 Bar.): Rt=1.446 min (>95% ee)
The second eluting fractions were evaporated under reduced
pressure to afford tert-butyl 2-[4-[3-(2,4-dioxohexahydropy-
rimidin-1-yl)-1-methyl-indazol-6-yl]-3-fluoro-1-piperidyl]
acetate, isomer 2 (260 mg, 537.53 µmol, 27.44% yield) as a
white solid. SFC (Column: Chiral OJ-3 50×4.6 mm, 3 m
particle size, Mobile phase: 5% to 40% EtOH in CO₂, Flow
rate: 3 mL/min, Temperature: 35° C., Pressure: 100 Bar.):
Rt=1.687 min. (99.6% ee).

Step 7: 2-[4-[3-(2,4-dioxohexahydropyrimidin-1-
yl)-1-methyl-indazol-6-yl]-3-fluoro-1-piperidyl]ace-
tic acid, isomer 1 tert-Butyl 2-[4-[3-(2,4-dioxohexahydropyrimidin-1-yl)-
1-methyl-indazol-6-yl]-3-fluoro-1-piperidyl]acetate, isomer
1 (170.0 mg, 369.96 µmol) was dissolved in dichlorometh-
ane (2 mL) and 4M hydrochloric acid in 1,4-dioxane (2 mL)
was added. The resulting mixture was stirred at 40° C. for 4
h. The reaction mixture was concentrated under reduced
pressure. The residue was triturated with diethyl ether and
filtered to give 2-[4-[3-(2,4-dioxohexahydropyrimidin-1-
yl)-1-methyl-indazol-6-yl]-3-fluoro-1-piperidyl]acetic acid
hydrochloride, isomer 1 (180 mg, 368.29 µmol, 99.55%
yield) as a white solid. LCMS (ESI+): 404.2 [M+H]⁺

Step 8: 2-(6,7-dihydro-5H-pyrrolo[1,2-c]imidazol-1-
yl)-2-[6-[4-[2-[2-[(4-[3-(2,4-dioxohexahydropyrimi-
din-1-yl)-1-methyl-indazol-6-yl]-3-fluoro-1-pip-
eridyl]acetyl]-2,6-diazaspiro[3.3]heptan-6-yl]
phenyl]-4-fluoro-1-oxo-isoindolin-2-yl]-N-thiazol-2-
yl-acetamide, isomer 1

To a solution of 2-[4-[3-(2,4-dioxohexahydropyrimidin-
1-yl)-1-methyl-indazol-6-yl]-3-fluoro-1-piperidyl]acetic
acid hydrochloride, isomer 1 (180 mg, 409.21 µmol) and
propylphosphonic anhydride solution (50 wt. % in ethyl
acetate) (182.4 µL, 195.31 mg, 613.82 µmol) in N,N-
dimethylformamide (2.5 mL) was added N,N-diisopropyl-
ethylamine (498.93 µL, 370.21 mg, 2.86 mmol). The mix-
ture was stirred at 0° C. for 20 min, 2-[6-[4-(2,6-diazaspiro
[3.3]heptan-2-yl)phenyl]-4-fluoro-1-oxo-isoindolin-2-yl]-2-
(6,7-dihydro-5H-pyrrolo[1,2-c]imidazol-1-yl)-N-thiazol-2-
yl-acetamide, trifluoroacetic acid salt (223.82 mg, 327.37
µmol) was added. The mixture was stirred at 0° C. for 1 h.
To the mixture was added propylphosphonic anhydride
solution (50 wt. % in ethyl acetate) (117.18 mg, 368.29
µmol). The mixture was stirred at 0° C. for 1 h. The reaction
mixture was purified by preparative HPLC (Column: Waters
Xbridge C18 150*50 mm, 10 m particle size, Mobile phase:
22%-52% acetonitrile in water, Run time: 10 min) to afford
Compound 124 (149.55 mg, 156.59 µmol, 38.27% yield) as
a white solid. LCMS (ES+): 955.6 [M+H]⁺, ¹H NMR (400
MHz, DMSO-d₆) δ=12.78-12.21 (m, 1H), 10.55 (s, 1H),
7.74 (s, 1H), 7.70 (d, J=10.8 Hz, 1H), 7.64 (d, J=8.4 Hz, 2H),
7.61-7.56 (m, 2H), 7.52-7.41 (m, 2H), 7.23 (br d, J=2.4 Hz,
1H), 7.12 (d, J=8.8 Hz, 1H), 6.54 (d, J=8.8 Hz, 2H), 6.13 (s,
1H), 4.99-4.72 (m, 2H), 4.47 (br d, J=4.0 Hz, 2H), 4.21 (d,
J=17.6 Hz, 1H), 4.09 (s, 2H), 4.06-3.95 (m, 9H), 3.91 (t,
J=6.8 Hz, 2H), 3.21-3.08 (m, 3H), 3.03-2.89 (m, 2H), 2.75
(br t, J=6.8 Hz, 3H), 2.58-2.54 (m, 2H), 2.48-2.42 (m, 2H),
2.38-2.27 (m, 2H), 1.78-1.66 (m, 1H).

Example 125

2-(6,7-dihydro-5H-pyrrolo[1,2-c]imidazol-1-yl)-2-
[6-[4-[2-[2-[4-[3-(2,4-dioxohexahydropyrimidin-1-
yl)-1-methyl-indazol-6-yl]-3-fluoro-1-piperidyl]
acetyl]-2,6-diazaspiro[3.3]heptan-6-yl]phenyl]-4-
fluoro-1-oxo-isoindolin-2-yl]-N-thiazol-2-yl-
acetamide, isomer 2, Compound 125

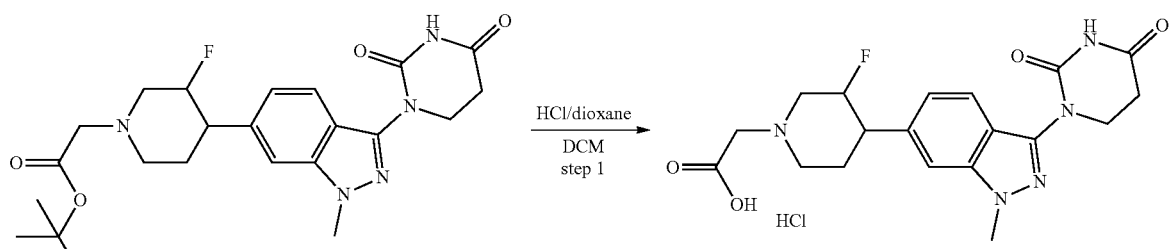

Isomer 2

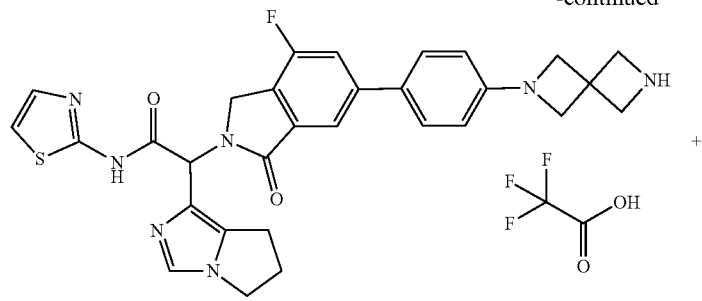

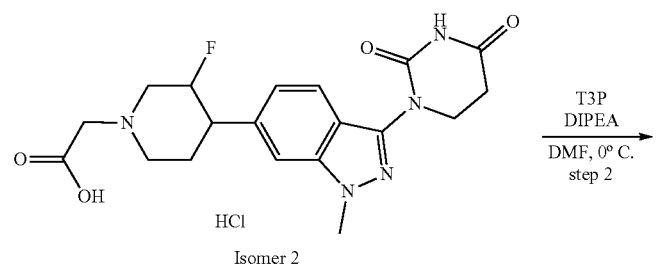

Isomer 2

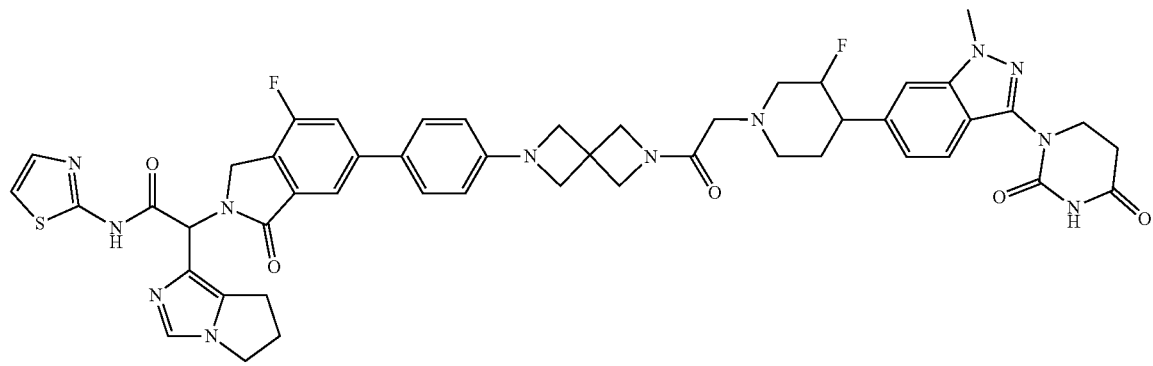

Isomer 2

Step 1: 2-[4-[3-(2,4-dioxohexahydropyrimidin-1-yl)-1-methyl-indazol-6-yl]-3-fluoro-1-piperidyl]acetic acid tert-butyl 2-[4-[3-(2,4-dioxohexahydropyrimidin-1-yl)-1-methyl-indazol-6-yl]-3-fluoro-1-piperidyl]acetate, isomer 2 (160.0 mg, 348.2 μmol) was dissolved in dichloromethane (2 mL) and hydrogen chloride (4M solution in 1,4-dioxane, 2 mL, 8 mmol) was added. The resulting mixture was stirred at 40° C. for 4 h. The reaction mixture was concentrated under reduced pressure. The residue was triturated with diethyl ether and filtered to give 2-[4-[3-(2,4-dioxohexahydropyrimidin-1-yl)-1-methyl-indazol-6-yl]-3-fluoro-1-piperidyl]acetic acid, isomer 2, hydrochloride (170 mg, 347.83 μmol, 99.90% yield) as a white solid. LCMS (ES+): m/z 404.2 [M+H]+

Step 2: 2-(6,7-dihydro-5H-pyrrolo[1,2-c]imidazol-1-yl)-2-[6-[4-[2-[2-[(3S,4R)-4-[3-(2,4-dioxohexahydropyrimidin-1-yl)-1-methyl-indazol-6-yl]-3-fluoro-1-piperidyl]acetyl]-2,6-diazaspiro[3.3]heptan-6-yl]phenyl]-4-fluoro-1-oxo-isoindolin-2-yl]-N-thiazol-2-yl-acetamide To a solution of 2-[(3S,4R)-4-[3-(2,4-dioxohexahydropyrimidin-1-yl)-1-methyl-indazol-6-yl]-3-fluoro-1-piperidyl]acetic acid hydrochloride (170 mg, 386.48 μmol) and propylphosphonic anhydride solution (50 wt. % in ethyl acetate) (184.46 mg, 579.72 μmol, 172 μL) in N,N-dimethylformamide (2.5 mL) was added N,N-diisopropylethylamine (349.64 mg, 2.71 mmol, 471.21 μL). the mixture was stirred at 0° C. for 20 min, 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (211.38 mg, 309.18 μmol) was added, the mixture was stirred at 0° C. for 1 h, To the mixture was added propylphosphonic anhydride solution (50 wt. % in ethyl acetate) (110.67 mg, 347.83 μmol). The mixture was stirred at 0° C. for 1 h. The residue was purified by preparative HPLC (Column: Waters Xbridge C18 150*50 mm; 10 μm, Mobile phase: 22%-52% acetonitrile in water, Run time: 10 min) to afford Compound 125 (118.69 mg, 124.28 μmol, 32.16% yield) as a white solid. LCMS (ES+): m/z 955.6[M+H]+, $^1$H NMR (400 MHz, DMSO-$d_6$) δ=12.72-12.27 (m, 1H), 10.55 (s, 1H), 7.74 (s, 1H), 7.73-7.68 (m, 1H), 7.65 (d, J=8.4 Hz, 2H), 7.62-7.56 (m, 2H), 7.51-7.45 (m, 2H), 7.23 (br s, 1H), 7.12 (d, J=8.4 Hz, 1H), 6.55 (d, J=8.4 Hz, 2H), 6.13 (s, 1H), 4.97-4.76 (m, 2H), 4.54-4.43 (m, 2H), 4.22 (d, J=17.6 Hz, 1H), 4.10 (s, 2H), 4.08-3.95 (m, 9H), 3.92 (t, J=6.8 Hz, 2H), 3.11 (s, 3H), 3.00 (br s, 2H), 2.76 (br t, J=6.8 Hz, 3H), 2.61-2.54 (m, 2H), 2.49-2.43 (m, 2H), 2.39-2.26 (m, 2H), 1.80-1.67 (m, 1H)

Example 126
2-(6,7-dihydro-5H-pyrrolo[1,2-c]imidazol-1-yl)-2-[6-[4-[2-[2-[1-[4-[[(3S)-2,6-dioxo-3-piperidyl]amino]-2-fluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide, Compound 126
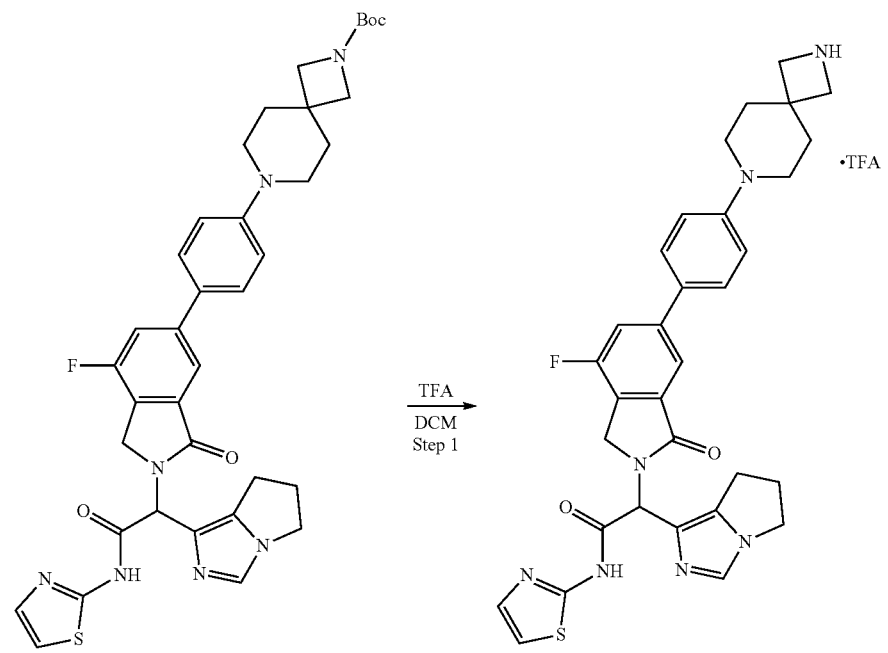
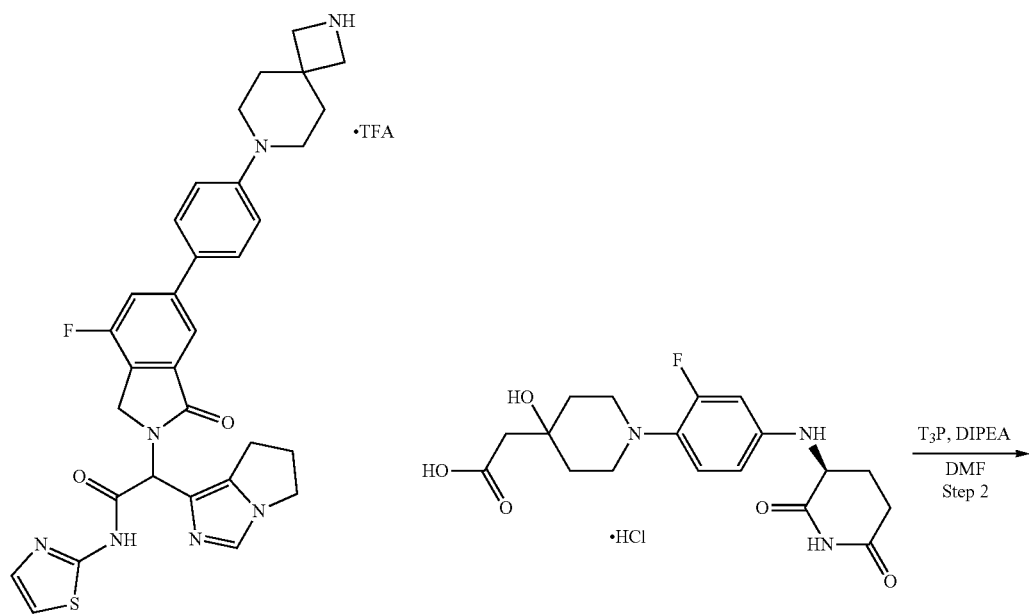

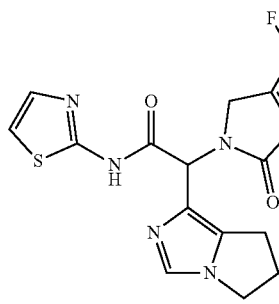

Step 1: 2-[6-[4-(2,7-diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide To a solution of tert-butyl 7-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonane-2-carboxylate (300 mg, 429.91 μmol) in dichloromethane (5 mL) was added trifluoroacetic acid (2.22 g, 19.47 mmol, 1.50 mL), the mixture was stirred at 25 for 1 h. The reaction mixture was concentrated under reduced pressure and the residue was triturated with diethyl ether and filtered to afford 2-[6-[4-(2,7-diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (300 mg, 421.51 μmol, 98.05% yield) as a yellow solid.

Step 2: 2-(6,7-dihydro-5H-pyrrolo[1,2-c]imidazol-1-yl)-2-[6-[4-[2-[2-[1-[4-[[(3S)-2,6-dioxo-3-piperidyl]amino]-2-fluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide To a solution of 2-[1-[4-[[(3S)-2,6-dioxo-3-piperidyl]amino]-2-fluoro-phenyl]-4-hydroxy-4-piperidyl]acetic acid hydrochloride (130 mg, 312.62 μmol) in N,N-dimethylformamide (6 mL) was added N,N-diisopropylethylamine (282.82 mg, 2.19 mmol, 381.16 μL) and propylphosphonic anhydride solution (50 wt. % in ethyl acetate) (298.41 mg, 468.93 μmol, 261 L) at 0° C. for 15 min, 2-[6-[4-(2,7-diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (200.25 mg, 281.36 μmol) was added, and the mixture was stirred at 0° C. for 1 h. Propylphosphonic anhydride solution (50 wt. % in ethyl acetate) (99.47 mg, 156.31 μmol) was added, the mixture was stirred at 0° C. for another 1 h. The mixture was poured into water (30 mL) and neutralized with saturated aqueous solution of sodium bicarbonate (20 mL). A white solid precipitated, which was collected by filtration. The solid was dissolved in dichloromethane and dried over sodium sulfate, filtered, and concentrated under reduced pressure. The residue was purified by preparative HPLC (Column: Phenomenex Gemini-NX C18 75*30 mm*3 um; mobile phase: [water-acetonitrile]; Gradient Time: 8 minutes) to afford Compound 126 (64.87 mg, 67.64 μmol, 21.64% yield) as a white solid. LCMS (ESI): m/z 959.6 [M+H]$^+$, $^1$H NMR (400 MHz, DMSO-d$_6$) δ=12.63-12.43 (m, 1H), 10.78 (s, 1H), 7.78-7.71 (m, 2H), 7.66 (d, J=8.8 Hz, 2H), 7.61 (s, 1H), 7.49 (d, J=3.6 Hz, 1H), 7.26 (br, 1H), 7.06 (d, J=8.8 Hz, 2H), 6.86 (t, J=9.2 Hz, 1H), 6.54-6.46 (m, 1H), 6.44-6.39 (m, 1H), 6.15 (s, 1H), 5.78 (d, J=8.0 Hz, 1H), 4.86-4.75 (m, 2H), 4.29-4.17 (m, 2H), 4.06-3.90 (m, 4H), 3.63 (s, 2H), 3.26-3.18 (m, 4H), 2.95-2.81 (m, 4H), 2.59 (s, 2H), 2.12-2.06 (m, 1H), 1.92-1.71 (m, 7H), 1.64 (br, 2H).

Example 127

2-(6,7-dihydro-5H-pyrrolo[1,2-c]imidazol-1-yl)-2-[6-[4-[2-[2-[1-[3-(2,4-dioxohexahydropyrimidin-1-yl)-5-fluoro-1-methyl-indazol-6-yl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, Compound 127

Step 1: 1-(5-fluoro-1-methyl-6-(1,4-dioxa-8-azaspiro[4.5]decan-8-yl)-1H-indazol-3-yl)dihydropyrimidine-2,4(1H,3H)-dione

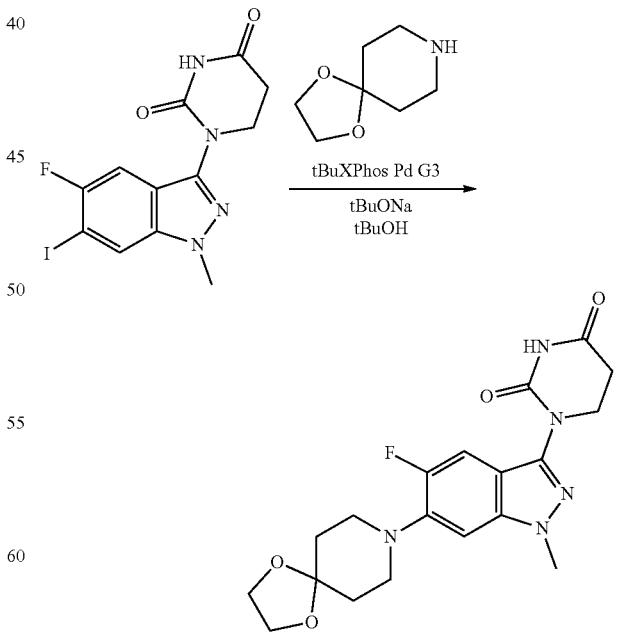

To a mixture of 1-(5-fluoro-6-iodo-1-methyl-1H-indazol-3-yl)dihydropyrimidine-2,4(1H,3H)-dione (10.0 g, 25.8 mmol) and 1,4-dioxa-8-azaspiro[4.5]decane (10.0 g, 69.8 mmol, 8.93 mL) in t-BuOH (150 mL) was added t-BuONa (7.43 g, 77.3 mmol), tBuXPhos (10.94 g, 25.76 mmol) and tBuXPhos Pd G3 (10.2 g, 12.9 mmol) under N$_2$ atmosphere at 25° C. Then the mixture was stirred at 105° C. for 12 h under nitrogen. The reaction mixture was quenched with aqueous saturated ammonium chloride (200 mL), extracted with ethyl acetate (200 mL×3). The combined organic layers were washed with brine (50 mL), dried over sodium sulfate, filtered, and concentrated under reduced pressure to give a residue. The residue was purified by column chromatography (silica gel, petroleum ether/ethyl acetate=1/1 to 1/5, TLC:petroleum ether/ethyl acetate=1/2, R$_f$=0.19) to give 1-(5-fluoro-1-methyl-6-(1,4-dioxa-8-azaspiro[4.5]decan-8-yl)-1H-indazol-3-yl)dihydropyrimidine-2,4(1H,3H)-dione (6.00 g, 10.3 mmol, 40.2% yield, 70% purity) as a light brown solid. LCMS: 404.2 (M+H), $^1$HNMR: (400 MHz, DMSO-d$_6$) δ 10.52 (s, 1H), 7.37-7.32 (m, 1H), 7.15 (d, J=7.2 Hz, 1H), 3.94 (s, 4H), 3.92-3.87 (m, 3H), 3.35-3.33 (m, 2H), 3.20-3.10 (m, 4H), 2.74 (t, J=6.7 Hz, 2H), 1.82 (br t, J 20=5.3 Hz, 4H)

Step 2: 1-(5-fluoro-1-methyl-6-(4-oxopiperidin-1-yl)-1H-indazol-3-yl)dihydropyrimidine-2,4(1H,3H)-dione

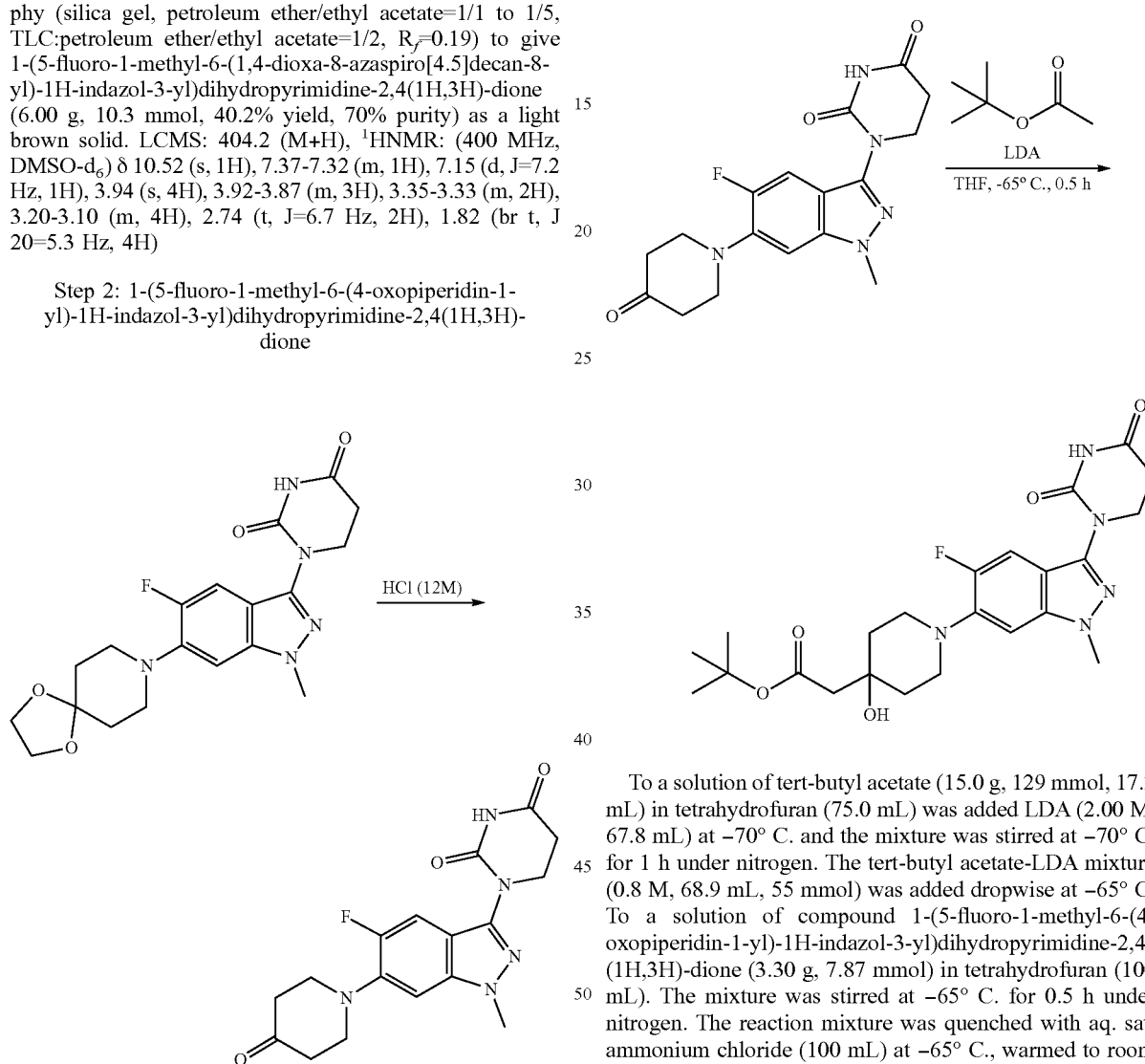

To a solution of 1-(5-fluoro-1-methyl-6-(1,4-dioxa-8-azaspiro[4.5]decan-8-yl)-1H-indazol-3-yl)dihydropyrimidine-2,4(1H,3H)-dione (5.00 g, 8.55 mmol) was added hydrochloric acid (Concentrated 36%, 70.4 g, 695 mmol, 69.0 mL). The mixture was stirred at 20° C. for 5 h. The reaction mixture was basified with saturated aqueous sodium bicarbonate to pH=7~8, extracted with ethyl acetate (200 mL×3). The combined organic layers were washed with brine (500 mL), dried over sodium sulfate, filtered and concentrated under reduced pressure. The residue was purified by column chromatography (SiO$_2$, petroleum ether/ethyl acetate=1/1 to 5/1, TLC:petroleum ether/ethyl acetate=1/2, R$_f$=0.19) to afford 1-(5-fluoro-1-methyl-6-(4-oxopiperidin-1-yl)-1H-indazol-3-yl)dihydropyrimidine-2,4 (1H,3H)-dione (3.60 g, crude) as a yellow solid and confirmed by LCMS (ESI+): 360.2 (M+H)

Step 3: tert-butyl 2-(1-(3-(2,4-dioxotetrahydropyrimidin-1(2H)-yl)-5-fluoro-1-methyl-1H-indazol-6-yl)-4-hydroxypiperidin-4-yl)acetate To a solution of tert-butyl acetate (15.0 g, 129 mmol, 17.3 mL) in tetrahydrofuran (75.0 mL) was added LDA (2.00 M, 67.8 mL) at −70° C. and the mixture was stirred at −70° C. for 1 h under nitrogen. The tert-butyl acetate-LDA mixture (0.8 M, 68.9 mL, 55 mmol) was added dropwise at −65° C. To a solution of compound 1-(5-fluoro-1-methyl-6-(4-oxopiperidin-1-yl)-1H-indazol-3-yl)dihydropyrimidine-2,4 (1H,3H)-dione (3.30 g, 7.87 mmol) in tetrahydrofuran (100 mL). The mixture was stirred at −65° C. for 0.5 h under nitrogen. The reaction mixture was quenched with aq. sat. ammonium chloride (100 mL) at −65° C., warmed to room temperature and extracted with ethyl acetate (100 mL×3). The combined organic layers were washed with brine (150 mL), dried over sodium sulfate, filtered, and concentrated under reduced pressure to give a residue. The residue was purified by reversed-phase HPLC (0.1% hydrochloric acid in water; acetonitrile) to give compound tert-butyl 2-(1-(3-(2,4-dioxotetrahydropyrimidin-1(2H)-yl)-5-fluoro-1-methyl-1H-indazol-6-yl)-4-hydroxypiperidin-4-yl)acetate (2.00 g, 4.21 mmol, 53.4% yield) as a white solid. LCMS (M+H): 476.4 (M+H), $^1$H-NMR: (400 MHz, CDCl3) δ 7.61 (br s, 1H), 7.51-7.33 (m, 1H), 4.18-4.07 (m, 2H), 3.98 (s, 3H), 3.45-3.22 (m, 2H), 2.89 (t, J=6.7 Hz, 2H), 2.50 (br s, 2H), 1.89 (br d, J=11.5 Hz, 2H), 1.67-1.60 (m, 4H), 1.50 (s, 9H)

1103

Step 4: 2-[1-[3-(2,4-dioxohexahydropyrimidin-1-yl)-5-fluoro-1-methyl-indazol-6-yl]-4-hydroxy-4-piperidyl]acetic acid

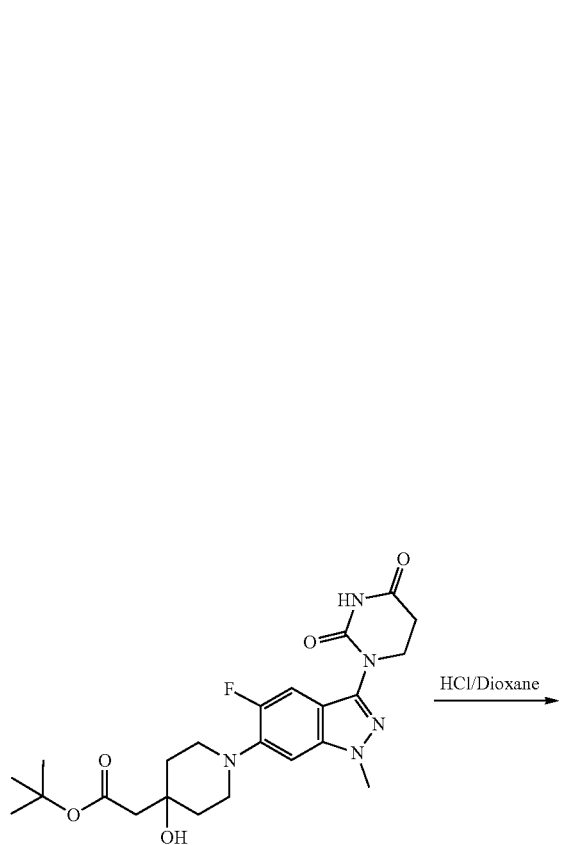

1104

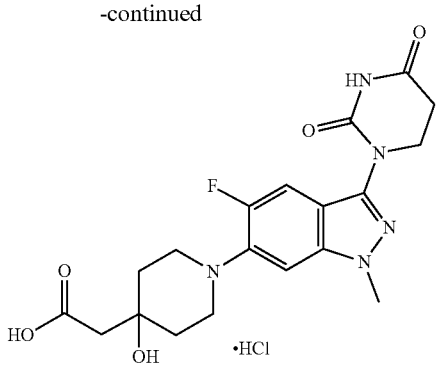

To a solution of compound tert-butyl 2-(1-(3-(2,4-dioxo-tetrahydropyrimidin-1(2H)-yl)-5-fluoro-1-methyl-1H-indazol-6-yl)-4-hydroxypiperidin-4-yl)acetate (2.00 g, 4.21 mmol) in dichloromethane (10.0 mL) was added hydrogen chloride (4.00 M in 1,4-dioxane, 42.1 mL, 168 mmol) and the mixture was stirred at 25° C. for 6 h. The reaction mixture was concentrated under reduced pressure. The residue was purified with preparative HPLC (0.1% hydrochloric acid) to give 2-[1-[3-(2,4-dioxohexahydropyrimidin-1-yl)-5-fluoro-1-methyl-indazol-6-yl]-4-hydroxy-4-piperidyl] acetic acid hydrochloride (1.00 g, 2.15 mmol, 51.11% yield) as a yellow solid. LCMS (ESI+): 420.1, $^1$HNMR: (400 MHz, DMSO-d$_6$) δ 10.52 (s, 1H), 7.40-7.30 (m, 1H), 7.19 (br d, J=6.0 Hz, 1H), 3.95 (s, 3H), 3.89 (t, J=6.7 Hz, 2H), 3.56 (s, 1H), 3.23-3.05 (m, 4H), 2.73 (t, J=6.6 Hz, 2H), 2.43 (s, 2H), 1.97-1.84 (m, 2H), 1.75 (br d, J=12.8 Hz, 2H)

Step 5: 2-(6,7-dihydro-5H-pyrrolo[1,2-c]imidazol-1-yl)-2-[6-[4-[2-[2-[1-[3-(2,4-dioxohexahydropyrimidin-1-yl)-5-fluoro-1-methyl-indazol-6-yl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide

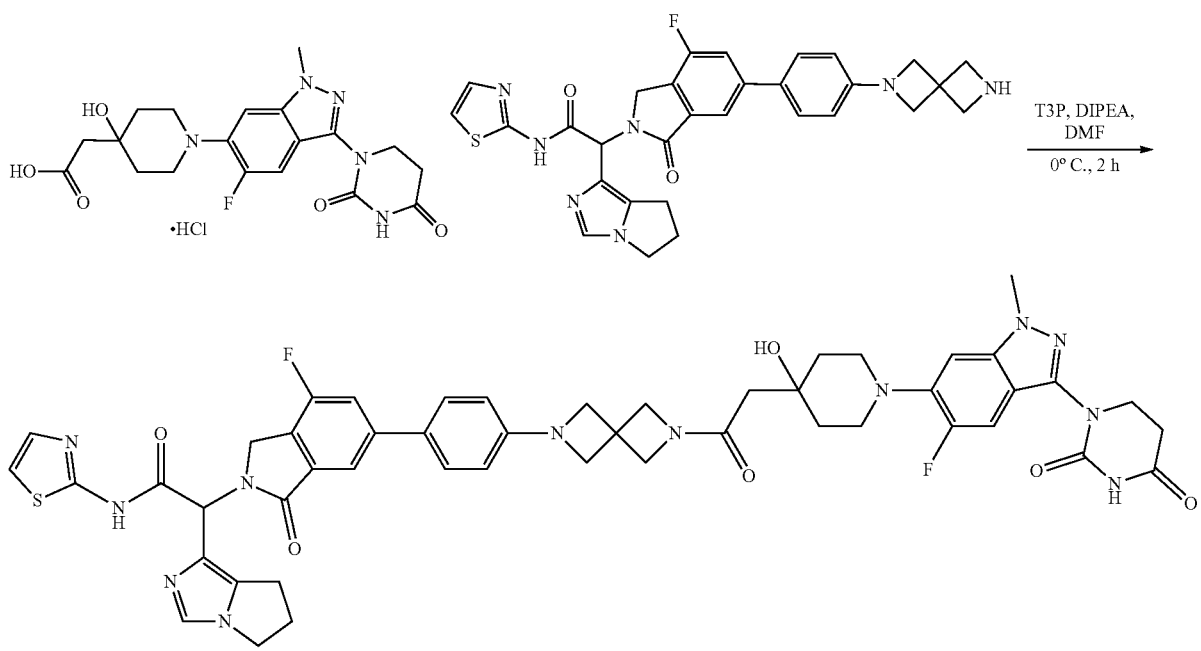

To a solution of 2-[1-[3-(2,4-dioxohexahydropyrimidin-1-yl)-5-fluoro-1-methyl-indazol-6-yl]-4-hydroxy-4-piperidyl]acetic acid hydrochloride (200 mg, 438.72 µmol) and Propylphosphonic anhydride solution (50 wt. % in ethyl acetate) (209.39 mg, 658.09 µmol) in N,N-dimethylformamide (3 mL) was added N,N-diisopropylethylamine (396.91 mg, 3.07 mmol, 534.93 µL). The mixture was stirred at 0° C. for 20 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide trifluoroacetic acid salt (239.96 mg, 350.98 µmol) was added. The mixture was stirred at 0° C. for 1 h. Propylphosphonic anhydride solution (50 wt. % in ethyl acetate) (125.63 mg, 394.85 µmol) was added. The mixture was stirred at 0° C. for 1 h. The reaction mixture was purified by preparative HPLC (Column: Phenomenex Gemini-NX C18 75*30 mm; 3 m; mobile phase: 22%-52% to acetonitrile in water; Run time: 8 min) to give Compound 127 (164.87 mg, 164.69 µmol, 37.54% yield) as a white solid. LCMS (ES+): m/z 971.4 [M+H]+, $^1$H NMR (400 MHz, DMSO-d$_6$) δ=12.49 (br s, 1H), 10.53 (br s, 1H), 7.78-7.68 (m, 2H), 7.68-7.56 (m, 3H), 7.48 (d, J=3.6 Hz, 1H), 7.33 (d, J=12.8 Hz, 1H), 7.24 (d, J=3.6 Hz, 1H), 7.12 (d, J=7.2 Hz, 1H), 6.54 (d, J=8.8 Hz, 2H), 6.14 (s, 1H), 4.87 (s, 1H), 4.80 (br d, J=17.6 Hz, 1H), 4.39 (s, 2H), 4.21 (d, J=17.6 Hz, 1H), 4.09 (s, 2H), 4.05-3.92 (m, 9H), 3.89 (t, J=6.8 Hz, 2H), 3.16 (br d, J=11.2 Hz, 2H), 3.10-2.99 (m, 2H), 2.73 (br t, J=6.8 Hz, 2H), 2.57-2.52 (m, 2H), 2.49-2.41 (m, 2H), 2.26 (s, 2H), 1.90-1.79 (m, 2H), 1.74-1.66 (m, 2H)

Example 128

2-[6-[4-[2-[2-[1-[2-chloro-4-[[2,6-dioxo-3-piperidyl]amino]phenyl]-4-hydroxy-4-piperidyl]acetyl]-2,7-diazaspiro[3.5]nonan-7-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, isomer 1, Compound 128

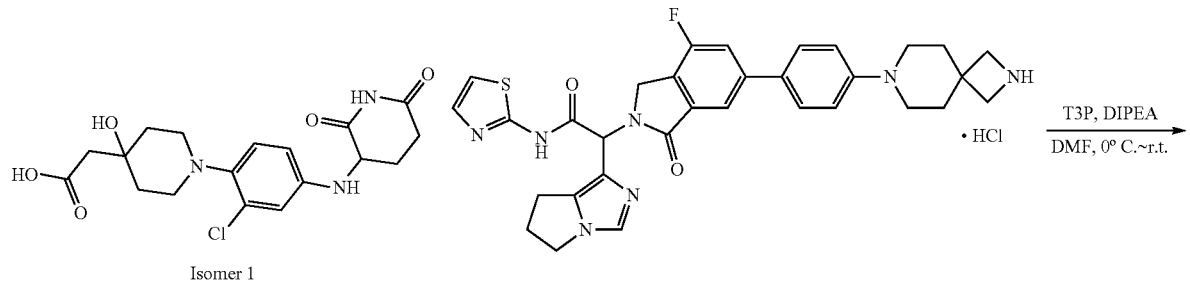

Isomer 1

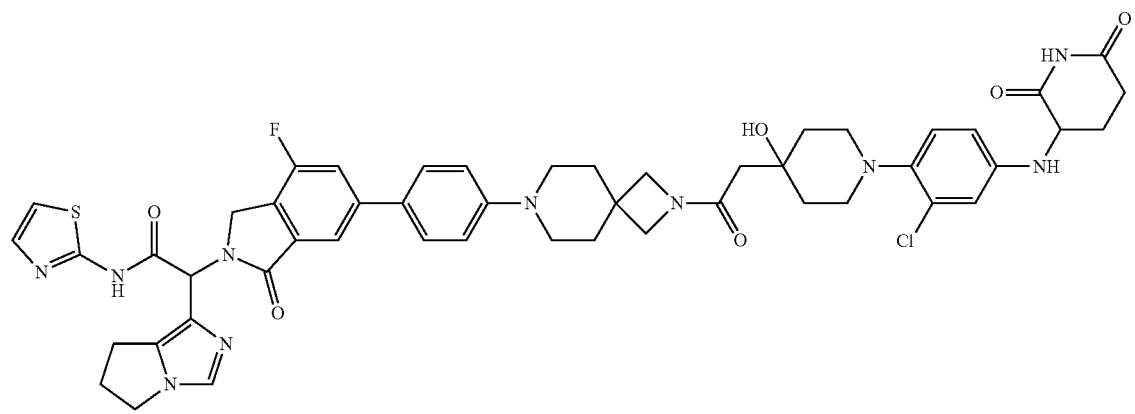

Isomer 1

To a solution of 2-[1-[2-chloro-4-[[(3S)-2,6-dioxo-3-piperidyl]amino]phenyl]-4-hydroxy-4-piperidyl]acetic acid hydrochloride (300 mg, 693.97 µmol) and propylphosphonic anhydride solution (50 wt. % in ethyl acetate) (331.21 mg, 1.04 mmol) in N,N-dimethylformamide (6 mL) was added N,N-diisopropylethylamine (627.83 mg, 4.86 mmol, 846.14 µL). The mixture was stirred at 0° C. for 20 min 2-[6-[4-(2,7-diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (370.44 mg, 520.47 µmol) was added. The mixture was stirred at 0° C. for 1 h, To the mixture was added propylphosphonic anhydride solution (50 wt. 00 in ethyl acetate) 198.73 mg, 624.57 µmol). The mixture was stirred at 0° C. for 1 h. The mixture was purified by prep-HPLC (Column: Phenomenex Gemini-NX C18 75*30 mm, 3 µm; mobile phase: 28%-58% acetonitrile in water, Run time: 8 min) to give Compound 128 (91.57 mg, 93.87 µmol, 13.53% yield) as a white solid. LCMS (ES+): m/z 975.4 [M+H], $^1$H-NM/R (400 MHz, DMSO-$d_6$) δ=12.51 (br s, 1H), 10.76 (s, 1H), 7.78-7.70 (m, 2H), 7.65 (d, J=8.8 Hz, 2H), 7.60 (s, 1H), 7.47 (br d, J=3.2 Hz, 1H), 7.30-7.18 (m, 1H), 7.05 (br d, J=8.8 Hz, 2H), 6.96 (d, J=8.8 Hz, 1H), 6.75 (d, J=2.4 Hz, 1H), 6.60 (dd, J=2.4, 8.8 Hz, 1H), 6.14 (s, 1H), 5.82 (d, J=7.6 Hz, 1H), 4.86-4.75 (m, 2H), 4.24 (s, 2H), 4.05-3.91 (m, 4H), 3.63 (s, 2H), 3.27-3.17 (m, 4H), 2.92-2.69 (m, 6H), 2.56-2.52 (m, 2H), 2.47-2.44 (m, 1H), 2.24 (s, 2H), 2.12-2.03 (m, 1H), 1.79 (br s, 8H), 1.68-1.61 (m, 2H).

Example 129

2-(6,7-dihydro-5H-pyrrolo[1,2-c]imidazol-1-yl)-2-[6-[4-[2-[2-[4-[3-(2,4-dioxohexahydropyrimidin-1-yl)-5-fluoro-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1, Compound 129

Step 1: tert-Butyl 3,3-difluoro-4-(4,4,5,5-tetramethyl-1,3,2-dioxaborolan-2-yl)-3,6-dihydropyridine-1(2H)-carboxylate

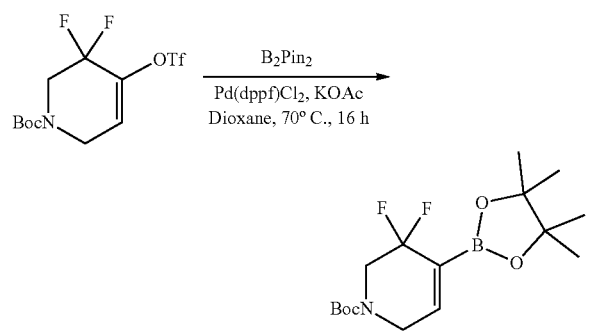

A mixture of compound tert-butyl 3,3-difluoro-4-(((trifluoromethyl)sulfonyl)oxy)-3,6-dihydropyridine-1(2H)-carboxylate (2.70 g, 7.35 mmol), B$_2$Pin$_2$ (2.24 g, 8.82 mmol), dppf (122 mg, 220 µmol), Pd(dppf)Cl$_2$ (161 mg, 220 µmol) and KOAc (2.53 g, 25.7 mmol) in 1,4-dioxane (30 mL) was degassed and purged with N$_2$ for 3 times, and the mixture was stirred at 80° C. for 12 h under N$_2$ atmosphere. The reaction mixture was filtered, the filtered cake was washed by ethyl acetate (50 mL). The filtrate was diluted with water (50 mL), extracted with ethyl acetate 100 mL (50 mL×2). The combined organic layers were washed with brine (30 mL), dried over sodium sulfate, filtered and concentrated under reduced pressure to give a residue, which was purified by column chromatography (SiO$_2$, petroleum ether/ethyl acetate=I/O to 10/1, TLC:petroleum ether/ethyl acetate=8/1, R$_f$=0.34) to give compound tert-butyl 3,3-difluoro-4-(4,4,5,5-tetramethyl-1,3,2-dioxaborolan-2-yl)-3,6-dihydropyridine-1(2H)-carboxylate (1.10 g, 3.19 mmol, 43.35% yield) as a yellow solid. $^1$H NMR (400 MHz, CDCl3) δ 6.92-6.70 (m, 1H), 3.99 (br s, 2H), 3.80-3.63 (m, 2H), 1.40 (s, 9H), 1.23 (s, 12H).

Step 2: tert-butyl 4-(3-(2,4-dioxotetrahydropyrimidin-1(2H)-yl)-5-fluoro-1-methyl-1H-indazol-6-yl)-3,3-difluoro-3,6-dihydropyridine-1(2H)-carboxylate

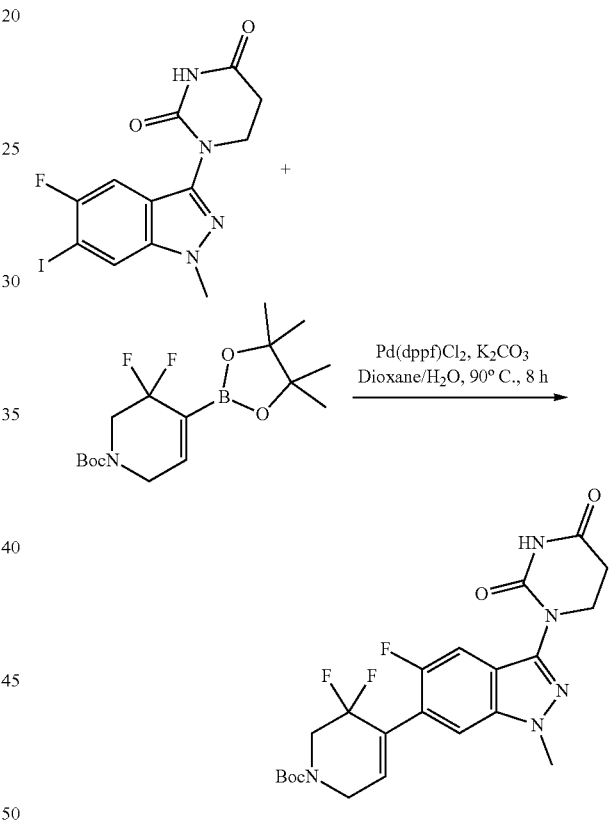

A mixture of compound tert-butyl 3,3-difluoro-4-(4,4,5,5-tetramethyl-1,3,2-dioxaborolan-2-yl)-3,6-dihydropyridine-1(2H)-carboxylate (1.07 g, 3.09 mmol), 1-(5-fluoro-6-iodo-1-methyl-1H-indazol-3-yl)dihydropyrimidine-2,4(1H,3H)-dione (1.00 g, 2.58 mmol), K$_2$CO$_3$ (1.07 g, 7.73 mmol) and Pd(dppf)Cl$_2$ (188 mg, 257 µmol) in dioxane (10.0 mL) and water (1.00 mL) was degassed and purged with N$_2$ for 3 times and stirred at 90° C. for 8 h under N$_2$ atmosphere. The reaction mixture was diluted with water (10 mL), extracted with ethyl acetate 100 mL (50 mL×2). The combined organic layers were washed with brine 50 mL (25 mL×2), dried over sodium sulfate, filtered, and concentrated under reduced pressure to give a residue. The residue was purified by preparative HPLC (trifluoroacetic acid used as a phase modifier) to give tert-butyl 4-(3-(2,4-dioxotetrahydropyrimidin-1(2H)-yl)-5-fluoro-1-methyl-1H-indazol-6-yl)-3, 3-difluoro-3,6-dihydropyridine-1(2H)-carboxylate (800 mg, 1.50 mmol, 58.2% yield) as a yellow solid. LCMS (ESI+): 480.2 (M+H).

Step 3: tert-butyl 4-(3-(2,4-dioxotetrahydropyrimi-din-1(2H)-yl)-5-fluoro-1-methyl-1H-indazol-6-yl)-3,3-difluoropiperidine-1-carboxylate

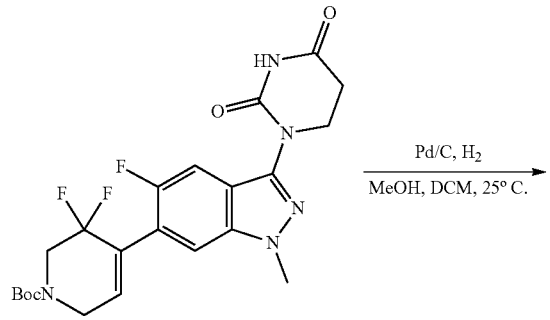

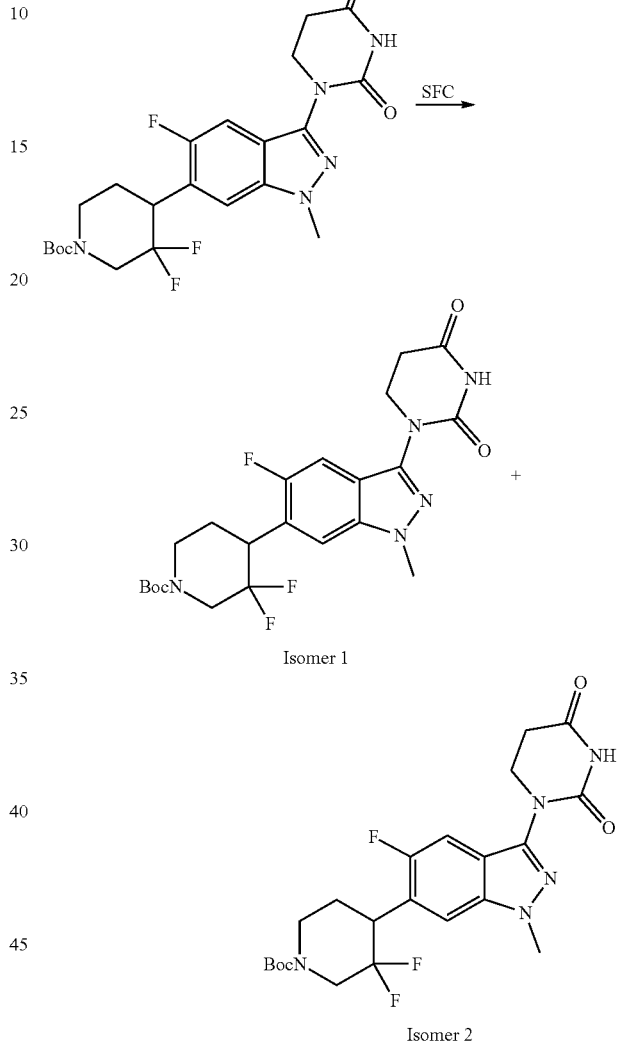

A mixture of tert-butyl 4-(3-(2,4-dioxotetrahydropyrimi-din-1(2H)-yl)-5-fluoro-1-methyl-1H-indazol-6-yl)-3,3-difluoro-3,6-dihydropyridine-1(2H)-carboxylate (800 mg, 1.67 mmol) in dichloromethane (5.00 mL) and methanol (10.0 mL) was added palladium, 10% on charcoal (800 mg) and the mixture was stirred at 25° C. for 12 h under hydrogen atmosphere (15 psi). The reaction mixture was filtered, the filtered cake was washed by methanol (50 mL) and dichloromethane (50 mL). The filtrate was concentrated under reduced pressure to give residue, which was triturated with tetrahydrofuran (5 mL) at 25° C. for 10 min to afford tert-butyl 4-(3-(2,4-dioxotetrahydropyrimidin-1(2H)-yl)-5-fluoro-1-methyl-1H-indazol-6-yl)-3,3-difluoropiperidine-1-carboxylate (485 mg, 926 µmol, 55.5% yield) was obtained as a yellow solid. LCMS (ESI+): 504.2 (M+Na), $^1$H NMR (400 MHz, DMSO-$d_6$) δ 10.56 (s, 1H), 7.76-7.72 (m, 1H), 7.42 (d, J=10.3 Hz, 1H), 4.37-4.06 (m, 3H), 4.01 (s, 3H), 4.06-3.96 (m, 1H), 3.90 (t, J=6.8 Hz, 2H), 3.84-3.69 (m, 1H), 2.74 (t, J=6.7 Hz, 2H), 2.31 (br d, J=1.6 Hz, 1H), 1.90-1.81 (m, 1H), 1.43 (s, 9H).

Step 4: tert-Butyl 4-(3-(2,4-dioxotetrahydropyrimi-din-1(2H)-yl)-5-fluoro-1-methyl-1H-indazol-6-yl)-3,3-difluoropiperidine-1-carboxylate, isomer 1 and tert-butyl 4-(3-(2,4-dioxotetrahydropyrimidin-1(2H)-yl)-5-fluoro-1-methyl-1H-indazol-6-yl)-3,3-difluoropiperidine-1-carboxylate, isomer 2 tert-Butyl 4-(3-(2,4-dioxotetrahydropyrimidin-1(2H)-yl)-5-fluoro-1-methyl-1H-indazol-6-yl)-3,3-difluoropiperidine-1-carboxylate (500 mg) was separated by prep-SFC. Instrument: Waters 80Q Preparative SFC system; Column: Chiralpak IG column, 250×30 mm I.D., 10 m particle size; Mobile Phase: Phase A for Supercritical $CO_2$, Phase B for isopropyl alcohol:acetonitrile (3:1); Isocratic elution: 30% Phase, B (70% Phase A); Flow rate: 60 g/min; cycle time: 5.35 min; Back Pressure: 100 bar to keep the $CO_2$ in Supercritical flow. The first set of fractions was evaporated to afford tert-butyl 4-(3-(2,4-dioxotetrahydropyrimidin-1 (2H)-yl)-5-fluoro-1-methyl-1H-indazol-6-yl)-3,3-difluoropiperidine-1-carboxylate, isomer 1 (210 mg, 99.9% ee). The second set of fractions was evaporated to afford tert-butyl 4-(3-(2,4-dioxotetrahydropyrimidin-1(2H)-yl)-5fluoro-1-methyl-1H-indazol-6-yl)-3,3-difluoropiperidine-1-carboxylate, isomer 2 (200 mg, 99.7% ee)

1111            1112
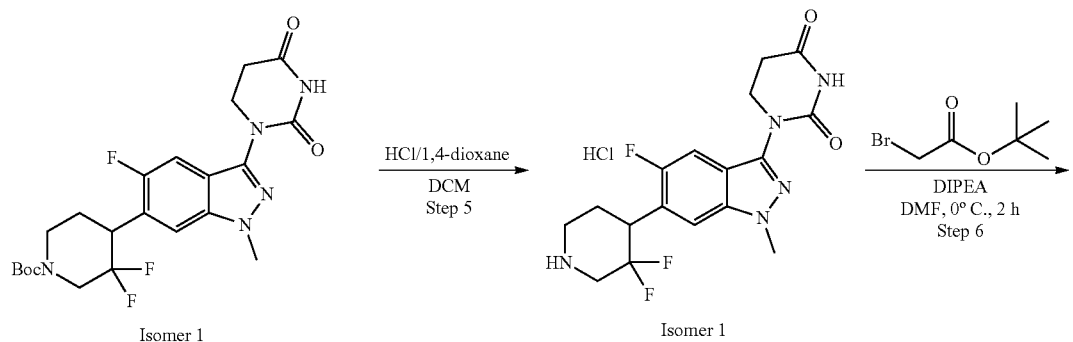
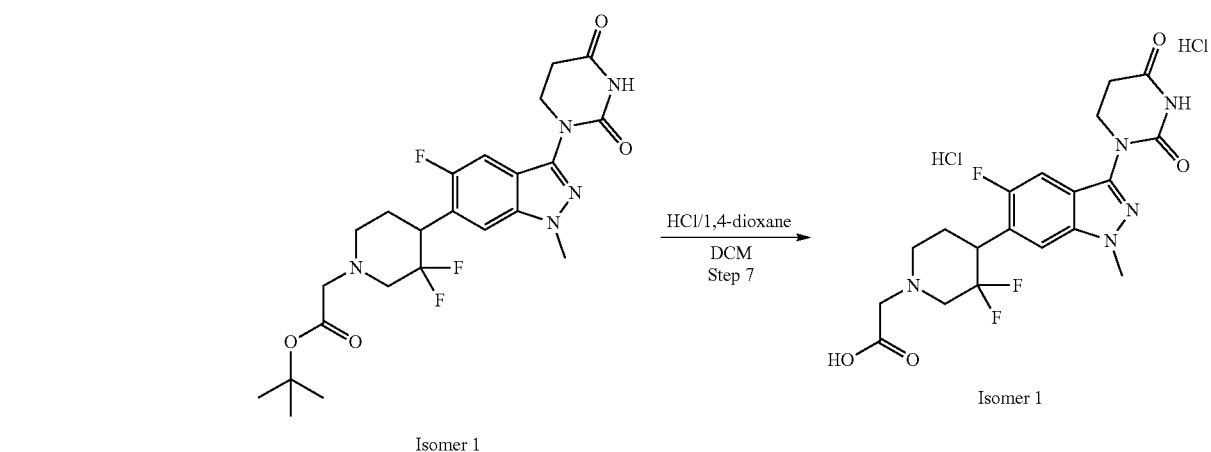
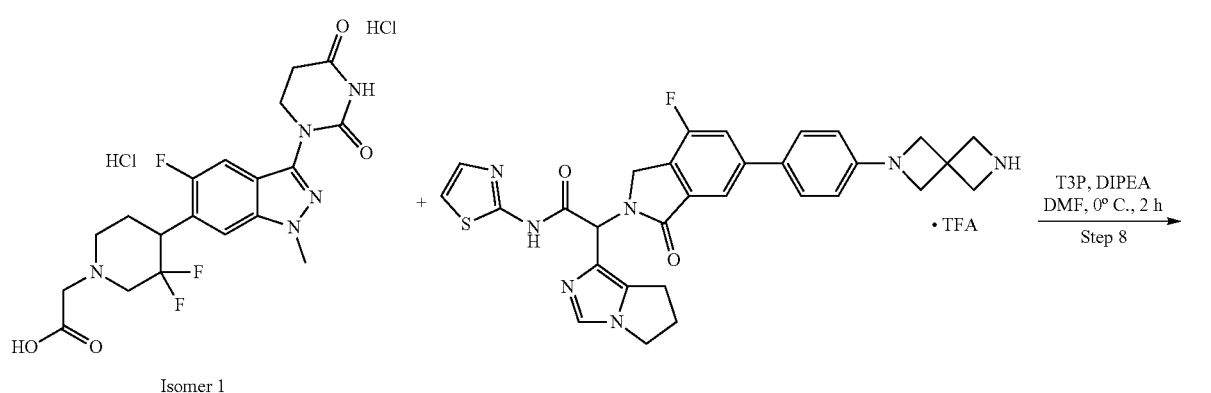
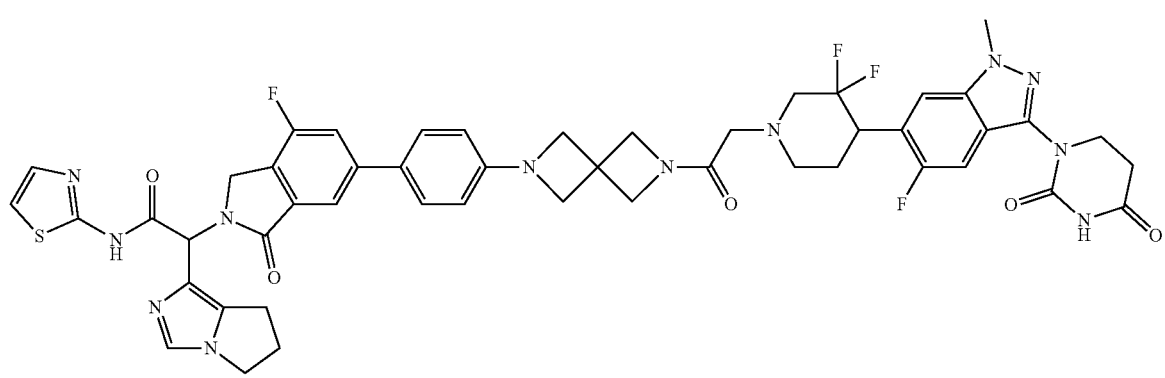

Step 5: 1-[6-[3,3-difluoro-4-piperidyl]-5-fluoro-1-methyl-indazol-3-yl]hexahydropyrimidine-2,4-dione, isomer 1

To a solution of tert-butyl 4-(3-(2,4-dioxotetrahydropyrimidin-1(2H)-yl)-5-fluoro-1-methyl-1H-indazol-6-yl)-3,3-difluoropiperidine-1-carboxylate, isomer 1 (200.00 mg, 415.40 µmol) in dichloromethane (2 mL) was added hydrochloric acid in dioxane (4 M, 2 mL), the mixture was stirred at 20° C. for 2 h. The reaction mixture was concentrated under reduced pressure to remove solvent. The crude product was triturated with petroleum ether (20 mL) for 15 min to afford 1-[6-[3,3-difluoro-4-piperidyl]-5-fluoro-1-methyl-indazol-3-yl]hexahydropyrimidine-2,4-dione hydrochloride, isomer 1 (150 mg, 359.01 µmol, 86.43% yield) as a white solid. LCMS (ESI): m/z 382.0 [M+H]+

Step 6: tert-Butyl 2-[4-[3-(2,4-dioxohexahydropyrimidin-1-yl)-5-fluoro-1-methyl-indazol-6-yl]-3,3-difluoro-1-piperidyl]acetate, isomer 1

To a solution of 1-[6-[3,3-difluoro-4-piperidyl]-5-fluoro-1-methyl-indazol-3-yl]hexahydropyrimidine-2,4-dione, isomer 1 hydrochloride (150 mg, 393.34 µmol) and N,N-diisopropylethylamine (305.01 mg, 2.36 mmol, 411.06 µL) in N,N-dimethylformamide (5 mL) was added tert-butyl 2-bromoacetate (191.80 mg, 983.34 µmol, 144.21 µL). The mixture was stirred at 0° C. for 2 h. The reaction mixture was poured into water (50 mL), extracted with ethyl acetate (30 mL×2). The combined organic layers were washed with brine (10 mL×2), dried over sodium sulfate, filtered and concentrated. The crude product was triturated with petroleum ether (6 mL) for 15 min to afford tert-butyl 2-[(4-[3-(2,4-dioxohexahydropyrimidin-1-yl)-5-fluoro-1-methyl-indazol-6-yl]-3,3-difluoro-1-piperidyl]acetate, isomer 1 (160 mg, 322.91 µmol, 82.09% yield) as an off-white solid. LCMS (ESI): m/z 496.2 [M+H]+

Step 7: 2-[4-[3-(2,4-dioxohexahydropyrimidin-1-yl)-5-fluoro-1-methyl-indazol-6-yl]-3,3-difluoro-1-piperidyl]acetic acid, isomer 1

To a solution of tert-butyl 2-[(4-[3-(2,4-dioxohexahydropyrimidin-1-yl)-5-fluoro-1-methyl-indazol-6-yl]-3,3-difluoro-1-piperidyl]acetate, isomer 1 (160.00 mg, 322.91 µmol) in dichloromethane (2 mL) was added hydrochloric acid in 1,4-dioxane (4 M, 2 mL), the mixture was stirred at 40° C. for 14 h. The reaction mixture was concentrated under reduced pressure to remove solvent. The crude product was triturated with Petroleum ether (50 mL) for 15 min to afford 2-[4-[3-(2,4-dioxohexahydropyrimidin-1-yl)-5-fluoro-1-methyl-indazol-6-yl]-3,3-difluoro-1-piperidyl]acetic acid hydrochloride, isomer 1 (150 mg, 315.23 µmol, 97.62% yield) as a white solid. LCMS (ESI): m/z 440.4 [M+H]+

Step 8: 2-(6,7-dihydro-5H-pyrrolo[1,2-c]imidazol-1-yl)-2-[6-[4-[2-[2-[4-[3-(2,4-dioxohexahydropyrimidin-1-yl)-5-fluoro-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1

To a solution of 2-[4-[3-(2,4-dioxohexahydropyrimidin-1-yl)-5-fluoro-1-methyl-indazol-6-yl]-3,3-difluoro-1-piperidyl]acetic acid hydrochloride, isomer 1 (150 mg, 315.23 µmol) and propylphosphonic anhydride solution (50 wt. % in ethyl acetate) (300.90 mg, 472.84 µmol) in N,N-dimethylformamide (6 mL) was added N,N-diisopropylethylamine (325.92 mg, 2.52 mmol, 439.24 µL) The mixture was stirred at 0° C. for 20 min, 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (179.57 mg, 262.65 µmol) was added, the mixture was stirred at 0° C. for 60 min. Propylphosphonic anhydride solution (50 wt. % in ethyl acetate) (100.30 mg, 157.61 µmol) was added, the mixture was stirred at 0° C. for 60 min. The reaction mixture was poured into water (50 mL). A white solid precipitated, which was collected by filtration. The solid was washed with water (10 mL), dried under reduced pressure to give a residue, the further was purified by preparative HPLC (Column: Phenomenex Gemini-NX C18 75*30 mm; 3 m particles; mobile phase: [water-acetonitrile]; Gradient Time (min) 8) to afford Compound 129 (120.13 mg, 120.37 mol, 56.80% yield) as a white solid. LCMS (ESI): m/z 496.5 [M/2+H]+, 1H-NMR (400 MHz, DMSO-d6) δ=12.52 (br, 1H), 10.58 (s, 1H), 7.77-7.69 (m, 3H), 7.65 (d, J=8.8 Hz, 2H), 7.61 (s, 1H), 7.50-7.40 (m, 2H), 7.26 (br, 1H), 6.56 (d, J=8.4 Hz, 2H), 6.15 (s, 1H), 4.80 (d, J=17.6 Hz, 1H), 4.45 (s, 2H), 4.22 (d, J=17.6 Hz, 1H), 4.11 (s, 2H), 4.08-3.95 (m, 9H), 3.92 (t, J=6.8 Hz, 2H), 3.60-3.40 (m, 4H), 3.22 (br, 4H), 3.02 (d, J=10.4 Hz, 1H), 2.82-2.71 (m, 4H), 2.65-2.54 (m, 4H), 2.41 (br, 2H), 1.90-1.78 (m, 1H).

Example 130

2-(6,7-dihydro-5H-pyrrolo[1,2-c]imidazol-1-yl)-2-[6-[4-[2-[2-[4-[3-(2,4-dioxohexahydropyrimidin-1-yl)-5-fluoro-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, isomer 2, Compound 130

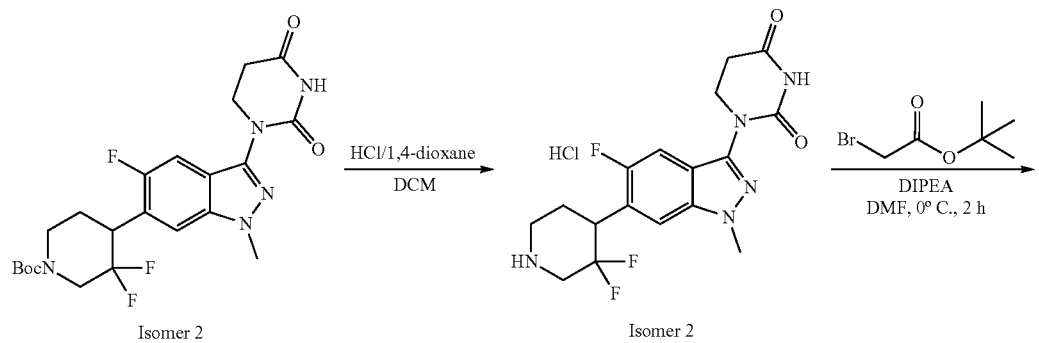

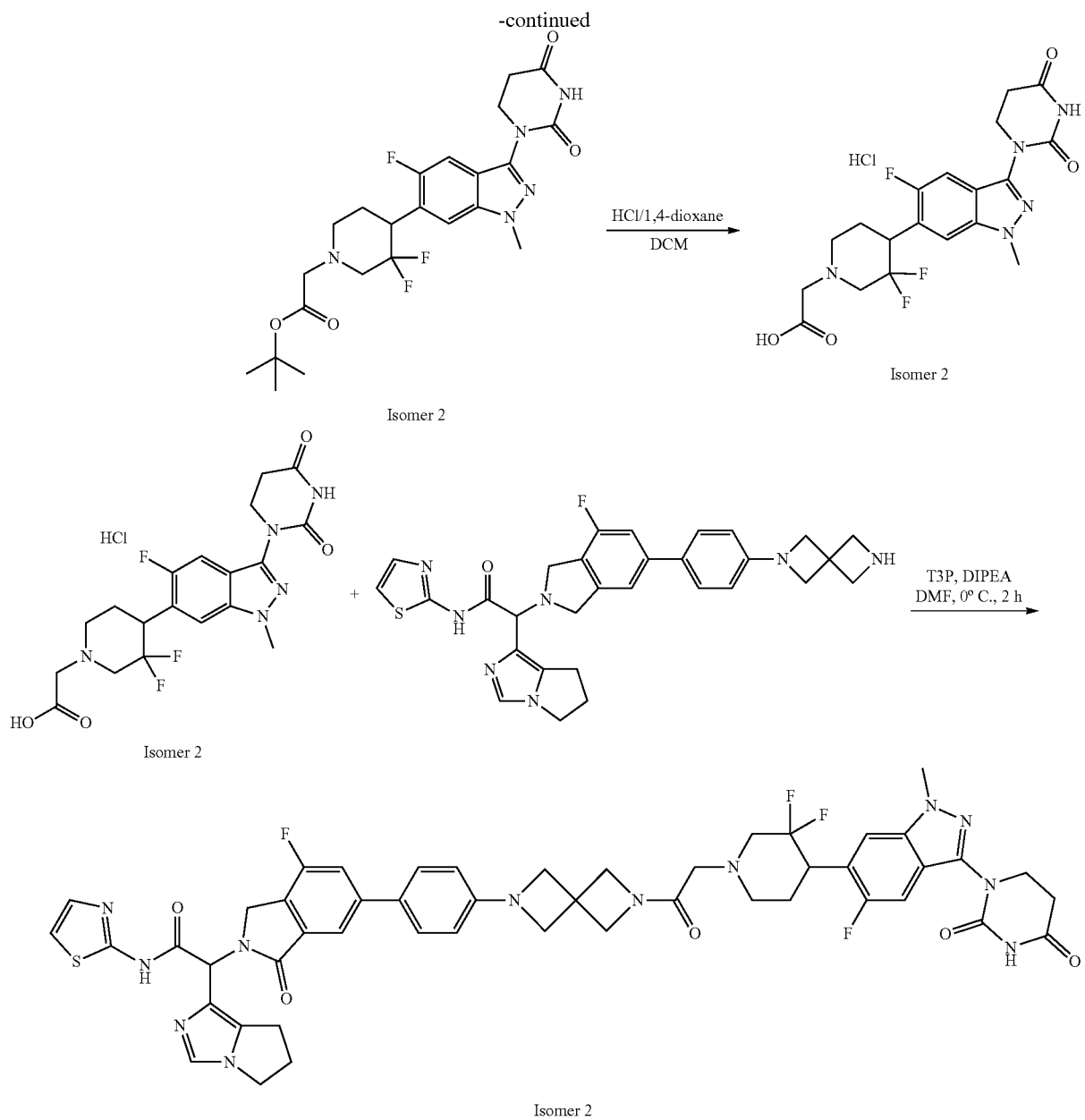

Step 1: 1-[6-[3,3-difluoro-4-piperidyl]-5-fluoro-1-methyl-indazol-3-yl]hexahydropyrimidine-2,4-dione hydrochloride, isomer 2

To a solution of tert-butyl 4-[3-(2,4-dioxohexahydropyrimidin-1-yl)-5-fluoro-1-methyl-indazol-6-yl]-3,3-difluoro-piperidine-1-carboxylate, isomer 2 (200.00 mg, 415.40 μmol) in dichloromethane (2 mL) was added hydrochloric acid in dioxane (4 M, 2 mL), the mixture was stirred at 20° C. for 2 h. The reaction mixture was concentrated under reduced pressure to remove solvent. The crude product was triturated with Petroleum ether (20 mL) for 15 min to afford 1-[6-[3,3-difluoro-4-piperidyl]-5-fluoro-1-methyl-indazol-3-yl]hexahydropyrimidine-2,4-dione hydrochloride, isomer 2 (150 mg, 359.01 μmol, 86.43% yield) as a white solid. LCMS (ESI). m/z 382.1 [M+H]+

Step 2: tert-butyl 2-[4-[3-(2,4-dioxohexahydropyrimidin-1-yl)-5-fluoro-1-methyl-indazol-6-yl]-3,3-difluoro-1-piperidyl]acetate, isomer 2

To a solution of 1-[6-[3,3-difluoro-4-piperidyl]-5-fluoro-1-methyl-indazol-3-yl]hexahydropyrimidine-2,4-dione hydrochloride, isomer 2 (150 mg, 393.34 μmol) and N,N-diisopropylethylamine (305.01 mg, 2.36 mmol, 411.06 μL) in N,N-dimethylformamide (5 mL) was added tert-butyl 2-bromoacetate (191.80 mg, 983.34 μmol, 144.21 μL). The mixture was stirred at 0° C. for 2 h. The reaction mixture was poured into water (50 mL), extracted with Ethyl acetate (30 mL×2). The combined organic layers were washed with brine (10 mL×2), dried over sodium sulfate, filtered and concentrated. The crude product was triturated with petroleum ether (6 mL) for 15 min to afford tert-butyl 2-[4-[3-(2,4-dioxohexahydropyrimidin-1-yl)-5-fluoro-1-methyl-indazol-6-yl]-3,3-difluoro-1-piperidyl]acetate, isomer 2 (160 mg, 322.91 μmol, 82.09% yield) as an off-white solid. LCMS (ESI): m/z 496.3 [M+H]⁺, ¹H NMR (400 MHz, DMSO-d₆) δ=10.57 (s, 1H), 7.74 (d, J=5.2 Hz, 1H), 7.43 (d, J=10.4 Hz, 1H), 4.06-4.00 (m, 3H), 3.92 (t, J=6.8 Hz, 2H), 3.40 (br, 2H), 3.27-3.22 (m, 1H), 3.07-2.99 (m, 1H), 2.91-2.79 (m, 1H), 2.76 (t, J=6.8 Hz, 2H), 2.66-2.59 (m, 1H), 2.44-2.36 (m, 2H), 1.88-1.76 (m, 1H), 1.45 (s, 9H).

Step 3: 2-[4-[3-(2,4-dioxohexahydropyrimidin-1-yl)-5-fluoro-1-methyl-indazol-6-yl]-3,3-difluoro-1-piperidyl]acetic acid hydrochloride, isomer 2

To a solution of tert-butyl 2-[4-[3-(2,4-dioxohexahydropyrimidin-1-yl)-5-fluoro-1-methyl-indazol-6-yl]-3,3-difluoro-1-piperidyl]acetate, isomer 2 (160.00 mg, 322.91 μmol) in dichloromethane (2 mL) was added hydrochloric acid in dioxane (4 M, 2 mL), the mixture was stirred at 40° C. for 14 h. The reaction mixture was concentrated under reduced pressure to remove solvent. The crude product was triturated with petroleum ether (50 mL) for 15 min to afford 2-[4-[3-(2,4-dioxohexahydropyrimidin-1-yl)-5-fluoro-1-methyl-indazol-6-yl]-3,3-difluoro-1-piperidyl]acetic acid hydrochloride, isomer 2 (150 mg, 341.38 μmol, >98% yield) as a white solid. LCMS (ESI): m/z 440.4 [M+H]+

Step 4: 2-(6,7-dihydro-5H-pyrrolo[1,2-c]imidazol-1-yl)-2-[6-[4-[2-[2-[(4S)-4-[3-(2,4-dioxohexahydropyrimidin-1-yl)-5-fluoro-1-methyl-indazol-6-yl]-3,3-difluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, isomer 2

To a solution of 2-[4-[3-(2,4-dioxohexahydropyrimidin-1-yl)-5-fluoro-1-methyl-indazol-6-yl]-3,3-difluoro-1-piperidyl]acetic acid hydrochloride, isomer 2 (150 mg, 341.38 μmol) and propylphosphonic anhydride solution (50 wt. % in ethyl acetate) (325.86 mg, 512.08 μmol) in N,N-dimethylformamide (6 mL) was added N,N-diisopropylethylamine (352.96 mg, 2.73 mmol, 475.69 μL) The mixture was stirred at 0° C. for 20 min, 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (210.06 mg, 307.25 μmol) was added, the mixture was stirred at 0° C. for 60 min. After that, Propylphosphonic anhydride solution (50 wt. % in ethyl acetate) (108.62 mg, 170.69 μmol) was added, the mixture was stirred at 0° C. for 60 min. The reaction mixture was poured into water (50 mL), a lot of white solid was precipitated, filtered and the solid was washed with water (10 mL), dried under reduced pressure to give a residue, the further was purified by prep-HPLC (neutral condition) (Column: Phenomenex Gemini-NX C18 75*30 mm, 3 m; mobile phase: acetonitrile:water; Run Time: 8 minutes) to afford Compound 130 (81.46 mg, 81.70 mol, 40.49% yield) as a white solid. LCMS (ESI): m/z 496.6 [M/2+H]⁺ ¹H NMR (400 MHz, DMSO-d₆) δ=12.52 (br, 1H), 10.58 (s, 1H), 7.77-7.69 (m, 3H), 7.65 (d, J=8.8 Hz, 2H), 7.61 (s, 1H), 7.50-7.40 (m, 2H), 7.26 (br, 1H), 6.56 (d, J=8.4 Hz, 2H), 6.15 (s, 1H), 4.80 (d, J=17.6 Hz, 1H), 4.45 (s, 2H), 4.22 (d, J=17.6 Hz, 1H), 4.11 (s, 2H), 4.08-3.95 (m, 9H), 3.92 (t, J=6.8 Hz, 2H), 3.60-3.40 (m, 4H), 3.22 (br, 4H), 3.02 (d, J=10.4 Hz, 1H), 2.82-2.71 (m, 4H), 2.65-2.54 (m, 4H), 2.41 (br, 2H), 1.90-1.78 (m, 1H).

Example 131

2-[6-[4-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide, Compound 131

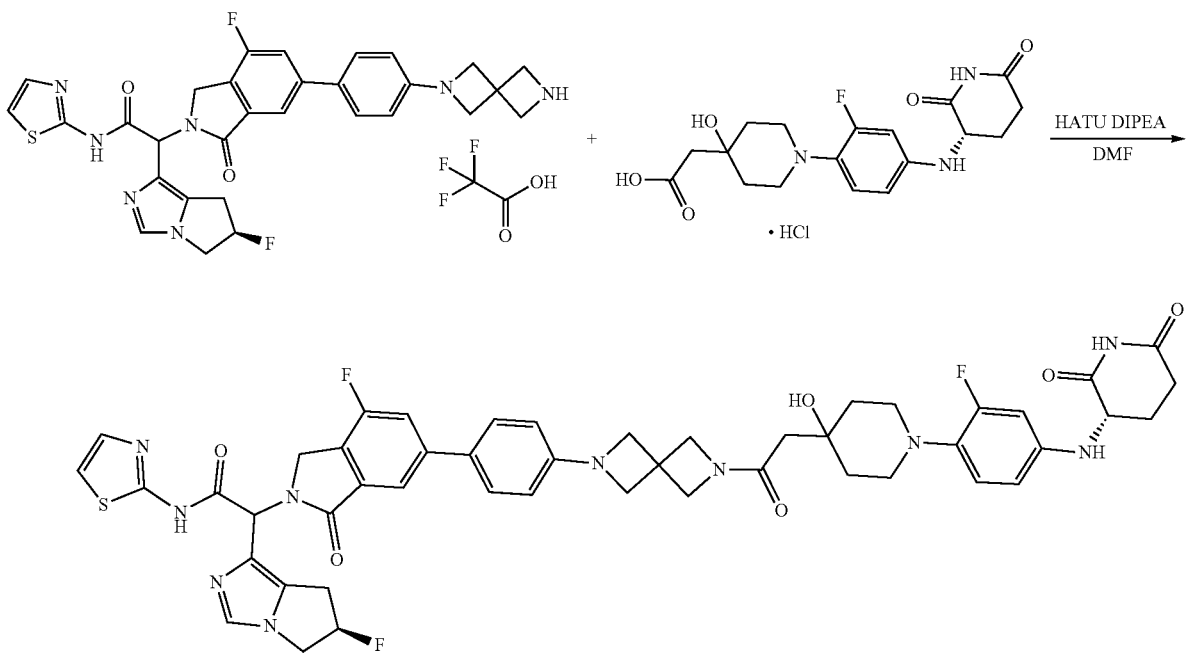

To a stirred solution of 2-[1-[4-[[(3S)-2,6-dioxo-3-piperidyl]amino]-2-fluoro-phenyl]-4-hydroxy-4-piperidyl]acetic acid hydrochloride (106.68 mg, 256.53 μmol) in N,N-dimethylformamide (4 mL) at 0° C. was added N,N-diisopropylethylamine (165.78 mg, 1.28 mmol, 223.42 μL) followed by 1-[bis(dimethylamino)methylene]-1H-1,2,3-triazolo[4,5-b]pyridinium 3-oxide hexafluorophosphate (121.93 mg, 320.67 μmol), reaction mixture was stirred for 5 minutes. 2-[6-[4-(2,6-diazaspiro[3.3]heptan-2-yl)phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide, trifluoroacetic acid salt (150 mg, 213.78 μmol) was added while maintaining 0° C., and the reaction mixture was stirred for 5 h while warming to room temperature. The crude reaction mixture was purified by C18 column (120 g) for purification (0% to 60% acetonitrile in water+0.1 ammonium acetate over 45 minutes, then steep gradient to 100% acetonitrile). The pure fractions were frozen and lyophilized to afford product Compound 131 (63.46 mg, 65.43 μmol, 30.61% yield) as light brown solid. LCMS (m/z: 948.7 [M+1]). $^1$H-NMR (400 MHz, DMSO-d6: 12.53 (s, 1H), 10.78 (s, 1H), 7.75 (s, 2H), 7.72 (s, 1H), 7.69 (d, J=5.20 Hz, 1H), 7.65 (d, J=8.40 Hz, 1H), 7.49 (s, 1H), 7.27 (s, 1H), 6.86 (t, J=Hz, 1H), 6.55 (d, J=8.40 Hz, 1H), 6.50 (dd, J=15.20, 2.00 Hz, 1H), 6.42 (d, J=8.80 Hz, 1H), 6.17 (d, J=4.80 Hz, 1H), 5.89 (s, 1H), 5.79-5.77 (m, 1H), 4.80 (dd, J=6.40, Hz, 1H), 4.76 (s, 1H), 4.20-4.39 (m, 6H), 4.09 (s, 2H), 4.03 (s, 4H), 2.90-2.87 (m, 5H), 2.74-2.71 (m, 3H), 2.60 (m, 1H), 2.23 (s, 2H), 2.08 (m, 1H), 1.79-1.76 (m, 3H), 1.63 (d, J=12.00 Hz, 2H).

Example 132

2-[6-[4-[2-[2-[1-[4-[[(3R)-2,6-dioxo-3-piperidyl]amino]-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide, Compound 132

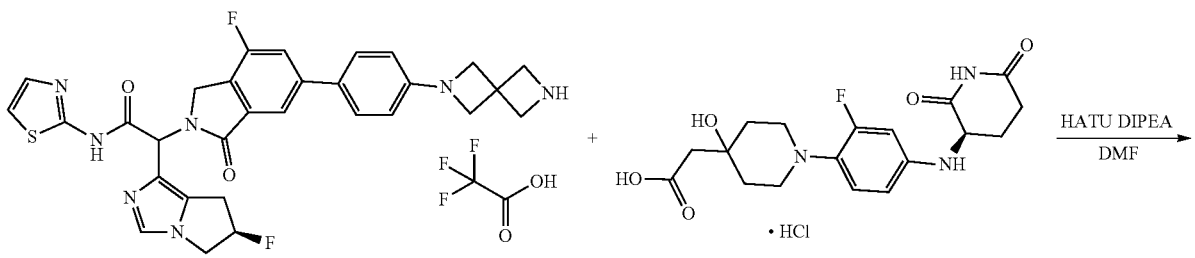

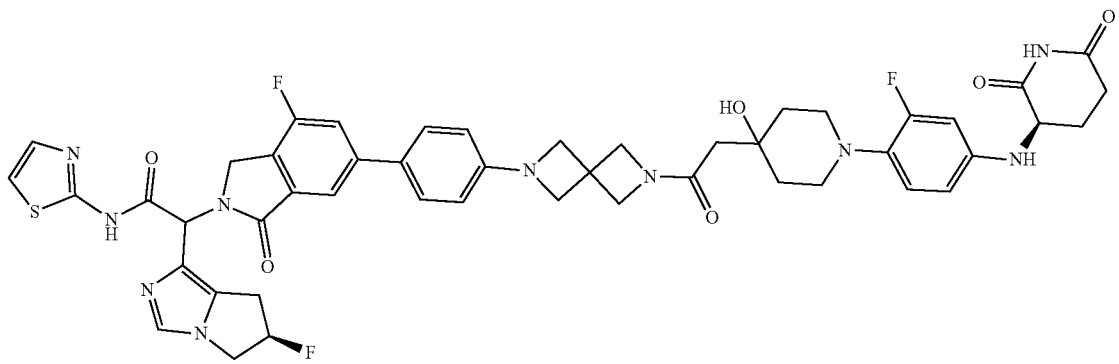

To a stirred solution of 2-[1-[4-[[(3R)-2,6-dioxo-3-piperidyl]amino]-2-fluoro-phenyl]-4-hydroxy-4-piperidyl]acetic acid hydrochloride (54.07 mg, 130.02 μmol) in N,N-dimethylformamide (3 mL) at 0° C. was added N,N-diisopropylethylamine (110.52 mg, 855.11 mol, 148.94 μL) followed by 1-[bis(dimethylamino)methylene]-1H-1,2,3-triazolo[4,5-b]pyridinium 3-oxide hexafluorophosphate (81.28 mg, 213.78 μmol). After 5 min then added 2-[6-[4-(2,6-diazaspiro[3.3]heptan-2-yl)phenyl]-4-fluoro-1-oxo-isoindolin-2-yl]-2-[(6R)-6-fluoro-6,7-dihydro-5H-pyrrolo[1,2-c]imidazol-1-yl]-N-thiazol-2-yl-acetamide, trifluoroacetic acid salt (100 mg, 142.52 μmol) while maintaining 0° C., and the reaction mixture was stirred for 5 h while warming to room temperature. The crude reaction mixture was purified by C18 column (120 g) for purification (0% to 60% acetonitrile in water+0.1 ammonium acetate over 45 minutes, then steep gradient to 100% acetonitrile). The pure fractions were frozen and lyophilized to afford product Compound 132 (37.2 mg, 37.51 μmol, 26.32% yield) as light brown solid. LCMS (m/z: 948.8 [M+1]). ¹H-NMR (400 MHz, DMSO-d6: 12.53 (s, 1H), 10.77 (s, 1H), 7.75 (s, 2H), 7.72 (s, 1H), 7.69 (d, J=4.80 Hz, 1H), 7.65 (d, J=8.80 Hz, 1H), 7.49 (s, 1H), 7.27 (s, 1H), 6.86 (t, J=Hz, 1H), δ 6.55 (d, J=8.80 Hz, 2H), 6.50 (dd, J=2.40, 14.80 Hz, 1H), 6.42 (dd, J=2.00, 8.60 Hz, 1H), 6.17 (d, J=4.00 Hz, 1H), 5.88 (d, J=2.80 Hz, 1H), 5.77 (d, J=8.00 Hz, 1H), 4.80 (dd, J=6.40, Hz, 1H), 4.76 (s, 1H), 4.39 (s, 2H), 4.27-4.25 (m, 4H), 4.09 (s, 2H), 4.03 (s, 4H), 3.08-2.88 (m, 5H), 2.69-2.68 (m, 2H), 2.23 (s, 2H), 2.08 (m, 1H), 1.91-1.76 (m, 3H), 1.63 (d, J=12.40 Hz, 2H).

Example 133

2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3-fluoro-1-piperidyl]acetyl]-2,6-diazaspiro[3.3]heptan-6-yl]phenyl]-4-fluoro-1-oxo-isoindolin-2-yl]-N-thiazol-2-yl-acetamide, Compound 133

Step 1: 1-[6-(3-fluoro-4-piperidyl)-1-methyl-indazol-3-yl]hexahydropyrimidine-2,4-dione

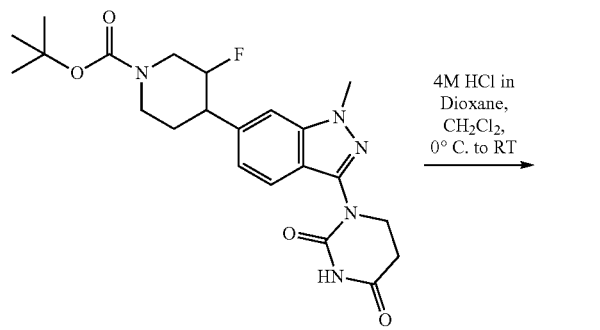

4M HCl in Dioxane, CH₂Cl₂, 0° C. to RT

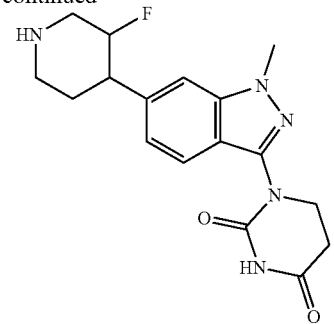

In a 25 mL single-necked round-bottomed flask containing a well-stirred solution of tert-butyl 4-[3-(2,4-dioxohexahydropyrimidin-1-yl)-1-methyl-indazol-6-yl]-3-fluoro-piperidine-1-carboxylate (100 mg, 224.47 μmol) in anhydrous dichloromethane (3 mL) was added hydrogen chloride, 4M in 1,4-dioxane, 99% (8.18 mg, 224.47 μmol, 10.23 μL) dropwise at 0° C. The reaction mixture stirred at room temperature for 5 h. The reaction mixture was concentrated under reduced pressure to afford crude. The crude mass was triturated with diethyl ether (2×10 mL) and dried under reducing pressure to get 1-[6-(3-fluoro-4-piperidyl)-1-methyl-indazol-3-yl]hexahydropyrimidine-2,4-dione; hydrochloride (80 mg, 208.30 μmol, 92.80% yield) as an off-white solid. LCMS (ESI+) m/z: 346.2 [M+H]⁺.

Step 2: tert-Butyl 2-[4-[3-(2,4-dioxohexahydropyrimidin-1-yl)-1-methyl-indazol-6-yl]-3-fluoro-1-piperidyl]acetate

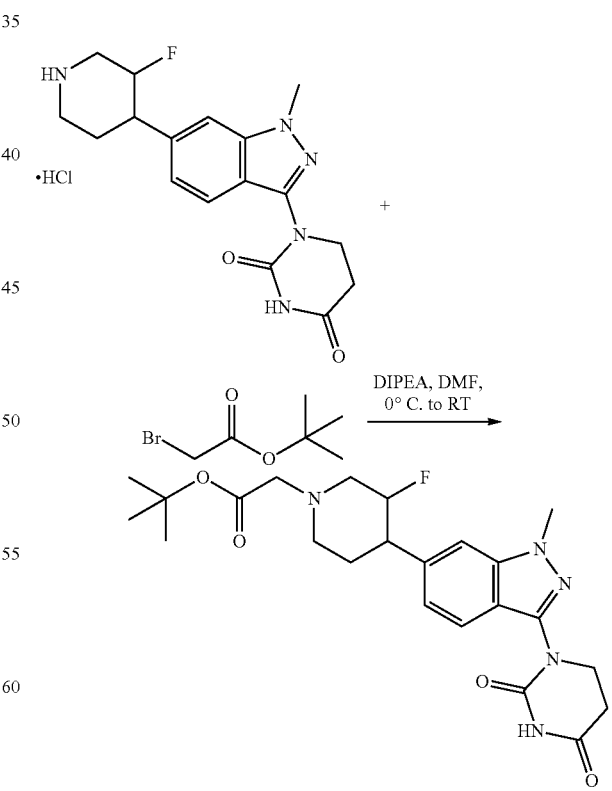

DIPEA, DMF, 0° C. to RT

Into a 25 mL single-necked round-bottomed flask containing a well-stirred solution of 1-[6-(3-fluoro-4-piperidyl)-

1-methyl-indazol-3-yl]hexahydropyrimidine-2,4-dione (80 mg, 209.52 mol) in DMF (3 mL) was added N,N-diisopropylethylamine (162.47 mg, 1.26 mmol, 218.96 L) under nitrogen atmosphere at 0° C. tert-butyl 2-bromoacetate (40.87 mg, 209.52 µmol, 30.73 µL) was added and the resulting mixture was stirred at ambient temperature for 20 h. The reaction mixture was poured into ice water (5 mL). The aqueous mixture was extracted using ethyl acetate (3×15 mL). The organic layer was washed with brine solution (15 mL), dried over sodium sulfate and concentrated under reduced pressure. The crude was purified by column chromatography using silica (0-3% methanol and dichloromethane) to get tert-butyl 2-[4-[3-(2,4-dioxohexahydropyrimidin-1-yl)-1-methyl-indazol-6-yl]-3-fluoro-1-piperidyl]acetate (80 mg, 172.25 µmol, 82.21% yield) as an off-white solid. LCMS (ESI+) m/z: 460.2 [M+H]$^+$.

Step 3: 2-[4-[3-(2,4-dioxohexahydropyrimidin-1-yl)-1-methyl-indazol-6-yl]-3-fluoro-1-piperidyl]acetic acid Step 7: 2-(6,7-dihydro-5H-pyrrolo[1,2-c]imidazol-1-yl)-2-[6-[4-[2-[2-[4-[3-(2,4-dioxohexahydropyrimidin-1-yl)-1-methyl-indazol-6-yl]-3-fluoro-1-piperidyl]acetyl]-2,6-diazaspiro[3.3]heptan-6-yl]phenyl]-4-fluoro-1-oxo-isoindolin-2-yl]-N-thiazol-2-yl-acetamide

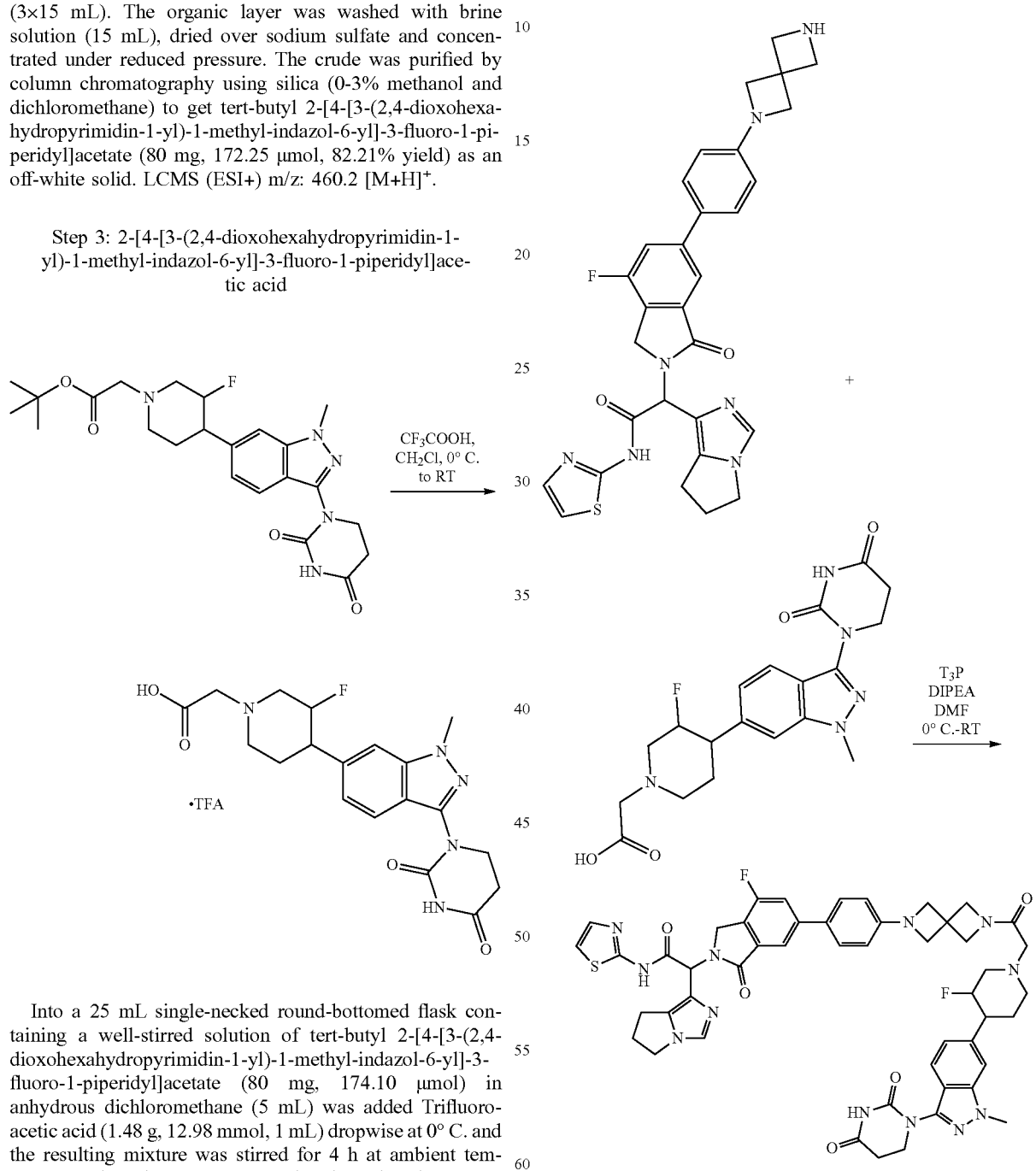

Into a 25 mL single-necked round-bottomed flask containing a well-stirred solution of tert-butyl 2-[4-[3-(2,4-dioxohexahydropyrimidin-1-yl)-1-methyl-indazol-6-yl]-3-fluoro-1-piperidyl]acetate (80 mg, 174.10 µmol) in anhydrous dichloromethane (5 mL) was added Trifluoroacetic acid (1.48 g, 12.98 mmol, 1 mL) dropwise at 0° C. and the resulting mixture was stirred for 4 h at ambient temperature. The solvent was removed under reduced pressure. Dichloromethane was added to the solid, evaporated under reduced pressure. The solid was triturated with Et$_2$O (10 mL) to get 2-[4-[3-(2,4-dioxohexahydropyrimidin-1-yl)-1-methyl-indazol-6-yl]-3-fluoro-1-piperidyl]acetic acid, trifluoroacetic acid (90 mg, 171.55 µmol, 98.54% yield) as an off-white solid. LCMS (ESI+) m/z: 404.2 [M+H]$^+$.

Into a 10 mL single-necked round-bottomed flask containing a well-stirred solution of 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide; 2,2,2-trifluoroacetic acid (100 mg, 146.27 µmol) and 2-[4-[3-(2,4-dioxohexahydropyrimidin-1-yl)-1-methylindazol-6-yl]-3-fluoro-1-piperidyl]acetic acid (75.68 mg, 146.27 μmol); 2,2,2-trifluoroacetic acid in N,N-dimethylformamide (2 mL) was added N,N-diisopropylethylamine (18.90 mg, 146.27 μmol, 25.48 μL) under nitrogen atmosphere at 0° C. Subsequently, Propylphosphonic anhydride solution (50 wt. % in ethyl acetate) (46.54 mg, 146.27 μmol) was added at the same temperature. The resulting mixture was stirred at room temperature for 2 h. The reaction mixture was directly injected on a C18 column (100 g) for purification (0-45% acetonitrile in water+0.1% ammonium acetate over 30 minutes, then steep gradient to 100% acetonitrile). The pure fractions were combined and lyophilized to get Compound 133 (65 mg, 67.51 μmol, 46.16% yield) as an off-white solid. LCMS(ESI+) m/z: 955.8 [M+H]+. 1H-NMR (400 MHz, DMSO-d6): δ 12.50 (s, 1H), 10.56 (s, 1H), 7.75 (s, 1H), 7.71 (d, J=10.40 Hz, 1H), 7.65 (d, J=8.80 Hz, 2H), 7.61 (s, 1H), 7.58 (d, J=8.80 Hz, 1H), 7.49 (d, J=3.60 Hz, 2H), 7.26 (d, J=3.60 Hz, 1H), 7.12 (d, J=8.80 Hz, 1H), 6.55 (d, J=8.80 Hz, 2H), 6.15 (s, 1H), 4.93 (bs, 1H), 4.80 (d, J=17.60 Hz, 1H), 4.51-4.45 (m, 2H), 4.22 (d, J=17.60 Hz, 1H), 4.10 (s, 2H), 4.05-3.95 (m, 10H), 3.92 (t, J=6.80 Hz, 2H), 3.17-3.14 (m, 1H), 3.11 (s, 2H), 3.02-3.00 (m, 2H), 2.97-2.91 (m, 1H), 2.78-2.76 (m, 3H), 2.64-2.60 (m, 2H), 2.37-2.33 (m, 2H), 1.76-1.71 (m, 1H).

Example 134

2-(6,7-dihydro-5H-pyrrolo[1,2-c]imidazol-1-yl)-2-[6-[4-[2-[2-[1-[4-[[2,6-dioxo-3-piperidyl]amino]-2,6-difluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide, isomer 1, Compound 134

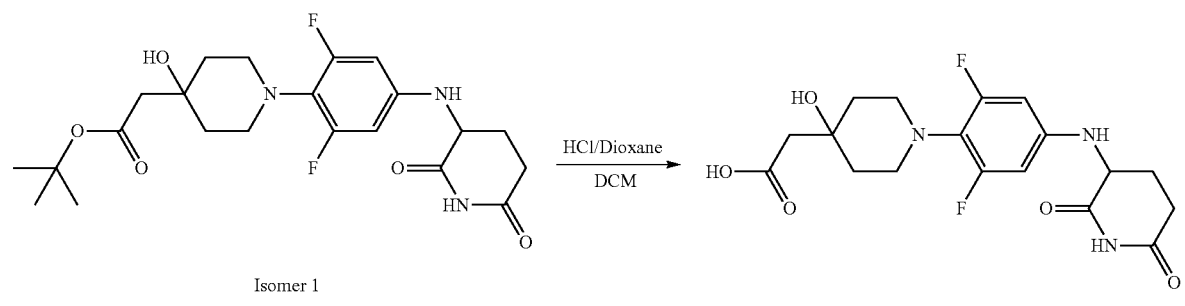

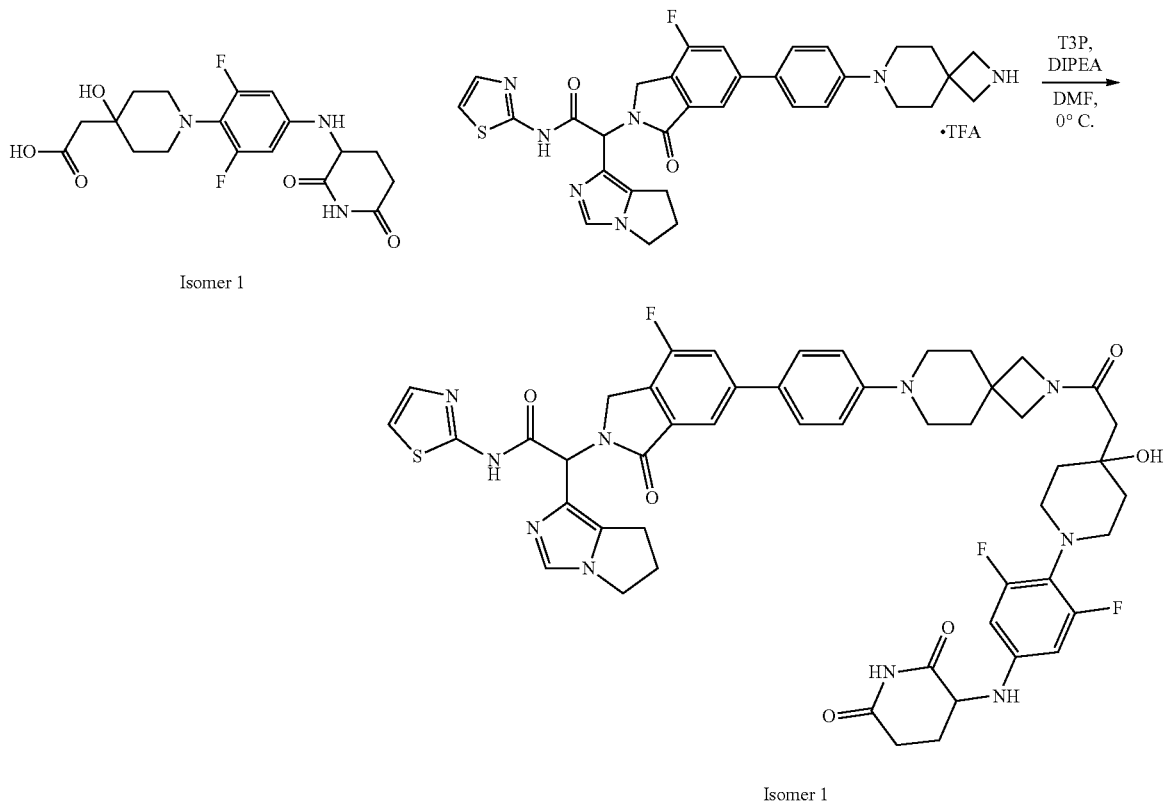

Step 1: 2-[1-[4-[[2,6-dioxo-3-piperidyl]amino]-2,6-difluoro-phenyl]-4-hydroxy-4-piperidyl]acetic acid, isomer 1

To a solution of tert-butyl 2-[1-[4-[[(3S)-2,6-dioxo-3-piperidyl]amino]-2,6-difluoro-phenyl]-4-hydroxy-4-piperidyl]acetate (Example 99, Step 3, 100 mg, 220.52 µmol) in dichloromethane (1 mL) was added hydrochloric acid (4 M in 1,4-dioxane, 1 mL, 4 mmol). The mixture was stirred at 25° C. for 12 h. The reaction mixture was concentrated under reduced pressure to remove solvent to afford 2-[1-[4-[[2,6-dioxo-3-piperidyl]amino]-2,6-difluoro-phenyl]-4-hydroxy-4-piperidyl]acetic acid hydrochloride, isomer 1 (100 mg, 230.50 µmol, >99% yield) as a white solid. LCMS (ESI): m/z 398.1 [M+H]+

Step 2: 2-(6,7-dihydro-5H-pyrrolo[1,2-c]imidazol-1-yl)-2-[6-[4-[2-[2-[1-[4-[[(3S)-2,6-dioxo-3-piperidyl]amino]-2,6-difluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide, isomer 1

To a solution of 2-[1-[4-[[(3S)-2,6-dioxo-3-piperidyl]amino]-2,6-difluoro-phenyl]-4-hydroxy-4-piperidyl]acetic acid hydrochloride (60.96 mg, 140.50 µmol) and propylphosphonic anhydride solution (50 wt. % in ethyl acetate) (134.12 mg, 210.75 µmol) in N,N-dimethylformamide (3 mL) was added N,N-diisopropylethylamine (127.11 mg, 983.52 µmol, 171.31 µL), The mixture was stirred at 0° C. for 20 minutes. 2-(6-(4-(2,7-diazaspiro[3.5]nonan-7-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide, trifluoroacetic acid salt (100 mg, 140.50 µmol) was added. The mixture was stirred at 0° C. for 60 minutes. Propylphosphonic anhydride solution (50 wt. % in ethyl acetate) (67.06 mg, 105.38 µmol) was added, the mixture was stirred at 0° C. for 60 min. The mixture was poured into water (50 mL) and neutralized with saturated aqueous solution of sodium bicarbonate (30 mL). A white solid precipitated, which was collected by filtration. The solid was dissolved in dichloromethane and dried over sodium sulfate, filtered, and concentrated under reduced pressure. The residue was purified by prep-HPLC (neutral condition). Column: Phenomenex Gemini-NX C18 75*30 mm*3 um; mobile phase: [water-acetonitrile]; Gradient Time (min) 8 to afford Compound 134 (68.33 mg, 69.93 µmol, 49.77% yield) as a white solid. LCMS (ESI): m/z 997.5 [M+H]+, 1H NMR (400 MHz, DMSO-d6) δ=12.53 (br, 1H), 10.81 (s, 1H), 7.78-7.71 (m, 2H), 7.66 (d, J=8.8 Hz, 2H), 7.61 (s, 1H), 7.49 (d, J=2.8 Hz, 1H), 7.26 (s, 1H), 7.06 (d, J=9.2 Hz, 2H), 6.32 (d, J=12.4 Hz, 2H), 6.22 (d, J=7.6 Hz, 1H), 6.15 (s, 1H), 4.88-4.71 (m, 2H), 4.36-4.27 (m, 1H), 4.22 (d, J=17.6 Hz, 1H), 4.06-3.92 (m, 4H), 3.63 (s, 2H), 3.29-3.20 (m, 6H), 2.76-2.67 (m, 4H), 2.59 (br, 2H), 2.45 (s, 1H), 2.23 (s, 1H), 2.13-2.02 (m, 1H), 1.92-1.67 (m, 8H), 1.59 (br, 2H).

Example 135

2-(6,7-dihydro-5H-pyrrolo[1,2-c]imidazol-1-yl)-2-[6-[4-[2-[2-[1-[4-[(2,6-dioxo-3-piperidyl)amino]-2,5-difluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, Compound 135

Step 1: tert-Butyl 2-[1-(2,5-difluoro-4-nitro-phenyl)-4-hydroxy-4-piperidyl]acetate

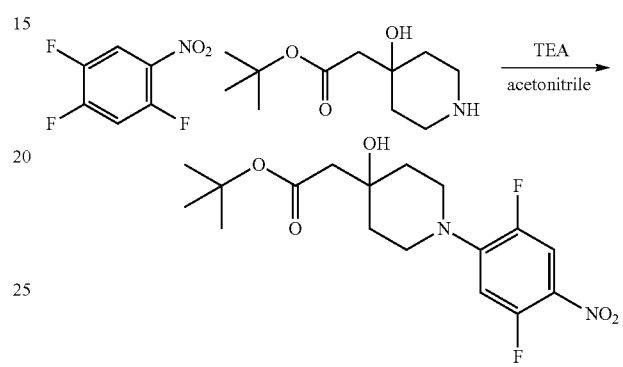

To a solution of 1,2,4-trifluoro-5-nitro-benzene (2 g, 11.29 mmol, 1.30 mL) and tert-butyl 2-(4-hydroxy-4-piperidyl)acetate (2.43 g, 11.29 mmol) in acetonitrile (30 mL) was added triethylamine (85.72 mg, 847.07 µmol, 118.06 µL). The mixture was stirred at 20° C. for 1 h. The mixture was concentrated under reduced pressure to give a residue. The residue was purified by column chromatography (Silica gel, Petroleum ether/Ethyl acetate=I/O to 1/1) to give tert-butyl 2-[1-(2,5-difluoro-4-nitro-phenyl)-4-hydroxy-4-piperidyl]acetate (2.5 g, 6.61 mmol, 58.55% yield) as a yellow solid. 1H-NMR (400 MHz, DMSO-d6) δ=7.95 (dd, J=13.9, 7.3 Hz, 1H), 7.10 (dd, J=14.6, 7.6 Hz, 1H), 4.72 (s, 1H), 3.56 (br d, J=12.8 Hz, 2H), 3.32-3.23 (s, 2H), 1.84-1.63 (m, 4H), 1.39 (s, 9H).

Step 2: tert-butyl 2-[1-(4-amino-2,5-difluoro-phenyl)-4-hydroxy-4-piperidyl]acetate

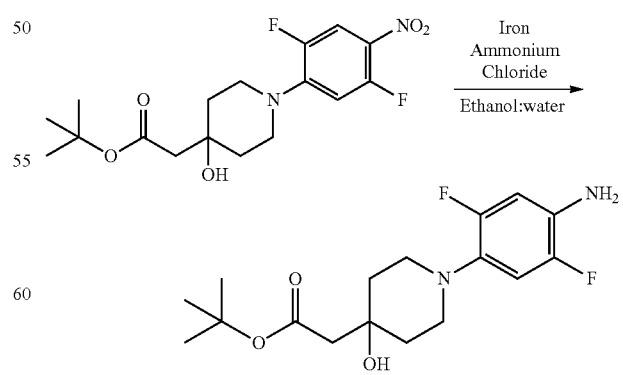

To a solution of tert-butyl 2-[1-(2,5-difluoro-4-nitro-phenyl)-4-hydroxy-4-piperidyl]acetate (2.5 g, 6.71 mmol) in Ethanol (25 mL) and Water (5 mL) was added iron (1.50 g, 26.86 mmol, 190.81 μL) and ammonium chloride (2.87 g, 53.71 mmol, 1.88 mL). The mixture was heated to 20° C. for 3 h. The mixture was filtered and concentrated under reduced pressure to afford tert-butyl 2-[1-(4-amino-2,5-difluoro-phenyl)-4-hydroxy-4-piperidyl]acetate (2.0 g, 5.55 mmol, 82.59% yield) as a brown solid. LCMS (ESI+): 343.0 (M+H)

Step 3: tert-butyl 2-[1-[4-[(2,6-dibenzyloxy-3-pyridyl)amino]-2,5-difluoro-phenyl]-4-hydroxy-4-piperidyl]acetate

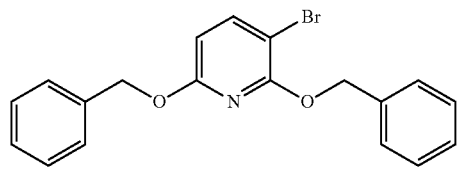

+

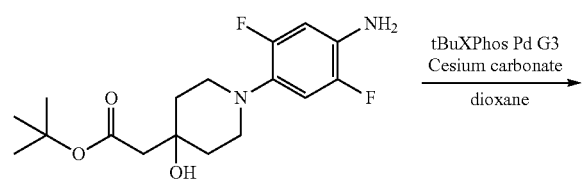

tBuXPhos Pd G3
Cesium carbonate
⎯⎯⎯⎯⎯⎯⎯⎯→
dioxane

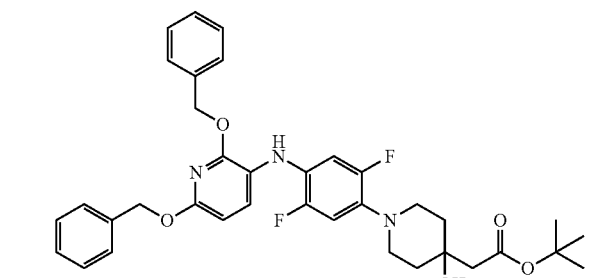

To a solution of 2,6-dibenzyloxy-3-bromo-pyridine (0.2 g, 540.19 μmol) and tert-butyl 2-[1-(4-amino-2,5-difluoro-phenyl)-4-hydroxy-4-piperidyl]acetate (203.45 mg, 594.21 μmol) in 1,4-dioxane (3 mL) was added Cesium carbonate (528.01 mg, 1.62 mmol) and tBuXPhos Pd G3 (42.97 mg, 54.02 μmol), the mixture was stirred at 90° C. for 16 h under nitrogen. The reaction mixture was quenched by water (5 mL), and extracted with ethyl acetate (3×5 mL). The combined organic layers were washed with brine (3×3 mL), dried over sodium sulfate, filtered, and concentrated under reduced pressure. The residue was purified by column chromatography (silica gel, Petroleum ether/Ethyl acetate=I/O to 1/1) to afford tert-butyl 2-[1-[4-[(2,6-dibenzyloxy-3-pyridyl)amino]-2,5-difluoro-phenyl]-4-hydroxy-4-piperidyl]acetate (200 mg, 286.53 μmol, 53.04% yield) was obtained as a brown oil. LCMS (ESI+): 632.8 [M+H]⁺

Step 4: tert-Butyl 2-[1-[4-[(2,6-dioxo-3-piperidyl)amino]-2,5-difluoro-phenyl]-4-hydroxy-4-piperidyl] acetate

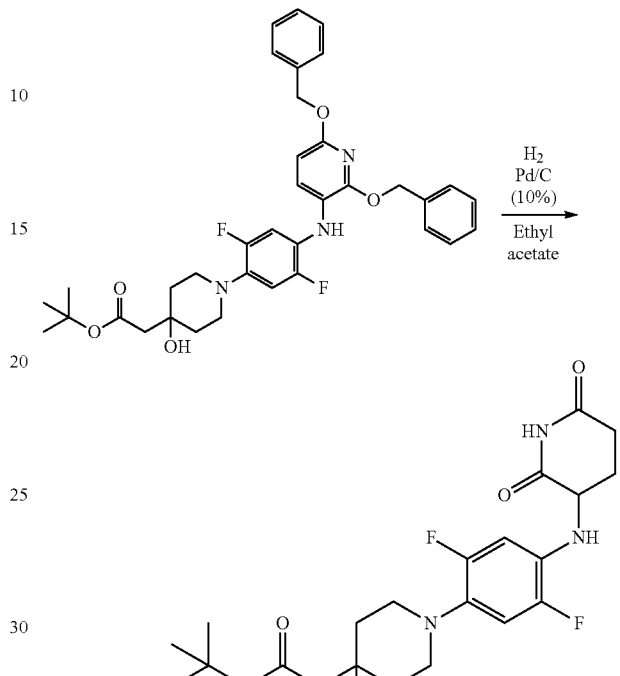

To a solution of tert-butyl 2-[1-[4-[(2,6-dibenzyloxy-3-pyridyl)amino]-2,5-difluoro-phenyl]-4-hydroxy-4-piperidyl]acetate (1.3 g, 2.06 mmol) in ethyl acetate (15 mL) was added Pd, 10% on charcoal (219.00 mg, 205.79 μmol). The mixture was stirred at 20° C. for 16 h under hydrogen gas (15 psi). The reaction mixture was filtered and concentrated under reduced pressure to afford tert-butyl 2-[1-[4-[(2,6-dioxo-3-piperidyl)amino]-2,5-difluoro-phenyl]-4-hydroxy-4-piperidyl]acetate (0.8 g, 1.76 mmol, 85.72% yield) was obtained as a brown oil. LCMS (ESI+): 454.3 [M+H]⁺

Step 5: 2-[1-[4-[(2,6-dioxo-3-piperidyl)amino]-2,5-difluoro-phenyl]-4-hydroxy-4-piperidyl]acetic acid hydrochloride

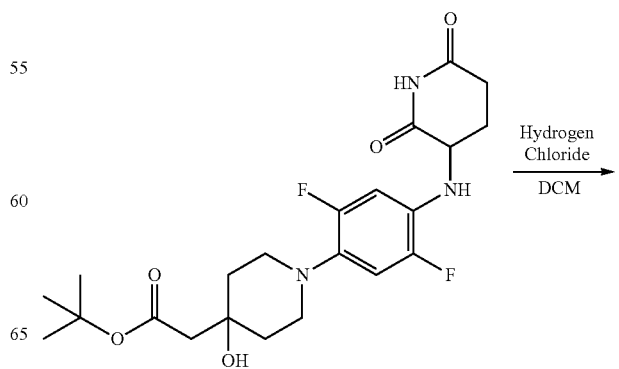

1131
-continued

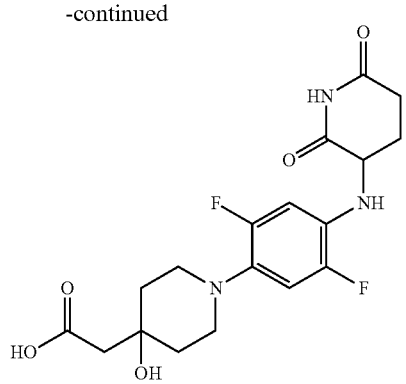

To a solution of tert-butyl 2-[1-[4-[(2,6-dioxo-3-piperidyl)amino]-2,5-difluoro-phenyl]-4-hydroxy-4-piperidyl]

1132 acetate (0.8 g, 1.76 mmol) in dichloromethane (8 mL) was added hydrochloric acid (12 M, 1.47 mL) at 0° C. The mixture was stirred at 25° C. for 1 h. The reaction mixture was concentrated under reduced pressure to give a residue. The residue was diluted with acetonitrile (5 mL) and stirred at 25° C. for 15 min, The solid was filtered and collected to afford 2-[1-[4-[(2,6-dioxo-3-piperidyl)amino]-2,5-difluoro-phenyl]-4-hydroxy-4-piperidyl]acetic acid hydrochloride (600 mg, 1.38 mmol, 78.40% yield) as a purple solid. LCMS (ESI+): 398.1 [M+H]$^+$ Step 6: 2-(6,7-dihydro-5H-pyrrolo[1,2-c]imidazol-1-yl)-2-[6-[4-[2-[2-[1-[4-[(2,6-dioxo-3-piperidyl)amino]-2,5-difluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide

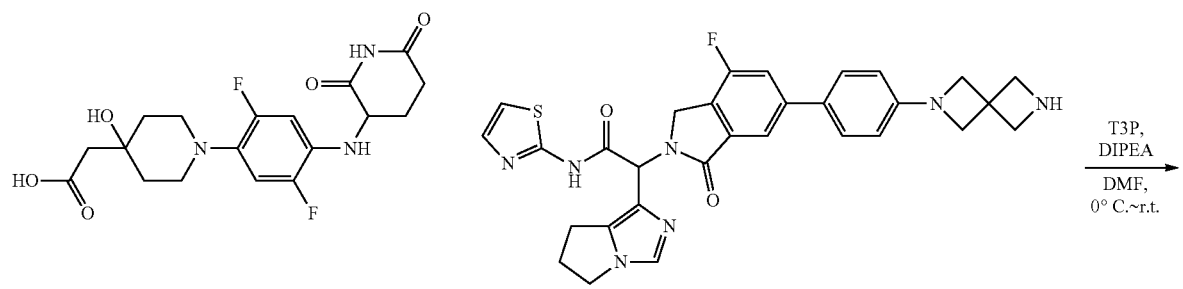

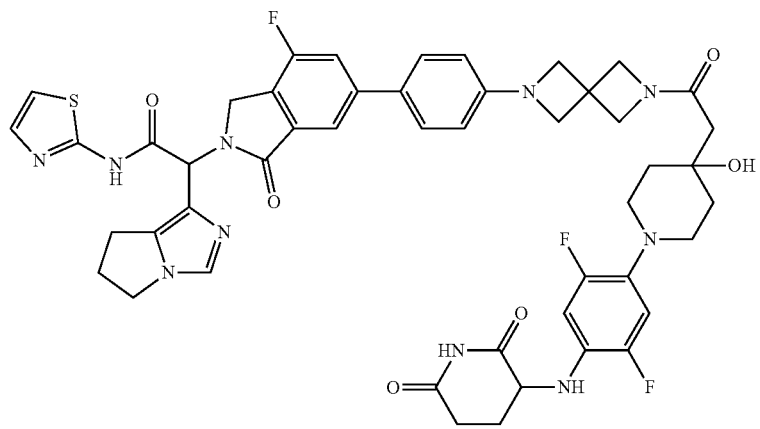

To a solution of 2-[1-[4-[(2,6-dioxo-3-piperidyl)amino]-2,5-difluoro-phenyl]-4-hydroxy-4-piperidyl]acetic acid hydrochloride (0.25 g, 576.26 μmol) and Propylphosphonic anhydride solution (50 wt. % in ethyl acetate) (275.03 mg, 864.39 μmol) in N,N-dimethylformamide (3 mL) was added N,N-diisopropylethylamine (521.34 mg, 4.03 mmol, 702.62 μL). The mixture was stirred at 0° C. for 15 min. Then to the mixture was added 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (295.48 mg, 432.19 μmol). The mixture was stirred at 0° C. for 1 h. Propylphosphonic anhydride solution (50 wt. % in ethyl acetate) (165.02 mg, 518.63 μmol) was added to the reaction mixture. The mixture was stirred at 0° C. for 1 h. The reaction mixture was purified by prep-HPLC (column: Phenomenex Luna C18 250*50 mm*10 m; mobile phase: Water-acetonitrile; B %: 35%-55%, 20 min) to give Compound 135 (127.84 mg, 127.97 μmol, 22.2% yield) as a white solid. LCMS (ES+): m/z 949.2 [M+H]+ 1H NMR (400 MHz, DMSO-$d_6$) δ=12.52 (br s, 1H), 10.79 (s, 1H), 7.78-7.59 (m, 5H), 7.48 (d, J=3.6 Hz, 1H), 7.26 (d, J=3.6 Hz, 1H), 6.85 (dd, J=8.0, 13.2 Hz, 1H), 6.72 (dd, J=8.4, 14.4 Hz, 1H), 6.54 (d, J=8.8 Hz, 2H), 6.15 (s, 1H), 5.46 (br d, J=8.0 Hz, 1H), 4.79 (d, J=17.6 Hz, 1H), 4.42-4.29 (m, 3H), 4.22 (br d, J=17.6 Hz, 1H), 4.12-3.93 (m, 8H), 2.93-2.84 (m, 4H), 2.80-2.68 (m, 2H), 2.52 (br d, J=1.6 Hz, 3H), 2.48-2.43 (m, 2H), 2.22 (s, 2H), 2.07-1.97 (m, 2H), 1.81-1.71 (m, 2H), 1.66-1.59 (m, 2H)

Example 136

2-[4-chloro-6-[4-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]phenyl]-1-oxo-isoindolin-2-yl]-2-(6,7-dihydro-5H-pyrrolo[1,2-c]imidazol-1-yl)-N-thiazol-2-yl-acetamide, Compound 136

Step 1: tert-butyl 6-[4-[7-chloro-2-[1-(6,7-dihydro-5H-pyrrolo[1,2-c]imidazol-1-yl)-2-ethoxy-2-oxo-ethyl]-3-oxo-isoindolin-5-yl]phenyl]-2,6-diazaspiro[3.3]heptane-2-carboxylate Ethyl 2-(4-chloro-6-iodo-1-oxo-isoindolin-2-yl)-2-(6,7-dihydro-5H-pyrrolo[1,2-c]imidazol-1-yl)acetate (500 mg, 1.03 mmol) and tert-butyl 6-[4-(4,4,5,5-tetramethyl-1,3,2-dioxaborolan-2-yl)phenyl]-2,6-diazaspiro[3.3]heptane-2-carboxylate (412.10 mg, 1.03 mmol) were dissolved in dioxane (6 mL) and tBuXPhos (64.98 mg, 102.94 μmol) was added, followed by Sodium carbonate (240.04 mg, 2.26 mmol, 94.88 μL) dissolved in Water (2 mL). The mixture was degassed with argon and Pd(dppf)Cl₂ (75.30 mg, 102.94 μmol) was added. The reaction was sealed and heated at 80° C. for 16 h. The organic layer was isolated, concentrated under reduced pressure and purified by flash column chromatography on silica gel (0-80% methanol in dichloromethane) to give tert-butyl 6-[4-[7-chloro-2-[1-(6,7-dihydro-5H-pyrrolo[1,2-c]imidazol-1-yl)-2-ethoxy-2-oxo-ethyl]-3-oxo-isoindolin-5-yl]phenyl]-2,6-diazaspiro[3.3]heptane-2-carboxylate (400 mg, 569.49 μmol, 55.32% yield). LCMS (ESI+): 632.5 (M+H).

Step 2: [2-[6-[4-(2-tert-butoxycarbonyl-2,6-diazaspiro[3.3]heptan-6-yl)phenyl]-4-chloro-1-oxo-isoindolin-2-yl]-2-(6,7-dihydro-5H-pyrrolo[1,2-c]imidazol-1-yl)acetyl]oxylithium

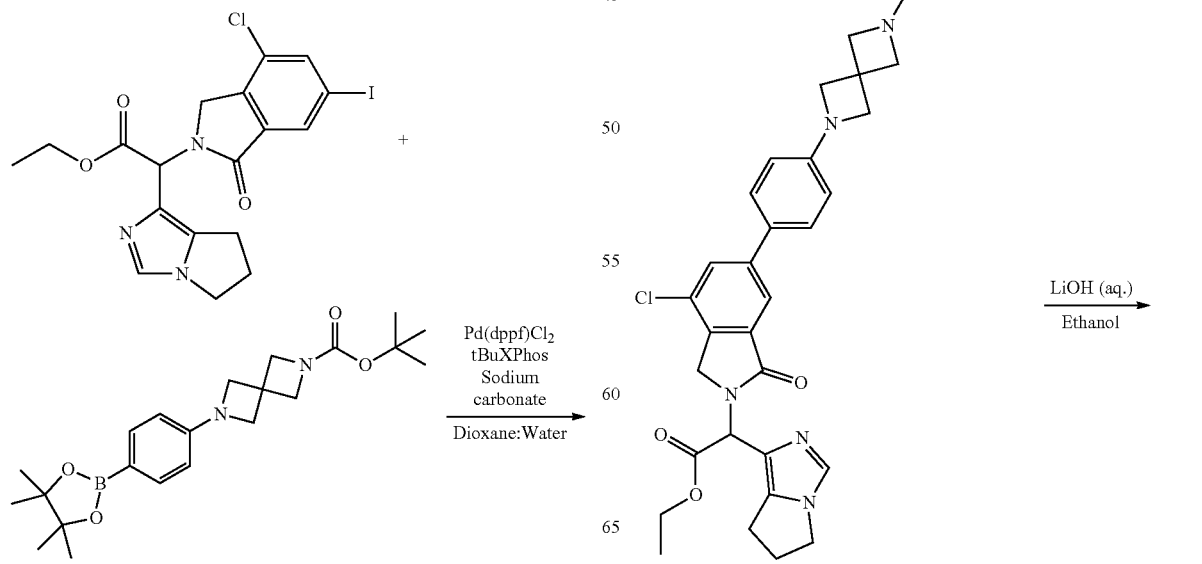

1135

-continued

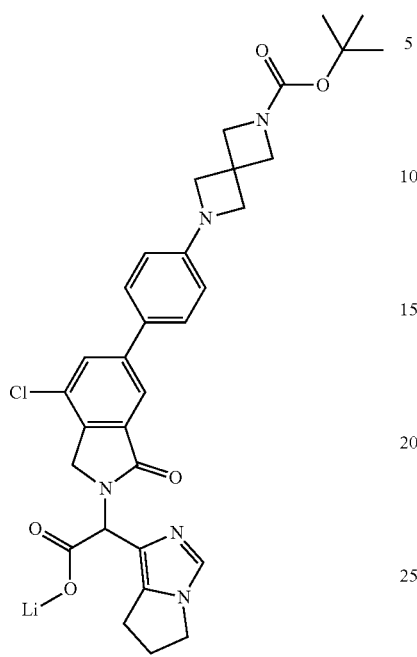

tert-butyl 6-[4-[7-chloro-2-[1-(6,7-dihydro-5H-pyrrolo[1,2-c]imidazol-1-yl)-2-ethoxy-2-oxo-ethyl]-3-oxo-isoindolin-5-yl]phenyl]-2,6-diazaspiro[3.3]heptane-2-carboxylate (409.05 mg, 647.08 µmol) was dissolved in Ethanol (2 mL), cooled to 0° C. and Lithium hydroxide monohydrate, 98% (1 M, 647.08 µL) was added. The reaction mixture was stirred for 3 h. The reaction mixture was acidified with sodium dihydrogen phosphate (aq., sat.), at which point the product precipitated. Brine was added to the reaction mixture, and the mixture was stirred for 5 minutes. The reaction mixture was extracted with ethyl acetate (3×). The organic layers were washed with brine, dried with sodium sulfate, filtered, and evaporated under reduced pressure. The crude residue was dissolved in dichloromethane (2 mL) with benzene (0.5 mL) and evaporated under reduced pressure, submitted to high vacuum to afford [2-[6-[4-(2-tert-butoxycarbonyl-2,6-diazaspiro[3.3]heptan-6-yl)phenyl]-4-chloro-1-oxo-isoindolin-2-yl]-2-(6,7-dihydro-5H-pyrrolo[1,2-c]imidazol-1-yl)acetyl]oxylithium (412 mg, 641.61 µmol, 99.16% yield). LCMS (ESI+): 604.4/606.4 (M+H)

1136

Step 3: tert-Butyl 6-[4-[7-chloro-2-[1-(6,7-dihydro-5H-pyrrolo[1,2-c]imidazol-1-yl)-2-oxo-2-(thiazol-2-ylamino)ethyl]-3-oxo-isoindolin-5-yl]phenyl]-2,6-diazaspiro[3.3]heptane-2-carboxylate

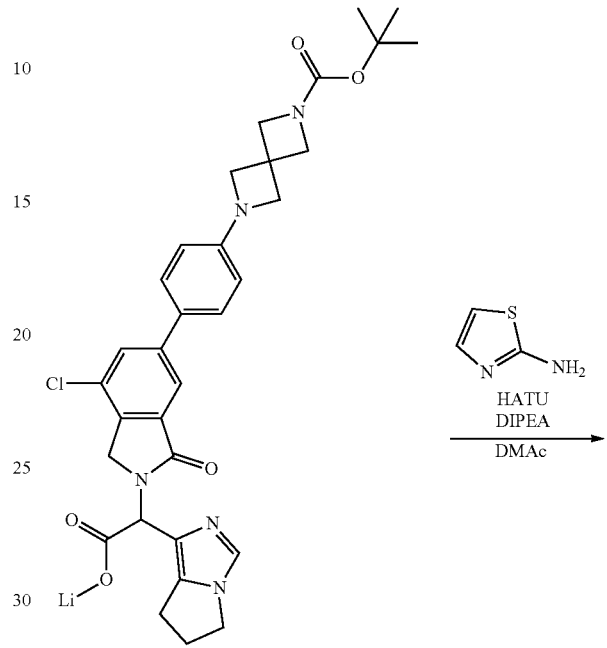

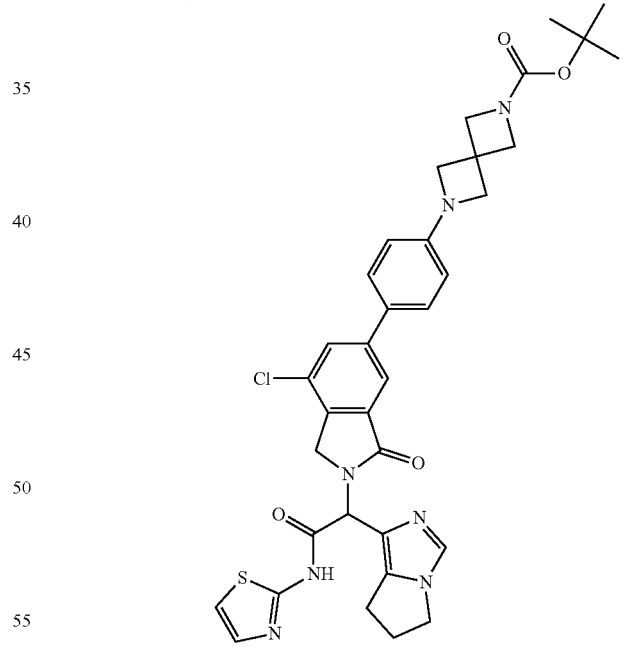

[2-[6-[4-(2-tert-butoxycarbonyl-2,6-diazaspiro[3.3]heptan-6-yl)phenyl]-4-chloro-1-oxo-isoindolin-2-yl]-2-(6,7-dihydro-5H-pyrrolo[1,2-c]imidazol-1-yl)acetyl]oxylithium (412 mg, 675.38 µmol) and thiazol-2-amine (81.16 mg, 810.45 µmol) were mixed in DMAc (6 mL), the reaction mixture was cooled to 0° C. N,N-diisopropylethylamine (174.57 mg, 1.35 mmol, 235.27 µL) was added to the reaction mixture, and 1-[bis(dimethylamino)methylene]-1H-1,2,3-triazolo[4,5-b]pyridinium 3-oxide hexafluorophosphate (295.32 mg, 776.69 µmol) was added, and the reaction mixture was stirred for 20 h. The reaction mixture was partitioned between ethyl acetate and sodium bicarbonate (aq., sat.). The organic layer was washed with brine, dried with sodium sulfate, filtered and evaporated under reduced pressure. The crude residue was purified by silica gel chromatography (24 g column, 0% to 20% methanol in dichloromethane). Pure fractions were evaporated under reduced pressure. The solid was dried under vacuum to afford tert-butyl 6-[4-[7-chloro-2-[1-(6,7-dihydro-5H-pyrrolo[1,2-c]imidazol-1-yl)-2-oxo-2-(thiazol-2-ylamino)ethyl]-3-oxo-isoindolin-5-yl]phenyl]-2,6-diazaspiro[3.3]heptane-2-carboxylate (295 mg, 408.40 μmol, 60.47% yield). LCMS (ESI+): 686.4/688.4 (M+H)

Step 4: 2-[4-chloro-6-[4-(2,6-diazaspiro[3.3]heptan-2-yl)phenyl]-1-oxo-isoindolin-2-yl]-2-(6,7-dihydro-5H-pyrrolo[1,2-c]imidazol-1-yl)-N-thiazol-2-yl-acetamide, trifluoroacetic acid salt To a solution of tert-butyl 6-[4-[7-chloro-2-[1-(6,7-dihydro-5H-pyrrolo[1,2-c]imidazol-1-yl)-2-oxo-2-(thiazol-2-ylamino)ethyl]-3-oxo-isoindolin-5-yl]phenyl]-2,6-diazaspiro[3.3]heptane-2-carboxylate (205 mg, 298.74 μmol) in dichloromethane (3 mL) was added Trifluoroacetic acid (681.24 mg, 5.97 mmol, 460.30 μL). The mixture was stirred at 20° C. for 1 h. The reaction mixture was added to methyl tert-butyl ether (20 mL) under stirring at 0-5° C. The resulting suspension was stirred for 2 minutes. The suspension was transferred to a vial for centrifugation, and the suspension was centrifugated at 3000 rpm for 3 minutes. The supernatant solvent was decanted and discarded. methyl tert-butyl ether (20 mL) was added the solid and the resulting suspension was stirred for 2 minutes. The suspension was transferred to a vial for centrifugation, and the suspension was centrifugated at 3000 rpm for 3 minutes. The supernatant solvent was decanted and discarded. The volatiles were evaporated in vacuo to give 2-[4-chloro-6-[4-(2,6-diazaspiro[3.3]heptan-2-yl)phenyl]-1-oxo-isoindolin-2-yl]-2-(6,7-dihydro-5H-pyrrolo[1,2-c]imidazol-1-yl)-N-thiazol-2-yl-acetamide, trifluoroacetic acid salt (205 mg, 292.80 μmol, 98.01% yield) as a yellow solid. LCMS (ES+): m/z 586.1 [M+H]+

Step 5: 2-[4-chloro-6-[4-[2-[2-[1-[4-[[(3S)-2,6-dioxo-3-piperidyl]amino]-2-fluoro-phenyl]-4-hydroxy-4-piperidyl]acetyl]-2,6-diazaspiro[3.3]heptan-6-yl]phenyl]-1-oxo-isoindolin-2-yl]-2-(6,7-dihydro-5H-pyrrolo[1,2-c]imidazol-1-yl)-N-thiazol-2-yl-acetamide

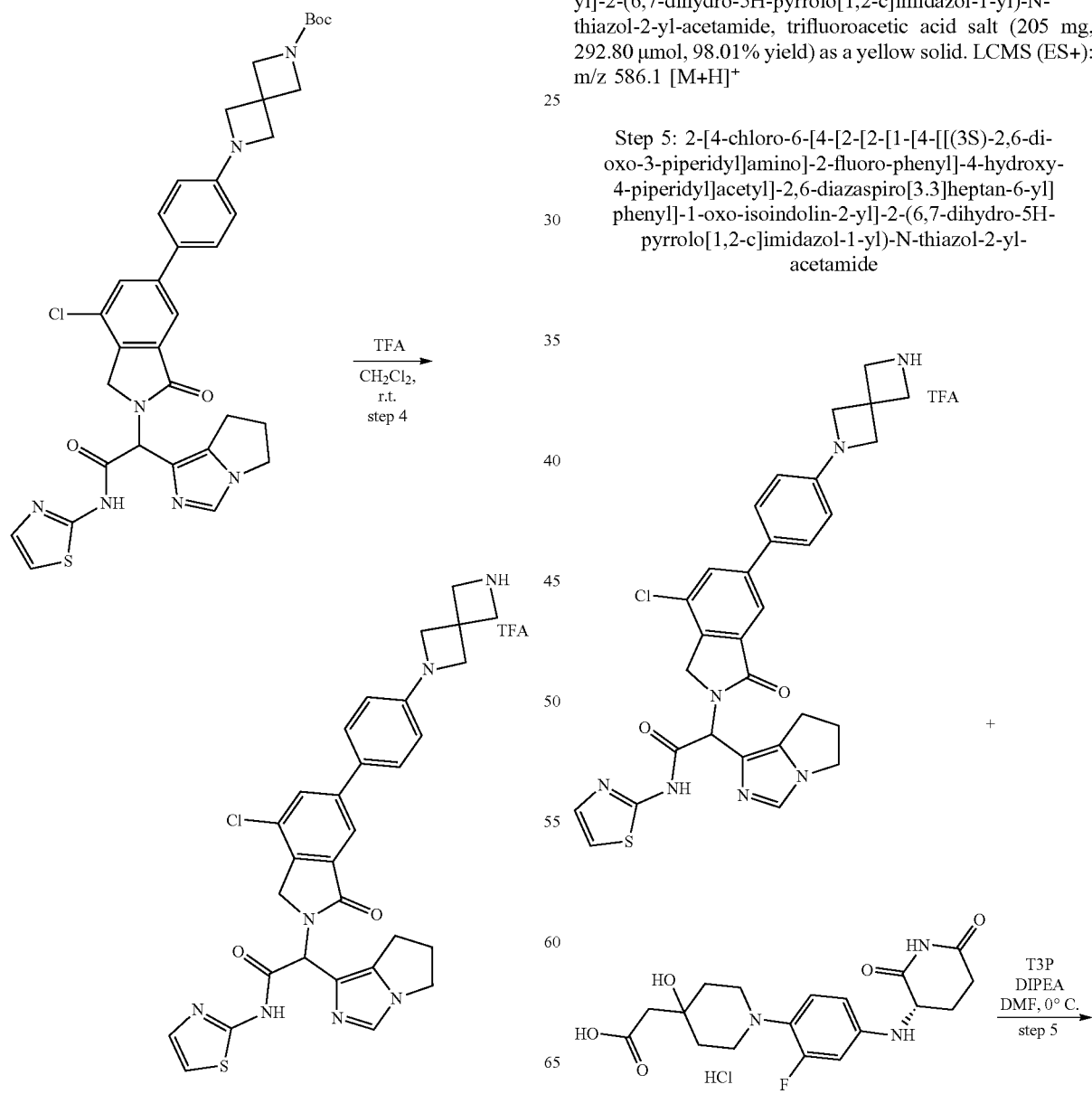

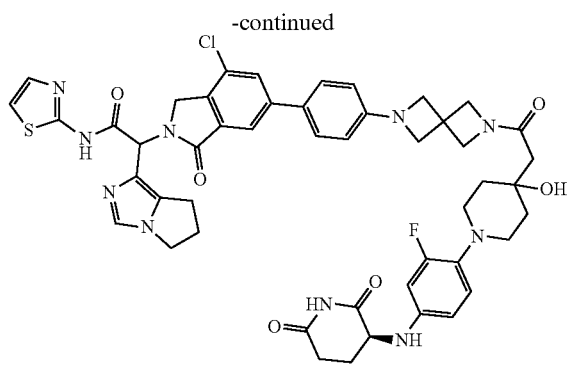

To a solution of 2-[1-[4-[[(3S)-2,6-dioxo-3-piperidyl]amino]-2-fluoro-phenyl]-4-hydroxy-4-piperidyl]acetic acid hydrochloride (121.76 mg, 292.80 μmol) and Propylphosphonic anhydride solution (50 wt. % in ethyl acetate) (139.75 mg, 439.20 μmol) in N,N-dimethylformamide (2 mL) was added N,N-diisopropylethylamine (264.90 mg, 2.05 mmol, 357.01 μL). The mixture was stirred at 0° C. for 20 minutes. 2-[4-chloro-6-[4-(2,6-diazaspiro[3.3]heptan-2-yl)phenyl]-1-oxo-isoindolin-2-yl]-2-(6,7-dihydro-5H-pyrrolo[1,2-c]imidazol-1-yl)-N-thiazol-2-yl-acetamide, trifluoroacetic acid salt (205 mg, 292.80 μmol) was added. The mixture was stirred at 0° C. for 1 h. To the mixture was added propylphosphonic anhydride solution (50 wt. % in ethyl acetate) (83.85 mg, 263.52 μmol). The mixture was stirred at 0° C. for 1 h. The reaction mixture was purified by prep-HPLC (column: Phenomenex luna C18 150*40 mm*15 m; mobile phase: 20%-50% acetonitrile in water (0.10% trifluoroacetic acid), 10 min run time) to give 30 mL solution. The solution was poured into an aqueous saturated sodium bicarbonate solution. The mixture was filtered and the filter cake was washed with water (5 mL), filter cake was lyophilized to give Compound 136 (142.05 mg, 149.93 μmol, 51.20% yield) as a white solid. LCMS (ES+): m/z 947.3 [M+H]+ $^1$H NMR (400 MHz, DMSO-d$_6$) δ=12.52 (s, 1H), 10.78 (s, 1H), 7.90 (d, J=1.2 Hz, 1H), 7.86-7.82 (m, 1H), 7.67-7.59 (m, 3H), 7.48 (d, J=3.6 Hz, 1H), 7.26 (d, J=3.6 Hz, 1H), 6.85 (t, J=9.2 Hz, 1H), 6.57-6.47 (m, 3H), 6.41 (dd, J=2.0, 8.8 Hz, 1H), 6.16 (s, 1H), 5.77 (d, J=7.6 Hz, 1H), 4.78-4.71 (m, 2H), 4.38 (s, 2H), 4.25 (m, 1H), 4.15 (d, J=18.0 Hz, 1H), 4.08 (s, 2H), 4.04-3.93 (m, 6H), 2.94-2.80 (m, 4H), 2.79-2.68 (m, 2H), 2.61-2.51 (m, 3H), 2.49-2.44 (m, 1H), 2.13-2.04 (m, 1H), 1.76 (br s, 3H), 1.62 (br d, J=12.8 Hz, 2H)

Example 137

2-(6,7-dihydro-5H-pyrrolo[1,2-c]imidazol-1-yl)-2-[6-[4-[7-[2-[1-[4-[[2,6-dioxo-3-piperidyl]amino]-2,6-difluoro-phenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide, isomer 1, Compound 137

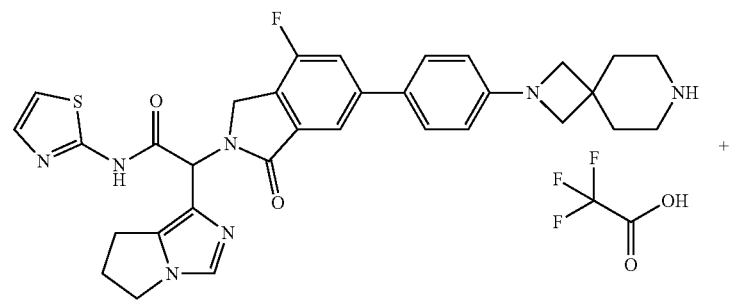

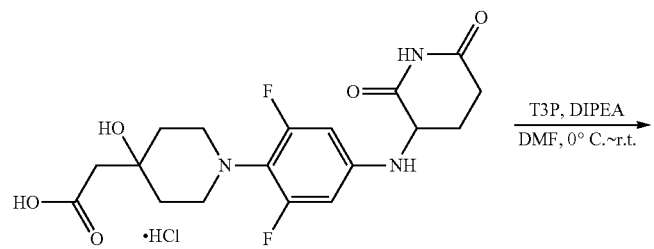

Isomer 1

-continued

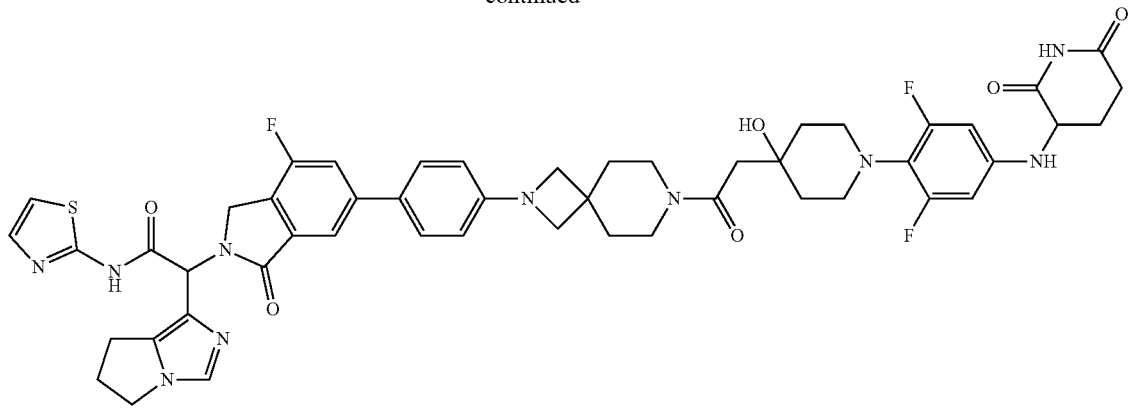

Isomer 1

Step 1: 2-(6,7-dihydro-5H-pyrrolo[1,2-c]imidazol-1-yl)-2-[6-[4-[7-[2-[1-[4-[[2,6-dioxo-3-piperidyl]amino]-2,6-difluoro-phenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide, isomer 1

To a solution of 2-[1-[4-[[2,6-dioxo-3-piperidyl]amino]-2,6-difluoro-phenyl]-4-hydroxy-4-piperidyl]acetic acid, isomer 1, hydrochloride (150 mg, 345.75 μmol) and propylphosphonic anhydride solution (50 wt. % in ethyl acetate) (165.02 mg, 518.63 μmol) in N,N-dimethylformamide (2 mL) was added N,N-diisopropylethylamine (312.80 mg, 2.42 mmol, 421.57 μL). The mixture was stirred at 0° C. for 20 minutes. 2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (221.47 mg, 311.18 μmol) was added. The mixture was stirred at 0° C. for 1 h. Then to the mixture was added propylphosphonic anhydride solution (50 wt. % in ethyl acetate) (99.01 mg, 311.18 μmol). The mixture was stirred at 0° C. for 1 h. The mixture was purified by prep-HPLC (column: Phenomenex luna C18 150*40 mm*15 um; mobile phase: water (0.1% trifluoroacetic acid)-acetonitrile; B %: 20%-50%, 10 min) to give 30 mL solution. The solution was neutralized with saturated aqueous sodium bicarbonate (5 mL) to pH=8, The mixture was filtered and the filter cake was washed with water (3 mL×2). The filter cake was lyophilized to give Compound 137 (183.74 mg, 184.29 μmol, 53.30% yield) as a white solid. LCMS (ES+): m/z 977.4 [M+H]+ 1H NMR (400 MHz, DMSO-$d_6$) δ=12.83-12.22 (m, 1H), 10.81 (br s, 1H), 7.76-7.67 (m, 2H), 7.66-7.60 (m, 3H), 7.49 (d, J=3.6 Hz, 1H), 7.26 (d, J=3.6 Hz, 1H), 6.53 (d, J=8.8 Hz, 2H), 6.34 (s, 1H), 6.32-6.28 (m, 1H), 6.21 (d, J=7.6 Hz, 1H), 6.15 (s, 1H), 4.92 (s, 1H), 4.80 (d, J=17.6 Hz, 1H), 4.39-4.27 (m, 1H), 4.22 (d, J=17.6 Hz, 1H), 4.06-3.93 (m, 2H), 3.67 (s, 4H), 3.48 (br s, 4H), 3.30-3.19 (m, 2H), 2.82-2.69 (m, 4H), 2.62-2.53 (m, 4H), 2.50-2.43 (m, 2H), 2.14-2.02 (m, 1H), 1.89-1.56 (m, 9H)

Example 138

2-[6-[4-[7-[2-[1-[2-chloro-4-[[2,6-dioxo-3-piperidyl]amino]phenyl]-4-hydroxy-4-piperidyl]acetyl]-2,7-diazaspiro[3.5]nonan-2-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, isomer 1, Compound 138

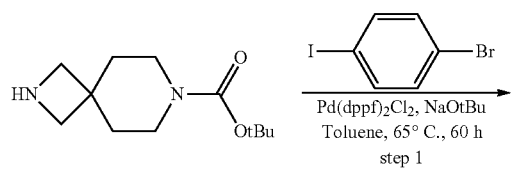

step 1

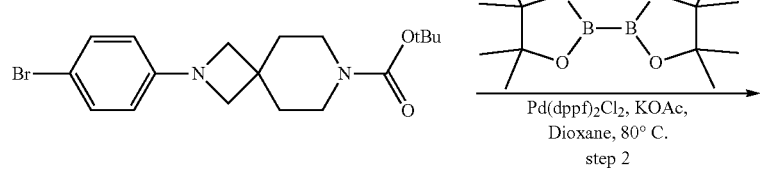

step 2

-continued
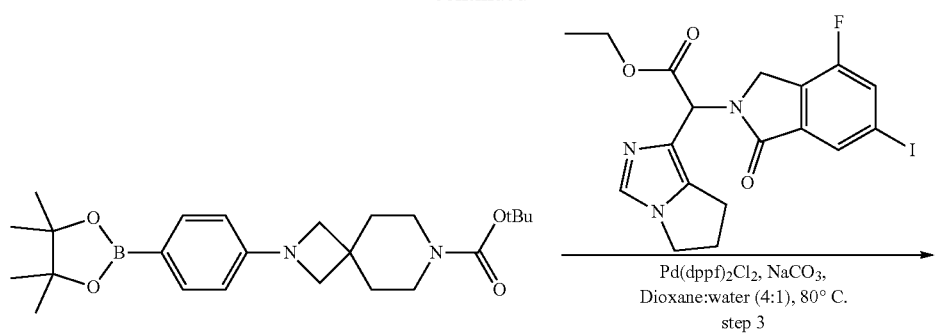
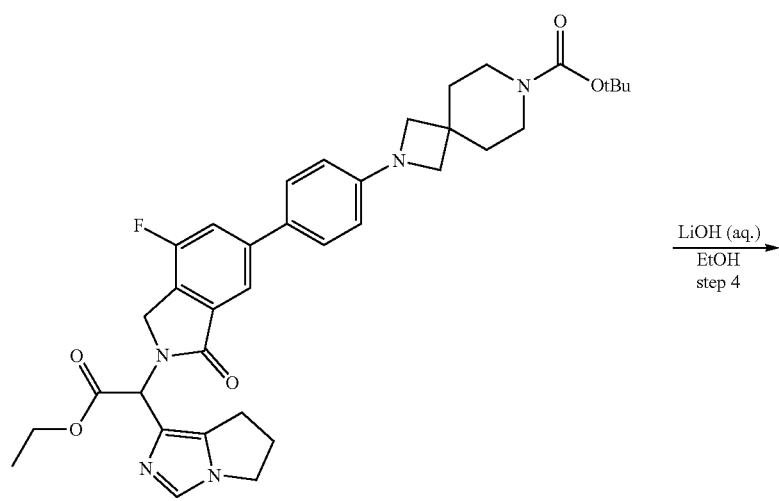
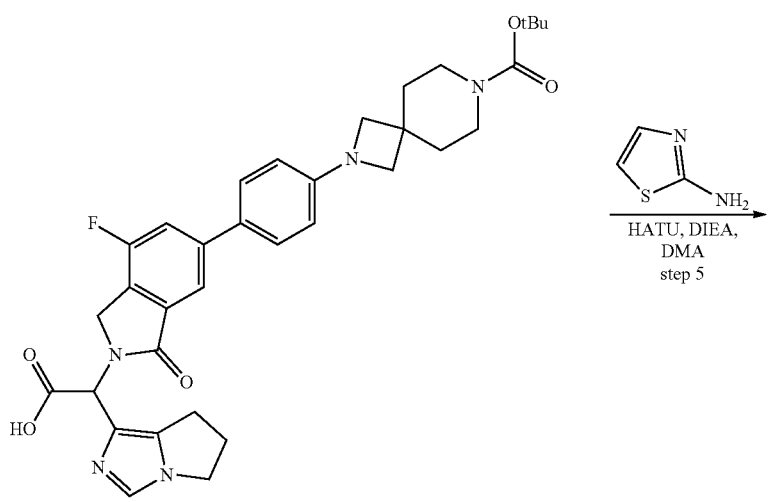

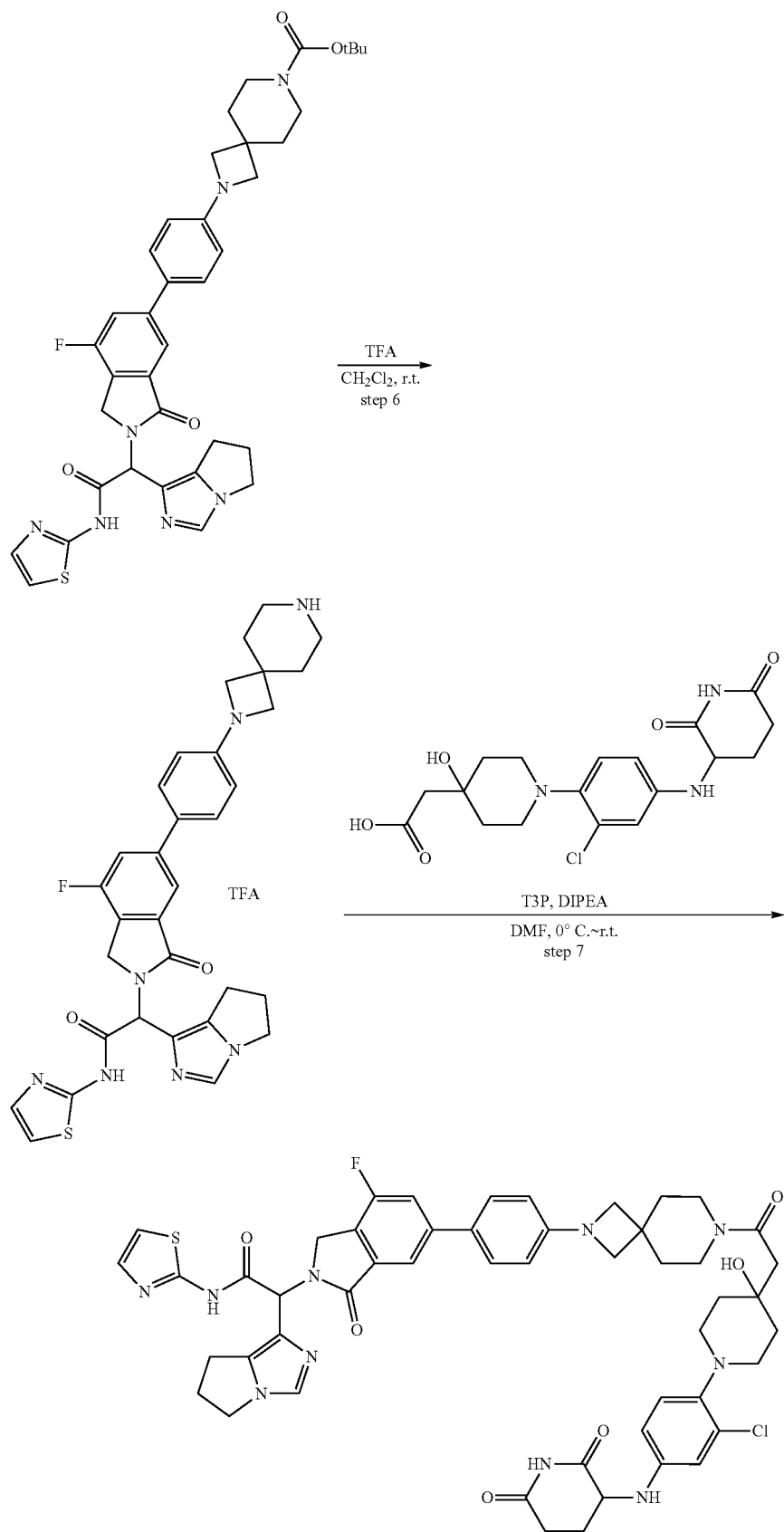
-continued

Step 1: tert-Butyl 2-(4-bromophenyl)-2,7-diazaspiro[3.5]nonane-7-carboxylate The mixture of tert-butyl 2,7-diazaspiro[3.5]nonane-7-carboxylate (1 g, 4.42 mmol), 1-bromo-4-iodo-benzene (1.25 g, 4.42 mmol), sodium tert-butoxide (849.29 mg, 8.84 mmol) and Pd(dppf)$_2$Cl$_2$ (323.31 mg, 441.86 µmol) in Toluene (10 mL). The mixture was stirred at 65° C. for 48 h under N$_2$ atmosphere. The reaction mixture was poured into water (200 mL). The mixture was extracted with ethyl acetate (100×2). The organic phase was washed with brine (100 mL), dried over anhydrous sodium sulfate, concentrated in vacuum to give a residue. The residue was pre-purified by flash silica gel chromatography (ISCO®; 10 g SepaFlash® Silica Flash Column, Eluent of 0~10% Ethyl acetate/Petroleum ether gradient @ 80 mL/min) to give tert-butyl 2-(4-bromophenyl)-2,7-diazaspiro[3.5]nonane-7-carboxylate (800 mg, 47.5% yield). $^1$H NMR (400 MHz, CDCl$_3$-d) δ=7.32-7.28 (m, 2H), 6.35 (d, J=8.8 Hz, 2H), 3.62 (s, 2H), 3.64-3.59 (m, 1H), 3.42-3.39 (m, 1H), 1.80-1.76 (m, 4H), 1.47 (s, 12H)

Step 2: tert-Butyl 2-[4-(4,4,5,5-tetramethyl-1,3,2-dioxaborolan-2-yl)phenyl]-2,7-diazaspiro[3.5]nonane-7-carboxylate A mixture of tert-butyl 2-(4-bromophenyl)-2,7-diazaspiro[3.5]nonane-7-carboxylate (18 g, 47.21 mmol), 4,4,5,5-tetramethyl-2-(4,4,5,5-tetramethyl-1,3,2-dioxaborolan-2-yl)-1,3,2-dioxaborolane (14.38 g, 56.65 mmol), Potassium Acetate (9.27 g, 94.41 mmol, 5.90 mL), Pd(dppf)Cl$_2$ (3.45 g, 4.72 mmol) in dioxane (180 mL). The mixture was stirred at 80° C. for 16 h under N$_2$ atmosphere. The mixture was diluted with water (400 mL) and extracted with ethyl acetate (200 mL×3). The combined organic layers were washed with brine (200 mL×2), dried over anhydrous sodium sulfate, filtered and concentrated under reduced pressure to give residue. The residue was purified by silica gel chromatography (SiO$_2$, Petroleum ether/Ethyl acetate=10/1) to give tert-butyl 2-[4-(4,4,5,5-tetramethyl-1,3,2-dioxaborolan-2-yl)phenyl]-2,7-diazaspiro[3.5]nonane-7-carboxylate (11 g, 49% yield) as white solid. $^1$H NMR (400 MHz, CDCl$_3$-d) δ=7.68 (d, J=8.4 Hz, 2H), 6.43 (d, J=8.4 Hz, 2H), 3.66 (s, 4H), 3.43-3.38 (m, 4H), 1.80-1.75 (m, 4H), 1.64 (br s, 4H), 1.47 (s, 9H), 1.33 (s, 12H)

Step 3: tert-Butyl 2-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]-2,7-diazaspiro[3.5]nonane-7-carboxylate A mixture of tert-butyl 2-[4-(4,4,5,5-tetramethyl-1,3,2-dioxaborolan-2-yl)phenyl]-2,7-diazaspiro[3.5]nonane-7-carboxylate (3 g, 7.00 mmol), ethyl 2-(6,7-dihydro-5H-pyrrolo[1,2-c]imidazol-1-yl)-2-(4-fluoro-6-iodo-1-oxo-isoindolin-2-yl)acetate (3.29 g, 7.00 mmol), Pd(dppf)Cl$_2$ (512.43 mg, 700.33 µmol), Na$_2$CO$_3$ (1.48 g, 14.01 mmol) in Dioxane (30 mL) and water (7.5 mL). The mixture was stirred at 80° C. for 16 h under N$_2$ atmosphere. The reaction mixture was concentrated under reduced pressure to remove solvent to give tert-butyl 2-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]-2,7-diazaspiro[3.5]nonane-7-carboxylate (4.51 g, crude product)

Step 4: 2-[6-[4-(7-tert-Butoxycarbonyl-2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)acetic acid tert-butyl 2-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]phenyl]-2,7-diazaspiro[3.5]nonane-7-carboxylate (4.5 g, 6.99 mmol) was dissolved in ethanol (40 mL), cooled to 0° C. and lithium hydroxide (1 M, 13.98 mmol, 13.98 mL) was added. The reaction mixture was stirred at 25° C. for 16 h. The reaction mixture was concentrated under reduced pressure to give a residue. The residue was purified by prep-HPLC (basic condition) to give 2-[6-[4-(7-tert-butoxycarbonyl-2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)acetic acid (3 g, 4.87 mmol, 69.70% yield) as a yellow solid. LCMS (ES+): 616.5 [M+H]$^+$

Step 5: tert-Butyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonane-7-carboxylate 2-[6-[4-(7-tert-butoxycarbonyl-2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)acetic acid (3 g, 4.87 mmol) and thiazol-2-amine (536.74 mg, 5.36 mmol) were mixed in DMA (30 mL), the reaction mixture was cooled to 0° C. N,N-diisopropylethylamine (2.52 g, 19.49 mmol, 3.39 mL) was added to the reaction mixture, and 1-[bis(dimethylamino)methylene]-1H-1,2,3-triazolo[4,5-b]pyridinium 3-oxide hexafluorophosphate (2.41 g, 6.33 mmol) was added, and the reaction mixture was stirred for 30 min at 0° C. The reaction mixture was warmed to 20° C. and stirred for 2 h. The reaction mixture was diluted with 200 mL of water. The precipitated solid was filtered and washed with water, the solid was dried. Methanol (30 mL) was added to the solid and stirred for 20 minutes at 20° C. solid was precipitated then it was filtered and washed with methanol, the solid was dried to give tert-butyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonane-7-carboxylate (2 g, 2.87 mmol, 58.82% yield) as a brown solid. LCMS (ES+): m/z 698.4 [M+H]$^+$, $^1$H NMR (400 MHz, CDCl$_3$-d) δ=7.87 (s, 1H), 7.56-7.46 (m, 4H), 7.39 (d, J=10.4 Hz, 1H), 6.97 (d, J=3.6 Hz, 1H), 6.53-6.50 (m, 2H), 6.42 (s, 1H), 4.81 (d, J=17.2 Hz, 1H), 4.45 (d, J=17.2 Hz, 1H), 4.05-3.94 (m, 2H), 3.68 (s, 4H), 3.45-3.38 (m, 4H), 2.85-2.74 (m, 1H), 2.69-2.53 (m, 3H), 1.84-1.77 (m, 4H), 1.47 (s, 9H)

Step 6: 2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide To the mixture of tert-butyl 2-[4-[2-[1-(6,7-dihydro-5H-pyrrolo[1,2-c]imidazol-1-yl)-2-oxo-2-(thiazol-2-ylamino)

ethyl]-7-fluoro-3-oxo-isoindolin-5-yl]phenyl]-2,7-diazaspiro[3.5]nonane-7-carboxylate (246 mg, 352.53 µmol) in dichloromethane (3 mL) was added trifluoroacetic acid (803.92 mg, 7.05 mmol, 543.19 µL). The mixture was stirred at 25° C. for 1 h. The reaction mixture was added to methyl tert-butyl ether (20 mL) under stirring at 0-5° C. The resulting suspension was stirred for 2 minutes. The suspension was transferred to a vial for centrifugation, and the suspension was centrifuged at 3000 rpm for 3 minutes. The supernatant solvent was decanted and discarded. methyl tert-butyl ether (20 mLs) was added the solid and the resulting suspension was stirred for 2 minutes. The suspension was transferred to a vial for centrifugation, and the suspension was centrifuged at 3000 rpm for 3 minutes. The supernatant solvent was decanted and discarded. The volatiles were evaporated in vacuo to give 2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (246 mg, 345.64 µmol, 98.05% yield) as a yellow solid. LCMS (ES+): m/z 598.2 [M+H]+

Step 7: 2-[6-[4-[7-[2-[1-[2-chloro-4-[[2,6-dioxo-3-piperidyl]amino]phenyl]-4-hydroxy-4-piperidyl]acetyl]-2,7-diazaspiro[3.5]nonan-2-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, isomer 1

To a solution of 2-[1-[2-chloro-4-[[(3S)-2,6-dioxo-3-piperidyl]amino]phenyl]-4-hydroxy-4-piperidyl]acetic acid hydrochloride, isomer 1 (150 mg, 346.98 µmol) and propylphosphonic anhydride solution (50 wt. % in ethyl acetate) (165.61 mg, 520.47 µmol) in N,N-dimethylformamide (3 mL) was added N,N-diisopropylethylamine (313.92 mg, 2.43 mmol, 423.07 µL). The mixture was stirred at 0° C. for 20 min. Then to the mixture was added 2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (246.96 mg, 346.98 µmol). The mixture was stirred at 0° C. for 1 h. To the mixture was added propylphosphonic anhydride solution (50 wt. % in ethyl acetate) (99.36 mg, 312.28 µmol). The mixture was stirred at 25° C. for 1 h. The mixture was purified by preparative HPLC (Column: Phenomenex luna C18 150*40 mm 15 µm, phase: water (0.1% trifluoroacetic acid)-acetonitrile, B %: 18%-48%, Run time: 10 min) to give 30 mL solution. The solution was poured into with saturated aqueous sodium bicarbonate solution to pH=8, The mixture was filtered and the filter cake was washed with water (2×5 mL), filter cake was lyophilized to give Compound 138 (117.90 mg, 118.44 µmol, 34.13% yield) as a white solid. LCMS (ES+): m/z 975.1 [M+H]+, 1H NMR (400 MHz, DMSO-d6) δ=12.52 (br s, 1H), 10.77 (s, 1H), 7.75-7.67 (m, 2H), 7.66-7.58 (m, 3H), 7.48 (d, J=3.6 Hz, 1H), 7.25 (d, J=3.6 Hz, 1H), 6.97 (d, J=8.8 Hz, 1H), 6.75 (d, J=2.4 Hz, 1H), 6.60 (dd, J=2.4, 8.8 Hz, 1H), 6.52 (br d, J=8.4 Hz, 2H), 6.14 (s, 1H), 5.83 (d, J=7.6 Hz, 1H), 4.96 (s, 1H), 4.79 (br d, J=17.6 Hz, 1H), 4.33-4.16 (m, 2H), 4.07-3.91 (m, 2H), 3.70-3.63 (m, 4H), 3.58-3.48 (m, 4H), 2.94-2.84 (m, 2H), 2.84-2.70 (m, 4H), 2.60-2.54 (m, 4H), 2.47-2.41 (m, 2H), 2.11-2.03 (m, 1H), 1.85-1.62 (m, 9H)

Example 139

2-(6,7-dihydro-5H-pyrrolo[1,2-c]imidazol-1-yl)-2-[6-[4-[2-[2-[1-[5-[[2,6-dioxo-3-piperidyl]amino]-3-fluoro-2-pyridyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1, Compound 139

Step 1: tert-Butyl 2-[1-[5-[[(2,6-dioxo-3-piperidyl)amino]-3-fluoro-2-pyridyl]-4-hydroxy-4-piperidyl]acetate, isomer 1 and tert-butyl 2-[1-[5-[[2,6-dioxo-3-piperidyl]amino]-3-fluoro-2-pyridyl]-4-hydroxy-4-piperidyl]acetate, isomer 2

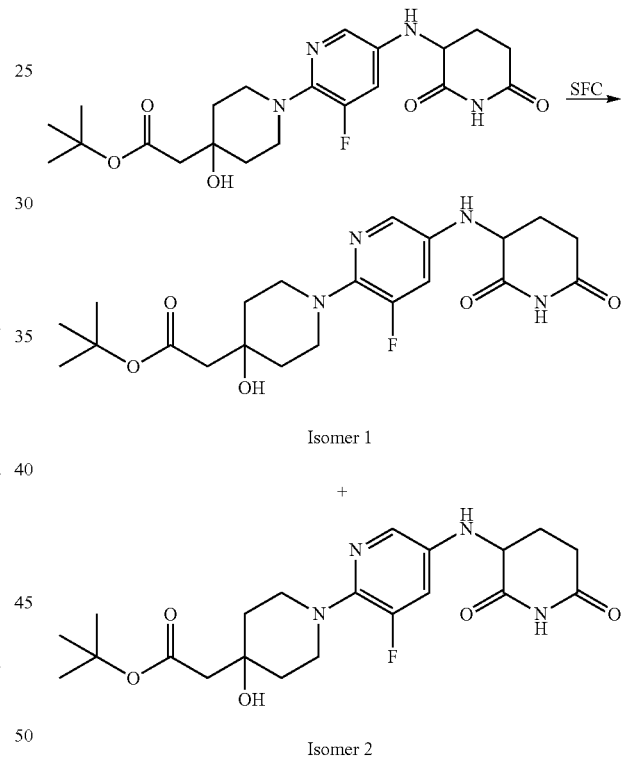

Isomer 1

+

Isomer 2

Racemic tert-Butyl 2-[1-[5-[[(2,6-dioxo-3-piperidyl]amino]-3-fluoro-2-pyridyl]-4-hydroxy-4-piperidyl]acetate was separated by Chiral SFC (35% isopropyl alcohol in supercritical CO2, column: DAICEL CHIRALCEL OJ (250 mm×30 mm, 10 µm); 90 min run time) to afford 2 sets of fractions.

First eluting set of fractions: tert-butyl 2-[1-[5-[[(3S)-2,6-dioxo-3-piperidyl]amino]-3-fluoro-2-pyridyl]-4-hydroxy-4-piperidyl]acetate, isomer 1 (660 mg, 1.50 mmol, 46% yield) as a brown solid LCMS (ESI): m/z 437.2 [M+H]+

Second eluting set of fractions: tert-Butyl 2-[1-[5-[[(3R)-2,6-dioxo-3-piperidyl]amino]-3-fluoro-2-pyridyl]-4-hydroxy-4-piperidyl]acetate (580 mg, 1.32 mmol, 40% yield) as a brown solid. LCMS (ESI): m/z 437.2 [M+H]+

1151

Step 2: 2-[1-[5-[[2,6-dioxo-3-piperidyl]amino]-3-fluoro-2-pyridyl]-4-hydroxy-4-piperidyl]acetic acid, isomer 1

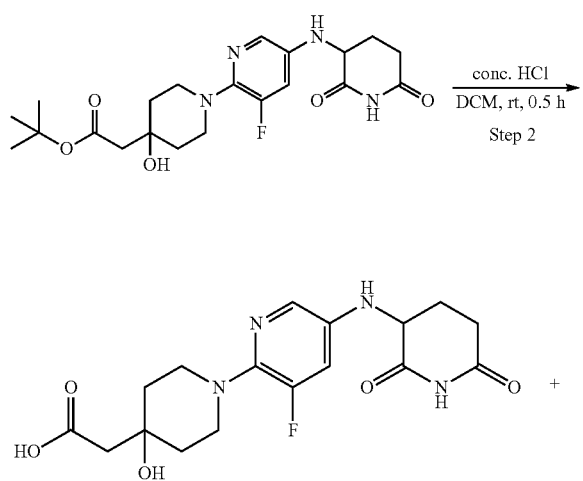

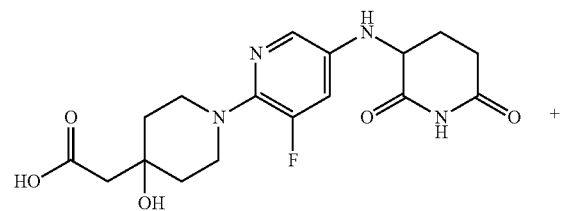

1152

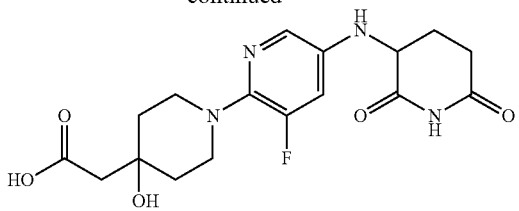

A mixture of tert-butyl 2-[1-[5-[[(3S)-2,6-dioxo-3-piperidyl]amino]-3-fluoro-2-pyridyl]-4-hydroxy-4-piperidyl]acetate (360 mg, 824.79 μmol) in dichloromethane (5.4 mL) was added hydrochloric acid (12 M, 360.00 μL). The mixture was stirred at 25° C. for 0.5 h. The mixture was concentrated under reduced pressure at 35° C. to give 2-[1-[5-[[(3S)-2,6-dioxo-3-piperidyl]amino]-3-fluoro-2-pyridyl]-4-hydroxy-4-piperidyl]acetic acid hydrochloride, isomer 1 (380 mg, 902.52 μmol) as a brown solid. LCMS (ESI): m/z 381.1 [M+H]$^+$ Step 3: 2-(6,7-dihydro-5H-pyrrolo[1,2-c]imidazol-1-yl)-2-[6-[4-[2-[2-[1-[5-[[(3S)-2,6-dioxo-3-piperidyl]amino]-3-fluoro-2-pyridyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1

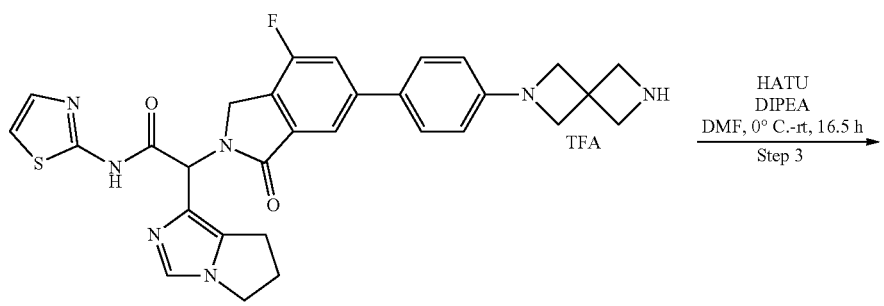

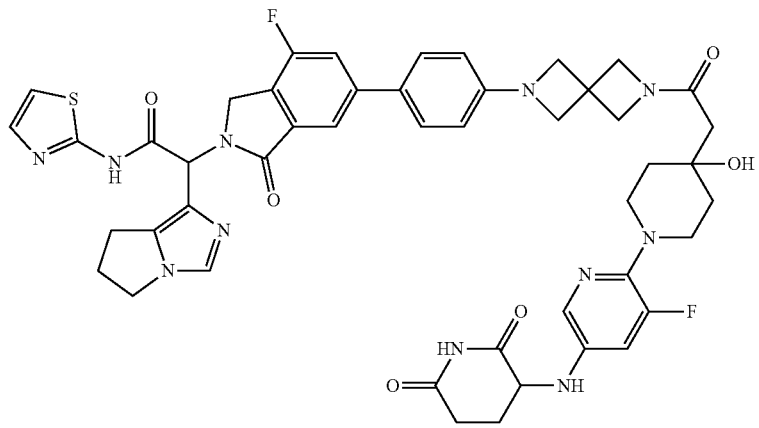

To a solution of 2-[1-[5-[[2,6-dioxo-3-piperidyl]amino]-3-fluoro-2-pyridyl]-4-hydroxy-4-piperidyl]acetic acid hydrochloride, isomer 1 hydrochloride (200 mg, 479.81 µmol) in N,N-dimethylformamide (3 mL) were added N,N-diisopropylethylamine (430.36 mg, 3.33 mmol, 580 µL) and 1-[bis(dimethylamino)methylene]-1H-1,2,3-triazolo[4,5-b]pyridinium 3-oxide hexafluorophosphate (183 mg, 481.29 µmol) at 0° C. The mixture was stirred at 0° C. for 0.5 h. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (260 mg, 380.30 µmol) was added to the mixture. The resulting mixture was stirred at 25° C. for 16 h. The mixture was filtered. The solid was purified by reversed phase column (water:acetonitrile). The fractions containing compound were frozen and lyophilized. The material was purified by preparative HPLC (flow: 25 mL/min; gradient: 26 to 56% acetonitrile in water over 9 min; column: Waters Xbridge 150×25 mm, 5 µm). Pure fractions were frozen and lyophilized to afford Compound 139 (147.08 mg, 156.23 µmol, 33% yield) as a white solid. LCMS (ESI): m/z 932.3 [M+H]$^+$, $^1$H NMR (400 MHz, DMSO-d$_6$) δ=12.51 (s, 1H), 10.80 (s, 1H), 7.74 (s, 1H), 7.70 (d, J=10.8 Hz, 1H), 7.64 (d, J=8.4 Hz, 2H), 7.60 (s, 1H), 7.56 (d, J=1.6 Hz, 1H), 7.48 (d, J=3.6 Hz, 1H), 7.24 (d, J=3.2 Hz, 1H), 6.98 (dd, J=2.4, 14.8 Hz, 1H), 6.54 (d, J=8.8 Hz, 2H), 6.14 (s, 1H), 5.88 (d, J=7.6 Hz, 1H), 4.84-4.71 (m, 2H), 4.37 (s, 2H), 4.32-4.24 (m, 1H), 4.21 (d, J=17.6 Hz, 1H), 4.07 (s, 2H), 4.05-3.88 (m, 6H), 3.28-3.19 (m, 2H), 3.11-3.01 (m, 2H), 2.82-2.68 (m, 2H), 2.62-2.58 (m, 1H), 2.57-2.52 (m, 2H), 2.47-2.42 (m, 1H), 2.21 (s, 2H), 2.10 (dt, J=4.0, 8.4 Hz, 1H), 1.93-1.82 (m, 1H), 1.73 (t, J=10.4 Hz, 2H), 1.66-1.55 (m, 2H).

Example 140

2-(6,7-dihydro-5H-pyrrolo[1,2-c]imidazol-1-yl)-2-[6-[4-[7-[2-[(4R)-4-[3-(2,4-dioxohexahydropyrimidin-1-yl)-1-methyl-indazol-6-yl]-3,3-difluoro-1-piperidyl]-2-oxo-ethyl]-2,7-diazaspiro[3.5]nonan-2-yl]phenyl]-4-fluoro-1-oxo-isoindolin-2-yl]-N-thiazol-2-yl-acetamide, Compound 140

Step 1: tert-Butyl 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-7-yl]acetate

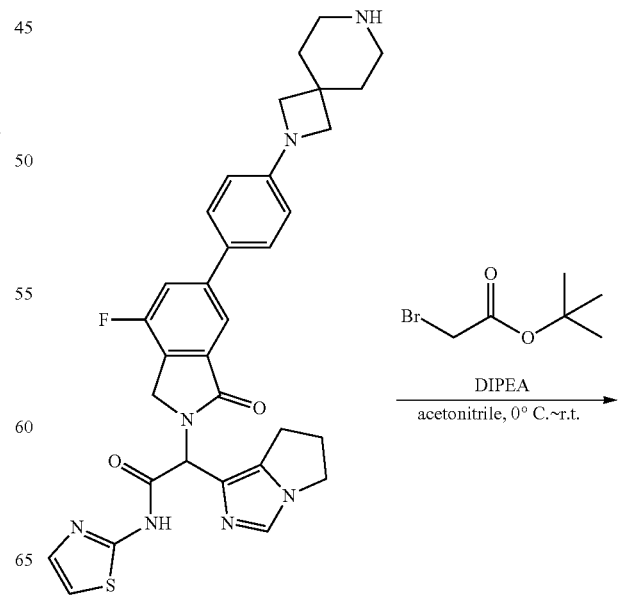

1155 -continued

1156

Step 2: 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-7-yl]acetic acid

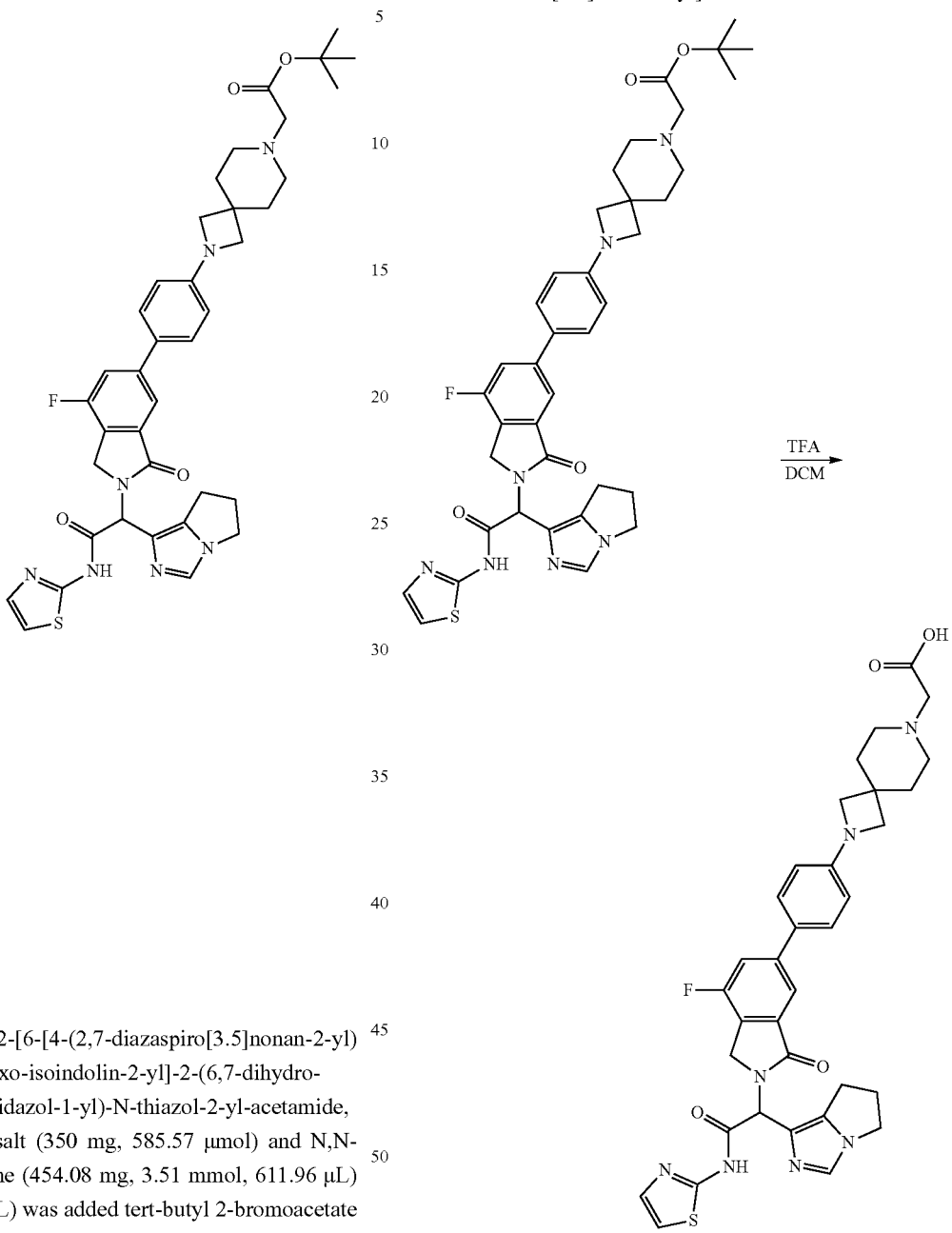

To a solution of 2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (350 mg, 585.57 μmol) and N,N-diisopropylethylamine (454.08 mg, 3.51 mmol, 611.96 μL) in acetonitrile (15 mL) was added tert-butyl 2-bromoacetate (171.33 mg, 878.36 mol, 128.82 μL) in acetonitrile (30 mL) at 0° C. The mixture was stirred at 20° C. for 2 h. The reaction mixture was poured into water (60 mL), extracted with ethyl acetate (60 mL×2). The combined organic layers were washed with brine (20 mL×2), dried over sodium sulfate, filtered and concentrated to afford tert-butyl 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-7-yl]acetate (440 mg, 618.11 μmol, 105.56% yield) as a off-white solid. LCMS (ESI): m/z 712.2 [M+H]$^+$ To a solution of tert-butyl 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-7-yl]acetate (440 mg, 618.11 μmol) in dichloromethane (2.5 mL) was added trifluoroacetic acid (2.60 g, 22.84 mmol, 1.76 mL). The mixture was stirred at 25° C. for 2 h. The reaction mixture was concentrated under reduced pressure to remove solvent and the crude product was triturated with Petroleum ether (30 mL) for 15 min to afford 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-7-yl]acetic acid, trifluoroacetic acid salt (440 mg, 585.00 μmol, 94.55% yield) as a yellow solid.

Step 3: 2-(6,7-dihydro-5H-pyrrolo[1,2-c]imidazol-1-yl)-2-[6-[4-[7-[2-[(4R)-4-[3-(2,4-dioxohexahydropyrimidin-1-yl)-1-methyl-indazol-6-yl]-3,3-difluoro-1-piperidyl]-2-oxo-ethyl]-2,7-diazaspiro[3.5]nonan-2-yl]phenyl]-4-fluoro-1-oxo-isoindolin-2-yl]-N-thiazol-2-yl-acetamide

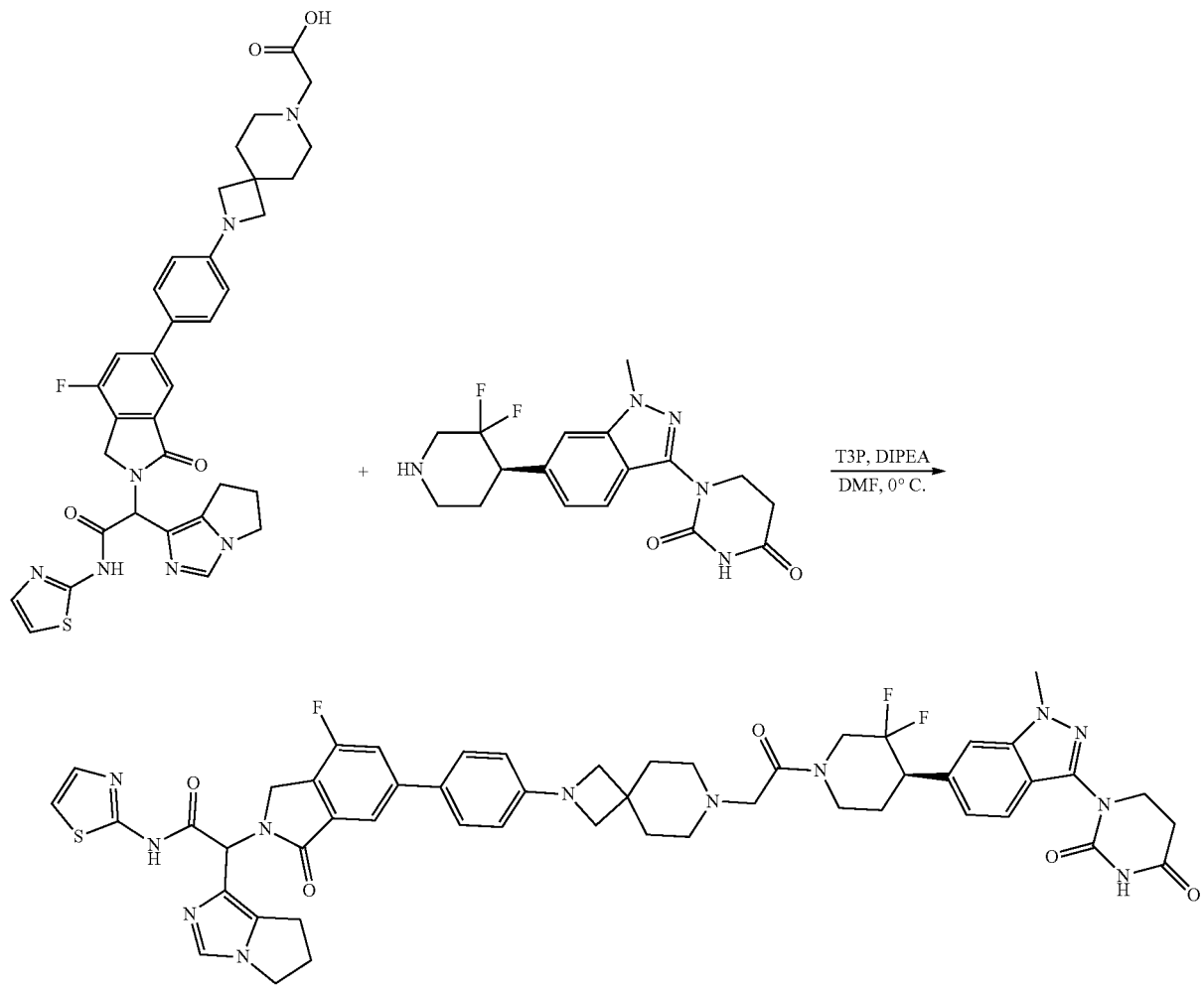

To a solution of 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-7-yl]acetic acid, trifluoroacetic acid salt (220 mg, 285.80 μmol) and propylphosphonic anhydride solution (50 wt. % in ethyl acetate) (272.81 mg, 428.70 μmol) in N,N-dimethylformamide (6 mL) was added N,N-diisopropylethylamine (295.50 mg, 2.29 mmol, 398.24 μL), The mixture was stirred at 0° C. for 20 minutes. 1-[6-[(4R)-3,3-difluoro-4-piperidyl]-1-methyl-indazol-3-yl]hexahydropyrimidine-2,4-dione hydrochloride (90 mg, 247.69 μmol) was added and the mixture was stirred at 0° C. for 60 min. Propylphosphonic anhydride solution (50 wt. % in ethyl acetate) (181.87 mg, 285.80 μmol) was added, the mixture was stirred at 0° C. for 60 min. The mixture was poured into water (50 mL) and neutralized with saturated aqueous solution of sodium bicarbonate (30 mL). A white solid precipitated, which was collected by filtration. The solid was dissolved in dichloromethane and dried over sodium sulfate, filtered and concentrated under reduced pressure. The residue was purified by prep-HPLC (trifluoroacetic acid was used as a phase modifier). Column: Phenomenex Synergi C18 150*25 mm, 10 m; mobile phase: water (+0.1% trifluoroacetic acid)-acetonitrile; gradient time: 10 min. The pure fractions were poured in a saturated aqueous solution of sodium bicarbonate (30 mL). A white solid precipitated, which was collected by filtration. The solid was washed with water (10 mL×2) and lyophilized to afford Compound 140 (55.9 mg, 55.84 μmol, 19.54% yield) as an off-white solid. LCMS (ESI): m/z 501.5 [M/2+H]$^+$, $^1$H NMR (400 MHz, DMSO-d6) δ=10.67-10.48 (m, 1H), 7.71 (s, 1H), 7.67-7.59 (m, 4H), 7.58-7.44 (m, 2H), 7.08 (d, J=8.4 Hz, 2H), 6.64-6.48 (m, 3H), 5.80 (br, 1H), 5.21-5.06 (m, 1H), 4.80-4.66 (m, 1H), 4.61-4.28 (m, 1H), 4.15 (d, J=17.6 Hz, 1H), 4.00 (s, 3H), 3.93 (t, J=6.8 Hz, 4H), 3.67-3.59 (m, 4H), 3.58-3.49 (m, 1H), 3.43-3.40 (m, 1H), 3.27-3.22 (m, 1H), 3.20-3.06 (m, 2H), 2.77 (t, J=6.8 Hz, 3H), 2.63-2.55 (m, 2H), 2.45 (s, 4H), 2.32-2.22 (m, 1H), 2.17-1.90 (m, 2H), 1.87-1.73 (m, 4H).

Example 141

2-(6,7-dihydro-5H-pyrrolo[1,2-c]imidazol-1-yl)-2-[6-[4-[7-[2-[(4S)-4-[3-(2,4-dioxohexahydropyrimidin-1-yl)-1-methyl-indazol-6-yl]-3,3-difluoro-1-piperidyl]-2-oxo-ethyl]-2,7-diazaspiro[3.5]nonan-2-yl]phenyl]-4-fluoro-1-oxo-isoindolin-2-yl]-N-thiazol-2-yl-acetamide, Compound 141

Step 1: 1-[6-[(4S)-3,3-difluoro-4-piperidyl]-1-methyl-indazol-3-yl]hexahydropyrimidine-2,4-dione

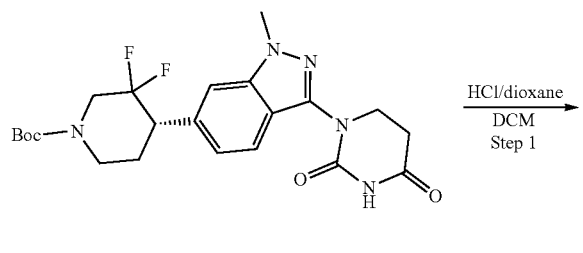

HCl/dioxane
DCM
Step 1

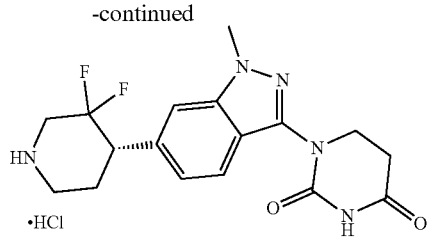

To a solution of tert-butyl (4S)-4-[3-(2,4-dioxohexahydropyrimidin-1-yl)-1-methyl-indazol-6-yl]-3,3-difluoro-piperidine-1-carboxylate (143 mg, 308.54 μmol) in dichloromethane (2 mL) was added hydrochloric acid in dioxane (4 M, 1 mL), the mixture was stirred at 25° C. for 2 h. The reaction mixture was concentrated under reduced pressure and the residue was triturated with diethyl ether and filtered to afford 1-[6-[(4S)-3,3-difluoro-4-piperidyl]-1-methyl-indazol-3-yl]hexahydropyrimidine-2,4-dione hydrochloride (116 mg, 290.13 μmol, 94.03% yield) as a white solid.

Step 2: 2-(6,7-dihydro-5H-pyrrolo[1,2-c]imidazol-1-yl)-2-[6-[4-[7-[2-[(4S)-4-[3-(2,4-dioxohexahydropyrimidin-1-yl)-1-methyl-indazol-6-yl]-3,3-difluoro-1-piperidyl]-2-oxo-ethyl]-2,7-diazaspiro[3.5]nonan-2-yl]phenyl]-4-fluoro-1-oxo-isoindolin-2-yl]-N-thiazol-2-yl-acetamide

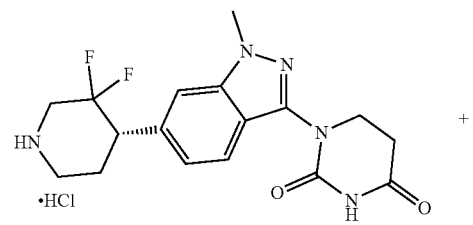

+

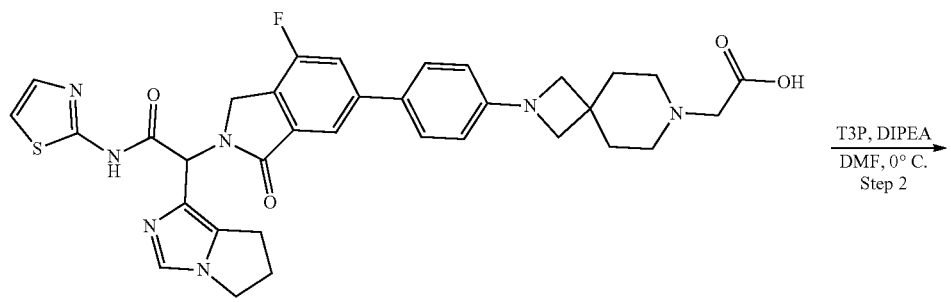

T3P, DIPEA
DMF, 0° C.
Step 2

-continued

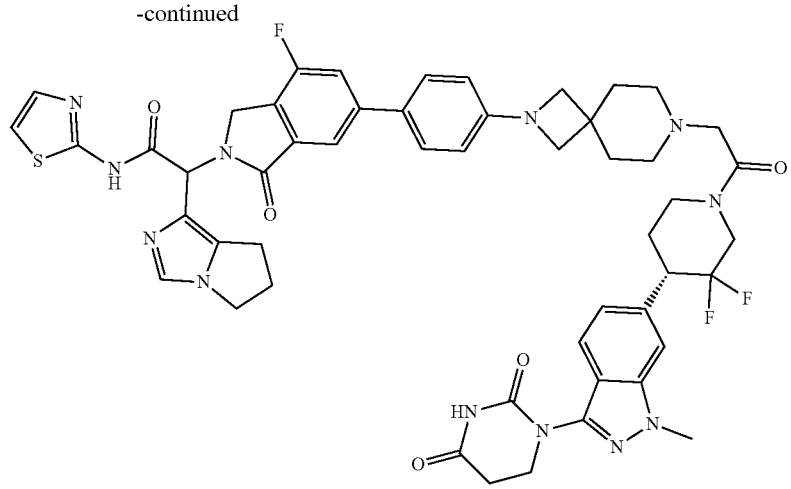

To a solution of 2-[2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-7-yl]acetic acid, trifluoroacetic acid salt (220 mg, 285.80 μmol) and propylphosphonic anhydride solution (50 wt. % in ethyl acetate) (272.81 mg, 428.70 μmol) in N,N-dimethylformamide (6 mL) was added N,N-diisopropylethylamine (295.50 mg, 2.29 mmol, 398.24 μL), The mixture was stirred at 0° C. for 20 minutes. 1-[6-[(4S)-3,3-difluoro-4-piperidyl]-1-methyl-indazol-3-yl]hexahydropyrimidine-2,4-dione hydrochloride (103.85 mg, 285.80 μmol) was added, the mixture was stirred at 0° C. for 60 min. Propylphosphonic anhydride solution (50 wt. % in ethyl acetate) (181.87 mg, 285.80 μmol) was added, the mixture was stirred at 0° C. for 60 min. The mixture was poured into water (50 mL) and neutralized with the saturated aqueous solution of sodium bicarbonate (30 mL). A white solid precipitated, which was collected by filtration. The solid was dissolved in dichloromethane and dried over sodium sulfate, filtered and concentrated under reduced pressure. The residue was purified by preparative HPLC. Column: Phenomenex Synergi C18 150*25 mm, 10 m; mobile phase: water (0.1% trifluoroacetic acid)-acetonitrile; gradient time: 10 min, then neutralized with saturated aqeuous solution of sodium bicarbonate (30 mL). A white solid precipitated, which was collected by filtration. The solid was washed with water (10 mL×2) and lyophilized to afford Compound 141 (57.22 mg, 57.16 μmol, 20.00% yield) as an off-white solid. LCMS (ESI): m/z 501.9 [M/2+H]$^+$, $^1$H NMR (400 MHz, DMSO-d$_6$) δ=10.57 (s, 1H), 7.76-7.67 (m, 2H), 7.66-7.58 (m, 4H), 7.57-7.47 (m, 2H), 7.26 (d, J=3.2 Hz, 1H), 7.08 (d, J=8.2 Hz, 1H), 6.56-6.49 (m, 2H), 6.15 (s, 1H), 4.88-4.65 (m, 2H), 4.59-4.27 (m, 1H), 4.22 (d, J=17.6 Hz, 1H), 4.05-3.96 (m, 5H), 3.93 (t, J=6.8 Hz, 2H), 3.62 (d, J=11.2 Hz, 4H), 3.58-3.47 (m, 1H), 3.46-3.40 (m, 1H), 3.30-3.23 (m, 1H), 3.22-3.04 (m, 2H), 2.84-2.74 (m, 3H), 2.64-2.54 (m, 2H), 2.39-2.39 (m, 1H), 2.47-2.37 (m, 4H), 2.33-2.20 (m, 1H), 2.18-1.89 (m, 2H), 1.89-1.73 (m, 4H).

Example 142

2-(6,7-dihydro-5H-pyrrolo[1,2-c]imidazol-1-yl)-2-[6-[1-[1-[2-[1-[4-[[(3S)-2,6-dioxo-3-piperidyl]amino]-2-fluoro-phenyl]-4-hydroxy-4-piperidyl]acetyl]-4-piperidyl]pyrazol-4-yl]-4-fluoro-1-oxo-isoindolin-2-yl]-N-thiazol-2-yl-acetamide, Compound 142

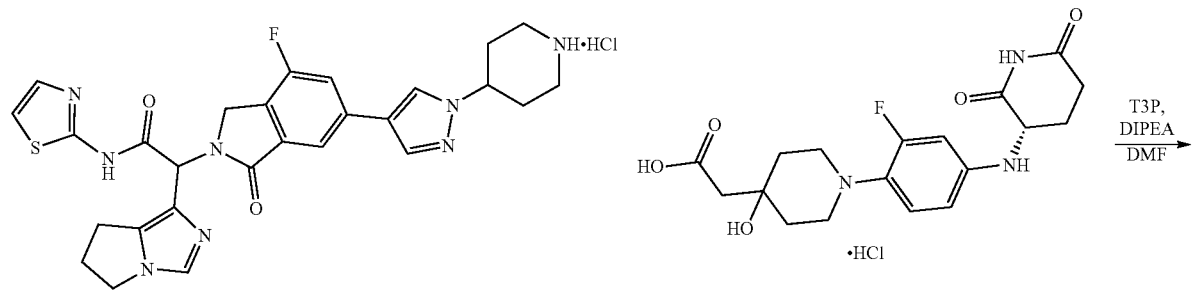

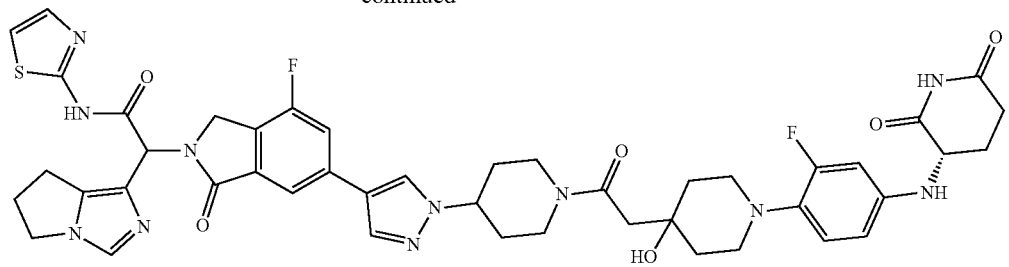

2-(6,7-dihydro-5H-pyrrolo[1,2-c]imidazol-1-yl)-2-[4-fluoro-1-oxo-6-[1-(4-piperidyl)pyrazol-4-yl]isoindolin-2-yl]-N-thiazol-2-yl-acetamide hydrochloride (310 mg, 531.66 umol) and 2-[1-[4-[[(3S)-2,6-dioxo-3-piperidyl]amino]-2-fluoro-phenyl]-4-hydroxy-4-piperidyl]acetic acid hydrochloride (265.30 mg, 637.99 umol) were mixed in DMF (4 mL). DIPEA (343.57 mg, 2.66 mmol, 463.03 uL) was added to the reaction mixture at 0° C. Propylphosphonic anhydride solution (422.91 mg, 1.33 mmol) was added to the reaction mixture at 0° C. The reaction mixture was stirred at rt for 1 h. The crude mixture was directly injected on a C-18 column (100 g) for purification while eluting (0% to 50% of Acetonitrile in water (with 0.1% NH$_4$OAc) over 50 minutes, then steep gradient to 100% acetonitrile). The pure fraction was frozen and lyophilized to afford Compound 142 (185.2 mg, 201.15 umol, 37.83% yield) as a free base off white solid. LCMS (ESI+): 908.8 [M+H]. $^1$H-NMR (400 MHz, DMSO-d6): δ 12.53 (s, 1H), 10.79 (s, 1H), 8.54 (s, 1H), 8.10 (s, 1H), 7.85 (s, 1H), 7.76 (d, J=10.40 Hz, 1H), 7.61 (s, 1H), 7.49 (d, J=3.20 Hz, 1H), 7.27 (d, J=3.60 Hz, 1H), 6.86 (t, J=9.60 Hz, 1H), 6.50 (d, J=16.80 Hz, 1H), 6.42 (d, J=8.80 Hz, 1H), 6.15 (s, 1H), 5.78 (d, J=7.20 Hz, 1H), 4.91 (s, 1H), 4.80 (d, J=17.60 Hz, 1H), 4.55 (d, J=12.00 Hz, 1H), 4.46 (t, J=11.20 Hz, 1H), 4.27-4.17 (m, 3H), 4.02-3.96 (m, 2H), 3.25 (s, 1H), 2.92-2.74 (m, 5H), 2.70 (d, J=5.60 Hz, 2H), 2.68 (s, 1H), 2.69 (s, 3H), 2.10 (t, J=4.80 Hz, 4H), 1.91 (d, J=12.00 Hz, 1H), 1.86 (d, J=3.20 Hz, 1H), 1.82 (t, J=12.80 Hz, 2H), 1.79-1.65 (m, 4H), [Expected H-47, Observed H-46].

Example 143

2-(6,7-dihydro-5H-pyrrolo[1,2-c]imidazol-1-yl)-2-[6-[4-[2-[2-[(4R)-4-[3-(2,4-dioxohexahydropyrimidin-1-yl)-1-methyl-indazol-6-yl]-3,3-difluoro-1-piperidyl]-2-oxo-ethyl]-2,7-diazaspiro[3.5]nonan-7-yl]phenyl]-4-fluoro-1-oxo-isoindolin-2-yl]-N-thiazol-2-yl-acetamide, Compound 143

Step 1: tert-Butyl 2-[7-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-2-yl]acetate

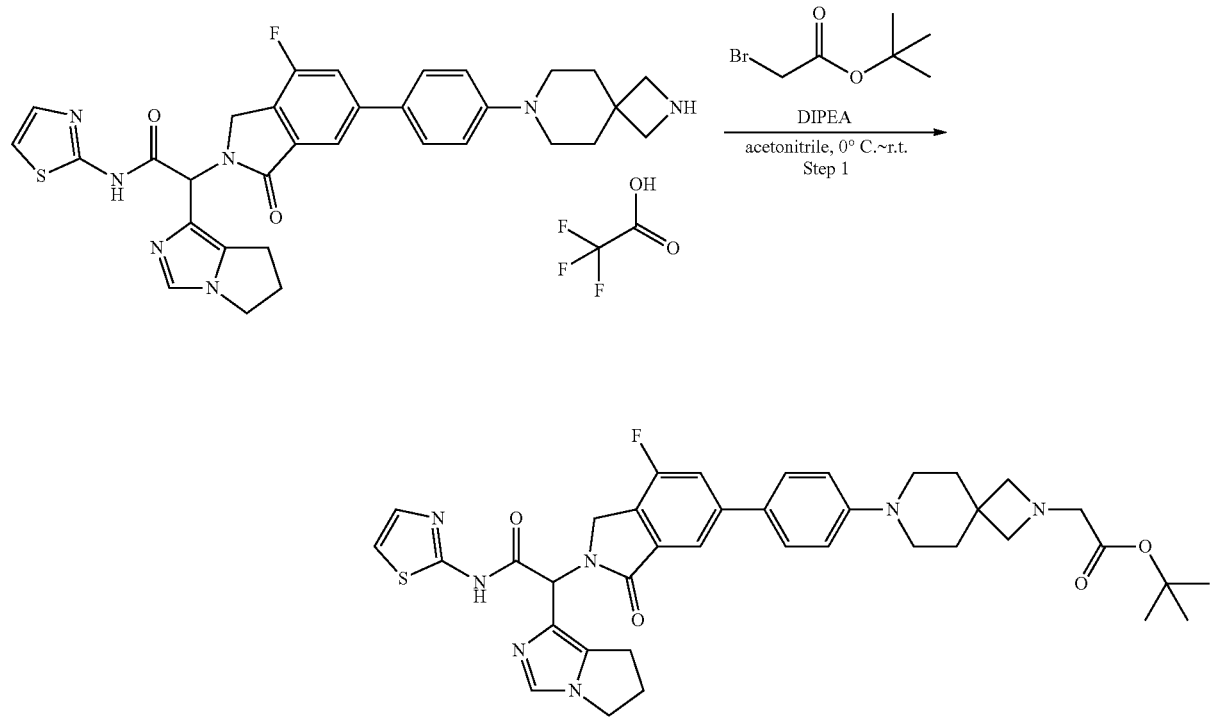

To a solution of 2-[6-[4-(2,7-diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (500 mg, 702.52 μmol) and N,N-diisopropylethylamine (544.76 mg, 4.22 mmol, 734.18 μL) in acetonitrile (20 mL) was added tert-butyl 2-chloroacetate (126.96 mg, 843.02 mol, 120.92 μL) in acetonitrile (10 mL) at 0° C. The mixture was warmed to 20° C. and stirred at 20° C. for 2 h. The reaction mixture was concentrated under reduced pressure to remove solvent, the reaction mixture was poured into a saturated sodium bicarbonate solution (50 mL), extracted with Ethyl acetate (50 mL×2). The combined organic layers were washed with brine (20 mL×2), dried over sodium sulfate, filtered and concentrated under reduced pressure to give a residue. The residue was purified by reverse phase flash chromatography (80 g Flash Column Welch Ultimate XB-C18 20-40 m, 5% to 32% acetonitrile in water, flow: 60 mL/min, 12 minutes) to afford tert-butyl 2-[7-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-2-yl]acetate (300 mg, 421.44 μmol, 59.99% yield) as a white solid. LCMS (ESI+): 712.3 (M+H)

Step 2: 2-[7-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-2-yl]acetic acid, trifluoroacetic acid salt

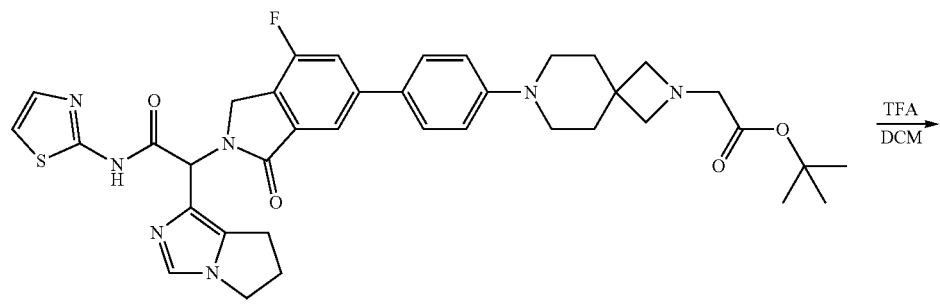

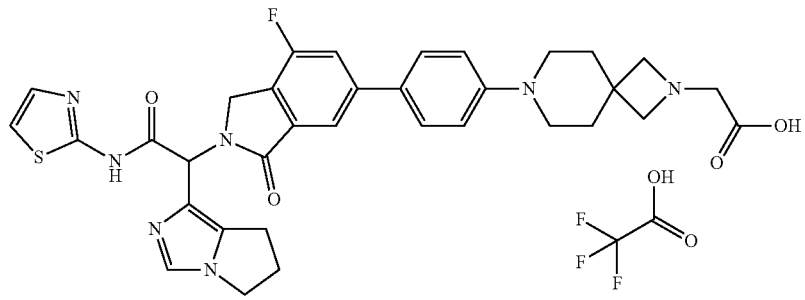

To a solution of tert-butyl 2-[7-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diaz-aspiro[3.5]nonan-2-yl]acetate (300 mg, 421.44 μmol) in dichloromethane (2 mL) was added trifluoroacetic acid (2.22 g, 19.47 mmol, 1.50 mL). The mixture was stirred at 25° C. for 3 h. The reaction mixture was concentrated under reduced pressure and the residue was triturated with diethyl ether and filtered to afford 2-[7-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diaz-aspiro[3.5]nonan-2-yl]acetic acid, trifluoroacetic acid salt (300 mg, 389.73 μmol, 92.48% yield) as a yellow solid. LCMS (ESI+): 656.2 (M+H).

Step 3: 2-(6,7-dihydro-5H-pyrrolo[1,2-c]imidazol-1-yl)-2-[6-[4-[2-[2-[(4R)-4-[3-(2,4-dioxohexahydropyrimidin-1-yl)-1-methyl-indazol-6-yl]-3,3-difluoro-1-piperidyl]-2-oxo-ethyl]-2,7-diazaspiro[3.5]nonan-7-yl]phenyl]-4-fluoro-1-oxo-isoindolin-2-yl]-N-thiazol-2-yl-acetamide

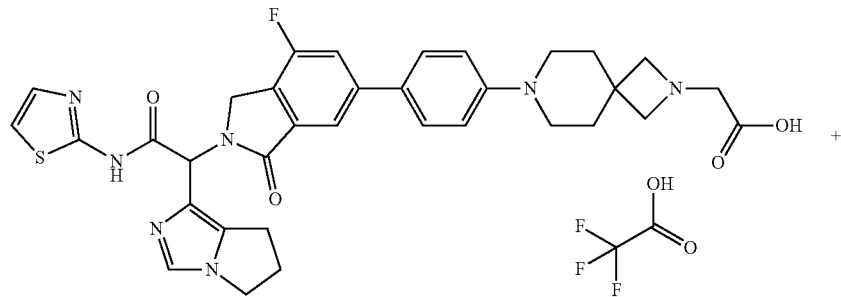

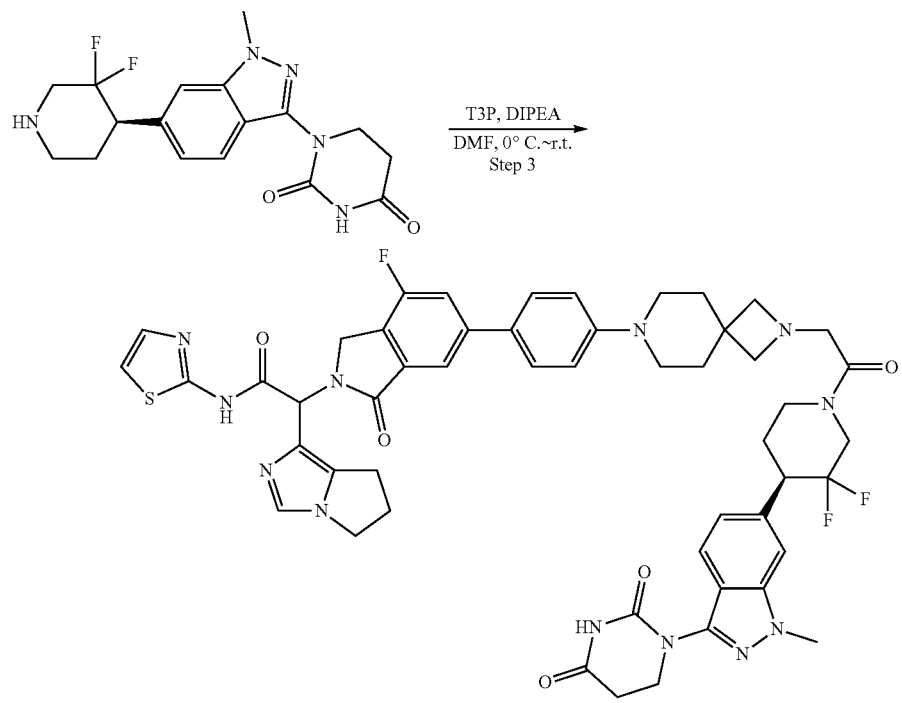

To a solution of 2-[7-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-2-yl]acetic acid, trifluoroacetic acid (80 mg, 103.93 µmol) and propylphosphonic anhydride solution, 50% in ethyl acetate (99.20 mg, 155.89 µmol) in N,N-dimethylformamide (2 mL) was added N,N-diisopropylethylamine (107.45 mg, 831.42 µmol, 144.82 µL). The mixture was stirred at 0° C. for 20 min; 1-[6-[(4R)-3,3-difluoro-4-piperidyl]-1-methyl-indazol-3-yl]hexahydropyrimidine-2,4-dione hydrochloride (41.55 mg, 103.93 µmol) was added, the mixture was stirred at 0° C. for 60 min. Propylphosphonic anhydride solution (50 wt. % in ethyl acetate) (66.14 mg, 103.93 µmol) was added, the mixture was stirred at 0° C. for 60 min. The mixture was poured into water (50 mL) and neutralized with a saturated aqueous solution of sodium bicarbonate (30 mL). A white solid precipitated, which was collected by filtration The solid was dissolved in dichloromethane and dried over sodium sulfate, filtered, and concentrated under reduced pressure. The residue was purified by preparative HPLC. (Column: Phenomenex Luna C18 150*40 mm 15 µm; eluent mixture: water (0.1% trifluoroacetic acid)-acetonitrile; gradient time: 10 minutes). The pure fractions were added to saturated aqueous solution of sodium bicarbonate (30 mL). The white precipitate was filtered. The solid was washed with water (10 mL×2) and submitted to high vacuum to afford Compound 143 (52.25 mg, 52.19 µmol, 50.22% yield) as a yellow solid. LCMS (ESI+): 501.8 (M/2+H), $^1$H NMR (400 MHz, DMSO-$d_6$) δ=12.53 (br s, 1H), 10.57 (s, 1H), 7.79-7.70 (m, 2H), 7.69-7.60 (m, 4H), 7.56-7.47 (m, 2H), 7.26 (d, J=3.6 Hz, 1H), 7.11-7.02 (m, 3H), 6.15 (s, 1H), 4.80 (d, J=17.6 Hz, 1H), 4.75-4.50 (m, 1H), 4.22 (d, J=17.6 Hz, 2H), 4.00 (s, 6H), 3.93 (t, J=6.8 Hz, 3H), 3.70-3.43 (m, 5H), 3.24 (br, 7H), 2.92-2.71 (m, 4H), 2.59-2.56 (m, 1H), 2.30 (br, 1H), 1.96 (d, J=2.0 Hz, 1H), 1.86 (br, 4H).

Example 144

2-(6,7-dihydro-5H-pyrrolo[1,2-c]imidazol-1-yl)-2-[6-[4-[2-[2-[(4S)-4-[3-(2,4-dioxohexahydropyrimidin-1-yl)-1-methyl-indazol-6-yl]-3,3-difluoro-1-piperidyl]-2-oxo-ethyl]-2,7-diazaspiro[3.5]nonan-7-yl]phenyl]-4-fluoro-1-oxo-isoindolin-2-yl]-N-thiazol-2-yl-acetamide, Compound 144

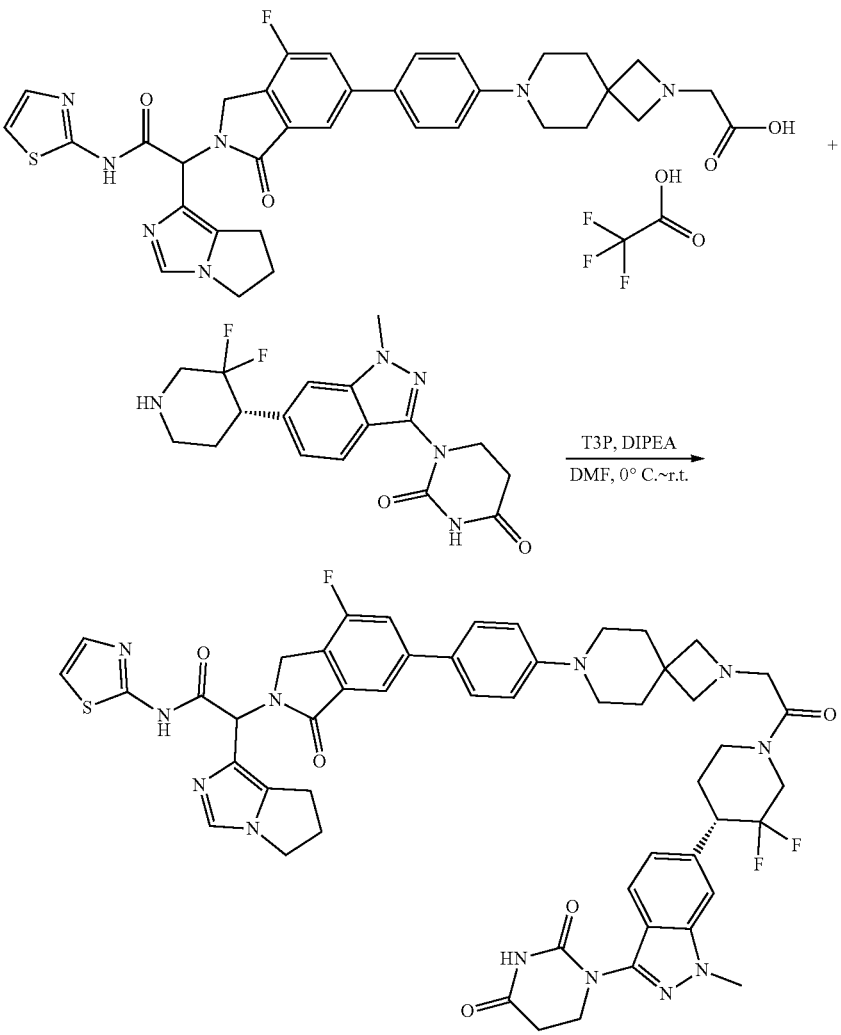

To a solution of 2-[7-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonan-2-yl]acetic acid, trifluoroacetic salt (220 mg, 285.80 µmol) and propylphosphonic anhydride solution (50 wt. % in ethyl acetate) (272.81 mg, 428.70 µmol) in N,N-dimethylformamide (5 mL) was added N,N-diisopropylethylamine (295.50 mg, 2.29 mmol, 398.24 µL). The mixture was stirred at 0° C. for 20 minutes. 1-[6-[(4S)-3,3-difluoro-4-piperidyl]-1-methyl-indazol-3-yl]hexahydropyrimidine-2,4-dione hydrochloride (103.85 mg, 285.80 µmol) was added, the mixture was stirred at 0° C. for 60 min. Propylphosphonic anhydride solution (50 wt. % in ethyl acetate) (181.87 mg, 285.80 µmol) was added, the mixture was stirred at 0° C. for 60 min. The mixture was poured into water (50 mL) and neutralized with a saturated aqueous solution of sodium bicarbonate (30 mL). The white solid precipitate was collected by filtration. The solid was dissolved in dichloromethane and dried over sodium sulfate, filtered, and concentrated under reduced pressure. The residue was purified by preparative HPLC: Column: Phenomenex luna C18 150*40 mm*15 m; mobile phase: [water (0.1% trifluoroacetic acid)-acetonitrile]; gradient time: 10 min). A saturated aqueous sodium bicarbonate solution (30 mL) was added to the pure fractions. The solid precipitate was collected by filtration. The solid was washed with water (10 mL×2) and lyophilized to afford Compound 144 (77.01 mg, 72.31 µmol, 25.30% yield) as a yellow solid. LCMS (ESI+): 501.2 (M/2+H), $^1$H NMR (400 MHz, DMSO-$d_6$) δ=12.76-12.23 (m, 1H), 10.57 (br s, 1H), 7.78-7.70 (m, 2H), 7.67-7.59 (m, 4H), 7.52 (s, 1H), 7.49 (d, J=3.6 Hz, 1H), 7.26 (d, J=3.6 Hz, 1H), 7.09-7.01 (m, 3H), 6.16 (s, 1H), 4.80 (d, J=17.6 Hz, 1H), 4.76-4.41 (m, 2H), 4.22 (d, J=17.6 Hz, 1H), 4.17-4.06 (m, 1H), 4.00 (s, 5H), 3.93 (t, J=6.8 Hz, 2H), 3.66-3.42 (m, 4H), 3.22 (br d, J=6.4 Hz, 5H), 3.16-3.06 (m, 4H), 2.77 (s, 3H), 2.59-2.55 (m, 1H), 2.29-2.06 (m, 1H), 1.98-1.90 (m, 1H), 1.85-1.77 (m, 4H), 1.24 (s, 1H)

Example 145

2-[6-[4-[2-[2-[1-[2-chloro-4-[[2,6-dioxo-3-piperidyl]amino]-6-fluoro-phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, isomer 1, Compound 145

Step 1: tert-butyl 2-[1-(2-chloro-6-fluoro-4-nitrophenyl)-4-hydroxy-4-piperidyl]acetate

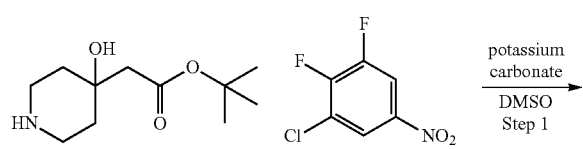

To a solution of tert-butyl 2-(4-hydroxy-4-piperidyl)acetate (8 g, 37.16 mmol) and 1-chloro-2,3-difluoro-5-nitrobenzene (6.54 g, 33.78 mmol) in DMSO (80 mL) was added potassium carbonate (14.01 g, 101.34 mmol, 6.12 mL). The mixture was stirred at 110° C. for 1 h. The reaction mixture was cooled to 20° C. and filtered. The filtrate was quenched with water (200 mL), precipitation was observed. the resulting mixture was filtered under vacuum to give a filter head and a filtrate. the filter head was concentrated under vacuum to afford tert-butyl 2-[1-(2-chloro-6-fluoro-4-nitro-phenyl)-4-hydroxy-4-piperidyl]acetate (13 g, 33.43 mmol, 98.97% yield) was obtained as a yellow. $^1$H-NMR (400 MHz, CDCl$_3$): 8.03-7.95 (m, 1H), 7.90-7.81 (m, 1H), 6.96-6.89 (m, 1H), 3.88 (s, 1H), 3.51-3.45 (m, 2H), 3.40-3.29 (m, 2H), 2.43 (s, 2H), 1.88-1.65 (m, 4H), 1.49 (s, 9H).

Step 2: tert-Butyl 2-[1-(4-amino-2-chloro-6-fluorophenyl)-4-hydroxy-4-piperidyl]acetate

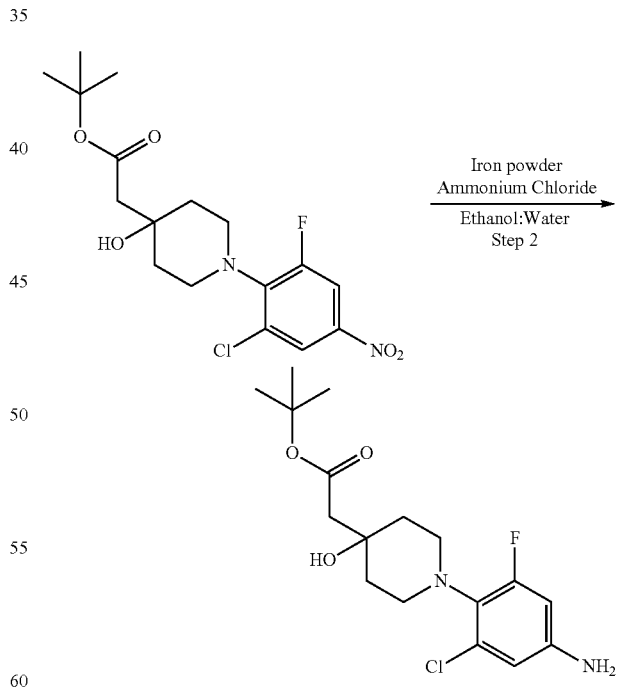

To the mixture of tert-butyl 2-[1-(2-chloro-6-fluoro-4-nitro-phenyl)-4-hydroxy-4-piperidyl]acetate (13 g, 33.43 mmol) in Water (40 mL), Ethanol (200 mL) was added Ammonium Chloride (8.94 g, 167.17 mmol, 5.84 mL). Iron powder (11.20 g, 200.61 mmol, 1.43 mL). The mixture was stirred at 90° C. for 1 h. The reaction mixture was cooled to 25° C. and Diatomite filtration. The reaction mixture was concentrated under reduced pressure to remove EtOH. The residue was diluted with water (300 mL) and extracted with ethyl acetate (300 mL×2). The combined organic layers were washed with brine (200 mL×2), dried over NaSO4, filtered and concentrated under reduced pressure to afford tert-butyl 2-[1-(4-amino-2-chloro-6-fluoro-phenyl)-4-hydroxy-4-piperidyl]acetate (11 g, 30.65 mmol, 91.69% yield) was obtained as an orange oil-). LCMS (ESI+): 359.2 (M+H)

Step 3: tert-Butyl 2-[1-[2-chloro-4-[(2,6-dibenzyloxy-3-pyridyl)amino]-6-fluoro-phenyl]-4-hydroxy-4-piperidyl]acetate

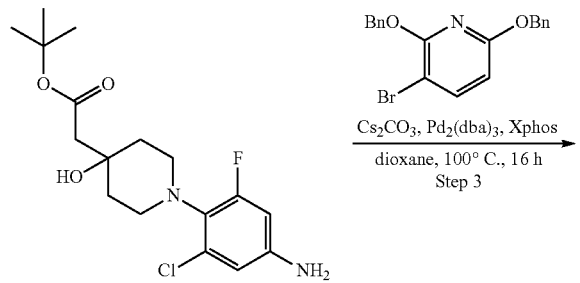

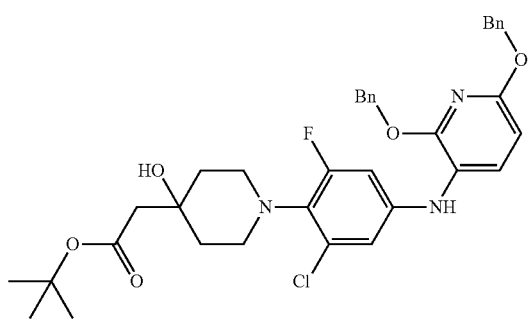

A stirred solution of tert-butyl 2-[1-(4-amino-2-chloro-6-fluoro-phenyl)-4-hydroxy-4-piperidyl]acetate (4.2 g, 11.70 mmol) and 2,6-dibenzyloxy-3-bromo-pyridine (6.50 g, 17.56 mmol) in 1,4-dioxane (45 mL), the reaction mixture was degassed with nitrogen for 15 minutes, cesium carbonate (11.44 g, 35.11 mmol), XPhos (557.97 mg, 1.17 mmol) and Pd2(dba)3 (1.07 g, 1.17 mmol) were added at 25° C. Degassing with nitrogen was continued for another 5 min. The reaction mixture was heated to 100° C. for 16 h under N2. The mixture was cooled to 25° C. and diluted with water (300 mL), extracted with ethyl acetate (2×200 mL). The combined organic layers were washed with brine (2×300 mL), dried over with sodium sulfate, filtered and concentrated under reduced pressure. The residue was purified by column chromatography (SiO2, Petroleum ether/Ethyl acetate=0/1 to 5/1) to afford tert-butyl 2-[1-[2-chloro-4-[(2,6-dibenzyloxy-3-pyridyl)amino]-6-fluoro-phenyl]-4-hydroxy-4-piperidyl]acetate (5.7 g, 8.79 mmol, 75.13% yield) was obtained as a yellow oil. LCMS (ES+): 648.2 [M+H]⁺

Step 4: tert-butyl 2-[1-[2-chloro-4-[(2,6-dioxo-3-piperidyl)amino]-6-fluoro-phenyl]-4-hydroxy-4-piperidyl]acetate

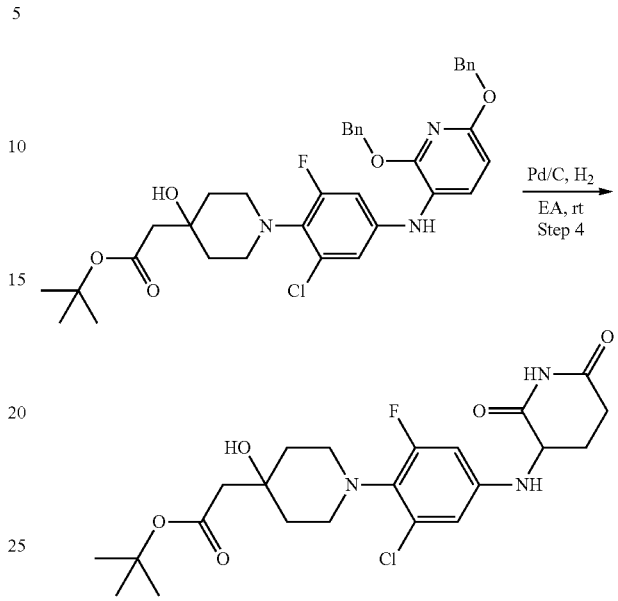

To the mixture of tert-butyl 2-[1-[2-chloro-4-[(2,6-dibenzyloxy-3-pyridyl)amino]-6-fluoro-phenyl]-4-hydroxy-4-piperidyl]acetate (5.6 g, 8.64 mmol) in Ethyl acetate (57 mL) was added palladium, 10% on charcoal (570 mg) and lithium chloride (732.55 mg, 17.28 mmol, 353.89 L) under N2. The mixture was stirred at 25° C. for 16 h under H2 atmosphere (35 Psi). The mixture was filtered, and the filter cake was washed with ethyl acetate. The filtrate was concentrated to give a residue. The residue was purified by column chromatography (silica gel, Petroleum ether/Ethyl acetate=5/1 to 2/1) to give tert-butyl 2-[1-[2-chloro-4-[(2,6-dioxo-3-piperidyl)amino]-6-fluoro-phenyl]-4-hydroxy-4-piperidyl] acetate (1.9 g, 4.04 mmol, 46.80% yield) as a blue solid. LCMS ¹H NMR (400 MHz, DMSO-d6) δ=10.80 (s, 1H), 6.60-6.56 (m, 1H), 6.44 (dd, J=2.4, 14.8 Hz, 1H), 6.21 (d, J=8.0 Hz, 1H), 4.44 (s, 1H), 4.39-4.28 (m, 1H), 3.30-3.17 (m, 2H), 2.78-2.64 (m, 3H), 2.55-2.51 (m, 1H), 2.33 (s, 2H), 2.11-2.01 (m, 1H), 1.92-1.83 (m, 1H), 1.79-1.69 (m, 2H), 1.62-1.55 (m, 2H), 1.41 (s, 9H)

Step 5: tert-butyl 2-[1-[2-chloro-4-[(2,6-dioxo-3-piperidyl)amino]-6-fluoro-phenyl]-4-hydroxy-4-piperidyl]acetate, isomer 1 and tert-butyl 2-[1-[2-chloro-4-[(2,6-dioxo-3-piperidyl)amino]-6-fluoro-phenyl]-4-hydroxy-4-piperidyl]acetate, isomer 2

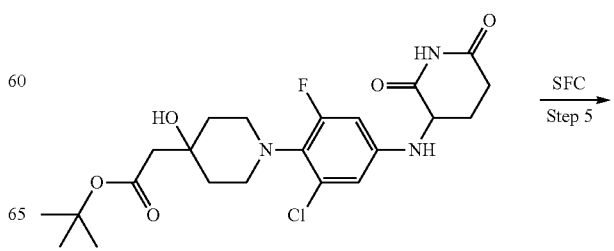

1175
-continued

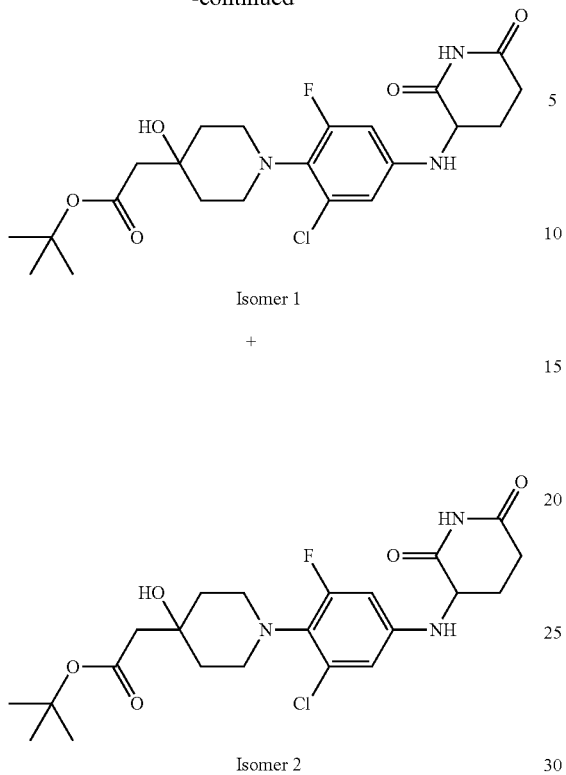

Isomer 1

+

Isomer 2

The tert-butyl 2-[1-[2-chloro-4-[(2,6-dioxo-3-piperidyl)amino]-6-fluoro-phenyl]-4-hydroxy-4-piperidyl]acetate (2.2 g, 4.68 mmol) was purified by prep-SFC (Sample preparation: add isopropyl alcohol and CH$_2$Cl$_2$ 100 mL into sample Instrument: Waters 80Q Mobile Phase: 50% isopropyl alcohol in Supercritical CO$_2$; Flow Rate: 70 g/min Cycle Time: 4.4 min, total time: 550 min Single injection volume: 1.5 mL Back Pressure: 100 bar to keep the CO$_2$ in Supercritical flow). To give tert-butyl 2-[1-[2-chloro-4-[[(3S)-2,6-dioxo-3-piperidyl]amino]-6-fluoro-phenyl]-4-hydroxy-4-piperidyl]acetate, isomer 1, (900 mg, 1.84 mmol, 39.27% yield) as a blue solid and tert-butyl 2-[1-[2-chloro-4-[[(3R)-2,6-dioxo-3-piperidyl]amino]-6-fluoro-phenyl]-4-hydroxy-4-piperidyl]acetate, isomer 2 (1 g, 2.13 mmol, 45.45% yield) as a blue solid.

1176

Step 6: 2-[1-[2-chloro-4-[[(3S)-2,6-dioxo-3-piperidyl]amino]-6-fluoro-phenyl]-4-hydroxy-4-piperidyl]acetate, isomer 1

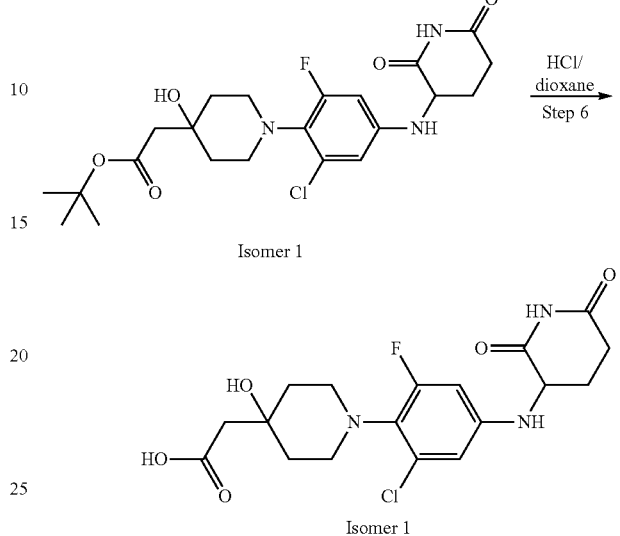

To a solution of tert-butyl 2-[1-[2-chloro-4-[[(3S)-2,6-dioxo-3-piperidyl]amino]-6-fluoro-phenyl]-4-hydroxy-4-piperidyl]acetate, isomer 1 (0.25 g, 531.99 µmol) in dichloromethane (3 mL) was added 4M hydrochloric acid in 1,4-dioxane (4 M, 3 mL). The mixture was stirred at 20° C. for 16 h. The reaction mixture was concentrated under reduced pressure. The residue was triturated with diethyl ether and filtered to give 2-[1-[2-chloro-4-[[(3S)-2,6-dioxo-3-piperidyl]amino]-6-fluoro-phenyl]-4-hydroxy-4-piperidyl]acetic acid hydrochloride (240 mg, 522.33 µmol, 98.18% yield) as a blue solid. LCMS (ES+): m/z 414.1 [M+H]$^+$ Step 7: 2-[6-[4-[2-[2-[1-[2-chloro-4-[[2,6-dioxo-3-piperidyl]amino]-6-fluoro-phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, isomer 1

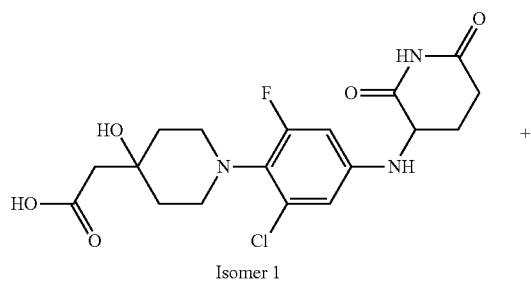

Isomer 1

+

Isomer 1

To a solution of 2-[1-[2-chloro-4-[[(3S)-2,6-dioxo-3-piperidyl]amino]-6-fluoro-phenyl]-4-hydroxy-4-piperidyl]acetic acid hydrochloride (240 mg, 532.99 μmol) and propylphosphonic anhydride solution (50 wt. % in ethyl acetate) 254.38 mg, 799.49 μmol) in N,N-dimethylformamide (4 mL) was added N,N-diisopropylethylamine (482.19 mg, 3.73 mmol, 649.85 μL). The mixture was stirred at 0° C. for 20 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (364.39 mg, 532.99 μmol) was added, the mixture was stirred at 0° C. for 1 h. To the mixture was added Propylphosphonic anhydride solution (50 wt. % in ethyl acetate) (152.63 mg, 479.69 μmol). The mixture was stirred at 0° C. for 1 h. The mixture was purified by preparative HPLC (Column: Phenomenex luna C18 150*40 mm*15 m, phase: water (+0.1% trifluoroacetic acid)-acetonitrile, B %: 23%-53%, 10 min) to give a solution. The solution was poured into saturated aqueous sodium bicarbonate aqueous solution. The mixture was filtered and the filter cake was washed with water (5 mL), filter cake was lyophilized to give Compound 145 (221.53 mg, 224.87 μmol, 42.19% yield) as a off-white solid. LCMS (ESI+): m/z 965.5 [M+H]+
1H NMR (400 MHz, DMSO-$d_6$) δ=12.51 (br s, 1H), 10.80 (s, 1H), 7.75-7.68 (m, 2H), 7.67-7.59 (m, 3H), 7.48 (d, J=3.6 Hz, 1H), 7.25 (d, J=3.6 Hz, 1H), 6.60-6.51 (m, 3H), 6.44 (dd, J=2.4, 14.8 Hz, 1H), 6.22 (d, J=8.0 Hz, 1H), 6.14 (s, 1H), 4.83-4.73 (m, 2H), 4.41-4.29 (m, 3H), 4.21 (d, J=17.6 Hz, 1H), 4.08 (s, 2H), 4.05-3.95 (m, 6H), 3.28-3.18 (m, 2H), 2.79-2.65 (m, 4H), 2.60-2.52 (m, 3H), 2.48-2.44 (m, 1H), 2.21 (s, 2H), 2.09-2.01 (m, 1H), 1.92-1.79 (m, 1H), 1.75-1.65 (m, 2H), 1.62-1.55 (m, 2H).

Example 146

2-(6,7-dihydro-5H-pyrrolo[1,2-c]imidazol-1-yl)-2-[6-[4-[2-[1-[4-[[2,6-dioxo-3-piperidyl]amino]-2-fluoro-phenyl]-4-hydroxy-piperidine-4-carbonyl]-2,6-diazaspiro[3.3]heptan-6-yl]phenyl]-4-fluoro-1-oxo-isoindolin-2-yl]-N-thiazol-2-yl-acetamide, isomer 1, Compound 146

Step 1: 1-(2-fluoro-4-nitro-phenyl)-4-hydroxy-piperidine-4-carbonitrile

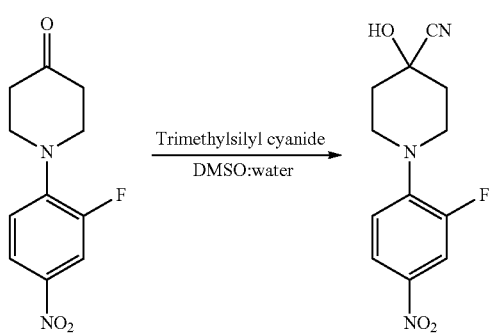 [SMILES: O=C1CCN(c2ccc([N+](=O)[O-])cc2F)CC1 ; N#CC1(O)CCN(c2ccc([N+](=O)[O-])cc2F)CC1]

To a stirred solution of 1-(2-fluoro-4-nitro-phenyl)piperidin-4-one (5.0 g, 20.99 mmol) in DMSO (50 mL) and water (5 mL) was added trimethylsilyl cyanide (4.16 g, 41.98 mmol) at room temperature, and the reaction mixture was stirred at ambient temperature for 16 h. The reaction mixture was poured in ice cold water and extracted with ethyl acetate (300 mL). Organic layer was washed with water (150 mL) followed by brine (50 mL). The residue was concentrated and purified over silica, using 10 to 50% ethyl acetate in petroleum ether as eluent. Collected fractions were distilled under reduced pressure to afford 1-(2-fluoro-4-nitro-phenyl)-4-hydroxy-piperidine-4-carbonitrile (4.6 g, 16.18 mmol, 77.09% yield) as yellow solid. LCMS m/z: 266.2 [M+1]

Step 2: 1-(2-fluoro-4-nitro-phenyl)-4-hydroxy-piperidine-4-carboxylic acid

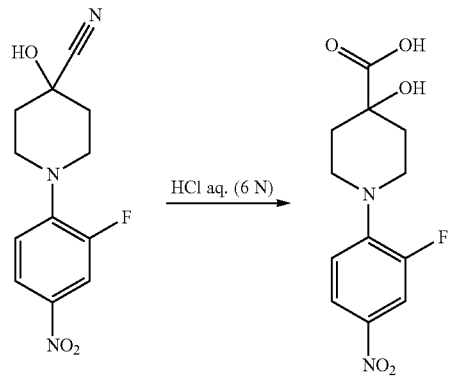 [SMILES: N#CC1(O)CCN(c2ccc([N+](=O)[O-])cc2F)CC1 ; O=C(O)C1(O)CCN(c2ccc([N+](=O)[O-])cc2F)CC1]

1-(2-fluoro-4-nitro-phenyl)-4-hydroxy-piperidine-4-carbonitrile (2.5 g, 9.43 mmol) was stirred in concentrated aqueous hydrochloric acid (6 N) (30 mL) in sealed tube at 85° C. for 16 h. The reaction was cooled to room temperature and reaction mass was quenched in crushed ice. The precipitated solid was filtered, washed with water, and dried to afford 1-(2-fluoro-4-nitro-phenyl)-4-hydroxy-piperidine-4-carboxylic acid (2.15 g, 7.06 mmol, 74.87% yield) as yellow solid. LCMS m/z: 285.2 [M+1]

Step 3: Benzyl 1-(2-fluoro-4-nitro-phenyl)-4-hydroxy-piperidine-4-carboxylate

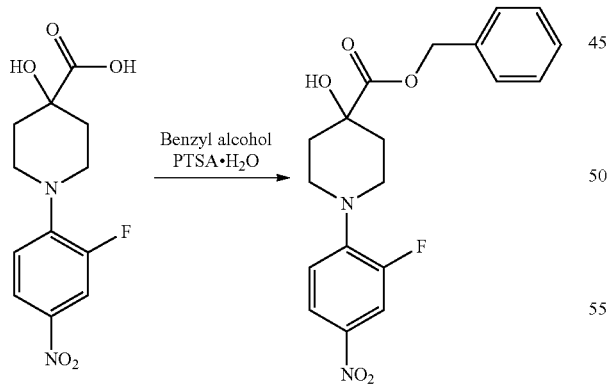

To a stirred suspension of 1-(2-fluoro-4-nitro-phenyl)-4-hydroxy-piperidine-4-carboxylic acid (2.1 g, 7.39 mmol) in Toluene (20 mL) was added p-toluenesulfonic acid monohydrate (140.52 mg, 738.81 µmol) followed by benzyl alcohol (3.99 g, 36.94 mmol, 3.82 mL) at ambient temperature. Reaction mixture was stirred at 60° C. for 12 h. The reaction mixture was cooled to room temperature and quenched with ice cold water. Extracted with ethyl acetate (200 mL×2). Organic layer was washed with water followed by brine (100 mL), concentrated and purified over silica, eluted compound using a 10 to 40% ethyl acetate in petroleum ether. The collected fractions were distilled to afford benzyl 1-(2-fluoro-4-nitro-phenyl)-4-hydroxy-piperidine-4-carboxylate (2.0 g, 5.01 mmol, 67.76% yield) as yellow solid. LCMS m/z: 375.2 [M+1]

Step 4: Benzyl 1-(4-amino-2-fluoro-phenyl)-4-hydroxy-piperidine-4-carboxylate

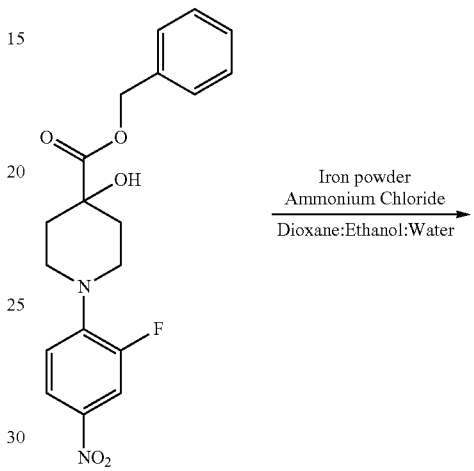

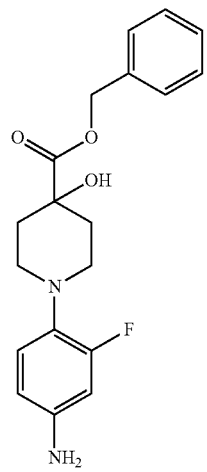

Benzyl 1-(4-amino-2-fluoro-phenyl)-4-hydroxy-piperidine-4-carboxylate was synthesized in 92.34% yield from benzyl 1-(2-fluoro-4-nitro-phenyl)-4-hydroxy-piperidine-4-carboxylate using a protocol similar to that used for the synthesis of tert-butyl 2-[1-(4-amino-2-fluoro-phenyl)-4-hydroxy-4-piperidyl]acetate. LCMS m/z: 345.2 [M+H]

Step 5: Benzyl 1-[4-[(2,6-dioxo-3-piperidyl)amino]-2-fluoro-phenyl]-4-hydroxy-piperidine-4-carboxylate

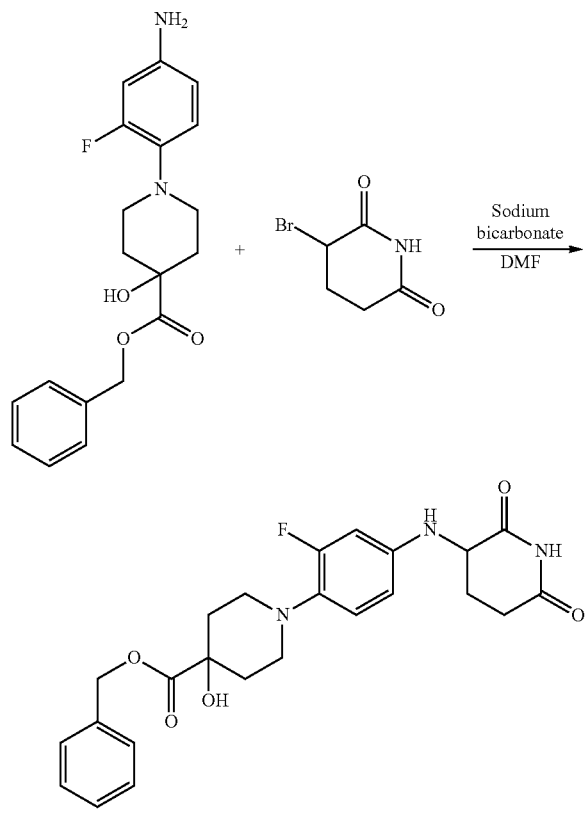

Benzyl 1-[4-[(2,6-dioxo-3-piperidyl)amino]-2-fluoro-phenyl]-4-hydroxy-piperidine-4-carboxylate was synthesized in 74% yield from benzyl 1-(4-amino-2-fluoro-phenyl)-4-hydroxy-piperidine-4-carboxylate using a protocol similar to that used for the synthesis tert-butyl 2-[1-[4-[(2,6-dioxo-3-piperidyl)amino]-2-fluoro-phenyl]-4-hydroxy-4-piperidyl]acetate. LCMS m/z: 456.0 [M+H]

Step 6: Benzyl 1-[4-[[2,6-dioxo-3-piperidyl]amino]-2-fluoro-phenyl]-4-hydroxy-piperidine-4-carboxylate, isomer 1 and benzyl 1-[4-[[2,6-dioxo-3-piperidyl]amino]-2-fluoro-phenyl]-4-hydroxy-piperidine-4-carboxylate, isomer 2

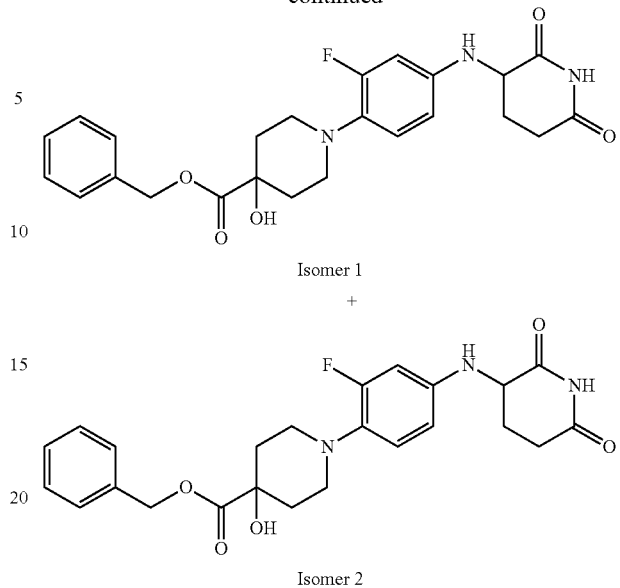

Racemic benzyl 1-[4-[(2,6-dioxo-3-piperidyl)amino]-2-fluoro-phenyl]-4-hydroxy-piperidine-4-carboxylate (1.9 g, 4.17 mmol) was submitted to chiral SFC (Column: YMC Cellulose-C [250*30 mm, 5 micron]; Mobile phase: CO2: 0.5% Isopropyl amine in isopropyl alcohol (60:40); flow rate: 100 g/min; cycle time: 6.3 min; back pressure: 100 bar; UV: 210 nm) to afford two sets of fractions.

The first eluting set of fractions was evaporated to afford benzyl 1-[4-[[2,6-dioxo-3-piperidyl]amino]-2-fluoro-phenyl]-4-hydroxy-piperidine-4-carboxylate, isomer 1 (750 mg, 1.63 mmol, 39.16% yield) as a brown solid. Analytical SFC (Column: YMC Cellulose-C [250*30 mm, 5 micron]; Mobile phase: CO2: 0.5% Isopropyl amine in isopropyl alcohol (60:40); flow rate: 100 g/min; cycle time: 6.3 min; back pressure: 100 bar; UV: 210 nm): Rt=3.73 min., 92.77% ee.

The second eluting set of fractions was evaporated to afford benzyl 1-[4-[[2,6-dioxo-3-piperidyl]amino]-2-fluoro-phenyl]-4-hydroxy-piperidine-4-carboxylate, isomer 2 (700 mg, 1.52 mmol, 36.54% yield) as brown solid. Analytical SFC (Column: YMC Cellulose-C [250*30 mm, 5 micron]; Mobile phase: CO2: 0.5% Isopropyl amine in isopropyl alcohol (60:40); flow rate: 100 g/min; cycle time: 6.3 min; back pressure: 100 bar; UV: 210 nm): Rt=4.53 min., 50.62% ee.

Step 7: 1-[4-[[2,6-dioxo-3-piperidyl]amino]-2-fluoro-phenyl]-4-hydroxy-piperidine-4-carboxylic acid, isomer 1

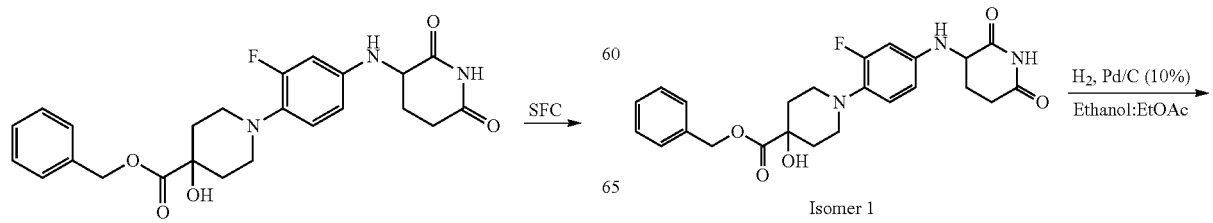

1183

-continued

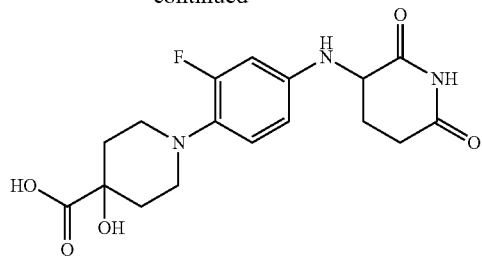

Isomer 1

To a stirred solution of benzyl 1-[4-[[(3S)-2,6-dioxo-3-piperidyl]amino]-2-fluoro-phenyl]-4-hydroxy-piperidine-4-carboxylate (200 mg, 439.10 µmol) in ethyl acetate (10 mL)

and ethanol (10 mL) was added palladium, 10% on carbon (100 mg, 439.10 µmol) and the reaction mixture was hydrogenated under balloon pressure at room temperature for 12 h. The reaction mixture was filtered over celite bed and washed with 10% methanol-dichloromethane. Filtrate was concentrated under reduced pressure afforded 1-[4-[[(3S)-2,6-dioxo-3-piperidyl]amino]-2-fluoro-phenyl]-4-hydroxy-piperidine-4-carboxylic acid, isomer 1 (145 mg, 313.93 µmol, 71.49% yield) as blue solid. LCMS (m/z: 366.1 [M+1])

Step 8: 2-(6,7-dihydro-5H-pyrrolo[1,2-c]imidazol-1-yl)-2-[6-[4-[2-[1-[4-[[2,6-dioxo-3-piperidyl]amino]-2-fluoro-phenyl]-4-hydroxy-piperidine-4-carbonyl]-2,6-diazaspiro[3.3]heptan-6-yl]phenyl]-4-fluoro-1-oxo-isoindolin-2-yl]-N-thiazol-2-yl-acetamide, isomer 1

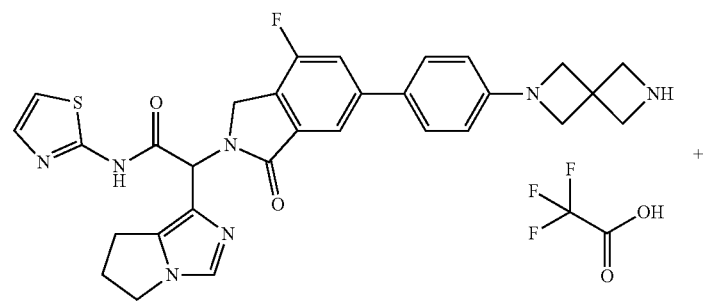

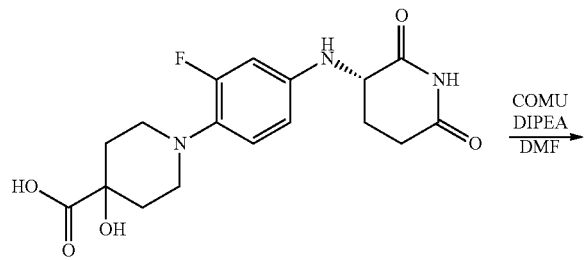

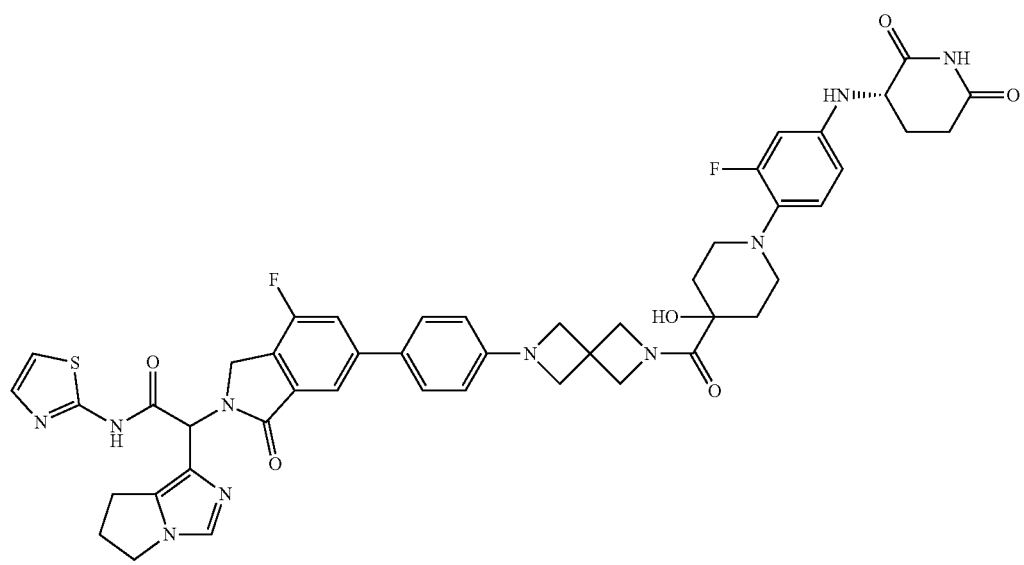

To a stirred solution of 1-[4-[[2,6-dioxo-3-piperidyl]amino]-2-fluoro-phenyl]-4-hydroxy-piperidine-4-carboxylic acid, isomer 1 (69.47 mg, 190.15 μmol) in N,N-dimethylformamide (3 mL) at 0° C. was added N,N-diisopropylethylamine (122.88 mg, 950.75 μmol, 165.60 L) followed by 1-[(1-(cyano-2-ethoxy-2-oxoethylideneaminooxy)-dimethylamino-morpholino)] uronium hexafluorophosphate (104.86 mg, 247.19 μmol). The reaction mixture was stirred for 5 minutes. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (130 mg, 190.15 μmol) was added while maintaining 0° C., and the reaction mixture was stirred for 45 min while warming to room temperature. The crude reaction mixture was purified by C18 column (120 g) for purification (0% to 60% acetonitrile in water (+0.1% ammonium acetate) over 45 minutes, then steep gradient to 100% acetonitrile). The pure fractions were frozen and lyophilized to afford product Compound 146 (19 mg, 18.47 mol, 9.72% yield) as an off white solid. LCMS m/z: 917.2 [M+H], $^1$H-NMR (400 MHz, DMSO-d6): δ 12.54 (s, 1H), 10.82 (s, 1H), 7.89-7.74 (m, 6H), 7.61 (s, 1H), 7.37 (s, 1H), 6.99 (t, J=9.20 Hz, 1H), 6.66 (t, J=17.20 Hz, 4H), 6.27 (s, 1H), 5.94 (d, J=7.60 Hz, 2H), 5.30 (s, 1H), 4.96 (d, J=18.40 Hz, 1H), 4.752 (s, 2H), 4.40-4.33 (m, 2H), 4.23-4.13 (m, 10H), 3.03 (t, J=11.20 Hz, 5H), 2.90-2.82 (m, 3H), 2.19-2.14 (m, 3H), 2.01-1.90 (m, 2H), 1.77 (d, J=12.80 Hz, 2H).

Example 147

2-(6,7-dihydro-5H-pyrrolo[1,2-c]imidazol-1-yl)-2-[6-[4-[2-[2-[1-[4-(2,4-dioxohexahydropyrimidin-1-yl)-2-fluoro-phenyl]-4-hydroxy-4-piperidyl]acetyl]-2,6-diazaspiro[3.3]heptan-6-yl]phenyl]-4-fluoro-indazol-2-yl]-N-thiazol-2-yl-acetamide, Compound 147

Step 1: 3-[3-fluoro-4-[4-hydroxy-4-(2-methoxy-2-oxo-ethyl)-1-piperidyl]anilino]propanoic acid

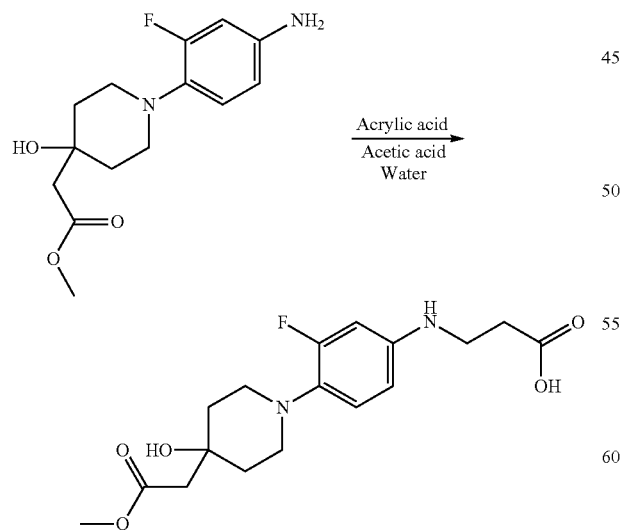

To a solution of methyl 2-[1-(4-amino-2-fluoro-phenyl)-4-hydroxy-4-piperidyl]acetate (3.5 g, 12.40 mmol) in water (24 mL) and acetic acid (6 mL) was added acrylic acid (1.07 g, 14.88 mmol, 1.02 mL). The reaction mixture was heated at 100° C. for 14 h. The reaction mixture was concentrated under reduced pressure. The residue was diluted with ethyl acetate (60 mL). The ethyl acetate layer was dried over sodium sulfate, filtered and concentrated under reduced pressure to afford 3-[3-fluoro-4-[4-hydroxy-4-(2-methoxy-2-oxo-ethyl)-1-piperidyl]anilino]propanoic acid (4.0 g, 6.66 mmol, 53.72% yield). LCMS: 355.1 [M+H]$^+$.

Step 2: Methyl 2-[1-[4-(2,4-dioxohexahydropyrimidin-1-yl)-2-fluoro-phenyl]-4-hydroxy-4-piperidyl]acetate

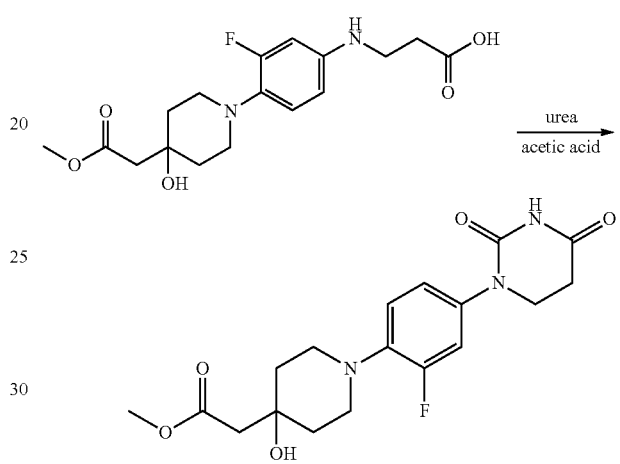

To a solution of 3-[3-fluoro-4-[4-hydroxy-4-(2-methoxy-2-oxo-ethyl)-1-piperidyl]anilino]propanoic acid (4.0 g, 11.29 mmol) in acetic acid (15 mL) was added urea (1.36 g, 22.58 mmol, 1.01 mL). The reaction mixture was heated to 110° C. in sealed tube for 14 h. The reaction mixture was concentrated under reduced pressure. The residue was diluted with ethyl acetate (100 mL), washed with a saturated sodium bicarbonate solution (30 mL), water (30 mL) and brine solution (30 mL). The organic layer was dried over sodium sulfate and concentrated under reduced. The residue was purified by column chromatography on silica gel, eluting with 60% ethyl acetate in petroleum ether, to afford methyl 2-[1-[4-(2,4-dioxohexahydropyrimidin-1-yl)-2-fluoro-phenyl]-4-hydroxy-4-piperidyl]acetate (1.6 g, 3.65 mmol, 32.36% yield) as a light brown solid. LCMS m/z: 380.1 [M+H]$^+$.

Step 3: 2-[1-[4-(2,4-dioxohexahydropyrimidin-1-yl)-2-fluoro-phenyl]-4-hydroxy-4-piperidyl]acetic acid hydrochloride

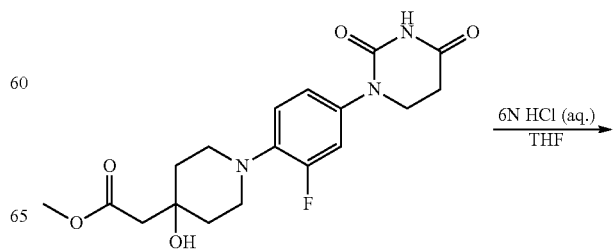

-continued

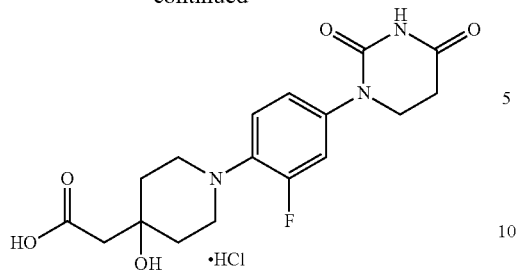

To a solution of methyl 2-[1-[4-(2,4-dioxohexahydropyrimidin-1-yl)-2-fluoro-phenyl]-4-hydroxy-4-piperidyl]acetate (300 mg, 790.76 μmol) in THE (2 mL) was added 6N HCl (6 M, 7.50 mL) and stirred at room temperature for 14 h. The reaction mixture was concentrated under reduced pressure to afford 2-[1-[4-(2,4-dioxohexahydropyrimidin-1-yl)-2-fluoro-phenyl]-4-hydroxy-4-piperidyl]acetic acid hydrochloride (280 mg, 648.06 μmol, 81.95% yield) as a brown gum. LCMS m/z 366.2 [M+H]$^+$ Step 4: 2-(6,7-dihydro-5H-pyrrolo[1,2-c]imidazol-1-yl)-2-[6-[4-[2-[2-[1-[4-(2,4-dioxohexahydropyrimidin-1-yl)-2-fluoro-phenyl]-4-hydroxy-4-piperidyl]acetyl]-2,6-diazaspiro[3.3]heptan-6-yl]phenyl]-4-fluoro-indazol-2-yl]-N-thiazol-2-yl-acetamide

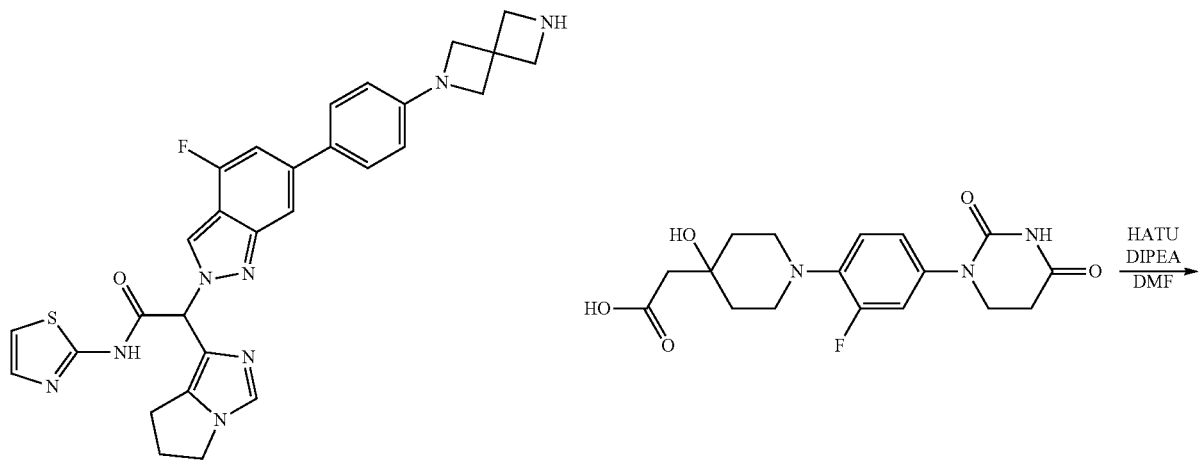

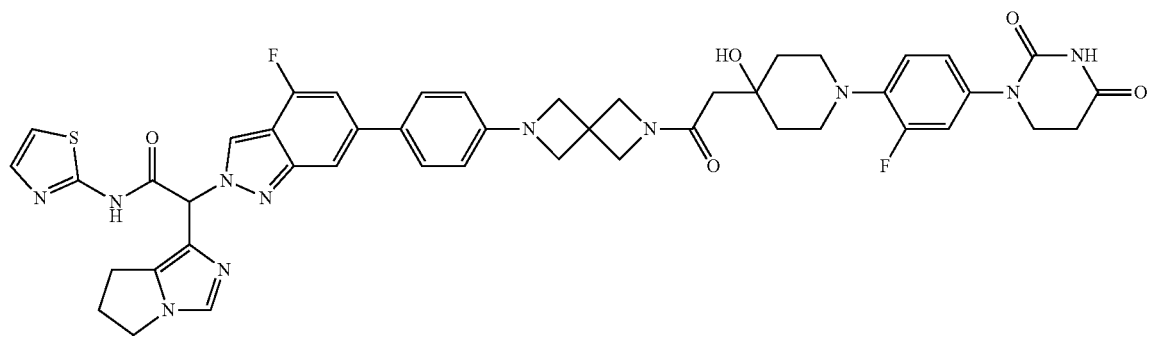

To a stirred solution of 2-[6-[4-(2,6-diazaspiro[3.3]heptan-2-yl)phenyl]-4-fluoro-indazol-2-yl]-2-(6,7-dihydro-5H-pyrrolo[1,2-c]imidazol-1-yl)-N-thiazol-2-yl-acetamide, trifluoroacetic acid salt (140 mg, 209.37 μmol) and 2-[1-[4-(2,4-dioxohexahydropyrimidin-1-yl)-2-fluoro-phenyl]-4-hydroxy-4-piperidyl]acetic acid hydrochloride (100.96 mg, 251.25 μmol) in N,N-dimethylformamide (1 mL) was cooled to 0° C. N,N-Diisopropylethylamine (162.36 mg, 1.26 mmol, 218.81 μL) was added to a reaction mixture followed by HATU (103.49 mg, 272.18 mol) at 0° C. The reaction mixture stirred at ambient temperature for 1 h. The reaction mixture was directly injected on a C-18 column (100 g) for purification (0-45% Acetonitrile in water (+0.1% ammonium acetate) over 30 minutes, then steep gradient to 100% acetonitrile). The pure fractions were combined and lyophilized to afford Compound 147 (50 mg, 54.46 μmol, 26.01% yield) as an off-white solid. LCMS m/z 901.8 (M+H)$^+$. $^1$H-NMR (400 MHz, DMSO-d6): δ 12.82 (d, J=3.20 Hz, 1H), 10.37 (s, 1H), 8.25 (s, 1H), 7.69 (s, 1H), 7.61-7.59 (m, 3H), 7.51 (d, J=3.60 Hz, 1H), 7.29-7.28 (m, 1H), 7.18-7.10 (m, 2H), 7.07-7.05 (m, 2H), 6.69 (s, 1H), 6.54 (d, J=8.80 Hz, 2H), 4.84 (s, 1H), 4.39 (s, 2H), 4.09 (s, 2H), 4.12-3.38 (m, 6H), 3.74 (t, J=6.80 Hz, 2H), 3.09-2.98 (m, 5H), 2.89-2.83 (m, 1H), 2.71-2.67 (m, 2H), 2.59-2.58 (m, 2H), 2.25 (s, 2H), 1.83-1.78 (m, 2H), 1.68-1.65 (m, 2H).

Example 148

2-(6,7-dihydro-5H-pyrrolo[1,2-c]imidazol-1-yl)-2-[6-[4-[2-[2-[(2s,6r)-1-[4-[(2,6-dioxo-3-piperidyl)amino]-2-fluoro-phenyl]-4-hydroxy-2,6-dimethyl-4-piperidyl]acetyl]-2,6-diazaspiro[3.3]heptan-6-yl]phenyl]-4-fluoro-indazol-2-yl]-N-thiazol-2-yl-acetamide, Compound 148

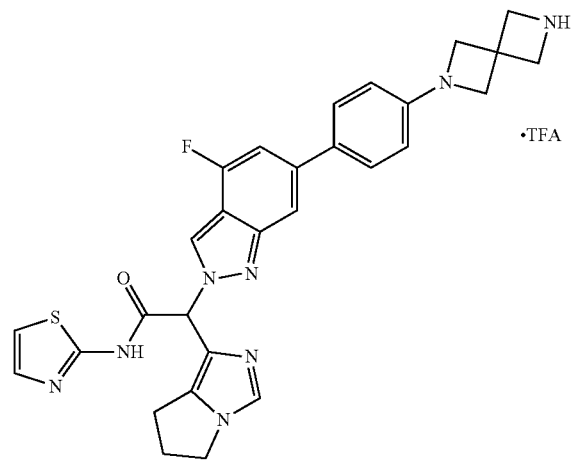 + 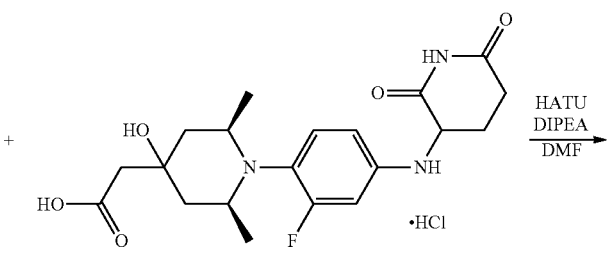

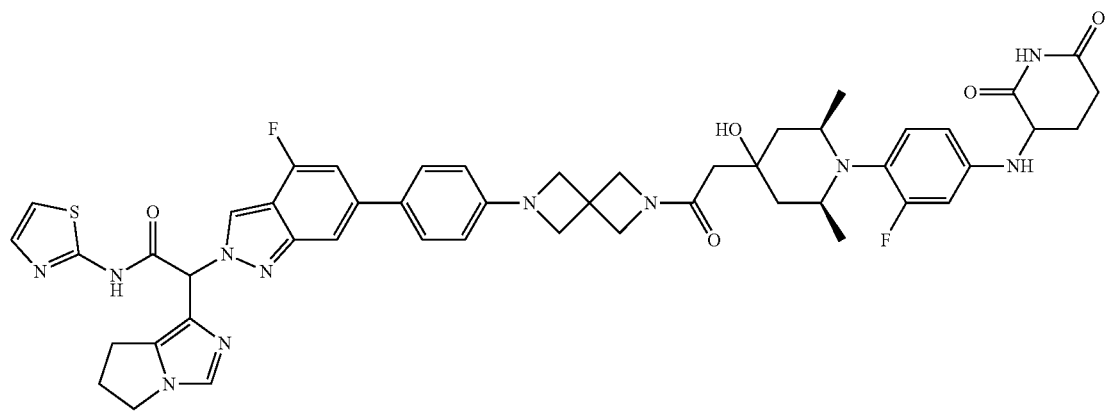

A stirred solution of 2-[6-[4-(2,6-diazaspiro[3.3]heptan-2-yl)phenyl]-4-fluoro-indazol-2-yl]-2-(6,7-dihydro-5H-pyrrolo[1,2-c]imidazol-1-yl)-N-thiazol-2-yl-acetamide, trifluoroacetic acid (70 mg, 104.69 μmol) and 2-[(2s,6r)-1-[4-[(2,6-dioxo-3-piperidyl)amino]-2-fluoro-phenyl]-4-hydroxy-2,6-dimethyl-4-piperidyl]acetic acid hydrochloride (55.76 mg, 125.62 μmol) in N,N-dimethylformamide (2 mL) was cooled to 0° C. N,N-Diisopropylethylamine (81.18 mg, 628.12 mol, 109.41 μL) was added to the reaction mixture followed by HATU (51.75 mg, 136.09 mol) at 0° C. The reaction mixture stirred at ambient temperature for 2 h. The reaction mixture was directly injected on a C-18 column (100 g) for purification (0-45% Acetonitrile in water (with 0.1% ammonium acetate) over 30 minutes, then steep gradient to 100% acetonitrile). The pure fractions were combined and lyophilized to afford Compound 148 (28 mg, 28.50 μmol, 27.23% yield) as an off-white solid. LCMS m/z 944.8 (M+H)⁺. ¹H-NMR (400 MHz, DMSO-d6): δ 12.83 (s, 1H), 10.81 (s, 1H), 8.26 (s, 1H), 7.70 (s, 1H), 7.60 (d, J=7.60 Hz, 3H), 7.52 (d, J=3.60 Hz, 1H), 7.29 (d, J=3.20 Hz, 1H), 7.14-7.11 (m, 1H), 6.88-6.83 (m, 1H), 6.70 (s, 1H), 6.55-6.53 (m, 2H), 6.45-6.41 (m, 2H), 5.91-5.90 (m, 1H), 4.83-4.81 (m, 1H), 4.39-4.34 (m, 2H), 4.31-4.22 (m, 1H), 4.11-4.07 (m, 2H), 3.68-3.57 (m, 1H), 3.28-3.18 (m, 1H), 2.86-2.71 (m, 2H), 2.68-2.55 (m, 5H), 2.18-2.09 (m, 4H), 1.90-1.87 (m, 3H), 1.73-1.60 (m, 3H), 1.40-1.37 (m, 1H), 1.05-1.03 (m, 4H).

Example 149

2-(6,7-dihydro-5H-pyrrolo[1,2-c]imidazol-1-yl)-2-[6-[4-[4-[2-[4-[[(3S)-2,6-dioxo-3-piperidyl]amino]-2-fluoro-phenyl]-1-piperidyl]-2-oxo-ethyl]-4-hydroxy-1-piperidyl]phenyl]-7-fluoro-indazol-2-yl]-N-thiazol-2-yl-acetamide, Compound 149

Step 1: [2-(6-bromo-7-fluoro-indazol-2-yl)-2-(6,7-dihydro-5H-pyrrolo[1,2-c]imidazol-1-yl)acetyl]oxylithium

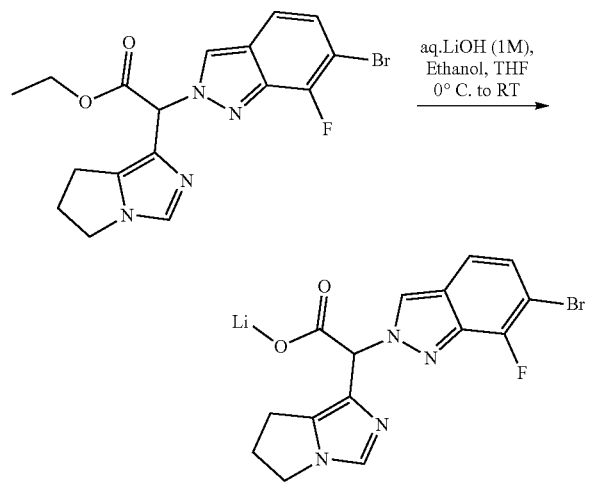

To a stirred solution of ethyl 2-(6-bromo-7-fluoro-indazol-2-yl)-2-(6,7-dihydro-5H-pyrrolo[1,2-c]imidazol-1-yl)acetate (500 mg, 1.23 mmol) in tetrahydrofuran (5 mL), Ethanol (5 mL) and Water (5 mL) was added Lithium hydroxide, monohydrate (77.28 mg, 1.84 mmol, 51.18 μL) at 0° C. The reaction mixture was stirred at room temperature for 2 h. The mixture was concentrated under reduced pressure, co-distilled with toluene (2×25 mL). The residue was stirred with diethyl ether (25 mL), decanted and dried to afford [2-(6-bromo-7-fluoro-indazol-2-yl)-2-(6,7-dihydro-5H-pyrrolo[1,2-c]imidazol-1-yl)acetyl]oxylithium (460 mg, 1.07 mmol, 86.95% yield) as a brown solid. LCMS (ESI+): 379.0 [M+H]⁺

Step 2: 2-(6-bromo-7-fluoro-indazol-2-yl)-2-(6,7-dihydro-5H-pyrrolo[1,2-c]imidazol-1-yl)-N-thiazol-2-yl-acetamide

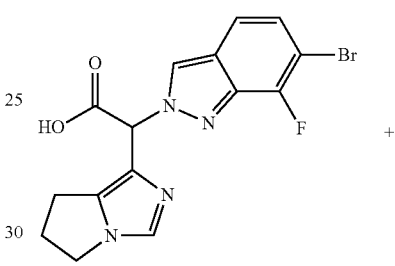

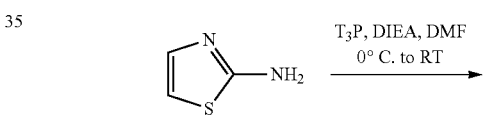

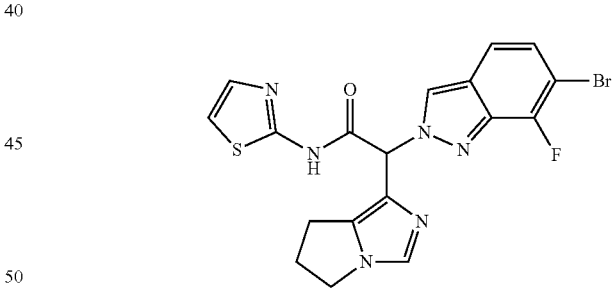

To a stirred solution of 2-(6-bromo-7-fluoro-indazol-2-yl)-2-(6,7-dihydro-5H-pyrrolo[1,2-c]imidazol-1-yl)acetic acid (450 mg, 1.19 mmol) and thiazol-2-amine (178.27 mg, 1.78 mmol) in N,N-dimethylformamide (10 mL) was added N,N-diisopropylethylamine (920.28 mg, 7.12 mmol, 1.24 mL). The reaction mixture was cooled to 0° C. Propylphosphonic anhydride solution (50 wt. % in ethyl acetate) (755.21 mg, 2.37 mmol) was added at 0° C. and stirred for 16 h at room temperature. The reaction mixture was poured into to ice cold water (50 mL). The solid was filtered, washed with ice water and dried to afford 2-(6-bromo-7-fluoro-indazol-2-yl)-2-(6,7-dihydro-5H-pyrrolo[1,2-c]imidazol-1-yl)-N-thiazol-2-yl-acetamide (390 mg, 795.99 μmol, 67.07% yield) as pale yellow solid. LCMS (ESI+): 461.0 [M+H]⁺.

Step 3: tert-butyl 2-[1-[4-[2-[1-(6,7-dihydro-5H-pyrrolo[1,2-c]imidazol-1-yl)-2-oxo-2-(thiazol-2-ylamino)ethyl]-7-fluoro-indazol-6-yl]phenyl]-4-hydroxy-4-piperidyl]acetate

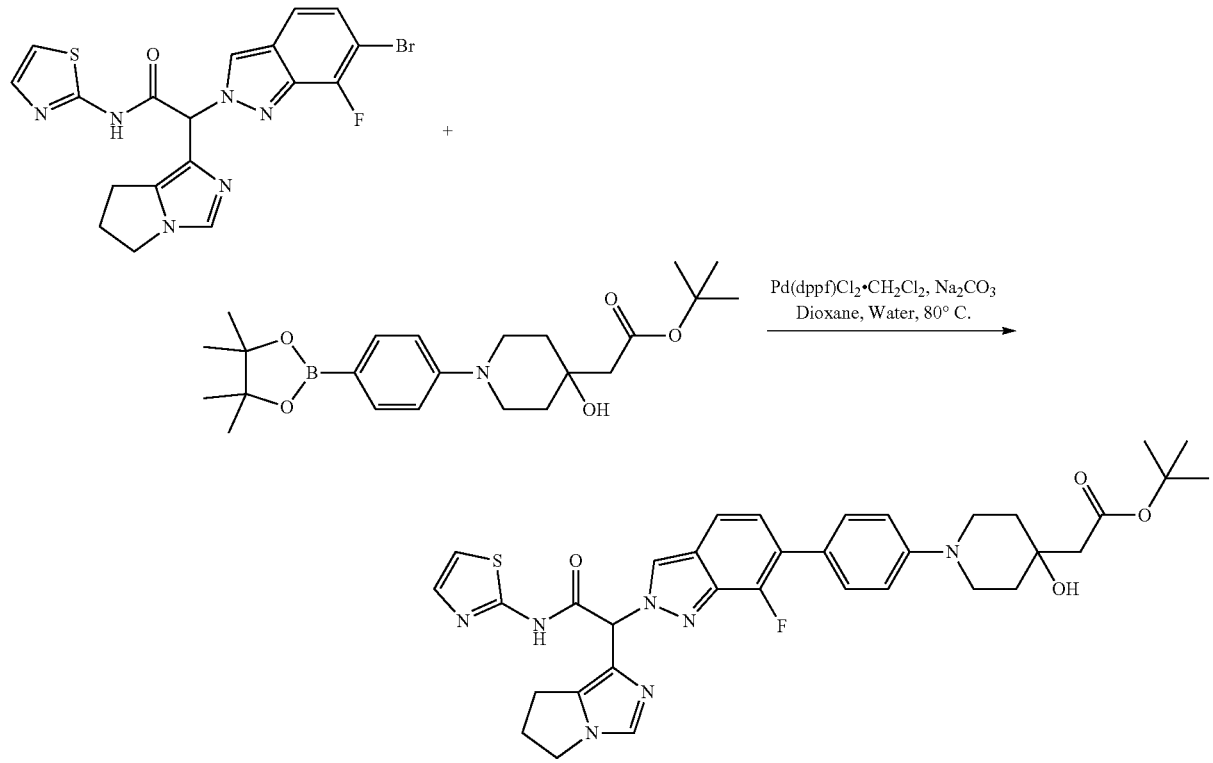

To a solution of 2-(6-bromo-7-fluoro-indazol-2-yl)-2-(6,7-dihydro-5H-pyrrolo[1,2-c]imidazol-1-yl)-N-thiazol-2-yl-acetamide (290 mg, 628.64 µmol) and tert-butyl 2-[4-hydroxy-1-[4-(4,4,5,5-tetramethyl-1,3,2-dioxaborolan-2-yl)phenyl]-4-piperidyl]acetate (262.36 mg, 628.64 µmol) in 1,4-Dioxane (10 mL) was added Sodium carbonate (199.89 mg, 1.89 mmol, 79.01 µL) in Water (3 mL). The mixture was degassed with nitrogen for 15 minutes. [1,1'-Bis(diphenylphosphino)ferrocene]dichloropalladium(II), complex with dichloromethane (87.02 mg, 106.55 µmol) was added to the reaction mixture and further degassed with nitrogen for 5 minutes and heated at 90° C. under nitrogen for 4 h. The reaction mixture was diluted with ethyl acetate and filtered through celite. The filtrate was added ice water (50 mL) and extracted using ethyl acetate (3×100 mL). The organic layer washed with brine solution (50 mL), dried over sodium sulfate and concentrated under reduced pressure. The residue was purified by flash column using silica (3% methanol in dichloromethane) to afford tert-butyl 2-[1-[4-[2-[1-(6,7-dihydro-5H-pyrrolo[1,2-c]imidazol-1-yl)-2-oxo-2-(thiazol-2-ylamino)ethyl]-7-fluoro-indazol-6-yl]phenyl]-4-hydroxy-4-piperidyl]acetate (120 mg, 163.62 µmol, 26.03% yield) as a pale brown solid. LCMS (ESI+): 672.2 [M+H]$^+$.

Step 4: 2-[1-[4-[2-[1-(6,7-dihydro-5H-pyrrolo[1,2-c]imidazol-1-yl)-2-oxo-2-(thiazol-2-ylamino)ethyl]-7-fluoro-indazol-6-yl]phenyl]-4-hydroxy-4-piperidyl]acetic acid; hydrochloride

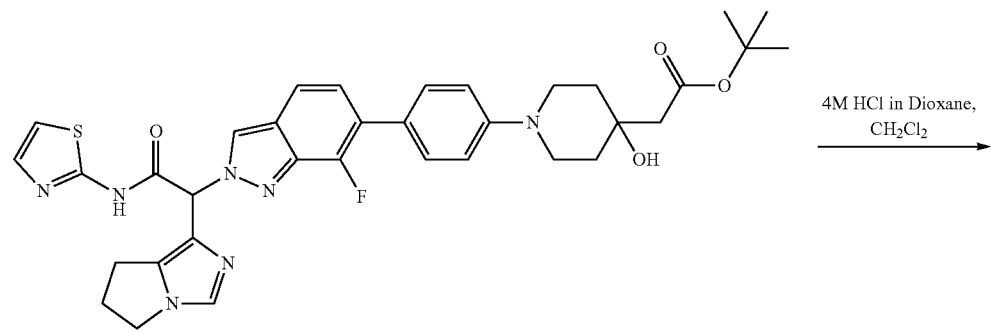

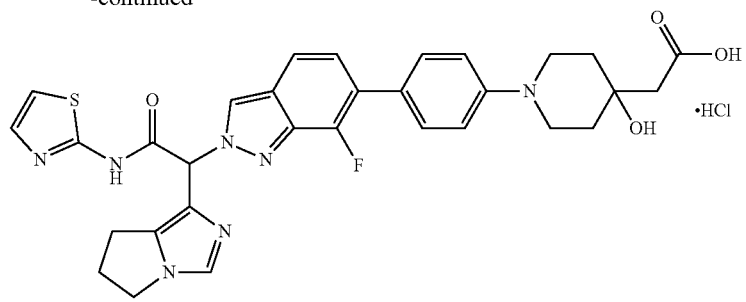

To the stirred solution of tert-butyl 2-[1-[4-[2-[1-(6,7-dihydro-5H-pyrrolo[1,2-c]imidazol-1-yl)-2-oxo-2-(thiazol-2-ylamino)ethyl]-7-fluoro-indazol-6-yl]phenyl]-4-hydroxy-4-piperidyl]acetate (120 mg, 178.63 μmol) in dichloromethane (5 mL) was added hydrogen chloride (4.0 M solution in 1,4-dioxane, 45 μL, 178.63 μmol) dropwise at 0° C. The reaction mixture stirred at ambient temperature for 2 h. The reaction mixture was concentrated under reduced pressure. The residue solid was triturated with diethyl ether (2×25 mL) and dried under reduced pressure to afford 2-[1-[4-[2-[1-(6,7-dihydro-5H-pyrrolo[1,2-c]imidazol-1-yl)-2-oxo-2-(thiazol-2-ylamino)ethyl]-7-fluoro-indazol-6-yl]phenyl]-4-hydroxy-4-piperidyl]acetic acid; hydrochloride (120 mg, 162.83 μmol, 91.15% yield) as a brown solid. LCMS (ESI+): 616.1 [M+H]⁺.

Step 5: 2-(6,7-dihydro-5H-pyrrolo[1,2-c]imidazol-1-yl)-2-[6-[4-[4-[2-[4-[4-[[(3S)-2,6-dioxo-3-piperidyl]amino]-2-fluoro-phenyl]-1-piperidyl]-2-oxo-ethyl]-4-hydroxy-1-piperidyl]phenyl]-7-fluoro-indazol-2-yl]-N-thiazol-2-yl-acetamide

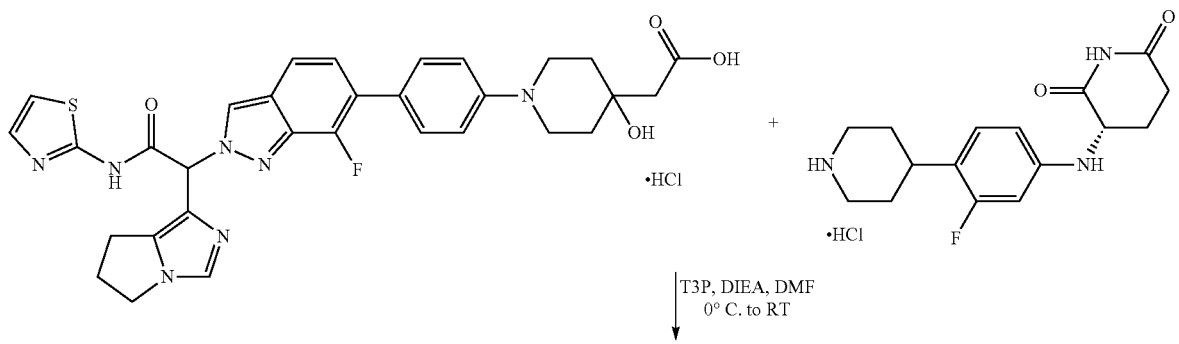

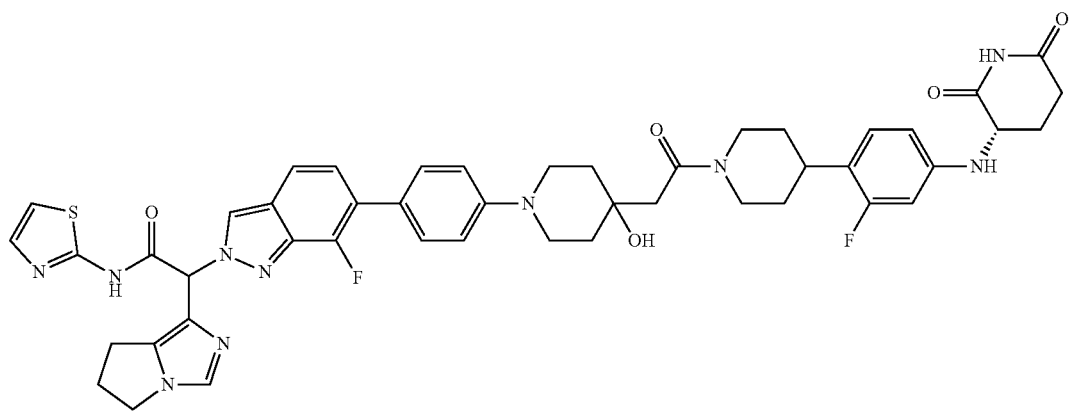

2-[1-[4-[2-[1-(6,7-dihydro-5H-pyrrolo[1,2-c]imidazol-1-yl)-2-oxo-2-(thiazol-2-ylamino)ethyl]-7-fluoro-indazol-6-yl]phenyl]-4-hydroxy-4-piperidyl]acetic acid; hydrochloride (100 mg, 153.34 µmol) and (3S)-3-[3-fluoro-4-(4-piperidyl)anilino]piperidine-2,6-dione; hydrochloride (62.90 mg, 184.01 µmol) were mixed in N,N-dimethylformamide (2 mL) and mixture was cooled to 0° C. N,N-Diisopropylethylamine (118.91 mg, 920.05 µmol, 160.25 µL) was added to the reaction mixture. Propylphosphonic anhydride solution (50 wt. % in ethyl acetate) (97.58 mg, 306.68 µmol) was added and the reaction mixture was stirred for 2 h while warming to room temperature. The reaction mixture was directly injected on a C-18 column (100 g) for purification (0-45% Acetonitrile in water (+0.1% ammonium acetate) over 30 minutes, then steep gradient to 100% acetonitrile). The pure fractions were combined and lyophilized to afford Compound 149 (57 mg, 62.78 µmol, 40.94% yield) as an off-white solid. LCMS (ESI+): 902.9 [M+H]⁺. ¹H-NMR (400 MHz, DMSO-d6): δ 12.82 (s, 1H), 10.80 (s, 1H), 8.30 (d, J=2.80 Hz, 1H), 7.70 (s, 1H), 7.56 (d, J=8.80 Hz, 1H), 7.52 (d, J=3.60 Hz, 1H), 7.47 (d, J=8.00 Hz, 2H), 7.29 (d, J=2.80 Hz, 1H), 7.13 (t, J=6.40 Hz, 1H), 7.06 (d, J=8.80 Hz, 2H), 6.98 (t, J=8.40 Hz, 1H), 6.72 (s, 1H), 6.47 (s, 1H), 6.44 (d, J=4.00 Hz, 1H), 6.04 (d, J=7.20 Hz, 1H), 5.09 (s, 1H), 4.60 (br d, J=12.80 Hz, 1H), 4.32-4.31 (m, 1H), 4.16-4.12 (m, 1H), 4.04-4.00 (m, 2H), 3.53-3.50 (m, 2H), 3.34-3.20 (m, 2H), 3.17-3.07 (m, 1H), 2.90-2.85 (m, 2H), 2.74-2.71 (m, 1H), 2.70-2.56 (m, 6H), 2.10-2.07 (m, 1H), 1.87-1.85 (m, 1H), 1.72-1.69 (m, 7H), 1.591-1.56 (m, 1H), 1.46-1.43 (m, 1H).

Example 150

2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]-2-oxo-ethyl]-4-hydroxy-1-piperidyl]-3-pyridyl]-4-fluoro-indazol-2-yl]-N-thiazol-2-yl-acetamide, Compound 150

Step 1: tert-butyl 2-[4-hydroxy-1-[5-(4,4,5,5-tetramethyl-1,3,2-dioxaborolan-2-yl)-2-pyridyl]-4-piperidyl]acetate

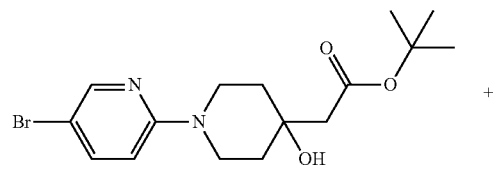

+

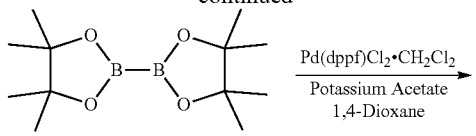

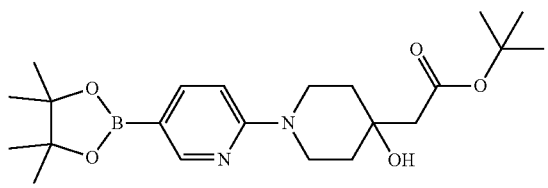

A solution of tert-butyl 2-[1-(5-bromo-2-pyridyl)-4-hydroxy-4-piperidyl]acetate (1.0 g, 2.69 mmol) and 4,4,5,5-tetramethyl-2-(4,4,5,5-tetramethyl-1,3,2-dioxaborolan-2-yl)-1,3,2-dioxaborolane (957.56 mg, 3.77 mmol) in 1,4-Dioxane (20 mL) was degassed with nitrogen for 15 min. Potassium acetate (793.03 mg, 8.08 mmol, 505.11 µL) and [1,1'-Bis(diphenylphosphino)ferrocene]dichloropalladium (II), complex with dichloromethane (219.96 mg, 269.35 µmol) were added to the reaction mixture and purged with nitrogen gas for mins. The reaction mixture was heated at 90° C. for 16 h under inert atmosphere. The reaction mixture was cooled and filtered under suction. The filtrate diluted with cold water (50 mL), and the mixture was extracted using ethyl acetate (3×150 mL). The organic layer washed with brine (100 mL), dried with sodium sulfate, filtered, and concentrated under reduced pressure. The residue was purified by column chromatography (0-80% ethyl acetate and petroleum ether) to afford tert-butyl 2-[4-hydroxy-1-[5-(4,4,5,5-tetramethyl-1,3,2-dioxaborolan-2-yl)-2-pyridyl]-4-piperidyl]acetate (350 mg, 786.81 µmol, 29.21% yield) as an off-white solid. LCMS m/z 337.2 (M (Boronic ester hydrolysis)+H)⁺.

Step 2: tert-butyl 2-[1-[5-[2-[1-(6,7-dihydro-5H-pyrrolo[1,2-c]imidazol-1-yl)-2-oxo-2-(thiazol-2-ylamino)ethyl]-4-fluoro-indazol-6-yl]-2-pyridyl]-4-hydroxy-4-piperidyl]acetate

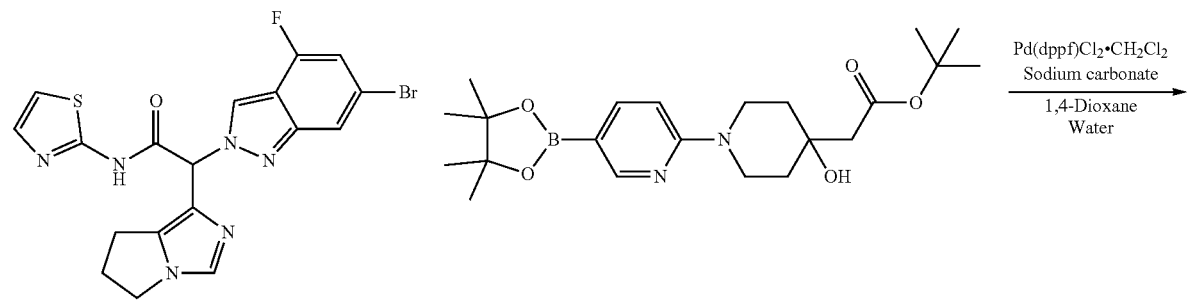

-continued

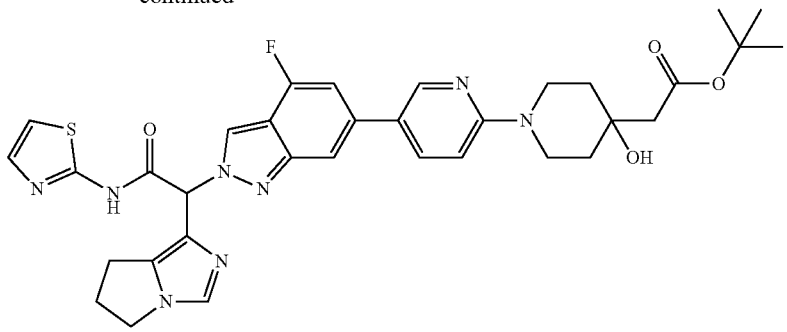

To a stirred solution of 2-(6-bromo-4-fluoro-indazol-2-yl)-2-(6,7-dihydro-5H-pyrrolo[1,2-c]imidazol-1-yl)-N-thiazol-2-yl-acetamide (400 mg, 867.10 µmol) and tert-butyl 2-[4-hydroxy-1-[5-(4,4,5,5-tetramethyl-1,3,2-dioxaborolan-2-yl)-2-pyridyl]-4-piperidyl]acetate (399.01 mg, 953.81 µmol) in 1,4-Dioxane (4 mL) was added sodium carbonate (229.76 mg, 2.17 mmol, 90.81 µL) in Water (1 mL), and the reaction mixture was purged with nitrogen gas for 15 minutes. [1,1'-Bis(diphenylphosphino)ferrocene]dichloropalladium(II), complex with dichloromethane (87.02 mg, 106.55 µmol) was added to the reaction mixture and purged with nitrogen gas for 5 mins. The reaction mixture was heated at 90° C. under nitrogen for 3 h. The reaction mixture was diluted with ethyl acetate and filtered through celite. The filtrate was washed with ice water (20 mL), and the filtrate was extracted using ethyl acetate (3×20 mL). The organic layer was washed with brine solution (30 mL), dried with sodium sulfate, filtered and concentrated under reduced pressure. The residue was purified by column chromatography using 230-400 silica gel, eluting with a 0 to 10% methanol in dichloromethane gradient to afford tert-butyl 2-[1-[5-[2-[1-(6,7-dihydro-5H-pyrrolo[1,2-c]imidazol-1-yl)-2-oxo-2-(thiazol-2-ylamino)ethyl]-4-fluoro-indazol-6-yl]-2-pyridyl]-4-hydroxy-4-piperidyl]acetate (150 mg, 95.87 µmol, 11.06% yield) as a brown solid. LCMS (m/z: 671.0 [M−H]).

Step 3: 2-[1-[5-[2-[1-(6,7-dihydro-5H-pyrrolo[1,2-c]imidazol-1-yl)-2-oxo-2-(thiazol-2-ylamino)ethyl]-4-fluoro-indazol-6-yl]-2-pyridyl]-4-hydroxy-4-piperidyl]acetic acid

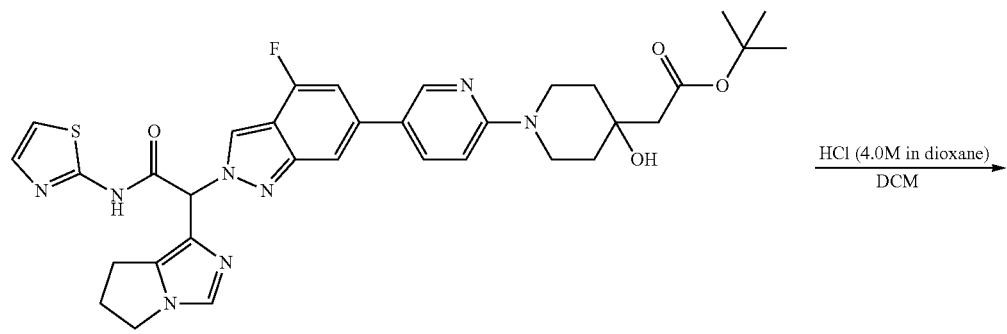

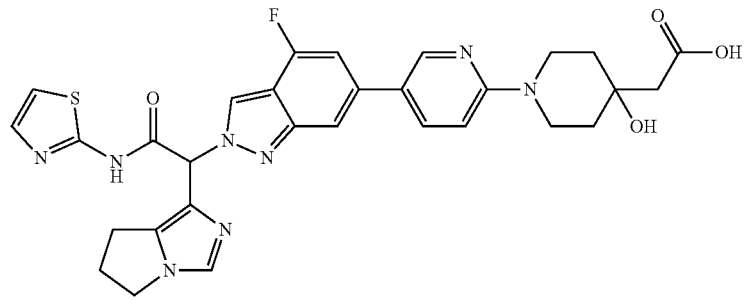

To a stirred solution of tert-butyl 2-[1-[5-[2-[1-(6,7-dihydro-5H-pyrrolo[1,2-c]imidazol-1-yl)-2-oxo-2-(thiazol-2-ylamino)ethyl]-4-fluoro-indazol-6-yl]-2-pyridyl]-4-hydroxy-4-piperidyl]acetate (145 mg, 215.53 μmol) in dichloromethane (2 mL) was added hydrogen chloride (4.0M solution in 1,4-dioxane, 110.01 mg, 3.02 mmol, 137.52 μL) dropwise at 0° C. The reaction mixture stirred at ambient temperature for 2 h. After completion, the reaction was evaporated to dryness under reduced pressure. The solid residue was triturated by diethyl ether (2×10 mL), and evaporated to dryness to afford 2-[1-[5-[2-[1-(6,7-dihydro-5H-pyrrolo[1,2-c]imidazol-1-yl)-2-oxo-2-(thiazol-2-ylamino)ethyl]-4-fluoro-indazol-6-yl]-2-pyridyl]-4-hydroxy-4-piperidyl]acetic acid hydrochloride (95 mg, 80.00 μmol, 37.12% yield) as a brown solid. LCMS (m/z: 617.0 [M+H]).

Step 4: 2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]-2-oxo-ethyl]-4-hydroxy-1-piperidyl]-3-pyridyl]-4-fluoro-indazol-2-yl]-N-thiazol-2-yl-acetamide

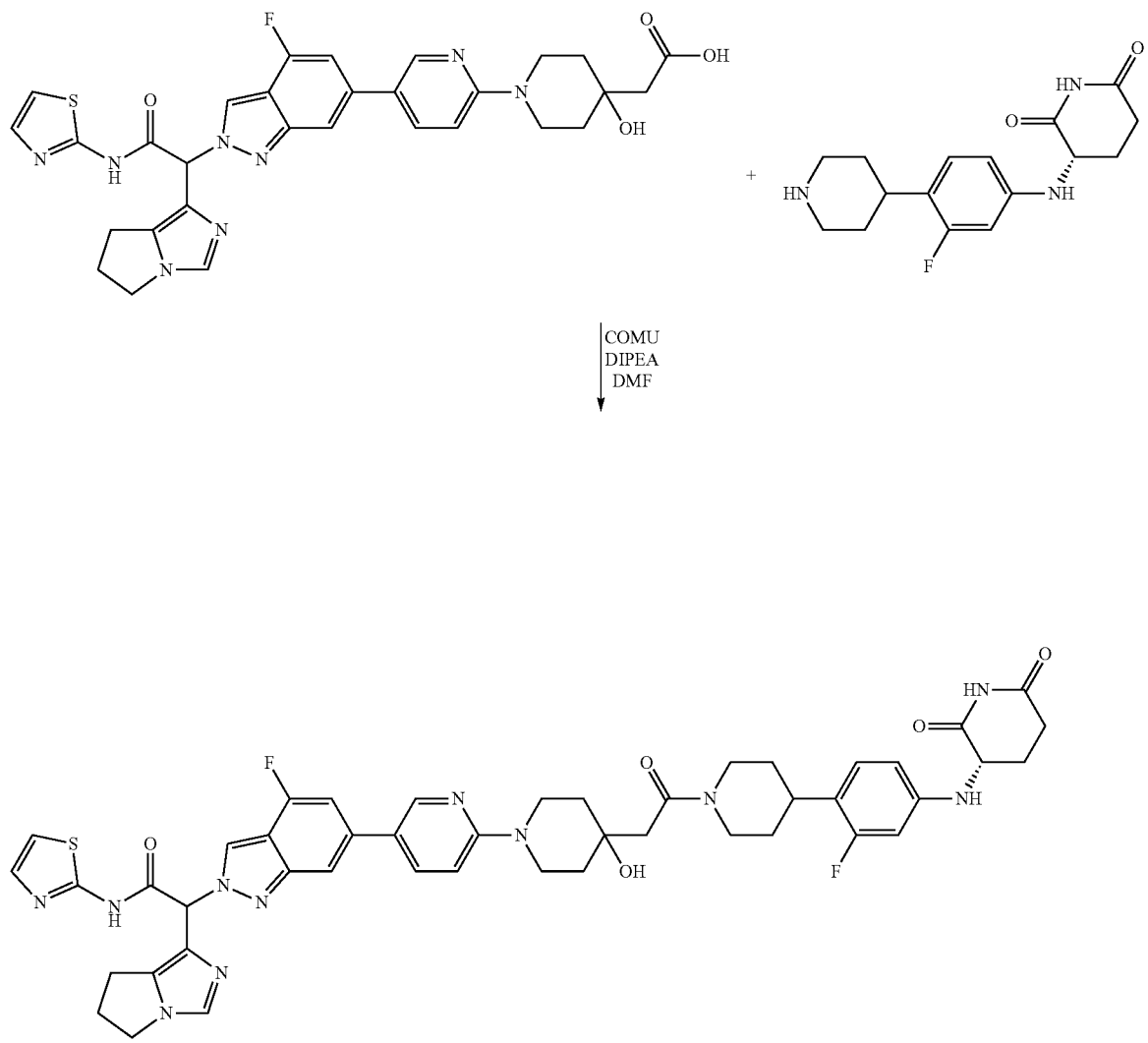

To a stirred solution of 2-[1-[5-[2-[1-(6,7-dihydro-5H-pyrrolo[1,2-c]imidazol-1-yl)-2-oxo-2-(thiazol-2-ylamino)ethyl]-4-fluoro-indazol-6-yl]-2-pyridyl]-4-hydroxy-4-piperidyl]acetic acid hydrochloride (80 mg, 122.49 µmol) and (3S)-3-[3-fluoro-4-(4-piperidyl)anilino]piperidine-2,6-dione hydrochloride (38.06 mg, 111.35 µmol) in N,N-dimethylformamide (1.5 mL) was added N,N-Diisopropylethylamine (71.96 mg, 556.76 µmol, 96.98 µL) at 0° C. and 1-Cyano-2-ethoxy-2-oxoethylidenaminooxy)dimethylamino-morpholino-carbenium hexafluorophosphate (57.23 mg, 133.62 µmol) was added at the same temperature and the reaction mixture stirred at room temperature for 1 h. The reaction mixture was directly injected on a C-18 column (100 g) for purification (0-45% acetonitrile in water (with 0.1% ammonium acetate) over 30 minutes, then steep gradient to 100% acetonitrile). The pure fractions were combined and lyophilized to afford Compound 150 (8.35 mg, 9.09 µmol, 8.17% yield) as an off-white solid. LCMS (ESI+): 915.8 [M+H]; $^1$H-NMR (400 MHz, DMSO-d6): δ 12.83 (s, 1H), 10.80 (s, 1H), 8.53 (d, J=2.00 Hz, 1H), 8.27 (s, 1H), 7.92 (dd, J=9.20, 1.60 Hz, 1H), 7.68 (d, J=12.80 Hz, 2H), 7.52 (d, J=3.60 Hz, 1H), 7.29 (d, J=3.20 Hz, 1H), 7.18 (d, J=12.00 Hz, 1H), 7.00-6.71 (m, 2H), 6.47 (s, 1H), 6.44 (d, J=5.60 Hz, 1H), 5.16 (s, 1H), 4.59 (d, J=12.80 Hz, 1H), 4.32-4.29 (m, 1H), 4.20-3.89 (m, 5H), 3.18-3.01 (m, 1H), 2.91-2.60 (m, 4H), 2.10-2.06 (m, 2H), 1.88-1.84 (m, 2H), 1.72-1.45 (m, 8H), 1.29-1.24 (m, 4H), 0.90-0.87 (m, 2H). (water obscuration).

Example 151

2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]-2-oxo-ethyl]-4-hydroxy-1-piperidyl]-3-pyridyl]-7-fluoro-indazol-2-yl]-N-thiazol-2-yl-acetamide, Compound 151

Step 1: tert-butyl 2-[1-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-4-hydroxy-4-piperidyl]acetate

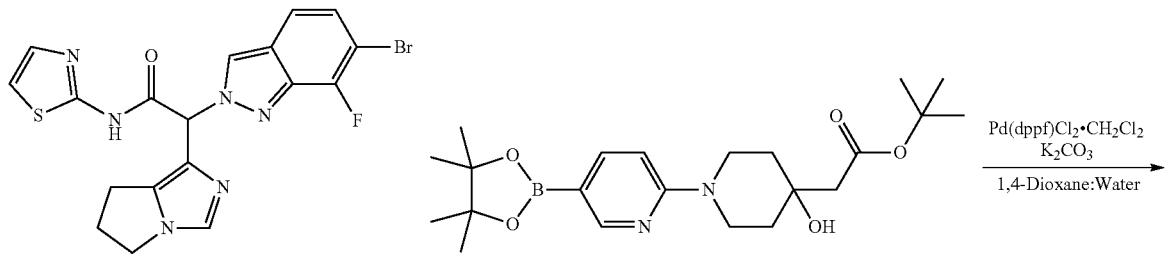

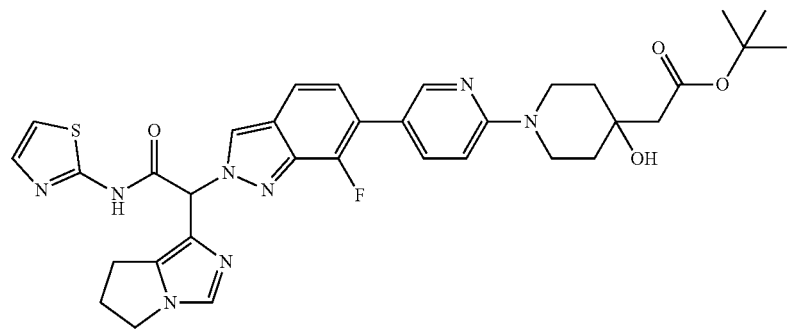

To a solution of 2-(6-bromo-7-fluoro-indazol-2-yl)-2-(6,7-dihydro-5H-pyrrolo[1,2-c]imidazol-1-yl)-N-thiazol-2-yl-acetamide (700 mg, 1.52 mmol) and tert-butyl 2-[4-hydroxy-1-[5-(4,4,5,5-tetramethyl-1,3,2-dioxaborolan-2-yl)-2-pyridyl]-4-piperidyl]acetate (888.70 mg, 2.12 mmol) in 1,4-dioxane (20 mL) and water (6 mL) was degassed with nitrogen for 15 mints. Potassium carbonate, anhydrous, 99% (629.15 mg, 4.55 mmol, 274.74 µL) and [1,1'-Bis(diphenylphosphino)ferrocene]dichloropalladium(II), complex with dichloromethane (87.02 mg, 106.55 µmol) was added to the reaction mixture and purged with nitrogen gas for mins then heated at 90° C. under nitrogen for 4 hr. The reaction mixture diluted with ethyl acetate and filtered through celite. The filtrate washed with ice water (50 mL) and extracted from ethyl acetate (3*100 mL). The organic layer washed with brine solution (50 mL), dried with sodium sulfate, and concentrated under reduced pressure. The residue was purified by column chromatography (3% methanol and dichloromethane) to afford tert-butyl 2-[1-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-4-hydroxy-4-piperidyl]acetate (300 mg, 353.29 µmol, 23.28% yield) as pale brown solid. LCMS m/z 673.2 (M+H)$^+$.

Step 2: 2-[1-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-4-hydroxy-4-piperidyl]acetic acid

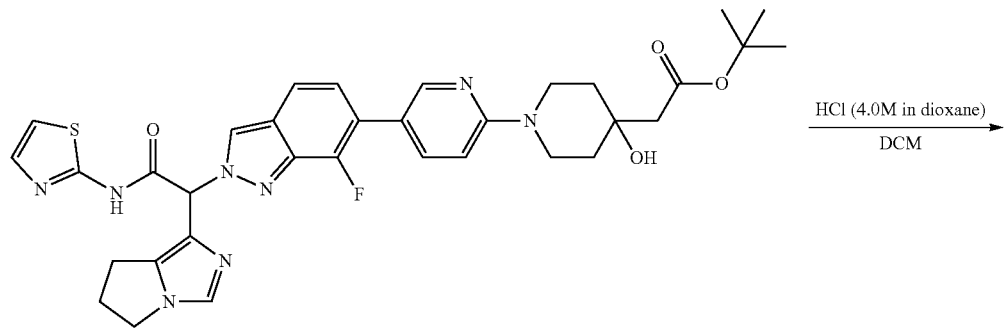

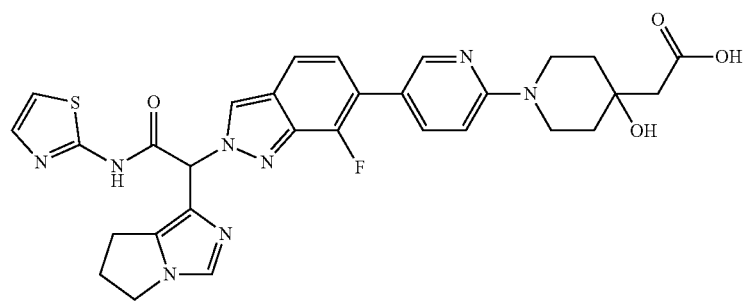

To a stirred solution of tert-butyl 2-[1-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-4-hydroxy-4-piperidyl]acetate (250 mg, 371.60 μmol) in dichloromethane (5 mL) was added hydrogen chloride (4.0M solution in dioxane, 10 mmol, 2.5 mL) dropwise at 0° C. The reaction mixture was concentrated under reduced pressure The solid was triturated with diethyl ether (2×25 mL) and dried under reducing pressure to give 2-[1-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-4-hydroxy-4-piperidyl]acetic acid (220 mg, 255.00 μmol, 68.62% yield) as a brown solid. LCMS m/z 617.2 (M+H)$^+$.

Step 3: 2-(6,7-dihydro-5H-pyrrolo[1,2-c]imidazol-1-yl)-2-[6-[6-[4-[2-[4-[4-[[(3S)-2,6-dioxo-3-piperidyl]amino]-2-fluoro-phenyl]-1-piperidyl]-2-oxo-ethyl]-4-hydroxy-1-piperidyl]-3-pyridyl]-7-fluoro-indazol-2-yl]-N-thiazol-2-yl-acetamide

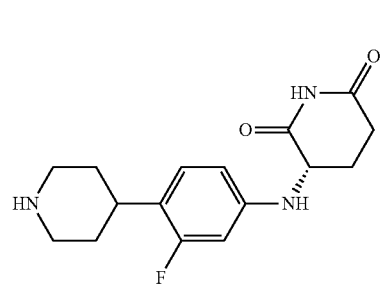

T3P (50 wt. % in ethyl acetate)
DIPEA
DMF

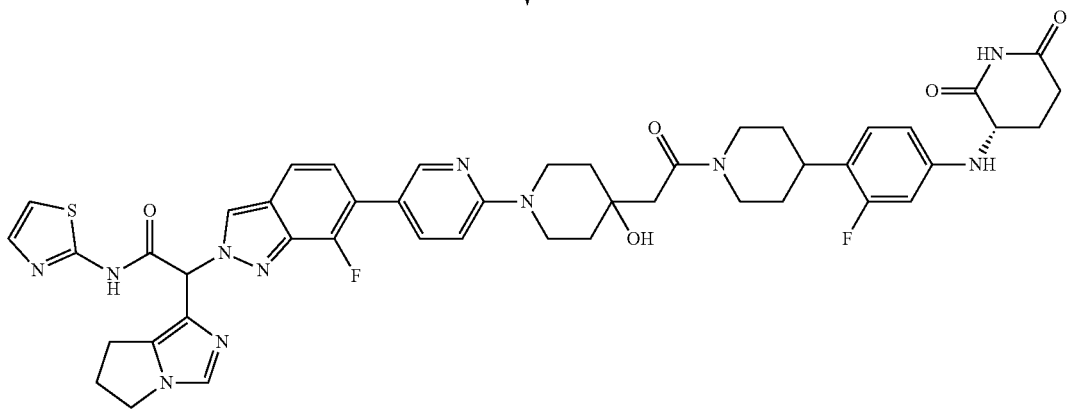

To a stirred solution of 2-[1-[5-[2-[1-(6,7-dihydro-5H-pyrrolo[1,2-c]imidazol-1-yl)-2-oxo-2-(thiazol-2-ylamino)ethyl]-7-fluoro-indazol-6-yl]-2-pyridyl]-4-hydroxy-4-piperidyl]acetic acid hydrochloride (100 mg, 153.11 μmol) and (3S)-3-[3-fluoro-4-(4-piperidyl)anilino]piperidine-2,6-dione hydrochloride (62.80 mg, 183.73 μmol) in N,N-dimethylformamide (2 mL) was cooled to 0° C. N,N-Diisopropylethylamine (118.73 mg, 918.66 μmol, 160.01 μL) was added to the reaction mixture followed by propylphosphonic anhydride solution (50 wt. %  in ethyl acetate) (97.43 mg, 306.22 μmol) at 0° C. The reaction mixture stirred at ambient temperature for 2 h. The reaction mixture was directly injected on a C-18 column (100 g) for purification (0-45% acetonitrile in water (0.1% ammonium acetate) over 30 minutes, then steep gradient to 100% acetonitrile). The pure fractions were combined and lyophilized to afford Compound 151 (36 mg, 39.67 μmol, 25.91% yield) as an off-white solid. LCMS m/z 903.8 (M+H)$^+$. $^1$H-NMR (400 MHz, DMSO-d6): δ 12.83 (s, 1H), 10.80 (s, 1H), 8.37 (s, 1H), 8.33 (d, J=10.40 Hz, 1H), 7.77 (d, J=8.80 Hz, 1H), 7.70 (s, 1H), 7.59 (d, J=8.80 Hz, 1H), 7.52 (d, J=3.20 Hz, 1H), 7.29 (d, J=2.80 Hz, 1H), 7.15 (t, J=7.60 Hz, 1H), 7.00-6.96 (m, 2H), 6.72 (s, 1H), 6.47-6.44 (m, 2H), 6.04 (d, J=7.60 Hz, 1H), 5.17 (s, 1H), 4.60 (d, J=13.20 Hz, 1H), 4.34-4.31 (m, 1H), 4.15-4.04 (m, 5H), 3.12-3.06 (m, 1H), 2.90-2.55 (m, 11H), 2.15-2.08 (m, 2H), 1.88-1.84 (m, 1H), 1.72-1.58 (m, 7H), 1.55-1.24 (m, 1H).

Example 152

2-(6,7-dihydro-5H-pyrrolo[1,2-c]imidazol-1-yl)-2-[6-[4-[1-[2-[4-[4-[(2,6-dioxo-3-piperidyl)amino]phenyl]-1-piperidyl]acetyl]-4-piperidyl]-2-methyl-phenyl]-4-fluoro-1-oxo-isoindolin-2-yl]-N-thiazol-2-yl-acetamide, Compound 152

Step 1: tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]-3-methyl-phenyl]-3,6-dihydro-2H-pyridine-1-carboxylate

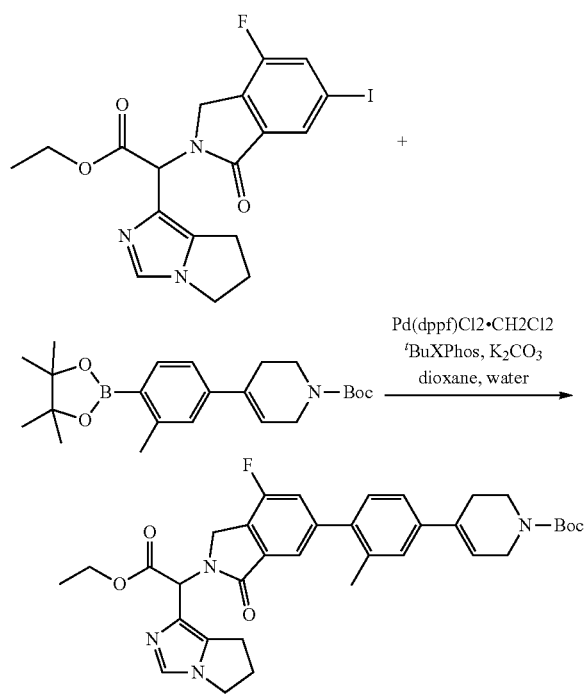

To ethyl 2-(6,7-dihydro-5H-pyrrolo[1,2-c]imidazol-1-yl)-2-(4-fluoro-6-iodo-1-oxo-isoindolin-2-yl)acetate (500 mg, 1.07 mmol) dissolved 1,4-dioxane (5 mL) and water (0.5 mL) was added tert-butyl 4-[3-methyl-4-(4,4,5,5-tetramethyl-1,3,2-dioxaborolan-2-yl)phenyl]-3,6-dihydro-2H-pyridine-1-carboxylate (CAS #1187313-16-1, 553.15 mg, 1.39 mmol). The reaction mixture was purged with nitrogen for 10 min. t-BuXPhos (45.25 mg, 106.55 μmol), Pd(dppf)Cl₂·CH₂Cl₂ (43.47 mg, 53.28 μmol) and potassium carbonate (441.79 mg, 3.20 mmol, 192.92 uL) were added under nitrogen atmosphere, and reaction mixture was stirred at 90° C. for 16 h. The reaction mixture was filtered through celite bed and the filtrate was diluted with ethyl acetate (150 mL). The organic layer was washed with water (50 mL) and brine (50 mL) solution and dried over the sodium sulfate and concentrated to afford tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]-3-methyl-phenyl]-3,6-dihydro-2H-pyridine-1-carboxylate. LCMS m/z: 615.3 (M+H).

Step 2: tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]-3-methyl-phenyl]piperidine-1-carboxylate

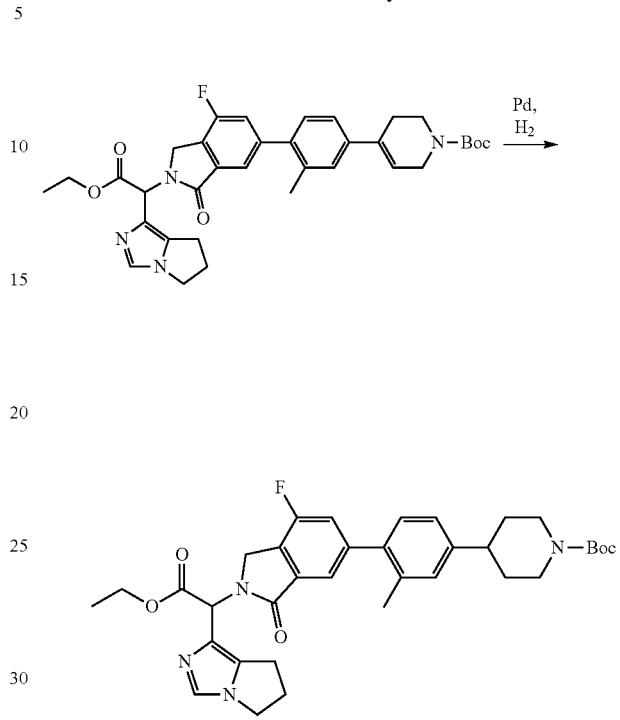

A round bottom flask was charged with tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]-3-methyl-phenyl]-3,6-dihydro-2H-pyridine-1-carboxylate (448 mg, 728.81 μmol) and methanol (10 mL). Palladium (10% on carbon, 77.56 mg, 728.81 μmol) was added. The reaction mixture was flushed with hydrogen gas for 5 min, and the reaction mixture was stirred at ambient temperature with hydrogen bladder gas flushing with pressure (3 bar) for 18 h. The reaction mixture was filtered through celite bed and washed with 20% methanol in dichloromethane. The filtrate was concentrated to afford tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]-3-methyl-phenyl]piperidine-1-carboxylate (370 mg, 277.8 μmol, 26.0% yield over 2 steps). LCMS m/z: 617.3 (M+H)⁺

Step 3: 2-[6-[4-(1-tert-butoxycarbonyl-4-piperidyl)-2-methyl-phenyl]-4-fluoro-1-oxo-isoindolin-2-yl]-2-(6,7-dihydro-5H-pyrrolo[1,2-c]imidazol-1-yl)acetic acid

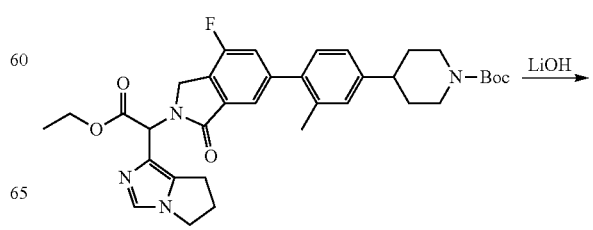

-continued

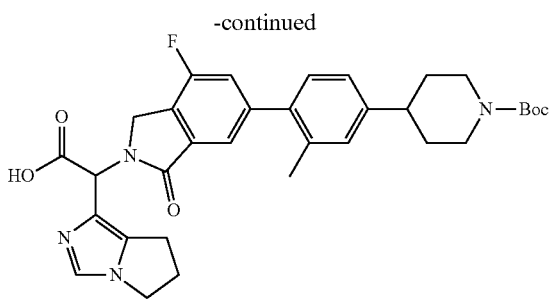

To a tert-butyl 4-[4-[2-[1-(6,7-dihydro-5H-pyrrolo[1,2-c]imidazol-1-yl)-2-ethoxy-2-oxo-ethyl]-7-fluoro-3-oxo-isoindolin-5-yl]-3-methyl-phenyl]piperidine-1-carboxylate (370 mg, 599.95 μmol) in ethanol (1 mL) and tetrahydrofuran (1 mL) and water (1 mL) reaction mixture was stirred for 10 min. Lithium hydroxide (28.74 mg, 1.20 mmol) added to the reaction was stirred at ambient temperature for 3 h. The reaction mixture was concentrated under reduced pressure and the residue was diluted with water (5 mL). The aqueous layer was acidified with potassium hydrogen sulfate and the solid material was filtered to afford 2-[6-[4-(1-tert-butoxycarbonyl-4-piperidyl)-2-methyl-phenyl]-4-fluoro-1-oxo-isoindolin-2-yl]-2-(6,7-dihydro-5H-pyrrolo[1,2-c]imidazol-1-yl)acetic acid (282 mg, 353.3 μmol, 33.2% yield) LCMS (ESI+): 589.3 (M+H)+

Step 4: tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-3-methyl-phenyl]piperidine-1-carboxylate

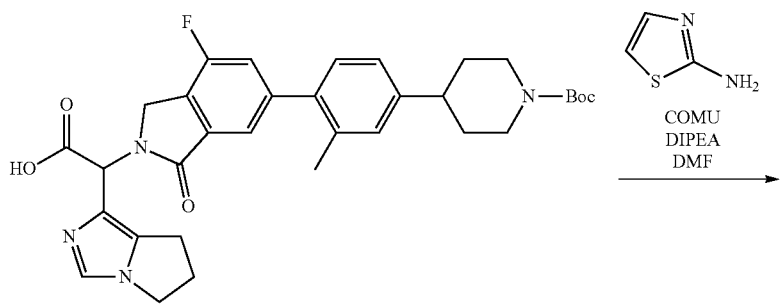

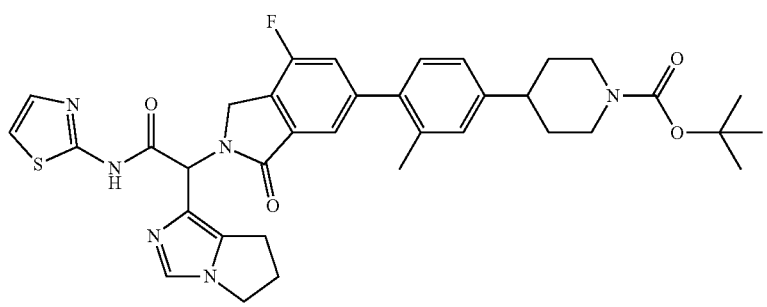

To a solution of 2-[6-[4-(1-tert-butoxycarbonyl-4-piperidyl)-2-methyl-phenyl]-4-fluoro-1-oxo-isoindolin-2-yl]-2-(6,7-dihydro-5H-pyrrolo[1,2-c]imidazol-1-yl)acetic acid (280 mg, 475.65 μmol) in N,N-dimethylformamide (5 mL) add N,N-Diisopropylethylamine (184.42 mg, 1.43 mmol, 248.55 uL) and [[(Z)-(1-cyano-2-ethoxy-2-oxo-ethylidene)amino]oxy-morpholino-methylene]-dimethyl-ammonium; hexafluorophosphate (305.56 mg, 713.48 mol) added the thiazol-2-amine (95.27 mg, 951.30 μmol) and the reaction mixture was stirred at 0° C. for 1.5 h. To the reaction mass added the cold ice and solid material was precipitated out and solid material was filtrated and solid was dried under suction. The residue was dissolved in dichloromethane (50 mL) and dried over sodium sulfate and evaporated to afford tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-3-methyl-phenyl]piperidine-1-carboxylate (245 mg, 207.1 mmol, 43.5% yield) as a brown solid. LCMS (ESI+) 671.3 (M+H)$^+$ Step 5: 2-(6,7-dihydro-5H-pyrrolo[1,2-c]imidazol-1-yl)-2-[4-fluoro-6-[2-methyl-4-(4-piperidyl)phenyl]-1-oxo-isoindolin-2-yl]-N-thiazol-2-yl-acetamide hydrochloride

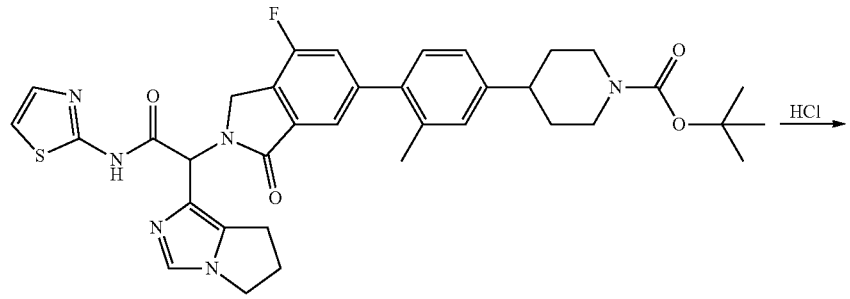

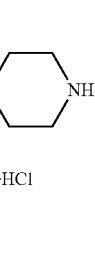

To a solution of tert-butyl 4-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]-3-methyl-phenyl]piperidine-1-carboxylate (240 mg, 357.78 μmol) in dichloromethane (5 mL) was added hydrogen chloride (4.0M in 1,4-dioxane, 0.5 mL, 2 mmol) at 0° C. The reaction mixture was stirred at ambient temperature for 3 h. Solvent was removed under reduced pressure and the solid was washed with diethyl ether (2×10 mL) and dried over vacuum to afford 2-(6,7-dihydro-5H-pyrrolo[1,2-c]imidazol-1-yl)-2-[4-fluoro-6-[2-methyl-4-(4-piperidyl)phenyl]-1-oxo-isoindolin-2-yl]-N-thiazol-2-yl-acetamide hydrochloride (138 mg, 129 μmol, 36% yield). LCMS m/z: 571.3 (M+H)⁺

Step 6: 2-(6,7-dihydro-5H-pyrrolo[1,2-c]imidazol-1-yl)-2-[6-[4-[1-[2-[4-[4-[(2,6-dioxo-3-piperidyl)amino]phenyl]-1-piperidyl]acetyl]-4-piperidyl]-2-methyl-phenyl]-4-fluoro-1-oxo-isoindolin-2-yl]-N-thiazol-2-yl-acetamide

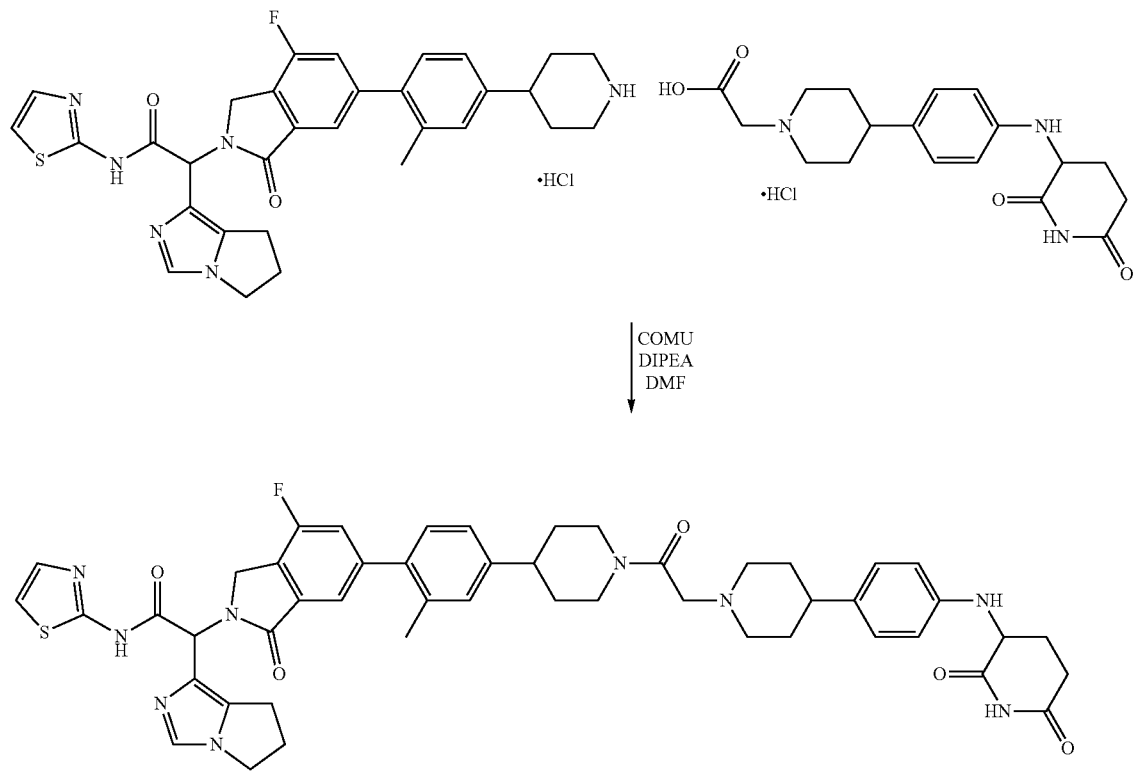 [SMILES: Cc1cc(C2CCNCC2)ccc1-c1cc(F)c2c(c1)C(=O)N(C(C(=O)Nc1nccs1)c1ncn3c1CCC3)C2 ; Cl ; O=C(O)CN1CCC(c2ccc(NC3CCC(=O)NC3=O)cc2)CC1 ; Cl ; Cc1cc(C2CCN(C(=O)CN3CCC(c4ccc(NC5CCC(=O)NC5=O)cc4)CC3)CC2)ccc1-c1cc(F)c2c(c1)C(=O)N(C(C(=O)Nc1nccs1)c1ncn3c1CCC3)C2]

To a solution of 2-(6,7-dihydro-5H-pyrrolo[1,2-c]imidazol-1-yl)-2-[4-fluoro-6-[2-methyl-4-(4-piperidyl)phenyl]-1-oxo-isoindolin-2-yl]-N-thiazol-2-yl-acetamide hydrochloride (110 mg, 181.18 μmol) in N,N-dimethylformamide (2 mL) were added N,N-diisopropylethylamine (70.25 mg, 543.53 μmol, 94.67 uL) and [[(Z)-(1-cyano-2-ethoxy-2-oxo-ethylidene)amino]oxy-morpholino-methylene]-dimethyl-ammonium hexafluorophosphate (116.39 mg, 271.77 μmol) at 0° C. The reaction mixture was stirred for 15 min. 2-[4-[4-[(2,6-dioxo-3-piperidyl)amino]phenyl]-1-piperidyl]acetic acid hydrochloride (69.18 mg, 181.18 μmol) was added. The reaction mixture was stirred for 1 h. Water (10 mL) was added to the reaction mixture. The solid was filtered. The solid was dissolved in dichloromethane. The volatiles were removed under reduced pressure. The residue was purified by reverse phase column chromatography using C18 column (50 g) for purification (5% to 75% acetonitrile in water (with 0.1% ammonium acetate)). Water (10 mL) and acetonitrile (5 mL) were added, and the mixture was thoroughly sonicated, vortexed, and sonicated again. The suspension was frozen and lyophilized to afford Compound 152 (24.6 mg, 26.16 μmol, 14.44% yield) as a white solid. LCMS m/z: 898.3 (M+H). ¹H-NMR (400 MHz, DMSO-d6) 11.86-12.97 (m, 1H), 10.79 (d, J=Hz, 1H), 7.56 (dd, J=, Hz, 2H), 7.46-7.48 (m, 1H), 7.15-7.23 (m, 3H), 6.94-7.03 (m, 3H), 6.60 (dd, J=−8.40, Hz, 2H), 6.01 (m, 1H), 5.66 (dd, J=−7.60, Hz, 1H), 4.94-4.98 (m, 1H), 4.52-4.55 (m, 1H), 4.20-4.28 (m, 3H), 3.92-4.01 (m, 3H), 3.09-3.37 (m, 3H), 2.94 (m, 2H), 2.71-2.83 (m, 3H), 2.65-2.70 (m, 2H), 2.25-2.34 (m, 3H), 2.08-2.11 (m, 3H), 1.83-1.89 (m, 3H), 1.69-1.76 (m, 6H), 1.59-1.61 (m, 4H).

Example 153

2-(6,7-dihydro-5H-pyrrolo[1,2-c]imidazol-1-yl)-2-[6-[4-[2-[2-[7-[3-(2,4-dioxohexahydropyrimidin-1-yl)-1-methyl-indazol-6-yl]-4-azaspiro[2.5]octan-4-yl]acetyl]-2,6-diazaspiro[3.3]heptan-6-yl]phenyl]-4-fluoro-1-oxo-isoindolin-2-yl]-N-(2-pyridyl)acetamide, Compound 153

Step 1: tert-butyl 7-[3-(2,4-dioxohexahydropyrimidin-1-yl)-1-methyl-indazol-6-yl]-4-azaspiro[2.5]oct-6-ene-4-carboxylate

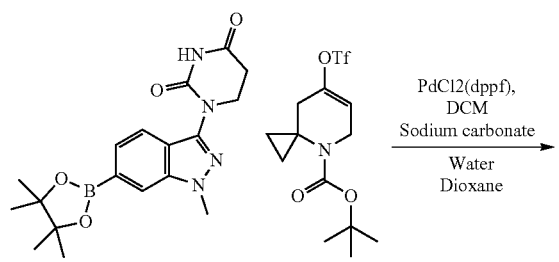

Step 2: tert-butyl 7-[3-(2,4-dioxohexahydropyrimidin-1-yl)-1-methyl-indazol-6-yl]-4-azaspiro[2.5]octane-4-carboxylate

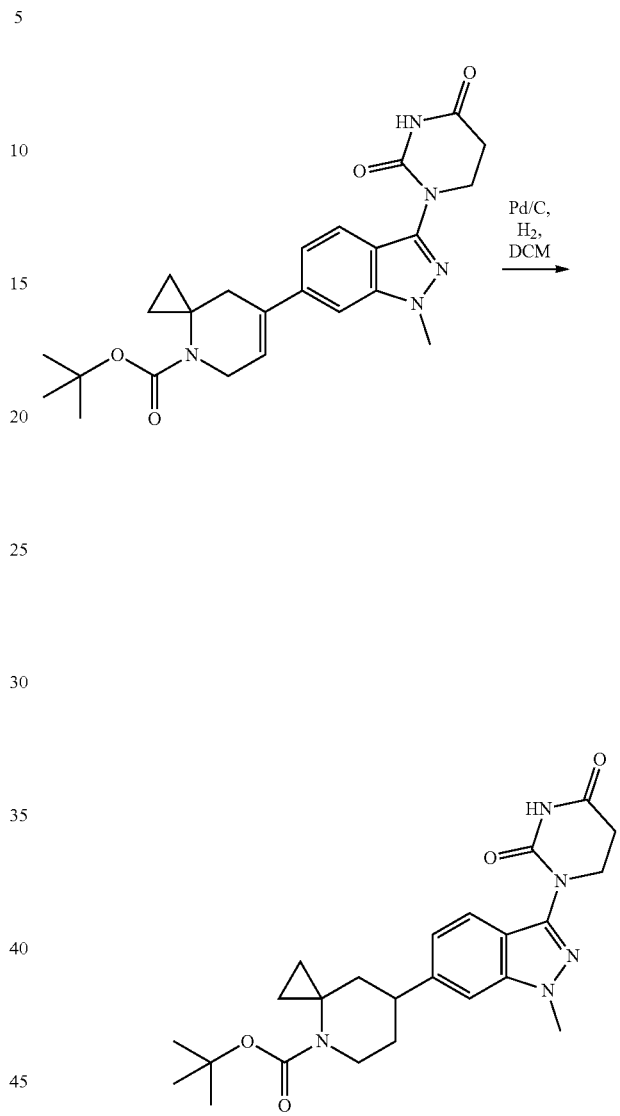

To a stirred solution of 1-[1-methyl-6-(4,4,5,5-tetramethyl-1,3,2-dioxaborolan-2-yl)indazol-3-yl]hexahydropyrimidine-2,4-dione (450 mg, 1.22 mmol) and tert-butyl 7-(trifluoromethylsulfonyloxy)-4-azaspiro[2.5]oct-6-ene-4-carboxylate (521.24 mg, 1.46 mmol) in 1,4-dioxane (7 mL) and Water (1.7 mL) was added sodium carbonate (322.08 mg, 3.04 mmol, 127.30 uL). The reaction mixture was degassed with nitrogen for 20 min. PdCl$_2$(dppf).dichloromethane (99.21 mg, 121.55 μmol) was added to the reaction mixture and further degassed for 10 min. The reaction mixture was heated at 80° C. under nitrogen for 6 h. The reaction mixture was filtered through celite, and the filter cake was washed with 10% methanol in dichloromethane (2×40 mL). Combined the organic layer, and concentrated under pressure. The residue was purified by silica gel (100-200 mesh) column chromatography, eluted with 5% methanol in dichloromethane. The fractions were collected and evaporated to afford tert-butyl 7-[3-(2,4-dioxohexahydropyrimidin-1-yl)-1-methyl-indazol-6-yl]-4-azaspiro[2.5]oct-6-ene-4-carboxylate (560 mg, 1.08 mmol, 88.71% yield) as a light brown color solid. LCMS m/z: 452.2 [M+H]$^+$ In a 25 ml clave flask, tert-butyl 7-[3-(2,4-dioxohexahydropyrimidin-1-yl)-1-methyl-indazol-6-yl]-4-azaspiro[2.5]oct-6-ene-4-carboxylate (550 mg, 1.22 mmol) was dissolved in methanol (15 mL). Palladium (10% on carbon (wet), 648.16 mg, 6.09 mmol) was added and reaction mixture was stirred under a hydrogen atmosphere (5 kg pressure) for 18 h. Dichloromethane (10 ml) was added and the mixture was stirred for 1 h. The reaction mixture was filtered through celite, washed by 10% methanol:dichloromethane (2×100 ml). The filtrate was evaporated under reduced pressure. The residue was purified by silica column, eluting with 6% methanol:dichloromethane. The collected fractions were evaporated on rotary vacuum afford tert-butyl 7-[3-(2,4-dioxohexahydropyrimidin-1-yl)-1-methyl-indazol-6-yl]-4-azaspiro[2.5]octane-4-carboxylate (460 mg, 853.30 μmol, 70.05% yield) as an off white solid. LCMS m/z: 398.1, [M−56+H]$^+$

Step 3: 1-[6-(4-azaspiro[2.5]octan-7-yl)-1-methyl-indazol-3-yl]hexahydropyrimidine-2,4-dione hydrochloride

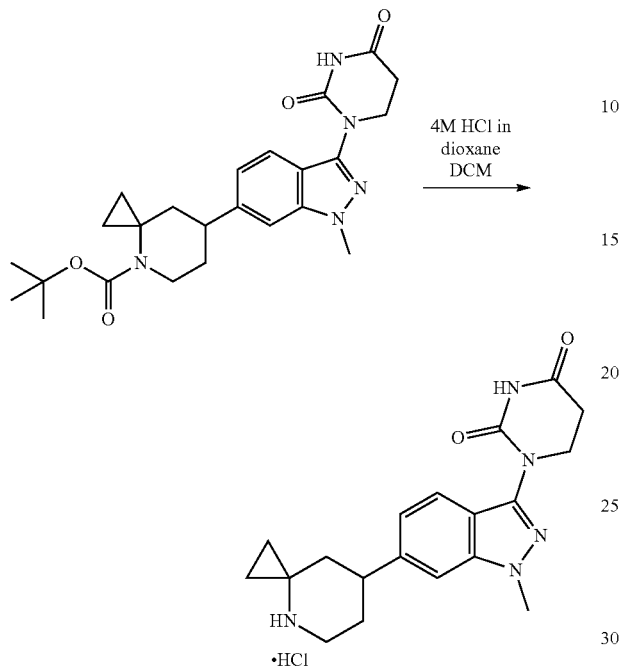

·HCl

To a stirred solution of tert-butyl 7-[3-(2,4-dioxohexahydropyrimidin-1-yl)-1-methyl-indazol-6-yl]-4-azaspiro[2.5]octane-4-carboxylate (460 mg, 1.01 mmol) in dichloromethane (5.0 mL) at 0° C. was added hydrogen chloride (4 M solution in 1,4-dioxane, 1.27 mL, 5.07 mmol) dropwise. The reaction mixture was stirred at ambient temperature for 3 h. The reaction mixture evaporated under reduced pressure. The obtained crude was triturated by diethyl ether (2×20 ml) afford 1-[6-(4-azaspiro[2.5]octan-7-yl)-1-methyl-indazol-3-yl]hexahydropyrimidine-2,4-dione hydrochloride (430 mg, 915.41 µmol, 90.25% yield) as an off-white solid. LCMS m/z: 354.1 [M+H]+

Step 4: tert-butyl 2-[7-[3-(2,4-dioxohexahydropyrimidin-1-yl)-1-methyl-indazol-6-yl]-4-azaspiro[2.5]octan-4-yl]acetate

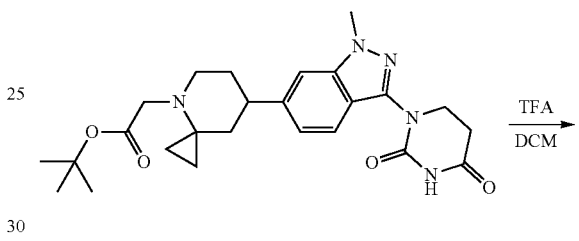

To a stirred solution of 1-[6-(4-azaspiro[2.5]octan-7-yl)-1-methyl-indazol-3-yl]hexahydropyrimidine-2,4-dione hydrochloride (430 mg, 1.10 mmol) in N,N-dimethylformamide (3.0 mL) at 0° C. were added triethylamine (558.02 mg, 5.51 mmol, 768.62 uL) fallowed by tert-butyl 2-bromoacetate (236.64 mg, 1.21 mmol, 177.92 uL). After addition allow reaction to stirred at ambient temperature for 8 h. The reaction mixture was poured in ice cold water (10 ml). The solid precipitate was filtered, collected and dried under rotary vacuum to afford tert-butyl 2-[7-[3-(2,4-dioxohexahydropyrimidin-1-yl)-1-methyl-indazol-6-yl]-4-azaspiro[2.5]octan-4-yl]acetate (250 mg, 479.08 µmol, 43.44% yield) as an off white solid. LCMS m/z: 468.3 [M+H]+

Step 5: 2-[7-[3-(2,4-dioxohexahydropyrimidin-1-yl)-1-methyl-indazol-6-yl]-4-azaspiro[2.5]octan-4-yl]acetic acid trifluoroacetic acid

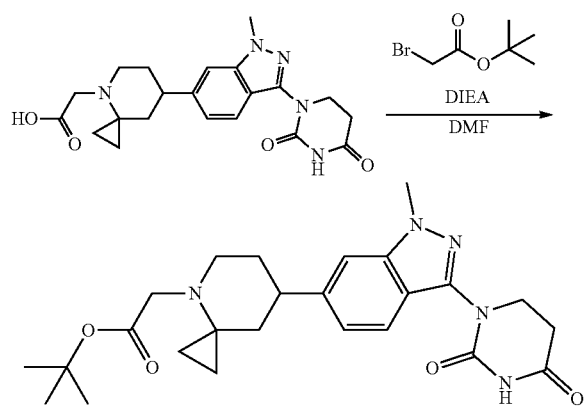

To a stirred solution of tert-butyl 2-[7-[3-(2,4-dioxohexahydropyrimidin-1-yl)-1-methyl-indazol-6-yl]-4-azaspiro[2.5]octan-4-yl]acetate (250 mg, 534.69 µmol) in dichloromethane (2.5 mL) at 0° C. was added trifluoroacetic acid (304.84 mg, 2.67 mmol, 205.97 uL) dropwise. The reaction was stirred at ambient temperature for 4 h. The mixture was evaporated to dryness under reduced pressure. The solid was triturated with diethyl ether (2×15 ml). The compound was dried under rotary vacuum to afford 2-[7-[3-(2,4-dioxohexahydropyrimidin-1-yl)-1-methyl-indazol-6-yl]-4-azaspiro[2.5]octan-4-yl]acetic acid trifluoroacetic acid (270 mg, 469.12 µmol, 87.74% yield) as an off white solid. LCMS m/z: 412.2, [M+H]+

Step 6: 2-(6,7-dihydro-5H-pyrrolo[1,2-c]imidazol-1-yl)-2-[6-[4-[2-[2-[7-[3-(2,4-dioxohexahydropyrimidin-1-yl)-1-methyl-indazol-6-yl]-4-azaspiro[2.5]octan-4-yl]acetyl]-2,6-diazaspiro[3.3]heptan-6-yl]phenyl]-4-fluoro-1-oxo-isoindolin-2-yl]-N-(2-pyridyl)acetamide
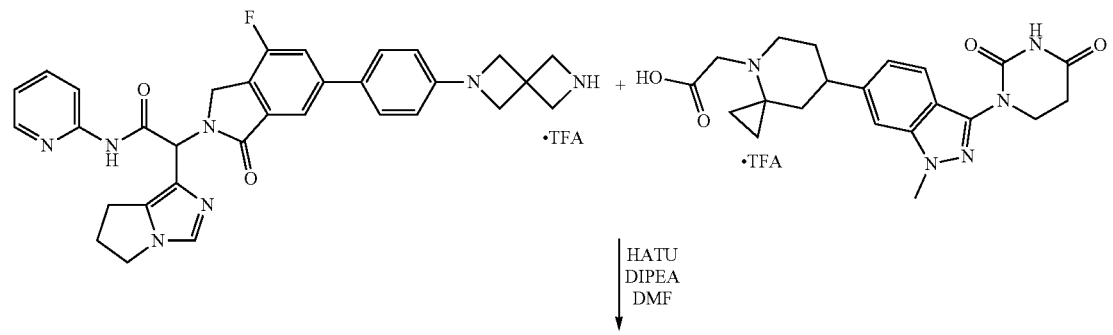
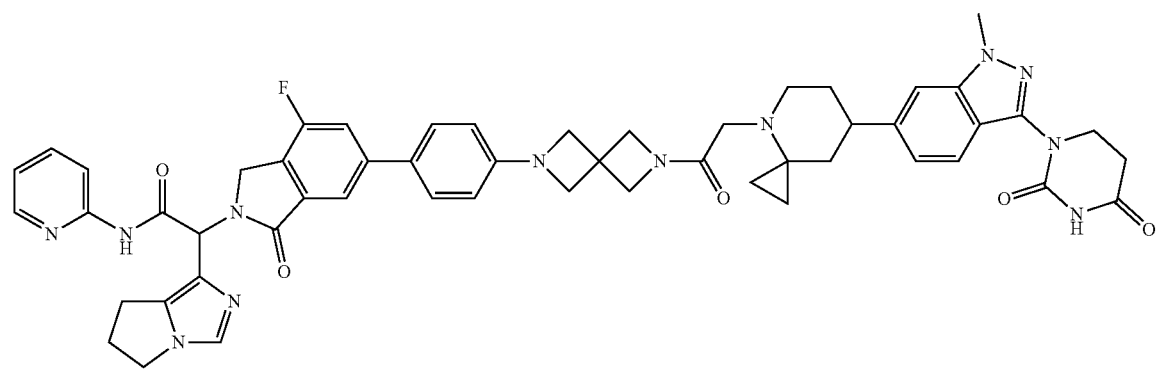

To a stirred solution of 2-[7-[3-(2,4-dioxohexahydropyrimidin-1-yl)-1-methyl-indazol-6-yl]-4-azaspiro[2.5]octan-4-yl]acetic acid, trifluoracetic acid salt (127.95 mg, 243.49 µmol) in N,N-dimethylformamide (1.5 mL) at 0° C. was added N,N-diisopropylethylamine (200.26 mg, 1.55 mmol, 269.89 uL) followed by HATU (126.25 mg, 332.03 µmol). The reaction mixture stirred reaction for 5 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-(2-pyridyl)acetamide, trifluoroacetic acid salt (150 mg, 221.35 µmol) was added. The reaction mixture was stirred at ambient temperature for 1 h. The compound was purified by reverse phase chromatography (C18 column, acetonitrile in water (10 mM ammonium acetate)). Pure fractions were lyophilized afforded Compound 153 (58 mg, 60.29 µmol, 27.24% yield) as a white solid. LCMS m/z: 957.3, [M+H]$^+$. $^1$H-NMR (400 MHz, DMSO-d6): δ 10.91 (s, 1H), 10.55 (s, 1H), 8.33 (d, J=0.80 Hz, 1H), 8.08 (d, J=8.40 Hz, 1H), 7.81 (t, J=7.20 Hz, 1H), 7.78-7.64 (m, 5H), 7.56 (d, J=8.40 Hz, 1H), 7.49 (s, 1H), 7.14-7.11 (m, 1H), 7.10 (d, J=7.60 Hz, 1H), 6.55 (d, J=8.80 Hz, 2H), 6.20 (s, 1H), 4.80 (d, J=17.60 Hz, 1H), 4.39 (q, J=9.60 Hz, 2H), 4.21 (d, J=17.60 Hz, 1H), 4.03-3.95 (m, 11H), 3.91 (t, J=6.40 Hz, 2H), 3.38 (s, 1H), 2.96 (s, 2H), 2.79-2.74 (m, 3H), 2.56-2.51 (m, 2H), 2.33 (t, J=1.60 Hz, 1H), 1.92 (m, 1H), 1.50 (m, 1H), 0.91 (d, J=11.60 Hz, 1H), 0.72-0.43 (m, 4H). Some proton signals were not observed due to water obscuration.

Example 154

2-(6,7-dihydro-5H-pyrrolo[1,2-c]imidazol-1-yl)-2-[6-[4-[2-[2-[7-[3-(2,4-dioxohexahydropyrimidin-1-yl)-1-methyl-indazol-6-yl]-4-azaspiro[2.5]octan-4-yl]acetyl]-2,6-diazaspiro[3.3]heptan-6-yl]phenyl]-4-fluoro-1-oxo-isoindolin-2-yl]-N-thiazol-2-yl-acetamide, Compound 154

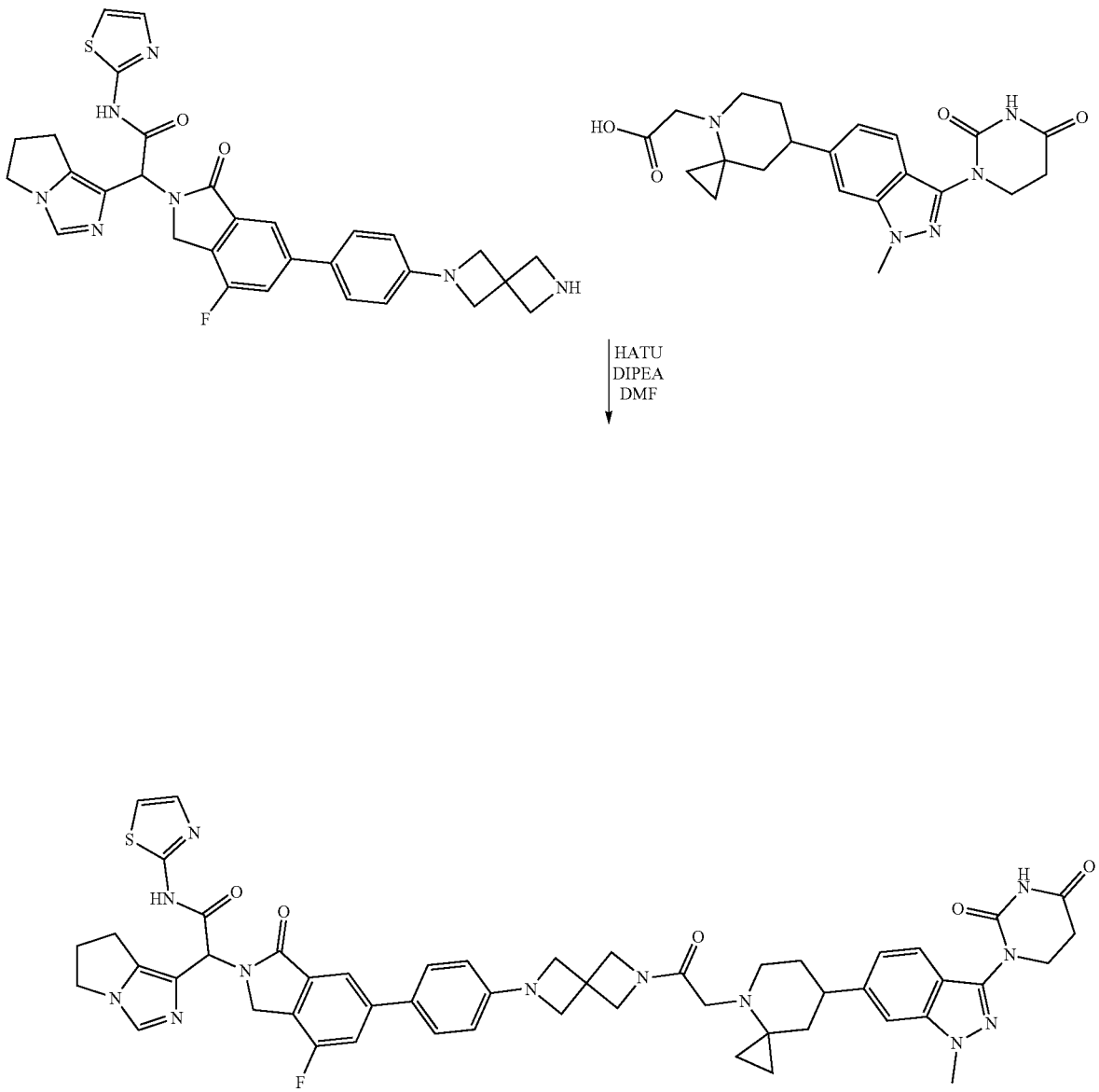

To a stirred solution of 2-[7-[3-(2,4-dioxohexahydropyrimidin-1-yl)-1-methyl-indazol-6-yl]-4-azaspiro[2.5]octan-4-yl]acetic acid, trifluoracetic acid salt (115.29 mg, 219.40 µmol) in N,N-dimethylformamide (1.5 mL) at 0° C. was added N,N-diisopropylethylamine (198.49 mg, 1.54 mmol, 267.51 uL) fallowed by HATU (125.14 mg, 329.10 µmol). The reaction mixture was stirred for 5 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid (150 mg, 219.40 µmol) was added. The reaction mixture was stirred ambient temperature for 1 h. The reaction mixture was purified (C18 column, Acetonitrile in water (10 mM ammonium acetate)). Pure fractions were lyophilized to afford Compound 154 (80 mg, 82.12 µmol, 37.43% yield) as a white color solid. LCMS m/z: 963.3, [M+H]+, 1H-NMR (400 MHz, DMSO-d6): δ 12.53 (s, 1H), 10.55 (s, 1H), 7.75 (s, 1H), 7.72 (d, J=10.80 Hz, 1H), 7.66 (s, 1H), 7.64 (s, 1H), 7.62 (s, 1H), 7.55 (d, J=8.80 Hz, 1H), 7.50 (s, 1H), 7.49 (s, 1H), 7.27 (d, J=3.60 Hz, 1H), 7.08 (d, J=8.40 Hz, 1H), 6.54 (d, J=8.40 Hz, 2H), 6.15 (s, 1H), 4.80 (d, J=17.60 Hz, 1H), 4.38 (q, J=9.60 Hz, 2H), 4.22 (d, J=17.60 Hz, 1H), 4.07-3.98 (m, 12H), 3.91 (t, J=6.80 Hz, 2H), 3.53 (d, J=14.80 Hz, 1H), 2.96-2.89 (m, 3H), 2.75 (t, J=6.40 Hz, 3H), 2.25 (t, J=Hz, 1H), 1.92 (m, 1H), 1.48-1.42 (m, 1H), 0.90 (d, J=12.00 Hz, 1H), 0.70 (d, J=5.60 Hz, 1H), 0.50 (d, J=4.40 Hz, 3H) (Some signals were not observed due to solvent obscuration).

Example 155

2-(6,7-dihydro-5H-pyrrolo[1,2-c]imidazol-1-yl)-2-[6-[4-[6-[4-[3-(2,4-dioxohexahydropyrimidin-1-yl)-1-methyl-indazol-6-yl]-3,3-difluoro-piperidine-1-carbonyl]-2-azaspiro[3.3]heptan-2-yl]phenyl]-4-fluoro-1-oxo-isoindolin-2-yl]-N-thiazol-2-yl-acetamide, Compound 155

Step 1: Methyl 2-(4-bromophenyl)-2-azaspiro[3.3]heptane-6-carboxylate

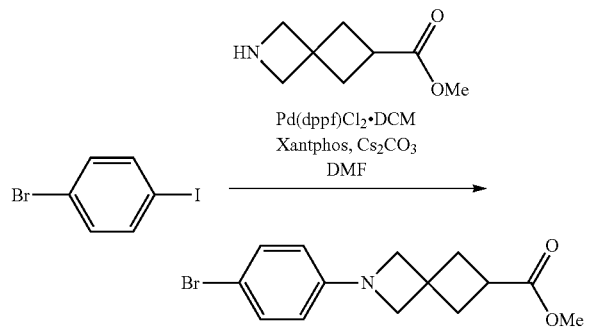

To a stirred solution of methyl 2-azaspiro[3.3]heptane-6-carboxylate (1.12 g, 4.16 mmol) and 1-bromo-4-iodo-benzene (1.41 g, 4.99 mmol) in N,N-dimethylformamide (15 mL) was added cesium carbonate (4.07 g, 12.48 mmol) and degassed with nitrogen for 15 min. Xantphos (481.42 mg, 832.04 µmol) and Pd(dppf)Cl2.dichloromethane (339.47 mg, 416.02 µmol) were added to the reaction mixture. The reaction mixture was purged with nitrogen gas for 5 mins. The reaction mixture was heated at 90° C. for 16 h under inert atmosphere. The reaction mixture cooled to ambient temperature and diluted with ethyl acetate. The mixture was filtered with celite bed and the filter cake was washed with ethyl acetate. The ethyl acetate layer was washed with water, brine, dried over sodium sulfate and concentrated under reduced pressure. The residue was purified by column chromatography using 50 g column, 230-400 silica gel using an ethyl acetate:petroleum ether eluent mixture to afford methyl 2-(4-bromophenyl)-2-azaspiro[3.3]heptane-6-carboxylate (510 mg, 1.40 mmol, 33.59% yield). LCMS (ESI+): 310.1/312.1 (M+H, Br pattern).

Step 2: Methyl 2-[4-(4,4,5,5-tetramethyl-1,3,2-dioxaborolan-2-yl)phenyl]-2-azaspiro[3.3]heptane-6-carboxylate

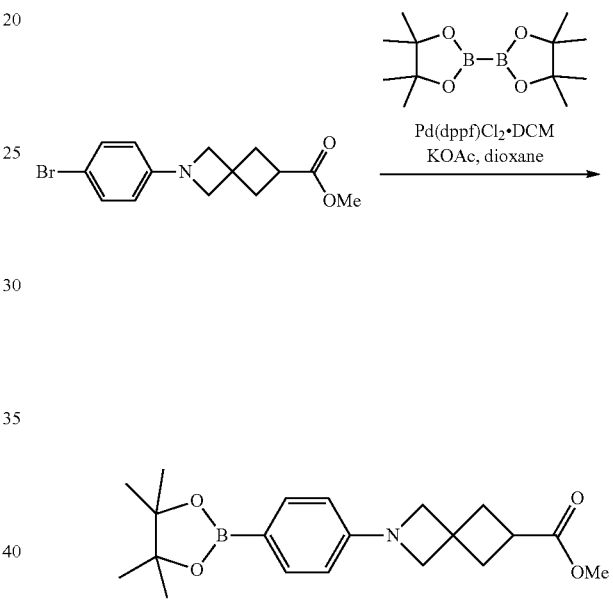

To a solution of methyl 2-(4-bromophenyl)-2-azaspiro [3.3]heptane-6-carboxylate (420 mg, 1.35 mmol) and 4,4,5,5-tetramethyl-2-(4,4,5,5-tetramethyl-1,3,2-dioxaborolan-2-yl)-1,3,2-dioxaborolane (515.76 mg, 2.03 mmol) in 1,4-dioxane (5 mL) was added Potassium Acetate (398.65 mg, 4.06 mmol, 253.92 uL) and degassed with nitrogen for 15 min. Pd(dppf)Cl2.dichloromethane (220.98 mg, 270.81 µmol) was added to the reaction mixture and purged with nitrogen gas for 5 min. The reaction mixture was heated at 90° C. for 16 h under inert atmosphere. The reaction mixture was cooled to ambient temperature and diluted with ethyl acetate. The mixture was filtered on celite and washed with ethyl acetate. The organic layer was washed with water and brine, and dried over sodium sulfate, filtered, and concentrated under reduced pressure. The residue was purified by column chromatography using a 25 g column, 230-400 silica gel, eluting in 13% ethyl acetate in petroleum ether, to afford product as methyl 2-[4-(4,4,5,5-tetramethyl-1,3,2-dioxaborolan-2-yl)phenyl]-2-azaspiro[3.3]heptane-6-carboxylate (310 mg, 685.51 µmol, 50.63% yield). LCMS m/z 358.0 (M+H+).

Step 3: Methyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptane-6-carboxylate

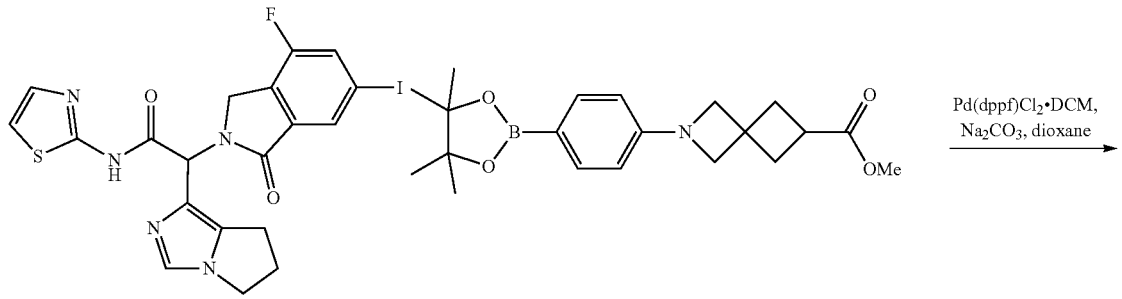

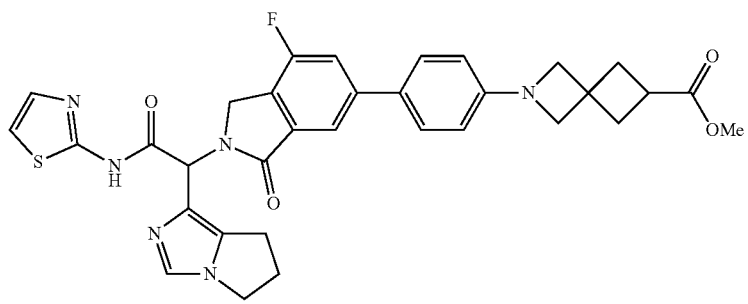

To a solution of methyl 2-[4-(4,4,5,5-tetramethyl-1,3,2-dioxaborolan-2-yl)phenyl]-2-azaspiro[3.3]heptane-6-carboxylate (310 mg, 867.74 µmol) and 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (302.74 mg, 578.49 µmol) in 1,4-dioxane (4 mL) was added sodium carbonate (61.31 mg, 578.49 µmol, 24.23 uL) in water (1 mL). The mixture was degassed with nitrogen for 15 min. Pd(dppf)Cl₂·CH₂Cl₂ (47.20 mg, 57.85 µmol) was added to the reaction mixture and purged with nitrogen gas for 5 mins. The reaction mixture was heated at 90° C. for 16 h under inert atmosphere. The reaction mixture cooled to ambient temperature and diluted with methanol, filtered through celite bed and washed with methanol, concentrated and crude was purified by column chromatography using 25 g column, 230-400 silica gel, eluted in 10% methanol:dichloromethane, to afford product as methyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptane-6-carboxylate (162 mg, 137.0 µmol, 23.68% yield). LCMS m/z 627.2 (M+H⁺).

Step 4: [2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptane-6-carbonyl]oxylithium

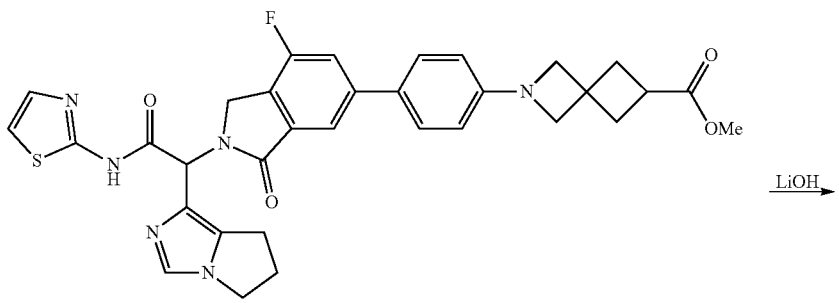

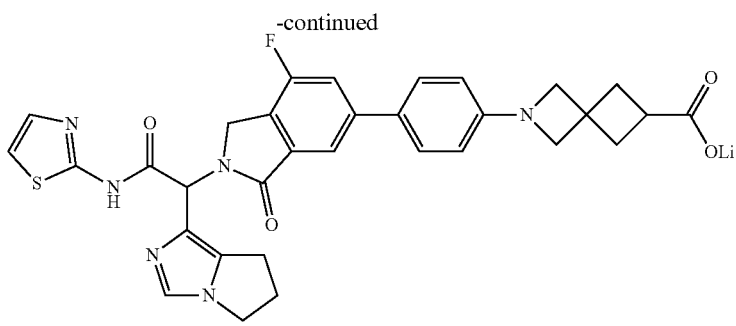

To a stirred solution of methyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptane-6-carboxylate (150 mg, 239.35 μmol) in methanol (1 mL) and tetrahydrofuran (1 mL) was added lithium hydroxide monohydrate, 98% (10.04 mg, 239.35 mol, 6.65 uL) dissolved in Water (1 mL). The reaction mixture was stirred at ambient temperature for 2 h. The reaction mixture was evaporated under high vacuum to afford [2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptane-6-carbonyl]oxylithium (145 mg, 117.20 μmol). LCMS m/z: 613.2 (M+H)⁺.

Step 5: 2-(6,7-dihydro-5H-pyrrolo[1,2-c]imidazol-1-yl)-2-[6-[4-[6-[4-[3-(2,4-dioxohexahydropyrimidin-1-yl)-1-methyl-indazol-6-yl]-3,3-difluoro-piperidine-1-carbonyl]-2-azaspiro[3.3]heptan-2-yl]phenyl]-4-fluoro-1-oxo-isoindolin-2-yl]-N-thiazol-2-yl-acetamide

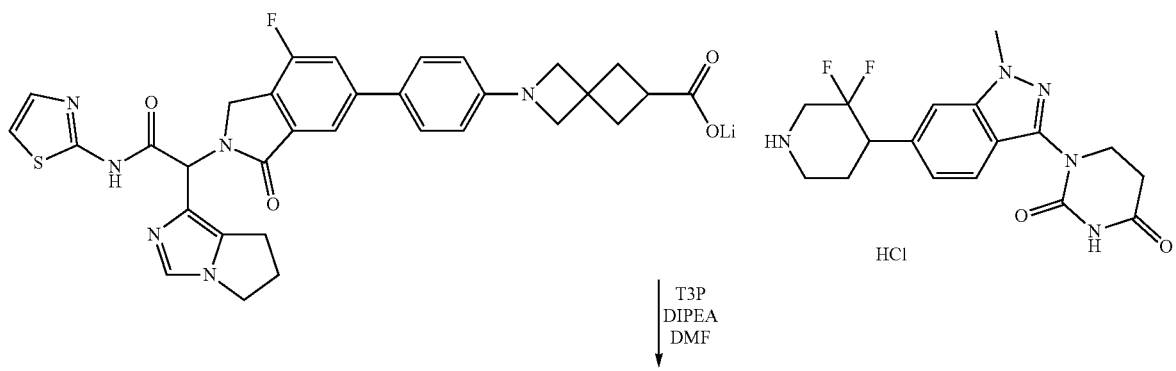

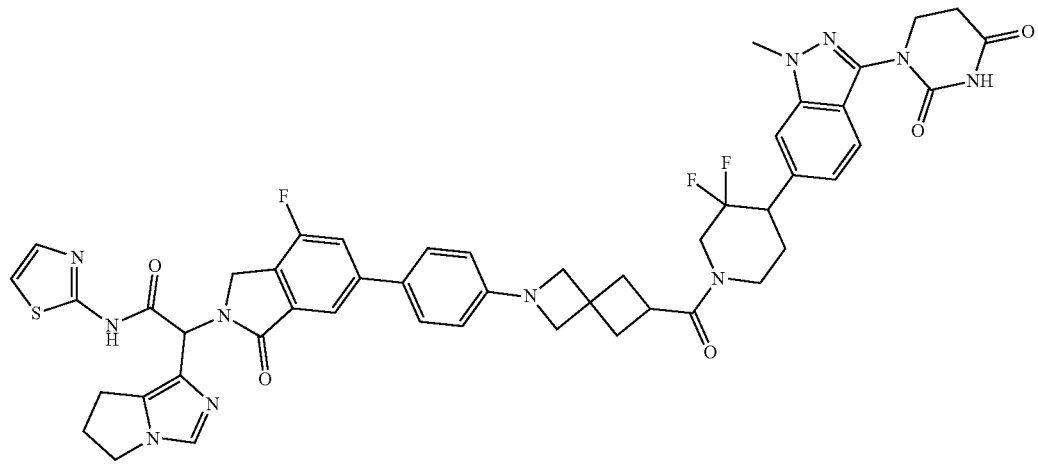

To a solution of [2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2-azaspiro[3.3]heptane-6-carbonyl]oxylithium (145 mg, 234.40 μmol) in N,N-dimethylformamide (2 mL) was added N,N-diisopropylethylamine (126.23 mg, 976.66 μmol, 170.12 uL) followed by propanephosphonic acid anhydride (50% in Ethyl acetate) (124.30 mg, 390.66 μmol) at 0° C. The reaction mixture was stirred for 15 min. 1-[6-(3,3-difluoro-4-piperidyl)-1-methyl-indazol-3-yl]hexahydropyrimidine-2,4-dione hydrochloride (78.10 mg, 195.33 μmol) was added and stirred for 1 h. The reaction mixture was directly injected on a C-18 column (100 g) for purification (0-50% acetonitrile in water (0.1% ammonium acetate) over 30 min, then steep gradient to 100% acetonitrile). The pure fractions were combined, frozen and lyophilized to get Compound 155 (13 mg, 13.30 μmol, 6.81% yield over 2 steps) as an off-white solid. LCMS (ESI+): 958.2 (M+H)+, $^1$H-NMR (400 MHz, DMSO-d6): 12.56 (s, 1H), 10.57 (s, 1H), 7.74 (s, 1H), 7.70 (d, J=10.40 Hz, 1H), 7.64-7.59 (m, 4H), 7.55 (d, J=3.60 Hz, 1H), 7.48 (s, 1H), 7.24 (s, 1H), 7.09-7.06 (m, 1H), 6.51 (t, J=7.20 Hz, 2H), 6.13 (s, 1H), 4.84-4.79 (m, 2H), 4.57 (d, J=32.00 Hz, 1H), 4.21 (d, J=17.60 Hz, 2H), 4.02-3.91 (m, 10H), 3.79 (d, J=8.80 Hz, 2H), 3.61-3.52 (m, 2H), 3.43-3.39 (m, 2H), 3.21-3.06 (m, 2H), 3.41 (t, J=8.80 Hz, 3H), 2.45-2.38 (m, 3H), 2.21-2.12 (m, 1H), 1.93-1.89 (m, 1H).

Example 156

2-(6,7-dihydro-5H-pyrrolo[1,2-c]imidazol-1-yl)-2-[6-[4-[2-[1-[4-(2,4-dioxohexahydropyrimidin-1-yl)-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, Compound 156

Step 1: 3-[3-fluoro-4-[4-hydroxy-4-(2-methoxy-2-oxo-ethyl)-1-piperidyl]anilino]propanoic acid

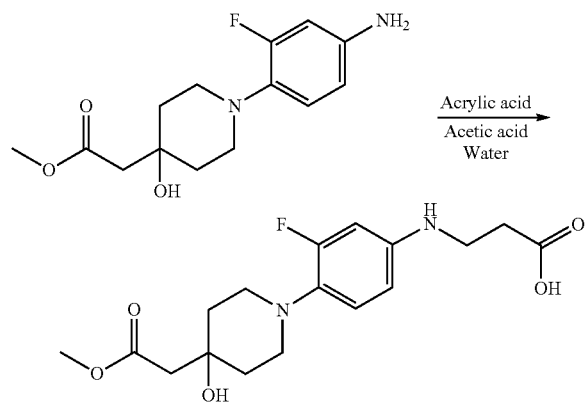

To a solution of methyl 2-[1-(4-amino-2-fluoro-phenyl)-4-hydroxy-4-piperidyl]acetate (3.5 g, 12.40 mmol) in water (24 mL), acetic acid (6 mL) was added acrylic acid (1.07 g, 14.88 mmol, 1.02 mL) and heated at 100° C. for 14 h. The reaction mixture was concentrated under reduced pressure. The solid was dissolved in ethyl acetate (60 mL). The ethyl acetate layer was dried over sodium sulfate and concentrated under reduced pressure to get crude 3-[3-fluoro-4-[4-hydroxy-4-(2-methoxy-2-oxo-ethyl)-1-piperidyl]anilino]propanoic acid (4.0 g, 6.66 mmol, 53.72% yield). LCMS: 355.1 [M+H]+.

Step 2: Methyl 2-[1-[4-(2,4-dioxohexahydropyrimidin-1-yl)-2-fluoro-phenyl]-4-hydroxy-4-piperidyl]acetate

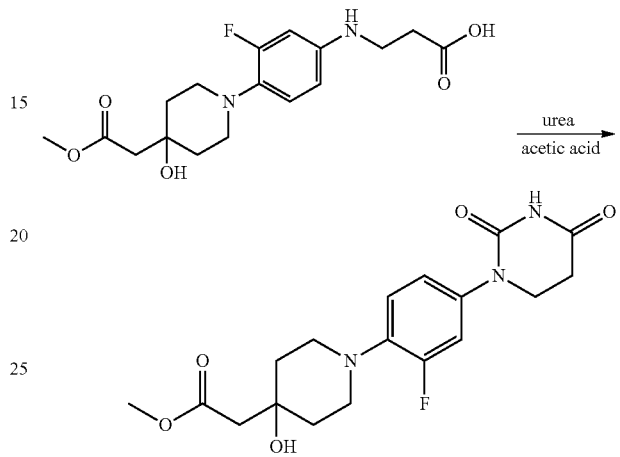

To a solution of 3-[3-fluoro-4-[4-hydroxy-4-(2-methoxy-2-oxo-ethyl)-1-piperidyl]anilino]propanoic acid (4.0 g, 11.29 mmol) in acetic acid (15 mL) was added urea (1.36 g, 22.58 mmol, 1.01 mL) and heated at 110° C. in sealed tube for 14 h. Hydrochloric acid (2M aqueous solution, 10 mL, 20 mmol) was added to the reaction mixture and heated at 100° C. for 1 h. The reaction mixture was concentrated under reduced pressure to get crude, which was diluted with ethyl acetate (100 mL), washed with a sodium bicarbonate solution (30 mL), water (30 ml) and brine (30 mL). The organic layer was dried over sodium sulfate and concentrated under reduced pressure to get crude which was purified by column chromatography on silica gel eluted with 60% ethyl acetate in petroleum ether to afford methyl 2-[1-[4-(2,4-dioxohexahydropyrimidin-1-yl)-2-fluoro-phenyl]-4-hydroxy-4-piperidyl]acetate (1.6 g, 3.65 mmol, 32.36% yield) as a light brown solid.

Step 3: 2-[1-[4-(2,4-dioxohexahydropyrimidin-1-yl)-2-fluoro-phenyl]-4-hydroxy-4-piperidyl]acetic acid hydrochloride

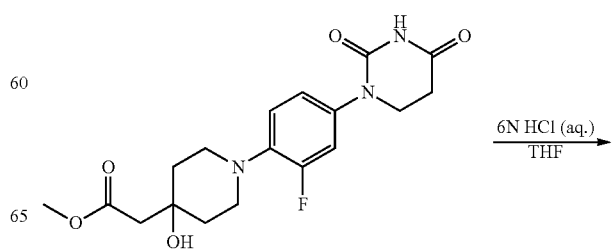

-continued

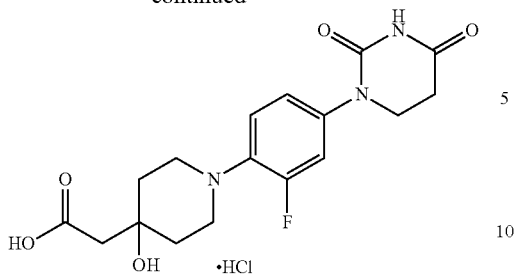

To a solution of methyl 2-[1-[4-(2,4-dioxohexahydropyrimidin-1-yl)-2-fluoro-phenyl]-4-hydroxy-4-piperidyl]acetate (300 mg, 790.76 μmol) in tetrahydrofuran (2 mL) was added hydrochloric acid (6M aqueous, 7.50 mL, 45 mmol) and the reaction mixture was stirred at ambient temperature for 14 h. The reaction mixture was concentrated under reduced pressure to afford 2-[1-[4-(2,4-dioxohexahydropyrimidin-1-yl)-2-fluoro-phenyl]-4-hydroxy-4-piperidyl]acetic acid hydrochloride (280 mg, 648.06 μmol, 81.95% yield) as a brown gum. LCMS m/z 366.2 [M+H]+

Step 4: 2-(6,7-dihydro-5H-pyrrolo[1,2-c]imidazol-1-yl)-2-[6-[4-[2-[2-[1-[4-(2,4-dioxohexahydropyrimidin-1-yl)-2-fluoro-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide

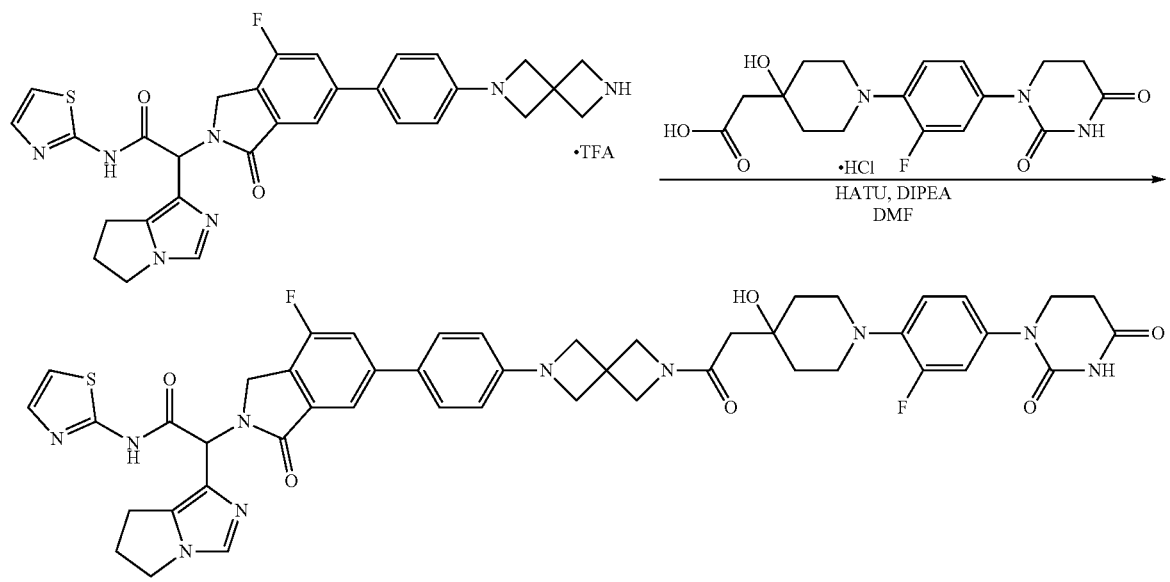

To the stirred solution of 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (80 mg, 117.01 μmol) and 2-[1-[4-(2,4-dioxohexahydropyrimidin-1-yl)-2-fluoro-phenyl]-4-hydroxy-4-piperidyl]acetic acid hydrochloride (61.12 mg, 152.12 mol) in N,N-dimethylformamide (2 mL) was cooled to 0° C. N,N-Diisopropylethylamine (90.74 mg, 702.09 μmol, 122.29 uL) was added to the reaction mixture followed by HATU (62.29 mg, 163.82 μmol) at 0° C. The reaction mixture stirred at ambient temperature for 1 h. The reaction mixture was directly injected on a C-18 column (100 g) for purification (0-45% Acetonitrile in water (+0.1% ammonium acetate) and over 30 min, then steep gradient to 100% acetonitrile). The pure fractions were combined and lyophilized to get Compound 156 (55 mg, 58.79 μmol, 50.24% yield) as an off-white solid. LCMS m/z 917.3 (M+H)+. 1H-NMR (400 MHz, DMSO-d6): δ 12.51 (s, 1H), 10.38 (s, 1H), 7.74-7.70 (m, 2H), 7.65 (d, J=8.40 Hz, 2H), 7.60 (s, 1H), 7.46 (s, 1H), 7.31-7.15 (m, 2H), 7.07-7.05 (m, 2H), 6.55 (d, J=8.40 Hz, 2H), 6.12 (s, 1H), 4.84 (s, 1H), 4.82-4.81 (m, 1H), 4.39 (s, 2H), 4.21 (d, J=17.60 Hz, 1H), 4.09 (s, 2H), 4.03-3.96 (m, 6H), 3.74 (t, J=6.80 Hz, 2H), 3.09-2.97 (m, 4H), 2.75-2.68 (m, 4H), 2.63-2.58 (m, 1H), 2.50-2.45 (m, 1H), 2.25 (s, 2H), 1.88-1.76 (m, 2H), 1.68-1.65 (m, 2H).

Example 157

2-(6,7-dihydro-5H-pyrrolo[1,2-c]imidazol-1-yl)-2-(6-(4-(6-(2-(1-(4-(2,6-dioxopiperidin-3-yl)-2-fluoro-phenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide, Compound 157

Step 1: tert-butyl 2-[1-(2-fluoro-4-iodo-phenyl)-4-hydroxy-4-piperidyl]acetate

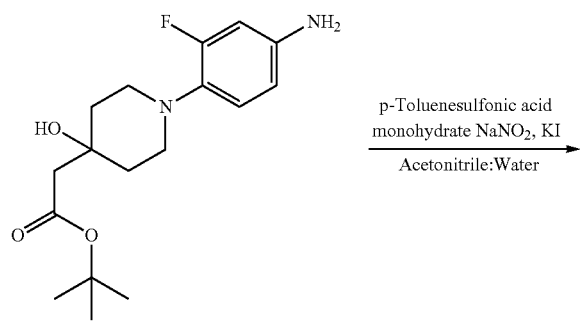

Step 2: tert-butyl 2-[1-[4-(2,6-dibenzyloxy-3-pyridyl)-2-fluoro-phenyl]-4-hydroxy-4-piperidyl]acetate

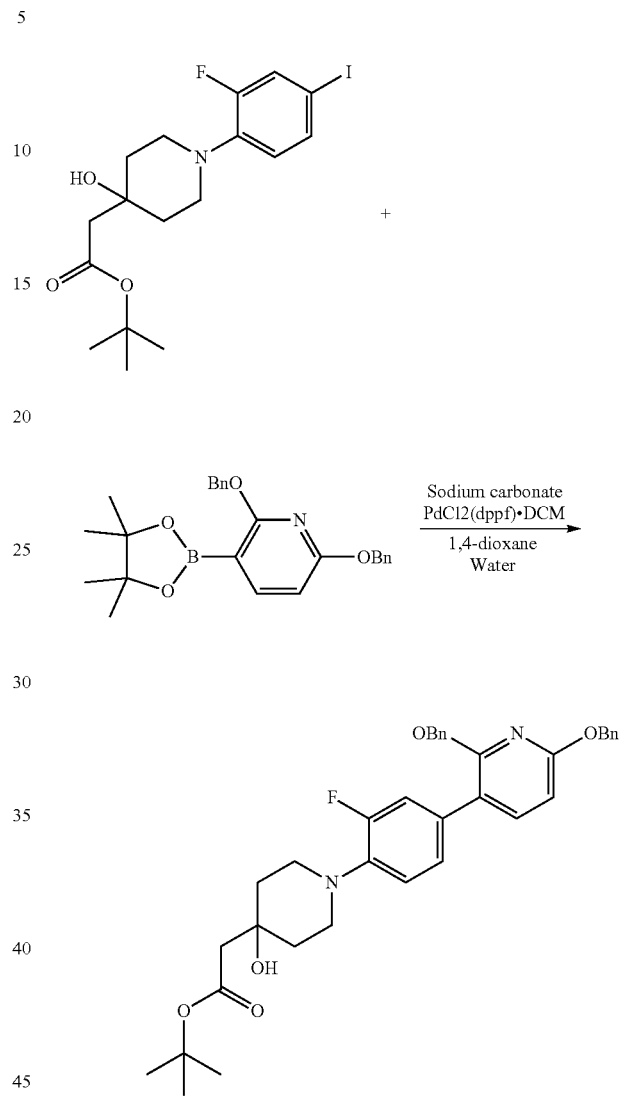

To a solution of tert-butyl 2-[1-(4-amino-2-fluoro-phenyl)-4-hydroxy-4-piperidyl]acetate (3.2 g, 9.86 mmol) in acetonitrile (40 mL) was added. Cooled the reaction mixture at 0° C. The p-toluenesulfonic acid monohydrate (1.88 g, 9.86 mmol) was added into traction mixture at single portion. A solution of sodium nitrite (680.66 mg, 9.86 mmol) in water (10 mL) was added dropwise over 2 min. Allow reaction mixture was stirred at same temperature for 30 min. The solution of potassium iodide, 99% (1.64 g, 9.86 mmol) in water (10 mL) was added dropwise into reaction mixture over 3 min. After addition stirred reaction mixture at 0° C. for 10 min. The reaction mixture was warmed to ambient temperature for 1.5 h. Potassium carbonate solution (10% in water) was added to the reaction mixture. The reaction mixture was extracted with ethyl acetate. The organic layer was dried over sodium sulfate, filtered, and concentrated under reduced pressure. The residue was purified by silica gel column chromatography (100-200 mesh), eluted with 10% Ethyl acetate:Petroleum ether. The pure fractions were evaporated to afford tert-butyl 2-[1-(2-fluoro-4-iodo-phenyl)-4-hydroxy-4-piperidyl]acetate (2.1 g, 4.34 mmol, 44.02% yield). LCMS m/z 436.0 (M+H$^+$)

To a solution of tert-butyl 2-[1-(2-fluoro-4-iodo-phenyl)-4-hydroxy-4-piperidyl]acetate (500 mg, 1.15 mmol) and 2,6-dibenzyloxy-3-(4,4,5,5-tetramethyl-1,3,2-dioxaborolan-2-yl)pyridine (575.23 mg, 1.38 mmol) in 1,4-dioxane (5 mL) and water (0.5 mL) was added Sodium carbonate (304.38 mg, 2.87 mmol, 120.31 uL) and solvent was purged with nitrogen for 10 min. PdCl$_2$(dppf).dichloromethane (93.81 mg, 114.87 μmol) was added and the reaction mixture purged with nitrogen gas for 5 mins and heated at 90° C. for 16 h. The reaction mixture diluted with ethyl acetate and filtered through celite. The filtrate washed with ice water and extracted with ethyl acetate. The organic layer washed with brine solution, dried with sodium sulfate, filtered, and concentrated under reduced pressure to get crude. The crude was purified by column chromatography by using 230-400 silica gel; eluting with 3% methanol in dichloromethane to afford tert-butyl 2-[1-[4-(2,6-dibenzyloxy-3-pyridyl)-2-fluoro-phenyl]-4-hydroxy-4-piperidyl]acetate (310 mg, 507.4 μmol, 44.17% yield). LCMS m/z 599.4 (M+H$^+$)

1237

Step 3: tert-butyl 2-[1-[4-(2,6-dioxo-3-piperidyl)-2-fluoro-phenyl]-4-hydroxy-4-piperidyl]acetate

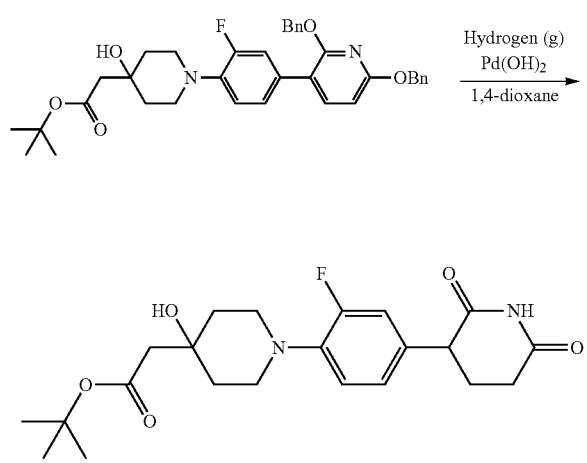

A stirred solution of tert-butyl 2-[1-[4-(2,6-dibenzyloxy-3-pyridyl)-2-fluoro-phenyl]-4-hydroxy-4-piperidyl]acetate (525 mg, 876.90 μmol) in 1,4-dioxane (6 mL) was purged with nitrogen for 5 min and palladium hydroxide (10% on carbon, 184.71 mg, 1.32 mmol) was added. The reaction mixture was put under a hydrogen atmosphere (1 atm). The reaction was stirred for 16 h at ambient temperature. The reaction mixture diluted with ethyl acetate and filtered through celite. the required filtrate was concentrated under reduced pressure to afford tert-butyl 2-[1-[4-(2,6-dioxo-3-piperidyl)-2-fluoro-phenyl]-4-hydroxy-4-piperidyl]acetate (310 mg, 685.66 μmol, 78.19% yield). LCMS m/z 421.3 (M+H)+.

1238

Step 4: 2-[1-[4-(2,6-dioxo-3-piperidyl)-2-fluoro-phenyl]-4-hydroxy-4-piperidyl]acetic acid hydrochloride

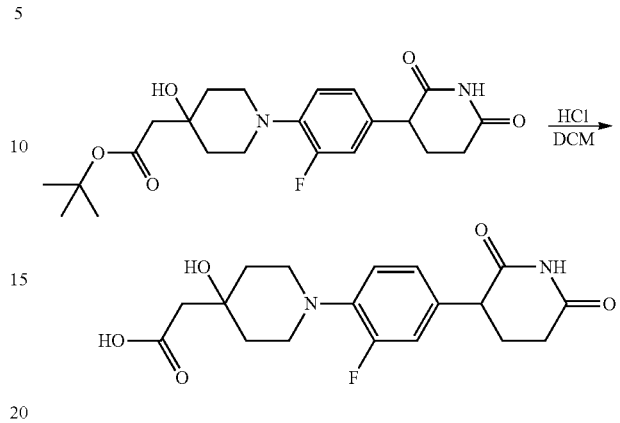

To the stirred solution of tert-butyl 2-[1-[4-(2,6-dioxo-3-piperidyl)-2-fluoro-phenyl]-4-hydroxy-4-piperidyl]acetate (310 mg, 737.26 μmol) in dichloromethane (5 mL) was added hydrogen chloride (4.0 M solution in 1,4-dioxane, 2.76 mL, 11.06 mmol) dropwise at 0° C. The reaction mixture stirred at ambient temperature for 6 h. The reaction mixture was concentrated under reduced pressure The solid was triturated with diethyl ether (2×10 ml) and dried under reducing pressure to give 2-[1-[4-(2,6-dioxo-3-piperidyl)-2-fluoro-phenyl]-4-hydroxy-4-piperidyl]acetic acid hydrochloride (250 mg, 597.15 μmol, 81.00% yield) as an off-white solid. LCMS m/z 365.2 (M+H)+.

Step 5: 2-(6,7-dihydro-5H-pyrrolo[1,2-c]imidazol-1-yl)-2-(6-(4-(6-(2-(1-(4-(2,6-dioxopiperidin-3-yl)-2-fluorophenyl)-4-hydroxypiperidin-4-yl)acetyl)-2,6-diazaspiro[3.3]heptan-2-yl)phenyl)-4-fluoro-1-oxoisoindolin-2-yl)-N-(thiazol-2-yl)acetamide

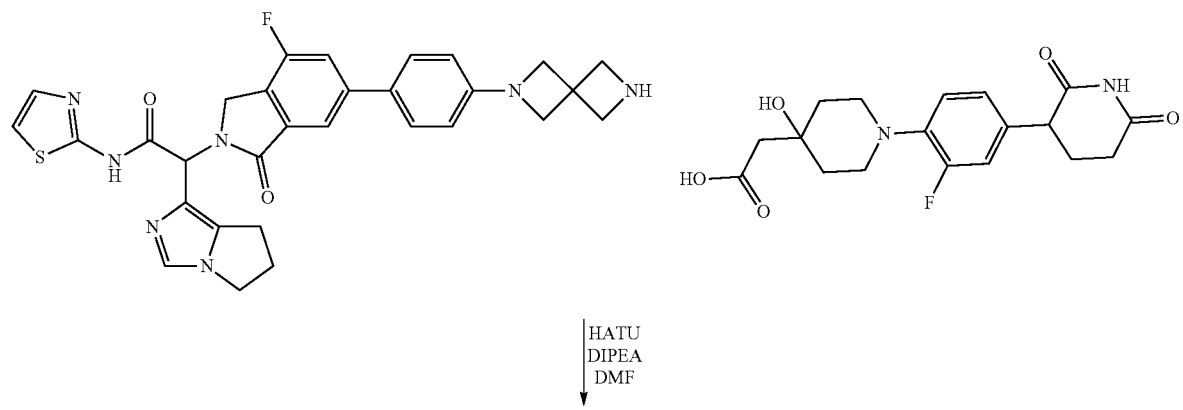

HATU
DIPEA
DMF

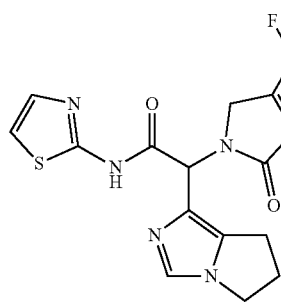
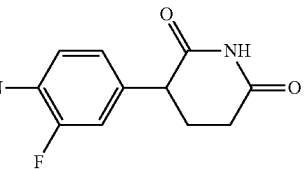

To the stirred solution of 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (80 mg, 117.01 μmol) and 2-[1-[4-(2,6-dioxo-3-piperidyl)-2-fluoro-phenyl]-4-hydroxy-4-piperidyl]acetic acid hydrochloride (60.97 mg, 152.12 μmol) in N,N-dimethylformamide (2 mL) was cooled to 0° C. N,N-Diisopropylethylamine (90.74 mg, 702.09 mol, 122.29 uL) was added to the reaction mixture followed by HATU (62.29 mg, 163.82 mol) at 0° C. The reaction mixture stirred at rt for 1 h. The reaction mixture was directly injected on a C-18 column (100 g) for purification (0-45% Acetonitrile in water (0.1% NH₄OAc) and over 30 min, then steep gradient to 100% acetonitrile). The pure fractions were combined and lyophilized to get Compound 157 (45 mg, 48.59 μmol, 41.53% yield) as an off-white solid. LCMS m/z 914.3 (M−H). ¹H-NMR (400 MHz, DMSO-d6): δ 12.62 (s, 1H), 10.83 (s, 1H), 7.74-7.60 (m, 5H), 7.47 (s, 1H), 7.23-7.21 (m, 1H), 7.03-6.93 (m, 3H), 6.55 (d, J=8.80 Hz, 2H), 6.12 (s, 1H), 4.83-4.88 (m, 2H), 4.39 (s, 2H), 4.21 (d, J=17.60 Hz, 1H), 4.09-4.03 (m, 2H), 3.80 (s, 6H), 3.79-3.78 (m, 1H), 3.05-2.99 (m, 5H), 2.81-2.74 (m, 5H), 2.34-2.19 (m, 3H), 2.01-1.99 (m, 1H), 1.88-1.76 (m, 2H), 1.67-1.64 (m, 2H).

Example 158

2-[6-[4-[2-[2-[1-[2-chloro-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, Compound Step 1: tert-butyl 2-[1-(2-chloro-4-nitro-phenyl)-4-hydroxy-4-piperidyl]acetate

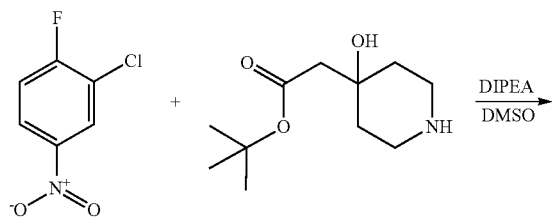

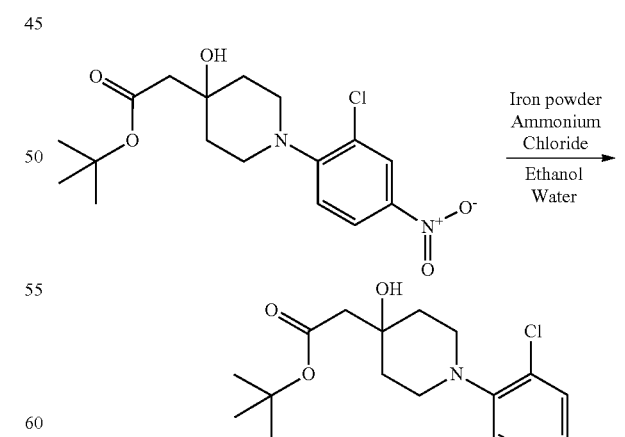

Into a 250 mL sealed tube containing a well-stirred solution of a mixture of 2-chloro-1-fluoro-4-nitro-benzene (6 g, 34.18 mmol) and tert-butyl 2-(4-hydroxy-4-piperidyl) acetate (8.09 g, 37.60 mmol) in anhydrous DMSO (60 mL) was added N,N-diisopropylethylamine (13.25 g, 102.54 mmol, 17.86 mL) at ambient temperature. The resulting content was stirred at 100° C. for 16 h. The reaction mixture was treated with ice cold water (250 mL) and the precipitated solid was filtered. The collected solid was dried under vacuum to afford tert-butyl 2-[1-(2-chloro-4-nitro-phenyl)-4-hydroxy-4-piperidyl]acetate (11.1 g, 29.04 mmol, 84.95% yield) as a brown solid. LCMS (ESI): m/z 371.8 [M+H]⁺

Step 2: tert-butyl 2-[1-(4-amino-2-chloro-phenyl)-4-hydroxy-4-piperidyl]acetate

To a 500 mL three-necked round-bottomed flask containing a well-stirred solution of tert-butyl 2-[1-(2-chloro-4-nitro-phenyl)-4-hydroxy-4-piperidyl]acetate (11 g, 29.66 mmol) in ethanol (120 mL) and water (20 mL), ammonium Chloride (3.17 g, 59.33 mmol, 2.07 mL) and iron powder (8.28 g, 148.32 mmol, 1.05 mL) were added at ambient temperature under nitrogen atmosphere. The contents were heated at 90° C. for 4 h. Reaction mixture was filtered through a pad of celite, and the celite bed was washed with ethyl acetate (150 mL), the filtrate was concentrated under reduced pressure to afford a residue. Water (100 mL) was added, and the aqueous layer was extracted with ethyl acetate (2×150 mL). Organic layers were combined, dried with sodium sulfate, filtered and concentrated under reduced pressure to afford tert-butyl 2-[1-(4-amino-2-chloro-phenyl)-4-hydroxy-4-piperidyl]acetate (10 g, 27.87 mmol, 93.96% yield) as a brown gummy liquid. LCMS (ESI): m/z 341.8 [M+H]$^+$ Step 3: 3-[4-[4-(2-tert-butoxy-2-oxo-ethyl)-4-hydroxy-1-piperidyl]-3-chloro-anilino]propanoic acid

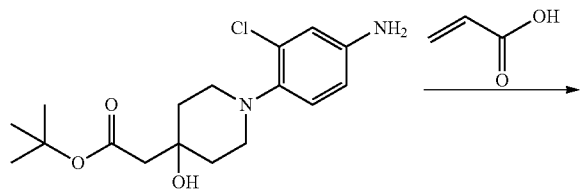

To a solution of tert-butyl 2-[1-(4-amino-2-chloro-phenyl)-4-hydroxy-4-piperidyl]acetate (1.8 g, 5.28 mmol) in toluene (13 mL) was added acrylic acid (457 mg, 6.34 mmol, 435.24 uL). The reaction mixture was stirred at 100° C. for 16 h. The reaction mixture was concentrated under vacuum to afford 3-[4-[4-(2-tert-butoxy-2-oxo-ethyl)-4-hydroxy-1-piperidyl]-3-chloro-anilino]propanoic acid (2.1 g, 4.02 mmol, 76.08% yield) was obtained as a black solid.

Step 4: 2-[1-[2-chloro-4-(2,4-dioxohexahydropyrimidin-1-yl)phenyl]-4-hydroxy-4-piperidyl]acetic acid

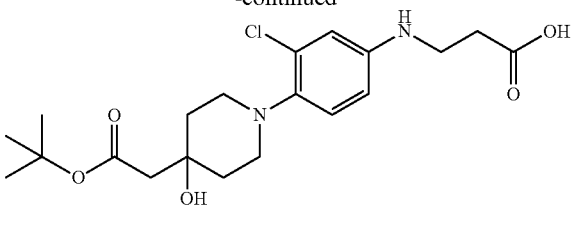

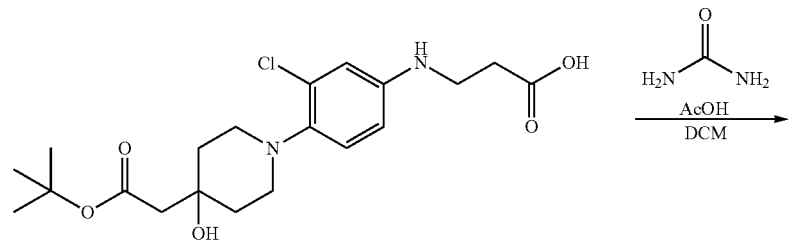

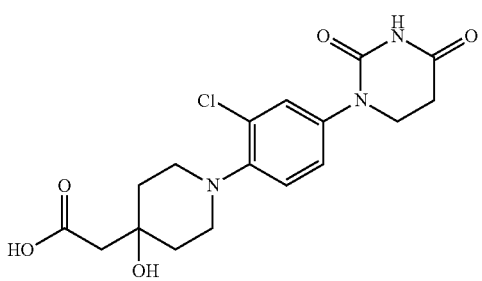

To a solution of 3-[4-[4-(2-tert-butoxy-2-oxo-ethyl)-4-hydroxy-1-piperidyl]-3-chloro-anilino]propanoic acid (1 g, 2.42 mmol) in acetic acid 10 mL) was added urea (582 mg, 9.69 mmol, 434.33 uL). The reaction mixture was stirred at 100° C. for 16 h. The reaction mixture was concentrated under vacuum. The residue was dissolved in dichloromethane (15 mL) and hydrochloric acid, 36% w/w (10 M aqueous solution, 2.4 mL) was added at 0° C. The reaction mixture was stirred at 20° C. for 1 h. The reaction mixture was concentrated under vacuum. The residue was purified by preparative HPLC (acetonitrile in 0.1% formic acid in water). The desired fraction was collected and lyophilized to afford 2-[1-[2-chloro-4-(2,4-dioxohexahydropyrimidin-1-yl)phenyl]-4-hydroxy-4-piperidyl]acetic acid (360 mg, 914.59 mol, 37.76% yield) was obtained as a yellow solid. LCMS (ESI+): 382.2 (M+H)+

Step 5: 2-[6-[4-[2-[2-[1-[2-chloro-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

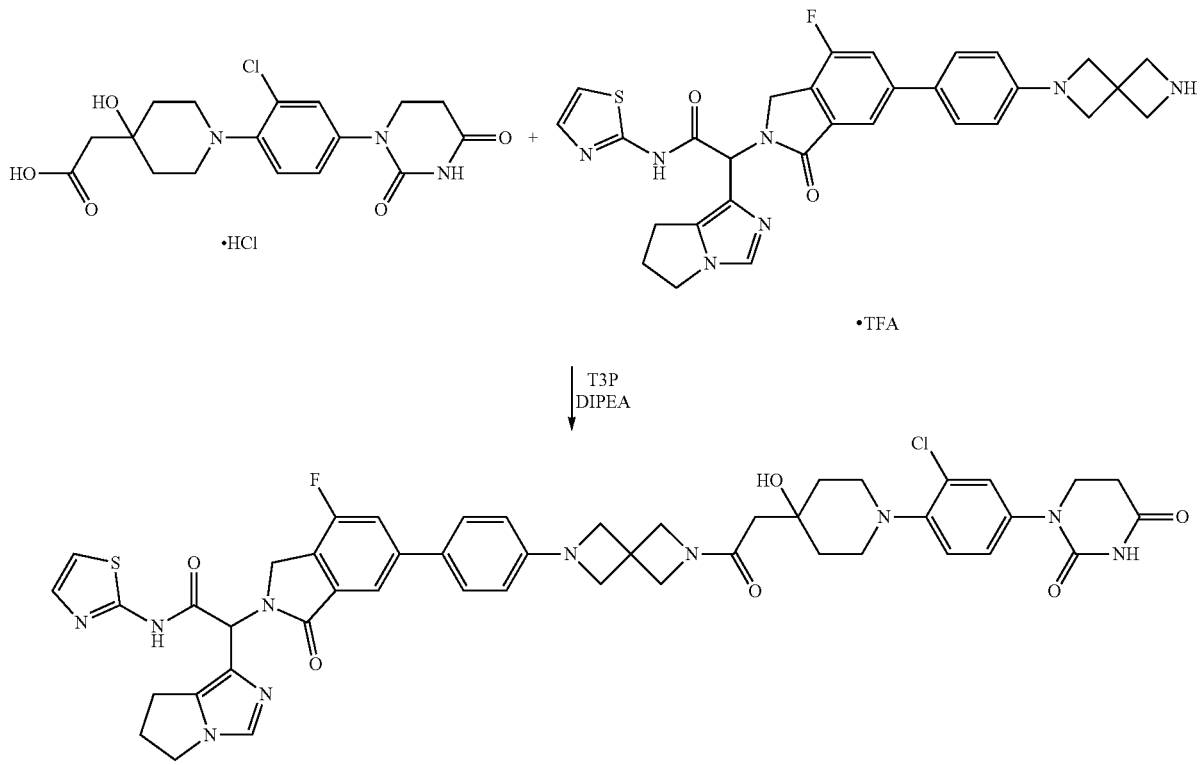

To a solution of 2-[1-[2-chloro-4-(2,4-dioxohexahydropyrimidin-1-yl)phenyl]-4-hydroxy-4-piperidyl]acetic acid (80 mg, 209.53 µmol) and propylphosphonic anhydride (50% ethyl acetate) (200.00 mg, 314.29 µmol) in N,N-dimethylformamide (0.3 mL) was added N-ethyl-N-propan-2-ylpropan-2-amine (189.56 mg, 1.47 mmol, 255.47 uL). The mixture was stirred at 0° C. for 20 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (121.76 mg, 178.10 µmol) was added, and the mixture was stirred at 0° C. for 1 h. Propylphosphonic anhydride (50% ethyl acetate) (120.00 mg, 188.58 µmol) was added to the reaction mixture. The mixture was stirred at 0° C. for 1 h. The reaction mixture was diluted with acetonitrile (2 mL). The reaction mixture was purified by preparative HPLC (Column: Waters Xbridge C18 150*50 mm*10 m phase, 27%-57% acetonitrile in water) to afford Compound 158 (15 mg, 195.58 µmol, 16.5% yield). LCMS (ESI+): 933.5 (M+H)+, 1H NMR (400 MHz, DMSO-d6) δ=12.60-12.45 (m, 1H), 10.38 (s, 1H), 7.74 (s, 1H), 7.70 (d, J=10.8 Hz, 1H), 7.64 (d, J=8.8 Hz, 2H), 7.60 (s, 1H), 7.48 (br d, J=2.8 Hz, 1H), 7.41 (d, J=2.4 Hz, 1H), 7.24 (dd, J=2.4, 8.8 Hz, 2H), 7.20-7.16 (m, 1H), 6.54 (d, J=8.8 Hz, 2H), 6.14 (s, 1H), 4.87-4.75 (m, 2H), 4.39 (s, 2H), 4.21 (d, J=17.6 Hz, 1H), 4.09 (s, 2H), 4.02 (s, 6H), 3.74 (t, J=6.8 Hz, 2H), 3.04-2.93 (m, 4H), 2.81-2.65 (m, 4H), 2.48-2.42 (m, 2H), 2.25 (s, 2H), 1.85-1.76 (m, 2H), 1.67 (br d, J=12.4 Hz, 2H)

Example 159

2-(6,7-dihydro-5H-pyrrolo[1,2-c]imidazol-1-yl)-2-[6-[4-[2-[2-[1-[4-(2,6-dioxo-3-piperidyl)-2-fluoro-phenyl]-4-hydroxy-4-piperidyl]acetyl]-2,7-diaz-aspiro[3.5]nonan-7-yl]phenyl]-4-fluoro-1-oxo-isoindolin-2-yl]-N-thiazol-2-yl-acetamide, Compound 159

Step 1: tert-butyl 2-[1-(2-fluoro-4-iodo-phenyl)-4-hydroxy-4-piperidyl]acetate

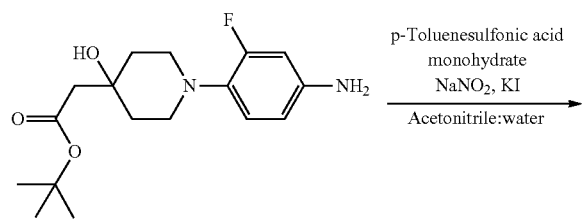

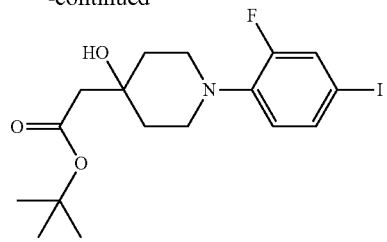

A solution of tert-butyl 2-[1-(4-amino-2-fluoro-phenyl)-4-hydroxy-4-piperidyl]acetate (3.2 g, 9.86 mmol) in acetonitrile (40 mL) was cooled to 0° C. p-Toluenesulfonic acid monohydrate (1.88 g, 9.86 mmol, 1.51 mL) was added into reaction mixture as a single portion. A sodium nitrite solution (680.66 mg, 9.86 mmol, 313.67 uL) in water (10 mL) was added dropwise over 2 min. The reaction mixture was stirred at 0° C. for 30 min. A potassium iodide solution (1.64 g, 9.86 mmol) in water (10 mL) was added dropwise to the reaction mixture over a period of 3 min. The reaction mixture was stirred at 0° C. for 10 min, and warmed to ambient temperature and stirred for 1.5 h. Potassium carbonate solution (10% in water) was added to the reaction mixture. The reaction mixture was extracted with ethyl acetate. The organic layer was dried over sodium sulfate, filtered, and concentrated under reduced pressure. The residue was purified by silica gel column chromatography (100-200 mesh), eluted at 10% ethyl acetate in petroleum ether. Pure fractions were evaporated under reduced pressure to afford tert-butyl 2-[1-(2-fluoro-4-iodo-phenyl)-4-hydroxy-4-piperidyl]acetate (2.1 g, 4.34 mmol, 44.02% yield). LCMS m/z 436.0 (M+H$^+$).

Step 2: tert-butyl 2-[1-[4-(2,6-dibenzyloxy-3-pyridyl)-2-fluoro-phenyl]-4-hydroxy-4-piperidyl]acetate

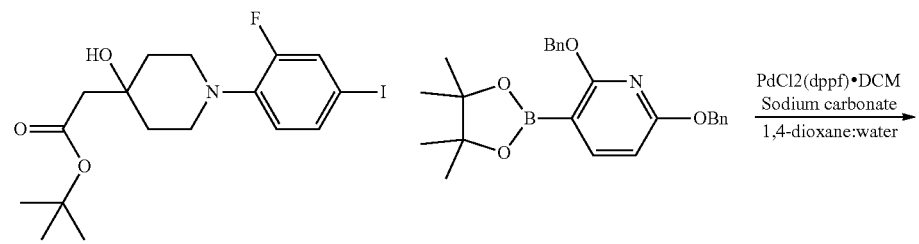

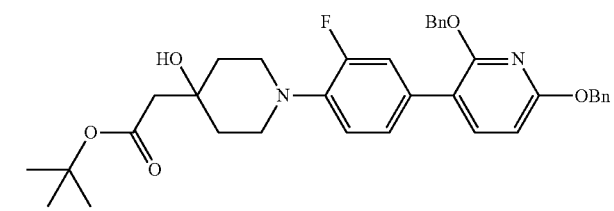

To a solution of tert-butyl 2-[1-(2-fluoro-4-iodo-phenyl)-4-hydroxy-4-piperidyl]acetate (500 mg, 1.15 mmol) and 2,6-dibenzyloxy-3-(4,4,5,5-tetramethyl-1,3,2-dioxaborolan-2-yl)pyridine (575.23 mg, 1.38 mmol) in 1,4-dioxane (5 mL) and water (0.5 mL) was added Sodium carbonate (304.38 mg, 2.87 mmol, 120.31 uL) and solution was purged with nitrogen for 10 min. PdCl$_2$(dppf).dichloromethane (93.81 mg, 114.87 µmol) was added to the reaction mixture and purged with nitrogen gas for 5 mins. The reaction mixture was heated to 90° C. for 16 h. The reaction mixture diluted with ethyl acetate and filtered through celite. The filtrate washed with ice cold water. The organic layer washed with brine solution, dried with sodium sulfate, filtered and concentrated under reduced pressure. The residue was purified by column chromatography by using (230-400 silica-gel) eluted compound with 3% methanol in dichloromethane to afford tert-butyl 2-[1-[4-(2,6-dibenzyloxy-3-pyridyl)-2-fluoro-phenyl]-4-hydroxy-4-piperidyl]acetate (310 mg, 687.74 µmol, 44.17% yield). LCMS m/z 599.4 (M+H$^+$)

Step 3: tert-butyl 2-[1-[4-(2,6-dioxo-3-piperidyl)-2-fluoro-phenyl]-4-hydroxy-4-piperidyl]acetate

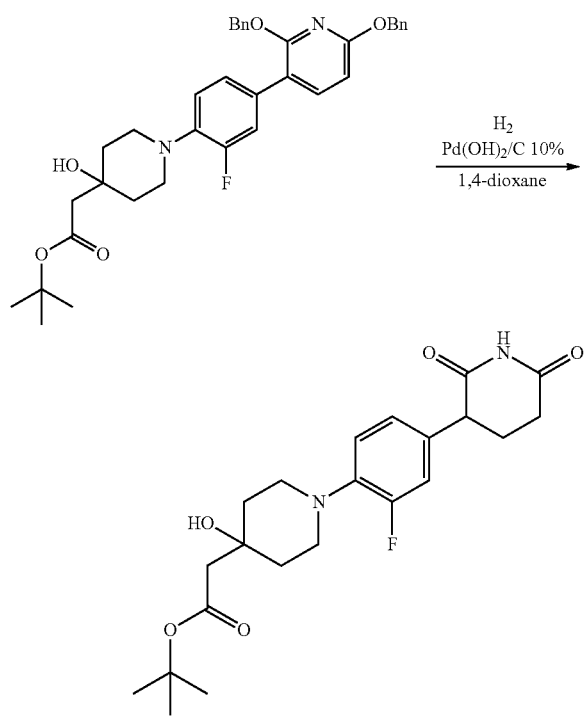

A stirred solution of tert-butyl 2-[1-[4-(2,6-dibenzyloxy-3-pyridyl)-2-fluoro-phenyl]-4-hydroxy-4-piperidyl]acetate (525 mg, 876.90 µmol) in 1,4-dioxane (6 mL) was purged with nitrogen for 5 min. Palladium hydroxide on carbon 10% (184.71 mg, 1.32 mmol) was added. The reaction mixture was put under an atmosphere of hydrogen gas (1 atm). The reaction was stirred for 16 h at ambient temperature. The reaction mixture was diluted with ethyl acetate and filtered through celite. The filtrate was concentrated under reduced pressure to afford tert-butyl 2-[1-[4-(2,6-dioxo-3-piperidyl)-2-fluoro-phenyl]-4-hydroxy-4-piperidyl]acetate (310 mg, 685.66 µmol, 78.19% yield). LCMS m/z 421.3 (M+H$^+$).

Step 4: 2-[1-[4-(2,6-dioxo-3-piperidyl)-2-fluoro-phenyl]-4-hydroxy-4-piperidyl]acetic acid

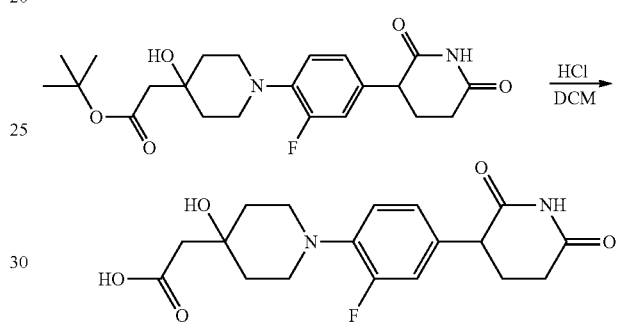

To a stirred solution of tert-butyl 2-[1-[4-(2,6-dioxo-3-piperidyl)-2-fluoro-phenyl]-4-hydroxy-4-piperidyl]acetate (310 mg, 737.26 µmol) in dichloromethane (5 mL) was added hydrogen chloride (4.0M in 1,4-dioxane, 5 mL, 20 mmol) dropwise at 0° C. The reaction mixture was concentrated under reduced pressure. The solid was triturated with diethyl ether (2×10 ml) and dried under reducing pressure to afford 2-[1-[4-(2,6-dioxo-3-piperidyl)-2-fluoro-phenyl]-4-hydroxy-4-piperidyl]acetic acid hydrochloride (250 mg, 597.15 µmol, 81.00% yield) as an off-white solid. LCMS m/z 365.2 (M+H)$^+$.

Step 5: 2-(6,7-dihydro-5H-pyrrolo[1,2-c]imidazol-1-yl)-2-[6-[4-[2-[2-[1-[4-(2,6-dioxo-3-piperidyl)-2-fluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide

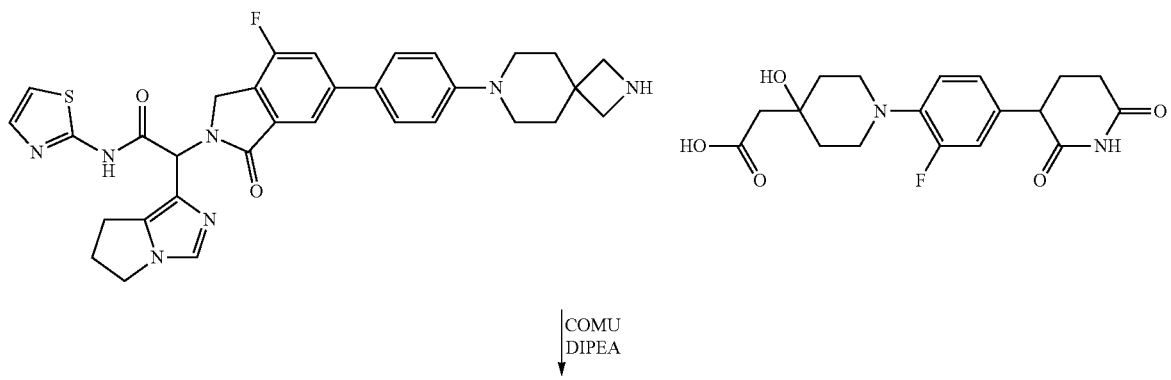

1249

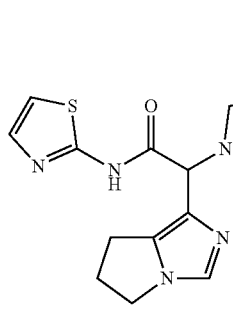

1250
-continued

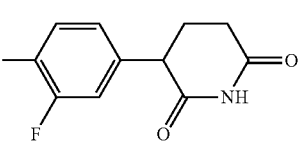

To a stirred solution of 2-[6-[4-(2,7-diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide hydrochloride (295 mg, 465.18 µmol) and 2-[1-[4-(2,6-dioxo-3-piperidyl)-2-fluoro-phenyl]-4-hydroxy-4-piperidyl]acetic acid hydrochloride (141.25 mg, 352.39 µmol) in N,N-dimethylformamide (3 mL) was cooled to 0° C. N,N-Diisopropylethylamine (250.50 mg, 1.94 mmol, 337.60 uL) was added to the reaction mixture followed by COMU (215.82 mg, 503.94 mol) at 0° C. The reaction mixture stirred at rt for 1 h. The reaction mixture was directly injected on a C-18 column (100 g) for purification (0-45% Acetonitrile in water (0.1% ammonium acetate) over 30 min, then steep gradient to 100% acetonitrile). The pure fractions were combined and lyophilized to get Compound 159 (35 mg, 36.15 µmol, 9.33% yield) as an off-white solid. LCMS m/z 943.8 (M+H), $^1$H-NMR (400 MHz, DMSO-d6): δ 12.52 (s, 1H), 10.81 (s, 1H), 7.77 (s, 1H), 7.73 (dd, J=12.0 Hz, 1.20 Hz, 1H), 7.65 (d, J=14.80 Hz, 2H), 7.61 (s, 1H), 7.49 (d, J=3.60 Hz, 1H), 7.26 (d, J=3.60 Hz, 1H), 7.07-6.93 (m, 6H), 6.16 (s, 1H), 4.84 (s, 1H), 4.82 (d, J=17.60 Hz, 1H), 4.23 (d, J=17.60 Hz, 1H), 4.09-3.95 (m, 4H), 3.81 (dd, J=28.40 Hz, 8.0 Hz, 1H), 3.64 (s, 2H), 3.35-3.22 (m, 5H), 3.06-3.00 (m, 4H), 2.82-2.74 (m, 1H), 2.69-2.67 (m, 2H), 2.26 (s, 2H), 2.21-2.10 (m, 1H), 2.05-1.99 (m, 1H), 1.81-1.69 (m, 6H), 1.68 (d, J=18.80 Hz, 3H).

Example 160

2-(6,7-dihydro-5H-pyrrolo[1,2-c]imidazol-1-yl)-2-[6-[4-[7-[2-[1-[4-(2,6-dioxo-3-piperidyl)-2-fluorophenyl]-4-hydroxy-4-piperidyl]acetyl]-2,7-diazaspiro[3.5]nonan-2-yl]phenyl]-4-fluoro-1-oxo-isoindolin-2-yl]-N-thiazol-2-yl-acetamide, Compound 160

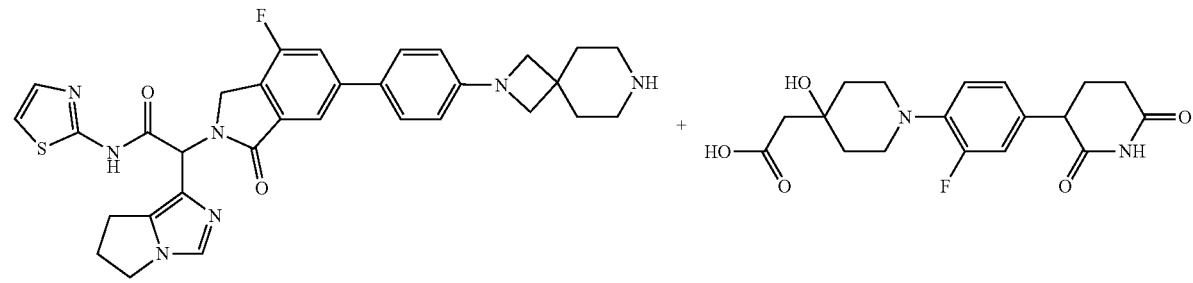

T3P
DIPEA
DMF

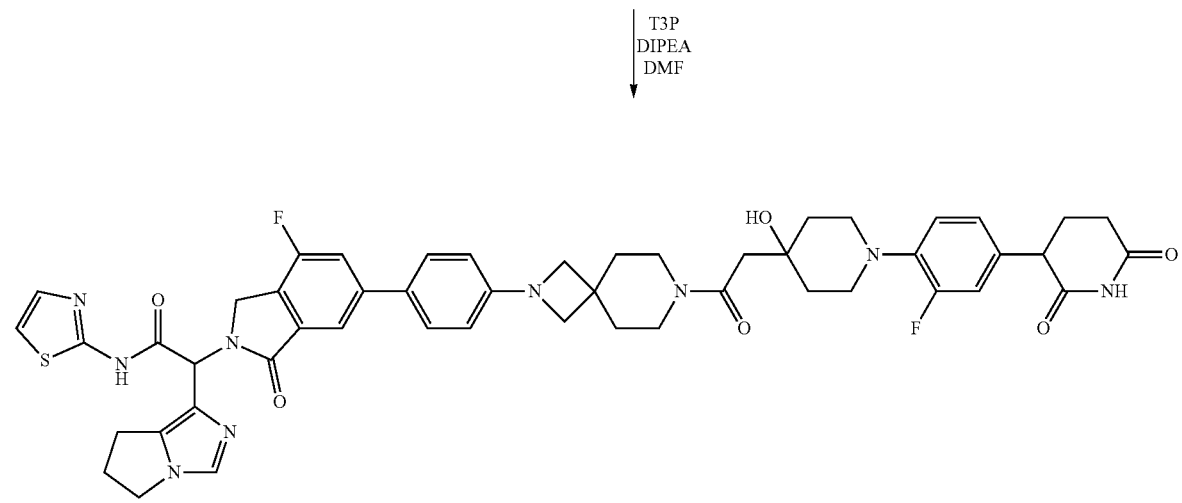

To a stirred solution of 2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (120 mg, 168.60 µmol) and 2-[1-[4-(2,6-dioxo-3-piperidyl)-2-fluoro-phenyl]-4-hydroxy-4-piperidyl]acetic acid hydrochloride (81.10 mg, 202.32 µmol) in N,N-dimethylformamide (2 mL) was cooled to 0° C. N,N-diisopropylethylamine (108.95 mg, 843.02 mol, 146.84 uL) was added to the reaction mixture followed by propylphosphonic anhydride, 50% in ethyl acetate (80.47 mg, 252.91 µmol) at 0° C. The reaction mixture stirred at ambient temperature for 1 h. The reaction mixture was directly injected on a C-18 column (100 g) for purification (0-45% of acetonitrile in water+0.1% NH₄OAc over 30 min, then steep gradient to 100% acetonitrile). The pure fractions were combined and lyophilized to get Compound 160 (32.2 mg, 33.74 µmol, 20.01% yield) as an off-white solid. LCMS m/z: 943.8 [M+H]

Example 161

2-(6,7-dihydro-5H-pyrrolo[1,2-c]imidazol-1-yl)-2-[6-[4-[2-[2-[(2s,6r)-1-[4-[(2,6-dioxo-3-piperidyl)amino]-2-fluoro-phenyl]-4-hydroxy-2,6-dimethyl-4-piperidyl]acetyl]-2,6-diazaspiro[3.3]heptan-6-yl]phenyl]-4-fluoro-1-oxo-isoindolin-2-yl]-N-thiazol-2-yl-acetamide, Compound 161

Step 1: (2s,6r)-1-[(4-methoxyphenyl)methyl]-2,6-dimethyl-piperidin-4-one

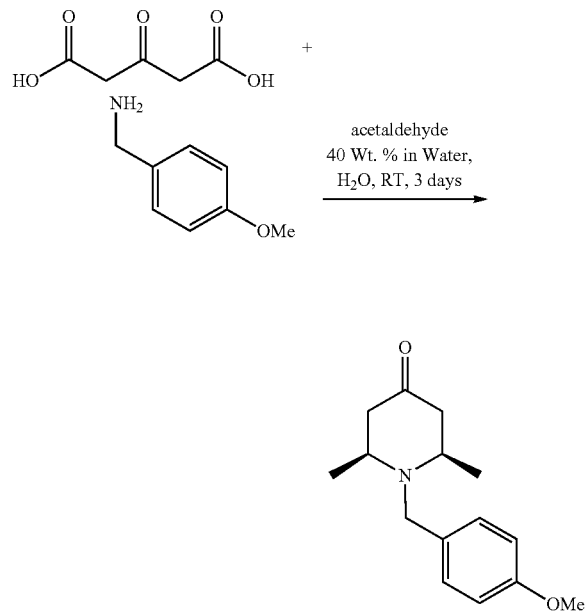

To a stirred solution of 3-oxopentanedioic acid (10 g, 68.45 mmol) in Water (50 mL) was added acetaldehyde solution, 40 w/w % in water (15.08 g, 136.89 mmol). 4-methoxyphenylmethanamine (9.39 g, 68.45 mmol, 8.94 mL) was added to the reaction mixture in small portions over 10 mins. The reaction mixture was stirred at ambient temperature for three days. The reaction mixture was extracted with dichloromethane (3×60 ml). Combined organic layers were washed with brine and dried over anhydrous sodium sulphate, concentrated under reduced pressure to afford brown residue. The residue was purified by flash column chromatography on silica gel (0-30% Ethyl acetate in petroleum ether) to give (2s,6r)-1-[(4-methoxyphenyl)methyl]-2,6-dimethyl-piperidin-4-one (6.7 g, 21.13 mmol, 30.87% yield) as a brown gummy liquid. LCMS (ESI+) m/z: 248.2 [M+H].

Step 2: tert-butyl 2-[(2s,6r)-4-hydroxy-1-[(4-methoxyphenyl)methyl]-2,6-dimethyl-4-piperidyl]acetate

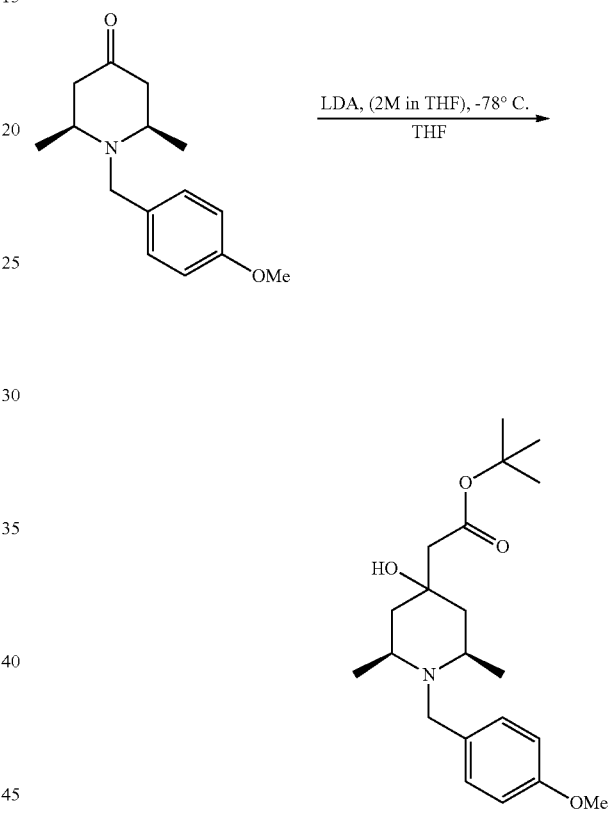

To a stirred solution of tert-butyl acetate (2.82 g, 24.26 mmol, 3.27 mL) in tetrahydrofuran (30 mL) at −78° C. was added lithium diisopropylamide (2M in tetrahydrofuran, 40.43 mmol, 20 mL) dropwise over a period of 5 min and the reaction mixture was stirred at −78° C. for 1 h. The solution of (2s,6r)-1-[(4-methoxyphenyl)methyl]-2,6-dimethyl-piperidin-4-one (5 g, 20.22 mmol) in tetrahydrofuran (20 mL) was added to the above solution dropwise and stirred at −78° C. for 2 h. The reaction mixture was warmed 0° C. and quenched with saturated ammonium chloride solution. The mixture was extracted with ethyl acetate (150 mL×2). The combined organic layer was washed with brine (50 mL), dried over sodium sulfate and concentrated under reduced pressure. The residue was purified by flash column chromatography on silica gel (0-30% ethyl acetate in petroleum ether) to give tert-butyl 2-[(2s,6r)-4-hydroxy-1-[(4-methoxyphenyl)methyl]-2,6-dimethyl-4-piperidyl]acetate (5.1 g, 12.38 mmol, 61.24% yield) as a gummy liquid. LCMS (ESI+) m/z: 364.4 [M+H]⁺.

1253

Step 3: tert-butyl 2-[(2s,6r)-4-hydroxy-2,6-dimethyl-4-piperidyl]acetate

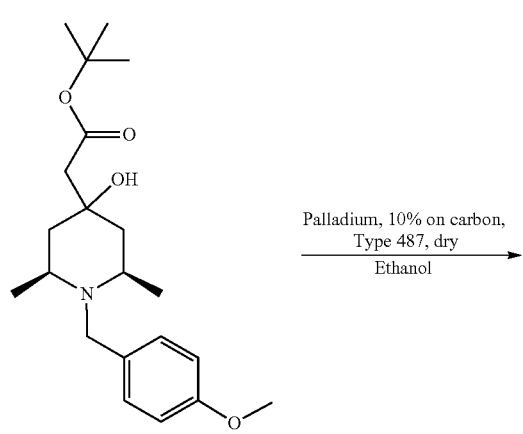

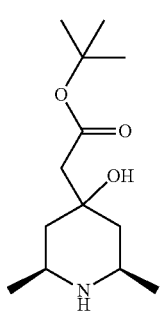

To a solution of tert-butyl 2-[(2s,6r)-4-hydroxy-1-[(4-methoxyphenyl)methyl]-2,6-dimethyl-4-piperidyl]acetate (5.1 g, 14.03 mmol) in Ethanol (60 mL) was added palladium, 10% on carbon (1.49 g, 14.03 mmol). The suspension was stirred under hydrogen balloon pressure at ambient temperature for 16 h. The reaction mixture was filtered through celite bed and washed with ethanol. The filtrate was concentrated under reduced pressure to afford tert-butyl 2-[(2s,6r)-4-hydroxy-2,6-dimethyl-4-piperidyl]acetate (3.4 g, 13.90 mmol, 99.04% yield). LCMS (ESI+) m/z: 244.2 [M+H]+.

1254

Step 4: tert-butyl 2-[(2s,6r)-1-(2-fluoro-4-nitro-phenyl)-4-hydroxy-2,6-dimethyl-4-piperidyl]acetate

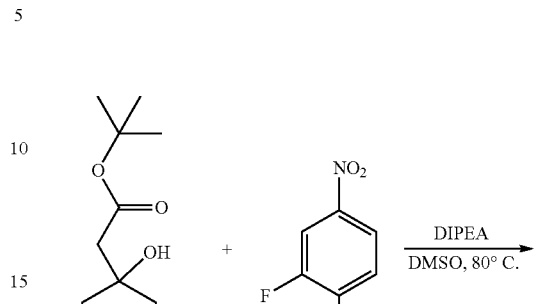

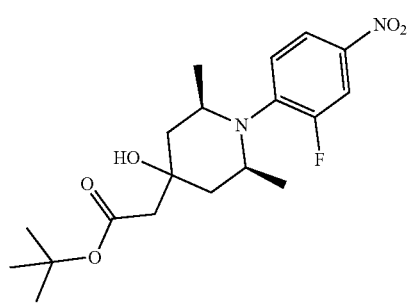

In a 100 mL sealed tube, tert-butyl 2-[(2s,6r)-4-hydroxy-2,6-dimethyl-4-piperidyl]acetate (3.4 g, 13.97 mmol) and 1,2-difluoro-4-nitro-benzene (2.22 g, 13.97 mmol, 1.54 mL) were mixed in dimethyl sulfoxide (40 mL). N, N-Diisopropylethylamine (3.61 g, 27.94 mmol, 4.87 mL) was added and the reaction mixture was heated in a heating block at 80° C. for 16 h. The reaction mixture was diluted with ethyl acetate and washed with ice cold water; and the organic layer was concentrated under reduced pressure. The residue was purified by flash chromatography using silica gel (0-30% ethyl acetate in petroleum ether) to afford tert-butyl 2-[(2s,6r)-1-(2-fluoro-4-nitro-phenyl)-4-hydroxy-2,6-dimethyl-4-piperidyl]acetate (2.4 g, 5.72 mmol, 40.92% yield) as a yellow coloured gummy liquid. LCMS (ESI+) m/z: 383.2 [M+H]+.

1255

Step 5: tert-butyl 2-[(2s,6r)-1-[4-[(2,6-dioxo-3-piperidyl)amino]-2-fluoro-phenyl]-4-hydroxy-2,6-dimethyl-4-piperidyl]acetate

1256

Step 6: 2-[(2s,6r)-1-[4-[(2,6-dioxo-3-piperidyl)amino]-2-fluoro-phenyl]-4-hydroxy-2,6-dimethyl-4-piperidyl]acetic acid

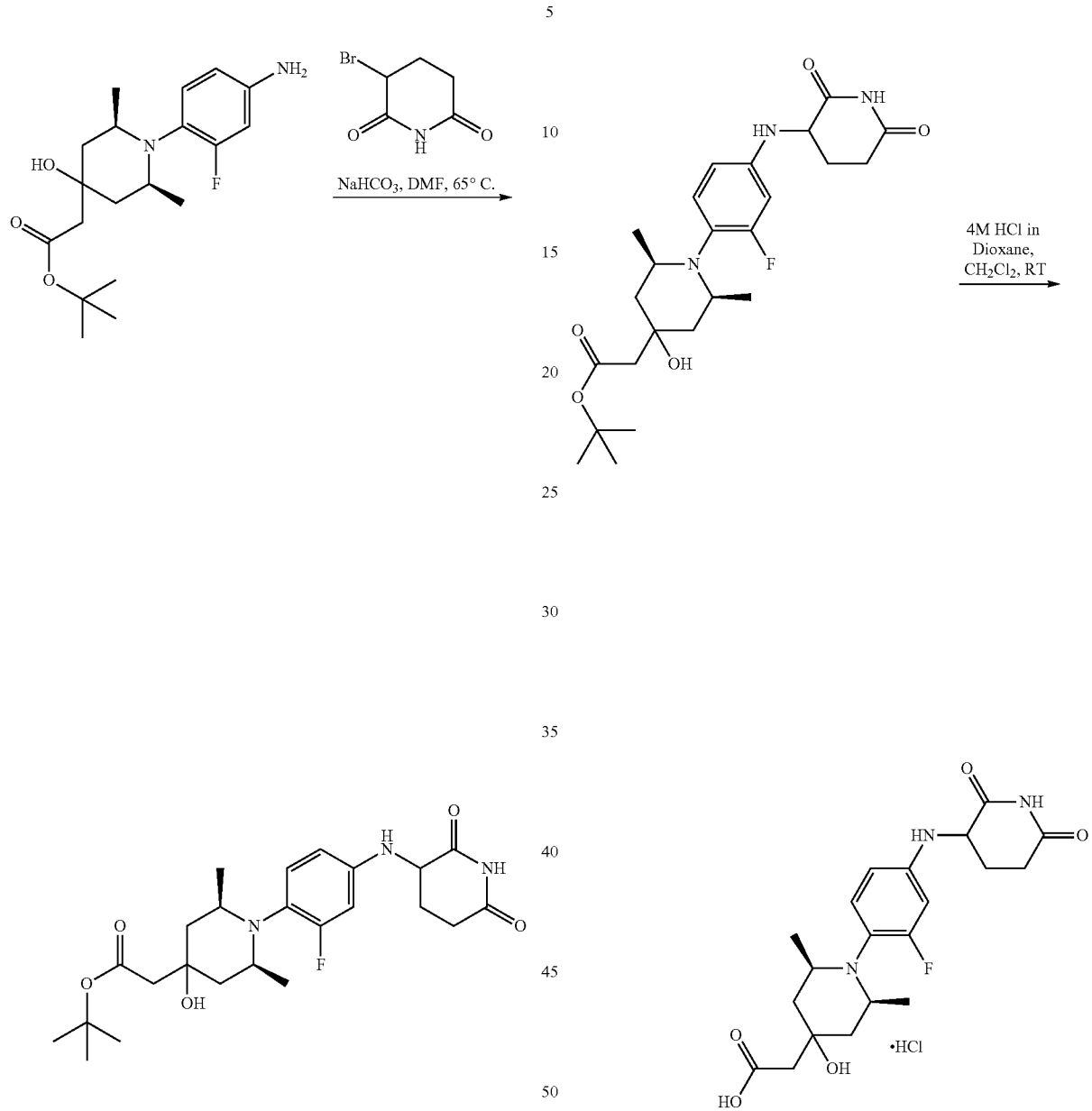

To a stirred solution of tert-butyl 2-[(2s,6r)-1-(4-amino-2-fluoro-phenyl)-4-hydroxy-2,6-dimethyl-4-piperidyl]acetate (2.10 g, 5.96 mmol) in N,N-dimethylformamide (25 mL) in a sealed tube were added sodium bicarbonate (1.50 g, 17.88 mmol) and 3-bromopiperidine-2,6-dione (2.29 g, 11.92 mmol) under nitrogen atmosphere. The reaction tube was sealed and heated at 65° C. for 16 h. The reaction mixture was diluted with ethyl acetate and washed with ice cold water, organic layer was dried over sodium sulphate and concentrated under reduced pressure. The residue was purified by flash column chromatography on silica gel (0-100% ethyl acetate in petroleum ether) to give butyl 2-[(2s,6r)-1-[4-[(2,6-dioxo-3-piperidyl)amino]-2-fluoro-phenyl]-4-hydroxy-2,6-dimethyl-4-piperidyl]acetate (1.7 g, 3.65 mmol, 61.26% yield) as off white solid. LCMS (ESI+) m/z: 464.2 [M+H]+.

To a stirred solution of tert-butyl 2-[(2s,6r)-1-[4-[(2,6-dioxo-3-piperidyl)amino]-2-fluoro-phenyl]-4-hydroxy-2,6-dimethyl-4-piperidyl]acetate (150 mg, 323.60 μmol) in dichloromethane (2 mL) was added hydrogen chloride (4 M in 1,4-dioxane, 6.44 mmol, 1.61 mL) at 0° C. and the reaction mixture was stirred at ambient temperature for 16 h. The reaction mixture was concentrated under reduced pressure and co-distilled with dichloromethane (2×5 mL). The solid was triturated with diethyl ether to afford 2-[(2s,6r)-1-[4-[(2,6-dioxo-3-piperidyl)amino]-2-fluoro-phenyl]-4-hydroxy-2,6-dimethyl-4-piperidyl]acetic acid hydrochloride (140 mg, 305.35 μmol, 94.36% yield) as an off white solid. LCMS (ESI+) m/z: 408.2 [M+H]+

Step 7: 2-(6,7-dihydro-5H-pyrrolo[1,2-c]imidazol-1-yl)-2-[6-[4-[2-[2-[(2s,6r)-1-[4-[(2,6-dioxo-3-piperidyl)amino]-2-fluoro-phenyl]-4-hydroxy-2,6-dimethyl-4-piperidyl]acetyl]-2,6-diazaspiro[3.3]heptan-6-yl]phenyl]-4-fluoro-1-oxo-isoindolin-2-yl]-N-thiazol-2-yl-acetamide

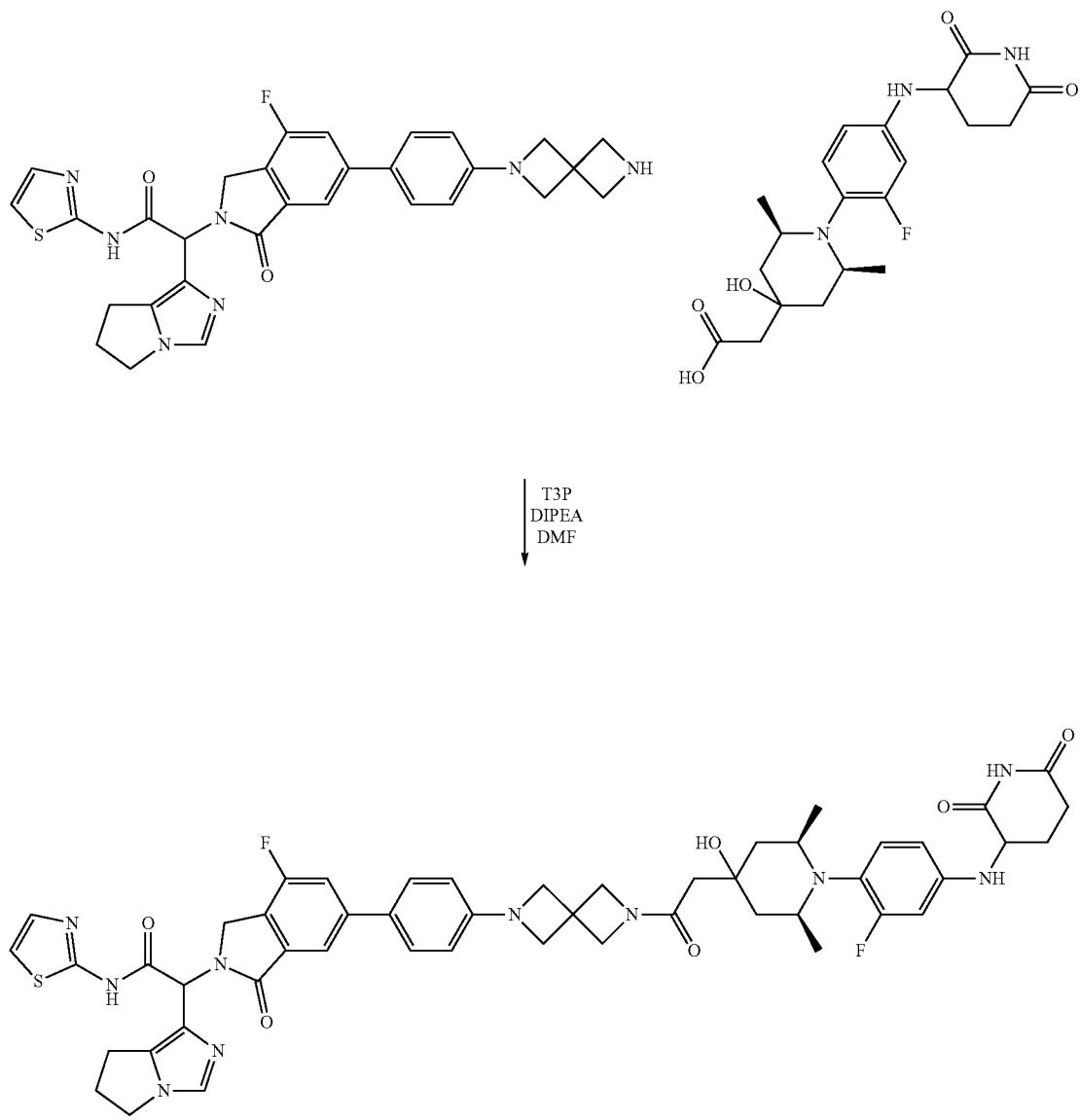

To the stirred solution of 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (170 mg, 248.66 μmol) and 2-[(2s,6r)-1-[4-[(2,6-dioxo-3-piperidyl)amino]-2-fluoro-phenyl]-4-hydroxy-2,6-dimethyl-4-piperidyl]acetic acid hydrochloride (121.42 mg, 273.52 μmol) in N,N-dimethylformamide (2 mL) was cooled to 0° C. N,N-diisopropylethylamine (192.82 mg, 1.49 mmol, 259.87 uL) was added to the reaction mixture followed by propylphosphonic anhydride (50% in ethyl acetate, 118.68 mg, 372.98 mol) at 0° C. The reaction mixture was stirred at ambient temperature for 1 h. The reaction mixture was directly injected on a C-18 column (100 g) for purification (0-45% of acetonitrile in water (0.1% ammonium acetate) over 30 min, then steep gradient to 100% acetonitrile). The pure fractions were combined and lyophilized to get Compound 161 (43.5 mg, 44.63 μmol, 17.95% yield) as an off-white solid. LCMS m/z: 959.2 [M+H], $^1$H-NMR (400 MHz, DMSO-d6): 12.52 (s, 1H), 10.79 (s, 1H), 7.45-7.61 (m, 5H), 7.49 (d, J=3.6 Hz, 1H), 7.26 (d, J=3.6 Hz, 1H), 6.85 (m, 1H), 6.55 (d, J=8.8 Hz, 1H), 6.43 (d, J=8.4 Hz, 1H), 6.15 (s, 1H), 4.82-4.78 (m, 2H), 4.58 (s, 2H), 4.47-3.99 (m, 9H), 3.72-3.60 (m, 1H), 3.30-3.18 (m, 2H), 2.78-2.52 (m, 3H), 2.34-2.18 (m, 3H), 1.97-1.85 (m, 2H), 1.82-1.65 (m, 2H), 1.50-1.31 (m, 1H), 1.04 (d, J=6.4 Hz, 3H), 0.82 (d, J=6.1 Hz, 3H).

Example 162

2-[6-[4-[2-[2-[4-amino-1-[4-[(2,6-dioxo-3-piperidyl)amino]-2-fluoro-phenyl]-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, Compound 162

Step 1: tert-Butyl 2-[1-benzyl-4-(tert-butoxycarbonylamino)-4-piperidyl]acetate

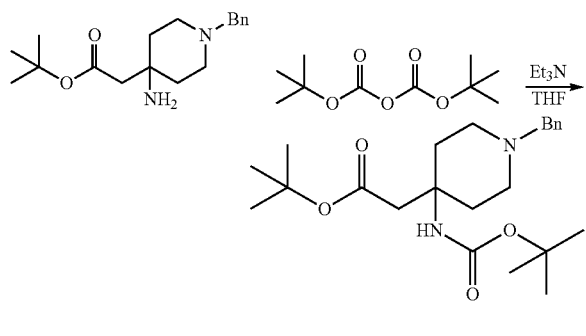

To a solution of tert-butyl 2-(4-amino-1-benzyl-4-piperidyl)acetate (CAS #: 2138234-11-2; 2.5 g, 8.21 mmol) and triethylamine (2.49 g, 24.64 mmol, 3.43 mL) in tetrahydrofuran (20 mL) was added di-tert-butyl dicarbonate (2.69 g, 12.32 mmol, 2.83 mL) at 25° C., and the mixture was stirred at 25° C. for 1 h. The reaction mixture was quenched by addition water 200 mL at 25° C. and extracted with ethyl acetate (3×50 mL). The combined organic layers were washed with brine (15 mL), dried with anhydrous sodium sulfate, filtered, and concentrated under reduced pressure. The residue was purified by column chromatography (silica gel, Petroleum Ether:Ethyl Acetate=20:1 to 5:1) to afford tert-butyl 2-[1-benzyl-4-(tert-butoxycarbonylamino)-4-piperidyl]acetate (2.9 g, 7.17 mmol, 87.29% yield) was obtained as white solid. TLC (Petroleum ether:Ethyl acetate=3:1): $R_f$=0.4, LCMS (ESI+): [M+H]$^+$ 405.1. $^1$H-NMR (400 MHz, Methanol-d4) δ 7.40-7.22 (m, 5H), 3.53 (s, 2H), 2.69-2.57 (m, 4H), 2.39-2.28 (m, 2H), 2.25-2.13 (m, 2H), 1.75-1.61 (m, 2H), 1.48-1.41 (m, 18H)

Step 2: tert-Butyl 2-[4-(tert-butoxycarbonylamino)-4-piperidyl]acetate

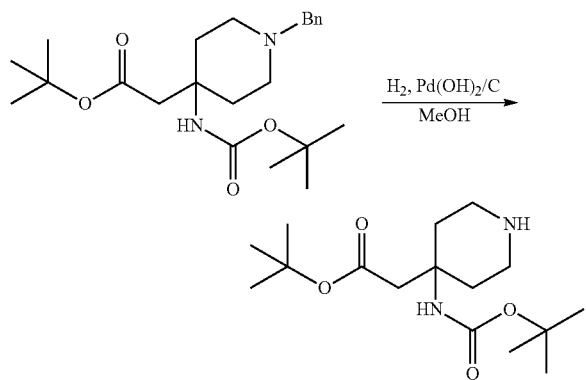

To a solution of methyl tert-butyl 2-[1-benzyl-4-(tert-butoxycarbonylamino)-4-piperidyl]acetate (500 mg, 1.24 mmol) in methanol (5 mL) was added palladium hydroxide, 10% on charcoal (50 mg, 494.39 μmol) under N$_2$. The suspension was degassed under vacuum and purged with H$_2$ several times. The mixture was stirred under H$_2$ (15 PSI) at 20° C. for 12 h. The reaction was filtered and filtrate was concentrated under vacuum to afford tert-butyl 2-[4-(tert-butoxycarbonylamino)-4-piperidyl]acetate (310 mg, 985.94 μmol, 79.77% yield) was obtained as colorless oil. LCMS (ESI+): 315.1 [M+H]$^+$, $^1$H-NMR (400 MHz, chloroform-d) δ=3.47 (s, 2H), 2.96-2.85 (m, 2H), 2.70-2.61 (m, 2H), 2.26-2.09 (m, 2H), 1.75-1.58 (m, 2H), 1.49-1.33 (m, 18H)

Step 3: tert-Butyl 2-(4-((tert-butoxycarbonyl)amino)-1-(2-fluoro-4-nitrophenyl)piperidin-4-yl)acetate

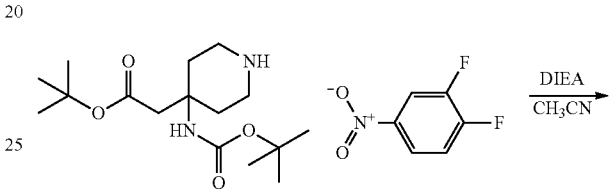

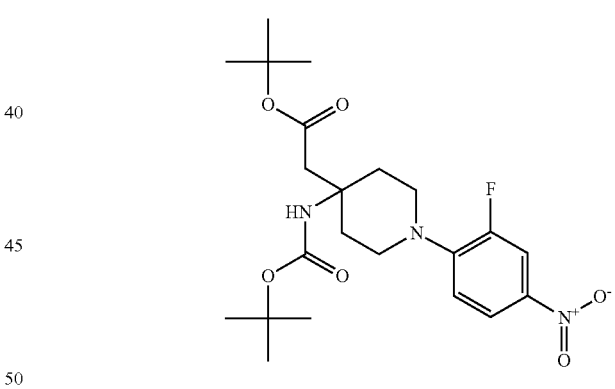

To a solution of tert-butyl 2-[4-(tert-butoxycarbonylamino)-4-piperidyl] acetate (250 mg, 795.12 μmol) and N,N-diisopropyl ethyl amine (402.29 mg, 3.98 mmol, 554.11 μL) in acetonitrile (3 mL) was added 1,2-difluoro-4-nitrobenzene (132.82 mg, 834.87 μmol, 92.24 L) at 25° C., and the mixture was stirred at 90° C. for 2 h. The reaction was concentrated under reduced pressure. The residue was purified by preparative TLC (Petroleum ether:Ethyl acetate=5:1) to afford tert-butyl 2-(4-((tert-butoxycarbonyl)amino)-1-(2-fluoro-4-nitrophenyl)piperidin-4-yl)acetate (305 mg, 672.54 μmol, 84.58% yield) was obtained as light-yellow solid. LCMS (ES+) m/z=454.1 [M+H]$^+$, $^1$H NMR (400 MHz, Chloroform-d) δ=8.03 20-7.95 (m, 1H), 7.94-7.85 (m, 1H), 7.01 (t, J=8.8 Hz, 1H), 4.59 (s, 1H), 3.52-3.38 (m, 2H), 3.28-3.15 (m, 2H), 2.72 (s, 2H), 2.46-2.34 (m, 2H), 1.92-1.80 (m, 2H), 1.48-1.43 (m, 18H).

Step 4: tert-Butyl 2-[1-(4-amino-2-fluoro-phenyl)-4-(tert-butoxycarbonylamino)-4-piperidyl]acetate

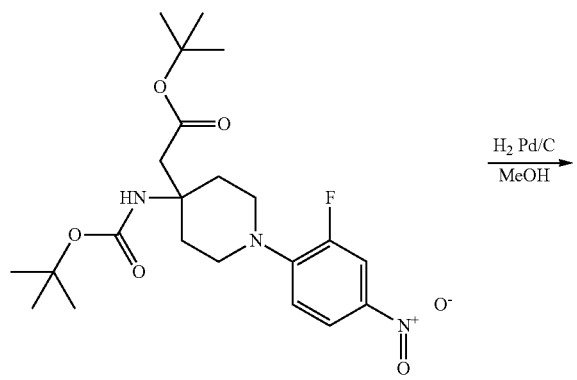

Step 5: tert-Butyl 2-(4-((tert-butoxycarbonyl)amino)-1-(4-((2,6-dioxopiperidin-3-yl)amino)-2-fluorophenyl)piperidin-4-yl)acetate

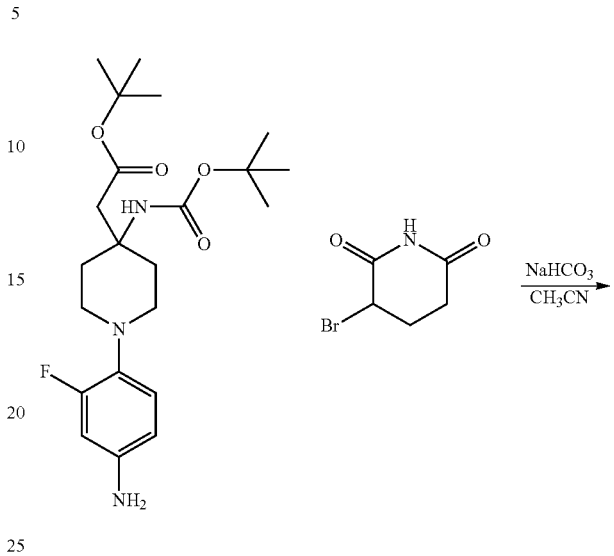

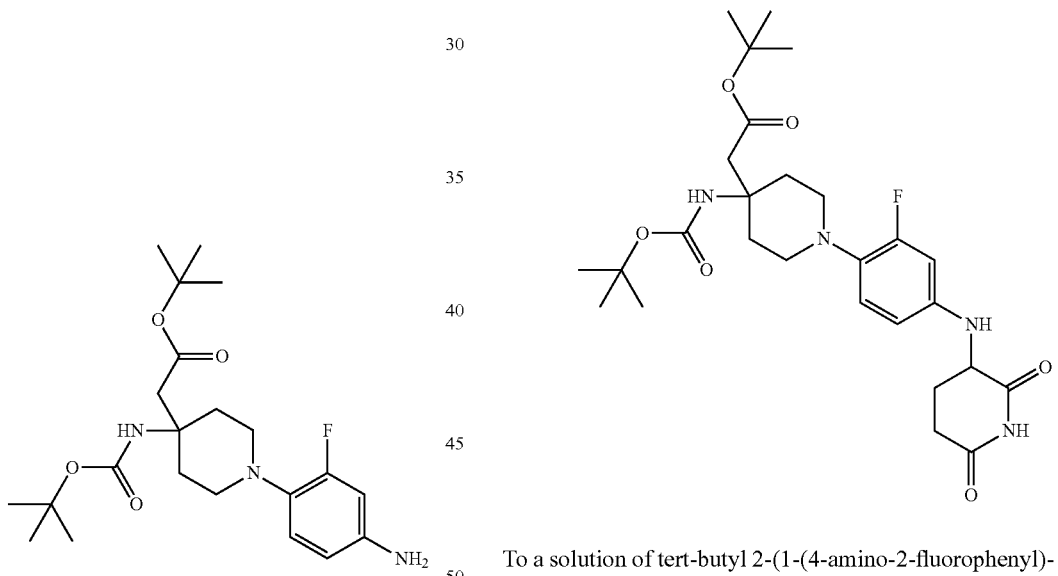

To a solution of methyl tert-butyl 2-[4-(tert-butoxycarbonylamino)-1-(2-fluoro-4-nitro-phenyl)-4-piperidyl]acetate (300 mg, 661.52 µmol) in methanol (5 mL) was added palladium, 10% on charcoal (80 mg) under $N_2$. The suspension was degassed under vacuum and purged with hydrogen several times. The mixture was stirred under hydrogen (15 psi) at 20° C. for 12 h. The reaction was filtered and filtrated was concentrated under vacuum to afford tert-butyl 2-[1-(4-amino-2-fluoro-phenyl)-4-(tert-butoxycarbonylamino)-4-piperidyl]acetate (220 mg, 467.51 µmol, 70.67% yield) was obtained as yellow solid. LCMS (ESI+) m/z 424.1 [M+H]$^+$. $^1$H-NMR (400 MHz, CHLOROFORM-d) δ=7.17-6.72 (m, 1H), 6.50-6.31 (m, 2H), 4.56 (br s, 1H), 3.26-2.85 (m, 4H), 2.71 (s, 2H), 2.42-2.26 (m, 2H), 2.05-1.78 (m, 2H), 1.45 (s, 18H)

To a solution of tert-butyl 2-(1-(4-amino-2-fluorophenyl)-4-((tert-butoxycarbonyl)amino)piperidin-4-yl)acetate (200 mg, 472.23 µmol) and sodium bicarbonate (198.35 mg, 2.36 mmol, 91.83 µL) in $CH_3CN$ (2 mL) was added 3-bromopiperidine-2,6-dione (90.67 mg, 472.23 µmol) at 25° C., and the mixture was stirred at 90° C. for 12 h. The reaction mixture was concentrated under reduced pressure. The residue was purified by preparative TLC (Petroleum ether:Ethyl acetate=5:1, product $R_f$=0.4) to afford tert-butyl 2-(4-((tert-butoxycarbonyl)amino)-1-(4-((2,6-dioxopiperidin-3-yl)amino)-2-fluorophenyl)piperidin-4-yl)acetate (180 mg, 306.39 µmol, 64.88% yield) was obtained as blue solid. LCMS (ESI+): m/z 535.2 [M+H]$^+$, $^1$H NMR (400 MHz, DMSO-d6) δ=11.06 (br s, 1H), 10.77 (s, 1H), 6.82 (t, J=9.2 Hz, 1H), 6.55-6.46 (m, 2H), 6.44-6.38 (m, 1H), 5.78 (d, J=7.6 Hz, 1H), 4.93-4.87 (m, 1H), 4.31-4.20 (m, 1H), 2.90-2.43 (m, 10H), 2.19-2.05 (m, 3H), 1.91-1.77 (m, 1H), 1.72-1.60 (m, 2H), 1.45-1.36 (m, 18H).

1263

Step 6: 2-[4-amino-1-[4-[(2,6-dioxo-3-piperidyl)amino]-2-fluoro-phenyl]-4-piperidyl]acetic

1264

-continued

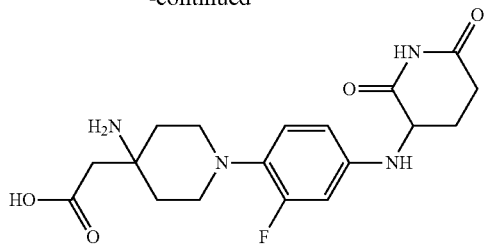

tert-butyl 2-[4-(tert-butoxycarbonylamino)-1-[4-[(2,6-dioxo-3-piperidyl)amino]-2-fluoro-phenyl]-4-piperidyl]acetate (600 mg, 1.12 mmol) was dissolved in dichloromethane (4 mL) and 4M hydrochloric acid in 1,4-dioxane (4 mL) was added. The reaction mixture was stirred at 40° C. for 4 h. The reaction mixture was concentrated under reduced pressure. The residue was triturated with diethyl ether and filtered to give 2-[4-amino-1-[4-[(2,6-dioxo-3-piperidyl)amino]-2-fluoro-phenyl]-4-piperidyl]acetic acid hydrochloride (460 mg, 1.11 mmol, 98.80% yield) as a blue solid. LCMS (ES+): m/z 379.1 [M+H]+

Step 7: 2-[6-[4-[2-[2-[4-amino-1-[4-[(2,6-dioxo-3-piperidyl)amino]-2-fluoro-phenyl]-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

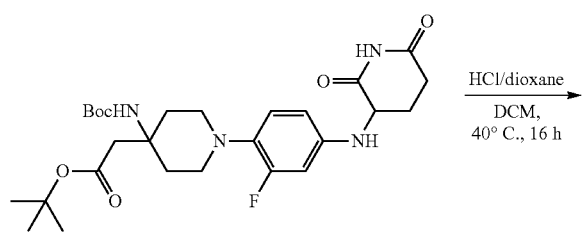

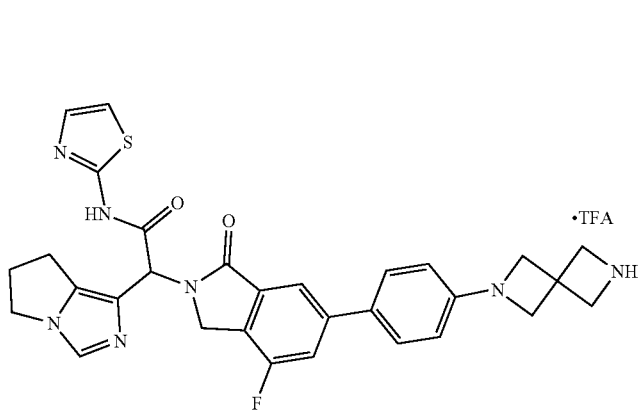

DIPEA
T3P
DMF,
0° C., 2 h

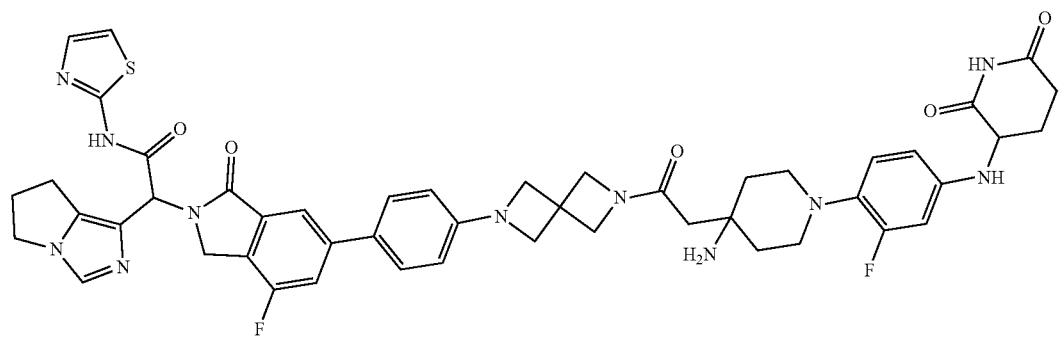

To a solution of 2-[4-amino-1-[4-[(2,6-dioxo-3-piperidyl)amino]-2-fluoro-phenyl]-4-piperidyl]acetic acid hydrochloride (200 mg, 482.09 μmol) and propylphosphonic anhydride solution (50 wt. % in ethyl acetate) (230.09 mg, 723.14 μmol) in N,N-dimethylformamide (4 mL) was added N,N-diisopropylethylamine (436.15 mg, 3.37 mmol, 587.80 μL). 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (263.68 mg, 385.67 μmol) was added to the reaction mixture. The mixture was stirred at 0° C. for 1 h. The reaction mixture was quenched by addition of water (20 mL) at 0° C. The mixture was filtered, and the filter cake was washed with water (2×5 mL). The collected solid was purified by preparative HPLC (Column: Phenomenex Luna C18 150 mm*25 mm, 10 m particle size, mobile phase: 13%-43% acetonitrile in water (0.225% formic acid), run time: 11 min) to afford Compound 162 (42.3 mg, 41.17 μmol, 8.54% yield) as a white solid. LCMS (ES+): m/z 930.7 [M+H]$^+$, $^1$H NMR (400 MHz, DMSO-d$_6$) δ=10.91-10.63 (m, 1H), 8.32 (s, 1H), 7.77-7.69 (m, 2H), 7.67-7.59 (m, 3H), 7.49 (d, J=3.6 Hz, 1H), 7.26 (d, J=3.6 Hz, 1H), 6.88 (t, J=9.2 Hz, 1H), 6.58-6.47 (m, 3H), 6.45-6.39 (m, 1H), 6.15 (s, 1H), 5.79 (d, J=8.0 Hz, 1H), 4.78 (s, 1H), 4.38 (s, 2H), 4.22 (d, J=18 Hz, 2H), 4.10-3.97 (m, 8H), 2.99-2.93 (m, 2H), 2.84-2.69 (m, 6H), 2.62-2.57 (m, 4H), 2.24 (s, 2H), 2.12-2.06 (m, 1H), 1.93-1.69 (m, 4H), 1.67-1.56 (m, 2H).

Example 163

2-(6,7-dihydro-5H-pyrrolo[1,2-c]imidazol-1-yl)-2-[6-[4-[2-[2-[1-[4-(2,4-dioxohexahydropyrimidin-1-yl)-2-fluoro-phenyl]-4-hydroxy-4-piperidyl]acetyl]-2,7-diazaspiro[3.5]nonan-7-yl]phenyl]-4-fluoro-1-oxo-isoindolin-2-yl]-N-thiazol-2-yl-acetamide, Compound 163

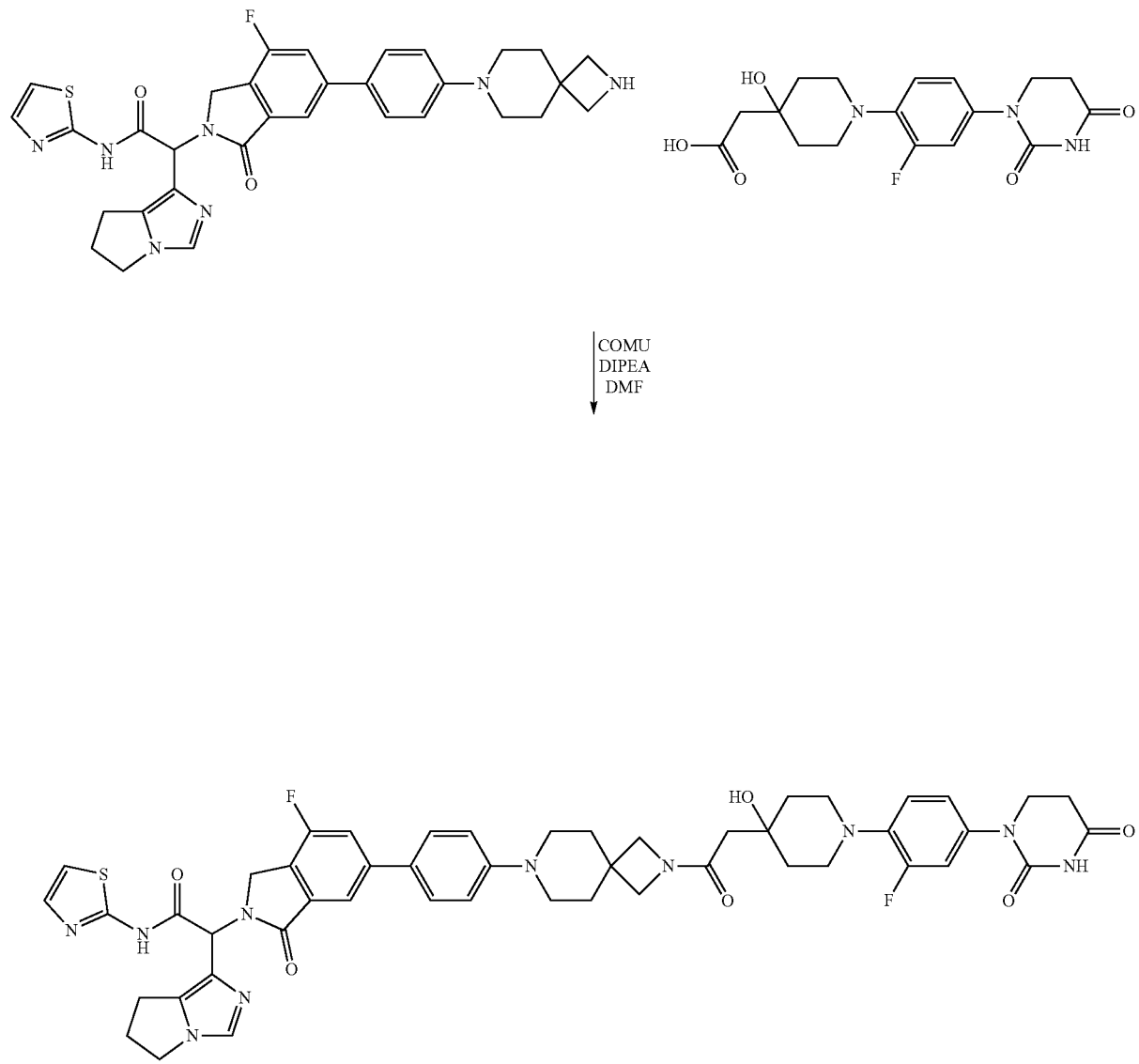

The stirred solution of 2-[6-[4-(2,7-diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide trifluoroacetic acid (200 mg, 281.01 μmol) and 2-[1-[4-(2,4-dioxohexahydropyrimidin-1-yl)-2-fluoro-phenyl]-4-hydroxy-4-piperidyl]acetic acid hydrochloride (129.85 mg, 323.16 mol) in N,N-dimethylformamide (3 mL) was added N,N-Diisopropylethylamine (181.59 mg, 1.41 mmol, 244.73 uL) at 0° C. 1-Cyano-2-ethoxy-2-oxoethylidenaminooxy) dimethylamino-morpholino-carbenium hexafluorophosphate (138.40 mg, 323.16 μmol) was added at the same temperature and the reaction mixture was stirred at ambient temperature for 1 h. The reaction mixture was directly injected on a C-18 column (100 g) for purification (0-45% acetonitrile in water (+0.1% ammonium acetate) over 30 min, then steep gradient to 100% acetonitrile). The pure fractions were combined and lyophilized to afford Compound 163 (51.1 mg, 53.59 μmol, 19.07% yield) as off-white solid. LCMS (ESI+): 944.9 [M+H]; ¹H-NMR (400 MHz, DMSO-d6):12.50 (s, 1H), 10.38 (s, 1H), 7.77 (s, 1H), 7.74 (d, J=12.00 Hz, 1H), 7.66 (d, J=8.80 Hz, 2H), 7.61 (s, 1H), 7.49 (d, J=3.60 Hz, 1H), 7.26 (d, J=2.40 Hz, 1H), 7.16 (d, J=13.60 Hz, 1H), 7.06 (d, J=5.20 Hz, 4H), 6.14 (s, 1H), 4.86 (s, 1H), 4.81 (d, J=17.60 Hz, 1H), 4.22 (d, J=18.00 Hz, 1H), 4.01-3.94 (m, 4H), 3.74 (t, J=6.40 Hz, 2H), 3.64 (s, 2H), 3.29-3.23 (m, 5H), 3.09-2.97 (m, 4H), 2.77-2.75 (m, 4H), 2.26 (s, 2H), 1.90-1.66 (m, 9H) (Water obscuration).

Example 164

2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, isomer A1, Compound 164

Step 1: tert-butyl 2-(1-benzyl-4-hydroxyazepan-4-yl)acetate

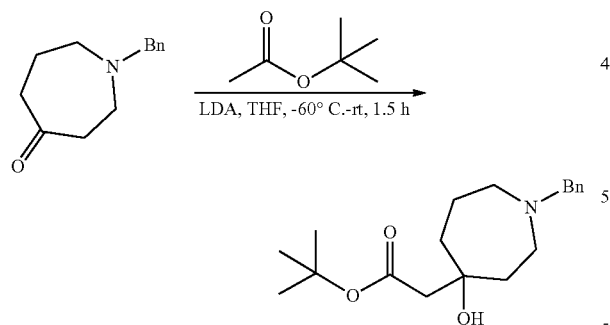

To a solution of tert-butyl acetate (10.80 g, 92.98 mmol, 12.51 mL) in tetrahydrofuran (100 mL) was added LDA (2 M in tetrahydrofuran, 53.1 mL, 106.26 mmol) at −60° C. The reaction mixture was stirred at −60° C. for 10 min. 1-benzylazepan-4-one (18 g, 88.55 mmol) in tetrahydrofuran (100 mL) was added to the reaction mixture and the resulting solution was stirred at −60° C. for 20 min. After that, the reaction mixture was stirred at 25° C. for another 1 h. The reaction mixture was quenched with NH₄Cl (100 mL) and diluted with ethyl acetate (500 mL) and water (500 mL). The layers were separated, and the aqueous layer was extracted with ethyl acetate (2×500 mL). The combined extracts were washed with brine (500 mL), dried over sodium sulfate, filtered and concentrated under reduced pressure. The residue was purified by column chromatography on silica gel to give tert-butyl 2-(1-benzyl-4-hydroxyazepan-4-yl) acetate (8.7 g, 23.69 mmol, 27% yield) as a yellow oil. LCMS (ESI+): m/z 320.3 [M+H]⁺

Step 2: tert-butyl 2-(4-hydroxyazepan-4-yl)acetate

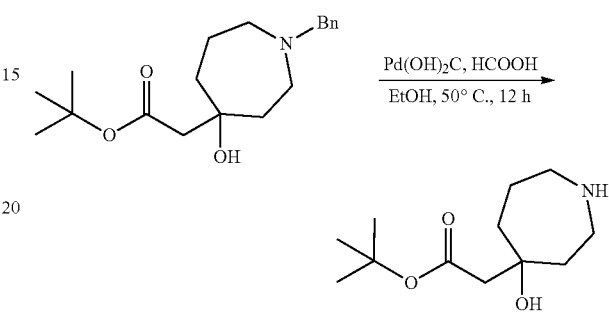

To a solution of tert-butyl 2-(1-benzyl-4-hydroxy-azepan-4-yl)acetate (8.7 g, 23.69 mmol) in EtOH (150 mL) was added formic acid (2.3 g, 47.88 mmol) and palladium hydroxide, 20% on charcoal (1.7 g, 23.69 mmol). The resulting mixture was stirred at 50° C. for 12 h. After being cooled to ambient temperature, the reaction mixture was filtered through a pad column of Celite. The filtrate was concentrated under reduced pressure to give tert-butyl 2-(4-hydroxyazepan-4-yl)acetate (6.6 g, 21.59 mmol, 91% yield) as a yellow oil. ¹H NMR (400 MHz, CHLOROFORM-d) δ=3.09-2.93 (m, 2H), 2.83-2.72 (m, 2H), 2.41 (s, 2H), 1.93-1.79 (m, 3H), 1.77-1.64 (m, 3H), 1.60-1.54 (m, 1H), 1.44-1.38 (m, 9H).

Step 3: tert-butyl 2-(1-(2-fluoro-4-nitrophenyl)-4-hydroxyazepan-4-yl)acetate

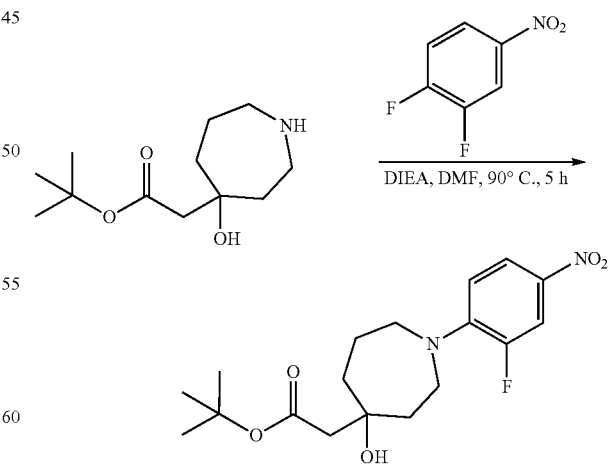

To a solution of tert-butyl 2-(4-hydroxyazepan-4-yl)acetate (6.6 g, 28.78 mmol) in N,N-dimethylformamide (80 mL) was added 1,2-difluoro-4-nitrobenzene (4.58 g, 28.76 mmol, 3.18 mL) and N-ethyl-N-isopropylpropan-2-amine (9.30 g, 71.95 mmol, 12.53 mL). The mixture was stirred at 90° C. for 5 h. After being cooled to ambient temperature, the mixture was concentrated in vacuo. The residue was diluted with ethyl acetate (50 mL) and water (50 mL). The layers were separated, and the aqueous layer was extracted with ethyl acetate (3×50 mL). The combined organic layer was dried over sodium sulfate, filtered, and concentrated in vacuo. The residue was purified by column chromatography on silica gel (petroleum ether/ethyl acetate=5/1) to give tert-butyl 2-(1-(2-fluoro-4-nitrophenyl)-4-hydroxyazepan-4-yl) acetate (9 g, 23.21 mmol, 81% yield) as a yellow solid. $^1$H NMR (400 MHz, CHLOROFORM-d) δ=7.98-7.80 (m, 2H), 6.70 (t, J=9.2 Hz, 1H), 3.95 (s, 1H), 3.64-3.50 (m, 3H), 3.47-3.37 (m, 1H), 2.42 (d, J=5.6 Hz, 2H), 2.38-2.23 (m, 1H), 1.99-1.85 (m, 4H), 1.63-1.55 (m, 1H), 1.47 (s, 9H).

Step 4: tert-butyl 2-(1-(2-fluoro-4-nitrophenyl)-4-hydroxyazepan-4-yl)acetate, Isomer A and tert-butyl 2-(1-(2-fluoro-4-nitrophenyl)-4-hydroxyazepan-4-yl) acetate, Isomer B

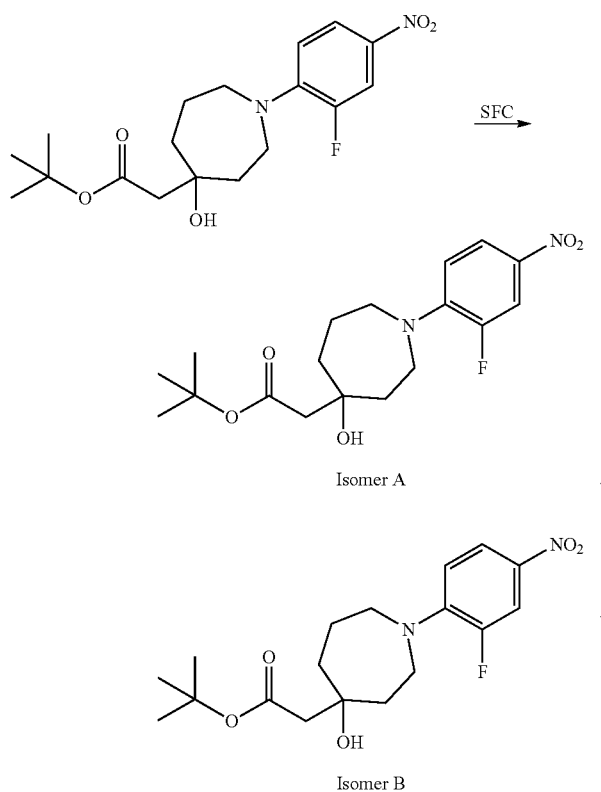

The racemic mixture of tert-butyl 2-(1-(2-fluoro-4-nitrophenyl)-4-hydroxyazepan-4-yl)acetate, Isomer A and tert-butyl 2-(1-(2-fluoro-4-nitrophenyl)-4-hydroxyazepan-4-yl) acetate, Isomer B was separated by Chiral SFC (20% 0.1% NH$_3$·H$_2$O-methanol condition; column: DAICEL CHIRALCEL OJ (250 mm×30 mm×10 μm) to afford two sets of fractions. The first eluting set of fractions was evaporated to afford tert-butyl 2-(1-(2-fluoro-4-nitrophenyl)-4-hydroxyazepan-4-yl)acetate, isomer A (4.15 g, 10.70 mmol, 44% yield) as a yellow solid. $^1$H NMR (400 MHz, CHLOROFORM-d) δ=7.97-7.80 (m, 2H), 6.70 (t, J=9.2 Hz, 1H), 3.95 (s, 1H), 3.70-3.52 (m, 3H), 3.46-3.35 (m, 1H), 2.48-2.36 (m, 2H), 2.35-2.22 (m, 1H), 1.99-1.77 (m, 4H), 1.62-1.50 (m, 2H), 1.47 (s, 9H).

The second eluting set of fractions was evaporated to afford tert-butyl 2-(1-(2-fluoro-4-nitrophenyl)-4-hydroxyazepan-4-yl)acetate, isomer B (4.27 g, 11.01 mmol, 45% yield) as a yellow solid. $^1$H NMR (400 MHz, CHLOROFORM-d) δ=7.96-7.79 (m, 2H), 6.70 (t, J=9.2 Hz, 1H), 3.96 (s, 1H), 3.68-3.51 (m, 3H), 3.41 (d, J=4.4 Hz, 1H), 2.47-2.37 (m, 2H), 2.30 (s, 1H), 1.99-1.79 (m, 4H), 1.61-1.50 (m, 2H), 1.47 (s, 9H).

Step 5: tert-butyl 2-(1-(4-amino-2-fluorophenyl)-4-hydroxyazepan-4-yl)acetate, Isomer A

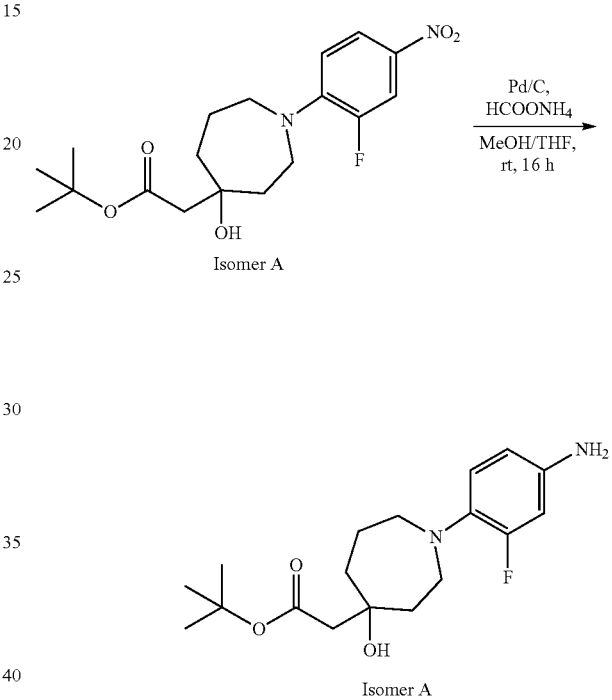

To a solution of tert-butyl 2-(1-(2-fluoro-4-nitrophenyl)-4-hydroxyazepan-4-yl)acetate, isomer A (4.15 g, 11.26 mmol) in methanol (8 mL) and tetrahydrofuran (32 mL) were added palladium, 10% on carbon (450 mg, 11.26 mmol) and ammonium formate (3.55 g, 56.33 mmol, 2.77 mL). The mixture was stirred at 25° C. for 16 h. The mixture was filtered through a pad of celite and washed with methanol (20 mL). The filtrate was concentrated under reduced pressure. The residue was diluted with ethyl acetate (250 mL) and water (250 mL). The layers were separated. Saturated aqueous sodium bicarbonate was added to the aqueous layer until pH 7 was reached. The mixture was extracted with ethyl acetate (2×250 mL). The combined organic layer was dried over anhydrous sodium sulfate, filtered and concentrated in vacuo to give tert-butyl 2-(1-(4-amino-2-fluorophenyl)-4-hydroxyazepan-4-yl)acetate, isomer A (3.6 g, 10.11 mmol, 90% yield) as a dark purple solid. $^1$H NMR (400 MHz, CHLOROFORM-d) δ=6.77 (dd, J=8.8, 9.6 Hz, 1H), 6.49-6.30 (m, 2H), 3.97 (s, 1H), 3.58-3.36 (m, 2H), 3.34-3.15 (m, 2H), 3.13-2.99 (m, 2H), 2.55-2.42 (m, 2H), 2.16-2.05 (m, 1H), 2.00-1.89 (m, 2H), 1.88-1.76 (m, 2H), 1.75-1.66 (m, 1H), 1.47 (s, 9H).

Step 6: tert-butyl 2-(1-(4-((2,6-dioxopiperidin-3-yl)amino)-2-fluorophenyl)-4-hydroxyazepan-4-yl)acetate, Isomer A

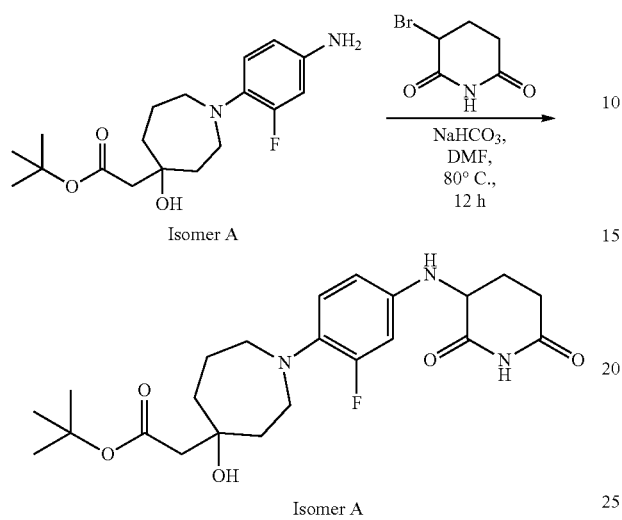

Isomer A

To a solution of tert-butyl 2-(1-(4-amino-2-fluorophenyl)-4-hydroxyazepan-4-yl) acetate, isomer A (3.6 g, 10.64 mmol) and 3-bromopiperidine-2,6-dione (4.09 g, 21.28 mmol) in N,N-dimethylformamide (40 mL) was added sodium bicarbonate (2.68 g, 31.91 mmol). The mixture was stirred at 80° C. for 12 h. The mixture was filtered through a pad of Celite and the filtrate was diluted with ethyl acetate (20 mL) and water (20 mL). The layers were separated, and the aqueous phase was extracted with ethyl acetate (3×20 mL). The combined organic layer was dried over sodium sulfate, filtered, and concentrated in vacuo. The residue was purified by reversed phase column (0.1% formic acid in water/acetonitrile) to give racemic tert-butyl 2-(1-(4-((2,6-dioxopiperidin-3-yl)amino)-2-fluorophenyl)-4-hydroxyazepan-4-yl)acetate (11, 3 g, 6.07 mmol, 57% yield) as a black solid. $^1$H NMR (400 MHz, CHLOROFORM-d) δ=8.15 (s, 1H), 6.82 (t, J=9.2 Hz, 1H), 6.48-6.34 (m, 2H), 4.52 (s, 1H), 4.03-3.89 (m, 2H), 3.37-3.17 (m, 2H), 3.15-3.00 (m, 2H), 2.91-2.80 (m, 1H), 2.79-2.66 (m, 1H), 2.56-2.50 (m, 1H), 2.48 (d, J=5.2 Hz, 2H), 2.17-2.05 (m, 1H), 1.98-1.90 (m, 2H), 1.89-1.79 (m, 2H), 1.76-1.59 (m, 3H), 1.47 (s, 9H).

Step 7: tert-butyl 2-[1-[4-[[2,6-dioxo-3-piperidyl]amino]-2-fluoro-phenyl]-4-hydroxy-azepan-4-yl]acetate, isomer A1 and tert-butyl 2-[1-[4-[[2,6-dioxo-3-piperidyl]amino]-2-fluoro-phenyl]-4-hydroxy-azepan-4-yl]acetate, isomer A2

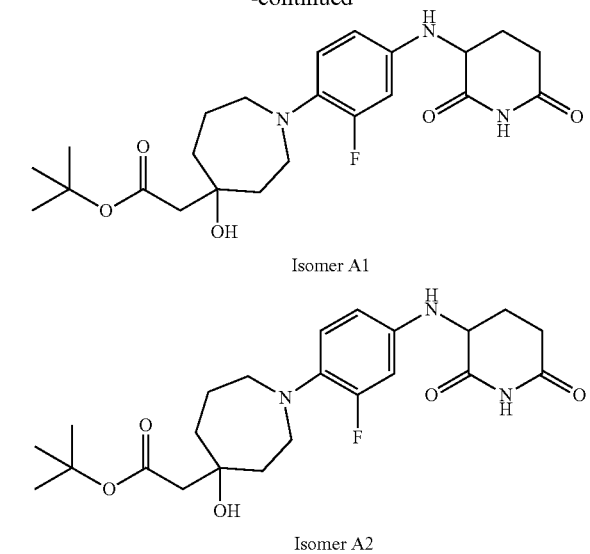

Isomer A1

Isomer A2

Racemic tert-butyl 2-[1-[4-[[2,6-dioxo-3-piperidyl]amino]-2-fluoro-phenyl]-4-hydroxy-azepan-4-yl]acetate was separated by Chiral SFC (Neu-EtOH condition, column: DAICEL CHIRALCEL OJ-H (250 mm×30 mm×5 µm); B %: 40%-40%; 4.3 min, 340 min) to afford two sets of fractions.

First set of fractions were evaporated to afford tert-butyl 2-(1-(4-((2,6-dioxopiperidin-3-yl)amino)-2-fluorophenyl)-4-hydroxyazepan-4-yl)acetate, isomer A1 (1.2 g, 2.54 mmol, 38% yield) as a yellow solid. $^1$H NMR (400 MHz, DMSO-d6) δ=10.77 (s, 1H), 6.76 (t, J=9.2 Hz, 1H), 6.49 (dd, J=2.4, 15.2 Hz, 1H), 6.38 (dd, J=2.4, 8.8 Hz, 1H), 5.66 (d, J=7.6 Hz, 1H), 4.42 (s, 1H), 4.28-4.15 (m, 1H), 3.25-3.07 (m, 2H), 3.03-2.82 (m, 2H), 2.79-2.67 (m, 1H), 2.63-2.53 (m, 1H), 2.36 (s, 2H), 2.08 (dt, J=4.8, 8.8 Hz, 1H), 2.03-1.90 (m, 2H), 1.88-1.77 (m, 2H), 1.77-1.66 (m, 2H), 1.63-1.51 (m, 1H), 1.39 (s, 9H).

Second set of fractions were evaporated to afford tert-butyl 2-((S)-1-(4-(((R)-2,6-dioxopiperidin-3-yl)amino)-2-fluorophenyl)-4-hydroxyazepan-4-yl)acetate (1.7 g, 3.40 mmol, 51% yield) as a yellow solid. $^1$H NMR (400 MHz, DMSO-d6) δ=10.76 (s, 1H), 6.76 (t, J=9.2 Hz, 1H), 6.48 (dd, J=2.4, 15.2 Hz, 1H), 6.38 (dd, J=2.4, 8.4 Hz, 1H), 5.65 (d, J=7.6 Hz, 1H), 4.42 (s, 1H), 4.22 (ddd, J=4.8, 7.2, 11.6 Hz, 1H), 4.03 (q, J=7.2 Hz, 1H), 3.23-3.05 (m, 2H), 3.01-2.83 (m, 2H), 2.72 (dt, J=6.4, 12.0 Hz, 1H), 2.56 (td, J=4.0, 17.6 Hz, 1H), 2.35 (s, 2H), 2.08 (dt, J=4.4, 8.8 Hz, 1H), 1.99 (s, 2H), 1.97-1.89 (m, 1H), 1.87-1.77 (m, 2H), 1.74-1.64 (m, 2H), 1.61 (dd, J=5.2, 8.8 Hz, 1H), 1.39 (s, 9H).

Step 8: 2-[1-[4-[[2,6-dioxo-3-piperidyl]amino]-2-fluoro-phenyl]-4-hydroxy-azepan-4-yl]acetic acid, Isomer A1

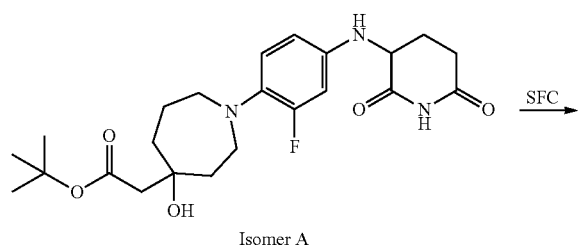

Isomer A

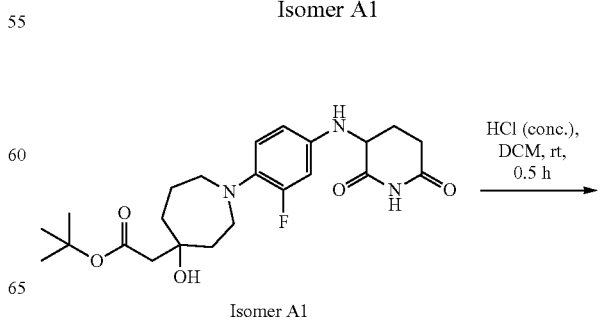

Isomer A1

1273

-continued

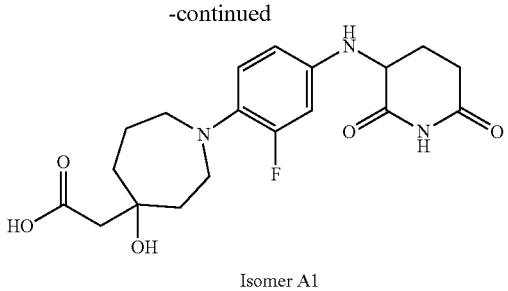

Isomer A1

To a solution of tert-butyl 2-[1-[4-[[2,6-dioxo-3-piperidyl]amino]-2-fluoro-phenyl]-4-hydroxy-azepan-4-yl]acetate, isomer A1 (300 mg, 667.39 μmol) in dichloromethane

1274

(4.5 mL) was added Hydrogen chloride (12 M, 0.3 mL, 3.6 mmol). The mixture was stirred at 25° C. for 0.5 h. The mixture was concentrated under reduced pressure at 35° C. to give 2-[1-[4-[[2,6-dioxo-3-piperidyl]amino]-2-fluoro-phenyl]-4-hydroxy-azepan-4-yl]acetic acid hydrochloride, isomer A1 (230 mg, 502.94 μmol, 75% yield, HCl salt) as a blue solid. LCMS (ESI): m/z 394.1 [M+H]$^+$ Step 9: 2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, Isomer A1

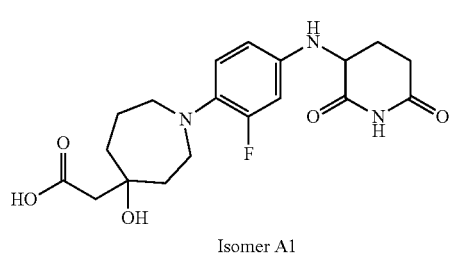

Isomer A1

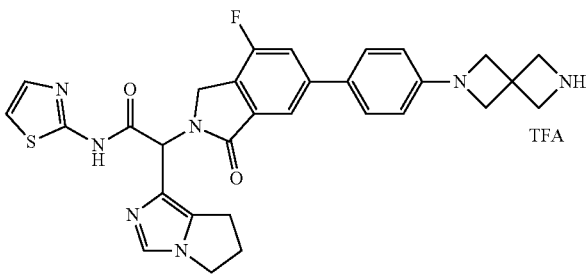

TFA

EDCl
HOBt
DIEA
DMF, 0° C.-rt, 16.5 h

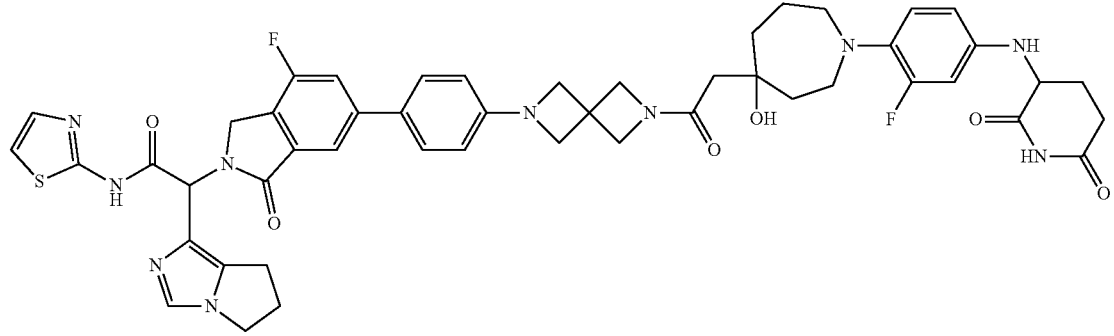

Isomer A1

To a solution of 2-[1-[4-[[2,6-dioxo-3-piperidyl]amino]-2-fluoro-phenyl]-4-hydroxy-azepan-4-yl]acetic acid hydrochloride, isomer A1 (206 mg, 479.22 μmol) in N,N-dimethylformamide (3 mL) were added N-ethyl-N-isopropylpropan-2-amine (437.78 mg, 3.39 mmol, 590 μL), N1-((ethylimino)methylene)-N3,N3-dimethylpropane-1,3-diamine hydrochloride (103 mg, 537.30 μmol) and HOBt (72 mg, 532.86 μmol) at 0° C. The mixture was stirred at 0° C. for 0.5 h. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (262 mg, 383.22 μmol) was added to the mixture. The resulting mixture was stirred at 25° C. for 16 h. The mixture was filtered. The filtrate was purified by preparative HPLC (flow: 60 mL/min; gradient: from 10%-40% acetonitrile in water (0.225% formic acid) over 10 min; column: Phenomenex Luna C18 150×40 mm×15 μm) and lyophilized to give Compound 164 (130.66 mg, 129.20 μmol, 27% yield) as a purple solid. LCMS (ESI): m/z 945.3 [M+H]+, 1H NMR (400 MHz, DMSO-d6) δ=12.52 (s, 1H), 10.76 (s, 1H), 7.74 (s, 1H), 7.70 (d, J=10.8 Hz, 1H), 7.63 (d, J=8.4 Hz, 2H), 7.60 (s, 1H), 7.48 (d, J=3.6 Hz, 1H), 7.25 (d, J=3.6 Hz, 1H), 6.78 (t, J=9.6 Hz, 1H), 6.53 (d, J=8.4 Hz, 2H), 6.47 (s, 1H), 6.39 (d, J=8.4 Hz, 1H), 6.14 (s, 1H), 5.66 (d, J=7.6 Hz, 1H), 4.83 (s, 1H), 4.79 (d, J=17.6 Hz, 1H), 4.40-4.30 (m, 2H), 4.27-4.16 (m, 2H), 4.07 (s, 2H), 4.03-3.92 (m, 6H), 3.26-3.09 (m, 3H), 3.02-2.85 (m, 2H), 2.81-2.65 (m, 2H), 2.61-2.56 (m, 1H), 2.54 (s, 1H), 2.47-2.42 (m, 1H), 2.29-2.17 (m, 2H), 2.08 (td, J=4.4, 8.4 Hz, 1H), 1.98-1.86 (m, 2H), 1.86-1.78 (m, 1H), 1.77-1.55 (m, 4H).

Example 165

2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, isomer A2, Compound 165

Step 1: 2-[(1-[4-[[2,6-dioxo-3-piperidyl]amino]-2-fluoro-phenyl]-4-hydroxy-azepan-4-yl]acetic acid hydrochloride, isomer A2

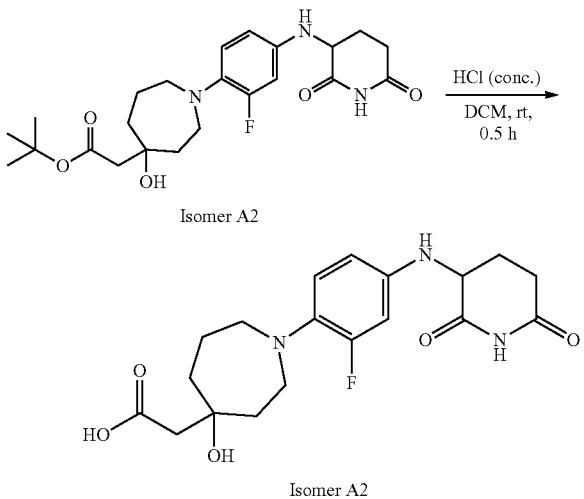

To a solution of tert-butyl 2-[1-[4-[[2,6-dioxo-3-piperidyl]amino]-2-fluoro-phenyl]-4-hydroxy-azepan-4-yl]acetate, isomer A2 (300 mg, 667.39 μmol) in dichloromethane (4.5 mL) was added HCl (12 M, 0.3 mL). The mixture was stirred at 25° C. for 0.5 h. The mixture was concentrated under reduced pressure at 35° C. to give 2-[1-[4-[[2,6-dioxo-3-piperidyl]amino]-2-fluoro-phenyl]-4-hydroxy-azepan-4-yl]acetic acid hydrochloride, isomer A2 (360 mg, 829.09 μmol) as a blue solid. LCMS (ESI): m/z 394.2 [M+H]+

Step 2: 2-(6,7-dihydro-5H-pyrrolo[1,2-c]imidazol-1-yl)-2-(6-(4-(6-(2-(1-(4-((2,6-dioxopiperidin-3-yl)amino)-2-fluorophenyl)-4-hydroxyazepan-4-yl)acetyl)-2,6-diazaspiro[3.3]heptan-2-yl)phenyl)-4-fluoro-1-oxoisoindolin-2-yl)-N-(thiazol-2-yl)acetamide

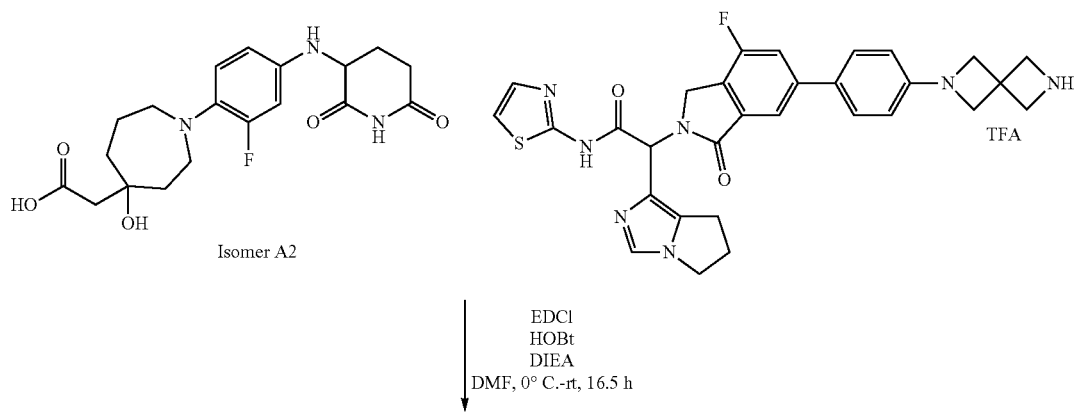

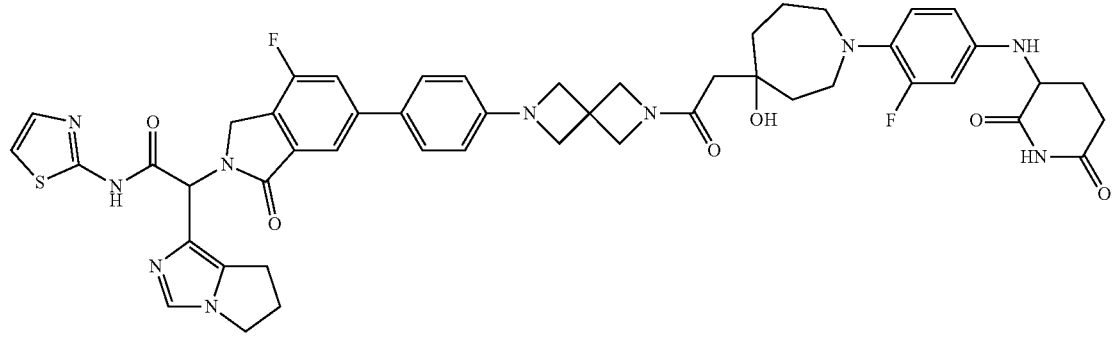

Isomer A2

To a solution of tert-butyl 2-(1-(4-((2,6-dioxopiperidin-3-yl)amino)-2-fluorophenyl)-4-hydroxyazepan-4-yl)acetate hydrochloride, isomer A2 (280 mg, 651.36 μmol) in N,N-dimethylformamide (0.3 mL) were added N-ethyl-N-isopropylpropan-2-amine (593.60 mg, 4.59 mmol, 800 μL) and HATU (248 mg, 652.24 μmol). The mixture was stirred at 0° C. for 30 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid (310 mg, 453.43 μmol) was added to the mixture. The resulting mixture was stirred at 25° C. for 16 h. The mixture was filtered. The filtrate was purified by preparative HPLC (flow: 25 mL/min; gradient: from 11%-44% acetonitrile in water (0.225% formic acid) over 11 min; column: Phenomenex luna C18 150×25 mm×10 μm). The desired fraction was frozen and lyophilized. The residue was dissolved in dichloromethane (4 mL), and the mixture was washed with saturated aqueous sodium bicarbonate (2×3 mL). The organic layer was dried over anhydrous sodium sulfate, filtered, and concentrated in vacuo. The residue was dissolved with acetonitrile (5 mL) and water (20 mL). The solution was lyophilized to give Compound 165 (60.45 mg, 63.33 μmol, 10% yield) as a brown solid. LCMS (ESI): m/z 945.5 [M+H]$^+$, $^1$H NMR (400 MHz, DMSO-d6) δ=12.51 (s, 1H), 10.77 (s, 1H), 7.73 (s, 1H), 7.69 (d, J=11.2 Hz, 1H), 7.63 (d, J=8.4 Hz, 2H), 7.58 (s, 1H), 7.42 (s, 1H), 7.25-7.06 (m, 1H), 6.78 (t, J=9.2 Hz, 1H), 6.60-6.44 (m, 3H), 6.39 (dd, J=2.0, 8.4 Hz, 1H), 6.09 (s, 1H), 5.66 (d, J=7.6 Hz, 1H), 4.91-4.76 (m, 2H), 4.42-4.29 (m, 2H), 4.27-4.14 (m, 2H), 4.11-3.89 (m, 8H), 3.24-3.08 (m, 2H), 3.03-2.84 (m, 2H), 2.79-2.66 (m, 2H), 2.61-2.53 (m, 2H), 2.45 (d, J=4.4 Hz, 2H), 2.29-2.18 (m, 2H), 2.12-2.05 (m, 1H), 1.97-1.68 (m, 6H), 1.63 (td, J=5.2, 13.6 Hz, 1H).

Example 166

2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, isomer B1, Compound 166

Step 1: tert-butyl 2-(1-(4-amino-2-fluorophenyl)-4-hydroxyazepan-4-yl)acetate, Isomer B

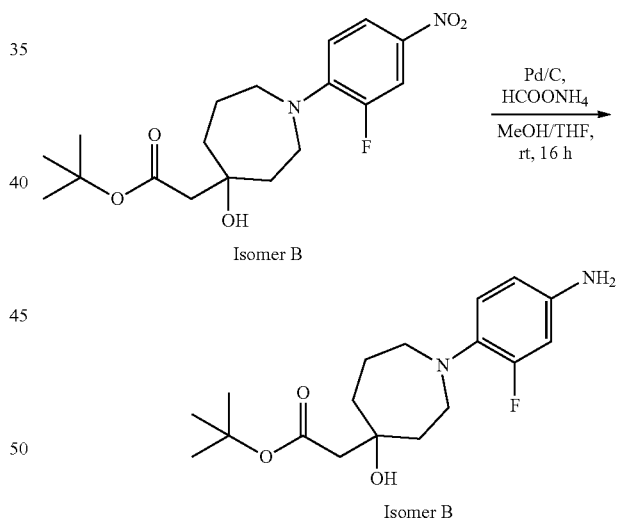

To a solution of tert-butyl 2-(1-(2-fluoro-4-nitrophenyl)-4-hydroxyazepan-4-yl)acetate (4.27 g, 11.59 mmol) in methanol (8 mL) and tetrahydrofuran (32 mL) were added palladium, 10% on carbon (450 mg, 11.26 mmol) and ammonium formate (3.65 g, 57.96 mmol, 2.86 mL). The mixture was stirred at 25° C. for 16 h. The mixture was filtered through a pad of Celite, the filter cake was washed with methanol (20 mL). The filtrate was concentrated under reduced pressure. The residue was diluted with ethyl acetate (250 mL). The mixture was adjusted to pH 7 with saturated aqueous sodium bicarbonate. The mixture was extracted with ethyl acetate (2×250 mL). The combined organic layer was dried over anhydrous sodium sulfate, filtered and concentrated in vacuo to give tert-butyl 2-(1-(4-amino-2-fluorophenyl)-4-hydroxyazepan-4-yl) acetate (3.85 g, 10.81 mmol, 93% yield) as a purple black solid. $^1$H NMR (400 MHz, CHLOROFORM-d) δ=6.77 (dd, J=8.4, 9.6 Hz, 1H), 6.46-6.32 (m, 2H), 4.02-3.92 (m, 1H), 3.57-3.41 (m, 1H), 3.19 (s, 2H), 3.13-2.98 (m, 2H), 2.53-2.42 (m, 2H), 2.13-2.05 (m, 1H), 1.97-1.91 (m, 2H), 1.87-1.76 (m, 2H), 1.76-1.68 (m, 1H), 1.47 (s, 9H).

Step 2: tert-butyl 2-(1-(4-((2,6-dioxopiperidin-3-yl)amino)-2-fluorophenyl)-4-hydroxyazepan-4-yl)acetate, Isomer B

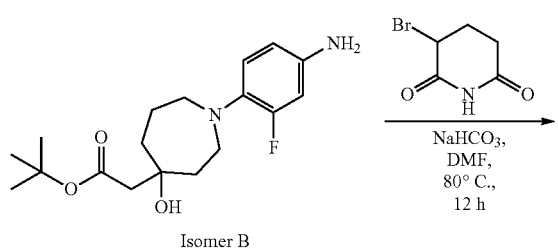

To a solution of 3-bromopiperidine-2,6-dione (4.37 g, 22.75 mmol) and (R)-tert-butyl 2-(1-(4-amino-2-fluorophenyl)-4-hydroxyazepan-4-yl)acetate (3.85 g, 11.38 mmol) in N,N-dimethylformamide (40 mL) was added sodium bicarbonate (2.87 g, 34.13 mmol, 1.33 mL). The mixture was stirred at 80° C. for 12 h. The mixture was filtered through a pad of Celite, and the filtrate was diluted with ethyl acetate (20 mL) and water (20 mL). The layers were separated, and the aqueous phase was extracted with ethyl acetate (3×20 mL). The combined organic layer was dried over sodium sulfate, filtered and concentrated in vacuo. The crude product was purified by reversed phase column (0.1% formic acid condition) to give tert-butyl 2-((1-(4-((2,6-dioxopiperidin-3-yl)amino)-2-fluorophenyl)-4-hydroxyazepan-4-yl)acetate, Isomer B (4 g, 8.54 mmol, 75% yield) as a black solid. LCMS (ESI): m/z 450.3 [M+H]$^+$ Step 3: tert-butyl 2-(1-(4-((2,6-dioxopiperidin-3-yl)amino)-2-fluorophenyl)-4-hydroxyazepan-4-yl) acetate, isomer B1 and tert-butyl 2-(1-(4-((2,6-dioxopiperidin-3-yl)amino)-2-fluorophenyl)-4-hydroxyazepan-4-yl)acetate, Isomer B2

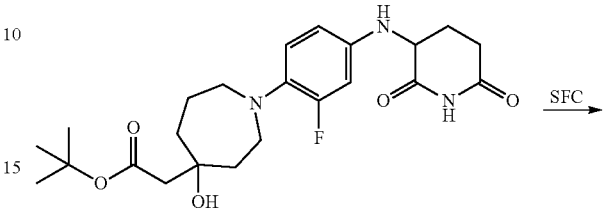

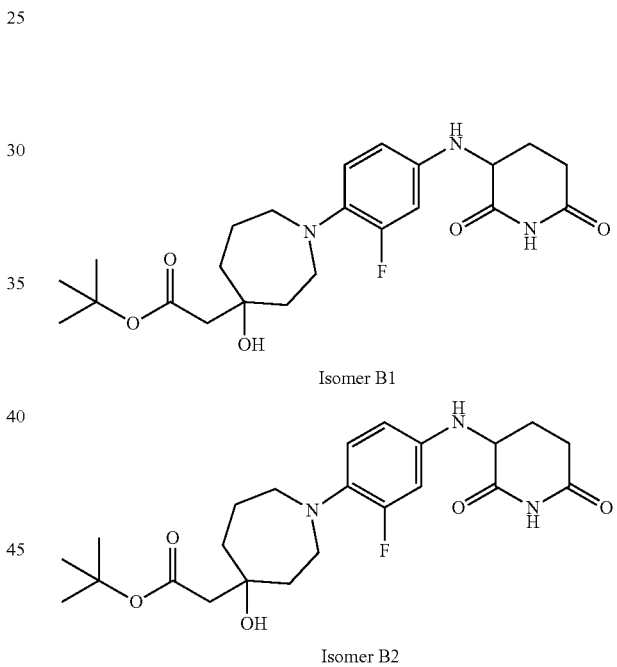

Racemic tert-butyl 2-(1-(4-((2,6-dioxopiperidin-3-yl)amino)-2-fluorophenyl)-4-hydroxyazepan-4-yl) acetate was separated by chiral SFC (Isopropanol condition, column: REGIS (S,S)-WHELK-O1 (250 mm×50 mm, 10 μm); B %: 60%; 8.1 min run time) to give two sets of fraction.

The first eluting set of fractions was evaporated to afford tert-butyl 2-(1-(4-((2,6-dioxopiperidin-3-yl)amino)-2-fluorophenyl)-4-hydroxyazepan-4-yl)acetate, isomer B1 (1.43 g, 3.12 mmol, 37% yield, LCMS (ESI): m/z 450.3 [M+H]$^+$ The second eluting set of fractions was evaporated to afford tert-butyl 2-((R)-1-(4-(((R)-2,6-dioxopiperidin-3-yl)amino)-2-fluorophenyl)-4-hydroxyazepan-4-yl)acetate, isomer B2 (1.24 g, 2.73 mmol, 32% yield, LCMS (ESI): m/z 450.3 [M+H]$^+$ Step 4: 2-[1-[4-[[2,6-dioxo-3-piperidyl]amino]-2-fluoro-phenyl]-4-hydroxy-azepan-4-yl]acetic acid hydrochloride, Isomer B1

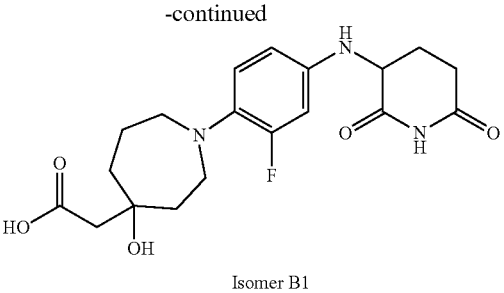

Isomer B1

To a solution of tert-butyl 2-[1-[4-[[2,6-dioxo-3-piperidyl]amino]-2-fluoro-phenyl]-4-hydroxy-azepan-4-yl]acetate, isomer B1 (300 mg, 667.39 μmol) in dichloromethane (4.5 mL) was added HCl (12 M, 0.3 mL). The mixture was stirred at 25° C. for 0.5 h. The mixture was concentrated under reduced pressure at 35° C. to give 2-[1-[4-[[2,6-dioxo-3-piperidyl]amino]-2-fluoro-phenyl]-4-hydroxy-azepan-4-yl]acetic acid hydrochloride, isomer B1 (360 mg, 829.09 μmol) as a blue solid. LCMS (ESI): m/z 394.2 [M+H]+

Step 5: 2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, isomer B1

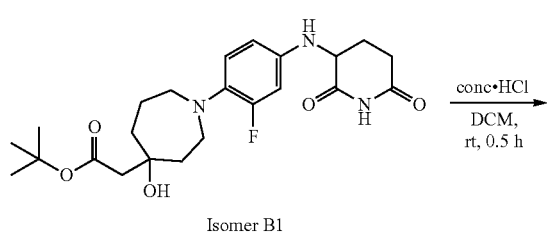

Isomer B1

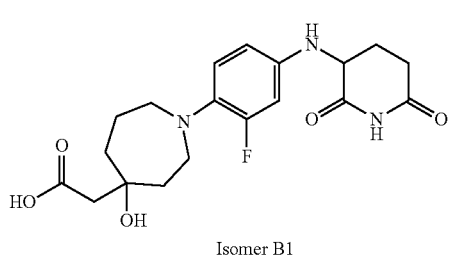

Isomer B1

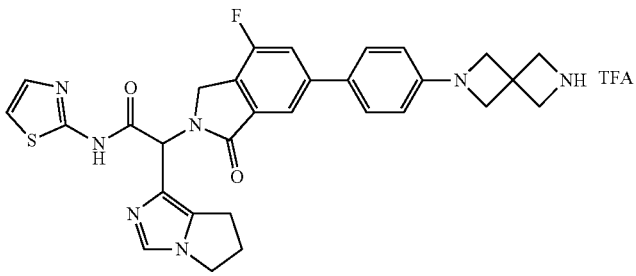

EDCl
HOBt
DIEA
DMF, 0° C.-rt, 16.5 h

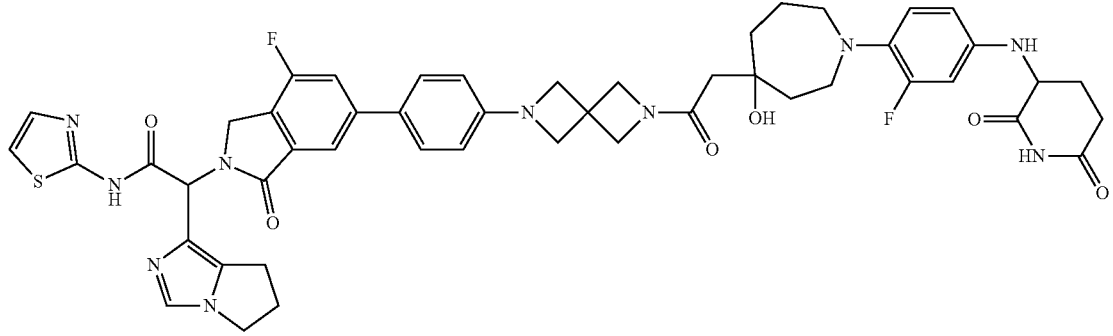

Isomer B1

To a solution of 2-[1-[4-[[2,6-dioxo-3-piperidyl]amino]-2-fluoro-phenyl]-4-hydroxy-azepan-4-yl]acetic acid hydrochloride, isomer B1 (200 mg, 465.26 μmol) in N,N-dimethylformamide (3 mL) were added N-ethyl-N-isopropylpropan-2-amine (422.94 mg, 3.27 mmol, 570 μL), $N_1$-((ethylimino)methylene)-$N_3$,$N_3$-dimethylpropane-1,3-diamine hydrochloride (100 mg, 521.64 μmol) and HOBt (70 mg, 518.05 μmol) at 0° C. The mixture was stirred at 0° C. for 0.5 h. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (255 mg, 372.98 μmol) was added to the mixture. The resulting mixture was stirred at 25° C. for 16 h. The reaction mixture was filtered. The filtrate was purified by preparative HPLC (column: Phenomenex Luna C18 150×40 mm×15 μm; mobile phase: water (0.225% formic acid)-acetonitrile; B %: 9%-39%, 10 min). The desired fraction was kept below 0° C. and lyophilized immediately to give Compound 166 (85.45 mg, 84.50 μmol, 18% yield) as a purple solid. LCMS (ESI): m/z 945.3 [M+H]$^+$, $^1$H NMR (400 MHz, DMSO-$d_6$) δ=12.96-12.00 (m, 1H), 10.77 (s, 1H), 8.23 (s, 1H), 7.74 (s, 1H), 7.70 (d, J=10.8 Hz, 1H), 7.66-7.58 (m, 3H), 7.48 (d, J=3.6 Hz, 1H), 7.25 (d, J=3.2 Hz, 1H), 6.78 (t, J=9.6 Hz, 1H), 6.58-6.45 (m, 3H), 6.39 (d, J=8.4 Hz, 1H), 6.14 (s, 1H), 5.66 (d, J=7.6 Hz, 1H), 4.79 (d, J=17.6 Hz, 2H), 4.39-4.30 (m, 2H), 4.27-4.16 (m, 2H), 4.07 (s, 2H), 4.04-3.91 (m, 6H), 3.23-3.09 (m, 3H), 3.03-2.94 (m, 1H), 2.90 (d d, J=6.0, 12.0 Hz, 1H), 2.81-2.66 (m, 2H), 2.61-2.52 (m, 2H), 2.47-2.42 (m, 1H), 2.23 (s, 2H), 2.08 (td, J=4.4, 8.8 Hz, 1H), 1.97-1.86 (m, 2H), 1.86-1.78 (m, 1H), 1.78-1.55 (m, 4H).

Example 167

2-(6,7-dihydro-5H-pyrrolo[1,2-c]imidazol-1-yl)-2-[6-[4-[2-[2-[1-[4-[[2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, isomer B2, Compound 167

Step 1: 2-[1-[4-[[2,6-dioxo-3-piperidyl]amino]-2-fluoro-phenyl]-4-hydroxy-azepan-4-yl]acetic acid hydrochloride, Isomer B2

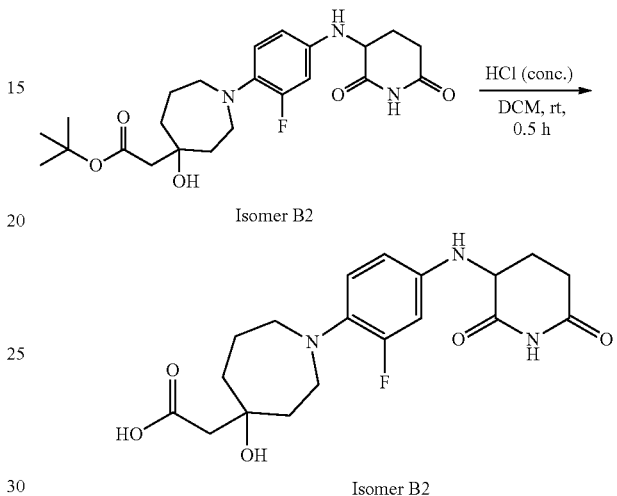

To a solution of tert-butyl 2-[1-[4-[[2,6-dioxo-3-piperidyl]amino]-2-fluoro-phenyl]-4-hydroxy-azepan-4-yl]acetate (300 mg, 667.39 μmol) in dichloromethane (4.5 mL) was added hydrochloric acid (12 M, 0.3 mL). The mixture was stirred at 25° C. for 0.5 h. The mixture was concentrated under reduced pressure at 35° C. to give 2-[1-[4-[[2,6-dioxo-3-piperidyl]amino]-2-fluoro-phenyl]-4-hydroxy-azepan-4-yl]acetic acid hydrochloride (350 mg, 806.06 μmol) as a blue solid. LCMS (ESI): m/z 394.2 [M+H]$^+$ Step 2: 2-(6,7-dihydro-5H-pyrrolo[1,2-c]imidazol-1-yl)-2-[6-[4-[2-[2-[(4R)-1-[4-[[(3R)-2,6-dioxo-3-piperidyl]amino]-2-fluoro-phenyl]-4-hydroxy-azepan-4-yl]acetyl]-2,6-diazaspiro[3.3]heptan-6-yl]phenyl]-4-fluoro-1-oxo-isoindolin-2-yl]-N-thiazol-2-yl-acetamide, Isomer B2

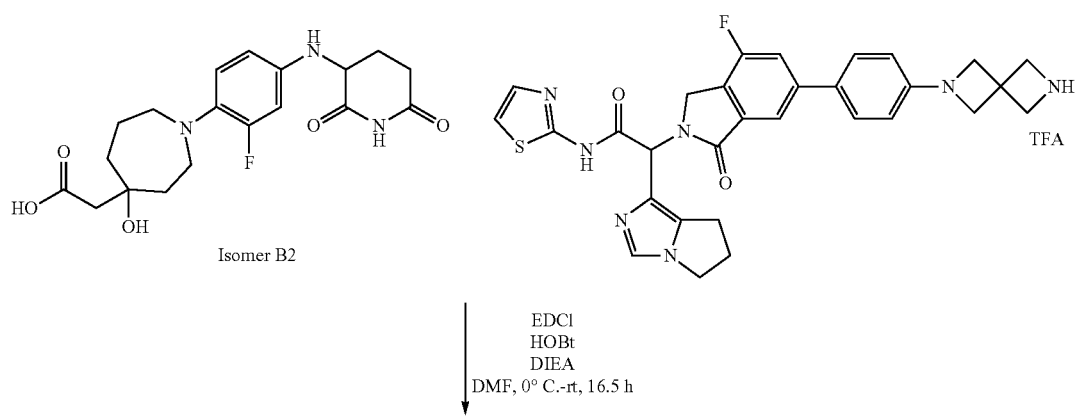

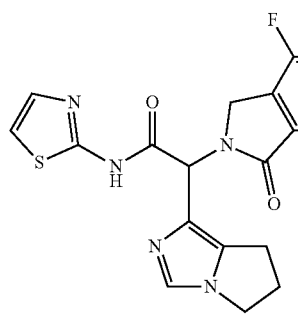
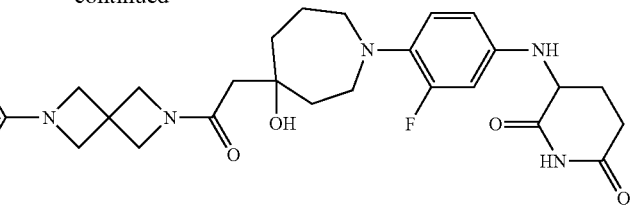

Isomer B2

To a solution of 2-[1-[4-[[2,6-dioxo-3-piperidyl]amino]-2-fluoro-phenyl]-4-hydroxy-azepan-4-yl]acetic acid hydrochloride (200 mg, 465.26 μmol) in N,N-dimethylformamide (3 mL) were added N-ethyl-N-isopropylpropan-2-amine (422.94 mg, 3.27 mmol, 0.57 mL), $N_1$-((ethylimino)methylene)-$N_3,N_3$-dimethylpropane-1,3-diamine hydrochloride (100 mg, 521.65 μmol) and HOBt (70 mg, 518.06 μmol) at 0° C. The mixture was stirred at 0° C. for 0.5 h. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (255 mg, 372.98 μmol) was added to the mixture. The resulting mixture was stirred at 25° C. for 16 h. The reaction mixture was filtered. The filtrate was purified by preparative HPLC (column: Phenomenex luna C18 150×40 mm×15 μm; mobile phase: water (0.225% formic acid)-acetonitrile; B %: 10%-40%, 10 min). The desired fraction was kept under below 0° C. and lyophilized immediately to give Compound 167 (78.81 mg, 77.93 μmol, 16% yield) as a purple solid. LCMS (ESI): m/z 945.3 [M+H]$^+$, $^1$H NMR (400 MHz, DMSO-$d_6$) δ=12.74-12.24 (m, 1H), 10.77 (s, 1H), 8.27 (s, 1H), 7.74 (s, 1H), 7.72-7.67 (m, 1H), 7.66-7.59 (m, 3H), 7.48 (d, J=3.6 Hz, 1H), 7.25 (d, J=3.6 Hz, 1H), 6.78 (t, J=9.2 Hz, 1H), 6.56-6.45 (m, 3H), 6.39 (d, J=8.8 Hz, 1H), 6.14 (s, 1H), 5.66 (d, J=7.6 Hz, 1H), 4.89-4.72 (m, 2H), 4.41-4.30 (m, 2H), 4.28-4.14 (m, 2H), 4.07 (s, 2H), 4.04-3.91 (m, 6H), 3.23-3.09 (m, 3H), 3.02-2.94 (m, 1H), 2.89 (d d, J=6.0, 13.2 Hz, 1H), 2.81-2.65 (m, 2H), 2.62-2.52 (m, 2H), 2.47-2.42 (m, 1H), 2.23 (s, 2H), 2.08 (td, J=4.4, 8.4 Hz, 1H), 1.96-1.86 (m, 2H), 1.86-1.78 (m, 1H), 1.77-1.55 (m, 4H).

Example 168

2-(6,7-dihydro-5H-pyrrolo[1,2-c]imidazol-1-yl)-2-[6-[4-[2-[2-[1-[4-(2,4-dioxohexahydropyrimidin-1-yl)-2-(trifluoromethyl)phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, Compound 168

Step 1: tert-butyl 2-[4-hydroxy-1-[4-nitro-2-(trifluoromethyl)phenyl]-4-piperidyl]acetate

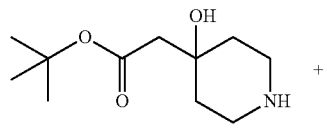 +

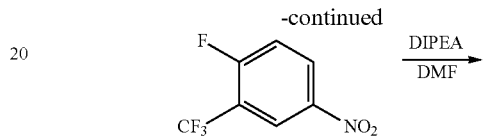

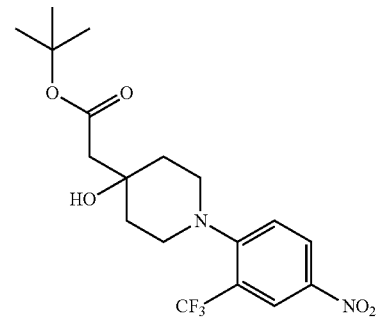

To a solution of tert-butyl 2-(4-hydroxy-4-piperidyl)acetate (10 g, 46.45 mmol) and 1-fluoro-4-nitro-2-(trifluoromethyl)benzene (10 g, 47.82 mmol, 6.58 mL) in N,N-dimethylformamide (50 mL) was added N,N-diisopropylethylamine (10.21 g, 78.96 mmol, 13.75 mL). The mixture was stirred at 80° C. for 1 h. The reaction mixture was diluted with water (100 mL) and extracted with ethyl acetate (3×100 mL). The combined organic layers were washed with brine (1×100 mL), dried over sodium sulfate, filtered and concentrated in vacuo. The residue was purified by column chromatography on silica gel (10:1 petroleum ether:ethyl acetate). tert-butyl 2-[4-hydroxy-1-[4-nitro-2-(trifluoromethyl)phenyl]-4-piperidyl]acetate (16.5 g, 38.76 mmol, 83.45% yield) was obtained as a yellow solid. LC-MS m/z 405.2 [M+H]$^+$ $^1$H NMR (400 MHz, CHLOROFORM-d) δ=8.50 (d, J=2.8 Hz, 1H), 8.31 (dd, J=2.8, 8.8 Hz, 1H), 7.32 (d, J=9.2 Hz, 1H), 3.89 (s, 1H), 3.37-3.25 (m, 2H), 3.14 (br d, J=12.0 Hz, 2H), 2.46 (s, 2H), 1.85-1.72 (m, 4H), 1.50 (s, 9H).

1287

Step 2: tert-butyl 2-[1-[4-amino-2-(trifluoromethyl)phenyl]-4-hydroxy-4-piperidyl]acetate

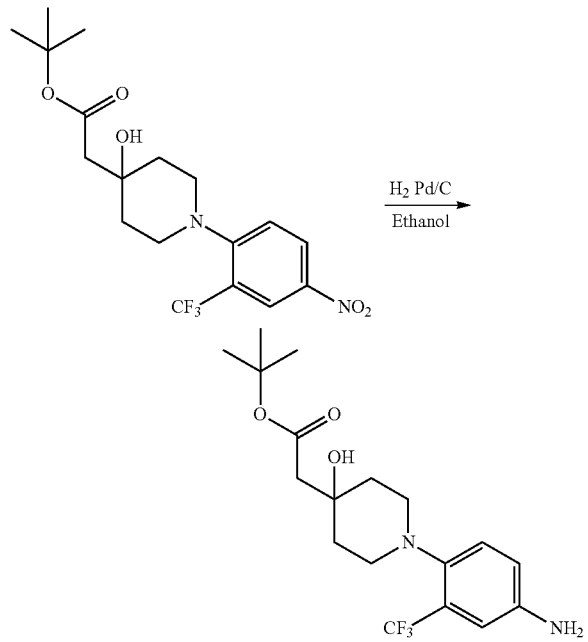

A mixture of tert-butyl 2-[4-hydroxy-1-[4-nitro-2-(trifluoromethyl)phenyl]-4-piperidyl]acetate (15.5 g, 38.33 mmol) in ethanol (160 mL) was added Palladium on carbon, 10% (1.6 g). The mixture was stirred at 25° C. under a hydrogen atmosphere (15 psi) for 12 h. The reaction mixture was filtered through a celite pad and the filter cake was washed with ethyl acetate. The filtrate was concentrated under reduced pressure. tert-Butyl 2-[1-[4-amino-2-(trifluoromethyl)phenyl]-4-hydroxy-4-piperidyl]acetate (13.8 g, 33.17 mmol, 86.55% yield) was obtained as an off-white solid. LCMS (ESI+) m/z 375.2 (M+H)+, $^1$H NMR (400 MHz, DMSO-d6) δ=7.20 (d, J=8.4 Hz, 1H), 6.79 (d, J=2.4 Hz, 1H), 6.75 (dd, J=2.4, 8.4 Hz, 1H), 5.29 (s, 2H), 4.45 (s, 1H), 2.92 (t, J=10.4 Hz, 2H), 2.54 (d, J=11.2 Hz, 2H), 2.34 (s, 2H), 1.81-1.70 (m, 2H), 1.58 (br d, J=12.4 Hz, 2H), 1.41 (s, 9H).

Step 3: 3-[4-[4-(2-tert-butoxy-2-oxo-ethyl)-4-hydroxy-1-piperidyl]-3-(trifluoromethyl)anilino]propanoic acid

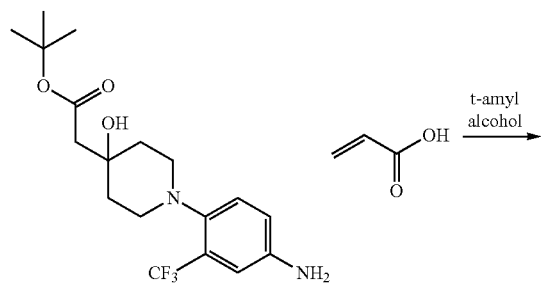

1288

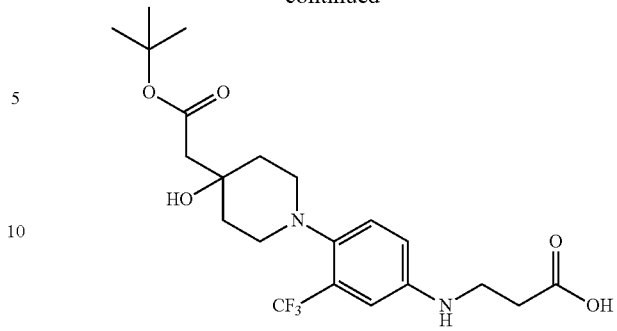

A mixture of tert-butyl 2-[1-[4-amino-2-(trifluoromethyl)phenyl]-4-hydroxy-4-piperidyl]acetate (13.8 g, 36.86 mmol) in t-amyl alcohol (140 mL) was added acrylic acid (6.64 g, 92.15 mmol, 6.32 mL). The mixture was stirred at 120° C. for 16 h. The reaction mixture was concentrated under reduced pressure. The residue was purified by column chromatography on silica gel (75:25 petroleum ether:ethyl acetate). 3-[4-[4-(2-tert-butoxy-2-oxo-ethyl)-4-hydroxy-1-piperidyl]-3-(trifluoromethyl)anilino]propanoic acid (12.6 g, 27.94 mmol, 75.80% yield) was obtained as an off-white solid. LC-MS (ESI+) m/z=447.1, $^1$H NMR (400 MHz, DMSO-d6) δ=12.64-11.87 (m, 1H), 7.40-7.18 (m, 1H), 6.77 (d, J=2.4 Hz, 2H), 5.91 (s, 1H), 4.47 (s, 1H), 3.23 (t, J=6.4 Hz, 2H), 2.93 (t, J=10.2 Hz, 2H), 2.59-2.52 (m, 2H), 2.49-2.44 (m, 2H), 2.34 (s, 2H), 1.81-1.71 (m, 2H), 1.59 (d, J=12.8 Hz, 2H), 1.41 (s, 9H).

Step 4: 2-[1-[4-(2,4-dioxohexahydropyrimidin-1-yl)-2-(trifluoromethyl)phenyl]-4-hydroxy-4-piperidyl]acetic acid hydrochloride

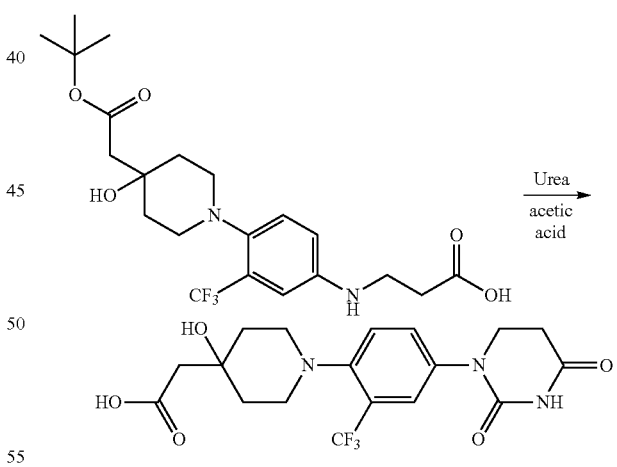

To a solution of 3-[4-[4-(2-tert-butoxy-2-oxo-ethyl)-4-hydroxy-1-piperidyl]-3-(trifluoromethyl)anilino]propanoic acid (1 g, 2.24 mmol) in acetic acid (10 mL) was added urea (444 mg, 7.39 mmol, 331.34 uL). The mixture was stirred at 120° C. for 12 h. The reaction mixture was concentrated under reduced pressure. The residue was purified by reverse phase chromatography (0.1% HCl in water/acetonitrile). The desired fraction was collected and concentrate under reduced pressure to afford 2-[1-[4-(2,4-dioxohexahydropyrimidin-1-yl)-2-(trifluoromethyl)phenyl]-4-hydroxy-4-piperidyl]acetic acid hydrochloride (510.79 mg, 1.12 mmol, 49.97% yield) was obtained as a white solid. LCMS m/z 416.1 (M+H), $^1$H NMR (400 MHz, DMSO-d6) δ=10.43 (s, 1H), 7.66-7.52 (m, 3H), 3.80 (t, J=6.8 Hz, 2H), 3.03 (t, J=10.0 Hz, 2H), 2.79-2.64 (m, 4H), 2.41 (s, 2H), 1.83-1.74 (m, 2H), 1.73-1.65 (m, 2H).

Step 5: 2-(6,7-dihydro-5H-pyrrolo[1,2-c]imidazol-1-yl)-2-[6-[4-[2-[2-[1-[4-(2,4-dioxohexahydropyrimidin-1-yl)-2-(trifluoromethyl)phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide

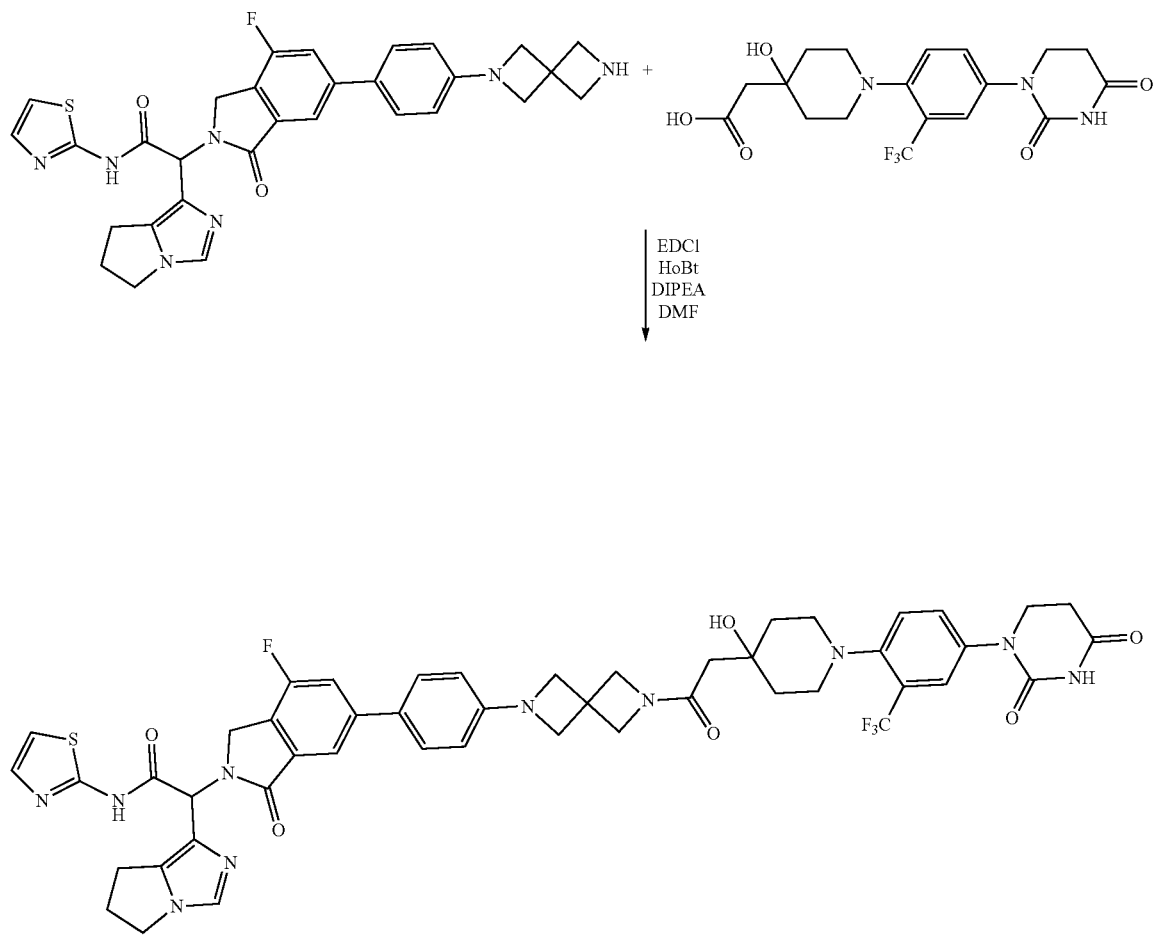

To a solution of 2-[1-[4-(2,4-dioxohexahydropyrimidin-1-yl)-2-(trifluoromethyl)phenyl]-4-hydroxy-4-piperidyl]acetic acid hydrochloride (300 mg, 663.98 μmol) in N,N-dimethylformamide (4 mL) were added N,N-diisopropylethylamine (601 mg, 4.65 mmol, 809.97 uL), N1-((ethylimino)methylene)-N3,N3-dimethylpropane-1,3-diamine hydrochloride (140 mg, 730.30 μmol) and HOBt (100 mg, 740.07 μmol) at 0° C. The mixture was stirred at 0° C. for 20 min. 2-[6-[4-[2-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (364 mg, 532.42 μmol) was added to the mixture and the mixture was stirred at 25° C. for 12 h. The reaction mixture was filtered. The filtrate was purified by preparative HPLC (Column: Phenomenex luna C18 150*40 mm*15 m; 10% to 50% acetonitrile in water (+0.225% formic acid), 10 min). The desired fraction was collected and lyophilized. The solid was purified by preparative HPLC (Column: Phenomenex Gemini-NX C18 75*30 mm*3 m; mobile phase: 28%-58% acetonitrile in water, 8 min). The desired fraction was collected and lyophilized to afford Compound 168 (97.56 mg, 99.88 μmol, 15.04% yield) was obtained as a white solid. LCMS (ESI+): 967.6 [M+H]$^+$, $^1$H NMR (400 MHz, DMSO-d6) δ=12.78-12.19 (m, 1H), 10.43 (s, 1H), 7.74 (s, 1H), 7.70 (d, J=10.8 Hz, 1H), 7.65 (s, 1H), 7.62 (d, J=1.6 Hz, 2H), 7.60 (s, 1H), 7.57 (s, 2H), 7.48 (d, J=3.6 Hz, 1H), 7.24 (d, J=3.6 Hz, 1H), 6.54 (d, J=8.4 Hz, 2H), 6.14 (s, 1H), 4.88 (s, 1H), 4.80 (d, J=17.6 Hz, 1H), 4.39 (s, 2H), 4.21 (d, J=17.6 Hz, 1H), 4.08 (s, 2H), 4.05-3.91 (m, 6H), 3.81 (t, J=6.8 Hz, 2H), 3.03 (t, J=9.8 Hz, 2H), 2.81-2.67 (m, 5H), 2.54 (s, 2H), 2.48-2.43 (m, 1H), 2.26 (s, 2H), 1.79-1.70 (m, 2H), 1.70-1.60 (m, 2H).

Example 169

2-[6-[4-[2-[2-[1-[2,6-dichloro-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, Compound 169

Step 1: tert-butyl 2-[1-(2-chloro-6-fluoro-4-nitrophenyl)-4-hydroxy-4-piperidyl]acetate

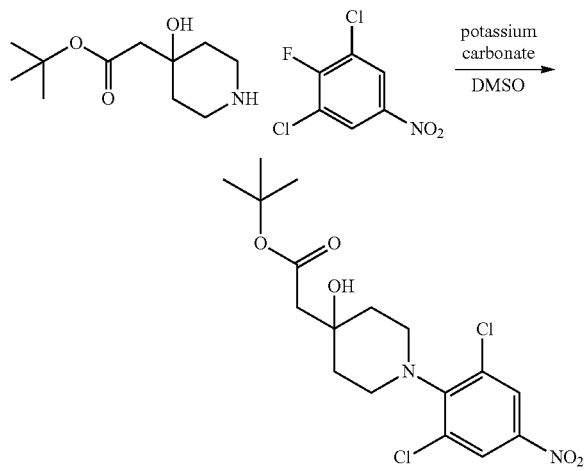

To a solution of 1,3-dichloro-2-fluoro-5-nitro-benzene (7.80 g, 37.16 mmol) and 1,3-dichloro-2-fluoro-5-nitro-benzene (7.80 g, 37.16 mmol) in DMSO (200 mL) was added potassium carbonate (15.41 g, 111.48 mmol, 6.73 mL). The mixture was stirred at 110° C. for 1 h. The reaction mixture was cooled to 20° C. and filtered. The filtrate was quenched with water (200 mL). The precipitated solid was filtered under suction. The solid was dried under vacuum to afford tert-butyl 2-[1-(2-chloro-6-fluoro-4-nitro-phenyl)-4-hydroxy-4-piperidyl]acetate (14 g, 36.01 mmol, 96.90% yield) was obtained as a yellow solid.

Step 2: tert-butyl 2-(1-(4-amino-2,6-dichlorophenyl)-4-hydroxypiperidin-4-yl)acetate

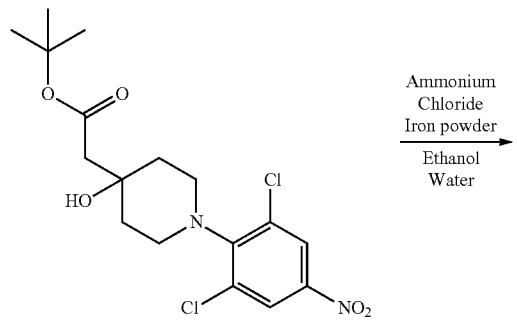

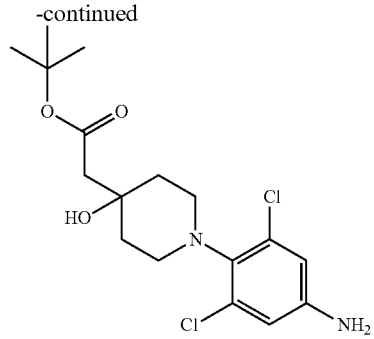

To a solution of $C_{17}H_{22}Cl_2N_2O_5$ (14 g, 34.54 mmol) in Water (40 mL) was added ammonium Chloride (9.24 g, 172.72 mmol, 6.04 mL) and Iron powder (11.58 g, 207.27 mmol, 1.47 mL). The mixture was stirred at 90° C. for 2 h. The reaction mixture was filtered, and the mother liquor was concentrated under reduced pressure to remove solvent. The residue was diluted with solvent (100 mL) and extracted with ethyl acetate (100 mL×2). The combined organic layers were washed with brine (50 mL), dried over sodium sulfate, filtered, and concentrated under reduced pressure. The residue was purified by flash silica gel chromatography (0 to 30% Ethyl acetate in petroleum ether) to afford tert-butyl 2-(1-(4-amino-2,6-dichlorophenyl)-4-hydroxypiperidin-4-yl)acetate (8 g, 21.32 mmol, 61.71% yield) was obtained as an orange oil. LCMS (ESI+) m/z: 375.0/377.0 (M+H, Cl pattern)

Step 3: 3-[4-[4-(2-tert-butoxy-2-oxo-ethyl)-4-hydroxy-1-piperidyl]-3,5-dichloro-anilino]propanoic acid

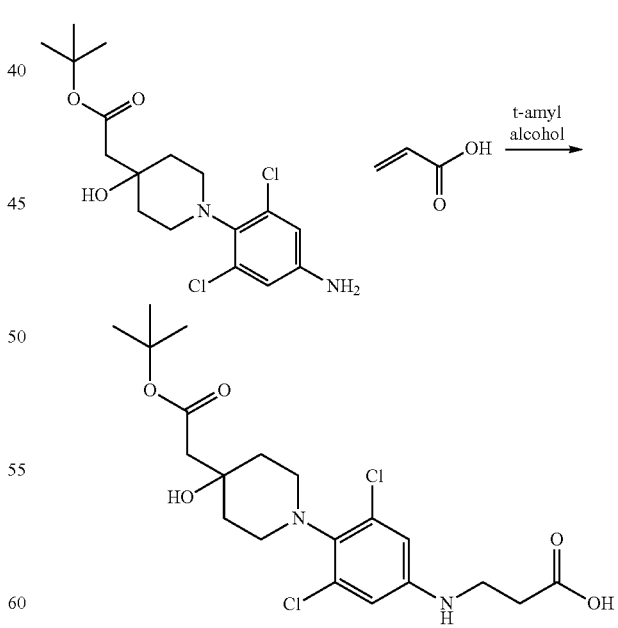

To a solution of tert-butyl 2-[1-(4-amino-2,6-dichlorophenyl)-4-hydroxy-4-piperidyl]acetate (2 g, 5.33 mmol) in t-amyl alcohol (20 mL) was added acrylic acid (576.06 mg, 7.99 mmol, 548.63 uL). The mixture was stirred at 100° C. for 12 h. The reaction mixture was concentrated under reduced pressure to remove solvent. The residue was purified by column chromatography (silica gel, dichloromethane/methanol=50/1 to 10/1 gradient) to afford 3-[4-[4-(2-tert-butoxy-2-oxo-ethyl)-4-hydroxy-1-piperidyl]-3,5-dichloro-anilino]propanoic acid (1.7 g, 3.80 mmol, 71.31% yield) as a black oil. LCMS (ESI+): 447.3 (M+H), $^1$H-NMR (400 MHz, CDCl$_3$) δ=6.48 (d, J=2.0 Hz, 1H), 6.40 (d, J=2.0 Hz, 1H), 3.49-3.40 (m, 2H), 3.35-3.25 (m, 2H), 2.77-2.68 (m, 2H), 2.56 (t, J=5.6 Hz, 2H), 2.39 (s, 2H), 1.71-1.62 (m, 4H), 1.41 (s, 9H)

Step 4: 2-[1-[2,6-dichloro-4-(2,4-dioxohexahydropyrimidin-1-yl)phenyl]-4-hydroxy-4-piperidyl]acetic acid

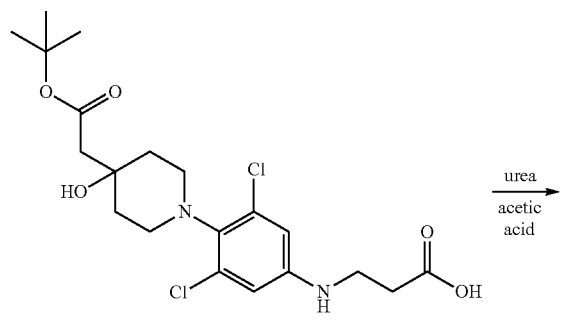

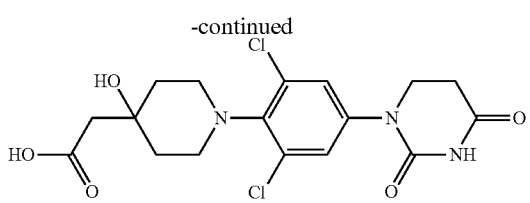

To a solution of 3-[4-[4-(2-tert-butoxy-2-oxo-ethyl)-4-hydroxy-1-piperidyl]-3,5-dichloro-anilino]propanoic acid (1.8 g, 4.02 mmol) in acetic acid (22 mL) was added urea (797.42 mg, 13.28 mmol, 595.09 uL). The mixture was stirred at 120° C. for 12 h. The reaction mixture was concentrated under reduced pressure to remove solvent and the solid was triturated with ethanol (80 mL) for 15 min to afford 2-[1-[2,6-dichloro-4-(2,4-dioxohexahydropyrimidin-1-yl)phenyl]-4-hydroxy-4-piperidyl]acetic acid (850 mg, 1.96 mmol, 48.72% yield) as a yellow solid. LCMS (ESI+): 417.9 (M+H), $^1$H NMR (400 MHz, DMSO-d$_6$) δ=7.45 (s, 1H), 7.39 (s, 1H), 3.77 (t, J=6.8 Hz, 2H), 3.51-3.41 (m, 3H), 2.84-2.76 (m, 2H), 2.69 (t, J=6.8 Hz, 2H), 2.21 (s, 2H), 1.72-1.55 (m, 4H).

Step 5: 2-[6-[4-[2-[2-[1-[2,6-dichloro-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

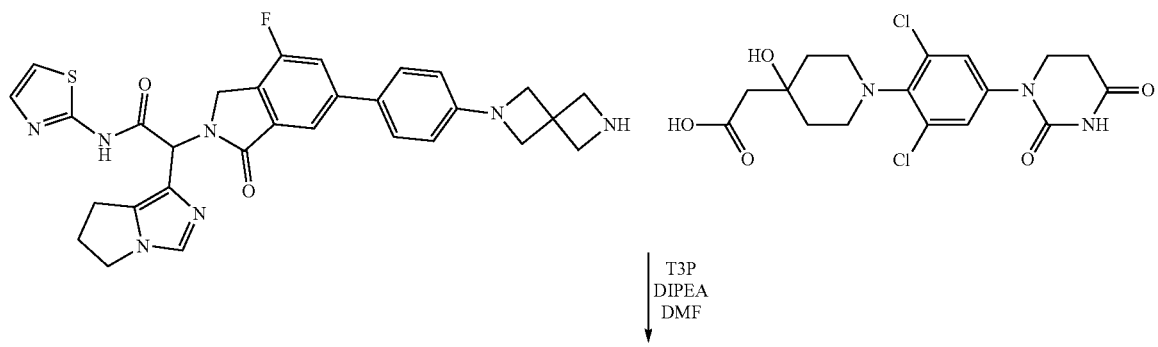

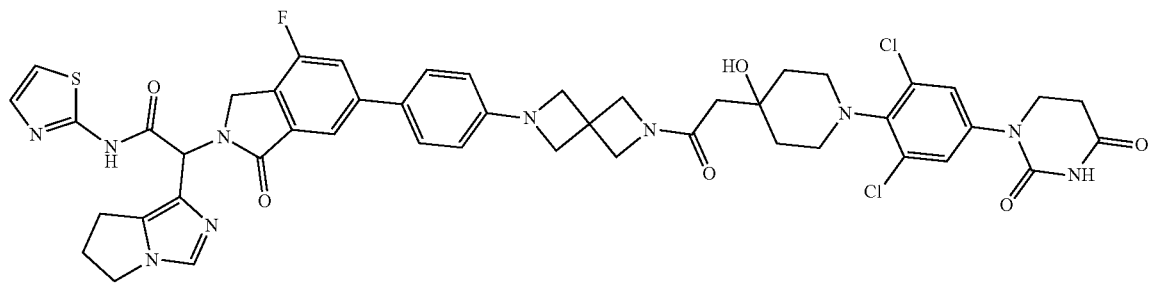

To a solution of 2-[1-[2,6-dichloro-4-(2,4-dioxohexahydropyrimidin-1-yl)phenyl]-4-hydroxy-4-piperidyl]acetic acid (124.04 mg, 298.00 µmol) and propylphosphonic anhydride (50% in ethyl acetate) (284.45 mg, 447.00 µmol) in N,N-dimethylformamide (5 mL) was added N,N-diisopropylethylamine (308.11 mg, 2.38 mmol, 415.24 uL). The mixture was stirred at 0° C. for 20 min. 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (176.61 mg, 298 µmol) was added, and the mixture was stirred at 0° C. for 60 min. Propylphosphonic anhydride (50% in ethyl acetate) (189.64 mg, 298.00 µmol) was added, the mixture was stirred at 0° C. for 60 min. The mixture was poured into water (50 mL) and saturated aqueous sodium bicarbonate solution (30 mL) was added. The solid was collected by filtration under suction. The solid was collected and dissolved in dichloromethane and dried over sodium sulfate, filtered, and concentrated under reduced pressure. The residue was purified by preparative HPLC (Column: Phenomenex luna C18 150*40 mm*15 m; mobile phase: water (0.1% trifluoroacetic acid)-acetonitrile; Gradient Time (min) 10). A saturated solution of sodium bicarbonate (30 mL) was added and the precipitated solid was washed with water (2×10 mL). The solid was dried under high vacuum to afford Compound 169 (60.54 mg, 61.92 µmol, 20.78% yield) as an off-white solid. LCMS (ESI+): 967.3 (M+H), 485.3 (M/2+H); $^1$H NMR (400 MHz, DMSO-$d_6$) δ=12.52 (br, 1H), 10.48 (s, 1H), 7.76-7.68 (m, 2H), 7.65 (d, J=8.8 Hz, 2H), 7.61 (s, 1H), 7.51-7.45 (m, 2H), 7.40 (s, 1H), 7.26 (s, 1H), 6.55 (d, J=8.8 Hz, 2H), 6.15 (s, 1H), 4.88-4.76 (m, 2H), 4.40 (s, 2H), 4.22 (d, J=17.6 Hz, 1H), 4.09 (s, 2H), 4.06-3.93 (m, 6H), 3.78 (t, J=6.8 Hz, 2H), 3.49 (t, J=9.6 Hz, 2H), 2.86-2.75 (m, 3H), 2.69 (t, J=6.8 Hz, 2H), 2.61-2.53 (m, 2H), 2.49-2.43 (m, 1H), 2.25 (s, 2H), 1.83-1.72 (m, 2H), 1.63 (d, J=12.4 Hz, 2H).

Example 170

2-[6-[4-[7-[2-[1-[2-chloro-4-(2,4-dioxohexahydropyrimidin-1-yl)phenyl]-4-hydroxy-4-piperidyl]acetyl]-2,7-diazaspiro[3.5]nonan-2-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, Compound 170

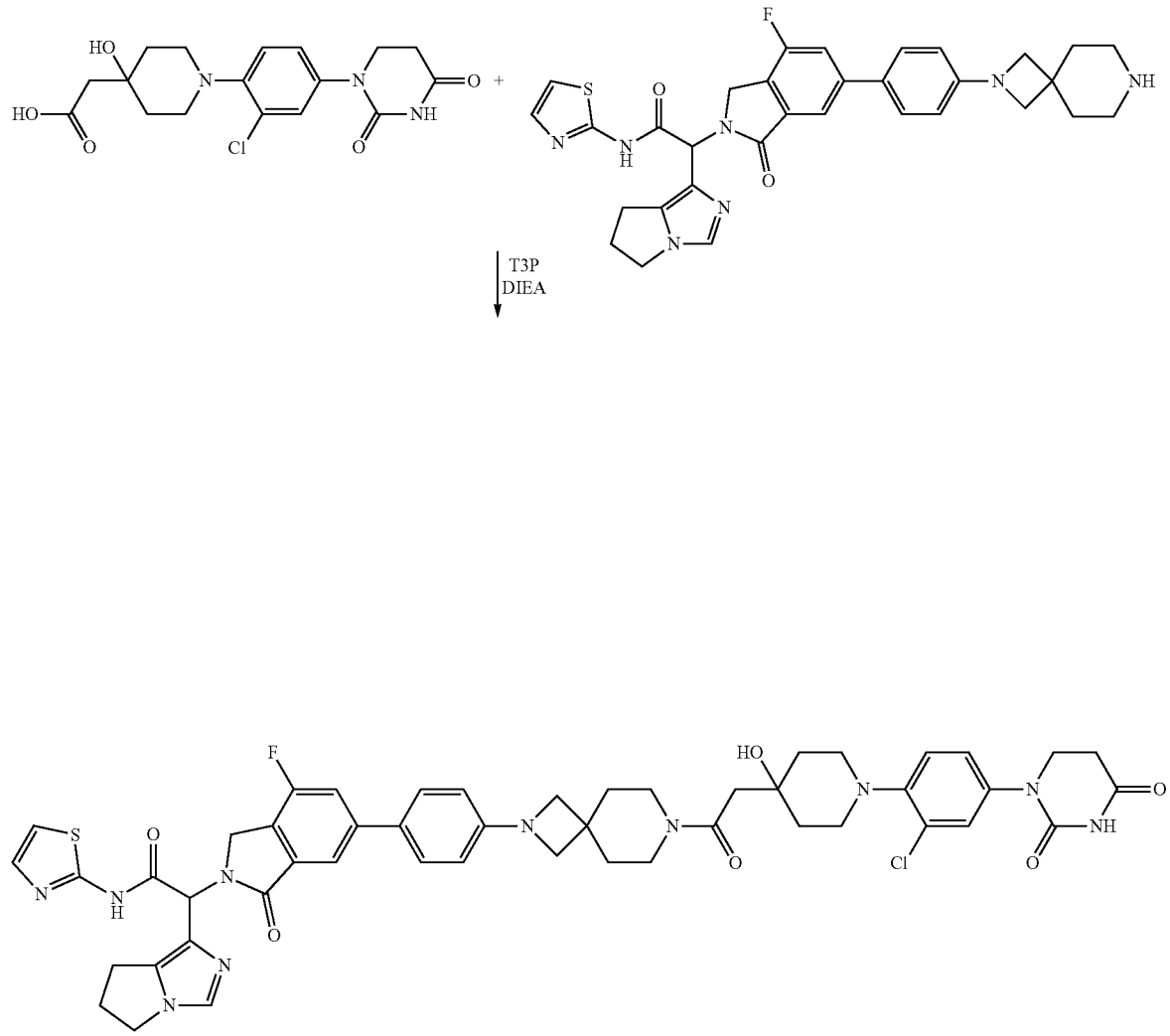

To a solution of 2-[1-[2-chloro-4-(2,4-dioxohexahydropyrimidin-1-yl)phenyl]-4-hydroxy-4-piperidyl]acetic acid, hydrochloride (220 mg, 525.97 μmol) in N,N-dimethylformamide (3 mL) were added N-ethyl-N-isopropylpropan-2-amine (482.30 mg, 3.73 mmol, 650 uL), propylphosphonic anhydride (50% ethyl acetate) (338 mg, 531.14 μmol) at 0° C. The mixture was stirred at 0° C. for 20 min. Then 2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (300 mg, 421.51 μmol) was added to the mixture and the mixture was stirred at 25° C. for 12 h. The reaction mixture was filtered. The filtrate was purified by reversed-phase column (water/acetonitrile). The desired fraction was lyophilized. The compound was purified by preparative HPLC (column: Phenomenex Gemini-NX C18 75*30 mm*3 m; 30% to 60% acetonitrile in water; 8 min). The desired fraction was collected, frozen and lyophilized to afford Compound 170 (78.92 mg, 80.44 μmol, 15.29% yield) was obtained as an off-white solid. LCMS m/z 961.2 [M+H]$^+$, $^1$H NMR (400 MHz, DMSO-d6) δ 12.69-12.35 (m, 1H), 10.37 (s, 1H), 7.73 (s, 1H), 7.69 (d, J=10.8 Hz, 1H), 7.63 (d, J=8.4 Hz, 2H), 7.60 (s, 1H), 7.47 (d, J=3.6 Hz, 1H), 7.41 (d, J=2.4 Hz, 1H), 7.27-7.21 (m, 2H), 7.20-7.15 (m, 1H), 6.52 (d, J=8.4 Hz, 2H), 6.13 (s, 1H), 5.03 (s, 1H), 4.80 (d, J=17.6 Hz, 1H), 4.21 (d, J=17.6 Hz, 1H), 4.06-3.90 (m, 2H), 3.74 (t, J=6.8 Hz, 2H), 3.66 (s, 4H), 3.53 (s, 4H), 3.40-3.37 (m, 1H), 3.07-2.93 (m, 4H), 2.80-2.72 (m, 1H), 2.69 (t, J=6.8 Hz, 2H), 2.57 (s, 3H), 2.46 (d, J=6.0 Hz, 1H), 1.78 (d, J=16.8 Hz, 4H), 1.75-1.64 (m, 4H).

Example 171

2-[6-[4-[2-[2-[1-[2-cyano-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, Compound 171

Step 1: tert-butyl 2-[1-(2-cyano-4-nitro-phenyl)-4-hydroxy-4-piperidyl]acetate

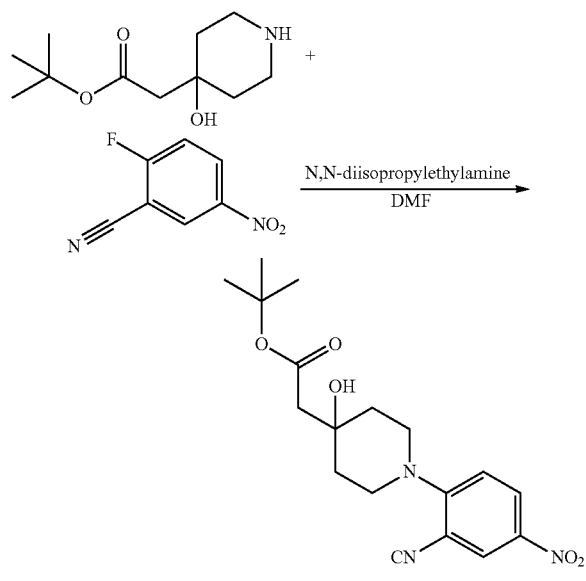

To a solution of tert-butyl 2-(4-hydroxy-4-piperidyl)acetate (10 g, 46.45 mmol) and 2-fluoro-5-nitro-benzonitrile (7.72 g, 46.45 mmol) in N,N-dimethylformamide (50 mL) was added N,N-diisopropylethylamine (10.21 g, 78.96 mmol, 13.75 mL). The mixture was stirred at 80° C. for 12 h. The reaction mixture was diluted with water (100 mL) and extracted with ethyl acetate (3×100 mL). The combined organic layers were washed with brine (1×100 mL), dried over Na$_2$SO$_4$, filtered and concentrated in vacuo. The residue was purified by column chromatography on silica gel (petroleum ether/ethyl acetate=5/1) to afford tert-butyl 2-[1-(2-cyano-4-nitro-phenyl)-4-hydroxy-4-piperidyl]acetate (15.5 g, 40.75 mmol, 87.72% yield) was obtained as a yellow solid. LCMS m/z=306.1 (M+H), $^1$H NMR (400 MHz, CHLOROFORM-d) 6=8.43 (d, J=2.8 Hz, 1H), 8.25 (dd, J=2.8, 9.2 Hz, 1H), 7.00 (d, J=9.2 Hz, 1H), 4.01 (s, 1H), 3.79-3.67 (m, 2H), 3.50 (dt, J=2.8, 12.4 Hz, 2H), 2.46 (s, 2H), 1.94-1.85 (m, 2H), 1.84-1.74 (m, 2H), 1.49 (s, 9H).

Step 2: tert-butyl 2-[1-(4-amino-2-cyano-phenyl)-4-hydroxy-4-piperidyl]acetate

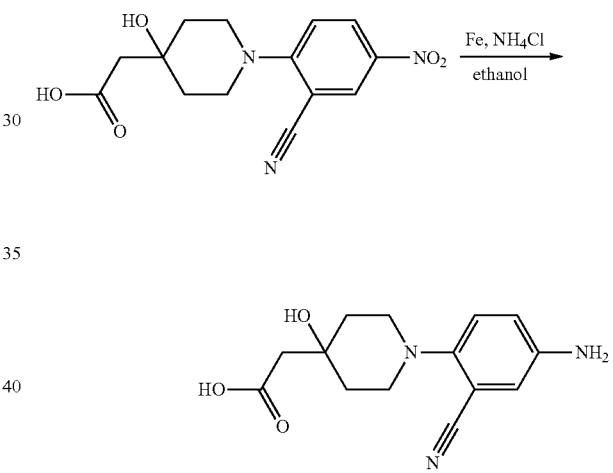

To a solution of tert-butyl 2-[1-(2-cyano-4-nitro-phenyl)-4-hydroxy-4-piperidyl]acetate (14.5 g, 40.12 mmol) in ethanol (145 mL) and water (29 mL) were added Fe (6.73 g, 120.48 mmol, 855.98 uL) and ammonium chloride (6.44 g, 120.36 mmol, 4.21 mL). The mixture was stirred at 90° C. for 3 h. The mixture was filtered through a pad of Celite, the filter cake was washed with ethanol (30 mL). The filtrate was concentrated under reduced pressure. The combined residue was diluted with ethyl acetate (100 mL) and water (100 mL). The layers were separated, and the aqueous layer was extracted with ethyl acetate (2×50 mL). The combined organic layer was washed with brine (2×50 mL), dried over Na$_2$SO$_4$, filtered and concentrated. The product was purified by flash silica gel chromatography (120 g Flash Column, Eluent mixture: 0 to 60% ethyl acetate in petroleum ether; 100 mL/min) to afford tert-butyl 2-[1-(4-amino-2-cyano-phenyl)-4-hydroxy-4-piperidyl]acetate (10.28 g, 30.71 mmol, 76.54% yield) was obtained as a yellow solid. LCMS (ESI): m/z 332.1 [M+H]$^+$, $^1$H NMR (400 MHz, DMSO-d6) δ=6.98-6.91 (m, 1H), 6.84-6.76 (m, 1H), 5.14 (s, 2H), 4.49 (s, 1H), 3.02-2.84 (m, 4H), 2.35 (s, 2H), 1.86-1.75 (m, 2H), 1.72-1.61 (m, 2H), 1.41 (s, 9H).

1299

Step 3: 3-[4-[4-(2-tert-butoxy-2-oxo-ethyl)-4-hydroxy-1-piperidyl]-3-cyano-anilino]propanoic acid

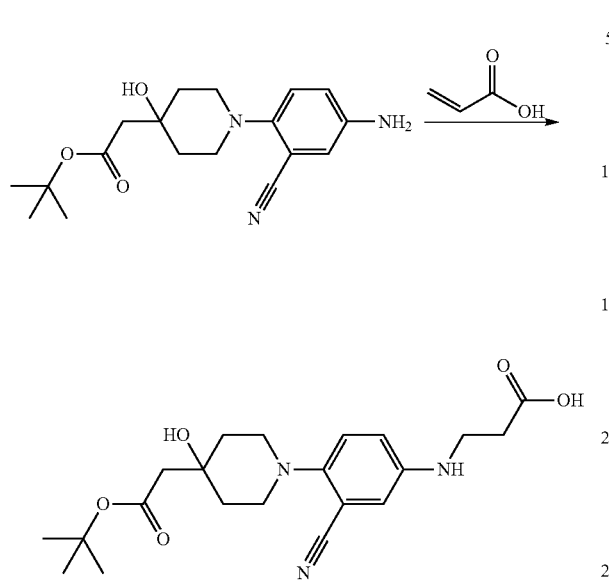

To a solution of tert-butyl 2-[1-(4-amino-2-cyano-phenyl)-4-hydroxy-4-piperidyl]acetate (9.28 g, 28.00 mmol) in t-amyl alcohol (100 mL) was added acrylic acid (6.05 g, 84.01 mmol, 5.77 mL). The mixture was stirred at 120° C. for 16 h. acrylic acid (2.02 g, 28.00 mmol, 1.92 mL) was added to the mixture. The mixture was stirred at 120° C. for another 24 h. The mixture was concentrated under reduced pressure. The product was purified by silica gel chromatography (120 g Column; Eluent: 0~60% PE/ethyl acetate gradient; 100 mL/min) to give 3-[4-[4-(2-tert-butoxy-2-oxo-ethyl)-4-hydroxy-1-piperidyl]-3-cyano-anilino]propanoic acid (8.8 g, 21.16 mmol, 75.55% yield) as a brown solid. LCMS (ESI): m/z 404.2 [M+H]$^+$, $^1$H NMR (400 MHz, DMSO-d$_6$) δ=12.22 (s, 1H), 7.01 (d, J=8.8 Hz, 1H), 6.87-6.76 (m, 2H), 5.73 (s, 1H), 4.50 (s, 1H), 3.22 (t, J=6.4 Hz, 2H), 3.02-2.85 (m, 4H), 2.46 (t, J=6.8 Hz, 2H), 2.36 (s, 2H), 1.86-1.76 (m, 2H), 1.67 (d, J=12.8 Hz, 2H), 1.42 (s, 9H).

1300

Step 4: 2-[1-[2-cyano-4-(2,4-dioxohexahydropyrimidin-1-yl)phenyl]-4-hydroxy-4-piperidyl]acetic acid hydrochloride

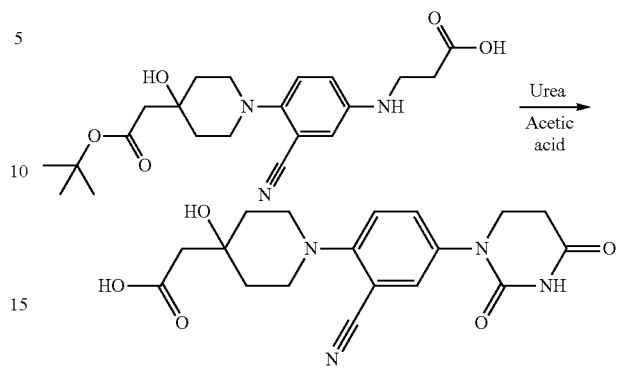

A mixture of 3-[4-[4-(2-tert-butoxy-2-oxo-ethyl)-4-hydroxy-1-piperidyl]-3-cyano-anilino]propanoic acid (7.8 g, 19.33 mmol) and urea (3.83 g, 63.80 mmol, 2.86 mL) in AcOH (70 mL) was stirred at 120° C. for 16 h. The mixture was concentrated under reduced pressure. The residue was purified by reversed phase column (HCl condition) followed by trituration with ethanol (50 mL) at 25° C. for 16 h. The mixture was filtered and the filter cake was washed with ethanol (15 mL). The filter cake was dried in vacuo to afford 2-[1-[2-cyano-4-(2,4-dioxohexahydropyrimidin-1-yl)phenyl]-4-hydroxy-4-piperidyl]acetic acid hydrochloride (4.88 g, 11.82 mmol, 61.13% yield) was obtained as a brown solid. LCMS (ESI+): m/z 373.1 [M+H]$^+$, $^1$H NMR (400 MHz, DMSO-d$_6$) δ=12.07 (s, 1H), 10.51-10.35 (m, 1H), 7.66 (d, J=2.4 Hz, 1H), 7.53 (dd, J=2.4, 8.8 Hz, 1H), 7.18 (d, J=8.8 Hz, 1H), 3.75 (t, J=6.8 Hz, 2H), 3.24 (d, J=11.6 Hz, 2H), 3.18-3.07 (m, 2H), 2.69 (t, J=6.8 Hz, 2H), 2.42 (s, 2H), 1.89-1.80 (m, 2H), 1.78-1.69 (m, 2H).

Step 5: 2-[6-[4-[2-[2-[1-[2-cyano-4-(2,4-dioxohexahydropyrimidin-1-yl)phenyl]-4-hydroxy-4-piperidyl]acetyl]-2,6-diazaspiro[3.3]heptan-6-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

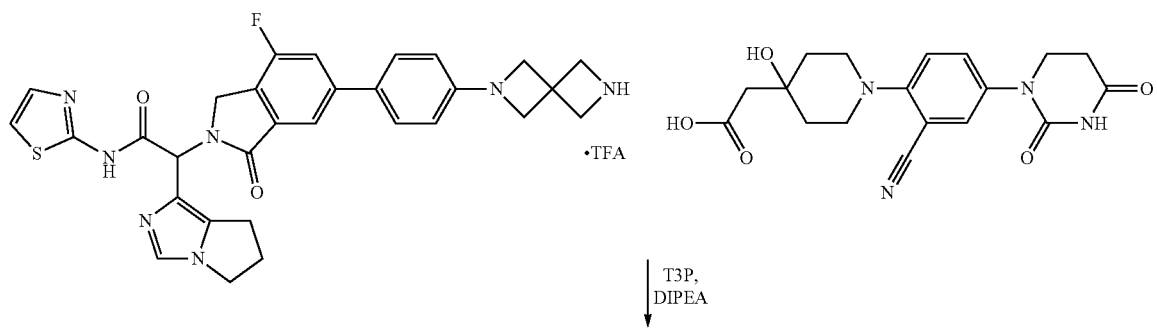

1301

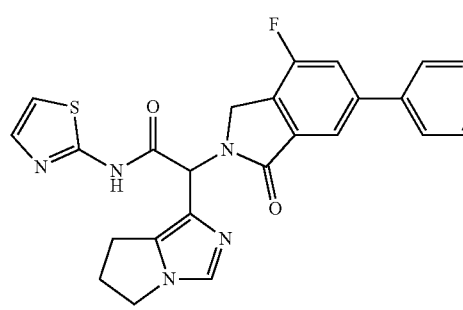

1302

-continued

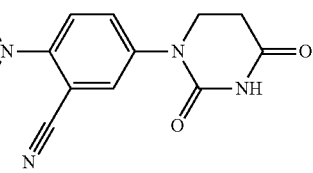

To a solution of 2-[1-[2-cyano-4-(2,4-dioxohexahydropyrimidin-1-yl)phenyl]-4-hydroxy-4-piperidyl]acetic acid hydrochloride (300 mg, 733.79 μmol) in N,N-dimethylformamide (4 mL) were added N,N-diisopropylethylamine (667.80 mg, 5.17 mmol, 900 uL) and propylphosphonic anhydride, 50% in ethyl acetate (480.00 mg, 754.29 μmol) at 0° C. The mixture was stirred at 0° C. for 0.5 h. Then 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (400 mg, 585.07 μmol) was added to the mixture. The resulting mixture was stirred at 25° C. for 16 h. The mixture was filtered. The filtrate was purified by preparative HPLC (flow: 60 mL/min; gradient: 20-50% acetonitrile in water (0.225% formic acid) over 10 min; column: Phenomenex luna C18 250×50 mm×15 μm) and lyophilized to give Compound 171 (41.66 mg, 42.52 μmol, 5.79% yield) as a white solid. LCMS m/z: 924.4 (M+H), $^1$H NMR (400 MHz, DMSO-d$_6$) δ=12.54 (s, 1H), 10.43 (s, 1H), 8.43 (s, 1H), 7.74 (s, 1H), 7.70 (d, J=10.8 Hz, 1H), 7.67 (d, J=2.4 Hz, 1H), 7.64 (d, J=8.8 Hz, 2H), 7.60 (s, 1H), 7.53 (dd, J=2.4, 8.8 Hz, 1H), 7.48 (d, J=3.6 Hz, 1H), 7.24 (d, J=3.6 Hz, 1H), 7.19 (d, J=8.8 Hz, 1H), 6.54 (d, J=8.8 Hz, 2H), 6.14 (s, 1H), 4.90 (s, 1H), 4.80 (d, J=18.0 Hz, 1H), 4.39 (s, 2H), 4.21 (d, J=17.6 Hz, 1H), 4.09 (s, 2H), 4.05-3.94 (m, 6H), 3.75 (t, J=6.8 Hz, 2H), 3.24 (d, J=12.0 Hz, 2H), 3.16-3.09 (m, 2H), 2.79-2.66 (m, 3H), 2.56 (d, J=0.8 Hz, 1H), 2.47-2.44 (m, 2H), 2.26 (s, 2H), 1.87-1.77 (m, 2H), 1.70 (d, J=12.0 Hz, 2H).

Example 172

2-[6-[4-[2-[2-[1-[2-chloro-4-(2,4-dioxohexahydropyrimidin-1-yl)phenyl]-4-hydroxy-4-piperidyl]acetyl]-2,7-diazaspiro[3.5]nonan-7-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide, Compound 172

Step 1: tert-butyl 2-[1-(2-chloro-4-nitro-phenyl)-4-hydroxy-4-piperidyl]acetate

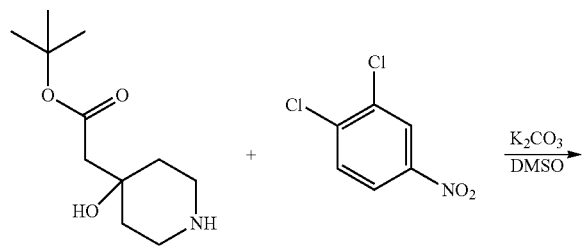

To a solution of 1,2-dichloro-4-nitro-benzene (10 g, 52.08 mmol) and 1,2-dichloro-4-nitro-benzene (10 g, 52.08 mmol) in dimethyl sulfoxide (100 mL) was added potassium carbonate (21.6 g, 156.25 mmol). The mixture was stirred at 110° C. for 1 h. The reaction was cooled to 20° C. and poured into water (500 mL). The mixture was extracted with ethyl acetate (3×200 mL). The combined organic phases were washed with brine (2×200 mL), dried with anhydrous sodium sulfate, filtered, and concentrated in vacuum to afford tert-butyl 2-[1-(2-chloro-4-nitro-phenyl)-4-hydroxy-4-piperidyl]acetate (18 g, 42.72 mmol, 82.01% yield). $^1$H NMR (400 MHz, DMSO-d$_6$) δ=8.20 (d, J=2.8 Hz, 1H), 8.12 (dd, J=2.8, 8.8 Hz, 1H), 7.29 (d, J=8.8 Hz, 1H), 4.65 (s, 1H), 3.29 (br d, J=8.8 Hz, 2H), 3.17-3.09 (m, 2H), 2.39 (s, 2H), 1.87-1.78 (m, 2H), 1.75-1.68 (m, 2H), 1.41 (s, 9H)

Step 2: tert-butyl 2-[1-(4-amino-2-chloro-phenyl)-4-hydroxy-4-piperidyl]acetate

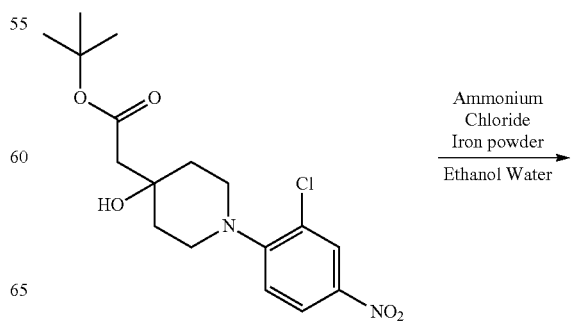

-continued

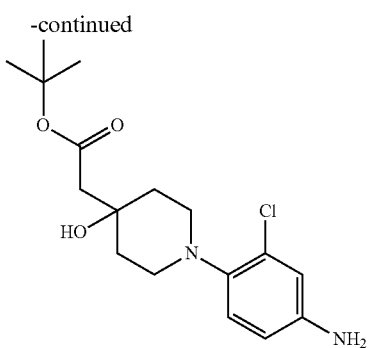

A mixture of tert-butyl 2-[1-(2-chloro-4-nitro-phenyl)-4-hydroxy-4-piperidyl]acetate (18 g, 48.54 mmol) and ethanol (400 mL), Water (80 mL) added ammonium chloride (7.79 g, 145.62 mmol, 5.09 mL). The reaction mixture was stirred at 90° C. for 16 h. The reaction mixture was concentrated to remove solvent, the mixture was poured into water (400 mL). The mixture was extracted with ethyl acetate (200 mL×3). the combined organic phase was washed with brine (200 mL×2), dried with anhydrous sodium sulfate, filtered, and concentrated in vacuum to give tert-butyl 2-[1-(4-amino-2-chloro-phenyl)-4-hydroxy-4-piperidyl]acetate. $^1$H NMR (400 MHz, DMSO-d$_6$) δ=6.88 (d, J=8.8 Hz, 1H), 6.61 (d, J=2.4 Hz, 1H), 6.46 (dd, J=2.4, 8.4 Hz, 1H), 4.97 (s, 2H), 4.42 (s, 1H), 2.89-2.80 (m, 2H), 2.79-2.72 (m, 2H), 2.34 (s, 2H), 1.81-1.72 (m, 2H), 1.68-1.60 (m, 2H), 1.41 (s, 9H)

Step 3: 3-[4-[4-(2-tert-butoxy-2-oxo-ethyl)-4-hydroxy-1-piperidyl]-3-chloro-anilino]propanoic acid

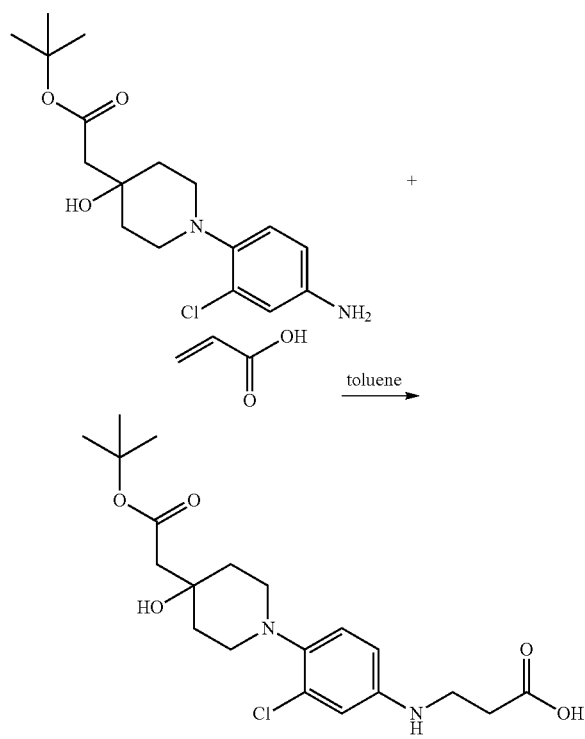

To a solution of tert-butyl 2-[1-(4-amino-2-chloro-phenyl)-4-hydroxy-4-piperidyl]acetate (13 g, 38.14 mmol) in toluene (91 mL) was added acrylic acid (3.30 g, 45.77 mmol, 3.14 mL). The mixture was stirred at 100° C. for 16 h. The mixture was concentrated under reduced pressure. The product was purified by reverse phase chromatography (C18 column, with formic acid as a phase modifier) to afford 3-[4-[4-(2-tert-butoxy-2-oxo-ethyl)-4-hydroxy-1-piperidyl]-3-chloro-anilino]propanoic acid (9.9 g, 22.54 mmol, 59.09% yield) was obtained as a brown solid. LCMS (ESI+): 413.2 (M+H)$^+$, $^1$H NMR (400 MHz, DMSO-d$_6$) δ=12.23 (s, 1H), 6.95 (d, J=8.4 Hz, 1H), 6.61 (d, J=2.4 Hz, 1H), 6.49 (dd, J=2.4, 8.8 Hz, 1H), 4.44 (s, 1H), 3.19 (t, J=6.8 Hz, 2H), 2.90-2.81 (m, 2H), 2.81-2.72 (m, 2H), 2.45 (t, J=6.8 Hz, 2H), 2.34 (s, 2H), 1.99 (s, 1H), 1.83-1.71 (m, 2H), 1.69-1.58 (m, 2H), 1.41 (s, 9H).

Step 4: 2-[1-[2-chloro-4-(2,4-dioxohexahydropyrimidin-1-yl)phenyl]-4-hydroxy-4-piperidyl]acetic acid hydrochloride

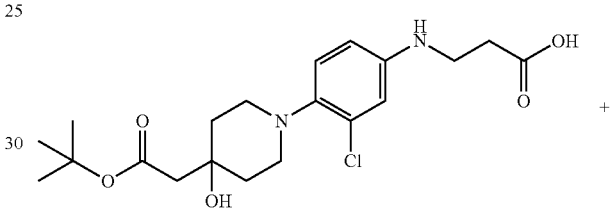

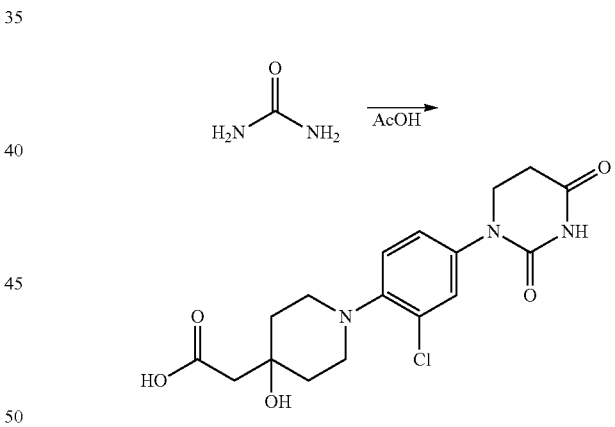

To a solution of 3-[4-[4-(2-tert-butoxy-2-oxo-ethyl)-4-hydroxy-1-piperidyl]-3-chloro-anilino]propanoic acid (9.9 g, 23.98 mmol) in acetic acid (100 mL) was added urea (4.75 g, 79.12 mmol, 3.55 mL). The mixture was stirred at 120° C. for 16 h. The reaction mixture was concentrated under reduced pressure. The solid was triturated with ethanol (40 mL) at 25° C. for 16 h. The solid was dried in vacuo to afford 2-[1-[2-chloro-4-(2,4-dioxohexahydropyrimidin-1-yl)phenyl]-4-hydroxy-4-piperidyl]acetic acid hydrochloride (3.87 g, 9.07 mmol, 37.82% yield) was obtained as an off-white solid. LCMS (ESI): m/z 382.1 [M+H]$^+$, $^1$H NMR (400 MHz, DMSO-d6) δ=10.39 (s, 1H), 7.41 (d, J=2.4 Hz, 1H), 7.27-7.17 (m, 2H), 3.74 (t, J=6.8 Hz, 2H), 3.00 (d, J=6.0 Hz, 4H), 2.68 (t, J=6.8 Hz, 2H), 2.41 (s, 2H), 1.91-1.79 (m, 2H), 1.77-1.65 (m, 2H).

Step 5: 2-[6-[4-[2-[2-[1-[2-chloro-4-(2,4-dioxohexa-hydropyrimidin-1-yl)phenyl]-4-hydroxy-4-piperidyl]acetyl]-2,7-diazaspiro[3.5]nonan-7-yl]phenyl]-4-fluoro-1-oxo-isoindolin-2-yl]-2-(6,7-dihydro-5H-pyrrolo[1,2-c]imidazol-1-yl)-N-thiazol-2-yl-acetamide

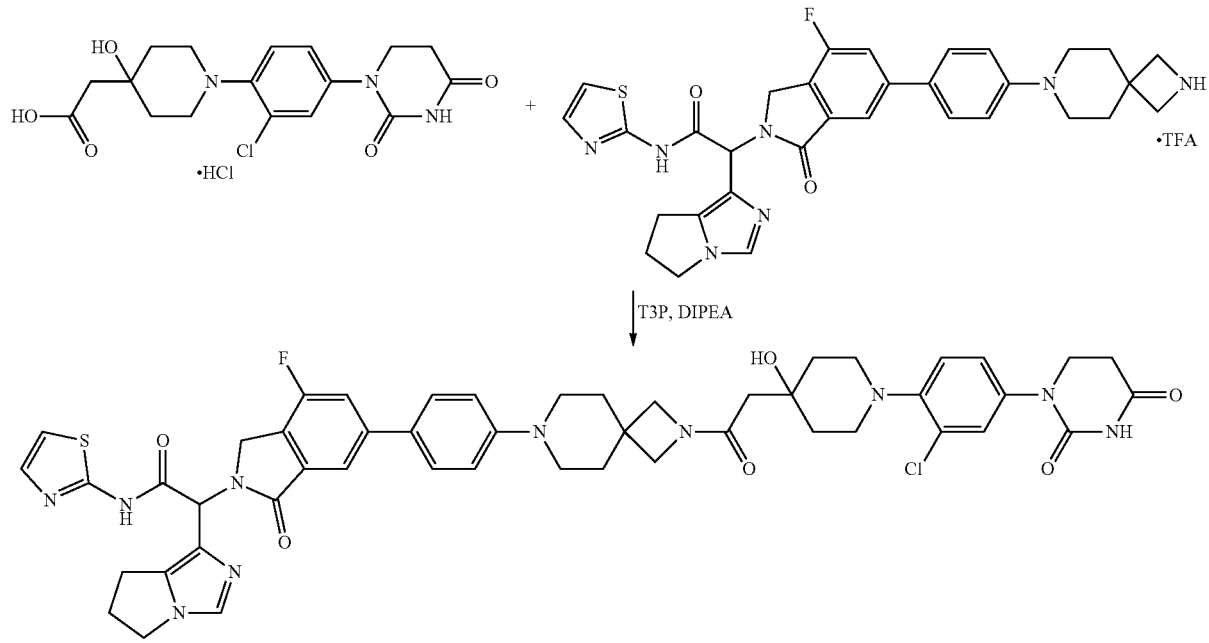 [SMILES: O=C(O)CC1(O)CCN(c2ccc(N3CCC(=O)NC3=O)cc2Cl)CC1 ; Cl ; O=C(Nc1nccs1)C(c1ncn2c1CCC2)N1Cc2c(F)cc(-c3ccc(N4CCC5(CC4)CNC5)cc3)cc2C1=O ; O=C1CCN(c2ccc(N3CCC(O)(CC(=O)N4CC5(CCN(c6ccc(-c7cc(F)c8c(c7)C(=O)N(C(C(=O)Nc7nccs7)c7ncn9c7CCC9)C8)cc6)CC5)C4)CC3)c(Cl)c2)C(=O)N1 ; "·TFA"]

To a solution of 2-[1-[2-chloro-4-(2,4-dioxohexahydro-pyrimidin-1-yl)phenyl]-4-hydroxy-4-piperidyl]acetic acid hydrochloride (200 mg, 478.16 μmol) in N,N-dimethylformamide (4 mL) were added N-ethyl-N-isopropylpropan-2-amine (430.36 mg, 3.33 mmol, 580 uL) and propylphosphonic anhydride (50% in ethyl acetate) (302 mg, 474.57 μmol). The mixture was stirred at 0° C. for 0.5 h. Then 2-[6-[4-(2,7-diazaspiro[3.5]nonan-7-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (270 mg, 379.36 μmol) was added to the mixture. The resulting mixture was stirred at 25° C. for 16 h. The mixture was filtered. The filtrate was purified by reversed phase column (flow: 40 mL/min; gradient: from 5-54% acetonitrile in water over 31 min; column: I.D. 31 mm×H140 mm, Welch Ultimate Xb C18 20-40 μm; 120 Å). The desired fraction was lyophilized to afford Compound 172 (76.22 mg, 78.48 μmol, 16.55% yield) was obtained as a light yellow solid. LCMS (ESI+): m/z 961.3 [M+H]+, $^1$H NMR (400 MHz, DMSO-d6) δ=12.52 (s, 1H), 10.38 (s, 1H), 7.76 (s, 1H), 7.73 (d, J=10.8 Hz, 1H), 7.65 (d, J=8.8 Hz, 2H), 7.60 (s, 1H), 7.48 (d, J=3.6 Hz, 1H), 7.41 (d, J=2.4 Hz, 1H), 7.24 (dd, J=2.8, 11.2 Hz, 2H), 7.20-7.15 (m, 1H), 7.05 (d, J=8.8 Hz, 2H), 6.14 (s, 1H), 4.87 (s, 1H), 4.80 (d, J=18.0 Hz, 1H), 4.21 (d, J=17.6 Hz, 1H), 4.05-3.91 (m, 4H), 3.74 (t, J=6.4 Hz, 2H), 3.63 (s, 2H), 3.28-3.19 (m, 4H), 2.98 (d, J=6.0 Hz, 4H), 2.77-2.66 (m, 3H), 2.54 (s, 1H), 2.46-2.41 (m, 2H), 2.27 (s, 2H), 1.85-1.74 (m, 6H), 1.71-1.65 (m, 2H).

Example 173

2-(6,7-dihydro-5H-pyrrolo[1,2-c]imidazol-1-yl)-2-[6-[4-[2-[2-[1-[4-[[2,6-dioxo-3-piperidyl]amino]-2-fluoro-5-methoxy-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1, Compound 173

Step 1: 1,2-difluoro-4-methoxy-5-nitro-benzene

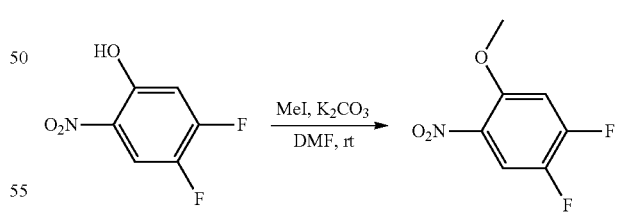

To a solution of 4,5-difluoro-2-nitro-phenol (500 mg, 2.86 mmol) in N,N-dimethylformamide (5 mL) were added potassium carbonate (1.18 g, 8.57 mmol, 517.04 μL) and iodomethane (1.22 g, 8.57 mmol, 533.33 μL). The mixture was stirred at 25° C. for 3 h. Ethyl acetate (20 mL) and water (20 mL) were added to the reaction mixture and layers were separated. The organic phase was washed with water (3×20 mL) followed by brine (3×20 mL), dried over anhydrous sodium sulfate, filtered and concentrated under reduced pressure to give 1,2-difluoro-4-methoxy-5-nitro-benzene (550 mg, 2.91 mmol) as a yellow solid. $^1$H NMR (400 MHz, DMSO-$d_6$) δ=8.23 (dd, J=8.4, 10.0 Hz, 1H), 7.62 (dd, J=6.8, 12.4 Hz, 1H), 3.93 (s, 3H).

Step 2: tert-butyl 2-[1-(2-fluoro-5-methoxy-4-nitro-phenyl)-4-hydroxy-4-piperidyl]acetate

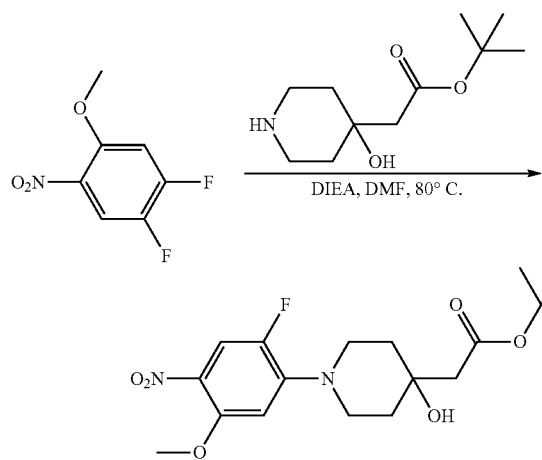

To a solution of 1,2-difluoro-4-methoxy-5-nitro-benzene (550 mg, 2.91 mmol) in N,N-dimethylformamide (5 mL) were added tert-butyl 2-(4-hydroxy-4-piperidyl)acetate (626 mg, 2.91 mmol) and N-ethyl-N-isopropylpropan-2-amine (645.54 mg, 4.99 mmol, 0.87 mL). The mixture was stirred at 80° C. for 12 h. After being cooled to 25° C., ethyl acetate (20 mL) and water (20 mL) were added to the reaction mixture and layers were separated. The organic phase was washed with water (3×20 mL) followed by brine (3×20 mL), dried over anhydrous sodium sulfate, filtered and concentrated under reduced pressure to give tert-butyl 2-[1-(2-fluoro-5-methoxy-4-nitro-phenyl)-4-hydroxy-4-piperidyl]acetate (1 g, 2.47 mmol, 85% yield) as a yellow solid. LCMS (ESI): m/z 385.1 [M+H]$^+$ Step 3: tert-butyl 2-[1-(4-amino-2-fluoro-5-methoxy-phenyl)-4-hydroxy-4-piperidyl]acetate

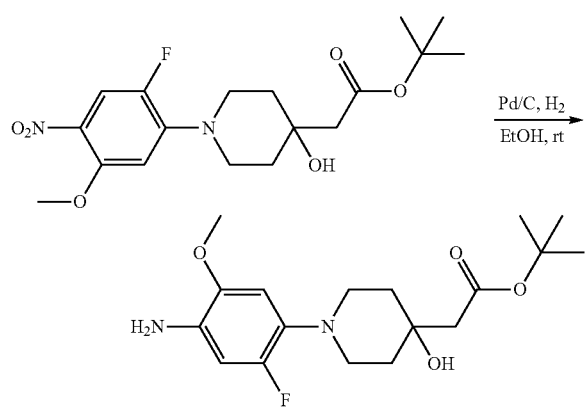

To a solution of tert-butyl 2-[1-(2-fluoro-5-methoxy-4-nitro-phenyl)-4-hydroxy-4-piperidyl]acetate (1 g, 2.60 mmol) in ethanol (10 mL) was added palladium, 10% in carbon (100 mg) under nitrogen. The mixture was stirred at 25° C. under hydrogen (15 psi) for 12 h. The reaction mixture was filtered through a pad of Celite and the filter cake was washed with ethanol (50 mL). The filtrate was concentrated under vacuum to give tert-butyl 2-[1-(4-amino-2-fluoro-5-methoxy-phenyl)-4-hydroxy-4-piperidyl]acetate (1 g, 2.60 mmol, >98% yield) as a brown solid. LCMS (ESI): m/z 355.1 [M+H]$^+$ Step 4: tert-butyl 2-[1-[4-[(2,6-dioxo-3-piperidyl)amino]-2-fluoro-5-methoxy-phenyl]-4-hydroxy-4-piperidyl]acetate

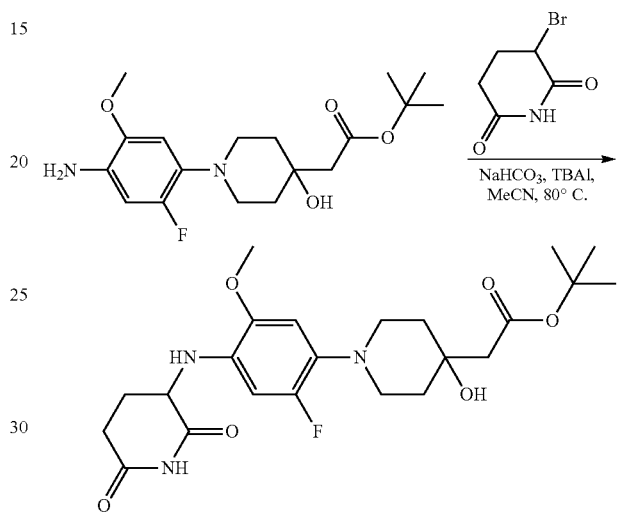

To a solution of tert-butyl 2-[1-(4-amino-2-fluoro-5-methoxy-phenyl)-4-hydroxy-4-piperidyl]acetate (200 mg, 564.31 μmol) and 3-bromopiperidine-2,6-dione (217 mg, 1.13 mmol) in acetonitrile (2 mL) were added sodium bicarbonate (142 mg, 1.69 mmol, 65.74 μL) and tetrabutylammonium iodide (21 mg, 56.85 μmol). The mixture was stirred at 80° C. for 16 h. After being cooled to 25° C., the reaction mixture was concentrated under reduce pressure. The residue was purified by column chromatography on silica gel (petroleum ether/ethyl acetate=5/1 to 1/4) to give tert-butyl 2-[1-[4-[(2,6-dioxo-3-piperidyl)amino]-2-fluoro-5-methoxy-phenyl]-4-hydroxy-4-piperidyl]acetate (200 mg, 421.04 μmol, 75% yield) as a brown solid. LCMS (ESI): m/z 466.2 [M+H]$^+$ Step 5: tert-butyl 2-[1-[4-[[2,6-dioxo-3-piperidyl]amino]-2-fluoro-5-methoxy-phenyl]-4-hydroxy-4-piperidyl]acetate, isomer 1 and tert-butyl 2-[1-[4-[[2,6-dioxo-3-piperidyl]amino]-2-fluoro-5-methoxy-phenyl]-4-hydroxy-4-piperidyl]acetate, isomer 2

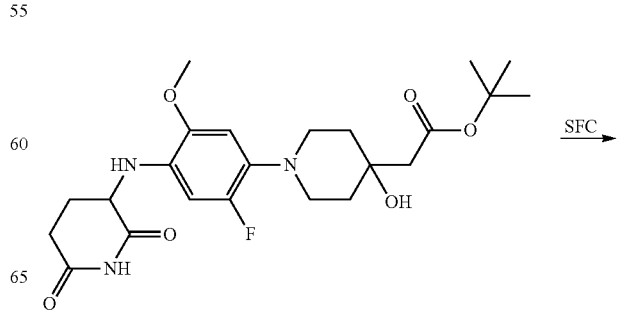

1309

-continued

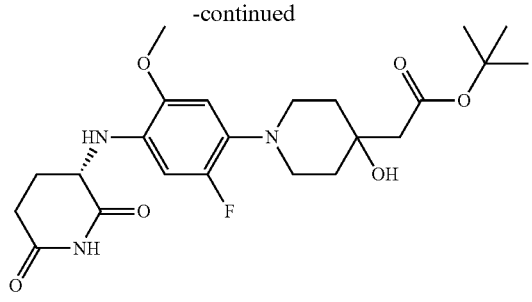

Isomer 1

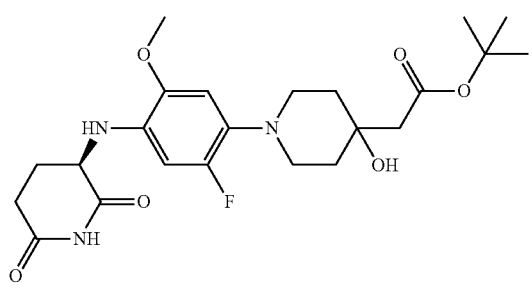

Isomer 2

Racemic tert-butyl 2-[1-[4-[(2,6-dioxo-3-piperidyl)amino]-2-fluoro-5-methoxy-phenyl]-4-hydroxy-4-piperidyl]acetate was separated by Chiral SFC (Isopropanol condition, column: Phenomenex-Cellulose-2 (250 mm×30 mm, 10 μm); B %: 50%-50%; 4.0 min, 25 min) to afford two sets of fractions. The first eluting set of fractions was evaporated to afford tert-butyl 2-[1-[4-[[2,6-dioxo-3-piperidyl]amino]-2-fluoro-5-methoxy-phenyl]-4-hydroxy-4-piperidyl]acetate, isomer 1 (100 mg, 212.67 μmol, 50% yield) as a brown solid (LCMS (ESI): m/z 466.1 [M+H]⁺). The second set of fractions was evaporated to afford tert-butyl 2-[1-[4-[[(3R)-2,6-dioxo-3-piperidyl]amino]-2-fluoro-5-methoxy-phenyl]-4-hydroxy-4-piperidyl]acetate (70 mg, 148.87 μmol, 35% yield) as a brown solid (LCMS (ESI): m/z 466.1 [M+H]⁺).

1310

Step 6: 2-[1-[4-[[2,6-dioxo-3-piperidyl]amino]-2-fluoro-5-methoxy-phenyl]-4-hydroxy-4-piperidyl]acetic acid, isomer 1

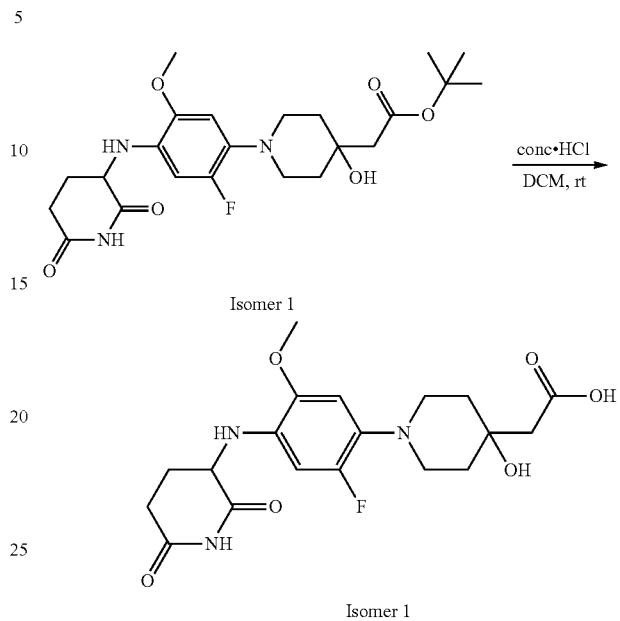

To a solution of tert-butyl 2-[1-[4-[[2,6-dioxo-3-piperidyl]amino]-2-fluoro-5-methoxy-phenyl]-4-hydroxy-4-piperidyl]acetate, isomer 1 (100 mg, 214.82 μmol) in dichloromethane (1.5 mL) was added hydrochloric acid (12 M, 0.1 mL). The mixture was stirred at 25° C. for 0.5 h. The mixture was concentrated under reduced pressure at 35° C. to give 2-[1-[4-[[2,6-dioxo-3-piperidyl]amino]-2-fluoro-5-methoxy-phenyl]-4-hydroxy-4-piperidyl]acetic acid, hydrochloride (92 mg, 196.02 μmol, 91% yield, HCl salt) as a brown oil. LCMS (ESI): m/z 410.1 [M+H]⁺

Step 7: 2-(6,7-dihydro-5H-pyrrolo[1,2-c]imidazol-1-yl)-2-[6-[4-[2-[2-[1-[4-[[(3S)-2,6-dioxo-3-piperidyl]amino]-2-fluoro-5-methoxy-phenyl]-4-hydroxy-4-piperidyl]acetyl]-2,6-diazaspiro[3.3]heptan-6-yl]phenyl]-4-fluoro-1-oxo-isoindolin-2-yl]-N-thiazol-2-yl-acetamide, isomer 1

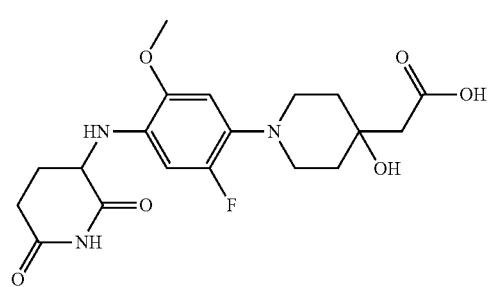

Isomer 1

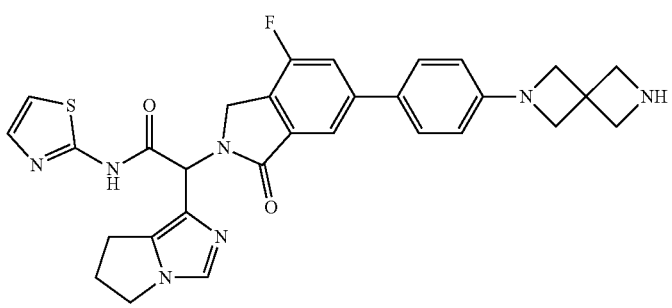

T3P
DIEA
DMF, 0° C.-rt

1311

1312

-continued

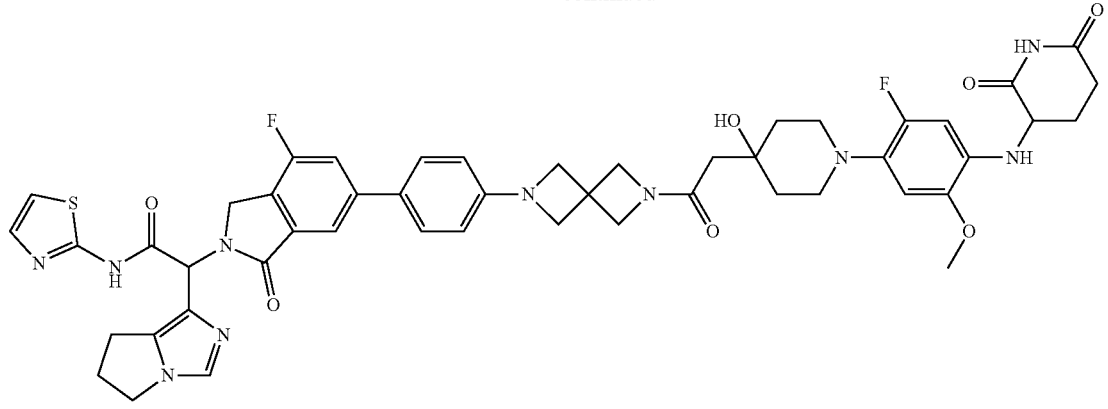

Isomer 1

To a solution of 2-[1-[4-[[2,6-dioxo-3-piperidyl]amino]-2-fluoro-5-methoxy-phenyl]-4-hydroxy-4-piperidyl]acetic acid, isomer 1, hydrochloride (92 mg, 206.34 μmol) in N,N-dimethylformamide (2 mL) were added N-ethyl-N-isopropylpropan-2-amine (192.92 mg, 1.49 mmol, 260.00 μL) and propylphosphonic anhydride, 50% in ethyl acetate (132 mg, 207.43 μmol) at 0° C. The mixture was stirred at 0° C. for 20 min. Then 2-[6-[4-(2,6-diazaspiro[3.3]heptan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide, trifluoroacetic acid salt (113 mg, 165.28 μmol) was added and the mixture was stirred at 25° C. for 12 h. The reaction mixture was filtered. The filtrate was purified by reversed phase column (flow: 40 mL/min; gradient: from 5-51% acetonitrile in water over 28 min; column: I.D. 31 mm×H 140 mm, Welch Ultimate Xb C18 20-40 m; 120 Å) and lyophilized to give Compound 173 (51.97 mg, 53.54 μmol, 26% yield) as a white solid. LCMS (ESI): m/z 961.3 [M+H]+, 1H NMR (400 MHz, DMSO-$d_6$) δ=12.50 (s, 1H), 10.84 (s, 1H), 7.74 (s, 1H), 7.70 (d, J=10.8 Hz, 1H), 7.64 (d, J=8.8 Hz, 2H), 7.60 (s, 1H), 7.48 (d, J=3.6 Hz, 1H), 7.25 (d, J=3.6 Hz, 1H), 6.62 (d, J=8.0 Hz, 1H), 6.58-6.50 (m, 3H), 6.14 (s, 1H), 5.07 (d, J=6.8 Hz, 1H), 4.83-4.74 (m, 2H), 4.38 (s, 2H), 4.28-4.18 (m, 2H), 4.08 (s, 2H), 4.04-3.92 (m, 6H), 3.79 (s, 3H), 3.23 (d, J=6.4 Hz, 2H), 3.00-2.91 (m, 2H), 2.91-2.82 (m, 2H), 2.82-2.82 (m, 1H), 2.82-2.72 (m, 2H), 2.56 (s, 1H), 2.43 (s, 1H), 2.23 (s, 2H), 2.17-2.08 (m, 1H), 1.98-1.84 (m, 1H), 1.82-1.72 (m, 2H), 1.63 (d, J=12.4 Hz, 2H).

Example 174. Synthesis of 2-(6,7-dihydro-5H-pyrrolo[1,2-c]imidazol-1-yl)-2-(6-(4-(7-(2-(4-(3-(2,4-dioxotetrahydropyrimidin-1(2H)-yl)-1-methyl-1H-indazol-6-yl)-3,3-difluoropiperidin-1-yl)acetyl)-2,7-diazaspiro[3.5]nonan-2-yl)phenyl)-4-fluoro-1-oxoisoindolin-2-yl)-N-(thiazol-2-yl)acetamide, Compound 175

Step 1: tert-Butyl 2-(4-(2-(1-(6,7-dihydro-5H-pyrrolo[1,2-c]imidazol-1-yl)-2-oxo-2-(thiazol-2-ylamino)ethyl)-7-fluoro-3-oxoisoindolin-5-yl)phenyl)-2,7-diazaspiro[3.5]nonane-7-carboxylate

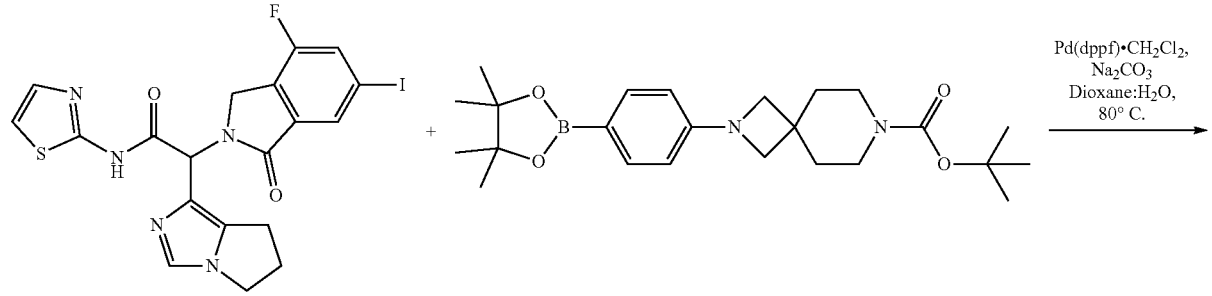

-continued

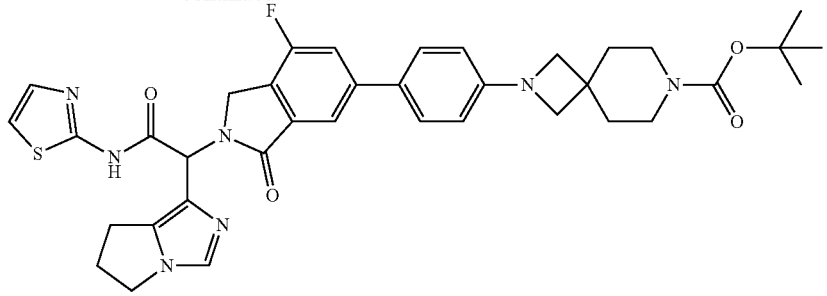

Into a 100 mL double-necked round-bottomed flask containing a well-stirred solution of 2-(6,7-dihydro-5H-pyrrolo[1,2-c]imidazol-1-yl)-2-(4-fluoro-6-iodo-1-oxo-isoindolin-2-yl)-N-thiazol-2-yl-acetamide (800 mg, 1.53 mmol) and tert-butyl 2-[4-(4,4,5,5-tetramethyl-1,3,2-dioxaborolan-2-yl)phenyl]-2,7-diazaspiro[3.5]nonane-7-carboxylate (785.82 mg, 1.83 mmol) in Dioxane (15 mL) was added Sodium carbonate (486.08 mg, 4.59 mmol, 192.12 μL) in Water (4 mL). The reaction mixture was degassed with nitrogen for 15 min and subsequently, [1,1' Bis(diphenylphosphino) ferrocene]dichloropalladium (II), complex with dichloromethane (124.77 mg, 152.87 μmol) was added and further degassed for 10 minutes. The resulting mixture was heated at 80° C. for 16 h. The reaction mixture was diluted with dichloromethane and filtered through celite, and the filtrate was concentrated under reduced pressure to get crude. The crude residue was purified by flash column chromatography using silica gel (100-200 mesh) eluting with 3% methanol in dichloromethane to get tert-butyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonane-7-carboxylate (400 mg, 549.14 μmol, 35.92% yield) as a light brown solid. LCMS (ESI+) m/z: 698.3 [M+H]+.

Step 2: 2-(6-(4-(2,7-diazaspiro[3.5]nonan-2-yl)phenyl)-4-fluoro-1-oxoisoindolin-2-yl)-2-(6,7-dihydro-5H-pyrrolo[1,2-c]imidazol-1-yl)-N-(thiazol-2-yl)acetamide

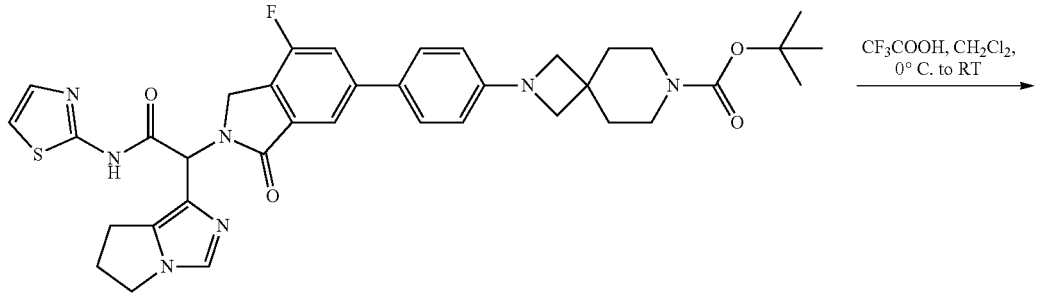

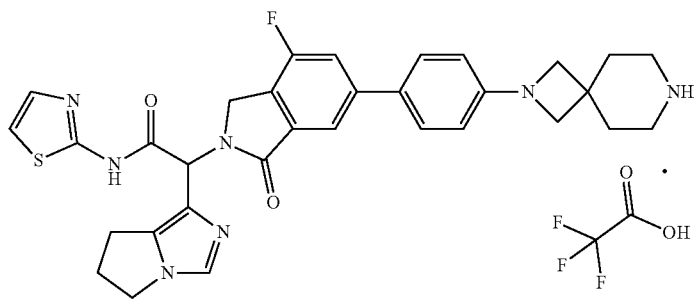

1315

Into a 100 mL single-necked round-bottomed flask containing a well-stirred solution of tert-butyl 2-[4-[2-[1-(6,7-dihydro-5H-pyrrolo[1,2-c]imidazol-1-yl)-2-oxo-2-(thiazol-2-ylamino)ethyl]-7-fluoro-3-oxo-isoindolin-5-yl]phenyl]-2,7-diazaspiro[3.5]nonane-7-carboxylate (400 mg, 573.21 µmol) in anhydrous dichloromethane (2.0 mL) at 0° C. was added trifluoroacetic acid (457.52 mg, 4.01 mmol, 309.13 µL) drop wise and the resulting mixture was stirred for 4 h at ambient temperature. Solvent was removed under reduced pressure. The residue was co-distilled with dichloromethane and triturated with Et$_2$O (50 mL) to afford 2-[6-[4-(2,7-diazaspiro[3.5]nonan-2-yl)phenyl]-4-fluoro-1-oxo-isoindo-

1316 lin-2-yl]-2-(6,7-dihydro-5H-pyrrolo[1,2-c]imidazol-1-yl)-N-thiazol-2-yl-acetamide; 2,2,2-trifluoroacetic acid (400 mg, 472.09 µmol, 82.36% yield) as an off white solid. LCMS (ESI+) m/z: 598.2 [M+H]$^+$.

Step 3: 2-(6,7-dihydro-5H-pyrrolo[1,2-c]imidazol-1-yl)-2-(6-(4-(7-(2-(4-(3-(2,4-dioxotetrahydropyrimidin-1(2H)-yl)-1-methyl-1H-indazol-6-yl)-3,3-difluoropiperidin-1-yl)acetyl)-2,7-diazaspiro[3.5]nonan-2-yl)phenyl)-4-fluoro-1-oxoisoindolin-2-yl)-N-(thiazol-2-yl)acetamide

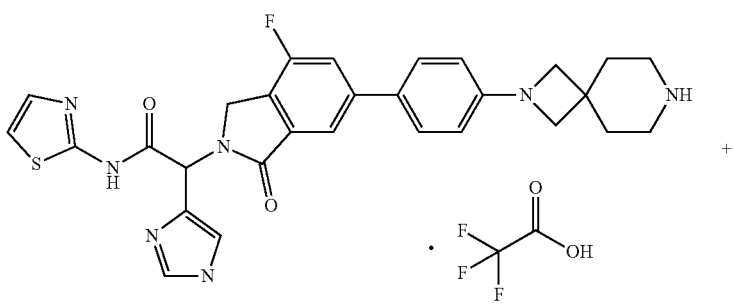

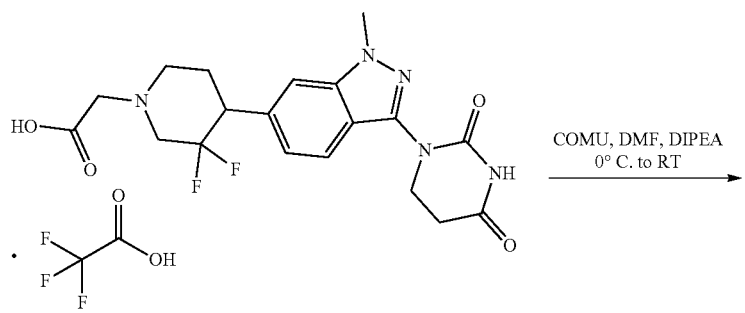

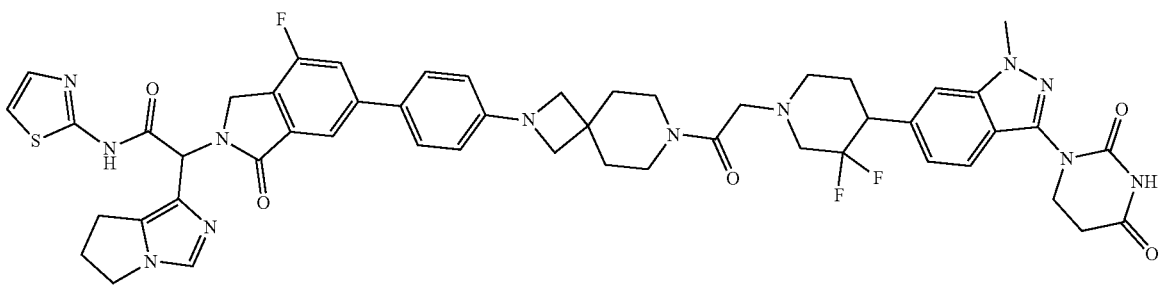

Into a 10 mL single-necked round-bottomed flask containing a well-stirred solution of 2-[6-[4-(2,7-diazaspiro[3.5]nonan-2-yl)phenyl]-4-fluoro-1-oxo-isoindolin-2-yl]-2-(6,7-dihydro-5H-pyrrolo[1,2-c]imidazol-1-yl)-N-thiazol-2-yl-acetamide; 2,2,2-trifluoroacetic acid (180 mg, 252.91 μmol) and 2-[4-[3-(2,4-dioxohexahydropyrimidin-1-yl)-1-methyl-indazol-6-yl]-3,3-difluoro-1-piperidyl]acetic acid; 2,2,2-trifluoroacetic acid (135.41 mg, 252.91 μmol) in N,N-dimethylformamide (2 mL) was added I-diisopropylethylamine (163.43 mg, 1.26 mmol, 220.26 μL) under nitrogen atmosphere at 0° C. Subsequently, (1-Cyano-2-ethoxy-2-oxoethylidenaminooxy)dimethylamino-morpholino-carbenium hexafluorophosphate (162.47 mg, 379.36 μmol) was added to the reaction mixture at 0° C. and the resulting mixture was stirred at ambient temperature for 1 h. The crude mixture was directly injected on a C18 column (100 g) for purification while eluting (0% to 50% of acetonitrile in water+ 0.1% ammonium acetate over 30 minutes, then steep gradient to 100% acetonitrile). The pure fraction was frozen and lyophilized to afford Compound 174 (130 mg, 129.47 μmol, 51.19% yield) as an off white solid. LCMS (ESI+) m/z: 1002.3 [M+H]$^+$. 1H-NMR (400 MHz, DMSO-d6): δ 12.50 (s, 1H), 10.58 (s, 1H), 7.75 (s, 1H), 7.71 (d, J=10.80 Hz, 1H), 7.65 (d, J=8.40 Hz, 2H), 7.61 (s, 1H), 7.59 (s, 1H), 7.55 (s, 1H), 7.48 (d, J=3.60 Hz, 1H), 7.26 (s, 1H), 7.10 (d, J=8.40 Hz, 1H), 6.54 (d, J=8.80 Hz, 2H), 6.14 (s, 1H), 4.81 (d, J=17.60 Hz, 1H), 4.21 (d, J=17.60 Hz, 1H), 4.02-3.96 (m, 4H), 3.93 (t, J=6.80 Hz, 3H), 3.70 (t, J=6.40 Hz, 4H), 3.51 (d, J=13.60 Hz, 5H), 3.42 (d, J=16.00 Hz, 3H), 3.29-3.21 (m, 2H), 3.02 (d, J=Hz, 1H), 2.68 (t, J=2.00 Hz, 3H), 2.34-2.33 (m, 1H), 1.89-1.84 (m, 3H), 1.73 (bs, 2H), (Water obscuration).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teaching of this invention that certain changes and modifications may be made thereto without departing from the spirit or scope of the invention as defined in the appended claims. Additionally, those skilled in the art will recognize, or be able to ascertain using no more than routine experimentation, many equivalents to the specific embodiments and methods described herein. Such equivalents are intended to be encompassed by the scope of the present application.

We claim:

1. A method of treating an EGFR mediated cancer comprising administering an effective amount of a compound of Formula:

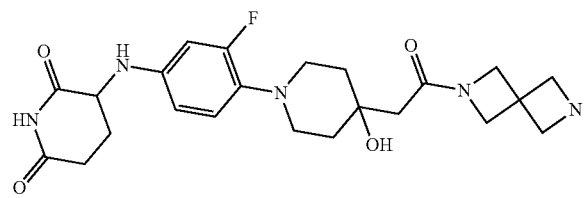

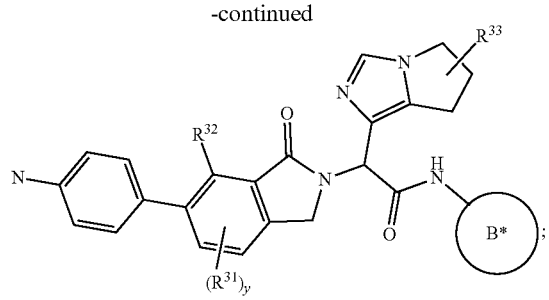

or a pharmaceutically acceptable salt thereof to a human in need thereof,
wherein:
y is 0, 1, 2, or 3;
B* is heteroaryl or aryl optionally substituted with 1, 2, or 3 $R^{31}$ substituents;
$R^{31}$ is independently selected at each occurrence from the group consisting of hydrogen, F, Cl, Br, I, $C_{1-6}$-alkyl, cyano, $C_{1-6}$-alkoxy, halo-$C_{1-6}$-alkoxy, halo-$C_{1-6}$-alkyl, $C_{3-8}$-cycloalkyl, and halo-$C_{3-8}$-cycloalkyl and can be located on either ring where present on a bicycle;
$R^{32}$ is hydrogen, F, Cl, Br, I, $C_{1-6}$-alkyl, halo-$C_{1-6}$-alkyl, $C_{3-8}$-cycloalkyl, or halo-$C_{3-8}$-cycloalkyl; and
$R^{33}$ is hydrogen, F, Cl, Br, I, $C_{1-6}$-alkyl, halo-$C_{1-6}$-alkyl, $C_{3-8}$-cycloalkyl, or halo-$C_{3-8}$-cycloalkyl and can be located on the dihydropyrrole or imidazole ring.

2. The method of claim 1, wherein B* is

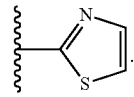

3. The method of claim 2, wherein y is 1.
4. The method of claim 3, wherein $R^{31}$ is selected from the group consisting of hydrogen, F, $C_{1-6}$-alkyl, cyano, $C_{1-6}$-alkoxy, and halo-$C_{1-6}$-alkyl.
5. The method of claim 3, wherein $R^{31}$ is F.
6. The method of claim 5, wherein $R^{32}$ is hydrogen.
7. The method of claim 6, wherein $R^{33}$ is hydrogen.
8. The method of claim 1, wherein B* is

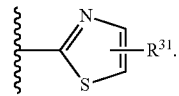

9. The method of claim 8, wherein $R^{31}$ is selected from the group consisting of hydrogen, F, $C_{1-6}$-alkyl, cyano, $C_{1-6}$-alkoxy, and halo-$C_{1-6}$-alkyl.
10. The method of claim 9, wherein $R^{32}$ is hydrogen.
11. The method of claim 10, wherein $R^{33}$ is hydrogen.
12. The method of claim 1, wherein $R^{32}$ is hydrogen.
13. The method of claim 12, wherein B* is

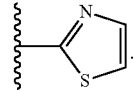

14. The method of claim 13, wherein y is 1.
15. The method of claim 1, wherein R$^{33}$ is hydrogen.
16. The method of claim 15, wherein B* is

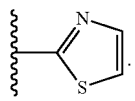

17. The method of claim 16, wherein y is 1.
18. The method of claim 1, wherein the compound is of structure:

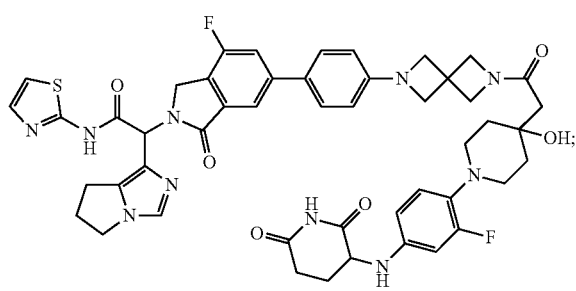 [SMILES: O=C1CCC(Nc2ccc(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1]

or a pharmaceutically acceptable salt thereof.

19. The method of claim 1, wherein the compound is of structure:

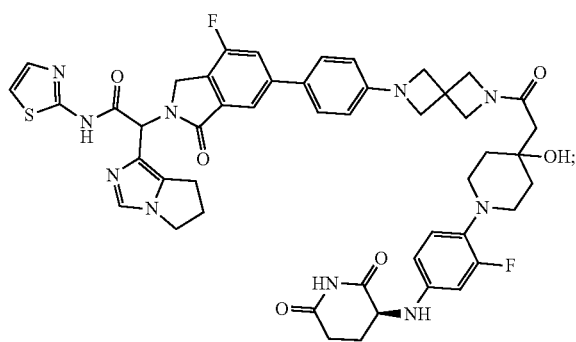 [SMILES: O=C1CC[C@H](Nc2ccc(N3CCC(O)(CC(=O)N4CC5(C4)CN(c4ccc(-c6cc(F)c7c(c6)C(=O)N(C(C(=O)Nc6nccs6)c6ncn8c6CCC8)C7)cc4)C5)CC3)c(F)c2)C(=O)N1]

or a pharmaceutically acceptable salt thereof.

20. The method of claim 1, wherein the compound is of structure:

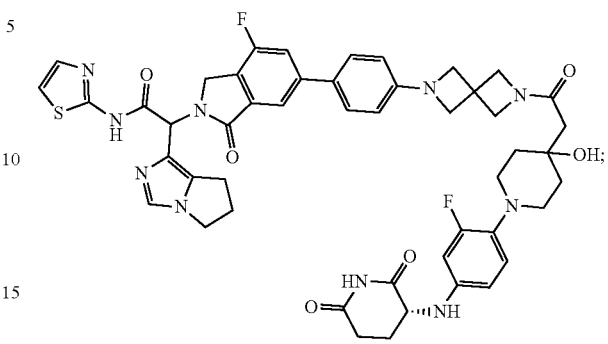

or a pharmaceutically acceptable salt thereof.

21. The method of claim 1, wherein the compound is administered orally.
22. The method of claim 19, wherein the compound is administered orally.
23. The method of claim 1, wherein the EGFR mediated cancer is selected from the group consisting of colon cancer, rectal cancer, lung cancer, breast cancer, head and neck cancer, glioblastoma, pancreatic cancer, thyroid cancer, astrocytoma, esophageal cancer, cervical cancer, synovial sarcoma, ovarian cancer, liver cancer, bladder cancer, and kidney cancer.
24. The method of claim 1, wherein the EGFR mediated cancer is a non-small-cell lung cancer.
25. The method of claim 1, wherein the EGFR mediated cancer is a small-cell lung cancer.
26. The method of claim 19, wherein the EGFR mediated cancer is selected from the group consisting of colon cancer, rectal cancer, lung cancer, breast cancer, head and neck cancer, glioblastoma, pancreatic cancer, thyroid cancer, astrocytoma, esophageal cancer, cervical cancer, synovial sarcoma, ovarian cancer, liver cancer, bladder cancer, and kidney cancer.
27. The method of claim 19, wherein the EGFR mediated cancer is a non-small-cell lung cancer.
28. The method of claim 19, wherein the EGFR mediated cancer is a small-cell lung cancer.

\* \* \* \* \*